US012570672B2

(12) United States Patent
Wurz et al.

(10) Patent No.: US 12,570,672 B2
(45) Date of Patent: Mar. 10, 2026

(54) MACROCYCLIC COMPOUNDS AND METHODS OF USE

(71) Applicant: AMGEN INC., Thousand Oaks, CA (US)

(72) Inventors: Ryan Paul Wurz, Newbury Park, CA (US); Yunxiao Li, Thousand Oaks, CA (US); Liping Pettus, Thousand Oaks, CA (US); Brian Alan Lanman, Woodland Hills, CA (US); Michael M. Yamano, Thousand Oaks, CA (US); Wei Zhao, Westford, MA (US); Benjamin Wigman, Woodland Hills, CA (US); Adriano Bauer, Newbury Park, CA (US); Andrew Smaligo, Thousand Oaks, CA (US); Shon K. Booker, Sherman Oaks, CA (US); John Stellwagen, Newbury Park, CA (US)

( * ) Notice: Subject to any disclaimer, the term of this patent is extended or adjusted under 35 U.S.C. 154(b) by 0 days.

(21) Appl. No.: 18/614,911

(22) Filed: Mar. 25, 2024

(65) Prior Publication Data

US 2024/0294551 A1 Sep. 5, 2024

Related U.S. Application Data

(63) Continuation of application No. PCT/US2023/079582, filed on Nov. 14, 2023.

(60) Provisional application No. 63/582,751, filed on Sep. 14, 2023, provisional application No. 63/497,978, filed on Apr. 24, 2023, provisional application No. 63/383,674, filed on Nov. 14, 2022.

(51) Int. Cl.

| | |
|---|---|
| *C07D 519/00* | (2006.01) |
| *A61K 31/519* | (2006.01) |
| *A61K 31/5377* | (2006.01) |
| *A61K 31/5383* | (2006.01) |
| *A61K 31/55* | (2006.01) |
| *A61K 31/551* | (2006.01) |
| *A61K 31/553* | (2006.01) |
| *C07D 471/22* | (2006.01) |
| *C07D 498/22* | (2006.01) |
| *C07D 513/22* | (2006.01) |

(52) U.S. Cl.

CPC .......... *C07D 519/00* (2013.01); *A61K 31/519* (2013.01); *A61K 31/5377* (2013.01); *A61K 31/5383* (2013.01); *A61K 31/55* (2013.01); *A61K 31/551* (2013.01); *A61K 31/553* (2013.01); *C07D 471/22* (2013.01); *C07D 498/22* (2013.01); *C07D 513/22* (2013.01)

(58) Field of Classification Search

CPC .. C07D 471/22; C07D 498/22; C07D 513/22; C07D 519/00; A61K 31/519; A61K 31/5377; A61K 31/5383; A61K 31/55; A61K 31/551; A61K 31/553

See application file for complete search history.

(56) References Cited

U.S. PATENT DOCUMENTS

| | | | |
|---|---|---|---|
| 10,519,146 B2 | 12/2019 | Lanman | |
| 10,590,090 B2 | 3/2020 | Koltun | |
| 10,640,504 B2 | 5/2020 | Lanman | |
| 2020/0017511 A1 | 1/2020 | Blank | |
| 2020/0239441 A1 | 7/2020 | Tamayo | |

FOREIGN PATENT DOCUMENTS

| | | |
|---|---|---|
| CA | 3211725 A1 | 9/2022 |
| WO | 2019075265 A1 | 4/2019 |
| WO | 2020132649 A1 | 6/2020 |
| WO | 2020132651 A1 | 6/2020 |
| WO | 2020132653 A1 | 6/2020 |
| WO | 2021041671 A1 | 3/2021 |
| WO | 2021147965 A1 | 7/2021 |
| WO | 2022133038 A1 | 6/2022 |
| WO | 2022246092 A1 | 11/2022 |
| WO | 2023040989 A1 | 3/2023 |
| WO | 2024040131 A1 | 2/2024 |

OTHER PUBLICATIONS

Caunt, C. J.; Sale, M. J.; Smith, P. D.; Cook, S. J. MEK1 and MEK2 inhibitors and cancer therapy: the long and winding road. Nat Rev Cancer 2015, 15, 577-592.

(Continued)

*Primary Examiner* — Sarah Pihonak
*Assistant Examiner* — Padmaja S Rao

(57) ABSTRACT

The present disclosure provides compounds useful for the inhibition of KRAS G12D, G12V, G12A, G12S, G13D, Q61H, Q61L or G12C. The compounds have a general Formula I':

(I')

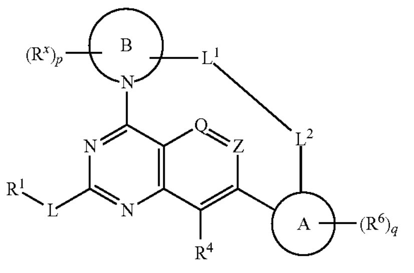

wherein the variables of Formula I' are defined herein. This disclosure also provides pharmaceutical compositions comprising the compounds, uses of the compounds, and compositions for treatment of, for example, cancer.

61 Claims, No Drawings

(56) References Cited

OTHER PUBLICATIONS

Cox, A. D.; Fesik, S. W.; Kimmelman, A. C.; Luo, J.; Der, C. J. Drugging the undruggable RAS: Mission possible? Nat Rev Drug Discov 2014, 13, 828-851.
Der, C. J.; Krontiris, T. G.; Cooper, G. M. Transforming genes of human bladder and lung carcinoma cell lines are homologous to the ras genes of Harvey and Kirsten sarcoma viruses. Proc Nat Acad Sci 1982, 79, 3637-3640.
Holderfield, M.; Deuker, M. M.; McCormick, F.; McMahon, M. Targeting RAF kinases for cancer therapy: BRAF-mutated melanoma and beyond. Nat Rev Cancer 2014, 14, 455-467.
Malumbres, M.; Barbacid, M. RAS oncogenes: the first 30 years. Nat Rev Cancer 2003, 3, 459-465. Sridhar, S. S.; Seymour, L.; Shepherd, F. A. Inhibitors of epidermal-growth-factor receptors: a review of clinical research with a focus on non-small-cell lung cancer. The Lancet Oncology 2003, 4, 397-406.
O'Bryan, J. P. Pharmacological targeting of RAS: Recent success with direct inhibitors. Pharmacol Res 2019, 139, 503-511.
Ostrem, J. M.; Peters, U.; Sos, M. L.; Wells, J. A.; Shokat, K. M. K-Ras(G12C) inhibitors allosterically control GTP affinity and effector interactions. Nature 2013, 503, 548-551.
Simanshu, D. K.; Nissley, D. V.; McCormick, F. RAS Proteins and Their Regulators in Human Disease. Cell 2017, 170, 17-33.
Sridhar, S. S.; Seymour, L.; Shepherd, F. A. Inhibitors of epidermal-growth-factor receptors: a review of clinical research with a focus on non-small-cell lung cancer. The Lancet Oncology 2003, 4, 397-406.
Vojtek, A. B.; Der, C. J. Increasing complexity of the Ras signaling pathway. J. Biol. Chem. 1998, 273, 19925-19928.

MACROCYCLIC COMPOUNDS AND METHODS OF USE

CROSS REFERENCE TO PRIOR APPLICATIONS

This application is a continuation of International Application PCT/US23/79582, filed Nov. 14, 2023, which claims the benefit of U.S. Provisional Patent Application No. 63/383,674, filed Nov. 14, 2022, U.S. Provisional Patent Application No. 63/497,978, filed Apr. 24, 2023 and U.S. Provisional Patent Application No. 63/582,751, filed Sep. 14, 2023, each of which is incorporated by reference in its entirety.

FIELD

The present disclosure provides compounds having activity as inhibitors of mutant KRAS proteins. This disclosure also provides pharmaceutical compositions comprising the compounds, uses and methods of treating certain disorders, such as cancer, including but not limited to non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

BACKGROUND

From its identification as one of the first human oncogenes in 1982 (Der et al., 1982), KRAS (the Kirsten rat sarcoma viral oncogene homologue) has been the focus of extensive academic and industrial research, as a key node in the MAPK signal transduction pathway, as a transforming factor in a network of parallel effector pathways (e.g., PI3K/AKT) (Vojtek et al., 1998) and as a potential target for anti-cancer agents (Malumbres et al., 2003). Despite progress in the development of inhibitors of upstream and downstream nodes in the MAPK pathway (e.g., EGFR (Sridhar et al., 2003), BRAF (Holderfield et al., 2014) and MEK (Caunt et al., 2015), the KRAS protein has historically proven resistant to direct inhibition.

KRAS is a G-protein that couples extracellular mitogenic signaling to intracellular, pro-proliferative responses. KRAS serves as an intracellular "on/off" switch. Mitogen stimulation induces the binding of GTP to KRAS, bringing about a conformational change which enables the interaction of KRAS with downstream effector proteins, leading to cellular proliferation. Normally, pro-proliferative signaling is regulated by the action of GTPase-activating proteins (GAPs), which return KRAS to its GDP-bound, non-proliferative state. Mutations in KRAS impair the regulated cycling of KRAS between these GDP- and GTP-bound states, leading to the accumulation of the GTP-bound active state and dysregulated cellular proliferation (Simanshu et al., 2017).

Attempts to develop inhibitors of mutated KRAS proteins have historically been thwarted by the absence of druggable pockets on the surface of the protein (Cox et al., 2014). In 2013, Shokat and colleagues identified covalent inhibitors of a common (O'Bryan, 2019) oncogenic mutant of KRAS, KRAS G12C, which bound to a previously unrecognized allosteric pocket on GDP-KRAS G12C and prevented its subsequent activation (Ostream et al., 2013). This discovery brought about significant new efforts in the KRAS inhibitor research, which have recently culminated in the entry of KRAS inhibitors in human clinical trials.

While some progress has been made on KRAS G12C inhibitors, there is a continued interest and effort to develop inhibitors of KRAS, particularly inhibitors of other KRAS such as KRAS G12D, G12V, G12A, G12S, G13D, Q61H, Q61L or G12C. Thus, there is a need to develop new inhibitors for KRAS G12D, G12V, G12A, G12S, G13D, Q61H, Q61L or G12C for the treatment of disorders, such as cancer.

SUMMARY

In a first aspect, the present application is directed to compound of formula (I'):

(I')

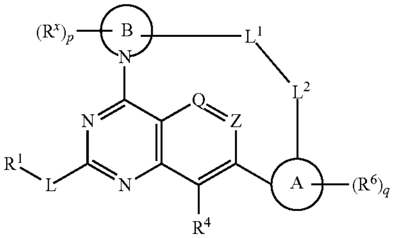

or a pharmaceutically acceptable salt of said compound, wherein;

Z is C—H, C-halogen, C—CN, C—$C_{1-4}$ alkyl, C—$C_{1-4}$ haloalkyl, C—$C_{1-4}$ alkoxy, C—$C_{1-4}$ haloalkoxy, C—$C_{3-7}$ cycloalkyl or N;

Q is CH, C-halogen, C—$C_{1-4}$ alkyl, C—$C_{1-4}$ haloalkyl or N;

B is a 4-15 membered heterocycloalkyl having 0-3 additional ring heteroatoms independently selected from O, S and N;

p is 0, 1, 2, 3 or 4;

q is 0, 1, 2 or 3;

each $R^x$ is independently hydroxyl, halogen, oxo, cyano, —$N(R^z)_2$, $C_{1-4}$ alkyl, $C_{1-4}$ deuteroalkyl, $C_{1-4}$ alkoxy, $C_{1-4}$ haloalkyl, $C_{1-4}$ haloalkoxy, $C_{1-4}$ hydroxyalkyl, 5-7 membered heteroaryl, —$S(O)_2$—$C_{1-4}$alkyl, —$S(O)_2N(R^z)_2$, —$C(O)R^z$, —$C(O)OR^z$, —$C(O)N(R^z)_2$, —$C_{1-4}$ alkylene-C(O)—$C_{1-4}$alkyl, —$C_{1-4}$ alkylene-$C(O)N(R^z)_2$, $C_{1-4}$ alkylene-$S(O)_2$—$C_{1-4}$alkyl, or —S—$C_{1-4}$alkyl;

L is a bond, $C_{1-6}$ alkylene, —O—$C_{1-6}$ alkylene, —S—$C_{1-6}$ alkylene, $NR^z$, O or S, wherein each $C_{1-6}$ alkylene, —O—$C_{1-6}$ alkylene and —S—$C_{1-6}$ alkylene chain is substituted with 0-2 occurrences of $R^2$;

$L^1$-$L^2$- is -$L^2$, —$N(R^z)C(O)$-$L^2$, —C(O)-$L^2$-, —OC(O)-$L^2$, —C(O)O-$L^2$, —OC(O)—O-$L^2$, —OC(S)—O-$L^2$, —O-$L^2$, —$N(R^z)C(O)O$-$L^2$, —$OC(O)N(R^z)$-$L^2$, —$N(R^z)$-$L^2$, —$S(O)_2$-$L^2$, —S-$L^2$, —S(O)-$L^2$, $C_{1-4}$ alkylene-C(O)-$L^2$, $C_{1-4}$ alkylene-C(O)O-$L^2$, —$C_{1-4}$ alkylene-OC(O)O-$L^2$, —$C_{1-4}$ alkylene-OC(O)-$L^2$, —$C_{1-4}$ alkylene-O-$L^2$, —$C_{1-4}$ alkylene-$S(O)_2$-$L^2$, —$C_{1-4}$ alkylene-S-$L^2$, —$C_{1-4}$ alkylene-S(O)-$L^2$, —O-5-6 membered heteroaryl-$L^2$, —$C_{1-4}$ alkylene-5-6 membered heteroaryl-$L^2$, —$C_{1-4}$ hydroxyalkylene-5-6-membered heteroaryl-$L^2$ or a 5-6 membered heteroaryl-$L^2$;

$L^2$ is $C_{1-6}$ alkylene, $C_{1-6}$ alkylene-O—, $C_{1-6}$ alkylene-O—$C_{1-6}$ alkylene, $C_{2-6}$ alkenylene, $C_{2-6}$ alkynylene, $C_{3-7}$ cycloalkylene, $C_{1-4}$ alkylene-$C_{3-7}$ cycloalkylene, $C_{1-4}$ haloalkylene-$C_{3-7}$ cycloalkylene, $C_{3-7}$ cycloalkylene-$C_{1-4}$ alkylene, $C_{1-6}$ hydroxyalkylene or $C_{1-6}$ haloalkylene;

$R^1$ is hydrogen, hydroxyl, $C_{6-10}$ aryl, 5-10 membered heteroaryl, $C_{3-8}$ cycloalkyl or 4-15 membered heterocycloalkyl, wherein each aryl, heteroaryl, cycloalkyl or heterocycloalkyl is substituted with 0-3 occurrences of $R^5$;

$R^2$ is halogen, hydroxyl, $C_{1-4}$ alkyl or two $R^2$ on the same or adjacent carbon atoms can be taken together to form a $C_{3-7}$ cycloalkyl; A is $C_{6-10}$ aryl or 5-10 membered heteroaryl and is substituted with q occurrences of $R^6$;

$R^4$ is hydrogen, hydroxyl, halogen, $C_{1-4}$ alkyl, $C_{1-4}$ alkoxy, $C_{1-4}$ haloalkyl, $C_{2-4}$ alkenyl, $C_{2-4}$ alkynyl, $C_{3-7}$ cycloalkyl or cyano;

each $R^5$ independently is halogen, cyano, oxo, -T-$R^y$, hydroxyl, —$N(R^z)_2$, $C_{1-4}$ alkyl, $C_{1-4}$ haloalkyl, $C_{1-4}$ alkoxy or —O—$C_{2-4}$ alkynyl;

each $R^6$ independently is halogen, hydroxyl, cyano, —$N(R^z)_2$, —C(O)$R^z$, —C(O)O$R^z$, $C_{1-4}$ alkyl, $C_{1-4}$ alkoxy, $C_{1-4}$ haloalkyl, $C_{1-4}$ haloalkoxy, $C_{2-4}$ alkynyl or $C_{3-6}$ cycloalkyl or two $R^6$ taken together on adjacent carbon atoms form a $C_{3-7}$ cycloalkyl;

T is $C_{1-4}$ alkylene, —$S(O)_2$—, —C(O)—, —$C_{1-4}$ alkylene-C(O)—, $C_{1-4}$ alkylene-$S(O)_2$— or —S—;

$R^y$ is $C_{1-4}$ alkyl, $C_{1-4}$ haloalkyl, hydroxyl, cyano or —$N(R^z)_2$; and each $R^z$ is hydrogen or $C_{1-4}$ alkyl.

In a second aspect, provided herein is a pharmaceutical composition comprising a compound described herein or a pharmaceutically acceptable salt of said compound and a pharmaceutically acceptable excipient.

In a third aspect, provided herein is a compound described herein, or a pharmaceutically acceptable salt of said compound, or the pharmaceutical composition as described herein for use in treating cancer (e.g., non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma).

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as embodiment 1 is a compound of formula (I'):

(I')

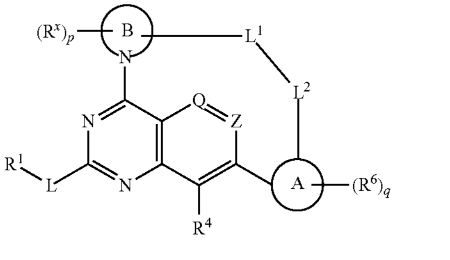

or a pharmaceutically acceptable salt of said compound, wherein;

Z is C—H, C-halogen, C—CN, C—$C_{1-4}$ alkyl, C—$C_{1-4}$ haloalkyl, C—$C_{1-4}$ alkoxy, C—$C_{1-4}$ haloalkoxy, C—$C_{3-7}$ cycloalkyl or N;

Q is CH, C-halogen, C—$C_{1-4}$ alkyl, C—$C_{1-4}$ haloalkyl or N;

B is a 4-15 membered heterocycloalkyl having 0-3 additional ring heteroatoms independently selected from O, S and N;

p is 0, 1, 2, 3 or 4;

q is 0, 1, 2 or 3;

each $R^x$ is independently hydroxyl, halogen, oxo, cyano, —$N(R^z)_2$, $C_{1-4}$ alkyl, $C_{1-4}$ deuteroalkyl, $C_{1-4}$ alkoxy, $C_{1-4}$ haloalkyl, $C_{1-4}$ haloalkoxy, $C_{1-4}$ hydroxyalkyl, 5-7 membered heteroaryl, —$S(O)_2$—$C_{1-4}$alkyl, —$S(O)_2N(R^z)_2$, —C(O)$R^z$, —C(O)O$R^z$, —C(O)$N(R^z)_2$, —$C_{1-4}$ alkylene-C(O)—$C_{1-4}$alkyl, —$C_{1-4}$ alkylene-C(O)$N(R^z)_2$, $C_{1-4}$ alkylene-$S(O)_2$—$C_{1-4}$alkyl, or —S—$C_{1-4}$alkyl;

L is a bond, $C_{1-6}$ alkylene, —O—$C_{1-6}$ alkylene, —S—$C_{1-6}$ alkylene, N$R^z$, O or S, wherein each $C_{1-6}$ alkylene, —O—$C_{1-6}$ alkylene and —S—$C_{1-6}$ alkylene chain is substituted with 0-2 occurrences of $R^2$;

-$L^1$-$L^2$- is -$L^2$, —$N(R^z)C(O)$-$L^2$, —C(O)-$L^2$-, —OC(O)-$L^2$, —C(O)O-$L^2$, —OC(O)—O-$L^2$, —OC(S)—O-$L^2$, —O-$L^2$, —$N(R^z)C(O)O$-$L^2$, —OC(O)$N(R^z)$-$L^2$, —$N(R^z)$-$L^2$, —$S(O)_2$-$L^2$, —S-$L^2$, —S(O)-$L^2$, $C_{1-4}$ alkylene-C(O)-$L^2$, $C_{1-4}$ alkylene-C(O)O-$L^2$, —$C_{1-4}$ alkylene-OC(O)O-$L^2$, —$C_{1-4}$ alkylene-OC(O)-$L^2$, —$C_{1-4}$ alkylene-O-$L^2$, —$C_{1-4}$ alkylene-$S(O)_2$-$L^2$, —$C_{1-4}$ alkylene-S-$L^2$, —$C_{1-4}$ alkylene-S(O)-$L^2$, —O-5-6 membered heteroaryl-$L^2$, —$C_{1-4}$ alkylene-5-6 membered heteroaryl-$L^2$, —$C_{1-4}$ hydroxyalkylene-5-6-membered heteroaryl-$L^2$ or a 5-6 membered heteroaryl-$L^2$;

$L^2$ is $C_{1-6}$ alkylene, $C_{1-6}$ alkylene-O—, $C_{1-6}$ alkylene-O—$C_{1-6}$ alkylene, $C_{2-6}$ alkenylene, $C_{2-6}$ alkynylene, $C_{3-7}$ cycloalkylene, $C_{1-4}$ alkylene-$C_{3-7}$ cycloalkylene, $C_{1-4}$ haloalkylene-$C_{3-7}$ cycloalkylene, $C_{3-7}$ cycloalkylene-$C_{1-4}$ alkylene, $C_{1-6}$ hydroxyalkylene or $C_{1-6}$ haloalkylene;

$R^1$ is hydrogen, hydroxyl, $C_{6-10}$ aryl, 5-10 membered heteroaryl, $C_{3-8}$ cycloalkyl or 4-15 membered heterocycloalkyl, wherein each aryl, heteroaryl, cycloalkyl or heterocycloalkyl is substituted with 0-3 occurrences of $R^5$;

$R^2$ is halogen, hydroxyl, $C_{1-4}$ alkyl or two $R^2$ on the same or adjacent carbon atoms can be taken together to form a $C_{3-7}$ cycloalkyl; A is $C_{6-10}$ aryl or 5-10 membered heteroaryl and is substituted with q occurrences of $R^6$;

$R^4$ is hydrogen, hydroxyl, halogen, $C_{1-4}$ alkyl, $C_{1-4}$ alkoxy, $C_{1-4}$ haloalkyl, $C_{2-4}$ alkenyl, $C_{2-4}$ alkynyl, $C_{3-7}$ cycloalkyl or cyano;

each $R^5$ independently is halogen, cyano, oxo, -T-$R^y$, hydroxyl, —$N(R^z)_2$, $C_{1-4}$ alkyl, $C_{1-4}$ haloalkyl, $C_{1-4}$ alkoxy or —O—$C_{2-4}$ alkynyl;

each $R^6$ independently is halogen, hydroxyl, cyano, —$N(R^z)_2$, —C(O)$R^z$, —C(O)O$R^z$, $C_{1-4}$ alkyl, $C_{1-4}$ alkoxy, $C_{1-4}$ haloalkyl, $C_{1-4}$ haloalkoxy, $C_{2-4}$ alkynyl or $C_{3-6}$ cycloalkyl or two $R^6$ taken together on adjacent carbon atoms form a $C_{3-7}$ cycloalkyl;

T is $C_{1-4}$ alkylene, —$S(O)_2$—, —C(O)—, —$C_{1-4}$ alkylene-C(O)—, $C_{1-4}$ alkylene-$S(O)_2$— or —S—;

$R^y$ is halogen, oxo, $C_{1-4}$ alkyl, $C_{1-4}$ haloalkyl, hydroxyl, cyano or —$N(R^z)_2$; and each $R^z$ is hydrogen or $C_{1-4}$ alkyl.

Provided herein as embodiment 2 is the compound or salt according to embodiment 1, wherein B is a 4-10 membered heterocycloalkyl having one additional oxygen heteroatom. Provided herein as embodiment 3 is the compound or salt according to embodiment 2, wherein p is 0. Provided herein as embodiment 4 is the compound or salt according to embodiment 3, wherein B-$L^1$ is

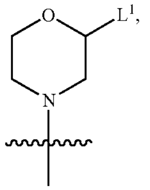
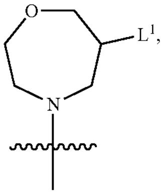
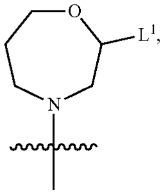

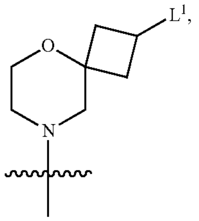
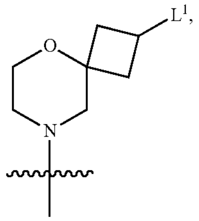

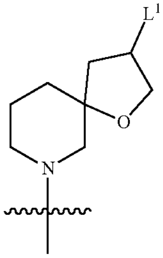
or
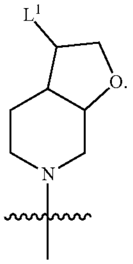

Provided herein as embodiment 5 is the compound or salt according to embodiment, wherein B-$L^1$ is

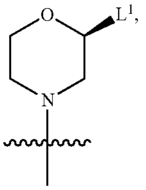
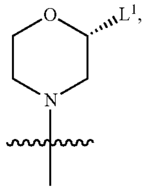
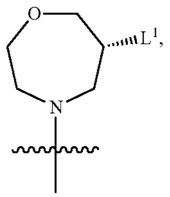
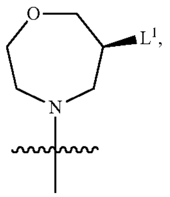
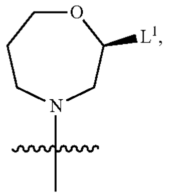
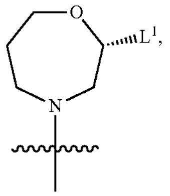

-continued

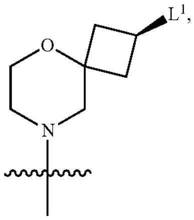
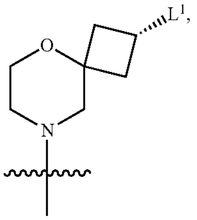
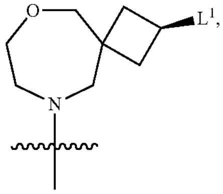
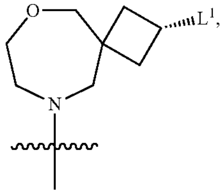
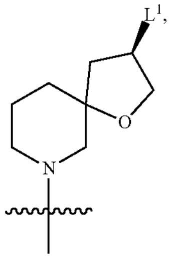
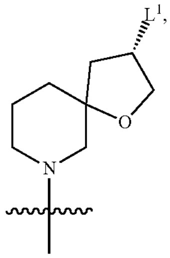
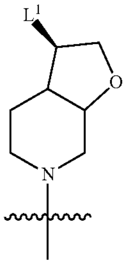
or
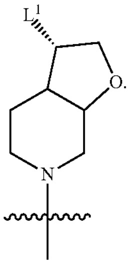

Provided herein as embodiment 6 is the compound or salt according to embodiment 5, wherein B-$L^1$ is

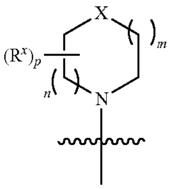
is
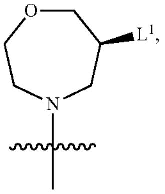

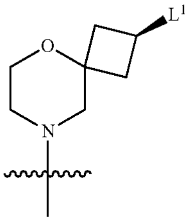
or
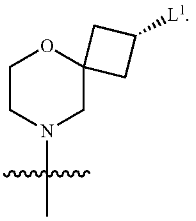

Provided herein as embodiment 7 is the compound or salt according to embodiment 6, wherein

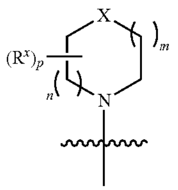 is 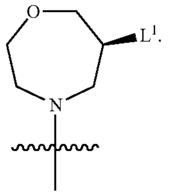

Provided herein as embodiment 8 is the compound or salt according to embodiment 6, wherein

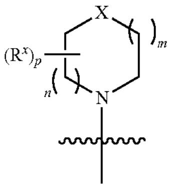 is 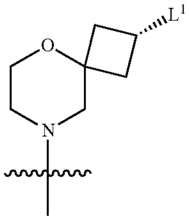 .

Provided herein as embodiment 9 is the compound or salt according to embodiment 6, wherein

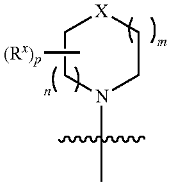 is 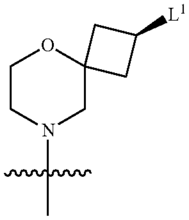 .

Provided herein as embodiment 10 is the compound or salt according to embodiment 1, wherein B is a 4-10 membered heterocycloalkyl having one additional nitrogen heteroatom. Provided herein as embodiment 11 is the compound or salt according to embodiment 10, wherein p is 0. Provided herein as embodiment 12 is the compound or salt according to embodiment 11, wherein B-$L^1$ is

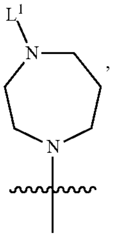 , 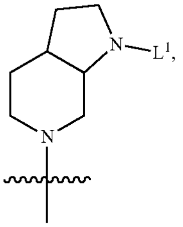 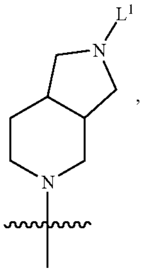 ,

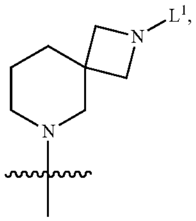 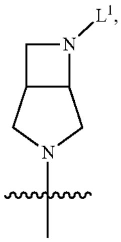

-continued

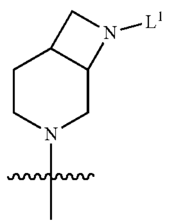 or 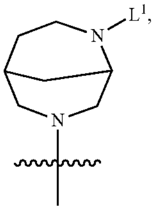

Provided herein as embodiment 13 is the compound or salt according to embodiment 12, wherein B-$L^1$ is

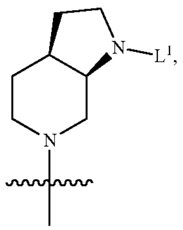 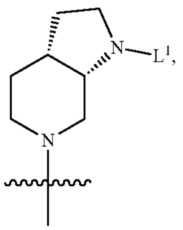 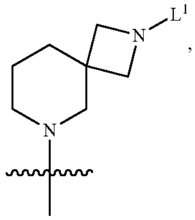 ,

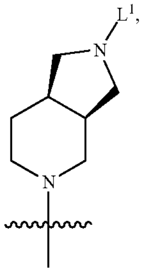 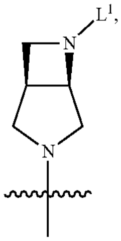 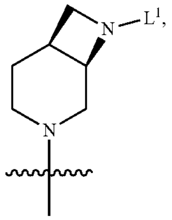

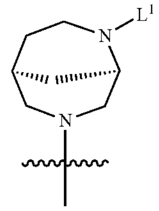 or 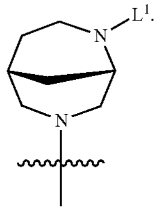

Provided herein as embodiment 14 is the compound or salt according to embodiment 13, wherein B-$L^1$ is

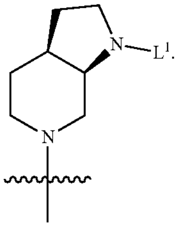

Provided herein as embodiment 15 is the compound or salt according to embodiment 1, wherein B is a 4-10 membered heterocycloalkyl having 0 additional heteroatoms. Provided herein as embodiment 16 is the compound or salt according to embodiment 15, wherein p is 0. Provided herein as embodiment 17 is the compound or salt according to embodiment 16, wherein B-$L^1$ is

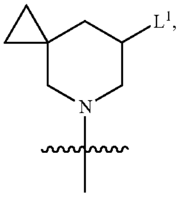
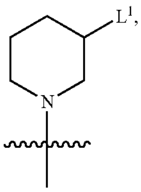
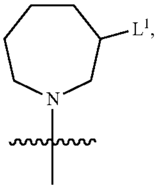
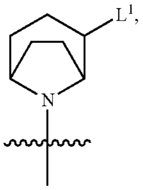
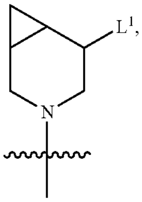
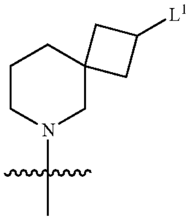
or
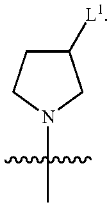

Provided herein as embodiment 18 is the compound or salt according to embodiment 17, wherein B-$L^1$ is,

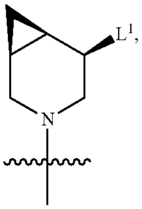
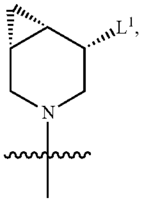
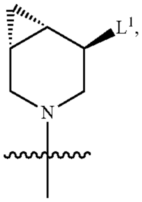
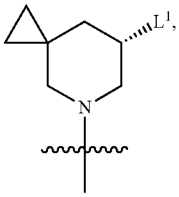
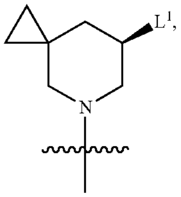
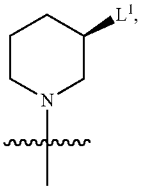
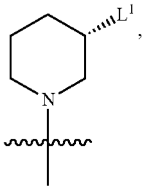
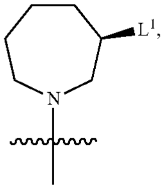
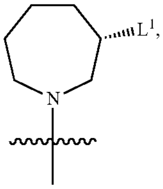
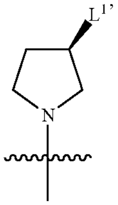
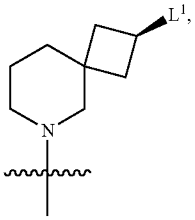
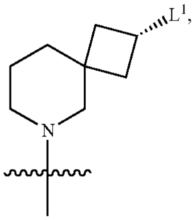

-continued

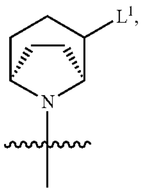
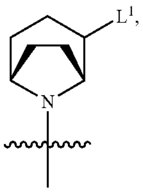
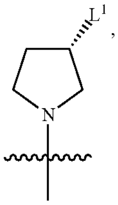
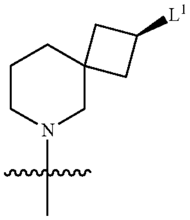
or
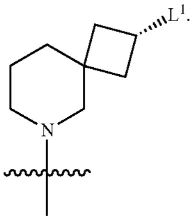

Provided herein as embodiment 19 is the compound or salt according to embodiment 18, wherein B-$L^1$ is

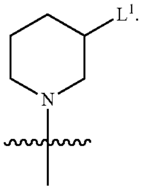

Provided herein as embodiment 20 is the compound or salt according to embodiment 18, wherein B-$L^1$ is

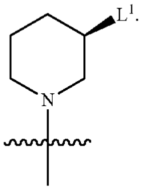

Provided herein as embodiment 21 is the compound or salt according to embodiment 18, wherein B-$L^1$ is

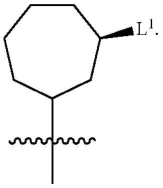

Provided herein as embodiment 22 is the compound or salt according to embodiment 18, wherein B-$L^1$ is

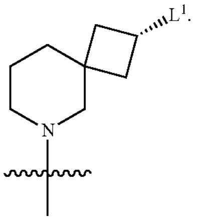

Provided herein as embodiment 23 is the compound or salt according to embodiment 1, wherein B is a 4-10 membered heterocycloalkyl having one additional oxygen heteroatom. Provided herein as embodiment 24 is the compound or salt according to embodiment 23, wherein p is 1. Provided herein as embodiment 25 is the compound or salt according to embodiment 24, wherein B-$L^1$ is

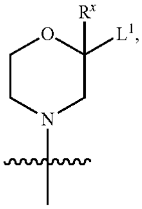 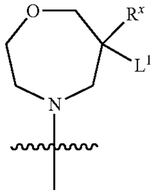 or

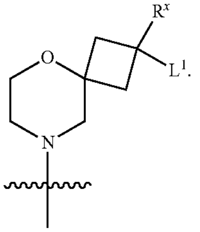

Provided herein as embodiment 26 is the compound or salt according to embodiment 24 or 25, wherein $R^x$ is $C_{1-4}$ alkyl, $C_{1-4}$ haloalkyl or $C_{1-4}$ deuteroalkyl. Provided herein as embodiment 27 is the compound or salt according to embodiment 26, wherein $R^x$ is methyl, $CD_3$ or monofluoromethyl.

Provided herein as embodiment 28 is the compound or salt according to embodiment 27, wherein B-$L^1$ is

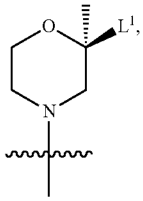 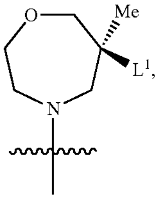 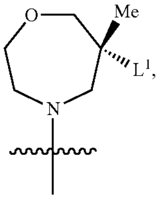

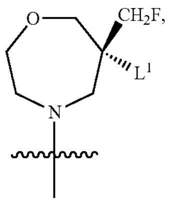 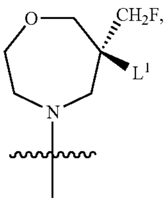 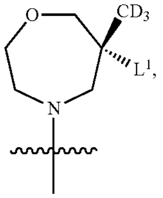

-continued

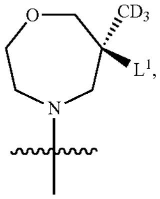 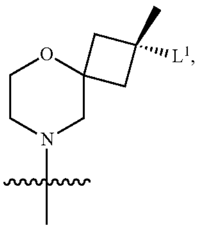 or

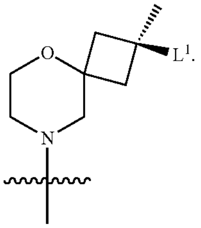

Provided herein as embodiment 29 is the compound or

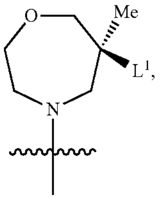 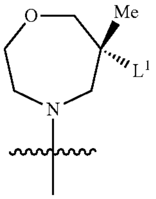 or

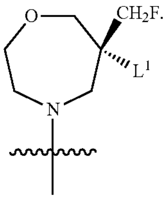

salt according to embodiment 28, wherein B-$L^1$ is Provided herein as embodiment 30 is the compound or salt according to embodiment 29, wherein B-$L^1$ is

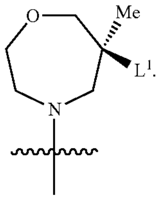

Provided herein as embodiment 31 is the compound or salt according to embodiment 29, wherein B-$L^1$ is

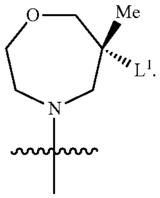

Provided herein as embodiment 32 is the compound or salt according to embodiment 29, wherein B-$L^1$ is

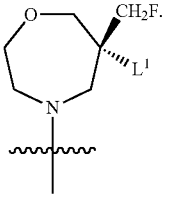

Provided herein as embodiment 33 is the compound or salt according to embodiment 1, wherein B is a 4-10 membered heterocycloalkyl having 0 additional heteroatoms. Provided herein as embodiment 34 is the compound or salt according to embodiment 33, wherein p is 1. Provided herein as embodiment 35 is the compound or salt according to embodiment 34, wherein B-$L^1$ is

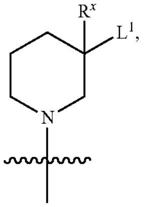 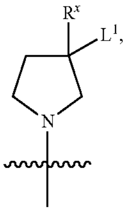 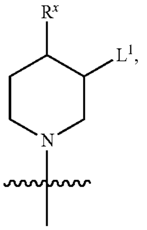

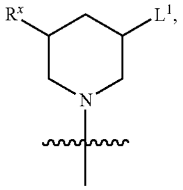 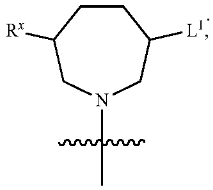

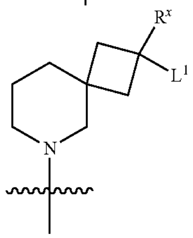 or 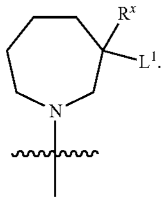

Provided herein as embodiment 36 is the compound or salt according to embodiment 35, wherein $R^x$ is halogen, hydroxyl, $C_{1-4}$ haloalkyl or $C_{1-4}$ alkyl. Provided herein as embodiment 37 is the compound or salt according to embodiment 36, wherein $R^x$ is fluorine, hydroxyl, methyl or monofluoromethyl.

Provided herein as embodiment 38 is the compound or salt according to embodiment 37, wherein B-$L^1$ is

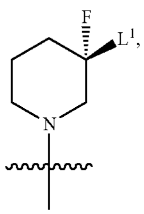 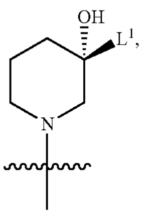 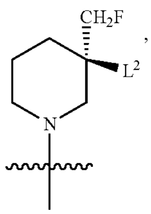 ,

-continued

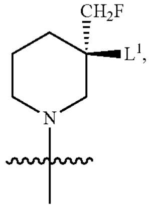 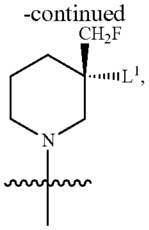 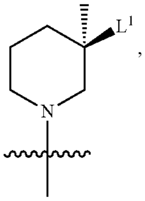 ,

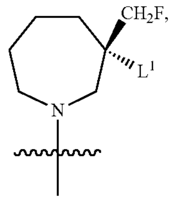 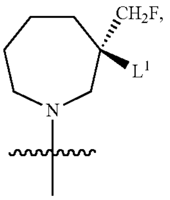 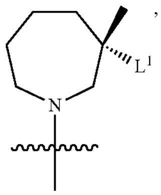 ,

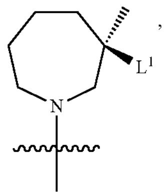 , 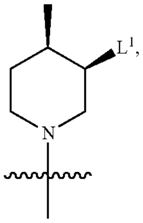 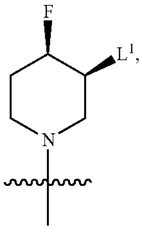

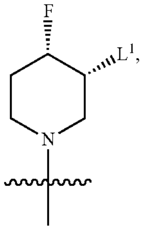 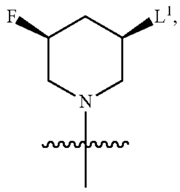 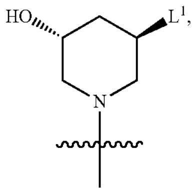

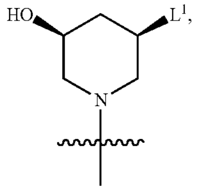 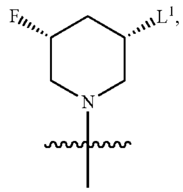

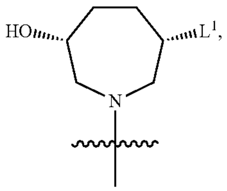 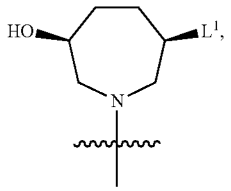

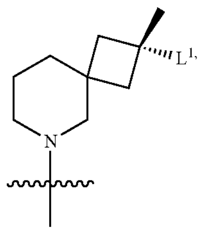 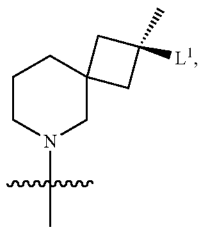

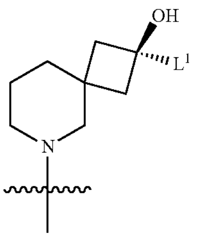 or 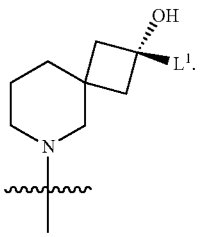

Provided herein as embodiment 39 is the compound or salt according to embodiment 38, wherein B-$L^1$ is

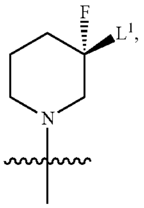
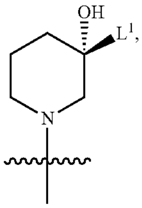
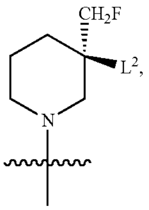
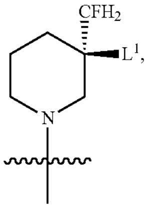
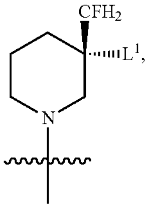
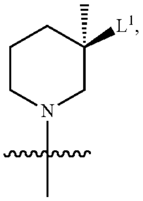
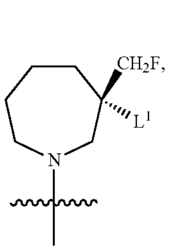
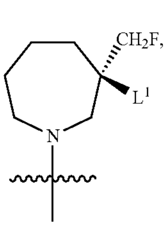
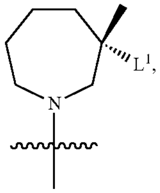
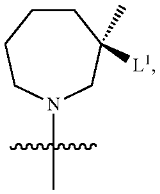
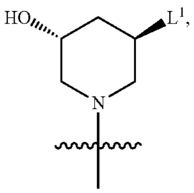
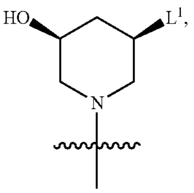
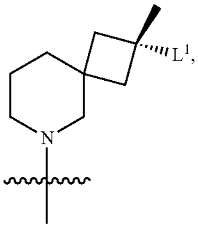
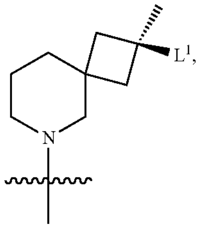
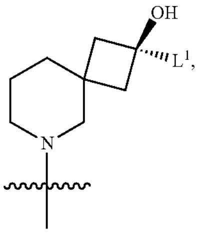
or
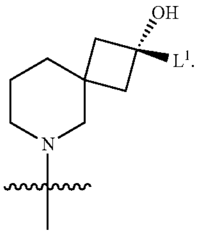

Provided herein as embodiment 40 is the compound or salt according to embodiment 39, wherein B-$L^1$ is

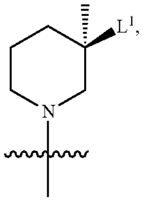
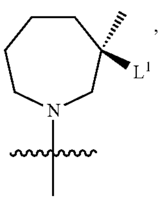
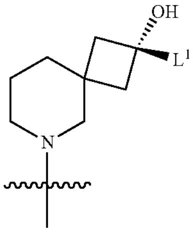
or
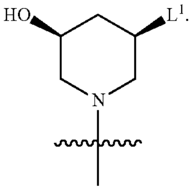

Provided herein as embodiment 41 is the compound or salt according to any one of embodiment 40, wherein B-$L^1$ is

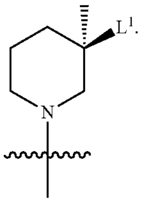

Provided herein as embodiment 42 is the compound or salt according to embodiment 40, wherein B-$L^1$ is

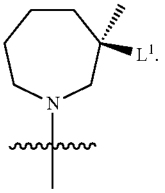

Provided herein as embodiment 43 is the compound or salt according to embodiment 40, wherein B-$L^1$ is

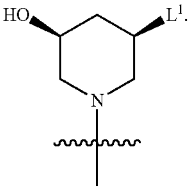

Provided herein as embodiment 44 is the compound or salt according to embodiment 40, wherein B-$L^1$ is

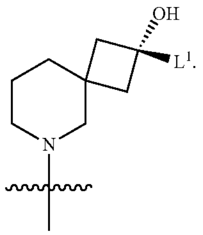

Provided herein as embodiment 45 is the compound or salt according to embodiment 1, wherein B is a 4-10 membered heterocycloalkyl having 0 additional heteroatoms. Provided herein as embodiment 46 is the compound or salt according to embodiment 45, wherein p is 2. Provided herein as embodiment 47 is the compound or salt according to embodiment 46, wherein B-$L^1$ is

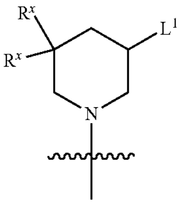

or

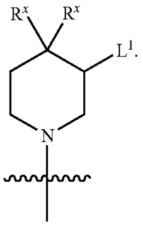

Provided herein as embodiment 48 is the compound or salt according to embodiment 47, wherein each $R^x$ is independently halogen. Provided herein as embodiment 49 is the compound or salt according to embodiment 48, wherein both $R^x$ are fluorine. Provided herein as embodiment 50 is the compound or salt according to embodiment 49, wherein B-$L^1$ is

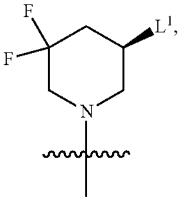

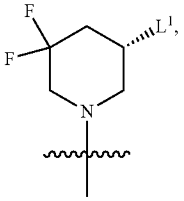

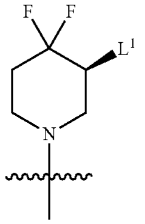

or

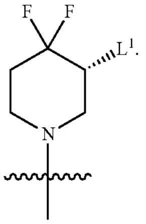

Provided herein as embodiment 51 is the compound or salt according to embodiment 1, wherein B is a 4-10 membered heterocycloalkyl having one additional nitrogen heteroatom. Provided herein as embodiment 52 is the compound or salt according to embodiment 51, wherein p is 2. Provided herein as embodiment 53 is the compound or salt according embodiment 52, wherein B-$L^1$ is

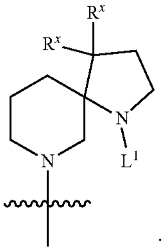

Provided herein as embodiment 54 is the compound or salt according to embodiment 53, wherein each $R^x$ is independently halogen. Provided herein as embodiment 55 is the compound or salt according to embodiment 54, wherein both $R^x$ are fluorine. Provided herein as embodiment 56 is the compound or salt according to embodiment 55, wherein B-$L^1$ is

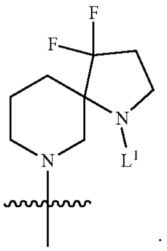

Provided herein as embodiment 57 is the compound or salt according to embodiment 1 and is a compound of formula (I):

(I)

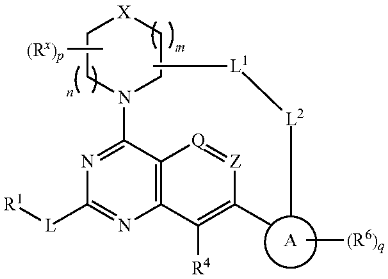

or a pharmaceutically acceptable salt of said compound, wherein;

X is N, $CH_2$, O, S, S(O), S(O)($NR^z$) or $S(O)_2$;

Z is C—H, C-halogen, C—CN, C—$C_{1-4}$ alkyl, C—$C_{1-4}$ haloalkyl, C—$C_{1-4}$ alkoxy, C—$C_{1-4}$ haloalkoxy, C—$C_{3-7}$ cycloalkyl or N;

Q is CH, C-halogen, C—$C_{1-4}$ alkyl, C—$C_{1-4}$ haloalkyl or N;

n is 0, 1, 2, or 3;

m is 0, 1, 2 or 3;

p is 0, 1, 2 or 3;

q is 0, 1, 2 or 3;

xhaloalkyl, $C_{1-4}$ haloalkoxy, 5-7 membered heteroaryl, -T-$R^y$ or two $R^x$ taken together with the same carbon or adjacent carbon atoms can form $C_{3-7}$ cycloalkyl, a 3-7 membered heterocycloalkyl, wherein each $C_{3-7}$ cycloalkyl or 3-7 membered heterocycloalkyl is further substituted with 0-3 occurrences of R or two $R^x$ taken together can form a bridged ring where the bridge is selected from one of the following: —$C_{1-4}$ alkylene, —$C_{1-4}$ alkylene-O—$C_{1-4}$ alkylene-, —O—, —S— or —$C_{1-4}$ alkylene-S—$C_{1-4}$ alkylene- and wherein each $C_{1-4}$ alkylene is further substituted with 0-2 occurrences of $R^y$;

L is a bond, $C_{1-6}$ alkylene, —O—$C_{1-6}$ alkylene, —S—$C_{1-6}$ alkylene, $NR^z$, O or S, wherein each $C_{1-6}$ alkylene, —O—$C_{1-6}$ alkylene and —S—$C_{1-6}$ alkylene chain is substituted with 0-2 occurrences of $R^2$;

-$L^1$-$L^2$- is -$L^2$, —N($R^z$)C(O)-$L^2$, —C(O)-$L^2$-, —OC(O)-$L^2$, —C(O)O-$L^2$, —OC(O)—O-$L^2$, —OC(S)—O-$L^2$, —O-$L^2$, —N($R^z$)C(O)O-$L^2$, —OC(O)N($R^z$)-$L^2$, —N($R^z$)-$L^2$, —$S(O)_2$-$L^2$, —S-$L^2$, —S(O)-$L^2$, $C_{1-4}$ alkylene-C(O)-$L^2$, $C_{1-4}$ alkylene-C(O)O-$L^2$, —$C_{1-4}$ alkylene-OC(O)O-$L^2$, —$C_{1-4}$ alkylene-OC(O)-$L^2$, —$C_{1-4}$ alkylene-O-$L^2$, —$C_{1-4}$ alkylene-$S(O)_2$-$L^2$, —$C_{1-4}$ alkylene-S-$L^2$, —$C_{1-4}$ alkylene-S(O)-$L^2$, —O-5-6 membered heteroaryl-$L^2$, —$C_{1-4}$ alkylene-5-6 membered heteroaryl-$L^2$, —$C_{1-4}$ hydroxyalkylene-5-6-membered heteroaryl-$L^2$ or a 5-6 membered heteroaryl-$L^2$;

$L^2$ is $C_{1-6}$ alkylene, $C_{1-6}$ alkylene-O—, $C_{1-6}$ alkylene-O—$C_{1-6}$ alkylene, $C_{2-6}$ alkenylene, $C_{2-6}$ alkynylene, $C_{3-7}$ cycloalkylene, $C_{1-4}$ alkylene-$C_{3-7}$ cycloalkylene, $C_{1-4}$ haloalkylene-$C_{3-7}$ cycloalkylene, $C_{3-7}$ cycloalkylene-$C_{1-4}$ alkylene, $C_{1-6}$ hydroxyalkylene or $C_{1-6}$ haloalkylene;

$R^1$ is hydrogen, hydroxyl, $C_{6-10}$ aryl, 5-10 membered heteroaryl, $C_{3-8}$ cycloalkyl or 4-15 membered heterocycloalkyl, wherein each aryl, heteroaryl, cycloalkyl or heterocycloalkyl is substituted with 0-3 occurrences of $R^5$;

$R^2$ is halogen, hydroxyl, $C_{1-4}$ alkyl or two $R^2$ on the same or adjacent carbon atoms can be taken together to form a $C_{3-7}$ cycloalkyl;

A is $C_{6-10}$ aryl or 5-10 membered heteroaryl and is substituted with q occurrences of $R^6$;

$R^4$ is hydrogen, hydroxyl, halogen, $C_{1-4}$ alkyl, $C_{1-4}$ alkoxy, $C_{1-4}$ haloalkyl, $C_{2-4}$ alkenyl, $C_{2-4}$ alkynyl, $C_{3-7}$ cycloalkyl or cyano;

each $R^5$ independently is halogen, cyano, oxo, -T-$R^y$, hydroxyl, —$N(R^z)_2$, $C_{1-4}$ alkyl, $C_{1-4}$ haloalkyl, $C_{1-4}$ alkoxy or —O—$C_{2-4}$ alkynyl;

each $R^6$ independently is halogen, hydroxyl, cyano, —$N(R^z)_2$, —C(O)$R^z$, —C(O)O$R^z$, $C_{1-4}$ alkyl, $C_{1-4}$ alkoxy, $C_{1-4}$ haloalkyl, $C_{1-4}$ haloalkoxy, $C_{2-4}$ alkynyl or $C_{3-6}$ cycloalkyl or two $R^6$ taken together on adjacent carbon atoms form a $C_{3-7}$ cycloalkyl;

T is $C_{1-4}$ alkylene, —$S(O)_2$—, —C(O)—, —$C_{1-4}$ alkylene-C(O)—, $C_{1-4}$ alkylene-$S(O)_2$— or —S—;

$R^y$ is halogen, oxo, $C_{1-4}$ alkyl, $C_{1-4}$ haloalkyl, hydroxyl, cyano or —$N(R^z)_2$; and each $R^z$ is hydrogen or $C_{1-4}$ alkyl.

Provided herein as embodiment 58 is the compound or salt according to any one of embodiments 1-57, wherein Z is C—H, C—F, C—CN, C—$CH_3$, C—$CF_3$, C—OMe, C—Cl or N. Provided herein as embodiment 59 is the compound or salt according to any one of embodiments 1-57, wherein Z is N. Provided herein as embodiment 60 is the compound or salt according to any one of embodiments 1-57, wherein Z is CH. Provided herein as embodiment 61 is the compound or salt according to any one of embodiments 1-57, wherein Z is CF.

Provided herein as embodiment 62 is the compound or salt according to any one of embodiment, 1-57, wherein Q is CH or N. Provided herein as embodiment 63 is the compound or salt according to any one of embodiments 1-57, wherein Q is CH. Provided herein as embodiment 64 is the compound or salt according to any one of embodiments 1-57, wherein Q is N. Provided herein as embodiment 65 is the compound or salt according to any one of embodiments 1-57, wherein Z is N and Q is CH. Provided herein as embodiment 66 is the compound or salt according to any one of embodiments 1-57, wherein Z is CH and Q is CH. Provided herein as embodiment 67 is the compound or salt according to any one of embodiments 1-57, wherein Z is CF and Q is CH. Provided herein as embodiment 68 is the compound or salt according to any one of embodiments 1-57, wherein Z is N and Q is N.

Provided herein as embodiment 69 is the compound or salt according to any one of embodiments 1-68, wherein L is —O-methylene or —O-ethylene substituted with 0-2 occurrences of $R^2$. Provided herein as embodiment 70 is the compound or salt according to embodiment 69, wherein L is —O-methylene substituted with 0 occurrences of $R^2$.

Provided herein as embodiment 71 is the compound or salt according to any one of embodiments 69-70, wherein $R^1$ is heterocycloalkyl substituted with 0-3 occurrences of $R^5$. Provided herein as embodiment 72 is the compound or salt according to embodiment 71, wherein $R^1$ is 7a-(hexahydro-1H-pyrrolizine), 6-(hexahydro-1H-pyrrolo[2,1-c][1,4]oxazinyl), 2-pyrrolidinyl, 1-(7-oxabicyclo[2.2.1]heptanyl), 2-morpholinyl, 1-(2-azabicyclo[2.2.2]octanyl) or 3-(2-azabicyclo[3.1.0]hexanyl) substituted with 0-3 occurrences of $R^5$. Provided herein as embodiment 73 is the compound or salt according to embodiment 71, wherein $R^1$ is 7a-(hexahydro-1H-pyrrolizine), 6-(hexahydro-1H-pyrrolo[2,1-c][1,4]oxazinyl) or 1-(7-oxabicyclo[2.2.1]heptanyl) substituted with 0 occurrences of $R^5$. Provided herein as embodiment 74 is the compound or salt according to embodiment 73, wherein $R^1$ is 7a-(hexahydro-1H-pyrrolizine) substituted with 0 occurrences of $R^5$.

Provided herein as embodiment 75 is the compound or salt according to embodiment 71, wherein $R^1$ is 7a-(hexahydro-1H-pyrrolizine), 6-(hexahydro-1H-pyrrolo[2,1-c][1,4]oxazinyl), 2-pyrrolidinyl, 1-(7-oxabicyclo[2.2.1]heptanyl), 2-morpholinyl, 1-(2-azabicyclo[2.2.2]octanyl) or 3-(2-azabicyclo[3.1.0]hexanyl) substituted with one occurrence of $R^5$. Provided herein as embodiment 76 is the compound or salt according to embodiment 75, wherein $R^5$ independently is halogen, oxo, methyl, methoxy or —O-(2-propynyl). Provided herein as embodiment 77 is the compound or salt according to embodiment 75, wherein $R^1$ is 7a-(hexahydro-1H-pyrrolizine) substituted with one occurrence of $R^5$. Provided herein as embodiment 78 is the compound or salt according to embodiment 77, wherein $R^5$ independently is fluoro or —O-(2-propynyl). Provided herein as embodiment 79 is the compound or salt according to embodiment 78, wherein $R^5$ is fluoro. Provided herein as embodiment 80 is the compound or salt according to embodiment 75, wherein $R^1$ is 2-pyridinyl substituted with one occurrence of $R^5$. Provided herein as embodiment 81 is the compound or salt according to embodiment 80, wherein $R^5$ is methyl.

Provided herein as embodiment 82 is the compound or salt according to embodiment 71, wherein $R^1$ is 2-pyrrolidinyl substituted with two occurrences of $R^5$. Provided herein as embodiment 83 is the compound or salt according to embodiment 82, wherein each $R^5$ independently is methyl, fluoro or methoxy.

Provided herein as embodiment 84 is the compound or salt according to embodiment 69, wherein L is —O-methylene substituted with 1 occurrence of $R^2$. Provided herein as embodiment 85 is the compound or salt according to embodiment 84, wherein $R^2$ is $C_{1-4}$ alkyl (e.g., methyl).

Provided herein as embodiment 86 is the compound or salt according to embodiment 85, wherein $R^1$ is 2-pyrrolidine substituted with 0-3 occurrences of $R^5$. Provided herein as embodiment 87 is the compound or salt according to embodiment 86, wherein $R^1$ is 2-pyrrolidine substituted with 1 occurrence of $R^5$. Provided herein as embodiment 88 is the compound or salt according to embodiment 87, wherein $R^5$ is $C_{1-4}$ alkyl (e.g., methyl).

Provided herein as embodiment 89 is the compound or salt according to embodiment 69, wherein L is —O-ethylene substituted with two occurrences of $R^2$. Provided herein as embodiment 90 is the compound or salt according to embodiment 89, wherein both $R^2$ are $C_{1-4}$ alkyl (e.g., methyl). Provided herein as embodiment 91 is the compound or salt according to embodiment 90, wherein $R^1$ is hydroxyl.

Provided herein as embodiment 92 is the compound or salt according to embodiment 69, wherein L is —O-n-propylene substituted with two occurrences of $R^2$. Provided herein as embodiment 93 is the compound or salt according to embodiment 92, wherein the two $R^2$ are taken together with the same carbon atom to form a $C_{3-7}$ cycloalkyl (e.g., cyclopropyl).

Provided herein as embodiment 94 is the compound or salt according to any one of embodiments 92-93, wherein $R^1$ is N-azetidinyl substituted with 0-3 occurrences of $R^5$ or —$N(R^z)_2$. Provided herein as embodiment 95 is the compound or salt according to embodiment 94, wherein $R^1$ is N-azetidinyl substituted with one occurrence of R. Provided herein as embodiment 96 is the compound or salt according to embodiment 95, wherein $R^5$ is fluorine. Provided herein as embodiment 97 is the compound or salt according to any one of embodiments 92-93, wherein $R^1$ is —$N(R^z)_2$ and $R^z$ are methyl.

Provided herein as embodiment 98 is the compound or salt according to any one of embodiments 1-68, wherein L is O.

Provided herein as embodiment 99 is the compound or salt according to embodiment 98, wherein $R^1$ is heterocycloalkyl substituted with 0-3 occurrences of $R^5$. Provided herein as embodiment 100 is the compound or salt according to embodiment 99, wherein $R^1$ is 3-tetrahydrofuranyl or 4-piperdinyl substituted with 0-3 occurrences of $R^5$. Provided herein as embodiment 101 is the compound or salt according to embodiment 100, wherein $R^1$ is 3-tetrahydrofuranyl substituted with 0 occurrences of $R^5$. Provided herein as embodiment 102 is the compound or salt according to embodiment 101, wherein $R^1$ is 4-piperidinyl substituted with one occurrence of $R^5$. Provided herein as embodiment 103 is the compound or salt according to embodiment 102, wherein $R^5$ is methyl.

Provided herein as embodiment 104 is the compound or salt according to any one of embodiments 1-68, wherein L is $C_{1-6}$ alkylene or —O—$C_{1-6}$ alkylene. Provided herein as embodiment 105 is the compound or salt according to embodiment 104, wherein L is methylene or —O-methylene. Provided herein as embodiment 106 is the compound or salt according to embodiment 105, wherein $R^1$ is hydrogen.

Provided herein as embodiment 107 is the compound or salt according to any one of embodiments 1-68, wherein L is a bond. Provided herein as embodiment 108 is the compound or salt according to embodiment 107, wherein $R^1$ is N-piperizinyl substituted with one occurrence of $R^5$. Provided herein as embodiment 109 is the compound or salt according to embodiment 108, wherein $R^5$ is methyl.

Provided herein as embodiment 110 is the compound or salt according to any one of embodiments 1-68, wherein -L-$R^1$ is

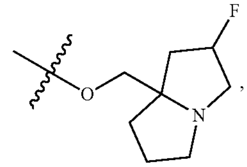,
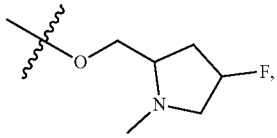,
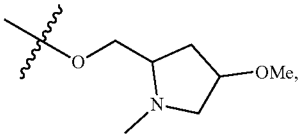,
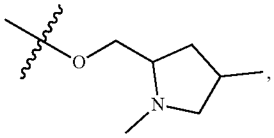,
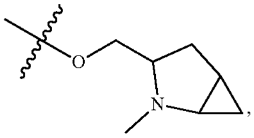,
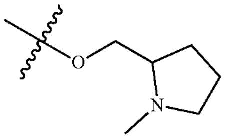,
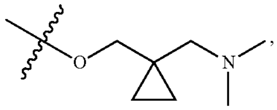,
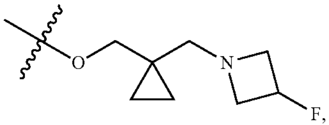,
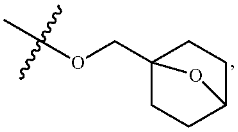,
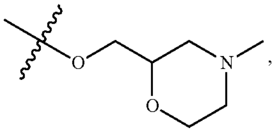,
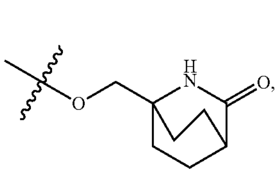,
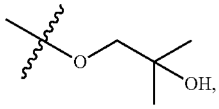,
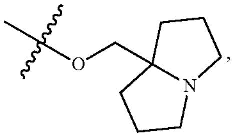,
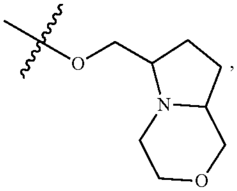,
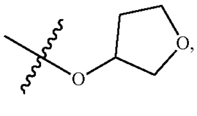,
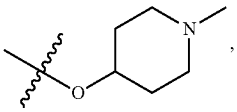,
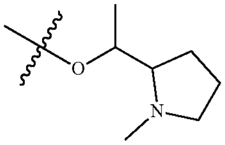,
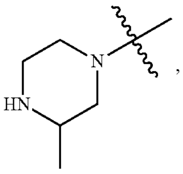,
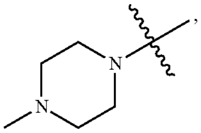, methoxy or methyl.

Provided herein as embodiment 111 is the compound or salt according to embodiment 110, wherein -L-$R^1$ is
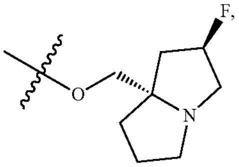,
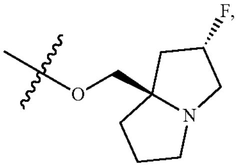,
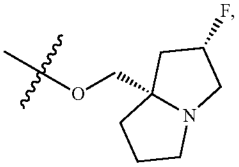,
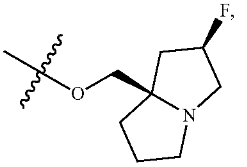,
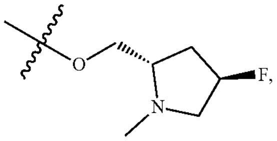,
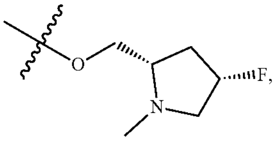,
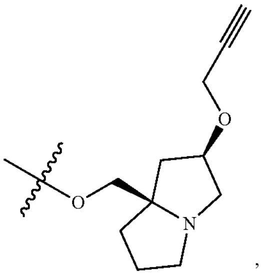,
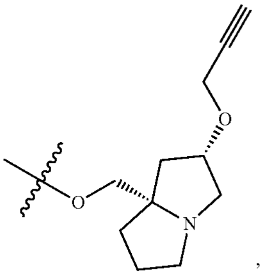,
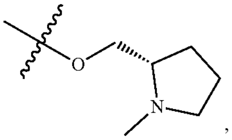,
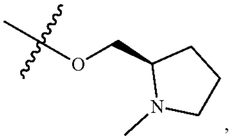,
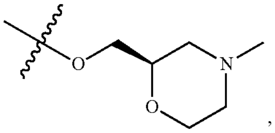,
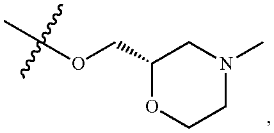,
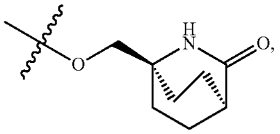,
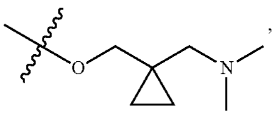,
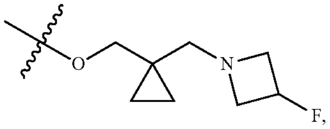,
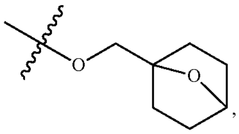,
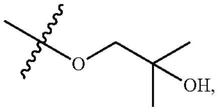,
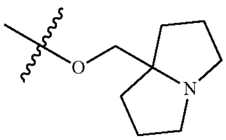,
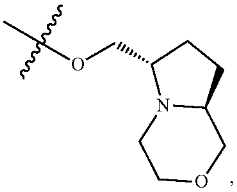,
-continued
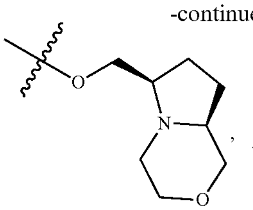,
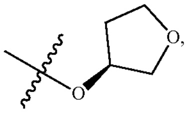,
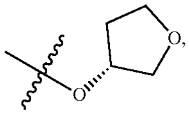,
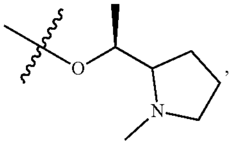,
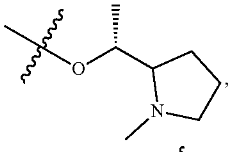,
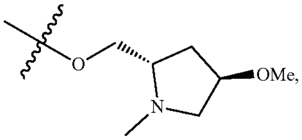,
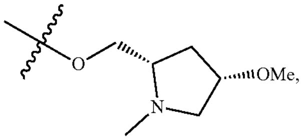,
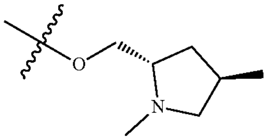,
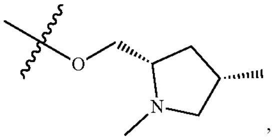,
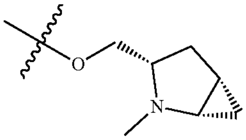,
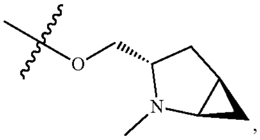,
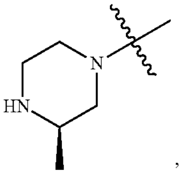,
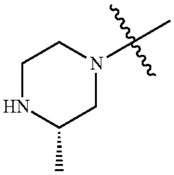,
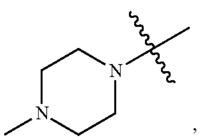,
methoxy or methyl.
Provided herein as embodiment 112 is the compound or salt according to embodiment 111, wherein -L-$R^1$ is
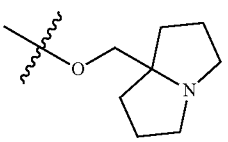,
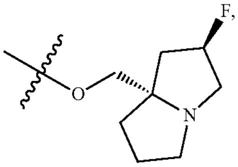,
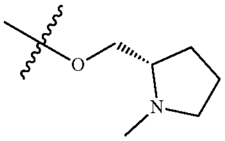
or -continued

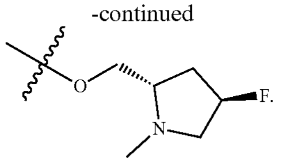

Provided herein as embodiment 113 is the compound or salt according to embodiment 112, wherein -L-$R^1$ is

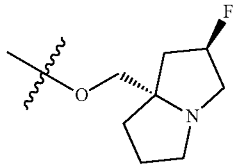

or

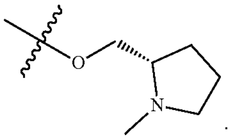

Provided herein as embodiment 114 is the compound or salt according to embodiment 112, wherein -L-$R^1$ is

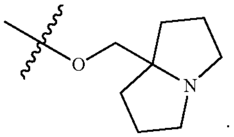 [SMILES: *OCC12CCCN1CCC2]

Provided herein as embodiment 115 is the compound or salt according to embodiment 112, wherein -L-$R^1$ is

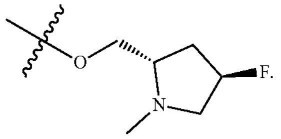 [SMILES: *OC[C@@H]1C[C@@H](F)CN1C]

Provided herein as embodiment 116 is the compound or salt according to embodiment 112, wherein -L-$R^1$ is

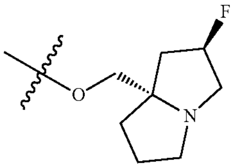 [SMILES: *OC[C@@]12CCCN1C[C@H](F)C2]

Provided herein as embodiment 117 is the compound or salt according to embodiment 112, wherein -L-$R^1$ is

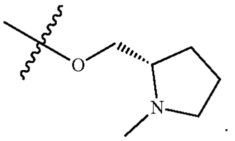 [SMILES: *OC[C@@H]1CCCN1C]

Provided herein as embodiment 118 is the compound or salt according to any one of embodiments 57-117, wherein X is O. Provided herein as embodiment 119 is the compound or salt according to embodiment 118, wherein n is 1 and m is 1. Provided herein as embodiment 120 is the compound or salt according to embodiment 119, wherein p is 0.

Provided herein as embodiment 121 is the compound or salt according to embodiment 119, wherein p is 1. Provided herein as embodiment 122 is the compound or salt according to embodiment 121, wherein $R^x$ is methyl, methoxy or hydroxyl. Provided herein as embodiment 123 is the compound or salt according to embodiment 122, wherein $R^x$ is hydroxyl. Provided herein as embodiment 124 is the compound or salt according to embodiment 122, wherein $R^x$ is methyl.

Provided herein as embodiment 125 is the compound or salt according to embodiment 119, wherein p is 2. Provided herein as embodiment 126 is the compound or salt according to embodiment 125, wherein two $R^x$ taken together with the same carbon atom forms cyclobutyl further substituted with 0 occurrences of $R^y$. Provided herein as embodiment 127 is the compound or salt according to embodiment 125, wherein two $R^x$ taken together with the same carbon atom forms cyclobutyl further substituted with one occurrence of $R^y$. Provided herein as embodiment 128 is the compound or salt according to embodiment 127, wherein $R^y$ is methyl.

Provided herein as embodiment 129 is the compound or salt according to embodiment 118, wherein n is 1 and m is 2 or n is 2 and m is 1. Provided herein as embodiment 130 is the compound or salt according to embodiment 129, wherein p is 0.

Provided herein as embodiment 131 is the compound or salt according to embodiment 129, wherein p is 1. Provided herein as embodiment 132 is the compound or salt according to embodiment 131, wherein $R^x$ is $C_{1-4}$ alkyl, $C_{1-4}$ deuteroalkyl, $C_{1-4}$ haloalkyl, $C_{1-4}$ alkoxy or hydroxyl. Provided herein as embodiment 133 is the compound or salt according to embodiment 132, wherein $R^x$ is methyl. Provided herein as embodiment 134 is the compound or salt according to embodiment 132, wherein $R^x$ is monofluoromethyl. Provided herein as embodiment 135 is the compound or salt according to embodiment 132, wherein $R^x$ is $-CD_3$.

Provided herein as embodiment 136 is the compound or salt according to embodiment 129, wherein p is 2. Provided herein as embodiment 137 is the compound or salt according to embodiment 136, wherein two $R^x$ taken together with the same carbon atom forms cyclobutyl further substituted with 0 occurrences of $R^y$.

Provided herein as embodiment 138 is the compound or salt according to any one of embodiments 118-137, wherein

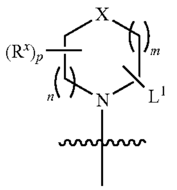

is

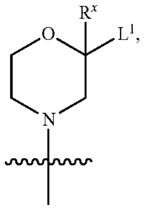

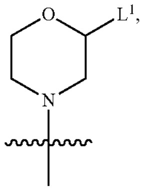

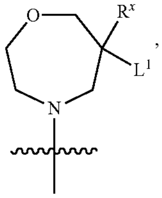

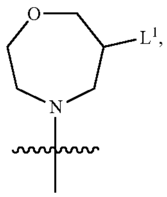

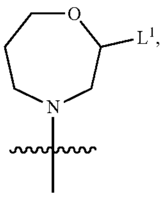

-continued
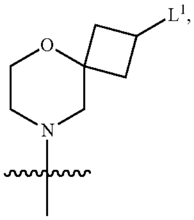
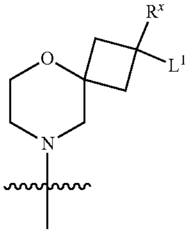
or
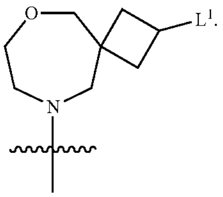
Provided herein as embodiment 139 is the compound or salt according to embodiment 138, wherein
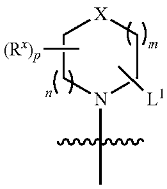
is
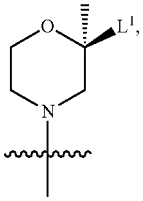
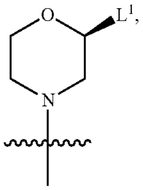
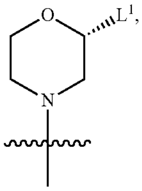
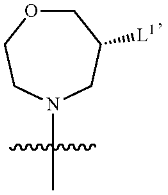
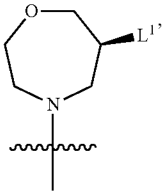
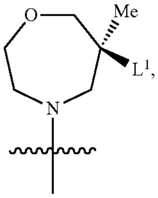
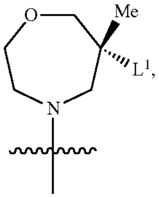
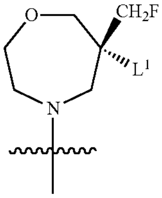
,
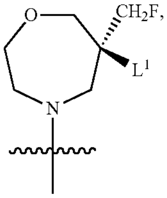
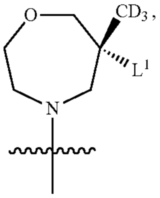
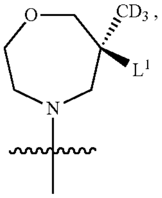
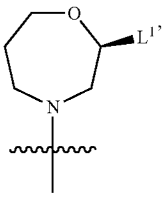
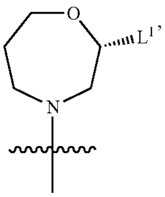
-continued
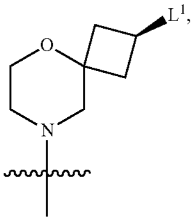
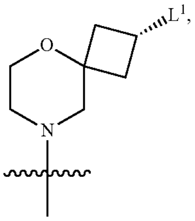
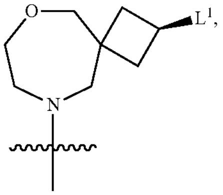
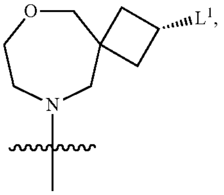
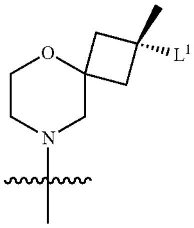
or
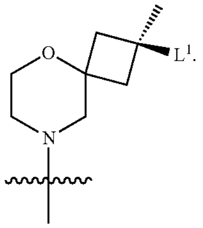
Provided herein as embodiment 140 is the compound or salt according to embodiment 139, wherein is
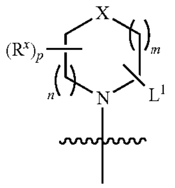
is
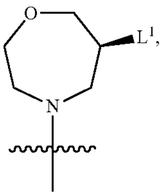
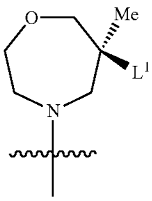
,
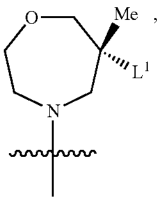
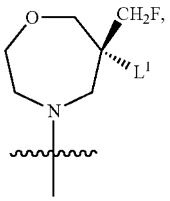
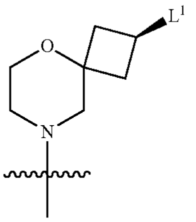
or
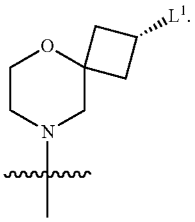
Provided herein as embodiment 141 is the compound or salt according to embodiment 140, wherein

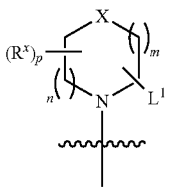

is

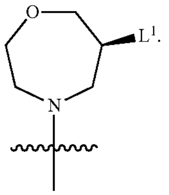

Provided herein as embodiment 142 is the compound or salt according to embodiment 140, wherein

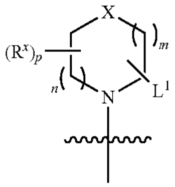

is

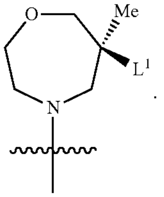

Provided herein as embodiment 143 is the compound or salt according to embodiment 140, wherein is

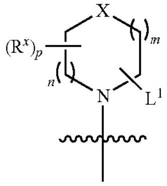

is

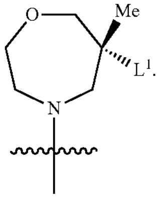

Provided herein as embodiment 144 is the compound or salt according to embodiment 140, wherein is

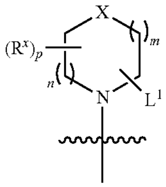

is

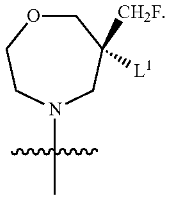

Provided herein as embodiment 145 is the compound or salt according to embodiment 140, wherein

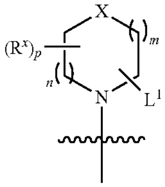

is

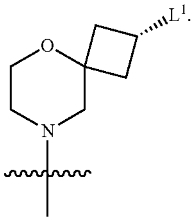

Provided herein as embodiment 146 is the compound or salt according to embodiment 140, wherein

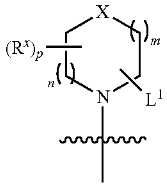

is

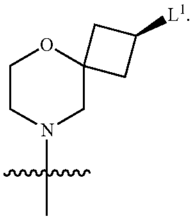

Provided herein as embodiment 147 is the compound or salt according to any one of embodiments 57-117, wherein X is N. Provided herein as embodiment 148 is the compound or salt according to embodiment 147, wherein n is 1 and m is 2. Provided herein as embodiment 149 is the compound or salt according to embodiment 148, wherein p is 0.

Provided herein as embodiment 150 is the compound or salt according to any one of embodiments 147-149, wherein is

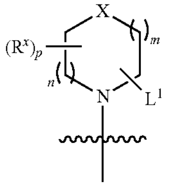

is

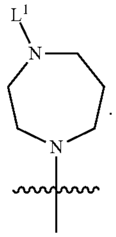

Provided herein as embodiment 151 is the compound or salt according to embodiment 147, wherein n is 3 and m is 1. Provided herein as embodiment 152 is the compound or salt according to embodiment 151, wherein p is 2. Provided herein as embodiment 153 is the compound or salt according to embodiment 152, wherein two $R^x$ taken together form a methylene bridged ring.

Provided herein as embodiment 154 is the compound or salt according to any one of embodiments 151-153, wherein

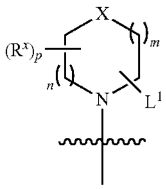

is

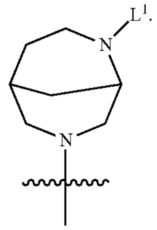

Provided herein as embodiment 155 is the compound or salt according to embodiment 154, wherein

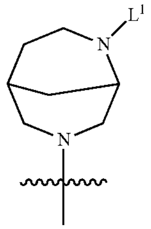

is

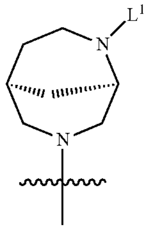

or

-continued

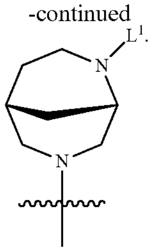

Provided herein as embodiment 156 is the compound or salt according to any one of embodiments 57-117, wherein X is $CH_2$. Provided herein as embodiment 157 is the compound or salt according to embodiment 156, wherein n is 0 and m is 1 or n is 1 and m is 0. Provided herein as embodiment 158 is the compound or salt according to embodiment 157, wherein p is 0.

Provided herein as embodiment 159 is the compound or salt according to embodiment 157, wherein p is 1. Provided herein as embodiment 160 is the compound or salt according to embodiment 159, wherein $R^x$ is $C_{1-4}$ alkyl (e.g., methyl).

Provided herein as embodiment 161 is the compound or salt according to embodiment 156, wherein n is 1 and m is 1. Provided herein as embodiment 162 is the compound or salt according to embodiment 161, wherein p is 0.

Provided herein as embodiment 163 is the compound or salt according to embodiment 161, wherein p is 1. Provided herein as embodiment 164 is the compound or salt according to embodiment 163, wherein $R^x$ is methyl, methoxy, hydroxyl, monofluoromethyl or fluorine. Provided herein as embodiment 165 is the compound or salt according to embodiment 164, wherein $R^x$ is hydroxyl. Provided herein as embodiment 166 is the compound or salt according to embodiment 164, wherein $R^x$ is methyl. Provided herein as embodiment 167 is the compound or salt according to embodiment 164, wherein $R^x$ is monofluoromethyl.

Provided herein as embodiment 168 is the compound or salt according to embodiment 161, wherein p is 2. Provided herein as embodiment 169 is the compound or salt according to embodiment 168, wherein both $R^x$ are halogen (e.g., fluorine).

Provided herein as embodiment 170 is the compound or salt according to embodiment 156, wherein n is 1 and m is 2 or n is 2 and m is 1. Provided herein as embodiment 171 is the compound or salt according to embodiment 170, wherein p is 0.

Provided herein as embodiment 172 is the compound or salt according to embodiment 170, wherein p is 1. Provided herein as embodiment 173 is the compound or salt according to embodiment 172, wherein $R^x$ is methyl, methoxy, monofluoromethyl, hydroxyl or fluorine. Provided herein as embodiment 174 is the compound or salt according to embodiment 173, wherein $R^x$ is methyl. Provided herein as embodiment 175 is the compound or salt according to embodiment 173, wherein $R^x$ is hydroxyl. Provided herein as embodiment 175 is the compound or salt according to embodiment 173, wherein $R^x$ is monofluoromethyl.

Provided herein as embodiment 177 is the compound or salt according to any one of embodiments 161-176, wherein

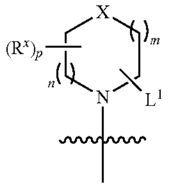

is

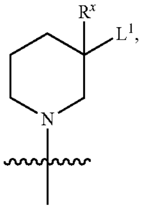

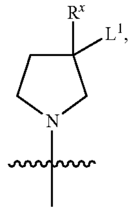

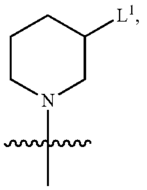

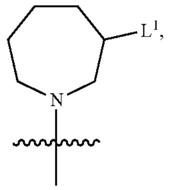

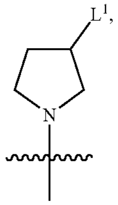

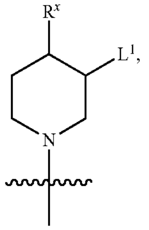

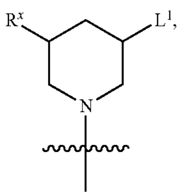

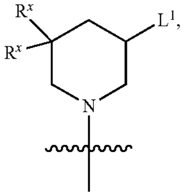

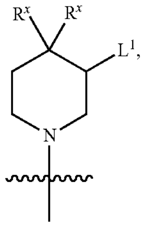

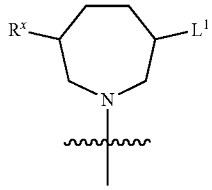

or

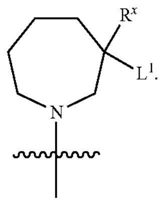

Provided herein as embodiment 178 is the compound or salt according to embodiment 177, wherein

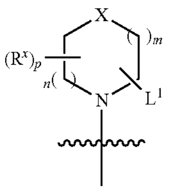

is

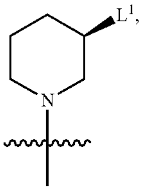

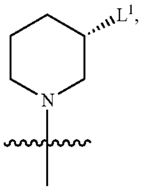

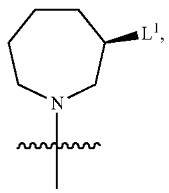

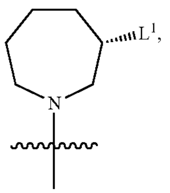

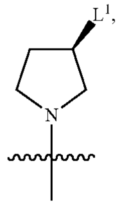

-continued
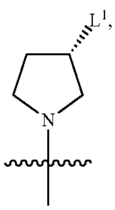
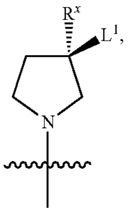
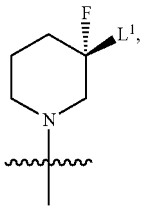
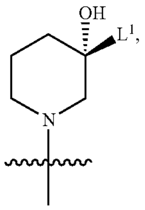
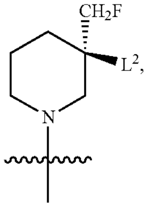
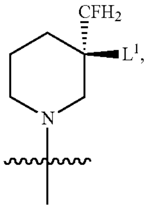
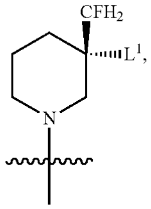
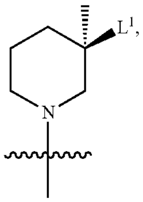
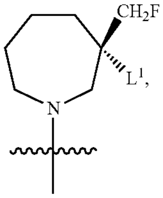
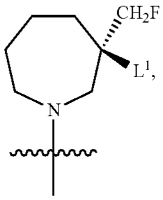
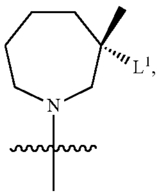
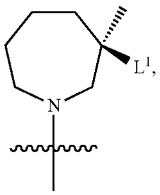
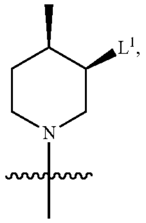
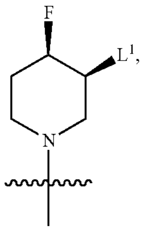
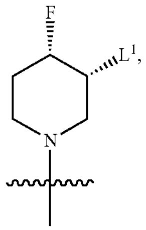
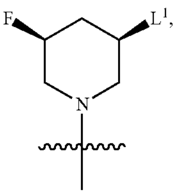
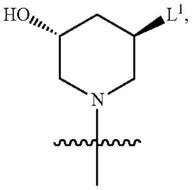
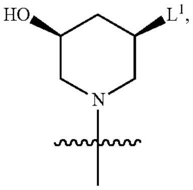
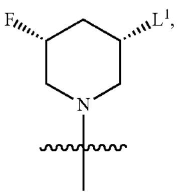
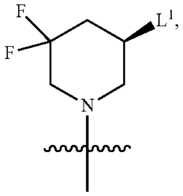
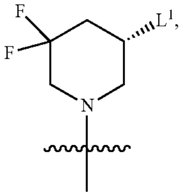
-continued
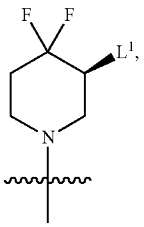
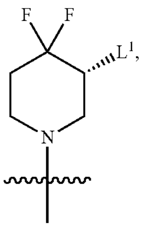
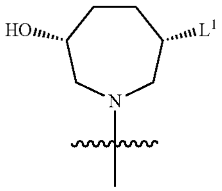
or
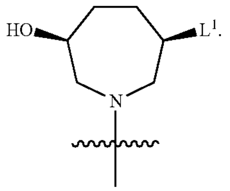
Provided herein as embodiment 179 is the compound or salt according to embodiment 178, wherein
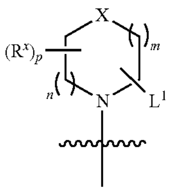
is
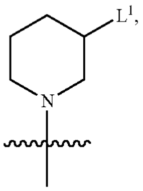
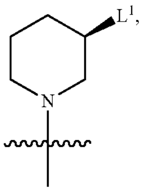
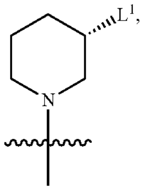
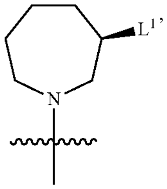
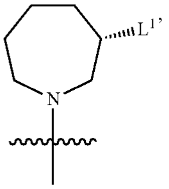
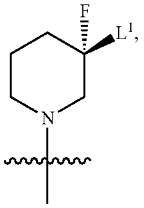
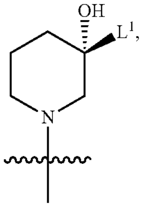
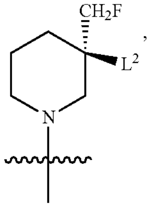
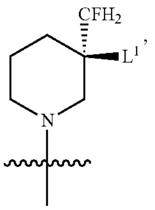
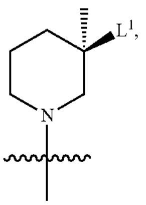
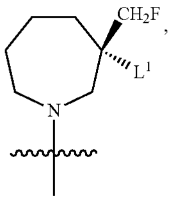
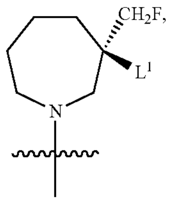
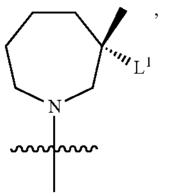
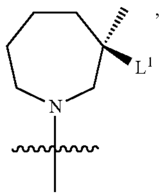

-continued

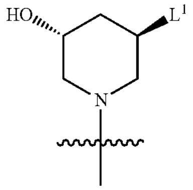 or 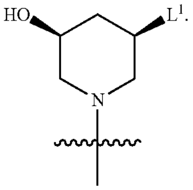

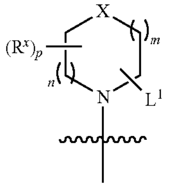 is 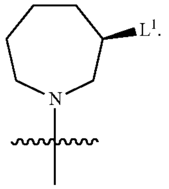

Provided herein as embodiment 180 is the compound or salt according to embodiment 179, wherein is

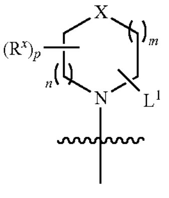 is 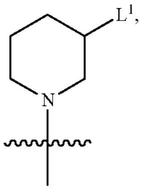 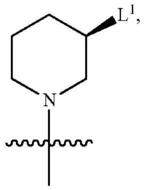

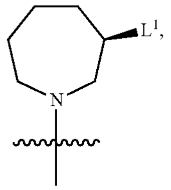 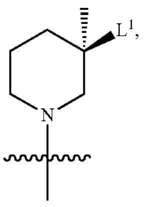 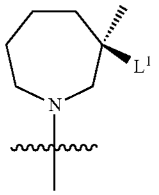 or

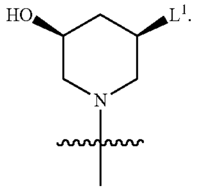

Provided herein as embodiment 181 is the compound or salt according to embodiment 180, wherein

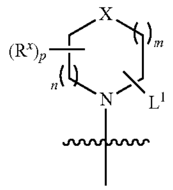 is 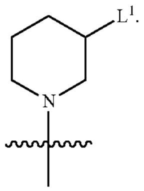

Provided herein as embodiment 182 is the compound or salt according to embodiment 180, wherein

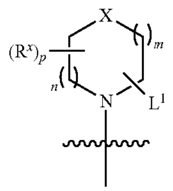 is 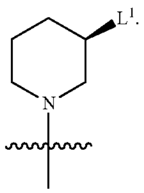

Provided herein as embodiment 183 is the compound or salt according to embodiment 180, wherein Provided herein as embodiment 184 is the compound or salt according to embodiment 180, wherein

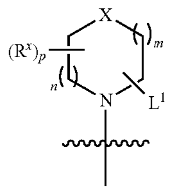 is 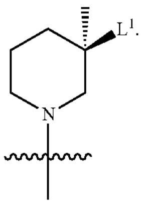

Provided herein as embodiment 185 is the compound or salt according to embodiment 180, wherein

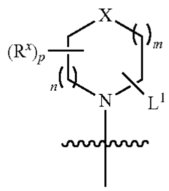 is 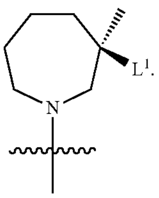

Provided herein as embodiment 186 is the compound or salt according to embodiment 180, wherein

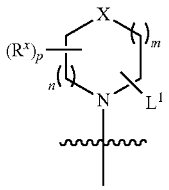 is 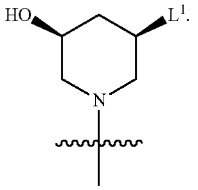

Provided herein as embodiment 187 is the compound or salt according to any one of embodiments 57-117, wherein X is $CH_2$. Provided herein as embodiment 188 is the compound or salt according to embodiment 187, wherein n is 1 and m is 0 or m is 0 and n is 1. Provided herein as embodiment 189 is the compound or salt according to embodiment 188, wherein two $R^x$ taken are together with the same carbon atom to form a 3-7 membered heterocycloalkyl (e.g., 2-azetidinyl) further substituted with 0 occurrences of $R^y$.

Provided herein as embodiment 190 is the compound or salt according to embodiment 187, wherein n is 1 and m is 1. Provided herein as embodiment 191 is the compound or salt according to embodiment 190, wherein p is 2. Provided herein as embodiment 192 is the compound or salt according to embodiment 191, wherein two $R^x$ taken are together with the same carbon atom to form $C_{3-7}$ cycloalkyl or a 3-7 membered heterocycloalkyl, wherein each $C_{3-7}$ cycloalkyl or 3-7 membered heterocycloalkyl is further substituted with 0-3 occurrences of $R^y$. Provided herein as embodiment 193 is the compound or salt according to embodiment 192, wherein two $R^x$ taken are together with the same carbon atom to form cyclopropyl or cyclobutyl further substituted with 0 occurrences of $R^y$. Provided herein as embodiment 194 is the compound or salt according to embodiment 192, wherein two $R^x$ taken are together with the same carbon atom to form cyclopropyl further substituted with 0 occurrences of $R^y$. Provided herein as embodiment 195 is the compound or salt according to embodiment 192, wherein two $R^x$ taken are together with the same carbon atom to form cyclobutyl further substituted with 0 occurrences of $R^y$. Provided herein as embodiment 196 is the compound or salt according to embodiment 192, wherein two $R^x$ taken are together with the same carbon atom to form cyclobutyl further substituted with one occurrence of $R^y$. Provided herein as embodiment 197 is the compound or salt according to embodiment 196, wherein $R^y$ is methyl or hydroxyl.

Provided herein as embodiment 198 is the compound or salt according to embodiment 192, wherein two $R^x$ taken are together with the same carbon atom to form a 3-7 membered heterocycloalkyl (e.g., 2-azetidinyl or 2-tetrahydrofuranyl) further substituted with 0 occurrences of $R^y$.

Provided herein as embodiment 199 is the compound or salt according to embodiment 191, wherein two $R^x$ taken are together with adjacent carbon atoms to form $C_{3-7}$ cycloalkyl or a 3-7 membered heterocycloalkyl, wherein each $C_{3-7}$ cycloalkyl or 3-7 membered heterocycloalkyl is further substituted with 0-3 occurrences of $R^y$. Provided herein as embodiment 200 is the compound or salt according to embodiment 199, wherein two $R^x$ taken are together with adjacent carbon atoms to form a $C_{3-7}$ cycloalkyl (e.g., cyclopropyl) further substituted with 0 occurrences of $R^y$. Provided herein as embodiment 201 is the compound or salt according to embodiment 199, wherein two $R^x$ taken are together with adjacent carbon atoms to form a 3-7 membered heterocycloalkyl (e.g., azetidinyl, 2-tetrahydrofuranyl, 2-pyrrolidinyl or 3-pyrrolidinyl) further substituted with 0 occurrences of $R^y$. Provided herein as embodiment 202 is the compound or salt according to embodiment 201, wherein two $R^x$ taken are together with adjacent carbon atoms to form a 2-pyrrolidinyl further substituted with 0 occurrences of $R^y$.

Provided herein as embodiment 203 is the compound or salt according to embodiment 191, wherein two $R^X$ are taken together to form a bridged ring where the bridge is selected from one of the following: —$C_{1-4}$ alkylene, —$C_{1-4}$ alkylene-O—$C_{1-4}$ alkylene-, —O—, —S— or —$C_{1-4}$ alkylene-S—$C_{1-4}$ alkylene- and wherein each $C_{1-4}$ alkylene is further substituted with 0-2 occurrences of $R^y$. Provided herein as embodiment 204 is the compound or salt according to embodiment 203, wherein two $R^X$ are taken together to form a $C_{1-4}$ alkylene (e.g., ethylene) bridged ring further substituted with 0 occurrences of $R^y$.

Provided herein as embodiment 205 is the compound or salt according to any one of embodiments 187-204, wherein

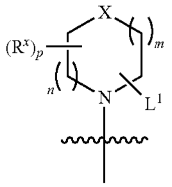

is

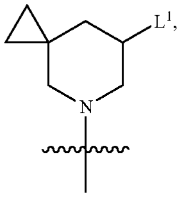

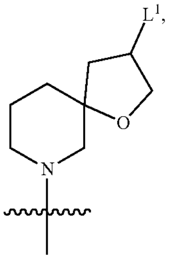

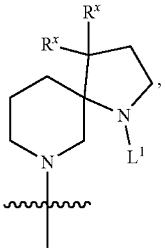

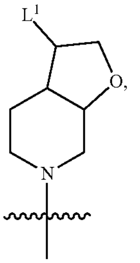

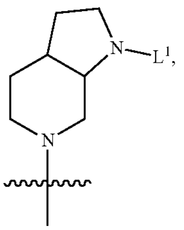

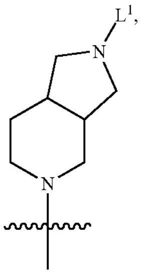

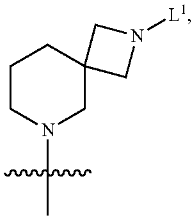

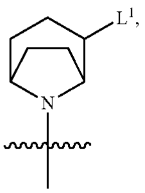

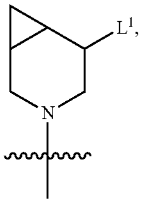

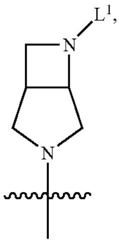

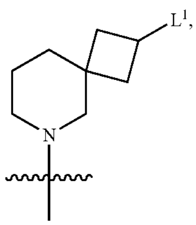

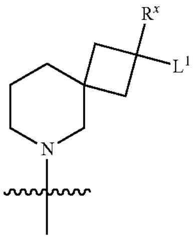

or

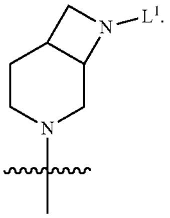

Provided herein as embodiment 206 is the compound or salt according to embodiment 205, wherein

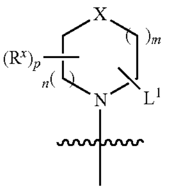
is
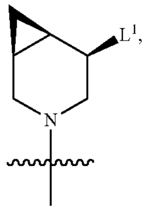 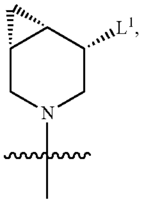
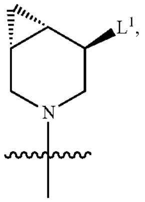 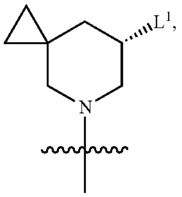 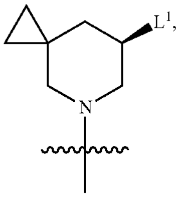
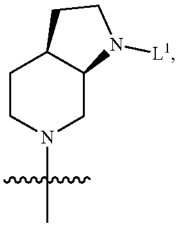 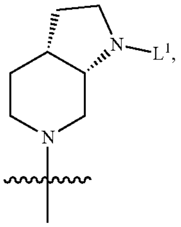 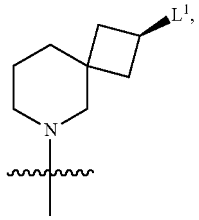
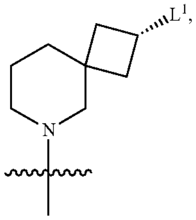 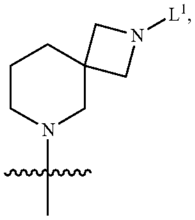
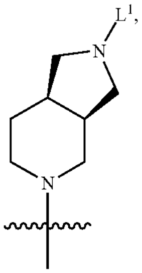 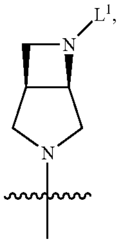 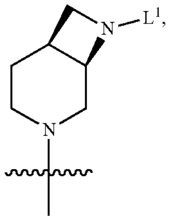
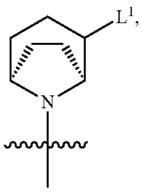 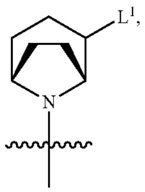 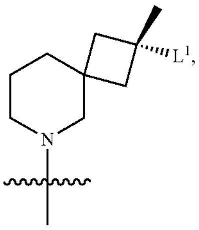
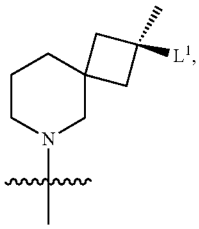 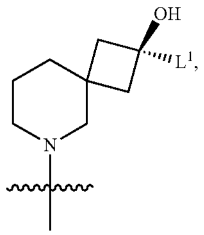
-continued
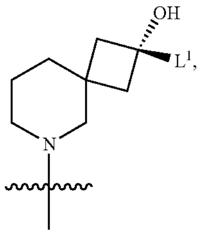 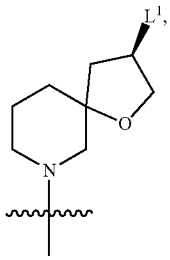 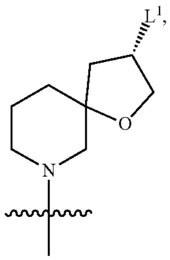
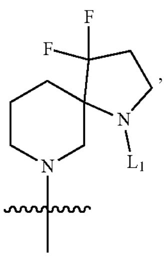 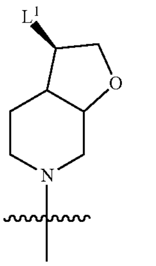 or 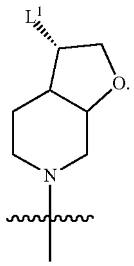
Provided herein as embodiment 207 is the compound or salt according to embodiment 206, wherein
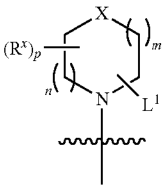
is
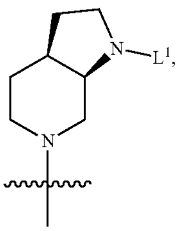 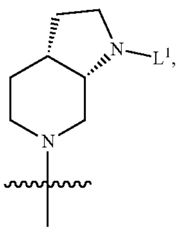
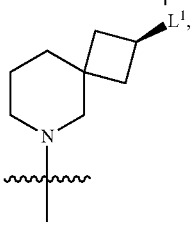 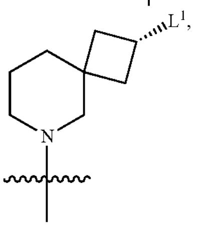
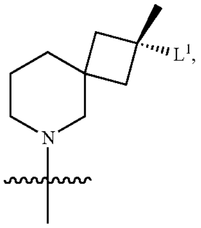 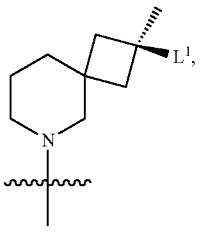
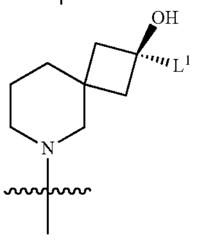 or 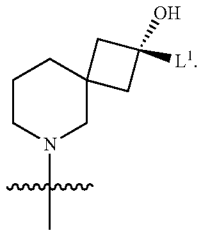

Provided herein as embodiment 208 is the compound or salt according to embodiment 207, wherein

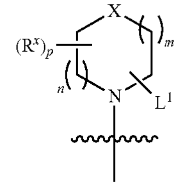 is 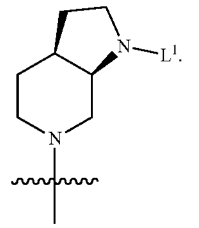

Provided herein as embodiment 209 is the compound or salt according to embodiment 207, wherein

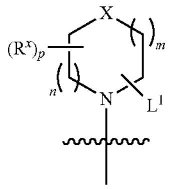 is 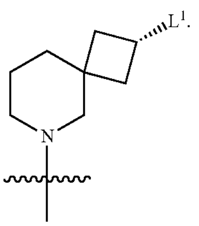

Provided herein as embodiment 210 is the compound or salt according to embodiment 207, wherein

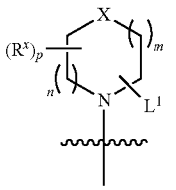 is 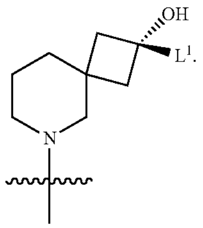

Provided herein as embodiment 211 is the compound or salt according to any one of embodiments 1-210, wherein A is $C_{6-10}$ aryl (e.g., phenyl, naphthyl, 8-(1,2,3,4-tetrahydroquinolinyl) or 5-(1,2,3,4-tetrahydronaphthalyl)). Provided herein as embodiment 212 is the compound or salt according to embodiment 211, wherein A is phenyl. Provided herein as embodiment 213 is the compound or salt according to embodiment 212, wherein q is 0.

Provided herein as embodiment 214 is the compound or salt according to embodiment 212, wherein q is 1. Provided herein as embodiment 215 is the compound or salt according to embodiment 214, wherein $R^6$ is halo (e.g., chlorine).

Provided herein as embodiment 216 is the compound or salt according to embodiment 212, wherein q is 2. Provided herein as embodiment 217 is the compound or salt according to embodiment 216, wherein each $R^6$ is halo (e.g., chloro or fluoro), hydroxyl or cyano. Provided herein as embodiment 218 is the compound or salt according to embodiment 217, wherein one $R^6$ is chloro and the other $R^6$ is cyano. Provided herein as embodiment 219 is the compound or salt according to embodiment 217, wherein one $R^6$ is chloro and the other $R^6$ is fluoro. Provided herein as embodiment 220 is the compound or salt according to embodiment 217, wherein one $R^6$ is chloro and the other $R^6$ is hydroxyl.

Provided herein as embodiment 221 is the compound or salt according to embodiment 212, wherein q is 3. Provided herein as embodiment 222 is the compound or salt according to embodiment 221, wherein one $R^6$ is halo (e.g., fluoro), another $R^6$ is $C_{1-4}$ alkyl (e.g., methyl) and the last $R^6$ is $—N(R^z)_2$ (e.g., $—NH_2$).

Provided herein as embodiment 223 is the compound or salt according to embodiment 211, wherein A is 5-(1,2,3,4-tetrahydronaphthalyl). Provided herein as embodiment 224 is the compound or salt according to embodiment 223, wherein q is 0. Provided herein as embodiment 225 is the compound or salt according to embodiment 224, wherein q is 1. Provided herein as embodiment 226 is the compound or salt according to embodiment 225, wherein $R^6$ is hydroxy.

Provided herein as embodiment 227 is the compound or salt according to embodiment 211, wherein A is 8-(1,2,3,4-tetrahydroquinolinyl). Provided herein as embodiment 228 is the compound or salt according to embodiment 227, wherein q is 0.

Provided herein as embodiment 229 is the compound or salt according to embodiment 211, wherein A is naphthyl. Provided herein as embodiment 230 is the compound or salt according to embodiment 229, wherein q is 0.

Provided herein as embodiment 231 is the compound or salt according to embodiment 229, wherein q is 1. Provided herein as embodiment 232 is the compound or salt according to embodiment 231, wherein $R^6$ is hydroxyl, halo, $C_{1-4}$ alkoxy or $C_{1-4}$ alkyl. Provided herein as embodiment 233 is the compound or salt according to embodiment 232, wherein $R^6$ is hydroxyl. Provided herein as embodiment 234 is the compound or salt according to embodiment 232, wherein $R^6$ is halo (e.g., fluorine or chlorine). Provided herein as embodiment 235 is the compound or salt according to embodiment 232, wherein $R^6$ is $C_{1-4}$ alkoxy (e.g., methoxy). Provided herein as embodiment 236 is the compound or salt according to embodiment 232, wherein $R^6$ is $C_{1-4}$ alkyl (e.g., methyl).

Provided herein as embodiment 237 is the compound or salt according to embodiment 229, wherein q is 2. Provided herein as embodiment 238 is the compound or salt according to embodiment 237, wherein each occurrence of $R^6$ is halogen, hydroxyl, cyano, $C_{1-4}$ alkoxy or $C_{1-4}$ alkyl. Provided herein as embodiment 239 is the compound or salt according to embodiment 238, wherein each occurrence of $R^6$ is fluorine, chlorine, cyano, hydroxyl or methoxy.

Provided herein as embodiment 240 is the compound or salt according to any one of embodiments 211-239, wherein A-$L^2$ is

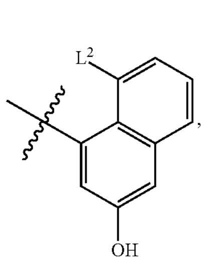, 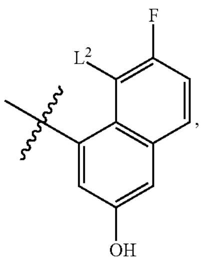,

-continued

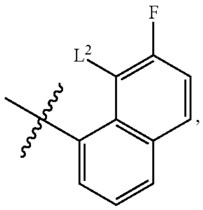,
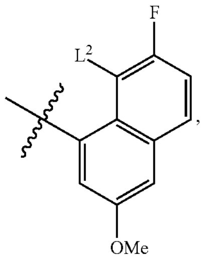,
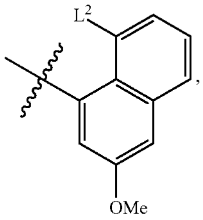,
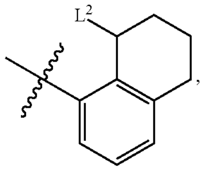,
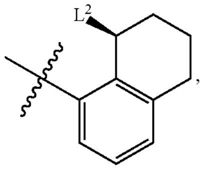,
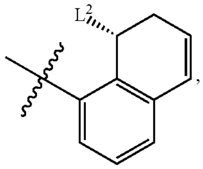,
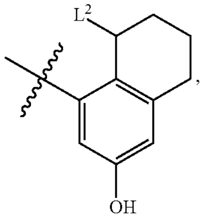,
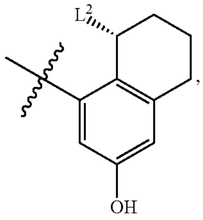,
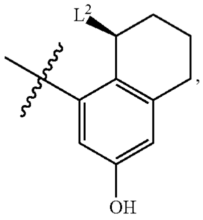,
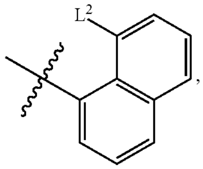,
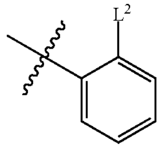,
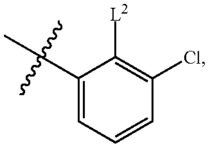,
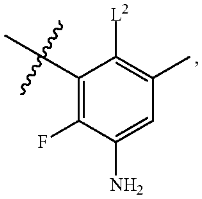,
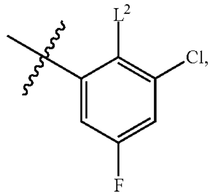,
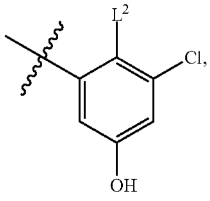,
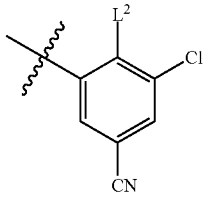
or -continued

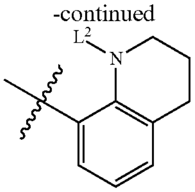.

Provided herein as embodiment 241 is the compound or salt according to embodiment 240, wherein A-$L^2$ is

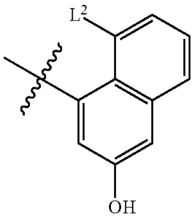.

Provided herein as embodiment 242 is the compound or salt according to embodiment 240, wherein A-$L^2$ is

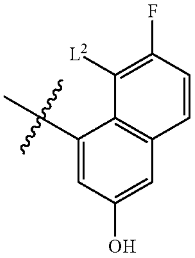.

Provided herein as embodiment 243 is the compound or salt according to embodiment 240, wherein A-$L^2$ is

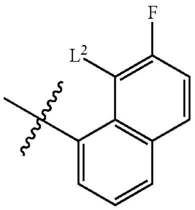.

Provided herein as embodiment 244 is the compound or salt according to embodiment 240, wherein A-$L^2$ is

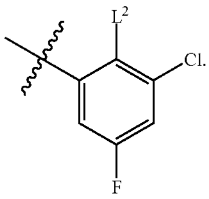.

Provided herein as embodiment 245 is the compound or salt according to embodiment 240, wherein A-$L^2$ is

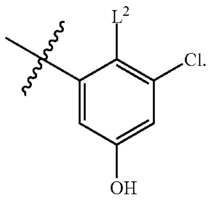

Provided herein as embodiment 246 is the compound or salt according to embodiment 240, wherein A-$L^2$ is

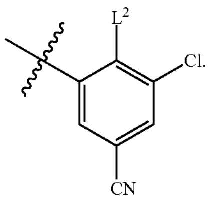

Provided herein as embodiment 247 is the compound or salt according to embodiment 240, wherein A-$L^2$ is

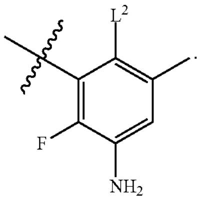

Provided herein as embodiment 248 is the compound or salt according to embodiment 240, wherein A-$L^2$ is

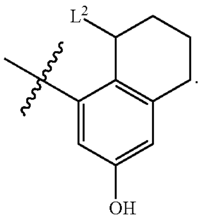

Provided herein as embodiment 249 is the compound or salt according to embodiment 248, wherein A-$L^2$ is

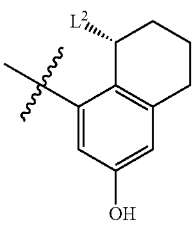

or

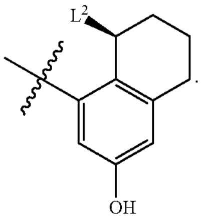

Provided herein as embodiment 250 is the compound or salt according to any one of embodiments 1-210, wherein A is 5-10 membered heteroaryl (e.g., 3-pyrimidinyl, 4-indazolyl, 4-isoquinolinyl, 4-(5,6,7,8)-tetrahydroisoquinolinyl or 7-indazolyl).

Provided herein as embodiment 251 is the compound or salt according to embodiment 250, wherein A is 3-pyrimidinyl. Provided herein as embodiment 252 is the compound or salt according to embodiment 251, wherein q is 1. Provided herein as embodiment 253 is the compound or salt according to embodiment 252, wherein $R^6$ halo (e.g., chlorine).

Provided herein as embodiment 254 is the compound or salt according to embodiment 250, wherein A is 4-isoquinolinyl. Provided herein as embodiment 255 is the compound or salt according to embodiment 252, wherein q is 0.

Provided herein as embodiment 256 is the compound or salt according to embodiment 250, wherein A is 4-(5,6,7,8)-tetrahydroisoquinolinyl. Provided herein as embodiment 257 is the compound or salt according to embodiment 256, wherein q is 0.

Provided herein as embodiment 258 is the compound or salt according to embodiment 250, wherein A is 4-indazolyl. Provided herein as embodiment 259 is the compound or salt according to embodiment 258, wherein q is 0.

Provided herein as embodiment 260 is the compound or salt according to embodiment 258, wherein q is 1. Provided herein as embodiment 261 is the compound or salt according to embodiment 260, wherein $R^6$ halo is $C_{1-4}$ alkyl, halo, $C_{1-4}$ haloalkyl or —C(O)$OR^z$. Provided herein as embodiment 262 is the compound or salt according to embodiment 261, wherein $R^6$ is halo (e.g., fluorine or chlorine). Provided herein as embodiment 263 is the compound or salt according to embodiment 261, wherein $R^6$ is $C_{1-4}$ alkyl (e.g., methyl). Provided herein as embodiment 264 is the compound or salt according to embodiment 261, wherein $R^6$ is $C_{1-4}$ haloalkyl (e.g., trifluoromethyl). Provided herein as embodiment 265 is the compound or salt according to embodiment 261, wherein $R^6$ is —C(O)$OR^z$ (e.g., —C(O)OtBu).

Provided herein as embodiment 266 is the compound or salt according to embodiment 258, wherein q is 2. Provided herein as embodiment 267 is the compound or salt according to embodiment 266, wherein one $R^6$ is halo (e.g., chloro) and the other $R^6$ is —C(O)$R^z$ (e.g., —C(O)$CH_3$). Provided herein as embodiment 268 is the compound or salt according to embodiment 266, wherein two $R^6$ are taken together on adjacent carbon atoms form a $C_{3-7}$ cycloalkyl (e.g., cyclopentyl).

Provided herein as embodiment 269 is the compound or salt according to embodiment 250, wherein A is 7-indazolyl. Provided herein as embodiment 270 is the compound or salt according to embodiment 269, wherein q is 2. Provided herein as embodiment 271 is the compound or salt according to embodiment 270, wherein one $R^6$ is chloro and the other $R^6$ is methyl.

Provided herein as embodiment 272 is the compound or salt according to any one of embodiments 250-271, wherein A-$L^2$ is

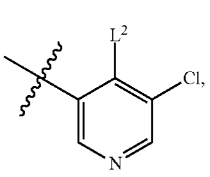

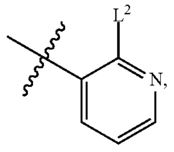

-continued

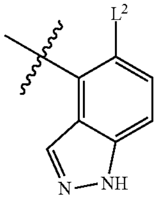
,
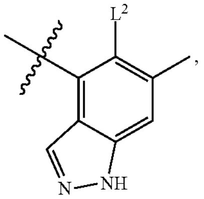

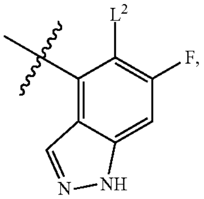
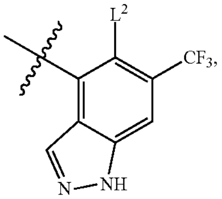

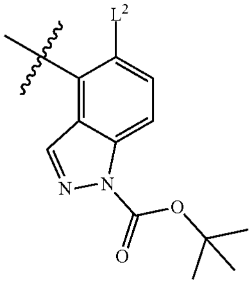
,
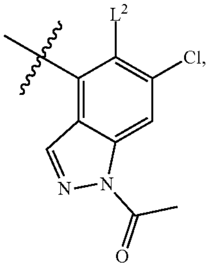

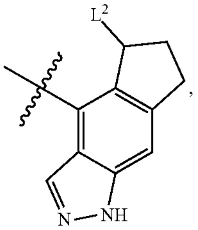
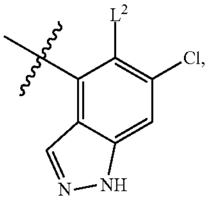

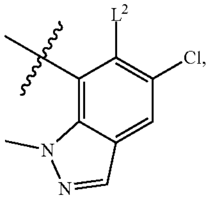
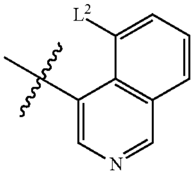
or

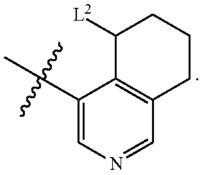

Provided herein as embodiment 273 is the compound or salt according to embodiment 272, wherein A-$L^2$ is

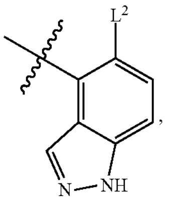
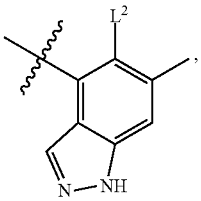

-continued

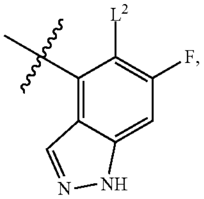
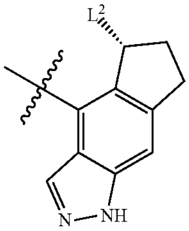
or

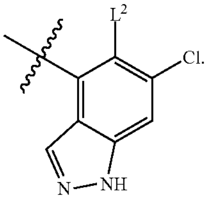

Provided herein as embodiment 274 is the compound or salt according to embodiment 273, wherein A-$L^2$ is

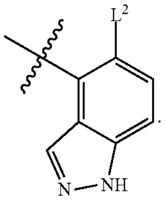

Provided herein as embodiment 275 is the compound or salt according to embodiment 273, wherein A-$L^2$ is

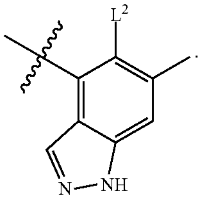

Provided herein as embodiment 276 is the compound or salt according to embodiment 273, wherein A-$L^2$ is

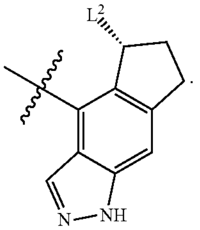

Provided herein as embodiment 277 is the compound or salt according to embodiment 273, wherein A-$L^2$ is

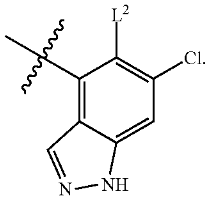

Provided herein as embodiment 278 is the compound or salt according to any one of embodiments 1-277, wherein $-L^1-L^2-$ is $—N(R^z)—C(O)-L^2$. Provided herein as embodiment 279 is the compound or salt according to embodiment 278, wherein $R^z$ is hydrogen. Provided herein as embodiment 280 is the compound or salt according to embodiment 279, wherein $L^2$ is n-propylene, 1-fluoro-n-propylene, n-butylene, 1-fluoro-n-butylene, 1-fluoro-n-pentylene, n-pentylene, methylene-O-ethylene, methylene-O-n-propylene, $—CHF—CH_2$-cyclopropylene- or $—CH_2CH_2$-cyclopropylene-.

Provided herein as embodiment 281 is the compound or salt according to embodiment 278, wherein $R^z$ is methyl. Provided herein as embodiment 282 is the compound or salt according to embodiment 281, wherein $L^2$ is n-propylene, n-butylene, 1-fluoro-n-butylene, $—CHF—CH_2$-cyclopropylene-, methylene-O-ethylene or $—CH_2CH_2$-cyclopropylene-. Provided herein as embodiment 283 is the compound or salt according to embodiment 278, wherein $-L^1-L^2-$ is

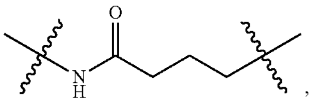
,
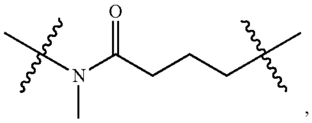
,
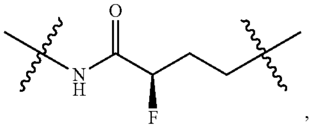
,
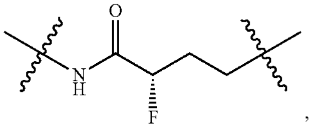
,
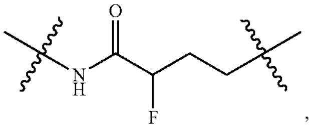
,
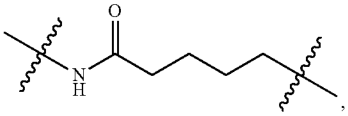
,
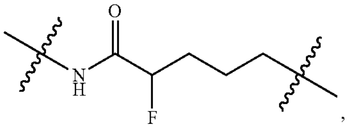
, -continued

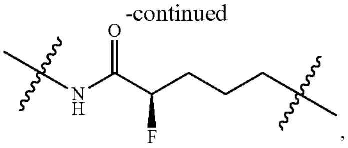
,
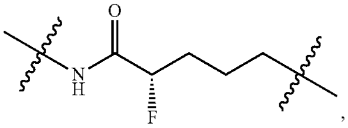
,
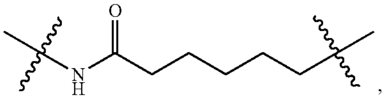
,
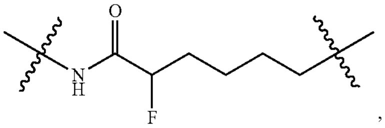
,
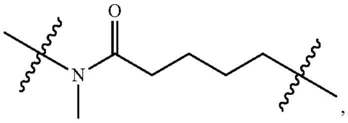
,
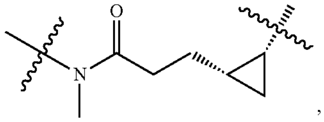
,
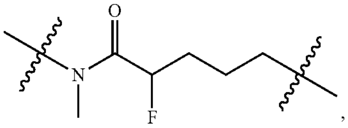
,
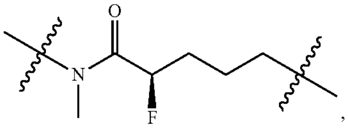
,
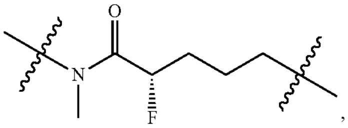
,
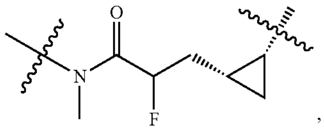
,
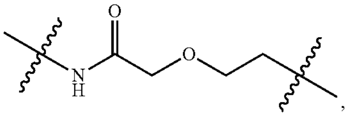
,
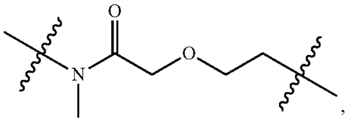
,
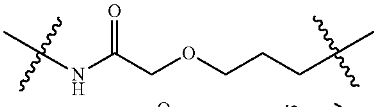
or
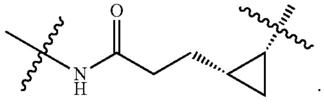
.

Provided herein as embodiment 284 is the compound or salt according to any one of embodiments 1-277, wherein -$L^1$-$L^2$- is —O—C(O)-$L^2$. Provided herein as embodiment 285 is the compound or salt according to embodiment 284, wherein $L^2$ is methylene-O-n-propylene, n-propylene-O—, n-butylene, 1-methyl-n-butylene, trans-n-propenylene, cis-n-butenylene, n-pentylene, —CHF—$CH_2$-cyclopropylene-, -methylene-O-ethylene, -ethylene-cyclopropylene- or n-propylene. Provided herein as embodiment 286 is the compound or salt according to embodiment 284, wherein -$L^1$-$L^2$- is

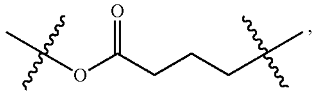,

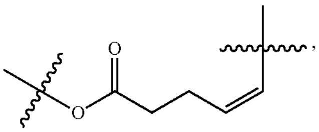,

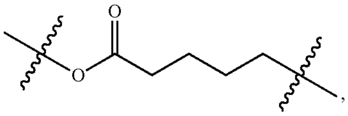,

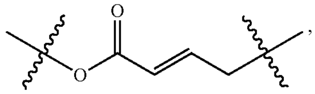,

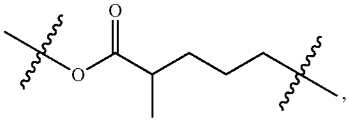,

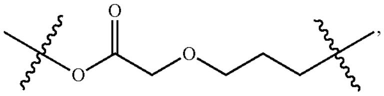,

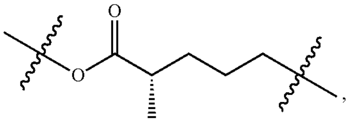,

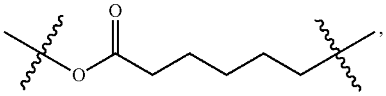,

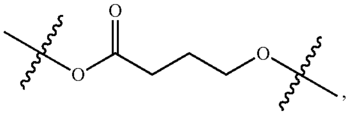,

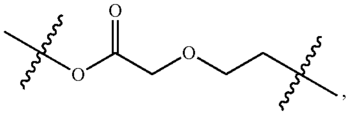,

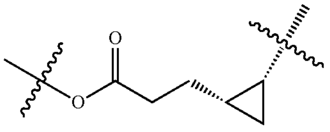 or

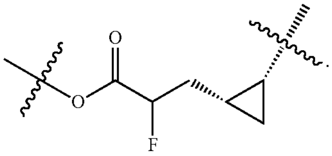.

Provided herein as embodiment 287 is the compound or salt according to any one of embodiments 1-277, wherein -$L^1$-$L^2$- is —O—C(O)—O-$L^2$. Provided herein as embodiment 288 is the compound or salt according to embodiment 287, wherein $L^2$ is ethylene, n-propylene, n-butylene, 2-methyl-n-propylene, cis-2-propenylene, trans-2-propenylene or —$CH_2$-cyclopropylene. Provided herein as embodiment 289 is the compound or salt according to embodiment 287, wherein -$L^1$-$L^2$- is

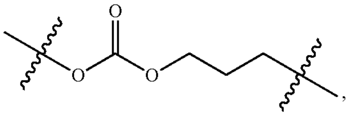,

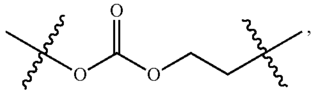,

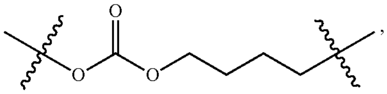,

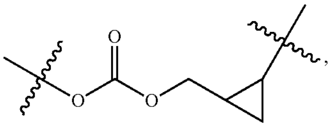,

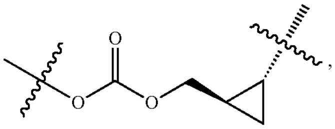,

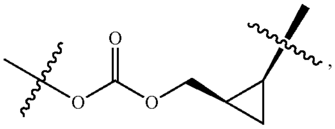,

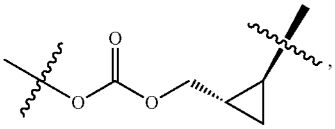,

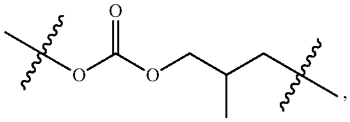,

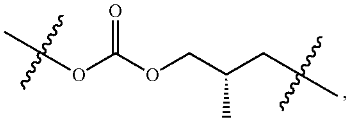,

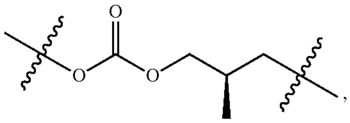,

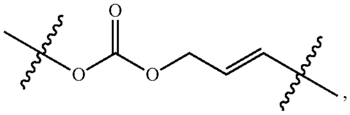,

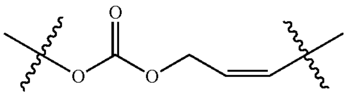 or

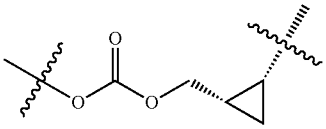.

Provided herein as embodiment 290 is the compound or salt according to embodiment 289, wherein $-L^1-L^2-$ is

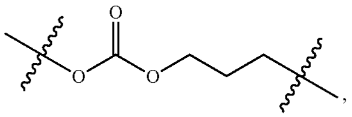

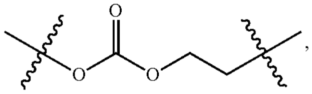

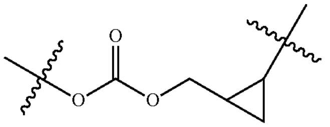

or

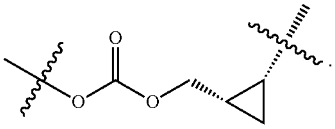

Provided herein as embodiment 291 is the compound or salt according to embodiment 290, wherein $-L^1-L^2-$ is

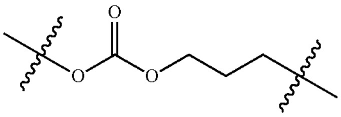

or

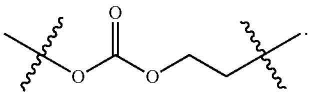

Provided herein as embodiment 292 is the compound or salt according to any one of embodiments 1-277, wherein $-L^1-L^2-$ is —$C_{1-4}$ alkylene-$S(O)_2$-$L^2$. Provided herein as embodiment 293 is the compound or salt according to embodiment 292, wherein $-L^1-L^2-$ is -methylene-$S(O)_2$-$L^2$. Provided herein as embodiment 294 is the compound or salt according to embodiment 293, wherein $L^2$ is n-butylene. Provided herein as embodiment 295 is the compound or salt according to embodiment 292, wherein $-L^1-L^2-$ is

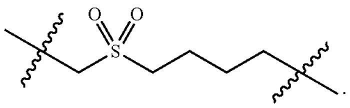 [SMILES: *CCCCS(=O)(=O)C*]

Provided herein as embodiment 296 is the compound or salt according to any one of embodiments 1-277, wherein $-L^1-L^2-$ is —$C_{1-4}$ alkylene-S(O)-$L^2$. Provided herein as embodiment 297 is the compound or salt according to embodiment 296, wherein $-L^1-L^2-$ is -methylene-S(O)-$L^2$. Provided herein as embodiment 298 is the compound or salt according to embodiment 297, wherein $L^2$ is n-butylene. Provided herein as embodiment 299 is the compound or salt according to embodiment 296, wherein $-L^1-L^2-$ is

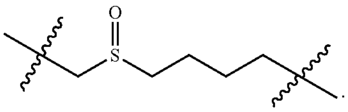 [SMILES: *CCCCS(=O)C*]

Provided herein as embodiment 300 is the compound or salt according to any one of embodiments 1-277, wherein $-L^1-L^2-$ is —$C_{1-4}$ alkylene-S-$L^2$. Provided herein as embodiment 301 is the compound or salt according to embodiment 300, wherein $-L^1-L^2-$ is -methylene-S-$L^2$. Provided herein as embodiment 302 is the compound or salt according to embodiment 301, wherein $L^2$ is n-butylene. Provided herein as embodiment 303 is the compound or salt according to embodiment 300, wherein $-L^1-L_2-$ is

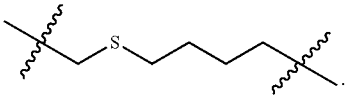 [SMILES: *CCCCSC*]

Provided herein as embodiment 304 is the compound or salt according to any one of embodiments 1-277, wherein-$L^1-L^2-$ is —O-$L^2$. Provided herein as embodiment 305 is the compound or salt according to embodiment 304, wherein $L^2$ is n-butylene, n-pentylene, cis-2-pentenylene or trans-2-pentenylene. Provided herein as embodiment 306 is the compound or salt according to embodiment 304, wherein $-L^1-L^2-$ is

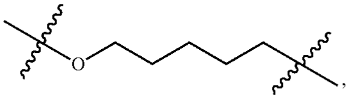

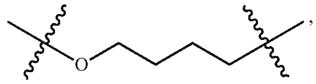

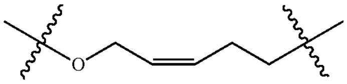

or

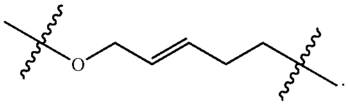

Provided herein as embodiment 307 is the compound or salt according to any one of embodiments 1-277, wherein $-L^1-L^2-$ is a single bond. Provided herein as embodiment 308 is the compound or salt according to embodiment 307, wherein $L^2$ is n-hexylene. Provided herein as embodiment 309 is the compound or salt according to embodiment 307, wherein $-L^1-L^2-$ is

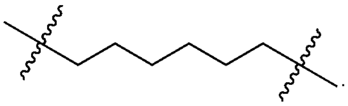 [SMILES: *CCCCCC*]

Provided herein as embodiment 310 is the compound or salt according to any one of embodiments 1-277, wherein $-L^1-L^2-$ is a single bond. Provided herein as embodiment 311 is the compound or salt according to embodiment 310, wherein $L^2$ is $C_{2-6}$ alkenylene. Provided herein as embodiment 312 is the compound or salt according to embodiment 311, wherein $L^2$ is trans-3-hexenylene. Provided herein as embodiment 313 is the compound or salt according to embodiment 310, wherein $-L^1-L^2-$ is

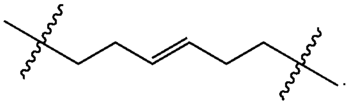 [SMILES: *CC/C=C/CC*]

Provided herein as embodiment 314 is the compound or salt according to any one of embodiments 1-277, wherein $-L^1-L^2-$ is —$NR^z$—C(O)—O-$L^2$. Provided herein as embodiment 315 is the compound or salt according to embodiment 314, wherein $R^z$ is hydrogen or methyl. Provided herein as embodiment 316 is the compound or salt according to embodiment 315, wherein $L^2$ is n-propylene, ethylene, n-butylene, —$CH_2$-cyclopropylene. Provided herein as embodiment 317 is the compound or salt according to embodiment 314, wherein $-L^1-L^2-$ is

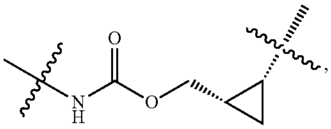,

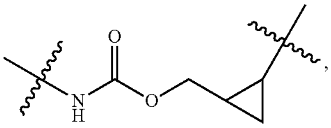,

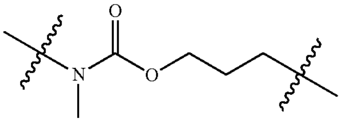,

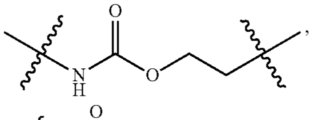,

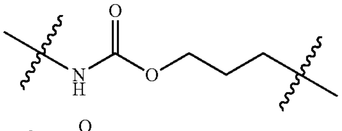,

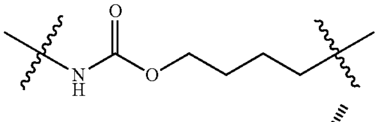 or

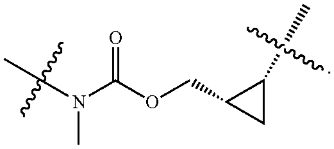.

Provided herein as embodiment 318 is the compound or salt according to embodiment 317, wherein $-L^1-L^2-$ is

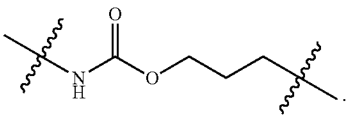 [SMILES: *CCCOC(=O)N*].

Provided herein as embodiment 319 is the compound or salt according to any one of embodiments 1-277, wherein $-L^1-L^2-$ is —C(O)—O-$L^2$. Provided herein as embodiment 320 is the compound or salt according to embodiment 319, wherein $L^2$ is n-propylene or n-butylene. Provided herein as embodiment 321 is the compound or salt according to embodiment 319, wherein $-L^1-L^2-$ is

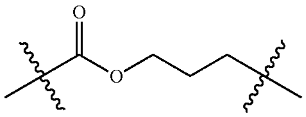 or

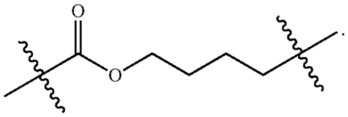.

Provided herein as embodiment 322 is the compound or salt according to any one of embodiments 1-277, wherein $-L^1-L^2-$ is —O—C(O)—$NR^z$-$L^2$. Provided herein as embodiment 323 is the compound or salt according to embodiment 322, wherein $R^z$ is hydrogen or methyl. Provided herein as embodiment 324 is the compound or salt according to embodiment 323, wherein $L^2$ is n-propylene or -methylene-cyclopropylene. Provided herein as embodiment 325 is the compound or salt according to embodiment 322, wherein $-L^1-L^2-$ is

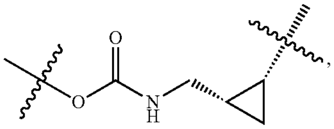,

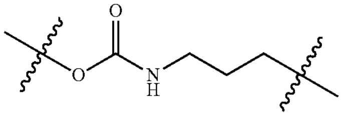 or

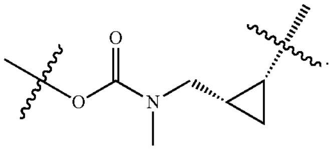.

Provided herein as embodiment 326 is the compound or salt according to any one of embodiments 1-277, wherein $-L^1-L^2-$ is a 5-6 membered heteroaryl-$L^2$. Provided herein as embodiment 327 is the compound or salt according to embodiment 326, wherein $-L^1-L^2-$ is

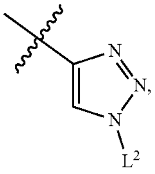,

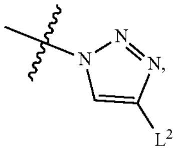,

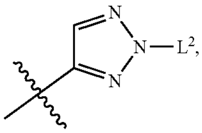,

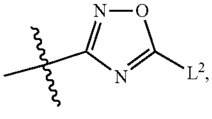,

-continued

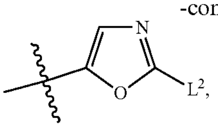

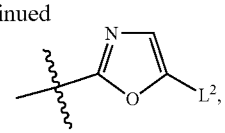

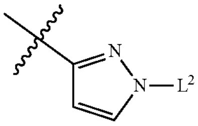

or

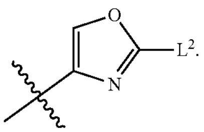

Provided herein as embodiment 328 is the compound or salt according to embodiment 327, wherein $L^2$ is n-propylene, ethylene, cis-2-propenylene or trans-2-propenylene. Provided herein as embodiment 329 is the compound or salt according to embodiment 326, wherein $-L^1-L^2-$ is

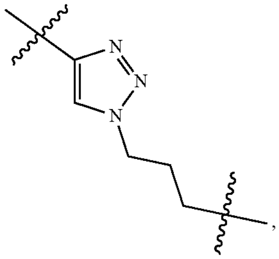

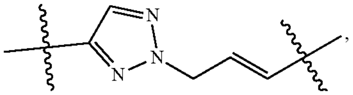

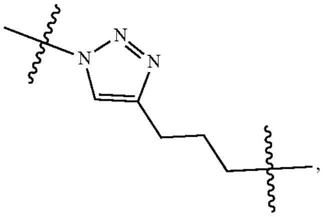

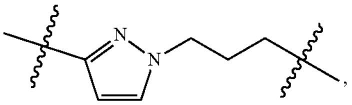

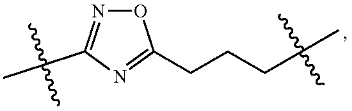

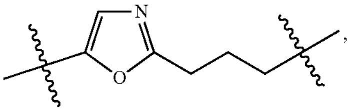

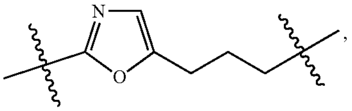

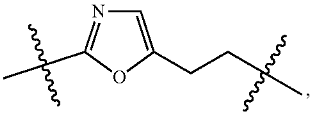

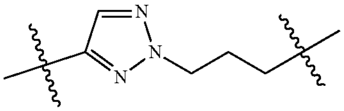

or

-continued

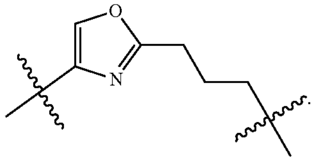

Provided herein as embodiment 330 is the compound or salt according to embodiment 329, wherein $-L^1-L^2-$ is

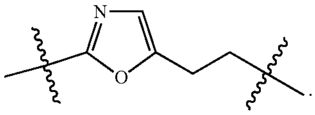 [SMILES: *CCc1cnc(*)o1]

Provided herein as embodiment 331 is the compound or salt according to any one of embodiments 1-277, wherein $-L^1-L^2-$ is a $-C_{1-4}$ alkylene-5-6 membered heteroaryl-$L^2$. Provided herein as embodiment 332 is the compound or salt according to embodiment 331, wherein $-L^1-L^2-$ is -methylene-5-6 membered heteroaryl-$L^2$. Provided herein as embodiment 333 is the compound or salt according to embodiment 332, wherein $-L^1-L^2-$ is

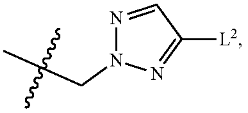

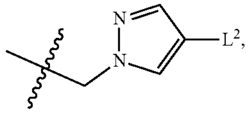

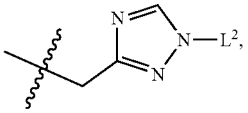

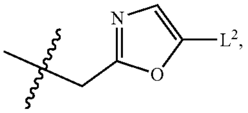

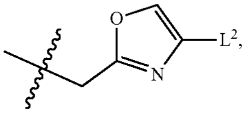

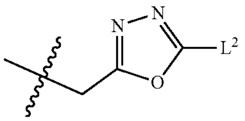

or

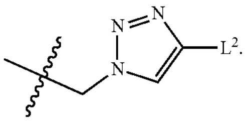

Provided herein as embodiment 334 is the compound or salt according to embodiment 333, wherein $L^2$ is ethylene, n-propylene, cyclopropylene, cis-2-propenylene or trans-2-propenylene. Provided herein as embodiment 335 is the compound or salt according to embodiment 331, wherein $-L^1-L^2-$ is

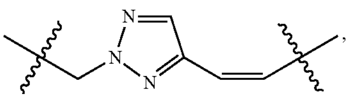

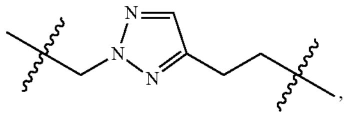

-continued

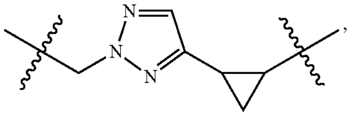

,

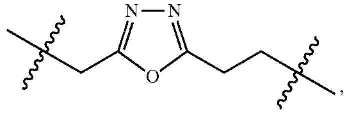

,

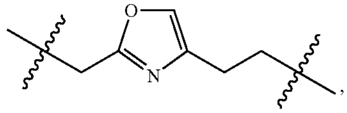

,

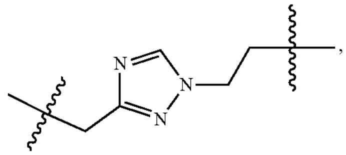

,

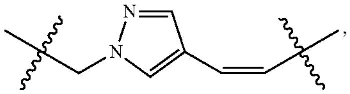

,

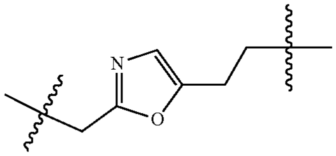

or

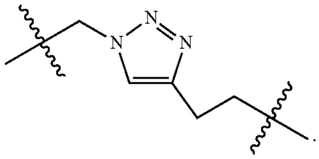

.

Provided herein as embodiment 336 is the compound or salt according to any one of embodiments 1-277, wherein -$L^1$-$L^2$- is a —$C_{1-4}$ hydroxyalkylene-5-6 membered heteroaryl-$L^2$. Provided herein as embodiment 337 is the compound or salt according to embodiment 336, wherein -$L^1$-$L^2$- is -hydroxymethylene-5-6 membered heteroaryl-$L^2$. Provided herein as embodiment 338 is the compound or salt according to embodiment 337, wherein -$L^1$-$L^2$- is

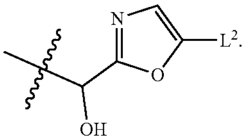

Provided herein as embodiment 339 is the compound or salt according to embodiment 338, wherein $L^2$ is ethylene. Provided herein as embodiment 340 is the compound or salt according to embodiment 336, wherein -$L^1$-$L^2$- is

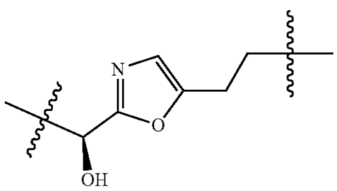

or

-continued

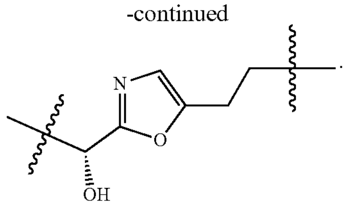

.

Provided herein as embodiment 341 is the compound or salt according to any one of embodiments 1-277, wherein -$L^1$-$L^2$- is —O-5-6 membered heteroaryl-$L^2$. Provided herein as embodiment 342 is the compound or salt according to embodiment 341, wherein -$L^1$-$L^2$- is

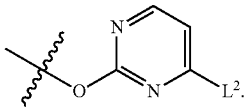

Provided herein as embodiment 343 is the compound or salt according to embodiment 342, wherein $L^2$ is ethylene. Provided herein as embodiment 344 is the compound or salt according to embodiment 341, wherein -$L^1$-$L^2$- is

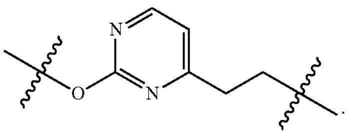 [SMILES: *CCc1ccnc(O*)n1]

.

Provided herein as embodiment 345 is the compound or salt according to any one of embodiments 1-277, wherein -$L^1$-$L^2$- is —C(O)—. Provided herein as embodiment 346 is the compound or salt according to embodiment 345, wherein $L^2$ is n-propylene, -methylene-O-ethylene, -methylene-O-n-propylene or n-butylene. Provided herein as embodiment 347 is the compound or salt according to embodiment 346, wherein -$L^1$-$L^2$- is

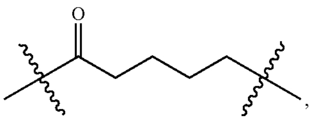

,

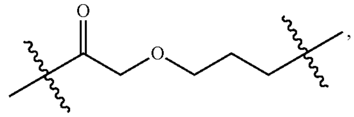 [SMILES: *CCCOCC(*)=O]

,

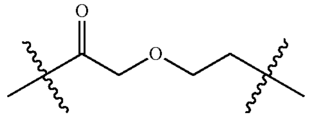

or

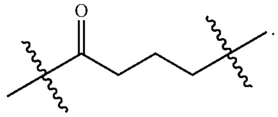

.

Provided herein as embodiment 348 is the compound or salt according to embodiment 347, wherein -$L^1$-$L^2$- is

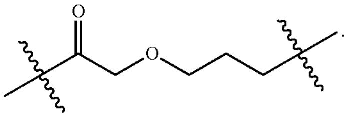

Provided herein as embodiment 349 is the compound or salt according to any one of embodiments 1-277, wherein $-L^1-L^2-$ is $C_{1-4}$ alkylene-C(O)-$L^2$. Provided herein as embodiment 350 is the compound or salt according to embodiment 349, wherein $-L^1-L^2-$ is -methylene-C(O)-$L^2$. Provided herein as embodiment 351 is the compound or salt according to embodiment 350, wherein $L^2$ is n-propylene or n-butylene. Provided herein as embodiment 352 is the compound or salt according to embodiment 349, wherein $-L^1-L^2-$ is

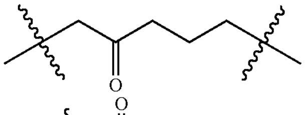

or

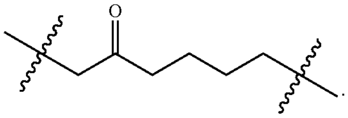

Provided herein as embodiment 353 is the compound or salt according to embodiment 349, wherein $-L^1-L^2-$ is -ethylene-C(O)-$L^2$. Provided herein as embodiment 354 is the compound or salt according to embodiment 353, wherein $L^2$ is ethylene or n-propylene. Provided herein as embodiment 355 is the compound or salt according to embodiment 349, wherein $-L^1-L^2-$ is

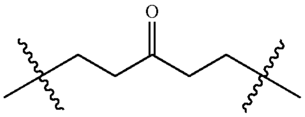

or

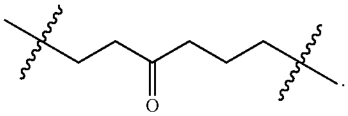

Provided herein as embodiment 356 is the compound or salt according to any one of embodiments 1-277, wherein $-L^1-L^2-$ is —$C_{1-4}$ alkylene-OC(O)O-$L^2$. Provided herein as embodiment 357 is the compound or salt according to embodiment 356, wherein $-L^1-L^2-$ is -methylene-OC(O)O-$L^2$. Provided herein as embodiment 358 is the compound or salt according to embodiment 357, wherein $L^2$ is ethylene. Provided herein as embodiment 359 is the compound or salt according to embodiment 356, wherein $-L^1-L^2-$ is

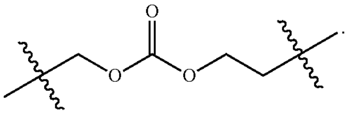 [SMILES: *CCOC(=O)OC*]

Provided herein as embodiment 360 is the compound or salt according to any one of embodiments 1-277, wherein $-L^1-L^2-$ is $C_{1-4}$ hydroxyalkylene-C(O)-$L^2$. Provided herein as embodiment 361 is the compound or salt according to embodiment 360, wherein $-L^1-L^2-$ is -hydroxymethylene-C(O)-$L^2$. Provided herein as embodiment 362 is the compound or salt according to embodiment 361, wherein $L^2$ is n-butylene. Provided herein as embodiment 363 is the compound or salt according to embodiment 360, wherein $-L^1-L^2-$ is

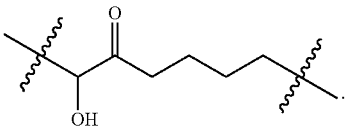 [SMILES: *CCCCC(=O)C(*)O]

Provided herein as embodiment 364 is the compound or salt according to any one of embodiments 1-277, wherein-$L^1-L^2-$ is —$C_{1-4}$ alkylene-O-$L^2$. Provided herein as embodiment 365 is the compound or salt according to embodiment 364, wherein $-L^1-L^2-$ is -methylene-O-$L^2$. Provided herein as embodiment 366 is the compound or salt according to embodiment 365, wherein $L^2$ is n-butylene, 2,2-difluoro-n-butylene, trans-2-butenylene, cis-2-butenylene, 3-methyl-n-butylene, -ethylene-cyclopropylene- or ethylene-O-methylene. Provided herein as embodiment 367 is the compound or salt according to embodiment 364, wherein $-L^1-L^2-$ is

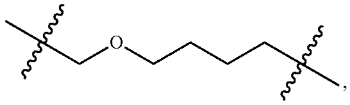,

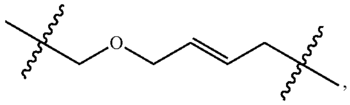,

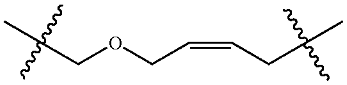,

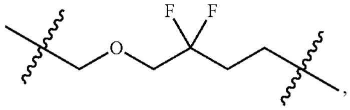,

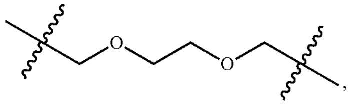,

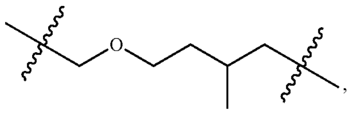,

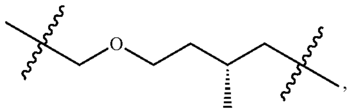,

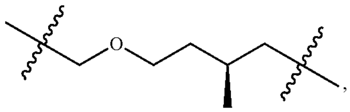,

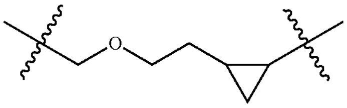,

-continued

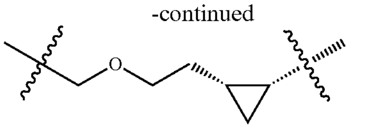
or
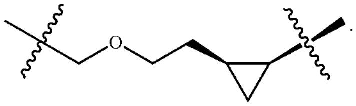

Provided herein as embodiment 368 is the compound or salt according to embodiment 367, wherein $-L^1-L^2-$ is

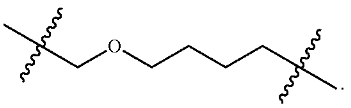 [SMILES: *CCCCOC*]

Provided herein as embodiment 369 is the compound or salt according to embodiment 364, wherein $-L^1-L^2-$ is methyl-methylene-O-$L^2$. Provided herein as embodiment 370 is the compound or salt according to embodiment 369, wherein $L^2$ is n-butylene. Provided herein as embodiment 371 is the compound or salt according to embodiment 364, wherein $-L^1-L^2-$ is

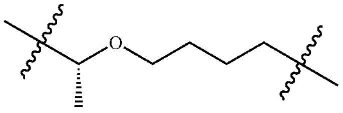
or
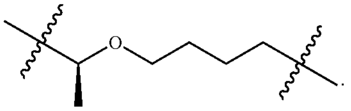

Provided herein as embodiment 372 is the compound or salt according to embodiment 364, wherein $-L^1-L^2-$ is ethylene-O-$L^2$. Provided herein as embodiment 373 is the compound or salt according to embodiment 372, wherein $L^2$ is ethylene, n-propylene or methylenecyclopropylene. Provided herein as embodiment 374 is the compound or salt according to embodiment 364, wherein $-L^1-L^2-$ is

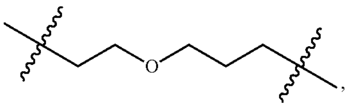
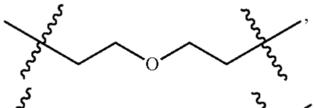
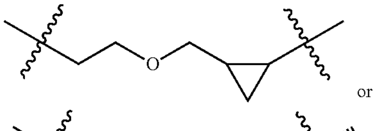
or
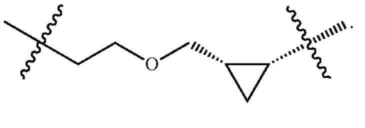

Provided herein as embodiment 375 is the compound or salt according to embodiment 374, wherein $-L^1-L^2-$ is

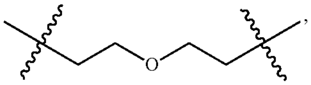
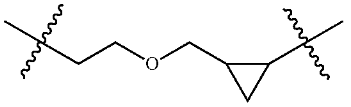
or
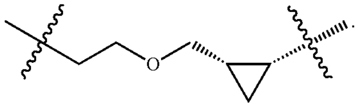

Provided herein as embodiment 376 is the compound or salt according to any one of embodiments 1-277, wherein $-L^1-L^2-$ is —$C_{1-4}$ alkylene-C(O)O-$L^2$. Provided herein as embodiment 377 is the compound or salt according to embodiment 376, wherein $-L^1-L^2-$ is -methylene-C(O)O-$L^2$. Provided herein as embodiment 378 is the compound or salt according to embodiment 377, wherein $L^2$ is ethylene, n-propylene or 2-methyl-n-propylene. Provided herein as embodiment 379 is the compound or salt according to embodiment 376, wherein $-L^1-L^2-$ is

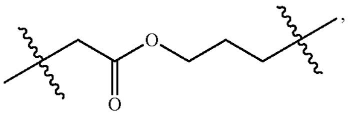
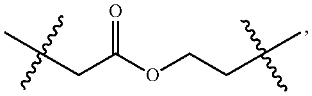
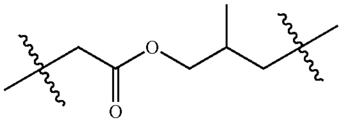
or
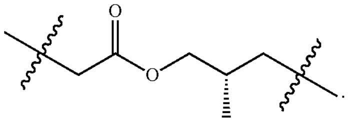

Provided herein as embodiment 380 is the compound or salt according to any one of embodiments 1-277, wherein $-L^1-L^2-$ is —$C_{1-4}$ alkylene-OC(O)-$L^2$. Provided herein as embodiment 381 is the compound or salt according to embodiment 380, wherein $-L^1-L^2-$ is -methylene-OC(O)O-$L^2$. Provided herein as embodiment 382 is the compound or salt according to embodiment 381, wherein $L^2$ is n-propylene. Provided herein as embodiment 383 is the compound or salt according to embodiment 380, wherein $-L^1-L^2-$ is -ethylene-OC(O)-$L^2$. Provided herein as embodiment 384 is the compound or salt according to embodiment 383, wherein $L^2$ is ethylene or n-propylene. Provided herein as embodiment 385 is the compound or salt according to embodiment 380, wherein $-L^1-L^2-$ is

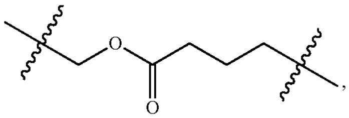

-continued

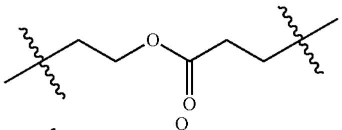

or

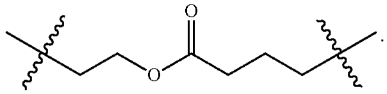

Provided herein as embodiment 386 is the compound or salt according to any one of embodiments 1-277, wherein $-L^1-L^2-$ is a single bond. Provided herein as embodiment 387 is the compound or salt according to embodiment 386, wherein $L^2$ is 2-hydroxy-n-hexylene or 3-hydroxy-n-hexylene. Provided herein as embodiment 388 is the compound or salt according to embodiment 386, wherein $-L^1-L^2-$ is

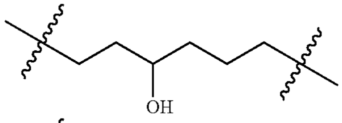

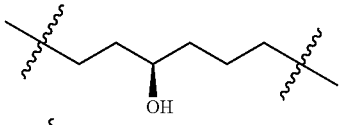

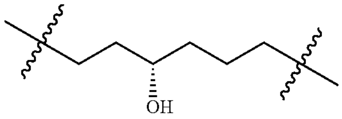

or

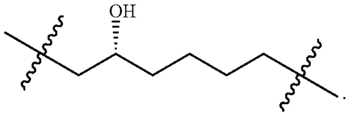

Provided herein as embodiment 389 is the compound or salt according to any one of embodiments 1-277, wherein $-L^1-L^2-$ is —O—C(S)—O-$L^2$. Provided herein as embodiment 390 is the compound or salt according to embodiment 389, wherein $L^2$ is n-propylene. Provided herein as embodiment 391 is the compound or salt according to embodiment 389, wherein $-L^1-L^2-$ is

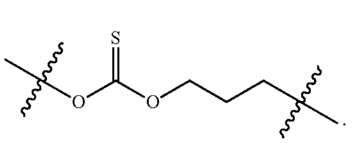 [SMILES: *CCCOC(=S)O*]

Provided herein as embodiment 392 is the compound or salt according to any one of embodiments 1-391, wherein $R^4$ is $C_{1-4}$ alkyl, $C_{1-4}$ alkoxy, hydroxyl, halogen or $C_{1-4}$ haloalkyl. Provided herein as embodiment 393 is the compound or salt according to embodiment 392, wherein $R^4$ is $C_{1-4}$ alkyl, hydroxyl or halogen. Provided herein as embodiment 394 is the compound or salt according to embodiment 393, wherein $R^4$ is $C_{1-4}$ alkyl or halogen. Provided herein as embodiment 395 is the compound or salt according to embodiment 394, wherein $R^4$ halogen (e.g., fluorine or chlorine). Provided herein as embodiment 396 is the compound or salt according to embodiment 395, wherein $R^4$ is fluorine.

Provided herein as embodiment 397 is the compound or salt according to embodiment 1, wherein is the compound is a compound of formula (II):

(II)

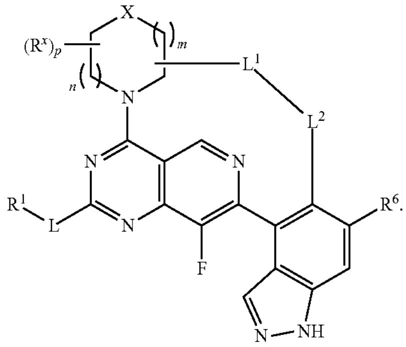

Provided herein as embodiment 398 is the compound or salt according to embodiment 1, wherein is the compound is a compound of formula (III):

(III)

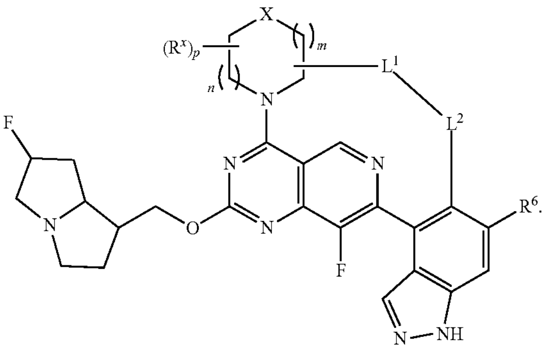

Provided herein as embodiment 399 is the compound or salt according to embodiment 1, wherein is the compound is a compound of formula (IV):

(IV)

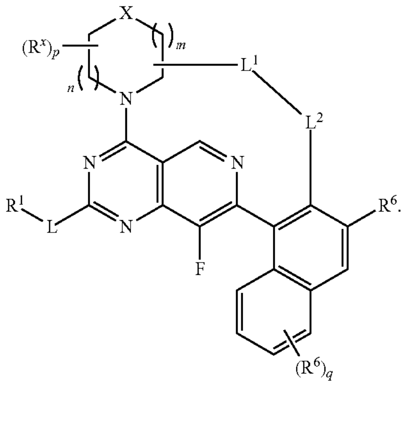

Provided herein as embodiment 400 is the compound or salt according to embodiment 1, wherein is the compound is a compound of formula (V):

(V)
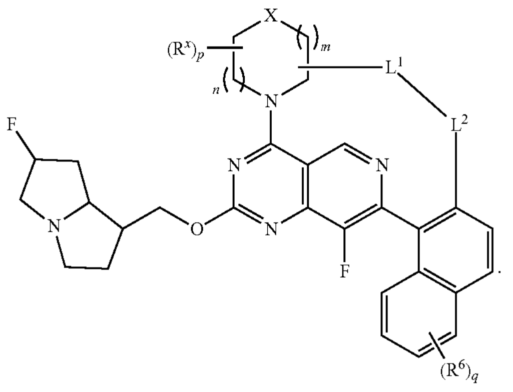
Provided herein as embodiment 401 is the compound or salt according to embodiment 1, wherein the compound is selected from a compound of Table 1:
TABLE 1
| Compound |
| --- |
| 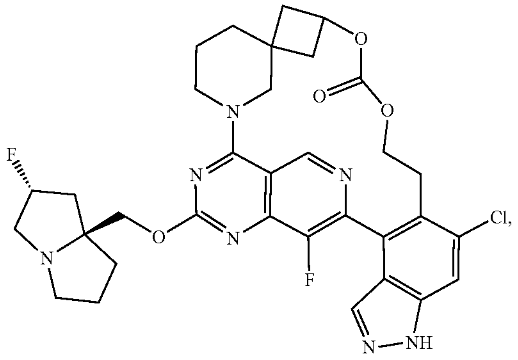 [SMILES: O=C1OCCc2c(Cl)cc3[nH]ncc3c2-c2ncc3c(nc(OC[C@@]45CCCN4C[C@H](F)C5)nc3c2F)N2CCCC3(CC(C3)O1)C2] |
| 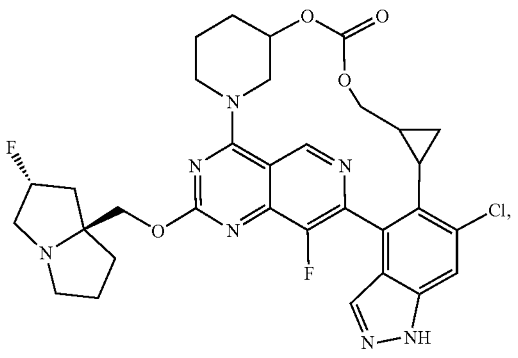 [SMILES: O=C1OCC2CC2c2c(Cl)cc3[nH]ncc3c2-c2ncc3c(nc(OC[C@@]45CCCN4C[C@H](F)C5)nc3c2F)N2CCCC(C2)O1] |
TABLE 1-continued
| Compound |
| --- |
| 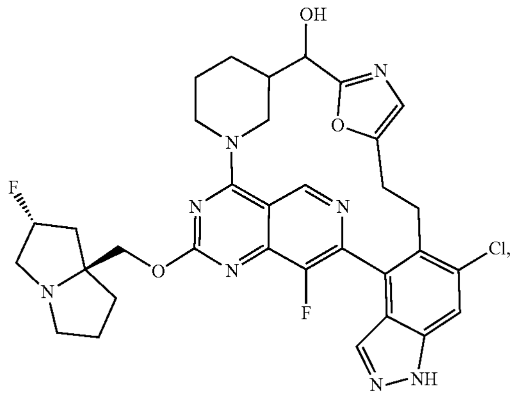 [SMILES: OC1c2ncc(o2)CCc2c(Cl)cc3[nH]ncc3c2-c2ncc3c(nc(OC[C@@]45CCCN4C[C@H](F)C5)nc3c2F)N2CCCC1C2] |
| 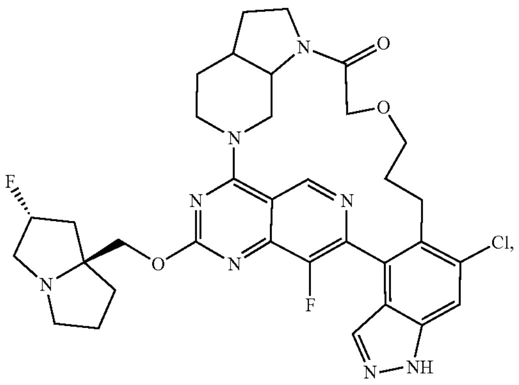 [SMILES: O=C1COCCCc2c(Cl)cc3[nH]ncc3c2-c2ncc3c(nc(OC[C@@]45CCCN4C[C@H](F)C5)nc3c2F)N2CCC3CCN1C3C2] |
| 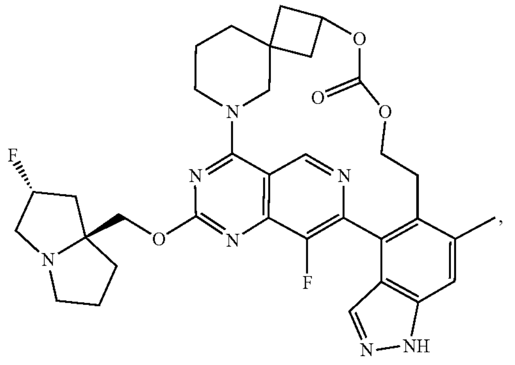 [SMILES: Cc1cc2[nH]ncc2c2c1CCOC(=O)OC1CC3(CCCN(C3)c3nc(OC[C@@]45CCCN4C[C@H](F)C5)nc4c(F)c-2ncc34)C1] |
| 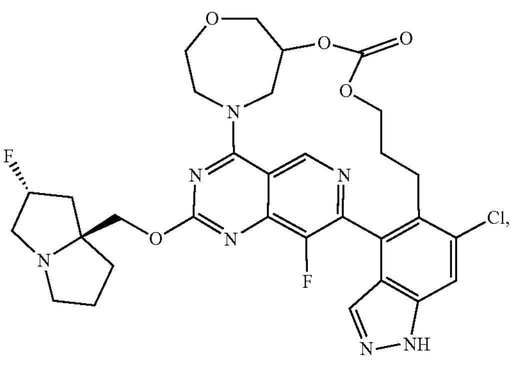 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] |

TABLE 1-continued
| Compound |
| --- |
| 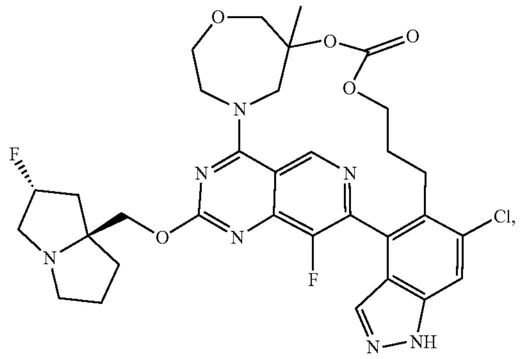 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2] |
| 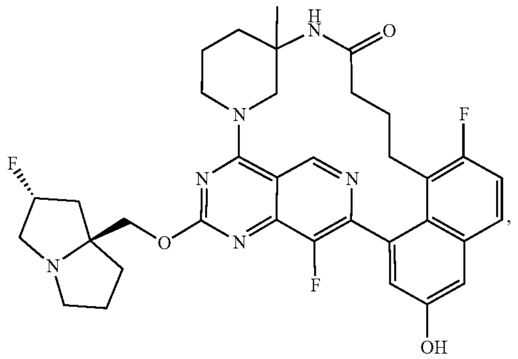 [SMILES: CC12CCCN(C1)c1nc(OC[C@@]34CCCN3C[C@H](F)C4)nc3c(F)c(ncc13)-c1cc(O)cc3ccc(F)c(c13)CCCC(=O)N2] |
| 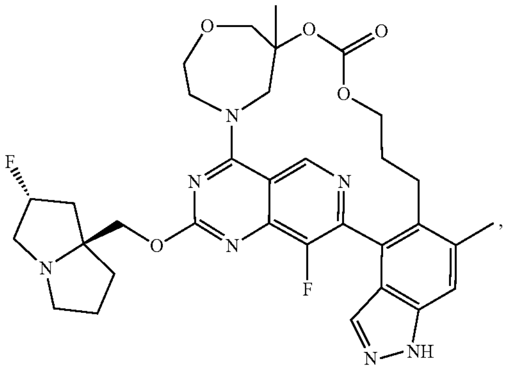 [SMILES: Cc1cc2[nH]ncc2c2c1CCCOC(=O)OC1(C)COCCN(C1)c1nc(OC[C@@]34CCCN3C[C@H](F)C4)nc3c(F)c-2ncc13] |
| 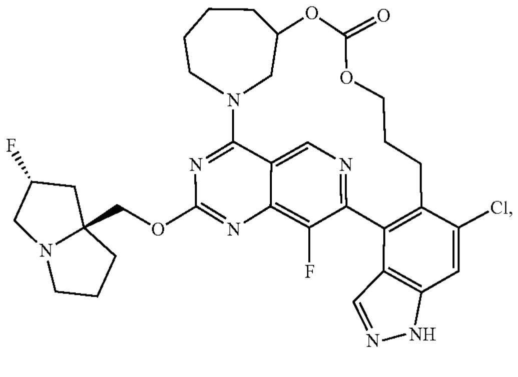 [SMILES: O=C1OCCCc2c(Cl)cc3[nH]ncc3c2-c2ncc3c(nc(OC[C@@]45CCCN4C[C@H](F)C5)nc3c2F)N2CCCCC(C2)O1] |
TABLE 1-continued
| Compound |
| --- |
| 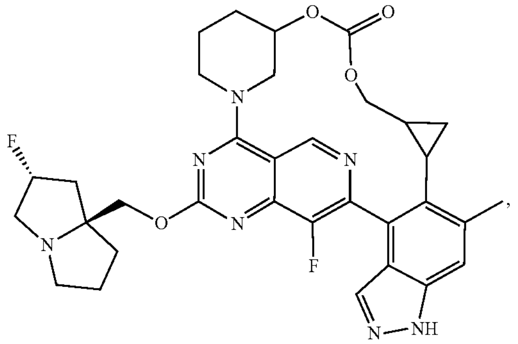 [SMILES: Cc1cc2[nH]ncc2c2c1C1CC1COC(=O)OC1CCCN(C1)c1nc(OC[C@@]34CCCN3C[C@H](F)C4)nc3c(F)c-2ncc13] |
| 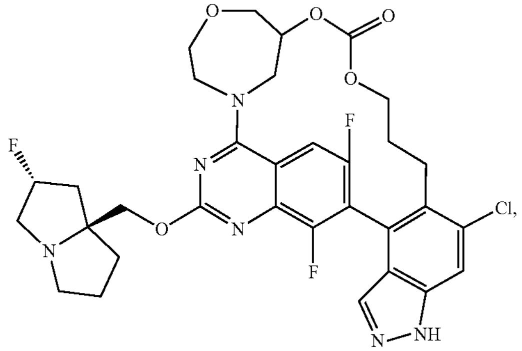 [SMILES: O=C1OCCCc2c(Cl)cc3[nH]ncc3c2-c2c(F)cc3c(nc(OC[C@@]45CCCN4C[C@H](F)C5)nc3c2F)N2CCOCC(C2)O1] |
| 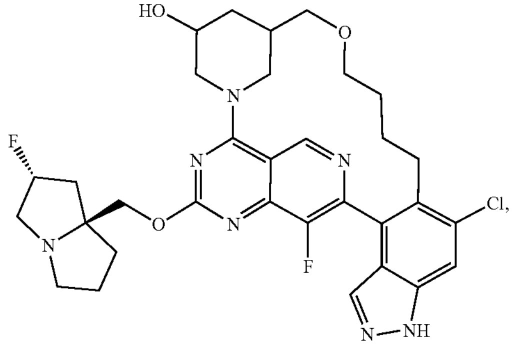 [SMILES: OC1CC2COCCCCc3c(Cl)cc4[nH]ncc4c3-c3ncc4c(nc(OC[C@@]56CCCN5C[C@H](F)C6)nc4c3F)N(C1)C2] |
| 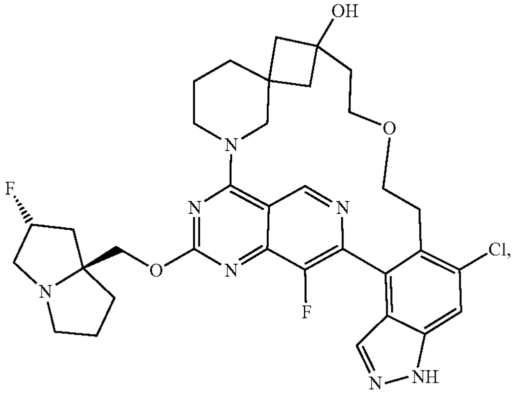 |

TABLE 1-continued
| Compound |
| --- |
| 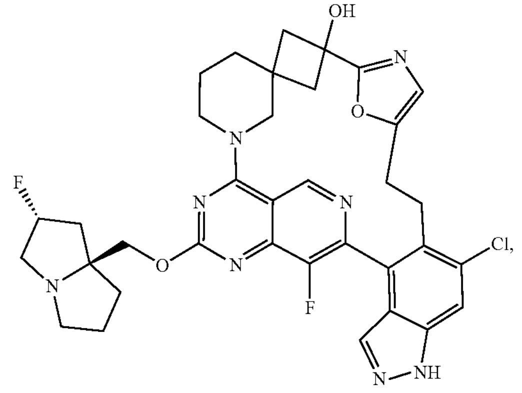 [SMILES: OC12CC3(CCCN(C3)c3nc(OC[C@@]45CCCN4C[C@H](F)C5)nc4c(F)c(ncc34)-c3c(c(Cl)cc4[nH]ncc34)CCc3cnc1o3)C2] , |
| 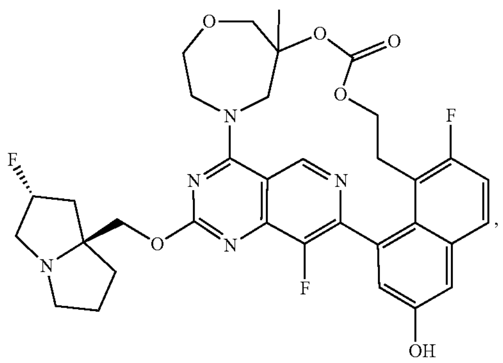 [SMILES: CC12COCCN(C1)c1nc(OC[C@@]34CCCN3C[C@H](F)C4)nc3c(F)c(ncc13)-c1cc(O)cc3ccc(F)c(c13)CCOC(=O)O2] , |
| 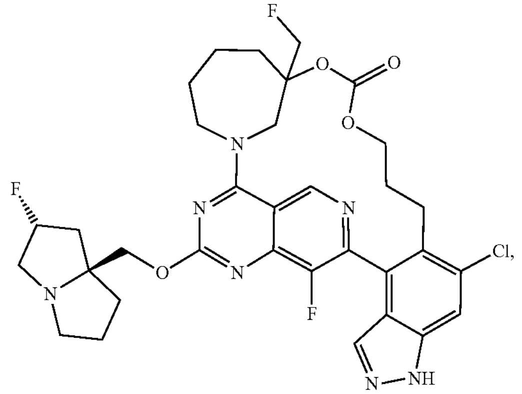 , |
| 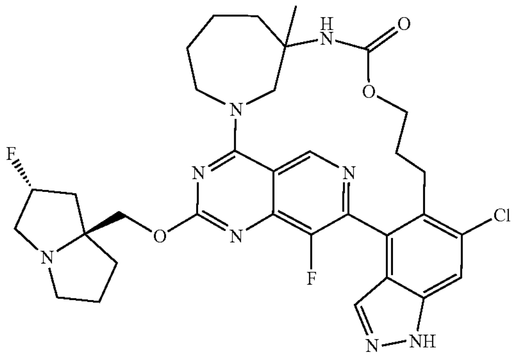 [SMILES: CC12CCCCN(C1)c1nc(OC[C@@]34CCCN3C[C@H](F)C4)nc3c(F)c(ncc13)-c1c(c(Cl)cc3[nH]ncc13)CCCOC(=O)N2] |
TABLE 1-continued
| Compound |
| --- |
| 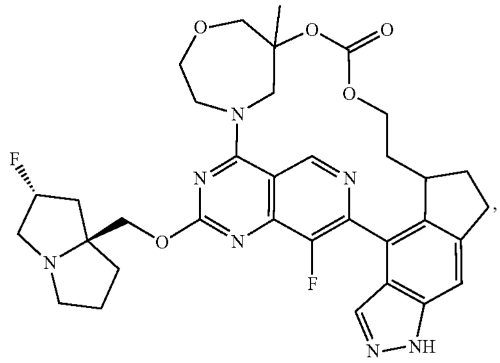 [SMILES: CC12COCCN(C1)c1nc(OC[C@@]34CCCN3C[C@H](F)C4)nc3c(F)c(ncc13)-c1c3c(cc4[nH]ncc14)CCC3CCOC(=O)O2] , |
| 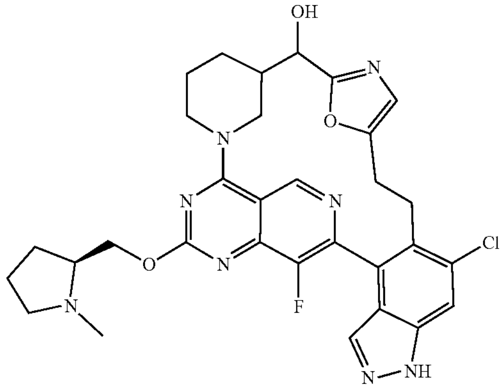 [SMILES: CN1CCC[C@H]1COc1nc2c3cnc(c(F)c3n1)-c1c(c(Cl)cc3[nH]ncc13)CCc1cnc(o1)C(O)C1CCCN2C1] |
| 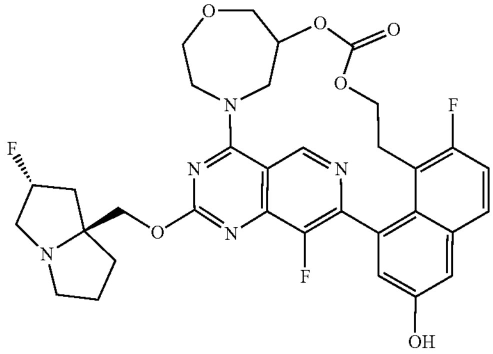 [SMILES: O=C1OCCc2c(F)ccc3cc(O)cc(c23)-c2ncc3c(nc(OC[C@@]45CCCN4C[C@H](F)C5)nc3c2F)N2CCOCC(C2)O1] |
| 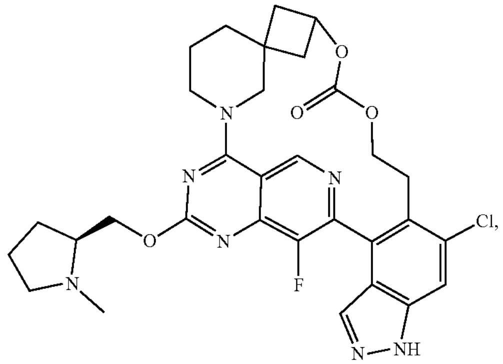 [SMILES: CN1CCC[C@H]1COc1nc2c3cnc(c(F)c3n1)-c1c(c(Cl)cc3[nH]ncc13)CCOC(=O)OC1CC3(CCCN2C3)C1] , |

TABLE 1-continued
| Compound |
| --- |
| 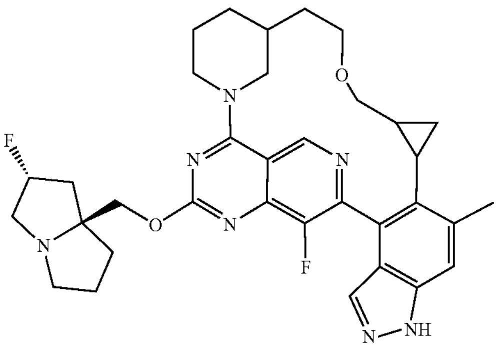 [SMILES: Cc1cc2[nH]ncc2c2c1C1CC1COCCC1CCCN(C1)c1nc(OC[C@@]34CCCN3C[C@H](F)C4)nc3c(F)c-2ncc13] |
| 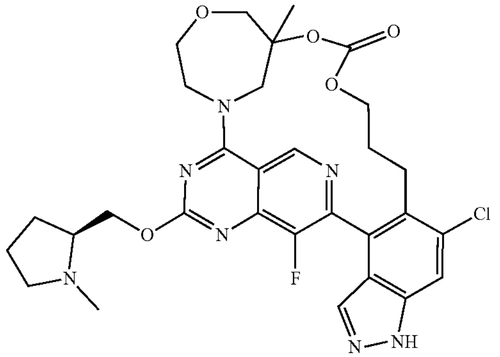 [SMILES: CN1CCC[C@H]1COc1nc2c3cnc(c(F)c3n1)-c1c(c(Cl)cc3[nH]ncc13)CCCOC(=O)OC1(C)COCCN2C1] |
| or |
| 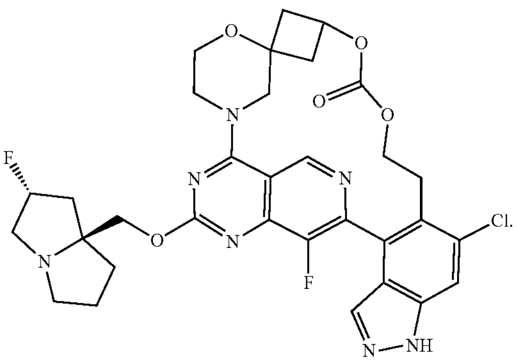 |
Provided herein as embodiment 402 is the compound or salt according to embodiment 1, wherein the compound is selected from a compound of Table 2:
TABLE 2
| Compound |
| --- |
| 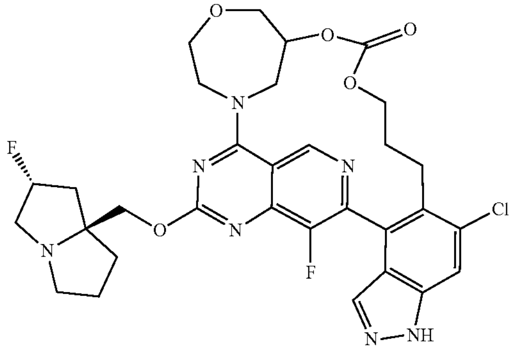 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] |
| 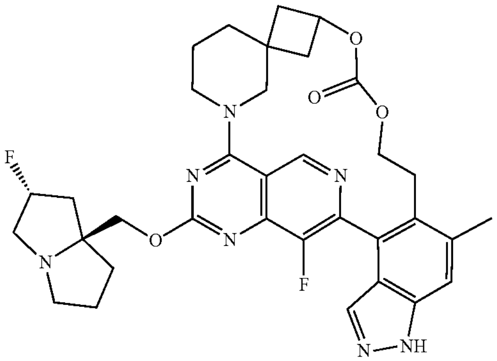 [SMILES: Cc1cc2[nH]ncc2c2c1CCOC(=O)OC1CC3(CCCN(C3)c3nc(OC[C@@]45CCCN4C[C@H](F)C5)nc4c(F)c-2ncc34)C1] |
| 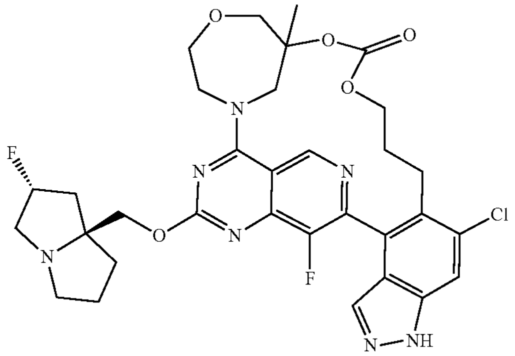 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2] |
| 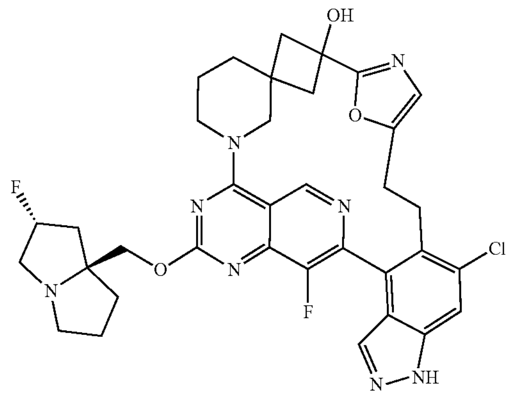 [SMILES: OC12CC3(CCCN(C3)c3nc(OC[C@@]45CCCN4C[C@H](F)C5)nc4c(F)c(ncc34)-c3c(c(Cl)cc4[nH]ncc34)CCc3cnc1o3)C2] |

TABLE 2-continued
| Compound |
| --- |
| 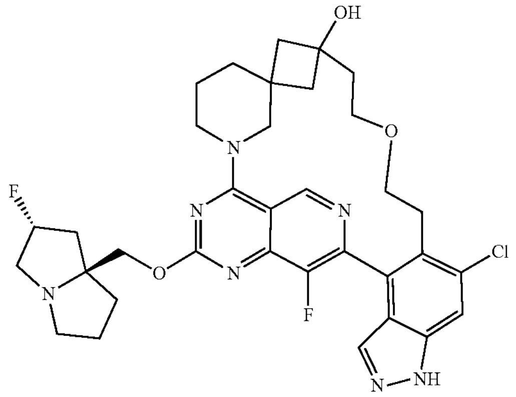 [SMILES: OC12CCOCCc3c(Cl)cc4[nH]ncc4c3-c3ncc4c(nc(OC[C@@]56CCCN5C[C@H](F)C6)nc4c3F)N3CCCC(C3)(C1)C2] |
| 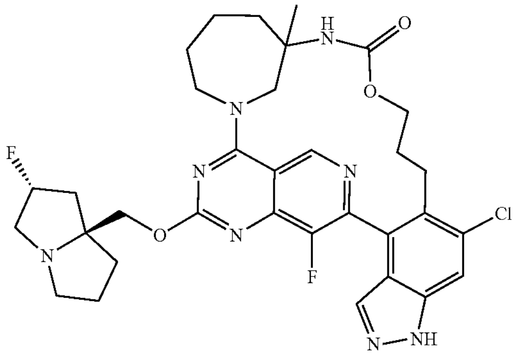 [SMILES: CC12CCCCN(C1)c1nc(OC[C@@]34CCCN3C[C@H](F)C4)nc3c(F)c(ncc13)-c1c(c(Cl)cc3[nH]ncc13)CCCOC(=O)N2] |
| 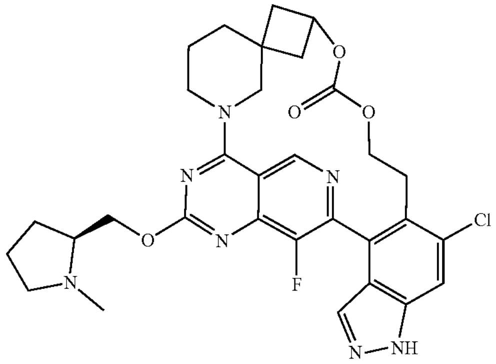 [SMILES: CN1CCC[C@H]1COc1nc2c3cnc(c(F)c3n1)-c1c(c(Cl)cc3[nH]ncc13)CCOC(=O)OC1CC3(CCCN2C3)C1] |
| 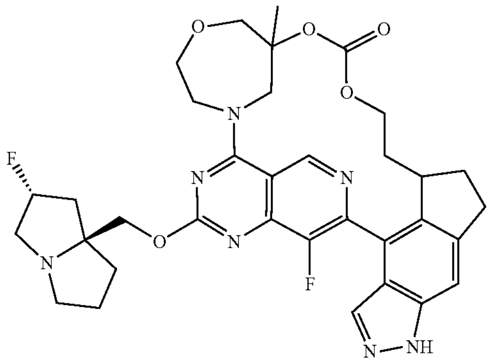 [SMILES: CC12COCCN(C1)c1nc(OC[C@@]34CCCN3C[C@H](F)C4)nc3c(F)c(ncc13)-c1c3c(cc4[nH]ncc14)CCC3CCOC(=O)O2] |
| 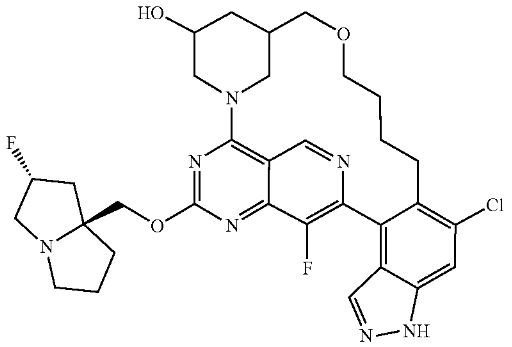 [SMILES: OC1CC2COCCCCc3c(Cl)cc4[nH]ncc4c3-c3ncc4c(nc(OC[C@@]56CCCN5C[C@H](F)C6)nc4c3F)N(C1)C2] |
| or |
| 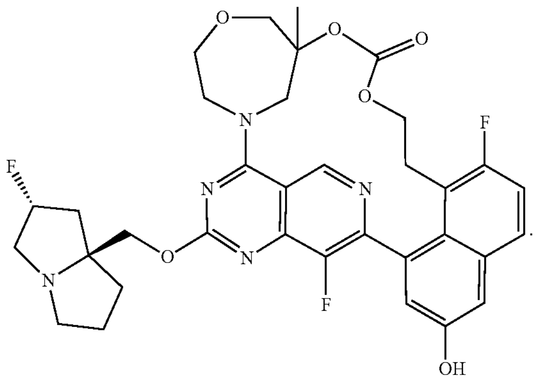 [SMILES: CC12COCCN(C1)c1nc(OC[C@@]34CCCN3C[C@H](F)C4)nc3c(F)c(ncc13)-c1cc(O)cc3ccc(F)c(c13)CCOC(=O)O2] |
Provided herein as embodiment 403 is the compound or salt according to embodiment 1, wherein the compound is
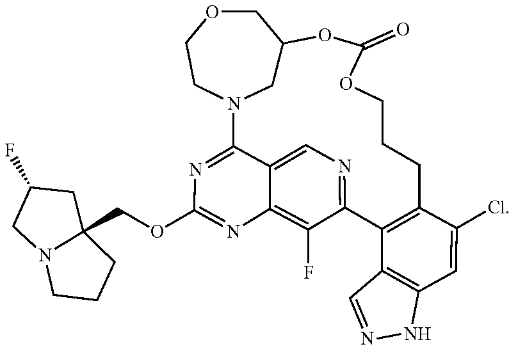 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1]
Provided herein as embodiment 404 is the compound or salt according to embodiment 1, wherein the compound is

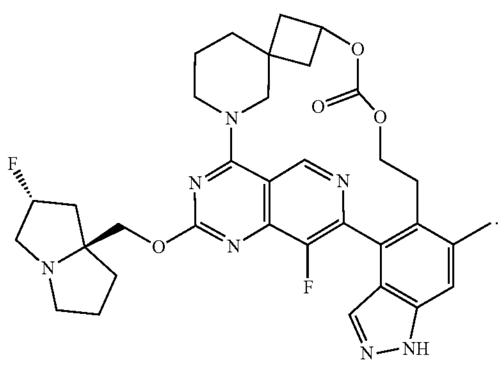 [SMILES: Cc1cc2[nH]ncc2c2c1CCOC(=O)OC1CC3(CCCN(C3)c3nc(OC[C@@]45CCCN4C[C@H](F)C5)nc4c(F)c-2ncc34)C1]

Provided herein as embodiment 405 is the compound or salt according to embodiment 1, wherein the compound is

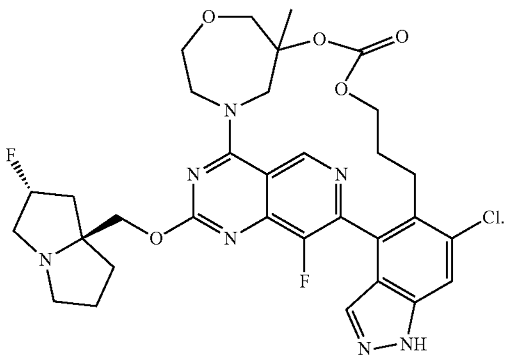 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2]

Provided herein as embodiment 406 is the compound or salt according to embodiment 1, wherein the compound is

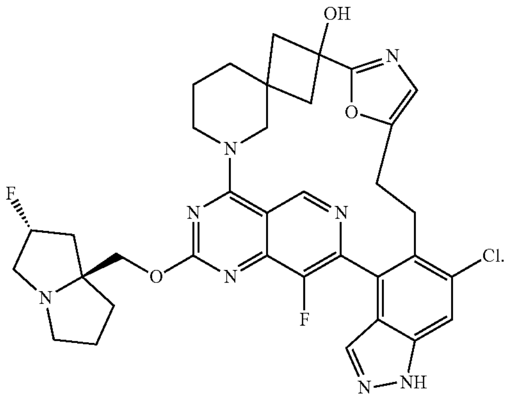 [SMILES: OC12CC3(CCCN(C3)c3nc(OC[C@@]45CCCN4C[C@H](F)C5)nc4c(F)c(ncc34)-c3c(c(Cl)cc4[nH]ncc34)CCc3cnc1o3)C2]

Provided herein as embodiment 407 is the compound or salt according to embodiment 1, wherein the compound is

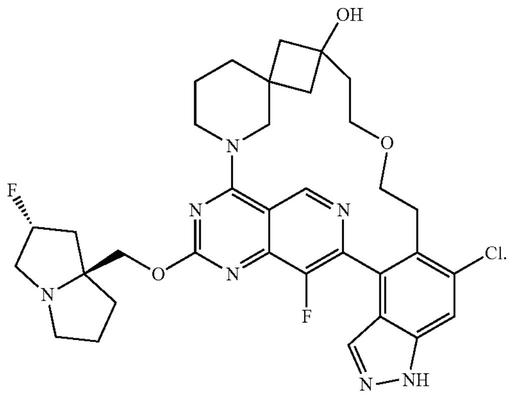 [SMILES: OC12CCOCCc3c(Cl)cc4[nH]ncc4c3-c3ncc4c(nc(OC[C@@]56CCCN5C[C@H](F)C6)nc4c3F)N3CCCC(C3)(C1)C2]

Provided herein as embodiment 408 is the compound or salt according to embodiment 1, wherein the compound is

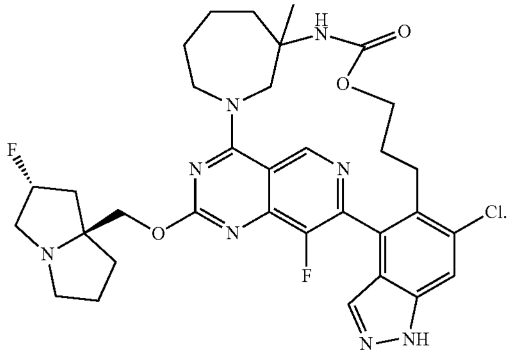 [SMILES: CC12CCCCN(C1)c1nc(OC[C@@]34CCCN3C[C@H](F)C4)nc3c(F)c(ncc13)-c1c(c(Cl)cc3[nH]ncc13)CCCOC(=O)N2]

Provided herein as embodiment 409 is the compound or salt according to embodiment 1, wherein the compound is

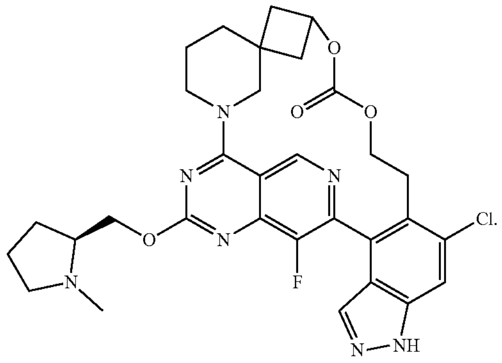 [SMILES: CN1CCC[C@H]1COc1nc2c3cnc(c(F)c3n1)-c1c(c(Cl)cc3[nH]ncc13)CCOC(=O)OC1CC3(CCCN2C3)C1]

Provided herein as embodiment 410 is the compound or salt according to embodiment 1, wherein the compound is

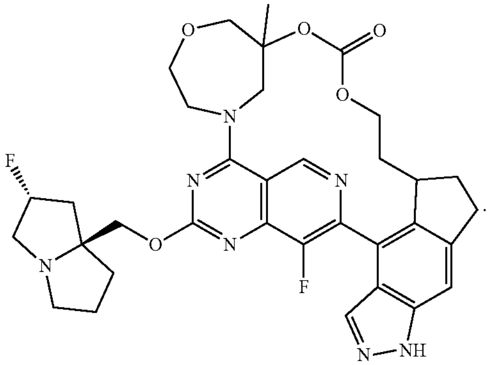 [SMILES: CC12COCCN(C1)c1nc(OC[C@@]34CCCN3C[C@H](F)C4)nc3c(F)c(ncc13)-c1c3c(cc4[nH]ncc14)CCC3CCOC(=O)O2]
Provided herein as embodiment 411 is the compound or salt according to embodiment 1, wherein the compound is
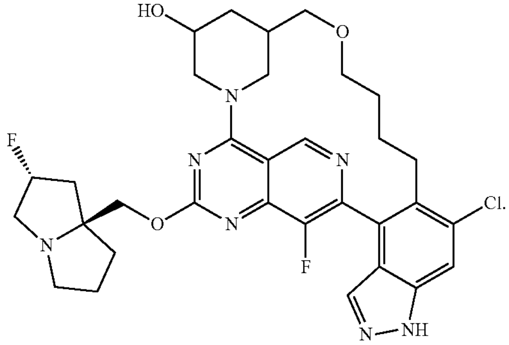 [SMILES: OC1CC2COCCCCc3c(Cl)cc4[nH]ncc4c3-c3ncc4c(nc(OC[C@@]56CCCN5C[C@H](F)C6)nc4c3F)N(C1)C2]
Provided herein as embodiment 412 is the compound or salt according to embodiment 1, wherein the compound is
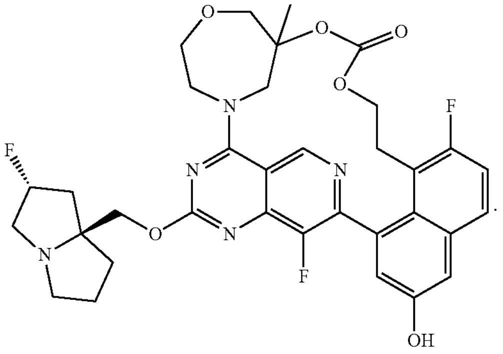 [SMILES: CC12COCCN(C1)c1nc(OC[C@@]34CCCN3C[C@H](F)C4)nc3c(F)c(ncc13)-c1cc(O)cc3ccc(F)c(c13)CCOC(=O)O2]
Provided herein as embodiment 413 is the compound or salt according to embodiment 1, wherein the compound is selected from a compound of Table 3:
TABLE 3
| Compound |
| --- |
| 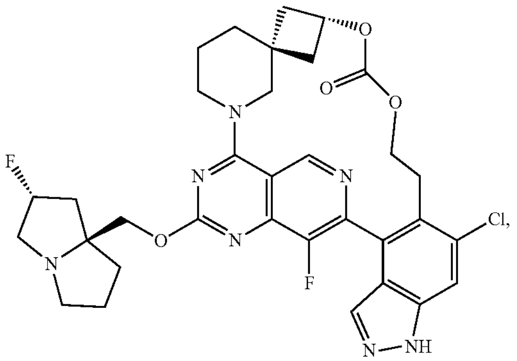 [SMILES: O=C1OCCc2c(Cl)cc3[nH]ncc3c2-c2ncc3c(nc(OC[C@@]45CCCN4C[C@H](F)C5)nc3c2F)N2CCC[C@]3(C2)C[C@H](C3)O1] |
| 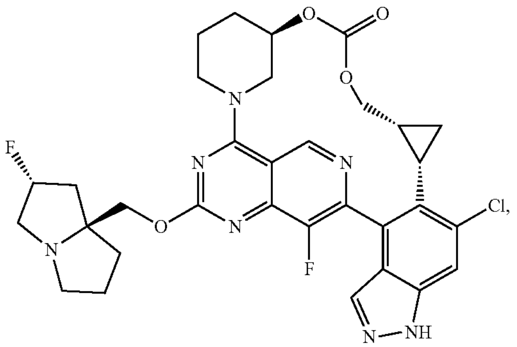 [SMILES: O=C1OC[C@@H]2C[C@@H]2c2c(Cl)cc3[nH]ncc3c2-c2ncc3c(nc(OC[C@@]45CCCN4C[C@H](F)C5)nc3c2F)N2CCC[C@H](C2)O1] |
| 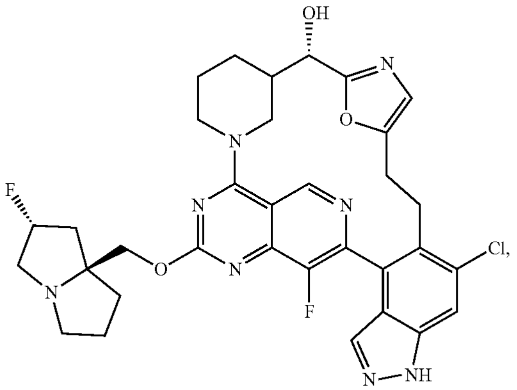 [SMILES: O[C@@H]1c2ncc(o2)CCc2c(Cl)cc3[nH]ncc3c2-c2ncc3c(nc(OC[C@@]45CCCN4C[C@H](F)C5)nc3c2F)N2CCCC1C2] |
| 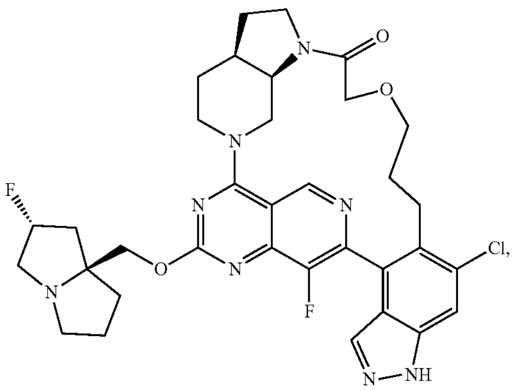 [SMILES: O=C1COCCCc2c(Cl)cc3[nH]ncc3c2-c2ncc3c(nc(OC[C@@]45CCCN4C[C@H](F)C5)nc3c2F)N2CC[C@H]3CCN1[C@H]3C2] |

TABLE 3-continued
| Compound |
| --- |
| 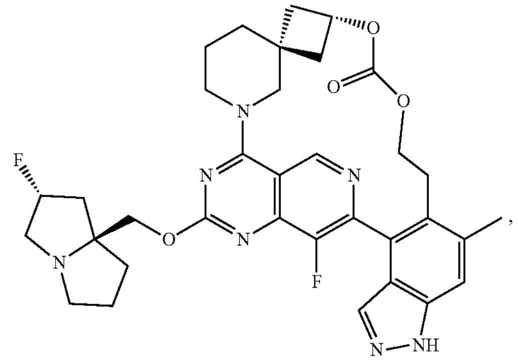 [SMILES: Cc1cc2[nH]ncc2c2c1CCOC(=O)O[C@H]1C[C@]3(CCCN(C3)c3nc(OC[C@@]45CCCN4C[C@H](F)C5)nc4c(F)c-2ncc34)C1] |
| 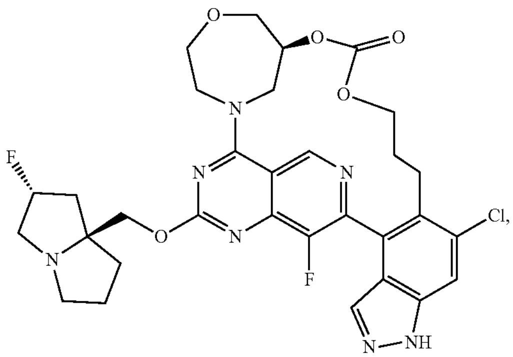 [SMILES: O=C1OCCCc2c(Cl)cc3[nH]ncc3c2-c2ncc3c(nc(OC[C@@]45CCCN4C[C@H](F)C5)nc3c2F)N2CCOC[C@H](C2)O1] |
| 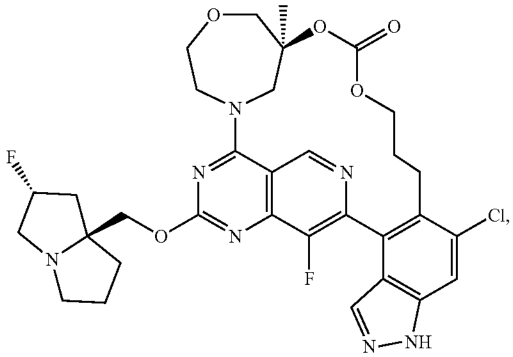 [SMILES: C[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2] |
| 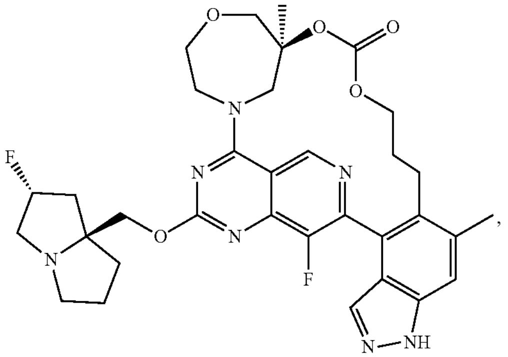 [SMILES: Cc1cc2[nH]ncc2c2c1CCCOC(=O)O[C@]1(C)COCCN(C1)c1nc(OC[C@@]34CCCN3C[C@H](F)C4)nc3c(F)c-2ncc13] |
TABLE 3-continued
| Compound |
| --- |
| 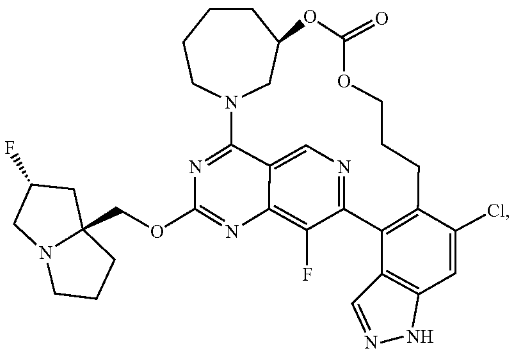 [SMILES: O=C1OCCCc2c(Cl)cc3[nH]ncc3c2-c2ncc3c(nc(OC[C@@]45CCCN4C[C@H](F)C5)nc3c2F)N2CCCC[C@H](C2)O1] |
| 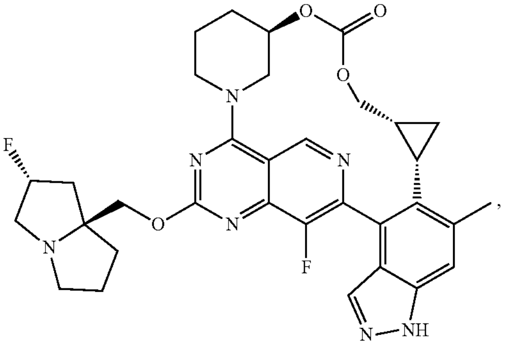 [SMILES: Cc1cc2[nH]ncc2c2c1[C@H]1C[C@H]1COC(=O)O[C@@H]1CCCN(C1)c1nc(OC[C@@]34CCCN3C[C@H](F)C4)nc3c(F)c-2ncc13] |
| 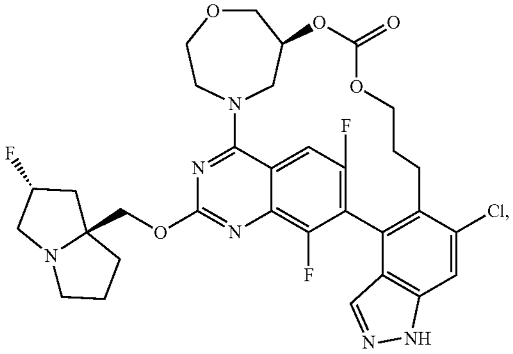 [SMILES: O=C1OCCCc2c(Cl)cc3[nH]ncc3c2-c2c(F)cc3c(nc(OC[C@@]45CCCN4C[C@H](F)C5)nc3c2F)N2CCOC[C@H](C2)O1] |
| 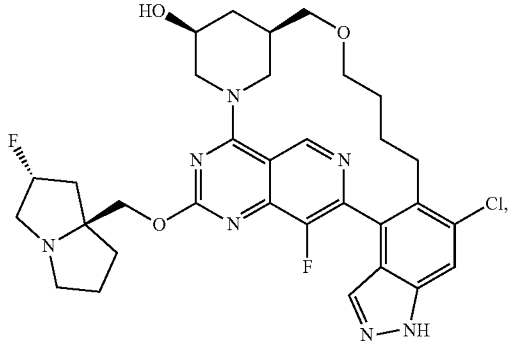

TABLE 3-continued
| Compound |
| --- |
| 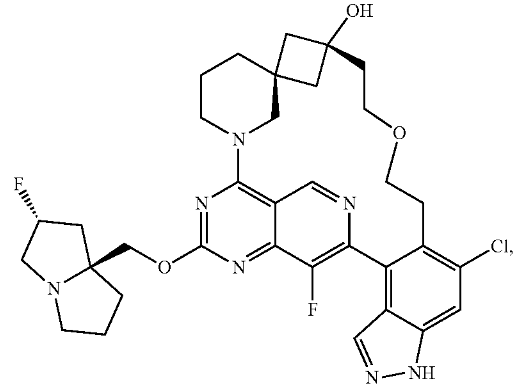 [SMILES: O[C@]12CCOCCc3c(Cl)cc4[nH]ncc4c3-c3ncc4c(nc(OC[C@@]56CCCN5C[C@H](F)C6)nc4c3F)N3CCC[C@@](C3)(C1)C2] |
| 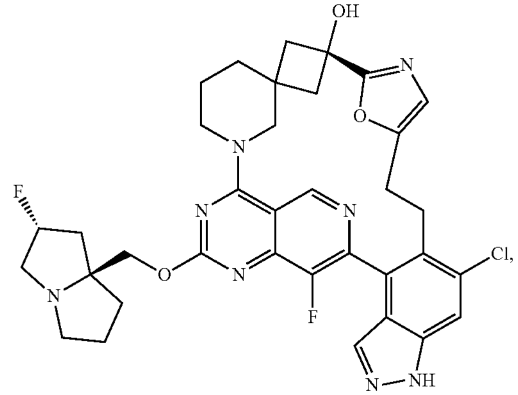 |
| 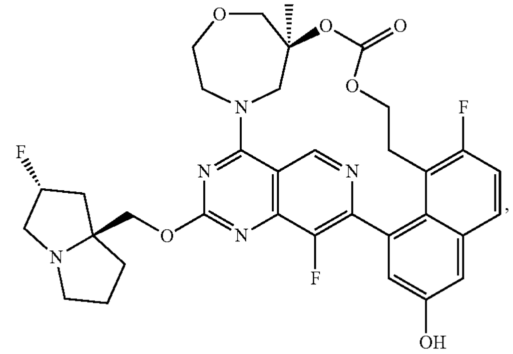 [SMILES: C[C@@]12COCCN(C1)c1nc(OC[C@@]34CCCN3C[C@H](F)C4)nc3c(F)c(ncc13)-c1cc(O)cc3ccc(F)c(c13)CCOC(=O)O2] |
| 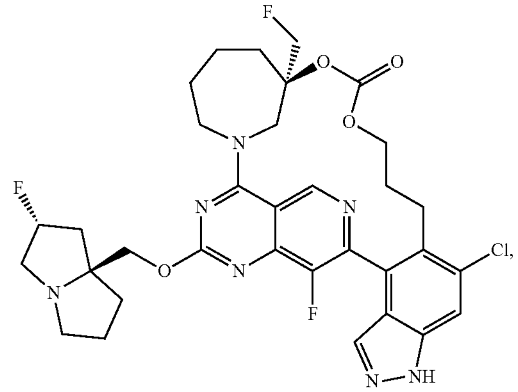 [SMILES: O=C1OCCCc2c(Cl)cc3[nH]ncc3c2-c2ncc3c(nc(OC[C@@]45CCCN4C[C@H](F)C5)nc3c2F)N2CCCC[C@](CF)(C2)O1] |
TABLE 3-continued
| Compound |
| --- |
| 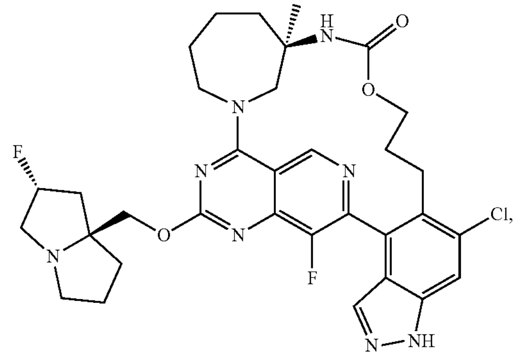 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCOC(=O)N2] |
| 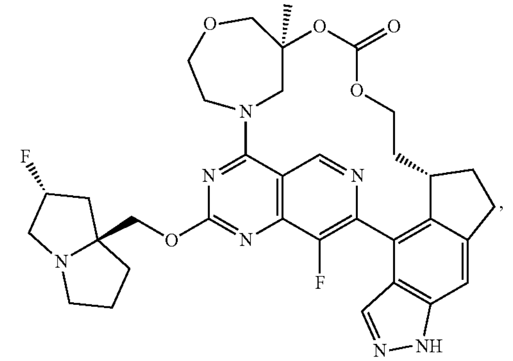 [SMILES: C[C@@]12COCCN(C1)c1nc(OC[C@@]34CCCN3C[C@H](F)C4)nc3c(F)c(ncc13)-c1c3c(cc4[nH]ncc14)CC[C@H]3CCOC(=O)O2] |
| 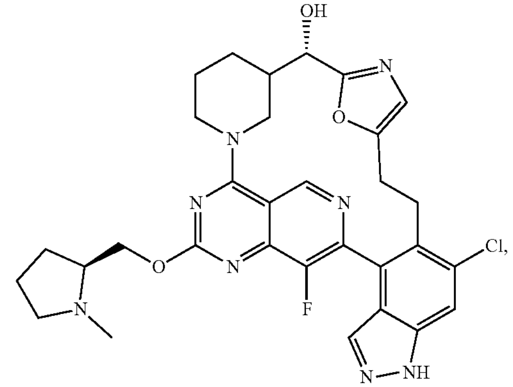 [SMILES: CN1CCC[C@H]1COc1nc2c3cnc(c(F)c3n1)-c1c(c(Cl)cc3[nH]ncc13)CCc1cnc(o1)[C@@H](O)C1CCCN2C1] |
| 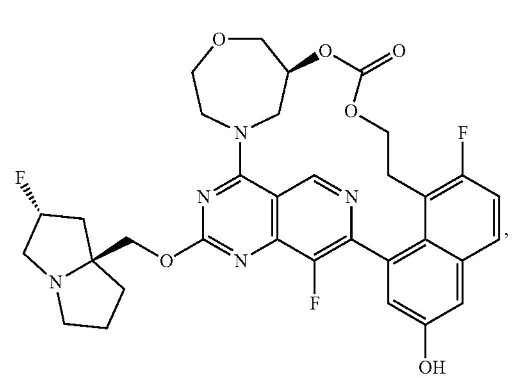 [SMILES: O=C1OCCc2c(F)ccc3cc(O)cc(c23)-c2ncc3c(nc(OC[C@@]45CCCN4C[C@H](F)C5)nc3c2F)N2CCOC[C@H](C2)O1]

TABLE 3-continued
| Compound |
| --- |
| 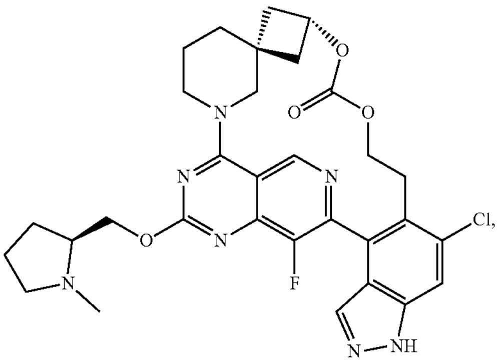 [SMILES: CN1CCC[C@H]1COc1nc2c3cnc(c(F)c3n1)-c1c(c(Cl)cc3[nH]ncc13)CCOC(=O)O[C@H]1C[C@]3(CCCN2C3)C1] , |
| 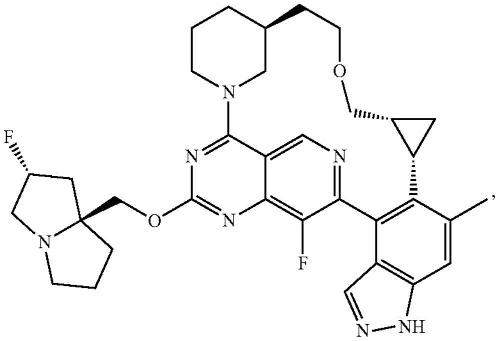 [SMILES: Cc1cc2[nH]ncc2c2c1[C@H]1C[C@H]1COCC[C@@H]1CCCN(C1)c1nc(OC[C@@]34CCCN3C[C@H](F)C4)nc3c(F)c-2ncc13] , |
| 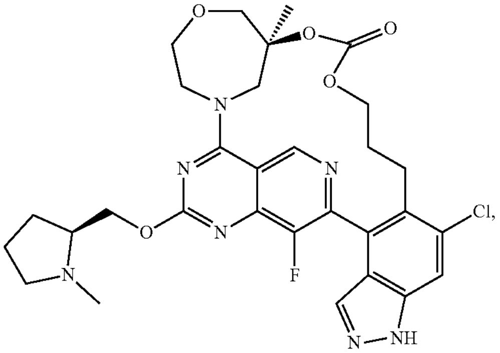 [SMILES: CN1CCC[C@H]1COc1nc2c3cnc(c(F)c3n1)-c1c(c(Cl)cc3[nH]ncc13)CCCOC(=O)O[C@]1(C)COCCN2C1] , |
| 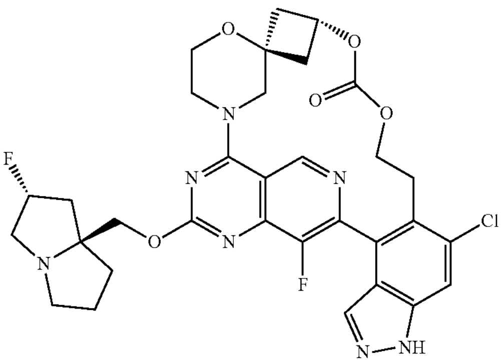 [SMILES: O=C1OCCc2c(Cl)cc3[nH]ncc3c2-c2ncc3c(nc(OC[C@@]45CCCN4C[C@H](F)C5)nc3c2F)N2CCO[C@]3(C2)C[C@H](C3)O1] |
| or |
TABLE 3-continued
| Compound |
| --- |
| 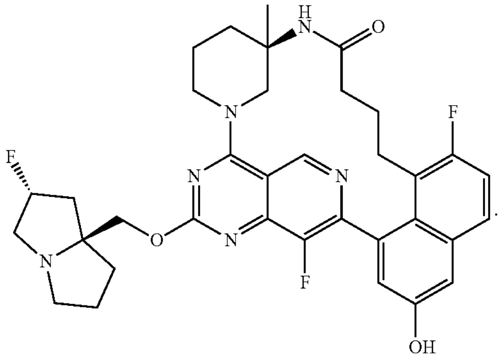 [SMILES: C[C@@]12CCCN(C1)c1nc(OC[C@@]34CCCN3C[C@H](F)C4)nc3c(F)c(ncc13)-c1cc(O)cc3ccc(F)c(c13)CCCC(=O)N2] . |
Provided herein as embodiment 414 is the compound or salt according to embodiment 1, wherein the compound is selected from a compound of Table 4:
TABLE 4
| Compound |
| --- |
| 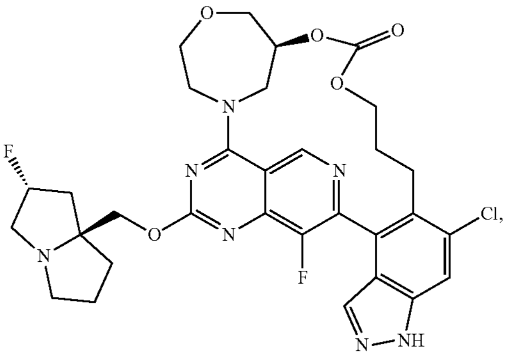 [SMILES: O=C1OCCCc2c(Cl)cc3[nH]ncc3c2-c2ncc3c(nc(OC[C@@]45CCCN4C[C@H](F)C5)nc3c2F)N2CCOC[C@H](C2)O1] , |
| 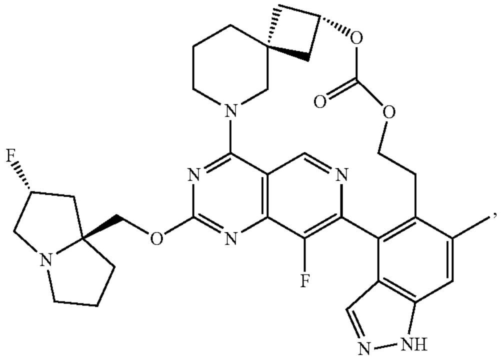 [SMILES: Cc1cc2[nH]ncc2c2c1CCOC(=O)O[C@H]1C[C@]3(CCCN(C3)c3nc(OC[C@@]45CCCN4C[C@H](F)C5)nc4c(F)c-2ncc34)C1] , |

TABLE 4-continued
| Compound |
| --- |
| 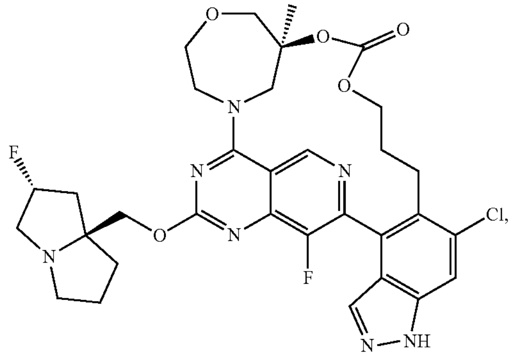 [SMILES: C[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2] , |
| 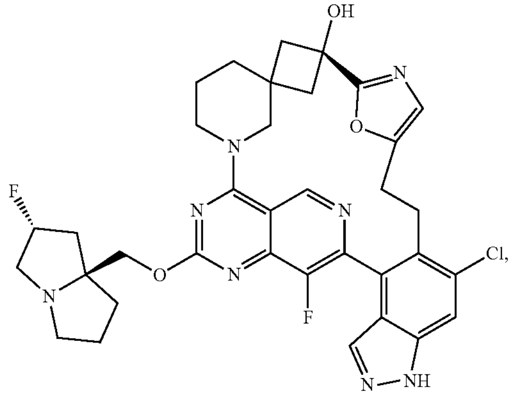 , |
| 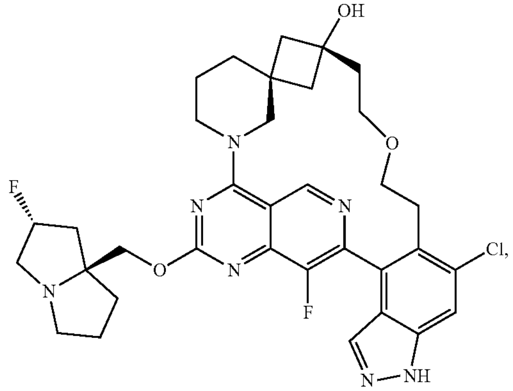 [SMILES: O[C@]12CCOCCc3c(Cl)cc4[nH]ncc4c3-c3ncc4c(nc(OC[C@@]56CCCN5C[C@H](F)C6)nc4c3F)N3CCC[C@@](C3)(C1)C2] , |
| 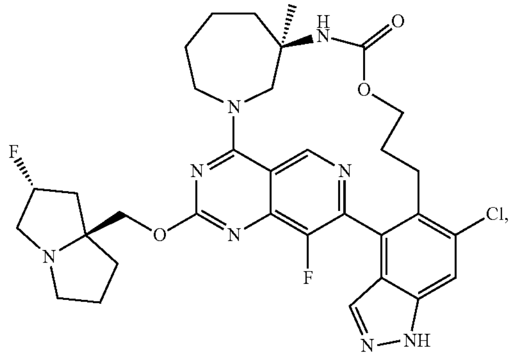 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCOC(=O)N2] , |
| 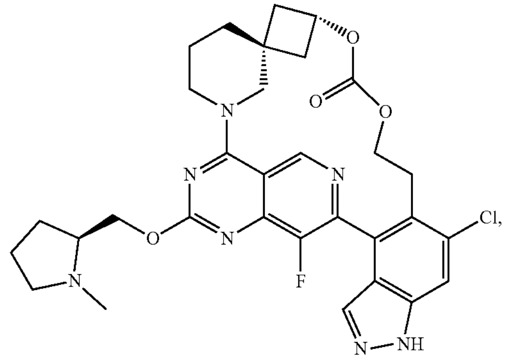 [SMILES: CN1CCC[C@H]1COc1nc2c3cnc(c(F)c3n1)-c1c(c(Cl)cc3[nH]ncc13)CCOC(=O)O[C@H]1C[C@]3(CCCN2C3)C1] , |
| 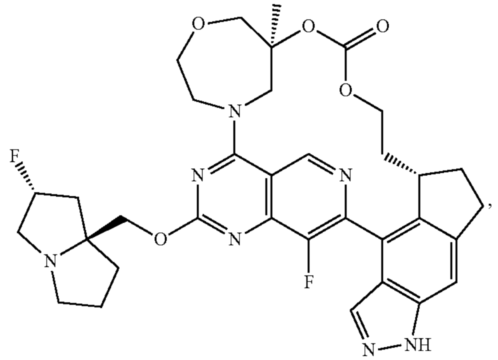 [SMILES: C[C@@]12COCCN(C1)c1nc(OC[C@@]34CCCN3C[C@H](F)C4)nc3c(F)c(ncc13)-c1c3c(cc4[nH]ncc14)CC[C@H]3CCOC(=O)O2] , |
| 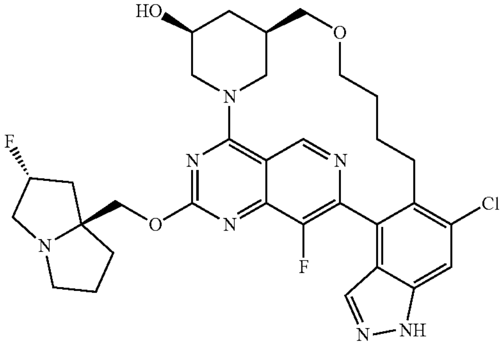 [SMILES: O[C@H]1C[C@H]2COCCCCc3c(Cl)cc4[nH]ncc4c3-c3ncc4c(nc(OC[C@@]56CCCN5C[C@H](F)C6)nc4c3F)N(C1)C2] |
| or |
| 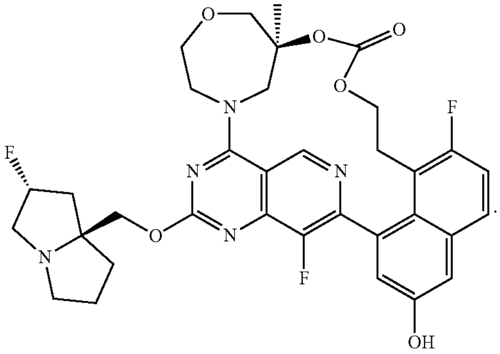 [SMILES: C[C@@]12COCCN(C1)c1nc(OC[C@@]34CCCN3C[C@H](F)C4)nc3c(F)c(ncc13)-c1cc(O)cc3ccc(F)c(c13)CCOC(=O)O2] . |
Provided herein as embodiment 415 is the compound or salt according to embodiment 1, wherein the compound is

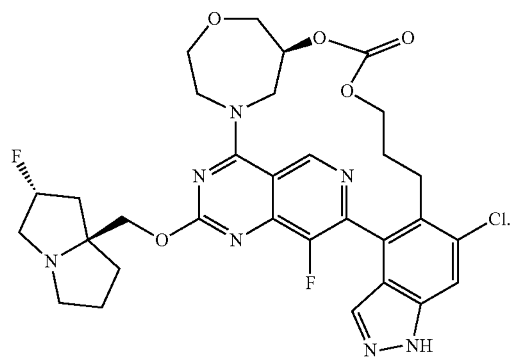

Provided herein as embodiment 416 is the compound or salt according to embodiment 1, wherein the compound is

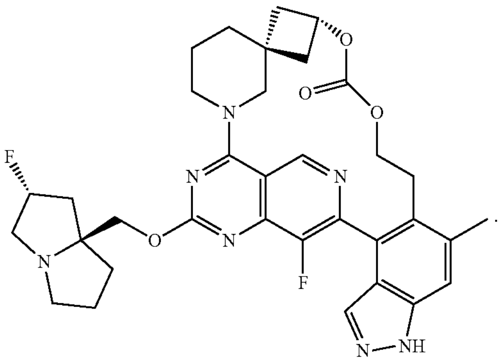 [SMILES: Cc1cc2[nH]ncc2c2c1CCOC(=O)O[C@H]1C[C@]3(CCCN(C3)c3nc(OC[C@@]45CCCN4C[C@H](F)C5)nc4c(F)c-2ncc34)C1]

Provided herein as embodiment 417 is the compound or salt according to embodiment 1, wherein the compound is

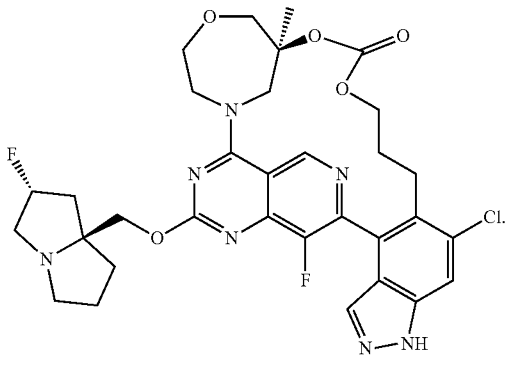 [SMILES: C[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2]

Provided herein as embodiment 418 is the compound or salt according to embodiment 1, wherein the compound is

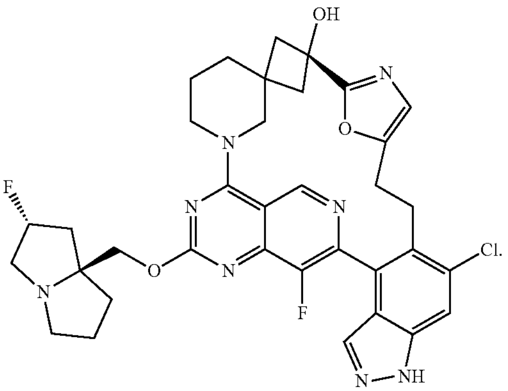

Provided herein as embodiment 419 is the compound or salt according to embodiment 1, wherein the compound is

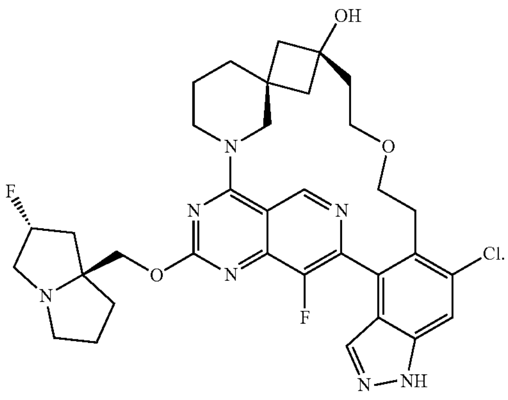 [SMILES: O[C@]12CCOCCc3c(Cl)cc4[nH]ncc4c3-c3ncc4c(nc(OC[C@@]56CCCN5C[C@H](F)C6)nc4c3F)N3CCC[C@@](C3)(C1)C2]

Provided herein as embodiment 420 is the compound or salt according to embodiment 1, wherein the compound is

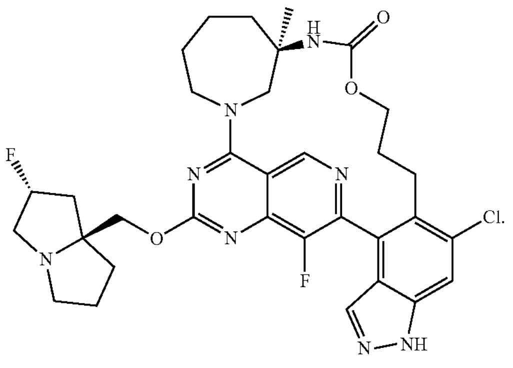 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCOC(=O)N2]

Provided herein as embodiment 421 is the compound or salt according to embodiment 1, wherein the compound is

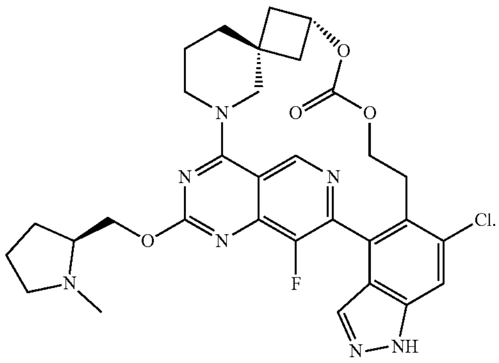 [SMILES: CN1CCC[C@H]1COc1nc2c3cnc(c(F)c3n1)-c1c(c(Cl)cc3[nH]ncc13)CCOC(=O)O[C@H]1C[C@]3(CCCN2C3)C1]

Provided herein as embodiment 422 is the compound or salt according to embodiment 1, wherein the compound is

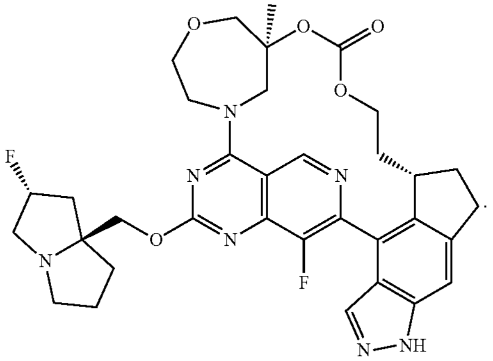 [SMILES: C[C@@]12COCCN(C1)c1nc(OC[C@@]34CCCN3C[C@H](F)C4)nc3c(F)c(ncc13)-c1c3c(cc4[nH]ncc14)CC[C@H]3CCOC(=O)O2]

Provided herein as embodiment 423 is the compound or salt according to embodiment 1, wherein the compound is

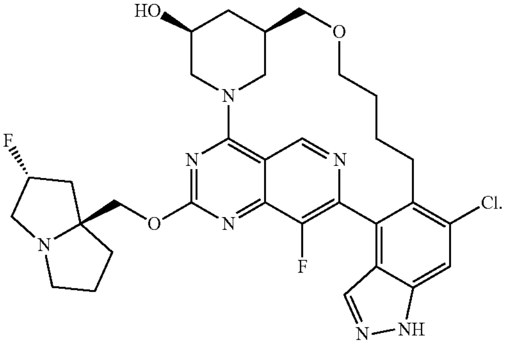 [SMILES: O[C@H]1C[C@H]2COCCCCc3c(Cl)cc4[nH]ncc4c3-c3ncc4c(nc(OC[C@@]56CCCN5C[C@H](F)C6)nc4c3F)N(C1)C2]

Provided herein as embodiment 424 is the compound or salt according to embodiment 1, wherein the compound is

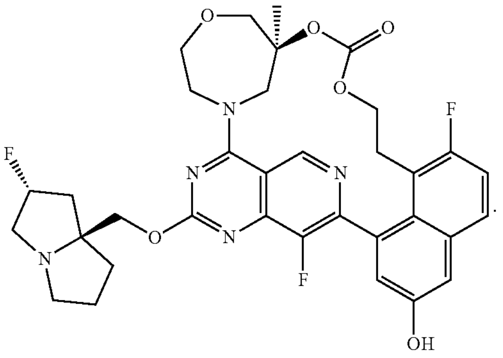 [SMILES: C[C@@]12COCCN(C1)c1nc(OC[C@@]34CCCN3C[C@H](F)C4)nc3c(F)c(ncc13)-c1cc(O)cc3ccc(F)c(c13)CCOC(=O)O2]

Further Embodiments

Provided herein as further embodiment B1 is a compound of Formula (B-I):

(B-I)

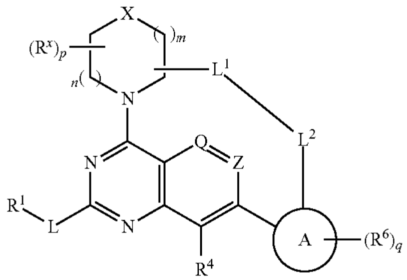

or a pharmaceutically acceptable salt of said compound, wherein;

X is N, $CH_2$, O, S, S(O), S(O)($NR^z$) or $S(O)_2$;

Z is CH, CF, C—CN, C—OMe, C—Cl or N;

Q is CH or N;

n is 0, 1, 2, or 3;

m is 0, 1, 2 or 3;

p is 0, 1, 2 or 3;

q is 0, 1, 2 or 3;

each $R^x$ is hydroxyl, halogen, oxo, cyano, —$N(R^z)_2$, $C_{1-4}$ alkyl, $C_{1-4}$ alkoxy, $C_{1-4}$ haloalkyl, $C_{1-4}$ haloalkoxy, 5-7 membered heteroaryl, -T-$R^y$ or two $R^x$ taken together with the same carbon or adjacent carbon atoms can form $C_{3-7}$ cycloalkyl, a 3-7 membered heterocycloalkyl, wherein each $C_{3-7}$ cycloalkyl or 3-7 membered heterocycloalkyl is further substituted with 0-3 occurrences of R or two $R^x$ taken together can form a bridged ring where the bridge is selected from one of the following: —$C_{1-4}$ alkylene, —$C_{1-4}$ alkylene-O—$C_{1-4}$ alkylene-, —O—, —S— or —$C_{1-4}$ alkylene-S—$C_{1-4}$ alkylene- and wherein each $C_{1-4}$ alkylene is further substituted with 0-2 occurrences of $R^y$;

L is $C_{1-6}$ alkyl, $C_{1-6}$ alkoxy, $C_{1-6}$ alkylene, —O—$C_{1-6}$ alkylene, —S—$C_{1-6}$ alkylene, $NR^z$, O or S, wherein each $C_{1-6}$ alkylene, —O—$C_{1-6}$ alkylene and —S—$C_{1-6}$ alkylene chain is substituted with 0-2 occurrences of $R^2$;

$L^1$ is a bond, —$N(R^z)C(O)$-$L^2$, —C(O)-$L^2$- —OC(O)-$L^2$, —C(O)O-$L^2$, —$C_{1-4}$ alkylene-C(O)O—, —OC(O)—O-$L^2$, —O-$L^2$, —$N(R^z)$-$L^2$, —$C_{1-4}$ alkylene-C(O)O-$L^2$, —$C_{1-4}$ alkylene-OC(O)-$L^2$ or a 5-6 membered heteroaryl;

$L^2$ is $C_{1-6}$ alkylene, $C_{1-6}$ alkylene-O—, $C_{1-6}$ alkylene-O—$C_{1-6}$ alkylene, $C_{2-6}$ alkenylene, $C_{2-6}$ alkynylene, $C_{3-7}$ cycloalkylene, $C_{1-4}$ alkylene-$C_{3-7}$ cycloalkylene, $C_{1-4}$ haloalkylene-$C_{3-7}$ cycloalkylene, $C_{3-7}$ cycloalkylene-$C_{1-4}$ alkylene or $C_{1-6}$ haloalkylene;

$R^1$ is hydrogen, hydroxyl, aryl, heteroaryl, $C_{3-8}$ cycloalkyl or heterocycloalkyl substituted with 0-3 occurrences of $R^5$;

$R^2$ is halogen, hydroxyl, $C_{1-4}$ alkyl or two $R^2$ on the same or adjacent carbon atoms can be taken together to form a $C_{3-7}$ cycloalkyl;

A is aryl or heteroaryl substituted with q occurrences of $R^6$;

$R^4$ is hydrogen, hydroxyl, halogen, $C_{1-4}$ alkyl, $C_{1-4}$ alkoxy, $C_{1-4}$ haloalkyl, $C_{2-4}$ alkenyl, $C_{2-4}$ alkynyl, $C_{3-7}$ cycloalkyl or cyano;

each $R^5$ independently is halogen, cyano, oxo, -T-$R^y$, hydroxyl, amino or $C_{1-4}$ alkyl;

each $R^6$ independently is halogen, hydroxyl, cyano, —$N(R^z)_2$, $C_{1-4}$ alkyl, $C_{1-4}$ alkoxy, $C_{1-4}$ haloalkyl, $C_{1-4}$ haloalkoxy, $C_{2-4}$ alkynyl or $C_{3-6}$ cycloalkyl;

T is $C_{1-4}$ alkylene, —$S(O)_2$—, —C(O)—, —$C_{1-4}$ alkylene-C(O)—, $C_{1-4}$ alkylene-$S(O)_2$— or —S—;

$R^y$ is halogen, oxo, $C_{1-4}$ alkyl, $C_{1-4}$ haloalkyl, hydroxyl, cyano or —$N(R^z)_2$; and $R^z$ is hydrogen or $C_{1-4}$ alkyl.

Provided herein as embodiment B2 is the compound of embodiment B1, wherein Z is N and Q is CH.

Provided herein as embodiment B3 is the compound of embodiment B1, wherein L is —O— methylene-, —O-ethylene-, —O-n-propylene or —O-isopentanylene substituted with 0-2 occurrences of $R^2$.

Provided herein as embodiment B4 is the compound of embodiment B1, wherein -L-$R^1$ is

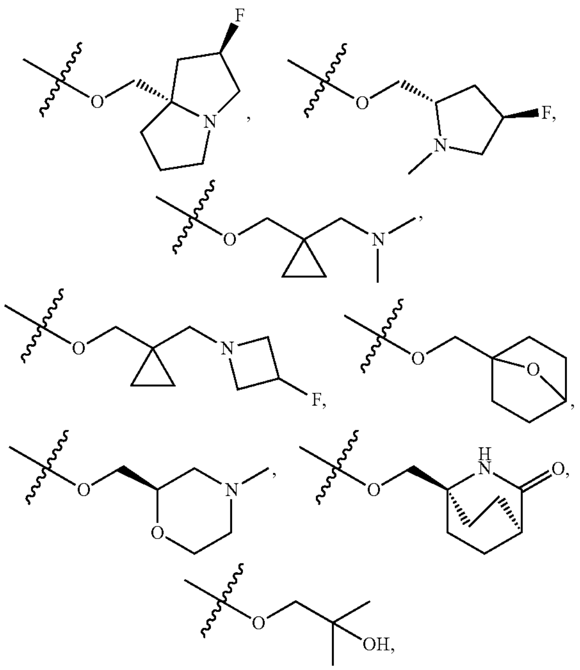

methoxy or methyl. Provided herein as embodiment B5 is the compound of embodiment B4, wherein -L-$R^1$ is

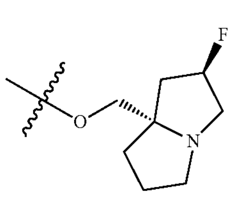

or

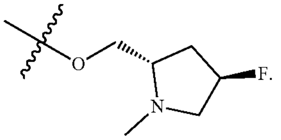

Provided herein as embodiment B6 is the compound of embodiment B1, wherein X is O. Provided herein as embodiment B7 is the compound of embodiment B6, wherein n is 0 and m is 1 or n is 1 and m is 1. Provided herein as embodiment B8 is the compound of embodiment B7, wherein

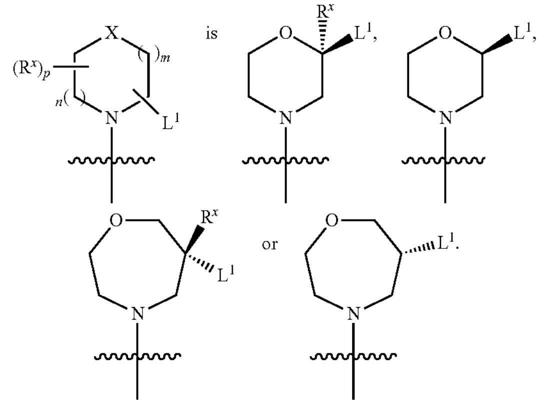

Provided herein as embodiment B9 is the compound of embodiment B1, wherein X is S. Provided herein as embodiment B10 is the compound of embodiment B9, wherein n is 0 and m is 1 or n is 1 and m is 1. Provided herein as embodiment B11 is the compound of embodiment B10, wherein

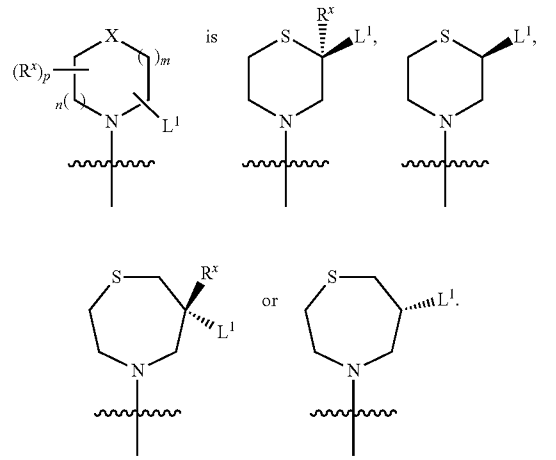

Provided herein as embodiment B12 is the compound of embodiment B1, wherein X is N. Provided herein as embodiment B13 is the compound of embodiment B12, wherein n is 1 and m is 2. Provided herein as embodiment B14 is the compound of embodiment B13, wherein

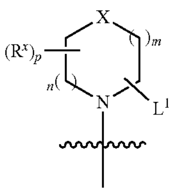

is

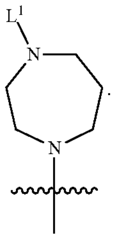

Provided herein as embodiment B15 is the compound of embodiment B1, wherein x is $CH_2$. Provided herein as embodiment B16 is the compound of embodiment B15, wherein n is 0 and m is 1; n is 1 and m is 0; n is 1 and m is 1; n is 1 and m is 2 or n is 2 and m is 1. Provided herein as embodiment B17 is the compound of embodiment B16, wherein

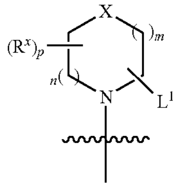

is

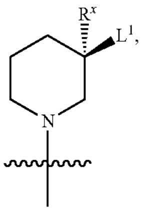

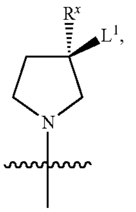

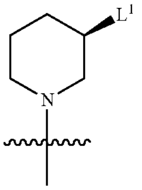

or

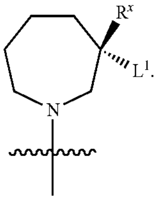

Provided herein as embodiment B18 is the compound of embodiment 366, wherein B1 is aryl (e.g., phenyl, naphthyl or 5-(1,2,3,4-tetrahydronaphthalyl)). Provided herein as embodiment B19 is the compound of embodiment B18, wherein A-$L^2$ is

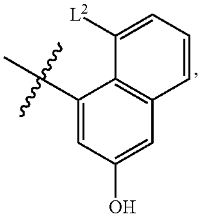

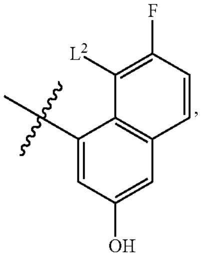

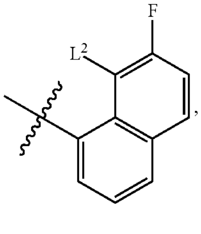

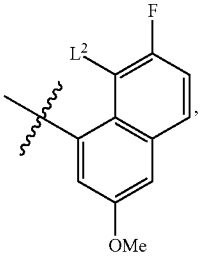

-continued

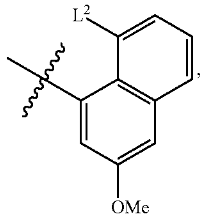

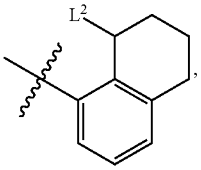

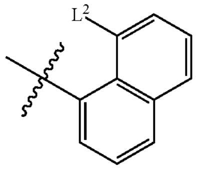

or

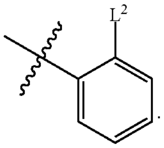

Provided herein as embodiment B20 is the compound of embodiment B1, wherein A-$L^2$ is heteroaryl (e.g., 4-indazolyl or 8-(1,2,3,4-tetrahydroquinolinyl). Provided herein as embodiment B21 is the compound of embodiment B20, wherein A-$L^2$ is

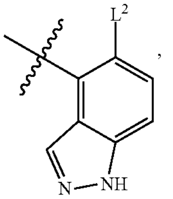

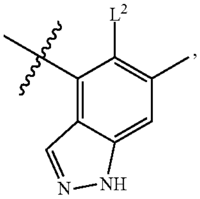

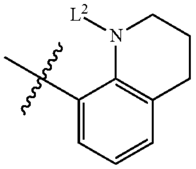

or

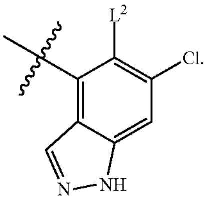

Provided herein as embodiment B22 is the compound of embodiment B1, wherein -$L^1$-$L^2$- is —N($R^z$)—C(O)-$L^2$. Provided herein as embodiment B23 is the compound of embodiment B22, wherein $R^z$ is hydrogen. Provided herein as embodiment B24 is the compound of embodiment B23, wherein $L^2$ is n-propylene, n-butylene, 1-fluoro-n-pentylene, n-pentylene or —$CH_2$-cyclopropylene-. Provided herein as embodiment B25 is the compound of embodiment B22, wherein -$L^1$-$L^2$- is

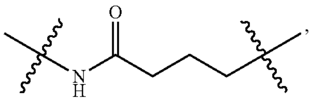

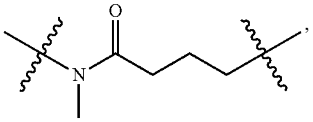

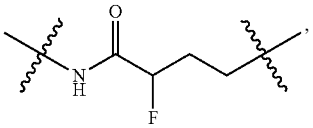

-continued

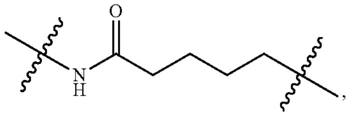

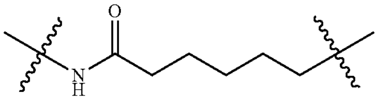

or

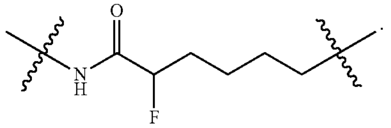

Provided herein as embodiment B26 is the compound of embodiment B1, wherein -$L^1$-$L^2$- is —O—C(O)-$L^2$. Provided herein as embodiment B27 is the compound of embodiment B26, wherein $L^2$ is n-propylene-O—, n-butylene, n-butenylene, n-pentylene or n-propylene. Provided herein as embodiment B28 is the compound of embodiment B26, wherein -$L^1$-$L^2$- is

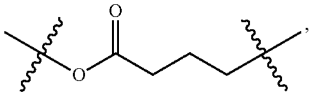

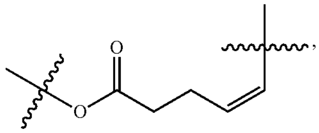

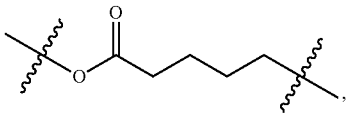

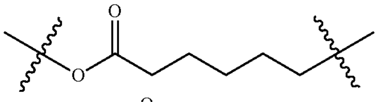

or

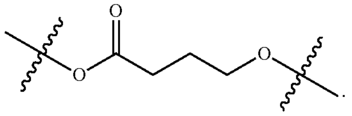

Provided herein as embodiment B29 is the compound of embodiment B1, wherein -$L^1$-$L^2$- is —O—C(O)—O-$L^2$. Provided herein as embodiment B30 is the compound of embodiment B29, wherein $L^2$ is n-propylene or —$CH_2$-cyclopropylene. Provided herein as embodiment B31 is the compound of embodiment B29, wherein -$L^1$-$L^2$- is

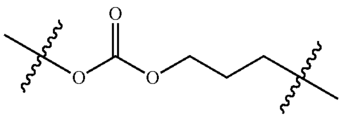

or

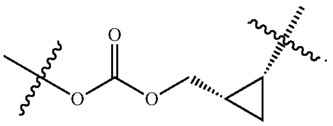

Provided herein as embodiment B32 is the compound of embodiment B1, wherein -$L^1$-$L^2$- is —O-$L^2$. Provided herein as embodiment B33 is the compound of embodiment B32, wherein $L^2$ is n-pentylene. Provided herein as embodiment B34 is the compound of embodiment B32, wherein -$L^1$-$L^2$- is

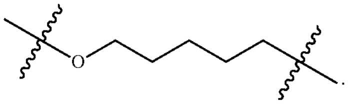 [SMILES: *CCCCCO*]

Provided herein as embodiment B35 is the compound of embodiment B1, wherein -$L^1$-$L^2$- is —$NR^z$—C(O)—O-$L^2$. Provided herein as embodiment B36 is the compound of embodiment B35, wherein $R^z$ is hydrogen. Provided herein as embodiment B37 is the compound of embodiment B36, wherein $L^2$ is n-propylene or —$CH_2$-cyclopropylene. Provided herein as embodiment B38 is the compound of embodiment B35, wherein -$L^1$-$L^2$- is

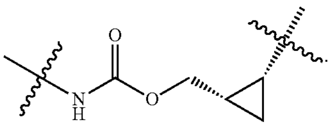 [SMILES: *NC(=O)OC[C@H]1C[C@H]1*]

Provided herein as embodiment B39 is the compound of embodiment B1, wherein -$L^1$-$L^2$- is —O—C(O)—$NR^z$-$L^2$. Provided herein as embodiment B40 is the compound of embodiment B39, wherein $L^2$ is n-propylene or —$CH_2$-cyclopropylene. Provided herein as embodiment B41 is the compound of embodiment B39, wherein -$L^1$-$L^2$ is

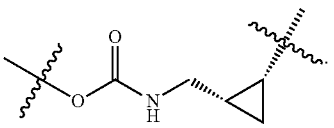 [SMILES: *OC(=O)NC[C@H]1C[C@H]1*]

Provided herein as embodiment B42 is the compound of embodiment B1, wherein -$L^1$-$L^2$- is a 5-6 membered heteroaryl. Provided herein as embodiment B43 is the compound of embodiment B42, wherein -$L^1$-$L^2$- is

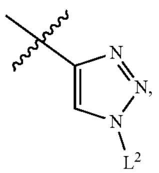

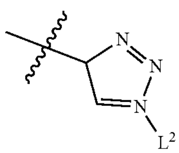

or

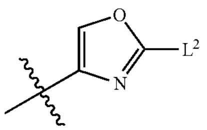

Provided herein as embodiment B44 is the compound of embodiment B42, wherein -$L^1$-$L^2$- is

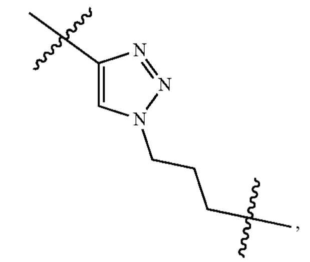
,

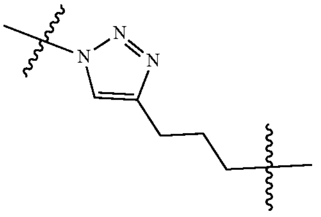
or

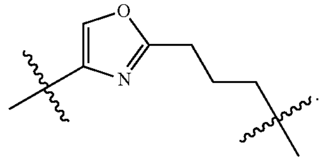
.

Provided herein as embodiment B45 is the compound of embodiment B1, wherein $-L^1-L^2-$ is absent. Provided herein as embodiment B46 is the compound of embodiment B45, wherein $L^2$ is n-hexylene.

Provided herein as embodiment B47 is the compound of embodiment B1, wherein $-L^1-L^2-$ is —C(O)—. Provided herein as embodiment B48 is the compound of embodiment B47, wherein $L^2$ is n-butylene. Provided herein as embodiment B49 is the compound of embodiment B47, wherein $-L^1-L^2-$ is

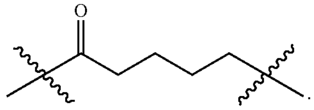 [SMILES: *CCCCC(*)=O]
.

Provided herein as embodiment B50 is the compound of embodiment B1, wherein $R^4$ is $C_{1-4}$ alkyl or halogen. Provided herein as embodiment B51 is the compound of embodiment B1, wherein $R^4$ is fluorine.

Provided herein as embodiment C1 is a compound of Formula (C-I):

(C-I)

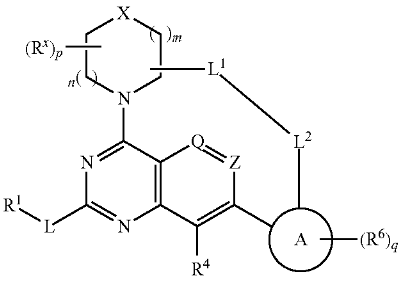

or a pharmaceutically acceptable salt of said compound, wherein;

X is N, $CH_2$, O, S, S(O), S(O)($NR^z$) or $S(O)_2$;

Z is CH, CF, C—CN, C—OMe, C—Cl or N;

Q is CH or N;

n is 0, 1, 2, or 3;

m is 0, 1, 2 or 3;

p is 0, 1, 2 or 3;

q is 0, 1, 2 or 3;

each $R^x$ is hydroxyl, halogen, oxo, cyano, —$N(R^z)_2$, $C_{1-4}$ alkyl, $C_{1-4}$ alkoxy, $C_{1-4}$ haloalkyl, $C_{1-4}$ haloalkoxy, 5-7 membered heteroaryl, $-T-R^y$ or two $R^x$ taken together with the same carbon or adjacent carbon atoms can form $C_{3-7}$ cycloalkyl, a 3-7 membered heterocycloalkyl, wherein each $C_{3-7}$ cycloalkyl or 3-7 membered heterocycloalkyl is further substituted with 0-3 occurrences of R or two $R^x$ taken together can form a bridged ring where the bridge is selected from one of the following: —$C_{1-4}$ alkylene, —$C_{1-4}$ alkylene-O—$C_{1-4}$ alkylene-, —O—, —S— or —$C_{1-4}$ alkylene-S—$C_{1-4}$ alkylene- and wherein each $C_{1-4}$ alkylene is further substituted with 0-2 occurrences of $R^y$;

L is $C_{1-6}$ alkyl, $C_{1-6}$ alkoxy, $C_{1-6}$ alkylene, —O—$C_{1-6}$ alkylene, —S—$C_{1-6}$ alkylene, $NR^z$, O or S, wherein each $C_{1-6}$ alkylene, —O—$C_{1-6}$ alkylene and —S—$C_{1-6}$ alkylene chain is substituted with 0-2 occurrences of $R^2$;

$L^1$ is a bond, —$N(R^z)C(O)-L^2$, —$C(O)-L^2$- —$OC(O)-L^2$, —$C(O)O-L^2$, —OC(O)—$O-L^2$, —OC(S)—$O-L^2$, —$O-L^2$, —$N(R^z)C(O)O-L^2$, —$OC(O)N(R^z)-L^2$, —$N(R^z)-L^2$, —$S(O)_2-L^2$, —$S-L^2$, —$S(O)-L^2$, $C_{1-4}$ alkylene-$C(O)-L^2$, $C_{1-4}$ alkylene-$C(O)O-L^2$, —$C_{1-4}$ alkylene-$OC(O)O-L^2$, —$C_{1-4}$ alkylene-$OC(O)-L^2$, —$C_{1-4}$ alkylene-$O-L^2$, —$C_{1-4}$ alkylene-$S(O)_2-L^2$, —$C_{1-4}$ alkylene-$S-L^2$, —$C_{1-4}$ alkylene-$S(O)-L^2$, —O-5-6 membered heteroaryl-$L^2$, —$C_{1-4}$ alkylene-5-6 membered heteroaryl-$L^2$, —$C_{1-4}$ hydroxyalkylene-5-6-membered heteroaryl-$L^2$ or a 5-6 membered heteroaryl-$L^2$;

$L^2$ is $C_{1-6}$ alkylene, $C_{1-6}$ alkylene-O—, $C_{1-6}$ alkylene-O—$C_{1-6}$ alkylene, $C_{2-6}$ alkenylene, $C_{2-6}$ alkynylene, $C_{3-7}$ cycloalkylene, $C_{1-4}$ alkylene-$C_{3-7}$ cycloalkylene, $C_{1-4}$ haloalkylene-$C_{3-7}$ cycloalkylene, $C_{3-7}$ cycloalkylene-$C_{1-4}$ alkylene, $C_{1-6}$ hydroxyalkylene or $C_{1-6}$ haloalkylene; $R^1$ is absent, hydroxyl, aryl, heteroaryl, $C_{3-8}$ cycloalkyl or heterocycloalkyl substituted with 0-3 occurrences of $R^5$;

$R^2$ is halogen, hydroxyl, $C_{1-4}$ alkyl or two $R^2$ on the same or adjacent carbon atoms can be taken together to form a $C_{3-7}$ cycloalkyl;

A is aryl or heteroaryl substituted with q occurrences of $R^6$;

$R^4$ is hydrogen, hydroxyl, halogen, $C_{1-4}$ alkyl, $C_{1-4}$ alkoxy, $C_{1-4}$ haloalkyl, $C_{2-4}$ alkenyl, $C_{2-4}$ alkynyl, $C_{3-7}$ cycloalkyl or cyano;

each $R^5$ independently is halogen, cyano, oxo, $-T-R^y$, hydroxyl, amino or $C_{1-4}$ alkyl;

each $R^6$ independently is halogen, hydroxyl, cyano, —$N(R^z)_2$, —$C(O)R^z$, —$C(O)OR^z$, $C_{1-4}$ alkyl, $C_{1-4}$ alkoxy, $C_{1-4}$ haloalkyl, $C_{1-4}$ haloalkoxy, $C_{2-4}$ alkynyl or $C_{3-6}$ cycloalkyl or two $R^6$ taken together on adjacent carbon atoms form a $C_{3-7}$ cycloalkyl;

T is $C_{1-4}$ alkylene, —$S(O)_2$—, —C(O)—, —$C_{1-4}$ alkylene-C(O)—, $C_{1-4}$ alkylene-$S(O)_2$— or —S—;

$R^y$ is halogen, oxo, $C_{1-4}$ alkyl, $C_{1-4}$ haloalkyl, hydroxyl, cyano or —$N(R^z)_2$; and $R^z$ is hydrogen or $C_{1-4}$ alkyl.

Provided herein as embodiment C2 is the compound according to embodiment C1, wherein Z is N and Q is CH.

Provided herein as embodiment C3 is the compound according to embodiment C2, wherein L is —O-methylene-, —O-ethylene-, —O-n-propylene or —O-isopentanylene substituted with 0-2 occurrences of $R^2$. Provided herein as embodiment C4 is the compound according to embodiment C3, wherein -L-$R^1$ is

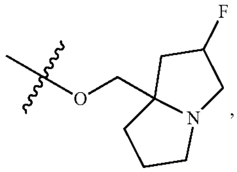,
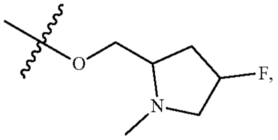,
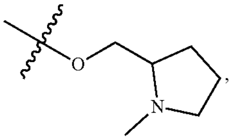,
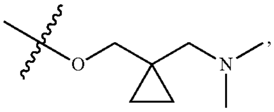,
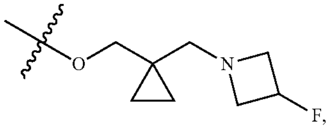,
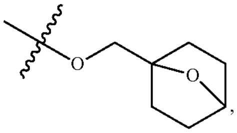,
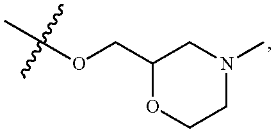,
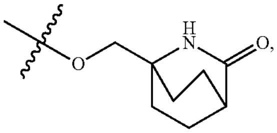,
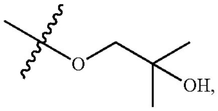,
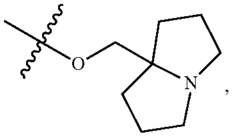,
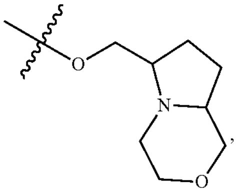,
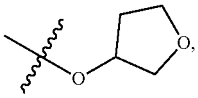,
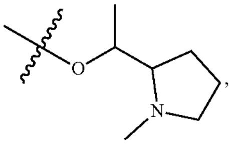, methoxy or methyl. Provided herein as embodiment C5 is the compound according to embodiment C4, wherein -L-$R^1$ is

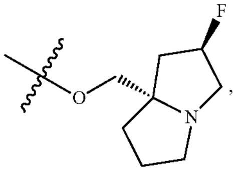,
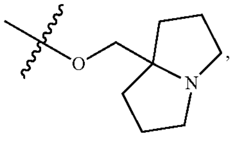,

-continued

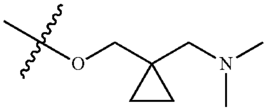
or
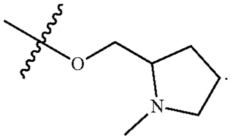.

Provided herein as embodiment C6 is the compound according to embodiment C1, wherein n is 1 and m is 1 or n is 1 and m is 2 or n is 2 and m is 1. Provided herein as embodiment C7 is the compound according to embodiment C6, wherein

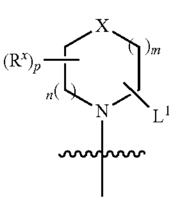
is
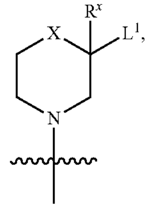,
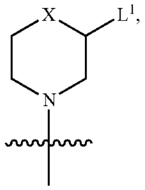,
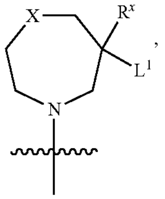,
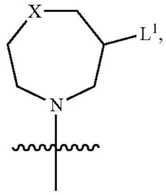,
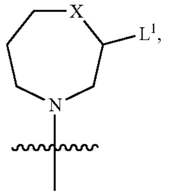,
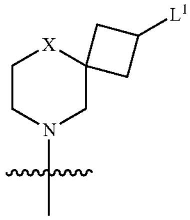
or
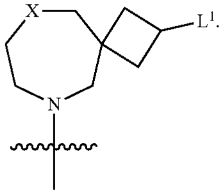.

Provided herein as embodiment C8 is the compound according to embodiment C7,

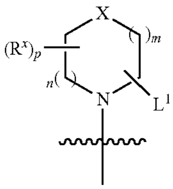
is
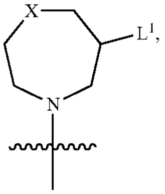,
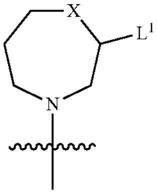
or
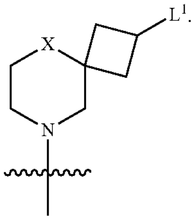.

Provided herein as embodiment C9 is the compound according to embodiment C1, X is O. Provided herein as embodiment C10 is the compound according to embodiment C9, wherein

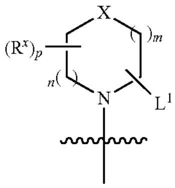

is

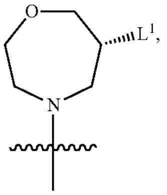

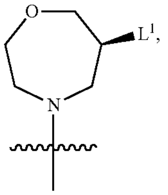

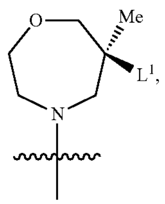

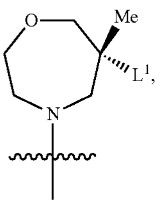

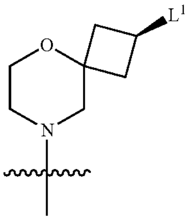

or

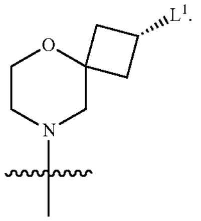

Provided herein as embodiment C11 is the compound according to embodiment C1, wherein X is $CH_2$. Provided herein as embodiment C12 is the compound according to embodiment C11, wherein n is 0 and m is 1; n is 1 and m is 0; n is 1 and m is 1; n is 1 and m is 2 or n is 2 and m is 1. Provided herein as embodiment C13 is the compound according to embodiment C12, wherein

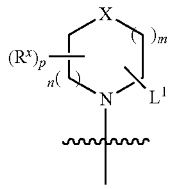

is

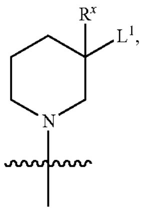

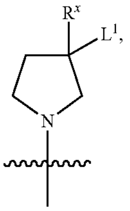

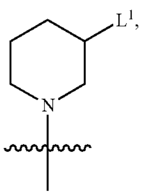

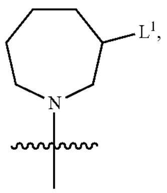

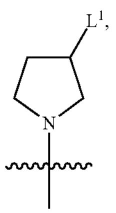

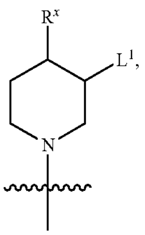

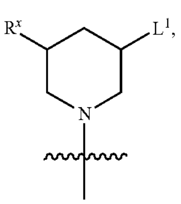

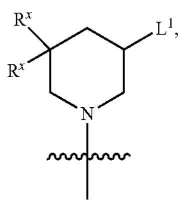

-continued

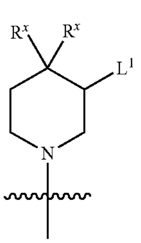

or

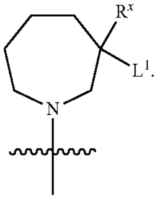

Provided herein as embodiment C13 is the compound according to embodiment C1, wherein A is aryl. Provided herein as embodiment C14 is the compound according to embodiment C13, wherein A-$L^2$ is

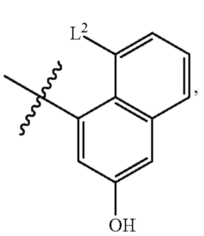

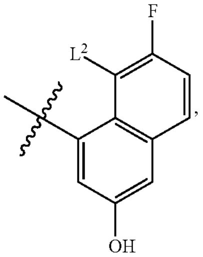

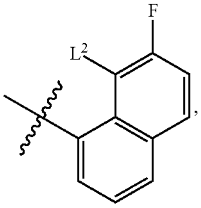

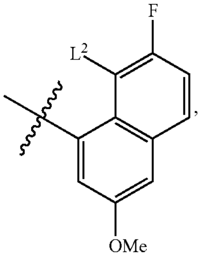

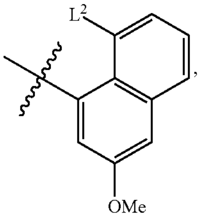

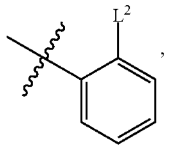

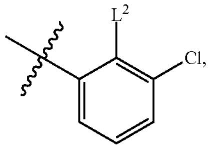

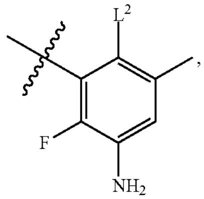

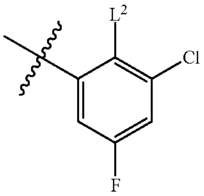

or

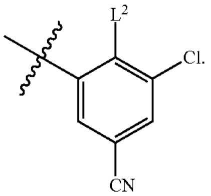

Provided herein as embodiment C15 is the compound according to embodiment C1, wherein A is heteroaryl. Provided herein as embodiment C16 is the compound according to embodiment C15, wherein A-$L^2$ is

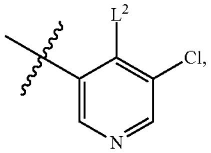

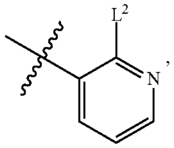

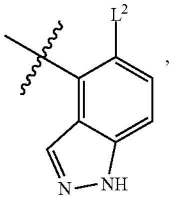

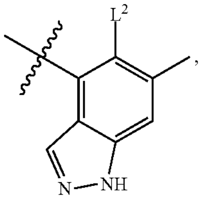

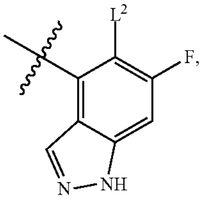

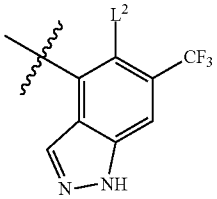

or

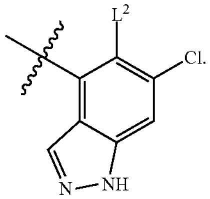

Provided herein as embodiment C17 is the compound according to embodiment C16, wherein A-$L^2$ is

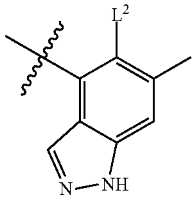

or

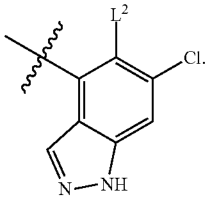

Provided herein as embodiment C18 is the compound according to embodiment C1, wherein -$L^1$-$L^2$- is —O—C(O)—O-$L^2$. Provided herein as embodiment C19 is the compound according to embodiment C18, wherein $L^2$ is ethylene, n-propylene, 2-methyl-n-propylene, cis-2-propenylene, trans-2-propenylene or —$CH_2$-cyclopropylene. Provided herein as embodiment C20 is the compound according to embodiment C19, wherein -$L^1$-$L^2$- is

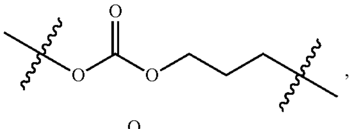

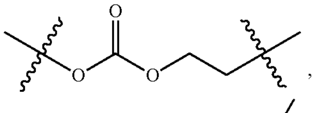

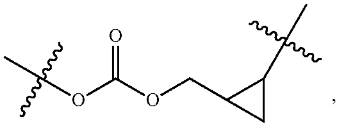

-continued

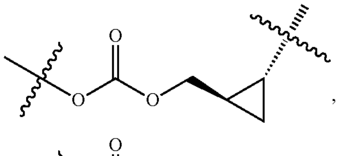

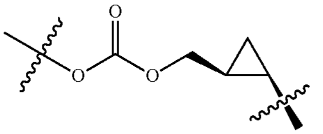

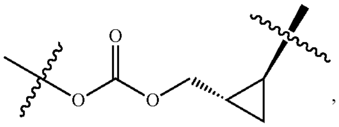

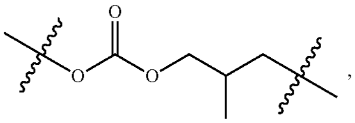

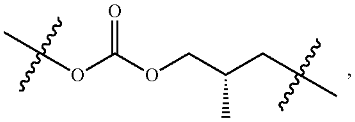

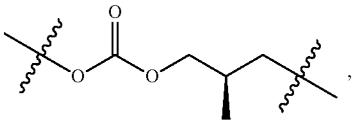

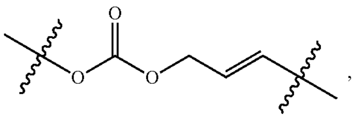

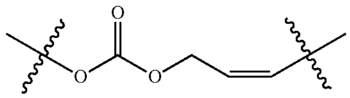

or

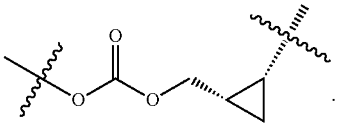

Provided herein as embodiment C21 is the compound according to embodiment C20, wherein -$L^1$-$L^2$- is

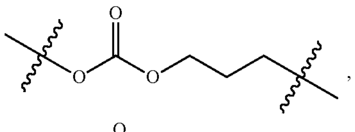

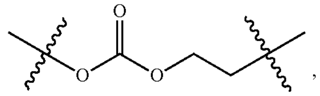

or

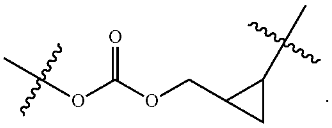

Provided herein as embodiment C22 is the compound according to embodiment C21, wherein -$L^1$-$L^2$- is

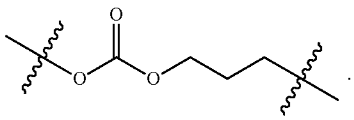 [SMILES: *CCCOC(=O)O* ; "."]
.

Provided herein as embodiment C23 is the compound according to embodiment C1, wherein $-L^1-L^2-$ is $—O-L^2$. Provided herein as embodiment C24 is the compound according to embodiment C23, wherein $L^2$ is n-butylene, n-pentylene, cis-2-pentenylene or trans-2-pentenylene. Provided herein as embodiment C25 is the compound according to embodiment C23, wherein $-L^1-L^2-$ is

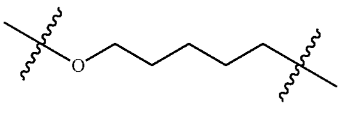
,

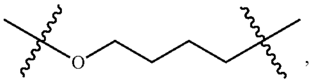 [SMILES: *CCCCO* ; "."]
,

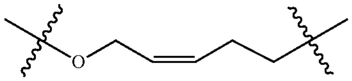
or

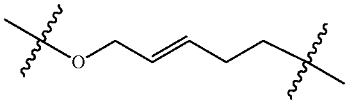
.

Provided herein as embodiment C26 is the compound according to embodiment C25, wherein $-L^1-L^2-$ is

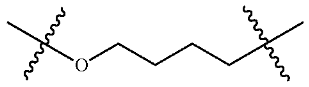
.

Provided herein as embodiment C27 is the compound according to embodiment C1, wherein $-L^1-L^2-$ is $—C_{1-4}$ alkylene-OC(O)O-$L^2$. Provided herein as embodiment C28 is the compound according to embodiment C27, wherein $L^2$ is ethylene. Provided herein as embodiment C29 is the compound according to embodiment C27, wherein $-L^1-L^2-$ is

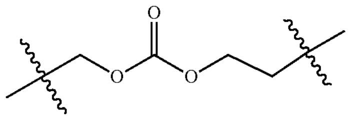
.

Provided herein as embodiment C30 is the compound according to embodiment C1, wherein $-L^1-L^2-$ is a $—C_{1-4}$ hydroxyalkylene-5-6 membered heteroaryl-$L^2$. Provided-herein as embodiment C31 is the compound according to embodiment C30, wherein $-L^1-L^2-$ is

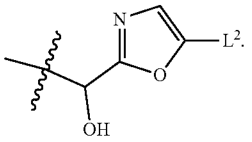

Provided herein as embodiment C32 is the compound according to embodiment C31, wherein $L^2$ is ethylene. Provided herein as embodiment C33 is the compound according to embodiment C30, wherein $-L^1-L^2-$ is

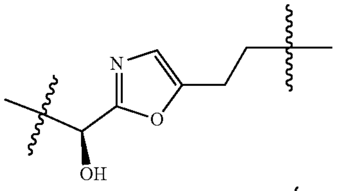
or

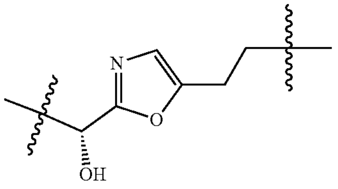
.

Provided herein as embodiment C34 is the compound according to embodiment C1, wherein $-L^1-L^2-$ is $—C_{1-4}$ alkylene-O-$L^2$. Provided herein as embodiment C35 is the compound according to embodiment C34, wherein $-L^1-L^2-$ is -methylene-O-$L^2$. Provided herein as embodiment C36 is the compound according to embodiment C35, wherein $L^2$ is n-butylene, 2,2-difluoro-n-butylene, trans-2-butenylene, cis-2-butenylene, 3-methyl-n-butylene, -ethylene-cyclopropylene- or ethylene-O-methylene. Provided herein as embodiment C37 is the compound according to embodiment C34, wherein $-L^1-L^2-$ is

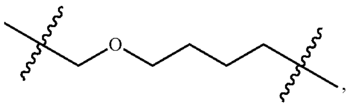
,

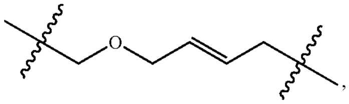
,

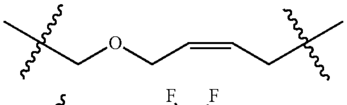
,

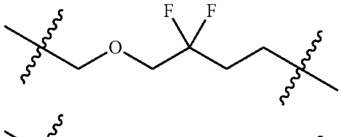
,

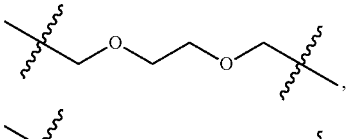
,

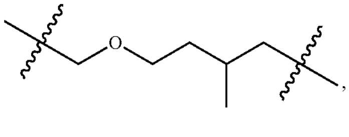
,

-continued

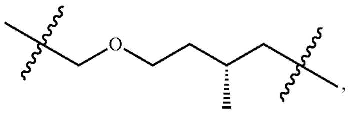

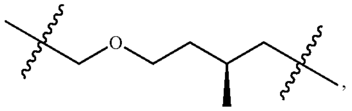

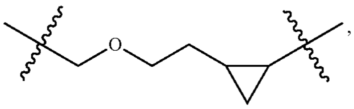

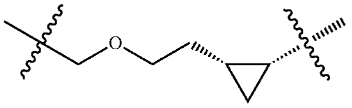

or

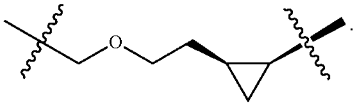

Provided herein as embodiment C38 is the compound according to embodiment C37, wherein $-L^1-L^2-$ is

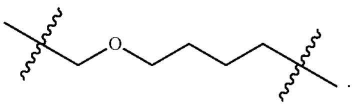 [SMILES: *CCCCOC* ; "."]

Provided herein as embodiment C39 is the compound according to embodiment C1, wherein $-L^1-L^2-$ is ethylene-O-$L^2$. Provided herein as embodiment C40 is the compound according to embodiment C39, wherein $L^2$ is ethylene, n-propylene or methylenecyclopropylene. Provided herein as embodiment C41 is the compound according to embodiment C39, wherein $-L^1-L^2-$ is

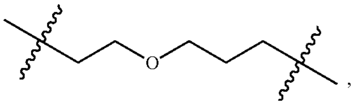

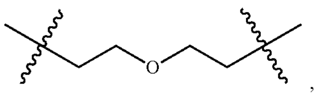

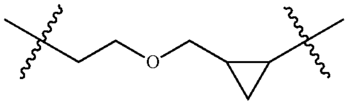

or

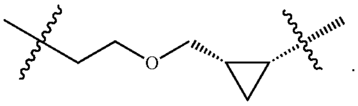

Provided herein as embodiment C42 is the compound according to embodiment C41, wherein $-L^1-L^2-$ is

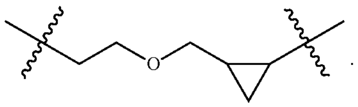 [SMILES: *CCOCC1CC1* ; "."]

Provided herein as embodiment C43 is the compound according to embodiment C1, wherein $-L^1-L^2-$ is —$NR^z$—C(O)—O-$L^2$. Provided herein as embodiment C44 is the compound according to embodiment C43, wherein $R^z$ is hydrogen or methyl. Provided herein as embodiment C45 is the compound according to embodiment C44, wherein $L^2$ is n-propylene, ethylene, —$CH_2$-cyclopropylene.

Provided herein as embodiment C46 is the compound according to embodiment C43, wherein $-L^1-L^2-$ is

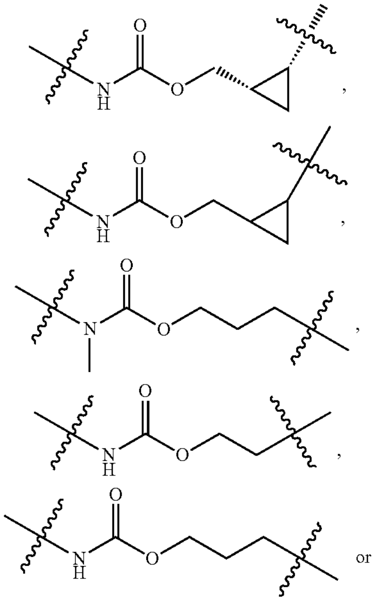

or

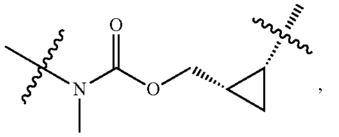

Provided herein as embodiment C47 is the compound according to embodiment C46, wherein $-L^1-L^2-$ is

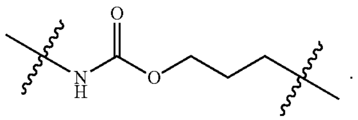 [SMILES: *CCCOC(=O)N* ; "."]

Provided herein as embodiment C48 is the compound according to embodiment C1, wherein $-L^1-L^2-$ is a 5-6 membered heteroaryl. Provided herein as embodiment C49 is the compound according to embodiment C48, wherein $-L^1-L^2-$ is

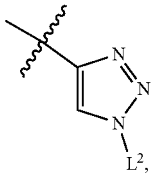

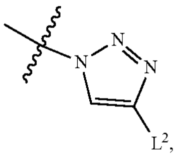

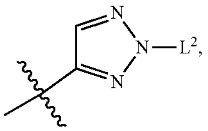

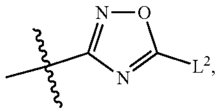

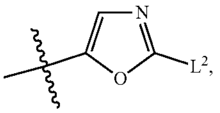

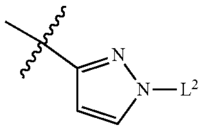

or

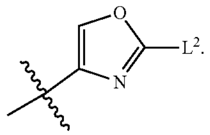

Provided herein as embodiment C50 is the compound according to embodiment C48, wherein $-L^1-L^2-$ is

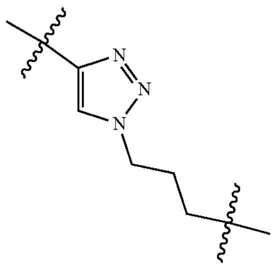

,

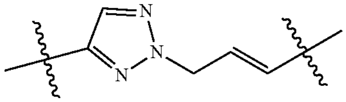

,

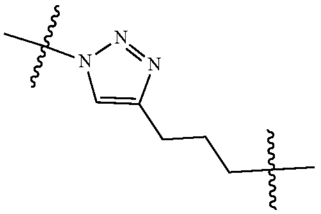

,

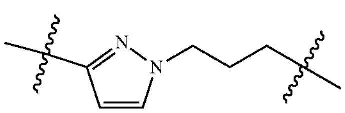

,

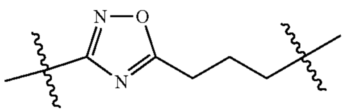

,

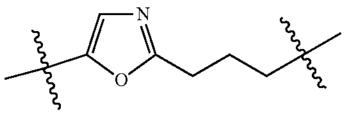

,

-continued

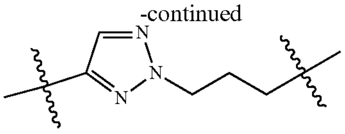

or

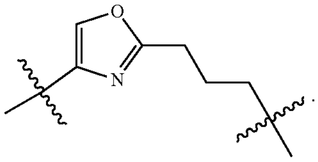

.

Provided herein as embodiment C51 is the compound according to embodiment C50, wherein $-L^1-L^2-$ is

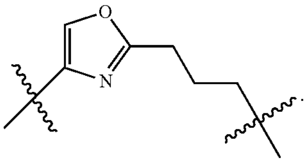 [SMILES: *CCCc1nc(*)co1]

.

Provided herein as embodiment C52 is the compound according to embodiment C1, wherein $-L^1-L^2-$ is —C(O)—. Provided herein as embodiment C53 is the compound according to embodiment C52, wherein $L^2$ is n-propylene, -methylene-O-n-propylene or n-butylene. Provided herein as embodiment C54 is the compound according to embodiment C52, wherein $-L^1-L^2-$ is

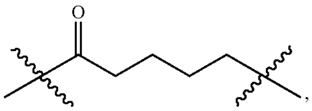

,

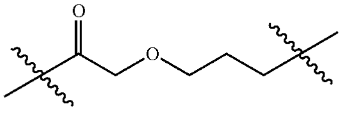

or

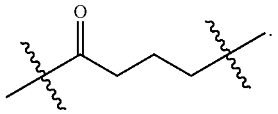

.

Provided herein as embodiment C55 is the compound according to embodiment C54, wherein $-L^1-L^2-$ is

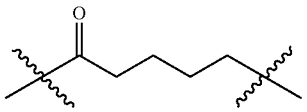

or

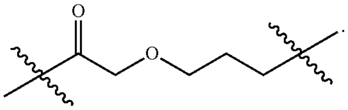

.

Provided herein as embodiment C56 is the compound according to embodiment C1, wherein $-L^1-L^2-$ is a $—C_{1-4}$ alkylene-5-6 membered heteroaryl-$L^2$. Provided herein as embodiment C57 is the compound according to embodiment C56, wherein $-L^1-L^2-$ is

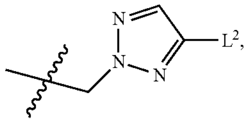

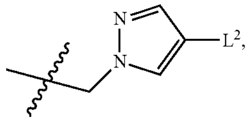

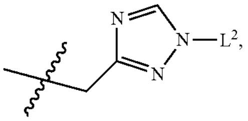

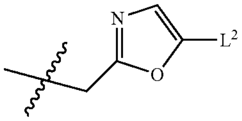

or

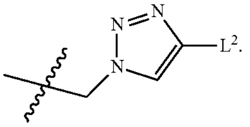

Provided herein as embodiment C58 is the compound according to embodiment C56, wherein $-L^1-L^2-$ is

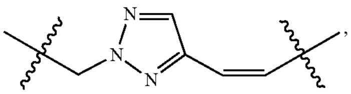

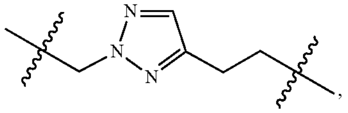

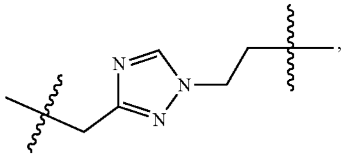

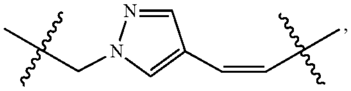

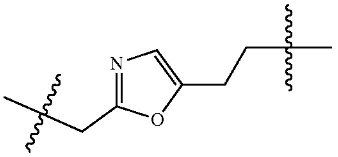

or

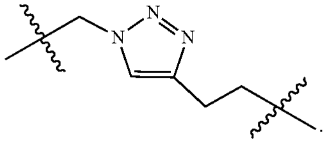

Provided herein as embodiment C59 is the compound according to embodiment C58, wherein $-L^1-L^2-$ is

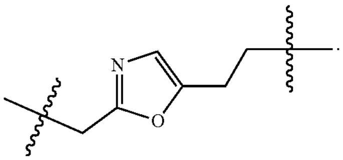 [SMILES: *CCc1cnc(C*)o1]

Provided herein as embodiment C60 is the compound according to embodiment C1, wherein $R^4$ is $C_{1-4}$ alkyl or halogen. Provided herein as embodiment C61 is the compound according to embodiment C1, wherein $R^4$ is fluorine.

Provided herein as embodiment C62 is the compound according to embodiment C1, wherein the compound is selected from a compound of Table 5:

TABLE 5

| Compound |
| --- |
| 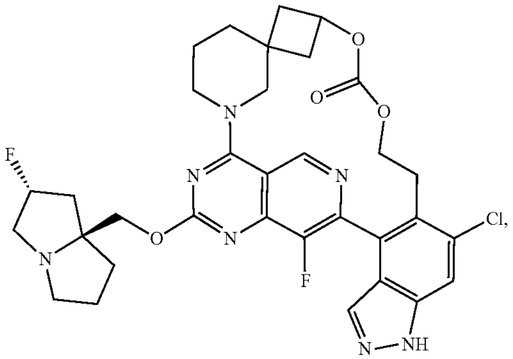 [SMILES: O=C1OCCc2c(Cl)cc3[nH]ncc3c2-c2ncc3c(nc(OC[C@@]45CCCN4C[C@H](F)C5)nc3c2F)N2CCCC3(CC(C3)O1)C2] |
| 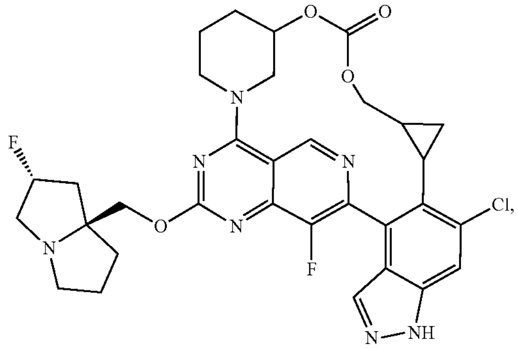 [SMILES: O=C1OCC2CC2c2c(Cl)cc3[nH]ncc3c2-c2ncc3c(nc(OC[C@@]45CCCN4C[C@H](F)C5)nc3c2F)N2CCCC(C2)O1] |
| 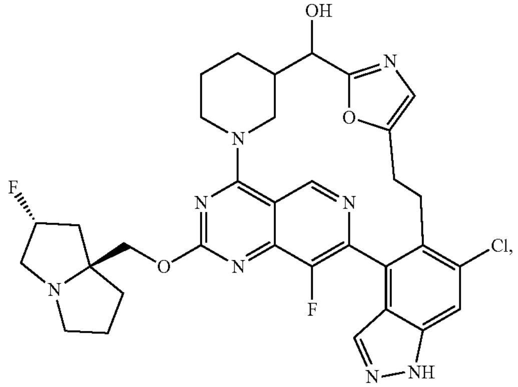 [SMILES: OC1c2ncc(o2)CCc2c(Cl)cc3[nH]ncc3c2-c2ncc3c(nc(OC[C@@]45CCCN4C[C@H](F)C5)nc3c2F)N2CCCC1C2] |
| 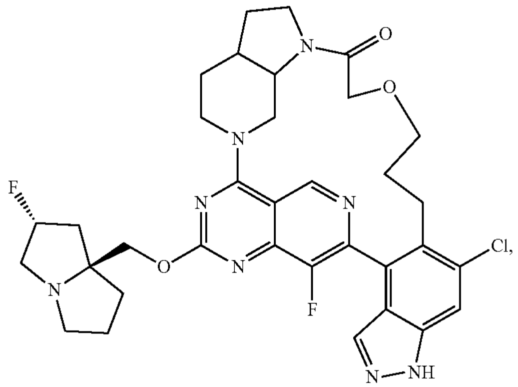 [SMILES: O=C1COCCCc2c(Cl)cc3[nH]ncc3c2-c2ncc3c(nc(OC[C@@]45CCCN4C[C@H](F)C5)nc3c2F)N2CCC3CCN1C3C2] |

TABLE 5-continued
| Compound |
| --- |
| 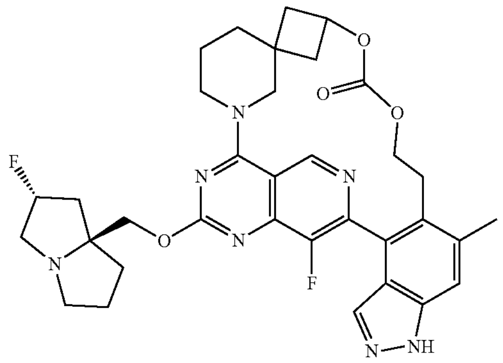 , |
| 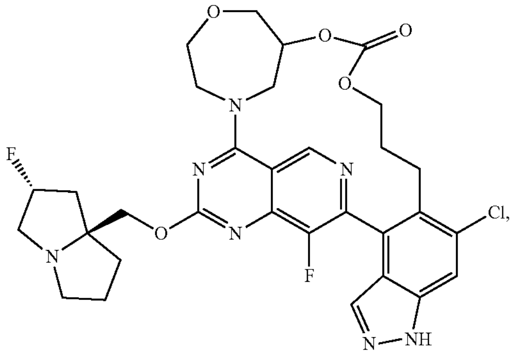 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] , |
| 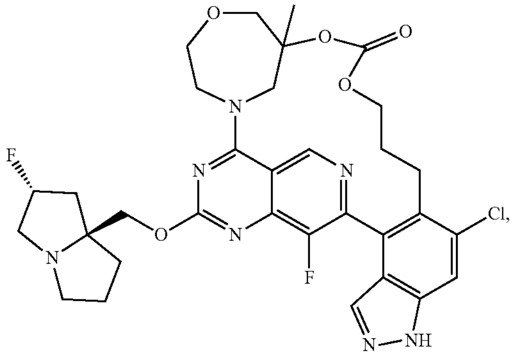 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2] , |
| 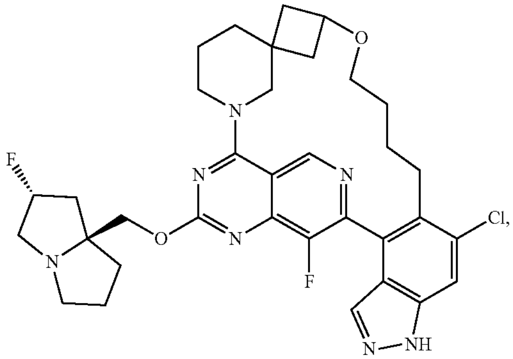 [SMILES: Fc1c2ncc3c(nc(OC[C@@]45CCCN4C[C@H](F)C5)nc13)N1CCCC3(CC(C3)OCCCCc3c(Cl)cc4[nH]ncc4c3-2)C1] , |
TABLE 5-continued
| Compound |
| --- |
| 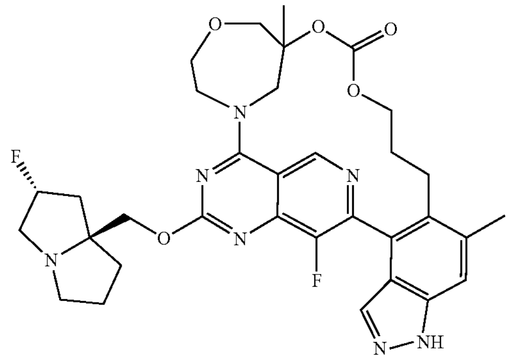 [SMILES: Cc1cc2[nH]ncc2c2c1CCCOC(=O)OC1(C)COCCN(C1)c1nc(OC[C@@]34CCCN3C[C@H](F)C4)nc3c(F)c-2ncc13] |
| 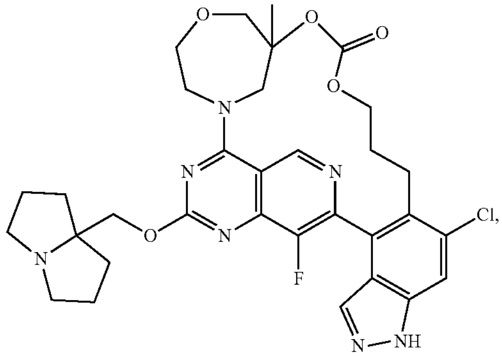 [SMILES: CC12COCCN(C1)c1nc(OCC34CCCN3CCC4)nc3c(F)c(ncc13)-c1c(c(Cl)cc3[nH]ncc13)CCCOC(=O)O2] , |
| 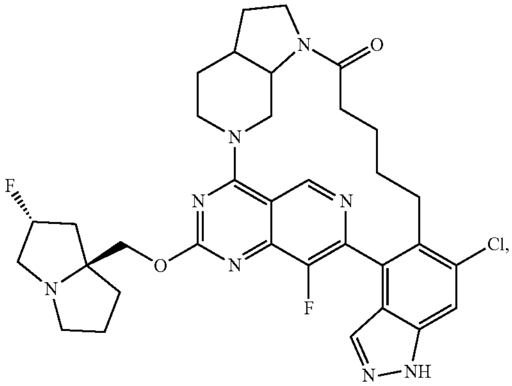 [SMILES: O=C1CCCCc2c(Cl)cc3[nH]ncc3c2-c2ncc3c(nc(OC[C@@]45CCCN4C[C@H](F)C5)nc3c2F)N2CCC3CCN1C3C2] , |
| 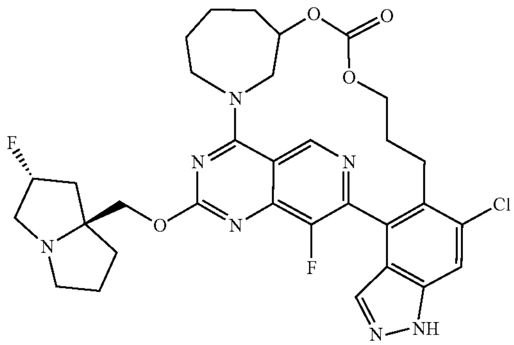 [SMILES: O=C1OCCCc2c(Cl)cc3[nH]ncc3c2-c2ncc3c(nc(OC[C@@]45CCCN4C[C@H](F)C5)nc3c2F)N2CCCCC(C2)O1] |

TABLE 5-continued
| Compound |
|---|
| 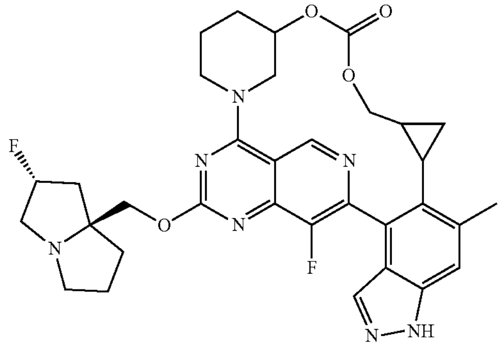 , |
| 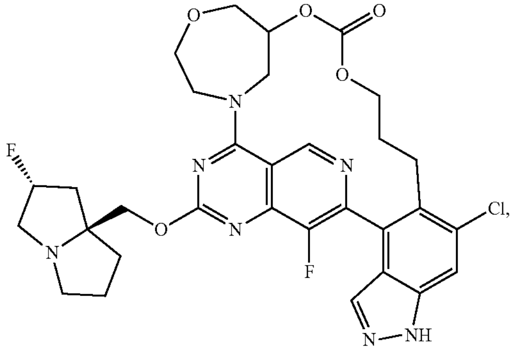 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] , |
| 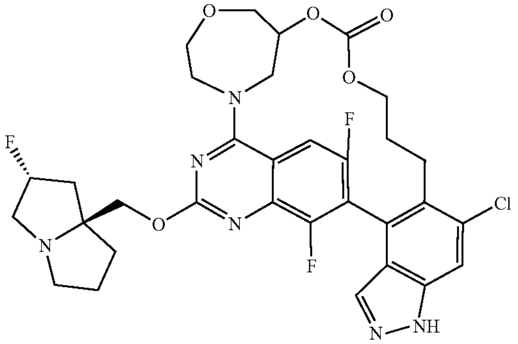 [SMILES: O=C1OCCCc2c(Cl)cc3[nH]ncc3c2-c2c(F)cc3c(nc(OC[C@@]45CCCN4C[C@H](F)C5)nc3c2F)N2CCOCC(C2)O1] |
| 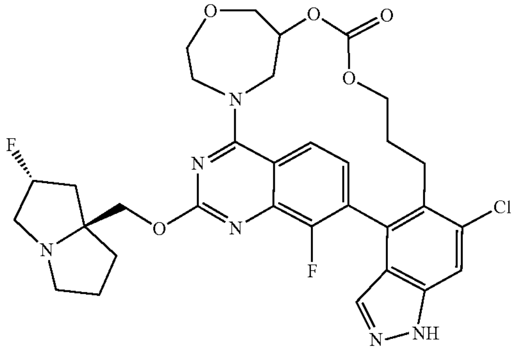 [SMILES: O=C1OCCCc2c(Cl)cc3[nH]ncc3c2-c2ccc3c(nc(OC[C@@]45CCCN4C[C@H](F)C5)nc3c2F)N2CCOCC(C2)O1] |
TABLE 5-continued
| Compound |
|---|
| 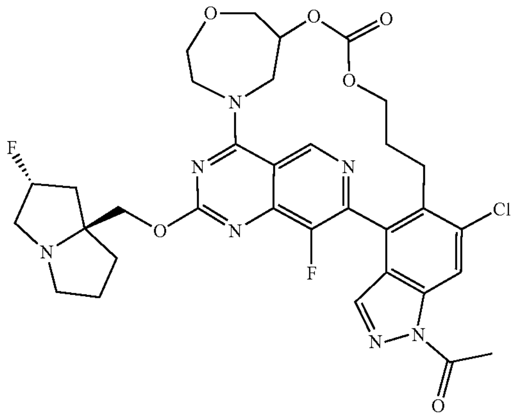 [SMILES: CC(=O)n1ncc2c3c(c(Cl)cc21)CCCOC(=O)OC1COCCN(C1)c1nc(OC[C@@]24CCCN2C[C@H](F)C4)nc2c(F)c-3ncc12] |
| 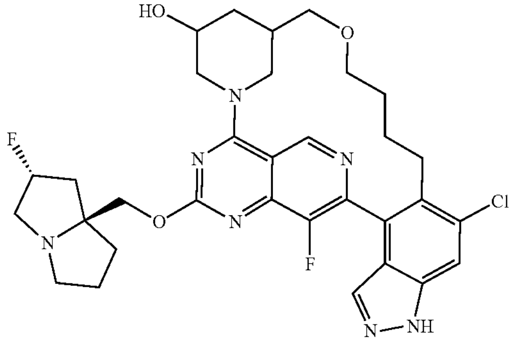 [SMILES: OC1CC2COCCCCc3c(Cl)cc4[nH]ncc4c3-c3ncc4c(nc(OC[C@@]56CCCN5C[C@H](F)C6)nc4c3F)N(C1)C2] |
| 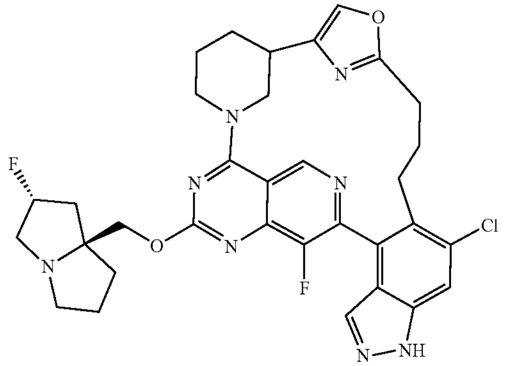 [SMILES: Fc1c2ncc3c(nc(OC[C@@]45CCCN4C[C@H](F)C5)nc13)N1CCCC(C1)c1coc(n1)CCCc1c(Cl)cc3[nH]ncc3c1-2] |
| 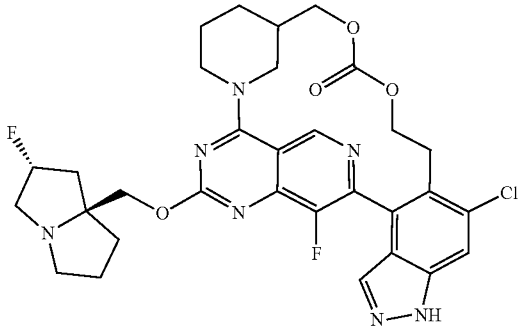 [SMILES: O=C1OCCc2c(Cl)cc3[nH]ncc3c2-c2ncc3c(nc(OC[C@@]45CCCN4C[C@H](F)C5)nc3c2F)N2CCCC(CO1)C2] |

TABLE 5-continued
| Compound |
| --- |
| 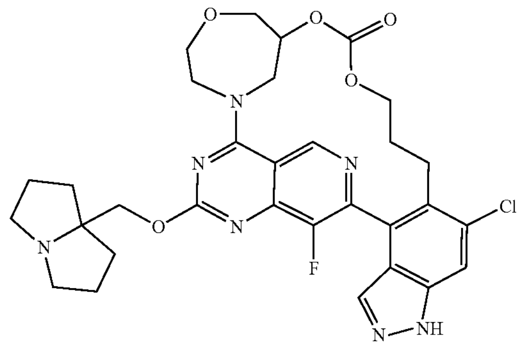 [SMILES: O=C1OCCCc2c(Cl)cc3[nH]ncc3c2-c2ncc3c(nc(OCC45CCCN4CCC5)nc3c2F)N2CCOCC(C2)O1] |
| 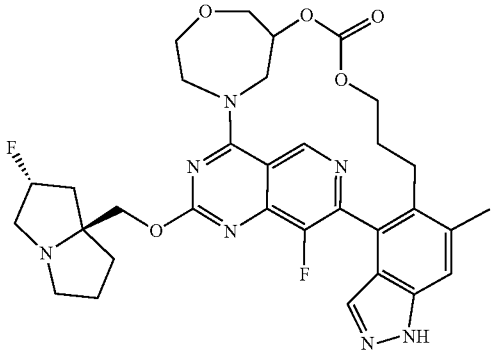 [SMILES: Cc1cc2[nH]ncc2c2c1CCCOC(=O)OC1COCCN(C1)c1nc(OC[C@@]34CCCN3C[C@H](F)C4)nc3c(F)c-2ncc13] |
| 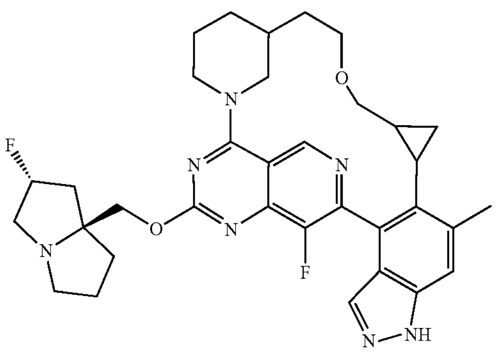 [SMILES: Cc1cc2[nH]ncc2c2c1C1CC1COCCC1CCCN(C1)c1nc(OC[C@@]34CCCN3C[C@H](F)C4)nc3c(F)c-2ncc13] |
| 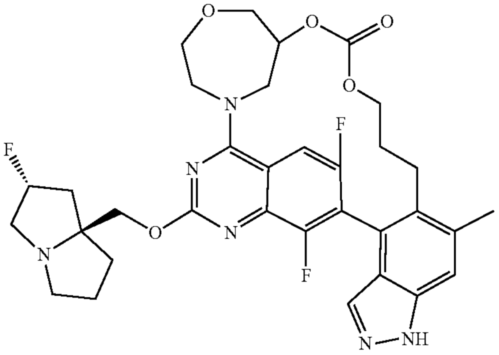 [SMILES: Cc1cc2[nH]ncc2c2c1CCCOC(=O)OC1COCCN(C1)c1nc(OC[C@@]34CCCN3C[C@H](F)C4)nc3c(F)c-2c(F)cc13] |
TABLE 5-continued
| Compound |
| --- |
| 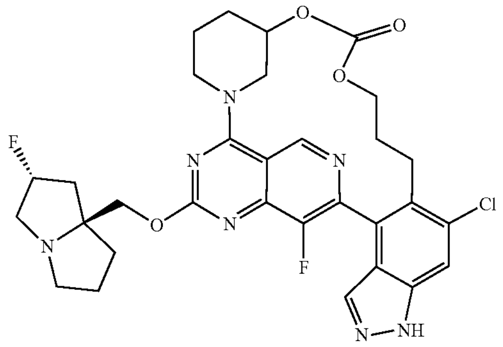 [SMILES: O=C1OCCCc2c(Cl)cc3[nH]ncc3c2-c2ncc3c(nc(OC[C@@]45CCCN4C[C@H](F)C5)nc3c2F)N2CCCC(C2)O1] |
| 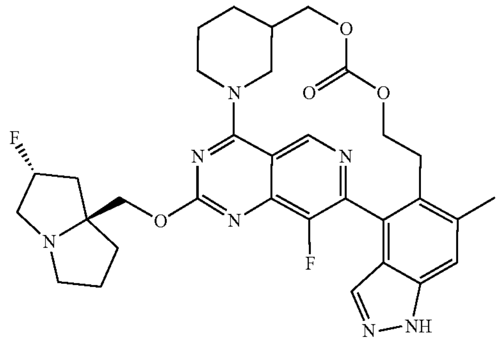 [SMILES: Cc1cc2[nH]ncc2c2c1CCOC(=O)OCC1CCCN(C1)c1nc(OC[C@@]34CCCN3C[C@H](F)C4)nc3c(F)c-2ncc13] |
| 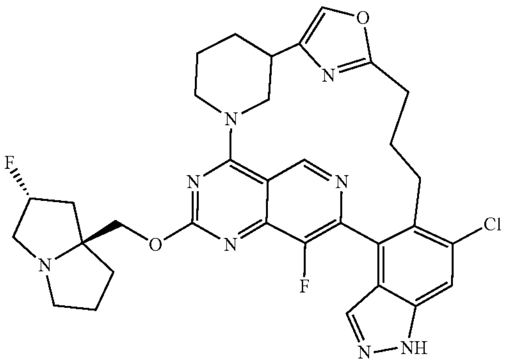 [SMILES: Fc1c2ncc3c(nc(OC[C@@]45CCCN4C[C@H](F)C5)nc13)N1CCCC(C1)c1coc(n1)CCCc1c(Cl)cc3[nH]ncc3c1-2] |
| 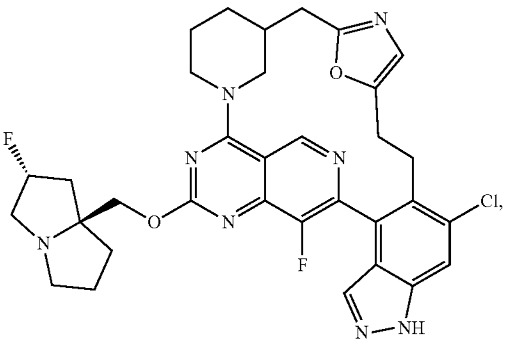 [SMILES: Fc1c2ncc3c(nc(OC[C@@]45CCCN4C[C@H](F)C5)nc13)N1CCCC(Cc3ncc(o3)CCc3c(Cl)cc4[nH]ncc4c3-2)C1] |

TABLE 5-continued
| Compound |
| --- |
| 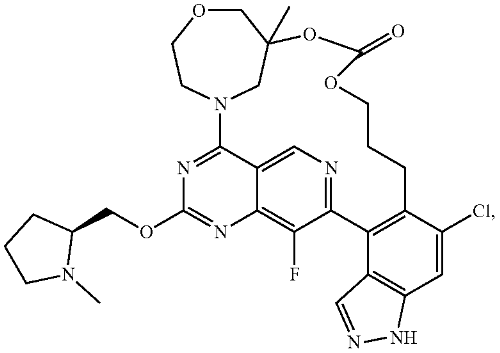 [SMILES: CN1CCC[C@H]1COc1nc2c3cnc(c(F)c3n1)-c1c(c(Cl)cc3[nH]ncc13)CCCOC(=O)OC1(C)COCCN2C1] |
| 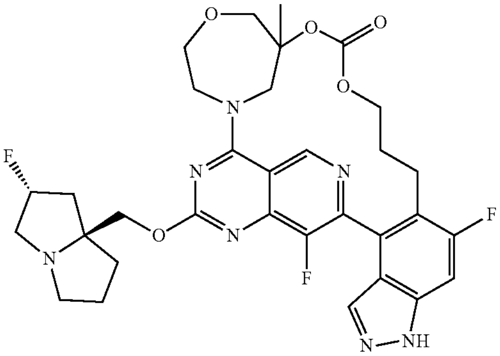 [SMILES: CC12COCCN(C1)c1nc(OC[C@@]34CCCN3C[C@H](F)C4)nc3c(F)c(ncc13)-c1c(c(F)cc3[nH]ncc13)CCCOC(=O)O2] |
| or |
| 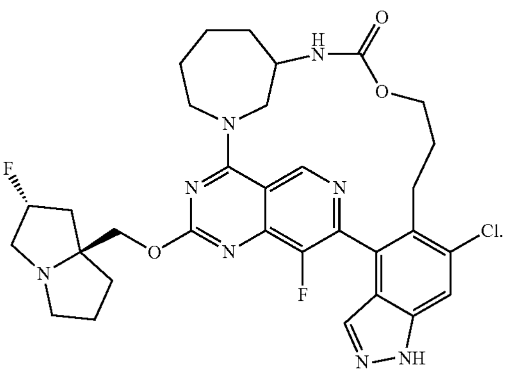 [SMILES: O=C1NC2CCCCN(C2)c2nc(OC[C@@]34CCCN3C[C@H](F)C4)nc3c(F)c(ncc23)-c2c(c(Cl)cc3[nH]ncc23)CCCO1] |
Provided herein as embodiment C63 is the compound according to embodiment C1, wherein the compound is selected from a compound of Table 6:
TABLE 6
| Compound |
| --- |
| 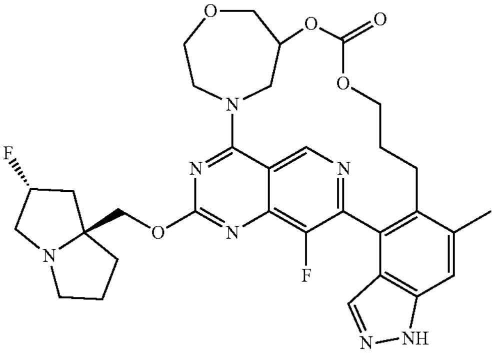 , |
| 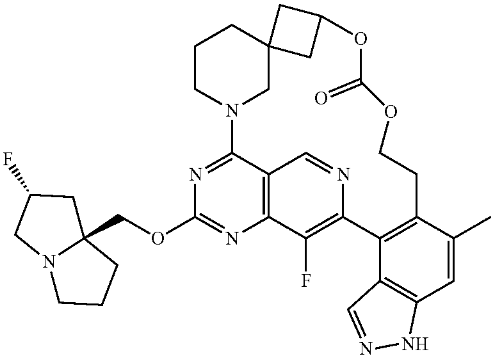 , |
| 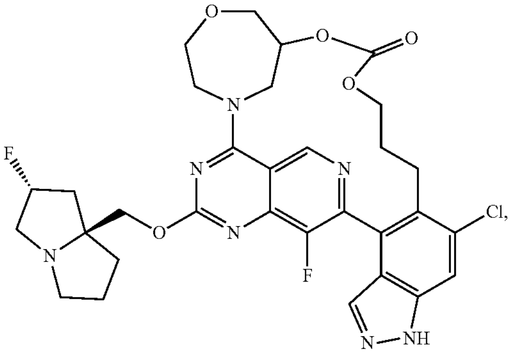 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] |
| 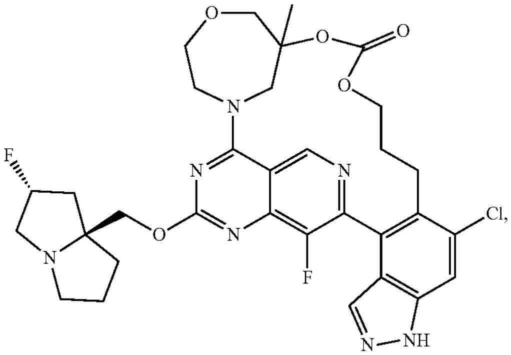 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2] |

TABLE 6-continued

| Compound |
| --- |
| 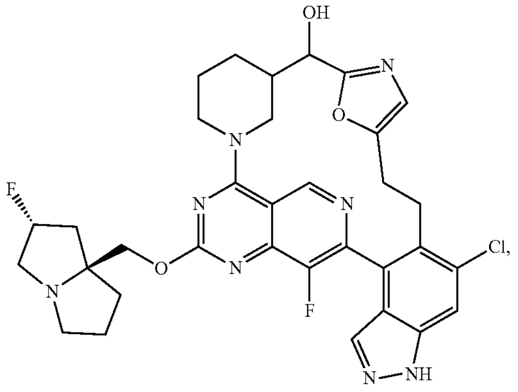 [SMILES: OC1c2ncc(o2)CCc2c(Cl)cc3[nH]ncc3c2-c2ncc3c(nc(OC[C@@]45CCCN4C[C@H](F)C5)nc3c2F)N2CCCC1C2] , |
| 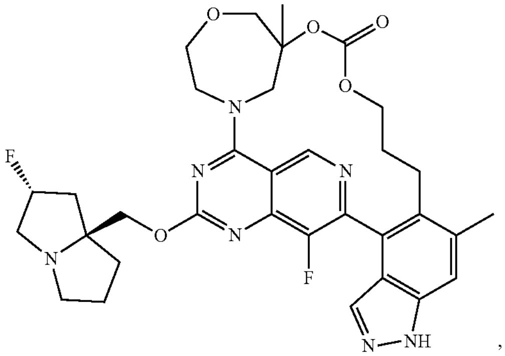 [SMILES: Cc1cc2[nH]ncc2c2c1CCCOC(=O)OC1(C)COCCN(C1)c1nc(OC[C@@]34CCCN3C[C@H](F)C4)nc3c(F)c-2ncc13] , |
| 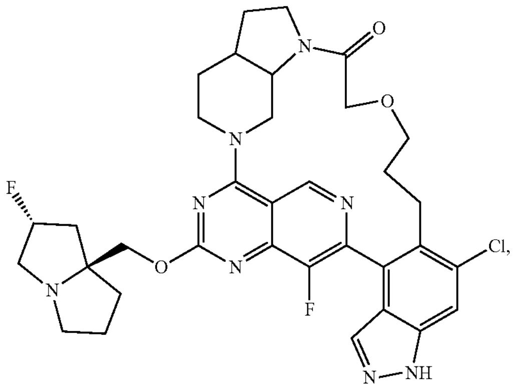 [SMILES: O=C1COCCCc2c(Cl)cc3[nH]ncc3c2-c2ncc3c(nc(OC[C@@]45CCCN4C[C@H](F)C5)nc3c2F)N2CCC3CCN1C3C2] , |
| 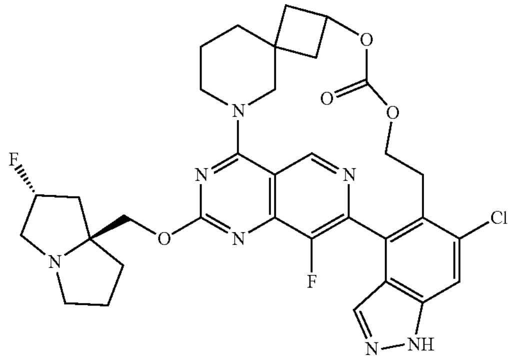 [SMILES: O=C1OCCc2c(Cl)cc3[nH]ncc3c2-c2ncc3c(nc(OC[C@@]45CCCN4C[C@H](F)C5)nc3c2F)N2CCCC3(CC(C3)O1)C2] |

TABLE 6-continued

| Compound |
| --- |
| 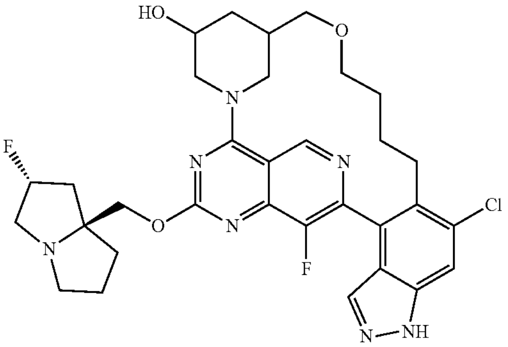 [SMILES: OC1CC2COCCCCc3c(Cl)cc4[nH]ncc4c3-c3ncc4c(nc(OC[C@@]56CCCN5C[C@H](F)C6)nc4c3F)N(C1)C2] |
| or |
| 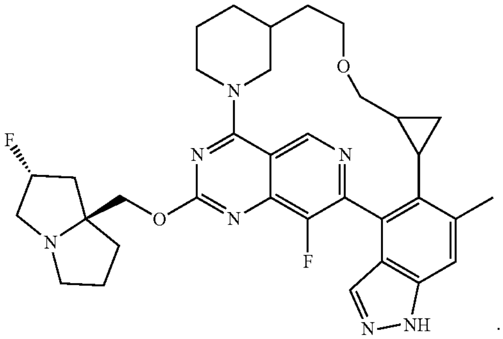 [SMILES: Cc1cc2[nH]ncc2c2c1C1CC1COCCC1CCCN(C1)c1nc(OC[C@@]34CCCN3C[C@H](F)C4)nc3c(F)c-2ncc13] . |

The foregoing merely summarizes certain aspects of this disclosure and is not intended, nor should it be construed, as limiting the disclosure in any way.

Formulation, and Route of Administration

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients, such as diluents, carriers, adjuvants and the like, and, if desired, other active ingredients. See, e.g., Remington: The Science and Practice of Pharmacy, Volume I and Volume II, twenty-second edition, edited by Loyd V. Allen Jr., Philadelphia, PA, Pharmaceutical Press, 2012; Pharmaceutical Dosage Forms (Vol. 1-3), Liberman et al., Eds., Marcel Dekker, New York, NY, 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by GD Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as embodiment 425 is a pharmaceutical composition comprising the compound or salt according to any one of embodiments 1-424, B1-B51 or C1-C63, or a tautomer thereof, or a pharmaceutically acceptable salt of said compound or said tautomer, and a pharmaceutically acceptable excipient.

Provided herein as embodiment 426 is a compound according to any one of Embodiments 1-424, B1-B51 or C1-C63, or a tautomer thereof, or a pharmaceutically acceptable salt of said compound or said tautomer, or the pharmaceutical composition according to embodiment 423 for use as a medicament.

Methods of Use

As discussed herein (see, section entitled "Definitions"), the compounds described herein are to be understood to include all stereoisomers, tautomers, or pharmaceutically acceptable salts of any of the foregoing or solvates of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

In one embodiment, the disclosure provides methods of using the compounds or pharmaceutical compositions of the present disclosure to treat disease conditions, including but not limited to conditions implicated by KRAS G12D, G12V, G12A, G12S, G13D, Q61H, Q61L or G12C mutation (e.g., cancer). The cancer types are non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

KRAS G12D mutations occur with the alteration frequencies shown in the table below (TCGA data sets. For example, the table shows that 32.4% of subjects with pancreatic cancer have a cancer wherein one or more cells express KRAS G12D mutant protein. Accordingly, the compounds provided herein, which bind to $KRAS^{G12D}$ (see Section entitled "Biological Evaluation" below) are useful for treatment of subjects having a cancer, including, but not limited to the cancers listed in the table below.

| Cancer Type | Alteration Frequency |
|---|---|
| Pancreatic Adenocarcinoma (PAAD) | 32.4 |
| Colon Adenocarcinoma (COAD) | 12.25 |
| Rectal adenocarcinoma (READ) | 8.03 |
| Uterine corpus endometrial carcinoma (UCEC) | 6.04 |

-continued

| Cancer Type | Alteration Frequency |
|---|---|
| Lung Adenocarcinoma (LUAD) | 3.53 |
| Plasma Cell Tumors | 2.92 |
| Stomach Adenocarcinoma (STAD) | 2.27 |
| Bladder urothelial carcinoma (BLCA) | 1.46 |
| Cervical Squamous carcinoma (CESC) | 1.38 |
| Kidney Adenocarcinoma | 1.07 |
| Thymic Cancer | 0.81 |
| Myeloid Leukemia (LAML) | 0.69 |
| Liver Hepatocellular Carcinoma (LIHC) | 0.55 |
| Glioblastoma multiforme (GBM) | 0.51 |
| Skin Cutaneous Melanoma (SKCM) | 0.43 |
| Bladder Cancer | 0.4 |
| Prostate Adenocarcinoma (PRAD) | 0.2 |
| Breast Invasive Carcinoma (BRCA) | 0.1 |

Provided herein as embodiment 427 is a compound according to any one of embodiments 1-424, B1-B51 or C1-C63 or a pharmaceutically acceptable salt thereof, or the pharmaceutical composition according to embodiment 425 for use in treating cancer.

Provided herein as Embodiment 428 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS G12D mutant protein.

Provided herein as Embodiment 429 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS G12V mutant protein.

Provided herein as Embodiment 430 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS G12A mutant protein.

Provided herein as Embodiment 431 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS G12S mutant protein.

Provided herein as Embodiment 432 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS G13D mutant protein.

Provided herein as Embodiment 433 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS Q61H mutant protein.

Provided herein as Embodiment 434 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS Q61L mutant protein.

Provided herein as Embodiment 435 is a compound according to any one of Embodiments 1-424, B1-B51 or C1-C63 or a pharmaceutically acceptable salt thereof, or the pharmaceutical composition according to Embodiment 425 for use in treating cancer, wherein one or more cells express KRAS G12C mutant protein.

Provided herein as Embodiment 436 is the compound or pharmaceutical composition for use of any one of embodiments 427-435, wherein the cancer is pancreatic cancer, colorectal cancer, non-small cell lung cancer, small bowel cancer, appendiceal cancer, cancer of unknown primary, endometrial cancer, mixed cancer types, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 437 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer.

Provided herein as Embodiment 438 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS G12D mutant protein.

Provided herein as Embodiment 439 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS G12V mutant protein.

Provided herein as Embodiment 440 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS G12A mutant protein.

Provided herein as Embodiment 441 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS G12S mutant protein.

Provided herein as Embodiment 442 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS G13D mutant protein.

Provided herein as Embodiment 443 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS Q61H mutant protein.

Provided herein as Embodiment 444 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS Q61L mutant protein.

Provided herein as Embodiment 445 is a use of the compound according to any one of Embodiments 1-424, B1-B51 or C1-C63 or a pharmaceutically acceptable salt thereof, or the pharmaceutical composition according to Embodiment 425 in the preparation of a medicament for treating cancer, wherein one or more cells express KRAS G12C mutant protein.

Provided herein as Embodiment 446 is the use according to any one of Embodiments 437-445, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 447 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof.

Provided herein as Embodiment 448 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS G12D mutant protein.

Provided herein as Embodiment 449 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS G12V mutant protein.

Provided herein as Embodiment 450 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS G12A mutant protein.

Provided herein as Embodiment 451 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS G12S mutant protein.

Provided herein as Embodiment 452 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS G13D mutant protein.

Provided herein as Embodiment 453 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS Q61H mutant protein.

Provided herein as Embodiment 454 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS Q61L mutant protein.

Provided herein as Embodiment 455 is a method of treating cancer in a subject in need thereof, the method comprising administering to the subject a therapeutically effective amount of the compound according to any one of to any one of Embodiments 1-424, B1-B51 or C1-C63 or a pharmaceutically acceptable salt thereof, wherein one or more cells express KRAS G12C mutant protein.

Provided herein as Embodiment 456 is the method according to any one of embodiments 447-455, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 457 is the method according to any one of embodiments 457-455, wherein the cancer is non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

Provided herein as Embodiment 458 is the method according to Embodiment 457, wherein the cancer is non-small cell lung cancer.

Provided herein as Embodiment 459 is the method according to Embodiment 457, wherein the cancer is colorectal cancer.

Provided herein as Embodiment 460 is the method according to Embodiment 457, wherein the cancer is pancreatic cancer.

Combination Therapy

The present disclosure also provides methods for combination therapies in which an agent known to modulate other pathways, or other components of the same pathway, or even overlapping sets of target enzymes are used in combination with a compound of the present disclosure or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect. See, e.g., U.S. Pat. No. 10,519,146 B2, issued Dec. 31, 2019; specifically, the sections from column 201 (line 37) to column 212 (line 46) and column 219 (line 64) to column 220 (line 39), which are herewith incorporated by reference.

Provided herein as Embodiment 461 is the method according to any one of embodiments 447-460, which further comprises simultaneous, separate, or sequential administration of an effective amount of a second compound, wherein the second compound is an Aurora kinase A inhibitor, AKT inhibitor, arginase inhibitor, CDK4/6 inhibitor, ErbB family inhibitor, ERK inhibitor, FAK inhibitor, FGFR inhibitor, glutaminase inhibitor, IGF-1R inhibitor, KIF18A inhibitor, MCL-1 inhibitor, MEK inhibitor, mTOR inhibitor, PD-1 inhibitor, PD-L1 inhibitor, PI3K inhibitor, Raf kinase inhibitor, SHP2 inhibitor, SOS1 inhibitor, Src kinase inhibitor, or one or more chemotherapeutic agent.

In one embodiment, the second compound is administered as a pharmaceutically acceptable salt. In another embodiment the second compound is administered as a pharmaceutical composition comprising the second compound or a pharmaceutically acceptable salt thereof and a pharmaceutically acceptable excipient.

Aurora Kinase A Inhibitors

Provided herein is the method according to any one of embodiments 447-460, which further comprises simultaneous, separate, or sequential administration of an effective amount of a second compound, wherein the second compound is an Aurora kinase A inhibitor.

Exemplary Aurora kinase A inhibitors for use in the methods provided herein include, but are not limited to, alisertib, cenisertib, danusertib, tozasertib, LY3295668 ((2R,4R)-1-[(3-chloro-2-fluorophenyl)methyl]-4-[[3-fluoro-6-[(5-methyl-1H-pyrazol-3-yl)amino]pyridin-2-yl]methyl]-2-methylpiperidine-4-carboxylic acid), ENMD-2076 (6-(4-methylpiperazin-1-yl)-N-(5-methyl-1H-pyrazol-3-yl)-2-[(E)-2-phenylethenyl]pyrimidin-4-amine), TAK-901 (5-(3-ethylsulfonylphenyl)-3,8-dimethyl-N-(1-methylpiperidin-4-yl)-9H-pyrido[2,3-b]indole-7-carboxamide), TT-00420 (4-[9-(2-chlorophenyl)-6-methyl-2,4,5,8,12-pentazatricyclo[8.4.0.03,7]tetradeca-1(14),3,6,8,10,12-hexaen-13-yl]morpholine), AMG 900 (N-[4-[3-(2-aminopyrimidin-4-yl)pyridin-2-yl]oxyphenyl]-4-(4-methylthiophen-2-yl)phthalazin-1-amine), MLN8054 (4-[[9-chloro-7-(2,6-difluorophenyl)-5H-pyrimido[5,4-d][2]benzazepin-2-yl]amino]benzoic acid), PF-03814735 (N-[2-[(1R,8S)-4-[[4-(cyclobutylamino)-5-(trifluoromethyl)pyrimidin-2-yl]amino]-11-azatricyclo[6.2.1.02,7]undeca-2(7),3,5-trien-11-yl]-2-oxoethyl]acetamide), SNS-314 (1-(3-chlorophenyl)-3-[5-[2-(thieno[3,2-d]pyrimidin-4-ylamino)ethyl]-1,3-thiazol-2-yl]urea), CYC116 (4-methyl-5-[2-(4-morpholin-4-ylanilino)pyrimidin-4-yl]-1,3-thiazol-2-amine), TAS-119, BI 811283, and TTP607.

AKT Inhibitors

Provided herein is the method according to any one of embodiments 447-460, which further comprises simultaneous, separate, or sequential administration of an effective amount of a second compound, wherein the second compound is an AKT inhibitor.

Exemplary AKT inhibitors for use in the methods provided herein include, but are not limited to, afuresertib, capivasertib, ipatasertib, uprosertib, BAY1125976 (2-[4-(1-aminocyclobutyl)phenyl]-3-phenylimidazo[1,2-b]pyridazine-6-carboxamide), ARQ 092 (3-[3-[4-(1-aminocyclobutyl)phenyl]-5-phenylimidazo[4,5-b]pyridin-2-yl]pyridin-2-amine), MK2206 (8-[4-(1-aminocyclobutyl)phenyl]-9-phenyl-2H-[1,2,4]triazolo[3,4-f][1,6]naphthyridin-3-one), SR13668 (indolo[2,3-b]carbazole-2,10-dicarboxylic acid, 5,7-dihydro-6-methoxy-, 2,10-diethyl ester), ONC201 (11-benzyl-7-[(2-methylphenyl)methyl]-2,5,7,11-tetrazatricyclo[7.4.0.02,6]trideca-1(9),5-dien-8-one), ARQ 751 (N-(3-aminopropyl)-N-[(1R)-1-(3-anilino-7-chloro-4-oxoquinazolin-2-yl)but-3-ynyl]-3-chloro-2-fluorobenzamide), RX-0201, and LY2780301.

Arginase Inhibitors

Provided herein is the method according to any one of embodiments 447-460, which further comprises simultaneous, separate, or sequential administration of an effective amount of a second compound, wherein the second compound is an arginase inhibitor.

Exemplary arginase inhibitors for use in the methods provided herein include, but are not limited to, numidargistat and CB 280.

CDK4/6 Inhibitors

Provided herein is the method according to any one of embodiments 447-460, which further comprises simultaneous, separate, or sequential administration of an effective amount of a second compound, wherein the second compound is a CDK4/6 inhibitor.

The term "CDK 4/6" as used herein refers to cyclin dependent kinases ("CDK") 4 and 6, which are members of the mammalian serine/threonine protein kinases.

The term "CDK 4/6 inhibitor" as used herein refers to a compound that is capable of negatively modulating or inhibiting all or a portion of the enzymatic activity of CDK 4 and/or 6.

Exemplary CDK 4/6 inhibitors for use in the methods provided herein include, but are not limited to, abemaciclib, palbociclib, ribociclib, trilaciclib, and PF-06873600 ((pyrido[2,3-d]pyrimidin-7(8H)-one, 6-(difluoromethyl)-8-[(1R,2R)-2-hydroxy-2-methylcyclopentyl]-2-[[1-(methylsulfonyl)-4-piperidinyl]amino]).

In one embodiment, the CDK4/6 inhibitor is palbociclib.

ErbB Family Inhibitors

Provided herein is the method according to any one of embodiments 447-460, which further comprises simultaneous, separate, or sequential administration of an effective amount of a second compound, wherein the second compound is an ErbB family inhibitor.

The term "ErbB family" as used herein refers to a member of a mammalian transmembrane protein tyrosine kinase family including: ErbB1 (EGFR HER1), ErbB2 (HER2), ErbB3 (HER3), and ErbB4 (HER4).

The term "ErbB family inhibitor" as used herein refers to an agent, e.g., a compound or antibody, that is capable of negatively modulating or inhibiting all or a portion of the activity of at least one member of the ErbB family. The modulation or inhibition of one or more ErbB tyrosine kinase may occur through modulating or inhibiting kinase enzymatic activity of one or more ErbB family member or by blocking homodimerization or heterodimerization of ErbB family members.

In one embodiment, the ErbB family inhibitor is an EGFR inhibitor, e.g., an anti-EGFR antibody. Exemplary anti-EGFR antibodies for use in the methods provided herein include, but are not limited to, zalutumumab, nimotuzumab, matuzumab, necitumumab, panitumumab, and cetuximab. In one embodiment, the anti-EGFR antibody is cetuximab. In one embodiment, the anti-EGFR antibody is panitumumab.

In another embodiment the ErbB family inhibitor is a HER2 inhibitor, e.g., an anti-HER2 antibody. Exemplary anti-HER-2 antibodies for use in the methods provided herein include, but are not limited to, pertuzumab, trastuzumab, and trastuzumab emtansine.

In yet another embodiment the ErbB family inhibitor is a HER3 inhibitor, e.g., an anti-HER3 antibody, such as HMBD-001 (Hummingbird Bioscience).

In one embodiment, the ErbB family inhibitor is a combination of an anti-EGFR antibody and anti-HER2 antibody.

In one embodiment, the ErbB family inhibitor is an irreversible inhibitor. Exemplary irreversible ErbB family inhibitors for use in the methods provided herein include, but are not limited to, afatinib, dacomitinib, canertinib, poziotinib, AV 412 ((N-[4-[(3-chloro-4-fluorophenyl)amino]-7-[3-methyl-3-(4-methyl-1-piperazinyl)-1-butyn-1-yl]-6-quinazolinyl]-2-propenamide)), PF 6274484 ((N-[4-[(3-chloro-4-fluorophenyl)amino]-7-methoxy-6-quinazolinyl]-2-propenamide), and HKI 357 ((E)-N-[4-[3-chloro-4-[(3-fluorophenyl)methoxy]anilino]-3-cyano-7-ethoxyquinolin-6-yl]-4-(dimethylamino)but-2-enamide).

In one embodiment, the irreversible ErbB family inhibitor is afatinib. In one embodiment, the irreversible ErbB family inhibitor is dacomitinib.

In one embodiment, the ErbB family inhibitor is a reversible inhibitor. Exemplary reversible ErbB family inhibitors for use in the methods provided herein include, but are not limited to erlotinib, gefitinib, sapitinib, varlitinib, tarloxotinib, TAK-285 (N-(2-(4-((3-chloro-4-(3-(trifluoromethyl)phenoxy)phenyl)amino)-5H-pyrrolo [3,2-d]pyrimidin-5-yl)ethyl)-3-hydroxy-3-methylbutanamide), AEE788 ((S)-6-(4-((4-ethylpiperazin-1-yl)methyl)phenyl)-N-(1-phenylethyl)-7H-pyrrolo[2,3-d]pyrimidin-4-amine), BMS 599626 ((3S)-3-morpholinylmethyl-[4-[[1-[(3-fluorophenyl)methyl]-1H-indazol-5-yl]amino]-5-methylpyrrolo[2,1-f][1,2,4]triazin-6-yl]-carbamate), and GW 583340 (N-[3-chloro-4-[(3-fluorophenyl)methoxy]phenyl]-6-[2-[(2-methylsulfonylethylamino)methyl]-1,3-thiazol-4-yl]quinazolin-4-amine).

In one embodiment, the reversible ErbB family inhibitor is sapitinib. In one embodiment, the reversible ErbB family inhibitor is tarloxotinib.

ERK Inhibitors

Provided herein is the method according to any one of embodiments 447-460, which further comprises simultaneous, separate, or sequential administration of an effective amount of a second compound, wherein the second compound is an ERK inhibitor.

Exemplary ERK inhibitors for use in the methods provided herein include, but are not limited to, ulixertinib, ravoxertinib, CC-90003 (N-[2-[[2-[(2-methoxy-5-methylpyridin-4-yl)amino]-5-(trifluoromethyl)pyrimidin-4-yl]amino]-5-methylphenyl]prop-2-enamide), LY3214996 (6,6-dimethyl-2-[2-[(2-methylpyrazol-3-yl)amino]pyrimidin-4-yl]-5-(2-morpholin-4-ylethyl)thieno[2,3-c]pyrrol-4-one), KO-947 (1,5,6,8-tetrahydro-6-(phenylmethyl)-3-(4-pyridinyl)-7H-pyrazolo[4,3-g]quinazolin-7-one), ASTX029, LTT462, and JSI-1187.

FAK Inhibitors

Provided herein is the method according to any one of embodiments 447-460, which further comprises simultaneous, separate, or sequential administration of an effective amount of a second compound, wherein the second compound is a FAK inhibitor.

Exemplary FAK inhibitors for use in the methods provided herein include, but are not limited to, GSK2256098 (2-[[5-chloro-2-[(5-methyl-2-propan-2-ylpyrazol-3-yl)amino]pyridin-4-yl]amino]-N-methoxybenzamide), PF-00562271 (N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide), VS-4718 (2-[[2-(2-methoxy-4-morpholin-4-ylanilino)-5-(trifluoromethyl)pyridin-4-yl]amino]-N-methylbenzamide), and APG-2449.

FGFR Inhibitors

Provided herein is the method according to any one of embodiments 447-460, which further comprises simultaneous, separate, or sequential administration of an effective amount of a second compound, wherein the second compound is an FGFR inhibitor.

Exemplary FGFR inhibitors for use in the methods provided herein include, but are not limited to, futibatinib, pemigatinib, ASP5878 (2-[4-[[5-[(2,6-difluoro-3,5-dimethoxyphenyl)methoxy]pyrimidin-2-yl]amino]pyrazol-1-yl]ethanol), AZD4547 (N-[5-[2-(3,5-dimethoxyphenyl)ethyl]-

1H-pyrazol-3-yl]-4-[(3S,5R)-3,5-dimethylpiperazin-1-yl] benzamide), debio 1347 ([5-amino-1-(2-methyl-3H-benzimidazol-5-yl)pyrazol-4-yl]-(1H-indol-2-yl) methanone), TNCB062079, H3B-6527 (N-[2-[[6-[(2,6-dichloro-3,5-dimethoxyphenyl)carbamoyl-methylamino] pyrimidin-4-yl]amino]-5-(4-ethylpiperazin-1-yl)phenyl] prop-2-enamide), ICP-105, CPL304110, HMPL-453, and HGS1036.

Glutaminase Inhibitors

Provided herein is the method according to any one of embodiments 447-460, which further comprises simultaneous, separate, or sequential administration of an effective amount of a second compound, wherein the second compound is a glutaminase inhibitor.

Exemplary glutaminase inhibitors for use in the methods provided herein include, but are not limited to, telaglenastat, IPN60090, and OP 330.

IGF-1R Inhibitors

Provided herein is the method according to any one of embodiments 447-460, which further comprises simultaneous, separate, or sequential administration of an effective amount of a second compound, wherein the second compound is an IGF-1R inhibitor.

Exemplary IGF-1R inhibitors for use in the methods provided herein include, but are not limited to, cixutumumab, dalotuzumab, linsitinib, ganitumab, robatumumab, BMS-754807 ((2S)-1-[4-[(5-cyclopropyl-1H-pyrazol-3-yl) amino]pyrrolo[2,1-f][1,2,4]triazin-2-yl]-N-(6-fluoropyridin-3-yl)-2-methylpyrrolidine-2-carboxamide), KW-2450 (N-[5-[[4-(2-hydroxyacetyl)piperazin-1-yl]methyl]-2-[(E)-2-(1H-indazol-3-yl)ethenyl]phenyl]-3-methylthiophene-2-carboxamide), PL225B, AVE1642, and BIIB022.

KIF18A Inhibitors

Provided herein is the method according to any one of embodiments 447-460, which further comprises simultaneous, separate, or sequential administration of an effective amount of a second compound, wherein the second compound is a KIF18A inhibitor.

Exemplary KIF18A inhibitors for use in the methods provided herein include, but are not limited to, the inhibitors disclosed in US 2020/0239441, WO 2020/132649, WO 2020/132651, and WO 2020/132653, each of which is herewith incorporated by reference in its entirety.

MCL-1 Inhibitors

Provided herein is the method according to any one of embodiments 447-460, which further comprises simultaneous, separate, or sequential administration of an effective amount of a second compound, wherein the second compound is an MCL-1 inhibitor.

Exemplary MEK inhibitors for use in the methods provided herein include, but are not limited to, murizatoclax, tapotoclax, AZD 5991 ((3aR)-5-chloro-2,11,12,24,27,29-hexahydro-2,3,24,33-tetramethyl-22H-9,4,8-(metheniminomethyno)-14,20:26,23-dimetheno-10H,20H-pyrazolo[4,3-1][2,15,22,18,19]benzoxadithiadiazacyclohexacosine-32-carboxylic acid), MIK 665 ((αR)-α-[[(5S)-5-[3-Chloro-2-methyl-4-[2-(4-methyl-1-piperazinyl)ethoxy]phenyl]-6-(4-fluorophenyl)thieno[2,3-d]pyrimidin-4-yl]oxy]-2-[[2-(2-methoxyphenyl)-4-pyrimidinyl]methoxy]benzenepropanoic acid), and ABBV-467.

In one embodiment, the MCL-1 inhibitor is murizatoclax. In another embodiment, the MCL-1 inhibitor is tapotoclax.

MEK Inhibitors

Provided herein is the method according to any one of embodiments 447-460, which further comprises simultaneous, separate, or sequential administration of an effective amount of a second compound, wherein the second compound is MEK inhibitor.

Exemplary MEK inhibitors for use in the methods provided herein include, but are not limited to, trametinib, cobimetinib, selumetinib, pimasertib, refametinib, PD-325901 (N-[(2R)-2,3-dihydroxypropoxy]-3,4-difluoro-2-(2-fluoro-4-iodoanilino)benzamide), AZD8330 (2-(2-fluoro-4-iodoanilino)-N-(2-hydroxyethoxy)-1,5-dimethyl-6-oxopyridine-3-carboxamide), GDC-0623 (5-(2-fluoro-4-iodoanilino)-N-(2-hydroxyethoxy)imidazo[1,5-a]pyridine-6-carboxamide), RO4987655 (3,4-difluoro-2-(2-fluoro-4-iodoanilino)-N-(2-hydroxyethoxy)-5-[(3-oxooxazinan-2-yl) methyl]benzamide), TAK-733 (3-[(2R)-2,3-dihydroxypropyl]-6-fluoro-5-(2-fluoro-4-iodoanilino)-8-methylpyrido[2,3-d]pyrimidine-4,7-dione), PD0325901 (N-[(2R)-2,3-dihydroxypropoxy]-3,4-difluoro-2-(2-fluoro-4-iodoanilino)benzamide), CI-1040 (2-(2-chloro-4-iodophenylamino)-N-(cyclopropylmethoxy)-3,4-difluorobenzamide), PD318088 (5-bromo-N-(2,3-dihydroxypropoxy)-3,4-difluoro-2-(2-fluoro-4-iodophenylamino)benzamide), PD98059 (2-(2-amino-3-methoxyphenyl)-4H-chromen-4-one), PD334581 (N-[5-[3,4-Difluoro-2-[(2-fluoro-4-iodophenyl)amino]phenyl]-1,3,4-oxadiazol-2-yl]-4-morpholineethanamine), FCN-159, CS3006, HL-085, SHR 7390, and WX-554.

In one embodiment, the MEK inhibitor is trametinib.

mTOR Inhibitors

Provided herein is the method according to any one of embodiments 447-460, which further comprises simultaneous, separate, or sequential administration of an effective amount of a second compound, wherein the second compound is an mTOR inhibitor.

Exemplary mTOR inhibitors for use in the methods provided herein include, but are not limited to, everolimus, rapamycin, zotarolimus (ABT-578), ridaforolimus (deforolimus, MK-8669), sapanisertib, buparlisib, pictilisib, vistusertib, dactolisib, Torin-1 (1-(4-(4-propionylpiperazin-1-yl)-3-(trifluoromethyl)cyclohexyl)-9-(quinolin-3-yl)benzo[h][1,6]naphthyridin-2(1H)-one), GDC-0349 ((S)-1-ethyl-3-(4-(4-(3-methylmorpholino)-7-(oxetan-3-yl)-5,6,7,8-tetrahydropyrido[3,4-d]pyrimidin-2-yl)phenyl)urea), and VS-5584 (SB2343, (5-(8-methyl-2-rnorpholin-4-yl-9-propan-2-ylpurin-6-yl)pyrimidin-2-amine).

In one embodiment, the mTOR inhibitor is everolimus.

PD-1 Inhibitors

Provided herein is the method according to any one of embodiments 447-460, which further comprises simultaneous, separate, or sequential administration of an effective amount of a second compound, wherein the second compound is a PD-1 inhibitor.

Exemplary PD-1 inhibitors for use in the methods provided herein include, but are not limited to, pembrolizumab, nivolumab, cemiplimab, spartalizumab (PDR001), camrelizumab (SHR1210), sintilimab (IBI308), tislelizumab (BGB-A317), toripalimab (JS 001), dostarlimab (TSR-042, WBP-285), INCMGA00012 (MGA012), AMP-224, AMP-514, and the anti-PD-1 antibody as described in U.S. Pat. No. 10,640,504 B2 (the "Anti-PD-1 Antibody A," column 66, line 56 to column 67, line 24 and column 67, lines 54-57), which is incorporated herein by reference.

In one embodiment, the PD-1 inhibitor is pembrolizumab. In another embodiment the PD-1 inhibitor is the Anti-PD-1 Antibody A.

PD-L1 Inhibitors

Provided herein is the method according to any one of embodiments 447-460, which further comprises simultaneous, separate, or sequential administration of an effective amount of a second compound, wherein the second compound is a PD-L1 inhibitor.

Exemplary PD-L1 inhibitors for use in the methods provided herein include, but are not limited to, atezolizumab, avelumab, durvalumab, ZKAB001, TG-1501, SHR-1316, MSB2311, MDX-1105, KN035, IMC-001, HLX20, FAZ053, CS1001, CK-301, CBT-502, BGB-A333, BCD-135, and A167.

In one embodiment, the PD-L1 inhibitor is atezolizumab.

PI3K Inhibitors

Provided herein is the method according to any one of embodiments 447-460, which further comprises simultaneous, separate, or sequential administration of an effective amount of a second compound, wherein the second compound is a PI3K inhibitor.

Exemplary PI3K inhibitors for use in the methods provided herein include, but are not limited to, idelalisib, copanlisib, duvelisib, alpelisib, taselisib, perifosine, buparlisib, umbralisib, pictilisib, dactolisib, voxtalisib, sonolisib, tenalisib, serabelisib, acalisib, CUDC-907 (N-hydroxy-2-[[2-(6-methoxypyridin-3-yl)-4-morpholin-4-ylthieno[3,2-d]pyrimidin-6-yl]methyl-methylamino]pyrimidine-5-carboxamide), ME-401 (N-[2-methyl-1-[2-(1-methylpiperidin-4-yl)phenyl]propan-2-yl]-4-(2-methylsulfonylbenzimidazol-1-yl)-6-morpholin-4-yl-1,3,5-triazin-2-amine), IPI-549 (2-amino-N-[(1S)-1-[8-[2-(1-methylpyrazol-4-yl)ethynyl]-1-oxo-2-phenylisoquinolin-3-yl]ethyl]pyrazolo[1,5-a]pyrimidine-3-carboxamide), SF1126 ((2S)-2-[[(2S)-3-carboxy-2-[[2-[[(2S)-5-(diaminomethylideneamino)-2-[[4-oxo-4-[[4-(4-oxo-8-phenylchromen-2-yl)morpholin-4-ium-4-yl]methoxy]butanoyl]amino]pentanoyl]amino]acetyl]amino]propanoyl]amino]-3-hydroxypropanoate), XL147 (N-[3-(2,1,3-benzothiadiazol-5-ylamino)quinoxalin-2-yl]-4-methylbenzenesulfonamide), GSK1059615 ((5Z)-5-[(4-pyridin-4-ylquinolin-6-yl)methylidene]-1,3-thiazolidine-2,4-dione), and AMG 319 (N-[(1S)-1-(7-fluoro-2-pyridin-2-ylquinolin-3-yl)ethyl]-7H-purin-6-amine).

Raf Kinase Inhibitors

Provided herein is the method according to any one of embodiments 447-460, which further comprises simultaneous, separate, or sequential administration of an effective amount of a second compound, wherein the second compound is a Raf kinase inhibitor.

The term "RAF kinase" as used herein refers to a member of a mammalian serine/threonine kinases composed of three isoforms (C-Raf, B-Raf and A-Raf) and includes homodimers of each isoform as well as heterodimers between isoforms, e.g., C-Raf/B-Raf heterodimers.

The term "Raf kinase inhibitor" as used herein refers to a compound that is capable of negatively modulating or inhibiting all or a portion of the enzymatic activity of one or more member of the Raf family kinases, or is capable of disrupting Raf homodimer or heterodimer formation to inhibit activity.

In one embodiment, the Raf kinase inhibitor includes, but is not limited to, encorafenib, sorafenib, lifirafenib, vemurafenib, dabrafenib, PLX-8394 (N-(3-(5-(2-cyclopropylpyrimidin-5-yl)-3a,7a-dihydro-1H-pyrrolo[2,3-b]pyridine-3-carbonyl)-2,4-difluorophenyl)-3-fluoropyrrolidine-1-sulfonamide), Raf-709 (N-(2-methyl-5,-morpholino-6'-((tetrahydro-2H-pyran-4-yl)oxy)-[3,3'-bipyridin]-5-yl)-3-(trifluoromethyl)benzamide), LXH254 (N-(3-(2-(2-hydroxyethoxy)-6-morpholinopyridin-4-yl)-4-methylphenyl)-2-(trifluoromethyl)isonicotinamide), LY3009120 (1-(3,3-dimethylbutyl)-3-(2-fluoro-4-methyl-5-(7-methyl-2-(methylamino)pyrido[2,3-d]pyrimidin-6-yl)phenyl)urea), Tak-632 (N-(7-cyano-6-(4-fluoro-3-(2-(3-(trifluoromethyl)phenyl)acetamido)phenoxy)benzo[d]thiazol-2-yl)cyclopropanecarboxamide), CEP-32496 (1-(3-((6,7-dimethoxyquinazolin-4-yl)oxy)phenyl)-3-(5-(1,1,1-trifluoro-2-methylpropan-2-yl)isoxazol-3-yl)urea), CCT196969 (1-(3-(tert-butyl)-1-phenyl-1H-pyrazol-5-yl)-3-(2-fluoro-4-((3-oxo-3,4-dihydropyrido[2,3-b]pyrazin-8-yl)oxy)phenyl)urea), and RO5126766 (N-[3-fluoro-4-[[4-methyl-2-oxo-7-(2-pyrimidinyloxy)-2H-1-benzopyran-3-yl]methyl]-2-pyridinyl]-N'-methyl-sulfamide).

In one embodiment, the Raf kinase inhibitor is encorafenib. In one embodiment, the Raf kinase inhibitor is sorafenib. In one embodiment, the Raf kinase inhibitor is lifirafenib.

SHP2 Inhibitors

Provided herein is the method according to any one of embodiments 447-460, which further comprises simultaneous, separate, or sequential administration of an effective amount of a second compound, wherein the second compound is a SHP2 inhibitor.

Exemplary SHP2 inhibitors for use in the methods provided herein include, but are not limited to, SHP-099 (6-(4-amino-4-methylpiperidin-1-yl)-3-(2,3-dichlorophenyl)pyrazin-2-amine dihydrochloride), RMC-4550 ([3-[(3S,4S)-4-amino-3-methyl-2-oxa-8-azaspiro[4.5]decan-8-yl]-6-(2,3-dichlorophenyl)-5-methylpyrazin-2-yl]methanol), TNO155, (3S,4S)-8-[6-amino-5-(2-amino-3-chloropyridin-4-yl)sulfanylpyrazin-2-yl]-3-methyl-2-oxa-8-azaspiro[4.5]decan-4-amine), and vociprotafib (RMC4630—Revolution Medicine). In one embodiment, the SHP inhibitor for use in the methods provided herein is vociprotafib (Revolution Medicine).

In another embodiment, exemplary SHP2 inhibitors for use in the methods provided herein include, but are not limited to, 3-[(1R,3R)-1-amino-3-methoxy-8-azaspiro[4.5]dec-8-yl]-6-(2,3-dichlorophenyl)-5-methyl-2-pyrazinemethanol (CAS 2172651-08-8), 3-[(3S,4S)-4-amino-3-methyl-2-oxa-8-azaspiro[4.5]dec-8-yl]-6-[(2,3-dichlorophenyl)thio]-5-methyl-2-pyrazinemethanol (CAS 2172652-13-8), 3-[(3S,4S)-4-amino-3-methyl-2-oxa-8-azaspiro[4.5]dec-8-yl]-6-[[3-chloro-2-(3-hydroxy-1-azetidinyl)-4-pyridinyl]thio]-5-methyl-2-pyrazinemethanol (CAS 2172652-38-7), and 6-[(2-amino-3-chloro-4-pyridinyl)thio]-3-[(3S,4S)-4-amino-3-methyl-2-oxa-8-azaspiro[4.5]dec-8-yl]-5-methyl-2-pyrazinemethanol (CAS 2172652-48-9).

In another embodiment, exemplary SHP2 inhibitors for use in the methods provided herein include, but are not limited to, 1-[5-(2,3-dichlorophenyl)-6-methylimidazo[1,5-a]pyrazin-8-yl]-4-methyl-4-piperidinamine (CAS 2240981-75-1), (1R)-8-[5-(2,3-dichlorophenyl)-6-methylimidazo[1,5-a]pyrazin-8-yl]-8-azaspiro[4.5]decan-1-amine (CAS 2240981-78-4), (3S,4S)-8-[7-(2,3-dichlorophenyl)-6-methylpyrazolo[1,5-a]pyrazin-4-yl]-3-methyl-2-oxa-8-azaspiro[4.5]decan-4-amine (CAS 2240982-45-8), (3S,4S)-8-[7-[(2-amino-3-chloro-4-pyridinyl)thio]pyrazolo[1,5-a]pyrazin-4-yl]-3-methyl-2-oxa-8-azaspiro[4.5]decan-4-amine (CAS 2240982-57-2), 4-[(3S,4S)-4-amino-3-methyl-2-oxa-8-azaspiro[4.5]dec-8-yl]-7-(2,3-dichlorophenyl)-6-methylpyrazolo[1,5-a]pyrazine-2-methanol (CAS 2240982-69-6), 7-[(2-amino-3-chloro-4-pyridinyl)thio]-4-[(3S,4S)-4-amino-3-methyl-2-oxa-8-azaspiro[4.5]dec-8-yl]-6-methylpyrazolo[1,5-a]pyrazine-2-methanol (CAS 2240982-73-2), and (3S,4S)-8-[7-[(2-amino-3-chloro-4-pyridinyl)thio]-6-methylpyrazolo[1,5-a]pyrazin-4-yl]-3-methyl-2-oxa-8-azaspiro[4.5]decan-4-amine (CAS 2240982-77-6).

In one embodiment, the SHP inhibitor for use in the methods provided herein is (1R)-8-[5-(2,3-dichlorophenyl)-6-methylimidazo[1,5-a]pyrazin-8-yl]-8-azaspiro[4.5]decan-1-amine (CAS 2240981-78-4).

In another embodiment, exemplary SHP2 inhibitors for use in the methods provided herein include, but are not limited to 3-[(1R)-1-amino-8-azaspiro[4.5]dec-8-yl]-6-(2,3-dichlorophenyl)-5-hydroxy-2-pyridinemethanol (CAS 2238840-54-3), 3-[(1R)-1-amino-8-azaspiro[4.5]dec-8-yl]-6-[(2,3-dichlorophenyl)thio]-5-hydroxy-2-pyridinemethanol (CAS 2238840-56-5), 5-[(1R)-1-amino-8-azaspiro[4.5]dec-8-yl]-2-(2,3-dichlorophenyl)-3-pyridinol (CAS 2238840-58-7), 3-[(1R)-1-amino-8-azaspiro[4.5]dec-8-yl]-6-(2,3-dichlorophenyl)-5-methyl-2-pyridinemethanol (CAS 2238840-60-1), (1R)-8-[6-(2,3-dichlorophenyl)-5-methyl-3-pyridinyl]-8-azaspiro[4.5]decan-1-amine (CAS 2238840-62-3), 3-[(1R)-1-amino-8-azaspiro[4.5]dec-8-yl]-6-[(2,3-dichlorophenyl)thio]-5-methyl-2-pyridinemethanol (CAS 2238840-63-4), (1R)-8-[6-[(2,3-dichlorophenyl)thio]-5-methyl-3-pyridinyl]-8-azaspiro[4.5]decan-1-amine (CAS 2238840-64-5), 5-(4-amino-4-methyl-1-piperidinyl)-2-[(2,3-dichlorophenyl)thio]-3-pyridinol (CAS 2238840-65-6), 5-[(1R)-1-amino-8-azaspiro[4.5]dec-8-yl]-2-[(2,3-dichlorophenyl)thio]-3-pyridinol (CAS 2238840-66-7), 6-[(2-amino-3-chloro-4-pyridinyl)thio]-3-[(3S,4S)-4-amino-3-methyl-2-oxa-8-azaspiro[4.5]dec-8-yl]-5-hydroxy-2-pyridinemethanol (CAS 2238840-67-8), 3-(4-amino-4-methyl-1-piperidinyl)-6-(2,3-dichlorophenyl)-5-hydroxy-2-pyridinemethanol (CAS 2238840-68-9), 3-[(3S,4S)-4-amino-3-methyl-2-oxa-8-azaspiro[4.5]dec-8-yl]-6-(2,3-dichlorophenyl)-5-methyl-2-pyridinemethanol (CAS 2238840-69-0), 6-[(2-amino-3-chloro-4-pyridinyl)thio]-3-[(3S,4S)-4-amino-3-methyl-2-oxa-8-azaspiro[4.5]dec-8-yl]-5-methyl-2-pyridinemethanol (CAS 2238840-70-3), 3-(4-amino-4-methyl-1-piperidinyl)-6-(2,3-dichlorophenyl)-5-methyl-2-pyridinemethanol (CAS 2238840-71-4), 6-[(2-amino-3-chloro-4-pyridinyl)thio]-3-(4-amino-4-methyl-1-piperidinyl)-2-pyridinemethanol (CAS 2238840-72-5), 5-[(2-amino-3-chloro-4-pyridinyl)thio]-2-[(3S,4S)-4-amino-3-methyl-2-oxa-8-azaspiro[4.5]dec-8-yl]-6-methyl-3-pyridinemethanol (CAS 2238840-73-6), 2-[(3S,4S)-4-amino-3-methyl-2-oxa-8-azaspiro[4.5]dec-8-yl]-5-(2,3-dichlorophenyl)-6-methyl-3-pyridinemethanol (CAS 2238840-74-7), 3-[(3S,4S)-4-amino-3-methyl-2-oxa-8-azaspiro[4.5]dec-8-yl]-6-(2,3-dichlorophenyl)-5-hydroxy-2-pyridinemethanol (CAS 2238840-75-8), and 2-[(2-amino-3-chloro-4-pyridyl)sulfanyl]-5-[(3S,4S)-4-amino-3-methyl-2-oxa-8-azaspiro[4.5]decan-8-yl]-6-(hydroxymethyl)pyridin-3-ol.

In one embodiment, the SHP inhibitor for use in the methods provided herein is 3-[(1R)-1-amino-8-azaspiro[4.5]dec-8-yl]-6-[(2,3-dichlorophenyl)thio]-5-hydroxy-2-pyridinemethanol (CAS 2238840-56-5).

In one embodiment, the SHP2 inhibitor for use in the methods provided herein is an inhibitor disclosed in U.S. Pat. No. 10,590,090 B2, US 2020/017517 A1, US 2020/017511 A1, or WO 2019/075265 A1, each of which is herewith incorporated by reference in its entirety.

SOS1 Inhibitors

Provided herein is the method according to any one of embodiments 447-460, which further comprises simultaneous, separate, or sequential administration of an effective amount of a second compound, wherein the second compound is an SOS1 inhibitor.

Exemplary SOS1 inhibitors for use in the methods provided herein include, but are not limited to, BI 3406 (N-[(1R)-1-[3-amino-5-(trifluoromethyl)phenyl]ethyl]-7-methoxy-2-methyl-6-[(3S)-oxolan-3-yl]oxyquinazolin-4-amine), and BI 1701963.

Src Kinase Inhibitors

Provided herein is the method according to any one of embodiments 447-460, which further comprises simultaneous, separate, or sequential administration of an effective amount of a second compound, wherein the second compound is a Src kinase inhibitor.

The term "Src kinase" as used herein refers to a member of a mammalian nonreceptor tyrosine kinase family including: Src, Yes, Fyn, and Fgr (SrcA subfamily); Lck, Hck, Blk, and Lyn (SrcB subfamily), and Frk subfamily.

The term "Src kinase inhibitor" as used herein refers to a compound that is capable of negatively modulating or inhibiting all or a portion of the enzymatic activity of one or more member of the Src kinases.

Exemplary Src kinase inhibitors for use in the methods provided herein include, but are not limited to, dasatinib, ponatinib, vandetanib, bosutinib, saracatinib, KX2-391 (N-benzyl-2-(5-(4-(2-morpholinoethoxy)phenyl)pyridin-2-yl)acetamide), SU6656 ((Z)—N,N-dimethyl-2-oxo-3-((4,5,6,7-tetrahydro-1H-indol-2-yl)methylene)indoline-5-sulfonamide), PP 1 (1-(tert-butyl)-3-(p-tolyl)-1H-pyrazolo[3,4-d]pyrimidin-4-amine), WH-4-023 (2,6-dimethylphenyl(2,4-dimethoxyphenyl)(2-((4-(4-methylpiperazin-1-yl)phenyl)amino)pyrimidin-4-yl)carbamate), and KX-01 (N-benzyl-2-(5-(4-(2-morpholinoethoxy)phenyl)pyridin-2-yl)acetamide).

In one embodiment, the Src kinase inhibitor is dasatinib. In one embodiment, the Src kinase inhibitor is saracatinib. In one embodiment, the Src kinase inhibitor is ponatinib. In one embodiment, the Src kinase inhibitor is vandetanib. In one embodiment, the Src kinase inhibitor is KX-01.

Chemotherapeutic Agents

Provided herein is the method according to any one of embodiments 447-460, which further comprises simultaneous, separate, or sequential administration of an effective amount of a second compound, wherein the second compound is one or more chemotherapeutic agent.

Exemplary chemotherapeutic agents for use in the methods provided herein include, but are not limited to, leucovorin calcium (calcium folinate), 5-fluorouracil, irinotecan, oxaliplatin, cisplatin, carboplatin, pemetrexed, docetaxel, paclitaxel, gemcitabine, vinorelbine, chlorambucil, cyclophosphamide, and methotrexate.

Definitions

The following definitions are provided to assist in understanding the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds, including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixture of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated. A bond drawn with a wavy line indicates that both stereoisomers are encompassed. This is not to be confused with a wavy line drawn perpendicular to a bond which indicates the point of attachment of a group to the rest of the molecule.

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of other enantiomers or diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. Further, this disclosure encompasses pharmaceutical compositions comprising mixtures of any of the compounds disclosed herein and one or more other active agents disclosed herein. See, for example, Jacques et al., Enantiomers, Racemates and Resolutions (Wiley-Interscience, New York, 1981); Wilen et al., Tetrahedron 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, IN, 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula I, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. Substitution with isotopes such as deuterium ($^{2}H$ or D) may afford certain therapeutic advantages resulting from greater metabolic stability, for example, increased in vivo half-life or reduced dosage requirements, and hence may be advantageous in some circumstances. Substitution with positron emitting isotopes, such as $^{11}C$, $^{18}F$, O and $^{13}N$, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagent in place of the non-labelled reagent previously employed.

Solvates

As discussed above, the compounds disclosed herein and the stereoisomers, tautomers, and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Miscellaneous Definitions

This section will define additional terms used to describe the scope of the compounds, compositions and uses disclosed herein.

The term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl, each of which may optionally be substituted with 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S— nitro, cyano, carboxy, alkyl-O—C(O)—, carbamoyl, alkyl-S(O)—, sulfonyl, sulfonamido, phenyl, and heterocycloalkyl.

The term "alkyl" refers to a saturated straight chain hydrocarbon or saturated branched chain hydrocarbon containing the indicated number of carbon atoms. For example, C3alkyl means an alkyl group that has 3 carbon atoms (e.g., n-propyl or isopropyl). For example, a $C_{1-6}$alkyl refers to an alkyl group having 1 to 6 carbon atoms. Where a range is indicated, all members of that range and all subgroups within that range are envisioned. For example, a $C_{1-6}$alkyl includes alkyl groups having 1, 2, 3, 4, 5, or 6 carbon atoms (or any combination of the foregoing), as well as all subgroups in the indicated range (e.g., 1-2, 1-3, 1-4, 1-5, 1-6, 2-3, 2-4, 2-5, 2-6, 3-4, 3-5, 3-6, 4-5, 4-6, or 5-6 carbon atoms, or any combination of the foregoing ranges)). A "$C_{1-4}$ alkyl" includes, for example, methyl, ethyl, n-propyl, isopropyl, n-butyl, isobutyl, sec-butyl, or t-butyl. Nonlimiting examples of alkyl groups include methyl, ethyl, n-propyl, isopropyl, n-butyl, sec-butyl, isobutyl, tert-butyl, n-pentyl, and n-hexyl.

The term alkylene (for example, "$C_{1-4}$alkylene" and "$C_{1-6}$alkylene") refers to a straight or branched divalent alkyl group as defined herein containing the indicated number of carbon atoms (for example, 1 to 4, or 1 to 6 carbon atoms). Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene and the like.

The term "alkenyl" refers to a straight or branched chain hydrocarbon containing the indicated number of carbon atoms and having one or more carbon-carbon double bonds. For example, $C_3$alkenyl means the alkenyl group has 3 carbon atoms (e.g., 1-propenyl or 2-propenyl). For example, a $C_{2-6}$alkenyl refers to an alkenyl group having 2 to 6 carbon atoms. Where a range is indicated, all members of that range and all subgroups within that range are envisioned. For example, a $C_{2-6}$alkenyl includes alkenyl groups having 2, 3, 4, 5, or 6 carbon atoms (or any combination of the foregoing), as well as all subgroups in the indicated range (e.g., 2-3, 2-4, 2-5, 2-6, 3-4, 3-5, 3-6, 4-5, 4-6, or 5-6 carbon atoms, or any combination of the foregoing ranges). A $C_{2-4}$alkenyl includes, for example, ethenyl, 1-propenyl, 2-propenyl, isopropenyl, 1-butenyl, 2-butenyl, or 3-butenyl. Non-limiting examples of alkenyl groups include ethenyl (vinyl), 1-propenyl, 2-propenyl (allyl), isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

The term "alkynyl" refers to a straight or branched chain hydrocarbon containing the indicated number of carbon atoms and having one or more carbon-carbon triple bonds. For example, $C_3$alkynyl means the alkynyl group has 3 carbon atoms. For example, a $C_{2-6}$alkynyl refers to an alkynyl group having 2 to 6 carbon atoms. Where a range is indicated, all members of that range and all subgroups within that range are envisioned. For example, a $C_{2-6}$alkynyl includes any alkynyl groups having 2, 3, 4, 5, or 6 carbon atoms (or any combination of the foregoing), as well as all subgroups in the indicated range (e.g., 2-3, 2-4, 2-5, 2-6, 3-4, 3-5, 3-6, 4-5, 4-6, or 5-6 carbon atoms, or any combination of the foregoing ranges). For illustration, $C_{2-4}$alkynyl includes, for example, ethynyl, 1-propynyl, 2-propynyl, 1-butynyl, 2-butynyl, or 3-butynyl. Nonlimiting examples of alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

The terms "alkoxy" and "alkoxyl" are interchangeable and refer to an —O-alkyl group, where the alkyl group is as defined elsewhere herein. For example, a $C_3$alkoxy group means the alkoxy group has 3 carbon atoms (e.g., $OCH_2CH_2CH_3$). Where a range is indicated, all members of that range and all subgroups within that range are envisioned. For example, a $C_{1-6}$alkoxy includes alkoxy groups having 2, 3, 4, 5, or 6 carbon atoms, or any combination of the foregoing, as well as all subgroups in the indicated range (e.g., 2-3, 2-4, 2-5, 2-6, 3-4, 3-5, 3-6, 4-5, 4-6, and 5-6 carbon atoms, or any combination of the foregoing). Non-limiting examples of alkoxy groups include methoxy, ethoxy, n-propoxy, 1-methylethyloxy (iso-propoxy), n-butoxy, isobutoxy, sec-butoxy, and tert-butoxy.

The term "cycloalkyl" refers to a saturated carbocyclic molecule containing the indicated number of carbon atoms. The term "$C_{3-8}$ cycloalkyl" or "$C_{3-7}$ cycloalkyl" as used herein refers to a saturated carbocyclic molecule wherein the cyclic framework has 3 to 8 carbons or 3 to 7 carbons. Representative examples of $C_{3-8}$cycloalkyl include, but are not limited to, cyclopropyl and cyclobutyl.

The term cycloalkylene (for example, "$C_{3-7}$ cycloalkylene") refers to a saturated carbocyclic divalent group as defined herein containing the indicated number of carbon atoms (for example, 3 to 7 carbon atoms). Representative examples of cycloalkylene include, but are not limited to, cyclopropylene, cyclobutylene, cyclopentylene, cyclohexylene and the like.

The term "cyano" refers to a —CN group.

The term "deutero" as used herein as a prefix to another term for a chemical group refers to a modification of the chemical group, wherein one or more hydrogen atoms are substituted with deuterium ("D" or "$^2$H"). For example, the term "$C_{1-4}$deuteroalkyl" refers to a $C_{1-4}$alkyl as defined herein, wherein one or more hydrogen atoms are substituted with D. Representative examples of $C_{1-4}$deuteroalkyl include, but are not limited to, $—CH_2D$, $—CHD_2$, $—CD_3$, $—CH_2CD_3$, $—CDHCD_3$, $—CD_2CD_3$, $—CH(CD_3)_2$, $—CD(CHD_2)_2$, and $—CH(CH_2D)(CD_3)$.

The term "halogen" as used herein refers to —F, —Cl, —Br, or —I.

The term "halo" as used herein as a prefix to another term for a chemical group refers to a modification of the chemical group, wherein one or more hydrogen atoms are substituted with a halogen as defined herein. The halogen is independently selected at each occurrence. For example, the term "$C_{1-4}$haloalkyl" refers to a $C_{1-4}$alkyl as defined herein, wherein one or more hydrogen atoms are substituted with a halogen. Representative examples of $C_{1-4}$haloalkyl include, but are not limited to, $—CH_2F$, $—CHF_2$, $—CF_3$, $—CHFCl$, $—CH_2CF_3$, $—CFHCF_3$, $—CF_2CF_3$, $—CH(CF_3)_2$, $—CF(CHF_2)_2$, and $—CH(CH_2F)(CF_3)$.

The term "haloalkyl" refers to an alkyl group in which one or more of the hydrogen atoms is replaced by a halogen. The halogen is independently selected at each occurrence. The term includes, for example, monohaloalkyl (e.g., $CH_2F$, $CH(CH_2F)CH_3$) dihaloalkyl (e.g., $CHF_2$, $CH(CHF_2)CH_3$), trihaloalkyl (e.g., $CF_3$, $CH(CF_3)CH_3$), and polyhaloalkyl (e.g., $CF(CF_3)CH_3$). A haloalkyl group may or may not be perhalogenated (e.g., perfluorinated, such as $CF(CF_3)CF_3$). For example, the term "$C_{1-4}$haloalkyl" refers to a $C_{1-4}$alkyl, wherein one or more hydrogen atoms is substituted with a halogen. For illustration, $C_{1-4}$haloalkyl includes, for example, $CH_2F$, $CHF_2$, $CF_3$, $CHFCl$, $CH_2CF_3$, $CFHCF_3$, $CF_2CF_3$, $CH(CF_3)_2$, $CF(CHF_2)_2$, $CH(CH_2F)(CF_3)$, $CH_2Cl$, $CHC_{1-2}$, $CCl_3$, $CHFCl$, $CH_2CCl_3$, $CClHCCl_3$, $CCl_2CCl_3$, $CH(CCl_3)_2$, $CCl(CHCl_2)_2$, $CH(CH_2Cl)CCl_3$, and $CH_2CF(CH_3)_2$.

The term haloalkylene refers to a divalent haloalkyl group in which one or more of the hydrogen atoms is replaced by a halogen (for example, "$C_{1-4}$ haloalkylene" and "$C_{1-6}$ haloalkylene"). Representative examples of haloalkylene include, but are not limited to —CHF—, —$CF_2$—, —CHCl—, —$CH_2CF_2$—, —$CF_2CF_2$—, —CHCl—, —$CCl_2$—, —CFCl— and the like.

The terms "haloalkoxy" and "haloalkoxyl" are interchangeable and refer to an alkoxy group in which one or more of the hydrogen atoms is replaced by a halogen. The halogen is independently selected at each occurrence. The term includes monohaloalkoxy (e.g., $OCH_2F$, $OCH(CH_2F)CH_3$) dihaloalkoxy (e.g., $OCHF_2$, $OCH(CHF_2)CH_3$), trihaloalkoxy (e.g., $OCF_3$, $OCH(CF_3)CH_3$), and polyhaloalkoxy (e.g., $OCF(CF_3)CH_3$). A haloalkoxy group may or may not be perhalogenated (e.g., perfluorinated, such as $OCF(CF_3)CF_3$). For example, the term "$C_{1-4}$haloalkoxy" refers to a $C_{1-4}$alkoxy as defined herein, wherein one or more hydrogen atoms is substituted with a halogen. Representative examples of $C_{1-4}$haloalkoxy include $OCH_2F$, $OCHF_2$, $OCF_3$, $OCHFCl$, $OCH_2CF_3$, $OCFHCF_3$, $OCF_2CF_3$, $OCH(CF_3)_2$, $OCF(CHF_2)_2$, $OCH(CH_2F)(CF_3)$, $OCH_2Cl$, $OCHCl_2$, $OCF_3$, $OCHFCl$, $OCH_2CCl_3$, $OCClHCCl_3$, $OCCl_2CCl_3$, $OCH(CCl_3)_2$, $OCCl(CHCl_2)_2$, $OCH(CH_2Cl)CCl_3$, and $OCH_2CF(CH_3)_2$.

As used herein, the term "heteroaryl" refers to a 5-20 membered monocyclic- or bicyclic- or tricyclic-aromatic ring system, having 1 to 8 heteroatoms selected from N, O and S. In certain preferred aspects, the heteroaryl is a 5-10 membered ring system (e.g., 5-7 membered monocycle, an 8-10 membered bicycle or a 11-14 membered tricycle) or a 5-7 membered ring system. Exemplary monocyclic heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, and 5-pyrimidinyl. Exemplary bicyclic heteroaryl groups include 1-, 3-, 4-, 5-, 6-, 7-, or 8-isoquinolinyl, 2-, 3-, 4-, 5-, 6-, 7-, or 8-quinolinyl, 1-, 3-, 4-, 5-, 6-, 7-, or 8-isoquinolinyl, 1-, 2-, 4-, 5-, 6-, 7-, or 8-benzimidazolyl and 1-, 2-, 3-, 4-, 5-, 6- or 7-indolyl.

The term "heteroaryl" also refers to a group in which a heteroaromatic ring is fused to one or more aryl, cycloaliphatic, or heterocycloalkyl rings.

As used herein, the term "heterocycloalkyl" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocycloalkyl can include fused or bridged rings as well as spirocyclic rings. For example, a heterocycloalkyl group having 5 total atoms and 2 heteroatoms independently selected from N, O, and S, refers to a ring having 3 carbon atoms and 2 heteroatoms, wherein each heteroatom of the ring independently is N, O, or S. Where a range is indicated, all members of that range and all subgroups within that range are envisioned. For example, a heterocycloalkyl group having 5-7 total ring atoms and 1-3 heteroatoms independently selected from N, O, and S includes rings having 5, 6, or 7 total atoms, or any combination of the foregoing, as well as all subgroups in the indicated range (e.g., 5-6 or 6-7 total ring atoms, or any combination of the foregoing), wherein 1, 2, or 3 of the atoms in the ring are heteroatoms and each heteroatom independently is selected from N, O, and S. Thus, a heterocycloalkyl having 5-7 total ring atoms and 1-3 heteroatoms independently selected from N, O, and S encompasses rings containing, for example, 4 carbon atoms and 1 heteroatom, 3 carbon atoms and 2 heteroatoms, 2 carbon atoms and 3 heteroatoms, 5 carbon atoms and 1 heteroatom, 4 carbon atoms and 2 heteroatoms, 3 carbon atoms and 3 heteroatoms, 6 carbon atoms and 1 heteroatom, 5 carbon atoms and 2 heteroatoms, and 4 carbon atoms and 3 heteroatoms, wherein each heteroatom of the foregoing is independently selected from N, O, and S. Nonlimiting examples of heterocycloalkyl groups include but are not limited to aziridinyl, oxiranyl, thiiranyl, azetidinyl, oxetanyl, thietanyl, pyrrolidinyl, tetrahydrofuranyl, tetrahydrothiophene-yl, pyrazolidinyl, imidazolidinyl, isoxazolidinyl, oxazolidinyl, isothiazolidinyl, thiazolidinyl, oxathiolidinyl, piperidinyl, tetrahydropyranyl, tetrahydrothiopyranyl, piperazinyl, dioxanyl, dithianyl, morpholinyl, thiomorpholinyl, azepanyl, hexahydro-1H-pyrrolizinyl and 1,4-diazepanyl.

The terms "hydroxy" and "hydroxyl" are interchangeable and refer to a —OH group.

The term "hydroxyatkyl" or "hydroxylalkyl" refers to a saturated straight chain alkyl or saturated branched chain alkyl containing the indicated number of carbon atoms substituted with one or two hydroxy groups in place of a hydrogen, provided that if two hydroxy groups are present they are not both on the same carbon atom. Nonlimiting examples hydroxyalkyl include but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethiv, 2,3-dihydroxybutyl 3,4-dihydroxybutyl and the like.

The term "hydroxyalkylene" or "hydroxylalkylene" refers to a saturated straight chain alkylene or saturated branched chain alkylene containing the indicated number of carbon atoms substituted with one or two hydroxy groups in place of a hydrogen, provided that if two hydroxy groups are present they are not both on the same carbon atom. Nonlimiting examples hydroxyalkylene include but are not limited to, hydroxymethylene, 2-hydroxyethylene, 2-hydroxypropylene, 3-hydroxypropylene, 1-(hydroxyrnethyl)-2-methylpropylene, 2-hydroxybutylene, 3-hydroxybutylene, 4-hydroxybutylene, 2,3-dihydroxypropylene, 1-(hydroxyrnethyl)-2-hydroxyethylene, 2,3-dihydroxybutylene, 3,4-dihydroxybutylene and the like.

The term "oxo" refers to a substituent oxygen atom connected to another atom by a double bond (e.g., =O). For example, an oxo substituent on a cyclopentyl ring can be depicted as:

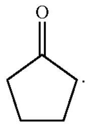

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, 2nd Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. Any variables used in the following schemes are the variables as defined for Formula I, unless otherwise noted. All starting materials are either commercially available, for example, from Merck Sigma-Aldrich Inc., Fluorochem Ltd, and Enamine Ltd. or known in the art and may be synthesized by employing known procedures using ordinary skill. Starting material may also be synthesized via the procedures disclosed herein. Suitable reaction conditions, such as, solvent, reaction temperature, and reagents, for the Schemes discussed in this section, may be found in the examples provided herein.

Scheme I

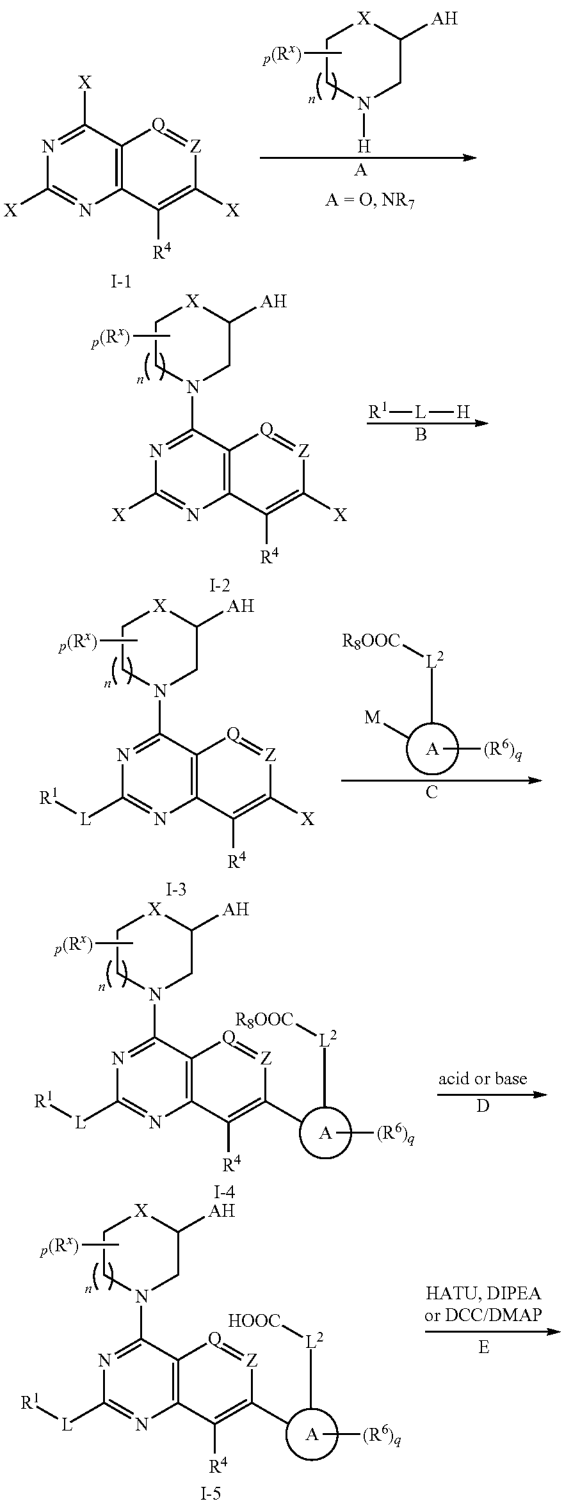

I-1
I-2
I-3
I-4
I-5

-continued

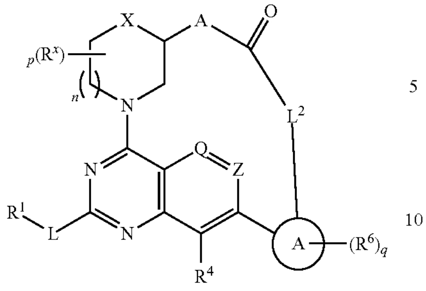

I

Compounds of Formula (I) can be prepared according to Scheme I. In step A, compound (I-1) undergoes $S_NAr$ reaction with an optionally substituted cyclic amine or aliphatic amine bearing an alcohol or protected amine in a solvent such as acetonitrile and in the presence of a base such as Hunig's base to give compound (I-2). In step B, compound (I-2) undergoes $S_NAr$ reaction with a nucleophile having the formula $R^1$-L-H in a solvent such as acetonitrile, in the presence of a base such as Hunig's base to give compound (I-3). In step C, compound (I-3) is coupled with an organometallic reagent or a boronic acid (ester) attached to a aryl or hetereoaryl bearing an terminal ester group to give compound (I-4). This coupling reaction proceeds in a solvent or mixture of solvents such as THF and water, and a catalyst such as cataCXium A Pd G3, with or without a base such as potassium phosphate. In step D, compound (I-4) is saponified to give compound (I-5). This reaction proceeds in TFA in solvent such as DCM or in LiOH in a mixture of solvents such as THF and water. In step E, compound (I-5) is cyclized under conditions such as HATU and DIPEA or DCC/DMAP in a solvent such as DMF or dichloromethane to give compounds of Formula (I).

Scheme II

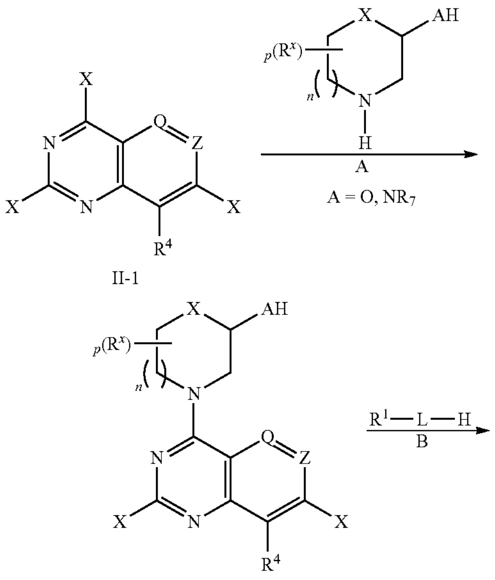

II-1

II-2

-continued

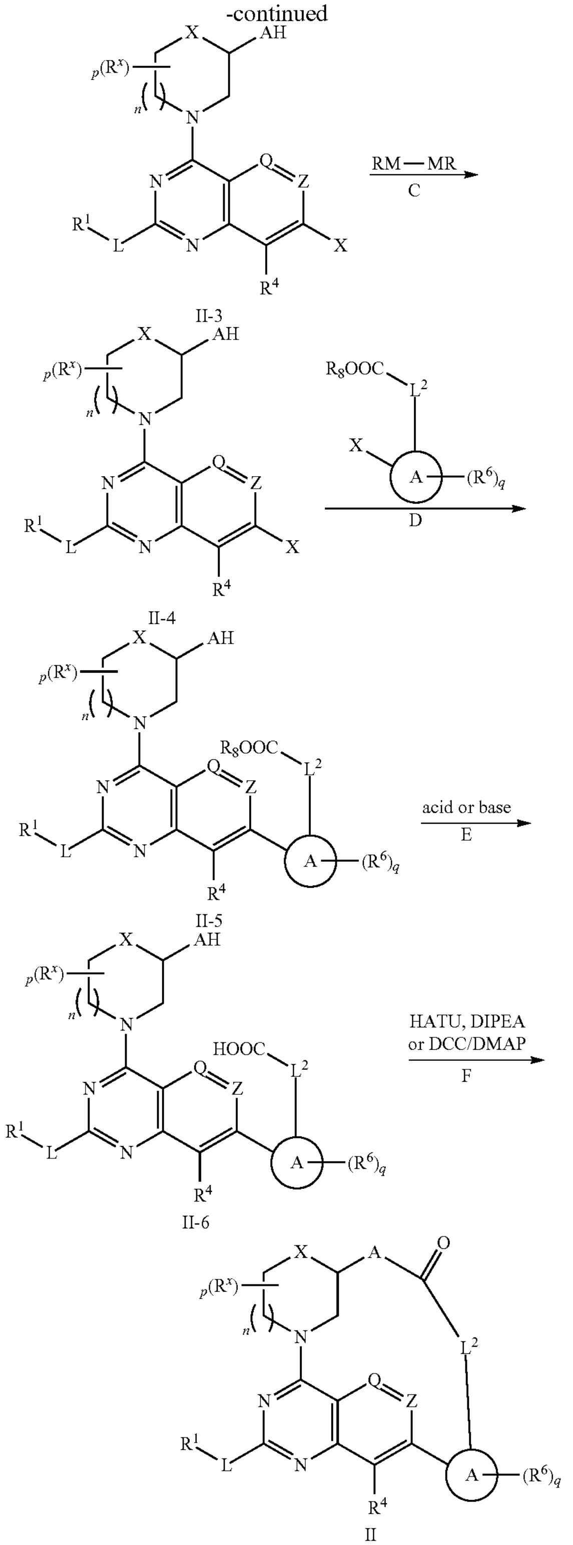

II-3

II-4

II-5

II-6

II

Compounds of Formula (II) can also be prepared according to Scheme II. In step A, compound (II-1) undergoes $S_NAr$ reaction with an optionally substituted cyclic amine or aliphatic amine bearing an alcohol or protected amine in a solvent such as acetonitrile and in the presence of a base such as Hunig's base to give compound (II-2). In step B, compound (II-2) undergoes $S_NAr$ reaction with a nucleophile having the formula $R^1$-L-H in a solvent such as acetonitrile, in the presence of a base such as Hunig's base to give compound (II-3). In step C, compound (II-3) is coupled with an organometallic reagent such as bis(tributyltin) to give compound (II-4). This coupling reaction proceeds in a solvent such as 1,4-dioxane, and a catalyst such as chloro[(tricyclohexylphosphine)-2-(2'-aminobiphenyl)] palladium(II), with or without additive such as lithium chloride. In step D, compound (11-4) is coupled with an organometallic reagent or a boronic acid (ester) attached to a aryl or hetereoaryl bearing an terminal ester group to give compound (II-5). This coupling reaction proceeds in a solvent or mixture of solvents such as THF and water, and a catalyst such as cataCXium A Pd G3, with or without a base such as potassium phosphate. In step E, compound (II-5) is saponified to give compound (II-6). This reaction proceeds in TFA in solvent such as DCM or in LiOH in a mixture of solvents such as THF and water. In step F, compound (II-6) is cyclized under conditions such as HATU and DIPEA or DCC/DMAP in a solvent such as DMF or dichloromethane to give compounds of Formula (II).

Scheme III

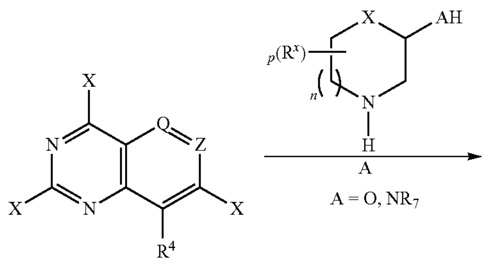

III-1

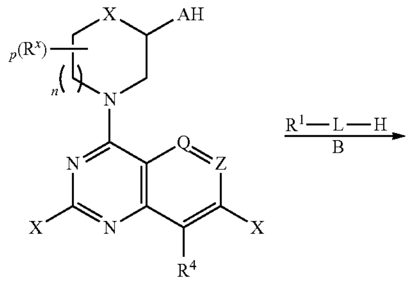

III-2

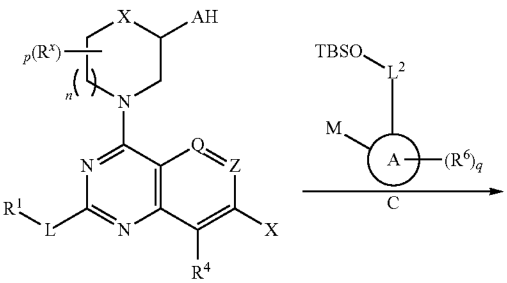

III-3

-continued

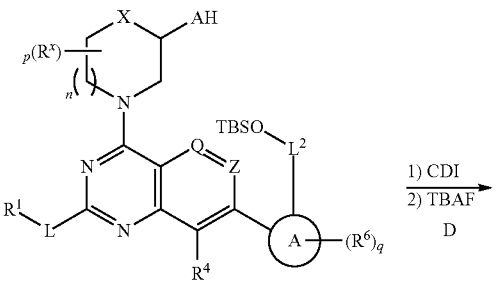

III-4

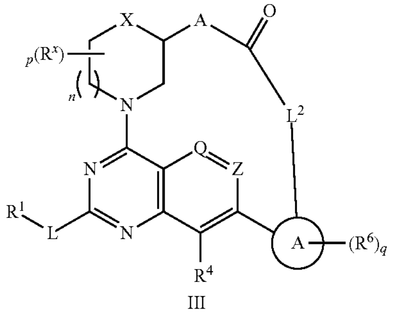

III

Compounds of Formula (III) can also be prepared according to Scheme III. In step A, compound (III-1) undergoes $S_NAr$ reaction with an optionally substituted cyclic amine or aliphatic amine bearing an alcohol or protected amine in a solvent such as acetonitrile and in the presence of a base such as Hunig's base to give compound (III-2). In step B, compound (III-2) undergoes $S_NAr$ reaction with a nucleophile having the formula $R^1$-L-H in a solvent such as acetonitrile, in the presence of a base such as Hunig's base to give compound (III-3). In step C, compound (III-3) is coupled with an organometallic reagent or a boronic acid (ester) attached to a aryl or hetereoaryl bearing a terminal TBS protected alcohol to give compound (III-4). This coupling reaction proceeds in a solvent or mixture of solvents such as THF and water, and a catalyst such as cataCXium A Pd G3, with or without a base such as potassium phosphate. In step D, compound (III-4) is reacted with CDI, followed by treated with a desilyated regent such as TBAF in solvent such as THF to give compounds of Formula (III).

Scheme IV

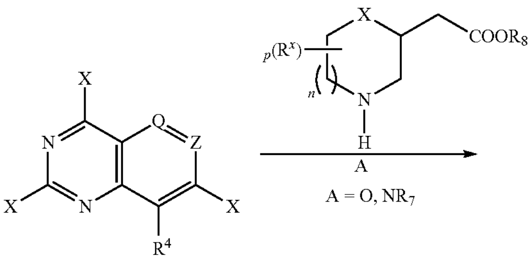

IV-1

-continued

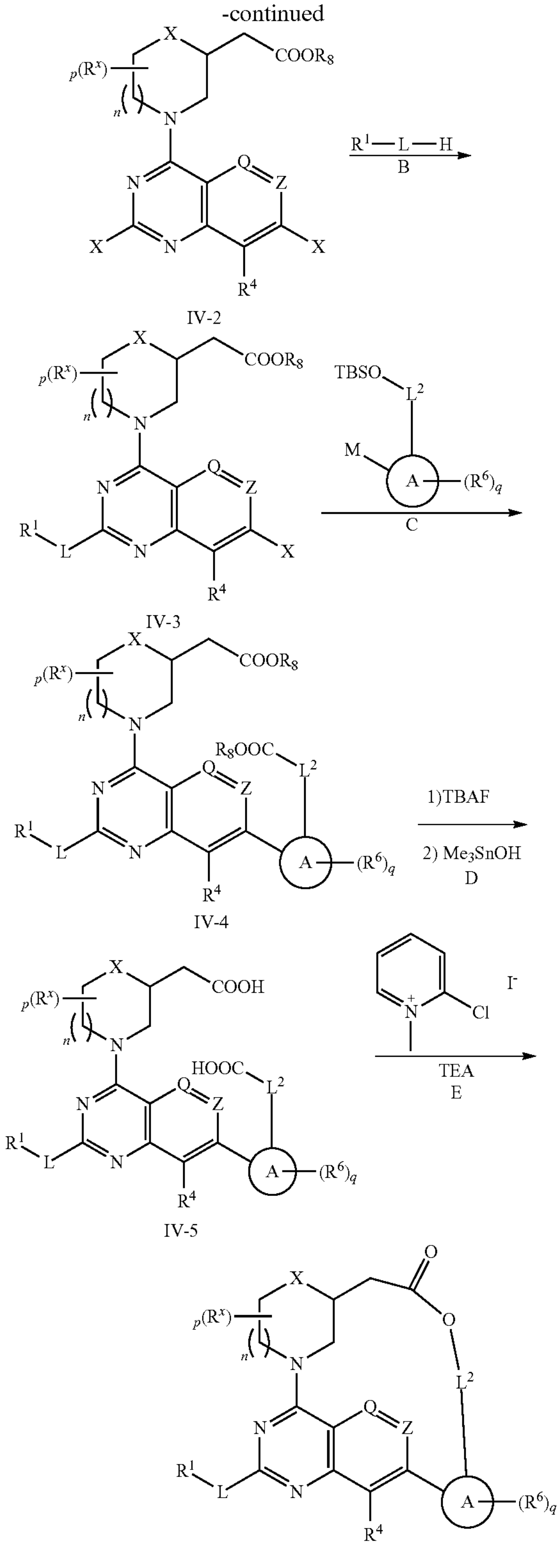

IV-2

IV-3

IV-4

IV-5

IV

Compounds of Formula (IV) can also be prepared according to Scheme IV. In step A, compound (IV-1) undergoes $S_NAr$ reaction with an optionally substituted cyclic amine or aliphatic amine bearing a terminal ester group in a solvent such as acetonitrile and in the presence of a base such as Hunig's base to give compound (IV-2). In step B, compound (IV-2) undergoes $S_NAr$ reaction with a nucleophile having the formula $R^1$-L-H in a solvent such as acetonitrile, in the presence of a base such as Hunig's base to give compound (IV-3). In step C, compound (IV-3) is coupled with an organometallic reagent or a boronic acid (ester) attached to a aryl or hetereoaryl bearing an terminal TBS protected alcohol to give compound (IV-4). This coupling reaction proceeds in a solvent or mixture of solvents such as THF and water, and a catalyst such as cataCXium A Pd G3, with or without a base such as potassium phosphate. In step D, compound (IV-4) is treated with a desilyated reagent such as TBAF in a solvent such as THF, followed by saponification using reagent such as $Me_3SnOH$ in a solvent such as DCE to give compound (IV-5). In step E, compound (IV-5) is cyclized using reagent such as 2-chloro-1-methylpyridinium iodide in a solvent such as DCE in the presence of a base such as TEA to give compounds of Formula (IV).

Scheme V

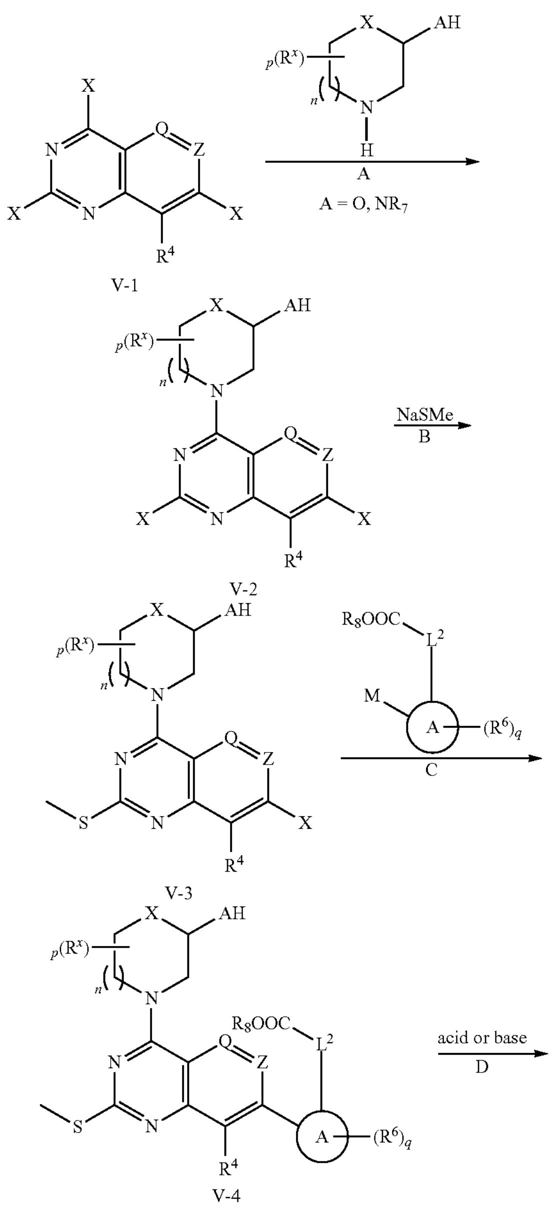

V-1

V-2

V-3

V-4

-continued

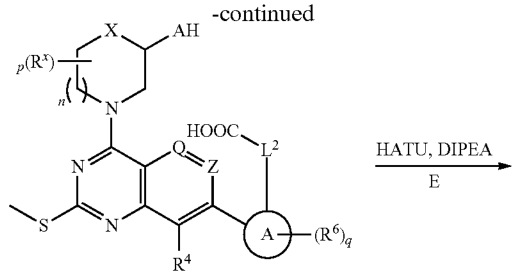

V-5

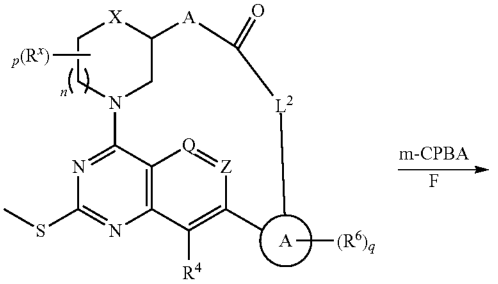

V-6

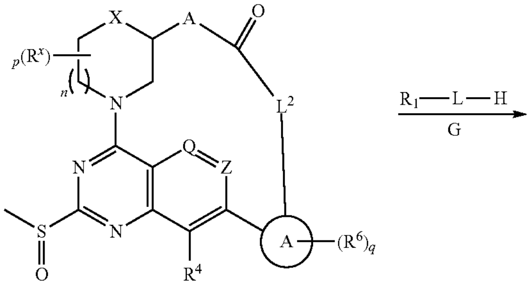

V-7

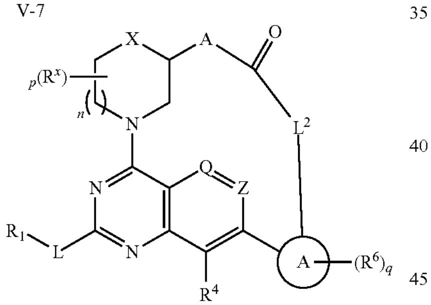

V

Compounds of Formula (V) can also be prepared according to Scheme V. In step A, compound (V-1) undergoes $S_NAr$ reaction with an optionally substituted cyclic amine or aliphatic amine bearing an alcohol or protected amine in a solvent such as acetonitrile and in the presence of a base such as Hunig's base to give compound (V-2). In step B, compound (V-2) undergoes $S_NAr$ reaction with a nucleophile such as sodium methanethiolate in a solvent such as THF, to give compound (V-3). In step C, compound (V-3) is coupled with an organometallic reagent or a boronic acid (ester) attached to a aryl or hetereoaryl bearing an terminal ester group to give compound (V-4). This coupling reaction proceeds in a solvent or mixture of solvents such as THF and water, and a catalyst such as cataCXium A Pd G3, with or without a base such as potassium phosphate. In step D, compound (V-4) is saponified to give compound (V-5). This reaction proceeds in TFA in solvent such as DCM or in LiOH in a mixture of solvents such as THF and water. In step E, compound (V-5) is cyclized under conditions such as HATU and DIPEA or DCC/DMAP in a solvent such as DMF or dichloromethane to give compound (V-6). In step F, compound (V-6) is oxidized using reagent such as m-CPBA in a solvent such as DCM to give compound (V-7). In step G, compound (V-7) undergoes $S_NAr$ reaction with a nucleophile having the formula $R^1$-L-H in a solvent such as acetonitrile and in the presence of a base such as Hunig's base to give compounds of Formula (V).

Scheme VI

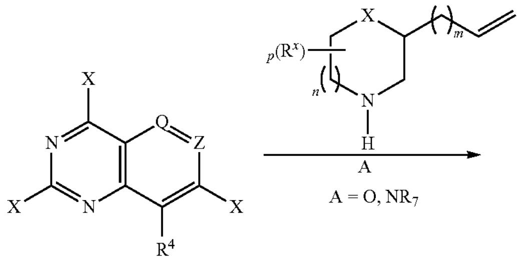

VI-1

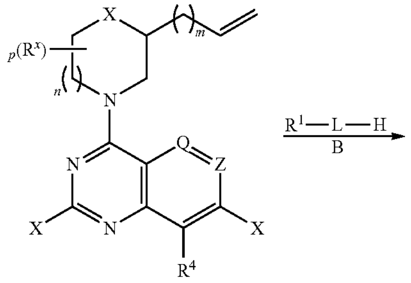

VI-2

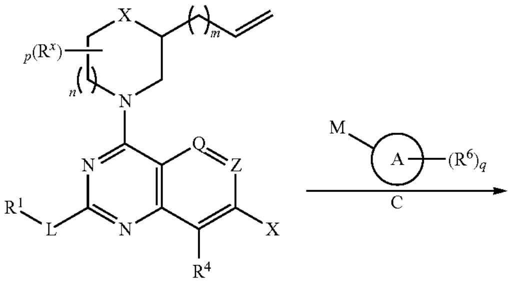

VI-3

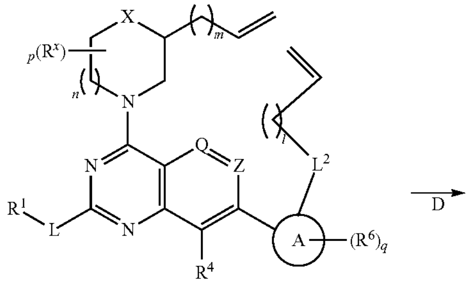

VI-4

-continued

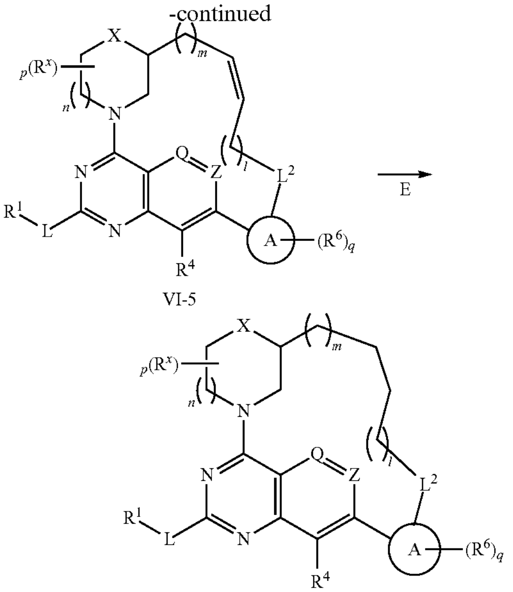

VI-5

VI

Compounds of Formula (VI) can also be prepared according to Scheme VI. In step A, compound (VI-1) undergoes $S_NAr$ reaction with an optionally substituted cyclic amine or aliphatic amine bearing an terminal alkene in a solvent such as acetonitrile and in the presence of a base such as Hunig's base to give compound (VI-2). In step B, compound (VI-2) undergoes $S_NAr$ reaction with a nucleophile having the formula $R^1$-L-H in a solvent such as acetonitrile, in the presence of a base such as Hunig's base to give compound (VI-3). In step C, compound (VI-3) is coupled with an organometallic reagent or a boronic acid (ester) attached to a aryl or hetereoaryl bearing an terminal alkene to give compound (VI-4). This coupling reaction proceeds in a solvent or mixture of solvents such as THF and water, and a catalyst such as cataCXium A Pd G3, with or without a base such as potassium phosphate. In step D, compound (VI-4) undergoes ring closure metathesis to give compound (VI-5). This reaction proceeds with Hoveyda-Grubbs $2^{nd}$ generation catalyst in a solvent such as DCE and in the presence of an acid such as TsOH. In step E, compound (VI-5) is hydrogenated under conditions such as Pd on carbon in hydrogen atmosphere in a solvent such as ethanol to give compounds of Formula (VI).

EXAMPLES

This section provides specific examples of compounds of Formula I and methods of making the same.

List of Abbreviations

TABLE 7

| | |
|---|---|
| Ac | acetyl |
| AcCl | acetyl chloride |
| AcOH | acetic acid |
| aq or aq. | aqueous |
| Bn | benzyl |
| $B_2pin_2$ | bis(pinacolato)diboron |
| BOC or Boc | tert-butyloxycarbonyl |
| BroP | bromotris(dimethylamino)phosphonium hexafluorophosphate |
| cataCXium A Pd G3 | mesylate[(di(1-adamantyl)-n-butylphosphine)-2-(2'-amino-1,1'-biphenyl)]palladium(II) |
| Cbz | benzyloxycarbonyl |
| CbzCl | benzyl chloroformate |
| CDI | carbonyldiimidazole |
| COD or cod | 1,5-cyclooctadiene |
| CuTC | copper(I) thiophene-2-carboxylate |
| DABCO | 1,4-diazabicyclo[2.2.2]octane |
| DBU | 1,8-diazabicyclo[5.4.0]undec-7-ene |
| DCE | 1,2-dichloroethane |
| DCM | dichloromethane |
| DHP | 3,4-dihydro-2H-pyran |
| DIPEA | Diisopropylethylamine |
| DMA | N,N-dimethylacetamide |
| DMAP | 4-(N,N-dimethylamino)pyridine |
| DMC | dimethyl carbonate |
| DMF | N,N-dimethylformamide |
| DMI | 1,3-dimethyl-2-imidazolidinone |
| DMSO | dimethyl sulfoxide |
| Dppf, DPPF or dppf | 1,1'-bis(diphenylphosphino)ferrocene |
| Dtbbpy | 4,4'-di-tert-butyl-2,2'-dipyridyl |
| eq or eq. or equiv. | equivalent |
| ESI or ES | electrospray ionization |
| Et | ethyl |
| EtOAc | ethyl acetate |
| G | gram(s) |
| H or h | hour(s) |
| HATU | O-(7-azabenzotriazol-1-yl)-N,N,N',N'-tetramethyluronium hexafluorophosphate |
| HBpin | 4,4,5,5-tetramethyl-1,3,2-dioxaborolane |
| HMPA | hexamethylphosphoramide |
| HOAc | acetic acid |
| Hoyeda-Grubbs II catalyst | (1,3-bis-(2,4,6-trimethylphenyl)-2-imidazolidinylidene)dichloro(o-isopropoxyphenylmethylene)ruthenium |
| HPLC | high pressure liquid chromatography |
| IBX | 2-iodoxybenzoic acid |
| iPr | iso-propyl |
| $iPr_2NEt$ or DIPEA | N-ethyl diisopropylamine (Hünig's base) |
| KOAc | potassium acetate |
| LC MS, LCMS, LC-MS or LC/MS | liquid chromatography mass spectroscopy |
| LHMDS or LiHMDS | lithium hexamethyldisilazide |
| m/z | mass divided by charge |
| Me | methyl |
| MeCN | acetonitrile |
| MeOH | methanol |
| mg | milligrams |
| min | minutes |
| mL | milliliters |
| MS | mass spectra |
| MTBE | methyl tert-butyl ether |
| NaHMDS | sodium hexamethyldisilazide |
| NFSI | N-fluorobenzenesulfonimide |
| NIS | N-iodosuccinimide |
| NMO | 4-methylmorpholine 4-oxide |
| NMP | N-methyl-2-pyrrolidone |
| NMR | nuclear magnetic resonance |
| $PCy_3$ Pd G2 | chloro[(tricyclohexylphosphine)-2-(2'-aminobiphenyl)]palladium(II) |
| $Pd(dppf)Cl_2$•DCM, $Pd(dppf)Cl_2$ | [1,1'-bis(diphenylphosphino)ferrocene]dichloropalladium(II), complex with dichloromethane |
| $Pd(dtbpf)Cl_2$ | [1,1'-bis(di-tert-butylphosphino)ferrocene]dichloropalladium(II) |
| $Pd(PPh_3)_4$ | tetrakis(triphenylphosphine)palladium(0) |
| PEPPSI—IPr | [1,3-bis(2,6-diisopropylphenyl)imidazol-2-ylidene](3-chloropyridyl)palladium(II) dichloride |
| Ph | phenyl |
| PhMe | toluene |
| Pin | pinacolato |
| Piv | pivaloyl |
| PivCl | pivaloyl chloride |
| PMB | 4-methoxybenzyl |
| PPNCI | bis(triphenylphosphoranylidene)ammonium chloride |
| PTSA or pTsOH | p-toluenesulfonic acid |
| Rbf | round-bottom flask |
| RP-HPLC | reverse phase high pressure liquid chromatography |

TABLE 7-continued

| | |
|---|---|
| RT or rt or r.t. | room temperature |
| sat. or satd. | saturated |
| SFC | supercritical fluid chromatography |
| TBACl | tetra-n-butylammonium chloride |
| TBAF | tetra-n-butylammonium fluoride |
| TBDPS | tert-butyldiphenylsilyl |
| TBDPSCl | tert-butyldiphenylsilyl chloride |
| TBS | tert-butyldimethylsilyl |
| TBSCl | tert-butyldimethylsilyl chloride |
| tBu | tert-butyl |
| TC | thiophene-2-carboxylate |
| TEA or $Et_3N$ | triethylamine |
| Tf | trifluoromethylsulfonyl |
| TFA | trifluoroacetic acid |
| THF | tetrahydrofuran |
| TIPS | triisopropylsilyl |
| TIPSCl | triisopropylsilyl chloride |
| UV | ultraviolet |
| XPhos | 2-dicyclohexylphosphino-2',4',6'-triisopropyl-1,1'-biphenyl |
| XPhos Pd G2 | chloro(2-dicyclohexylphosphino-2',4',6'-triisopropyl-1,1'-biphenyl)[2-(2'-amino-1,1'-biphenyl)]palladium(II) |

General Analytical and Purification Methods

Provided in this section are descriptions of the general analytical and purification methods used to prepare the specific examples provided herein.

Chromatography: Unless otherwise indicated, crude product-containing residues were purified by passing the crude material or concentrate through either a Biotage or ISCO brand silica gel column pre-packed with flash silica ($SiO_2$) and eluting the product from the column with a solvent gradient as indicated.

Preparative HPLC Method: Where indicated, the compounds described herein were purified via reverse phase HPLC using Waters FractionLynx or Gilson semi-preparative HPLC-MS system using one of the following two HPLC columns: (a) Phenomenex Gemini column (5 micron, C18, 150×30 mm) or (b) Waters X-select CSH column (5 micron, C18, 100×30 mm). A typical run through the instrument included: eluting at 45 mL/min with a linear gradient of 10% (v/v) to 100% MeCN (0.1% v/v formic acid) in water (0.1% formic acid) over 10 minutes; conditions can be varied to achieve optimal separations.

Proton NMR Spectra: Unless otherwise indicated, all $^1H$ NMR spectra were collected on a Bruker NMR instrument at 300, 400 or 500 MHz. All observed protons are reported as parts-per-million (ppm) downfield from tetramethylsilane (TMS) using the internal solvent peak as reference. Some $^1H$ signals may be missing due to exchange with D from MeOD, or due to signal suppression.

Mass Spectra (MS): Unless otherwise indicated, all mass spectral data for starting materials, intermediates and/or exemplary compounds are reported as mass/charge (m/z), having an [M+H]+ molecular ion. The molecular ion reported was obtained by electrospray detection method (commonly referred to as an ESI MS) utilizing a Waters Acquity UPLC/MS system. Compounds having an isotopic atom, such as bromine and the like, are generally reported according to the detected isotopic pattern, as appreciated by those skilled in the art.

Preparation of Intermediates

Intermediate A: tert-Butyl 4-(6-(methoxymethoxy)-8-(4,4,5,5-tetramethyl-1,3,2-dioxaborolan-2-yl)naphthalen-1-yl)butanoate

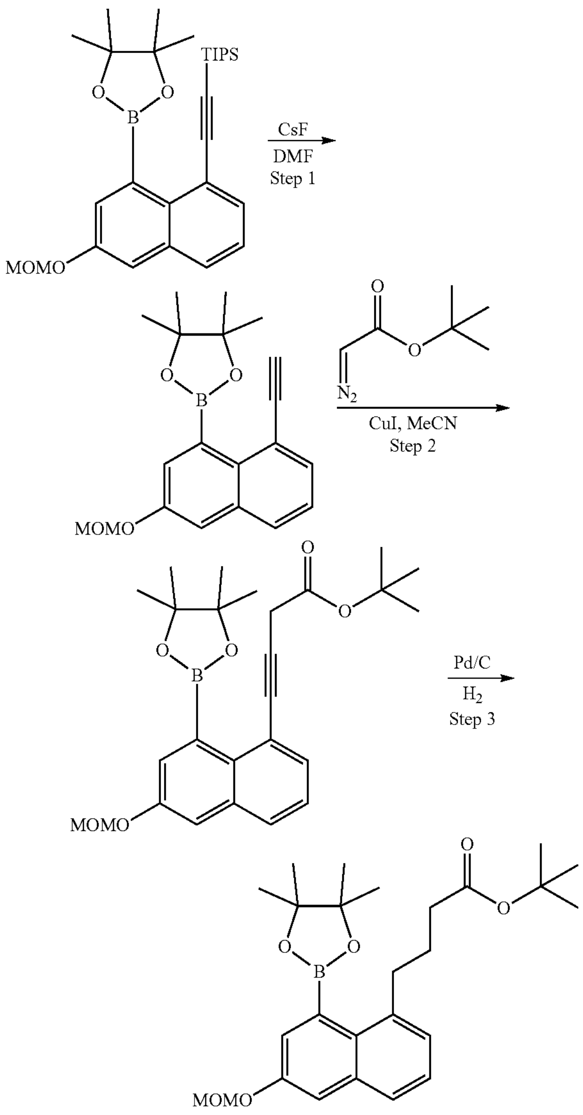

Intermediate A

Step 1. 2-(8-Ethynyl-3-(methoxymethoxy)naphthalen-1-yl)-4,4,5,5-tetramethyl-1,3,2-dioxaborolane. To a mixture of triisopropyl((6-(methoxymethoxy)-8-(4,4,5,5-tetramethyl-1,3,2-dioxaborolan-2-yl)naphthalen-1-yl)ethynyl)silane (1.00 g, 2.00 mmol, LabNetwork Inc.) in N,N-dimethylformamide (4.0 mL) was added cesium fluoride (4.61 g, 30.3 mmol) and stirred at rt overnight. Water was added to the reaction mixture and the aqueous phase was extracted with EtOAc. The combined organic layers were dried over $Na_2SO_4$, filtered and volatiles were removed in vacuo. The crude residue was purified by column chromatography on silica gel, eluting with a gradient of 0-30% EtOAc in heptane, to provide 2-(8-ethynyl-3-(methoxymethoxy)naphthalen-1-yl)-4,4,5,5-tetramethyl-1,3,2-dioxaborolane (0.60 g, 1.77 mmol, 88% yield) as white solid. m/z (ESI): 339.2 $(M+H)^+$.

Step 2. tert-Butyl 4-(6-(methoxymethoxy)-8-(4,4,5,5-tetramethyl-1,3,2-dioxaborolan-2-yl)naphthalen-1-yl)but-3-ynoate. 2-(8-Ethynyl-3-(methoxymethoxy)naphthalen-1-yl)-4,4,5,5-tetramethyl-1,3,2-dioxaborolane (0.18 g, 0.52 mmol), copper (I) iodide (9.9 mg, 0.05 mmol) was dissolved in acetonitrile (1.5 mL) and tert-butyl diazoacetate (0.15 g, 0.14 mL, 1.04 mmol, Sigma-Aldrich Corporation) was added dropwise. The mixture was stirred at rt for 5 h. Water was added, and the aqueous layer was extracted with EtOAc. The combined organic layers were dried over $Na_2SO_4$, filtered and the volatiles removed in vacuo. The residue was purified by column chromatography on silica gel, eluting with a gradient of 0-30% EtOAc in heptane, to provide tert-butyl 4-(6-(methoxymethoxy)-8-(4,4,5,5-tetramethyl-1,3,2-dioxaborolan-2-yl)naphthalen-1-yl)but-3-ynoate (0.14 g, 0.30 mmol, 58% yield) as clear oil. m/z (ESI): 397.0 $(M-t-Bu+H)^+$.

Step 3. tert-Butyl 4-(6-(methoxymethoxy)-8-(4,4,5,5-tetramethyl-1,3,2-dioxaborolan-2-yl)naphthalen-1-yl)butanoate. tert-Butyl 4-(6-(methoxymethoxy)-8-(4,4,5,5-tetramethyl-1,3,2-dioxaborolan-2-yl)naphthalen-1-yl)but-3-ynoate (0.11 g, 0.24 mmol) was dissolved in ethyl acetate (3.0 mL) and 5% Pd/C (52 mg, 0.024 mmol, Alfa Aesar) was added. The mixture was placed under an atmosphere of hydrogen (15 psi) and stirred at rt for 4 h. The reaction mixture was filtered through celite, and the filter cake washed with EtOAc. Volatiles were removed in vacuo and the residue was purified by column chromatography on silica gel, eluting with a gradient of 0-50% EtOAc in heptane, to provide tert-butyl 4-(6-(methoxymethoxy)-8-(4,4,5,5-tetramethyl-1,3,2-dioxaborolan-2-yl)naphthalen-1-yl)butanoate (94 mg, 0.21 mmol, 85% yield) as colorless oil. $^1$H NMR (400 MHz, CHLOROFORM-d) δ ppm 7.62 (d, J=7.5 Hz, 1H), 7.43 (d, J=2.7 Hz, 1H), 7.35-7.41 (m, 2H), 7.26 (d, J=6.7 Hz, 1H), 5.30-5.31 (m, 2H), 3.53 (s, 3H), 3.18-3.27 (m, 2H), 2.22-2.29 (m, 2H), 2.04-2.12 (m, 2H), 1.45-1.48 (m, 21H).

Intermediate B: Ethyl 4-(6-(methoxymethoxy)-8-(4,4,5,5-tetramethyl-1,3,2-dioxaborolan-2-yl)naphthalen-1-yl)butanoate

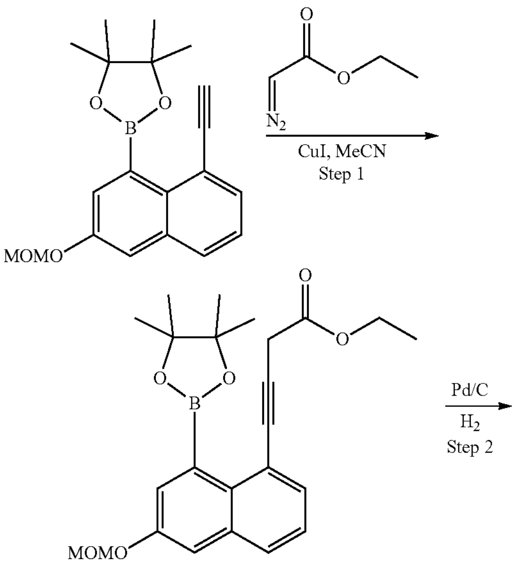

-continued

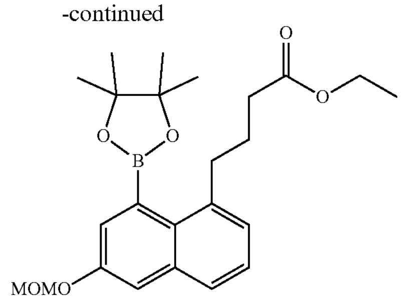

Intermediate B

Step 1. Ethyl 4-(6-(methoxymethoxy)-8-(4,4,5,5-tetramethyl-1,3,2-dioxaborolan-2-yl)naphthalen-1-yl)but-3-ynoate. 2-(8-Ethynyl-3-(methoxymethoxy)naphthalen-1-yl)-4,4,5,5-tetramethyl-1,3,2-dioxaborolane (1.00 g, 2.96 mmol, Intermediate A Step 1), copper (I) iodide (0.08 g, 0.44 mmol) was dissolved in acetonitrile (7.0 mL) and 15% ethyl diazoacetate (4.50 g, 4.17 mL, 5.91 mmol, Sigma-Aldrich Corporation) solution in toluene was added. The mixture was stirred at rt for 3 h. Saturated $NH_4Cl$ was added, and the aqueous layer was extracted with EtOAc. The combined organic phases were dried over $Na_2SO_4$, filtered and volatiles removed in vacuo. The mixture was then purified by column chromatography on silica gel, eluting with a gradient of 0-30% EtOAc in heptane, to provide ethyl 4-(6-(methoxymethoxy)-8-(4,4,5,5-tetramethyl-1,3,2-dioxaborolan-2-yl)naphthalen-1-yl)but-3-ynoate (1.10 g, 2.59 mmol, 88% yield) as clear oil. m/z (ESI): 425.0 $(M+2H)^+$.

Step 2. Ethyl 4-(6-(methoxymethoxy)-8-(4,4,5,5-tetramethyl-1,3,2-dioxaborolan-2-yl)naphthalen-1-yl)butanoate. Ethyl 4-(6-(methoxymethoxy)-8-(4,4,5,5-tetramethyl-1,3,2-dioxaborolan-2-yl)naphthalen-1-yl)but-3-ynoate (1.03 g, 2.43 mmol) was dissolved in ethyl acetate (25 mL) and 5% Pd/C (0.52 g, 0.24 mmol, Alfa Aesar) was added. The mixture was placed under an atmosphere of hydrogen (15 psi) and stirred at rt for 4 h. The reaction mixture was filtered through celite, and the filter cake washed with EtOAc. Volatiles were removed in vacuo and the residue was purified by column chromatography on silica gel, eluting with a gradient of 0-50% EtOAc in heptane, to provide ethyl 4-(6-(methoxymethoxy)-8-(4,4,5,5-tetramethyl-1,3,2-dioxaborolan-2-yl)naphthalen-1-yl)butanoate (0.80 g, 1.87 mmol, 77% yield) as colorless oil. $^1$H NMR (400 MHz, CHLOROFORM-d) δ ppm 7.61-7.65 (m, 1H), 7.43 (d, J=2.7 Hz, 1H), 7.40 (d, J=2.7 Hz, 1H), 7.37 (d, J=7.9 Hz, 1H), 7.24-7.28 (m, 1H), 5.30--5.31 (m, 2H), 4.13 (q, J=7.1 Hz, 2H), 3.53 (s, 3H), 3.23 (t, J=7.3 Hz, 2H), 2.32 (d, J=7.7 Hz, 2H), 2.12 (t, J=7.4 Hz, 2H), 1.46 (s, 12H), 1.25 (t, J=7.2 Hz, 3H).

Intermediate C: tert-Butyl 4-(2-fluoro-8-(4,4,5,5-tetramethyl-1,3,2-dioxaborolan-2-yl)naphthalen-1-yl)butanoate

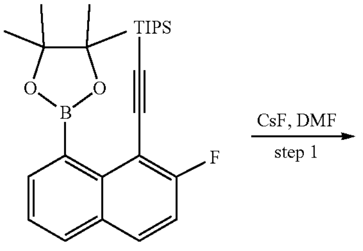

-continued

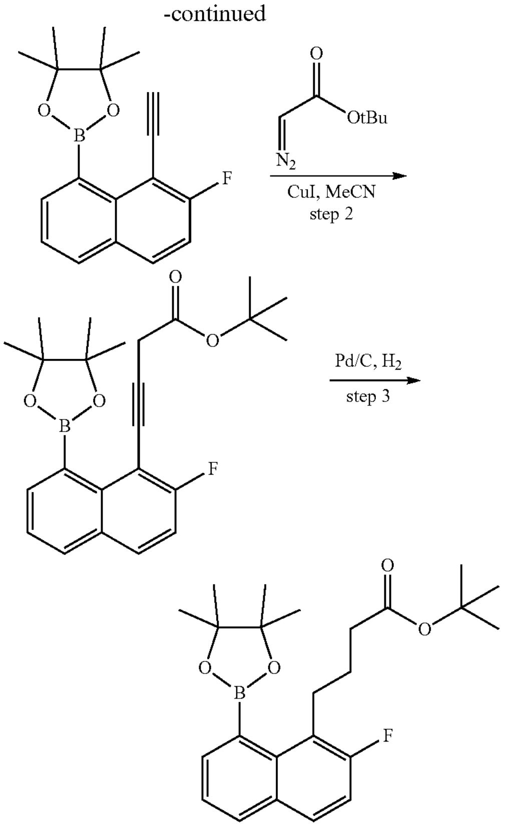

Intermediate C

Step 1. 2-(8-Ethynyl-7-fluoronaphthalen-1-yl)-4,4,5,5-tetramethyl-1,3,2-dioxaborolane. ((2-Fluoro-8-(4,4,5,5-tetramethyl-1,3,2-dioxaborolan-2-yl)naphthalen-1-yl)ethynyl)triisopropylsilane (2.00 g, 4.42 mmol, LabNetwork Inc.) and cesium fluoride (13.4 g, 88 mmol) were dissolved in N,N-dimethylformamide (10 mL) and the mixture was stirred at 50° C. for 3 h. Water was added, and the aqueous phase was extracted with EtOAc. The combined organic phases were dried over $Na_2SO_4$, filtered and volatiles were removed in vacuo. The residue was then purified by column chromatography on silica gel, eluting with a gradient of 0-30% EtOAc in heptane, to provide 2-(8-ethynyl-7-fluoronaphthalen-1-yl)-4,4,5,5-tetramethyl-1,3,2-dioxaborolane (0.80 g, 2.70 mmol, 61% yield) as white solid. m/z (ESI): 297.2 $(M+H)^+$ Step 2. tert-Butyl 4-(2-fluoro-8-(4,4,5,5-tetramethyl-1,3,2-dioxaborolan-2-yl)naphthalen-1-yl)but-3-ynoate. 2-(8-Ethynyl-7-fluoronaphthalen-1-yl)-4,4,5,5-tetramethyl-1,3,2-dioxaborolane (0.86 g, 2.90 mmol) was dissolved in acetonitrile (10 mL), tert-butyl diazoacetate (0.83 mg, 5.81 mmol, Sigma-Aldrich Corporation) was added, followed by copper (I) iodide (0.11 g, 0.58 mmol). The reaction mixture was stirred at rt for 16 h. Saturated $NH_4Cl$ and water were added, and the aqueous phase was extracted with EtOAc. The combined organic layers were dried over $Na_2SO_4$, filtered and volatiles were removed in vacuo. The crude material was purified by column chromatography on silica gel, eluting with a gradient of 0-25% EtOAc in heptane, to provide tert-butyl 4-(2-fluoro-8-(4,4,5,5-tetramethyl-1,3,2-dioxaborolan-2-yl)naphthalen-1-yl)but-3-ynoate (0.52 g, 1.27 mmol, 44% yield) as colorless oil. m/z (ESI): 355.0 $(M-t-Bu+H)^+$ Step 3. tert-Butyl 4-(2-fluoro-8-(4,4,5,5-tetramethyl-1,3,2-dioxaborolan-2-yl)naphthalen-1-yl)butanoate. tert-Butyl 4-(2-fluoro-8-(4,4,5,5-tetramethyl-1,3,2-dioxaborolan-2-yl)naphthalen-1-yl)but-3-ynoate (0.52 g, 1.27 mmol) was dissolved in ethyl acetate (10 mL) and 5% Pd/C (0.27 g, 0.13 mmol) was added. The mixture was placed under an atmosphere of hydrogen (15 psi) and stirred at rt for 6 h. The reaction mixture was filtered through celite, and the filter cake washed with EtOAc. Volatiles were removed in vacuo and the residue was purified by column chromatography on silica gel, eluting with a gradient of 0-30% EtOAc in heptane, to provide tert-butyl 4-(2-fluoro-8-(4,4,5,5-tetramethyl-1,3,2-dioxaborolan-2-yl)naphthalen-1-yl)butanoate (0.25 g, 0.60 mmol, 48% yield) as colorless oil. m/z (ESI): 359.2 $(M-t-Bu+H)^+$.

Intermediate D: Ethyl 4-(2-fluoro-6-(methoxymethoxy)-8-(4,4,5,5-tetramethyl-1,3,2-dioxaborolan-2-yl)naphthalen-1-yl)butanoate

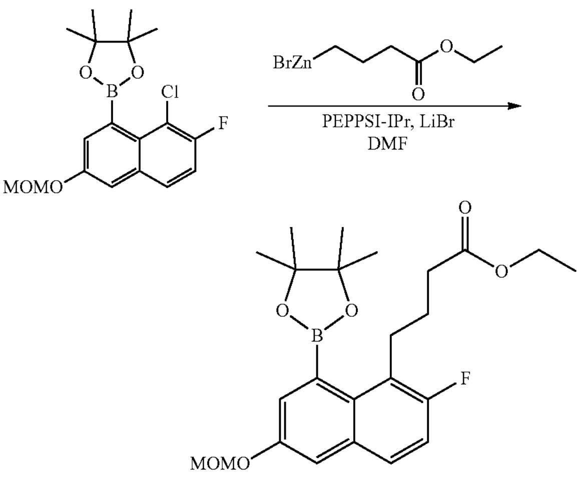

Intermediate D

In a 100 mL round-bottom flask were charged with 2-(8-chloro-7-fluoro-3-(methoxymethoxy)naphthalen-1-yl)-4,4,5,5-tetramethyl-1,3,2-dioxaborolane (2.10 g, 5.70 mmol, Labnetwork), PEPPSI-IPr catalyst (0.39 g, 0.57 mmol, Sigma-Aldrich Corporation) and anhydrous DMF (45 mL) under nitrogen. Lithium bromide (4 M in THF, 4.6 mL, 18.4 mmol) was added, followed by (4-ethoxy-4-oxobutyl)zinc (II) bromide (0.5 M solution in THF, 23 mL, 11.5 mmol, Rieke Metal) dropwise. The reaction mixture was stirred at 60° C. for 5 h. After cooling to rt, the reaction mixture was quenched with aqueous $NH_4Cl$, extracted with EtOAc. The combined organics were dried ($Na_2SO_4$) and concentrated. The crude material was purified by column chromatography on silica gel, eluting with a gradient of 5-20% of ethyl acetate in heptane, to provide ethyl 4-(2-fluoro-6-(methoxymethoxy)-8-(4,4,5,5-tetramethyl-1,3,2-dioxaborolan-2-yl)naphthalen-1-yl)butanoate as colorless oil. m/z (ESI): 464.4 $(M+Na)^+$. $^1H$ NMR (400 MHz, CHLOROFORM-d) δ ppm 7.51-7.67 (m, 1H), 7.35-7.47 (m, 2H), 7.18-7.26 (m, 1H), 5.11-5.31 (m, 2H), 3.95-4.18 (m, 2H), 3.44-3.60 (m, 3H), 3.04--3.34 (m, 2H), 2.14-2.31 (m, 2H), 1.86-2.07 (m, 2H), 1.41-1.53 (m, 12H), 1.17-1.27 (m, 3H).

Intermediate E: Methyl 5-(6-(methoxymethoxy)-8-(4,4,5,5-tetramethyl-1,3,2-dioxaborolan-2-yl)naphthalen-1-yl)pentanoate

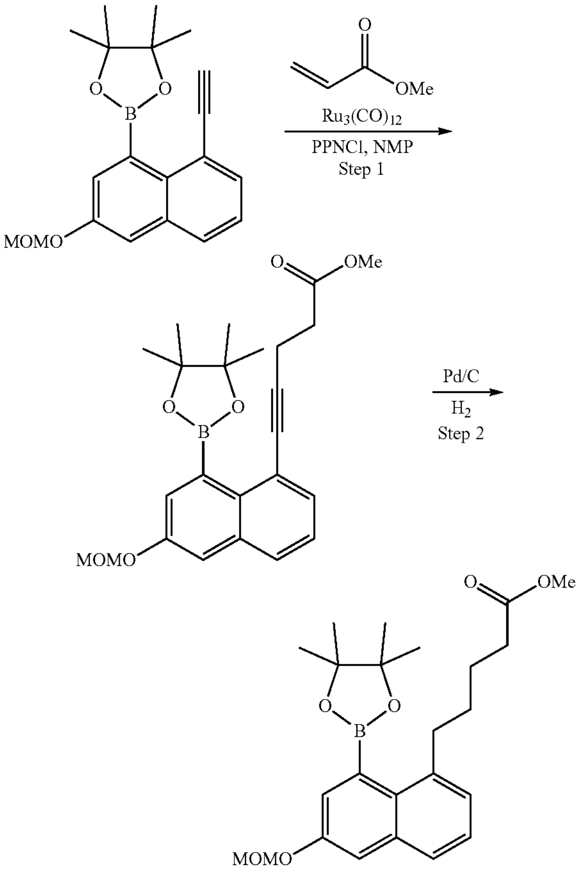

Intermediate E

Step 1. Methyl 5-(6-(methoxymethoxy)-8-(4,4,5,5-tetramethyl-1,3,2-dioxaborolan-2-yl)naphthalen-1-yl)pent-4-ynoate. A vial was charged with bis(triphenylphosphoranylidene)ammonium chloride (0.22 g, 0.39 mmol), triruthenium dodecacarbonyl (39 mg, 0.061 mmol) and NMP (0.7 mL). The reaction mixture was sparged with argon and stirred at 60° C. After 15 minutes, methyl acrylate (0.63 mL, 6.95 mmol) and 2-(8-ethynyl-3-(methoxymethoxy)naphthalen-1-yl)-4,4,5,5-tetramethyl-1,3,2-dioxaborolane (0.47 g, 1.39 mmol, Intermediate A, Step 1) were added to the mixture. The reaction was stirred at 65° C. After 5 days, the reaction mixture was partitioned between water and ethyl acetate; the organic layer was concentrated. The crude product was purified by column chromatography on silica gel, eluting with 0-100% ethyl acetate in heptane, to provide methyl 5-(6-(methoxymethoxy)-8-(4,4,5,5-tetramethyl-1,3,2-dioxaborolan-2-yl)naphthalen-1-yl)pent-4-ynoate (0.42 g, 0.99 mmol, 71% yield) as light-yellow solid. m/z (ESI): 425.2 $(M+H)^+$.

Step-2: Methyl 5-(6-(methoxymethoxy)-8-(4,4,5,5-tetramethyl-1,3,2-dioxaborolan-2-yl)naphthalen-1-yl)pentanoate. A solution of methyl 5-(6-(methoxymethoxy)-8-(4,4,5,5-tetramethyl-1,3,2-dioxaborolan-2-yl)naphthalen-1-yl)pent-4-ynoate (0.84 g, 1.98 mmol) in ethyl acetate (10 mL) was transferred to a hydrogenation flask, flushed with argon, and 5% Pd/C (0.42 g, 0.20 mmol) was added. The mixture was placed under an atmosphere of hydrogen (20 psi) and stirred at rt. After 2 h, the reaction mixture was filtered through celite; the filtrate was concentrated. The crude product was purified by column chromatography on silica gel, eluting with 0-50% ethyl acetate in heptane, to provide methyl 5-(6-(methoxymethoxy)-8-(4,4,5,5-tetramethyl-1,3,2-dioxaborolan-2-yl)naphthalen-1-yl)pentanoate (0.41 g, 0.96 mmol, 49% yield) as colorless oil. m/z (ESI): 450.1 $(M+Na)^+$.

Intermediate F: Ethyl 2-fluoro-4-(2-fluoro-6-(methoxymethoxy)-8-(4,4,5,5-tetramethyl-1,3,2-dioxaborolan-2-yl)naphthalen-1-yl)butanoate

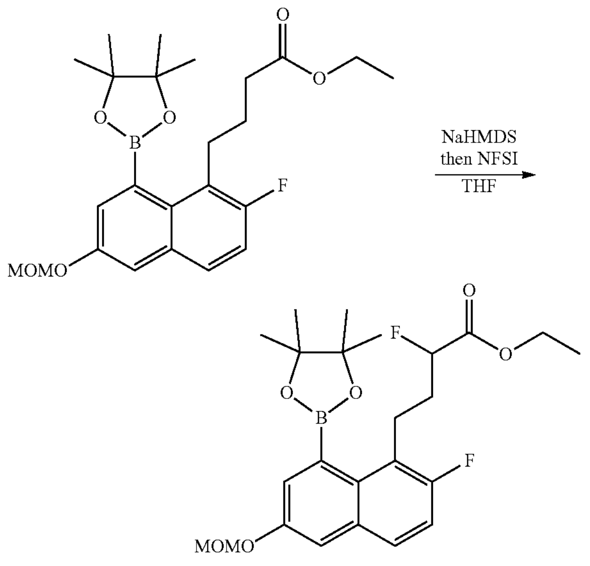

Intermediate F

A round-bottom flask was charged with NaHMDS (1 M in THF, 0.32 mL, 0.32 mmol) and the contents were cooled to −78° C. Ethyl 4-(2-fluoro-6-(methoxymethoxy)-8-(4,4,5,5-tetramethyl-1,3,2-dioxaborolan-2-yl)naphthalen-1-yl)butanoate (0.12 g, 0.27 mmol, Intermediate D) dissolved in 1.0 mL of THF was added dropwise to the solution. The reaction mixture was stirred −78° C. for 30 minutes and then N-fluorobenzenesulfonimide (0.10 g, 0.32 mmol) dissolved in 1.0 mL of THF was added slowly over 15 minutes. The mixture was allowed to slowly warm to rt with stirring for 16 h. The reaction was then cooled to −78° C. and MeOH (3 mL) was added to quench to the reaction. After warming to rt, the volatiles were removed in vacuo and the residue was purified via reverse phase chromatography to provide ethyl 2-fluoro-4-(2-fluoro-6-(methoxymethoxy)-8-(4,4,5,5-tetramethyl-1,3,2-dioxaborolan-2-yl)naphthalen-1-yl)butanoate (40 mg, 0.086 mmol, 32% yield). $^1H$ NMR (400 MHz, CHLOROFORM-d) δ ppm 7.63 (dd, J=9.0, 5.9 Hz, 1H), 7.48 (d, J=2.5 Hz, 1H), 7.43 (d, J=2.7 Hz, 1H), 7.23 (t, J=9.2 Hz, 1H), 5.28-5.31 (m, 2H), 4.82-4.98 (m, 1H), 4.22 (qd, J=7.1, 1.2 Hz, 2H), 3.52-3.54 (m, 3H), 3.30-3.38 (m, 2H), 2.24-2.31 (m, 1H), 2.17-2.23 (m, 1H), 1.46 (d, J=1.9 Hz, 12H), 1.27 (t, J=7.2 Hz, 3H). $^{19}F$ NMR (377 MHz, CHLOROFORM-d) δ ppm −76.59--74.96 (m, 3 F), −117.11 (br s, 1 F), −192.09--191.74 (m, 1 F).

Intermediate G: Ethyl 4-(2-fluoro-8-(4,4,5,5-tetramethyl-1,3,2-dioxaborolan-2-yl)naphthalen-1-yl)butanoate

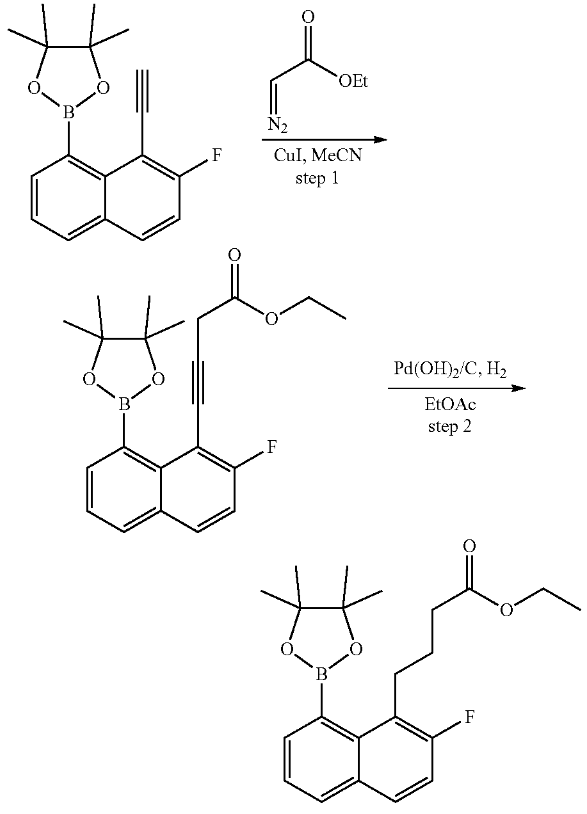

Intermediate G

Step 1. Ethyl 4-(2-fluoro-8-(4,4,5,5-tetramethyl-1,3,2-dioxaborolan-2-yl)naphthalen-1-yl)but-3-ynoate. A vial was charged with 2-(8-ethynyl-7-fluoronaphthalen-1-yl)-4,4,5,5-tetramethyl-1,3,2-dioxaborolane (1.76 g, 5.94 mmol, Intermediate C, step 1) and copper (I) iodide (0.11 g, 0.59 mmol) in acetonitrile (15 mL). Ethyl diazoacetate solution (15% in toluene, 6.1 mL, 7.1 mmol) was added slowly and the reaction mixture was stirred at rt for 16 h. The mixture was diluted with saturated aqueous $NH_4Cl$ solution and water and extracted with EtOAc. The combined organics were dried over $MgSO_4$, filtered, and concentrated. The crude residue was purified by column chromatography on silica gel, eluting with a gradient of 25-100% EtOAc in heptane, to provide ethyl 4-(2-fluoro-8-(4,4,5,5-tetramethyl-1,3,2-dioxaborolan-2-yl)naphthalen-1-yl)but-3-ynoate (1.11 g, 2.90 mmol, 49% yield). $^1$H NMR (400 MHz, CHLOROFORM-d) δ ppm 7.77-7.89 (m, 3H), 7.41-7.47 (m, 1H), 7.28-7.32 (m, 1H), 4.27 (d, J=7.1 Hz, 2H), 3.66 (s, 2H), 1.44 (s, 12H), 1.32-1.37 (m, 3H).

Step 2. Ethyl 4-(2-fluoro-8-(4,4,5,5-tetramethyl-1,3,2-dioxaborolan-2-yl)naphthalen-1-yl)butanoate. A 250 mL pressure tube was charged with ethyl 4-(2-fluoro-8-(4,4,5,5-tetramethyl-1,3,2-dioxaborolan-2-yl)naphthalen-1-yl)but-3-ynoate (1.00 g, 2.62 mmol), palladium hydroxide on carbon (0.18 g, 0.26 mmol) and ethyl acetate (6.5 mL). The system was sparged with nitrogen and then pressurized with H2 (25 psi). The reaction was vigorously stirred for 2.5 h. The reaction mixture was filtered over $SiO_2$, and the filtrate was concentrated. The residue was purified by column chromatography on silica gel, eluting with a gradient of 10-100% EtOAc in heptane, to provide ethyl 4-(2-fluoro-8-(4,4,5,5-tetramethyl-1,3,2-dioxaborolan-2-yl)naphthalen-1-yl)butanoate (0.81 g, 2.07 mmol, 79% yield) as white solid. $^1$H NMR (500 MHz, CHLOROFORM-d) δ ppm 7.87 (dd, J=8.2, 1.3 Hz, 1H), 7.68-7.75 (m, 2H), 7.38-7.46 (m, 1H), 7.26 (s, 1H), 4.06-4.12 (m, 2H), 3.29 (br d, J=2.5 Hz, 2H), 2.21-2.30 (m, 2H), 1.98-2.07 (m, 2H), 1.47 (s, 12H), 1.20-1.23 (m, 3H).

Intermediate H: Ethyl 2-fluoro-4-(2-fluoro-8-(4,4,5,5-tetramethyl-1,3,2-dioxaborolan-2-yl)naphthalen-1-yl)butanoate

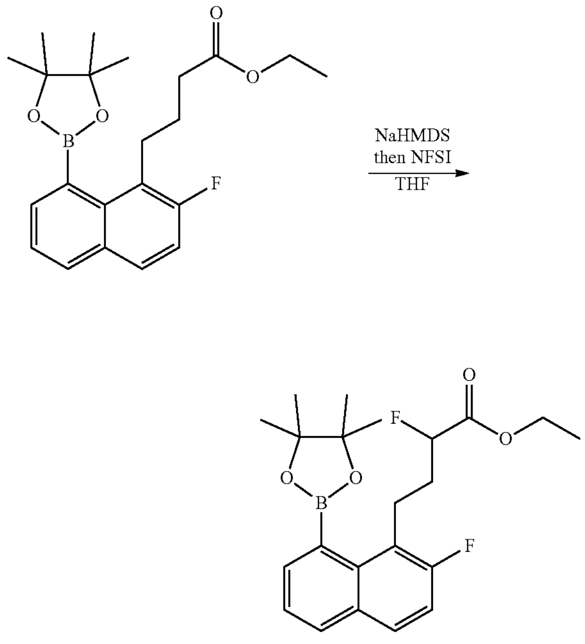

Intermediate H

A round-bottom flask was charged with NaHMDS (1 M in THF, 1.55 mL, 1.55 mmol) and the contents were cooled to −78° C. Ethyl 4-(2-fluoro-8-(4,4,5,5-tetramethyl-1,3,2-dioxaborolan-2-yl)naphthalen-1-yl)butanoate (0.50 g, 1.30 mmol, Intermediate G) dissolved in 1.0 mL of THF was then added to the solution. The reaction mixture was stirred at −78° C. for 30 minutes and then N-fluorobenzenesulfonimide (0.57 g, 1.81 mmol) dissolved in THF (1 mL) was added slowly over 15 minutes. The mixture was allowed to slowly warm to rt with stirring for 16 h. The reaction was then cooled to −78° C. and MeOH (3 mL) was added to quench to the reaction. After warming to rt, the volatiles were removed in vacuo and the residue was purified via reverse phase chromatography to provide ethyl 2-fluoro-4-(2-fluoro-8-(4,4,5,5-tetramethyl-1,3,2-dioxaborolan-2-yl)naphthalen-1-yl)butanoate (0.35 g, 0.87 mmol, 67% yield). m/z (ESI): $(M+H)^+$ 405.1.

Intermediate I: tert-Butyl 6-(6-methyl-1-(tetrahydro-2H-pyran-2-yl)-4-(4,4,5,5-tetramethyl-1,3,2-dioxaborolan-2-yl)-1H-indazol-5-yl)hexanoate

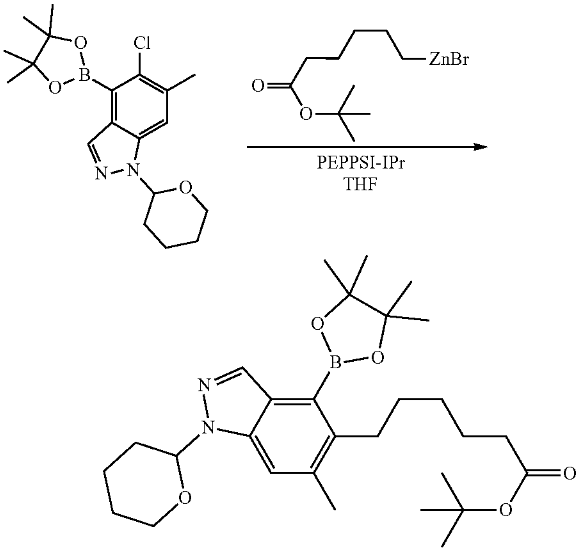

Example I

A 100 mL RBF was charged with 5-chloro-6-methyl-1-tetrahydropyran-2-yl-4-(4,4,5,5-tetramethyl-1,3,2-dioxaborolan-2-yl)indazole (1.00 g, 2.65 mmol, Advanced ChemBlocks Inc.), PEPPSI-IPr catalyst (0.18 g, 0.27 mmol, Sigma-Aldrich Corporation) in tetrahydrofuran (26.5 mL). 6-tert-Butoxy-6-oxohexylzinc bromide (0.5 M THF, 10.6 mL, 5.3 mmol, Rieke Metals, Inc.) was added. The reaction was stirred at rt for 16 h. The reaction mixture was then quenched with saturated aqueous ammonium chloride solution and extracted with DCM. The combined organic layers were dried over sodium sulfate, filtered, and concentrated. The residue was purified by column chromatography on silica gel, eluting with a gradient of 0-20% EtOAc in heptane, to provide tert-butyl 6-(6-methyl-1-(tetrahydro-2H-pyran-2-yl)-4-(4,4,5,5-tetramethyl-1,3,2-dioxaborolan-2-yl)-1H-indazol-5-yl)hexanoate (0.60 g, 1.18 mmol, 44% yield). m/z (ESI): 513.2 $(M+H)^+$.

Intermediate J: Ethyl 5-(6-methyl-1-(tetrahydro-2H-pyran-2-yl)-4-(4,4,5,5-tetramethyl-1,3,2-dioxaborolan-2-yl)-1H-indazol-5-yl)pentanoate

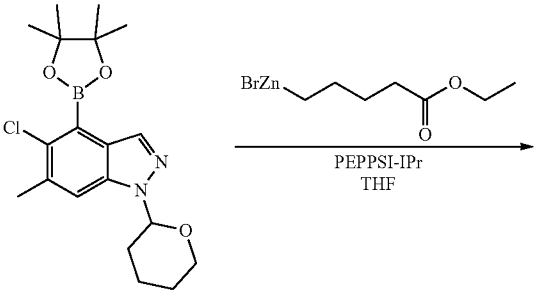

-continued

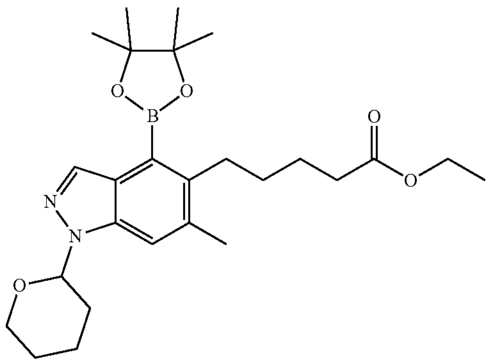

Intermediate J

To an oven dried round-bottom flask was charged with 5-chloro-6-methyl-1-(tetrahydro-2H-pyran-2-yl)-4-(4,4,5,5-tetramethyl-1,3,2-dioxaborolan-2-yl)-1H-indazole (3.90 g, 10.40 mmol, Ambeed, Inc.) and tetrahydrofuran (52 mL). 5-Ethoxy-5-oxopentylzinc bromide (0.5 M in THF, 52 mL, 25.5 mmol) was added. To this stirring solution was added PEPPSI-IPr catalyst (2.05 g, 2.59 mmol) and the reaction mixture was stirred at rt for 16 h. The reaction was diluted with saturated aqueous ammonium chloride solution and extracted with EtOAc. The combined organic layers were dried over sodium sulfate, filtered, and concentrated. The crude material was purified by column chromatography on silica gel, eluting with 0-25% EtOAc in heptane, to provide ethyl 5-(6-methyl-1-(tetrahydro-2H-pyran-2-yl)-4-(4,4,5,5-tetramethyl-1,3,2-dioxaborolan-2-yl)-1H-indazol-5-yl)pentanoate (1.21 g, 2.57 mmol, 25% yield) as yellow oil. m/z (ESI): 471.2 $(M+H)^+$.

Intermediate K: 5-(3-((tert-Butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole

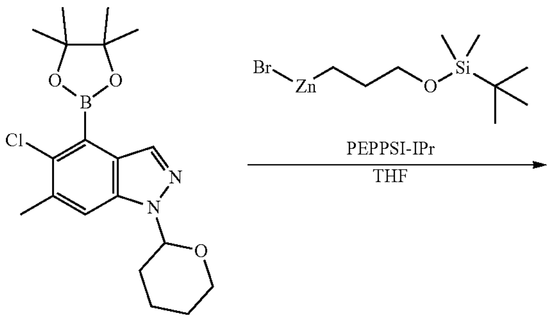

-continued

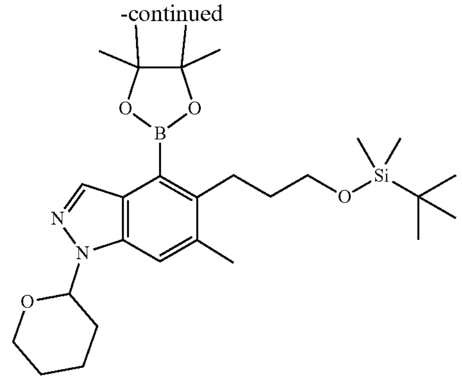

Intermediate K

To a 250 mL round-bottom flask was charged with 5-chloro-6-methyl-1-(tetrahydro-2H-pyran-2-yl)-4-(4,4,5,5-tetramethyl-1,3,2-dioxaborolan-2-yl)-1H-indazole (5.00 g, 13.30 mmol, Ambeed, Inc.) and the flask was loaded into a nitrogen box. Then PEPPSI-IPr (1.05 g, 1.33 mmol, Labnetwork) was added, followed by THF (1.5 mL). Then (3-((tert-butyldimethylsilyl)oxy)propyl)zinc(II) bromide (66.5 mL, 33.2 mmol, Rieke metals) was added slowly while swirling the flask. The reaction flask was then removed from the nitrogen box and stirred under nitrogen at rt for 3 h. The reaction was quenched by the addition of saturated $NH_4Cl$ solution with vigorous stirring for 10 minutes. The mixture was then diluted with water and extracted with EtOAc. The combined organic layers were dried over sodium sulfate, filtered, and concentrated. The crude was sequentially purified by column chromatography on silica gel with a gradient of 0-10% EtOAc in heptane and reverse phase chromatography with a gradient of 0-80% MeCN (0.1% formic acid) in water (0.1% formic acid), to provide 5-(3-((tert-butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole (1.24 g, 2.40 mmol, 18% yield) as pale yellow oil. m/z (ESI): 515.2 $(M+H)^+$.

Intermediate L: Ethyl 4-(6-(pivaloyloxy)-8-(4,4,5,5-tetramethyl-1,3,2-dioxaborolan-2-yl)-1,2,3,4-tetrahydronaphthalen-1-yl)butanoate

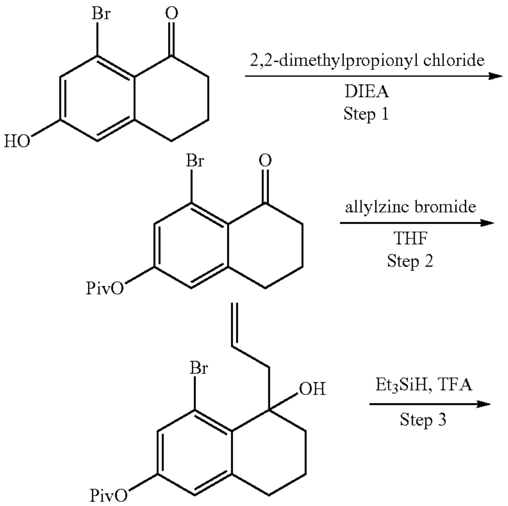

-continued

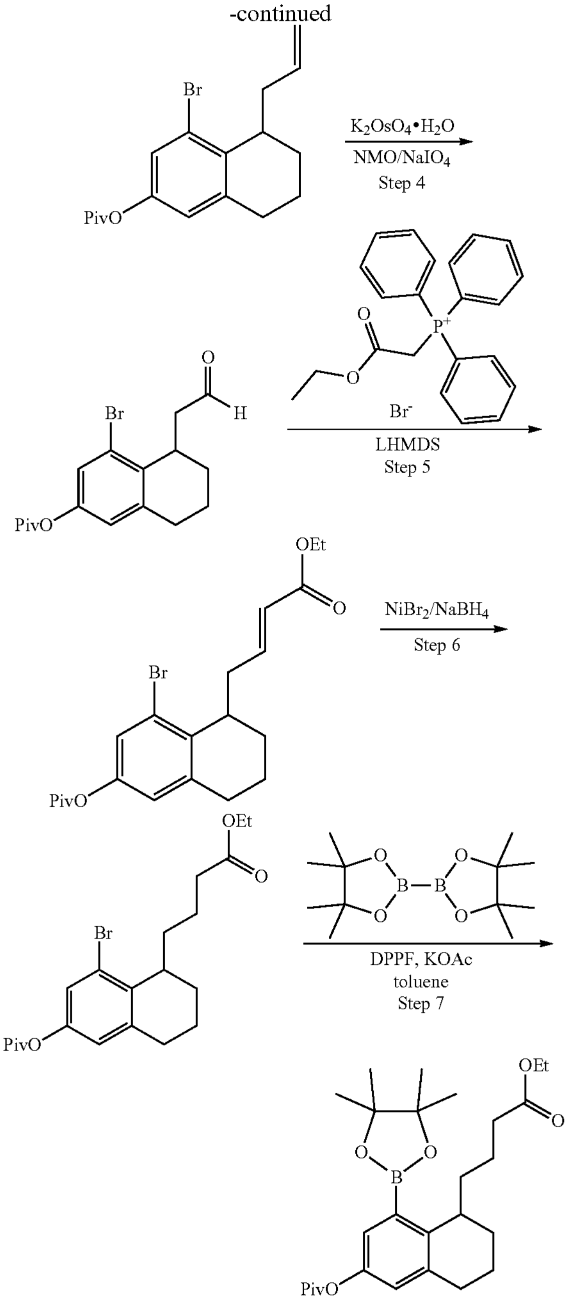

Intermediate L

Step 1. 4-Bromo-5-oxo-5,6,7,8-tetrahydronaphthalen-2-yl pivalate. To a 250-mL round-bottomed flask was added 8-bromo-6-hydroxy-tetralin-1-one (5.00 g, 20.70 mmol, PharmaBlock, Inc.) and DIEA (9.1 mL, 51.8 mmol) in 2-MeTHF (104 mL). The mixture was cooled to at 0° C. and 2,2-dimethyl-propanoyl chloride (2.88 g, 23.9 mmol) was slowly added. The reaction was stirred at at 0° C. for 1 h and was diluted with saturated $NH_4Cl$ solution and extracted with EtOAc. The organic extract was washed with saturated NaCl solution, dried over $MgSO_4$, filtered, and concentrated in vacuo. The crude material was purified by column chromatography on silica gel, eluting with a gradient of 0-50% EtOAc in hexane, to provide 4-bromo-5-oxo-5,6,7,8-tetrahydronaphthalen-2-yl pivalate as a brown oil (6.30 g, 18 mmol, 93% yield). m/z (ESI): 324.8/326.8 $(M+H)^+$.

Step 2. 5-Allyl-4-bromo-5-hydroxy-5,6,7,8-tetrahydronaphthalen-2-yl pivalate. To a 250-mL round-bottom flask was added 4-bromo-5-oxo-5,6,7,8-tetrahydronaphthalen-2-yl pivalate (4.20 g, 12.90 mmol) in THF (52 mL). The mixture was cooled to at 0° C. and allylzinc bromide (0.5 M in THF, 33.6 mL, 16.7 mmol) was added. The reaction was stirred for 1 h and was then diluted with saturated $NH_4Cl$ solution and extracted with EtOAc. The organic extract was concentrated, and the crude material was purified by column chromatography on silica gel, eluting with a gradient of 0-50% EtOAc in hexane, to provide 5-allyl-4-bromo-5-hydroxy-5,6,7,8-tetrahydronaphthalen-2-yl pivalate (4.20 g, 11.4 mmol, 89% yield) as colorless oil. m/z (ESI): 388.8/390.8 $(M+Na)^+$.

Step 3. 5-Allyl-4-bromo-5,6,7,8-tetrahydronaphthalen-2-yl pivalate. To a 25-mL round-bottomed flask was added 5-allyl-4-bromo-5-hydroxy-5,6,7,8-tetrahydronaphthalen-2-yl pivalate (4.20 g, 11.4 mmol) in DCM (57 mL). The mixture was cooled to at 0° C. and triethylsilane (3.99 g, 34.3 mmol) was added, followed by TFA (1.8 mL, 23 mmol). The reaction was stirred at 0° C. to rt for 3 h and was then diluted with water and extracted with EtOAc. The organic extract was washed with brine, dried over $MgSO_4$, filtered, and concentrated. The crude material was purified by column chromatography on silica gel, eluting with a gradient of 0-60% EtOAc in heptane, to provide 5-allyl-4-bromo-5,6,7,8-tetrahydronaphthalen-2-yl pivalate (3.00 g, 8.54 mmol, 75% yield) as colorless oil. m/z (ESI): 373.0/375.0 $(M+Na)^+$.

Step 4. 4-Bromo-5-(2-oxoethyl)-5,6,7,8-tetrahydronaphthalen-2-yl pivalate. To a 25-mL round-bottomed flask was added 5-allyl-4-bromo-5,6,7,8-tetrahydronaphthalen-2-yl pivalate (0.20 g, 0.57 mmol) and 4-methylmorpholine 4-oxide (0.10 g, 0.85 mmol) in acetone (2.1 mL) and water (0.7 mL). Potassium dioxidodioxoosmium dihydrate (2.1 mg, 5.7 μmol, Oakwood Products, Inc.) was added and the reaction mixture was stirred at rt for 2 h. Sodium (meta)periodate (0.24 g, 1.14 mmol) was added and stirring was continued for an additional hour. The reaction mixture was diluted with water and extracted with EtOAc. The organic extract was washed with saturated NaCl solution, dried over $MgSO_4$, filtered, and concentrated in vacuo. The crude material was purified by column chromatography, eluting with a gradient of 0-45% EtOAc in heptane, to provide 4-bromo-5-(2-oxoethyl)-5,6,7,8-tetrahydronaphthalen-2-yl pivalate (0.10 g, 0.28 mmol, 50% yield) as colorless oil. m/z (ESI): 374.8/376.8 $(M+Na)^+$. $^1H$ NMR (400 MHz, CHLOROFORM-d) δ ppm 9.85 (m, 1H), 7.04-7.22 (m, 1H), 6.57-6.89 (m, 1H), 3.61-3.82 (m, 1H), 2.76-2.98 (m, 3H), 2.51-2.68 (m, 1H), 1.70-1.94 (m, 4H), 1.36 (s, 9H).

Step 5. Ethyl (E/Z)-4-(8-bromo-6-(pivaloyloxy)-1,2,3,4-tetrahydronaphthalen-1-yl)but-2-enoate. To a 25-mL round-bottomed flask was added (carbethoxymethyl)triphenylphosphonium bromide (0.24 g, 0.57 mmol) in THF (1.4 mL). The mixture was cooled to at 0° C. and lithium bis(trimethylsilyl)amide solution, (1 M in THF, 0.50 mL, 0.5 mmol) was added. The reaction mixture was stirred for 30 minutes and then 4-bromo-5-(2-oxoethyl)-5,6,7,8-tetrahydronaphthalen-2-yl pivalate (0.10 g, 0.28 mmol) was added. The reaction mixture was stirred at rt for 16 h. The crude material was purified by column chromatography, eluting with a gradient of 0-25% EtOAc in heptane, to provide ethyl (E/Z)-4-(8-bromo-6-(pivaloyloxy)-1,2,3,4-tetrahydronaphthalen-1-yl)but-2-enoate as colorless oil. m/z (ESI): 422.8/424.8 $(M+H)^+$. NMR indicated a mixture of cis/trans (~1:2 ratio) isomers.

Step 6. Ethyl 4-(8-bromo-6-(pivaloyloxy)-1,2,3,4-tetrahydronaphthalen-1-yl)butanoate. To a 25-mL round-bottom flask was added ethyl (E/Z)-4-(8-bromo-6-(pivaloyloxy)-1,2,3,4-tetrahydronaphthalen-1-yl)but-2-enoate (0.28 g, 0.66 mmol) in THF (1.6 mL) and methanol (1.6 mL). The mixture was cooled to at 0° C. and nickel (II) bromide (0.17 g, 0.79 mmol) was added. After stirring at 0° C. for 15 min sodium borohydride (63 mg, 1.65 mmol) was added. The mixture was stirred for 1 h and was quenched with water and extracted with EtOAc. The organic layer was separated, dried ($Na_2SO_4$) and concentrated. The crude material was purified by column chromatography on silica gel, eluting with a gradient of 0-45% EtOAc in heptane, to provide ethyl 4-(8-bromo-6-(pivaloyloxy)-1,2,3,4-tetrahydronaphthalen-1-yl)butanoate. m/z (ESI): 446.8/448.8 $(M+Na)^+$.

Step 7. Ethyl 4-(6-(pivaloyloxy)-8-(4,4,5,5-tetramethyl-1,3,2-dioxaborolan-2-yl)-1,2,3,4-tetrahydronaphthalen-1-yl)butanoate. To a 20-mL vial was added ethyl 4-(8-bromo-6-(pivaloyloxy)-1,2,3,4-tetrahydronaphthalen-1-yl)butanoate (0.25 g, 0.59 mmol), bis(pinacalato)diboron (0.15 g, 0.59 mmol), potassium acetate (0.17 g, 1.76 mmol), and 1,1'-bis(diphenylphosphino)ferrocene-palladium dichloride (43 mg, 0.059 mmol) in toluene (2.9 mL). The reaction mixture was purged with nitrogen and then stirred at 90° C. for 3 h. After cooling to rt, the crude material was purified by column chromatography on silica gel, eluting with a gradient of 0-45% EtOAc in heptane, to provide ethyl 4-(6-(pivaloyloxy)-8-(4,4,5,5-tetramethyl-1,3,2-dioxaborolan-2-yl)-1,2,3,4-tetrahydronaphthalen-1-yl)butanoate (0.20 g, 0.42 mmol, 50% yield). m/z (ESI): 473.1 $(M+H)^+$.

Intermediate M: 5-(But-3-en-1-yl)-6-methyl-1-(tetrahydro-2H-pyran-2-yl)-4-(4,4,5,5-tetramethyl-1,3,2-dioxaborolan-2-yl)-1H-indazole

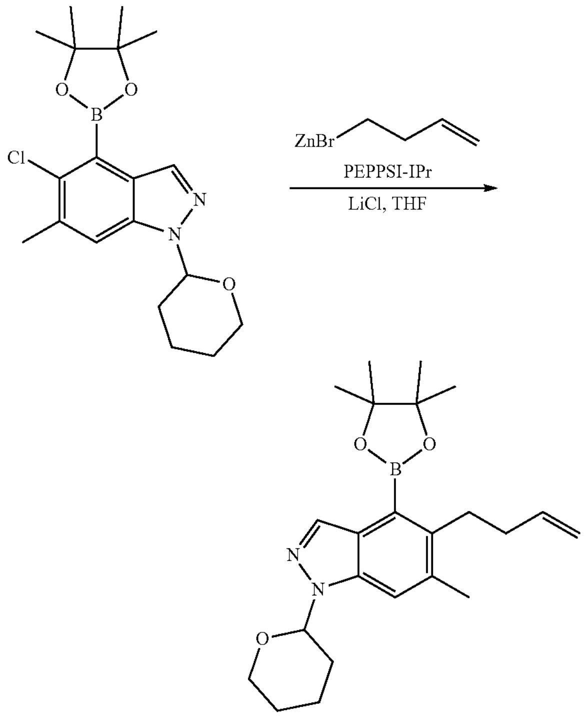

Intermediate M

A flask was charged with 5-chloro-6-methyl-1-(tetrahydro-2H-pyran-2-yl)-4-(4,4,5,5-tetramethyl-1,3,2-dioxaborolan-2-yl)-1H-indazole (1.00 g, 2.65 mmol, Ambeed, Inc.) and PEPPSI-IPr (0.42 g, 0.53 mmol, LabNetwork). Then, but-3-en-1-ylzinc(II) bromide (0.5 M in THF, 10.6 mL, 5.3 mmol) and LiCl (0.5 M in THF, 5.3 mL, 2.6 mmol) were added subsequently. The mixture was purged with nitrogen for 10 min and then heated to 40° C. for 16 h. Upon completion, the reaction was quenched with water and extracted with EtOAc. The organic layer was concentrated and purified via reverse phase chromatography, to provide 5-(but-3-en-1-yl)-6-methyl-1-(tetrahydro-2H-pyran-2-yl)-4-(4,4,5,5-tetramethyl-1,3,2-dioxaborolan-2-yl)-1H-indazole (0.59 g, 1.49 mmol, 56% yield) as light yellow solid. m/z (ESI): 397.2 $(M+H)^+$.

Intermediate N: 2-(8-Allylnaphthalen-1-yl)-4,4,5,5-tetramethyl-1,3,2-dioxaborolane

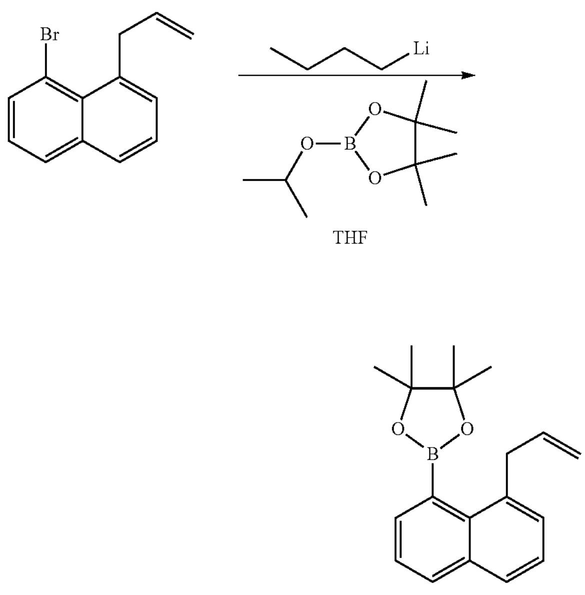

Intermediate N

A 250 mL round-bottom flask was charged with 1-allyl-8-bromonaphthalene (2.33 g, 9.43 mmol, CombiBlocks) and dry THF (100 mL). The mixture was cooled to −78° C. and n-BuLi (2.5 M in hexanes, 4.9 mL, 12.3 mmol) was added dropwise. The resulting mixture was stirred at −78° C. for 30 min. Then, 2-isopropoxy-4,4,5,5-tetramethyl-1,3,2-dioxaborolane (2.6 mL, 14.1 mmol, Sigma-Aldrich Corporation) was added and the reaction mixture was allowed to warm to rt over 1 h. The reaction mixture was quenched with water and extracted with EtOAc. The combined organic layers were dried and concentrated. The crude mixture was purified by column chromatography on silica gel, eluting with a gradient of 0-50% EtOAc in heptane, to provide 2-(8-allylnaphthalen-1-yl)-4,4,5,5-tetramethyl-1,3,2-dioxaborolane (2.70 g, 9.18 mmol, 97% yield), which was contaminated with des-allyl impurity. $^1H$ NMR (400 MHz, METHANOL-$d_4$) δ ppm 7.92 (d, J=8.2 Hz, 1H), 7.76 (d, J=7.9 Hz, 1H), 7.64 (d, J=6.7 Hz, 1H), 7.37-7.48 (m, 3H), 6.14 (ddt, J=16.9, 10.2, 6.7, 6.7 Hz, 1H), 5.08-5.24 (m, 2H), 3.97 (d, J=6.7 Hz, 2H), 1.45 (s, 12H).

Intermediate O: Methyl (Z)-5-(4-bromo-6-chloro-1-(tetrahydro-2H-pyran-2-yl)-1H-indazol-5-yl)pent-4-enoate and Intermediate P: Methyl 5-(4-bromo-6-chloro-1-(tetrahydro-2H-pyran-2-yl)-1H-indazol-5-yl)pentanoate

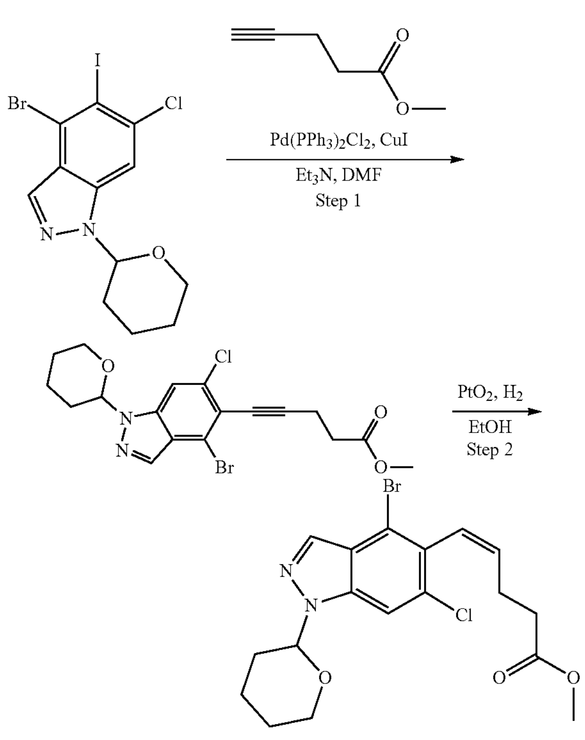

Intermediate O

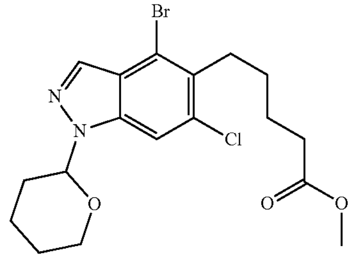

Intermediate P

Step 1. Methyl 5-(4-bromo-6-chloro-1-(tetrahydro-2H-pyran-2-yl)-1H-indazol-5-yl)pent-4-ynoate. To a 40-mL vial was charged with methyl pent-4-ynoate (1.52 g, 13.6 mmol), 4-bromo-6-chloro-5-iodo-1-(tetrahydro-2H-pyran-2-yl)-1H-indazole (3.00 g, 6.80 mmol, Lab Network), triethylamine (9.5 mL, 68 mmol), and N,N-dimethylformamide (14 mL). This solution was sparged with nitrogen for 20 minutes, and copper iodide (39 mg, 0.20 mmol) and bis(triphenylphosphine)palladium dichloride (0.24 g, 0.34 mmol) were added. The reaction mixture was stirred at rt for 16 h, then heated to 35° C. for 6 h. The reaction was diluted with saturated aqueous ammonium chloride solution and extracted with EtOAc. The aqueous layer was extracted with EtOAc, washed with brine, and the organics were dried over sodium sulfate and concentrated. The crude material was purified by column chromatography on silica gel, eluting with 0-30% EtOAc in heptane, to provide methyl 5-(4-bromo-6-chloro-1-(tetrahydro-2H-pyran-2-yl)-1H-indazol-5-yl)pent-4-ynoate (2.23 g, 5.24 mmol, 77% yield) as off-white solid.

Step 2. Methyl (Z)-5-(4-bromo-6-chloro-1-(tetrahydro-2H-pyran-2-yl)-1H-indazol-5-yl)pent-4-enoate & methyl 5-(4-bromo-6-chloro-1-(tetrahydro-2H-pyran-2-yl)-1H-indazol-5-yl)pentanoate. To a 60 mL hydrogenation reactor was charged with methyl 5-(4-bromo-6-chloro-1-(tetrahydro-2H-pyran-2-yl)-1H-indazol-5-yl)pent-4-ynoate (0.60 g, 1.41 mmol) and platinum(IV) oxide (6.4 mg, 0.028 mmol). The reactor was purged with nitrogen and then charged with EtOH (7 mL). The reaction vessel was charged with hydrogen (20 psi), and the reaction was stirred at rt for 18 h. Upon completion, the reaction mixture was diluted with EtOAc, filtered through celite, and the filtrate was concentrated. The crude material was purified by column chromatography on silica gel, eluting with 0-30% EtOAc in heptane, to provide methyl (Z)-5-(4-bromo-6-chloro-1-(tetrahydro-2H-pyran-2-yl)-1H-indazol-5-yl)pent-4-enoate (0.22 g, 0.51 mmol, 36% yield, Intermediate O) as colorless oil. m/z (ESI): 427.8 $(M+H)^+$. Also isolated was methyl 5-(4-bromo-6-chloro-1-(tetrahydro-2H-pyran-2-yl)-1H-indazol-5-yl)pentanoate (0.28 g, 0.65 mmol, 46% yield, Intermediate P). m/z (ESI): 429.0 $(M+H)^+$ Intermediate Q: Ethyl 2-(3-(4-bromo-6-chloro-1-(tetrahydro-2H-pyran-2-yl)-1H-indazol-5-yl)propoxy)acetate

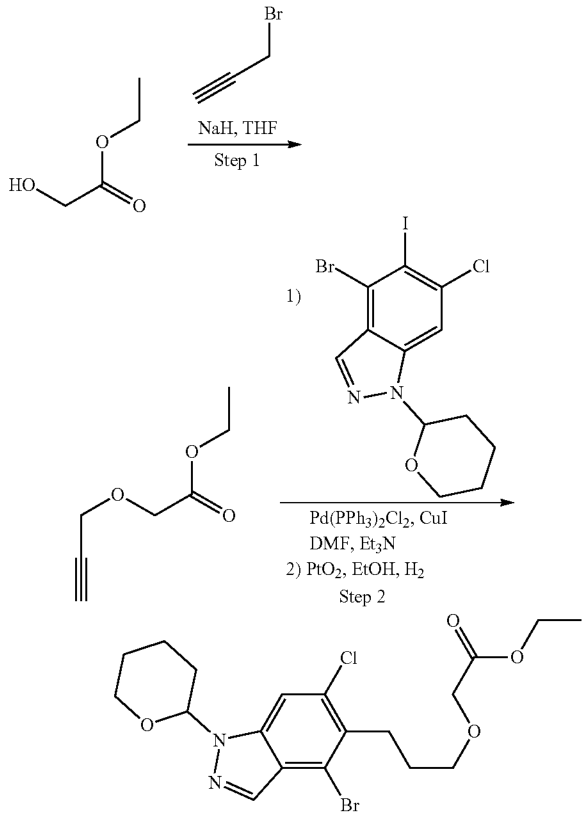

Intermediate Q

Step 1. Ethyl 2-(prop-2-yn-1-yloxy)acetate. To an oven dried 3-necked flask under nitrogen was charged with ethyl glycolate (3.49 mL, 33.6 mmol) and THF (96 mL). Sodium hydride, 60% dispersion in mineral oil (1.61 g, 40.3 mmol) was added portionwise and the reaction mixture was stirred at rt for 1 h. Propargyl bromide (5.0 mL, 33.6 mmol) was then added dropwise, and the reaction was stirred at rt for 48 h. The mixture was diluted with saturated aqueous ammonium chloride and extracted with EtOAc. The organic layers were dried over sodium sulfate, filtered, and concentrated. The crude material was purified by column chromatography on silica gel, eluting with 0-20% ethyl acetate in heptane, to provide ethyl 2-(prop-2-yn-1-yloxy)acetate (1.90 g, 13.40 mmol, 40% yield) as light-yellow oil. $^1H$ NMR (400 MHz, CHLOROFORM-d) δ ppm 4.34 (d, J=2.5 Hz, 2H), 4.20-4.29 (m, 4H), 2.49 (t, J=2.4 Hz, 1H), 1.32 (t, J=7.2 Hz, 3H).

Step 2. Ethyl 2-(3-(4-bromo-6-chloro-1-(tetrahydro-2H-pyran-2-yl)-1H-indazol-5-yl)propoxy)acetate. To a 40 mL vial was charged with 4-bromo-6-chloro-5-iodo-1-(tetrahydro-2H-pyran-2-yl)-1H-indazole (2.00 g, 4.53 mmol, LabNetwork), DMF (9.06 mL), and triethylamine (6.4 mL, 45.3 mmol). This solution was sparged with nitrogen and bis(triphenylphosphine)palladium(II) dichloride (0.16 g, 0.23 mmol) and copper iodide (26 mg, 0.14 mmol) were added. This solution was stirred at 35° C. for 24 h. The reaction mixture was diluted with saturated aqueous ammonium chloride and extracted with EtOAc. The organics were dried over sodium sulfate, concentrated, and the crude material was purified by column chromatography on silica gel, eluting with 0-40% EtOAc in heptane, to provide ethyl 2-((3-(4-bromo-6-chloro-1-(tetrahydro-2H-pyran-2-yl)-1H-indazol-5-yl)prop-2-yn-1-yl)oxy)acetate (0.86 g, 1.89 mmol, 42% yield) as orange oil. m/z (ESI): 455.0 $(M+H)^+$.

To a 60 mL ChemGlass reactor tube was charged ethyl 2-((3-(4-bromo-6-chloro-1-(tetrahydro-2H-pyran-2-yl)-1H-indazol-5-yl)prop-2-yn-1-yl)oxy)acetate (0.86 g, 1.89 mmol) and platinum(IV) oxide (21 mg, 0.094 mmol). This tube was purged with nitrogen and then charged with ethanol (9.5 mL). The reaction vessel was charged with hydrogen (30 psi) and stirred at rt for 14 h. The reaction mixture was filtered through celite washing with EtOAc. The crude material was purified by column chromatography on silica gel, eluting with 0-30% EtOAc in heptane, to provide ethyl 2-(3-(4-bromo-6-chloro-1-(tetrahydro-2H-pyran-2-yl)-1H-indazol-5-yl)propoxy)acetate (0.26 g, 0.57 mmol, 30% yield) as colorless oil. m/z (ESI): 459.0 $(M+H)^+$.

Intermediate R. 3-(But-3-en-1-yl)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol

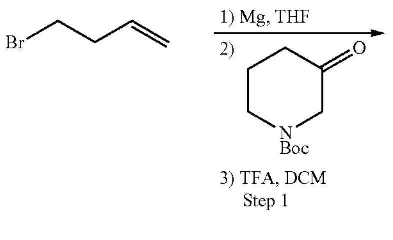

-continued

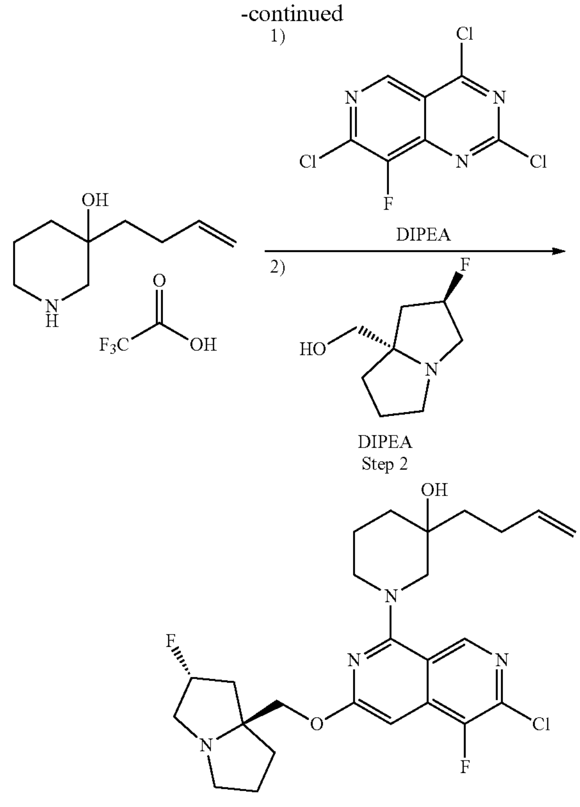

Intermediate R

Step 1. 3-(But-3-en-1-yl)piperidin-3-ol 2,2,2-trifluoroacetate. To a 250-mL round-bottom flask was added magnesium turnings (0.73 g, 30.1 mmol), THF (150 mL), and 4-bromobut-1-ene (4.07 g, 30.1 mmol, CombiBlocks). The mixture was heated to 80° C. After 2 h, the mixture was cooled to −78° C. and a solution of tert-butyl 3-oxopiperidine-1-carboxylate (3.00 g, 15.1 mmol, CombiBlocks) in THF (10 mL) was added. The mixture was allowed to slowly warm to rt. After 1 h, the mixture was quenched with saturated $NH_4Cl$, extracted with EtOAc, and concentrated. The resulting red oil was dissolved in DCM (100 mL) and TFA (11.6 mL, 151 mmol) was added. The mixture was stirred at 35° C. for 16 h. Upon completion, the mixture was concentrated and purified via reverse phase chromatography, to provide 3-(but-3-en-1-yl)piperidin-3-ol 2,2,2-trifluoroacetate salt (1.24 g, 4.61 mmol, 31% yield) as orange oil. m/z (ESI): 156.3 $(M+H)^+$.

Step 2. 3-(But-3-en-1-yl)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. To a round-bottom flask was added 2,4,7-trichloro-8-fluoropyrido[4,3-d]pyrimidine (1.20 g, 4.75 mmol, Enamine) in acetonitrile (30 mL). The mixture was cooled to 0° C. and 3-(but-3-en-1-yl)piperidin-3-ol 2,2,2-trifluoroacetate salt (1.28 g, 4.75 mmol) in MeCN (10 mL) was added, followed by N-ethyl-N-isopropylpropan-2-amine (2.48 mL, 14.3 mmol). The mixture was allowed to warm to rt over 20 min. ((2R,7aS)-2-fluorotetrahydro-1H-pyrrolizin-7a(5H)-yl)methanol (1.14 g, 7.13 mmol, LabNetwork) was added and the mixture was heated to 80° C. for 16 h. After cooling to rt, the mixture was concentrated and the residue was purified by column chromatography on silica gel, eluting with a gradient of 0-50% (3:1 EtOAc:EtOH, 2% TEA) in heptane to give 3-(but-3-en-1-yl)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.76 g, 1.54 mmol, 32% yield) as orange solid. m/z (ESI): 494.2 $(M+H)^+$.

Intermediate S: Methyl 4-(8-bromo-3,4-dihydroquinolin-1(2H)-yl)butanoate

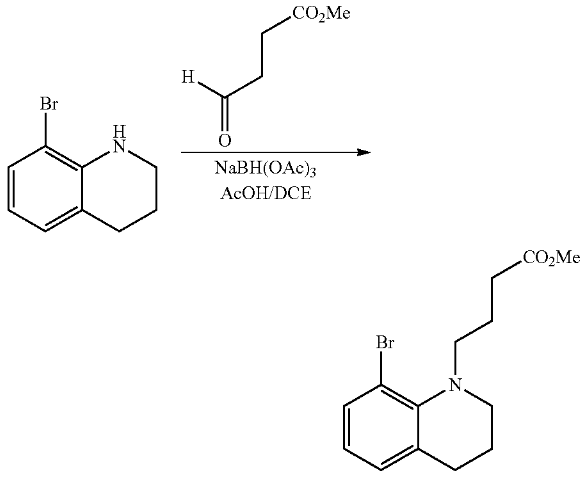

Intermediate S

A solution of 8-bromo-1,2,3,4-tetrahydroquinoline (1.25 mL, 5.89 mmol, Aurum Pharmatech LLC), 4-oxobutanoic acid methyl ester (1.37 g, 11.8 mmol, CombiBlocks Inc.), and acetic acid (0.14 mL, 2.36 mmol) in DCE (10 mL) was stirred at rt for 20 min. Sodium triacetoxyborohydride (1.50 g, 7.10 mmol) was added in one portion. The resulting mixture was stirred at rt for 3.5 h and at then at 50° C. for 20 h. The crude mixture was poured into ice cold saturated sodium carbonate solution and extracted with 20% MeOH/DCM. The combined organics were dried over sodium sulfate and concentrated in vacuo. The crude material was purified by column chromatography on silica gel, eluting with a gradient of 0-50% EtOAc in heptane, to provide methyl 4-(8-bromo-3,4-dihydroquinolin-1(2H)-yl)butanoate (0.64 g, 2.03 mmol, 35% yield) as colorless oil. $^1H$ NMR (CHLOROFORM-d, 400 MHz) δ 7.3-7.4 (m, 1H), 6.98 (dd, 1H, J=1.0, 7.5 Hz), 6.75 (t, 1H, J=7.6 Hz), 3.70 (s, 3H), 3.1-3.2 (m, 2H), 3.0-3.0 (m, 2H), 2.79 (t, 2H, J=6.7 Hz), 2.42 (t, 2H, J=7.5 Hz), 2.1-2.2 (m, 2H), 1.8-1.9 (m, 2H). m/z (ESI): 312.2 and 314.2 $(M+H)^+$.

Intermediate T: tert-Butyl 5-hydroxy-4-(4,4,5,5-tetramethyl-1,3,2-dioxaborolan-2-yl)-1H-indazole-1-carboxylate

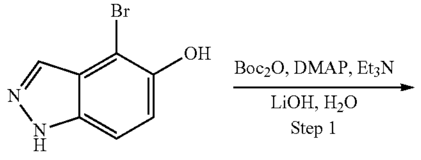

-continued

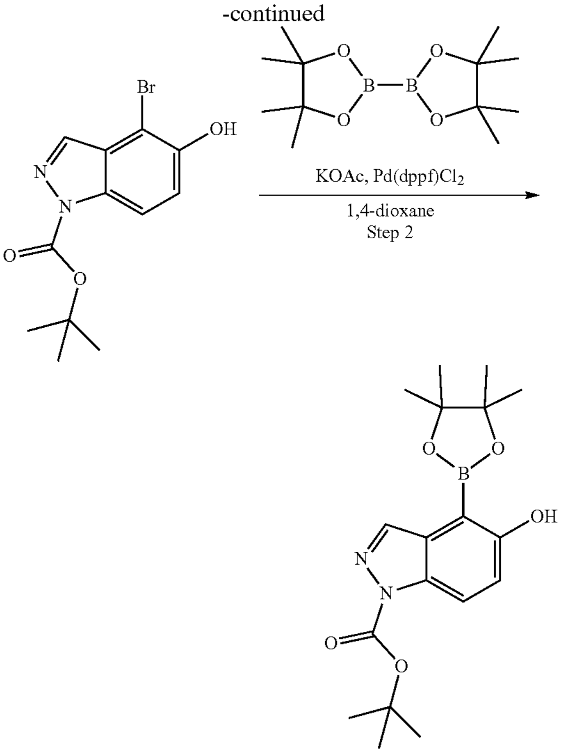

Intermediate T

Step 1: tert-Butyl 4-bromo-5-hydroxy-1H-indazole-1-carboxylate. To a 250-mL round-bottom flask was added 4-bromo-1H-indazol-5-ol (6.30 g, 29.6 mmol, Enamine) and triethylamine (12.5 mL, 89 mmol) in tetrahydrofuran (70 mL). A solution of di-tert-butyl dicarbonate (14.2 g, 65.1 mmol) in tetrahydrofuran (70 mL) was slowly added via syringe. After the addition was completed, 4-dimethylaminopyridine (0.18 g, 1.48 mmol) was added. The reaction mixture was stirred at rt for 1 h, then cooled to 0° C. Lithium hydroxide, monohydrate (7.45 g, 177 mmol) in water (30 mL) was added slowly. The reaction mixture was allowed to warm rt and stirred for 2 days. The mixture was slowly diluted with 2 M HCl (90 mL) to pH-6 at 0° C. and extracted with EtOAc. The combined organic layers were washed with brine, dried over $MgSO_4$, filtered, and concentrated in vacuo. The crude material was purified by column chromatography on silica gel, eluting with a gradient of 0-40% [3:1 EtOAc:EtOH] in heptane, to provide tert-butyl 4-bromo-5-hydroxy-1H-indazole-1-carboxylate (3.80 g, 12.10 mmol, 41% yield) as off-white solid. m/z (ESI): 257.1 $(M-^tBu)^+$. $^1$H NMR (400 MHz, DMSO-$d_6$) δ ppm 9.98-10.84 (m, 1H), 8.21 (d, J=0.6 Hz, 1H), 7.91 (d, J=8.9 Hz, 1H), 7.27 (d, J=8.8 Hz, 1H), 1.65 (s, 9H).

Step 2: tert-Butyl 5-hydroxy-4-(4,4,5,5-tetramethyl-1,3,2-dioxaborolan-2-yl)-1H-indazole-1-carboxylate. A 20-mL vial was charged with tert-butyl 4-bromo-5-hydroxy-1H-indazole-1-carboxylate (0.86 g, 2.75 mmol), potassium acetate (0.54 mg, 5.49 mmol), 4,4,4',4',5,5,5',5'-octamethyl-2,2'-bi(1,3,2-dioxaborolane) (0.98 g, 3.84 mmol) and Pd(dppf)$Cl_2$ (0.16 g, 0.22 mmol) in 1,4-dioxane (10 mL). The reaction mixture was heated to 80° C. for 6 h. The crude mixture was cooled to rt and filtered through a Whatman PTFE 0.45 μm filter. The crude was directly used in the next step without further purification.

Intermediate U: (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol

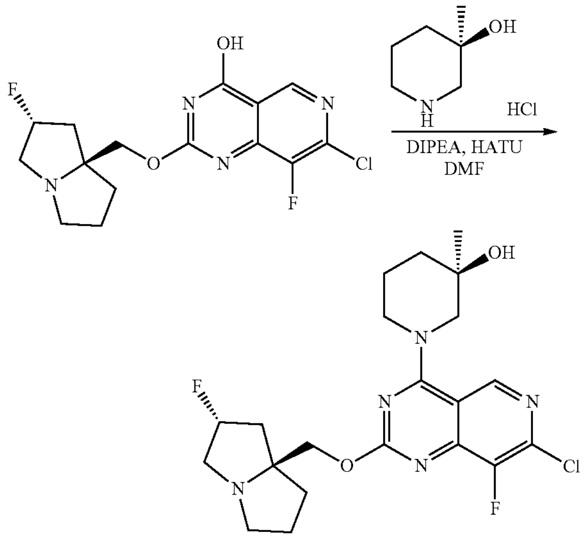

Intermediate U

To a 100 mL round-bottom flask was charged with 7-chloro-8-fluoro-2-(((2R,7aS)-2-fluorotetrahydro-1H-pyrrolizin-7a(5H)-yl)methoxy)pyrido[4,3-d]pyrimidin-4-ol (2.10 g, 5.90 mmol, Intermediate Z) and N-ethyl-N-isopropylpropan-2-amine (3.1 mL, 18 mmol) in DMF (29 mL). HATU (3.36 g, 8.8 mmol) was added in one portion and the reaction mixture was stirred at rt for 30 minutes. (R)-3-Methylpiperidin-3-ol hydrochloride (0.98 g, 6.5 mmol) was then added. The reaction mixture was stirred at rt for 2 h. The mixture was partitioned between ethyl acetate and saturated aqueous sodium chloride solution. The aqueous layer was extracted with EtOAc, and the combined organics were washed with brine, dried, and concentrated. The crude material was purified by column chromatography on silica gel, eluting with 0-100% 3:1 (EtOAc:EtOH with 2% triethylamine) in heptane, to provide (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol (2.60 g, 5.80 mmol, 98% yield) as brown solid. m/z (ESI): 455.0 $(M+H)^+$.

Intermediate V: (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-3-(fluoromethyl)piperidin-3-ol

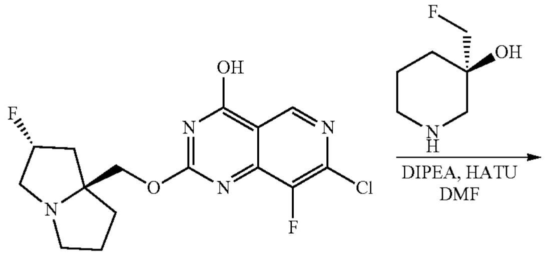

-continued

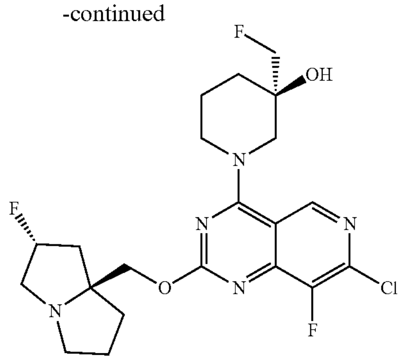

Intermediate V

To a 100 mL round-bottom flask was charged with 7-chloro-8-fluoro-2-(((2R,7aS)-2-fluorotetrahydro-1H-pyrrolizin-7a(5H)-yl)methoxy)pyrido[4,3-d]pyrimidin-4-ol (3.00 g, 8.41 mmol, Intermediate Z) and N-ethyl-N-isopropylpropan-2-amine (4.4 mL, 25.2 mmol) in DMF (34 mL). HATU (4.80 g, 12.60 mmol) was added, and the reaction mixture was stirred at rt for 20 minutes. (R)-3-(Fluoromethyl)piperidin-3-ol (1.23 g, 9.25 mmol) was then added in one portion. The reaction mixture was stirred at rt for 16 h. The mixture was partitioned between ethyl acetate and brine. The aqueous layer was extracted with EtOAc, and the combined organics were washed with brine, dried, and concentrated. The crude material was purified by column chromatography on silica gel, eluting with 0-100% 3:1 (EtOAc:EtOH with 2% triethylamine) in heptane, to provide (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-(fluoromethyl)piperidin-3-ol (2.71 g, 5.74 mmol, 68% yield) as orange solid. m/z (ESI): 472.0 $(M+H)^+$.

Intermediate W: (R)-1-(8-Fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-ol

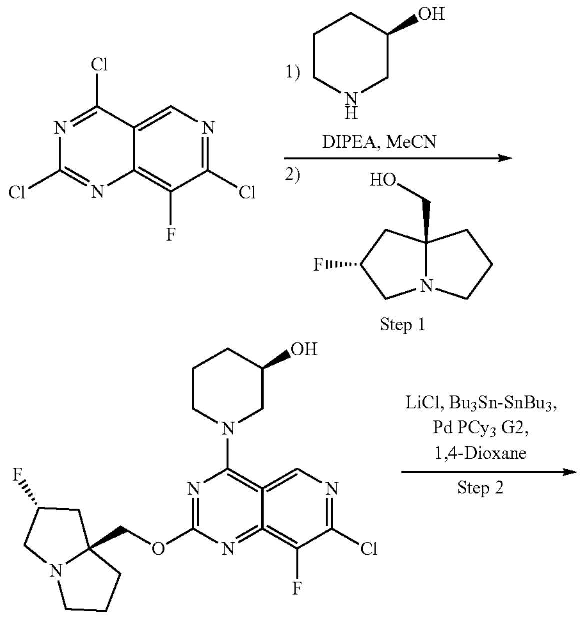

-continued

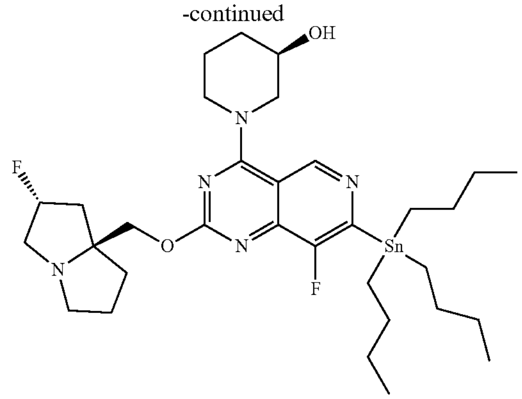

Intermediate W

Step 1. (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. To a suspension of 2,4,7-trichloro-8-fluoropyrido[4,3-d]pyrimidine (2.00 g, 7.92 mmol, Enamine) in acetonitrile (22.5 mL) at 0° C. was added (3R)-piperidin-3-ol (0.80 g, 7.92 mmol, CombiBlocks Inc.) and DIPEA (6.9 mL, 39.6 mmol). The reaction mixture was stirred at 0° C. for 40 min. The desired intermediate (R)-1-(2,7-dichloro-8-fluoropyrido[4,3-d]pyrimidin-4-yl)piperidin-3-ol was observed via LCMS (m/z (ESI): 317.2 $(M+H)^+$). A solution of ((2R,7aS)-2-fluorotetrahydro-1H-pyrrolizin-7a(5H)-yl)methanol (2.27 g, 14.3 mmol, BLD Pharmatech) in acetonitrile (2 mL) was added and reaction mixture was stirred at 80° C. for 16 h. After cooling to rt, the reaction mixture was concentrated under reduced pressure. The crude material was purified by column chromatography on silica gel, eluting with a gradient of 0-75% (3:1 EtOAc:EtOH with 2% triethylamine) in heptane, to provide (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (2.45 g, 5.57 mmol, 70% yield) as yellow solid. m/z (ESI): 440.0 $(M+H)^+$.

Step 2. (R)-1-(8-Fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-ol. To a 40 mL vial was charged with (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (1.00 g, 2.27 mmol), LiCl (0.48 g, 11.4 mmol), and 1,4-dioxane (8.5 mL). The solution was degassed by sparging with nitrogen for 15 min. [2-(2-Aminophenyl)phenyl]-chloro-palladium tricyclohexylphosphane (0.54 g, 0.91 mmol) and bis(tributyltin) (3.4 mL, 6.82 mmol) were added and the reaction was sealed and heated to 100° C. for 15 h. After cooling to rt, the mixture was filtered through celite and washed with EtOAc. The filtrate was concentrated, and the crude material was purified by column chromatography on silica gel column, eluting with a gradient of 0-100% (3:1 EtOAc:EtOH with 2% triethylamine) in heptane, to provide (R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-ol (0.85 g, 1.22 mmol, 54% yield) as yellow semi-solid. m/z (ESI): 696.0 $(M+H)^+$.

Intermediate X: 7-Bromo-6,8-difluoro-2-(((2R,7aS)-2-fluorotetrahydro-1H-pyrrolizin-7a(5H)-yl)methoxy)quinazolin-4-ol

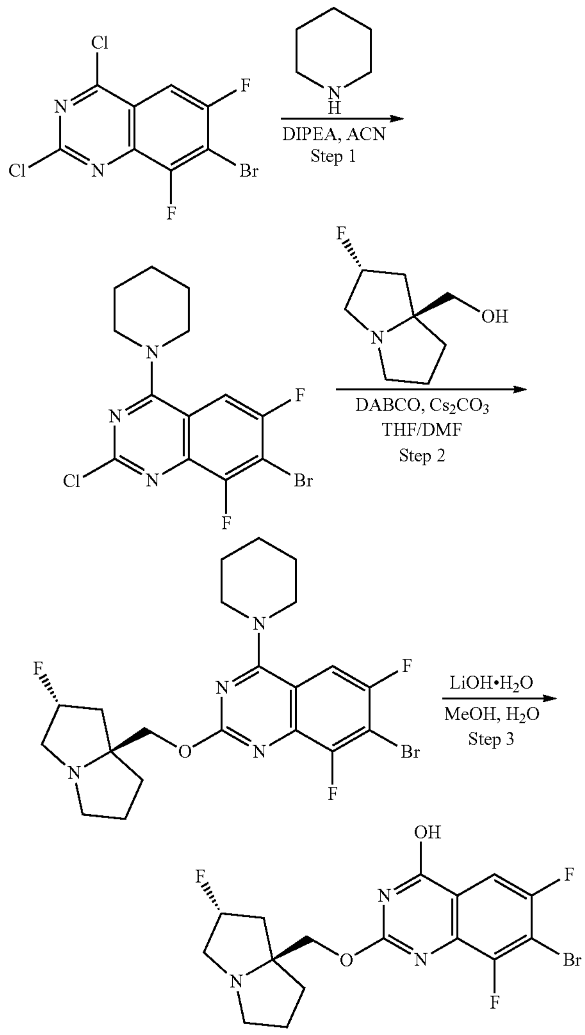

Intermediate X

Step 1. 7-Bromo-2-chloro-6,8-difluoro-4-(piperidin-1-yl)quinazoline. To a solution of 7-bromo-2,4-dichloro-6,8-difluoroquinazoline (50.0 g, 159 mmol) in acetonitrile (800 mL) at 0° C. was added piperidine (15.8 mL, 159 mmol) and DIPEA (55.6 mL, 319 mmol) in portions at 0° C. The mixture was stirred at 0° C. for 30 min, then was concentrated under reduced pressure. The crude product was triturated with petroleum ether (100 mL) at 20° C. for 1 h. The suspension was filtered, and the filter cake was washed with petroleum ether, dried under vacuum to give 7-bromo-2-chloro-6,8-difluoro-4-(piperidin-1-yl)quinazoline (52.6 g, 145 mmol, 91% yield) as yellow solid. m/z (ESI): 362.1/364.1 $(M+H)^+$.

Step 2. 7-Bromo-6,8-difluoro-2-(((2R,7aS)-2-fluorotetrahydro-1H-pyrrolizin-7a(5H)-yl)methoxy)-4-(piperidin-1-yl)quinazoline. To a solution of 7-bromo-2-chloro-6,8-difluoro-4-(piperidin-1-yl)quinazoline (55.0 g, 152 mmol) in THF (550 mL) and DMF (550 mL) was added ((2R,7aS)-2-fluorotetrahydro-1H-pyrrolizin-7a(5H)-yl)methanol (29.0 g, 182 mmol, LabNetwork), $Cs_2CO_3$ (59.3 g, 182 mmol) and DABCO (5.10 g, 45.5 mmol) in sequence. The reaction mixture was stirred at 25° C. for 10 h and was then diluted with $H_2O$ and extracted with EtOAc. The combined organic layers were dried over $Na_2SO_4$, filtered, and the filtrate was concentrated under reduced pressure. The crude product was triturated with MTBE (80 mL) at 20° C. for 1 h. The suspension was filtered and the filter cake was washed with MTBE, dried in vacuum to give 7-bromo-6,8-difluoro-2-(((2R,7aS)-2-fluorotetrahydro-1H-pyrrolizin-7a(5H)-yl)methoxy)-4-(piperidin-1-yl)quinazoline (41.3 g, 85 mmol 56% yield) as white solid. m/z (ESI): 485.1/487.1 $(M+H)^+$.

Step 3. 7-Bromo-6,8-difluoro-2-(((2R,7aS)-2-fluorotetrahydro-1H-pyrrolizin-7a(5H)-yl)methoxy)quinazolin-4-ol. To a solution of 7-bromo-6,8-difluoro-2-(((2R,7aS)-2-fluorotetrahydro-1H-pyrrolizin-7a(5H)-yl)methoxy)-4-(piperidin-1-yl)quinazoline (50.0 g, 103 mmol) in methanol (1 L) and water (500 mL) was added LiOH hydrate (15.14 g, 361 mmol). The reaction mixture was stirred at 100° C. for 10 h. This procedure was repeated on this scale three additional times.

After cooling to rt, the reaction mixtures were combined and concentrated under reduced pressure before the residue was diluted with $H_2O$ and extracted with EtOAc. The combined organic layers were washed with brine, dried over $Na_2SO_4$, filtered, and concentrated. The crude product was triturated with a mixed solvents of petroleum ether and EtOAc (1:1, 200 mL) at rt for 30 min. The suspension was filtered, and the filter cake was washed with the mixed solvents of petroleum ether and EtOAc (1:1), dried under vacuum to give 7-bromo-6,8-difluoro-2-(((2R,7aS)-2-fluorotetrahydro-1H-pyrrolizin-7a(5H)-yl)methoxy)quinazolin-4-ol (150 g, 358 mmol 87% yield) as white solid. m/z (ESI): 418.0/420.0 $(M+H)^+$.

Intermediate Y: 7-Bromo-8-fluoro-2-(((2R,7aS)-2-fluorotetrahydro-1H-pyrrolizin-7a(5H)-yl)methoxy)quinazolin-4-ol hydrobromide

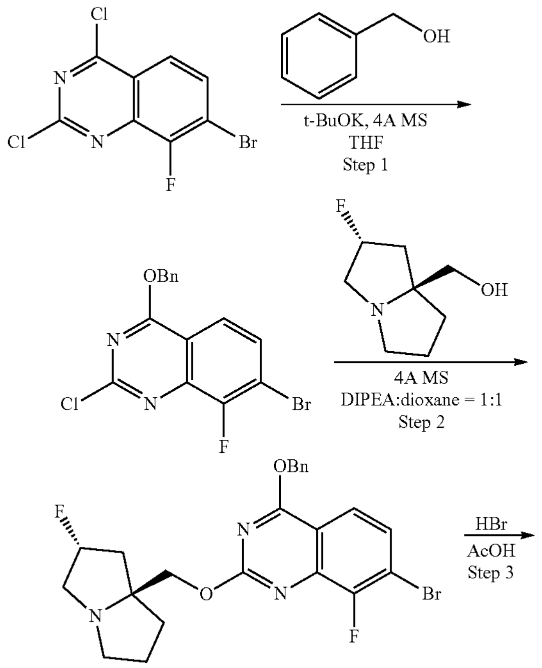

-continued

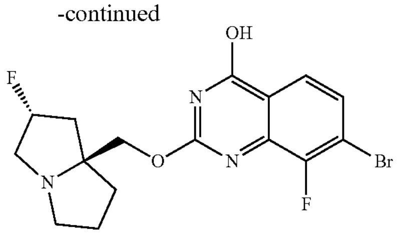

Intermediate Y

Step 1. 4-(Benzyloxy)-7-bromo-2-chloro-8-fluoroquinazoline. A solution of 7-bromo-2,4-dichloro-8-fluoroquinazoline (50.0 g, 169 mmol) in tetrahydrofuran (2 L) was treated with 4 Å molecular sieves (30 g), and then cooled to −60° C. The solution of phenylmethanol (16.6 mL, 161 mmol), pre-reacted with t-BuOK (1 M in THF, 161 mL, 161 mmol) at −60° C. was added dropwise. The mixture was stirred at −60° C. for 2 h. This procedure was repeated on this scale three additional times.

The reaction mixtures were combined and poured into water and then extracted with ethyl acetate. The combined organic layers were dried over $Na_2SO_4$, filtered, and concentrated under reduced pressure. The crude product was triturated with petroleum ether (800 mL) at 20° C. for 50 min. The suspension was filtered, and the filter cake was washed with petroleum ether, dried under vacuum to give 4-(benzyloxy)-7-bromo-2-chloro-8-fluoroquinazoline (220 g, 589 mmol, 88% yield) as yellow solid. m/z (ESI): 367.1/369.1 $(M+H)^+$.

Step 2. 4-(Benzyloxy)-7-bromo-8-fluoro-2-(((2R,7aS)-2-fluorotetrahydro-1H-pyrrolizin-7a(5H)-yl)methoxy)quinazoline. To a solution of 4-(benzyloxy)-7-bromo-2-chloro-8-fluoroquinazoline (70 g, 190 mmol) and 4 Å molecular sieves (30 g) in 1,4-dioxane (700 mL) was added ((2R,7aS)-2-fluorotetrahydro-1H-pyrrolizin-7a(5H)-yl)methanol (42.4 g, 267 mmol) and DIPEA (700 mL) in sequence. The mixture was stirred at 120° C. for 12 h. This procedure was repeated on similar scale 2 additional times.

After cooling to rt, the reaction mixtures were poured into water and extracted with ethyl acetate. The combined organic layers were dried over $Na_2SO_4$, filtered, and concentrated. The crude product was triturated with MTBE (800 mL) at 20° C. for 30 min. The suspension was filtered, and the filter cake was washed with MTBE, dried under vacuum to give 4-(benzyloxy)-7-bromo-8-fluoro-2-(((2R,7aS)-2-fluorotetrahydro-1H-pyrrolizin-7a(5H)-yl)methoxy)quinazoline (115 g, 235 mmol, 41% yield) as yellow solid. m/z (ESI): 490.3/492.2 $(M+H)^+$.

Step 3. 7-Bromo-8-fluoro-2-(((2R,7aS)-2-fluorotetrahydro-1H-pyrrolizin-7a(5H)-yl)methoxy)quinazolin-4-ol hydrobromide. 4-(Benzyloxy)-7-bromo-8-fluoro-2-(((2R,7aS)-2-fluorotetrahydro-1H-pyrrolizin-7a(5H)-yl)methoxy)quinazoline (35.0 g, 71.4 mmol) in 33% HBr in AcOH (33% solution, 250 mL, 71.4 mmol) was stirred at rt for 4 h. This procedure was repeated on similar scale 2 additional times.

The reaction mixtures were diluted with EtOAc, and the suspension was filtered. The filter cake was triturated with EtOAc (100 mL) at rt for 20 min. The suspension was filtered, and the filter cake was washed with EtOAc, dried under vacuum to give 7-bromo-8-fluoro-2-(((2R,7aS)-2-fluorotetrahydro-1H-pyrrolizin-7a(5H)-yl)methoxy)quinazolin-4-ol hydrobromide (105 g, 219 mmol, HBr salt) as white solid. m/z (ESI): 400.1/402.1 $(M+H)^+$.

Intermediate Z: 7-Chloro-8-fluoro-2-(((2R,7aS)-2-fluorotetrahydro-1H-pyrrolizin-7a(5H)-yl)methoxy)pyrido[4,3-d]pyrimidin-4-ol hydrobromide Intermediate Z

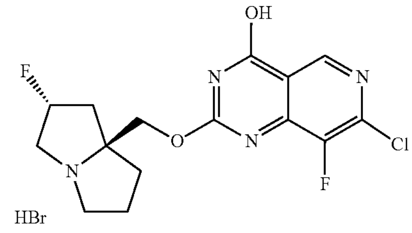

The title compound was synthesized in an analogous fashion to Intermediate Y, using 2,4,7-trichloro-8-fluoropyrido[4,3-d]pyrimidine (CAS #: 2454396-80-4, Enamine) in step 1. m/z (ESI): 357.2 $(M+H)^+$.

Intermediate AA: Ethyl 4-(2-fluoro-8-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-(methoxymethoxy)naphthalen-1-yl)butanoate

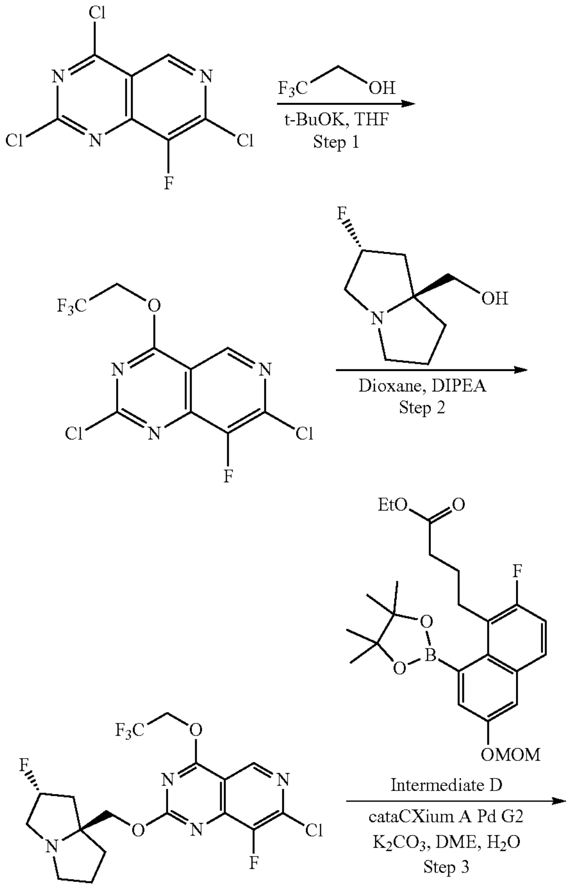

-continued

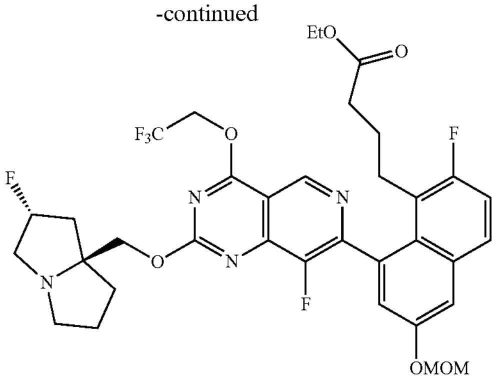

Intermediate AA

Step 1. 2,7-Dichloro-8-fluoro-4-(2,2,2-trifluoroethoxy)pyrido[4,3-d]pyrimidine. To a solution of 2,4,7-trichloro-8-fluoropyrido[4,3-d]pyrimidine (50.0 g, 198 mmol, Enamine) in tetrahydrofuran (750 mL) cooled to −60° C. was added 2,2,2-trifluoroethan-1-ol (18.82 g, 188 mmol), followed by t-BuOK (1 M in THF, 188 mL, 188 mmol) dropwise. The mixture was stirred at −60° C. for 2 h. The reaction mixture was quenched by addition of $H_2O$ (1 L) at 20° C. and extracted with EtOAc. The combined organic layers were dried over $Na_2SO_4$, filtered, and concentrated. The residue was washed with petroleum ether (50 mL), then filtered. The filter cake was concentrated under reduced pressure to give 2,7-dichloro-8-fluoro-4-(2,2,2-trifluoroethoxy)pyrido[4,3-d]pyrimidine (50 g, 158 mmol, 84% yield) as yellow solid. $^1H$ NMR (400 MHz, CHLOROFORM-d) δ ppm 9.18 (s, 1H), 5.06-5.12 (m, 2H).

Step 2. 7-Chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine. To a solution of 2,7-dichloro-8-fluoro-4-(2,2,2-trifluoroethoxy)pyrido[4,3-d]pyrimidine (28 g, 89 mmol) in 1,4-dioxane (280 mL) was added ((2R,7aS)-2-fluorotetrahydro-1H-pyrrolizin-7a(5H)-yl)methanol (16.93 g, 106 mmol) and DIPEA (46.4 mL, 266 mmol) in sequence. Then the mixture was stirred at 80° C. for 10 h. The reaction mixture was concentrated under reduced pressure and the residue was diluted with water and extracted with EtOAc. The combined organic layers were dried over $Na_2SO_4$, filtered, and concentrated. The residue was purified by column chromatography on silica gel, eluting with a gradient of 5-100% EtOAc in petroleum ether, to provide 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (28 g, 63.8 mmol, 72% yield) as yellow solid. m/z (ESI): 439.1/441.1 $(M+H)^+$.

Step 3. Ethyl 4-(2-fluoro-8-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-(methoxymethoxy)naphthalen-1-yl)butanoate. A mixture of ethyl 4-(2-fluoro-6-(methoxymethoxy)-8-(4,4,5,5-tetramethyl-1,3,2-dioxaborolan-2-yl)naphthalen-1-yl)butanoate (1.12 g, 2.51 mmol, Intermediate D), 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (1.00 g, 2.28 mmol), cataCXium A Pd G2 (0.15 g, 0.23 mmol) and $Cs_2CO_3$ (1.86 g, 5.70 mmol) in 1,2-dimethoxyethane (10 mL) and water (2 mL) was degassed and purged with nitrogen. The reaction mixture was heated at 100° C. for 1 h. After cooling to rt, the reaction mixture was diluted with water and extracted with EtOAc. The combined organic layers were washed with brine, dried over $Na_2SO_4$, filtered, and concentrated. The residue was purified by column chromatography on silica gel, eluting with a gradient of 5-100% ethyl acetate in petroleum ether, to provide ethyl 4-(2-fluoro-8-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-(methoxymethoxy)naphthalen-1-yl)butanoate (0.56 g, 0.77 mmol, 34% yield) as yellow solid. m/z (ESI): 725.3/723.2 $(M+H)^+$.

Intermediate BB: Ethyl 4-(2-fluoro-8-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-1-yl)butanoate Intermediate BB

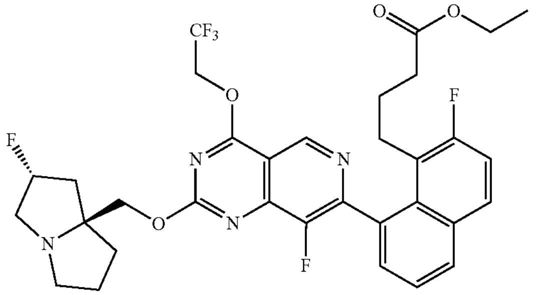

Synthesized in an analogous manner to Intermediate AA using ethyl 4-(2-fluoro-8-(4,4,5,5-tetramethyl-1,3,2-dioxaborolan-2-yl)naphthalen-1-yl)butanoate (Intermediate G) as the boronic acid in Step 3. m/z (ESI): 663.2 $(M+H)^+$.

Intermediate CC: Methyl 5-(2-fluoro-6-(methoxymethoxy)-8-(4,4,5,5-tetramethyl-1,3,2-dioxaborolan-2-yl)naphthalen-1-yl)pentanoate

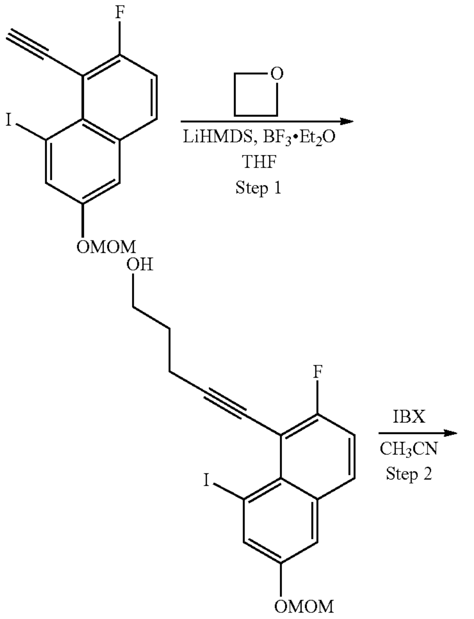

-continued

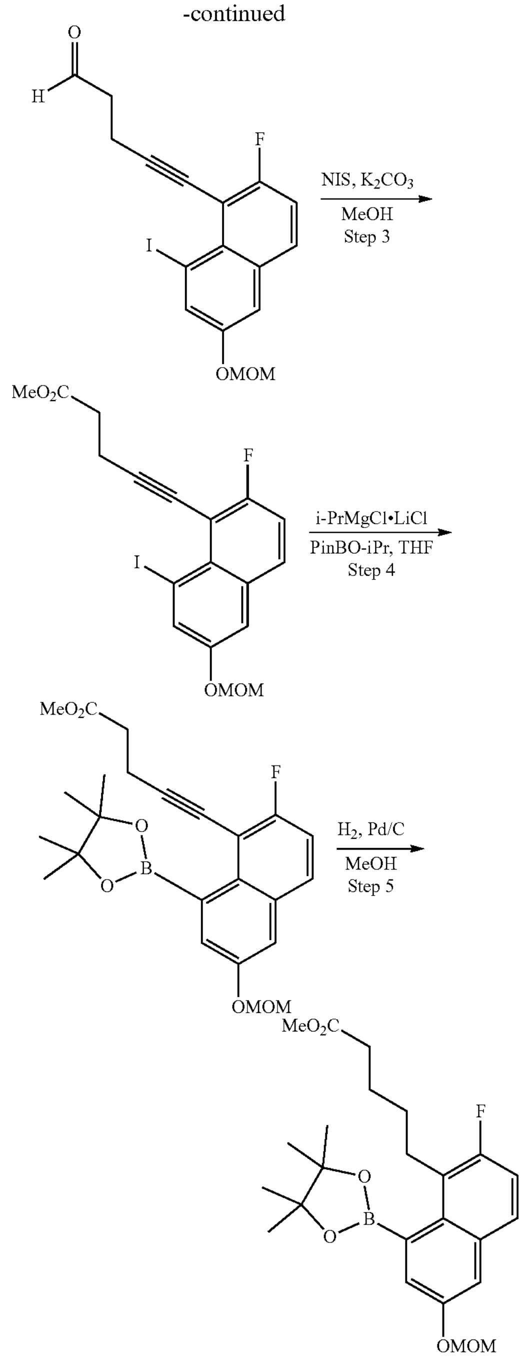

Intermediate CC

Step 1. 5-(2-Fluoro-8-iodo-6-(methoxymethoxy)naphthalen-1-yl)pent-4-yn-1-ol. To a solution of 1-ethynyl-2-fluoro-8-iodo-6-(methoxymethoxy)naphthalene (5.5 g, 15.4 mmol, Lab Network) in tetrahydrofuran (60 mL) was added lithium bis(trimethylsilyl)amide (1 M in THF, 46.5 mL, 46.5 mmol) and the reaction mixture was stirred for 30 min at −78° C. under $N_2$. $BF_3OEt_2$ (3.0 mL, 24 mmol) was added and after stirring for 30 min, oxetane (2.5 g, 43 mmol) was added and the mixture was stirred at rt for 2 h. The reaction mixture was quenched by aqueous $NH_4Cl$ and extracted with EtOAc. The combined organic layers were dried over $Na_2SO_4$, filtered, and concentrated under reduced pressure. The residue was purified by column chromatography on silica gel, eluting with 1-20% EtOAc in petroleum ether to provide 5-(2-fluoro-8-iodo-6-(methoxymethoxy)naphthalen-1-yl)pent-4-yn-1-ol (1.80 g, 4.40 mmol, 28% yield) as yellow solid. $^1$H NMR (400 MHz, DMSO-$d_6$) δ ppm 8.05 (d, J=2.3 Hz, 1H), 7.89 (dd, J=6.1, 9.0 Hz, 1H), 7.62 (d, J=2.5 Hz, 1H), 7.51 (t, J=8.8 Hz, 1H), 5.31 (s, 2H), 4.56 (t, J=5.2 Hz, 1H), 3.50-3.65 (m, 3H), 3.42 (s, 3H), 2.62 (t, J=7.1 Hz, 2H), 1.70-1.90 (m, 3H).

Step 2. 5-(2-Fluoro-8-iodo-6-(methoxymethoxy)naphthalen-1-yl)pent-4-ynal. To a solution of 5-(2-fluoro-8-iodo-6-(methoxymethoxy)naphthalen-1-yl)pent-4-yn-1-ol (1.70 g, 4.10 mmol) in acetonitrile (20 mL) was added 2-iodoxybenzoic acid (5.75 g, 20.5 mmol). The reaction mixture was stirred at 70° C. for 0.5 h. Water was added and the mixture was extracted with EtOAc. The combined organic phase was washed with brine, dried over sodium sulfate, filtered, and concentrated. The residue was purified by column chromatography on silica gel, eluting with 0-10% EtOAc in petroleum ether to give 5-(2-fluoro-8-iodo-6-(methoxymethoxy)naphthalen-1-yl)pent-4-ynal (1.70 g, 4.10 mmol, 100% yield) as yellow solid. $^1$H NMR (400 MHz, DMSO-$d_6$) δ ppm 9.75-9.78 (m, 1H), 8.04 (d, J=2.5 Hz, 1H), 7.80-7.90 (m, 1H), 7.61 (d, J=2.6 Hz, 1H), 7.50 (t, J=8.8 Hz, 1H), 5.30 (s, 2H), 3.42 (s, 3H), 2.80-2.91 (m, 4H).

Step 3. Methyl 5-(2-fluoro-8-iodo-6-(methoxymethoxy)naphthalen-1-yl)pent-4-ynoate. To a solution of 5-(2-fluoro-8-iodo-6-(methoxymethoxy)naphthalen-1-yl)pent-4-ynal (1.70 g, 4.10 mmol) in methanol (20 mL) was added $K_2CO_3$ (1.43 g, 10.3 mmol) and NIS (2.32 g, 10.3 mmol). The reaction mixture was stirred at rt for 2 h. The reaction mixture was quenched by water and extracted with EtOAc. The combined organic layers were dried over $Na_2SO_4$, filtered, and concentrated under reduced pressure. The residue was purified by column chromatography on silica gel, eluting with 0-20% EtOAc in petroleum ether to give methyl 5-(2-fluoro-8-iodo-6-(methoxymethoxy)naphthalen-1-yl)pent-4-ynoate (1.70 g, 3.10 mmol, 75% yield) as light yellow solid. $^1$H NMR (400 MHz, DMSO-$d_6$) δ ppm 8.03 (s, 1H), 7.89 (dd, J=6.3, 9.0 Hz, 1H), 7.61 (d, J=2.5 Hz, 1H), 7.50 (t, J=8.9 Hz, 1H), 5.30 (s, 2H), 3.64 (s, 3H), 3.41 (s, 3H), 2.80-2.85 (m, 2H), 2.70-2.76 (m, 2H).

Step 4. Methyl 5-(2-fluoro-6-(methoxymethoxy)-8-(4,4,5,5-tetramethyl-1,3,2-dioxaborolan-2-yl)naphthalen-1-yl)pent-4-ynoate. To a solution of methyl 5-(2-fluoro-8-iodo-6-(methoxymethoxy)naphthalen-1-yl)pent-4-ynoate (1.40 g, 3.20 mmol) in tetrahydrofuran (15 mL) was added isopropyl magnesium chloride/lithium chloride (4.9 mL, 6.3 mmol) dropwise at −78° C. The reaction mixture was stirred at −78° C. for 0.5 h. Then 2-isopropoxy-4,4,5,5-tetramethyl-1,3,2-dioxaborolane (2.95 g, 15.8 mmol) was added. The mixture was stirred at 0° C. for 1 h. The reaction mixture was quenched by addition of aqueous $NH_4Cl$ at 0° C., and then diluted with EtOAc. The mixture was extracted with EtOAc, and the combined organic layers were dried over $Na_2SO_4$, filtered, and concentrated. The residue was purified by column chromatography on silica gel, eluting with 0-10% EtOAc in petroleum ether to give methyl 5-(2-fluoro-6-(methoxymethoxy)-8-(4,4,5,5-tetramethyl-1,3,2-dioxaborolan-2-yl)naphthalen-1-yl)pent-4-ynoate (0.70 g, 1.58 mmol, 50% yield) as yellow solid.

Step 5. Methyl 5-(2-fluoro-6-(methoxymethoxy)-8-(4,4,5,5-tetramethyl-1,3,2-dioxaborolan-2-yl)naphthalen-1-yl)pentanoate. To a solution of methyl 5-(2-fluoro-6-(methoxymethoxy)-8-(4,4,5,5-tetramethyl-1,3,2-dioxaborolan-2-yl)naphthalen-1-yl)pent-4-ynoate (0.70 g, 1.58 mmol) in methanol (10 mL) was added Pd/C (0.40 g, 3.17 mmol) under argon. The suspension was degassed and purged with $H_2$ 2 times. The mixture was stirred under $H_2$ (15 psi) at rt for 2 h. The reaction mixture was filtered, and the filtrate was concentrated under reduced pressure. The residue was purified by column chromatography on silica gel, eluting with 0-20% EtOAc in petroleum ether to give methyl 5-(2-fluoro-6-(methoxymethoxy)-8-(4,4,5,5-tetramethyl-1,3,2-dioxaborolan-2-yl)naphthalen-1-yl)pentanoate (0.65 g, 1.46 mmol, 92% yield) as colorless oil. $^1H$ NMR (400 MHz, DMSO-$d_6$) δ ppm 7.77 (dd, J=6.1, 8.9 Hz, 1H), 7.53 (d, J=2.5 Hz, 1H), 7.37 (t, J=9.3 Hz, 1H), 7.29 (d, J=2.5 Hz, 1H), 5.30 (s, 2H), 3.53 (s, 3H), 3.41 (s, 3H), 3.02-3.11 (m, 2H), 2.25 (t, J=6.9 Hz, 2H), 1.44-1.56 (m, 4H), 1.38 (s, 12H).

Intermediate DD: Ethyl 2-fluoro-5-(6-methyl-1-(tetrahydro-2H-pyran-2-yl)-4-(4,4,5,5-tetramethyl-1,3,2-dioxaborolan-2-yl)-1H-indazol-5-yl)pentanoate

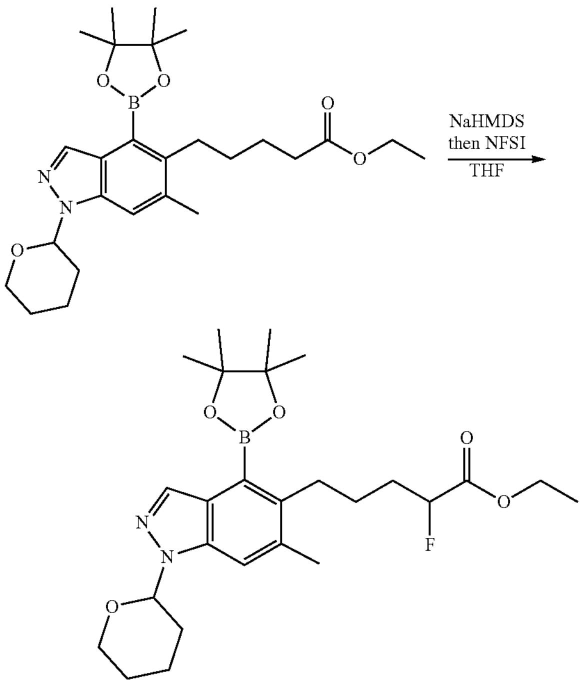

Intermediate DD

A solution of NaHMDS (1 M in THF, 2.5 mL, 2.5 mmol) was cooled to −78° C. Ethyl 5-(6-methyl-1-(tetrahydro-2H-pyran-2-yl)-4-(4,4,5,5-tetramethyl-1,3,2-dioxaborolan-2-yl)-1H-indazol-5-yl)pentanoate (0.99 g, 2.10 mmol, Intermediate J) dissolved in 3 mL of THF was then added to the solution. The solution was stirred at −78° C. for 30 min and then NFSI (0.93 g, 2.94 mmol) dissolved in 2 mL of THF was added slowly over 15 min. The mixture was slowly warmed to rt with stirring for 16 h. The reaction was then cooled to −78° C. and MeOH (3 mL) was added. The volatiles were removed in vacuo and the residue was purified via reverse phase column chromatography (10-100% $MeCN/H_2O$+0.1% TFA) to yield ethyl 2-fluoro-5-(6-methyl-1-(tetrahydro-2H-pyran-2-yl)-4-(4,4,5,5-tetramethyl-1,3,2-dioxaborolan-2-yl)-1H-indazol-5-yl)pentanoate (0.49 g, 0.99 mmol, 47% yield). m/z (ESI): (M+H)+489.2.

Intermediate EE: tert-Butyl ((S)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-yl)carbamate

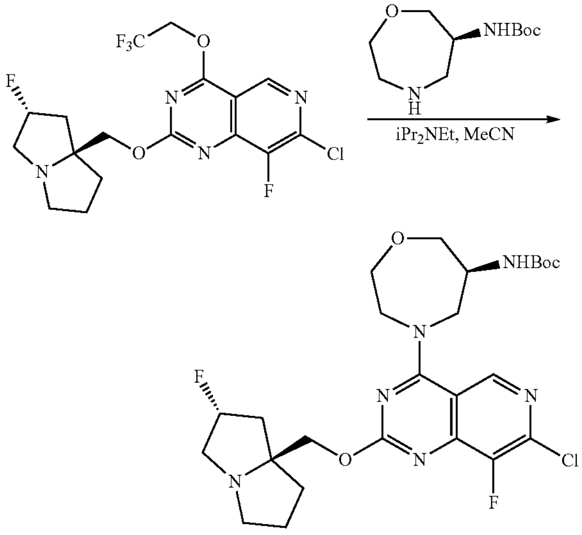

Intermediate EE

A 40-mL vial was charged with 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (2.00 g, 4.56 mmol, Intermediate AA, Step 2), tert-butyl (S)-(1,4-oxazepan-6-yl)carbamate (1.7 mL, 9.12 mmol, Enamine), DIPEA (3.2 mL, 18 mmol), and N,N-dimethylformamide (20 mL). The reaction was stirred at rt for 1 h. Water and DCM were then added. The organic layer was separated, dried ($Na_2SO_4$) and concentrated. The residue was purified by column chromatography on silica gel, eluting with 0-85% 3:1 EtOAc/EtOH (with 2% triethylamine) in heptane, to yield tert-butyl ((S)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-yl)carbamate (1.40 g, 3.10 mmol, 68% yield). m/z (ESI): 456.0 $(M+H)^+$.

Intermediate FF: tert-Butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)azepan-3-yl)carbamate

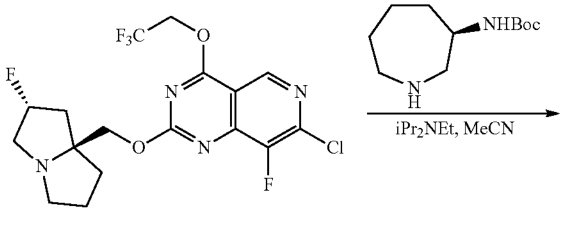

-continued

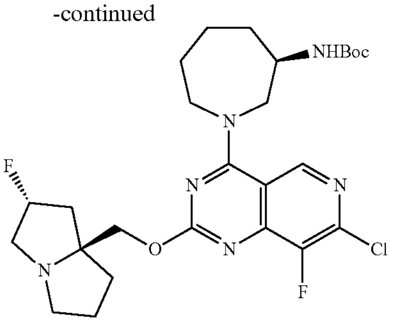

Intermediate FF

Synthesized in an analogous manner to Intermediate EE using (R)-tert-butyl azepan-3-ylcarbamate (CAS #: 1354351-56-6, Ambeed, Inc.). m/z (ESI): 553.0 $(M+H)^+$.

Intermediate GG: tert-Butyl 6-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.5]nonane-2-carboxylate Intermediate GG

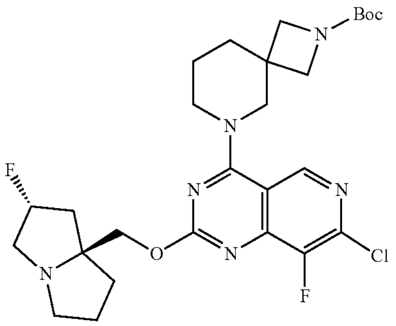

Synthesized in an analogous manner to Intermediate V using tert-butyl 2,6-diazaspiro[3.5]nonane-2-carboxylate (CAS #: 1086394-57-1, Enamine). m/z (ESI): 564.9 $(M+H)^+$.

Intermediate HH: tert-Butyl 5-(7-chloro-8-fluoro-2-(((2R,7aS)-2-fluorotetrahydro-1H-pyrrolizin-7a(5H)-yl)methoxy)pyrido[4,3-d]pyrimidin-4-yl)octahydro-2H-pyrrolo[3,4-c]pyridine-2-carboxylate Intermediate HH

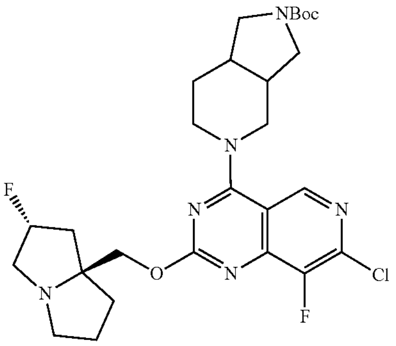

Synthesized in an analogous manner to Intermediate EE using tert-butyl hexahydro-1H-pyrrolo[3,4-c]pyridine-2(3H)-carboxylate hydrochloride (CAS #: 236406-56-7, eNovation Chemicals LLC). m/z (ESI): 565.0 $(M+H)^+$.

Intermediate II: Ethyl 5-(2-chloro-6-(4,4,5,5-tetramethyl-1,3,2-dioxaborolan-2-yl)phenyl)pentanoate

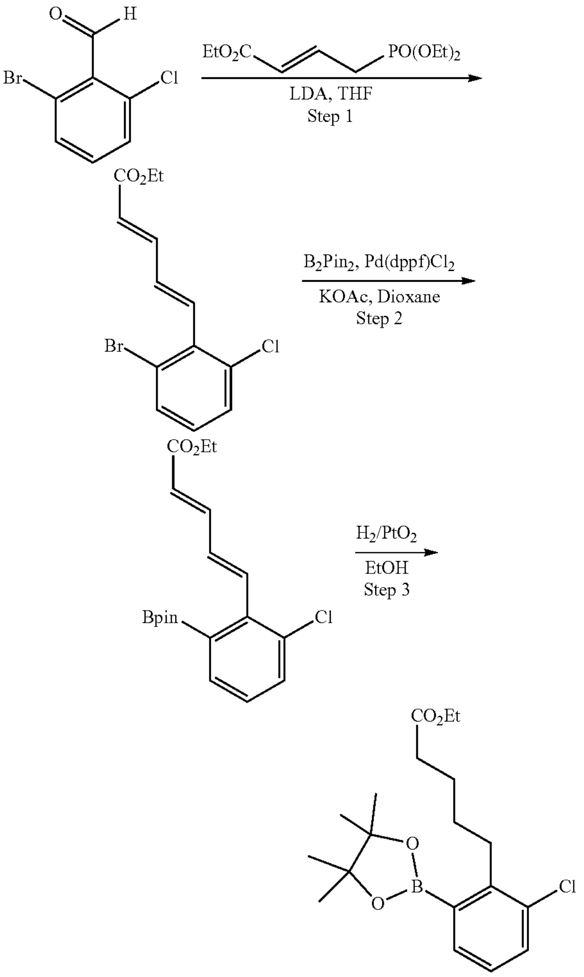

Intermediate II

Step 1. Ethyl (2E,4E)-5-(2-bromo-6-chlorophenyl)penta-2,4-dienoate. To a solution of LDA (2 M in THF, 8.8 mL, 17.7 mmol) in THF (80 mL) was added ethyl (E)-4-(diethoxyphosphoryl)but-2-enoate (4.79 g, 19.1 mmol) in tetrahydrofuran (50 mL) under $N_2$ at −78° C. The mixture was stirred at −78° C. for 0.5 h, then a solution of 2-bromo-6-chlorobenzaldehyde (3.23 g, 14.7 mmol) in THF (30 mL) was added via syringe. The mixture was stirred at 0° C. for 2 h then quenched with $H_2O$ and extracted with EtOAc. The combined organic layers were dried over $Na_2SO_4$, filtered, and concentrated under reduced pressure. The residue was purified by column chromatography on silica gel, eluting with 0-100% EtOAc in petroleum ether to give ethyl (2E,4E)-5-(2-bromo-6-chlorophenyl)penta-2,4-dienoate (3.93 g, 12.5 mmol, 85% yield) as yellow solid. $^1H$ NMR ((400 MHz, $CDCl_3$) δ ppm 7.54 (d, J=8.40 Hz, 1H), 7.42-7.50 (m, 1H), 7.35-7.40 (m, 1H), 7.02-7.10 (m, 1H), 6.85-6.95 (m, 2H), 6.05 (d, J=8.40 Hz, 1H), 4.20-4.30 (m, 2H), 1.30-1.35 (t, J=7.20 Hz, 3H). m/z (ESI): 315/317 $(M+H)^+$.

Step 2. Ethyl (2E,4E)-5-(2-chloro-6-(4,4,5,5-tetramethyl-1,3,2-dioxaborolan-2-yl)phenyl)penta-2,4-dienoate. To a solution of ethyl (2E,4E)-5-(2-bromo-6-chlorophenyl) penta-2,4-dienoate (3.93 g, 12.5 mmol) in 1,4-dioxane (40 mL) was added 4,4,4',4',5,5,5',5'-octamethyl-2,2'-bi(1,3,2-dioxaborolane) (9.49 g, 37.4 mmol), KOAc (4.28 g, 43.6 mmol), and $Pd(dppf)Cl_2$ (91 mg, 0.13 mmol). The mixture was stirred at 120° C. for 12 h then concentrated under reduced pressure. The residue was purified by column chromatography on silica gel, eluting with 5-20% EtOAc in petroleum ether, to give ethyl (2E,4E)-5-(2-chloro-6-(4,4,5,5-tetramethyl-1,3,2-dioxaborolan-2-yl)phenyl)penta-2,4-dienoate (2.36 g, 10 mmol, 83% yield) as colorless oil. m/z (ESI): 236.2 $(M-BPin)^+$.

Step 3. Ethyl 5-(2-chloro-6-(4,4,5,5-tetramethyl-1,3,2-dioxaborolan-2-yl)phenyl)pentanoate. To a solution of platinum(IV) oxide (0.19 g, 0.83 mmol) in ethanol (30 mL) was added ethyl (2E,4E)-5-(2-chloro-6-(4,4,5,5-tetramethyl-1,3,2-dioxaborolan-2-yl)phenyl)penta-2,4-dienoate (1.95 g, 8.27 mmol) under argon. The suspension was purged with H2 then stirred under H2 (15 psi) at rt for 2 h. The mixture was filtered through a pad of celite, and the filtrate was concentrated under reduced pressure. The residue was purified by column chromatography on silica gel, eluting with 5-20% EtOAc in petroleum ether, to give ethyl 5-(2-chloro-6-(4,4,5,5-tetramethyl-1,3,2-dioxaborolan-2-yl)phenyl)pentanoate (0.78 g, 3.3 mmol, 40% yield) as colorless oil. m/z (ESI): 240.2 $(M-BPin)^+$.

Intermediate JJ: 4-(tert-Butoxy)-7-chloro-8-fluoro-2-(((2R,7aS)-2-fluorotetrahydro-1H-pyrrolizin-7a(5H)yl)methoxy)pyrido[4,3-d]pyrimidine

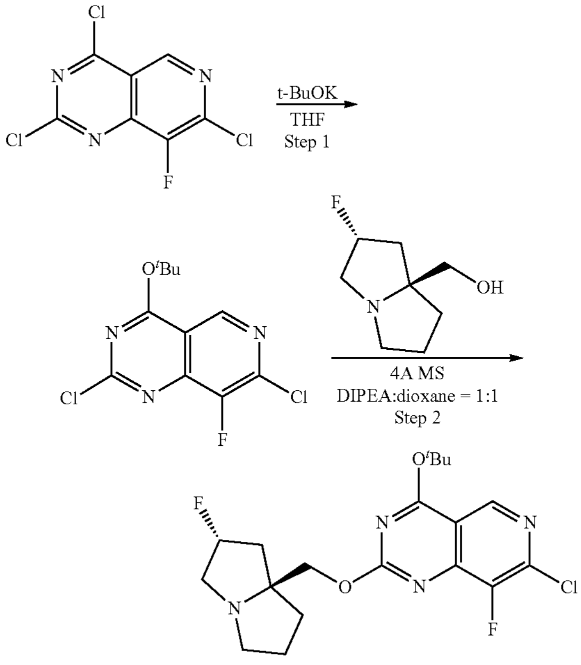

Intermediate JJ

Step 1. To a solution of 2,4,7-trichloro-8-fluoropyrido[4,3-d]pyrimidine (50.0 g, 198 mmol, Enamine) in tetrahydrofuran (1.5 L) was added t-BuOK (1 M in THF, 190 mL, 190 mmol) dropwise at −60° C. and the reaction mixture was stirred at −60° C. for 2 h. The mixture was diluted with EtOAc and water and extracted with EtOAc. The combined organic layers were washed with brine, dried over $Na_2SO_4$, filtered and the filtrate was concentrated under reduced pressure. The crude product was triturated with petroleum ether at rt for 1 h. The suspension was filtered, and the cake was concentrated under reduced pressure to give 4-(tert-butoxy)-2,7-dichloro-8-fluoropyrido[4,3-d]pyrimidine (30 g, 103 mmol, 54% yield) as yellow solid. $^1H$ NMR (400 MHz, $CDCl_3$) δ ppm 9.08 (s, 1H), 1.74 (s, 9H).

Step 2. 4-(tert-Butoxy)-7-chloro-8-fluoro-2-(((2R,7aS)-2-fluorotetrahydro-1H-pyrrolizin-7a(5H)yl)methoxy)pyrido[4,3-d]pyrimidine. To a solution of 4-(tert-butoxy)-2,7-dichloro-8-fluoropyrido[4,3-d]pyrimidine (50.0 g, 172 mmol) and 4 Å MS (10 g) in 1,4-dioxane (1 L) was added ((2R,7aS)-2-fluorotetrahydro-1H-pyrrolizin-7a(5H)-yl) methanol (30.2 g, 190 mmol) and DIPEA (60.0 g, 431 mmol) in sequence. Then the mixture was stirred at 80° C. for 5 h. After cooling to rt, the reaction mixture was diluted with EtOAc and water and extracted with EtOAc. The combined organic layers were washed with brine, dried over $Na_2SO_4$, filtered and the filtrate was concentrated under reduced pressure. The crude product was triturated with MTBE at rt for 1 h. The suspension was filtered, and the cake was concentrated under reduced pressure to give 4-(tert-butoxy)-7-chloro-8-fluoro-2-(((2R,7aS)-2-fluorotetrahydro-1H-pyrrolizin-7a(5H)yl)methoxy)pyrido[4,3-d]pyrimidine (40 g, 97 mmol, 56% yield) as yellow solid. m/z (ESI): 413.2/415.2 $(M+H)^+$.

Intermediate KK: 8-Fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d] pyrimidine

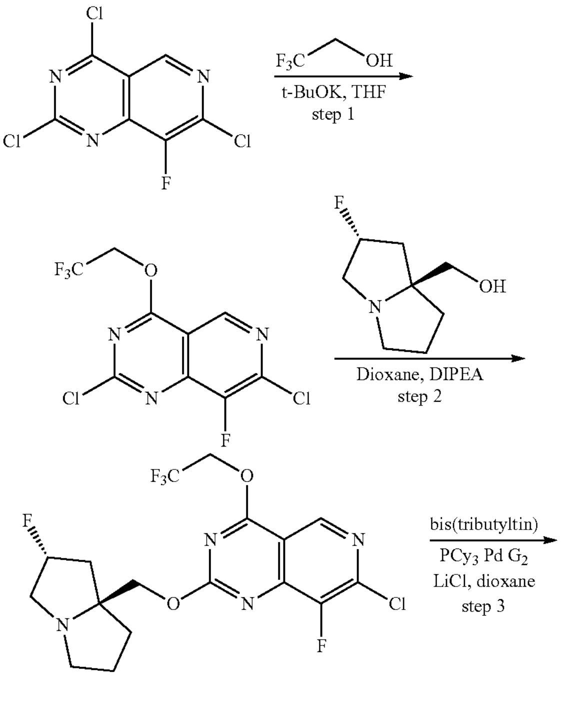

-continued

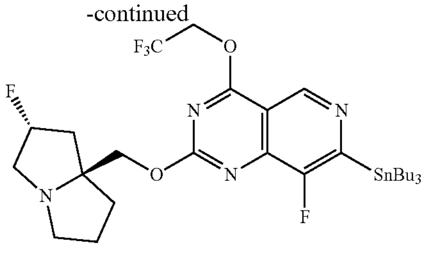

Intermediate KK

Step 1. 2,7-Dichloro-8-fluoro-4-(2,2,2-trifluoroethoxy)pyrido[4,3-d]pyrimidine. To a solution of 2,4,7-trichloro-8-fluoropyrido[4,3-d]pyrimidine (40.0 g, 158 mmol, Enamine) in tetrahydrofuran (600 mL) was added the mixture of 2,2,2-trifluoroethan-1-ol (15.1 g, 151 mmol) and t-BuOK (1 M in THF, 151 mL, 151 mmol) dropwise at −60° C. The reaction mixture was stirred at −60° C. for 2 h, then diluted with water and extracted with EtOAc. The combined organic layers were washed with brine, dried over $Na_2SO_4$, filtered and the filtrate was concentrated under reduced pressure. The crude product was triturated with petroleum ether at rt for 30 min. The suspension was filtered, and the filter cake was concentrated under reduced pressure to give 2,7-dichloro-8-fluoro-4-(2,2,2-trifluoroethoxy)pyrido[4,3-d]pyrimidine (46 g, 145 mmol, 96% yield) as white solid.

Step 2. 7-Chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine. To a solution of 2,7-dichloro-8-fluoro-4-(2,2,2-trifluoroethoxy)pyrido[4,3-d]pyrimidine (40 g, 127 mmol) in 1,4-dioxane (400 mL) was added ((2R,7aS)-2-fluorotetrahydro-1H-pyrrolizin-7a(5H)-yl)methanol (24.2 g, 152 mmol) and DIPEA (55.3 mL, 316 mmol) in sequence. The reaction mixture was stirred at 65° C. for 1.5 h. After cooling to rt, the mixture was diluted with water, and then extracted with EtOAc. The combined organic layers were dried over $Na_2SO_4$, filtered and the filtrate was concentrated under reduced pressure. The crude product was triturated with a mixed solvent (petroleum ether/EtOAc=2/1) at rt for 3 h. The suspension was filtered, and the filter cake was concentrated under reduced pressure to give 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (41 g, 93.4 mmol, 74% yield) as white solid.

Step 3. 8-Fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d]pyrimidine. To a solution of 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (10.0 g, 22.8 mmol) in 1,4-dioxane (200 mL) was added $PCy_3$ Pd G2 (5.38 g, 9.12 mmol) and LiCl (4.83 g, 114 mmol), then bis(tri-n-butyltin) (39.7 g, 68.4 mmol) in one portion under $N_2$. The mixture was stirred at 80° C. for 12 h under nitrogen. The suspension was filtered, and the filter cake was washed with EtOAc. The filtrate was diluted with water, extracted with EtOAc. The combined organic layers were dried over $Na_2SO_4$, filtered and the filtrate was concentrated under reduced pressure. The residue was purified by column chromatography on silica gel, eluting with a gradient of 0-100% EtOAc in petroleum ether. The crude product was triturated with DMSO at rt for 1 h. The suspension was filtered, and the filter cake was concentrated under reduced pressure to give 8-fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d]pyrimidine (2.68 g, 3.87 mmol, 17% yield) as white solid. m/z (ESI): 695.3/693.3 $(M+H)^+$.

Intermediate LL: Methyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate

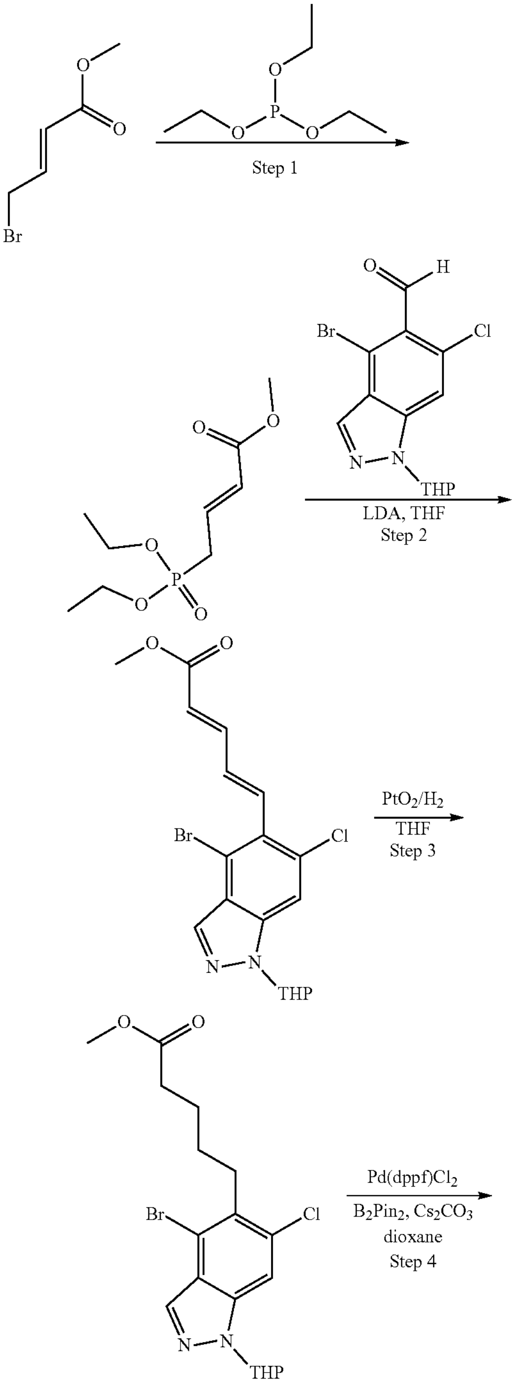

-continued

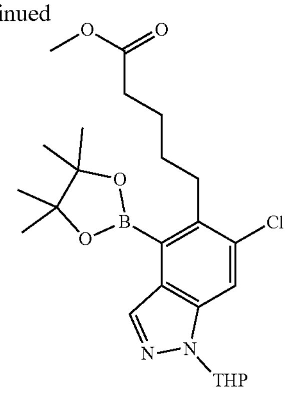

Intermediate LL

Step 1. Methyl (E)-4-(diethoxyphosphoryl) but-2-enoate. In a 3-L round-bottom flask was charged with methyl (E)-4-bromobut-2-enoate (150 g, 838 mmol). The contents were heated to 120° C. and triethyl phosphite (167 g, 1.00 mol) was added dropwise. The resulting mixture was stirred at 120° C. for 4 h under $N_2$ atmosphere. After cooling to rt, the reaction mixture was diluted with water and extracted with EtOAc. The combined organic layers were dried over $Na_2SO_4$, filtered, and concentrated under reduced pressure. The crude product methyl (E)-4-(diethoxyphosphoryl) but-2-enoate (150 g) as yellow oil was used in the next step without further purification.

Step 2. Methyl (2E, 4E)-5-(4-bromo-6-chloro-1-(tetrahydro-2H-pyran-2-yl)-1H-indazol-5-yl) penta-2, 4-dienoate. To a solution of LDA (2 M in THF, 175 mL, 350 mmol) in tetrahydrofuran (360 mL) was added the solution of methyl (E)-4-(diethoxyphosphoryl)but-2-enoate (82.0 g, 349 mmol) in tetrahydrofuran (600 mL) dropwise at −78° C. under $N_2$. The reaction mixture was stirred at −78° C. for 30 min, then the solution of 4-bromo-6-chloro-1-(tetrahydro-2H-pyran-2-yl)-1H-indazole-5-carbaldehyde (100 g, 291 mmol, Intermediate ZZZ) in tetrahydrofuran (600 mL) was added dropwise at −78° C. Then the mixture was stirred at 0° C. for 1.5 h. The mixture was quenched by addition of water at 0° C., and then extracted with EtOAc. The combined organic layers were dried over $Na_2SO_4$, filtered, and concentrated under reduced pressure. The residue was purified by column chromatography on silica gel, eluting with a gradient of 0-100% EtOAc in petroleum ether, to give methyl (2E, 4E)-5-(4-bromo-6-chloro-1-(tetrahydro-2H-pyran-2-yl)-1H-indazol-5-yl) penta-2,4-dienoate (91 g, 214 mmol, 73% yield) as white solid.

Step 3. Methyl 5-(4-bromo-6-chloro-1-(tetrahydro-2H-pyran-2-yl)-1H-indazol-5-yl) pentanoate. In a hydrogenation reactor was charged with $PtO_2$ (7.47 g, 32.9 mmol) in tetrahydrofuran (1.4 L). Methyl (2E, 4E)-5-(4-bromo-6-chloro-1-(tetrahydro-2H-pyran-2-yl)-1H-indazol-5-yl) penta-2,4-dienoate (70 g, 164 mmol) was added under argon and the suspension was degassed and purged with H2 for 3 times. The mixture was hydrogenated under H2 (15 psi) at rt for 72 h. The mixture was filtered through a pad of celite, and the filtrate was concentrated under reduced pressure. The residue was purified by column chromatography on silica gel, eluting with a gradient of 2-100% EtOAc in petroleum ether, to give methyl 5-(4-bromo-6-chloro-1-(tetrahydro-2H-pyran-2-yl)-1H-indazol-5-yl) pentanoate (37.5 g, 87 mmol, 53% yield) as white solid. m/z (ESI): 429.1/431.1 $(M+H)^+$.

Step 4. Methyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate. To a solution of methyl 5-(4-bromo-6-chloro-1-(tetrahydro-2H-pyran-2-yl)-1H-indazol-5-yl) pentanoate (25 g, 58.2 mmol) in 1,4-dioxane (250 mL) was added bis(pinacolato)diboron (44.3 g, 175 mmol) and $Cs_2CO_3$ (56.9 g, 175 mmol) under nitrogen. Pd(dppf)$Cl_2$ (4.26 g, 5.82 mmol) was added, and the reaction mixture was stirred at 120° C. for 2 h. The reaction mixture was diluted with water and extracted with EtOAc. The combined organic layers were dried over $Na_2SO_4$, filtered, and concentrated under reduced pressure. The residue was purified by column chromatography on silica gel, eluting with a gradient of 10-35% EtOAc in petroleum ether, to give methyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate (12 g, 25 mmol, 43% yield) as white solid. m/z (ESI): 477.2 $(M+H)^+$.

Intermediate MM: 5-(6-Chloro-4-(8-fluoro-2-(((2R, 7aS)-2-fluorotetrahydro-1H-pyrrolizin-7a(5H)-yl) methoxy)-4-hydroxypyrido[4,3-d]pyrimidin-7-yl)-1-(tetrahydro-2H-pyran-2-yl)-1H-indazol-5-yl) pentanoic acid

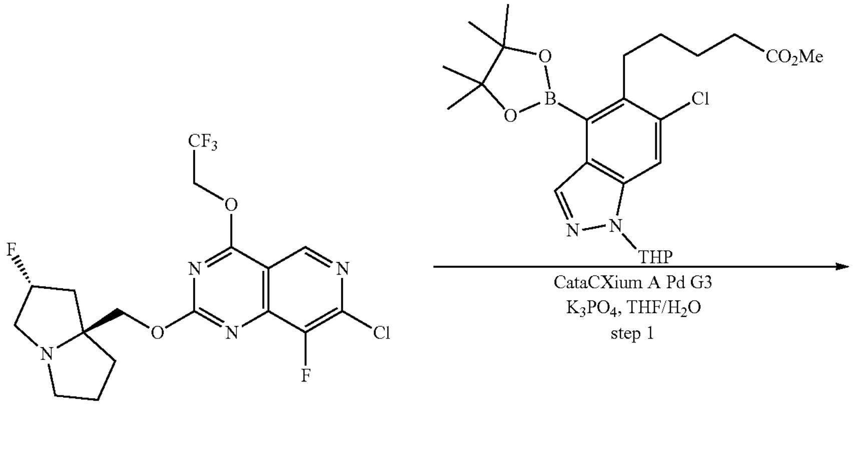

-continued

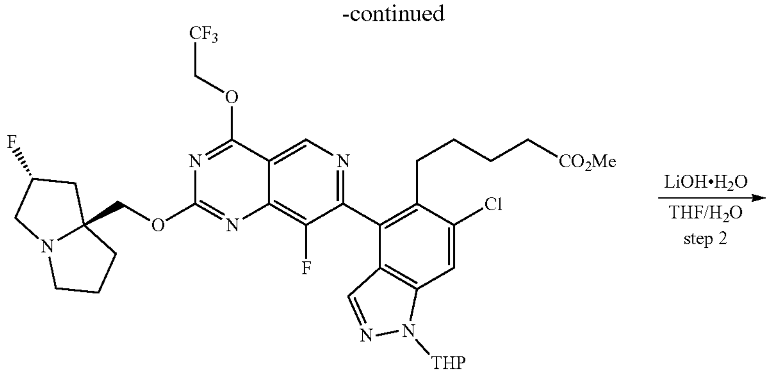

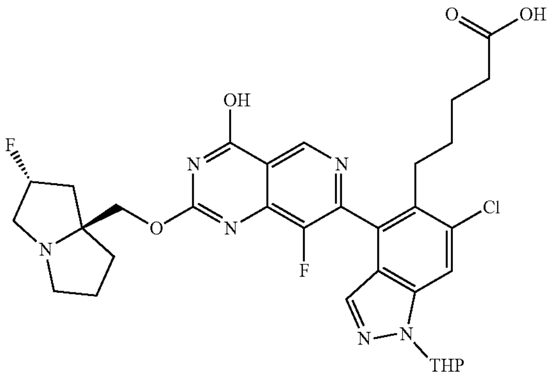

Intermediate MM

Step 1. Methyl 5-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)pentanoate. To a solution of 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.50 g, 1.14 mmol, Step 2 in Intermediate AA) and methyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate (0.56 g, 1.17 mmol, Intermediate LL) in THF (8 mL) and water (1 mL) was added $K_3PO_4$ (0.73 g, 3.42 mmol) and CataCXium A Pd G3 (83 mg, 0.13 mmol) in sequence under $N_2$. Then the mixture was stirred at 80° C. for 3 h. After cooling to rt, the reaction mixture was diluted with water and extracted with EtOAc. The combined organic layers were washed with brine, dried over $Na_2SO_4$, filtered, and concentrated. The residue was purified by column chromatography on silica gel, eluting with a gradient of 0-50% EtOAc in petroleum ether, to give methyl 5-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)pentanoate (0.47 g, 0.63 mmol, 55% yield) as colorless oil.

Step 2. 5-(6-Chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1-(tetrahydro-2H-pyran-2-yl)-1H-indazol-5-yl)pentanoic acid. To a solution of methyl 5-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)pentanoate (0.47 g, 0.62 mmol) in THF (8 mL) and water (1.6 mL) was added $LiOH{\cdot}H_2O$ (0.26 g, 2.45 mmol). The mixture was stirred at 60° C. for 5 h. After cooling to rt, the reaction was adjusted to pH 5 with 1N HCl, and then the mixture was extracted with EtOAc. The combined organic layers were washed with brine, dried over $Na_2SO_4$, filtered, and concentrated. The crude product was triturated with a mixed solvent (EtOAc/EtOH=5:1) at rt for 30 min. The suspension was filtered and filter cake was concentrated under reduced pressure to give 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1-(tetrahydro-2H-pyran-2-yl)-1H-indazol-5-yl)pentanoic acid (0.15 g, 0.23 mmol, 37% yield) as yellow solid. m/z (ESI): 657.2/659.2 $(M+H)^+$.

Intermediate NN: 5-(4-(8-Fluoro-2-(((2R,7aS)-2-fluorotetrahydro-1H-pyrrolizin7a(5H)-yl)methoxy)-4-hydroxypyrido[4,3-d]pyrimidin-7-yl)-6-methyl-1-(tetrahydro-2H-pyran-2-yl)-1H-indazol-5-yl) pentanoic acid

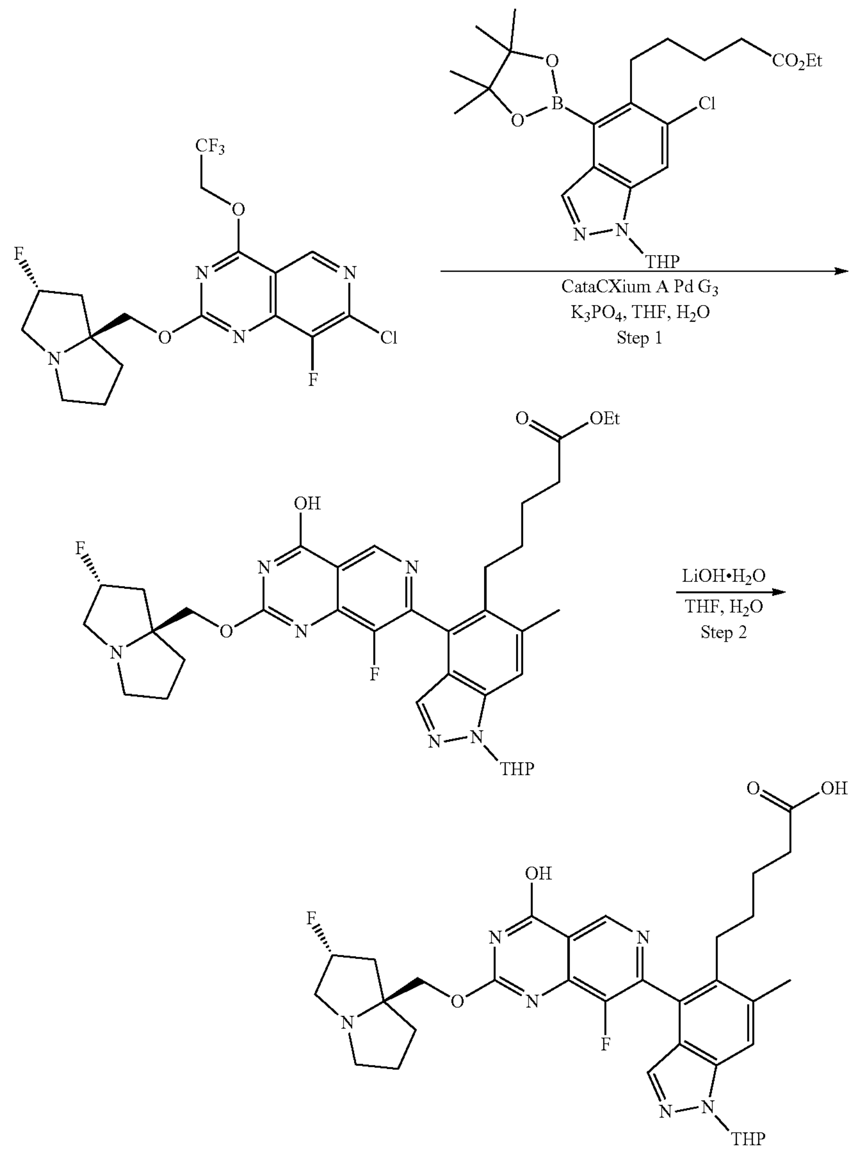

Intermediate NN

Step 1. Ethyl 5-(4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-methyl-1-(tetrahydro-2H-pyran-2-yl)-1H-indazol-5-yl)pentanoate. To a solution of 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (20 g, 45.6 mmol, Intermediate AA, Step 2) and ethyl 5-(6-methyl-1-(tetrahydro-2H-pyran-2-yl)-4-(4,4,5,5-tetramethyl-1,3,2-dioxaborolan-2-yl)-1H-indazol-5-yl)pentanoate (23.6 g, 50.1 mmol, Intermediate J) in tetrahydrofuran (400 mL) and water (10 mL) was added $K_3PO_4$ (29.0 g, 137 mmol) and cataCXium A Pd G3 (3.32 g, 4.56 mmol) under $N_2$. The reaction mixture was stirred at 80° C. for 10 h. After cooling to rt, the reaction mixture was diluted with water and extracted with EtOAc. The combined organic layers were washed with brine, dried over $Na_2SO_4$, filtered, and concentrated under reduced pressure. The residue was purified by column chromatography on silica gel, eluting with a gradient of 10-100% EtOAc in petroleum ether, to give ethyl 5-(4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-methyl-1-(tetrahydro-2H-pyran-2-yl)-1H-indazol-5-yl)pentanoate (20 g, 26.8 mmol, 59% yield) as yellow solid. m/z (ESI): 747.4 $(M+H)^+$.

Step 2. 5-(4-(8-Fluoro-2-(((2R,7aS)-2-fluorotetrahydro-1H-pyrrolizin7a(5H)-yl)methoxy)-4-hydroxypyrido[4,3-d]pyrimidin-7-yl)-6-methyl-1-(tetrahydro-2H-pyran-2-yl)-1H-indazol-5-yl)pentanoic acid. To a solution of ethyl 5-(4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-methyl-1-(tetrahydro-2H-pyran-2-yl)-1H-indazol-5-yl)pentanoate (11.0 g, 14.7 mmol) in tetrahydrofuran (220 mL) and water (44 mL) was added $LiOH \cdot H_2O$ (2.48 g, 58.9 mmol). The reaction mixture was stirred at 60° C. for 5 h. After cooling to rt, the reaction mixture was diluted with water and extracted with EtOAc. The aqueous layer was neutralized to pH to 5 using 1 M HCl and the resulting suspension was filtered. The filter cake was washed by $H_2O$ and concentrated under reduced pressure to give 5-(4-(8-fluoro-2-(((2R,7aS)-2-fluorotetrahydro-1H-pyrrolizin7a(5H)-yl)methoxy)-4-hydroxypyrido[4,3-d]pyrimidin-7-yl)-6-methyl-1-(tetrahydro-2H-pyran-2-yl)-1H-indazol-5-yl)pentanoic acid (5.00 g, 7.85 mmol, 53% yield) as yellow solid. m/z (ESI): 637.4 $(M+H)^+$.

Intermediate OO: 3,6,8-Trichloropyrimido[5,4-c]pyridazine

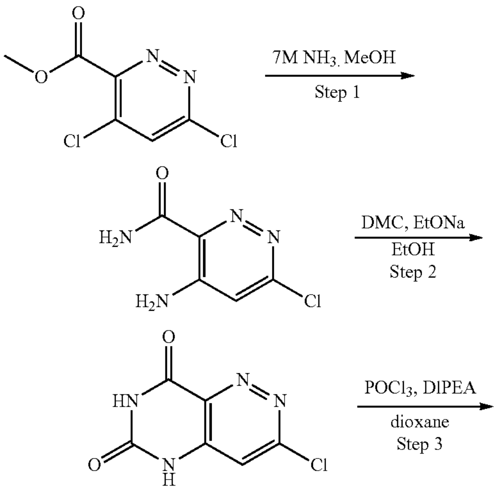

-continued

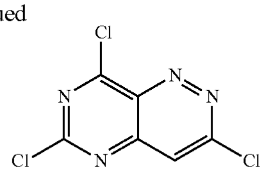

Intermediate OO

Step 1. 4-Amino-6-chloro-pyridazine-3-carboxamide. A solution of methyl 4,6-dichloropyridazine-3-carboxylate (50.0 g, 242 mmol) in $NH_3$-MeOH (7 M, 500 mL, 14.5 equiv.) was stirred at 100° C. for 12 h in a 2-L sealed tube. After cooling to rt, the reaction mixture was concentrated under reduced pressure. The crude product was triturated with a mixed solvent (petroleum ether: ethyl acetate=3:1) at rt for 1 h. The suspension was filtered, and the filter cake was washed with petroleum ether, dried to give 4-amino-6-chloro-pyridazine-3-carboxamide (50 g, crude) as yellow solid. m/z (ESI): 173.0/175.0 $(M+H)^+$.

Step 2. 3-Chloro-5H-pyrimido[5,4-c]pyridazine-6,8-dione. To a mixture of 4-amino-6-chloro-pyridazine-3-carboxamide (55.0 g, 319 mmol) in EtOH (660 mL) was added dimethyl carbonate (143.5 g, 1.59 mol) and EtONa (108 g, 1.59 mol). The reaction mixture stirred at 80° C. for 5 h. After cooling to rt, the reaction mixture was adjusted to pH 6 by addition of 1M HCl to give a suspension. It was filtered and the filter cake was concentrated under reduced pressure. The crude product was triturated with EtOAc at rt for 1 h. Then the mixture was filtered, and the filter cake was washed with EtOAc, dried to give 3-chloro-5H-pyrimido[5,4-c]pyridazine-6,8-dione (40.0 g, 201 mmol, 63% yield) as yellow solid. m/z (ESI): 196.9 $(M+H)^+$.

Step 3. 3,6,8-Trichloropyrimido[5,4-c]pyridazine. To a mixture of 3-chloro-5H-pyrimido[5,4-c]pyridazine-6,8-dione (34.5 g, 174 mmol) in dioxane (350 mL) was added $POCl_3$ (81 mL, 869 mmol) dropwise, followed by DIPEA (91 mL, 521 mmol). The reaction mixture was stirred at 100° C. for 3 h. After cooling, the reaction mixture was concentrated under reduced pressure. The residue was purified by column chromatography on silica gel, eluting with a gradient of 0-100% EtOAc in petroleum ether, to give 3,6,8-trichloropyrimido[5,4-c]pyridazine (8.50 g, 36.2 mmol, 21% yield) as green solid. m/z (ESI): 337.0/339.0 (quenching with morpholine, M+2 morpholine+H)$^+$.

Intermediate PP: rac-6-(tert-Butyl) 1-(3-(6-methyl-1-(tetrahydro-2H-pyran-2-yl)-4-(4,4,5,5-tetramethyl-1,3,2-dioxaborolan-2-yl)-1H-indazol-5-yl)propyl) (3aS,7aR)-hexahydro-1H-pyrrolo[2,3-c]pyridine-1,6(2H)-dicarboxylate

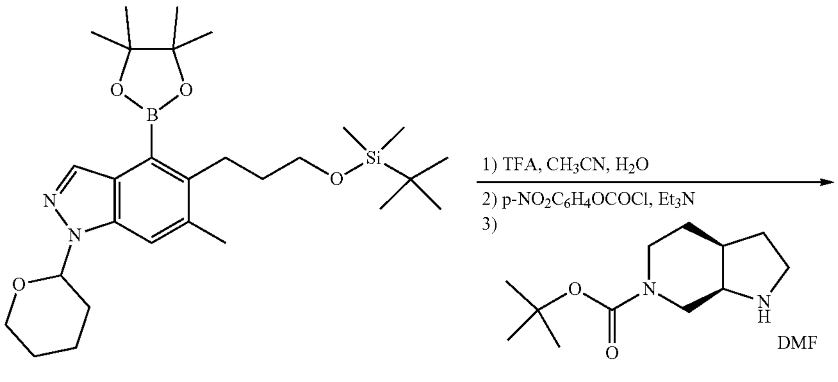

-continued

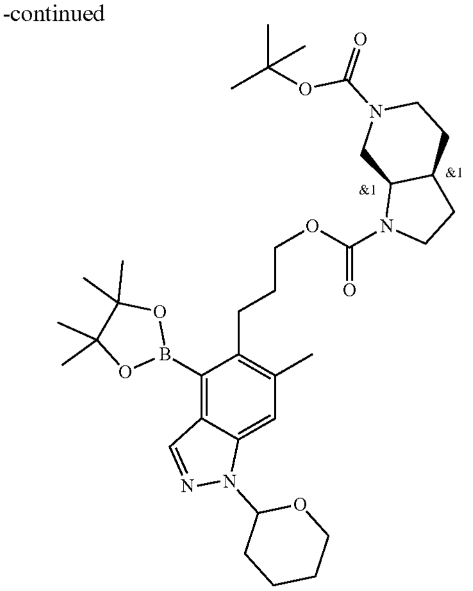

Intermediate PP

To a 100-mL round-bottom flask was added 5-(3-((tert-butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole (0.33 g, 0.65 mmol, Intermediate K) in a mixture of water (5 mL) and 2,2,2-trifluoroacetic acid (0.1% in acetonitrile) (22.5 mL, 0.197 mmol). The mixture was stirred at rt for 1 h and immediately quenched with saturated $NaHCO_3$ solution under vigorous stirring. The mixture was stirred at rt for additional 10 min, then was diluted with water and extracted with EtOAc. The combined organic layers were washed with saturated NaCl solution, dried over $Na_2SO_4$, and concentrated. To the crude material was added dichloromethane (3 mL), followed by triethylamine (0.17 mL, 1.3 mmol). The mixture was cooled to 0° C. and 4-nitrophenyl carbonochloridate (0.13 g, 0.65 mmol) was added and the mixture was stirred at rt for 2 h. rac-tert-butyl cis-1,2,3,3a,4,5,7,7a-octahydropyrrolo[2,3-c]pyridine-6-carboxylate (0.44 g, 1.95 mmol, Angel Pharmatech Ltd.) in N,N-dimethylformamide (0.5 mL) was added and the mixture was warmed at 40° C. for 1 h. After cooling to rt, the crude material was concentrated and purified by chromatography column on silica gel, eluting with 0-50% EtOAc in heptane to provide rac-6-(tert-butyl) 1-(3-(6-methyl-1-(tetrahydro-2H-pyran-2-yl)-4-(4,4,5,5-tetramethyl-1,3,2-dioxaborolan-2-yl)-1H-indazol-5-yl)propyl) (3aS,7aR)-hexahydro-1H-pyrrolo[2,3-c]pyridine-1,6(2H)-dicarboxylate (0.27 g, 0.42 mmol, 64% yield) as white solid. m/z (ESI): 653.2 $(M+H)^+$.

Intermediate QQ: tert-Butyl (R)-3-(((2-(2-fluoro-8-iodonaphthalen-1-yl)ethoxy)carbonyl)amino)-3-methylpiperidine-1-carboxylate

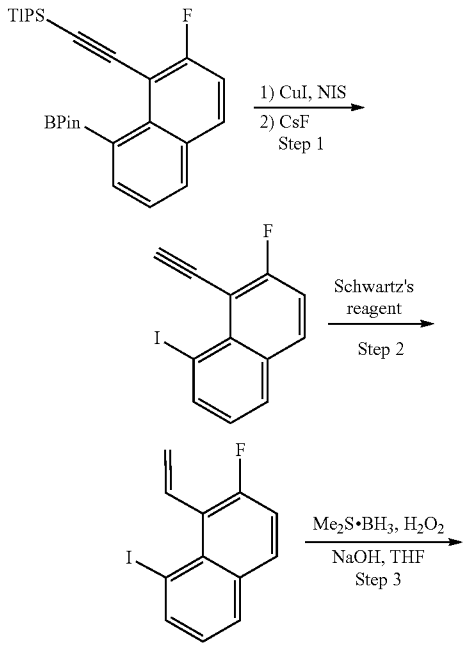

-continued

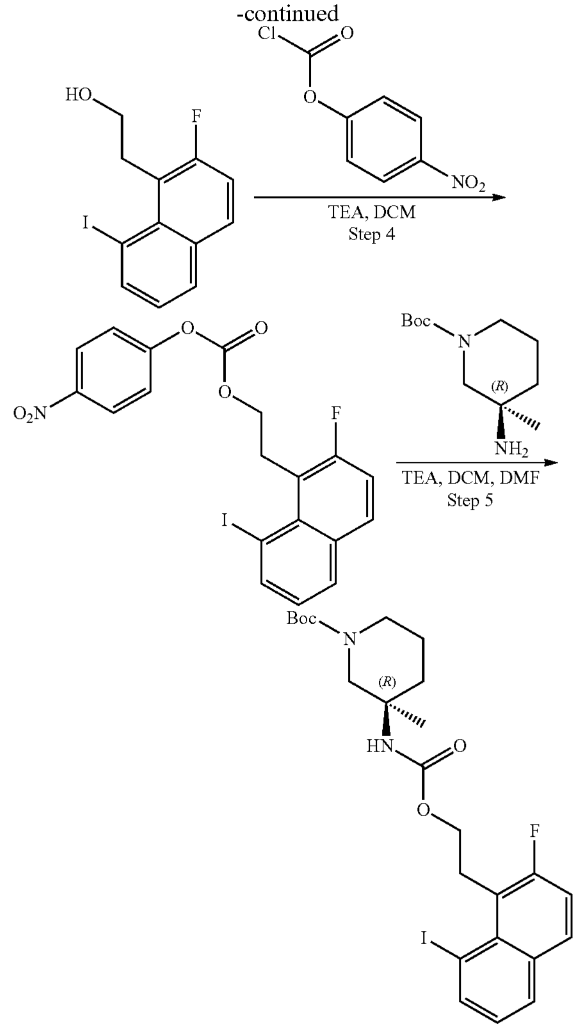

Intermediate QQ

Step 1. 1-Ethynyl-2-fluoro-8-iodonaphthalene. To a solution of ((2-fluoro-8-(4,4,5,5-tetramethyl-1,3,2-dioxaborolan-2-yl)naphthalen-1-yl)ethynyl)triisopropylsilane (15.0 g, 33.1 mmol, LabNetwork Inc.) in DMF (200 mL) and toluene (100 mL) was added CuI (9.47 g, 49.7 mmol), followed by NIS (8.95 g, 39.8 mmol). The reaction mixture was stirred at 110° C. for 4 h, cooled to rt, then quenched with water and extracted with EtOAc. The combined organic phase was washed with brine, dried over $Na_2SO_4$, filtered, and concentrated to give ((2-fluoro-8-iodonaphthalen-1-yl)ethynyl) trimethylsilane (20 g) as a brown solid, which was used in the next step without purification. To the above crude brown solid dissolved in N,N-dimethylacetamide (100 mL) was added CsF (30.0 g, 197 mmol). The mixture was stirred at 80° C. for 2 h then cooled to rt. Water was added and the mixture was extracted with EtOAc. The combined organic phase was washed with brine, dried over $Na_2SO_4$, filtered, and concentrated. The residue was purified by column chromatography on silica gel, eluting with 100% petroleum ether to provide 1-ethynyl-2-fluoro-8-iodonaphthalene (5.90 g, 19.9 mmol, 45% yield) as yellow solid. $^1$H NMR (400 MHz, DMSO-$d_6$) δ ppm 8.35 (d, J=7.4 Hz, 1H), 8.03-8.12 (m, 2H), 7.61 (t, J=8.8 Hz, 1H), 7.23 (t, J=8.0 Hz, 1H), 5.07 (d, J=1.2 Hz, 1H). m/z (ESI): 296.6 $(M+H)^+$.

Step 2. 2-Fluoro-8-iodo-1-vinylnaphthalene. To a suspension of bis(cyclopentadienyl)zirconium chloride hydride (5.23 g, 20.3 mmol) in dichloromethane (60 mL) was added 1-ethynyl-2-fluoro-8-iodonaphthalene (3.00 g, 10.1 mmol) in dichloromethane (2 mL) dropwise with stirring at 0° C., then the reaction mixture was stirred at 15° C. for 20 h. The reaction was quenched with water and extracted with EtOAc. The combined organic phase was washed with brine, dried ($Na_2SO_4$), filtered and concentrated. The reaction was repeated twice. The residue was purified by column chromatography on silica gel, eluting with 100% petroleum ether to provide 2-fluoro-8-iodo-1-vinylnaphthalene (3.53 g, 11.8 mmol, 58% yield) as brown solid. $^1$H NMR (400 MHz, DMSO-$d_6$) δ ppm 8.32 (d, J=7.2 Hz, 1H), 8.00-8.05 (m, 2H), 7.50-7.55 (m, 2H), 7.18 (t, J=8.0 Hz, 1H), 5.73 (d, J=1.2 Hz, 1H), 5.40-5.50 (t, J=17.6 Hz, 1H). m/z (ESI): 298.6 $(M+H)^+$.

Step 3. 2-(2-Fluoro-8-iodonaphthalen-1-yl) ethan-1-ol. To a solution of 2-fluoro-8-iodo-1-vinylnaphthalene (7.20 g, 24.2 mmol) in THF (60 mL) at rt was added $BH_3$-$Me_2S$ (10 M in THF solution, 12.1 mL, 121 mmol). The mixture was stirred for 12 h then treated with $H_2O_2$ (24.7 mL, 242 mmol) and NaOH (121 mL of 1 M solution). After stirring for 12 h, the reaction mixture was diluted with saturated $Na_2SO_3$ and extracted with EtOAc. The combine organic phase was washed with brine, filtered and concentrated. The residue was purified by column chromatography on silica gel, eluting with 20-50% EtOAc in petroleum ether, to provide 2-(2-fluoro-8-iodonaphthalen-1-yl) ethan-1-ol (1.44 g, 4.56 mmol, 19% yield) as yellow solid. $^1$H NMR (400 MHz, DMSO-$d_6$) δ ppm 8.36 (d, J=7.3 Hz, 1H), 8.01 (d, J=8.0 Hz, 1H), 7.90-7.95 (m, 1H), 7.49 (t, J=9.20 Hz, 1H), 7.13 (t, J=7.60 Hz, 1H), 4.79-4.85 (m, 1H), 3.76-3.67 (m, 4H). m/z (ESI): 316.6 $(M+H)^+$.

Step 4. 2-(2-Fluoro-8-iodonaphthalen-1-yl)ethyl (4-nitrophenyl) carbonate. To a solution of 4-nitrophenyl carbonochloridate (0.61 g, 3.04 mmol) and 2-(2-fluoro-8-iodonaphthalen-1-yl) ethan-1-ol (0.96 g, 3.04 mmol) in dichloromethane (10 mL) at 0° C. was added TEA (0.85 mL, 6.1 mmol). The mixture was stirred at rt for 2 h then diluted with DCM and washed with water. The organic phase was dried over $Na_2SO_4$, filtered, and concentrated. The residue was purified by column chromatography on silica gel, eluting with 40-80% EtOAc in petroleum ether, to provide 2-(2-fluoro-8-iodonaphthalen-1-yl)ethyl(4-nitrophenyl)carbonate (1.31 g, 1.97 mmol, 65% yield) as yellow oil. m/z (ESI): 481.5 $(M+H)^+$.

Step 5. tert-Butyl (R)-3-(((2-(2-fluoro-8-iodonaphthalen-1-yl)ethoxy)carbonyl)amino)-3-methylpiperidine-1-carboxylate. To a solution of 2-(2-fluoro-8-iodonaphthalen-1-yl)ethyl (4-nitrophenyl) carbonate (1.31 g, 1.97 mmol) and tert-butyl (R)-3-amino-3-methylpiperidine-1-carboxylate (1.16 g, 5.4 mmol) in dichloromethane (15 mL) and N,N-dimethylformamide (1.5 mL) was added TEA (1.3 mL, 9.33 mmol). The mixture was stirred at 80° C. for 12 h then concentrated under reduced pressure. The residue was purified by column chromatography on silica gel, eluting with 50-80% EtOAc in petroleum ether, to provide tert-butyl (R)-3-(((2-(2-fluoro-8-iodonaphthalen-1-yl)ethoxy)carbonyl)amino)-3-methylpiperidine-1-carboxylate (1.38 g, 2.48 mmol, 91% yield) as colorless oil. m/z (ESI): 579.0 $(M+Na)^+$.

Intermediate RR: (R)-1-(7-chloro-8-fluoro-2-(((2S, 4R)-4-fluoro-1-methylpyrrolidin-2-yl)methoxy) pyrido[4,3-d]pyrimidin-4-yl)azepan-3-ol

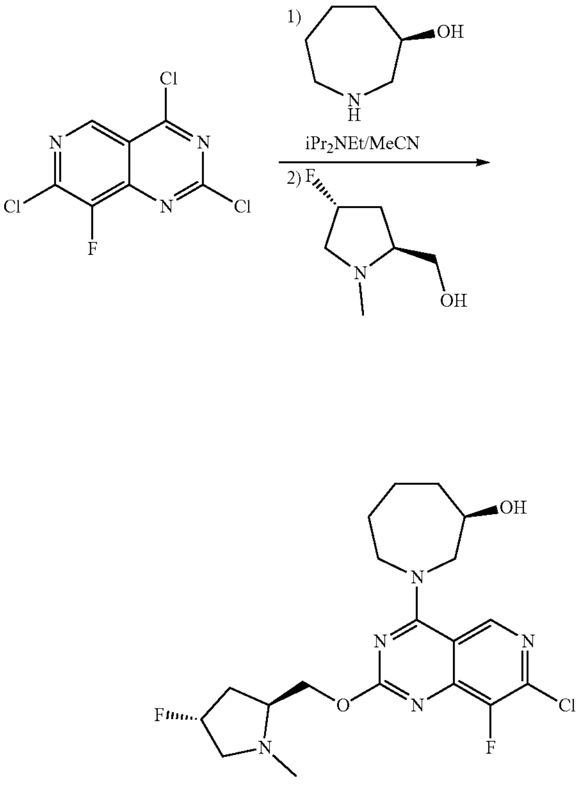

Intermediate RR

To a 0° C. suspension of 2,4,7-trichloro-8-fluoropyrido [4,3-d]pyrimidine (0.50 g, 1.98 mmol, Enamine) in acetonitrile (8 mL) at was added (3R)-azepan-3-ol (0.23 g, 1.98 mmol, PharmaBlock) and DIPEA (1.7 mL, 9.9 mmol). The reaction mixture was stirred at 0° C. for 15 minutes. Separately, a solution of [(2S,4R)-4-fluoro-1-methyl-pyrrolidin-2-yl]methanol (0.48 mL, 3.6 mmol, Synnovator, Inc.) in acetonitrile (2 mL) was dried over anhydrous magnesium sulfate. The mixture was stirred for 15 minutes at rt, and then filtered through celite to remove the magnesium sulfate. The filtrate of the solution containing [(2S,4R)-4-fluoro-1-methyl-pyrrolidin-2-yl]methanol was added, and the reaction mixture was stirred at 80° C. for 16 h. After cooling to rt, the reaction mixture was concentrated under reduced pressure and the crude material purified by column chromatography on silica gel, eluting with a gradient of 0-75% of a 3:1 EtOAc/EtOH (with 2% triethylamine) in heptane, to provide (R)-1-(7-chloro-8-fluoro-2-(((2S,4R)-4-fluoro-1-methylpyrrolidin-2-yl)methoxy)pyrido[4,3-d]pyrimidin-4-yl)azepan-3-ol (0.48 g, 1.10 mmol, 57% yield) as yellow solid. m/z (ESI): 428.1 $(M+H)^+$.

Intermediate SS: (1R,2S,5S)-8-(7-Chloro-8-fluoro-2-(((2R,7aS)-2-fluorotetrahydro-1H-pyrrolizin-7a (5H)-yl)methoxy)pyrido[4,3-d]pyrimidin-4-yl)-8-azabicyclo[3.2.1]octan-2-ol and (1S,2R,5R)-8-(7-chloro-8-fluoro-2-(((2R,7aS)-2-fluorotetrahydro-1H-pyrrolizin-7a(5H)-yl)methoxy)pyrido[4,3-d] pyrimidin-4-yl)-8-azabicyclo[3.2.1]octan-2-ol

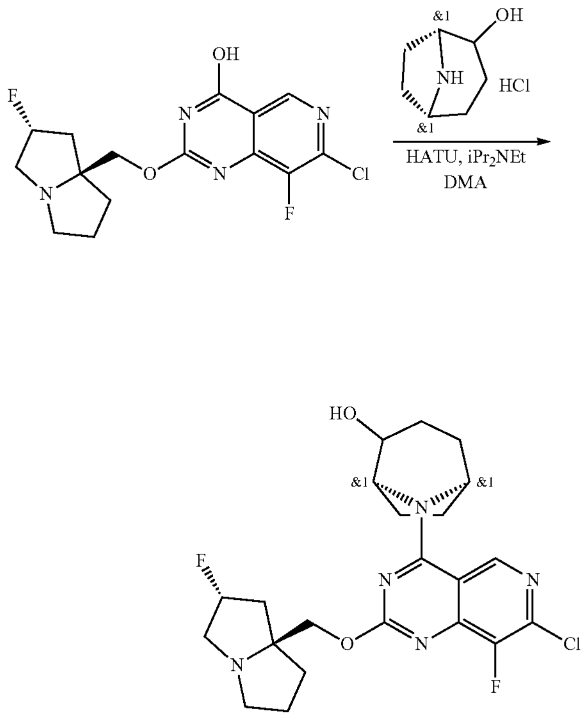

Intermediate SS

A 40-mL vial was charged with 7-chloro-8-fluoro-2-(((2R, 7aS)-2-fluorotetrahydro-1H-pyrrolizin-7a(5H)-yl)methoxy) pyrido[4,3-d]pyrimidin-4-ol (0.20 g, 0.56 mmol, Intermediate Z), 1,1'-dimethyltriethylamine (0.39 mL, 2.2 mmol) and N,N-dimethylacetamide (5.5 mL). The solution was stirred at rt for 10 min before HATU (0.26 g, 0.67 mmol) was added. After stirring for 50 min, exo-azabicyclo[3.2.1]octan-2-ol hydrochloride (0.12 g, 0.73 mmol, PharmaBlock, Inc.) was added and the reaction mixture was stirred at rt for 1 h. The mixture was purified by column chromatography on silica gel, eluting with 0-80% 3:1 EtOAc/EtOH with 2% triethylamine in heptane, to provide (1R,2S,5S)-8-(7-chloro-8-fluoro-2-(((2R,7aS)-2-fluorotetrahydro-1H-pyrrolizin-7a (5H)-yl)methoxy)pyrido[4,3-d]pyrimidin-4-yl)-8-azabicyclo[3.2.1]octan-2-ol and (1S,2R,5R)-8-(7-chloro-8-fluoro-2-(((2R,7aS)-2-fluorotetrahydro-1H-pyrrolizin-7a(5H)-yl) methoxy)pyrido[4,3-d]pyrimidin-4-yl)-8-azabicyclo[3.2.1] octan-2-ol (0.15 g, 0.33 mmol, 58% yield) as yellow solid. m/z (ESI): 466.0 $(M+H)^+$.

Intermediate TT: Ethyl 5-(1-(tetrahydro-2H-pyran-2-yl)-4-(4,4,5,5-tetramethyl-1,3,2-dioxaborolan-2-yl)-6-(trifluoromethyl)-1H-indazol-5-yl)pentanoate

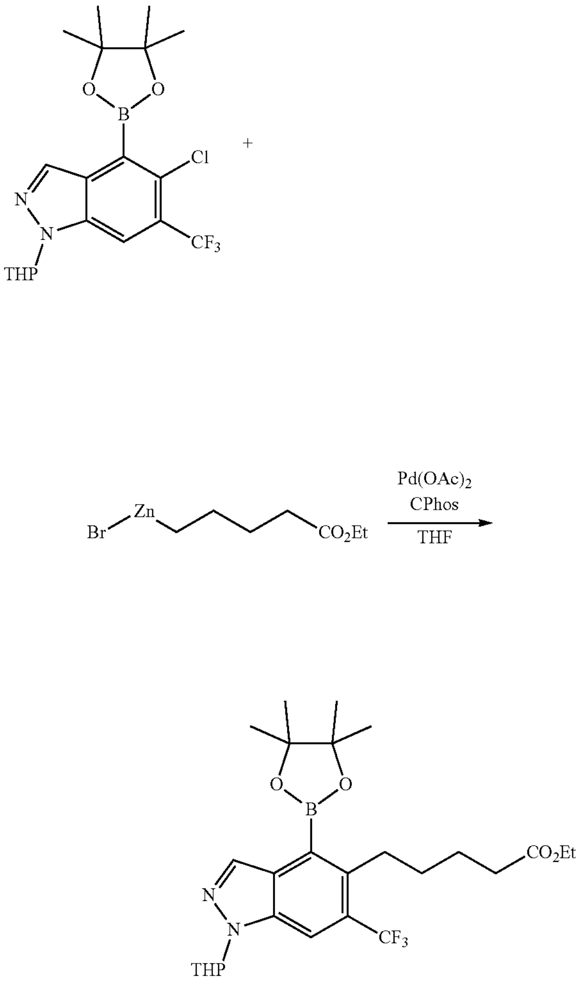

Intermediate TT

A vial was charged with palladium (II) acetate (52 mg, 0.23 mmol), CPhos (0.20 g, 0.46 mmol, Strem Chemicals) and 5-chloro-1-(tetrahydro-2H-pyran-2-yl)-4-(4,4,5,5-tetramethyl-1,3,2-dioxaborolan-2-yl)-6-(trifluoromethyl)-1H-indazole (1.00 g, 2.32 mmol, PharmaBlock). 5-Ethoxy-5-oxopentylzinc bromide (0.5 M in THF, 14 mL, 7 mmol, Rieke Metals) was added dropwise while vigorously stirring, and the mixture was stirred at rt for 3 h. The reaction was quenched with half-saturated aqueous ammonium chloride. The aqueous layer was extracted with EtOAc, and the combined organic phases were washed with brine, dried over anhydrous sodium sulfate, filtered, and concentrated. The crude material was dissolved in MeOH (2 mL) and injected into a C18 column (50 g), eluting with a gradient of 5-80% (0.1% formic acid MeCN)/(0.1% formic acid water). The desired fractions were concentrated under reduced pressure to provide ethyl 5-(1-(tetrahydro-2H-pyran-2-yl)-4-(4,4,5,5-tetramethyl-1,3,2-dioxaborolan-2-yl)-6-(trifluoromethyl)-1H-indazol-5-yl)pentanoate (0.33 g, 0.63 mmol, 27% yield) as orange oil.

Intermediate UU: (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)azepan-3-ol

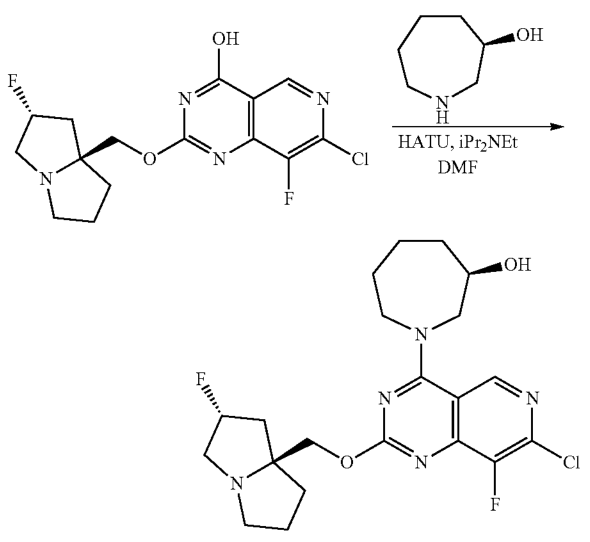

Intermediate UU

The title compound was synthesized in an analogous fashion to Intermediate V using (3R)-azepan-3-ol (CAS #: 1573085-99-0, PharmaBlock, Inc.). m/z (ESI): 454.0 $(M+H)^+$.

Intermediate VV: (S)-4-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol

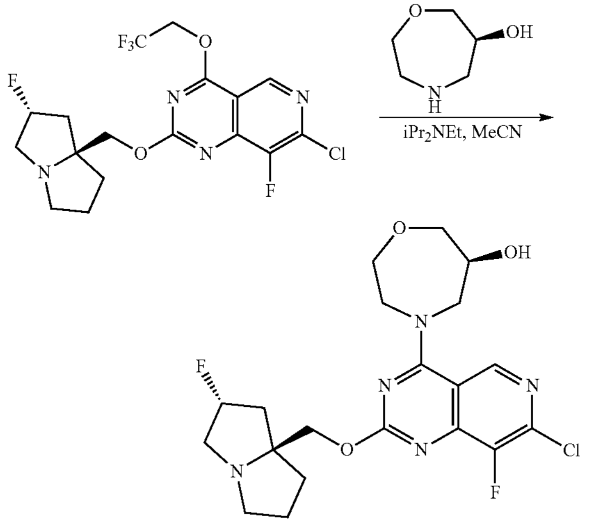

Intermediate VV

The title compound was synthesized in an analogous fashion to Intermediate EE using (S)-[1,4]oxazepan-6-ol (CAS #: 1373232-31-5, J&W Pharmlab). m/z (ESI): 456.0 $(M+H)^+$.

Intermediate WW: Methyl 5-(4-bromo-6-chloro-1-(tetrahydro-2H-pyran-2-yl)-1H-indazol-5-yl)-2-methylpentanoate

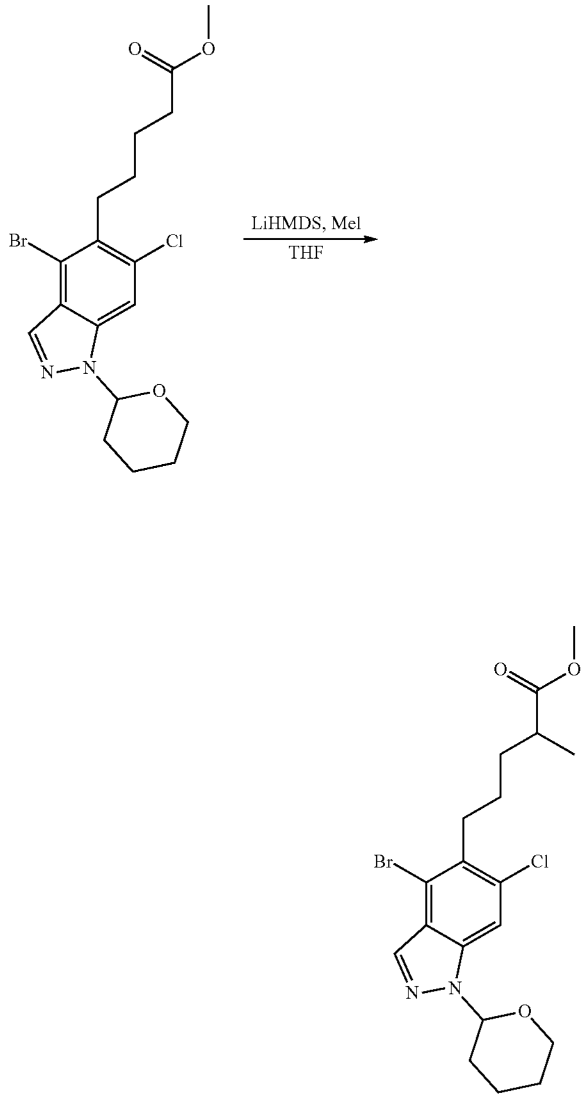

Intermediate WW

To an oven dried round-bottom flask was charged with methyl 5-(4-bromo-6-chloro-1-(tetrahydro-2H-pyran-2-yl)-1H-indazol-5-yl)pentanoate (0.80 g, 1.90 mmol, Intermediate P) in tetrahydrofuran (9 mL). The contents were cooled to −78° C. and LiHMDS (1 M in THF, 2.0 mL, 2.0 mmol) was added dropwise. The reaction mixture was stirred at −78° C. for 15 min and then iodomethane (0.14 mL, 2.2 mmol) was added and the reaction was stirred at −78° C. for 1 h. After warming the reaction was diluted with saturated aqueous ammonium chloride and extracted with EtOAc. The organics were dried ($Na_2SO_4$) and concentrated and the residue was purified by column chromatography on silica gel, eluting with 0-35% EtOAc in heptane, to give methyl 5-(4-bromo-6-chloro-1-(tetrahydro-2H-pyran-2-yl)-1H-indazol-5-yl)-2-methylpentanoate (0.15 g, 0.33 mmol, 18% yield) as colorless oil. m/z (ESI): 443.0 $(M+H)^+$.

Intermediate XX: Ethyl 2-(2-(4-bromo-6-chloro-1-(tetrahydro-2H-pyran-2-yl)-1H-indazol-5-yl)ethoxy) acetate

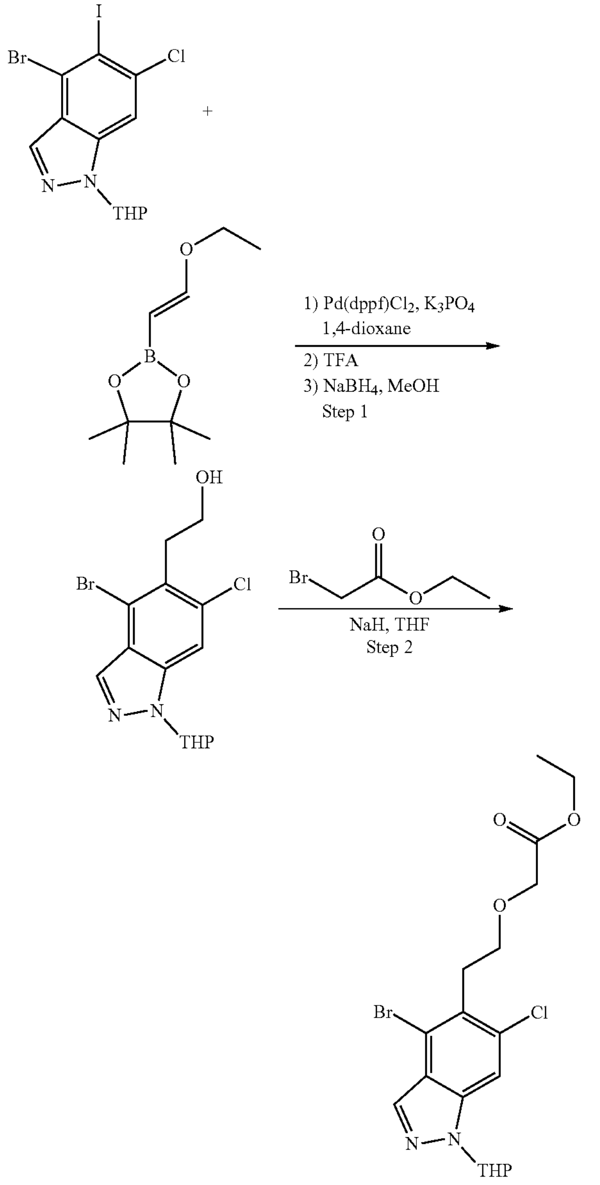

Intermediate XX

Step 1. 2-(4-Bromo-6-chloro-1-(tetrahydro-2H-pyran-2-yl)-1H-indazol-5-yl)ethan-1-ol. A vial was charged with (E)-1-ethoxyethene-2-boronic acid pinacol ester (2.02 g, 10.2 mmol, Aurum Pharmatech), 4-bromo-6-chloro-5-iodo-1-(tetrahydro-2H-pyran-2-yl)-1H-indazole (3.00 g, 6.80 mmol, LabNetwork), tripotassium phosphate (5.05 g, 23.8 mmol), 1,1'-bis(diphenylphosphino)ferrocene-palladium dichloride (0.50 g, 0.68 mmol), water (4 mL) and 1,4-dioxane (19 mL). The reaction mixture was heated to 100° C. for 1.5 h. After cooling to rt, the crude material was diluted with EtOAc and saturated aqueous sodium bicarbonate. The aqueous layer was extracted with EtOAc, and the combined organics were dried ($Na_2SO_4$) and concentrated. This crude product was then diluted with 1,4-dioxane (18 mL) and water (1 mL) and to it was added trifluoroacetic acid (7.8 mL, 102 mmol) dropwise. The reaction mixture was stirred at 40° C. for 6 h. After cooling to rt, the reaction mixture was concentrated and the residue was purified by column chromatography on silica gel, eluting with 0-100% (3:1 EtOAc:EtOH+2% triethylamine) in heptane, to provide 2-(4-bromo-6-chloro-1-(tetrahydro-2H-pyran-2-yl)-1H-indazol-5-yl)acetaldehyde (2.40 g, 6.71 mmol, 99% yield) as impure brown oil, which was treated with triethyl amine and filtered to neutralize the remaining TFA. m/z (ESI): 357.0 $(M+H)^+$. To a 250 mL round-bottom flask was charged with the above aldehyde (2.40 g, 6.71 mmol) and ethanol (70 mL). The reaction mixture was cooled to 0° C. and sodium borohydride (0.53 g, 14 mmol) was added portionwise. The solution was allowed to warm to rt and and stir for 30 min. The reaction was then carefully quenched by the addition of methanol, water, and saturated aqueous ammonium chloride. The resulting solution was extracted with EtOAc. The combined organics were dried ($Na_2SO_4$) and concentrated. The residue was purified by reverse phase chromatography using a 50 g C18 column, eluting with 0-100% acetonitrile+0.1% TFA in water+0.1% TFA to give 2-(4-bromo-6-chloro-1-(tetrahydro-2H-pyran-2-yl)-1H-indazol-5-yl)ethan-1-ol (0.20 g, 0.56 mmol, 8% yield). m/z (ESI): 359.0 $(M+H)^+$.

Step 2. Ethyl 2-(2-(4-bromo-6-chloro-1-(tetrahydro-2H-pyran-2-yl)-1H-indazol-5-yl)ethoxy)acetate. To an oven dried 100 mL round-bottom flask was charged with 2-(4-bromo-6-chloro-1-(tetrahydro-2H-pyran-2-yl)-1H-indazol-5-yl)ethan-1-ol (0.34 g, 0.95 mmol) in tetrahydrofuran (9.5 mL). The contents were cooled to 0° C. and sodium hydride, 60% dispersion in mineral oil (0.12 g, 3.0 mmol) was added. The reaction mixture was allowed to stir at 0° C. for 20 min, then ethyl bromoacetate (0.42 mL, 3.8 mmol) was added dropwise and the reaction was allowed to warm up to rt and stir for 4.5 h. The reaction mixture was carefully quenched by addition of saturated aqueous ammonium chloride and then extracted with EtOAc. The combined organics were dried ($Na_2SO_4$) and concentrated. The residue was purified by column chromatography on silica gel, eluting with 0-40% EtOAc in heptane, to provide ethyl 2-(2-(4-bromo-6-chloro-1-(tetrahydro-2H-pyran-2-yl)-1H-indazol-5-yl)ethoxy)acetate (0.20 g, 0.45 mmol, 48% yield) as colorless oil. m/z (ESI): 445.8 $(M+H)^+$.

Intermediate YY: Methyl 2-((S)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-yl)acetate

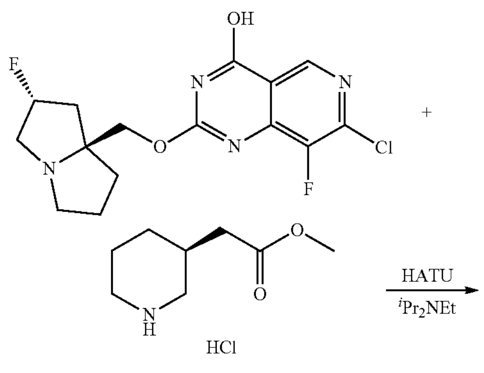

-continued

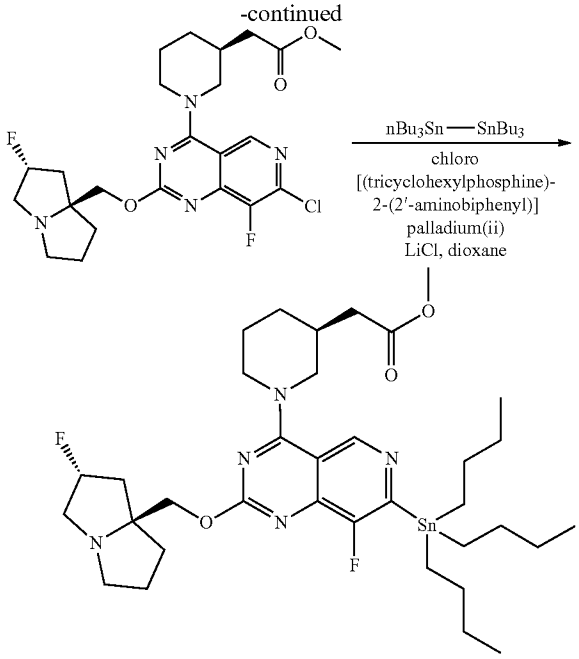

Intermediate YY

Step 1. Methyl 2-((S)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate. A 250 mL round-bottom flask was charged with 7-chloro-8-fluoro-2-(((2R,7aS)-2-fluorotetrahydro-1H-pyrrolizin-7a(5H)-yl)methoxy)pyrido[4,3-d]pyrimidin-4-ol (4.00 g, 11 mmol, Intermediate Z), N-ethyl-N-isopropylpropan-2-amine (7.8 mL, 45 mmol) and HATU (6.39 g, 16.8 mmol) in N,N-dimethylformamide (45 mL). The solution was stirred at rt for 10 min, then methyl 2-[(3S)-piperidin-3-yl]acetate hydrochloride (2.82 g, 14.6 mmol, Enamine) was added. The reaction mixture was stirred at rt for 16 h and was diluted with satd $NH_4Cl$ and extracted with EtOAc. The organic extract was washed with saturated NaCl, dried over $MgSO_4$, and concentrated. The crude material was purified by column chromatography on silica gel column, eluting with a gradient of 0-100% EtOAc/EtOH (3:1) with 1% TEA in heptane, to provide methyl 2-((S)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (5.00 g, 10 mmol, 90% yield) as orange solid. m/z (ESI): 496.0 $(M+H)^+$.

Step 2. Methyl 2-((S)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-yl)acetate. To a 40-mL vial was added methyl 2-((S)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (0.80 g, 1.6 mmol) and lithium chloride (0.34 g, 8.07 mmol) in 1,4-dioxane (8 mL). The reaction mixture was sparged with nitrogen for 15 min, then, 1,1,1,2,2,2-hexabutyl-distannane (2.5 mL, 4.8 mmol) and chloro[(tricyclohexylphosphine)-2-(2'-aminobiphenyl)]palladium(II) (0.38 g, 0.65 mmol) was added. The reaction mixture was stirred at 100° C. for 16 h. After cooling to rt, the reaction was concentrated under reduced pressure and the residue was purified by column chromatography on silica gel, eluting with a gradient of 0-75% of a 3:1 EtOAc/EtOH (containing 2% triethylamine) in heptane to provide methyl 2-((S)-1-(8- fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-yl)acetate (0.60 g, 0.80 mmol, 50% yield) as clear oil. m/z (ESI): 751.8 $(M+H)^+$.

Intermediate ZZ: 4-Bromo-5-(3-((tert-butyldimethylsilyl)oxy)-2-methylpropyl)-6-methyl-1-(tetrahydro-2H-pyran-2-yl)-1H-indazole

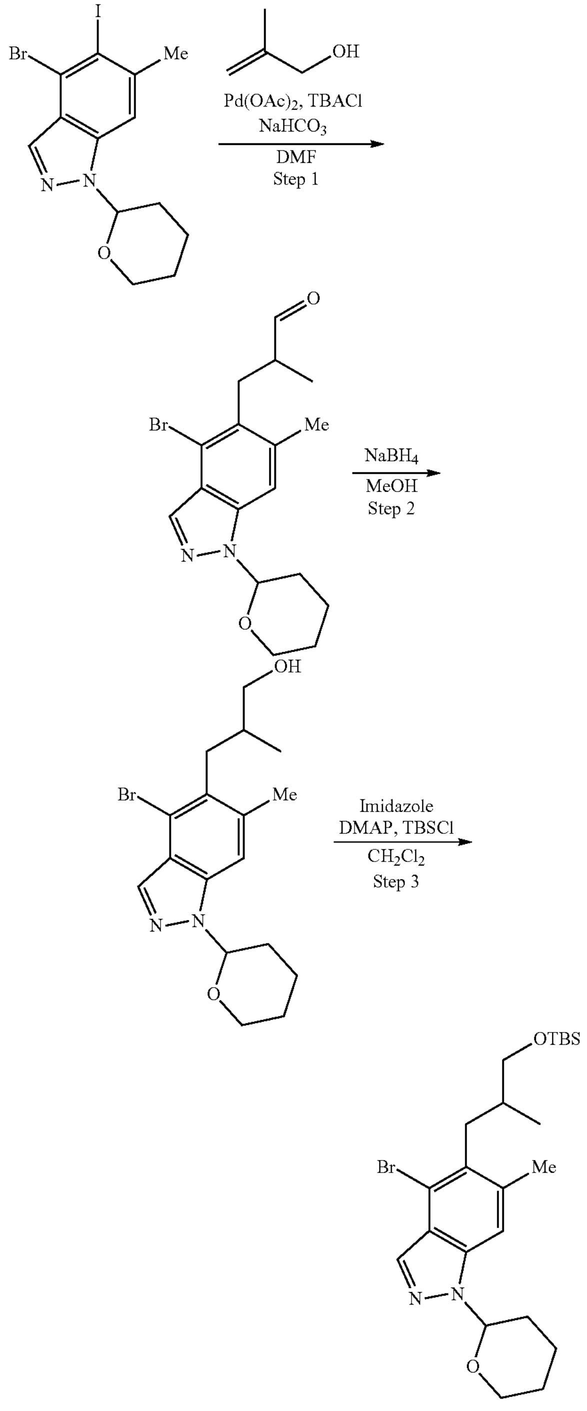

Intermediate ZZ

Step 1. 3-(4-Bromo-6-methyl-1-(tetrahydro-2H-pyran-2-yl)-1H-indazol-5-yl)-2-methylpropanal. To a 40 mL vial was charged with 4-bromo-5-iodo-6-methyl-1-(tetrahydro-2H-pyran-2-yl)-1H-indazole (1.50 g, 3.56 mmol, Advanced ChemBlocks), sodium bicarbonate (0.75 g, 8.91 mmol), TBACl (0.99 g, 3.56 mmol), and palladium(II) acetate (40 mg, 0.18 mmol). The vial was purged with nitrogen and then N,N-dimethylformamide (7 mL) and methallyl alcohol (0.45 mL, 5.3 mmol, Combi-Blocks) were added and the reaction mixture was stirred at 65° C. for 2 days. After cooling to rt, the reaction was diluted with 10% aqueous LiCl and EtOAc. The layers were separated, and the organic layer was washed once more using 10% aqueous LiCl. The organic layer was dried with sodium sulfate, filtered, and concentrated. The crude material was purified by column chromatography on silica gel, eluting with 0-35% EtOAc in heptane to give 3-(4-bromo-6-methyl-1-(tetrahydro-2H-pyran-2-yl)-1H-indazol-5-yl)-2-methylpropanal (0.99 g, 2.7 mmol, 76% yield) as clear oil. m/z (ESI): 365.1/367.0 $(M+H)^+$.

Step 2. 3-(4-Bromo-6-methyl-1-(tetrahydro-2H-pyran-2-yl)-1H-indazol-5-yl)-2-methylpropan-1-ol. A solution of 3-(4-bromo-6-methyl-1-(tetrahydro-2H-pyran-2-yl)-1H-indazol-5-yl)-2-methylpropanal (0.99 g, 2.70 mmol) in methanol (27 mL) was cooled to 0° C. and then sodium borohydride (0.13 g, 3.38 mmol) was added. The reaction was allowed to stir at 0° C. for 15 min and was then quenched via the addition of saturated aqueous ammonium chloride. The mixture was diluted with EtOAc and warmed to rt. The layers were separated, and the aqueous layer was extracted with EtOAc. The combined organic layers were dried with sodium sulfate, filtered, and concentrated. The crude product was purified by column chromatography on silica gel, eluting with a gradient of 0-40% EtOAc in heptane to provide 3-(4-bromo-6-methyl-1-(tetrahydro-2H-pyran-2-yl)-1H-indazol-5-yl)-2-methylpropan-1-ol (0.90 g, 2.40 mmol, 91% yield) as colorless oil. m/z (ESI): 367.0/368.95 $(M+H)^+$.

Step 3. 4-Bromo-5-(3-((tert-butyldimethylsilyl)oxy)-2-methylpropyl)-6-methyl-1-(tetrahydro-2H-pyran-2-yl)-1H-indazole. The mixture of 3-(4-bromo-6-methyl-1-(tetrahydro-2H-pyran-2-yl)-1H-indazol-5-yl)-2-methylpropan-1-ol (0.9 g, 2.4 mmol), tert-butyldimethylsilyl chloride (0.44 g, 2.94 mmol), imidazole (0.42 g, 6.12 mmol), and DMAP (30 mg, 0.25 mmol) in dichloromethane (16 mL) was stirred at rt for 16 h. The reaction was then quenched via the addition of saturated aqueous sodium bicarbonate, and the aqueous layer was extracted with $CH_2Cl_2$. The combined organic layers were dried over sodium sulfate, filtered, and concentrated. The crude product was purified by column chromatography, eluting with a gradient of 0-20% EtOAc/heptane to afford 4-bromo-5-(3-((tert-butyldimethylsilyl)oxy)-2-methylpropyl)-6-methyl-1-(tetrahydro-2H-pyran-2-yl)-1H-indazole (1.20 g, 2.40 mmol, 99% yield) as colorless oil. m/z (ESI, +ve ion): 481.0/483.0 $(M+H)^+$.

Intermediate AAA: 3-(4-Bromo-6-chloro-1-(tetrahydro-2H-pyran-2-yl)-1H-indazol-5-yl)-2-methylpropan-1-ol Intermediate AAA

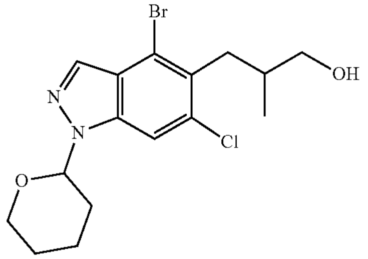

This compound was prepared in an analogous fashion as Intermediate ZZ in step 1 using 4-bromo-6-chloro-5-iodo-1-(tetrahydro-2H-pyran-2-yl)-1H-indazole (Lab Network). m/z (ESI): 408.8/410.8 $(M+Na)^+$.

Intermediate BBB: rac-(3S,4R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-4-fluoropiperidin-3-ol

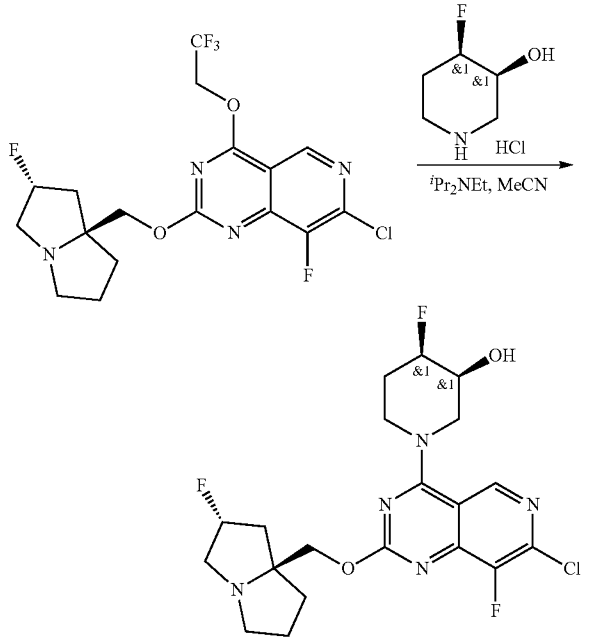

Intermediate BBB

A vial was charged with 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.75 g, 1.71 mmol, Intermediate AA, Step 2), rel-(3R,4S)-4-fluoropiperidin-3-ol hydrochloride (0.29 g, 1.88 mmol, Advanced ChemBlocks Inc.) and acetonitrile (7 mL). N-ethyl-N-isopropylpropan-2-amine (1.0 mL, 6.0 mmol) was added, and the reaction was heated to 50° C. for 5 h. After cooling to rt, the reaction was concentrated and the crude product was purified by column chromatography on silica gel, eluting with a gradient of 0-75% of a 3:1 EtOAc/EtOH (containing 2% triethylamine) in heptane to provide rac-(3S,4R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-4-fluoropiperidin-3-ol (0.57 g, 1.24 mmol, 72% yield) as orange solid. m/z (ESI): 458.0 $(M+H)^+$.

Intermediate CCC: (3R,4R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-4-methylpiperidin-3-ol

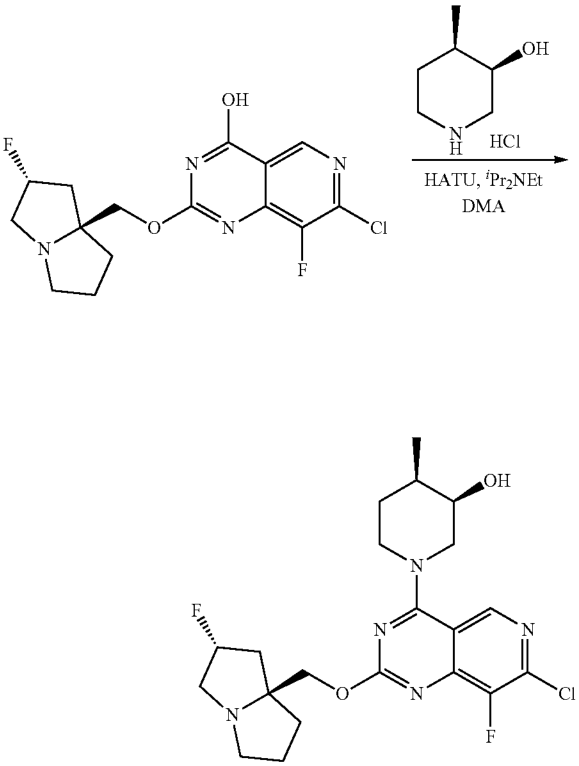

Intermediate CCC

A 40 mL vial was charged with 7-chloro-8-fluoro-2-(((2R,7aS)-2-fluorotetrahydro-1H-pyrrolizin-7a(5H)-yl)methoxy)pyrido[4,3-d]pyrimidin-4-ol (0.28 g, 0.77 mmol, Intermediate Z), 1,1'-dimethyltriethylamine (0.67 mL, 3.9 mmol) and N,N-dimethylacetamide (5 mL). The solution was stirred at rt for 10 min before HATU (0.35 g, 0.93 mmol) was added. After 50 min, (3R,4R)-4-methylpiperidin-3-ol hydrochloride (0.15 g, 1.00 mmol, Enamine) was added and the reaction was stirred at rt for 16 h. The reaction mixture was diluted with $CH_2Cl_2$, and the organic layer was washed with water, dried $(Na_2SO_4)$, filtered, and concentrated. The residue was purified by column chromatrography on silica gel, eluting with 0-75% EtOAc/EtOH 3:1 blend in heptane with 2% triethylamine as additive to provide (3R,4R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-4-methylpiperidin-3-ol (0.18 g, 0.39 mmol, 50% yield) as orange solid. m/z (ESI): 454.0 $(M+H)^+$.

Intermediate DDD: rac-(3R,5S)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-5-fluoropiperidin-3-ol

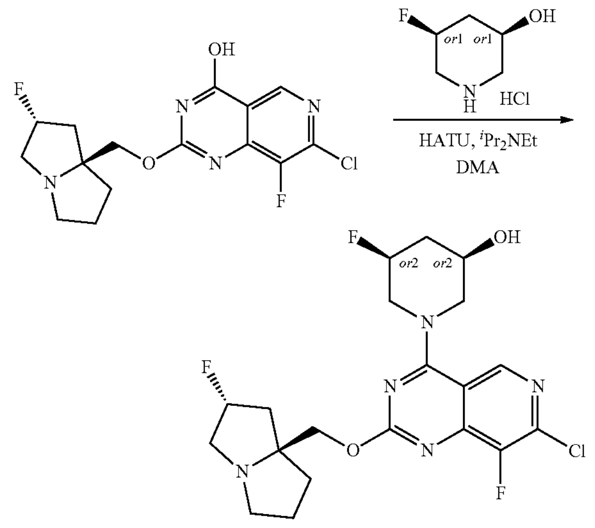

Intermediate DDD

A 40 mL vial was charged with 7-chloro-8-fluoro-2-(((2R,7aS)-2-fluorotetrahydro-1H-pyrrolizin-7a(5H)-yl)methoxy)pyrido[4,3-d]pyrimidin-4-ol (0.20 g, 0.56 mmol, Intermediate Z), 1,1'-dimethyltriethylamine (0.39 mL, 2.2 mmol) and N,N-dimethylacetamide (5.5 mL). The solution was stirred at rt for 10 min before HATU (0.26 g, 0.67 mmol) was added. After 50 min, rel-(3R,5S)-5-fluoropiperidin-3-ol hydrochloride (0.11 g, 0.73 mmol, AK scientific) was added and the reaction mixture was stirred at rt for 16 h. The reaction was diluted with $CH_2Cl_2$, and the organic layer was washed with water, dried ($Na_2SO_4$), filtered, and concentrated. The residue was purified by column chromatography on silica gel, eluting with 0-80% EtOAc/EtOH 3:1 blend in heptane with 2% triethylamine additive to provide rac-(3R,5S)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-5-fluoropiperidin-3-ol (89 mg, 0.20 mmol, 35% yield) as yellow solid. m/z (ESI): 458.0 $(M+H)^+$.

Intermediate EEE: (3R)-1-(7-(5-((E)-3-((tert-Butyldimethylsilyl)oxy)prop-1-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol

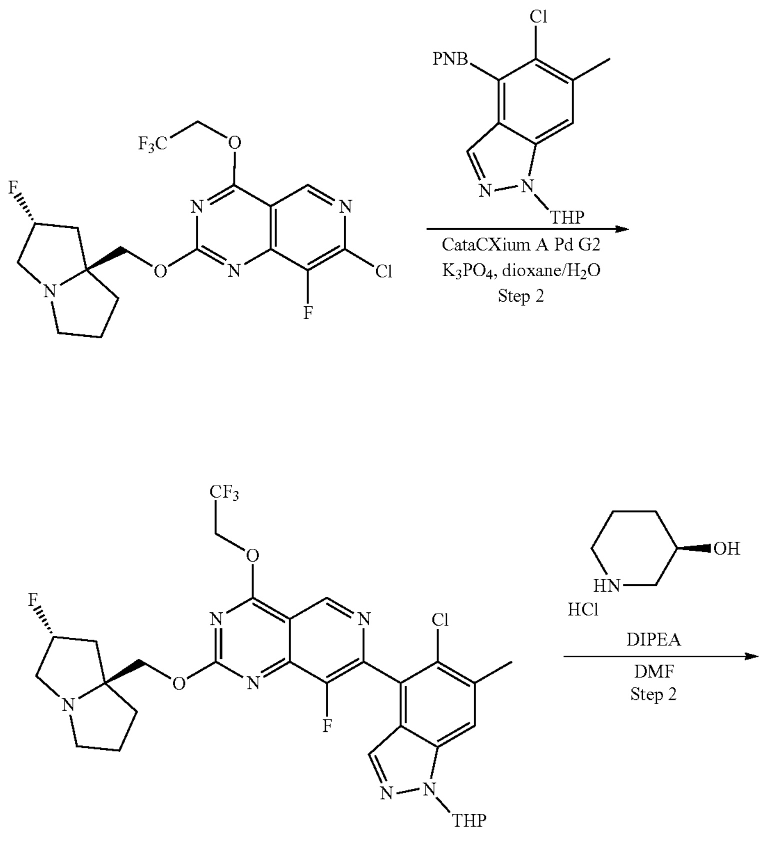

-continued

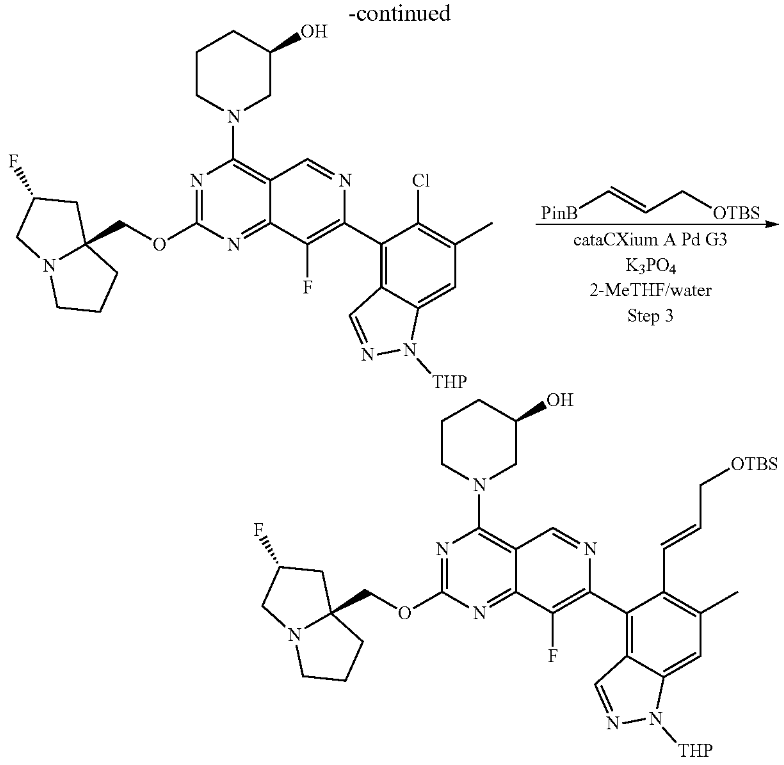

Intermediate EEE

Step 1. 7-(5-Chloro-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine. To a solution of 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (8.50 g, 19.4 mmol, Intermediate AA, Step 2) in 1,4-dioxane (170 mL) and water (21 mL) was added 5-chloro-6-methyl-1-(tetrahydro-2H-pyran-2-yl)-4-(4,4,5,5-tetramethyl-1,3,2-dioxaborolan-2-yl)-1H-indazole (8.76 g, 23.3 mmol, Ambeed, Inc.), $K_3PO_4$ (18.9 g, 58.1 mmol) and cataCXium A Pd G2 (1.30 g, 1.90 mmol) under $N_2$. Then the mixture was stirred at 100° C. for 5 h. After cooling to rt, the mixture was diluted with water and extracted with EtOAc. The combined organic layers were washed with brine, dried over $Na_2SO_4$, filtered, and concentrated under reduced pressure. The residue was purified by column chromatography on silica gel, eluting with a gradient of 30-100% EtOAc in petroleum ether, to give 7-(5-chloro-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (5 g, 7.67 mmol, 39% yield) as yellow solid. m/z (ESI): 653.2 $(M+H)^+$.

Step 2. (3R)-1-(7-(5-Chloro-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. A vial was charged with 7-(5-chloro-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.50 g, 0.77 mmol), (R)-piperidin-3-ol hydrochloride (0.11 g, 0.77 mmol) and N,N-dimethylformamide (2.5 mL). N-Ethyl-N-isopropylpropan-2-amine (0.3 mL, 1.7 mmol) was added dropwise, and the reaction mixture was stirred at rt for 3 h, diluted with water and extracted with DCM. The combined organic phases were washed with water, brine, dried over anhydrous sodium sulfate, filtered, and concentrated under reduced pressure. The crude material was dissolved in MeOH (2 mL) and injected into a pre-packed C18 column (50 g), eluting with a gradient of 5-100% (0.1% formic acid MeCN)/(0.1% formic acid water) over 10 min. The desired fractions were basified with saturated aqueous sodium bicarbonate, extracted with DCM. The combined organic layers were dried over anhydrous sodium sulfate, filtered and concentrated under reduced pressure to provide (3R)-1-(7-(5-chloro-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.30 g, 0.46 mmol, 60% yield) as off-white solid. m/z (ESI): 653.8 $(M+H)^+$.

Step 3. (3R)-1-(7-(5-((E)-3-((tert-Butyldimethylsilyl)oxy)prop-1-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. A vial was charged with (3R)-1-(7-(5-chloro-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.30 g, 0.46 mmol), (E)-tert-butyldimethyl((3-(4,4,5,5-tetramethyl-1,3,2-dioxaborolan-2-yl)allyl)oxy)silane (0.68 g, 2.29 mmol, Enamine), cataCXium A Pd G3 (50 mg, 0.069 mmol), potassium phosphate tribasic (0.34 g, 1.61 mmol), water (0.8 mL) and 2-methyltetrahydrofuran (3.8 mL). The reaction mixture was heated to 100° C. for 3 h, cooled, diluted with water, and extracted with DCM. The combined organic phases were washed with brine, dried over anhydrous sodium sulfate, filtered, and concentrated under reduced pressure. The crude material was dissolved in minimal MeOH and injected into a pre-packed C18 column (50 g), eluting with a gradient of 5-80% (0.1% formic acid MeCN)/(0.1% formic acid water) over 20 min. The desired fractions were basified with saturated aqueous sodium bicarbonate, extracted with DCM, dried over anhydrous sodium sulfate, filtered and concentrated under reduced pressure to provide (3R)-1-(7-(5-((E)-3-((tert-butyldimethylsilyl)oxy)prop-1-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (58 mg, 0.073 mmol, 16% yield) as off-white solid. m/z (ESI): 789.9 $(M+H)^+$.

Intermediate FFF: 5-(3-((tert-Butyldimethylsilyl)oxy)propyl)-6-chloro-1-(tetrahydro-2H-pyran-2-yl)-4-(4,4,5,5-tetramethyl-1,3,2-dioxaborolan-2-yl)-1H-indazole

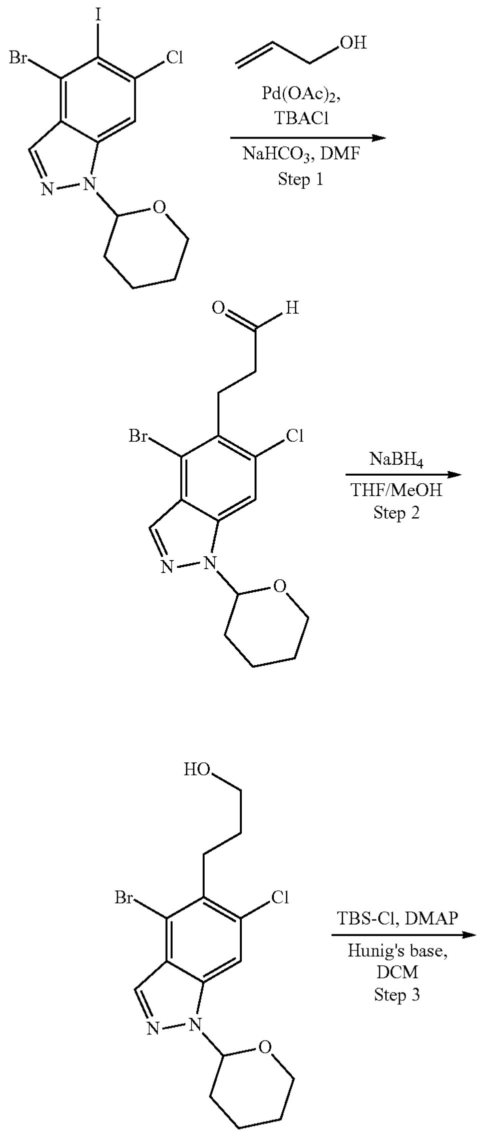

-continued

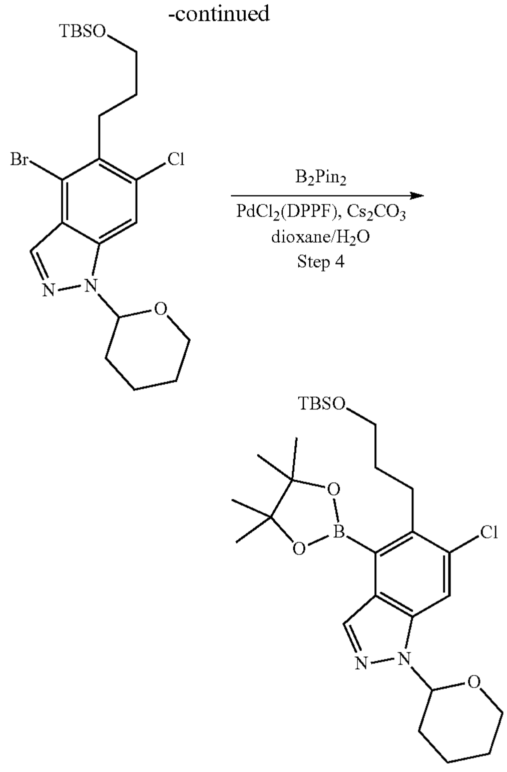

Intermediate FFF

Step 1. 3-(4-Bromo-6-chloro-1-(tetrahydro-2H-pyran-2-yl)-1H-indazol-5-yl)propanal. To a 40 mL vial was charged with 4-bromo-6-chloro-5-iodo-1-(tetrahydro-2H-pyran-2-yl)-1H-indazole (3.00 g, 6.80 mmol, Lab Network), sodium bicarbonate (1.43 g, 17.0 mmol), TBACl (1.95 g, 6.82 mmol), and N,N-dimethylformamide (14 mL). The solution was degassed by nitrogen bubbling for 10 min. Then palladium(II) acetate (77 mg, 0.34 mmol) and allyl alcohol (0.7 mL, 10 mmol) were added at 50° C. The reaction mixture was stirred at 50° C. for 18 h. After cooling to rt, the reaction was diluted with saturated aqueous ammonium chloride and extracted with EtOAc. The organic layer was washed with saturated aqueous sodium chloride, dried over sodium sulfate, and concentrated. The crude material was purified by column chromatography on silica gel, eluting with a gradient of 0-50% 3:1 EtOAc/EtOH in heptane, to provide 3-(4-bromo-6-chloro-1-(tetrahydro-2H-pyran-2-yl)-1H-indazol-5-yl)propanal (2.12 g, 5.70 mmol, 84% yield) as light-orange oil. m/z (ESI): 371.0 $(M+H)^+$.

Step 2: 3-(4-Bromo-6-chloro-1-(tetrahydro-2H-pyran-2-yl)-1H-indazol-5-yl)propan-1-ol. To a 100-mL round-bottom flask was added 3-(4-bromo-6-chloro-1-(tetrahydro-2H-pyran-2-yl)-1H-indazol-5-yl)propanal (1.06 g, 2.86 mmol) in tetrahydrofuran (5 mL)/methanol (5 mL). The reaction mixture was cooled to 0° C. Then, sodium borohydride (0.11 g, 2.86 mmol) was slowly added in portion. The reaction mixture was stirred at 0° C. for 30 min, then was slowly quenched with saturated $NH_4Cl$ and extracted with EtOAc. The combined organic layers were washed with brine, dried over $MgSO_4$, filtered, and concentrated under reduced pressure. 3-(4-Bromo-6-chloro-1-(tetrahydro-2H-pyran-2-yl)-1H-indazol-5-yl)propan-1-ol (1.03 g, 2.76 mmol, 97% yield) was obtained as light-yellow oil without further purification. m/z (ESI): 289.0 $(M-THP+H)^+$.

Step 3: 4-Bromo-5-(3-((tert-butyldimethylsilyl)oxy)propyl)-6-chloro-1-(tetrahydro-2H-pyran-2-yl)-1H-indazole. To a stirred solution of 3-(4-bromo-6-chloro-1-(tetrahydro-2H-pyran-2-yl)-1H-indazol-5-yl)propan-1-ol (1.03 g, 2.76 mmol) and 1,1'-dimethyltriethylamine (0.53 mL, 3.0 mmol) in dichloromethane (10 mL) in a 40 mL vial was added tert-butyldimethylsilyl chloride (0.46 g, 3.03 mmol) and 4-(dimethylamino)pyridine (34 mg, 0.28 mmol) at 0° C. After stirring at 0° C. for 2 h, the crude material was purified by column chromatography on silica gel, eluting with a gradient of 0-30% 3:1 EtOAc/EtOH in heptane, to provide 4-bromo-5-(3-((tert-butyldimethylsilyl)oxy)propyl)-6-chloro-1-(tetrahydro-2H-pyran-2-yl)-1H-indazole (1.12 g, 2.3 mmol, 83% yield) as colorless oil. m/z (ESI): 487.1 $(M+H)^+$.

Step 4. 5-(3-((tert-Butyldimethylsilyl)oxy)propyl)-6-chloro-1-(tetrahydro-2H-pyran-2-yl)-4-(4,4,5,5-tetramethyl-1,3,2-dioxaborolan-2-yl)-1H-indazole. To a solution of 4-bromo-5-(3-((tert-butyldimethylsilyl)oxy)propyl)-6-chloro-1-(tetrahydro-2H-pyran-2-yl)-1H-indazole (3.4 g, 7.0 mmol), 4,4,4',4',5,5,5',5'-octamethyl-2,2'-bi(1,3,2-dioxaborolane) (8.85 g, 34.8 mmol) in 1,4-dioxane (80 mL) and water (10 mL) was added Pd(dppf)$Cl_2$ (0.51 g, 0.7 mmol) and $Cs_2CO_3$ (6.81 g, 20.9 mmol) under $N_2$. The reaction mixture was heated at 120° C. for 5 h. After cooling to rt, the reaction mixture was diluted with water and extracted with EtOAc. The combined organic layers were washed with brine, dried over $Na_2SO_4$, filtered, and concentrated. The residue was purified by column chromatography on silica gel, eluting with a gradient of 10-100% EtOAc in petroleum ether, to give 5-(3-((tert-butyldimethylsilyl)oxy)propyl)-6-chloro-1-(tetrahydro-2H-pyran-2-yl)-4-(4,4,5,5-tetramethyl-1,3,2-dioxaborolan-2-yl)-1H-indazole (3.3 g, 6.2 mmol, 88% yield) as yellow oil. m/z (ESI): 535.3/537.2 $(M+H)^+$.

Intermediate GGG: (S)-4-(7-Bromo-6,8-difluoro-2-(((2R,7aS)-2-fluorotetrahydro-1H-pyrrolizin-7a(5H)-yl)methoxy)quinazolin-4-yl)-1,4-oxazepan-6-ol

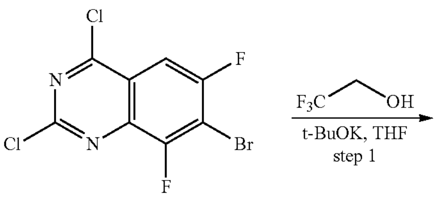

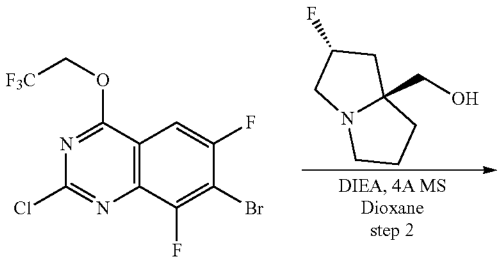

-continued

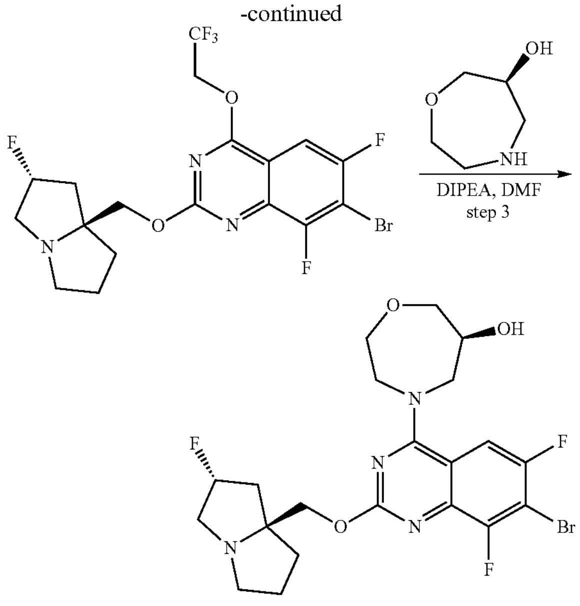

Intermediate GGG

Step 1. 7-Bromo-2-chloro-6,8-difluoro-4-(2,2,2-trifluoroethoxy)quinazoline. To a solution of 7-bromo-2,4-dichloro-6,8-difluoroquinazoline (20.0 g, 63.7 mmol) in tetrahydrofuran (300 mL) was added the mixture of 2,2,2-trifluoroethan-1-ol (6.06 g, 60.5 mmol) and t-BuOK (1 M in THF, 60.5 mL, 60.5 mmol) dropwise at −60° C. The mixture was stirred at −60° C. for 2 h, then was quenched by addition of water, and extracted with EtOAc. The combined organic layers were dried over $Na_2SO_4$, filtered, and concentrated under reduced pressure. The crude product was triturated with petroleum ether at rt for 30 min. The suspension was filtered, and the filter cake was concentrated under reduced pressure to give 7-bromo-2-chloro-6,8-difluoro-4-(2,2,2-trifluoroethoxy)quinazoline (17 g, 45 mmol, 74% yield) as yellow solid.

Step 2. 7-Bromo-6,8-difluoro-2-(((2R,7aS)-2-fluorotetrahydro-1H-pyrrolizin-7a(5H)-yl)methoxy)-4-(2,2,2-trifluoroethoxy)quinazoline. A mixture of 7-bromo-2-chloro-6,8-difluoro-4-(2,2,2-trifluoroethoxy)quinazoline (5.00 g, 13.2 mmol), ((2R,7aS)-2-fluorotetrahydro-1H-pyrrolizin-7a(5H)-yl)methanol (2.53 g, 15.9 mmol), DIPEA (6.9 mL, 40 mmol), 4 Å MS (5 g) in 1,4-dioxane (70 mL) was stirred at 100° C. for 12 h under nitrogen. After cooling to rt, the reaction mixture was filtered and concentrated under reduced pressure. The mixture was diluted by addition of water, and then extracted with EtOAc. The combined organic layers were dried over $Na_2SO_4$, filtered and the filtrate was concentrated under reduced pressure. The residue was purified by column chromatography on silica gel, eluting with a gradient of 10-100% EtOAc in petroleum ether, to give 7-bromo-6,8-difluoro-2-(((2R,7aS)-2-fluorotetrahydro-1H-pyrrolizin-7a(5H)-yl)methoxy)-4-(2,2,2-trifluoroethoxy)quinazoline (1.50 g, 3.00 mmol, 23% yield) as white solid. m/z (ESI): 500.0/502.1 $(M+H)^+$.

Step 3. (S)-4-(7-Bromo-6,8-difluoro-2-(((2R,7aS)-2-fluorotetrahydro-1H-pyrrolizin-7a(5H)-yl)methoxy)quinazolin-4-yl)-1,4-oxazepan-6-ol. A 40-mL vial was charged with (S)-[1,4]oxazepan-6-ol (0.94 g, 8.0 mmol, J&W Pharmlab), 7-bromo-6,8-difluoro-2-(((2R,7aS)-2-fluorotetrahydro-1H-pyrrolizin-7a(5H)-yl)methoxy)-4-(2,2,2-trifluoroethoxy) quinazoline (2.00 g, 4.00 mmol), N,N-diisopropylethylamine (2.8 mL, 16 mmol), and DMF (20 mL). The reaction was stirred at 100° C. for 24 h. Water and DCM were added. The organic layer was separated, dried ($Na_2SO_4$) and concentrated. The crude material was purified by column chromatography on silica gel, eluting with a gradient of 0-80% 3:1 EtOAc/EtOH (with 2% $Et_3N$) in heptane, to provide (S)-4-(7-bromo-6,8-difluoro-2-(((2R,7aS)-2-fluorotetrahydro-1H-pyrrolizin-7a(5H)-yl)methoxy)quinazolin-4-yl)-1,4-oxazepan-6-ol (1.00 g, 1.90 mmol, 48% yield) as light-yellow solid. m/z (ESI): 517.1 $(M+H)^+$.

Intermediate HHH: Ethyl 4-(6-methyl-1-(tetrahydro-2H-pyran-2-yl)-4-(4,4,5,5-tetramethyl-1,3,2-dioxaborolan-2-yl)-1H-indazol-5-yl)butanoate

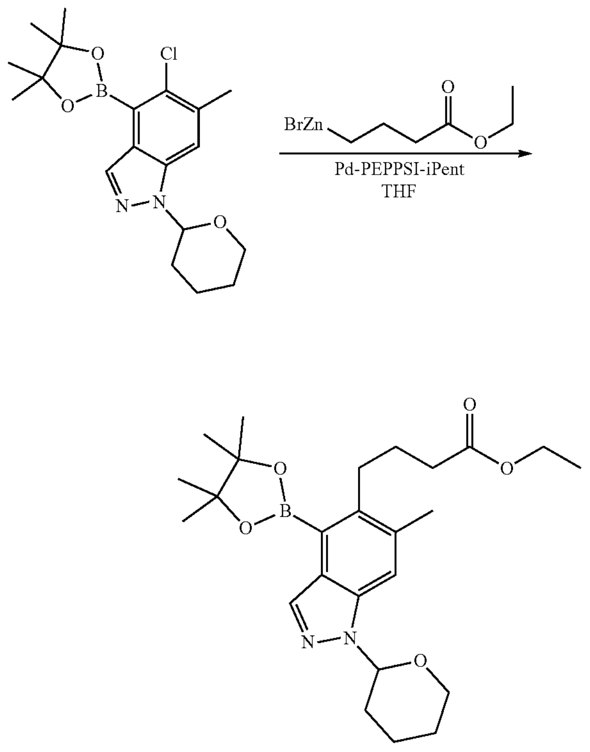

Intermediate HHH

To an oven dried round-bottom flask was added 5-chloro-6-methyl-1-(tetrahydro-2H-pyran-2-yl)-4-(4,4,5,5-tetramethyl-1,3,2-dioxaborolan-2-yl)-1H-indazole (1.50 g, 4.00 mmol, Ambeed, Inc.) and Pd-PEPPSI-IPENT catalyst (0.32 g, 0.4 mmol) in tetrahydrofuran (3 mL) under nitrogen. To this stirring solution was added 4-ethoxy-4-oxobutylzinc bromide (0.5 M in THF, 17.5 mL, 8.75 mmol, Rieke Metals, Inc.) and the reaction was stirred at rt for 1 h. The reaction was diluted with saturated $NH_4Cl$ and extracted with EtOAc. The combined organic layers were washed with brine, dried over $MgSO_4$, filtered, and concentrated under reduced pressure. The crude material was purified by column chromatography on silica gel, eluting with a gradient of 0-50% 3:1 EtOAc/EtOH in heptanes, to provide ethyl 4-(6-methyl-1-(tetrahydro-2H-pyran-2-yl)-4-(4,4,5,5-tetramethyl-1,3,2-dioxaborolan-2-yl)-1H-indazol-5-yl)butanoate (1.80 g, 3.90 mmol, 98% yield) as light-yellow oil. m/z (ESI): 457.0 $(M+H)^+$.

Intermediate III: Methyl 3-(6-methyl-1-(tetrahydro-2H-pyran-2-yl)-4-(4,4,5,5-tetramethyl-1,3,2-dioxaborolan-2-yl)-1H-indazol-5-yl)propanoate

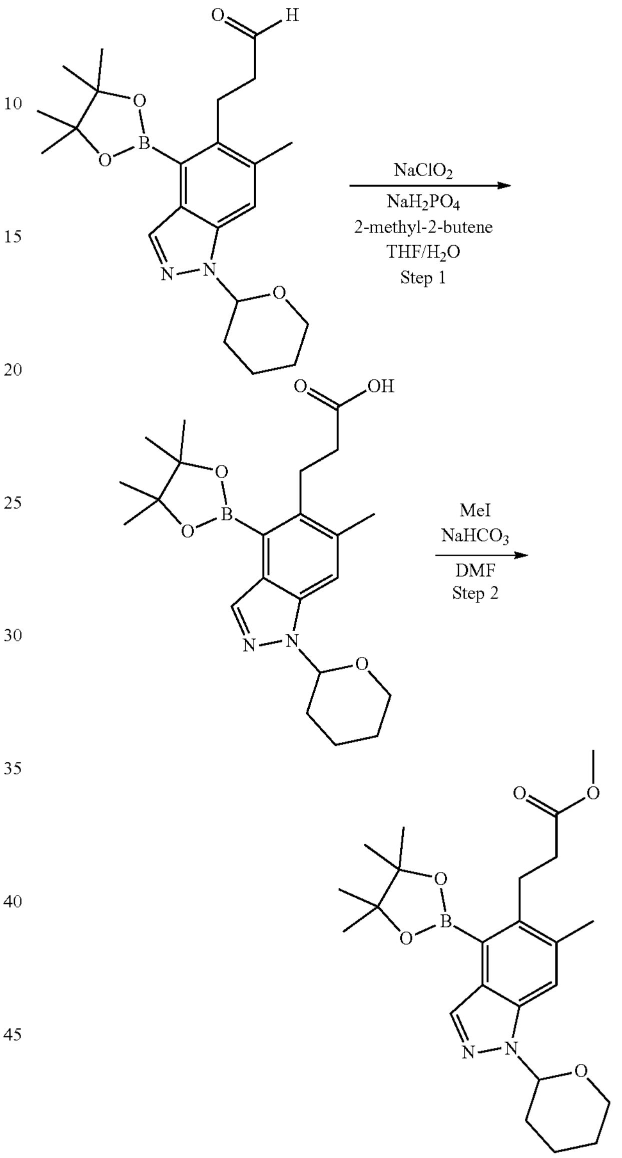

Intermediate III

Step 1. 3-(6-Methyl-1-(tetrahydro-2H-pyran-2-yl)-4-(4,4,5,5-tetramethyl-1,3,2-dioxaborolan-2-yl)-1H-indazol-5-yl)propanoic acid. To a 10-mL vial containing 3-(6-methyl-1-(tetrahydro-2H-pyran-2-yl)-4-(4,4,5,5-tetramethyl-1,3,2-dioxaborolan-2-yl)-1H-indazol-5-yl)propanal (0.28 g, 0.69 mmol, Intermediate FFF, Step 1) in tetrahydrofuran (0.5 mL)/tert-butanol (1 mL) was added 2-methyl-2-butene (0.24 mL, 2.2 mmol). A solution of sodium chlorite (0.25 g, 2.2 mmol) and sodium phosphate monobasic monohydrate (0.96 g, 6.9 mmol) in water (5 mL) was prepared and added slowly to the previous mixture at 0° C. After 15 min, the reaction was diluted with water and extracted with EtOAc. The combined organic layers were washed with brine, dried over $MgSO_4$, filtered, and concentrated under reduced pressure. Crude 3-(6-methyl-1-(tetrahydro-2H-pyran-2-yl)-4-(4,4,5, 5-tetramethyl-1,3,2-dioxaborolan-2-yl)-1H-indazol-5-yl) propanoic acid was obtained as yellow oil and was used directly in the next step. m/z (ESI): 415.0 $(M+H)^+$.

Step 2. Methyl 3-(6-methyl-1-(tetrahydro-2H-pyran-2-yl)-4-(4,4,5,5-tetramethyl-1,3,2-dioxaborolan-2-yl)-1H-indazol-5-yl)propanoate. To a 20-mL vial was added 3-(6-methyl-1-(tetrahydro-2H-pyran-2-yl)-4-(4,4,5,5-tetramethyl-1,3,2-dioxaborolan-2-yl)-1H-indazol-5-yl) propanoic acid (0.29 g, 0.69 mmol) in N,N-dimethylformamide (3.5 mL). Then, sodium bicarbonate (0.18 g, 2.08 mmol) was added followed by iodomethane (65 mL, 1.0 mmol). The reaction was stirred at for 18 h, then was diluted with water and extracted with EtOAc. The combined organic layers were washed with brine, dried over $MgSO_4$, filtered, and concentrated under reduced pressure. The crude material was purified by column chromatography on silica gel, eluting with a gradient of 0-40% 3:1 EtOAc/EtOH in heptane, to provide methyl 3-(6-methyl-1-(tetrahydro-2H-pyran-2-yl)-4-(4,4,5,5-tetramethyl-1,3,2-dioxaborolan-2-yl)-1H-indazol-5-yl)propanoate (0.11 g, 0.25 mmol, 37% yield) as yellow oil. m/z (ESI): 429.1 $(M+H)^+$.

Intermediate JJJ: 4-(6-Methyl-1-(tetrahydro-2H-pyran-2-yl)-4-(4,4,5,5-tetramethyl-1,3,2-dioxaborolan-2-yl)-1H-indazol-5-yl)butan-1-ol

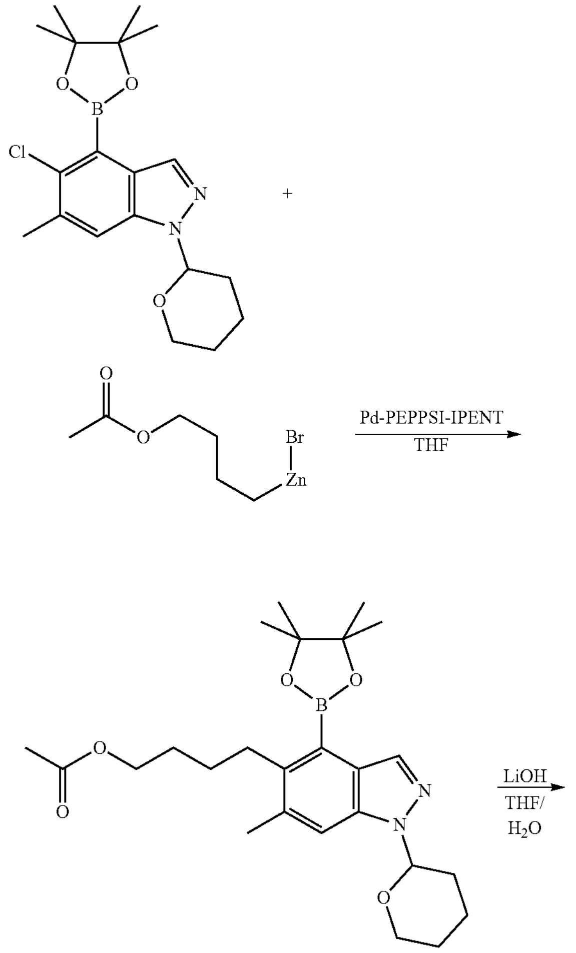

-continued

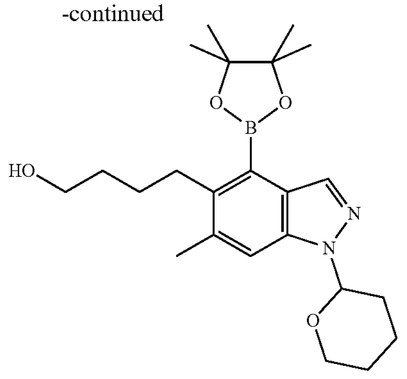

Intermediate JJJ

Step 1. 4-(6-Methyl-1-(tetrahydro-2H-pyran-2-yl)-4-(4,4,5,5-tetramethyl-1,3,2-dioxaborolan-2-yl)-1H-indazol-5-yl) butyl acetate. To a 40-mL vial was charged with 5-chloro-6-methyl-1-(tetrahydro-2H-pyran-2-yl)-4-(4,4,5,5-tetramethyl-1,3,2-dioxaborolan-2-yl)-1H-indazole (1.02 g, 2.71 mmol, Ambeed, Inc.), Pd-PEPPSI-IPENT (0.32 g, 0.41 mmol, Lab-Network), and tetrahydrofuran (7 mL). The mixture was purged with nitrogen for 5 min, then 4-acetoxybutylzinc bromide (0.5 M in tetrahydrofuran, 12 mL, 6 mmol, Rieke Metals, Inc.) was added. The mixture was heated at 55° C. for 16 h under nitrogen. After cooling to rt, the crude material was purified by column chromatography on silica gel, eluting with a gradient of 0-75% 3:1 EtOAc/EtOH in heptane, to provide 4-(6-methyl-1-(tetrahydro-2H-pyran-2-yl)-4-(4,4,5,5-tetramethyl-1,3,2-dioxaborolan-2-yl)-1H-indazol-5-yl)butyl acetate (1.20 g, 2.63 mmol, 97% yield) as yellow oil. $^1$H NMR (400 MHz, CHLOROFORM-d) δ ppm 8.34 (s, 1H), 7.47 (s, 1H), 5.70 (dd, J=9.0, 2.7 Hz, 1H), 4.14 (t, J=6.8 Hz, 2H), 3.95-4.07 (m, 1H), 3.66-3.89 (m, 1H), 2.92-3.17 (m, 2H), 2.53-2.65 (m, 1H), 2.49 (s, 3H), 2.13-2.25 (m, 1H), 2.03-2.09 (m, 4H), 1.64-1.86 (m, 6H), 1.58-1.63 (m, 1H), 1.43 (s, 12H).

Step 2. 4-(6-Methyl-1-(tetrahydro-2H-pyran-2-yl)-4-(4,4,5,5-tetramethyl-1,3,2-dioxaborolan-2-yl)-1H-indazol-5-yl) butan-1-ol. Lithium hydroxide monohydrate (0.11 g, 2.6 mmol) was added to a solution of 4-(6-methyl-1-(tetrahydro-2H-pyran-2-yl)-4-(4,4,5,5-tetramethyl-1,3,2-dioxaborolan-2-yl)-1H-indazol-5-yl)butyl acetate (0.60 g, 1.30 mmol) in tetrahydrofuran (3.3 mL) and water (3.3 mL). The reaction mixture was stirred at rt for 3 h, then was diluted with water and extracted with EtOAc. The combined organics were dried ($Na_2SO_4$) and concentrated. The residue was purified by column chromatography on silica gel, eluting with a gradient of 0-100% 3:1 EtOAc/EtOH in heptane, to give 4-(6-methyl-1-(tetrahydro-2H-pyran-2-yl)-4-(4,4,5,5-tetramethyl-1,3,2-dioxaborolan-2-yl)-1H-indazol-5-yl)butan-1-ol (0.53 g, 1.30 mmol, 97% yield) as colorless oil. m/z (ESI): 415.0 $(M+H)^+$.

Intermediate KKK: 4-Bromo-5-(3-((tert-butyldimethylsilyl)oxy)propyl)-6-fluoro-1-(tetrahydro-2H-pyran-2-yl)-1H-indazole

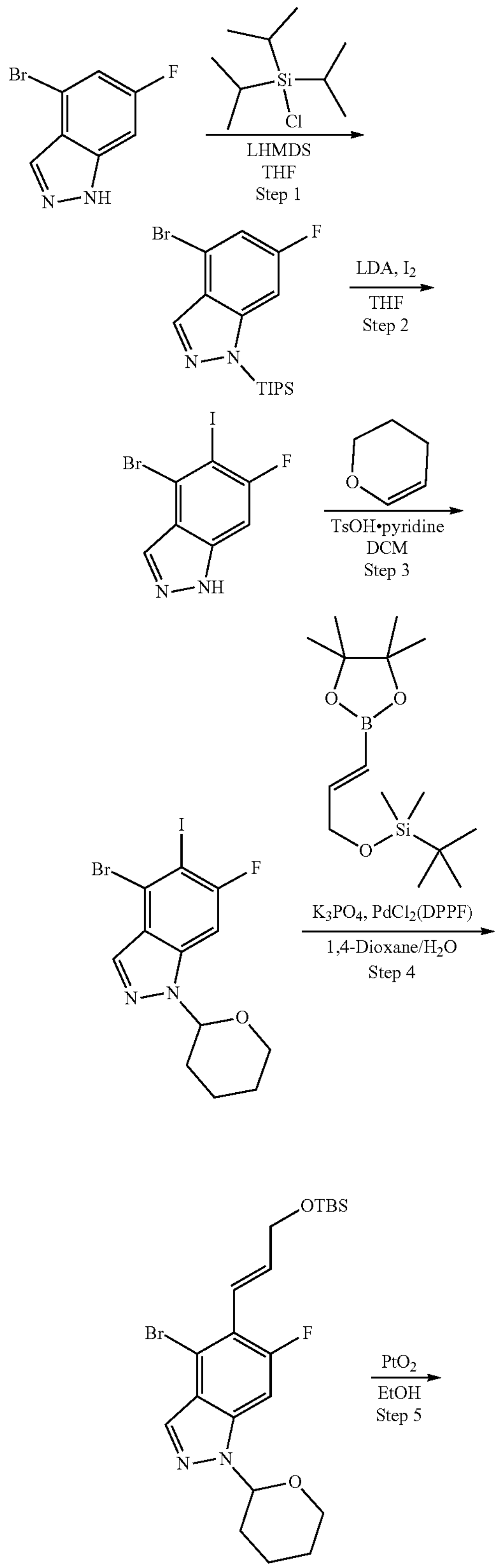

-continued

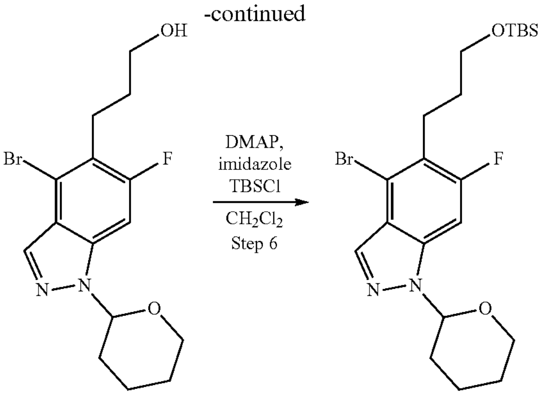

Intermediate KKK

Step 1. 4-Bromo-6-fluoro-1-(triisopropylsilyl)-1H-indazole. To a solution of 4-bromo-6-fluoro-1H-indazole (15.0 g, 69.8 mmol) in tetrahydrofuran (400 mL) was added to LiHMDS (1 M in THF, 84 mL, 84 mmol) under nitrogen at −78° C. The mixture was stirred at −78° C. for 1 h. TIPSCl (17.5 mL, 84 mmol) was added dropwise, the reaction mixture was stirred at −78° C. for 0.5 h, then slowly warmed to rt with stirring for another 3.5 h. The reaction was quenched by addition of saturated $NH_4Cl$ at 0° C., and then diluted with water and extracted with EtOAc. The combined organic layers were washed with brine, dried over $Na_2SO_4$, filtered, and concentrated. The residue was purified by column chromatography on silica gel, eluting with a gradient of 0-20% EtOAc in petroleum ether, to give 4-bromo-6-fluoro-1-(triisopropylsilyl)-1H-indazole (17 g, 46 mmol, 66%) as white solid.

Step 2. 4-Bromo-6-fluoro-5-iodo-1H-indazole. A solution of 4-bromo-6-fluoro-1-(triisopropylsilyl)-1H-indazole (20.0 g, 53.9 mmol) in tetrahydrofuran (300 mL) was added to LDA (2 M in THF, 67.5 mL, 135 mmol) under nitrogen at −78° C. The mixture was stirred at −78° C. for 1 h, then $I_2$ (27.3 g, 108 mmol) in tetrahydrofuran (100 mL) was added, and the mixture was warmed to rt with stirring for 12 h. The reaction mixture was quenched by addition of aqueous $NH_4Cl$, water, then extracted with EtOAc. The combined organic layers were washed with brine, dried over $Na_2SO_4$, filtered, and concentrated. The residue was purified by column chromatography on silica gel, eluting with a gradient of 5-20% EtOAc in petroleum ether, to provide 4-bromo-6-fluoro-5-iodo-1H-indazole (17 g, 50 mmol, 93%) as brown solid.

Step 3. 4-Bromo-6-fluoro-5-iodo-1-(tetrahydro-2H-pyran-2-yl)-1H-indazole. To a solution of 4-bromo-6-fluoro-5-iodo-1H-indazole (5.00 g, 14.7 mmol) in dichloromethane (50 mL) was added DHP (4.0 mL, 44 mmol) and pyridine 4-methylbenzenesulfonate hydrate (0.20 g, 0.73 mmol) under nitrogen. The reaction mixture was stirred at rt for 2 h and was diluted with water and extracted with DCM. The combined organic layers were washed with brine, dried over $Na_2SO_4$, filtered, and concentrated. The crude product was triturated with 10:1 petroleum ether/EtOAc at rt for 30 min. The mixture was filtered, and the cake was concentrated under reduced pressure to give 4-bromo-6-fluoro-5-iodo-1-(tetrahydro-2H-pyran-2-yl)-1H-indazole (5.00 g, 11.8 mmol, 80% yield) as white solid.

Step 4. (E)-4-Bromo-5-(3-((tert-butyldimethylsilyl)oxy)prop-1-en-1-yl)-6-fluoro-1-(tetrahydro-2H-pyran-2-yl)-1H-indazole. A vial was charged with 4-bromo-6-fluoro-5-iodo-1-(tetrahydro-2H-pyran-2-yl)-1H-indazole (0.53 g, 1.25 mmol), tert-butyldimethyl([(2E)-3-(tetramethyl-1,3,2-dioxaborolan-2-yl)prop-2-en-1-yl]oxy)silane (0.47 g, 1.57 mmol, Enamine), potassium phosphate tribasic (0.93 g, 4.38 mmol), 1,1'-bis(diphenylphosphino)ferrocene-palladium dichloride (69 mg, 0.094 mmol), water (1.0 mL) and 1,4-dioxane (5.0 mL). The reaction mixture was sparged with nitrogen and then heated to 100° C. for 1.5 h. After cooling to rt, the reaction was concentrated under reduced pressure and the crude material was purified by column chromatography on silica gel, eluting with a gradient of 0-10% EtOAc in heptane to provide (E)-4-bromo-5-(3-((tert-butyldimethylsilyl)oxy)prop-1-en-1-yl)-6-fluoro-1-(tetrahydro-2H-pyran-2-yl)-1H-indazole (0.36 g, 0.76 mmol, 61% yield) as light yellow oil. m/z (ESI): 469.0/471.0 $(M+H)^+$.

Step 5. 3-(4-Bromo-6-fluoro-1-(tetrahydro-2H-pyran-2-yl)-1H-indazol-5-yl)propan-1-ol. To a 60-mL hydrogenation reactor was charged (E)-4-bromo-5-(3-((tert-butyldimethylsilyl)oxy)prop-1-en-1-yl)-6-fluoro-1-(tetrahydro-2H-pyran-2-yl)-1H-indazole (0.35 g, 0.75 mmol) and platinum (IV) oxide (17 mg, 0.075 mmol). The reactor was purged with nitrogen and then charged with ethanol (7.5 mL). The reaction vessel was charged with hydrogen gas to 10 psi and allowed to vent. The reaction vessel was again charged with hydrogen gas to 30 psi, sealed, and stirred at rt for 16 h. The reaction mixture was filtered through celite and washed with EtOAc. The filtrate was concentrated, and the residue was purified by column chromatography on silica gel, eluting with 0-40% EtOAc in heptane, to provide 3-(4-bromo-6-fluoro-1-(tetrahydro-2H-pyran-2-yl)-1H-indazol-5-yl)propan-1-ol (51 mg, 0.14 mmol, 19% yield) as clear oil. m/z (ESI): 357.0/359.0 $(M+H)^+$.

Step 6. 4-Bromo-5-(3-((tert-butyldimethylsilyl)oxy)propyl)-6-fluoro-1-(tetrahydro-2H-pyran-2-yl)-1H-indazole. A mixture of 3-(4-bromo-6-fluoro-1-(tetrahydro-2H-pyran-2-yl)-1H-indazol-5-yl)propan-1-ol (51 mg, 0.14 mmol), tert-butyldimenhylsilyl chloride (26 mg, 0.17 mmol), imidazole (24 mg, 0.36 mmol), and DMAP (1.7 mg, 0.014 mmol) in dichloromethane (1.5 mL) was stirred at rt for 2 h. The reaction was then quenched by the addition of saturated aqueous sodium bicarbonate. The mixture was further diluted with dichloromethane and layers were separated. The aqueous layer was extracted with DCM, and the combined organic layers were dried with sodium sulfate, filtered, and concentrated. The crude oil was purified by column chromatography on silica gel, eluting with a gradient of 0-10% EtOAc in heptane, to afford 4-bromo-5-(3-((tert-butyldimethylsilyl)oxy)propyl)-6-fluoro-1-(tetrahydro-2H-pyran-2-yl)-1H-indazole (64 mg, 0.14 mmol, 95% yield) as colorless oil. m/z (ESI, +ve ion): 471.0/473.0 $(M+H)^+$.

Intermediate LLL: (E)-4-Bromo-5-(3-((tert-butyldimethylsilyl)oxy)prop-1-en-1-yl)-6-chloro-1-(tetrahydro-2H-pyran-2-yl)-1H-indazole

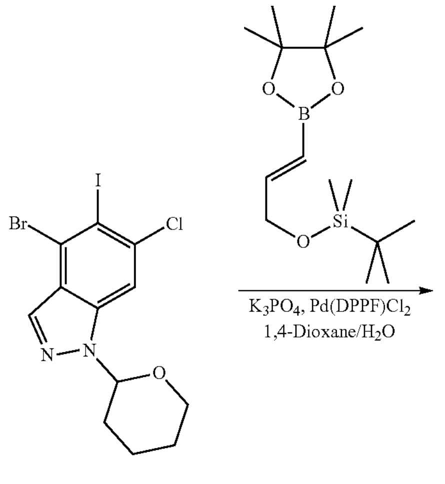

-continued

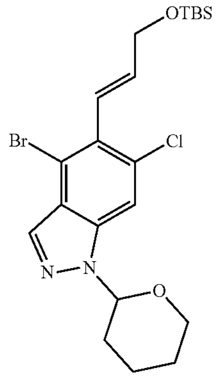

Intermediate LLL

A vial was charged with 4-bromo-6-chloro-5-iodo-1-(tetrahydro-2H-pyran-2-yl)-1H-indazole (1.00 g, 2.27 mmol, Lab-Network), tert-butyldimethyl([(2E)-3-(tetramethyl-1,3,2-dioxaborolan-2-yl)prop-2-en-1-yl]oxy)silane (0.85 mL, 2.8 mmol, Enamine), potassium phosphate tribasic (1.68 g, 7.93 mmol), 1,1'-bis(diphenylphosphino)ferrocene-palladium dichloride (0.12 g, 0.17 mmol), water (1.9 mL) and degassed 1,4-dioxane (9.4 mL). The reaction mixture was sparged with nitrogen before heating to 100° C. for 3 h. After cooling to rt, the reaction was concentrated under reduced pressure and the crude material was purified by column chromatography on silica gel, eluting with a gradient of 0-10% EtOAc in heptane to provide (E)-4-bromo-5-(3-((tert-butyldimethylsilyl)oxy)prop-1-en-1-yl)-6-chloro-1-(tetrahydro-2H-pyran-2-yl)-1H-indazole (0.77 g, 1.59 mmol, 70% yield) as clear oil. m/z (ESI): 485.0/487.0 $(M+H)^+$.

Intermediate MMM: (R)-1-(8-Fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-3-methylpiperidin-3-ol

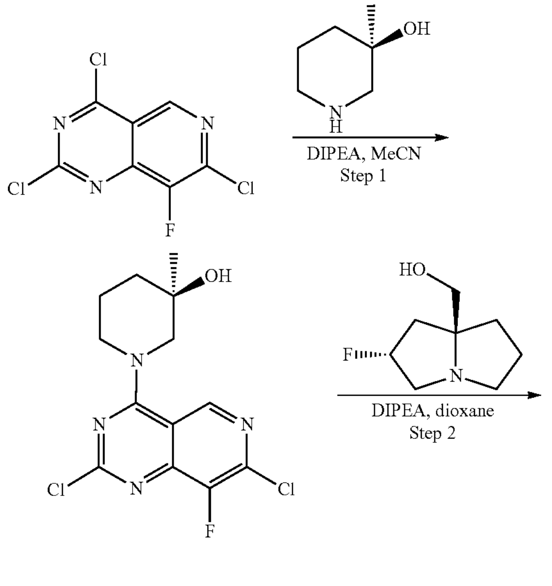

-continued

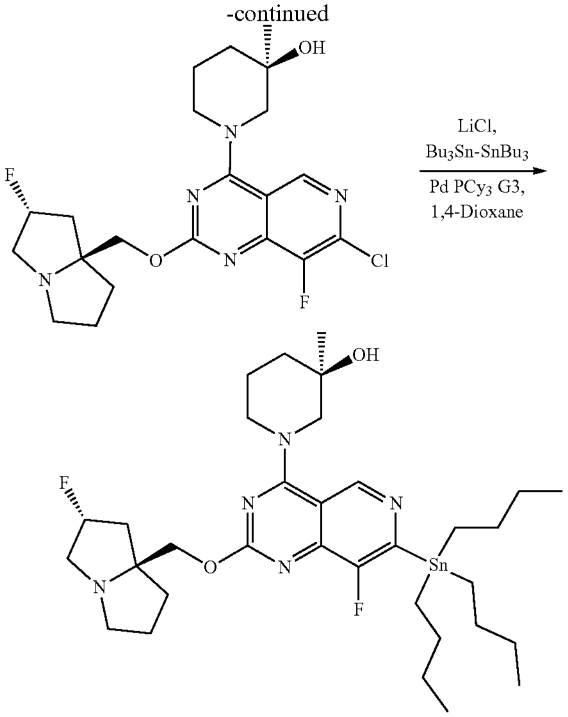

Intermediate MMM

Step 1. (R)-1-(2,7-Dichloro-8-fluoropyrido[4,3-d]pyrimidin-4-yl)-3-methylpiperidin-3-ol. To a mixture of 2,4,7-trichloro-8-fluoropyrido[4,3-d]pyrimidine (25 g, 99 mmol, Enamine) in acetonitrile (500 mL) was added DIPEA (86 mL, 495 mmol) and (R)-3-methylpiperidin-3-ol hydrochloride (15 g, 99 mmol). The mixture was stirred at 0° C. for 0.5 h under $N_2$. The reaction mixture was diluted with water and extracted with EtOAc. The combined organic layers were dried over $Na_2SO_4$, filtered and the filtrate was concentrated under reduced pressure. The residue was purified by chromatography on silica gel, eluting with a gradient of 2-100% ethyl acetate/petroleum ether to give (R)-1-(2,7-dichloro-8-fluoropyrido[4,3-d]pyrimidin-4-yl)-3-methylpiperidin-3-ol (28 g, 85 mmol, 85% yield) as yellow solid.

Step 2. (R)-1-(7-Chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol. To a solution of (R)-1-(2,7-dichloro-8-fluoropyrido[4,3-d]pyrimidin-4-yl)-3-methylpiperidin-3-ol (20 g, 60 mmol) in 1,4-dioxane (300 mL) was added DIPEA (20 g, 151 mmol) and ((2R,7aS)-2-fluorotetrahydro-1H-pyrrolizin-7a(5H)-yl)methanol (14 g, 85 mmol). The resulting mixture was stirred at 100° C. for 12 h under $N_2$. After cooling to rt, the reaction mixture was diluted with water and extracted with EtOAc. The combined organic layers were dried over $Na_2SO_4$, filtered, and concentrated under reduced pressure. The residue was purified by column chromatography on silica gel, eluting with a gradient of 10-100% ethyl acetate/petroleum ether to give (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (14 g, 31 mmol, 51% yield). m z (ESI): 454.2, 456.2 $(M+H)^+$.

Step 3. (R)-1-(8-Fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-3-methylpiperidin-3-ol. To a 500 mL three-neck bottle containing the solution of (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol (14 g, 31 mmol) in 1,4-dioxane (210 mL) was added chloro[(tricyclohexylphosphine)-2-(2'-aminobiphenyl)]palladium(II) (7.3 g, 12 mmol) and LiCl (6.5 g, 154 mmol). Bis(tributyltin) (54 g, 93 mmol) was added dropwise under $N_2$. The mixture was stirred at 100° C. for 12 h under $N_2$. After cooling to rt, the reaction mixture was diluted with water and extracted with EtOAc. The combined organic layers were dried over $Na_2SO_4$, filtered, and concentrated under reduced pressure. The residue was purified by column chromatography on silica gel, eluting with a gradient of 10-100% of ethyl acetate in petroleum ether to give (R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-3-methylpiperidin-3-ol (9.10 g, 13.0 mmol, 42% yield) as yellow oil. m z (ESI): 710.3 $(M+H)^+$.

Intermediate NNN: (3-(8-Bromonaphthalen-1-yl)propoxy)(tert-butyl)dimethylsilane

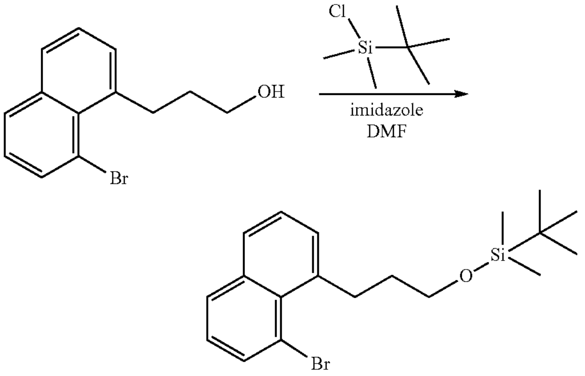

Intermediate NNN

A 40-mL vial was charged with imidazole (0.77 g, 11 mmol), (1,1-dimethylethyl)dimethylsilyl chloride (0.68 g, 4.5 mmol), 3-(8-bromonaphthalen-1-yl)propan-1-ol (1.00 g, 3.80 mmol, Enamine) and N,N-dimethylformamide (4 mL). The reaction mixture was stirred at rt for 16 h. Water and DCM were added to the mixture and the organic layer was separated, dried ($Na_2SO_4$) and concentrated. The crude product was purified by column chromatography on silica gel, eluting with a gradient of 0-85% 3:1 EtOAc/EtOH (with 2% triethylamine additive) in heptane to yield (3-(8-bromonaphthalen-1-yl)propoxy)(tert-butyl)dimethylsilane (1.10 g, 2.90 mmol, 75% yield). m/z (ESI): 379.1 $(M+H)^+$.

Intermediate OOO: (Z)-4-Bromo-5-(3-((tert-butyldimethylsilyl)oxy)prop-1-en-1-yl)-6-chloro-1-(tetrahydro-2H-pyran-2-yl)-1H-indazole

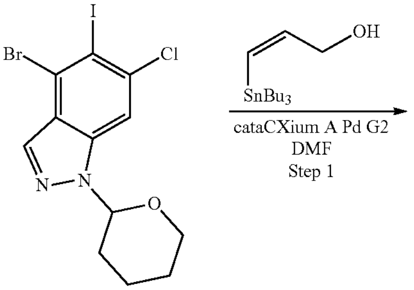

-continued

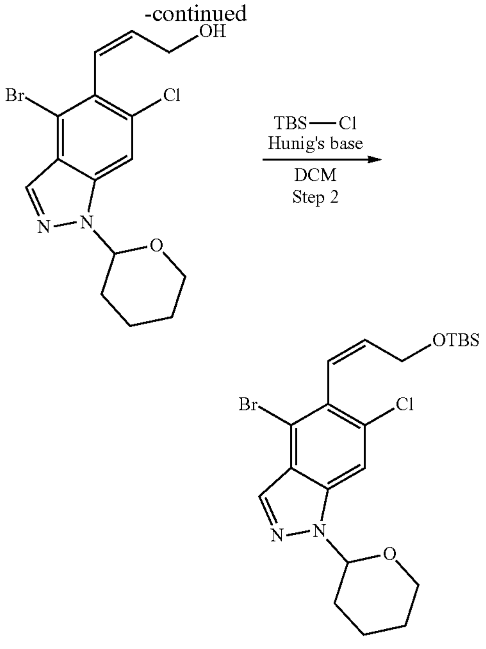

Intermediate OOO

Step 1. (Z)-3-(4-Bromo-6-chloro-1-(tetrahydro-2H-pyran-2-yl)-1H-indazol-5-yl)prop-2-en-1-ol. A vial was charged with cataCXium A Pd G2 (0.17 g, 0.23 mmol), 4-bromo-6-chloro-5-iodo-1-(tetrahydro-2H-pyran-2-yl)-1H-indazole (2.00 g, 4.53 mmol, Lab Network), (Z)-3-(tributylstannyl)prop-2-en-1-ol (2.0 mL, 5.8 mmol, Synthonix Inc.) and N,N-dimethylformamide (8 mL). The reaction mixture was heated to 100° C. for 1 h. After cooling to rt, the reaction mixture was diluted with water and extracted with EtOAc. The combined organic layers were washed with brine, dried over $MgSO_4$, filtered, and concentrated. The crude material was purified by column chromatography on silica gel, eluting with a gradient of 0-100% 3:1 EtOAc/EtOH in heptane, to provide (Z)-3-(4-bromo-6-chloro-1-(tetrahydro-2H-pyran-2-yl)-1H-indazol-5-yl)prop-2-en-1-ol (1.19 g, 3.19 mmol, 70% yield) as orange oil. m/z (ESI): 371.2 $(M+H)^+$.

Step 2. (Z)-4-Bromo-5-(3-((tert-butyldimethylsilyl)oxy)prop-1-en-1-yl)-6-chloro-1-(tetrahydro-2H-pyran-2-yl)-1H-indazole. In a 20-mL vial was charged with (Z)-3-(4-bromo-6-chloro-1-(tetrahydro-2H-pyran-2-yl)-1H-indazol-5-yl)prop-2-en-1-ol (1.10 g, 3.00 mmol), 1,1'-dimethyltriethylamine (0.63 mL, 3.5 mmol) and dichloromethane (10 mL). tert-Butyldimethylsilyl chloride (0.54 g, 3.58 mmol) and 1,1'-dimethyltriethylamine (0.63 mL, 3.6 mmol) were added at 0° C. and the reaction mixture was stirred at 0° C. for 3 h. The reaction was diluted with water and extracted with DCM. The combined organic layers were dried over $MgSO_4$ and concentrated under reduced pressure. The crude material was purified by column chromatography on silica gel, eluting with a gradient of 0-100% 3:1 EtOAc/EtOH in heptane, to provide (Z)-4-bromo-5-(3-((tert-butyldimethylsilyl)oxy)prop-1-en-1-yl)-6-chloro-1-(tetrahydro-2H-pyran-2-yl)-1H-indazole as light-yellow oil (1.20 g, 2.50 mmol, 84% yield). m/z (ESI): 485.2 $(M+H)^+$.

Intermediate PPP: (Z)-4-Bromo-5-(3-((tert-butyldimethylsilyl)oxy)prop-1-en-1-yl)-6-methyl-1-(tetrahydro-2H-pyran-2-yl)-1H-indazole

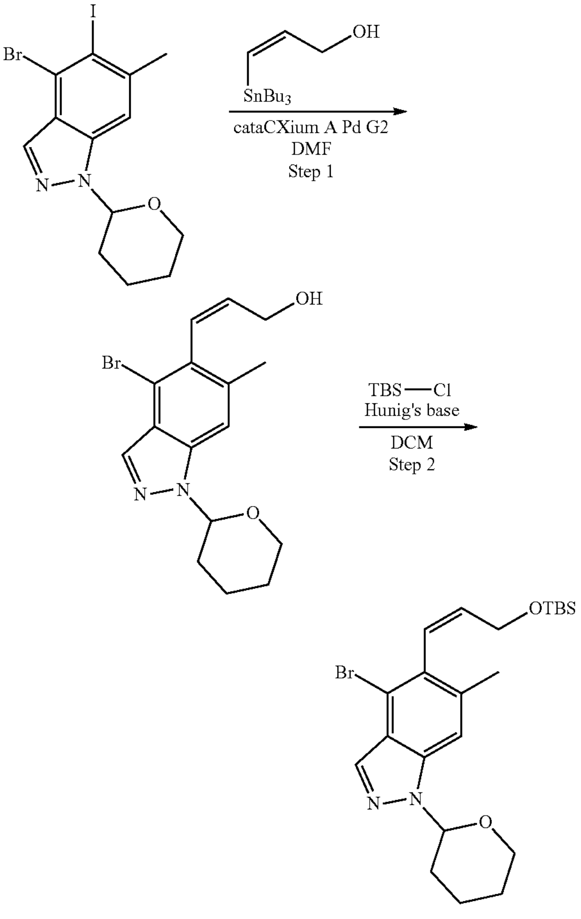

Intermediate PPP

Synthesized similarly to Intermediate OOO with 4-bromo-5-iodo-6-methyl-1-(tetrahydro-2H-pyran-2-yl)-1H-indazole (Advanced ChemBlocks). $^1H$ NMR (400 MHz, CHLOROFORM-d) δ ppm 7.98 (s, 1H), 7.37 (s, 1H), 6.34 (d, J=11.4 Hz, 1H), 6.01 (dd, J=11.2, 5.6 Hz, 1H), 5.68 (dd, J=9.3, 2.7 Hz, 1H), 3.97-4.08 (m, 3H), 3.69-3.83 (m, 1H), 2.50-2.62 (m, 1H), 2.41 (s, 3H), 2.12-2.23 (m, 1H), 2.05-2.12 (m, 1H), 1.73-1.81 (m, 2H), 1.63-1.71 (m, 1H), 0.84 (s, 9H), 0.01 (s, 3H), −0.03 (s, 3H). m/z (ESI): 465.3 $(M+H)^+$.

Intermediate QQQ: (S)-4-(7-Chloro-8-fluoro-2-(((R)-4-methylmorpholin-2-yl)methoxy)pyrido[4,3-d]pyrimidin-4-yl)-1,4-oxazepan-6-ol

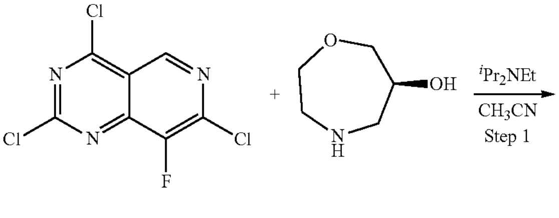

-continued

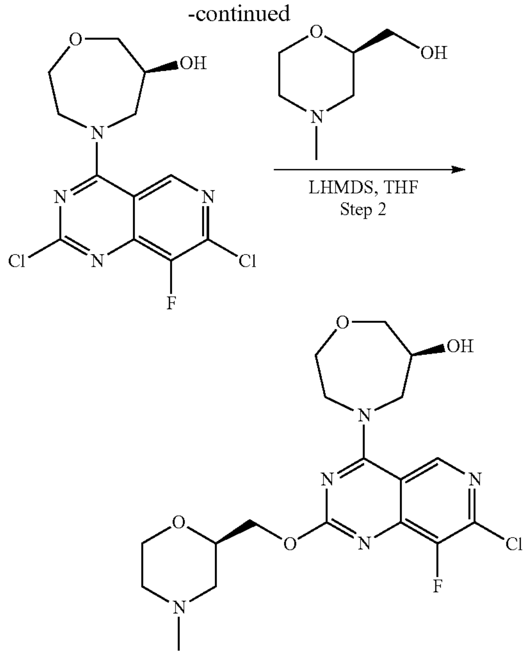

Intermediate QQQ

Step 1. (S)-4-(2,7-Dichloro-8-fluoropyrido[4,3-d]pyrimidin-4-yl)-1,4-oxazepan-6-ol. A 40-mL vial was charged with DIPEA (4.1 mL, 23 mmol) and 2,4,7-trichloro-8-fluoropyrido[4,3-d]pyrimidine (1.96 g, 7.76 mmol, Enamine) in acetonitrile (26 mL). The mixture was cooled to 0° C. and (S)-[1,4]oxazepan-6-ol (1.0 mL, 8.5 mmol, J&W Pharmlab) was added slowly. The reaction mixture was stirred at 0° C. for 1 h, then was concentrated under reduced pressure. The crude material was purified by column chromatography on silica gel, eluting with a gradient of 0-100% 3:1 EtOAc/EtOH in heptane, to provide (S)-4-(2,7-dichloro-8-fluoropyrido[4,3-d]pyrimidin-4-yl)-1,4-oxazepan-6-ol (1.90 g, 5.70 mmol, 74% yield) as light-yellow solid. m/z (ESI, +ve ion): 333.1 $(M+H)^+$.

Step 2. (S)-4-(7-Chloro-8-fluoro-2-(((R)-4-methylmorpholin-2-yl)methoxy)pyrido[4,3-d]pyrimidin-4-yl)-1,4-oxazepan-6-ol. To a 20-mL vial was added (R)-(4-methylmorpholin-2-yl)methanol (0.83 g, 6.3 mmol) in tetrahydrofuran (7 mL). The reaction mixture was cooled to 0° C. and lithium bis(trimethylsilyl)amide (1 M in THF, 7.0 mL, 7.0 mmol) was added dropwise. After stirring at 0° C. for 10 min, a suspension of (S)-4-(2,7-dichloro-8-fluoropyrido[4,3-d]pyrimidin-4-yl)-1,4-oxazepan-6-ol (0.70 g, 2.10 mmol) in tetrahydrofuran (2 mL) was added. The reaction mixture was allowed to warm to rt with stirring for 4 h. The reaction was diluted with saturated $NH_4Cl$ and water and extracted with EtOAc. The combined organic layers were washed with brine, dried over $MgSO_4$, filtered, and concentrated. The crude material was dissolved in DMSO (2.5 mL) and purified by reverse-phase column chromatography using a C18 column, eluting with a gradient 5-100% 0.1% formic acid in $CH_3CN$/0.1% formic acid in $H_2O$ over 10 min to provide (S)-4-(7-chloro-8-fluoro-2-(((R)-4-methylmorpholin-2-yl)methoxy)pyrido[4,3-d]pyrimidin-4-yl)-1,4-oxazepan-6-ol (0.24 g, 0.55 mmol, 26% yield) as colorless oil. m/z (ESI): 428.2 $(M+H)^+$.

Intermediate RRR: 4-Bromo-5-(2-((tert-butyldimethylsilyl)oxy)ethyl)-1-(tetrahydro-2H-pyran-2-yl)-1,5,6,7-tetrahydrocyclopenta[f]indazole

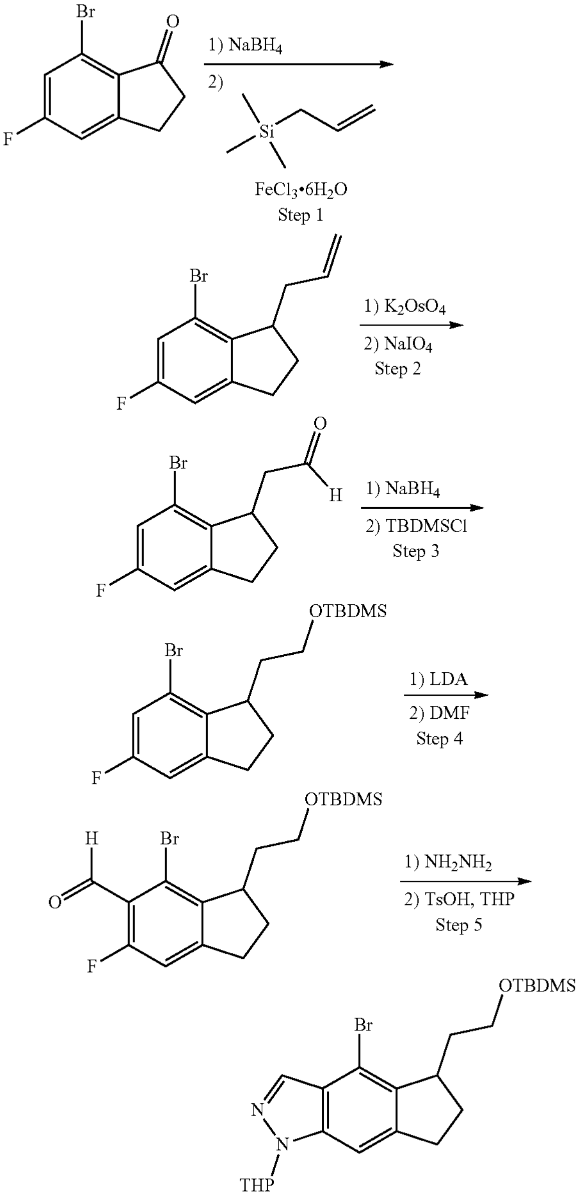

Intermediate RRR

Step 1. 1-Allyl-7-bromo-5-fluoro-2,3-dihydro-1H-indene. To a solution of 7-bromo-5-fluoro-2,3-dihydro-1H-inden-1-one (6.00 g, 26.2 mmol, Enamine) in methanol (20 mL) at 0° C. was added sodium borohydride (1.19 g, 31.4 mmol) portionwise. The reaction mixture was stirred at rt for 4 h, then was diluted with slow addition of water. The mixture was concentrated, and the residue was treated with water and extracted with EtOAc. The organic layer was dried ($Na_2SO_4$) and concentrated to afford crude 7-bromo-5-fluoro-2,3-dihydro-1H-inden-1-ol (6.00 g, 26.0 mmol, 99% yield). The crude material dissolved in dichloromethane (20 mL) was treated with iron(III) chloride hexahydrate (0.35 g, 1.30 mmol) and allyltrimethylsilane (7.4 mL, 65 mmol). The reaction mixture was stirred at rt for 12 h and concentrated. The residue was purified by column chromatography on silica gel, eluting with a gradient of 0-60% 3:1 EtOAc/EtOH in heptane to afford 1-allyl-7-bromo-5-fluoro-2,3-dihydro-1H-indene (5.90 g, 23 mmol, 89% yield). $^1$H NMR (400 MHz, CHLOROFORM-d) δ 7.07 (dd, J=2.3, 8.6 Hz, 1H), 6.87 (dd, J=0.8, 8.4 Hz, 1H), 5.87-5.76 (m, 1H), 5.13-5.03 (m, 2H), 3.35-3.27 (m, 1H), 3.12-3.00 (m, 1H), 2.93-2.84 (m, 1H), 2.59-2.51 (m, 1H), 2.26-2.14 (m, 2H), 2.11-2.00 (m, 1H). $^{19}$F NMR (376 MHz, CHLOROFORM-d) 6-115.07 (s).

Step 2. 2-(7-Bromo-5-fluoro-2,3-dihydro-1H-inden-1-yl) acetaldehyde. To a solution of 1-allyl-7-bromo-5-fluoro-2,3-dihydro-1H-indene (4.00 g, 15.7 mmol) and potassium osmate (VI) dihydrate (0.58 g, 1.57 mmol) in acetone (20 mL) and water (4 mL) was added 4-methylmorpholine 4-oxide (6.43 g, 54.9 mmol). The reaction mixture was allowed to stir under nitrogen for 2 h, then was quenched with the addition of solid sodium sulfite and stirred at rt for 10 min. The content was partially concentrated in vacuo and was diluted with EtOAc and brine solution. The aqueous layer was extracted with EtOAc, and the combined organics were dried ($Na_2SO_4$) and concentrated to afford crude 3-(7-bromo-5-fluoro-2,3-dihydro-1H-inden-1-yl)propane-1,2-diol. The crude material dissolved in THF (80 mL) was treated with sodium metaperiodate (8.38 g, 39.2 mmol), followed by addition of water (15 mL). The resulting reaction mixture was allowed to stir under nitrogen for 4 h, diluted with a mixture of EtOAc/heptane (1:1). The mixture was filtered through a pad of celite, and the filtrate was treated with sat. aqueous $NaHCO_3$ and extracted with EtOAc. The combined organic extracts were washed with brine, then dried over $MgSO_4$, filtered, and concentrated in vacuo. The residue was purified by column chromatography on silica gel, eluting with a gradient of 0-80% 3:1 EtOAc/EtOH in heptane, to afford 2-(7-bromo-5-fluoro-2,3-dihydro-1H-inden-1-yl)acetaldehyde (3.39 g, 13.2 mmol, 84% yield). $^1$H NMR (500 MHz, CHLOROFORM-d) δ 9.85 (dd, J=1.0, 2.3 Hz, 1H), 7.09 (dd, J=2.2, 8.6 Hz, 1H), 6.90 (td, J=1.0, 8.3 Hz, 1H), 3.78-3.72 (m, 1H), 3.13-3.03 (m, 1H), 2.99-2.92 (m, 2H), 2.58 (ddd, J=2.3, 10.5, 17.2 Hz, 1H), 2.42-2.33 (m, 1H), 1.94 (tdd, J=1.8, 8.0, 13.2 Hz, 1H). $^{19}$F NMR (471 MHz, CHLOROFORM-d) 6-114.03 (s).

Step 3. (2-(7-Bromo-5-fluoro-2,3-dihydro-1H-inden-1-yl)ethoxy)(tert-butyl)dimethylsilane. To a solution of 2-(7-bromo-5-fluoro-2,3-dihydro-1H-inden-1-yl)acetaldehyde (2.40 g, 9.33 mmol) in methanol (15 mL) at 0° C. was added sodium tetrahydroborate (0.42 g, 11.2 mmol) portionwise. The reaction mixture was stirred at rt for 2 h, diluted with slow addition of water and concentrated. The residue was partitioned between water and EtOAc. The organic was dried ($Na_2SO_4$) and concentrated to afford crude 2-(7-bromo-5-fluoro-2,3-dihydro-1H-inden-1-yl)ethan-1-ol. The crude material dissolved in DMF (5 mL) at 0° C. was treated with 1H-imidazole (0.76 g, 11.2 mmol) and (1,1-dimethylethyl)dimethylsilyl chloride (1.41 g, 9.33 mmol). The reaction mixture was stirred at rt for 2 h, diluted with water and extracted with EtOAc. The combined organic extracts were dried ($Na_2SO_4$), concentrated and the residue was purified by column chromatography on silica gel, eluting with a gradient of 0-40% EtOAc in heptane, to afford (2-(7-bromo-5-fluoro-2,3-dihydro-1H-inden-1-yl)ethoxy)(tert-butyl)dimethylsilane (3.12 g, 8.36 mmol, 90% yield). $^1$H NMR (500 MHz, CHLOROFORM-d) δ 7.06 (dd, J=2.3, 8.6 Hz, 1H), 6.87 (td, J=1.1, 8.3 Hz, 1H), 3.79-3.72 (m, 2H), 3.34-3.27 (m, 1H), 3.14-3.02 (m, 1H), 2.93-2.85 (m, 1H), 2.24-2.14 (m, 1H), 2.10-1.98 (m, 2H), 1.61-1.56 (m, 1H), 0.93 (s, 9H), 0.09 (d, J=2.6 Hz, 6H).

Step 4. 4-Bromo-3-(2-((tert-butyldimethylsilyl)oxy)ethyl)-6-fluoro-2,3-dihydro-1H-indene-5-carbaldehyde. To a solution of (2-(7-bromo-5-fluoro-2,3-dihydro-1H-inden-1-yl)ethoxy)(tert-butyl)dimethylsilane (3.12 g, 8.36 mmol) in tetrahydrofuran (15 mL) at −78° C. was added LDA (1 M in tetrahydrofuran/hexanes, 11.6 mL, 11.6 mmol) dropwise. After stirring at −78° C. for 30 mins, DMF (0.9 mL, 11.6 mmol) was added, and the resulting solution was stirred at −78° C. for another 30 mins before being quenched with saturated $NH_4Cl$ solution and warmed to rt. The reaction mixture was extracted with EtOAc, and the combined organic layers were dried ($Na_2SO_4$) and concentrated. The residue was purified by column chromatography on silica gel, eluting with a gradient of 0-50% EtOAc in heptane, to afford 4-bromo-3-(2-((tert-butyldimethylsilyl)oxy)ethyl)-6-fluoro-2,3-dihydro-1H-indene-5-carbaldehyde (3.05 g, 7.6 mmol, 92% yield). m/z (ESI): 401.0/403.0 $(M+H)^+$. $^1$H NMR (400 MHz, CHLOROFORM-d) δ 10.36 (s, 1H), 6.98 (d, J=10.0 Hz, 1H), 3.83-3.73 (m, 2H), 3.45 (br t, J=9.2 Hz, 1H), 3.21-3.09 (m, 1H), 3.03-2.90 (m, 1H), 2.29-2.11 (m, 2H), 2.05-1.95 (m, 1H), 1.61-1.52 (m, 1H), 0.94 (s, 9H), 0.10 (d, J=2.3 Hz, 6H). $^{19}$F NMR (376 MHz, CHLOROFORM-d) 6-117.11 (s, 1F).

Step 5. 4-Bromo-5-(2-((tert-butyldimethylsilyl)oxy)ethyl)-1-(tetrahydro-2H-pyran-2-yl)-1,5,6,7-tetrahydrocyclopenta[f]indazole. A mixture of 4-bromo-3-(2-((tert-butyldimethylsilyl)oxy)ethyl)-6-fluoro-2,3-dihydro-1H-indene-5-carbaldehyde (1.00 g, 2.49 mmol) and hydrazine (0.24 mL, 7.5 mmol) in 1,2-dimethoxyethane (3 mL) was heated in microwave at 75° C. for 18 h. After cooling to rt, the reaction mixture was purified by column chromatography on silica gel, eluting with a gradient of 0-80% 3:1 EtOAc/EtOH in heptane to afford 4-bromo-5-(2-((tert-butyldimethylsilyl)oxy)ethyl)-1,5,6,7-tetrahydrocyclopenta[f]indazole (0.43 g, 1.1 mmol, 44% yield). m/z (ESI): 395.0/397.0 $(M+H)^+$.

A mixture of the 4-bromo-5-(2-((tert-butyldimethylsilyl)oxy)ethyl)-1,5,6,7-tetrahydrocyclopenta[f]indazole (0.90 g, 2.28 mmol), 3,4-dihydro-2H-pyran (0.29 mL, 3.4 mmol), and 4-methylbenzenesulfonic acid hydrate (43 mg, 0.23 mmol) in dichloromethane (8 mL) was stirred at rt for 18 h. The reaction mixture was quenched with saturated sodium bicarbonate solution and extracted with EtOAc. The organic layer was dried ($Na_2SO_4$), concentrated and the residue was purified by column chromatography on silica gel, eluting with a gradient of 0-50% EtOAc in heptane to afford 4-bromo-5-(2-((tert-butyldimethylsilyl)oxy)ethyl)-1-(tetrahydro-2H-pyran-2-yl)-1,5,6,7-tetrahydrocyclopenta[f]indazole (0.98 g, 2.0 mmol, 90% yield). m/z (ESI): 479.0/481.0 $(M+H)^+$.

Intermediate SSS: tert-Butyl ((R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-yl)(methyl)carbamate

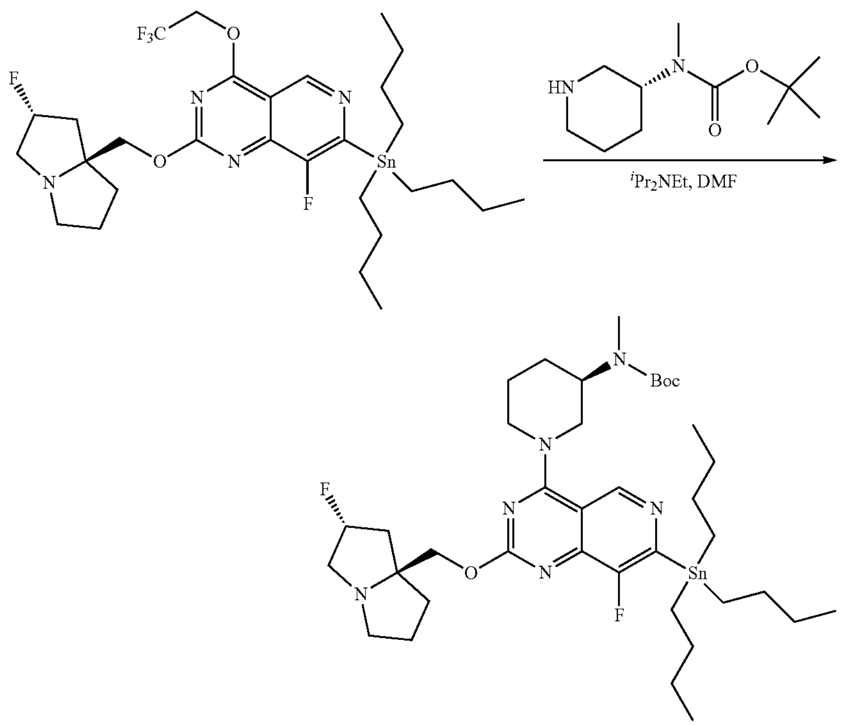

Intermediate SSS

The mixture of 8-fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d]pyrimidine (0.50 g, 0.72 mmol, Intermediate KK)), (R)-3-N-Boc-3-(methylamino) piperidine (0.31 g, 1.44 mmol), and DIPEA (0.5 mL, 2.9 mmol) in N,N-dimethylformamide (4 mL) was stirred at rt for 16 h, then heated at 50° C. for 3 h. After cooling to rt, the reaction mixture was diluted with water and extracted with EtOAc. The organic layer was dried ($Na_2SO_4$), concentrated and the residue was purified by column chromatography in silica gel, eluting with a gradient of 0-50% (3:1 EtOAc/EtOH, with 2% $Et_3N$)/heptane to afford tert-butyl ((R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-yl)(methyl)carbamate (0.41 g, 0.51 mmol, 70% yield) as colorless sticky solid. m/z (ESI, +ve ion): 807.2 $(M+H)^+$.

Intermediate TTT: 5-Allyl-6-methyl-1-(tetrahydro-2H-pyran-2-yl)-4-(4,4,5,5-tetramethyl-1,3,2-dioxaborolan-2-yl)-1H-indazole

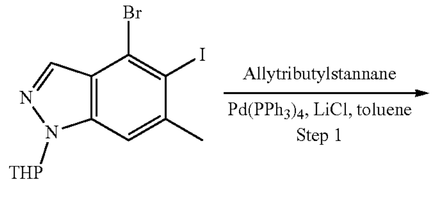

-continued

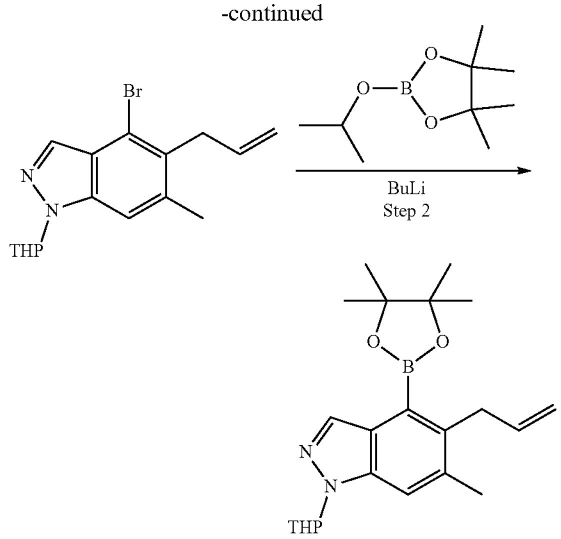

Intermediate TTT

Step 1. 5-Allyl-4-bromo-6-methyl-1-(tetrahydro-2H-pyran-2-yl)-1H-indazole. A 20-mL vial was charged with 4-bromo-5-iodo-6-methyl-1-(tetrahydro-2H-pyran-2-yl)-1H-indazole (0.26 g, 0.62 mmol, Advanced ChemBlocks), allyltributylstannane (0.21 mL, 0.68 mmol), lithium chloride (0.13 g, 3.09 mmol) and tetrakis triphenylphosphine (71 mg, 0.062 mmol) in toluene (2.5 mL). The reaction mixture was stirred at 90° C. for 16 h. After cooling to rt, the crude material was purified by column chromatography on silica gel, eluting with a gradient of 0-40% 3:1 EtOAc/EtOH (with 1% TEA) in heptane, to provide 5-allyl-4-bromo-6-methyl-1-(tetrahydro-2H-pyran-2-yl)-1H-indazole (0.24 g, 0.72 mmol) as yellow oil. m/z (ESI): 334.9/337.0 $(M+H)^+$. $^1H$ NMR (400 MHz, METHANOL-$d_4$) δ ppm 7.93 (s, 1H), 7.51 (s, 1H), 5.87-6.12 (m, 1H), 5.72-5.83 (m, 1H), 4.99-5.09 (m, 1H), 4.84-4.92 (m, 1H), 3.98-4.12 (m, 1H), 3.78-3.90 (m, 1H), 3.62-3.76 (m, 2H), 2.52 (s, 3H), 1.94-2.22 (m, 2H), 1.59-1.89 (m, 4H).

Step 2. 5-Allyl-6-methyl-1-(tetrahydro-2H-pyran-2-yl)-4-(4,4,5,5-tetramethyl-1,3,2-dioxaborolan-2-yl)-1H-indazole. 5-Allyl-4-bromo-6-methyl-1-(tetrahydro-2H-pyran-2-yl)-1H-indazole (1.90 g, 5.70 mmol) dissolved in THF (23 mL) was cooled to −78° C. Butyl lithium (2.5 M in hexane, 2.7 mL, 6.8 mmol) was added dropwise and the reaction mixture was stirred at −78° C. for 10 min. 2-Isopropoxy-4,4,5,5-tetramethyl-1,3,2-dioxaborolane (1.5 mL, 7.4 mmol) was then added dropwise and the reaction mixture was stirred at −78° C. for 1 h. Water was added and the mixture was warmed to rt, and the aqueous phase was extracted with EtOAc. The combined organic phases were dried over $Na_2SO_4$, filtered and volatiles were removed in vacuo. The crude material was purified by column chromatography on silica gel, eluting with a gradient of 0-55% 3:1 EtOAc/EtOH (with 1% TEA) in heptane, to provide 5-allyl-6-methyl-1-(tetrahydro-2H-pyran-2-yl)-4-(4,4,5,5-tetramethyl-1,3,2-dioxaborolan-2-yl)-1H-indazole (1.80 g, 4.70 mmol, 83% yield) as yellow oil. m/z (ESI): 383.0 $(M+H)^+$. $^1H$ NMR (400 MHz, METHANOL-$d_4$): δ ppm 8.25 (s, 1H), 7.51-7.64 (m, 1H), 5.90-6.07 (m, 1H), 5.63-5.80 (m, 1H), 4.91-5.01 (m, 1H), 4.81-4.86 (m, 1H), 3.98-4.08 (m, 1H), 3.74-3.90 (m, 3H), 2.42-2.52 (m, 5H), 2.08-2.19 (m, 1H), 1.98-2.07 (m, 1H), 1.62-1.94 (m, 2H), 1.42 (s, 12H).

Intermediate UUU: (R)-3-((Allyloxy)methyl)piperidine hydrochloride

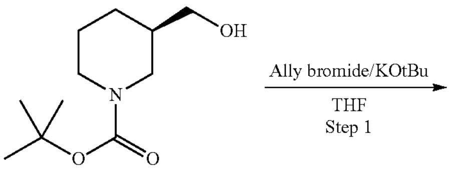

-continued

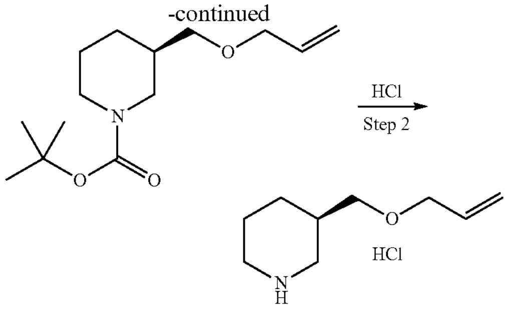

Intermediate UUU

Step 1. tert-Butyl (R)-3-((allyloxy)methyl)piperidine-1-carboxylate. A 100-mL round-bottomed flask was charged with (R)-tert-butyl 3-(hydroxymethyl)piperidine-1-carboxylate (0.50 g, 2.30 mmol, Ambeed, Inc.) in THF (12 mL). The solution was cooled to 0° C. and potassium tert-butoxide solution (1 M in THF, 3.3 mL, 3.3 mmol) was added. The reaction mixture was stirred for 10 min then allyl bromide (0.4 mL, 4.6 mmol) was added. The reaction was stirred at rt for 2 h, then was diluted with saturated $NH_4Cl$ and extracted with EtOAc. The organic extract was washed with saturated NaCl and dried over $MgSO_4$, filtered, and concentrated in vacuo. The crude material was purified by column chromatography on silica gel, eluting with a gradient of 0-60% 3:1 EtOAc/EtOH (with 1% TEA) in heptane, to provide tert-butyl (R)-3-((allyloxy)methyl)piperidine-1-carboxylate as a colorless oil. m/z (ESI): 278.2 $(M+Na)^+$.

Step 2. (R)-3-((Allyloxy)methyl)piperidine hydrochloride. tert-Butyl (R)-3-((allyloxy)methyl)piperidine-1-carboxylate from step 1 was dissolved in 10 mL of 1,4-dioxane. To the solution was added HCl, 4 M in 1,4-dioxane (5.8 mL, 23 mmol). The mixture was stirred at rt for 2 h. The solution was fully concentrated to give (R)-3-((allyloxy)methyl)piperidine hydrochloride (0.41 g, 2.1 mmol, 92% yield) as white oil. m/z (ESI): 156.2 $(M+H)^+$. $^1H$ NMR (400 MHz, METHANOL-$d_4$): δ ppm 5.81-6.06 (m, 1H), 5.28 (dd, J=17.2, 1.7 Hz, 1H), 5.18 (dd, J=10.5, 1.8 Hz, 1H), 3.99 (dq, J=5.5, 1.3 Hz, 2H), 3.34-3.50 (m, 1H), 3.34-3.57 (m, 1H), 3.34-3.49 (m, 4H), 2.93 (d, J=3.3 Hz, 1H), 2.72-2.83 (m, 1H), 2.03-2.23 (m, 1H), 1.92-2.02 (m, 1H), 1.68-1.91 (m, 2H), 1.23-1.53 (m, 1H).

Intermediate VVV: 4-((R)-3-(Allyloxy)piperidin-1-yl)-7-(5-(but-3-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine

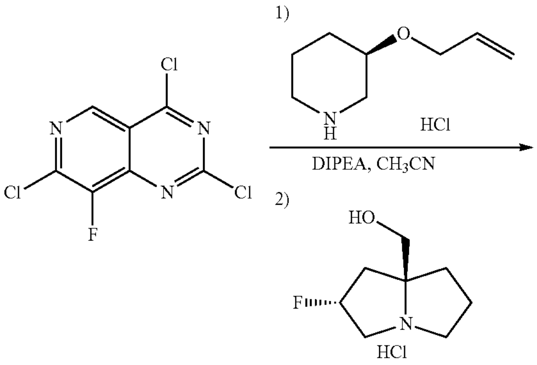

-continued

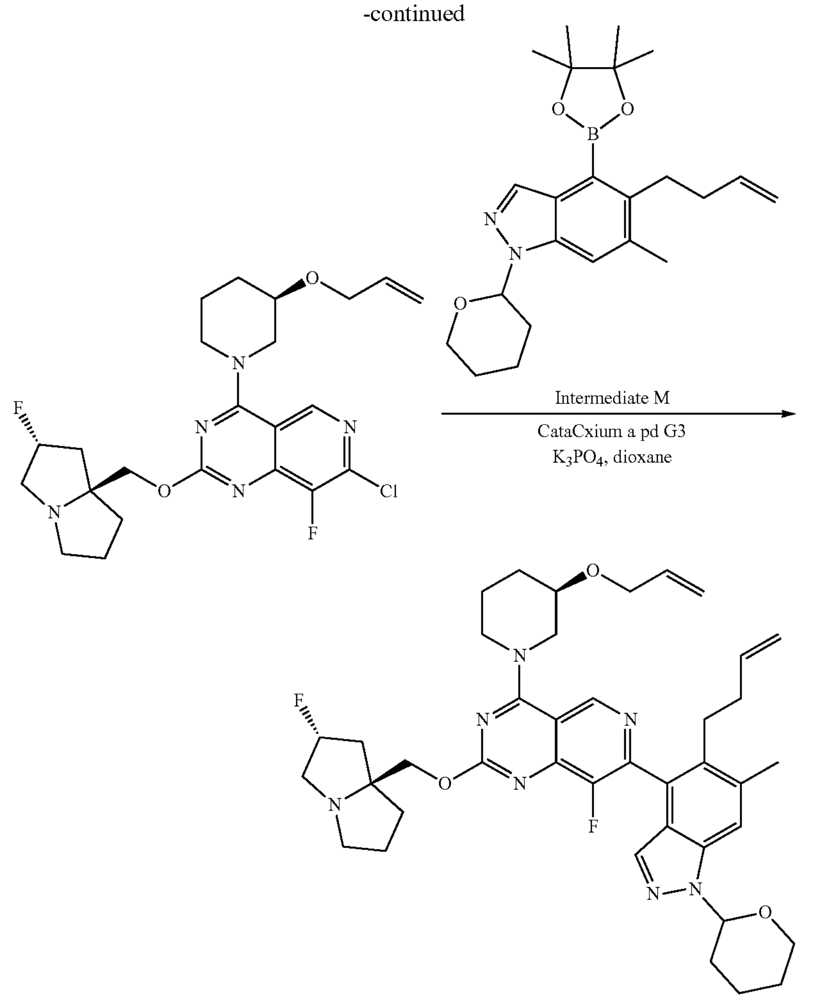

Intermediate VVV

Step 1. 4-((R)-3-(Allyloxy)piperidin-1-yl)-7-chloro-8-fluoro-2-(((2R,7aS)-2-fluorotetrahydro-1H-pyrrolizin-7a(5H)-yl)methoxy)pyrido[4,3-d]pyrimidine. To a stirred solution of 2,4,7-trichloro-8-fluoropyrido[4,3-d]pyrimidine (1.10 g, 4.36 mmol, Enamine) in acetonitrile (18 mL) at 0° C. was added (R)-3-(allyloxy)piperidine hydrochloride (0.85 g, 4.8 mmol), followed by Hunig's base (3.8 mL, 22 mmol). The reaction mixture was stirred at 0° C. for 0.5 h, then ((2R,7aS)-2-fluorotetrahydro-1H-pyrrolizin-7a(5H)-yl)methanol hydrochloride (0.85, 4.4 mmol) was added. The reaction mixture was stirred at 80° C. for 18 h. After cooling to rt, the reaction mixture was concentrated and the residue was purified by column chromatography on silica gel, eluting with a gradient of 0-50% (20% MeOH in DCM)/DCM, to afford 4-((R)-3-(allyloxy)piperidin-1-yl)-7-chloro-8-fluoro-2-(((2R,7aS)-2-fluorotetrahydro-1H-pyrrolizin-7a(5H)-yl)methoxy)pyrido[4,3-d]pyrimidine (1.22 g, 2.54 mmol, 58% yield) as yellow solid. m/z (ESI, +ve ion): 480.0 $(M+H)^+$.

Step 2. 4-((R)-3-(Allyloxy)piperidin-1-yl)-7-(5-(but-3-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine. In a vial was charged with 4-((R)-3-(allyloxy)piperidin-1-yl)-7-chloro-8-fluoro-2-(((2R,7aS)-2-fluorotetrahydro-1H-pyrrolizin-7a(5H)-yl)methoxy)pyrido[4,3-d]pyrimidine (0.59 g, 1.24 mmol), 5-(but-3-en-1-yl)-6-methyl-1-(tetrahydro-2H-pyran-2-yl)-4-(4,4,5,5-tetramethyl-1,3,2-dioxaborolan-2-yl)-1H-indazole (0.64 g, 1.61 mmol, Intermediate M), cataCXium A Pd G3 (90 mg, 0.12 mmol), and potassium phosphate tribasic hydrate (0.86 g, 3.71 mmol) in 1,4-dioxane (6 mL) and water (0.6 mL). The reaction mixture was flushed with nitrogen and stirred at 80° C. for 3.5 h. After cooling to rt, the reaction mixture was concentrated and the residue was purified by column chromatography on silica gel, eluting with a gradient of 0-80% (3:1 EtOAc/EtOH, with 2% $Et_3N$) in heptane, to afford 4-((R)-3-(allyloxy)piperidin-1-yl)-7-(5-(but-3-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (0.59 g, 0.83 mmol, 67% yield) as yellow solid. m/z (ESI, +ve ion): 714.0 $(M+H)^+$. $^1H$ NMR (400 MHz, METHANOL-$d_4$) δ ppm 9.33-9.37 (m, 1H), 7.70 (s, 1H), 7.51-7.59 (m, 1H), 5.80-5.93 (m, 2H), 5.63-5.74 (m, 1H), 5.34-5.57 (m, 1H), 5.06-5.24 (m, 2H), 4.83-4.92 (m, 2H), 4.67-4.80 (m, 2H), 4.27-4.46 (m, 2H), 3.91-4.13 (m, 6H), 3.76-3.89 (m, 4H), 3.35-3.52 (m, 1H), 2.78-2.89 (m, 1H), 2.54-2.76 (m, 6H), 2.33-2.53 (m, 4H), 2.10-2.27 (m, 4H), 1.95-2.10 (m, 3H), 1.65-1.91 (m, 4H), 1.44-1.54 (m, 1H).

Intermediate WWW: 4-(4-Bromo-6-chloro-1-(tetrahydro-2H-pyran-2-yl)-1H-indazol-5-yl)butan-1-ol

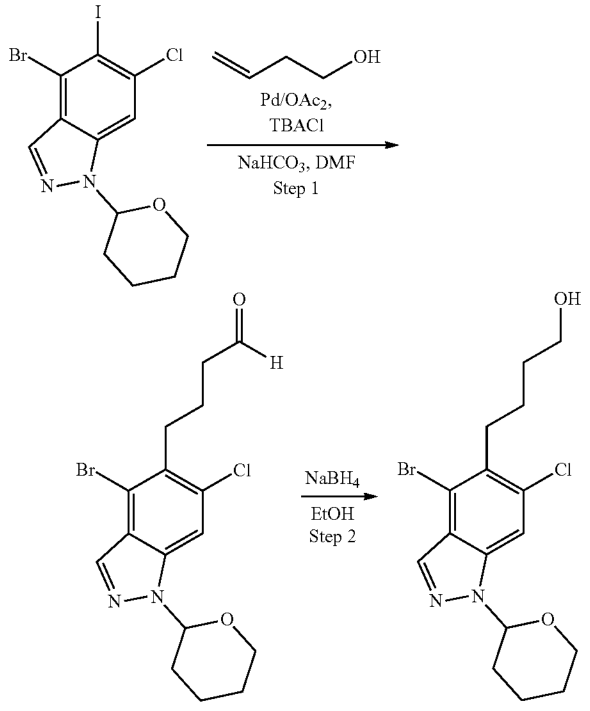

Intermediate WWW

Step 1. 4-(4-Bromo-6-chloro-1-(tetrahydro-2H-pyran-2-yl)-1H-indazol-5-yl)butanal. To a solution of 4-bromo-6-chloro-5-iodo-1-(tetrahydro-2H-pyran-2-yl)-1H-indazole (25.0 g, 56.6 mmol, Lab Network) in N,N-dimethylformamide (300 mL) was added $NaHCO_3$ (11.9 g, 142 mmol) and TBACl (14.8 g, 56.6 mmol) under $N_2$. Then the mixture was stirred at rt for 15 min, then but-3-en-1-ol (8.17 g, 113 mmol) and $Pd(OAc)_2$ (1.27 g, 5.66 mmol) was added under $N_2$. The mixture was stirred at 80° C. for 12 h under $N_2$. The residue was diluted with $H_2O$ and extracted with EtOAc. The combined organic layers were washed with brine, dried over $Na_2SO_4$, filtered and the filtrate was concentrated under reduced pressure. The residue was purified by column chromatography on silica gel, eluting with a gradient of 5-10% ethyl acetate in petroleum ether, to give 4-(4-bromo-6-chloro-1-(tetrahydro-2H-pyran-2-yl)-1H-indazol-5-yl)butanal (15 g, 39 mmol, 70% yield) as colorless oil. m/z (ESI): 385.1/387.1 $(M+H)^+$.

Step 2. 4-(4-Bromo-6-chloro-1-(tetrahydro-2H-pyran-2-yl)-1H-indazol-5-yl)butan-1-ol. To a solution of 4-(4-bromo-6-chloro-1-(tetrahydro-2H-pyran-2-yl)-1H-indazol-5-yl)butanal (15 g, 39 mmol) in EtOH (300 mL) was added $NaBH_4$ (4.41 g, 117 mmol) in portions at 0° C. The mixture was stirred at rt for 2 h, then was quenched by addition of saturated $NH_4Cl$ and $H_2O$. The aqueous layer was extracted with EtOAc, and the combined organic layers were washed with brine, dried over $Na_2SO_4$, filtered and concentrated. The residue was purified by column chromatography on silica gel, eluting with a gradient of 5-10% ethyl acetate in petroleum ether, to give 4-(4-bromo-6-chloro-1-(tetrahydro-2H-pyran-2-yl)-1H-indazol-5-yl)butan-1-ol (11 g, 28 mmol, 73% yield) as colorless oil. m/z (ESI): 387.0/389.0 $(M+H)^+$.

Intermediate XXX: 4-Bromo-5-(3-bromopropyl)-6-chloro-1-(tetrahydro-2H-pyran-2-yl)-1H-indazole

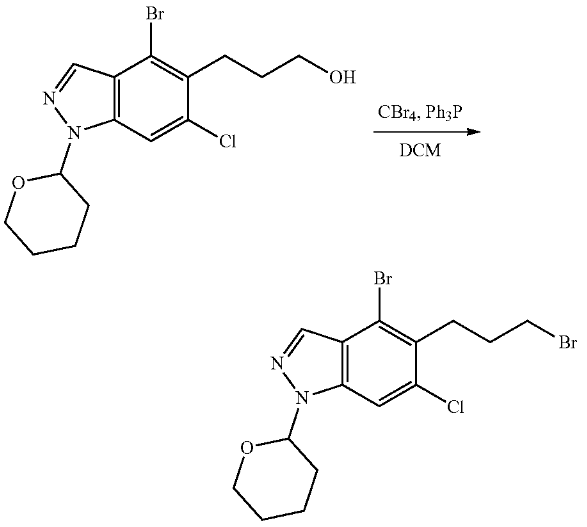

Intermediate XXX

To a 40 mL vial was charged with triphenylphosphine (1.25 g, 4.78 mmol) in dichloromethane (8 mL). Carbon tetrabromide (1.65 g, 4.98 mmol) was added and the reaction mixture was stirred at rt for 10 minutes. 3-(4-Bromo-6-chloro-1-(tetrahydro-2H-pyran-2-yl)-1H-indazol-5-yl)propan-1-ol (0.74 g, 2.0 mmol, Intermediate FFF, Step 2) was then added. The reaction was stirred at rt for 16 h, was then filtered and the filtrate concentrated in vacuo. The residue was purified by column chromatography on silica gel, eluting with a gradient of 0-45% ethyl acetate in heptane to give 4-bromo-5-(3-bromopropyl)-6-chloro-1-(tetrahydro-2H-pyran-2-yl)-1H-indazole (0.46 g, 1.10 mmol, 53% yield) as a colorless oil. m/z (ESI): 434.7 $(M+H)^+$.

Intermediate YYY: tert-Butyl (3S)-3-(2-(3-(4-bromo-6-chloro-1-(tetrahydro-2H-pyran-2-yl)-1H-indazol-5-yl)propoxy)ethyl)piperidine-1-carboxylate

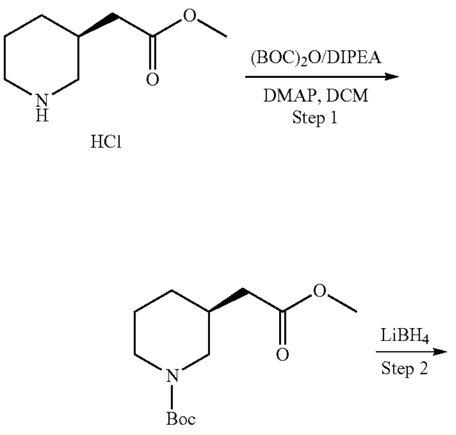

-continued

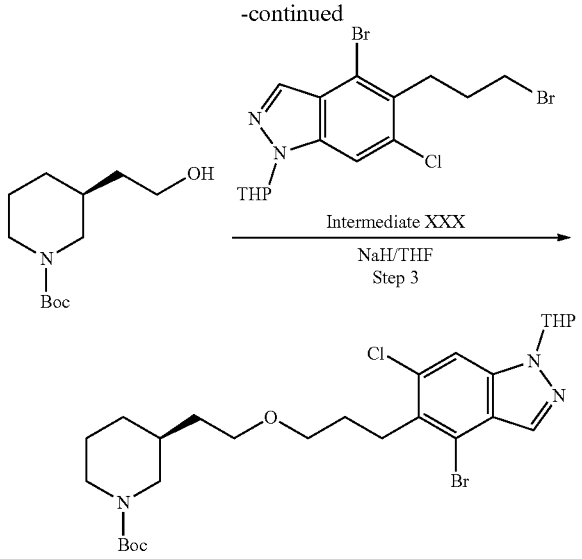

Intermediate YYY

Step 1. tert-Butyl (S)-3-(2-methoxy-2-oxoethyl)piperidine-1-carboxylate. A 250 mL round-bottom flask was charged with methyl 2-[(3S)-piperidin-3-yl]acetate hydrochloride (1.42 g, 7.33 mmol, Enamine), N-ethyl-N-isopropylpropan-2-amine (3.9 mL, 23 mmol) and DMAP (0.35 g, 2.82 mmol) in DCM (23 mL). The solution was stirred at rt for 10 min before di-tert-butyl dicarbonate (1.85 g, 8.46 mmol) was added. The reaction mixture was stirred at rt for 16 h, then was diluted with saturated $NH_4Cl$ and extracted with EtOAc. The organic extract was washed with saturated NaCl, dried over $MgSO_4$, filtered, and concentrated in vacuo. The crude material was purified by column chromatography on silica gel, eluting with a gradient of 0-80% 3:1 EtOAc/EtOH (with 1% TEA) in heptane, to provide tert-butyl (S)-3-(2-methoxy-2-oxoethyl)piperidine-1-carboxylate (1.30 g, 5.10 mmol, 90% yield) as colorless oil. m/z (ESI): 280.0 $(M+Na)^+$.

Step 2. tert-Butyl (S)-3-(2-hydroxyethyl)piperidine-1-carboxylate. A 250 mL round-bottom flask was charged with tert-butyl (S)-3-(2-methoxy-2-oxoethyl)piperidine-1-carboxylate (0.70 g, 2.72 mmol) in MeOH (1 mL) and DCM (10 mL). Lithium borohydride (2 M solution in THF, 4.1 mL, 8.2 mmol) was added slowly. The reaction mixture was stirred at rt for 16 h, then was diluted with saturated $NH_4Cl$ and extracted with EtOAc. The organic extract was washed with saturated NaCl, dried over $MgSO_4$, filtered, and concentrated in vacuo. The crude material was purified by column chromatography on silica gel, eluting with a gradient of 0-80% 3:1 EtOAc/EtOH (with 1% TEA) in heptane, to provide tert-butyl (S)-3-(2-hydroxyethyl)piperidine-1-carboxylate (0.52 g, 2.3 mmol, 83% yield) as colorless oil. m/z (ESI): 252.0 $(M+Na)^+$. $^1H$ NMR (400 MHz, METHANOL-$d_4$): δ ppm 4.35 (s, 1H), 3.65-3.84 (m, 2H), 3.39-3.51 (m, 2H), 2.68-2.90 (m, 1H), 1.70-1.81 (m, 1H), 1.45-1.62 (m, 2H), 1.37 (s, 9H), 1.23-1.36 (m, 3H), 1.01-1.15 (m, 1H).

Step 3. tert-Butyl (3S)-3-(2-(3-(4-bromo-6-chloro-1-(tetrahydro-2H-pyran-2-yl)-1H-indazol-5-yl)propoxy)ethyl)piperidine-1-carboxylate. To an oven dried 40 mL vial was charged with tert-butyl (S)-3-(2-hydroxyethyl)piperidine-1-carboxylate (0.39 g, 1.68 mmol) in THF (9 mL). Sodium hydride, 60% dispersion in mineral oil (0.12 g, 2.90 mmol) was added and the reaction mixture was stirred at rt for 15 min. To this was charged with 4-bromo-5-(3-bromopropyl)-6-chloro-1-(tetrahydro-2H-pyran-2-yl)-1H-indazole (0.49 g, 1.10 mmol, Intermediate XXX) in THF (4.5 mL). The reaction mixture was stirred at 55° C. for 16 h. After cooling to rt, the reaction was concentrated and the residue was purified by column chromatography on silica gel, eluting with 0-60% EtOAc in heptane to give tert-butyl (3S)-3-(2-(3-(4-bromo-6-chloro-1-(tetrahydro-2H-pyran-2-yl)-1H-indazol-5-yl)propoxy)ethyl)piperidine-1-carboxylate (0.30 g, 0.51 mmol, 46% yield) as yellow oil. m/z (ESI): 606.0/608.0 $(M+Na)^+$. $^1H$ NMR (400 MHz, CHLOROFORM-d): 6 ppm 7.97 (s, 1H), 7.60-7.77 (m, 1H), 5.53-5.74 (m, 1H), 3.68-4.07 (m, 4H), 3.44-3.59 (m, 4H), 3.00-3.23 (m, 2H), 2.74-2.88 (m, 1H), 2.42-2.59 (m, 2H), 2.10-2.21 (m, 2H), 1.61-1.94 (m, 8H), 1.58 (s, 6H), 1.47 (s, 10H), 1.08--1.20 (m, 1H).

Intermediate ZZZ: (4-Bromo-6-chloro-1-(tetrahydro-2H-pyran-2-yl)-1H-indazol-5-yl)methanol

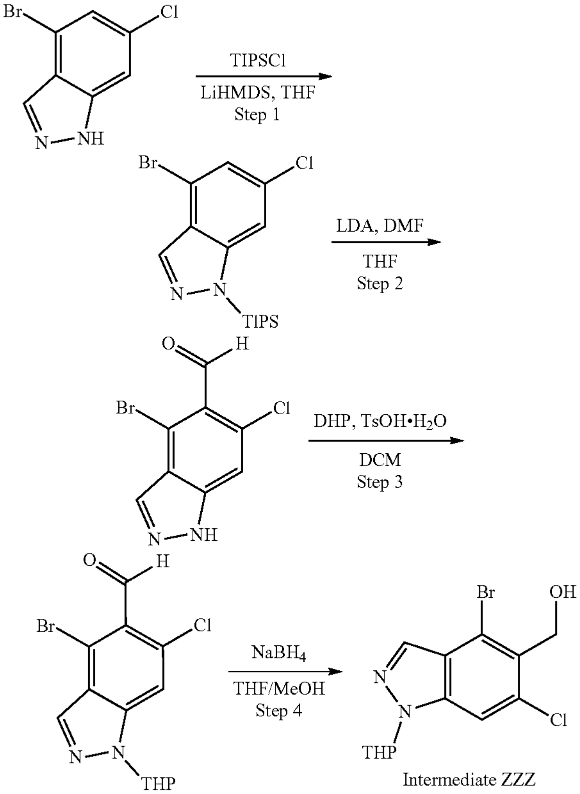

Intermediate ZZZ

Step 1. 4-Bromo-6-chloro-1-(triisopropylsilyl)-1H-indazole. To a solution of 4-bromo-6-chloro-1H-indazole (50 g, 216 mmol) in tetrahydrofuran (500 mL) was added LiHMDS (1 M in THF, 259 mL, 259 mmol) dropwise under nitrogen at −78° C. The reaction mixture was stirred for 1 h. Then TIPSCl (55 mL, 259 mmol) was added dropwise at −78° C. under $N_2$. The reaction mixture was stirred at −78° C. for 0.5 h, then at rt for 3.5 h. The reaction mixture was poured into water at 0° C. and extracted with EtOAc. The combined organic layers were dried over $Na_2SO_4$, filtered, and concentrated under reduced pressure. The residue was purified by column chromatography on silica gel, eluting with a gradient of 0-100% EtOAc in petroleum ether, to give 4-bromo-6-chloro-1-(triisopropylsilyl)-1H-indazole (50 g, 60% yield) as yellow solid. $^1$H NMR (400 MHz, DMSO-d$_6$): δ ppm 8.20 (s, 1H), 7.48 (s, 1H), 7.32 (s, 1H), 1.71-1.80 (m, 3H), 1.13-1.17 (d, J=1.6 Hz, 6H).

Step 2. 4-Bromo-6-chloro-1H-indazole-5-carbaldehyde. To a solution of 4-bromo-6-chloro-1-(triisopropylsilyl)-1H-indazole (50 g, 129 mmol) in tetrahydrofuran (500 mL) was added LDA (2 M in THF, 97 mL, 194 mmol) dropwise at −78° C. The reaction mixture was stirred at −78° C. under $N_2$ for 1 h. Then the solution of DMF (50 mL, 645 mmol) in tetrahydrofuran (50 mL) was added dropwise to the above mixture under $N_2$. The reaction mixture was stirred at −78° C. for 0.5 h, then at 0° C. for 2.5 h. The reaction mixture was quenched by addition of saturated $NH_4Cl$ at 0° C., then extracted with EtOAc. The combined organic layers were dried over $Na_2SO_4$, filtered, and concentrated under reduced pressure. The residue was triturated with a mixed solvent (petroleum ether/EtOAc=15:1) at rt for 1 h. The suspension was filtered, and the filter cake was washed with 30:1 petroleum ether/EtOAc and concentrated under reduced pressure to give 4-bromo-6-chloro-1H-indazole-5-carbaldehyde (30 g, 116 mmol, 90% yield) as yellow solid. $^1$H NMR (400 MHz, DMSO-d$_6$): δ ppm 13.87 (s, 1H), 10.36 (s, 1H), 8.32 (s, 1H), 7.82 (s, 1H).

Step 3. 4-Bromo-6-chloro-1-(tetrahydro-2H-pyran-2-yl)-1H-indazole-5-carbaldehyde. To a solution of 4-bromo-6-chloro-1H-indazole-5-carbaldehyde (50 g, 193 mmol) in dichloromethane (700 mL) was added DHP (53 mL, 578 mmol) and TsOH-$H_2O$ (6.64 g, 38.5 mmol). The reaction mixture was stirred at rt for 2 h, was then diluted with water and extracted with DCM. The combined organic layers were dried over $Na_2SO_4$, filtered, and concentrated under reduced pressure. The residue was triturated with a mixed solvent (petroleum ether/EtOAc=30:1) at rt for 1 h. The suspension was filtered, and the filter cake was washed with petroleum ether, and concentrated under reduced pressure to give 4-bromo-6-chloro-1-(tetrahydro-2H-pyran-2-yl)-1H-indazole-5-carbaldehyde (50 g, 75% yield) as yellow solid.

Step 4. (4-Bromo-6-chloro-1-(tetrahydro-2H-pyran-2-yl)-1H-indazol-5-yl)methanol. To a stirred suspension of 4-bromo-6-chloro-1-(tetrahydro-2H-pyran-2-yl)-1H-indazole-5-carbaldehyde (2.50 g, 7.30 mmol) in THF (23 mL) and methanol (35 mL) in a round-bottom flask at 0° C. under nitrogen was added sodium borohydride (0.28 g, 7.3 mmol) portionwise. After stirring for 30 min, the reaction mixture was quenched with saturated $NH_4Cl$ the partitioned between EtOAc and water. The organic was dried over $MgSO_4$, then concentrated under reduced pressure to provide (4-bromo-6-chloro-1-(tetrahydro-2H-pyran-2-yl)-1H-indazol-5-yl) methanol (2.30 g, 6.60 mmol, 91% yield) as pale yellow solid. m/z (ESI): 344.8 (M+H)$^+$.

Intermediate AAAA: tert-Butyl (3R)-3-((2-((4-bromo-6-chloro-1-(tetrahydro-2H-pyran-2-yl)-1H-indazol-5-yl)methoxy)ethoxy)methyl)piperidine-1-carboxylate

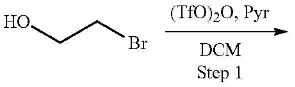

-continued

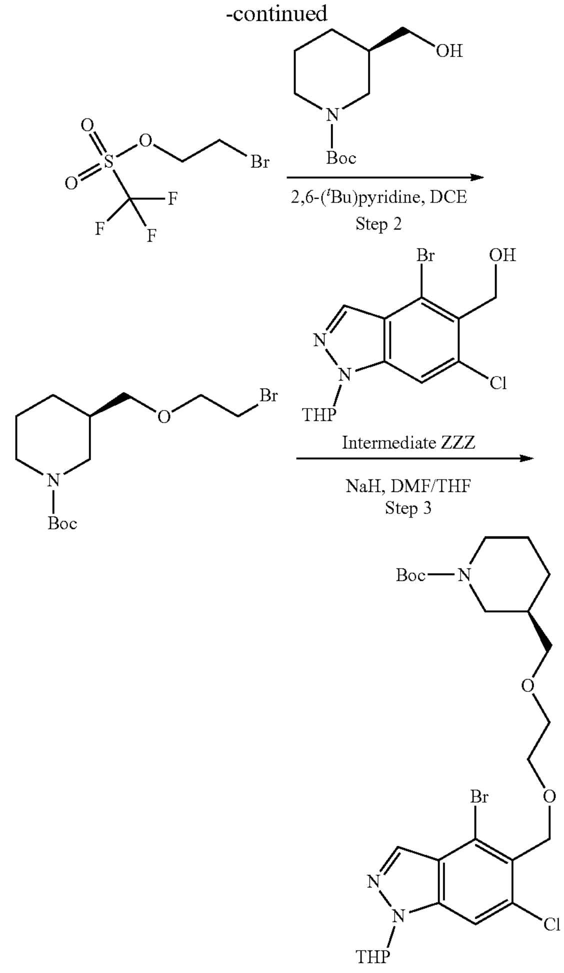

Intermediate AAA

Step 1. 2-Bromoethyl trifluoromethanesulfonate. To a stirred solution of 2-bromoethanol (2.00 g, 16 mmol) and pyridine (1.5 mL, 19 mmol) in DCM (16 mL) under nitrogen at 0° C. was added trifluoromethanesulfonic anhydride solution (1 M in DCM, 17.5 mL, 17.5 mmol) dropwise at a rate not to exceed an internal temp of 8° C. After 30 min, the reaction was diluted with ethyl acetate and washed with 1 M HCl, followed by 10% saturated sodium bicarbonate and saturated NaCl. The organic layer was dried over $MgSO_4$, filtered, then concentrated under reduced pressure to provide 2-bromoethyl trifluoromethanesulfonate (2.70 g, 10 mmol, 65% yield) as yellow oil. $^1$H NMR (CHLOROFORM-d, 400 MHz) δ 4.76 (t, 2H, J=6.4 Hz), 3.63 (t, 2H, J=6.4 Hz).

Step 2. tert-Butyl (R)-3-((2-bromoethoxy)methyl)piperidine-1-carboxylate. A stirred solution of (R)-1-Boc-3-hydroxymethylpiperidine (1.00 g, 4.60 mmol), 2-bromoethyl trifluoromethanesulfonate (1.80 g, 7.00 mmol), 2,6-di-tert-butylpyridine (4.40 g, 23 mmol) in 1,2-dichloroethane (6 mL) in a 40 mL vial was heated to 60° C. for 12 h. DMSO (5 mL) was added, and the mixture was concentrated under reduced pressure. The crude material was purified by C-18 column, eluting with a gradient of 5-100% water/MeCN (with 0.1% formic acid). The collected fractions were first concentrated then partitioned between EtOAc and saturated $NaHCO_3$. The aqueous layer was then further extracted with EtOAc, and the combined organics were washed with brine, dried over $MgSO_4$, then concentrated under reduced pressure to provide tert-butyl (R)-3-((2-bromoethoxy)methyl) piperidine-1-carboxylate (1.10 g, 3.50 mmol, 75% yield) as colorless oil. $^{1}H$ NMR (CHLOROFORM-d, 400 MHz) δ 3.9-4.1 (m, 1H), 3.8-3.9 (m, 1H), 3.7-3.8 (m, 2H), 3.47 (t, 2H, J=6.3 Hz), 3.38 (dd, 2H, J=2.6, 6.2 Hz), 2.8-2.9 (m, 1H), 2.6-2.7 (m, 1H), 1.8-1.9 (m, 2H), 1.6-1.8 (m, 1H), 1.4-1.5 (m, 11H), 1.2-1.3 (m, 1H).

Step 3. tert-Butyl (3R)-3-((2-((4-bromo-6-chloro-1-(tetrahydro-2H-pyran-2-yl)-1H-indazol-5-yl)methoxy)ethoxy) methyl)piperidine-1-carboxylate. To a stirred solution of (4-bromo-6-chloro-1-(tetrahydro-2H-pyran-2-yl)-1H-indazol-5-yl)methanol (1.80 g, 5.10 mmol, Intermediate ZZZ) in DMF (17 mL) at 0° C. was added sodium hydride, 60% dispersion in mineral oil (0.61 g, 15 mmol) in one portion. After 30 min, a solution of tert-butyl (R)-3-((2-bromoethoxy)methyl)piperidine-1-carboxylate (1.10 g, 3.40 mmol) in THF (10 mL) was added and cooling bath was removed. The reaction mixture was stirred at rt for 15 h, was then chilled to 0° C. and quenched with saturated $NH_4Cl$ and water. The aqueous layer was extracted with EtOAc, and the combined organic layers were washed with brine, dried over $MgSO_4$, then concentrated. The crude material was purified by C-18 column, eluting with a gradient of 5-100% water/MeCN (with 0.1% formic acid). The collected fractions were first concentrated then partitioned between EtOAc and saturated $NaHCO_3$. The aqueous layer was then further extracted with EtOAc and the combined organics were washed with brine, dried over $MgSO_4$, then concentrated under reduced pressure to provide tert-butyl (3R)-3-((2-((4-bromo-6-chloro-1-(tetrahydro-2H-pyran-2-yl)-1H-indazol-5-yl)methoxy) ethoxy)methyl)piperidine-1-carboxylate (0.45 g, 0.77 mmol, 22% yield) as colorless film. $^{1}H$ NMR (CHLOROFORM-d, 400 MHz) δ 8.0-8.0 (m, 1H), 7.69 (s, 1H), 5.67 (dd, 1H, J=2.7, 8.8 Hz), 4.96 (s, 2H), 3.9-4.1 (m, 2H), 3.8-3.9 (m, 1H), 3.7-3.8 (m, 3H), 3.6~3.7 (m, 2H), 3.35 (d, 2H, J=5.9 Hz), 2.8-2.9 (m, 1H), 2.4-2.5 (m, 1H), 2.1-2.2 (m, 2H), 1.6-1.8 (m, 6H), 1.46 (s, 9H), 1.3-1.4 (m, 5H).

Intermediate BBBB: tert-Butyl (2R)-2-((2-((4-bromo-6-chloro-1-(tetrahydro-2H-pyran-2-yl)-1H-indazol-5-yl)methoxy)ethoxy)methyl)morpholine-4-carboxylate Intermediate BBBB

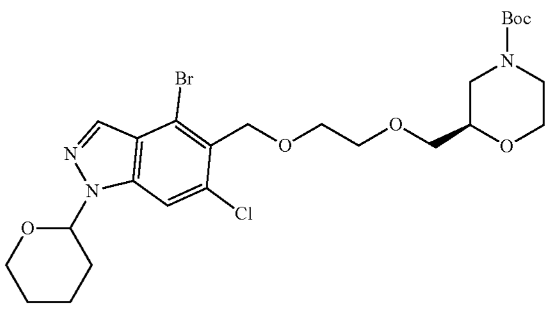

The compound was synthesized using an analogous method to Intermediate AAAA using (R)-tert-butyl 2-(hydroxymethyl)morpholine-4-carboxylate (Ambeed, Inc.) in step 2. m/z (ESI): 589.2 $(M+H)^+$.

Intermediate CCCC: tert-Butyl (3R)-3-(((4-(4-bromo-6-chloro-1-(tetrahydro-2H-pyran-2-yl)-1H-indazol-5-yl)butyl)thio)methyl)piperidine-1-carboxylate

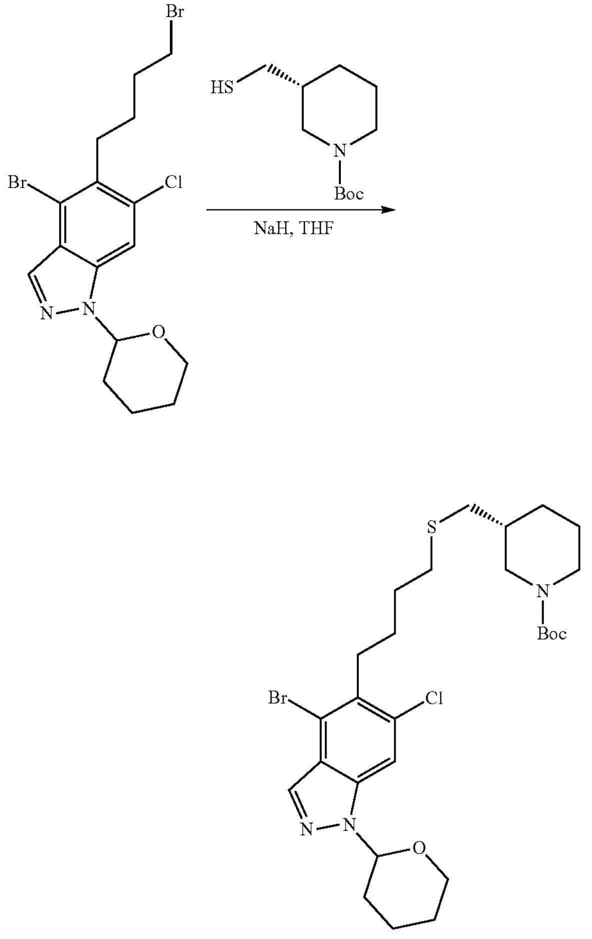

Intermediate CCCC

To a 40 mL vial purged with nitrogen was charged tert-butyl (3R)-3-(sulfanylmethyl)piperidine-1-carboxylate (1.1 mL, 4.9 mmol) and tetrahydrofuran (25 mL). To this was added sodium hydride, 60% dispersion in mineral oil (0.23 g, 5.7 mmol) and the reaction was stirred for 10 min. 4-Bromo-5-(4-bromobutyl)-6-chloro-1-(tetrahydro-2H-pyran-2-yl)-1H-indazole (1.99 g, 4.42 mmol, Step 1 in Example 135) in tetrahydrofuran (5 mL) was added. The reaction mixture was stirred at rt for 48 h. The reaction was carefully quenched with saturated aqueous ammonium chloride, filtered, concentrated. The residue was purified by flash column chromatography on silica gel, eluting with a gradient of 0-25% EtOAc in heptane, to give tert-butyl (3R)-3-(((4-(4-bromo-6-chloro-1-(tetrahydro-2H-pyran-2-yl)-1H-indazol-5-yl) butyl)thio)methyl)piperidine-1-carboxylate as a colorless oil (1.52 g, 2.53 mmol, 57% yield). m/z (ESI): 500.0 $(M-Boc+H)^+$. $^{1}H$ NMR (400 MHz, CHLOROFORM-d) δ ppm 7.91-8.06 (m, 1H), 7.54-7.75 (m, 1H), 5.55-5.70 (m, 1H), 3.93-4.10 (m, 2H), 3.69-3.91 (m, 2H), 3.07 (br t, J=7.4 Hz, 2H), 2.78-2.88 (m, 1H), 2.43-2.62 (m, 5H), 2.04-2.26 (m, 2H), 1.88-2.00 (m, 1H), 1.62-1.83 (m, 10H), 1.48 (s, 9H), 1.22-1.34 (m, 2H).

Intermediate DDDD: tert-Butyl (3R)-3-(((4-(4-bromo-6-chloro-1-(tetrahydro-2H-pyran-2-yl)-1H-indazol-5-yl)butyl)sulfinyl)methyl)piperidine-1-carboxylate

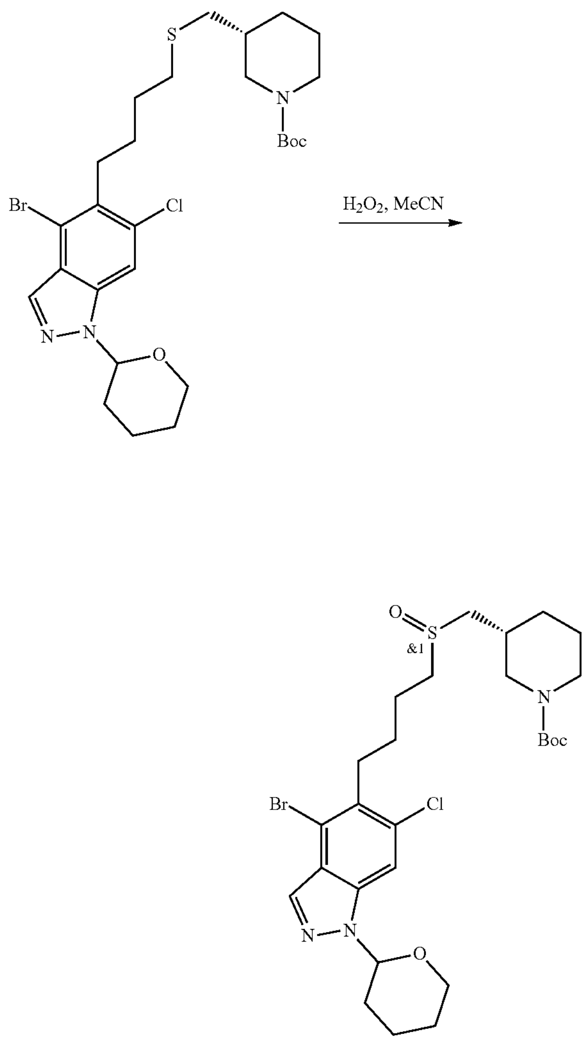

Intermediate DDDD

To a 40 mL vial was charged with tert-butyl (3R)-3-(((4-(4-bromo-6-chloro-1-(tetrahydro-2H-pyran-2-yl)-1H-indazol-5-yl)butyl)thio)methyl)piperidine-1-carboxylate (1.0 g, 1.7 mmol, Intermediate CCCC), acetonitrile (3.5 mL), and hydrogen peroxide (30%, 33.4 mL, 33.3 mmol). The reaction mixture was stirred at rt for 4.5 h, then was diluted with saturated aqueous sodium thiosulfate and extracted with DCM. The organics were dried over sodium sulfate and concentrated to give tert-butyl (3R)-3-(((4-(4-bromo-6-chloro-1-(tetrahydro-2H-pyran-2-yl)-1H-indazol-5-yl) butyl)sulfinyl)methyl)piperidine-1-carboxylate (0.97 g, 1.6 mmol, 94% yield) as white solid. m/z (ESI): 616.0 $(M+H)^+$. $^1H$ NMR (400 MHz, CHLOROFORM-d) δ ppm 7.92-8.01 (m, 1H), 7.67 (s, 1H), 5.60-5.70 (m, 1H), 3.71-4.15 (m, 1H), 3.69-4.06 (m, 3H), 2.93-3.19 (m, 4H), 2.71-2.90 (m, 1H), 2.68-2.87 (m, 2H), 2.48-2.66 (m, 1H), 2.39-2.69 (m, 1H), 2.26-2.92 (m, 1H), 2.04-2.23 (m, 4H), 1.94-2.02 (m, 2H), 1.60-1.89 (m, 7H), 1.42-1.48 (m, 9H).

Intermediate EEEE: tert-Butyl (3R)-3-(((4-(4-bromo-6-chloro-1-(tetrahydro-2H-pyran-2-yl)-1H-indazol-5-yl)butyl)sulfonyl)methyl)piperidine-1-carboxylate

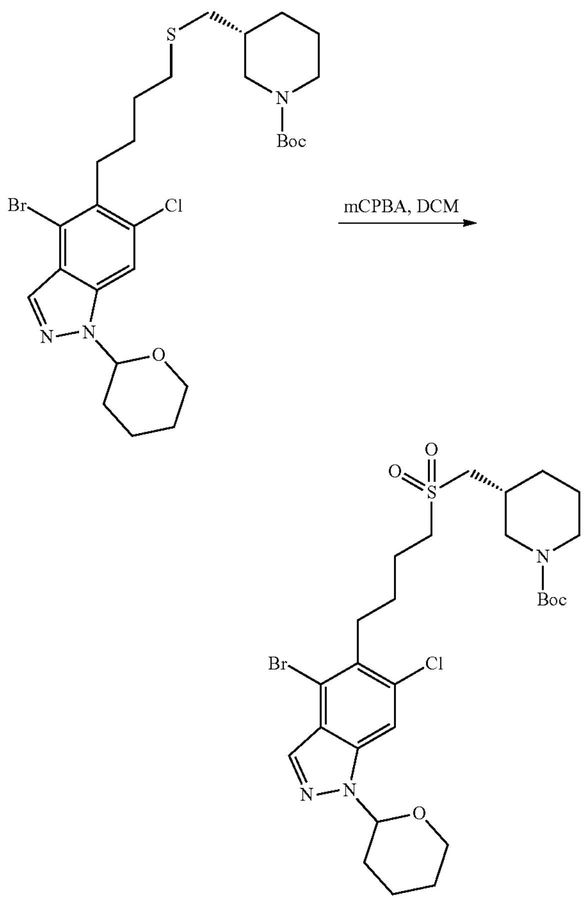

Intermediate EEEE

To a 20 mL vial was charged with tert-butyl (3R)-3-(((4-(4-bromo-6-chloro-1-(tetrahydro-2H-pyran-2-yl)-1H-indazol-5-yl)butyl)thio)methyl)piperidine-1-carboxylate (0.40 g, 0.67 mmol) and dichloromethane (7 mL). To this was added 3-chlorobenzene-1-carboperoxoic acid (0.37 g, 1.66 mmol) cautiously. The reaction mixture was stirred at rt for 1 h, was then diluted with DCM and a solution of sodium thiosulfate. The peroxides were checked with peroxide test strips before further extraction of the aqueous layer with dichloromethane. The combined organics were concentrated and the crude oil was purified by column chromatography on silica gel, eluting with a gradient of 0-50% 3:1 EtOAc/EtOH with 2% triethylamine in heptane, to give tert-butyl (3R)-3-(((4-(4-bromo-6-chloro-1-(tetrahydro-2H-pyran-2-yl)-1H-indazol-5-yl)butyl)sulfonyl)methyl)piperidine-1-carboxylate (0.39 g, 0.62 mmol, 93% yield) as white solid. m/z (ESI): 532.0 $(M-Boc+H)^+$. $^1H$ NMR (400 MHz, CHLOROFORM-d) δ ppm 7.89-8.02 (m, 1H), 7.67 (s, 1H), 5.60-5.72 (m, 1H), 3.87-4.07 (m, 2H), 3.60-3.84 (m, 2H), 2.85-3.16 (m, 8H), 2.26-2.55 (m, 2H), 2.02-2.19 (m, 6H), 1.64-1.80 (m, 6H), 1.49 (s, 10H).

Intermediate FFFF: tert-Butyl (R)-3-(azidomethyl)piperidine-1-carboxylate

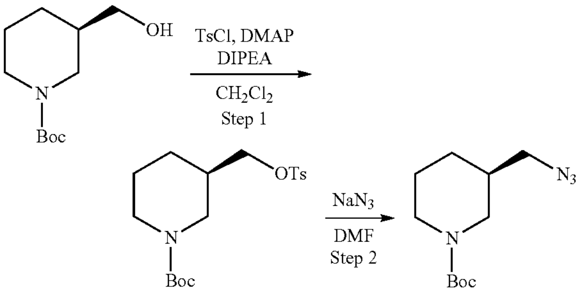

Intermediate FFFF

Step 1. tert-Butyl (R)-3-((tosyloxy)methyl)piperidine-1-carboxylate. para-Toluenesulfonyl chloride (3.90 g, 20.4 mmol) was added to a solution of (R)-tert-butyl 3-(hydroxymethyl)piperidine-1-carboxylate (2.00 g, 9.30 mmol, Ambeed, Inc.) and N,N-diisopropylethylamine (3.6 mL, 28 mmol) in dichloromethane (23 mL). 4-(N,N-Dimethylamino)-pyridine (0.11 g, 0.93 mmol) was added, and the reaction mixture was stirred at rt for 16 h. The reaction was quenched with saturated aqueous $NaHCO_3$ and extracted with DCM. The organics were dried and concentrated in vacuo. The crude material was purified by chromatography on silica gel, eluting with a gradient of 0-75% 3:1 EtOAc/EtOH in heptane, to provide tert-butyl (R)-3-((tosyloxy)methyl)piperidine-1-carboxylate (3.00 g, 8.10 mmol, 87% yield) as light-yellow oil.

Step 2. tert-Butyl (R)-3-(azidomethyl)piperidine-1-carboxylate. Sodium azide (0.26 g, 4.10 mmol) was added to a solution of tert-butyl (R)-3-((tosyloxy)methyl)piperidine-1-carboxylate (1.00 g, 2.71 mmol) in N,N-dimethylformamide (14 mL). The reaction mixture was heated to 65° C. for 2 h. After cooling to rt, the reaction was diluted with water and extracted with EtOAc. The organic layer was washed with water, then brine, dried over sodium sulfate and the EtOAc solution was used in the next step without further purification. m/z (ESI): 185.1 $(M+H-tBu)^+$.

Intermediate GGGG: tert-Butyl (3R)-3-((4-(2-(4-bromo-6-chloro-1-(tetrahydro-2H-pyran-2-yl)-1H-indazol-5-yl)ethyl)-1H-1,2,3-triazol-1-yl)methyl) piperidine-1-carboxylate

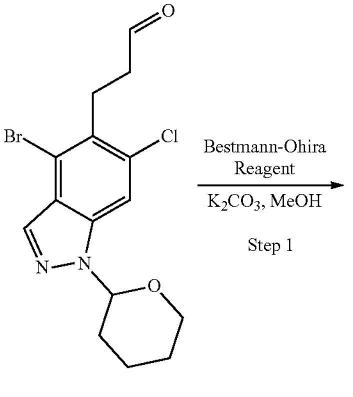

-continued

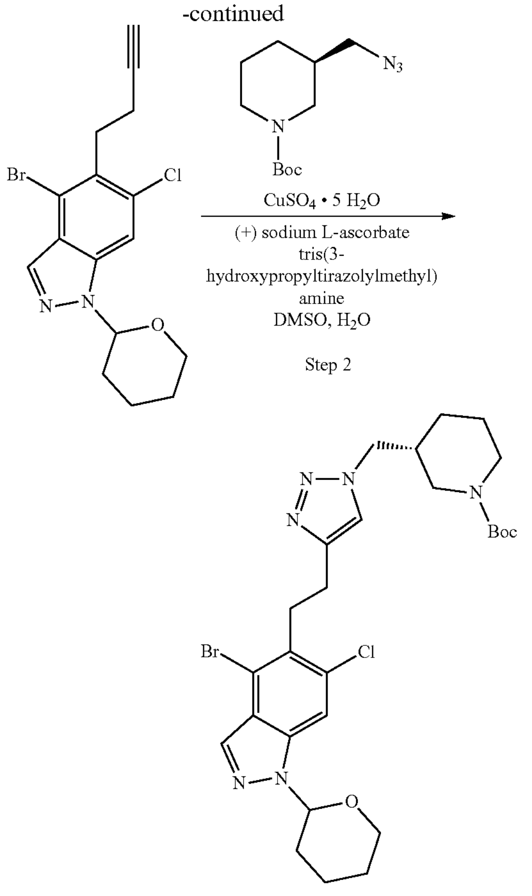

Intermediate GGGG

Step 1. 4-Bromo-5-(but-3-yn-1-yl)-6-chloro-1-(tetrahydro-2H-pyran-2-yl)-1H-indazole. Dimethyl (1-diazo-2-oxopropyl)phosphonate (10 wt % in MeCN, 11.9 mL, 6.20 mmol) was added to a suspension of 3-(4-bromo-6-chloro-1-(tetrahydro-2H-pyran-2-yl)-1H-indazol-5-yl)propanal (1.54 g, 4.13 mmol, Step 1 in Example 74) and potassium carbonate (1.14 g, 8.26 mmol) in methanol (10 mL) and stirred at rt for 4 h. The reaction was diluted with DCM, washed with saturated aqueous $NaHCO_3$. The organics were dried ($Na_2SO_4$), filtered and concentrated. The crude material was purified by column chromatography on silica gel, eluting with a gradient of 0-75% 3:1 EtOAc/EtOH in heptane, to provide 4-bromo-5-(but-3-yn-1-yl)-6-chloro-1-(tetrahydro-2H-pyran-2-yl)-1H-indazole (1.17 g, 3.18 mmol, 77% yield) as light-yellow oil. m/z (ESI): 367.1 $(M+H)^+$.

Step 2. tert-Butyl (3R)-3-((4-(2-(4-bromo-6-chloro-1-(tetrahydro-2H-pyran-2-yl)-1H-indazol-5-yl)ethyl)-1H-1,2,3-triazol-1-yl)methyl)piperidine-1-carboxylate. Copper (II) sulfate pentahydrate (45 mg, 0.18 mmol) and tris(3-hydroxypropyltriazolylmethyl)amine (78 mg, 0.18 mmol, Ambeed, Inc.) were dissolved in 1:1 DMSO/$H_2O$ (1.4 mL) and stirred for 30 minutes. The solution was added to a mixture of 4-bromo-5-(but-3-yn-1-yl)-6-chloro-1-(tetrahydro-2H-pyran-2-yl)-1H-indazole (0.33 g, 0.90 mmol) and (+)-sodium L-ascorbate (0.16 g, 0.81 mmol) in DMSO (1 mL), then tert-butyl (R)-3-(azidomethyl)piperidine-1-carboxylate (0.32 g, 1.35 mmol, Intermediate FFFF) in DMSO (1 mL) was added. The reaction mixture was heated to 40° C. for 45 min. The reaction was cooled then diluted with saturated aqueous $NH_4Cl$ and extracted with EtOAc. The organics were dried ($Na_2SO_4$), filtered and concentrated. The crude material was purified by column chromatography on silica gel, eluting with a gradient of 0-100% 3:1 EtOAc/EtOH in heptane, to provide tert-butyl (3R)-3-((4-(2-(4-bromo-6-chloro-1-(tetrahydro-2H-pyran-2-yl)-1H-indazol-5-yl)ethyl)-1H-1,2,3-triazol-1-yl)methyl)piperidine-1-carboxylate (0.50 g, 0.82 mmol, 92% yield) as white solid. m/z (ESI): 607.2 $(M+H)^+$.

Intermediate HHHH: tert-Butyl (Z)-3-((4-(2-(4-bromo-6-chloro-1-(tetrahydro-2H-pyran-2-yl)-1H-indazol-5-yl)vinyl)-1H-pyrazol-1-yl)methyl)piperidine-1-carboxylate

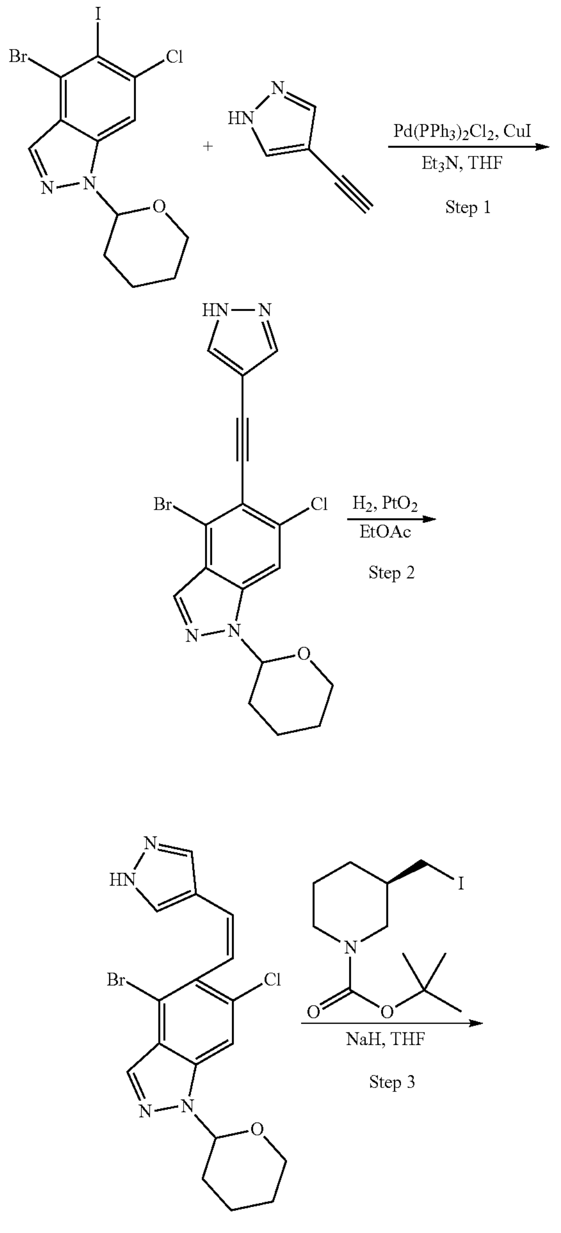

-continued

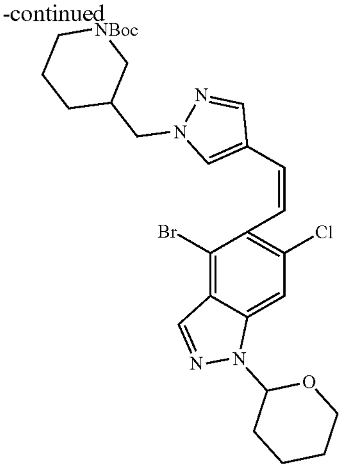

Intermediate HHHH

Step 1. 5-((1H-Pyrazol-4-yl)ethynyl)-4-bromo-6-chloro-1-(tetrahydro-2H-pyran-2-yl)-1H-indazole. In a 20-mL microwave reaction vessel was charged with 4-bromo-6-chloro-5-iodo-1-(tetrahydro-2H-pyran-2-yl)-1H-indazole (1.90 g, 4.30 mmol, LabNetwork), 4-ethynyl-1H-pyrazole (0.40 g, 4.30 mmol, Enamine), bis(triphenylphosphine)palladium(II) dichloride (0.23 g, 0.32 mmol) and copper (I) iodide (61 mg, 0.32 mmol) in THF (10 mL). Triethylamine (3.0 mL, 21 mmol) was added under nitrogen and the resulting mixture was purged with nitrogen for 5 min before the vessel was sealed and subjected to irradiation for 4 h at 70° C. After cooling to rt, the crude mixture was directly onto a silica gel precolumn and purified by column chromatography on silica gel, eluting with a gradient of 0-5% MeOH/DCM, to give 5-((1H-pyrazol-4-yl)ethynyl)-4-bromo-6-chloro-1-(tetrahydro-2H-pyran-2-yl)-1H-indazole (0.50 g, 1.23 mmol, 29% yield) as off-white solid. $^1H$ NMR (CHLOROFORM-d, 400 MHz) δ 10.18 (br s, 1H), 8.00 (d, 1H, J=0.6 Hz), 7.88 (br s, 2H), 7.71 (d, 1H, J=0.8 Hz), 5.67 (dd, 1H, J=2.6, 8.9 Hz), 4.0-4.1 (m, 1H), 3.7-3.8 (m, 1H), 2.4-2.5 (m, 1H), 2.1-2.2 (m, 2H), 1.7-1.8 (m, 3H). m/z (ESI): 405.0/407.0 $(M+H)^+$.

Step 2. (Z)-5-(2-(1H-Pyrazol-4-yl)vinyl)-4-bromo-6-chloro-1-(tetrahydro-2H-pyran-2-yl)-1H-indazole. A mixture of 5-((1H-pyrazol-4-yl)ethynyl)-4-bromo-6-chloro-1-(tetrahydro-2H-pyran-2-yl)-1H-indazole (0.50 g, 1.23 mmol) and platinum (IV) oxide (0.11 g, 0.50 mmol) in ethyl acetate (50 mL) was hydrogenated at 35 psi for 18 h. The solids were filtered off and the filtrate was concentrated in vacuo. The crude residue was purified by column chromatography on silica gel, eluting with a gradient of 0-3% MeOH/DCM, to give (Z)-5-(2-(1H-pyrazol-4-yl)vinyl)-4-bromo-6-chloro-1-(tetrahydro-2H-pyran-2-yl)-1H-indazole (0.46 g, 1.13 mmol, 92% yield) as off-white solid. $^1H$ NMR (CHLOROFORM-d, 400 MHz) δ 8.01 (s, 1H), 7.75 (s, 1H), 7.13 (s, 2H), 6.73 (d, 1H, J=11.5 Hz), 6.37 (d, 1H, J=11.7 Hz), 5.7-5.8 (m, 1H), 4.0-4.2 (m, 1H), 3.7-3.8 (m, 1H), 2.5-2.6 (m, 1H), 2.1-2.2 (m, 2H), 1.6-1.9 (m, 4H). m/z (ESI): 407.0/409.0 $(M+H)^+$.

Step 3. tert-Butyl (Z)-3-((4-(2-(4-bromo-6-chloro-1-(tetrahydro-2H-pyran-2-yl)-1H-indazol-5-yl)vinyl)-1H-pyrazol-1-yl)methyl)piperidine-1-carboxylate. To a stirred solution of (Z)-5-(2-(1H-pyrazol-4-yl)vinyl)-4-bromo-6-chloro-1-(tetrahydro-2H-pyran-2-yl)-1H-indazole (0.46 g, 1.13 mmol) in THF (11 mL) was added sodium hydride, 60% dispersion in mineral oil (0.20 g, 5.1 mmol) under nitrogen.

After 5 min, (3R)-1-Boc-3-(iodomethyl)piperidine (1.21 g, 3.7 mmol) was added and the resulting mixture was stirred at 0° C. for 20 min and then at rt for 8 days. The volatiles were removed and the crude was purified by column chromatography on silica gel, eluting with 0-100% EtOAc in heptane to give tert-butyl (Z)-3-((4-(2-(4-bromo-6-chloro-1-(tetrahydro-2H-pyran-2-yl)-1H-indazol-5-yl)vinyl)-1H-pyrazol-1-yl)methyl)piperidine-1-carboxylate (0.24 g, 0.40 mmol, 35% yield) as white solid. $^1$H NMR (CHLOROFORM-d, 400 MHz) δ 7.99 (s, 1H), 7.73 (s, 1H), 6.9-7.1 (m, 1H), 6.88 (s, 1H), 6.66 (d, 1H, J=11.7 Hz), 6.29 (d, 1H, J=11.5 Hz), 5.68 (br s, 1H), 4.03 (br s, 1H), 3.6-3.9 (m, 5H), 2.8-2.9 (m, 1H), 2.4-2.7 (m, 2H), 2.1-2.2 (m, 2H), 1.9-2.0 (m, 1H), 1.6-1.9 (m, 4H), 1.58 (br d, 2H, J=9.6 Hz), 1.42 (s, 9H), 1.05 (q, 1H, J=10.0 Hz). m/z (ESI): 603.8/605.8 $(M+H)^+$.

Intermediate IIII: tert-Butyl 3-(2-(3-(4-bromo-6-chloro-1-(tetrahydro-2H-pyran-2-yl)-1H-indazol-5-yl)propyl)-2H-1,2,3-triazol-4-yl)piperidine-1-carboxylate

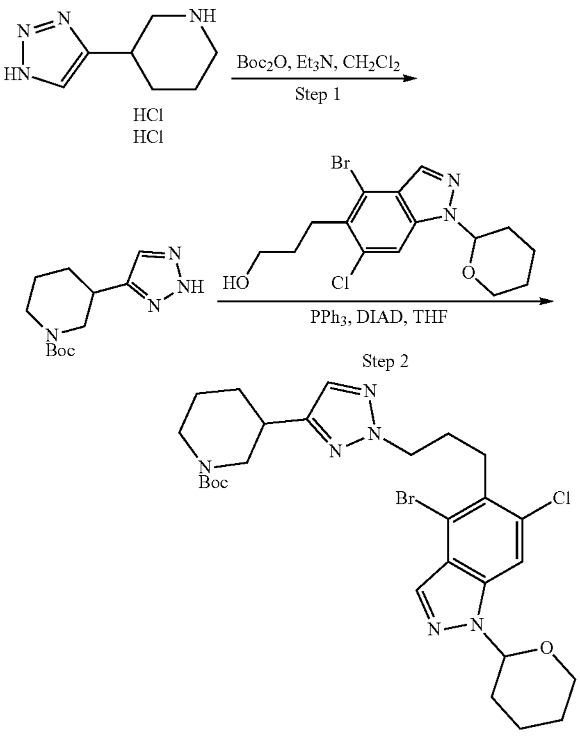

Intermediate IIII

Step 1. tert-Butyl 3-(1H-1,2,3-triazol-4-yl)piperidine-1-carboxylate. To a stirred solution of 3-(1H-1,2,3-triazol-4-yl)piperidine dihydrochloride (0.96 g, 4.26 mmol, Enamine) and triethylamine (3.0 mL, 21.3 mmol) in DCM (6 mL) at 0° C. was added a solution of di-tert-butyl dicarbonate (0.93 g, 4.26 mmol) in DCM (4 mL). The resulting mixture was stirred at 0° C. for 30 min and at rt for 48 h. The crude material was purified by column chromatography on silica gel, eluting with 0-55% (20% MeOH/DCM with 1% TEA)/DCM to give tert-butyl 3-(1H-1,2,3-triazol-4-yl)piperidine-1-carboxylate (1.16 g, 4.6 mmol, 100% yield) as colorless film. $^1$H NMR (CHLOROFORM-d, 400 MHz) δ 7.57 (s, 1H), 4.18 (br s, 1H), 3.92 (br s, 1H), 2.9-3.2 (m, 3H), 2.14 (br d, 1H, J=9.7 Hz), 1.7-1.8 (m, 2H), 1.5-1.6 (m, 1H), 1.47 (s, 9H). m/z (ESI): 275.0 $(M+Na)^+$.

Step 2. tert-Butyl 3-(2-(3-(4-bromo-6-chloro-1-(tetrahydro-2H-pyran-2-yl)-1H-indazol-5-yl)propyl)-2H-1,2,3-triazol-4-yl)piperidine-1-carboxylate. To a stirred ice-cooled solution of 3-(4-bromo-6-chloro-1-(tetrahydro-2H-pyran-2-yl)-1H-indazol-5-yl)propan-1-ol (0.49 g, 1.31 mmol, Intermediate FFF, Step 2), and tert-butyl 3-(1H-1,2,3-triazol-4-yl)piperidine-1-carboxylate (0.33 g, 1.31 mmol) in THF (7 mL) was added triphenylphosphine (0.45 mg, 1.71 mmol) in one portion, followed by (E)-diisopropyl diazene-1,2-dicarboxylate (0.35 g, 1.71 mmol) in THF (2 mL) slowly via a syringe under nitrogen atmosphere. The resulting mixture was stirred at 0° C. for 30 min and at rt for 1.5 h. The volatiles were removed and the crude residue was purified by column chromatography on silica gel, eluting with 5-40% EtOAc in heptane to give tert-butyl 3-(2-(3-(4-bromo-6-chloro-1-(tetrahydro-2H-pyran-2-yl)-1H-indazol-5-yl)propyl)-2H-1,2,3-triazol-4-yl)piperidine-1-carboxylate (0.55 g, 0.91 mmol, 69% yield) as white solid. $^1$H NMR (CHLOROFORM-d, 400 MHz) δ 7.94 (d, 1H, J=0.6 Hz), 7.63 (s, 1H), 7.42 (s, 1H), 5.64 (dd, 1H, J=2.7, 9.0 Hz), 4.51 (t, 2H, J=6.9 Hz), 4.1-4.3 (m, 1H), 3.99 (br d, 2H, J=11.7 Hz), 3.7-3.8 (m, 1H), 2.8-3.1 (m, 5H), 2.4-2.6 (m, 1H), 2.0-2.3 (m, 5H), 1.7-1.8 (m, 5H), 1.48 (s, 10H). m/z (ESI): 628.8/630.8 $(M+Na)^+$.

Intermediate JJJJ: tert-Butyl (Z)-3-(2-(3-(4-bromo-6-chloro-1-(tetrahydro-2H-pyran-2-yl)-1H-indazol-5-yl)allyl)-2H-1,2,3-triazol-4-yl)piperidine-1-carboxylate

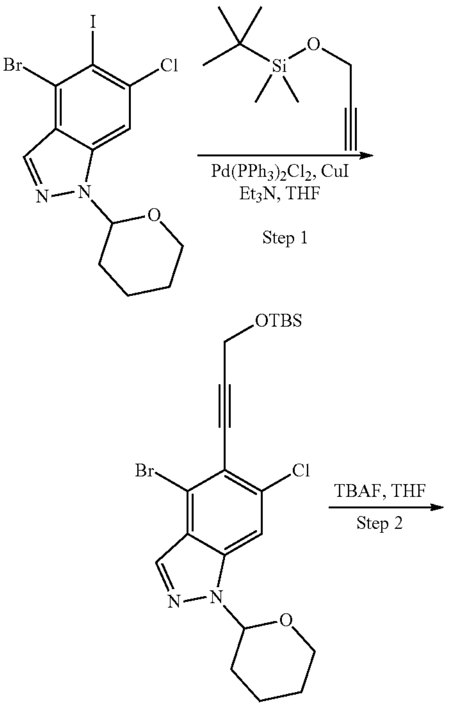

-continued

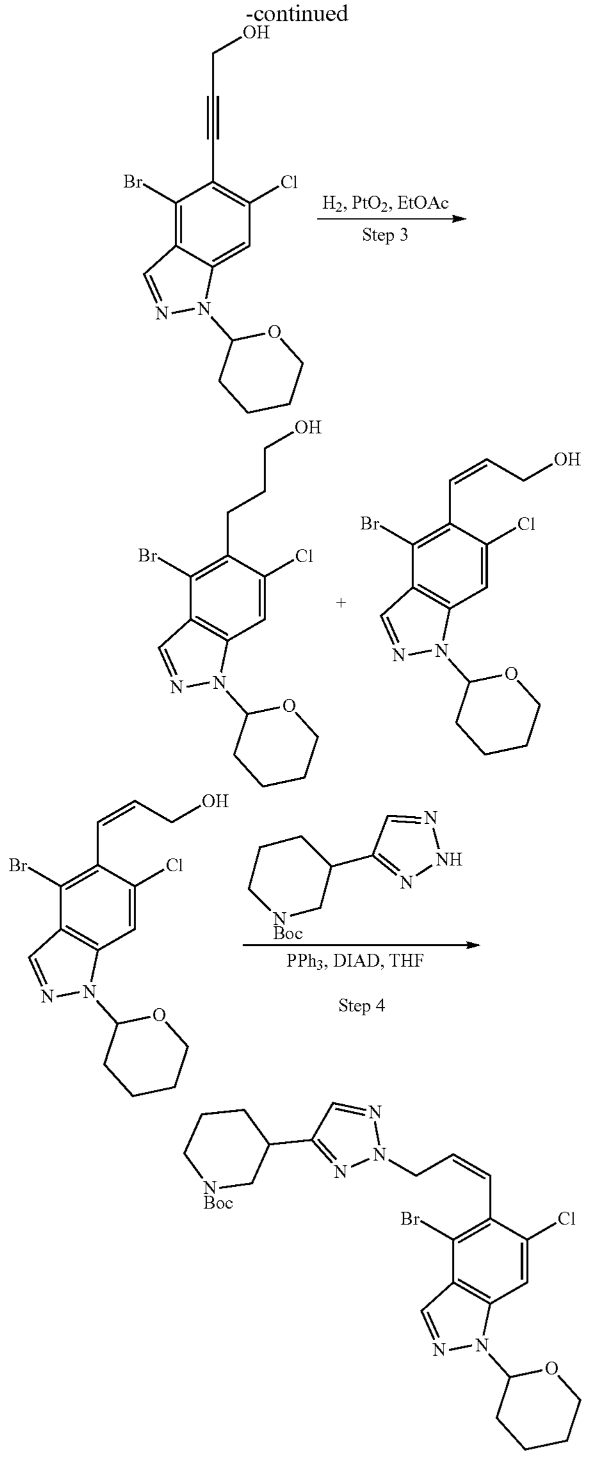

Intermediate JJJJ

Step 1. 4-Bromo-5-(3-((tert-butyldimethylsilyl)oxy)prop-1-yn-1-yl)-6-chloro-1-(tetrahydro-2H-pyran-2-yl)-1H-indazole. In a stirred solution of 4-bromo-6-chloro-5-iodo-1-(tetrahydro-2H-pyran-2-yl)-1H-indazole (5.00 g, 11.3 mmol, Lab Network), bis(triphenylphosphine)palladium(II) dichloride (0.60 g, 0.85 mmol), copper (I) iodide (0.16 g, 0.85 mmol), triethylamine (8.0 mL, 57 mmol) in THF (25 mL) was added propargyl alcohol (0.8 mL, 13.6 mmol) under nitrogen. The resulting mixture was stirred at rt for 2 h. tert-Butyldimethyl(2-propynyloxy)silane (2.8 mL, 13.6 mmol) was added, and the mixture was heated at 50° C. for 48 h. The volatiles were removed in vacuo and the crude residue was purified by column chromatography on silica gel, eluting with 0-100% EtOAc in heptane, to give 4-bromo-5-(3-((tert-butyldimethylsilyl)oxy)prop-1-yn-1-yl)-6-chloro-1-(tetrahydro-2H-pyran-2-yl)-1H-indazole (3.50 g, 7.20 mmol, 64% yield) as orange oil. m/z (ESI): 483.0/485.0 $(M+H)^+$.

Step 2. 3-(4-Bromo-6-chloro-1-(tetrahydro-2H-pyran-2-yl)-1H-indazol-5-yl)prop-2-yn-1-ol. To a stirred solution of 4-bromo-5-(3-((tert-butyldimethylsilyl)oxy)prop-1-yn-1-yl)-6-chloro-1-(tetrahydro-2H-pyran-2-yl)-1H-indazole (3.70 g, 7.65 mmol) in THF (30 mL) was added tetrabutylammonium fluoride solution (1 M in tetrahydrofuran, 22.9 mL, 22.9 mmol) slowly through a syringe. The resulting mixture was stirred at rt for 16 h. The volatiles were removed in vacuo and the crude residue was purified by column chromatography on silica gel, eluting with 0-90% 3:1 EtOAc/EtOH in heptane, to give 3-(4-bromo-6-chloro-1-(tetrahydro-2H-pyran-2-yl)-1H-indazol-5-yl)prop-2-yn-1-ol (1.37 g, 3.71 mmol, 49% yield) as colorless film. $^1$H NMR (CHLOROFORM-d, 400 MHz) δ 7.99 (d, 1H, J=0.6 Hz), 7.68 (d, 1H, J=0.8 Hz), 5.66 (dd, 1H, J=2.7, 8.8 Hz), 4.63 (s, 2H), 3.9-4.0 (m, 1H), 3.7-3.8 (m, 1H), 2.4-2.5 (m, 1H), 2.1-2.2 (m, 2H), 1.7-1.8 (m, 4H). m/z (ESI): 369.0/370.8 $(M+H)^+$.

Step 3. (Z)-3-(4-Bromo-6-chloro-1-(tetrahydro-2H-pyran-2-yl)-1H-indazol-5-yl)prop-2-en-1-ol. A mixture of 3-(4-bromo-6-chloro-1-(tetrahydro-2H-pyran-2-yl)-1H-indazol-5-yl)prop-2-yn-1-ol (1.38 g, 3.73 mmol) and platinum (IV) oxide (0.17 g, 0.75 mmol) in ethyl acetate (50 mL) was hydrogenated at 18 psi (initial pressure, ended at 15 psi) for 30 min. The solids were filtered off and the filtrate was concentrated in vacuo. The crude residue purified by column chromatography on silica gel, eluting with 0-3% MeOH in DCM, to give (Z)-3-(4-bromo-6-chloro-1-(tetrahydro-2H-pyran-2-yl)-1H-indazol-5-yl)prop-2-en-1-ol (0.95 g, 2.60 mmol, 69% yield) as off-white solid. m/z (ESI): 371.0/373.0 $(M+H)^+$.

Step 4. tert-Butyl (Z)-3-(2-(3-(4-bromo-6-chloro-1-(tetrahydro-2H-pyran-2-yl)-1H-indazol-5-yl)allyl)-2H-1,2,3-triazol-4-yl)piperidine-1-carboxylate. To a stirred ice-cooled solution of (Z)-3-(4-bromo-6-chloro-1-(tetrahydro-2H-pyran-2-yl)-1H-indazol-5-yl)prop-2-en-1-ol (0.36 g, 0.97 mmol) and tert-butyl 3-(2H-1,2,3-triazol-4-yl)piperidine-1-carboxylate (0.24 g, 0.97 mmol, from step 1 in Intermediate IIII) in THF (5 mL) was added triphenylphosphine (0.33 g, 1.26 mmol), followed by (E)-diisopropyl diazene-1,2-dicarboxylate (0.26 g, 1.26 mmol) slowly via a syringe under nitrogen atmosphere. The resulting mixture was stirred at 0° C. for 30 min and at rt for 1 h. The volatiles were removed in vacuo and the crude residue was purified by column chromatography on silica gel, eluting with 0-40% EtOAc in heptane, to give tert-butyl (Z)-3-(2-(3-(4-bromo-6-chloro-1-(tetrahydro-2H-pyran-2-yl)-1H-indazol-5-yl)allyl)-2H-1,2,3-triazol-4-yl)piperidine-1-carboxylate (0.36 g, 0.59 mmol, 61% yield) as white solid. $^1$H NMR (CHLOROFORM-d, 400 MHz) δ 8.00 (s, 1H), 7.71 (s, 1H), 7.35 (s, 1H), 6.59 (d, 1H, J=11.3 Hz), 6.27 (td, 1H, J=6.5, 11.3 Hz), 5.67 (dd, 1H, J=2.6, 8.9 Hz), 4.89 (dd, 2H, J=1.7, 6.5 Hz), 4.1-4.3 (m, 1H), 3.9-4.1 (m, 2H), 3.7-3.8 (m, 1H), 2.8-3.1 (m, 3H), 2.4-2.6 (m, 1H), 2.0-2.2 (m, 3H), 1.5-1.8 (m, 6H), 1.46 (s, 9H). m/z (ESI): 626.8/628.8 $(M+Na)^+$.

Intermediate KKKK: tert-Butyl (3S)-3-((4-(4-bromo-6-chloro-1-(tetrahydro-2H-pyran-2-yl)-1H-indazol-5-yl)butoxy)methyl)-3-fluoropiperidine-1-carboxylate

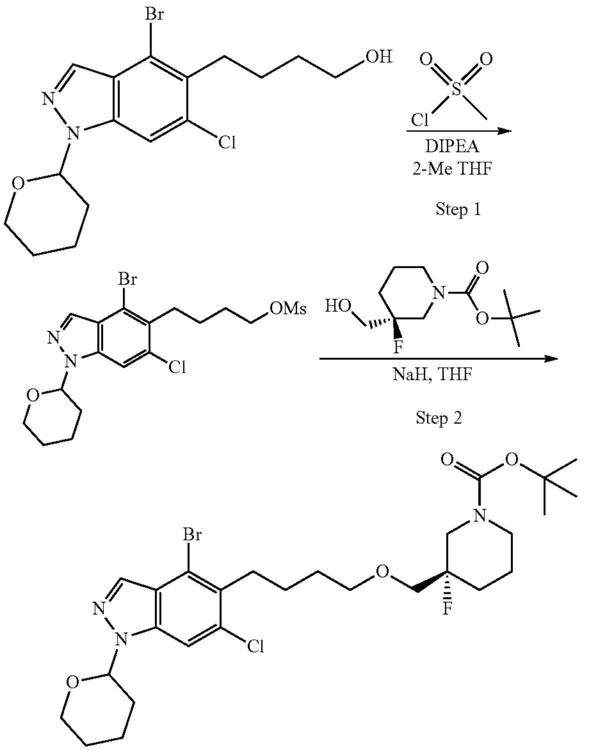

Intermediate KKKK

Step 1. 4-(4-Bromo-6-chloro-1-(tetrahydro-2H-pyran-2-yl)-1H-indazol-5-yl)butyl methanesulfonate. To a solution of 4-(4-bromo-6-chloro-1-(tetrahydro-2H-pyran-2-yl)-1H-indazol-5-yl)butan-1-ol (0.50 g, 1.30 mmol, Intermediate WWW) and DIEA (0.45 mL, 2.6 mmol) in 2-methyltetrahydrofuran (6.5 mL) was added methanesulfonyl chloride (0.17 mL, 2.1 mmol). The reaction mixture was stirred at rt for 1.5 h. The reaction mixture was partitioned between EtOAc and saturated aqueous sodium bicarbonate. The organic layer was separated, dried ($Na_2SO_4$) and concentrated. The crude product was purified by column chromatography on silica gel, eluting with 0-100% EtOAc in heptane, to provide 4-(4-bromo-6-chloro-1-(tetrahydro-2H-pyran-2-yl)-1H-indazol-5-yl)butyl methanesulfonate (0.63 g, 1.3 mmol, 100% yield) as colorless oil.

Step 2. tert-Butyl (3S)-3-((4-(4-bromo-6-chloro-1-(tetrahydro-2H-pyran-2-yl)-1H-indazol-5-yl)butoxy)methyl)-3-fluoropiperidine-1-carboxylate. To a 0° C. solution of tert-butyl (3S)-3-fluoro-3-(hydroxymethyl)piperidine-1-carboxylate (0.30 g, 1.29 mmol) in tetrahydrofuran (8.5 mL) was added sodium hydride, 60% dispersion in mineral oil (62 mg, 1.60 mmol). The reaction was stirred at 0° C. for 10 min, and then a solution of 4-(4-bromo-6-chloro-1-(tetrahydro-2H-pyran-2-yl)-1H-indazol-5-yl)butyl methanesulfonate (0.40 g, 0.86 mmol) in tetrahydrofuran (2 mL) was added. The reaction was stirred at 60° C. for 6 h. The reaction was quenched with saturated aqueous ammonium chloride and extracted with ethyl acetate. The organic layer was concentrated and the crude product was purified by column chromatography on silica gel, eluting with 0-100% EtOAc in heptane, to provide tert-butyl (3S)-3-((4-(4-bromo-6-chloro-1-(tetrahydro-2H-pyran-2-yl)-1H-indazol-5-yl)butoxy)methyl)-3-fluoropiperidine-1-carboxylate (0.32 g, 0.52 mmol, 61% yield) as colorless oil. m/z (ESI): 623.8/625.8 $(M+Na)^+$.

Intermediate LLLL: rac-((1R,2S)-2-(4-Bromo-6-methyl-1-(tetrahydro-2H-pyran-2-yl)-1H-indazol-5-yl)cyclopropyl) methanol

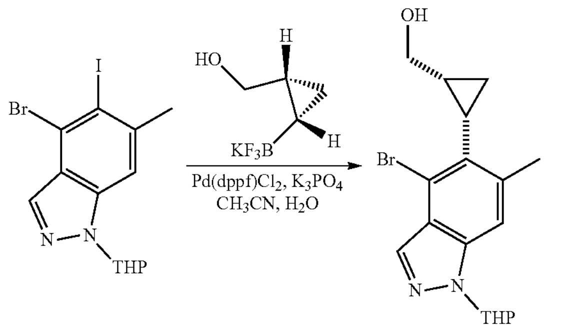

Intermediate LLLL

To a solution of 4-bromo-5-iodo-6-methyl-1-(tetrahydro-2H-pyran-2-yl)-1H-indazole (45 g, 107 mmol, Advanced ChemBlocks) in acetonitrile (1 L) and water (250 mL) was added potassium trifluoro ((1S,2R)-2-(hydroxymethyl)cyclopropyl) borate (38.0 g, 214 mmol, Lab Network), $K_3PO_4$ (113 g, 534 mmol) and $Pd(dppf)Cl_2$ (15.64 g, 21.37 mmol) in sequence under nitrogen. Then the mixture was stirred at 80° C. for 12 h. After cooling to rt, the reaction mixture was diluted with water and extracted with EtOAc. The combined organic layers were dried over $Na_2SO_4$, filtered and the filtrate was concentrated under reduced pressure. The residue was purified by column chromatography on silica gel, eluting with 10-35% EtOAc in petroleum ether, to give rac-((1R,2S)-2-(4-bromo-6-methyl-1-(tetrahydro-2H-pyran-2-yl)-1H-indazol-5-yl)cyclopropyl) methanol (12.9 g, 35.6 mmol, 33% yield) as yellow solid. m/z (ESI): 365.0/367.0 $(M+H)^+$.

Intermediate MMMM: tert-Butyl (3S)-3-(2-(((1R,2S)-2-(4-bromo-6-methyl-1-(tetrahydro-2H-pyran-2-yl)-1H-indazol-5-yl)cyclopropyl)methoxy)ethyl) piperidine-1-carboxylate

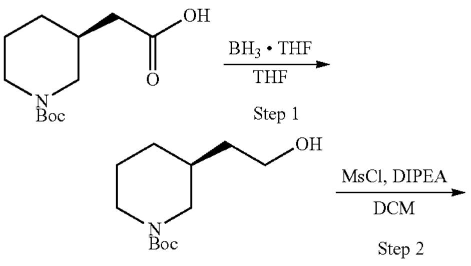

-continued

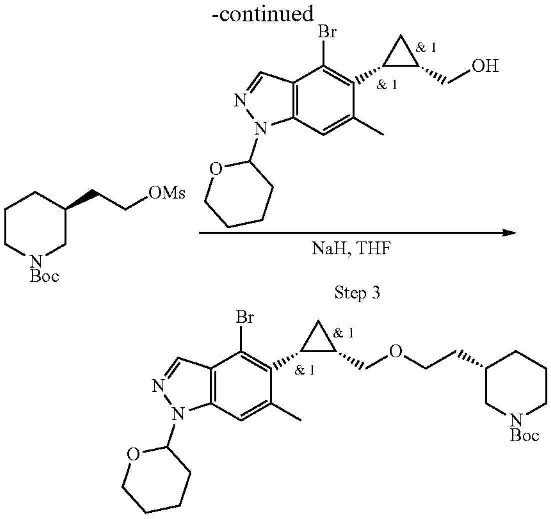

Intermediate MMMM

Step 1. tert-Butyl (S)-3-(2-hydroxyethyl)piperidine-1-carboxylate. In a 250-mL round-bottom flask under nitrogen was charged with (S)-2-(1-(tert-butoxycarbonyl)piperidin-3-yl)acetic acid (2.00 g, 8.22 mmol) in tetrahydrofuran (16 mL). At 0° C., (tetrahydro-1H-furan-1-ium-1-yl)trihydroborate (1 M in THF, 16.5 mL, 16.5 mmol) was added slowly. The reaction was stirred at 0° C. and slowly allowed to reach rt for 18 h. MeOH was slowly added and stirring continued for 2 h. The solvent was removed under reduced pressure and the residue was purified by column chromatography on silica gel, eluting with a gradient of 0-100% (3:1 EtOAc/EtOH, with 2% $Et_3N$) in heptane, to provide tert-butyl (S)-3-(2-hydroxyethyl)piperidine-1-carboxylate (1.89 g, 8.22 mmol, 100% yield) as colorless oil. m/z (ESI, +ve ion): 130.3 $(M+H-Boc)^+$.

Step 2. tert-Butyl (S)-3-(2-((methylsulfonyl)oxy)ethyl)piperidine-1-carboxylate. To a vial was added tert-butyl (S)-3-(2-hydroxyethyl)piperidine-1-carboxylate (0.30 g, 1.31 mmol) and DIPEA (0.29 mL, 1.7 mmol) in dichloromethane (3 mL). Methanesulfonyl chloride (0.11 mL, 1.4 mmol) was added slowly at 0° C. and the resulting mixture was allowed to stir at rt for 1 h. The reaction mixture was diluted with water and extracted with DCM. The organic layer was dried over $Na_2SO_4$, filtered, and concentrated under reduced pressure. The crude residue was purified by column chromatography on silica gel, eluting with a gradient of 0-100% (3:1 EtOAc/EtOH, with 2% $Et_3N$) in heptane, to give tert-butyl (S)-3-(2-((methylsulfonyl)oxy)ethyl)piperidine-1-carboxylate (0.40 g, 1.31 mmol, 100% yield) as colorless oil. m/z (ESI, +ve ion): 208.2 $(M+H-Boc)^+$.

Step 3. tert-Butyl (3S)-3-(2-(((1R,2S)-2-(4-bromo-6-methyl-1-(tetrahydro-2H-pyran-2-yl)-1H-indazol-5-yl)cyclopropyl)methoxy)ethyl)piperidine-1-carboxylate. To a vial was charged with rac-((1R,2S)-2-(4-bromo-6-methyl-1-(tetrahydro-2H-pyran-2-yl)-1H-indazol-5-yl)cyclopropyl) methanol (0.43 g, 1.19 mmol, Intermediate LLLL) in tetrahydrofuran (3.0 mL). Sodium hydride, 60% dispersion in mineral oil (56 mg, 1.40 mmol) was added and the reaction mixture was stirred at rt for 15 min. To it was added tert-butyl (S)-3-(2-((methylsulfonyl)oxy)ethyl)piperidine-1-carboxylate (0.33 g, 1.08 mmol) as a solution in tetrahydrofuran (0.5 mL). The reaction was then stirred at 50° C. for 16 h. After cooling to rt, the reaction mixture was quenched with saturated $NH_4Cl$ and extracted with EtOAc. The combined organic layers were dried over $Na_2SO_4$, filtered, and concentrated under reduced pressure. The crude residue was purified by column chromatography on silica gel, eluting with a gradient of 0-100% (3:1 EtOAc/EtOH, with 2% $Et_3N$) in heptane, to afford tert-butyl (3S)-3-(2-(((1R,2S)-2-(4-bromo-6-methyl-1-(tetrahydro-2H-pyran-2-yl)-1H-indazol-5-yl)cyclopropyl)methoxy)ethyl)piperidine-1-carboxylate (0.37 g, 0.64 mmol, 59% yield). m/z (ESI, +ve ion): 576.0 $(M+H)^+$.

Intermediate NNNN: rac-tert-Butyl 3-(1-(3-(6-methyl-1-(tetrahydro-2H-pyran-2-yl)-4-(4,4,5,5-tetramethyl-1,3,2-dioxaborolan-2-yl)-1H-indazol-5-yl)propyl)-1H-pyrazol-3-yl)piperidine-1-carboxylate

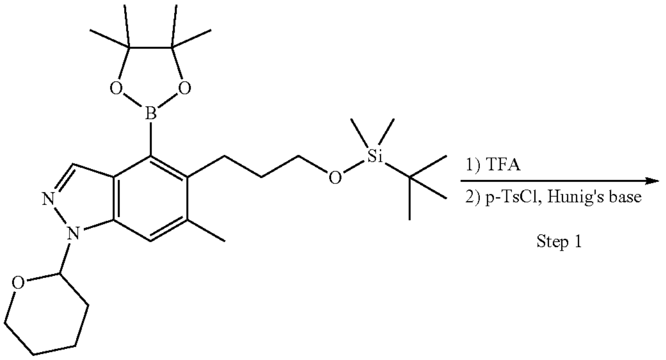

Intermediate K

-continued

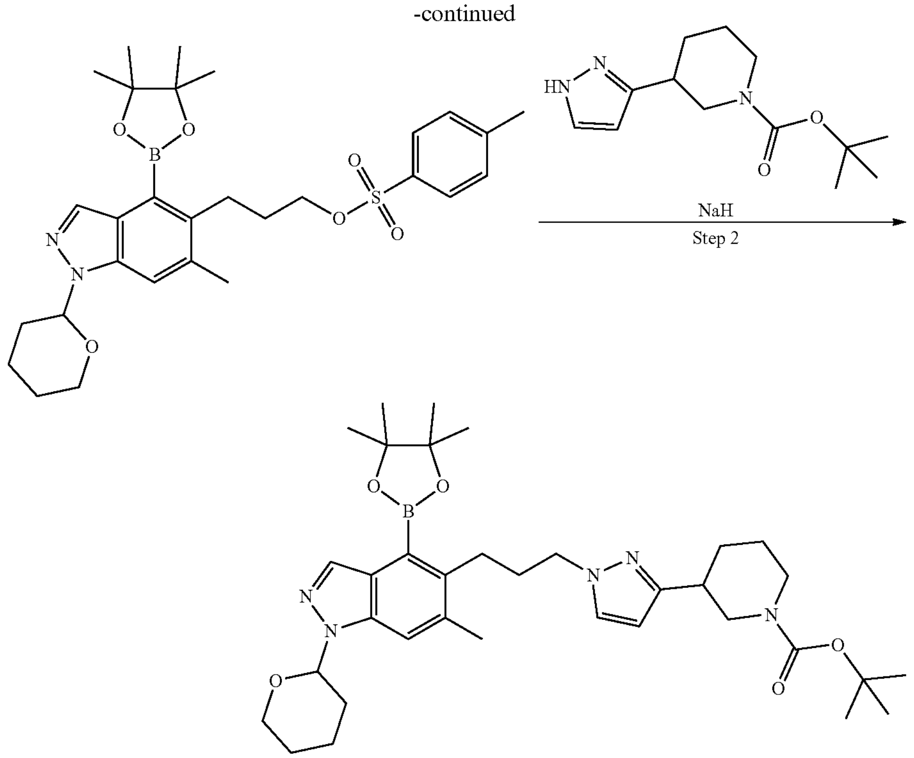

Intermediate NNNN

Step 1. 3-(6-Methyl-1-(tetrahydro-2H-pyran-2-yl)-4-(4,4,5,5-tetramethyl-1,3,2-dioxaborolan-2-yl)-1H-indazol-5-yl)propyl 4-methylbenzenesulfonate. To a 250-mL round-bottom flask was added 5-(3-((tert-butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole (Intermediate K, 0.97 g, 1.9 mmol) in 2,2,2-trifluoroacetic acid (0.1% in acetonitrile, 90 mL, 0.79 mmol). Water (10 mL) was added, and reaction mixture was stirred at rt for 1 h, then quenched with saturated aqueous $NaHCO_3$ and brine. The mixture was extracted with EtOAc, and the organics were dried over $Na_2SO_4$, concentrated. The residue was dissolved in dichloromethane (20 mL), and triethylamine (1.1 mL, 7.5 mmol), 4-methylbenzenesulfonyl chloride (1.08 g, 5.65 mmol) and N,N-dimethylpyridin-4-amine (46 mg, 0.38 mmol) was added sequentially. The resulting mixture was stirred at rt for 20 h. The reaction mixture was then quenched with water and the aqueous layer was extracted with $CH_2Cl_2$. The combined organic layers were dried over $Na_2SO_4$ and concentrated. The crude material was purified by column chromatography on silica gel, eluting with 0-60% EtOAc in heptane to provide 3-(6-methyl-1-(tetrahydro-2H-pyran-2-yl)-4-(4,4,5,5-tetramethyl-1,3,2-dioxaborolan-2-yl)-1H-indazol-5-yl)propyl 4-methylbenzenesulfonate (0.66 g, 1.20 mmol, 63% yield) as orange oil. m/z (ESI): 555.0 $(M+H)^+$.

Step 2. rac-tert-butyl 3-(1-(3-(6-methyl-1-(tetrahydro-2H-pyran-2-yl)-4-(4,4,5,5-tetramethyl-1,3,2-dioxaborolan-2-yl)-1H-indazol-5-yl)propyl)-1H-pyrazol-3-yl)piperidine-1-carboxylate. To a 8-mL vial was added sodium hydride, 60% dispersion in mineral oil (54 mg, 1.40 mmol). Under nitrogen atmosphere, tetrahydrofuran (1.5 mL) was added, followed by the addition of rac-tert-butyl 3-(1H-pyrazol-3-yl)piperidine-1-carboxylate (0.18 g, 0.72 mmol, Enamine) in tetrahydrofuran (1.5 mL) at 0° C. The mixture was stirred at 0° C. for 5 min, then 3-(6-methyl-1-(tetrahydro-2H-pyran-2-yl)-4-(4,4,5,5-tetramethyl-1,3,2-dioxaborolan-2-yl)-1H-indazol-5-yl)propyl 4-methylbenzenesulfonate (0.37 g, 0.67 mmol) in tetrahydrofuran (1.5 mL) was added at 0° C. The mixture was stirred at rt under $N_2$ atmosphere for 22 h. The mixture was quenched with sequential addition of MeOH and saturated $NH_4Cl$ solution. The mixture was fully concentrated and the residue was purified by column chromatography on silica gel, eluting with 0-60% EtOAc in heptane, to afford rac-tert-butyl 3-(1-(3-(6-methyl-1-(tetrahydro-2H-pyran-2-yl)-4-(4,4,5,5-tetramethyl-1,3,2-dioxaborolan-2-yl)-1H-indazol-5-yl)propyl)-1H-pyrazol-3-yl)piperidine-1-carboxylate (0.31 g, 0.48 mmol, 72% yield) as colorless oil. m/z (ESI): 634.2 $(M+H)^+$.

Intermediate OOOO and PPPP: tert-Butyl (3R)-3-((4-((Z)-2-(6-chloro-1-(tetrahydro-2H-pyran-2-yl)-4-(4,4,5,5-tetramethyl-1,3,2-dioxaborolan-2-yl)-1H-indazol-5-yl)vinyl)-2H-1,2,3-triazol-2-yl)methyl)piperidine-1-carboxylate and tert-butyl (3R)-3-((4-(2-(6-chloro-1-(tetrahydro-2H-pyran-2-yl)-4-(4,4,5,5-tetramethyl-1,3,2-dioxaborolan-2-yl)-1H-indazol-5-yl)ethyl)-2H-1,2,3-triazol-2-yl)methyl)piperidine-1-carboxylate

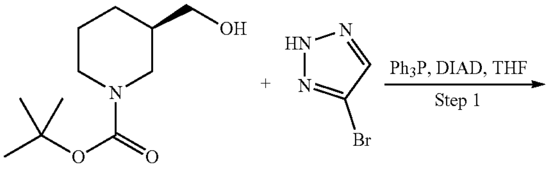

-continued

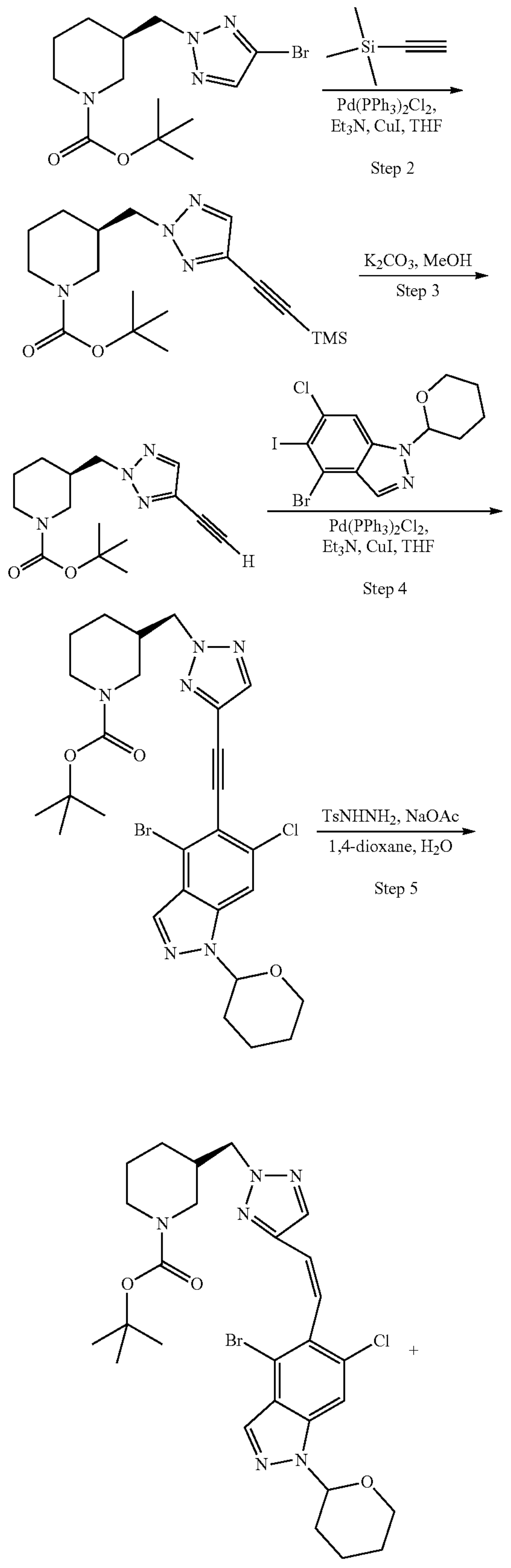

-continued

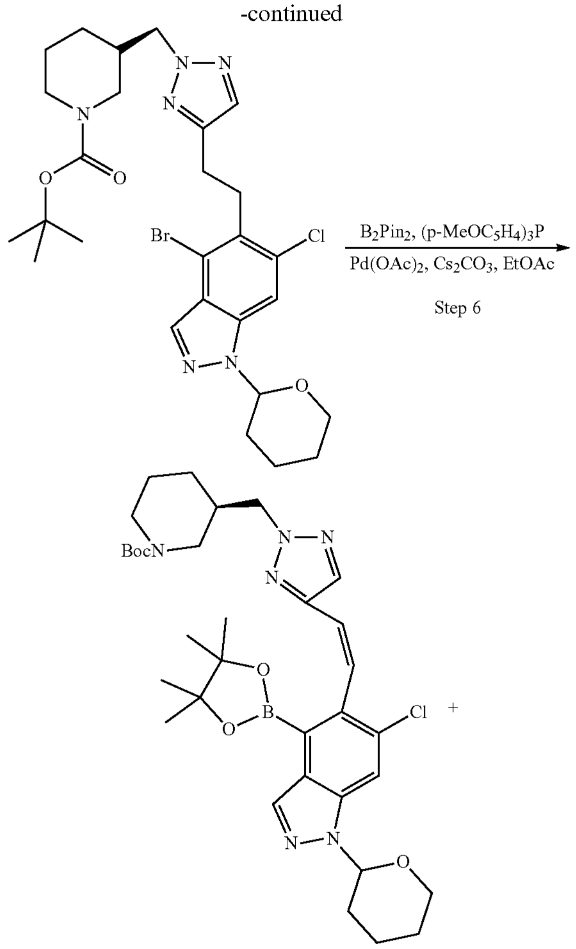

Intermediate OOOO

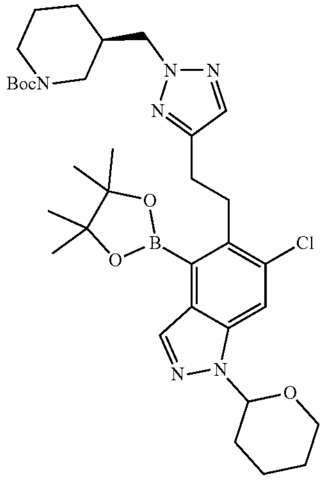

Intermediate PPPP

Step 1. tert-Butyl (R)-3-((4-bromo-2H-1,2,3-triazol-2-yl)methyl)piperidine-1-carboxylate. To a 40-mL vial was added (E)-diisopropyl diazene-1,2-dicarboxylate (1.23 g, 6.10 mmol) in tetrahydrofuran (11 mL). Triphenylphosphine (1.59 g, 6.06 mmol), (R)-tert-butyl 3-(hydroxymethyl)piperidine-1-carboxylate (1.19 g, 5.51 mmol, Ambeed, Inc.) and 4-bromo-2H-1,2,3-triazole (0.82 g, 5.51 mmol, Ambeed, Inc.) was added sequentially. The reaction mixture was stirred at rt for 3 h. The mixture was concentrated and purified by column chromatography on silica gel, eluting with 0-40% EtOAc in heptane, to provide tert-butyl (R)-3-((4-bromo-2H-1,2,3-triazol-2-yl)methyl)piperidine-1-carboxylate (1.45 g, 4.20 mmol, 76% yield) as colorless oil. m/z (ESI): 366.7 $(M+Na)^+$ Step 2. tert-Butyl (R)-3-((4-((trimethylsilyl)ethynyl)-2H-1,2,3-triazol-2-yl)methyl)piperidine-1-carboxylate. To a 20-mL microwave vial was added tert-butyl (R)-3-((4-bromo-2H-1,2,3-triazol-2-yl)methyl)piperidine-1-carboxylate (1.45 g, 4.20 mmol), bis(triphenylphosphine)palladium (II) dichloride (0.22 g, 0.32 mmol), and copper(I) iodide (60 mg, 0.32 mmol) in toluene (8.5 mL). The resulting mixture was purged with nitrogen for 5 min, then triethylamine (3.0 mL, 21 mmol) was added, followed by (trimethylsilyl) acetylene (0.9 mL, 6.3 mmol). The mixture was irradiated in a microwave at 85° C. for 4 h. After cooling to rt, the mixture was concentrated and the crude material was purified by column chromatography on silica gel, eluting with 0-40% EtOAc in hexane, to provide tert-butyl (R)-3-((4-((trimethylsilyl)ethynyl)-2H-1,2,3-triazol-2-yl)methyl)piperidine-1-carboxylate (1.50 g, 4.20 mmol, 100% yield) as yellow oil. m/z (ESI): 384.9 $(M+Na)^+$.

Step 3. tert-Butyl (R)-3-((4-ethynyl-2H-1,2,3-triazol-2-yl)methyl)piperidine-1-carboxylate. A mixture of tert-butyl (R)-3-((4-((trimethylsilyl)ethynyl)-2H-1,2,3-triazol-2-yl) methyl)piperidine-1-carboxylate (1.50 g, 4.20 mmol) and potassium carbonate (2.90 g, 21 mmol) in methanol (23 mL) was stirred under nitrogen at rt for 1 h. The precipitate was filtered off and the filtrate was concentration in vacuo. The residue was purified by column chromatography on silica gel, eluting with 0-50% EtOAc in heptane, to provide tert-butyl (R)-3-((4-ethynyl-2H-1,2,3-triazol-2-yl)methyl) piperidine-1-carboxylate (1.20 g, 3.5 mmol, 84% yield) as colorless oil. m/z (ESI): 313.0 $(M+Na)^+$.

Step 4. tert-Butyl (3S)-3-((4-((4-bromo-6-chloro-1-(tetrahydro-2H-pyran-2-yl)-1H-indazol-5-yl)ethynyl)-2H-1,2,3-triazol-2-yl)methyl)piperidine-1-carboxylate. To a 40-mL microwave vial was added 4-bromo-6-chloro-5-iodo-1-(tetrahydro-2H-pyran-2-yl)-1H-indazole (1.44 g, 3.27 mmol, Lab Network), tert-butyl (R)-3-((4-ethynyl-2H-1,2,3-triazol-2-yl)methyl)piperidine-1-carboxylate (0.95 g, 3.3 mmol), and copper(I) iodide (47 mg, 0.25 mmol). THF (6.5 mL) was added under nitrogen, followed by the addition of triethylamine (2.3 mL, 16 mmol). The resulting mixture was purged with nitrogen for 10 min and irradiated in microwave at 65° C. for 15 h. After cooling to rt, the mixture was concentrated and purified by column chromatography on silica gel, eluting with 0-70% EtOAc in DCM, to provide tert-butyl (3S)-3-((4-((4-bromo-6-chloro-1-(tetrahydro-2H-pyran-2-yl)-1H-indazol-5-yl)ethynyl)-2H-1,2,3-triazol-2-yl)methyl)piperidine-1-carboxylate (0.88 g, 1.50 mmol, 45% yield) as colorless oil. m/z (ESI): 546.5 $(M-{}^tBu+H)^+$.

Step 5. tert-Butyl (3S)-3-((4-((Z)-2-(4-bromo-6-chloro-1-(tetrahydro-2H-pyran-2-yl)-1H-indazol-5-yl)vinyl)-2H-1,2,3-triazol-2-yl)methyl)piperidine-1-carboxylate and tert-butyl (3S)-3-((4-(2-(4-bromo-6-chloro-1-(tetrahydro-2H-pyran-2-yl)-1H-indazol-5-yl)ethyl)-2H-1,2,3-triazol-2-yl) methyl)piperidine-1-carboxylate. To a 40-mL vial was added tert-butyl (3S)-3-((4-((4-bromo-6-chloro-1-(tetrahydro-2H-pyran-2-yl)-1H-indazol-5-yl)ethynyl)-2H-1,2,3-triazol-2-yl)methyl)piperidine-1-carboxylate (0.47 g, 0.78 mmol) in 1,4-dioxane (8 mL), p-toluenesulfonyl hydrazide (2.90 g, 15.6 mmol) was added and the mixture was degassed with nitrogen for 10 min. The mixture was stirred at 85° C., then sodium acetate (1.28 g, 15.6 mmol) in water (8 mL) was added via a syringe pump over 8 h. The reaction mixture was stirred at 85° C. for another 7 h. After cooling to rt, the mixture was diluted with saturated NaCl solution and extracted with EtOAc. The organic layers were combined, dried over $Na_2SO_4$, filtered, and concentrated. The residue was purified by column chromatography on silica gel, eluting with 0-40% EtOAc in heptane, to provide a 9:1 mixture of tert-butyl (3S)-3-((4-((Z)-2-(4-bromo-6-chloro-1-(tetrahydro-2H-pyran-2-yl)-1H-indazol-5-yl)vinyl)-2H-1,2,3-triazol-2-yl)methyl)piperidine-1-carboxylate and tert-butyl (3S)-3-((4-(2-(4-bromo-6-chloro-1-(tetrahydro-2H-pyran-2-yl)-1H-indazol-5-yl)ethyl)-2H-1,2,3-triazol-2-yl) methyl)piperidine-1-carboxylate (0.47 g, 0.78 mmol, 100% yield) as colorless oil. m/z (ESI): 626.7, 628.7 $(M+Na)^+$. $^1$H NMR (400 MHz, CHLOROFORM-d) δ ppm 1.40-1.47 (m, 12H) 1.65 (br d, J=11.82 Hz, 3H) 1.80 (br s, 2H) 2.30 (s, 4H) 2.88 (s, 2H) 3.80 (br s, 3H) 4.23 (t, J=6.32 Hz, 2H) 5.69-5.73 (m, 1H) 6.63 (d, J=11.61 Hz, 1H) 6.93 (d, J=11.60 Hz, 1H) 7.76 (s, 1H) 8.02 (s, 1H).

Step 6. tert-Butyl (3R)-3-((4-((Z)-2-(6-chloro-1-(tetrahydro-2H-pyran-2-yl)-4-(4,4,5,5-tetramethyl-1,3,2-dioxaborolan-2-yl)-1H-indazol-5-yl)vinyl)-2H-1,2,3-triazol-2-yl) methyl)piperidine-1-carboxylate and tert-butyl (3R)-3-((4-(2-(6-chloro-1-(tetrahydro-2H-pyran-2-yl)-4-(4,4,5,5-tetramethyl-1,3,2-dioxaborolan-2-yl)-1H-indazol-5-yl) ethyl)-2H-1,2,3-triazol-2-yl)methyl)piperidine-1-carboxylate. A vial was charged with tris(4-methoxyphenyl) phosphine (27 mg, 0.078 mmol), palladium acetate (8.7 mg, 0.039 mmol), 4,4,4',4',5,5,5',5'-octamethyl-2,2'-bi(1,3,2-dioxaborolane) (0.24 g, 0.93 mmol), cesium carbonate (0.38 g, 1.16 mmol), and a 9:1 mixture of tert-butyl (3S)-3-((4-((Z)-2-(4-bromo-6-chloro-1-(tetrahydro-2H-pyran-2-yl)-1H-indazol-5-yl)vinyl)-2H-1,2,3-triazol-2-yl)methyl)piperidine-1-carboxylate and tert-butyl (3S)-3-((4-(2-(4-bromo-6-chloro-1-(tetrahydro-2H-pyran-2-yl)-1H-indazol-5-yl) ethyl)-2H-1,2,3-triazol-2-yl)methyl)piperidine-1-carboxylate (0.47 g, 0.78 mmol) and ethyl acetate (1.5 mL). The reaction mixture was sparged with $N_2$ and heated to 80° C. for 2.5 h. After cooling to rt, the mixture was filtered, and the residue was concentrated. The residue purified by column chromatography on silica gel, eluting with 0-40% EtOAc in DCM, to provide a 9:1 mixture of tert-butyl (3R)-3-((4-((Z)-2-(6-chloro-1-(tetrahydro-2H-pyran-2-yl)-4-(4,4,5,5-tetramethyl-1,3,2-dioxaborolan-2-yl)-1H-indazol-5-yl)vinyl)-2H-1,2,3-triazol-2-yl)methyl)piperidine-1-carboxylate (Intermediate OOOO) and tert-butyl (3R)-3-((4-(2-(6-chloro-1-(tetrahydro-2H-pyran-2-yl)-4-(4,4,5,5-tetramethyl-1,3,2-dioxaborolan-2-yl)-1H-indazol-5-yl) ethyl)-2H-1,2,3-triazol-2-yl)methyl)piperidine-1-carboxylate (Intermediate PPPP) (0.28 g, 0.43 mmol, 55% yield) as white foam. m/z (ESI): 652.7/654.7 $(M+H)^+$.

Intermediate QQQQ: tert-Butyl (3R)-3-(2-(3-(6-chloro-1-(tetrahydro-2H-pyran-2-yl)-4-(4,4,5,5-tetramethyl-1,3,2-dioxaborolan-2-yl)-1H-indazol-5-yl) propyl)oxazol-4-yl)piperidine-1-carboxylate

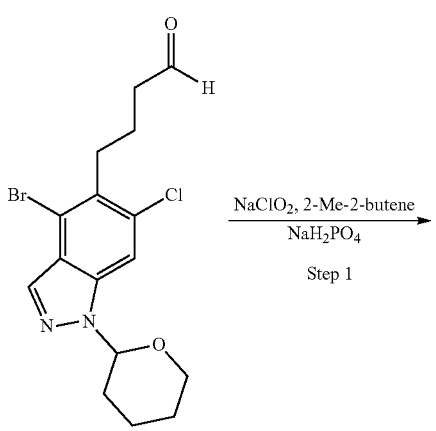

-continued

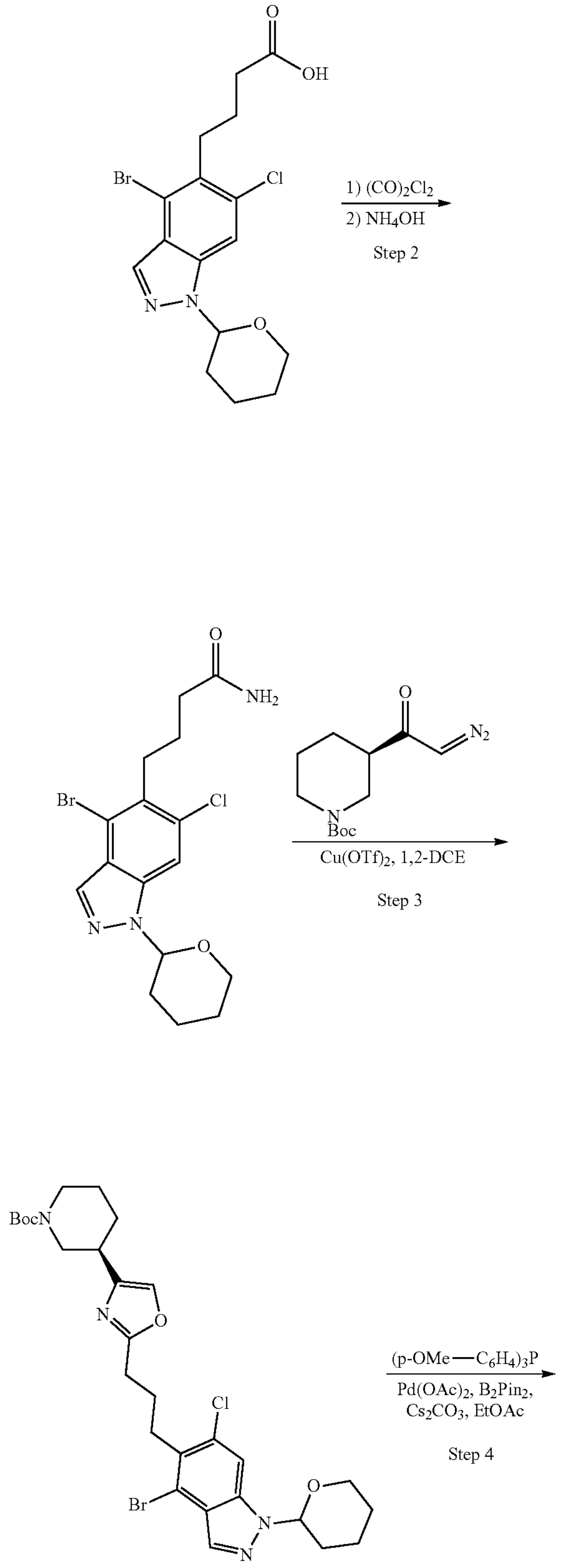

-continued

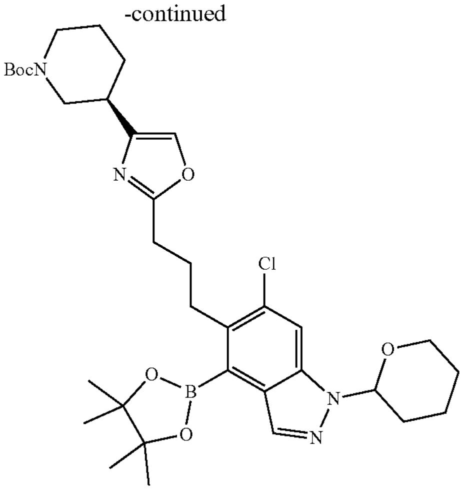

Intermediate QQQQ

Step 1. 4-(4-Bromo-6-chloro-1-(tetrahydro-2H-pyran-2-yl)-1H-indazol-5-yl)butanoic acid. To a 40 mL vial was charged 4-(4-bromo-6-chloro-1-(tetrahydro-2H-pyran-2-yl)-1H-indazol-5-yl)butanal (0.61 g, 1.60 mmol, Intermediate WWW, Step 1) in THF and tert-butanol (9 mL). To this was added 2-methyl-2-butene (0.18 mL, 1.6 mmol), and sodium chlorite (0.60 g, 6.60 mmol) and sodium phosphate monobasic, anhydrous (0.19 g, 1.60 mmol) in water (18 mL) at 0° C. The reaction mixture was allowed to warm to rt with stirring for 1 h. The reaction mixture was concentrated and taken up in MeOH, and was directly injected onto a C18 column, eluting with 5-100% acetonitrile+0.1% formic acid/(water+0.1% formic acid), to give 4-(4-bromo-6-chloro-1-(tetrahydro-2H-pyran-2-yl)-1H-indazol-5-yl)butanoic acid (0.38 g, 0.95 mmol, 60% yield) as white solid. m/z (ESI): 401.8 $(M+H)^+$.

Step 2. 4-(4-Bromo-6-chloro-1-(tetrahydro-2H-pyran-2-yl)-1H-indazol-5-yl)butanamide. To a 40 mL vial was charged 4-(4-bromo-6-chloro-1-(tetrahydro-2H-pyran-2-yl)-1H-indazol-5-yl)butanoic acid (1.57 g, 3.91 mmol), to this was added dichloromethane (20 mL), N,N-dimethylformamide (0.03 mL, 0.39 mmol), and oxalyl chloride (2.3 mL, 4.7 mmol) dropwise. The reaction mixture was stirred at rt for 1.5 h. A aqueous ammonium hydroxide solution (7.4 mL, 59 mmol) was added dropwise. The reaction mixture was stirred for 2.5 h and was concentrated. The residue was purified by reverse phase column chromatography using a C18 column, eluting with 5-100% acetonitrile+0.1% formic acid/(water+0.1% formic acid), to give 4-(4-bromo-6-chloro-1-(tetrahydro-2H-pyran-2-yl)-1H-indazol-5-yl)butanamide (0.40 g, 1.00 mmol, 26% yield). m/z (ESI): 423.9 $(M+Na)^+$.

Step 3. tert-Butyl (3R)-3-(2-(3-(4-bromo-6-chloro-1-(tetrahydro-2H-pyran-2-yl)-1H-indazol-5-yl)propyl)oxazol-4-yl)piperidine-1-carboxylate. To a 20 mL vial was charged with 4-(4-bromo-6-chloro-1-(tetrahydro-2H-pyran-2-yl)-1H-indazol-5-yl)butanamide (0.26 g, 0.64 mmol), copper(II) trifluoromethanesulfonate (46 mg, 0.13 mmol), tert-butyl (3R)-3-(2-diazoacetyl)piperidine-1-carboxylate (0.19 g, 0.77 mmol, BenchChem), and 1,2-dichloroethane (6.5 mL). The reaction was placed on a preheated 85° C. hot plate and stirred for 19 h. The reaction was repeated 4 times simultaneously and all 5 reactions were combined, filtered, and concentrated. The crude oil was purified by column chromatography on silica gel, eluting with 0-80% 3:1 EtOAc/EtOH+2% triethylamine in heptane, followed by reverse phase column chromatography using a C18 column, eluting with 5-100% acetonitrile+0.1% formic acid in water+0.1% formic acid, to give tert-butyl (3R)-3-(2-(3-(4-bromo-6-chloro-1-(tetrahydro-2H-pyran-2-yl)-1H-indazol-5-yl)propyl)oxazol-4-yl)piperidine-1-carboxylate (98 mg, 0.16 mmol, 5% yield) as yellow solid. m/z (ESI): 607.9 $(M+H)^+$. $^1H$ NMR (400 MHz, CHLOROFORM-d) δ ppm 7.94-8.05 (m, 1H), 7.62-7.73 (m, 1H), 7.36-7.42 (m, 1H), 5.61-5.76 (m, 1H), 3.95-4.09 (m, 2H), 3.71-3.91 (m, 2H), 3.10-3.19 (m, 3H), 2.90-3.06 (m, 3H), 2.68-2.82 (m, 1H), 2.42-2.57 (m, 1H), 1.97-2.23 (m, 6H), 1.41-1.52 (m, 12H), 1.21-1.37 (m, 2H).

Step 4. tert-Butyl (3R)-3-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)piperidine-1-carboxylate. To a 20 mL vial was charged with tert-butyl (3R)-3-(2-(3-(4-bromo-6-chloro-1-(tetrahydro-2H-pyran-2-yl)-1H-indazol-5-yl)propyl)oxazol-4-yl)piperidine-1-carboxylate (96 mg, 0.16 mmol), 4,4,4',4',5,5,5',5'-octamethyl-2,2'-bi(1,3,2-dioxaborolane) (48 mg, 0.19 mmol,), tris(4-methoxyphenyl)phosphine (5.6 mg, 0.016 mmol), palladium acetate (1.8 mg, 7.90 μmol), cesium carbonate (77 mg, 0.24 mmol), and ethyl acetate (1.5 mL). The reaction mixture was sparged with nitrogen and then heated to 80° C. for 3.5 h. After cooling to rt, the reaction was diluted with ethyl acetate, filtered, and concentrated. The crude material was purified by column chromatography on silica gel, eluting with 0-70% EtOAc in heptane, to give tert-butyl (3R)-3-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)piperidine-1-carboxylate (44 mg, 0.067 mmol, 43% yield) as yellow solid. m/z (ESI): 655.0 $(M+H)^+$.

Intermediate RRRR: 4-Bromo-6-methyl-1-(tetrahydro-2H-pyran-2-yl)-1H-indazole-5-carbaldehyde

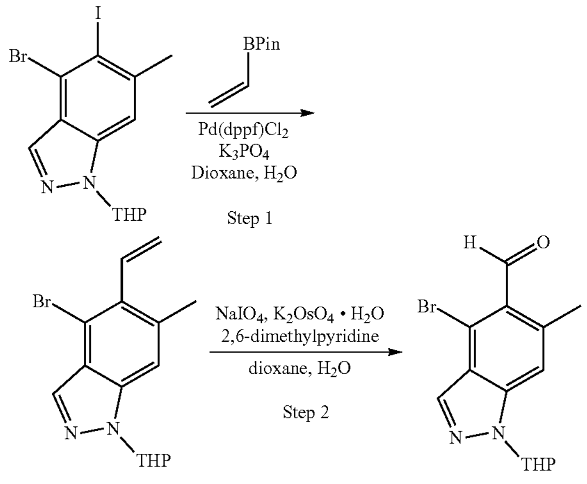

Intermediate RRRR

Step 1. 4-Bromo-6-methyl-1-(tetrahydro-2H-pyran-2-yl)-5-vinyl-1H-indazole. To a solution of 4-bromo-5-iodo-6-methyl-1-(tetrahydro-2H-pyran-2-yl)-1H-indazole (40 g, 95 mmol) in dioxane (1 L) and water (125 mL) was added 4,4,5,5-tetramethyl-2-vinyl-1,3,2-dioxaborolane (14.6 g, 95 mmol), $K_3PO_4$ (70.5 g, 332 mmol) and Pd(dppf)$Cl_2$ (6.95 g, 9.5 mmol) under $N_2$. The resulting mixture was stirred at 100° C. for 12 h under nitrogen. After cooling to rt, the reaction mixture was diluted with water and extracted with EtOAc. The combined organic layers were washed with brine, dried over $Na_2SO_4$, filtered, and concentrated. The residue was purified by column chromatography on silica gel, eluting with a gradient of 10-20% EtOAc in petroleum ether, to give 4-bromo-6-methyl-1-(tetrahydro-2H-pyran-2-yl)-5-vinyl-1H-indazole (20 g, 62 mmol, 65% yield) as yellow oil.

Step 2. 4-Bromo-6-methyl-1-(tetrahydro-2H-pyran-2-yl)-1H-indazole-5-carbaldehyde. To the mixture of 4-bromo-6-methyl-1-(tetrahydro-2H-pyran-2-yl)-5-vinyl-1H-indazole (30 g, 93 mmol), 2,6-dimethylpyridine (20.0 g, 187 mmol), $K_2OsO_4$ (3.74 g, 9.34 mmol) in 1,4-dioxane (830 mL) and water (200 mL) was added $NaIO_4$ (60.0 g, 280 mmol) in portions at rt. The reaction mixture was stirred at 50° C. for 4 h. After cooling to rt, the reaction mixture was diluted with water and extracted with EtOAc. The combined organic layers were washed with brine, dried over $Na_2SO_4$, filtered, and concentrated under reduced pressure. The residue was purified by column chromatography on silica gel, eluting with a gradient of 10-20% EtOAc in petroleum ether, to give 4-bromo-6-methyl-1-(tetrahydro-2H-pyran-2-yl)-1H-indazole-5-carbaldehyde (17 g, 53 mmol, 56% yield) as white solid. m/z (ESI): 322.9/325.0 $(M+H)^+$.

Intermediate SSSS: Methyl 5-(2-bromo-6-chlorophenyl)pentanoate

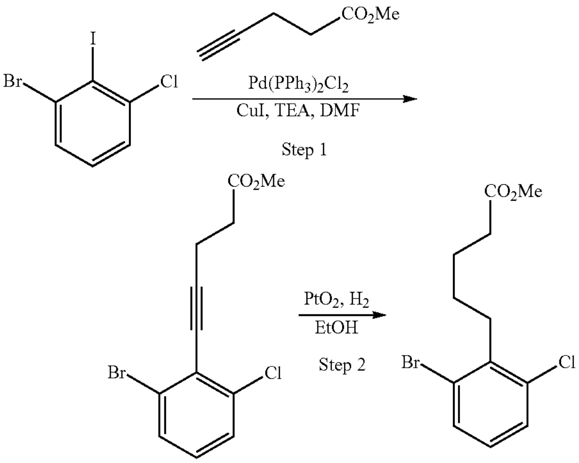

Intermediate SSSS

Step 1. Methyl 5-(2-bromo-6-chlorophenyl)pent-4-ynoate. A vial was charged with 1-bromo-3-chloro-2-iodobenzene (1.00 g, 3.15 mmol, Synthonix), methyl pent-4-ynoate (1.1 mL, 9.5 mmol, Ambeed, Inc.) and N,N-dimethylformamide (6.5 mL), then degassed with nitrogen for 15 min. Bis(triphenylphosphine)palladium(II) dichloride (111 mg, 0.16 mmol), triethylamine (4.4 mL, 31.5 mmol) and copper iodide (18 mg, 0.095 mmol) was added. The reaction mixture was stirred at rt for 90 h, then was diluted with water and extracted with DCM. The combined organic phases were washed with 0.5 N HCl, water, brine, dried over anhydrous sodium sulfate, filtered, and concentrated. The crude material was dissolved in DMSO (2 mL) and injected into a C18 column, eluting with a gradient of 5-100% (0.1% formic acid MeCN)/(0.1% formic acid water) over 20 min. The desired fractions were basified, extracted with EtOAc, and concentrated under reduced pressure to provide methyl 5-(2-bromo-6-chlorophenyl)pent-4-ynoate (626 mg, 2.08 mmol, 66% yield) as orange oil. m/z (ESI): 301.0/303.0 $(M+H)^+$.

Step 2. Methyl 5-(2-bromo-6-chlorophenyl)pentanoate. A 250-mL reactor tube was charged with methyl 5-(2-bromo-6-chlorophenyl)pent-4-ynoate (0.63 g, 2.07 mmol) and platinum(IV) oxide (47 mg, 0.21 mmol). The vessel was purged with nitrogen, then charged with ethanol (10 mL). The vessel was pressurized with hydrogen gas to 40 psi, sealed and stirred at rt for 16 h. The reaction was vented then filtered through a Celite plug. The filter cake was rinsed with EtOAc, and the organic phase was concentrated to provide methyl 5-(2-bromo-6-chlorophenyl)pentanoate (0.59 g, 1.93 mmol, 93% yield) as yellow oil. m/z (ESI): 644.8/646.8 $(M+Na)^+$.

Intermediate TTTT: 4-Benzyl-6-methyl-1,4-oxazepan-6-amine hydrochloride

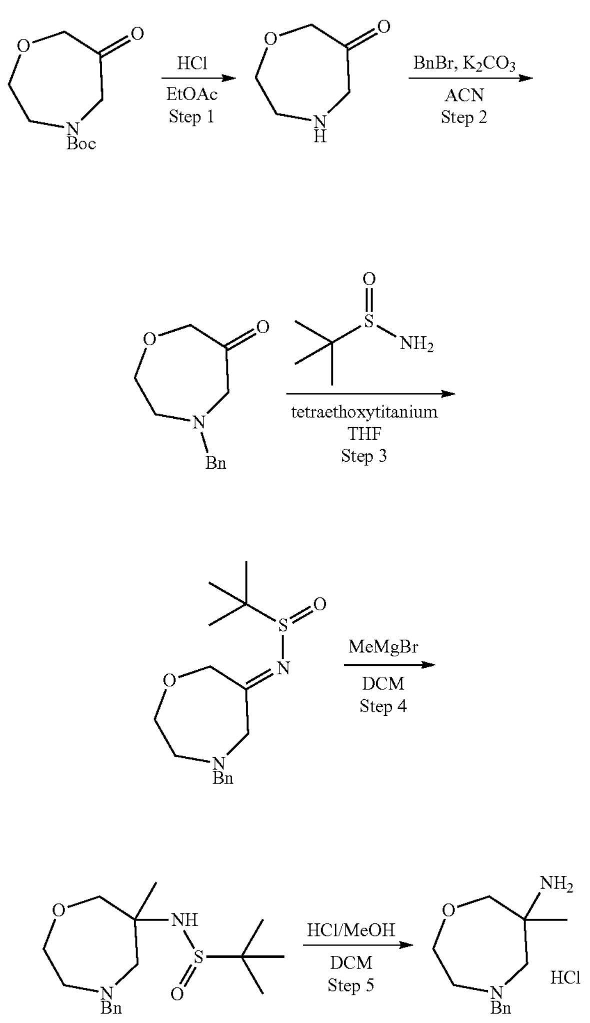

Intermediate TTTT

Step 1. 1,4-Oxazepan-6-one hydrochloride. A mixture of tert-butyl 6-oxo-1,4-oxazepane-4-carboxylate (6.50 g, 30.2 mmol) in HCl/EtOAc (4 M, 40 mL, 160 mmol) was degassed and purged with $N_2$. The mixture was stirred at rt for 1 h, then was concentrated under reduced pressure to give 1,4-oxazepan-6-one hydrochloride (4 g, crude) as a yellow solid.

Step 2. 4-Benzyl-1,4-oxazepan-6-one. To the mixture of 1,4-oxazepan-6-one hydrochloride (3.8 g, 25 mmol), $K_2CO_3$ (6.93 g, 50.1 mmol) in acetonitrile (20 mL) was added (bromomethyl)benzene (5.14 g, 30.1 mmol). The reaction mixture was purged with $N_2$ and then stirred at 40° C. for 2 h. The reaction mixture was diluted with water and extracted with EtOAc. The combined organic layers were washed with brine, dried over $Na_2SO_4$, filtered, and concentrated. The residue was purified by column chromatography on silica gel, eluting with a gradient of 5-100% ethyl acetate in petroleum ether, to provide 4-benzyl-1,4-oxazepan-6-one (3.8 g, 18.5 mmol, 74% yield) as a yellow oil.

Step 3. (Z)—N-(4-benzyl-1,4-oxazepan-6-ylidene)-2-methylpropane-2-sulfinamide. A mixture of 4-benzyl-1,4-oxazepan-6-one (2.00 g, 9.74 mmol), 2-methylpropane-2-sulfinamide (1.42 g, 11.7 mmol), tetraethoxytitanium (4.45 g, 19.5 mmol) in tetrahydrofuran (40 mL) was degassed and purged with $N_2$. The mixture was stirred at rt for 10 h and was quenched by the addition of water. The aqueous layer was extracted with EtOAc, and the combined organic layers were washed with brine, dried over $Na_2SO_4$, filtered, and concentrated. The residue was purified by column chromatography on silica gel, eluting with a gradient of 10-100% ethyl acetate in petroleum ether, to provide (Z)—N-(4-benzyl-1,4-oxazepan-6-ylidene)-2-methylpropane-2-sulfinamide (1.50 g, 4.86 mmol, 50% yield) as yellow oil.

Step 4. N-(4-Benzyl-6-methyl-1,4-oxazepan-6-yl)-2-methylpropane-2-sulfinamide. To a solution of (Z)—N-(4-benzyl-1,4-oxazepan-6-ylidene)-2-methylpropane-2-sulfinamide (1.50 g, 4.86 mmol) in dichloromethane (3 mL) was added MeMgBr (3 M in DCM, 9.7 mL, 29.1 mmol) slowly at 0° C. The reaction mixture was stirred at rt for 12 h, was then quenched by addition of water and extracted with dichloromethane. The combined organic layers were washed with brine, dried over $Na_2SO_4$, filtered, and concentrated. The residue was purified by prep-TLC on silica gel, eluting with 50% ethyl acetate in petroleum ether, to give N-(4-benzyl-6-methyl-1,4-oxazepan-6-yl)-2-methylpropane-2-sulfinamide (0.78 g, 2.4 mmol, 49% yield) as yellow oil. $^1H$ NMR (400 MHz, CHLOROFORM-d) δ ppm 7.31-7.34 (m, 5H), 4.24 (s, 1H), 4.06 (s, 1H), 3.57-3.79 (m, 5H), 2.80-2.87 (m, 1H), 2.68 (s, 2H), 2.50-2.55 (m, 1H), 1.15 (s, 3H), 1.11 (s, 9H).

Step 5. 4-Benzyl-6-methyl-1,4-oxazepan-6-amine hydrochloride. To the mixture of N-(4-benzyl-6-methyl-1,4-oxazepan-6-yl)-2-methylpropane-2-sulfinamide (0.10 g, 0.31 mmol) in dichloromethane (5 mL) was added HCl (4 M in MeOH, 2.5 mL, 10 mmol), and purged with $N_2$. The reaction mixture was stirred at rt for 12 h and was concentrated under reduced pressure to give 4-benzyl-6-methyl-1,4-oxazepan-6-amine hydrochloride (50 mg, 0.23 mmol, 74% yield) as white solid. $^1H$ NMR (400 MHz, MeOH-$d_4$) δ ppm 7.73 (s, 2H), 7.52 (t, J=5.2 Hz, 3H), 4.55-4.65 (m, 1H), 4.40-4.50 (m, 1H), 4.05-4.25 (m, 2H), 3.90-4.00 (m, 1H), 3.85-3.90 (m, 1H), 3.55-3.75 (m, 2H), 1.33 (s, 3H), 1.18 (s, 1H), 1.16 (s, 1H).

Intermediate UUUU: Methyl 5-(6-chloro-1-(tetrahydro-2H-pyran-2-yl)-4-(4,4,5,5-tetramethyl-1,3,2-dioxaborolan-2-yl)-1H-indazol-5-yl)-2-fluoropentanoate

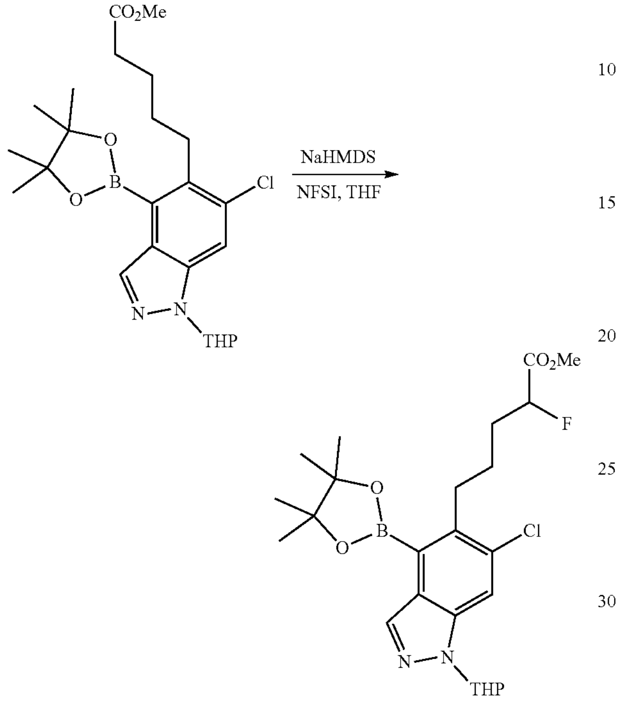

Intermediate UUUU

The solution of methyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate (Intermediate LL, 25 g, 52.4 mmol) in tetrahydrofuran (200 mL) was added dropwise NaHMDS (1 M in THF, 115 mL, 115 mmol) at −78° C. under $N_2$. The solution was stirred at −78° C. for 1 h under $N_2$. Then the solution of NFSI (28.9 g, 92 mmol) in tetrahydrofuran (200 mL) was added dropwise over to the above mixture during 15 minutes at −78° C. The mixture was stirred at −78° C. for 2 h. The reaction mixture was quenched by addition of water at rt and extracted with EtOAc. The combined organic layers were washed with brine, dried over $Na_2SO_4$, filtered, and concentrated. The crude product was purified by column chromatography on silica gel, eluting with 1-20% ethyl acetate in petroleum ether, followed by MPLC (neutral condition; column: stationary phase: 15 μm Luna C18, 70 mm ID×310 mm length (720G), solvent system: A: $H_2O$; B: ACN, gradient (the percent of B): 60%-80%), to give methyl 5-(6-chloro-1-(tetrahydro-2H-pyran-2-yl)-4-(4,4,5,5-tetramethyl-1,3,2-dioxaborolan-2-yl)-1H-indazol-5-yl)-2-fluoropentanoate (15.6 g, 31.6 mmol, 65% yield) as yellow oil. $^1H$ NMR (400 MHz, CHLOROFORM-d) δ ppm 8.36 (s, 1H), 7.74 (s, 1H), 5.66 (dd, J=9.2, 2.8 Hz, 1H), 4.90-5.05 (m, 1H), 3.97-4.02 (m, 1H), 3.79 (s, 3H), 3.67-3.77 (m, 1H), 3.15-3.24 (m, 2H), 2.47-2.56 (m, 1H), 2.10-2.16 (m, 1H), 1.96-2.06 (m, 3H), 1.66-1.79 (m, 5H), 1.41 (s, 12H). m/z (ESI): 495.2/497.2 $(M+H)^+$.

Intermediate VVVV: 3-(4-(4-(tert-Butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)propan-1-ol

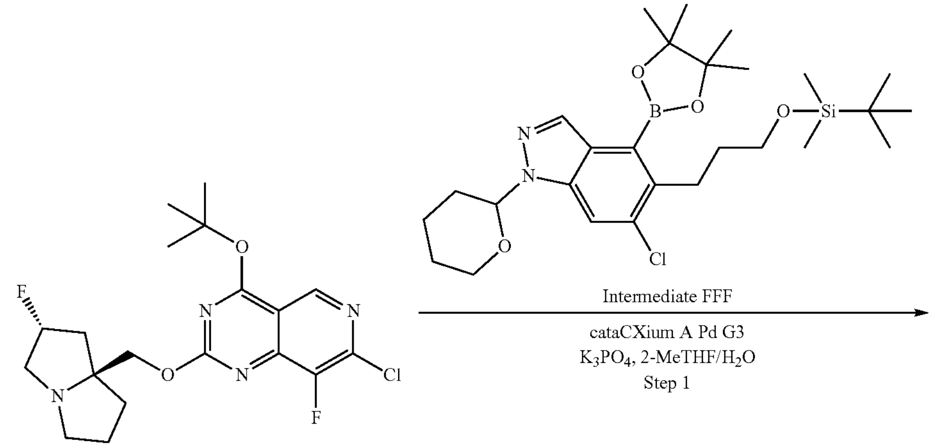

Intermediate JJ

-continued

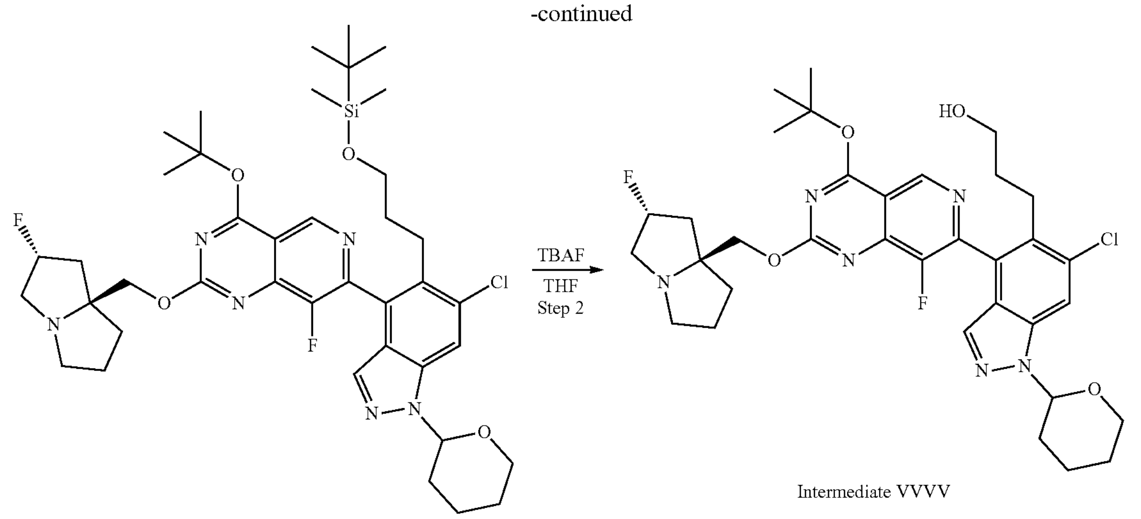

Intermediate VVVV

Step 1. 4-(tert-Butoxy)-7-(5-(3-((tert-butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine. A vial was charged with potassium phosphate tribasic (0.54 g, 2.54 mmol), cataCXium A Pd G3 (93 mg, 0.13 mmol), 5-(3-((tert-butyldimethylsilyl)oxy)propyl)-6-chloro-1-(tetrahydro-2H-pyran-2-yl)-4-(4,4,5,5-tetramethyl-1,3,2-dioxaborolan-2-yl)-1H-indazole (0.45 g, 0.85 mmol, Intermediate FFF), 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (0.35 g, 0.85 mmol, Intermediate JJ), water (0.5 mL) and 2-methyltetrahydrofuran (4.5 mL). The reaction mixture was heated to 80° C. for 1.5 h. After cooling to rt, the crude material was purified by column chromatography on silica gel, eluting with a gradient of 0-80% (2% $Et_3N$ 3:1 EtOAc:EtOH)/heptane, to provide 4-(tert-butoxy)-7-(5-(3-((tert-butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (0.40 g, 0.51 mmol, 60% yield) as light-yellow film. m/z (ESI): 785.3 $(M+H)^+$.

Step 2. 3-(4-(4-(tert-Butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)propan-1-ol. To a pressure release vial was added 4-(tert-butoxy)-7-(5-(3-((tert-butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (0.40 g, 0.51 mmol) in tetrahydrofuran (5 mL). Then, tetrabutylammonium fluoride solution (1.0 M in THF, 0.77 mL, 0.77 mmol) was added and the reaction was stirred at rt for 16 h. The crude material was purified by column chromatography on silica gel, eluting with a gradient of 0-100% [3:1 EtOAc:EtOH] in heptane with 2% $Et_3N$, to provide 3-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)propan-1-ol (0.18 g, 0.27 mmol, 53% yield) as light-yellow oil. m/z (ESI): 671.3 $(M+H)^+$.

Intermediate WWWW: tert-Butyl (6S)-6-((3-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)propyl)(methyl)amino)-1,4-oxazepane-4-carboxylate

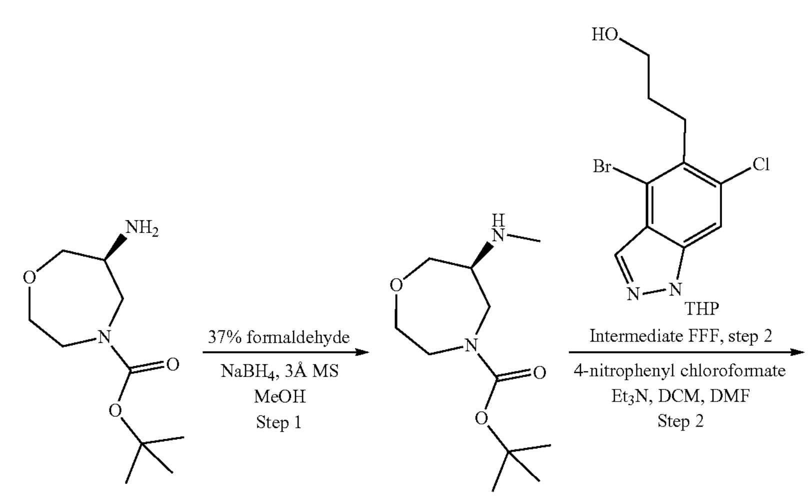

-continued
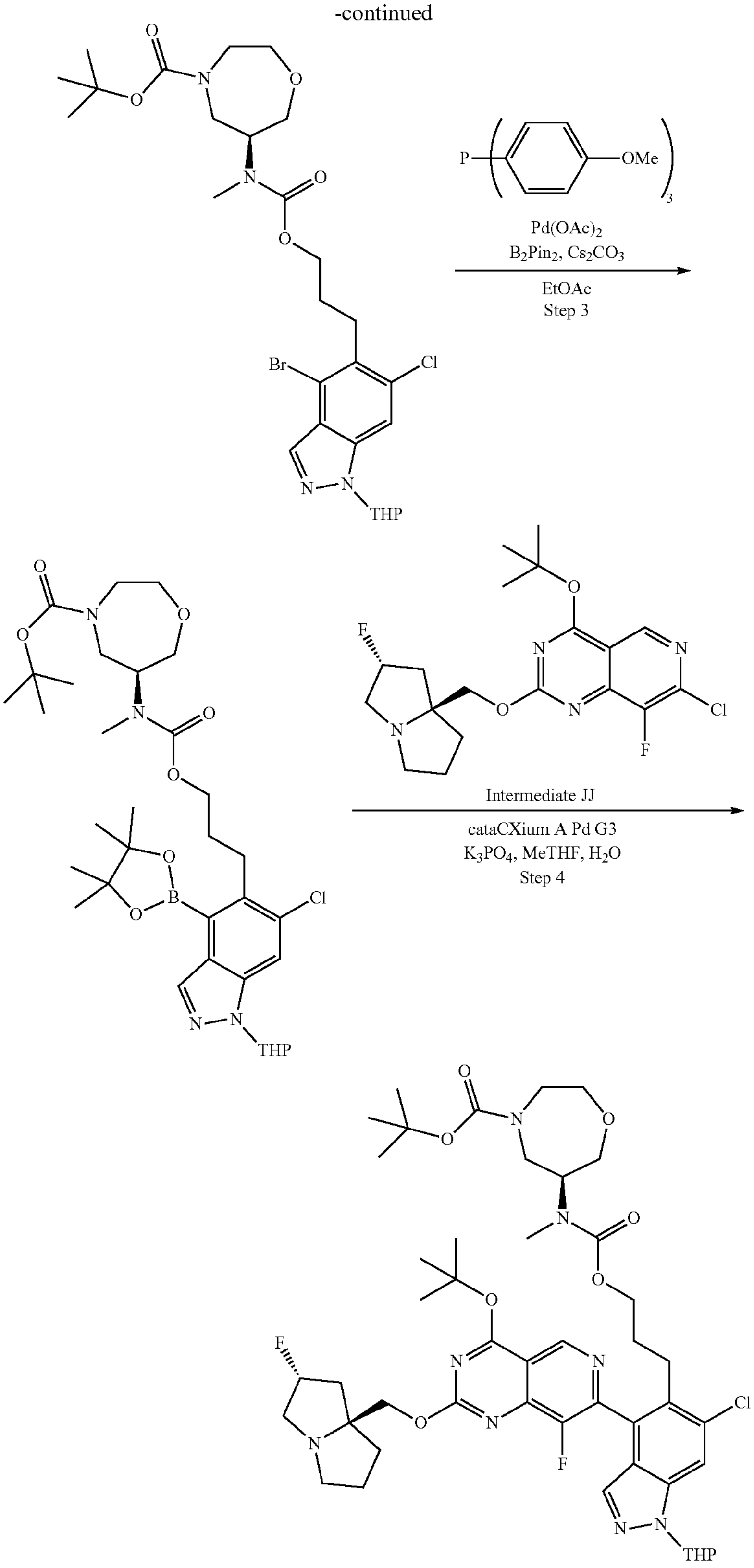
Intermediate WWWW
Step 1. tert-Butyl (S)-6-(methylamino)-1,4-oxazepane-4-carboxylate. (S)-4-Boc-6-amino-[1,4]oxazepane (1.00 g, 4.62 mmol, J & W Pharmlab, LLC) was added to a solution of formaldehyde, 37% solution (0.44 mL, 4.39 mmol) in MeOH (20 mL) containing 3 Å MS. The mixture was stirred at rt for 72 h. Sodium borohydride (0.28 g, 7.4 mmol) was added and the mixture was stirred for 30 min. The reaction was quenched by the addition of 1 N NaOH and extracted with DCM. The organic extract was washed with saturated NaCl and dried over $Na_2SO_4$, filtered, and concentrated. The crude product was used in the next step without further purification. m/z (ESI): 231.2 $(M+H)^+$.

Step 2. tert-Butyl (6S)-6-(((3-(4-bromo-6-chloro-1-(tetrahydro-2H-pyran-2-yl)-1H-indazol-5-yl)propoxy)carbonyl)(methyl)amino)-1,4-oxazepane-4-carboxylate. To a stirred solution of 3-(4-bromo-6-chloro-1-(tetrahydro-2H-pyran-2-yl)-1H-indazol-5-yl)propan-1-ol (0.30 g, 0.80 mmol, Intermediate FFF, Step 2) and triethylamine (0.21 mL, 1.46 mmol) in DCM (2.5 mL) was added 4-nitrophenyl chloroformate (0.19 g, 0.95 mmol) at 0° C. The reaction mixture was warmed to rt and stirred for 1 h. To the reaction was added DMF and tert-butyl (S)-6-(methylamino)-1,4-oxazepane-4-carboxylate (0.46 g, 2.01 mmol), and the reaction was stirred at 40° C. for 2 h. The reaction mixture was partitioned between water and ethyl acetate. The organic layer was separated, dried over $Na_2SO_4$, filtered, and concentrated. The crude material was purified by column chromatography on silica gel, eluting with 0-100% EtOAc in heptane, to afford tert-butyl (6S)-6-(((3-(4-bromo-6-chloro-1-(tetrahydro-2H-pyran-2-yl)-1H-indazol-5-yl)propoxy)carbonyl)(methyl)amino)-1,4-oxazepane-4-carboxylate (0.30 g, 0.48 mmol, 65% yield) as colorless oil. m/z (ESI): 651.0 $(M+Na)^+$.

Step 3. tert-Butyl (6S)-6-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)(methyl)amino)-1,4-oxazepane-4-carboxylate. A vial was charged with tris(4-methoxyphenyl)phosphine (20 mg, 0.056 mmol), palladium acetate (6 mg, 0.028 mmol), 4,4,4',4',5,5,5',5'-octamethyl-2,2'-bi(1,3,2-dioxaborolane) (0.17 g, 0.68 mmol), cesium carbonate (0.28 g, 0.85 mmol), tert-butyl (6S)-6-(((3-(4-bromo-6-chloro-1-(tetrahydro-2H-pyran-2-yl)-1H-indazol-5-yl)propoxy)carbonyl)(methyl)amino)-1,4-oxazepane-4-carboxylate (0.36 mg, 0.56 mmol) and ethyl acetate (2.5 mL). The reaction mixture was sparged with $N_2$ and heated to 80° C. for 6 h. After cooling to rt, the reaction mixture was passed through a syringe filter, the filtrate was concentrated, and the crude was used directly in the next step without further purification. m/z (ESI): 677.3 $(M+H)^+$.

Step 4. tert-Butyl (6S)-6-(((3-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)propoxy)carbonyl)(methyl)amino)-1,4-oxazepane-4-carboxylate. A vial was charged with potassium phosphate tribasic (0.36 g, 1.67 mmol), cataCXium A Pd G3 (61 mg, 0.084 mmol), tert-butyl (6S)-6-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)(methyl)amino)-1,4-oxazepane-4-carboxylate (0.38 g, 0.56 mmol), 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (0.23 g, 0.56 mmol, Intermediate JJ), water (0.2 mL) and 2-methyltetrahydrofuran (2 mL). The reaction mixture was heated to 80° C. for 2 h. After cooling to rt, the mixture was diluted with water and extracted with DCM. The combined organic phases were washed with brine, dried over anhydrous sodium sulfate, filtered, and concentrated under reduced pressure. The crude material was purified by column chromatography through silica gel, eluting with a gradient of 0-80% (3:1 EtOAc:EtOH with 2% $Et_3N$)/heptane, to provide tert-butyl (6S)-6-(((3-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)propoxy)carbonyl)(methyl)amino)-1,4-oxazepane-4-carboxylate (0.19 g, 0.21 mmol, 37% yield) as yellow solid. m/z (ESI): 927.4 $(M+H)^+$.

Intermediate XXXX: 4-(7-Chloro-8-fluoro-2-(((S)-1-methylpyrrolidin-2-yl)methoxy)pyrido[4,3-d]pyrimidin-4-yl)-6-methyl-1,4-oxazepan-6-ol

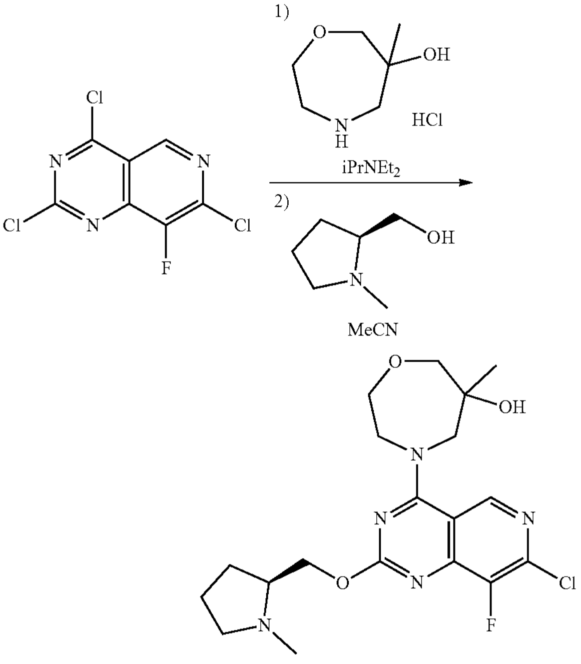

Intermediate XXXX

Synthesized in an analogous manner as Step 1 of Intermediate W using 6-methyl-1,4-oxazepan-6-ol hydrochloride (CAS #: 1823315-50-9, Ambeed, Inc.) and (2S)-1-methyl-2-pyrrolidinemethanol (CAS #: 34381-71-0, Sigma-Aldrich Corporation). Yield: 80%. m/z (ESI): 426.0 $(M+H)^+$.

Intermediate YYYY: (S)-4-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol

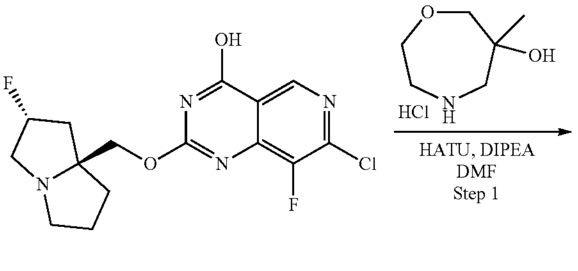

-continued

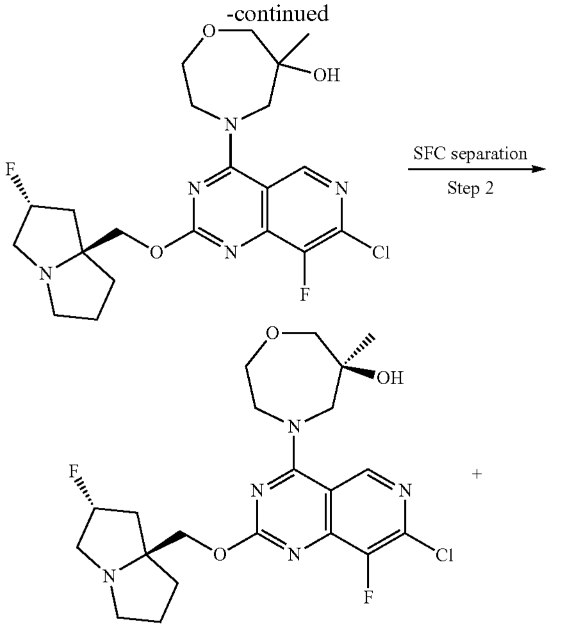

Intermediate YYYY

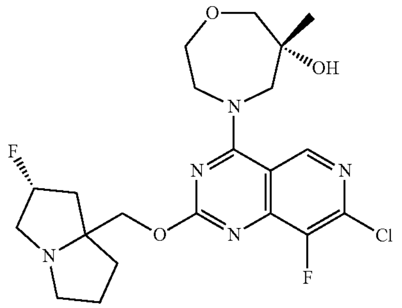

Step 1. 4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol. To a solution of 7-chloro-8-fluoro-2-(((2R,7aS)-2-fluorotetrahydro-1H-pyrrolizin-7a(5H)-yl)methoxy)pyrido[4,3-d]pyrimidin-4-ol (20.0 g, 56.1 mmol, Intermediate Z) in N,N-dimethylformamide (300 mL) was added N-ethyl-N-isopropylpropan-2-amine (36.2 g, 280 mmol) and HATU (32.0 g, 84 mmol). The reaction mixture was stirred at rt for 15 min. Then 6-methyl-1,4-oxazepan-6-ol hydrochloride (9.40 g, 56.1 mmol) was added. The mixture was stirred at rt for 10 h. Four batches were carried out in parallel. The reaction mixture was diluted with water and extracted with EtOAc. The combined organic layers were washed with brine, dried over $Na_2SO_4$, filtered, and concentrated. The crude product was purified by reverse-phase MPLC (Gradient $H_2O$ % 30-60% 30 min to 60-60% 30 min) to give 4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (58 g, 123 mmol, 55% yield) as yellow solid. m/z (ESI): 470.0 $(M+H)^+$.

Step 2. (S)-4-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol. 4-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (87.0 g, 185 mmol) was separated by SFC (conditions: 0.1% $NH_3{\cdot}H_2O$ IPA Begin B 35% End B 35% Gradient Time (min) 4.5 100% B Hold Time (min) Flow Rate (mL/min) 200 Injections 10 HPLC 96) to give peak 1 as (S)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (28.9 g, 61.6 mmol, 33% yield) as brown solid. $^1H$ NMR (400 MHz, DMSO-$d_6$) δ ppm 9.31 (s, 1H), 5.20-5.34 (m, 1H), 5.16 (s, 1H), 4.33-4.35 (m, 1H), 4.15-4.22 (m, 2H), 3.98-4.14 (m, 3H), 3.90-3.94 (m, 1H), 3.70-3.75 (m, 1H), 3.52-3.54 (m, 2H), 3.08-3.09 (m, 2H), 3.01-3.07 (m, 1H), 2.75-2.80 (m, 1H), 2.20-2.24 (m, 1H), 1.98-2.11 (m, 2H), 1.76-1.85 (m, 3H), 1.13 (s, 3H). $^{19}F$ NMR (400 MHz, DMSO-$d_6$) δ ppm −136.84 (s), −172.13 (s). m/z (ESI): 470.1 $(M+H)^+$.

Peak 2 as (R)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (26.9 g, 57.3 mmol, 31% yield) was also obtained as brown solid.

Intermediate ZZZZ: 5-(3-((tert-Butyldimethylsilyl)oxy)propyl)-6-fluoro-1-(tetrahydro-2H-pyran-2-yl)-4-(4,4,5,5-tetramethyl-1,3,2-dioxaborolan-2-yl)-1H-indazole

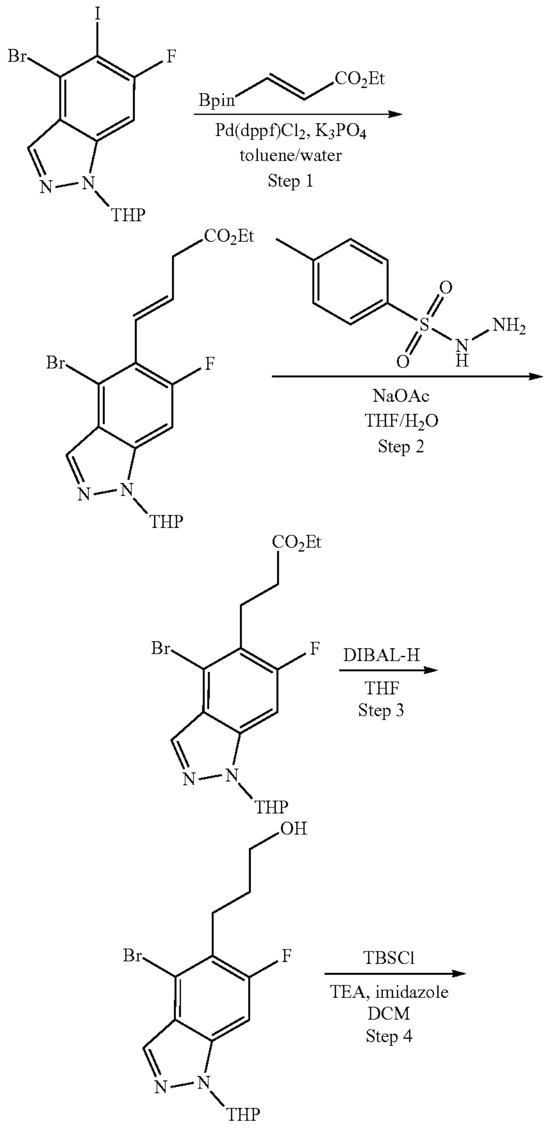

-continued

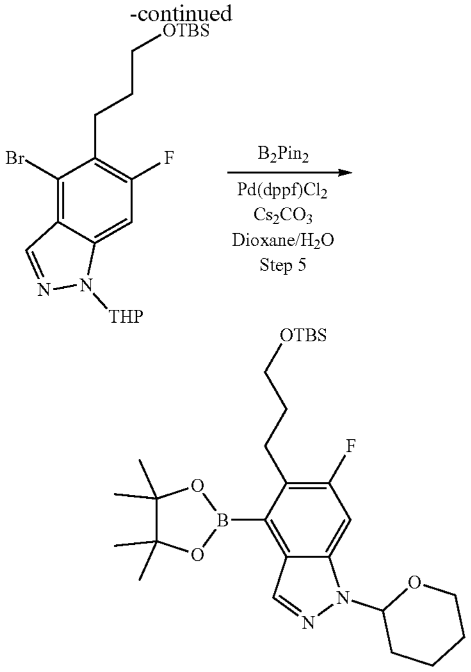

Intermediate ZZZZ

Step 1. Ethyl (E)-3-(4-bromo-6-fluoro-1-(tetrahydro-2H-pyran-2-yl)-1H-indazol-5yl)acrylate. To a solution of 4-bromo-6-fluoro-5-iodo-1-(tetrahydro-2H-pyran-2-yl)-1H-indazole (10.0 g, 23.5 mmol) in toluene (300 mL) and water (30 mL) was added $K_3PO_4$ (14.9 g, 70.6 mmol), ethyl (E)-3-(4,4,5,5-tetramethyl-1,3,2-dioxaborolan-2-yl)acrylate (6.91 g, 30.6 mmol) and Pd(dppf)$Cl_2$ (1.72 g, 2.35 mmol) in sequence. Then the mixture was stirred at 100° C. for 12 h under $N_2$. After cooling to rt, the reaction mixture was diluted with water and extracted with EtOAc. The combined organic layers were dried over $Na_2SO_4$, filtered, and concentrated. The residue was purified by column chromatography on silica gel, eluting with a gradient of 2-5% ethyl acetate in petroleum ether, to give ethyl (E)-3-(4-bromo-6-fluoro-1-(tetrahydro-2H-pyran-2-yl)-1H-indazol-5yl)acrylate (4.83 g, 12.2 mmol, 52% yield) as white solid. m/z (ESI): 397.1/399.1 $(M+H)^+$.

Step 2. Ethyl 3-(4-bromo-6-fluoro-1-(tetrahydro-2H-pyran-2-yl)-1H-indazol-5-yl)propanoate. To a solution of ethyl (E)-3-(4-bromo-6-fluoro-1-(tetrahydro-2H-pyran-2-yl)-1H-indazol-5yl)acrylate (9.00 g, 22.7 mmol) in tetrahydrofuran (180 mL) and water (180 mL) was added NaOAc (7.43 g, 91.0 mmol) and 4-methylbenzenesulfonohydrazide (12.7 g, 68.0 mmol) in sequence. The mixture was stirred at 80° C. for 12 h. After cooling to rt, the reaction mixture was diluted with water and extracted with EtOAc. The combined organic layers were dried over $Na_2SO_4$, filtered, and concentrated. The residue was purified by column chromatography on silica gel, eluting with a gradient of 2-10% ethyl acetate in petroleum ether, to give ethyl 3-(4-bromo-6-fluoro-1-(tetrahydro-2H-pyran-2-yl)-1H-indazol-5-yl)propanoate (8.68 g, 21.75 mmol, 96% yield) as brown oil.

Step 3. 3-(4-Bromo-6-fluoro-1-(tetrahydro-2H-pyran-2-yl)-1H-indazol-5-yl)propan-1-ol. To a solution of ethyl 3-(4-bromo-6-fluoro-1-(tetrahydro-2H-pyran-2-yl)-1H-indazol-5-yl)propanoate (9.0 g, 22.5 mmol) in tetrahydrofuran (90 mL) was added DIBAL-H (1 M in THF, 67.6 mL, 67.6 mmol) dropwise at 0° C. The resulting mixture was stirred at 0° C. for 2 h. The reaction mixture was quenched by addition of water, and then extracted with EtOAc. The combined organic layers were washed with brine, dried over $Na_2SO_4$, filtered, and concentrated. The residue was purified by column chromatography on silica gel, eluting with a gradient of 3-100% ethyl acetate in petroleum ether, to give 3-(4-bromo-6-fluoro-1-(tetrahydro-2H-pyran-2-yl)-1H-indazol-5-yl)propan-1-ol (7.71 g, 21.6 mmol, 96% yield) as brown oil.

Step 4. 4-Bromo-5-(3-((tert-butyldimethylsilyl)oxy)propyl)-6-fluoro-1-(tetrahydro-2H-pyran-2-yl)-1H-indazole. To a solution of 3-(4-bromo-6-fluoro-1-(tetrahydro-2H-pyran-2-yl)-1H-indazol-5-yl)propan-1-ol (10.0 g, 28.0 mmol) in dichloromethane (200 mL) was added TBS-Cl (6.33 g, 42.0 mmol), imidazole (3.81 g, 56.0 mmol) and TEA (5.5 mL, 39 mmol) in sequence. The reaction mixture was stirred at rt for 12 h. The reaction mixture was diluted with water and extracted with DCM. The combined organic layers were dried over $Na_2SO_4$, filtered and concentrated under reduced pressure. The residue was purified by column chromatography on silica gel, eluting with a gradient of 1-2% ethyl acetate in petroleum ether, to 4-bromo-5-(3-((tert-butyldimethylsilyl)oxy)propyl)-6-fluoro-1-(tetrahydro-2H-pyran-2-yl)-1H-indazole (12.17 g, 25.83 mmol, 93% yield) as a brown oil.

Step 5. 5-(3-((tert-Butyldimethylsilyl)oxy)propyl)-6-fluoro-1-(tetrahydro-2H-pyran-2-yl)-4-(4,4,5,5-tetramethyl-1,3,2-dioxaborolan-2-yl)-1H-indazole. To a solution of 4-bromo-5-(3-((tert-butyldimethylsilyl)oxy)propyl)-6-fluoro-1-(tetrahydro-2H-pyran-2-yl)-1H-indazole (7.00 g, 14.9 mmol) in 1,4-dioxane (70 mL) was added bis(pinacolato)diboron (18.9 g, 74.2 mmol) and $Cs_2CO_3$ (14.5 g, 44.5 mmol) in water (7 mL) under $N_2$. Then Pd(dppf)$Cl_2$ (1.09 g, 1.49 mmol) was added in one portion under $N_2$. Then the mixture was stirred at 120° C. for 5 h. After cooling to rt, the reaction mixture was diluted with water and extracted with EtOAc. The combined organic layers were washed with brine, dried over $Na_2SO_4$, filtered, and concentrated under reduced pressure. The crude product was purified by reversed-phase MPLC (0.1% $NH_3 \cdot H_2O$) to give 5-(3-((tert-butyldimethylsilyl)oxy)propyl)-6-fluoro-1-(tetrahydro-2H-pyran-2-yl)-4-(4,4,5,5-tetramethyl-1,3,2-dioxaborolan-2-yl)-1H-indazole (7.00 g, 13.5 mmol, 90% yield) as brown oil. $^1H$ NMR (400 MHz, DMSO-$d_6$) δ ppm 8.17 (s, 1H), 7.65 (d, J=10.8 Hz, 1H), 5.79-5.76 (m, 1H), 3.87-3.84 (m, 1H), 3.74-3.71 (m, 1H), 3.69-3.62 (m, 2H), 3.00-2.90 (m, 2H), 2.48-2.25 (m, 1H), 1.70-1.69 (m, 1H), 1.69-1.68 (m, 1H), 1.64-1.60 (m, 3H), 1.59-1.57 (m, 2H), 1.36 (s, 12H), 0.86 (s, 9H), 0.02 (s, 6H). $^{19}F$ NMR (400 MHz, DMSO-$d_6$) δ ppm −118.79 (s). m/z (ESI): 519.4 $(M+H)^+$.

Intermediate BA: (S)-4-(7-Chloro-8-fluoro-2-(((6S,8aS)-hexahydro-1H-pyrrolo[2,1-c][1,4]oxazin-6-yl)methoxy)pyrido[4,3-d]pyrimidin-4-yl)-1,4-oxazepan-6-ol

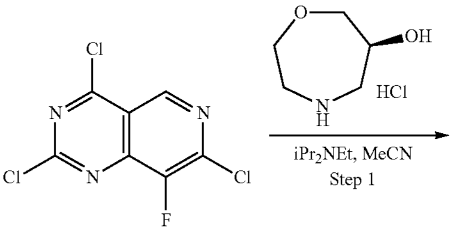

-continued

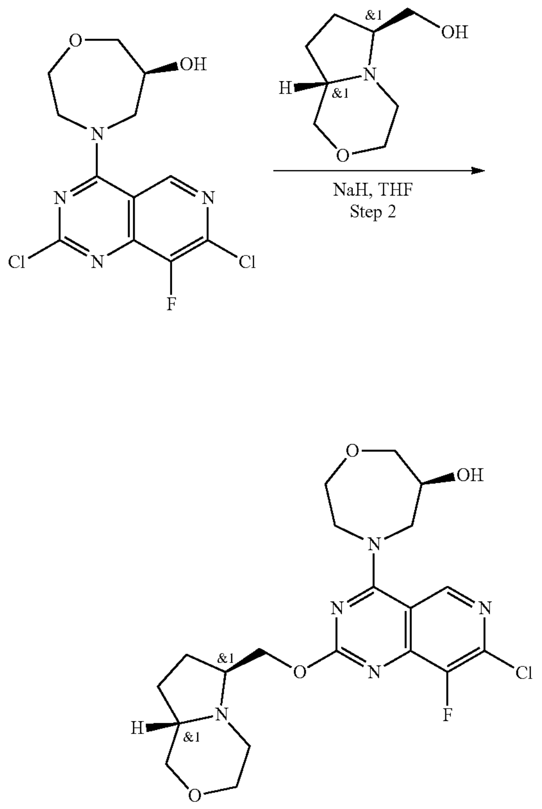

Intermediate BA

Step 1. (S)-4-(2,7-Dichloro-8-fluoropyrido[4,3-d]pyrimidin-4-yl)-1,4-oxazepan-6-ol. To a 100-mL round bottom flask was added 2,4,7-trichloro-8-fluoropyrido[4,3-d]pyrimidine (2.00 g, 7.92 mmol, Enamine), (S)-1,4-oxazepan-6-ol hydrochloride (1.28 g, 8.32 mmol) in acetonitrile (40 mL). The mixture was cooled to 0° C. before N-ethyl-N-isopropylpropan-2-amine (5.5 mL, 31.7 mmol) was added. The reaction mixture was stirred for 15 min while warming up to rt. The crude material was purified by column chromatography on silica gel, eluting with 0-80% EtOAc in heptane, to yield (S)-4-(2,7-dichloro-8-fluoropyrido[4,3-d]pyrimidin-4-yl)-1,4-oxazepan-6-ol (1.01 g, 3.03 mmol, 38% yield). m/z (ESI): 333.0 $(M+H)^+$.

Step 2. (S)-4-(7-chloro-8-fluoro-2-(((6S,8aS)-hexahydro-1H-pyrrolo[2,1-c][1,4]oxazin-6-yl)methoxy)pyrido[4,3-d]pyrimidin-4-yl)-1,4-oxazepan-6-ol. To a 40-mL vial was added [cis-3,4,6,7,8,8a-hexahydro-1h-pyrrolo[2,1-c][1,4]oxazin-6-yl]methanol (0.47 g, 2.97 mmol, Synnovator, Inc.) in tetrahydrofuran (14 mL). The mixture was cooled to 0° C., sodium hydride (60% in mineral oil, 0.12 g, 2.97 mmol) was added. The reaction mixture was stirred for 15 min while warming up. (S)-4-(2,7-dichloro-8-fluoropyrido[4,3-d]pyrimidin-4-yl)-1,4-oxazepan-6-ol (0.90 g, 2.7 mmol) was then added and the reaction mixture was stirred at rt for 1 h. The reaction was quenched by addition of sat. $NH_4Cl$ and concentrated. The mixture was purified by column chromatography on silica gel, eluting with with a gradient of 0-75% 3:1 EtOAc/EtOH (with 2% triethylamine) in heptane, to yield (S)-4-(7-chloro-8-fluoro-2-(((6S,8aS)-hexahydro-1H-pyrrolo[2,1-c][1,4]oxazin-6-yl)methoxy)pyrido[4,3-d]pyrimidin-4-yl)-1,4-oxazepan-6-ol (0.42 g, 0.93 mmol, 35% yield). m/z (ESI): 454.0 $(M+H)^+$.

Intermediate BC: tert-Butyl (3-(2-chloro-6-(4,4,5,5-tetramethyl-1,3,2-dioxaborolan-2-yl)phenyl) propoxy)dimethylsilane

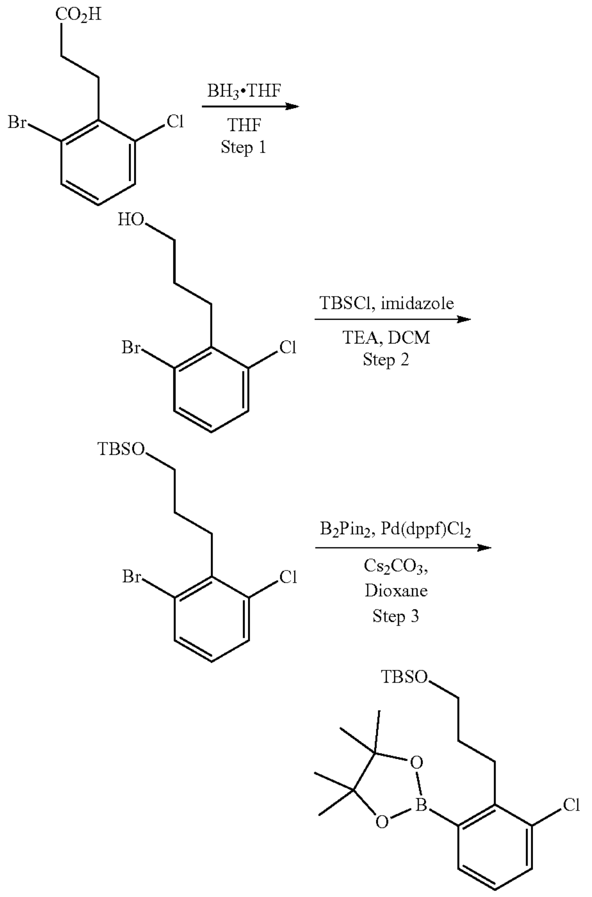

Intermediate BC

Step 1. 3-(2-Bromo-6-chlorophenyl) propan-1-ol. To the mixture of 3-(2-bromo-6-chlorophenyl) propanoic acid (8.00 g, 30.4 mmol) in tetrahydrofuran (80 mL) at 0° C. was added $BH_3$·THF (42.5 mL of 1 M solution, 42.5 mmol) dropwise. The reaction mixture was stirred at 0° C. for 2 h then quenched by the addition of 20 mL of MeOH at 0° C. The reaction mixture was stirred at 0° C. for 0.5 h followed by at rt for 0.5 h, then diluted with $H_2O$ and extracted with EtOAc. The combined organic layers were washed with brine, dried over $Na_2SO_4$, filtered, and concentrated. The residue was purified by column chromatography on silica gel, eluting with a gradient of 1-33% ethyl acetate in petroleum ether, to give 3-(2-bromo-6-chlorophenyl) propan-1-ol (6.60 g, 26 mmol, 87% yield) as yellow oil. m/z (ESI): 250.2/252.2 $(M+H)^+$.

Step 2. (3-(2-Bromo-6-chlorophenyl)propoxy)(tert-butyl) dimethylsilane. To a mixture of 3-(2-bromo-6-chlorophenyl) propan-1-ol (6.6 g, 26 mmol) and 1H-imidazole (3.60 g, 52.9 mmol) in dichloromethane (70 mL) at 0° C. was added TBSCl (5.98 g, 39.7 mmol) and TEA (5.2 mL, 37 mmol). After stirring at 0° C. for 1 h, the reaction mixture was diluted with $H_2O$ and extracted with EtOAc. The combined organic layers were washed with brine, dried over $Na_2SO_4$, filtered, and concentrated under reduced pressure. The residue was purified by column chromatography on silica gel, eluting with a gradient of 0.5-1% ethyl acetate in petroleum ether, to afford (3-(2-bromo-6-chlorophenyl)propoxy)(tert-butyl)dimethylsilane (7.50 g, 20.6 mmol, 78% yield) as yellow oil. m/z (ESI): 364.2/366.2 $(M+H)^+$.

Step 3. tert-Butyl(3-(2-chloro-6-(4,4,5,5-tetramethyl-1,3,2-dioxaborolan-2-yl)phenyl)propoxy)dimethylsilane. To the mixture of (3-(2-bromo-6-chlorophenyl)propoxy)(tert-butyl)dimethylsilane (1.00 g, 2.75 mmol), $Cs_2CO_3$ (2.69 g, 8.25 mmol) and 4,4,4',4',5,5,5',5'-octamethyl-2,2'-bi(1,3,2-dioxaborolane) (3.49 g, 13.7 mmol) in 1,4-dioxane (80 mL) was added $Pd(dppf)Cl_2$ (0.20 g, 0.28 mmol). The reaction mixture was stirred at 120° C. for 4 h. After cooling to rt, the reaction was diluted with $H_2O$ and extracted with EtOAc. The combined organic layers were washed with brine, dried over $Na_2SO_4$, filtered, and concentrated. The residue was purified by column chromatography on silica gel, eluting with a gradient of 1-10% ethyl acetate in petroleum ether, to give tert-butyl (3-(2-chloro-6-(4,4,5,5-tetramethyl-1,3,2-dioxaborolan-2-yl)phenyl)propoxy)dimethylsilane (1.00 g, 2.43 mmol, 89% yield) as yellow oil. $^1H$ NMR (400 MHz, $CDCl_3$-d) δ ppm 7.66 (d, J=7.2 Hz, 1H), 7.41 (d, J=8.0 Hz, 1H), 7.11 (t, J=7.6 Hz 1H), 3.73 (t, J=6.8 Hz, 2H), 3.03-3.17 (m, 2H), 1.72-1.83 (m, 2H), 1.35 (s, 12H), 0.92 (s, 9H), 0.08 (s, 6H). m/z (ESI): 284.3 $(M+H)^+$.

Intermediate BD: (S)-4-(7-Bromo-8-fluoro-2-(((2R,7aS)-2-fluorotetrahydro-1H-pyrrolizin-7a(5H)-yl)methoxy)quinazolin-4-yl)-1,4-oxazepan-6-ol

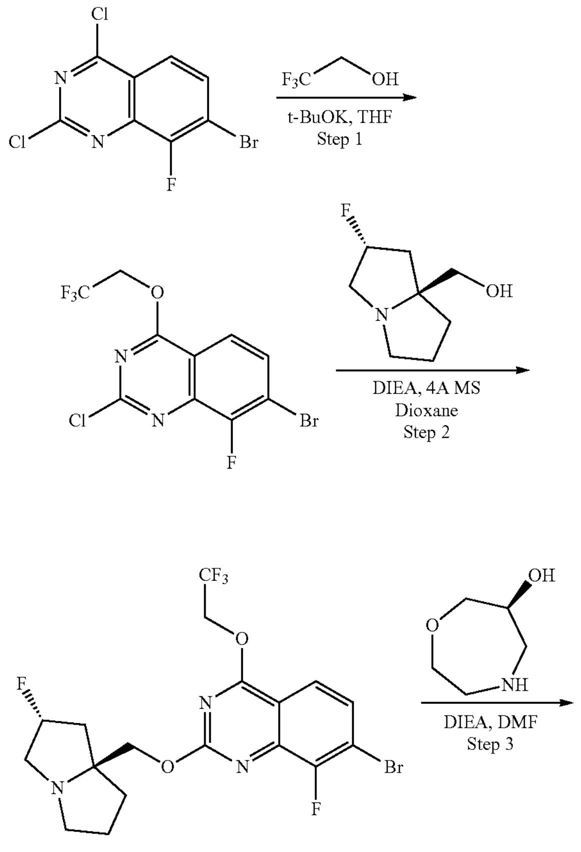

-continued

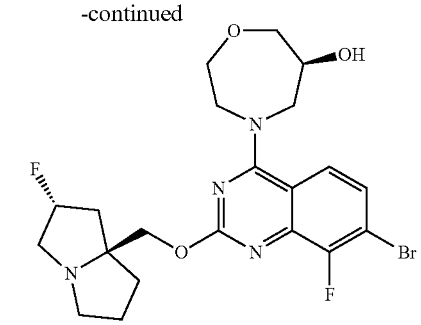

Intermediate BD

Step 1. 7-Bromo-2-chloro-8-fluoro-4-(2,2,2-trifluoroethoxy)quinazoline. To a solution of 7-bromo-2,4-dichloro-8-fluoroquinazoline (10.0 g, 33.8 mmol) in tetrahydrofuran (150 mL) was added slowly the mixed solution of 2,2,2-trifluoroethan-1-ol (3.21 g, 32.1 mmol) and t-BuOK (1 M in THF, 32.1 mL, 32.1 mmol,) at −65° C. under $N_2$. The mixture was stirred at −65° C. for 3 h. After warming to rt, the residue was diluted with water and extracted with EtOAc. The combined organic layers were dried over $Na_2SO_4$, filtered, and concentrated. The residue was triturated with petroleum ether at 25° C. for 60 min. The suspension was filtered, and the cake was concentrated under reduced pressure to give 7-bromo-2-chloro-8-fluoro-4-(2,2,2-trifluoroethoxy) quinazoline (9.50 g, 26.5 mmol, 78% yield) as white solid.

Step 2. 7-Bromo-8-fluoro-2-(((2R,7aS)-2-fluorotetrahydro-1H-pyrrolizin-7a(5H)-yl)methoxy)-4-(2,2,2-trifluoroethoxy)quinazoline. To a solution of 7-bromo-2-chloro-8-fluoro-4-(2,2,2-trifluoroethoxy)quinazoline (10.0 g, 27.8 mmol) in 1,4-dioxane (75 mL) was added ((2R,7aS)-2-fluorotetrahydro-1H-pyrrolizin-7a(5H)-yl)methanol (6.20 g, 38.9 mmol), DIPEA (75 mL, 83 mmol) and 4 Å MS (0.5 g). The mixture was stirred at 120° C. for 10 h. After cooling to rt, the reaction mixture was diluted with water and extracted with EtOAc. The combined organic layers were dried over $Na_2SO_4$, filtered, and concentrated. The residue was purified by column chromatography on silica gel, eluting with a gradient of 1-10% ethyl acetate in petroleum ether. The crude product was further purified by trituration with MTBE (20 mL) at rt for 1 h. The suspension was filtered, and the filter cake was concentrated under reduced pressure to give 7-bromo-8-fluoro-2-(((2R,7aS)-2-fluorotetrahydro-1H-pyrrolizin-7a(5H)-yl)methoxy)-4-(2,2,2-trifluoroethoxy)quinazoline (5.10 g, 10.6 mmol, 38% yield) as white solid. $^1H$ NMR (400 MHz, DMSO-$d_6$) δ ppm 7.71-7.78 (m, 2H), 5.22-5.36 (m, 3H), 4.09-4.21 (m, 2H), 3.03-3.12 (m, 3H), 2.83-2.99 (m, 1H), 1.95-2.15 (m, 3H), 1.79-1.86 (m, 3H). $^{19}F$ NMR (376 MHz, DMSO-$d_6$) δ ppm −72.10 (s, 3F), −119.82 (s, 1F), −172.17 (s, 1F). m/z (ESI): 482.1/484.0 $(M+H)^+$.

Step 3. (S)-4-(7-bromo-8-fluoro-2-(((2R,7aS)-2-fluorotetrahydro-1H-pyrrolizin-7a(5H)-yl)methoxy)quinazolin-4-yl)-1,4-oxazepan-6-ol. A 40-mL vial was charged with N,N-diisopropylethylamine (4.4 mL, 25 mmol), (S)-[1,4] oxazepan-6-ol (1.33 g, 11.4 mmol, J&W Pharmlab), 7-bromo-8-fluoro-2-(((2R,7aS)-2-fluorotetrahydro-1H-pyrrolizin-7a(5H)-yl)methoxy)-4-(2,2,2-trifluoroethoxy) quinazoline (3.05 g, 6.32 mmol) and DMF (20 mL). The reaction was stirred at 100° C. for 24 h. Water and DCM were added. The organic layer was separated, dried over $Na_2SO_4$, filtered, and concentrated. The crude material was purified by column chromatography on silica gel, eluting with a gradient of 0-80% 3:1 EtOAc:EtOH with 2% $Et_3N$ in heptane, to provide (S)-4-(7-bromo-8-fluoro-2-(((2R,7aS)-2-fluorotetrahydro-1H-pyrrolizin-7a(5H)-yl)methoxy)quinazolin-4-yl)-1,4-oxazepan-6-ol (1.30 g, 2.60 mmol, 41% yield) as light-yellow solid. m/z (ESI): 499.1 $(M+H)^+$.

Intermediate BE: 6-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol

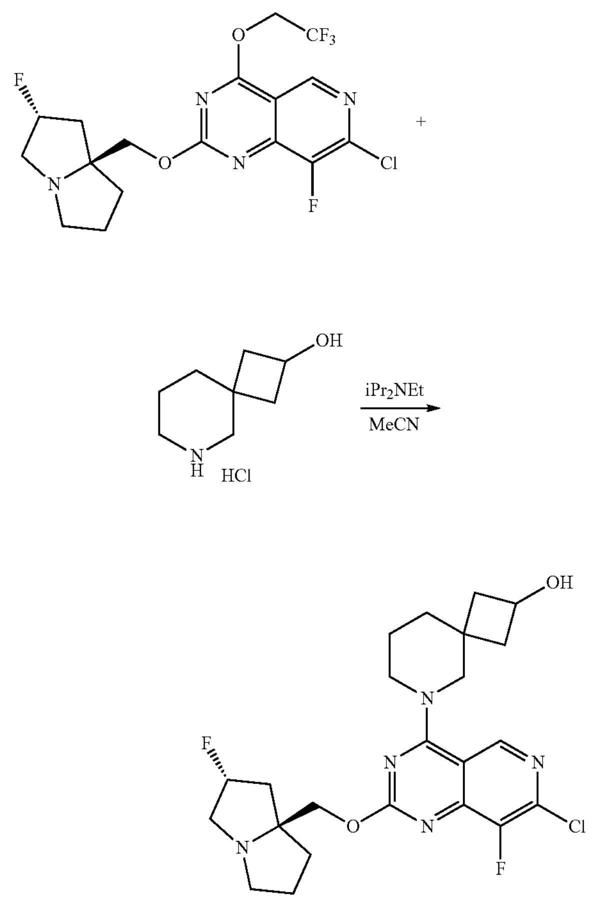

Intermediate BE

To a 20 mL vial was charged with 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.50 g, 1.14 mmol, Step 2 for Intermediate AA), N,N-diisopropylethylamine (0.78 mL, 4.56 mmol), and acetonitrile (4.5 mL). To this was added 6-azaspiro[3.5]nonan-2-ol hydrochloride (0.20 g, 1.14 mmol, Ambeed, Inc.) and the reaction mixture was stirred at 50° C. for 1 h. After cooling to rt, the mixture was concentrated and the residue was purified by column chromatography on silica gel, eluting with a gradient of 0-85% 3:1 EtOAc:EtOH with 2% triethylamine in heptane, to give 6-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol (0.33 g, 0.69 mmol, 60% yield) as white solid. m/z (ESI): 480.0 $(M+H)^+$.

Intermediate BF: (S)-4-(2-Chloro-7-((1-((dimethylamino)methyl)cyclopropyl)methoxy)-8-fluoropyrido[4,3-d]pyrimidin-4-yl)-1,4-oxazepan-6-ol

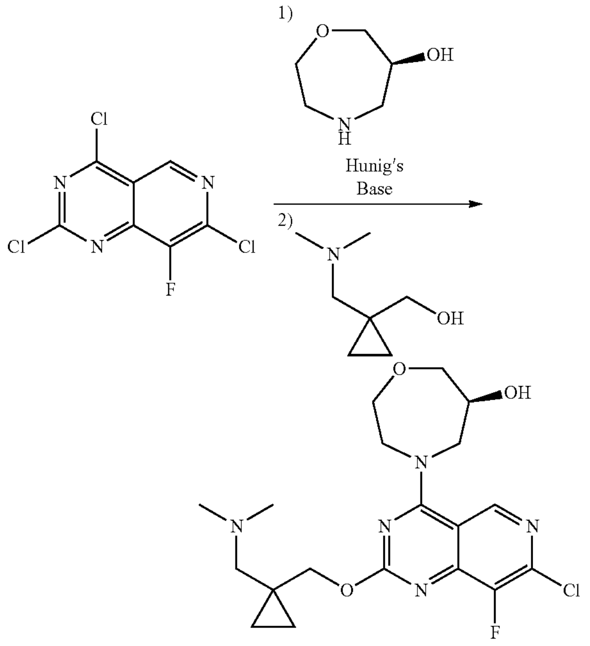

Intermediate BF

To a 20 mL vial was charged with 2,4,7-trichloro-8-fluoropyrido[4,3-d]pyrimidine (0.75 g, 2.97 mmol, Enamine), N,N-diisopropylethylamine (2.0 mL, 11.9 mmol) and acetonitrile (15 mL). The contents were cooled to 0° C. and (S)-1,4-oxazepan-6-ol (0.35 g, 2.97 mmol) was added. The mixture was stirred at rt for 15 min, then (1-((dimethylamino)methyl)cyclopropyl)methanol (0.38 mL, 3.0 mmol) was added and the reaction was heated to 80° C. for 16 h. After cooling to rt, the reaction was concentrated and the residue was purified by column chromatography on silica gel, eluting with 0-85% 3:1 EtOAc:EtOH+2% triethylamine in heptane, followed by reverse phase column chromatography using a C18 column, eluting with 5-100% acetonitrile+0.1% formic acid in water+0.1% formic acid, to give (S)-4-(2-chloro-7-((1-((dimethylamino)methyl)cyclopropyl)methoxy)-8-fluoropyrido[4,3-d]pyrimidin-4-yl)-1,4-oxazepan-6-ol (0.17 g, 0.4 mmol, 13% yield) as white solid. m/z (ESI): 426.0 $(M+H)^+$.

Intermediate BG: (S)-4-(7-Chloro-8-fluoro-2-(((S)-tetrahydrofuran-3-yl)oxy)pyrido[4,3-d]pyrimidin-4-yl)-1,4-oxazepan-6-ol

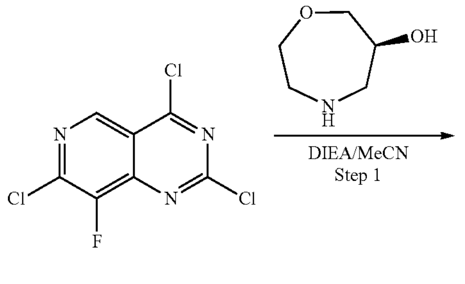

-continued

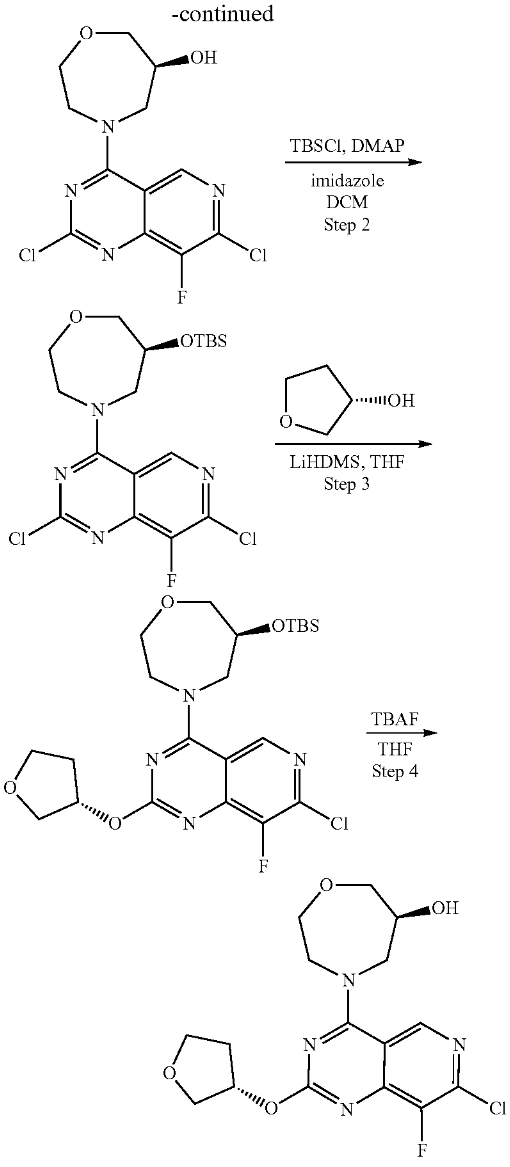

Intermediate BG

Step 1. (S)-4-(2,7-Dichloro-8-fluoropyrido[4,3-d]pyrimidin-4-yl)-1,4-oxazepan-6-ol. To a stirred solution of 2,4,7-trichloro-8-fluoropyrido[4,3-d]pyrimidine (1.96 g, 7.76 mmol, Enamine) in acetonitrile (8 mL) was added (S)-[1,4] oxazepan-6-ol (1.00 g, 8.54 mmol, J&W Pharmlab) and DIEA (4.1 mL, 23.3 mmol). The reaction mixture was stirred at 0° C. for 1 h. The crude reaction mixture was concentrated and the residue was purified by column chromatography on silica gel, eluting with a gradient of 0-70% (3:1 EtOAc/EtOH+2% TEA) in heptane, to yield (S)-4-(2,7-dichloro-8-fluoropyrido[4,3-d]pyrimidin-4-yl)-1,4-oxazepan-6-ol (1.9 g, 5.70 mmol, 74% yield) as light-yellow solid. m/z (ESI): 333.1 $(M+H)^+$.

Step 2. (S)-6-((tert-Butyldimethylsilyl)oxy)-4-(2,7-dichloro-8-fluoropyrido[4,3-d]pyrimidin-4-yl)-1,4-oxazepane. The mixture of (S)-4-(2,7-dichloro-8-fluoropyrido[4,3-d]pyrimidin-4-yl)-1,4-oxazepan-6-ol (1.2 g, 3.6 mmol), TBSCl (0.65 g, 4.32 mmol), imidazole (0.61 g, 9.01 mmol), and DMAP (0.044 mg, 0.36 mmol) in dichloromethane (18 mL) was stirred at rt for 16 h. The reaction mixture was then quenched with saturated sodium bicarbonate solution. The layers were separated, and the aqueous layer was extracted with DCM. The combined organic layers were dried with $Na_2SO_4$, filtered, and concentrated under reduced pressure. The crude oil was purified by column chromatography on silica gel, eluting with a gradient of 0-20% EtOAc/heptane to afford (S)-6-((tert-butyldimethylsilyl)oxy)-4-(2,7-dichloro-8-fluoropyrido[4,3-d]pyrimidin-4-yl)-1,4-oxazepane (0.95 g, 2.12 mmol, 59% yield) as colorless oil. m/z (ESI, +ve ion): 447.0 $(M+H)^+$.

Step 3. (S)-6-((tert-butyldimethylsilyl)oxy)-4-(7-chloro-8-fluoro-2-(((S)-tetrahydrofuran-3-yl)oxy)pyrido[4,3-d]pyrimidin-4-yl)-1,4-oxazepane. To a stirred solution of (S)-3-hydroxytetrahydrofuran (0.19 g, 2.12 mmol) in tetrahydrofuran (3.5 mL) was added lithium bis(trimethylsilyl)amide (1 M in THF, 2.2 mL, 2.2 mmol) dropwise at 0° C. After 10 min, a suspension of (S)-6-((tert-butyldimethylsilyl)oxy)-4-(2,7-dichloro-8-fluoropyrido[4,3-d]pyrimidin-4-yl)-1,4-oxazepane (0.48 g, 1.06 mmol) in tetrahydrofuran (2 mL) was added. The reaction mixture was allowed to warm to rt overnight. Volatiles were removed under reduced pressure and the crude material was purified by column chromatography on silica gel, eluting with a gradient of 0-60% (3:1 EtOAc:EtOH+2% TEA) in heptane, to provide (S)-6-((tert-butyldimethylsilyl)oxy)-4-(7-chloro-8-fluoro-2-(((S)-tetrahydrofuran-3-yl)oxy)pyrido[4,3-d]pyrimidin-4-yl)-1,4-oxazepane (0.53 g, 1.06 mmol, 100% yield) as light-yellow oil. m/z (ESI, +ve ion): 499.0 $(M+H)^+$.

Step 4. (S)-4-(7-Chloro-8-fluoro-2-(((S)-tetrahydrofuran-3-yl)oxy)pyrido[4,3-d]pyrimidin-4-yl)-1,4-oxazepan-6-ol. To a solution of (S)-6-((tert-butyldimethylsilyl)oxy)-4-(7-chloro-8-fluoro-2-(((S)-tetrahydrofuran-3-yl)oxy)pyrido[4,3-d]pyrimidin-4-yl)-1,4-oxazepane (0.53 g, 1.06 mmol) in tetrahydrofuran (5.3 mL) was added TBAF (1 M in THF, 1.6 mL, 1.6 mmol). The reaction was stirred at rt for 2 h. The reaction mixture was partitioned between EtOAc and half-saturated aqueous sodium bicarbonate. The organic layer was dried ($Na_2SO_4$), concentrated and the residue was purified by column chromatography on silica gel, eluting with a gradient of 0-100% (3:1 EtOAc:EtOH+2% TEA) in heptane, to provide (S)-4-(7-chloro-8-fluoro-2-(((S)-tetrahydrofuran-3-yl)oxy)pyrido[4,3-d]pyrimidin-4-yl)-1,4-oxazepan-6-ol (0.32 g, 0.82 mmol, 78% yield). m/z (ESI): 385.0 $(M+H)^+$.

Intermediate BH: (S)-4-(7-chloro-8-fluoro-2-(((R)-tetrahydrofuran-3-yl)oxy)pyrido[4,3-d]pyrimidin-4-yl)-1,4-oxazepan-6-ol

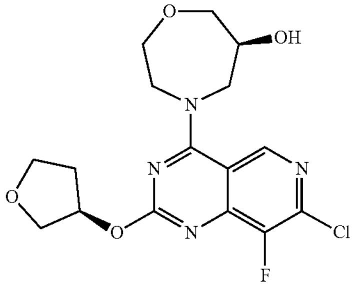 [SMILES: O[C@@H]1COCCN(c2nc(O[C@@H]3CCOC3)nc3c(F)c(Cl)ncc23)C1]

The compound was prepared in an analogous fashion as Intermediate BG using (R)-3-hydroxytetrahydrofuran (CAS #: 86087-24-3, AA Blocks LLC) in Step 3 to provide (S)-4-(7-chloro-8-fluoro-2-(((R)-tetrahydrofuran-3-yl)oxy)pyrido[4,3-d]pyrimidin-4-yl)-1,4-oxazepan-6-ol (m/z (ESI): 385.0 (M+H)$^+$.

Intermediate BI: (S)-4-(7-chloro-8-fluoro-2-((tetrahydro-1H-pyrrolizin-7a(5H)-yl)methoxy)pyrido[4,3-d]pyrimidin-4-yl)-1,4-oxazepan-6-ol

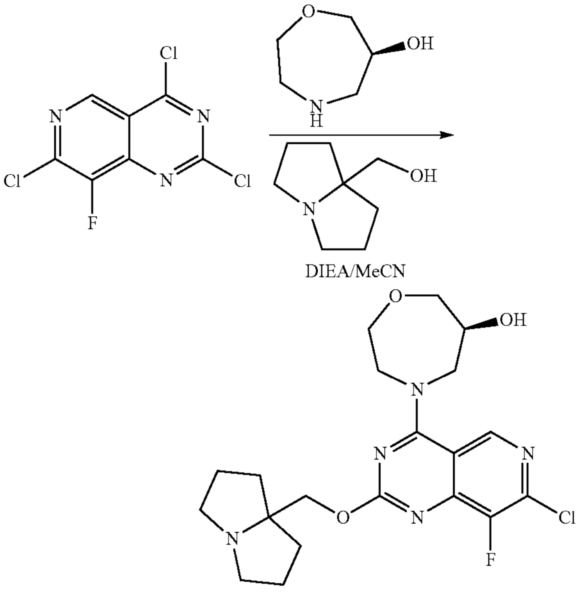

Intermediate BI

To a stirred solution of 2,4,7-trichloro-8-fluoropyrido[4,3-d]pyrimidine (0.50 g, 1.98 mmol, Enamine) in acetonitrile (8 mL) was added (S)-[1,4]oxazepan-6-ol (0.23 g, 1.98 mmol, J&W Pharmlab) and DIEA (1.7 mL, 9.9 mmol). The reaction mixture was stirred at 0° C. for 90 min. To the reaction was added then added hexahydro-1H-pyrrolizin-7a-ylmethanol (0.50 g, 3.57 mmol, Combi-Blocks Inc.), and the mixture was stirred at 80° C. for 8 h. After cooling to rt, the reaction mixture was concentrated under reduced pressure. The crude material was was purified by column chromatography on silica gel, eluting with a gradient of 0-70% (3:1 EtOAc: EtOH+2% TEA) in heptane, to yield (S)-4-(7-chloro-8-fluoro-2-((tetrahydro-1H-pyrrolizin-7a(5H)-yl)methoxy)pyrido[4,3-d]pyrimidin-4-yl)-1,4-oxazepan-6-ol (0.62 g, 1.41 mmol, 71% yield) as a yellow solid. m/z (ESI): 437.9 (M+H)$^+$.

Intermediate BJ: 3-Bromo-4-(3-((tert-butyldimethylsilyl)oxy)propyl)-5-chlorobenzonitrile

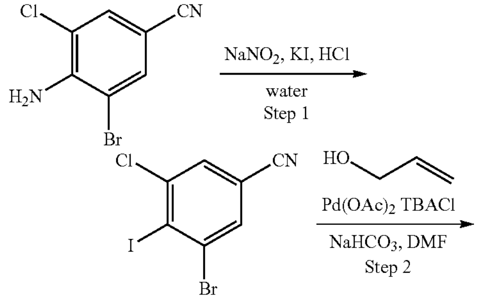

-continued

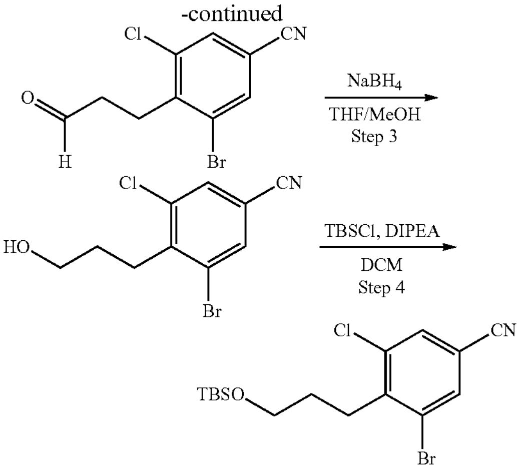

Intermediate BJ

Step 1. 3-Bromo-5-chloro-4-iodobenzonitrile. A 500-mL round-bottom flask was charged with 4-amino-3-bromo-5-chlorobenzonitrile (8.00 g, 34.6 mmol, Oakwood), water (40 mL) and hydrochloric acid, 37% (8.1 mL, 97 mmol). The reaction mixture was cooled to 0° C. and a solution of sodium nitrite (2.62 g, 38.0 mmol) in water (2 mL) was added dropwise, then the reaction mixture was stirred at 0° C. for 10 min. A solution of potassium iodide (6.88 g, 41.5 mmol) in water (2 mL) was then added dropwise, and the resulting slurry was removed from the cooling bath and warmed to rt and stirred for 4 h. The reaction was quenched via slow addition of saturated aqueous sodium thiosulfate (10%) and the mixture was extracted with EtOAc. The combined organic phases were washed with brine, dried over anhydrous sodium sulfate, filtered, and concentrated. The crude material was purified by column chromatography on silica gel, eluting with a gradient of 0-30% (3:1 EtOAc: EtOH) in heptane, to provide 3-bromo-5-chloro-4-iodobenzonitrile (4.34 g, 12.7 mmol, 37% yield) as light-yellow fluffy solid.

Step 2. 3-Bromo-5-chloro-4-(3-oxopropyl)benzonitrile. To a 20-mL vial was charged with 3-bromo-5-chloro-4-iodobenzonitrile (2.1 g, 6.1 mmol), sodium bicarbonate (1.29 g, 15.3 mmol), tetrabutylammonium chloride (1.71 g, 6.13 mmol), and N,N-dimethylformamide (12 mL). This reaction mixture was sparged with nitrogen, and then palladium(II) acetate (69 mg, 0.31 mmol) and allyl alcohol (0.63 mL, 9.2 mmol) were added at 50° C. The reaction was heated at 50° C. for 18 h. After cooling to rt, the reaction was diluted with saturated aqueous ammonium chloride and water. The aqueous layer was extracted with EtOAc, and the organics were washed with saturated aqueous sodium chloride, dried over sodium sulfate, and concentrated. The crude material was purified by column chromatography on silica gel, eluting with a gradient of 0-50% [3:1 EtOAc:EtOH] in heptane, to provide 3-bromo-5-chloro-4-(3-oxopropyl)benzonitrile (1.2 g, 4.4 mmol, 72% yield) as light-yellow solid.

Step 3. 3-Bromo-5-chloro-4-(3-hydroxypropyl)benzonitrile. To a 150-mL round-bottom flask was added 3-bromo-5-chloro-4-(3-oxopropyl)benzonitrile (2.24 g, 8.22 mmol) in tetrahydrofuran (12 mL)/methanol (12 mL). The reaction mixture was cooled to 0° C. Then, sodium borohydride (0.311 g, 8.22 mmol) was added in one portion. The reaction mixture was stirred at 0° C. for 15 min and was slowly quenched with saturated $NH_4Cl$ and extracted with EtOAc. The combined organic layers were washed with brine, dried over $MgSO_4$, filtered, and concentrated under reduced pressure. The crude material was purified by chromatography on silica gel, eluting with a gradient of 0-100% [3:1 EtOAc:EtOH] in heptane, to provide 3-bromo-5-chloro-4-(3-hydroxypropyl)benzonitrile (1.57 g, 5.72 mmol, 70% yield) as light-yellow solid.

Step 4. 3-Bromo-4-(3-((tert-butyldimethylsilyl)oxy)propyl)-5-chlorobenzonitrile. To a stirred solution of 3-bromo-5-chloro-4-(3-hydroxypropyl)benzonitrile (1.57 g, 5.72 mmol) and Hunig's base (1.1 mL, 6.3 mmol) in dichloromethane (20 mL) in a 100-mL round-bottom flask was added tert-butyldimethylsilyl chloride (0.95 g, 6.29 mmol) and 4-(dimethylamino)pyridine (35 mg, 0.29 mmol) at 0° C. The reaction was allowed to warm to rt. After 1 h, the reaction was concentrated under reduced pressure and the crude material was purified by chromatography on silica gel, eluting with a gradient of 0-40% [3:1 EtOAc:EtOH] in heptanes, to provide 3-bromo-4-(3-((tert-butyldimethylsilyl)oxy)propyl)-5-chlorobenzonitrile (2.03 g, 5.22 mmol, 91% yield) as colorless oil. $^1$H NMR (CHLOROFORM-d, 400 MHz) δ 7.75 (d, 1H, J=1.5 Hz), 7.61 (d, 1H, J=1.7 Hz), 3.74 (t, 2H, J=6.1 Hz), 3.0-3.1 (m, 2H), 1.7-1.8 (m, 2H), 0.92 (s, 9H), 0.08 (s, 6H). $^{13}$C NMR (CHLOROFORM-d, 101 MHz) δ 146.0, 135.8, 134.4, 131.8, 125.9, 116.2, 112.1, 62.5, 31.9, 31.5, 30.8, 25.9, 22.7, 18.3, 14.1, −5.3.

Intermediate BK: (S)-4-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-1,4-oxazepan-6-ol

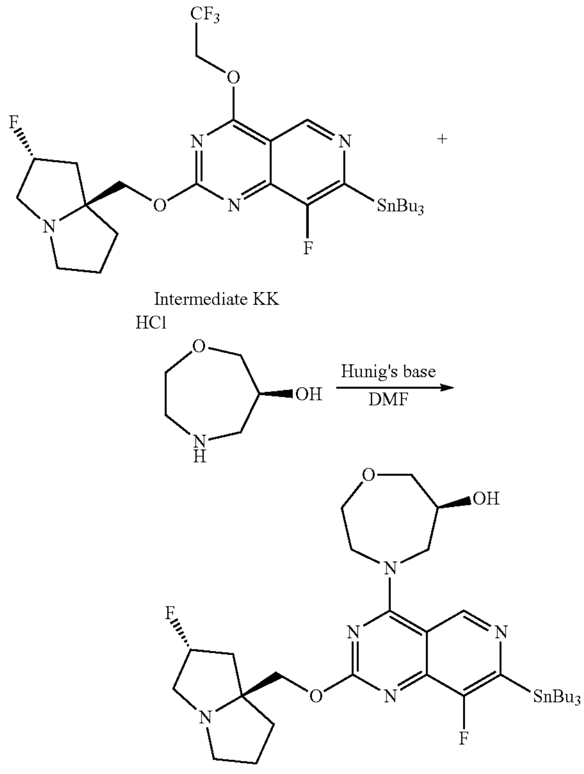

Intermediate BK

A screw-cap vial was charged with 8-fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d]pyrimidine (4.00 g, 5.77 mmol, Intermediate KK), (S)-1,4-oxazepan-6-ol hydrochloride (1.06 g, 6.92 mmol) and N,N-dimethylformamide (29 mL). N-ethyl-N-isopropylpropan-2-amine (5.0 mL, 28.8 mmol) was added dropwise, and the reaction mixture was heated to 40° C. for 3 h. The crude material was diluted with water and extracted with EtOAc. The combined organic phases were washed with aqueous LiCl, brine, dried over anhydrous sodium sulfate, filtered, and concentrated. The crude material was purified by chromatography on silica gel, eluting with a gradient of 0-50% (2% TEA in 3:1 EtOAc:EtOH)/heptane, to provide (S)-4-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-1,4-oxazepan-6-ol (0.30 g, 0.42 mmol, 7% yield) as light-yellow oil. m/z (ESI): 711.9 (M+H)$^+$.

Intermediate BL: (3-(2-Bromo-6-chlorophenyl)propoxy)(tert-butyl)dimethylsilane

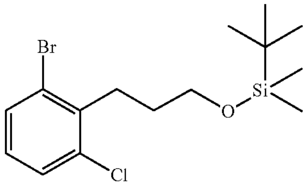 [SMILES: CC(C)(C)[Si](C)(C)OCCCc1c(Cl)cccc1Br]

This compound was made according to procedure described for Intermediate BJ Steps 2-4.

Intermediate BM: tert-Butyl(3-(2-chloro-6-(4,4,5,5-tetramethyl-1,3,2-dioxaborolan-2-yl)phenyl)propoxy)dimethylsilane

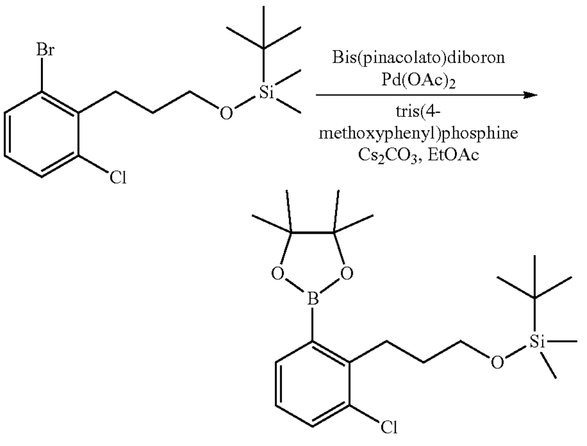

Intermediate BM

To a 6-mL vial was added cesium carbonate (443 mg, 1.36 mmol), 4,4,5,5-tetramethyl-1,3,2-dioxaborolane (0.35 g, 1.36 mmol) and (3-(2-bromo-6-chlorophenyl)propoxy)(tert-butyl)dimethylsilane (0.33 g, 0.91 mmol, Intermediate BL) in ethyl acetate (1.5 mL). The reaction was sparged with $N_2$ and $Pd(OAc)_2$ (20 mg, 0.091 mmol) and tris(4-methoxyphenyl)phosphine (35 mg, 0.10 mmol) were added. The vial was sealed under nitrogen and the reaction mixture was heated to 80° C. for 1 h. After cooling to rt, the reaction mixture was filtered through a pad of celite, rinsed with EtOAc. The filtrate was concentrated, and the residue was used in the next step without further purification.

Intermediate BN: 5-(2-((tert-Butyldimethylsilyl)oxy)ethyl)-6-methyl-1-(tetrahydro-2H-pyran-2-yl)-4-(4,4,5,5-tetramethyl-1,3,2-dioxaborolan-2-yl)-1H-indazole

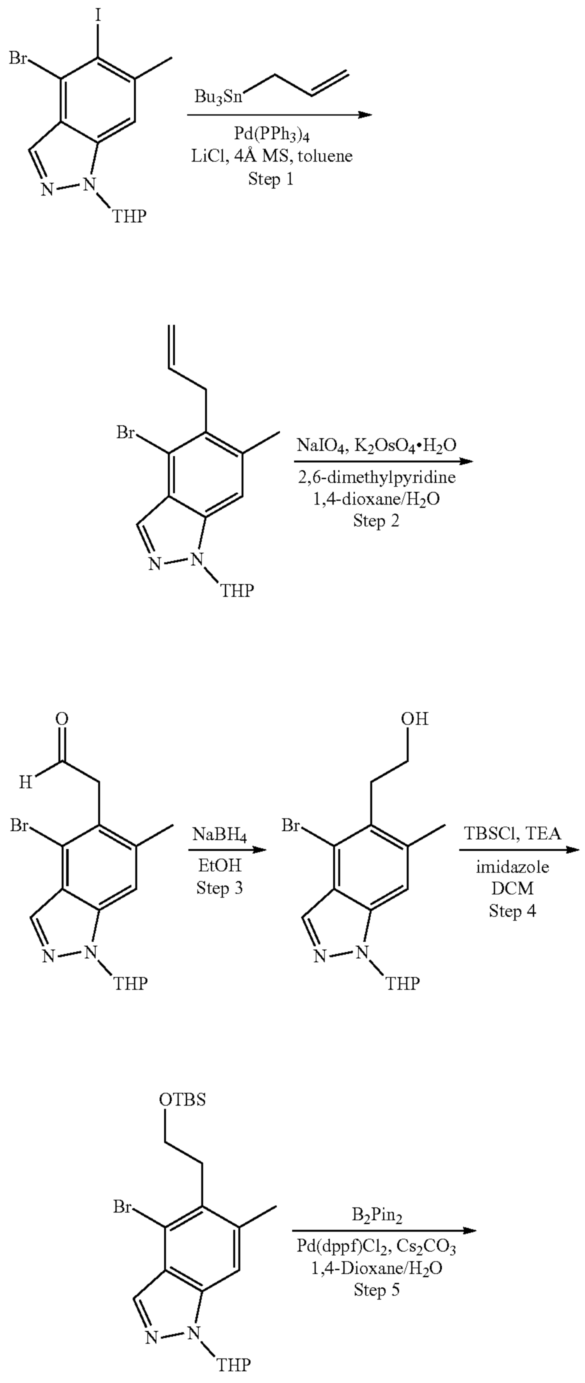

-continued

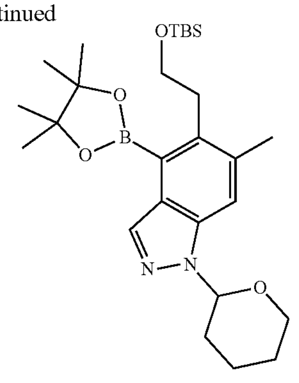

Intermediate BN

Step 1. 5-Allyl-4-bromo-6-methyl-1-(tetrahydro-2H-pyran-2-yl)-1H-indazole. To a solution of 4-bromo-5-iodo-6-methyl-1-(tetrahydro-2H-pyran-2-yl)-1H-indazole (120 g, 285 mmol) in toluene (1.2 L) was added 4 Å MS (40 g, 285 mmol), LiCl (59.8 g, 1.43 mol) and $Pd(PPh_3)_4$ (32.9 g, 28.5 mmol) under $N_2$. Then allyltributylstannane (132 g, 399 mmol) was added in one portion under $N_2$. The mixture was stirred at 110° C. for 12 h. After cooling to rt, the reaction mixture was diluted with water and extracted with ethyl acetate. The combined organics were dried over $Na_2SO_4$, filtered and the filtrate was concentrated under reduced pressure. The residue was purified by column chromatography on silica gel, eluting with a gradient of 1-100% ethyl acetate in petroleum ether, to give 5-allyl-4-bromo-6-methyl-1-(tetrahydro-2H-pyran-2-yl)-1H-indazole (80 g, 250 mmol, 87% yield) as yellow oil.

Step 2. 2-(4-Bromo-6-methyl-1-(tetrahydro-2H-pyran-2-yl)-1H-indazol-5-yl)acetaldehyde. To a solution of 5-allyl-4-bromo-6-methyl-1-(tetrahydro-2H-pyran-2-yl)-1H-indazole (40.0 g, 119 mmol) in 1,4-dioxane (800 mL) and water (400 mL) was added $K_2OsO_4 \cdot H_2O$ (1.98 g, 5.97 mmol) and 2,6-dimethylpyridine (38.4 g, 358 mmol), then sodium periodate (77.0 g, 358 mmol) was added and the reaction was stirred at rt for 2 h. The reaction mixture was quenched by addition of sat. $Na_2SO_3$ at 0° C. for 1 h. The reaction mixture was diluted with water and extracted with ethyl acetate. The combined organics were dried over $Na_2SO_4$, filtered and the filtrate was concentrated under reduced pressure. The residue was purified by column chromatography on silica gel, eluting with a gradient of 1-100% ethyl acetate in petroleum ether, to give 2-(4-bromo-6-methyl-1-(tetrahydro-2H-pyran-2-yl)-1H-indazol-5-yl)acetaldehyde (27.5 g, 82 mmol, 69% yield) as colorless oil.

Step 3. 2-(4-Bromo-6-methyl-1-(tetrahydro-2H-pyran-2-yl)-1H-indazol-5-yl)ethan-1-ol. To a solution of 2-(4-bromo-6-methyl-1-(tetrahydro-2H-pyran-2-yl)-1H-indazol-5-yl)acetaldehyde (40.0 g, 119 mmol) in ethanol (800 mL) was added sodium tetrahydroborate (13.5 g, 356 mmol) in portions at 0° C. Then the reaction was stirred at rt for 2 h under $N_2$. The reaction mixture was quenched by addition of sat. $NH_4Cl$ (1 L) at 0° C. The reaction mixture was diluted with water and extracted with ethyl acetate. The combined organics were dried over $Na_2SO_4$, filtered and the filtrate was concentrated under reduced pressure. The residue was purified by column chromatography on silica gel, eluting with a gradient of 1-100% ethyl acetate in petroleum ether, to give 2-(4-bromo-6-methyl-1-(tetrahydro-2H-pyran-2-yl)-1H-indazol-5-yl)ethan-1-ol (36.2 g, 107 mmol, 90% yield) as colorless oil. m/z (ESI): 339.0/341.0 $(M+H)^+$.

Step 4. 4-Bromo-5-(2-((tert-butyldimethylsilyl)oxy)ethyl)-6-methyl-1-(tetrahydro-2H-pyran-2-yl)-1H-indazole. To the mixture of 2-(4-bromo-6-methyl-1-(tetrahydro-2H-pyran-2-yl)-1H-indazol-5-yl)ethan-1-ol (40.0 g, 118 mmol) in dichloromethane (800 mL) was added imidazole (16.1 g, 236 mmol) and tert-butylchlorodimethylsilane (26.7 g, 177 mmol) in portions at 0° C., then TEA (23.0 mL, 165 mmol) was added dropwise under $N_2$. The mixture was stirred at rt for 4 h. The residue was diluted with water and extracted with dichloromethane. The combined organic layers were washed with brine, dried over $Na_2SO_4$, filtered, and concentrated under reduced pressure. The residue was purified by column chromatography on silica gel, eluting with a gradient of 1-100% ethyl acetate in petroleum ether, to give 4-bromo-5-(2-((tert-butyldimethylsilyl)oxy)ethyl)-6-methyl-1-(tetrahydro-2H-pyran-2-yl)-1H-indazole (52 g, 115 mmol, 97% yield) as colorless oil.

Step 5. 5-(2-((tert-Butyldimethylsilyl) oxy)ethyl)-6-methyl-1-(tetrahydro-2H-pyran-2-yl)-4-(4,4,5,5-tetramethyl-1,3,2-dioxaborolan-2-yl)-1H-indazole. To a solution of 4-bromo-5-(2-((tert-butyldimethylsilyl)oxy)ethyl)-6-methyl-1-(tetrahydro-2H-pyran-2-yl)-1H-indazole (40 g, 88 mmol) in 1,4-dioxane (800 mL) and water (100 mL) was added 4,4,4',4',5,5,5',5'-octamethyl-2,2'-bi(1,3,2-dioxaborolane) (112 g, 441 mmol), $Cs_2CO_3$ (119 mL, 265 mmol) and $Pd(dppf)Cl_2$ (6.45 g, 8.82 mmol) under $N_2$. The mixture was stirred at 120° C. for 2 h under $N_2$. After cooling to rt, the residue was diluted with water and extracted with dichloromethane. The combined organic layers were washed with brine, dried over $Na_2SO_4$, filtered, and concentrated. The residue was purified by reversed-phase MPLC to give 5-(2-((tert-butyldimethylsilyl) oxy)ethyl)-6-methyl-1-(tetrahydro-2H-pyran-2-yl)-4-(4,4,5,5-tetramethyl-1,3,2-dioxaborolan-2-yl)-1H-indazole (27.18 g, 54 mmol, 62% yield) as a colorless oil. $^1H$ NMR (400 MHz, $CDCl_3$) δ ppm 8.32 (s, 1H), 7.45 (s, 1H), 5.67-5.70 (m, 1H), 3.98-4.01 (m, 1H), 3.70-3.74 (m, 3H), 3.25-3.29 (m, 2H), 2.55-2.59 (m, 1H), 2.53 (s, 3H), 2.16-2.20 (m, 1H), 2.06-2.16 (m, 1H), 1.73-1.78 (m, 2H), 1.66-1.67 (m, 1H), 1.41 (s, 12H), 0.88 (s, 9H), 0.00 (s, 6H). m/z (ESI): 501.3/502.3 $(M+H)^+$.

Intermediate BO: tert-Butyldimethyl(2-(8-(4,4,5,5-tetramethyl-1,3,2-dioxaborolan-2-yl)naphthalen-1-yl)ethoxy)silane

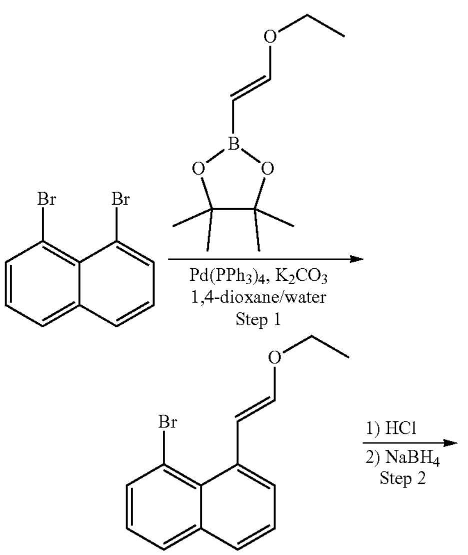

-continued

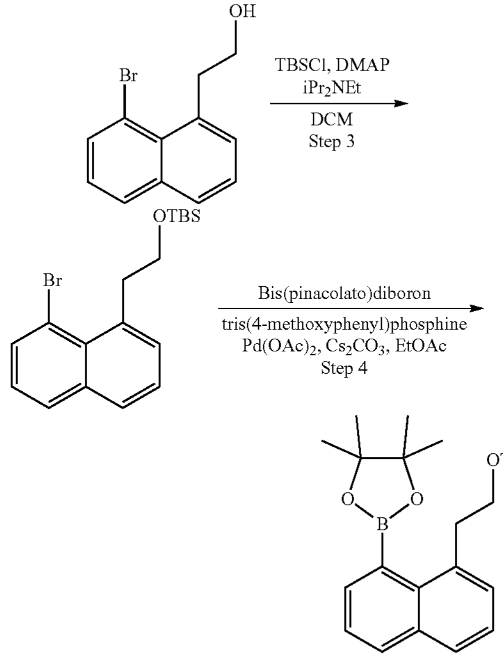

Intermediate BO

Step 1. (E)-1-Bromo-8-(2-ethoxyvinyl)naphthalene. A vial was charged with (E)-1-ethoxyethene-2-boronic acid pinacol ester (0.83 g, 4.20 mmol, Combi-Blocks Inc.), 1,8-dibromonaphtalene (1.00 g, 3.50 mmol), potassium carbonate (1.45 g, 10.5 mmol), $Pd(PPh_3)_4$ (0.20 g, 0.18 mmol) and degassed 1,4-dioxane (12 mL)/water (1.7 mL), then heated to 90° C. for 18 h. After cooling to rt, the reaction was diluted with water and extracted with EtOAc. The combined organic layers were washed with brine, dried over $MgSO_4$, filtered, and concentrated. The crude material was purified by column chromatography on silica gel, eluting with a gradient of 0-5% EtOAc in hexane, to provide (E)-1-bromo-8-(2-ethoxyvinyl)naphthalene (0.750 g, 2.71 mmol, 26% yield) as light yellow oil. $^1H$ NMR (400 MHz, CHLOROFORM-d) δ ppm 7.83 (dd, J=7.4, 1.1 Hz, 1H), 7.79 (dd, J=8.2, 1.0 Hz, 1H), 7.73 (t, J=4.8 Hz, 1H), 7.36-7.43 (m, 2H), 7.20-7.26 (m, 1H), 7.13 (d, J=12.3 Hz, 1H), 6.56 (d, J=12.5 Hz, 1H), 4.04 (q, J=7.0 Hz, 2H), 1.41 (t, J=7.0 Hz, 3H).

Step 2. 2-(8-Bromonaphthalen-1-yl)ethan-1-ol. To a 100-mL flask charged with (E)-1-bromo-8-(2-ethoxyvinyl)naphthalene (0.75 g, 2.71 mmol) in tetrahydrofuran (5 mL). Hydrochloric acid, 37% (1 mL) was added and the reaction mixture was stirred at rt for 1 h. The reaction was diluted with saturated aqueous $NaHCO_3$ and extracted with EtOAc. The combined organic layers were washed with brine, dried over $MgSO_4$, filtered, and concentrated. The crude mixture was dissolved in tetrahydrofuran (5 mL)/methanol (5 mL) and cooled down to 0° C. Sodium borohydride (0.15 g, 4.06 mmol) was added, and the reaction was stirred for 1 h, then diluted with water and extracted with EtOAc. The combined organic layers were washed with brine, dried over $MgSO_4$, filtered, and concentrated. The crude material was purified by column chromatography on silica gel, eluting with a gradient of 0-100% [3:1 EtOAc:EtOH] in heptane, to provide 2-(8-bromonaphthalen-1-yl)ethan-1-ol (0.51 g, 2.04 mmol, 75% yield) as yellow solid. m/z (ESI): 251.0 $(M+H)^+$. H NMR (400 MHz, CHLOROFORM-d) δ ppm 7.87 (dd, J=7.5, 1.3 Hz, 1H), 7.83 (dd, J=8.0, 1.1 Hz, 1H), 7.79 (dd, J=7.9, 1.7 Hz, 1H), 7.40-7.48 (m, 2H), 7.21-7.26 (m, 1H), 4.04 (t, J=6.8 Hz, 2H), 3.84-3.91 (m, 2H), 1.44 (br s, 1H).

Step 3. (2-(8-Bromonaphthalen-1-yl)ethoxy)(tert-butyl)dimethylsilane. To a stirred solution of 2-(8-bromonaphthalen-1-yl)ethan-1-ol (0.51 g, 2.04 mmol) and 1,1'-dimethyltriethylamine (0.39 mL, 2.24 mmol) in dichloromethane (7 mL) in a 40-mL vial was added tert-butyldimethylsilyl chloride (0.34 g, 2.24 mmol) and 4-(dimethylamino)pyridine (25 mg, 0.20 mmol) at 0° C. The reaction mixture was allowed to stir at 0° C. to rt for 4 h. The crude material was purified by column chromatography on silica gel, eluting with a gradient of 0-30% [3:1 EtOAc:EtOH] in heptane, to provide (2-(8-bromonaphthalen-1-yl)ethoxy)(tert-butyl)dimethylsilane (0.66 mg, 1.79 mmol, 88% yield) as yellow oil. m/z (ESI): 233.0 $(M+H-OTBS)^+$.

Step 4. tert-Butyldimethyl(2-(8-(4,4,5,5-tetramethyl-1,3,2-dioxaborolan-2-yl)naphthalen-1-yl)ethoxy)silane. To a 40 mL vial was charged with cesium carbonate (0.88 g, 2.69 mmol), 4,4,5,5-tetramethyl-1,3,2-dioxaborolane (0.55 g, 2.15 mmol) and (2-(8-bromonaphthalen-1-yl)ethoxy)(tert-butyl)dimethylsilane (0.66 g, 1.79 mmol) in ethyl acetate (1.8 mL). The reaction was flushed with $N_2$ for 5 minutes. To this was added $Pd(OAc)_2$ (40 mg, 0.18 mmol) and tris(4-methoxyphenyl)phosphine (70 mg, 0.20 mmol). The vial was sealed under $N_2$ and the reaction mixture was heated to 80° C. for 3 h. After cooling to rt, the reaction mixture was filtered through a pad of celite and rinsed with EtOAc. The filtrate was purified by chromatography on silica gel, eluting with a gradient of 0-50% [3:1 EtOAc:EtOH] in heptane, to provide tert-butyldimethyl(2-(8-(4,4,5,5-tetramethyl-1,3,2-dioxaborolan-2-yl)naphthalen-1-yl)ethoxy)silane (0.64 g, 1.55 mmol, 87% yield) as light-yellow oil. m/z (ESI): 413.3 $(M+H)^+$. $^1H$ NMR (400 MHz, CHLOROFORM-d) δ ppm 7.86 (dd, J=8.2, 1.3 Hz, 1H), 7.71 (dd, J=7.2, 2.2 Hz, 1H), 7.67 (dd, J=6.8, 1.4 Hz, 1H), 7.34-7.46 (m, 3H), 3.96 (t, J=7.4 Hz, 2H), 3.45 (t, J=7.4 Hz, 2H), 1.47 (s, 12H), 0.88 (s, 9H), 0.01-0.02 (s, 6H).

Intermediate BP: (R)-1-(7-chloro-8-fluoro-2-(((S)-1-methylpyrrolidin-2-yl)methoxy)pyrido[4,3-d]pyrimidin-4-yl)azepan-3-ol

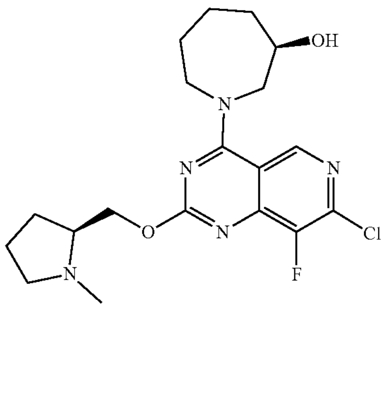 [SMILES: CN1CCC[C@H]1COc1nc(N2CCCC[C@@H](O)C2)c2cnc(Cl)c(F)c2n1]

The compound was prepared in an analogous fashion as Intermediate_UU adding (2S)-1-methyl-2-pyrrolidinemethanol (CAS #: 34381-71-0, Sigma-Aldrich Corporation) last in the procedure. m/z (ESI): 410.0 $(M+H)^+$.

Intermediate BQ: (S)-4-(7-Chloro-8-fluoro-2-(((S)-1-methylpyrrolidin-2-yl)methoxy)pyrido[4,3-d]pyrimidin-4-yl)-1,4-oxazepan-6-ol

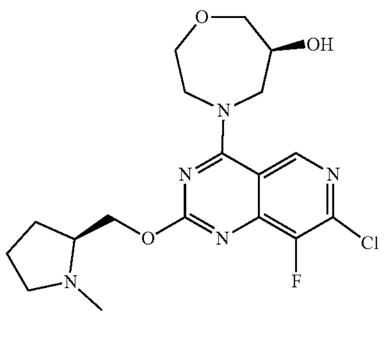 [SMILES: CN1CCC[C@H]1COc1nc(N2CCOC[C@@H](O)C2)c2cnc(Cl)c(F)c2n1]

The compound was prepared in an analogous fashion as Intermediate_BI adding (2S)-1-methyl-2-pyrrolidinemethanol (CAS #: 34381-71-0, Sigma-Aldrich Corporation) last in the procedure. m/z (ESI): 412.0 $(M+H)^+$.

Intermediate BR: (S)-4-(7-Chloro-8-fluoro-2-((tetrahydro-1H-pyrrolizin-7a(5H)-yl)methoxy)pyrido[4,3-d]pyrimidin-4-yl)-6-methyl-1,4-oxazepan-6-ol

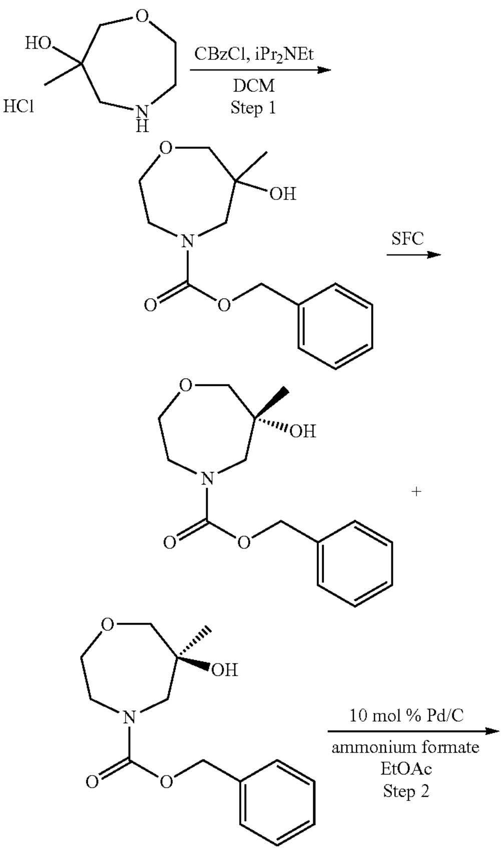

peak 1
eutomer

-continued

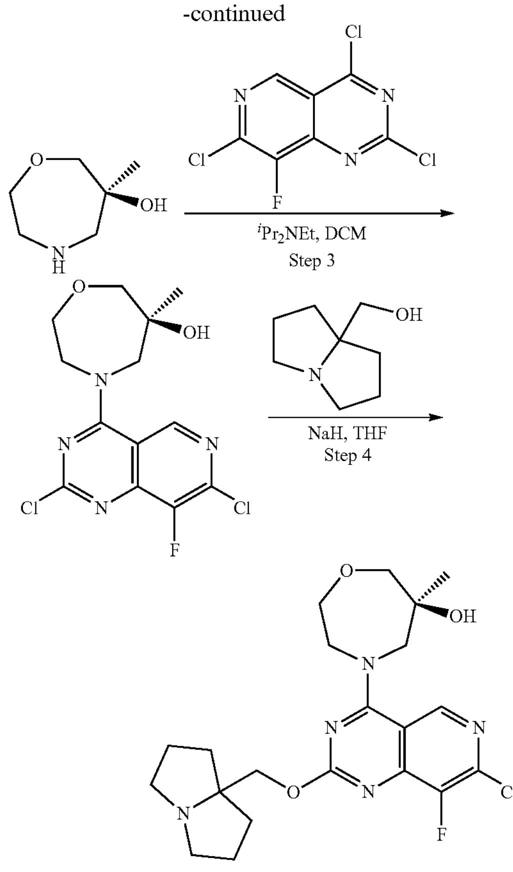

Intermediate BR

Step 1. Benzyl (S)-6-hydroxy-6-methyl-1,4-oxazepane-4-carboxylate. A 500-mL round-bottom flask was charged with 6-methyl-1,4-oxazepan-6-ol hydrochloride (10.0 g, 59.7 mmol, Ambeed, Inc.) and N,N-diisopropylethylamine (22.9 mL, 131 mmol) in dichloromethane (200 mL) at 0° C. under nitrogen. Benzyl chloroformate (8.9 mL, 63 mmol) was added dropwise and the mixture was stirred at 0° C. to rt for 2 h. The reaction was quenched with saturated aqueous ammonium chloride and extracted with DCM. The organic layer was washed with brine, dried over $Na_2SO_4$, filtered, and concentrated. The crude material was purified by column chromatography on silica gel, eluting with a gradient of 0-50% EtOAc in heptane, to provide the product as colorless oil. The reaction mixture was purified via SFC using a ChiralPak IF, 3×25 cm, 5 μm column with a mobile phase of 20% iPrOH with 0.2% DEA and using a flowrate of 160 mL/min. to generate 7.13 g of peak 1 with an ee of 99% as benzyl (S)-6-hydroxy-6-methyl-1,4-oxazepane-4-carboxylate and 7.26 g of peak 2 with an ee of 99% as benzyl (R)-6-hydroxy-6-methyl-1,4-oxazepane-4-carboxylate. m/z (ESI): 266.2 $(M+H)^+$.

Step 2. (S)-6-Methyl-1,4-oxazepan-6-ol. A mixture of benzyl (S)-6-hydroxy-6-methyl-1,4-oxazepane-4-carboxylate (6.00 g, 22.6 mmol), ammonium formate (7.13 g, 113 mmol), and palladium 5% on activated carbon (4.81 g, 2.26 mmol) in ethyl acetate (56 mL) was stirred at rt for 3 h. The mixture was filtered through a pad of celite, washed with EtOAc:EtOH (3:1). The filtrate was concentrated to yield (S)-6-methyl-1,4-oxazepan-6-ol (2.68 g, 20.4 mmol, 90% yield). m/z (ESI): 132.1 $(M+H)^+$.

Step 3. (S)-4-(2,7-Dichloro-8-fluoropyrido[4,3-d]pyrimidin-4-yl)-6-methyl-1,4-oxazepan-6-ol. A 20 ml vial was charged with 2,4,7-trichloro-8-fluoropyrido[4,3-d]pyrimidine (1.93 g, 7.62 mmol, Enamine), (S)-6-methyl-1,4-oxazepan-6-ol (1.00 g, 7.62 mmol), 1,1'-dimethyltriethylamine (7.6 mL, 31 mmol) in DCM (4 mL) at −78° C. After stirring for 5 min, the reaction was warmed to rt, then diluted with water and brine and extracted with DCM. The combined organic layers were dried with sodium sulfate, filtered, and concentrated. The crude was purified by column chromatography on silica gel, eluting with a gradient of 5-10% 3:1 EtOAc:EtOH in heptane, to afford (S)-4-(2,7-dichloro-8-fluoropyrido[4,3-d]pyrimidin-4-yl)-6-methyl-1,4-oxazepan-6-ol (1.57 g, 4.53 mmol, 59% yield) as white solid. m/z (ESI): 347.1 $(M+H)^+$.

Step 4. (S)-4-(7-Chloro-8-fluoro-2-((tetrahydro-1H-pyrrolizin-7a(5H)-yl)methoxy)pyrido[4,3-d]pyrimidin-4-yl)-6-methyl-1,4-oxazepan-6-ol. A 20 ml vial was charged with (tetrahydro-1H-pyrrolizin-7a(5H)-yl)methanol (0.70 g, 4.98 mmol, Combi-Blocks Inc.) in tetrahydrofuran (15 mL). The reaction mixture was cooled 0° C. and sodium hydride (60% in oil, 0.2 g, 5 mmol) was added. The reaction was stirred at 0° C. for 10 min. Then, (S)-4-(2,7-dichloro-8-fluoropyrido[4,3-d]pyrimidin-4-yl)-6-methyl-1,4-oxazepan-6-ol (1.57 g, 4.53 mmol) was added and the reaction mixture was stirred at 0° C. for 1 h. The mixture was carefully quenched with water and extracted with ethyl acetate. The combined organic layers were dried over $Na_2SO_4$, filtered, and concentrated. The crude was purified by column chromatography on silica gel, eluting with a gradient of 5-10% MeOH (with 10% 2 M $NH_3$) in DCM, to afford (S)-4-(7-chloro-8-fluoro-2-((tetrahydro-1H-pyrrolizin-7a(5H)-yl)methoxy)pyrido[4,3-d]pyrimidin-4-yl)-6-methyl-1,4-oxazepan-6-ol (0.57 g, 1.26 mmol, 28% yield) as yellow solid. m/z (ESI): 452.1 $(M+H)^+$.

Intermediate BS: (S)-4-(7-Chloro-8-fluoro-2-methylpyrido[4,3-d]pyrimidin-4-yl)-1,4-oxazepan-6-ol

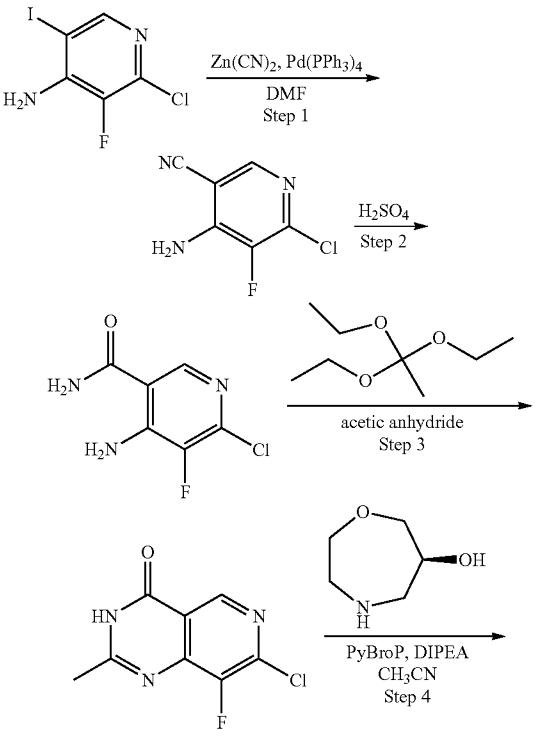

-continued

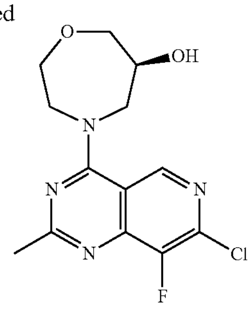

Intermediate BS

Step 1. 4-Amino-6-chloro-5-fluoronicotinonitrile. The mixture of 2-chloro-3-fluoro-5-iodopyridin-4-amine (3.00 g, 11.0 mmol), zinc cyanide (3.88 g, 33.0 mmol), and $Pd(PPh_3)_4$ (0.64 g, 0.55 mmol) in DMF (45 mL) was sparged with nitrogen and the reaction was stirred at 100° C. for 2 h. After cooling to rt, the reaction mixture was diluted with water and EtOAc. The precipitate was filtered off and the organic layer was separated, dried over $Na_2SO_4$, filtered, and concentrated to give 4-amino-6-chloro-5-fluoronicotinonitrile (2.2 g, crude) as white solid which was used directly for next step. m/z (ESI, +ve ion): 172.2 $(M+H)^+$.

Step 2. 4-Amino-6-chloro-5-fluoronicotinamide. 4-amino-6-chloro-5-fluoronicotinonitrile (1.89 g, 11.0 mmol) was dissolved in sulfuric acid (5.8 mL, 110 mmol) and the reaction mixture was stirred at 60° C. for 2 h. After cooling to rt, the mixture was slowly poured into ice water and neutralized with 10 M NaOH aqueous solution. The aqueous phase was extracted with EtOAc, and the combined organic phases were dried over $Na_2SO_4$ and concentrated to yield 4-amino-6-chloro-5-fluoronicotinamide (2.04 g, 10.8 mmol, 98% yield) as white solid. m/z (ESI, +ve ion): 190.2 $(M+H)^+$.

Step 3. 7-Chloro-8-fluoro-2-methylpyrido[4,3-d]pyrimidin-4(3H)-one. 4-Amino-6-chloro-5-fluoronicotinamide (0.94 g, 4.96 mmol) was suspended in acetic anhydride (3 mL) and 1,1,1-triethoxyethane (6.0 mL, 37 mmol). The reaction mixture was irradiated in microwave at 135° C. for 10 h. The yellow precipitate was collected by filtration and washed with heptane. The filtrate was concentrated and purified by column chromatography on silica gel, eluting with a gradient of 0-50% 3:1 EtOAc: EtOH with 2% $Et_3N$ in heptane, to afford 7-chloro-8-fluoro-2-methylpyrido[4,3-d]pyrimidin-4(3H)-one (0.77 g, 3.6 mmol, 73% yield) as yellow solid. m/z (ESI, +ve ion): 214.0 $(M+H)^+$.

Step 4. (S)-4-(7-Chloro-8-fluoro-2-methylpyrido[4,3-d]pyrimidin-4-yl)-1,4-oxazepan-6-ol.

To a stirred solution of 7-chloro-8-fluoro-2-methylpyrido[4,3-d]pyrimidin-4(3H)-one (0.21 g, 1.00 mmol) and bromotripyrrolidinophosphonium hexafluorophosphate (0.70 g, 1.50 mmol) in acetonitrile (4 mL) was added the solution of (S)-[1,4]oxazepan-6-ol (0.18 mL, 1.5 mmol) and N,N-diisopropylethylamine (0.87 mL, 4.99 mmol) in acetonitrile (3 mL). The resulting mixture was stirred at rt for 1 h. The reaction mixture was concentrated to yield (S)-4-(7-chloro-8-fluoro-2-methylpyrido[4,3-d]pyrimidin-4-yl)-1,4-oxazepan-6-ol which was used directly in the following step. m/z (ESI, +ve ion): 313.0 $(M+H)^+$.

Intermediate BT: rac-2-((1R,2R)-2-(4-Bromo-6-methyl-1-(tetrahydro-2H-pyran-2-yl)-1H-indazol-5-yl)cyclopropyl)ethyl methanesulfonate

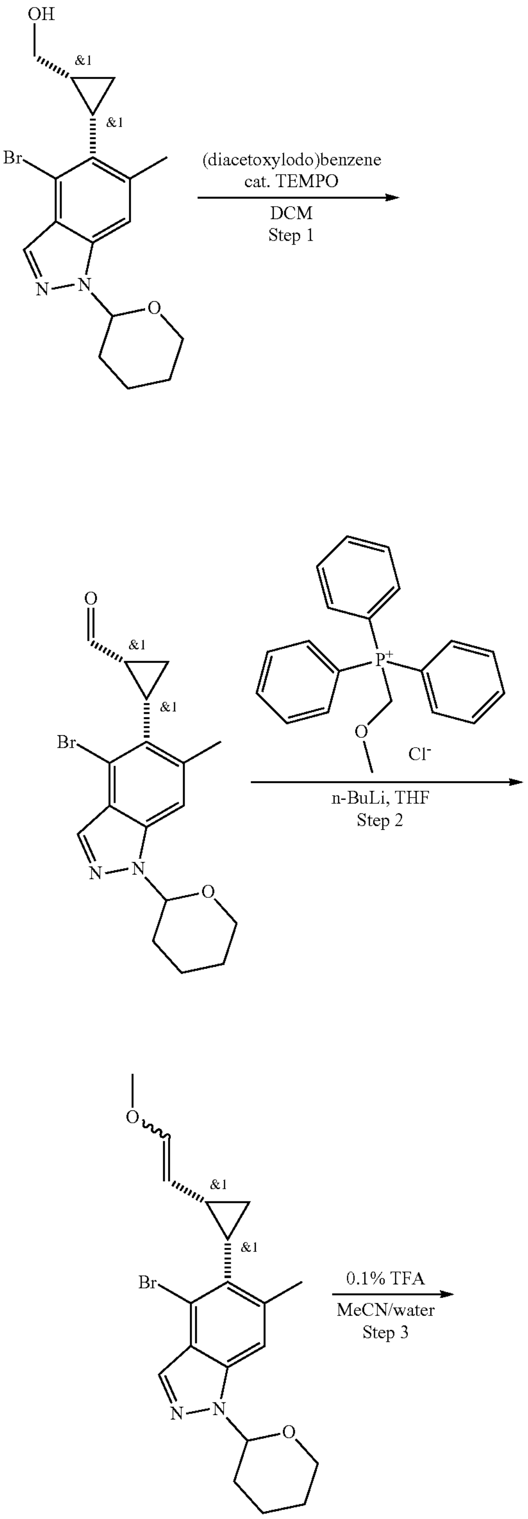

-continued

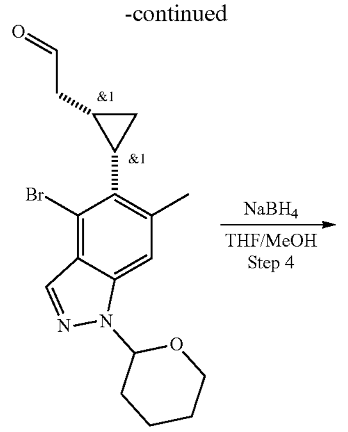

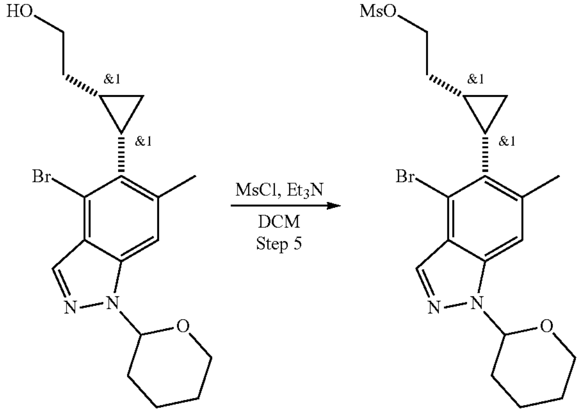

Intermediate BT

Step 1. rac-(1R,2S)-2-(4-Bromo-6-methyl-1-(tetrahydro-2H-pyran-2-yl)-1H-indazol-5-yl)cyclopropane-1-carbaldehyde. To a stirred solution of rac-((1R,2S)-2-(4-bromo-6-methyl-1-(tetrahydro-2H-pyran-2-yl)-1H-indazol-5-yl)cyclopropyl)methanol (3.82 g, 10.44 mmol, Intermediate LLLL) and (diacetoxyiodo)benzene (4.04 g, 12.5 mmol) in dichloromethane (35 mL) was added TEMPO, purified by sublimation (0.16 g, 1.04 mmol). The resulting mixture was stirred at rt for 72 h. The crude material was purified by chromatography on silica gel, eluting with a gradient of 0-100% [3:1 EtOAc:EtOH] in heptane, to provide rac-(1R,2S)-2-(4-bromo-6-methyl-1-(tetrahydro-2H-pyran-2-yl)-1H-indazol-5-yl)cyclopropane-1-carbaldehyde (3.60 g, 9.90 mmol, 95% yield) as light-yellow oil. m/z (ESI): 363.1 $(M+H)^+$.

Step 2. rac-4-Bromo-5-((1R,2S)-2-(2-methoxyvinyl)cyclopropyl)-6-methyl-1-(tetrahydro-2H-pyran-2-yl)-1H-indazole. In an oven-dried 250-mL round-bottom flask under nitrogen, a suspension of (methoxymethyl)triphenylphosphonium chloride (5.52 g, 16.1 mmol) and tetrahydrofuran (41 mL) was cooled to 0° C. and then n-butyl lithium (1.6 M in hexanes, 10.3 mL, 16.5 mmol) was added slowly (1 drop/second) and the reaction was allowed to stir at 0° C. After 20 min a solution of rac-(1R,2S)-2-(4-bromo-6-methyl-1-(tetrahydro-2H-pyran-2-yl)-1H-indazol-5-yl)cyclopropane-1-carbaldehyde (3.00 g, 8.26 mmol) in tetrahydrofuran (5 mL) was added dropwise and the reaction was allowed to stir at 0° C. to rt for 18 h. The reaction was quenched via the addition of saturated aqueous ammonium chloride and water. The layers were separated, and the aqueous layer was extracted with EtOAc. The organic layers were combined, dried with sodium sulfate, filtered, and concentrated. The crude material was purified by chromatography on silica gel, eluting with a gradient of 0-50% [3:1 EtOAc:EtOH] in heptanes, to provide a ~1:1 (E)/(Z) mixture of rac-4-bromo-5-((1R,2S)-2-((E)-2-methoxyvinyl)cyclopropyl)-6-methyl-1-(tetrahydro-2H-pyran-2-yl)-1H-indazole and rac-4-bromo-5-((1R,2S)-2-((Z)-2-methoxyvinyl)cyclopropyl)-6-methyl-1-(tetrahydro-2H-pyran-2-yl)-1H-indazole (1.51 g, 3.86 mmol, 47% yield). m/z (ESI): 391.1 $(M+H)^+$. $^1H$ NMR (400 MHz, CHLOROFORM-d) δ ppm 7.97 (s, 2H), 7.30-7.34 (m, 2H), 6.39 (d, J=12.5 Hz, 1H), 5.81 (d, J=6.3 Hz, 1H), 5.65 (dt, J=9.2, 3.0 Hz, 2H), 4.00-4.07 (m, 2H), 3.89-3.99 (m, 1H), 3.75 (td, J=11.0, 2.7 Hz, 2H), 3.62 (s, 3H), 3.46 (dt, J=10.1, 6.0 Hz, 1H), 3.26 (d, J=2.3 Hz, 3H), 2.50-2.59 (m, 9H), 2.33-2.43 (m, 1H), 2.03-2.19 (m, 6H), 1.88-1.96 (m, 1H), 1.49-1.82 (m, 10H).

Step 3. rac-2-((1R,2R)-2-(4-Bromo-6-methyl-1-(tetrahydro-2H-pyran-2-yl)-1H-indazol-5-yl)cyclopropyl)acetaldehyde. To a 20-mL vial was added rac-4-bromo-5-((1R,2S)-2-((E)-2-methoxyvinyl)cyclopropyl)-6-methyl-1-(tetrahydro-2H-pyran-2-yl)-1H-indazole (1.50 g, 3.83 mmol) in acetonitrile with 0.1% TFA (15 mL)/water with 0.1% TFA (7.5 mL). The reaction mixture was stirred at 55° C. for 12 h, the reaction was diluted with water and extracted with EtOAc. The combined organic layers were washed with brine, dried over $MgSO_4$, filtered, and concentrated. The crude material was purified by column chromatography on silica gel, eluting with a gradient of 0-40% [3:1 EtOAc:EtOH] in heptane, to provide rac-2-((1R,2R)-2-(4-bromo-6-methyl-1-(tetrahydro-2H-pyran-2-yl)-1H-indazol-5-yl)cyclopropyl)acetaldehyde (0.80 g, 2.12 mmol, 55% yield) as colorless oil. m/z (ESI): 377.1 $(M+H)^+$.

Step 4. rac-2-((1R,2R)-2-(4-Bromo-6-methyl-1-(tetrahydro-2H-pyran-2-yl)-1H-indazol-5-yl)cyclopropyl)ethan-1-ol. To a 100-mL round-bottom flask was added rac-2-((1R,2R)-2-(4-bromo-6-methyl-1-(tetrahydro-2H-pyran-2-yl)-1H-indazol-5-yl)cyclopropyl)acetaldehyde (0.80 g, 2.12 mmol) in tetrahydrofuran (5 mL)/methanol (5 mL). The reaction mixture was cooled to 0° C. Sodium borohydride (96 mg, 2.54 mmol) was slowly added in portions. The reaction was stirred at 0° C. for 1 h, then was quenched with slow addition of saturated $NH_4Cl$ and extracted with EtOAc. The combined organic layers were washed with brine, dried over $MgSO_4$, filtered, and concentrated to give rac-2-((1R,2R)-2-(4-bromo-6-methyl-1-(tetrahydro-2H-pyran-2-yl)-1H-indazol-5-yl)cyclopropyl)ethan-1-ol (0.80 g, 2.10 mmol, 99% yield) as colorless oil without further purification. m/z (ESI, +ve ion): 379.0 $(M+H)^+$.

Step 5. rac-2-((1R,2R)-2-(4-Bromo-6-methyl-1-(tetrahydro-2H-pyran-2-yl)-1H-indazol-5-yl)cyclopropyl)ethyl methanesulfonate. To a 40-mL pressure relief vial was added rac-2-((1R,2R)-2-(4-bromo-6-methyl-1-(tetrahydro-2H-pyran-2-yl)-1H-indazol-5-yl)cyclopropyl)ethan-1-ol (0.41 g, 1.07 mmol) and triethylamine (0.18 mL, 1.3 mmol) in dichloromethane (4 mL). Methanesulfonyl chloride (0.10 mL, 1.3 mmol) was added slowly at 0° C. and the resulting mixture was stirred at 0° C. for 1 h. The reaction mixture was diluted with water and extracted with DCM. The organic layer was dried over $MgSO_4$, filtered, and concentrated under reduced pressure to give rac-2-((1R,2R)-2-(4-bromo-6-methyl-1-(tetrahydro-2H-pyran-2-yl)-1H-indazol-5-yl)cyclopropyl)ethyl methanesulfonate (0.48 g, 1.04 mmol, 97% yield) was obtained as light yellow oil without further purification. m/z (ESI): 457.1 $(M+H)^+$.

Intermediate BU: rac-5-((1S, 2R)-2-(((tert-Butyldimethylsilyl)oxy)methyl) cyclopropyl)-6-methyl-1-(tetrahydro-2H-pyran-2-yl)-4-(4,4,5,5-tetramethyl-1,3,2-dioxaborolan-2-yl)-1H-indazole

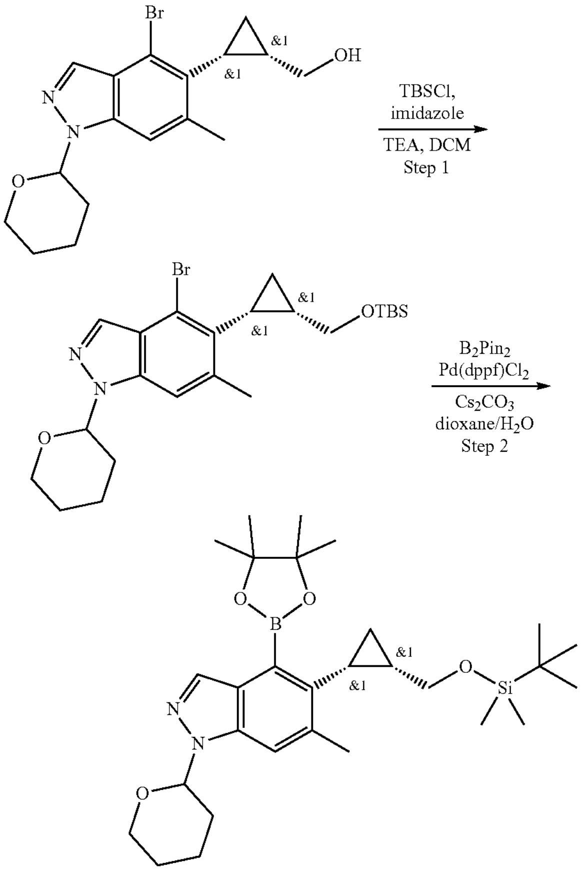

Intermediate BU

Step 1. 4-Bromo-5-((1R, 2S)-2-(((tert-butyldimethylsilyl)oxy) methyl)cyclopropyl)-6-methyl-1-(tetrahydro-2H-pyran-2-yl)-1H-indazole. To a solution of ((1S,2R)-2-(4-bromo-6-methyl-1-(tetrahydro-2H-pyran-2-yl)-1H-indazol-5-yl)cyclopropyl)methanol (50.00 g, 137 mmol) in dichloromethane (1-L) was added tert-butylchlorodimethylsilane (30.9 g, 205 mmol), TEA (26.7 mL, 192 mmol) and imidazole (18.6 g, 274 mmol) in sequence at 0° C. The mixture was stirred at rt for 12 h. The residue was diluted with water and extracted with DCM. The combined organic layers were washed with brine, dried over $Na_2SO_4$, filtered, and concentrated under reduced pressure. The residue was purified by column chromatography on silica gel, eluting with a gradient of 1-50% ethyl acetate in petroleum ether, to give 4-bromo-5-((1R, 2S)-2-(((tert-butyldimethylsilyl)oxy) methyl)cyclopropyl)-6-methyl-1-(tetrahydro-2H-pyran-2-yl)-1H-indazole (61.90 g, 129 mmol, 95% yield) as yellow oil.

Step 2. rac-5-((1S, 2R)-2-(((tert-Butyldimethylsilyl)oxy) methyl) cyclopropyl)-6-methyl-1-(tetrahydro-2H-pyran-2-yl)-4-(4,4,5,5-tetramethyl-1,3,2-dioxaborolan-2-yl)-1H-indazole. To a solution of 4-bromo-5-((1R, 2S)-2-(((tert-butyldimethylsilyl)oxy) methyl)cyclopropyl)-6-methyl-1-(tetrahydro-2H-pyran-2-yl)-1H-indazole (40 g, 83 mmol) in 1,4-dioxane (800 mL) was added 4,4,4',4',5,5,5',5'-octamethyl-2,2'-bi(1,3,2-dioxaborolane) (127 g, 500 mmol) and $Cs_2CO_3$ (82 g, 250 mmol) in water (50 mL) under $N_2$. Then Pd(dppf)C2 (6.10 g, 8.34 mmol) was added in one portion under $N_2$. Then the mixture was stirred at 120° C. for 2 h. After cooling to rt, the reaction mixture was diluted with water and extracted with EtOAc. The combined organic layers were washed with brine, dried over $Na_2SO_4$, filtered, and concentrated under reduced pressure. The residue was purified by column chromatography on silica gel, eluting with a gradient of 1-10% ethyl acetate in petroleum ether, to give rac-5-((1S, 2R)-2-(((tert-butyldimethylsilyl)oxy) methyl) cyclopropyl)-6-methyl-1-(tetrahydro-2H-pyran-2-yl)-4-(4,4,5,5-tetramethyl-1,3,2-dioxaborolan-2-yl)-1H-indazole as (29.0 g, 55.1 mmol, 66% yield) as brown oil. $^1H$ NMR (400 MHz, DMSO-$d_6$) δ ppm 7.93 (s, 1H), 7.52 (s, 1H), 5.76 (d, J=9.6 Hz, 1H), 3.84-3.87 (m, 1H), 3.71-3.74 (m, 1H), 2.90-3.10 (m, 2H), 2.52 (s, 3H), 2.37-2.41 (m, 2H), 2.22-2.24 (m, 1H), 2.01-2.11 (m, 1H), 1.92-1.98 (m, 1H), 1.65-1.75 (m, 1H), 1.47-1.57 (m, 2H) 1.41 (s, 6H), 1.34 (s, 6H), 1.15-1.17 (m, 1H), 0.74 (s, 9H), 0.62-0.72 (m, 1H), −0.2-(−0.18) (m, 6H). m/z (ESI): 527.4/528.4 $(M+H)^+$.

Intermediate BV: tert-Butyl (S)-3-(2-(2-(2-fluoro-8-iodonaphthalen-1-yl)ethoxy)ethyl)piperidine-1-carboxylate

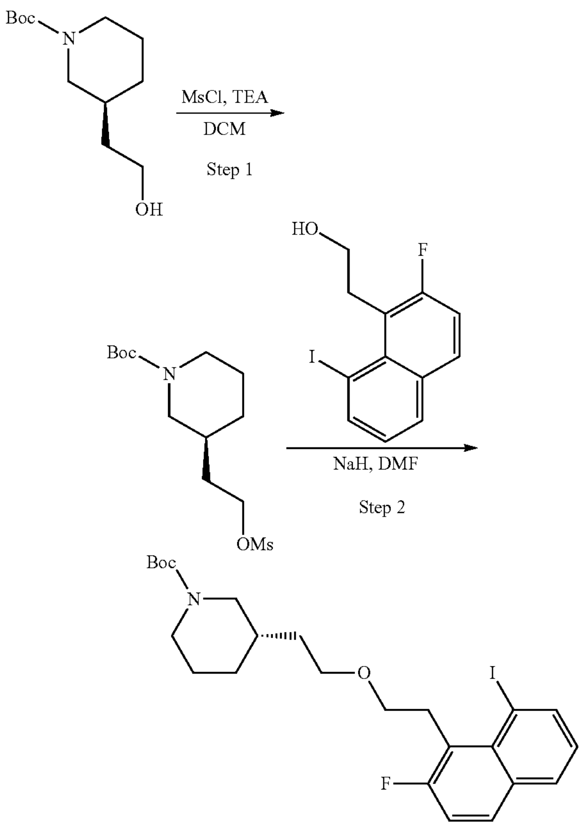

Intermediate BV

Step 1. tert-Butyl (S)-3-(2-((methylsulfonyl)oxy)ethyl)piperidine-1-carboxylate. To a solution of tert-butyl (S)-3-(2-hydroxyethyl)piperidine-1-carboxylate (2.00 g, 8.72 mmol, Enamine) in dichloromethane (20 mL) at 0° C. was added TEA (3.6 mL, 26.2 mmol) followed by methanesulfonyl chloride (2.65 g, 23.1 mmol). The resulting mixture was stirred at 0° C. for 5 h then treated with water and extracted with DCM. The combined organic layers were dried over $Na_2SO_4$, filtered, and concentrated under reduced pressure. The residue was purified by column chromatography on silica gel, eluting with a gradient of 0-5% EtOAc in petroleum ether, to provide tert-butyl (S)-3-(2-((methylsulfonyl)oxy)ethyl)piperidine-1-carboxylate (2.20 g, 7.16 mmol, 82% yield) as yellow oil. m/z (ESI): 308.1 $(M+H)^+$.

Step 2. tert-Butyl (S)-3-(2-(2-(2-fluoro-8-iodonaphthalen-1-yl)ethoxy)ethyl)piperidine-1-carboxylate. To a solution of 2-(2-fluoro-8-iodonaphthalen-1-yl)ethan-1-ol (Intermediate QQ, Step 3, 0.2 g, 0.63 mmol) in N,N-dimethylformamide (5 mL) at 0° C. was added NaH (60 wt % in mineral oil, 89 mg, 2.2 mmol). After stirring at rt for 1 h, the mixture was treated with tert-butyl (S)-3-(2-((methylsulfonyl)oxy)ethyl)piperidine-1-carboxylate (0.41 g, 1.33 mmol), then stirred at rt for 2 h. The reaction mixture was cooled in an ice bath and quenched by the addition of saturated $NH_4Cl$ solution and extracted with ethyl acetate. The combined organic layers were dried over $Na_2SO_4$, filtered, and concentrated. The residue was purified by column chromatography on silica gel, eluting with a gradient of 0-5% EtOAc in petroleum ether, to give tert-butyl (S)-3-(2-(2-(2-fluoro-8-iodonaphthalen-1-yl)ethoxy)ethyl)piperidine-1-carboxylate (0.12 g, 0.22 mmol, 34% yield) as yellow oil. m/z (ESI): 528.1 $(M+H)^+$.

Intermediate BW: 3-(4-Bromo-6-chloro-1-(tetrahydro-2H-pyran-2-yl)-1H-indazol-5-yl)propyl methanesulfonate

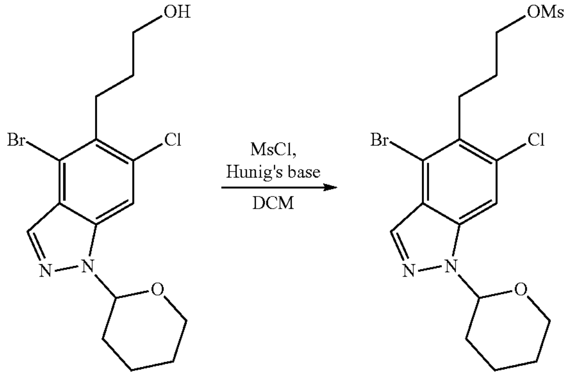

Intermediate BW

To a 40-mL pressure relief vial was charged with 3-(4-bromo-6-chloro-1-(tetrahydro-2H-pyran-2-yl)-1H-indazol-5-yl)propan-1-ol (0.97 g, 2.61 mmol, Intermediate FFF Step 2) and 1,1'-dimethyltriethylamine (0.59 mL, 3.4 mmol) in dichloromethane (5 mL). Then, methanesulfonyl chloride (0.22 mL, 2.9 mmol) was added slowly at 0° C. and the resulting mixture was stirred at 0° C. for 1.5 h. The reaction mixture was diluted with water and extracted with DCM. The organic layer was dried over $MgSO_4$, filtered, and concentrated under reduced pressure to give 3-(4-bromo-6-chloro-1-(tetrahydro-2H-pyran-2-yl)-1H-indazol-5-yl)propyl methanesulfonate (1.18 g, 2.61 mmol, 100% yield) as orange oil. m/z (ESI): 451.1 $(M+H)^+$.

Intermediate BX: 4-(tert-Butoxy)-8-fluoro-2-(((2R,7aS)-2-fluorotetrahydro-1H-pyrrolizin-7a(5H)-yl)methoxy)-7-(tributylstannyl)pyrido[4,3-d]pyrimidine

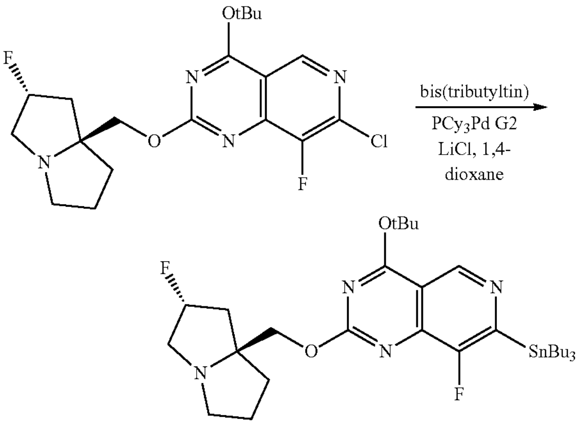

Intermediate BX

To a solution of 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (34 g, 82 mmol, Intermediate JJ) in 1,4-dioxane (680 mL) was added $PCy_3$ Pd G2 (19.5 g, 32.9 mmol) and LiCl (17.5 g, 412 mmol), then bis(tributyltin) (177 g, 305 mmol) was added in one portion under $N_2$. The mixture was stirred at 80° C. for 36 h under $N_2$. After cooling to rt, the reaction was filtered, and the filtrate was diluted with water and extracted with ethyl acetate. The combined organic layers were dried over $Na_2SO_4$, filtered, and concentrated under reduced pressure. The residue was purified by column chromatography on silica gel, eluting with 0-7% ethyl acetate in petroleum ether, to provide 4-(tert-butoxy)-8-fluoro-2-(((2R,7aS)-2-fluorotetrahydro-1H-pyrrolizin-7a(5H)-yl)methoxy)-7-(tributylstannyl)pyrido[4,3-d]pyrimidine (29.8 g, 44.7 mmol, 54% yield) as yellow oil. $^1H$ NMR (400 MHz, $CDCl_3$) δ ppm 9.21 (s, 1H), 5.21-5.36 (m, 1H), 4.20-4.29 (m, 2H), 3.24-3.28 (m, 2H), 2.05-2.30 (m, 3H), 1.80-2.05 (m, 4H), 1.34-1.60 (m, 9H), 1.20-1.32 (m, 18H), 0.86-0.93 (m, 9H). m/z (ESI): 667.4/669.4 $(M+H)^+$.

Intermediate BY: tert-Butyl 6-(6-(4-bromo-6-chloro-1-(tetrahydro-2H-pyran-2-yl)-1H-indazol-5-yl)-2-oxohexyl)-1,4-oxazepane-4-carboxylate

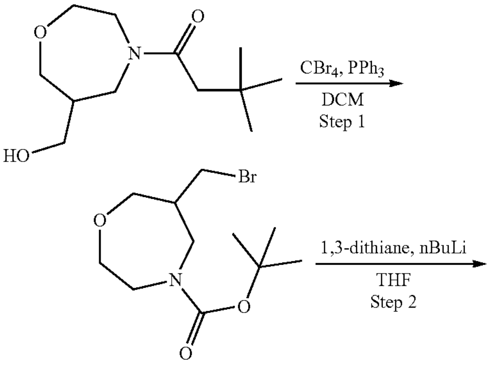

-continued

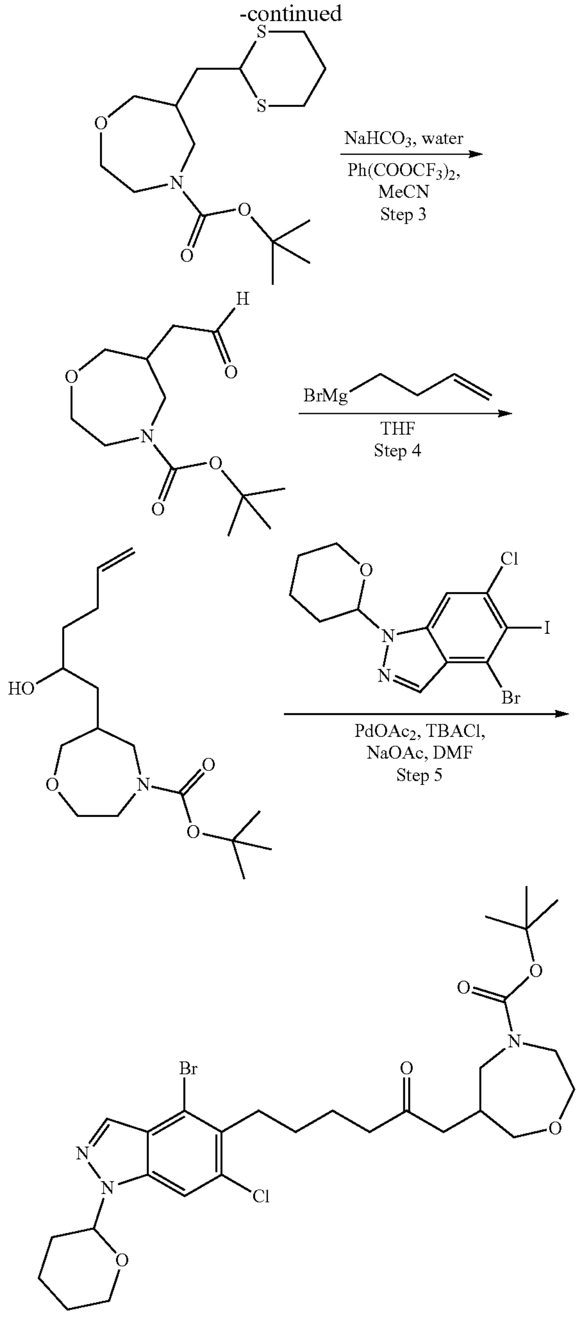

Intermediate BY

Step 1. tert-Butyl 6-(Bromomethyl)-1,4-oxazepane-4-carboxylate. A 150 mL flask was charged with tert-butyl 6-(hydroxymethyl)-1,4-oxazepane-4-carboxylate (3.50 g, 15.1 mmol, Pharmablock, Inc.), triphenylphosphine (7.94 g, 30.3 mmol), and dichloromethane (56 mL). The mixture was cooled to 0° C. and carbon tetrabromide (10.0 g, 30.3 mmol) in dichloromethane (19 mL) was added dropwise. The mixture was stirred for 4 h at rt. The volatiles were removed under reduced pressure to give yellow sticky oil which was purified by column chromatography on silica gel, eluting with a gradient of 0-80% EtOAc in heptane, to provide tert-butyl 6-(bromomethyl)-1,4-oxazepane-4-carboxylate (4.45 g, 15.1 mmol, 100% yield). $^1$H NMR (400 MHz, CHLOROFORM-d) δ ppm 3.57-3.82 (m, 6H), 3.32-3.48 (m, 4H), 2.36-2.49 (m, 1H), 1.50 (br d, J=8.2 Hz, 9H).

Step 2. tert-Butyl 6-((1,3-dithian-2-yl)methyl)-1,4-oxazepane-4-carboxylate. A dried 50 mL flask was charged with 1,3-dithiane (0.83 g, 6.90 mmol, CombiBlocks) and tetrahydrofuran (21 mL). The mixture was cooled to −20° C. and n-butyllithium (2.5 M in hexanes, 2.70 mL, 6.75 mmol) was added dropwise. The mixture was stirred at −20° C. for 2 h. The mixture was cooled to −78° C. and tert-butyl 6-(bromomethyl)-1,4-oxazepane-4-carboxylate (1.44 g, 4.93 mmol) in THF (2 mL) was added. After 2.5 h of stirring at −78° C. the reaction was quenched by the addition of aq. saturated ammonium chloride solution and the mixture was extracted with EtOAc. The combined organic phases were dried with sodium sulfate, filtered, and concentrated. The residue purified by column chromatography on silica gel, eluting with a gradient of 0-60% EtOAc in heptane, to provide tert-butyl 6-((1,3-dithian-2-yl)methyl)-1,4-oxazepane-4-carboxylate (1.30 g, 3.92 mmol, 80% yield) as white solid. m/z (ESI): 356.2 $(M+Na)^+$.

Step 3. tert-Butyl 6-(2-oxoethyl)-1,4-oxazepane-4-carboxylate. A vial was charged with tert-butyl 6-((1,3-dithian-2-yl)methyl)-1,4-oxazepane-4-carboxylate (0.30 g, 0.90 mmol), acetonitrile (1.6 mL) and water (180 μL). Sodium hydrogen carbonate (0.23 g, 2.70 mmol) was added and the reaction was cooled to 0° C. Phenyl-13-iodanediyl bis(2,2,2-trifluoroacetate) (0.87 g, 2.02 mmol) was added and the reaction mixture was stirred at 0° C. for 1.5 h. The reaction was quenched with saturated aqueous sodium thiosulfate solution and extracted with EtOAc. The combined organic phases were dried over sodium sulfate, filtered, and concentrated. The residue purified by column chromatography on silica gel, eluting with a gradient of 0-100% EtOAc in heptane, to provide to yield tert-butyl 6-(2-oxoethyl)-1,4-oxazepane-4-carboxylate (70 mg, 0.29 mmol, 32% yield) as colorless oil. m/z (ESI): 266.2 $(M+Na)^+$.

Step 4. tert-Butyl 6-(2-hydroxyhex-5-en-1-yl)-1,4-oxazepane-4-carboxylate. A 20 mL vial was charged with tert-butyl 6-(2-oxoethyl)-1,4-oxazepane-4-carboxylate (70 mg, 0.29 mmol) in tetrahydrofuran (1.5 mL) and the mixture was cooled to 0° C. But-3-en-1-ylmagnesium bromide (1.2 mL, 0.58 mmol) was added dropwise. After 10 minutes the reaction was poured into a saturated aqueous ammonium chloride solution and extracted with EtOAc. The combined organic layers were dried over sodium sulfate, filtered, and concentrated. The crude was purified by column chromatogrphy on silica gel, eluting with a gradient of 0-100% EtOAc in heptane, to give tert-butyl 6-(2-hydroxyhex-5-en-1-yl)-1,4-oxazepane-4-carboxylate (85 mg, 0.30 mmol, 98% yield) as colorless liquid. m/z (ESI): 322.2 $(M+Na)^+$.

Step 5. tert-Butyl 6-(6-(4-bromo-6-chloro-1-(tetrahydro-2H-pyran-2-yl)-1H-indazol-5-yl)-2-oxohexyl)-1,4-oxazepane-4-carboxylate. A 5 mL vial was charged with tert-butyl 6-(2-hydroxyhex-5-en-1-yl)-1,4-oxazepane-4-carboxylate (85 mg, 0.30 mmol), 4-bromo-6-chloro-5-iodo-1-(tetrahydro-2H-pyran-2-yl)-1H-indazole (0.16 g, 0.36 mmol, Pharmablock, Inc.), sodium bicarbonate (62 mg, 0.74 mmol), tetrabutylammonium chloride (78 mg, 0.30 mmol), and N,N-dimethylformamide (0.6 mL). The solution was degased for 10 minutes and then heated at 65° C. Palladium (II) acetate (3.3 mg, 0.015 mmol) was added. The reaction mixture was heated at 65° C. for 15 h. After cooling to rt, the reaction was diluted with ethyl acetate and saturated aqueous ammonium chloride. The aqueous layer was extracted with ethyl acetate and the combined organic layers were dried over sodium sulfate, filtered, and concentrated. The crude was purified by column chromatogrphy on silica gel, eluting with a gradient of 0-40% EtOAc in heptane, to give tert-butyl 6-(6-(4-bromo-6-chloro-1-(tetrahydro-2H-pyran- 2-yl)-1H-indazol-5-yl)-2-oxohexyl)-1,4-oxazepane-4-carboxylate (81 mg, 0.14 mmol, 46% yield) as yellow oil. m/z (ESI): 634.2 $(M+Na)^+$.

Intermediate BZ: tert-Butyl (3S)-3-((5-(2-(4-bromo-6-chloro-1-(tetrahydro-2H-pyran-2-yl)-1H-indazol-5-yl)ethyl)oxazol-2-yl)methyl)piperidine-1-carboxylate

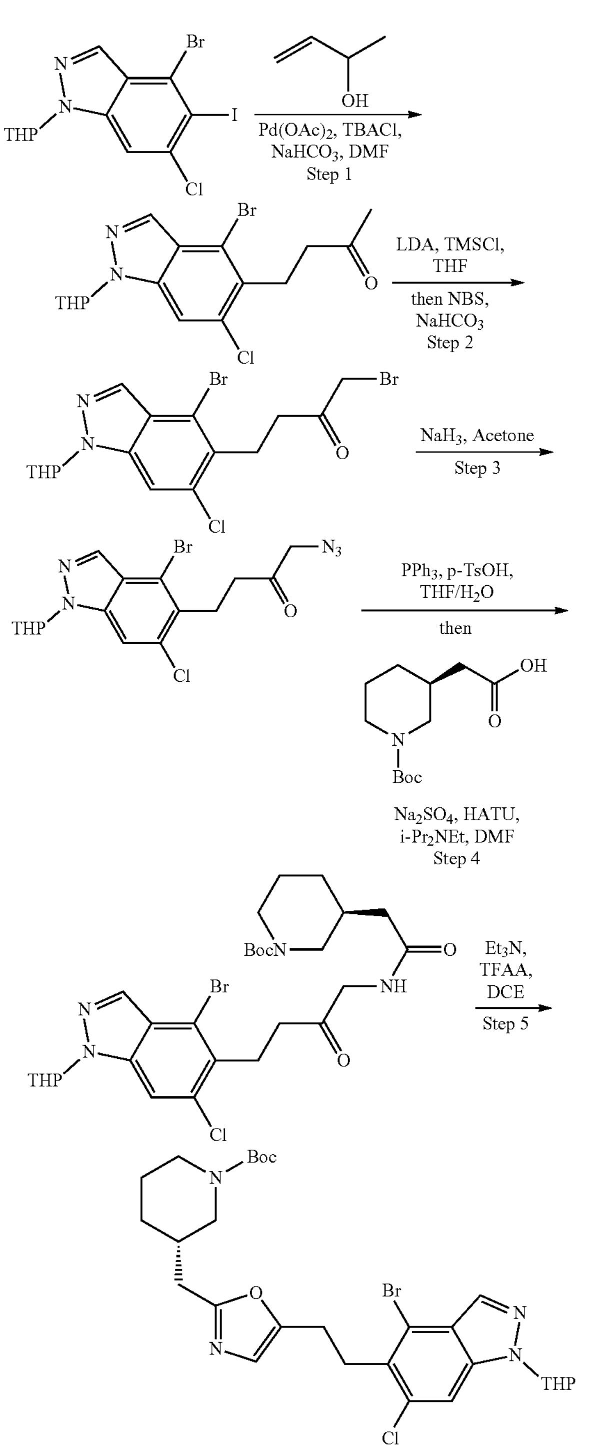

Intermediate BZ

Step 1. 4-(4-Bromo-6-chloro-1-(tetrahydro-2H-pyran-2-yl)-1H-indazol-5-yl)butan-2-one. To a 40 mL vial was charged with 4-bromo-6-chloro-5-iodo-1-(tetrahydro-2H-pyran-2-yl)-1H-indazole (2.04 g, 4.62 mmol, Pharmablock, Inc.), sodium bicarbonate (0.97 g, 11.6 mmol), TBACl (1.28 g, 4.62 mmol), palladium(II) acetate (52 mg, 0.23 mmol), 3-buten-2-ol (0.6 mL, 6.9 mmol) and N,N-dimethylformamide (10 mL). The reaction mixture was heated at 65° C. for 68 h. After cooling to rt, the reaction was diluted with saturated aqueous ammonium chloride and extracted with ethyl acetate. The organic layer was washed with water, dried over sodium sulfate, filtered, and concentrated. The crude material was purified by column chromatography on silica gel, eluting with 0-50% EtOAc in heptane to provide 4-(4-bromo-6-chloro-1-(tetrahydro-2H-pyran-2-yl)-1H-indazol-5-yl)butan-2-one (1.42 g, 3.68 mmol, 80% yield) as white solid. m/z (ESI): 406.9/408.9 $(M+Na)^+$.

Step 2. 1-Bromo-4-(4-bromo-6-chloro-1-(tetrahydro-2H-pyran-2-yl)-1H-indazol-5-yl)butan-2-one. To a 250-mL round-bottom flask was charged with lithium diisopropylamide (1 M solution in THF/hexanes, 4.1 mL, 4.1 mmol) in anhydrous tetrahydrofuran (35 mL). The mixture was cooled to 78° C. and 4-(4-bromo-6-chloro-1-(tetrahydro-2H-pyran-2-yl)-1H-indazol-5-yl)butan-2-one (1.33 g, 3.45 mmol) in 8 mL anhydrous THF was added dropwise under nitrogen. The reaction mixture was stirred at −78° C. for 30 minutes. Chlorotrimethylsilane (0.70 mL, 5.5 mmol) was then added dropwise at −78° C. The reaction mixture was stirred at −78° C. for additional 30 minutes. Saturated $NaHCO_3$ solution was added, and the mixture was warmed to rt. EtOAc was added, the layers were separated, and the organic layer was dried over $Na_2SO_4$, filtered, and concentrated. The crude product was diluted in anhydrous THF (10 mL) and cooled to 0° C. Sodium bicarbonate (0.44 g, 5.17 mmol) and N-bromosuccinimide (0.61 g, 3.45 mmol) was then added and the mixture was stirred at rt for 15 h. The reaction mixture was filtered and concentrated. The crude material was purified by column chromatography on silica gel, eluting with 0-100% EtOAc in heptane, to provide 1-bromo-4-(4-bromo-6-chloro-1-(tetrahydro-2H-pyran-2-yl)-1H-indazol-5-yl)butan-2-one (1.16 g, 2.50 mmol, 72% yield) as colorless viscous oil. m/z (ESI): 462.8/464.8/466.8 $(M+H)^+$.

Step 3. 1-Azido-4-(4-bromo-6-chloro-1-(tetrahydro-2H-pyran-2-yl)-1H-indazol-5-yl)butan-2-one. To a 40-mL vial was added 1-bromo-4-(4-bromo-6-chloro-1-(tetrahydro-2H-pyran-2-yl)-1H-indazol-5-yl)butan-2-one (1.16 g, 2.50 mmol) in acetone (10 mL). Sodium azide (0.21 g, 3.25 mmol) was then added, and the mixture was stirred at rt for 2 h. The reaction mixture was filtered over celite, concentrated, and the residue was purified by column chromatography on silica gel, eluting with 0-50% EtOAc in heptane, to provide 1-azido-4-(4-bromo-6-chloro-1-(tetrahydro-2H-pyran-2-yl)-1H-indazol-5-yl)butan-2-one (0.70 g, 1.64 mmol, 66% yield) as colorless oil. m/z (ESI): 448.0/450.0 $(M+Na)^+$.

Step 4. tert-Butyl (3S)-3-(2-((4-(4-bromo-6-chloro-1-(tetrahydro-2H-pyran-2-yl)-1H-indazol-5-yl)-2-oxobutyl) amino)-2-oxoethyl)piperidine-1-carboxylate. To a 40-mL vial was charged with 1-azido-4-(4-bromo-6-chloro-1-(tetrahydro-2H-pyran-2-yl)-1H-indazol-5-yl)butan-2-one (0.68 g, 1.58 mmol), water (0.43 mL), tetrahydrofuran (13 mL), and triphenylphosphine (0.44 g, 1.66 mmol), and p-toluenesulfonic acid monohydrate (0.30 g, 1.58 mmol) sequentially. The reaction mixture was stirred at rt for 6 h. Sodium sulfate, anhydrous (1.70 g, 11.9 mmol), N,N-dimethylformamide (2.6 mL), (S)-(1-Boc-piperidino)acetic acid (0.46 g, 1.90 mmol), HATU (1.20 g, 3.16 mmol) and diisopropylethylamine (1.38 mL, 7.91 mmol) were added sequentially. The mixture was stirred at rt for 18 h. Water was added, and the mixture was extracted with EtOAc. The combined organic layers were dried over $Na_2SO_4$, filtered, and concentrated. The crude material was purified by column chromatography on silica gel, eluting with 0-50% EtOAc in dichloromethane, to provide tert-butyl (3S)-3-(2-((4-(4-bromo-6-chloro-1-(tetrahydro-2H-pyran-2-yl)-1H-indazol-5-yl)-2-oxobutyl) amino)-2-oxoethyl)piperidine-1-carboxylate (1.31 g, 2.09 mmol, crude) as off-white solid. m/z (ESI): 625.1/627.1 $(M+H)^+$.

Step 5. tert-Butyl (3S)-3-((5-(2-(4-bromo-6-chloro-1-(tetrahydro-2H-pyran-2-yl)-1H-indazol-5-yl)ethyl)oxazol-2-yl) methyl)piperidine-1-carboxylate. To a 40-mL vial was charged with tert-butyl (3S)-3-(2-((4-(4-bromo-6-chloro-1-(tetrahydro-2H-pyran-2-yl)-1H-indazol-5-yl)-2-oxobutyl) amino)-2-oxoethyl)piperidine-1-carboxylate (0.97 g, 1.55 mmol), triethylamine (5.18 mL, 37.2 mmol) in 1,2-dichloroethane (20 mL). The mixture was cooled to 0° C., trifluoroacetic anhydride (2.15 mL, 15.5 mmol) was added dropwise and the mixture was stirred at 0° C. for 1.5 h. The mixture was quenched by slow addition of saturated $NaHCO_3$ solution at 0° C. The phases were separated, and the aqueous phase was extracted by DCM. The combined organic layers were dried over $Na_2SO_4$ and filtered and concentrated. The crude material was purified by reverse phase HPLC using a C18 column, eluting with 0-100% $CH_3CN$ (0.1% FA)/water (0.1% FA), to provide tert-butyl (3S)-3-((5-(2-(4-bromo-6-chloro-1-(tetrahydro-2H-pyran-2-yl)-1H-indazol-5-yl)ethyl)oxazol-2-yl)methyl)piperidine-1-carboxylate (84 mg, 0.14 mmol, 9% yield) as yellow oil. m/z (ESI): 607.1/609.1 $(M+H)^+$. $^1H$ NMR (500 MHz, CHLOROFORM-d) δ ppm 7.99-7.94 (m, 1H), 7.69-7.64 (m, 1H), 6.64 (s, 1H), 5.65 (dd, J=9.1, 2.7 Hz, 1H), 5.31 (s, 2H), 4.06-4.00 (m, 1H), 3.89 (dt, J=13.1, 3.9 Hz, 1H), 3.78-3.72 (m, 1H), 3.40-3.33 (m, 2H), 2.96-2.87 (m, 2H), 2.87-2.79 (m, 1H), 2.75-2.57 (m, 2H), 2.54-2.44 (m, 1H), 2.18-1.99 (m, 4H), 1.91-1.69 (m, 4H), 1.68-1.65 (m, 1H), 1.50-1.39 (m, 9H).

Intermediate CA: tert-Butyl 3-((1-(2-(4-bromo-6-chloro-1-(tetrahydro-2H-pyran-2-yl)-1H-indazol-5-yl)ethyl)-1H-1,2,4-triazol-3-yl)methyl)piperidine-1-carboxylate

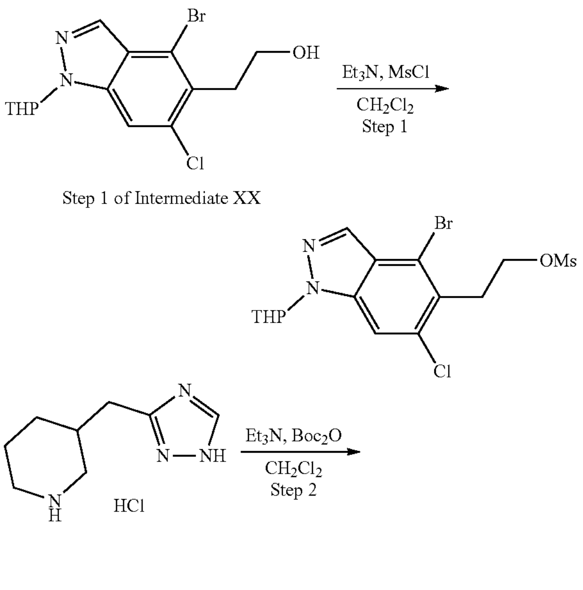

-continued

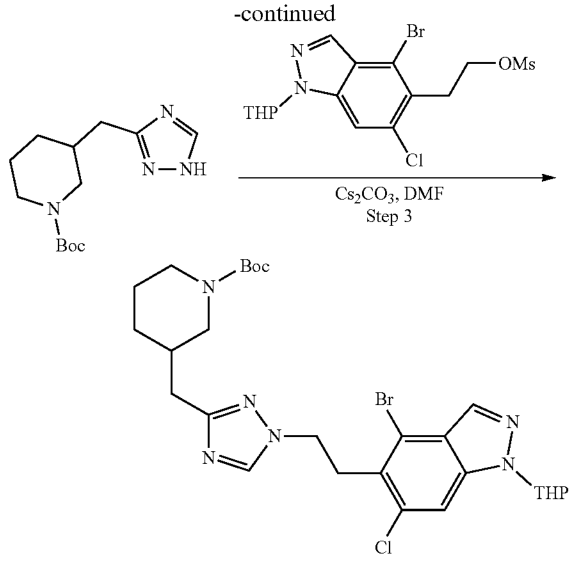

Intermediate CA

Step 1. 2-(4-Bromo-6-chloro-1-(tetrahydro-2H-pyran-2-yl)-1H-indazol-5-yl)ethyl methanesulfonate. To a 40-mL vial was added 2-(4-bromo-6-chloro-1-(tetrahydro-2H-pyran-2-yl)-1H-indazol-5-yl)ethan-1-ol (0.26 g, 0.72 mmol, Step 1 of Intermediate XX) and triethylamine (0.20 mL, 1.4 mmol) in dichloromethane (2 mL). Methanesulfonyl chloride (0.12 g, 1.08 mmol) in dichloromethane (2 mL) was added dropwise, and the resulting mixture was stirred at rt for 1 h. The reaction was quenched with water and extracted with $CH_2Cl_2$. The combined organic layers were dried over $Na_2SO_4$ and concentrated. The crude material was purified by column chromatography on silica gel, eluting with 0-100% EtOAc in heptane, to provide 2-(4-bromo-6-chloro-1-(tetrahydro-2H-pyran-2-yl)-1H-indazol-5-yl)ethyl methanesulfonate (0.31 g, 0.71 mmol, 98% yield) as pale yellow oil. m/z (ESI): 436.9/438.9 $(M+H)^+$. $^1H$ NMR (400 MHz, CHLOROFORM-d) δ ppm 8.01 (s, 1H), 7.71 (s, 1H), 5.68 (dd, J=2.7, 8.9 Hz, 1H), 4.45 (t, J=7.5 Hz, 2H), 4.02 (br d, J=10.0 Hz, 1H), 3.7-3.8 (m, 1H), 3.58 (t, 2H, J=7.5 Hz), 3.00 (s, 3H), 2.4-2.5 (m, 1H), 2.1-2.2 (m, 2H), 1.7-1.8 (m, 3H).

Step 2. tert-Butyl 3-((1H-1,2,4-triazol-3-yl)methyl)piperidine-1-carboxylate. To a stirred suspension of 3-((1H-1,2,4-triazol-3-yl)methyl)piperidine hydrochloride (0.63 g, 3.10 mmol, Angel Pharmatech Ltd.) and triethylamine (2.2 mL, 15.5 mmol) in DCM (8 mL) was added di-tert-butyl dicarbonate (0.47 g, 2.17 mmol) at 0° C. The resulting mixture was stirred at 0° C. for 30 min and was allowed to warm to rt with stirring for 4 h. The mixture was washed with water, the organic layer dried over $Na_2SO_4$, filtered, and concentrated to provide tert-butyl 3-((1H-1,2,4-triazol-3-yl)methyl)piperidine-1-carboxylate (0.75 g, 2.80 mmol, 90% yield) as yellow oil. m/z (ESI): 267.2 $(M+H)^+$.

Step 3. tert-Butyl 3-((1-(2-(4-bromo-6-chloro-1-(tetrahydro-2H-pyran-2-yl)-1H-indazol-5-yl)ethyl)-1H-1,2,4-triazol-3-yl)methyl)piperidine-1-carboxylate. To a 8-mL vial was charged with tert-butyl 3-((1H-1,2,4-triazol-3-yl) methyl)piperidine-1-carboxylate (0.21 g, 0.78 mmol), 2-(4-bromo-6-chloro-1-(tetrahydro-2H-pyran-2-yl)-1H-indazol-5-yl)ethyl methanesulfonate (0.31 g, 0.71 mmol) in N,N-dimethylformamide (2 mL). Cesium carbonate (0.46 g, 1.42 mmol) was added, and the mixture was stirred under nitrogen atmosphere and at 50° C. for 65 h. After cooling to rt, the mixture was filtered over Celite and the filtrate was concentrated and purified by chromatography using a C18 column, eluting with 0-100% $CH_3CN$ with 0.1% formic acid/water with 0.1% formic acid, to provide tert-butyl 3-((1-(2-(4-bromo-6-chloro-1-(tetrahydro-2H-pyran-2-yl)-1H-indazol-5-yl)ethyl)-1H-1,2,4-triazol-3-yl)methyl)piperidine-1-carboxylate (0.26 g, 0.43 mmol, 60% yield) as colorless oil. m/z (ESI): 607.1/609.1 $(M+H)^+$ Intermediate CB: tert-Butyl (3R)-3-((5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)piperidine-1-carboxylate

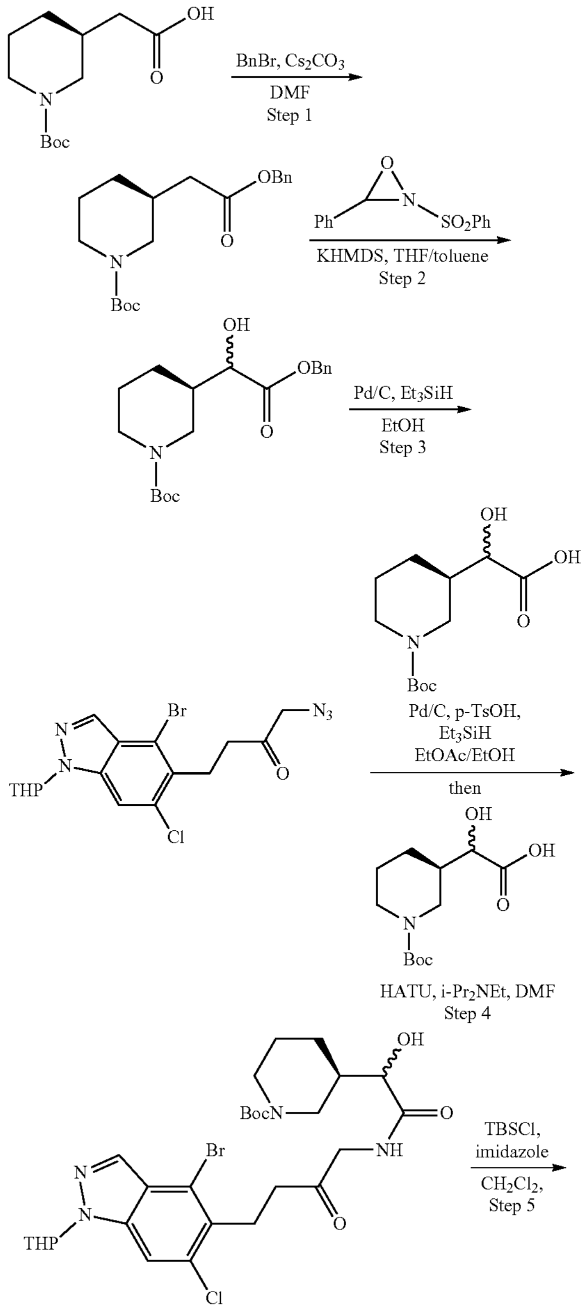

-continued

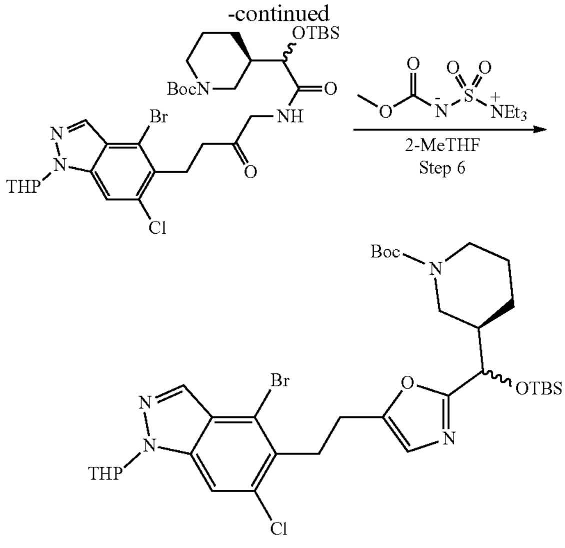

Intemediate CB

Step 1. tert-Butyl (S)-3-(2-(benzyloxy)-2-oxoethyl)piperidine-1-carboxylate. A 40 mL vial was charged with (S)-(1-Boc-piperidino)acetic acid (4.00 g, 16.4 mmol, Combi-Blocks Inc.) and N,N-dimethylformamide (20 mL). The solution was cooled to 0° C. and cesium carbonate (5.62 g, 17.3 mmol) was added and the reaction mixture was stirred for 1 h at 0° C. Then (bromomethyl)benzene (2.95 g, 17.3 mmol, Oakwood Chemicals) was added, and the mixture was stirred at 0° C. for additional 30 minutes, and then warmed to rt with stirring for 24 h. Water was added and the mixture was extracted with EtOAc. The combined organic layers were dried with $Na_2SO_4$, filtered and concentrated and the residue was purified by column chromatography on silica gel, eluting with 0-50% EtOAc in heptane, to provide tert-butyl (S)-3-(2-(benzyloxy)-2-oxoethyl)piperidine-1-carboxylate (4.75 g, 14.3 mmol, 87% yield) as colorless oil. m/z (ESI): 356.2 $(M+Na)^+$.

Step 2. tert-Butyl (3R)-3-(2-(benzyloxy)-1-hydroxy-2-oxoethyl)piperidine-1-carboxylate. To a 250-mL round-bottom flask was added tetrahydrofuran (16 mL) under nitrogen. The vial was cooled to −78° C. and potassium bis (trimethylsilyl)amide solution (0.5 M in toluene, 37.0 mL, 18.5 mmol) was added. A solution of tert-butyl (S)-3-(2-(benzyloxy)-2-oxoethyl)piperidine-1-carboxylate (4.75 g, 14.3 mmol) in tetrahydrofuran (16 mL) was added dropwise at −78° C. and the mixture was stirred at −78° C. for 10 min. 3-Phenyl-2-(phenylsulfonyl)-1,2-oxaziridine (4.84 g, 18.5 mmol, Synthonix Inc.) in tetrahydrofuran (16 mL) was then added and the mixture was stirred at −78° C. for 1 h. The mixture was quenched by the addition of saturated $NH_4Cl$ solution and warmed to 0° C. The mixture was partitioned between EtOAc and saturated NaCl solution. The combined organic layer was dried over $Na_2SO_4$, filtered and concentrated and the residue was purified by column chromatography on silica gel, eluting with 0-50% EtOAc in heptane, to provide tert-butyl (3R)-3-(2-(benzyloxy)-1-hydroxy-2-oxoethyl)piperidine-1-carboxylate (4.06 g, 11.6 mmol, 82% yield) as white solid. m/z (ESI): 372.1 $(M+Na)^+$.

Step 3. 2-((R)-1-(tert-Butoxycarbonyl)piperidin-3-yl)-2-hydroxyacetic acid. In a 250-mL round-bottom flask was charged with palladium on activated carbon (0.41 g, 3.81 mmol). The flask was back-filled with $N_2$ and tert-butyl (3R)-3-(2-(benzyloxy)-1-hydroxy-2-oxoethyl)piperidine-1- carboxylate (1.90 g, 5.44 mmol) in ethanol (16 mL) was added. 3-Ethyl-3-silapentane (4.0 mL, 25 mmol) was then added dropwise via a syringe pump over 30 minutes. The reaction mixture was then stirred at rt for 30 min. The resulting mixture was then filtered over celite and concentrated. The residue was dissolved in EtOAc and treated with saturated $NaHCO_3$ solution. The aqueous layer was acidified by 1 M $KHSO_4$ solution to pH 2 and extracted with EtOAc. The combined organic layers were dried over $Na_2SO_4$, filtered, and concentrated to provide 2-((R)-1-(tert-butoxycarbonyl)piperidin-3-yl)-2-hydroxyacetic acid (0.96 g, 3.70 mmol, 68% yield) as colorless viscous oil. m/z (ESI): 282.1 $(M+Na)^+$. $^1H$ NMR (400 MHz, CHLOROFORM-d) δ ppm 4.03-4.11 (m, 1H), 3.19-3.89 (m, 4H), 2.88-3.16 (m, 1H), 1.82-2.03 (m, 2H), 1.62-1.81 (m, 3H), 1.50 (s, 9H).

Step 4. tert-Butyl (3R)-3-(2-((4-(4-bromo-6-chloro-1-(tetrahydro-2H-pyran-2-yl)-1H-indazol-5-yl)-2-oxobutyl)amino)-1-hydroxy-2-oxoethyl)piperidine-1-carboxylate. To a 250-mL round-bottom flask containing 1-azido-4-(4-bromo-6-chloro-1-(tetrahydro-2H-pyran-2-yl)-1H-indazol-5-yl)butan-2-one (2.08 g, 4.87 mmol, Step 3 in Intermediate BZ) in ethyl acetate (20 mL) and ethanol (20 mL) was added palladium on activated carbon (0.36 g, 3.41 mmol). Under nitrogen atmosphere, 3-ethyl-3-silapentane (3.6 mL, 22.4 mmol) was added dropwise through a syringe pump over 30 minutes, and the mixture was stirred at rt for an additional 30 minutes. The resulting mixture was filtered over Celite, and the volatiles were evaporated. The residue was dissolved in N,N-dimethylformamide (10 mL). 2-((R)-1-(tert-butoxycarbonyl)piperidin-3-yl)-2-hydroxyacetic acid (1.39 g, 5.36 mmol), HATU (2.41 g, 6.34 mmol), and diisopropylethylamine (4.3 mL, 24.4 mmol) was added sequentially added. The reaction mixture was stirred at rt for 16 h, concentrated and the crude material was purified by column chromatography on silica gel, eluting with 0-100% EtOAc in heptane, to provide tert-butyl (3R)-3-(2-((4-(4-bromo-6-chloro-1-(tetrahydro-2H-pyran-2-yl)-1H-indazol-5-yl)-2-oxobutyl)amino)-1-hydroxy-2-oxoethyl)piperidine-1-carboxylate (2.01 g, 3.13 mmol, 64% yield) as colorless oil. m/z (ESI): 662.8/664.9 $(M+H)^+$.

Step 5. tert-Butyl (3R)-3-(2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)piperidine-1-carboxylate. To a 100-mL round-bottom flask was added tert-butyl (3R)-3-(2-((4-(4-bromo-6-chloro-1-(tetrahydro-2H-pyran-2-yl)-1H-indazol-5-yl)-2-oxobutyl)amino)-1-hydroxy-2-oxoethyl)piperidine-1-carboxylate (2.01 g, 3.13 mmol) in dichloromethane (20 mL). Imidazole (0.38 g, 5.64 mmol) and (1,1-dimethylethyl)dimethylsilyl chloride (0.85 g, 5.64 mmol) was sequentially added at 0° C. and the mixture was stirred at rt for 90 h. The resulting mixture was filtered, concentrated, and the crude product was purified by column chromatography on silica gel, eluting with 0-50% EtOAc in heptane, to provide tert-butyl (3R)-3-(2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)piperidine-1-carboxylate (1.64 g, 2.17 mmol, 69% yield) as white foam. m/z (ESI): 755.2/757.3 $(M+H)^+$.

Step 6. tert-Butyl (3R)-3-((5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)piperidine-1-carboxylate. In a 40-mL vial was added tert-butyl (3R)-3-(2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)piperidine-1-carboxylate (1.64 g, 2.17 mmol) and Burgess reagent (2.07 g, 8.67 mmol, Combi-Blocks Inc.) in 2-methyltetrahydrofuran (16 mL). The mixture was purged with $N_2$, then heated at 75° C. for 3 h. After cooling to rt, water was added to quench the reaction and the mixture was extracted by EtOAc. The combined organic layers were dried with $Na_2SO_4$, concentrated, and the residue was purified by column chromatography on silica gel, eluting with 0-50% EtOAc in heptane, to provide tert-butyl (3R)-3-((5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)piperidine-1-carboxylate (1.30 g, 1.76 mmol, 81% yield) as colorless oil. m/z (ESI): 737.1/739.2 $(M+H)^+$.

Intermediate CD: tert-Butyl 3-((4-(6-fluoro-1-(tetrahydro-2H-pyran-2-yl)-4-(4,4,5,5-tetramethyl-1,3,2-dioxaborolan-2-yl)-1H-indazol-5-yl)butoxy)methyl)azepane-1-carboxylate

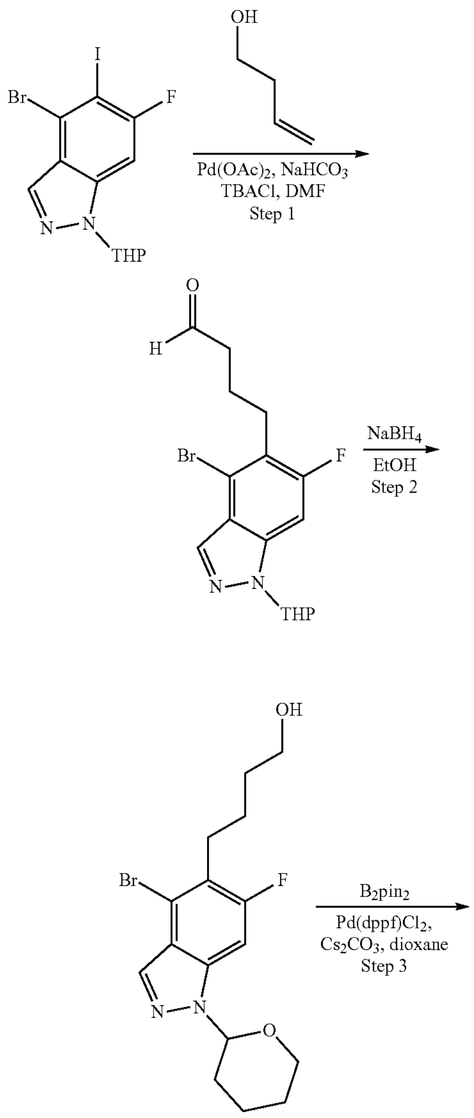

-continued

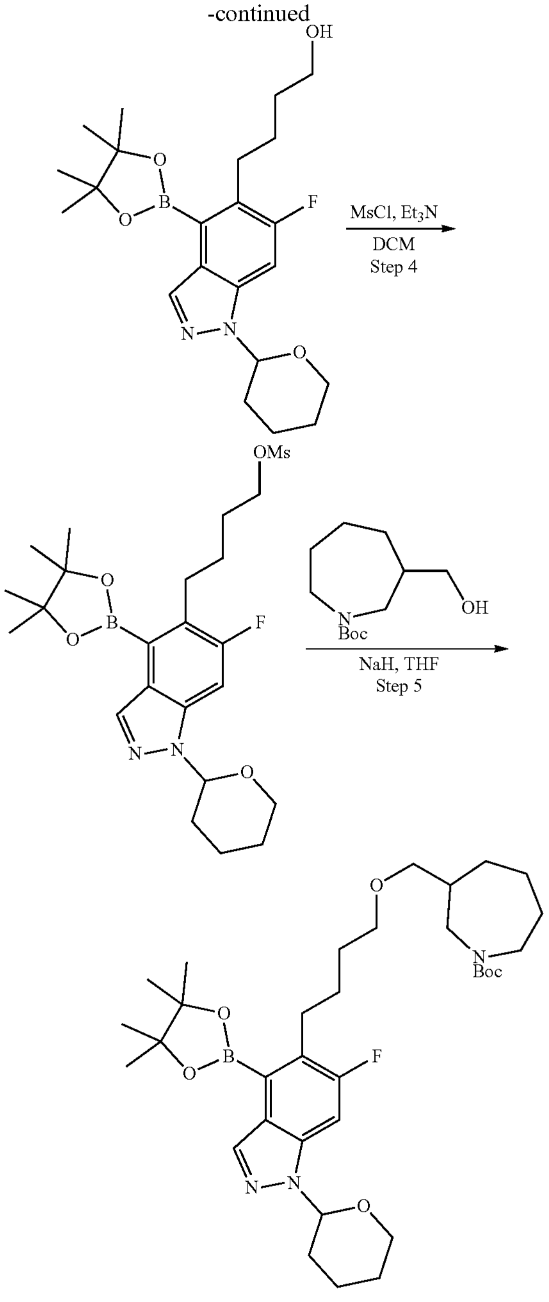

Intermediate CD

Step 1. 4-(4-Bromo-6-fluoro-1-(tetrahydro-2H-pyran-2-yl)-1H-indazol-5-yl)butanal. To a solution of 4-bromo-6-fluoro-5-iodo-1-(tetrahydro-2H-pyran-2-yl)-1H-indazole (48 g, 113 mmol) in N,N-dimethylformamide (600 mL) was added $NaHCO_3$ (28.5 g, 339 mmol) and TBACl (29.6 g, 113 mmol) under $N_2$. Then but-3-en-1-ol (16.3 g, 226 mmol) and $Pd(OAc)_2$ (2.54 g, 11.3 mmol) was added in one portion under $N_2$. The mixture was stirred at 80° C. for 12 h under $N_2$. The residue was diluted with $H_2O$ and extracted with ethyl acetate. The combined organic layers were washed with brine, dried over $Na_2SO_4$, filtered, and concentrated under reduced pressure. The residue was purified by column chromatography on silica gel, eluting with a gradient of 5-50% ethyl acetate in petroleum ether, to provide 4-(4-bromo-6-fluoro-1-(tetrahydro-2H-pyran-2-yl)-1H-indazol-5-yl)butanal (32.0 g, 86.9 mmol, 74% yield) as yellow oil.

Step 2. 4-(4-Bromo-6-fluoro-1-(tetrahydro-2H-pyran-2-yl)-1H-indazol-5-yl) butan-1-ol. To a solution of 4-(4-bromo-6-fluoro-1-(tetrahydro-2H-pyran-2-yl)-1H-indazol-5-yl)butanal (37.5 g, 102 mmol) in ethanol (600 mL) was added $NaBH_4$ (11.5 g, 305 mmol) in portions at 0° C. Then the mixture was stirred at rt for 2 h. The reaction mixture was quenched by addition of sat. $NH_4Cl$ solution, and then diluted with water and extracted with ethyl acetate. The combined organic layers were washed with brine, dried over $Na_2SO_4$, filtered, and concentrated under reduced pressure. The residue was was purified by column chromatography on silica gel, eluting with a gradient of 33-100% ethyl acetate in petroleum ether, to provide 4-(4-bromo-6-fluoro-1-(tetrahydro-2H-pyran-2-yl)-1H-indazol-5-yl) butan-1-ol (37.5 g, 101 mmol, 99% yield) was obtained as yellow oil. m/z (ESI): 371.1/373.1 $(M+H)^+$. $^1H$ NMR: (400 MHz, DMSO-$d_6$) δ ppm 8.04 (s, 1H), 7.68 (d, J=10.0 Hz, 1H), 5.80 (dd, J=9.6 Hz, 2.4 Hz, 1H), 4.38 (t, J=5.2 Hz, 1H), 3.81-3.85 (m, 1H), 3.65-3.75 (m, 1H), 3.38-3.42 (m, 2H), 2.82 (t, J=6.4 Hz, 2H), 2.31-2.45 (m, 1H), 2.00-2.02 (m, 1H), 1.97-1.99 (m, 1H), 1.60-1.75 (m, 1H), 1.45-1.49 (m, 4H), 1.41-1.45 (m, 2H). $^{19}F$ NMR: (400 MHz, DMSO-$d_6$) δ ppm −113.65 (s).

Step 3. 4-(6-Fluoro-1-(tetrahydro-2H-pyran-2-yl)-4-(4,4,5,5-tetramethyl-1,3,2-dioxaborolan-2-yl)-1H-indazol-5-yl) butan-1-ol. To a solution of 4-(4-bromo-6-fluoro-1-(tetrahydro-2H-pyran-2-yl)-1H-indazol-5-yl)butan-1-ol (5.00 g, 13.5 mmol) in 1,4-dioxane (150 mL) was added bis(pinacolato)diboron (20.52 g, 81 mmol) and $Cs_2CO_3$ (13.16 g, 40.4 mmol) in water (5 mL) under $N_2$. Then $Pd(dppf)Cl_2$ (0.99 g, 1.35 mmol) was added in one portion under $N_2$. The reaction mixture was stirred at 120° C. for 2 h under $N_2$. After cooling to rt, the residue was diluted with water and extracted with EtOAc. The combined organic layers were washed with brine, dried over $Na_2SO_4$, filtered, and concentrated under reduced pressure. The residue was purified by column chromatography on silica gel, eluting with a gradient of 0-10% ethyl acetate in petroleum ether, to provide 4-(6-fluoro-1-(tetrahydro-2H-pyran-2-yl)-4-(4,4,5,5-tetramethyl-1,3,2-dioxaborolan-2-yl)-1H-indazol-5-yl) butan-1-ol (2.3 g, 5.5 mmol, 41% yield) as brown oil. $^1H$ NMR (400 MHz, $CDCl_3$) δ ppm 8.37 (s, 1H), 7.32 (d, J=4.0 Hz, 1H), 5.64 (dd, J=9.2 Hz, 2.8 Hz, 1H), 4.00-3.98 (m, 1H), 3.73-3.70 (m, 3H), 3.03-3.00 (m, 2H), 2.53-2.50 (m, 1H), 2.15-2.13 (m, 1H), 2.05-1.99 (m, 1H), 1.68-1.66 (m, 3H), 1.67-1.65 (m, 5H), 1.42 (s, 12H). $^{19}F$ NMR (400 MHz, $CDCl_3$) δ ppm −118.45 (s). m/z (ESI): 419.3 $(M+H)^+$.

Step 4. 4-(6-Fluoro-1-(tetrahydro-2H-pyran-2-yl)-4-(4,4,5,5-tetramethyl-1,3,2-dioxaborolan-2-yl)-1H-indazol-5-yl) butyl methanesulfonate. To a 40 mL vial was charged with 4-(6-fluoro-1-(tetrahydro-2H-pyran-2-yl)-4-(4,4,5,5-tetramethyl-1,3,2-dioxaborolan-2-yl)-1H-indazol-5-yl)butan-1-ol (0.40 g, 0.96 mmol), dichloromethane (6.5 mL), and triethylamine (0.2 mL, 1.4 mmol). To this was added methanesulfonyl chloride (89 μL, 1.15 mmol) dropwise. The reaction mixture was stirred at rt for 16 h. Upon completion the reaction was diluted with water and concentrated. The crude mixture was purified by flash column chromatography on silica gel, eluting with a gradient of 0-85% ethyl acetate in heptane, to give 4-(6-fluoro-1-(tetrahydro-2H-pyran-2-yl)-4-(4,4,5,5-tetramethyl-1,3,2-dioxaborolan-2-yl)-1H-indazol-5-yl)butyl methanesulfonate (0.23 g, 0.46 mmol, 48% yield) as a colorless oil. m/z (ESI): 497.0 $(M+H)^+$.

Step 5. tert-Butyl 3-((4-(6-fluoro-1-(tetrahydro-2H-pyran-2-yl)-4-(4,4,5,5-tetramethyl-1,3,2-dioxaborolan-2-yl)-1H-indazol-5-yl)butoxy)methyl)azepane-1-carboxylate. To a 20 mL vial was charged with tert-butyl 3-(hydroxymethyl)azepane-1-carboxylate (0.37 g, 1.61 mmol), tetrahydrofuran (4.0 mL), and sodium hydride (60% in mineral oil, 64.5 mg, 1.61 mmol). The reaction was stirred at rt for 15 min. Then 4-(6-fluoro-1-(tetrahydro-2H-pyran-2-yl)-4-(4,4,5,5-tetramethyl-1,3,2-dioxaborolan-2-yl)-1H-indazol-5-yl)butyl methanesulfonate (0.40 g, 0.81 mmol) was added as a solution in tetrahydrofuran (4.0 mL). The reaction mixture was warmed to 50° C. for 4 h. After cooling to rt, the reaction mixture was carefully quenched with saturated ammonium chloride and concentrated. The crude oil was purified by flash column chromatography on silica gel, eluting with a gradient of 0-75% ethyl acetate in heptane, to give tert-butyl 3-((4-(6-fluoro-1-(tetrahydro-2H-pyran-2-yl)-4-(4,4,5,5-tetramethyl-1,3,2-dioxaborolan-2-yl)-1H-indazol-5-yl)butoxy)methyl)azepane-1-carboxylate (0.28 g, 0.45 mmol, 56% yield) as colorless oil. m/z (ESI): 630.2 $(M+H)^+$.

Intermediate CE: tert-Butyl-2-1-(4-(6-methyl-1-(tetrahydro-2H-pyran-2-yl)-4-(4,4,5,5-tetramethyl-1,3,2-dioxaborolan-2-yl)-1H-indazol-5-yl)butoxy)ethyl)morpholine-4-carboxylate

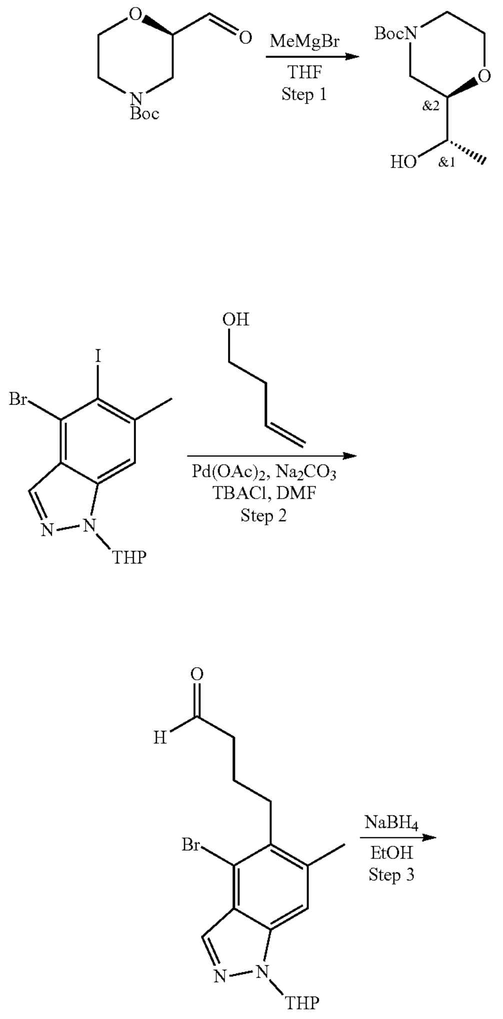

-continued

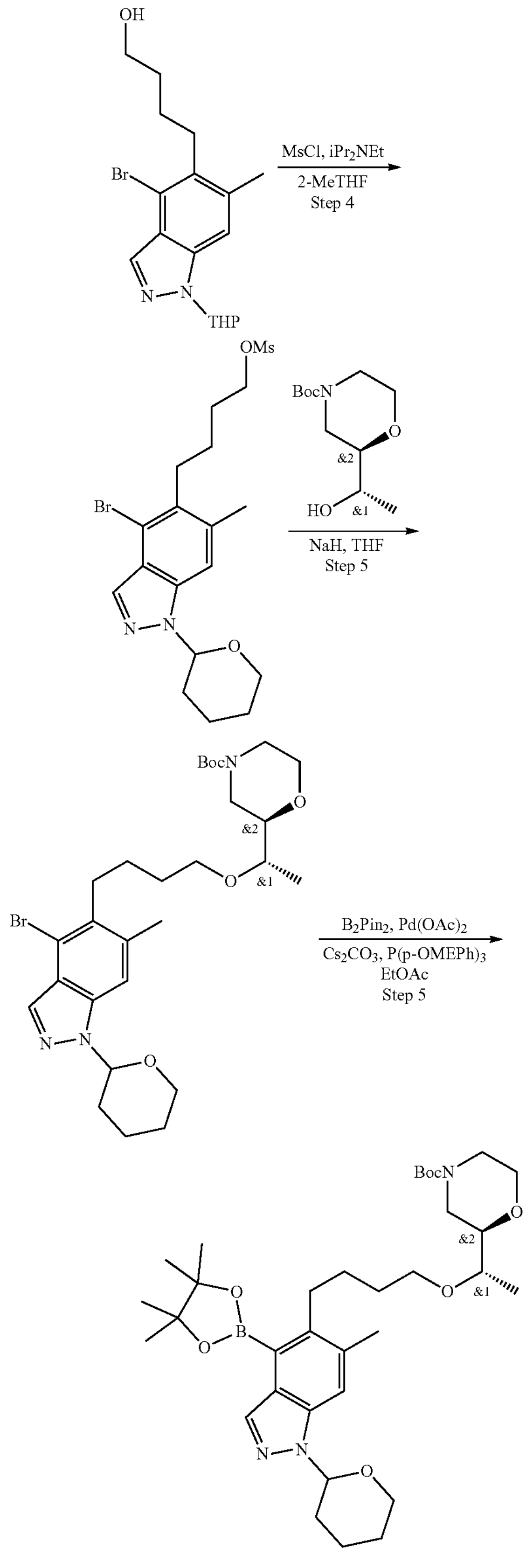

Intermediate CE

Step 1. tert-Butyl-2-(1-hydroxyethyl)morpholine-4-carboxylate. To an oven dried 40 mL vial was charged with tert-butyl (R)-2-formylmorpholine-4-carboxylate (0.50 g, 2.32 mmol) and tetrahydrofuran (23 mL). The content was cooled to −78° C. and methylmagnesium bromide (3 M in THF, 0.85 mL, 2.56 mmol) was added dropwise. The reaction mixture was allowed to warm to 0° C. over 3 h. Saturated aqueous ammonium chloride was added, and the mixture was stirred and warmed to rt. Sodium sulfate was added and the crude mixture was filtered through another pad of sodium sulfate and concentrated. This material was purified by column chromatography on silica gel, eluting with a gradient of 0-65% ethyl acetate in heptane, to give tert-butyl-2-(1-hydroxyethyl)morpholine-4-carboxylate (0.28 g, 1.21 mmol, 52% yield) as colorless oil. $^1$H NMR (400 MHz, CHLOROFORM-d) δ ppm 3.80-4.20 (m, 3H), 3.65-3.72 (m, 1H), 3.50-3.63 (m, 1H), 2.65-2.99 (m, 2H), 1.90-2.48 (m, 1H), 1.47 (s, 9H), 1.25-1.19 (m, 3H).

Step 2. 4-(4-Bromo-6-methyl-1-(tetrahydro-2H-pyran-2-yl)-1H-indazol-5-yl) butanal. To a solution of 4-bromo-5-iodo-6-methyl-1-(tetrahydro-2H-pyran-2-yl)-1H-indazole (50 g, 119 mmol) in N,N-dimethylformamide (600 mL) was added $Na_2CO_3$ (31.5 g, 297 mmol) and TBACl (31.0 g, 119 mmol) under $N_2$. Then the mixture was stirred at 15° C. for 15 min. Then but-3-en-1-ol (13.75 g, 185.6 mmol) and $Pd(OAc)_2$ (1.33 g, 5.94 mmol) was added under $N_2$, the mixture was stirred at 80° C. for 5 h. After cooling to rt, the reaction mixture was quenched by addition of water and extracted with EtOAc. The combined organic layers were washed with brine, dried over $Na_2SO_4$, filtered, and concentrated to give 4-(4-bromo-6-methyl-1-(tetrahydro-2H-pyran-2-yl)-1H-indazol-5-yl) butanal (45 g, 90% purity) as yellow oil.

Step 3. 4-(4-Bromo-6-methyl-1-(tetrahydro-2H-pyran-2-yl)-1H-indazol-5-yl) butan-1-ol. To a solution of 4-(4-bromo-6-methyl-1-(tetrahydro-2H-pyran-2-yl)-1H-indazol-5-yl) butanal (30 g, 82 mmol) in ethanol (600 mL) was added $NaBH_4$ (9.32 g, 246 mmol) in portions at 0° C. The reaction mixture was stirred at rt for 2 h, was then quenched by addition of sat. $NH_4Cl$, and then diluted with water and extracted with EtOAc. The combined organic layers were washed with brine, dried over $Na_2SO_4$, filtered, and concentrated. The residue was purified by column chromatography on silica gel, eluting with a gradient of 10-100% ethyl acetate in petroleum ether, to give 4-(4-bromo-6-methyl-1-(tetrahydro-2H-pyran-2-yl)-1H-indazol-5-yl) butan-1-ol (30 g, 81.97 mmol, 99% yield) as yellow oil. $^1$H NMR (400 MHz, DMSO-$d_6$) δ ppm 7.94 (s, 1H), 7.33 (s, 1H), 5.63-5.67 (m, 1H), 4.00-4.03 (m, 1H), 3.71-3.77 (m, 2H), 2.92-2.96 (m, 2H), 2.52 (s, 3H), 2.15-2.25 (m, 1H), 2.01-2.11 (m, 1H), 1.69-1.77 (m, 4H), 1.50-1.64 (m, 6H). m/z (ESI): 367.0/369.0 $(M+H)^+$.

Step 4. 4-(4-Bromo-6-methyl-1-(tetrahydro-2H-pyran-2-yl)-1H-indazol-5-yl)butyl methanesulfonate. To a solution of 4-(4-bromo-6-methyl-1-(tetrahydro-2H-pyran-2-yl)-1H-indazol-5-yl)butan-1-ol (0.5 g, 1.29 mmol) and DIPEA (0.45 mL, 2.58 mmol) in 2-methyltetrahydrofuran (6.5 mL) was added methanesulfonyl chloride (0.17 mL, 2.1 mmol). The reaction mixture was stirred at rt for 2 h. The reaction mixture was partitioned between ethyl acetate and saturated aqueous sodium bicarbonate; the organic layer was dried with $Na_2SO_4$ and concentrated. The crude product was purified by column chromatography on silica gel, eluting with a gradient of 0-100% ethyl acetate in heptane, to provide 4-(4-bromo-6-methyl-1-(tetrahydro-2H-pyran-2-yl)-1H-indazol-5-yl)butyl methanesulfonate (0.62 g, 1.34 mmol, 100% yield) as colorless oil. m/z (ESI): 464.0 $(M+H)^+$.

Step 5. tert-Butyl 2-(1-(4-(4-bromo-6-methyl-1-(tetrahydro-2H-pyran-2-yl)-1H-indazol-5-yl)butoxy)ethyl)morpholine-4-carboxylate. To an oven dried 40 mL vial was charged with tert-butyl 2-(1-hydroxyethyl)morpholine-4-carboxylate (0.43 mg, 1.86 mmol), tetrahydrofuran (8.5 mL), and sodium hydride (60% in oil, 0.12 g, 2.97 mmol) under nitrogen. The contents were stirred at rt for 10 minutes, then 4-(4-bromo-6-methyl-1-(tetrahydro-2H-pyran-2-yl)-1H-indazol-5-yl)butyl methanesulfonate (1.24 g, 2.79 mmol) was added as a solution in tetrahydrofuran (4 mL). The reaction mixture was stirred at 50° C. for 48 h. After cooling to rt, the reaction mixture was carefully quenched with saturated aqueous ammonium chloride, the solid filtered, and the filtrate concentrated. The crude oil was purified by flash column chromatography on silica gel, eluting with a gradient of 0-35% ethyl acetate in heptane, to give tert-butyl 2-(1-(4-(4-bromo-6-methyl-1-(tetrahydro-2H-pyran-2-yl)-1H-indazol-5-yl)butoxy)ethyl)morpholine-4-carboxylate (0.42 g, 0.73 mmol, 39% yield) as colorless oil. m/z (ESI): 580.0 $(M+H)^+$.

Step 6. tert-Butyl-2-1-(4-(6-methyl-1-(tetrahydro-2H-pyran-2-yl)-4-(4,4,5,5-tetramethyl-1,3,2-dioxaborolan-2-yl)-1H-indazol-5-yl)butoxy)ethyl)morpholine-4-carboxylate. To a 20 mL vial was charged with tert-butyl 2-(1-(4-(4-bromo-6-methyl-1-(tetrahydro-2H-pyran-2-yl)-1H-indazol-5-yl)butoxy)ethyl)morpholine-4-carboxylate (0.42 g, 0.73 mmol), 4,4,4',4',5,5,5',5'-octamethyl-2,2'-bi(1,3,2-dioxaborolane) (0.22 g, 0.88 mmol), tris(4-methoxyphenyl) phosphine (26 mg, 0.073 mmol), palladium acetate (8.2 mg, 0.037 mmol), cesium carbonate (0.36 g, 1.10 mmol), and ethyl acetate (3.0 mL). The reaction mixture was sparged with nitrogen and then heated to 80° C. for 1.5 h. After cooling to rt, the mixture was diluted with ethyl acetate, filtered, and concentrated to give crude tert-butyl-2-1-(4-(6-methyl-1-(tetrahydro-2H-pyran-2-yl)-4-(4,4,5,5-tetramethyl-1,3,2-dioxaborolan-2-yl)-1H-indazol-5-yl)butoxy) ethyl)morpholine-4-carboxylate (0.44 g, 0.70 mmol, 96% yield) which was used without further purification. m/z (ESI): 572.0 (M+Na-pinacol)$^+$.

Intermediate CF: tert-Butyl 3-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)piperidine-1-carboxylate

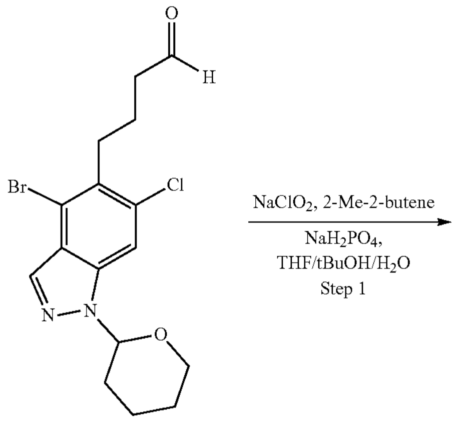

-continued

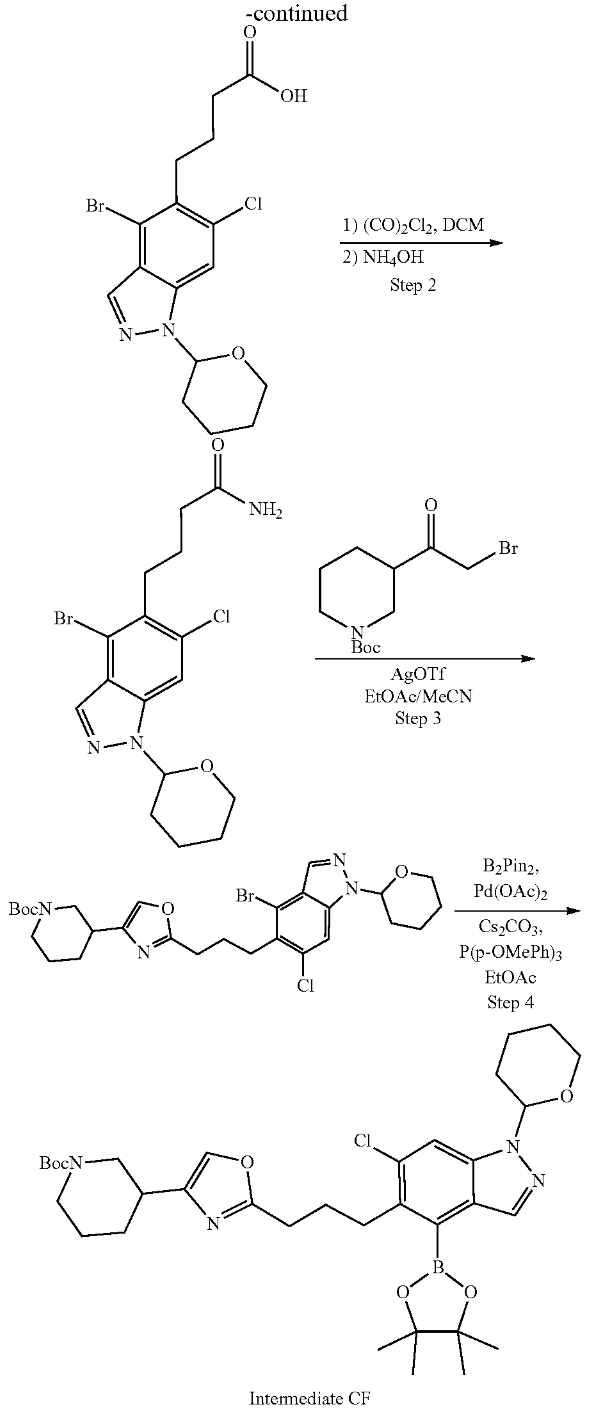

Intermediate CF

Step 1. 4-(4-Bromo-6-chloro-1-(tetrahydro-2H-pyran-2-yl)-1H-indazol-5-yl)butanoic acid. To a 40 mL vial was charged with 4-(4-bromo-6-chloro-1-(tetrahydro-2H-pyran-2-yl)-1H-indazol-5-yl)butanal (0.61 g, 1.58 mmol, Step 2 in Intermediate WWW), (9 mL) and tert-butanol (9 mL). To this was added 2-methyl-2-butene (0.18 mL, 1.58 mmol), and then sodium chlorite (0.60 g, 6.6 mmol) and sodium phosphate monobasic, anhydrous (0.19 g, 1.58 mmol) in water (18 mL) at 0° C. The reaction mixture was allowed to warm to rt for 1 h, was then concentrated and dissolved in MeOH. The crude was injected onto a C18 column and eluted with 5-100% acetonitrile+0.1% formic acid in water+0.1% formic acid, to give 4-(4-bromo-6-chloro-1-(tetrahydro-2H-pyran-2-yl)-1H-indazol-5-yl)butanoic acid (0.38 g, 0.95 mmol, 60% yield) as white solid after lyophilization. m/z (ESI): 401.8 $(M+H)^+$.

Step 2. 4-(4-Bromo-6-chloro-1-(tetrahydro-2H-pyran-2-yl)-1H-indazol-5-yl)butanamide. To a 40 mL vial was charged with 4-(4-bromo-6-chloro-1-(tetrahydro-2H-pyran-2-yl)-1H-indazol-5-yl)butanoic acid (1.57 g, 3.91 mmol) in dichloromethane (20 mL). DMF (30 mL, 0.39 mmol) was added, followed by oxalyl chloride (2.3 mL, 4.7 mmol) dropwise. The reaction mixture was stirred at rt for 1.5 h. Upon completion ammonium hydroxide (8 N, 7.4 mL, 58.6 mmol) was added dropwise. The reaction was stirred for 2.5 h. Upon completion the mixture was concentrated under reduced pressure and purified by reverse phase column chromatography using a C18 column, eluting with 5-100% acetonitrile+0.1% formic acid in water+0.1% formic acid, to give 4-(4-bromo-6-chloro-1-(tetrahydro-2H-pyran-2-yl)-1H-indazol-5-yl)butanamide (0.40 g, 1.00 mmol, 26% yield). m/z (ESI): 423.9 $(M+Na)^+$.

Step 3. tert-Butyl 3-(2-(3-(4-bromo-6-chloro-1-(tetrahydro-2H-pyran-2-yl)-1H-indazol-5-yl)propyl)oxazol-4-yl) piperidine-1-carboxylate. To a 20 mL vial was charged with tert-butyl 3-(2-bromoacetyl)piperidine-1-carboxylate (0.20 g, 0.65 mmol, Enamine), 4-(4-bromo-6-chloro-1-(tetrahydro-2H-pyran-2-yl)-1H-indazol-5-yl)butanamide (0.31 g, 0.78 mmol), ethyl acetate (1.6 mL)/acetonitrile (1.6 mL), and silver trifluoromethanesulfonate (0.34 g, 1.31 mmol). The reaction mixture was heated to 70° C. for 24 h. After cooling to rt, triethylamine (0.37 mL, 2.6 mmol), 4-(N,N-dimethylamino)-pyridine (8.0 mg, 0.065 mmol), and di-tert-butyl dicarbonate (0.43 g, 1.96 mmol,) were added. The reaction was stirred at rt for 1.5 h. The precipitate was filtered, and the filtrate concentrated. The residue was purified by reverse phase column chromatography C18 column, eluting with 5-100% acetonitrile+0.1% formic acid in water+0.1% formic acid, to give tert-butyl 3-(2-(3-(4-bromo-6-chloro-1-(tetrahydro-2H-pyran-2-yl)-1H-indazol-5-yl)propyl)oxazol-4-yl)piperidine-1-carboxylate (0.18 g, 0.30 mmol, 45% yield) as yellow solid. m/z (ESI): 607.0 $(M+H)^+$.

Step 4. tert-Butyl 3-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)piperidine-1-carboxylate. To a 20 mL vial was charged with tert-butyl 3-(2-(3-(4-bromo-6-chloro-1-(tetrahydro-2H-pyran-2-yl)-1H-indazol-5-yl)propyl)oxazol-4-yl)piperidine-1-carboxylate (0.18 g, 0.29 mmol), 4,4,4',4',5,5,5',5'-octamethyl-2,2'-bi(1,3,2-dioxaborolane) (0.13 g, 0.52 mmol), tris(4-methoxyphenyl)phosphine (20 mg, 0.058 mmol), palladium acetate (6.5 mg, 0.029 mmol), cesium carbonate (0.19 g, 0.58 mmol), and ethyl acetate (2.9 mL). The contents were sparged with nitrogen and then heated to 80° C. for 3.5 h. After cooling to rt, the reaction mixture was diluted with ethyl acetate, filtered, and the filtrate concentrated. The crude material was purified by flash column chromatography on silica gel, eluting with 0-70% ethyl acetate in heptane, to give tert-butyl 3-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)piperidine-1-carboxylate (70 mg, 0.11 mmol, 37% yield) as yellow solid. m/z (ESI): 655.2 $(M+H)^+$.

Intermediate CG: tert-Butyl (3R)-3-(5-(3-(4-bromo-6-chloro-1-(tetrahydro-2H-pyran-2-yl)-1H-indazol-5-yl)propyl)-1,2,4-oxadiazol-3-yl)piperidine-1-carboxylate

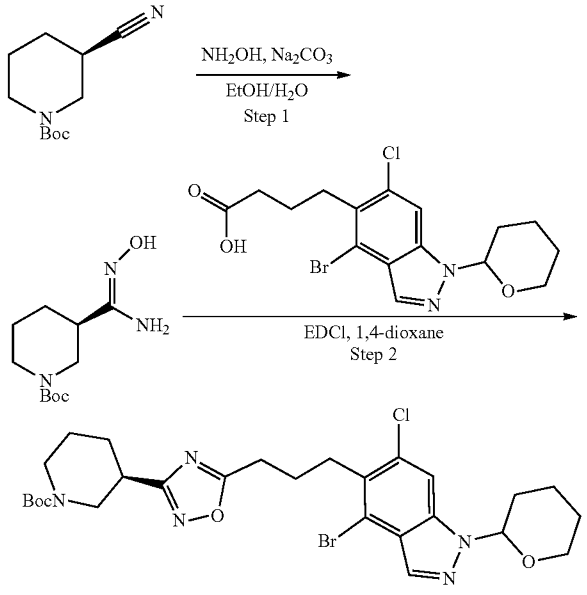

Intermediate CG

Step 1. tert-Butyl (R,E)-3-(N'-hydroxycarbamimidoyl)piperidine-1-carboxylate. To a 40 mL vial was charged with sodium carbonate (1.01 g, 9.51 mmol), tert-butyl (3R)-3-cyanopiperidine-1-carboxylate (1.0 g, 4.76 mmol), hydroxylamine hydrochloride (1.32 g, 19.0 mmol), ethanol (18 mL), and water (12 mL). The reaction mixture was heated to 80° C. for 4 h. After cooling to rt, the mixture was concentrated, and the residue was diluted with saturated aqueous sodium chloride and extracted with EtOAc. The combined organics were dried over $Na_2SO_4$, concentrated to give tert-butyl (R,E)-3-(N'-hydroxycarbamimidoyl)piperidine-1-carboxylate (0.83 g, 3.41 mmol, 72% yield) as white solid. m/z (ESI): 244.2 $(M+H)^+$.

Step 2. tert-Butyl (3R)-3-(5-(3-(4-bromo-6-chloro-1-(tetrahydro-2H-pyran-2-yl)-1H-indazol-5-yl)propyl)-1,2,4-oxadiazol-3-yl)piperidine-1-carboxylate. To a 40 mL vial was charged with tert-butyl (R,E)-3-(N'-hydroxycarbamimidoyl)piperidine-1-carboxylate (0.60 g, 2.47 mmol), 4-(4-bromo-6-chloro-1-(tetrahydro-2H-pyran-2-yl)-1H-indazol-5-yl)butanoic acid (0.99 g, 2.47 mmol, step 1 in Intermediate CF), and 1,4-dioxane (25 mL). To this stirring solution was added 1-(3-dimethylaminopropyl)-3-ethylcarbodiimide hydrochloride (0.52 g, 2.71 mmol) and the reaction mixture was heated to 100° C. for 18 h. After cooling to rt, the mixture was concentrated, diluted with ethyl acetate, and then washed with aqueous 0.1 M acetic acid, followed by saturated aqueous sodium bicarbonate. The organics were dried over $Na_2SO_4$, concentrated and the residue was purified by reverse phase column chromatography using a C18 column, eluting with 5-100% acetonitrile+0.1% formic acid in water+0.1% formic acid, to give tert-butyl (3R)-3-(5-(3-(4-bromo-6-chloro-1-(tetrahydro-2H-pyran-2-yl)-1H-indazol-5-yl)propyl)-1,2,4-oxadiazol-3-yl)piperidine-1-carboxylate (0.70 g, 1.15 mmol, 47% yield) as white solid. m/z (ESI): 607.0 $(M+H)^+$.

Intermediate CH: tert-Butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)-5-oxa-8-azaspiro[3.5]nonane-8-carboxylate

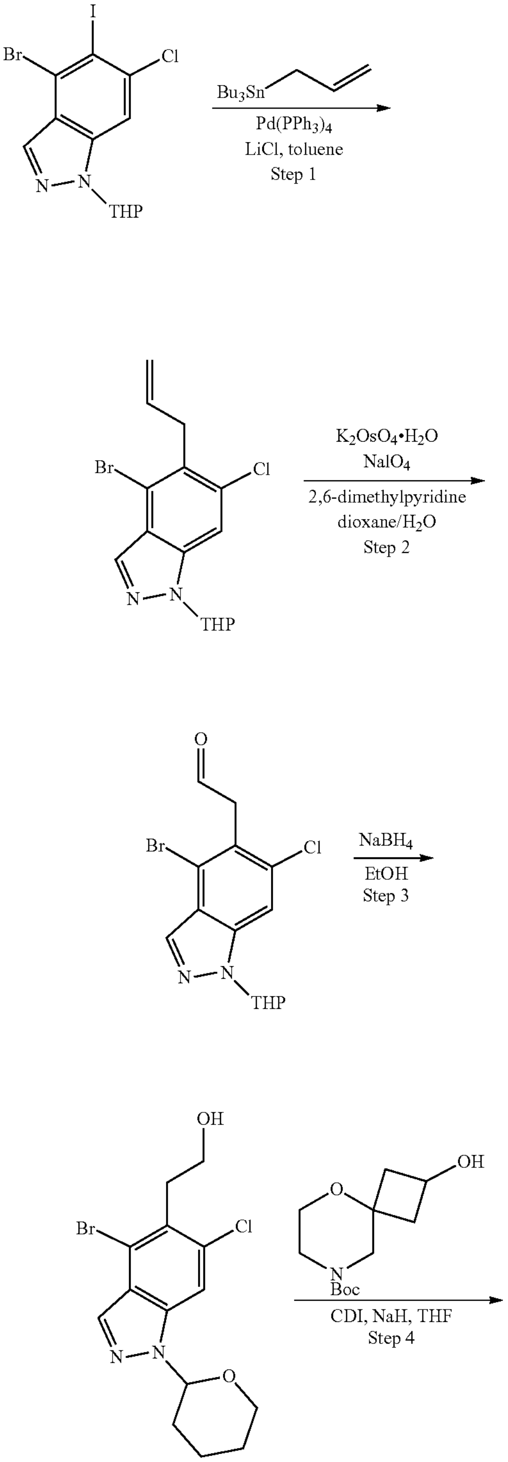

-continued

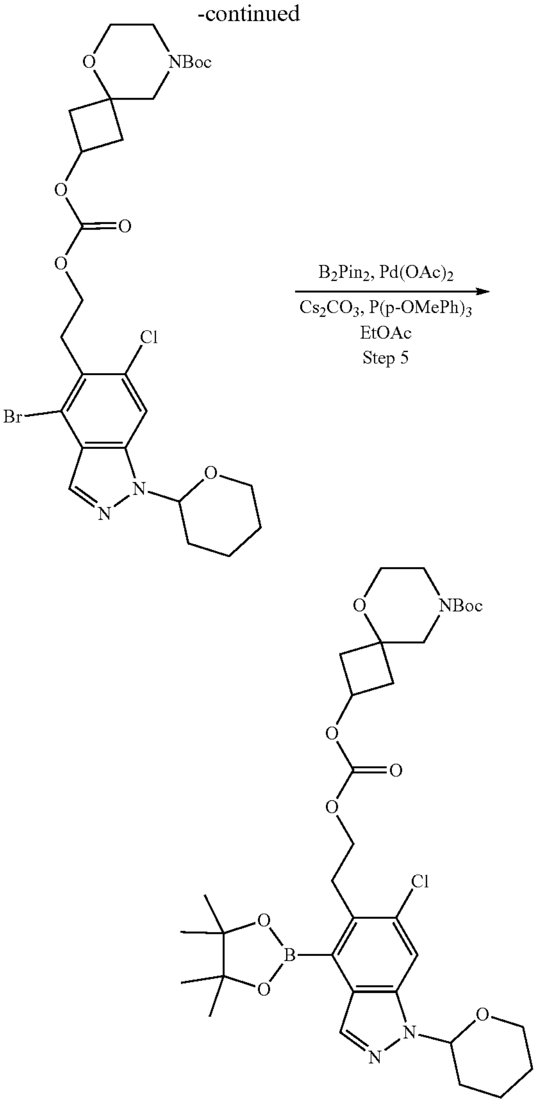

Intermediate CH

Step 1. 5-Allyl-4-bromo-6-chloro-1-(tetrahydro-2H-pyran-2-yl)-1H-indazole. To a solution of 4-bromo-6-chloro-5-iodo-1-(tetrahydro-2H-pyran-2-yl)-1H-indazole (100 g, 227 mmol) in toluene (1 L) was added allyltributylstannane (83.0 g, 249 mmol) and LiCl (48.0 g, 1.13 mol), then $Pd(PPh_3)_4$ (26.2 g, 22.65 mmol) was added in one portion under $N_2$. The mixture was stirred at 110° C. for 12 h. 5 reactions were carried out in parallel. After cooling to rt, the reactions were filtered and the filtrate was quenched by addition of water, and then extracted with EtOAc. The combined organic layers were dried over $Na_2SO_4$, filtered, and concentrated under reduced pressure. The residue was purified by column chromatography on silica gel, eluting with a gradient of 1-100% ethyl acetate in petroleum ether, to give 5-allyl-4-bromo-6-chloro-1-(tetrahydro-2H-pyran-2-yl)-1H-indazole (450 g, 80% purity on TLC) as a yellow solid.

Step 2. 2-(4-Bromo-6-chloro-1-(tetrahydro-2H-pyran-2-yl)-1H-indazol-5-yl)acetaldehyde. To a solution of 5-allyl-4-bromo-6-chloro-1-(tetrahydro-2H-pyran-2-yl)-1H-indazole (30 g, 84 mmol) in 1,4-dioxane (600 mL) and water (200 mL) was added $K_2OsO_4$ (0.56 g, 1.69 mmol) and 2,6-lutidine (18.1 g, 169 mmol) and sodium periodate (72.2 g, 337 mmol) under $N_2$. The reaction mixture was stirred at rt for 2 h. 15 reactions were carried out in parallel. The mixture was partitioned between water and ethyl acetate (1-L). The aqueous layer was extracted with EtOAc, and the combined organic layers were washed with sat. $Na_2S_2O_3$, dried over $Na_2SO_4$, filtered, and concentrated. The residue was purified by column chromatography on silica gel, eluting with a gradient of 1-100% ethyl acetate in petroleum ether, to give 2-(4-bromo-6-chloro-1-(tetrahydro-2H-pyran-2-yl)-1H-indazol-5-yl)acetaldehyde (210 g, 587 mmol, 46% yield) as yellow oil. $^1H$ NMR (400 MHz, CHLOROFORM-d) δ ppm 9.77 (s, 1H), 8.03 (s, 1H), 7.73 (s, 1H), 5.66-5.69 (m, 1H), 4.24 (s, 2H), 3.98-4.01 (m, 1H), 3.74-3.78 (m, 1H), 2.70-2.77 (m, 1H), 2.11-2.15 (m, 2H), 1.75-1.94 (m, 3H).

Step 3. 2-(4-Bromo-6-chloro-1-(tetrahydro-2H-pyran-2-yl)-1H-indazol-5-yl)ethan-1-ol. To a solution of 2-(4-bromo-6-chloro-1-(tetrahydro-2H-pyran-2-yl)-1H-indazol-5-yl)acetaldehyde (50 g, 140 mmol) in ethanol (500 mL) was added $NaBH_4$ (15.87 g, 419 mmol) in portions at 0° C. under $N_2$. Then the mixture was stirred at rt for 2 h. Four reactions were carried out in parallel. The reaction mixture was diluted with water and extracted with EtOAc. The combined organic layers were dried over $Na_2SO_4$, filtered, and concentrated. The residue was purified by column chromatography on silica gel, eluting with a gradient of 1-100% ethyl acetate in petroleum ether, to give 2-(4-bromo-6-chloro-1-(tetrahydro-2H-pyran-2-yl)-1H-indazol-5-yl)ethan-1-ol (167 g, 464 mmol, 84% yield) as white solid. $^1H$ NMR (400 MHz, CHLOROFORM-d) δ ppm 7.97 (s, 1H), 7.67 (s, 1H), 5.63-5.66 (m, 1H), 4.01-4.06 (m, 1H), 3.86-3.98 (m, 2H), 3.70-3.75 (m, 1H), 3.38 (t, J=7.6 Hz, 2H), 2.42-2.52 (m, 1H), 2.05-2.14 (m, 2H), 1.69-1.77 (m, 3H), 1.47 (t, J=6.0 Hz, 1H). m/z (ESI): 358.9/360.9 $(M+H)^+$.

Step 4. tert-Butyl 2-(((2-(4-bromo-6-chloro-1-(tetrahydro-2H-pyran-2-yl)-1H-indazol-5-yl)ethoxy)carbonyl)oxy)-5-oxa-8-azaspiro[3.5]nonane-8-carboxylate. To a stirred solution of 2-(4-bromo-6-chloro-1-(tetrahydro-2H-pyran-2-yl)-1H-indazol-5-yl)ethan-1-ol (1.20 g, 3.34 mmol) in tetrahydrofuran (6.5 mL) was added carbonyldiimidazole (0.81 g, 5.00 mmol). The reaction mixture was stirred at rt for 30 min. To a separate solution of tert-butyl 2-hydroxy-5-oxa-8-azaspiro[3.5]nonane-8-carboxylate (1.62 g, 6.67 mmol) in tetrahydrofuran (10 mL) at 0° C. was added sodium hydride (60% in mineral oil, 0.40 g, 10.0 mmol). The resulting mixture was stirred at 0° C. for 30 min and then the above mixture was added, and the resulting mixture was stirred at 0° C. for 40 min. The reaction mixture was quenched via the slow addition of saturated aqueous ammonium chloride and the reaction was allowed to warm to rt. The layers were separated, and the aqueous layer was extracted with DCM and the combined organic layers were dried with sodium sulfate, filtered, and concentrated under reduced pressure. The residue was purified by reverse phase chromatography, eluting with a gradient of 10-100% MeCN (0.1% formic acid) in water (0.1% formic acid), to afford tert-butyl 2-(((2-(4-bromo-6-chloro-1-(tetrahydro-2H-pyran-2-yl)-1H-indazol-5-yl)ethoxy)carbonyl)oxy)-5-oxa-8-azaspiro[3.5]nonane-8-carboxylate (1.86 g, 2.96 mmol, 89% yield) as light yellow oil. m/z (ESI): 628.0 $(M+H)^+$.

Step 5. tert-Butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)-5-oxa-8-azaspiro[3.5]nonane-8-carboxylate. To a 20 mL vial was charged with bis(pinacolato)diboron (1.13 g, 4.44 mmol), cesium carbonate (1.73 g, 5.32 mmol), tert-butyl 2-(((2-(4-bromo-6-chloro-1-(tetrahydro-2H-pyran-2-yl)-1H-indazol- 5-yl)ethoxy)carbonyl)oxy)-5-oxa-8-azaspiro[3.5]nonane-8-carboxylate (1.86 g, 2.96 mmol), palladium acetate (66 mg, 0.30 mmol), tris(4-methoxyphenyl)phosphine (0.21 g, 0.59 mmol), and ethyl acetate (6 mL). The content was degassed by sparging with nitrogen for 10 minutes. The reaction mixture was placed on a preheated (80° C.) hotplate and stirred for 2 h. After cooling to rt, the mixture was diluted with EtOAc and saturated aqueous ammonium chloride. The aqueous layer was extracted with EtOAc, and the combined organics were dried over sodium sulfate and concentrated. The crude oil was purified by flash column chromatography on silica gel, eluting with a gradient of 0-70% ethyl acetate in heptane, to give tert-butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)-5-oxa-8-azaspiro[3.5]nonane-8-carboxylate (1.85 g, 2.74 mmol, 93% yield) as colorless oil mixed with tert-butyl 2-(((2-(6-chloro-1-(tetrahydro-2H-pyran-2-yl)-1H-indazol-5-yl)ethoxy)carbonyl)oxy)-5-oxa-8-azaspiro[3.5]nonane-8-carboxylate. m/z (ESI): 676.2 $(M+H)^+$.

Intermediate CI: tert-Butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)-6-azaspiro[3.5]nonane-6-carboxylate

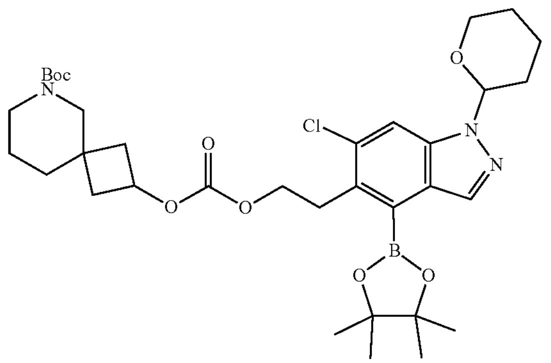 [SMILES: CC(C)(C)OC(=O)N1CCCC2(CC(OC(=O)OCCc3c(Cl)cc4c(cnn4C4CCCCO4)c3B3OC(C)(C)C(C)(C)O3)C2)C1]

This compound was prepared in an analogous manner to Intermediate CH using 6-Boc-2-hydroxy-6-azaspiro[3.5]nonane (CAS #: 1419101-54-4, Combi-Blocks Inc.) in Step 4. m/z (ESI): 673.2 $(M+H)^+$.

Intermediate CJ: tert-Butyl (3R)-3-((4-(4-bromo-6-methyl-1-(tetrahydro-2H-pyran-2-yl)-1H-indazol-5-yl)-3-methylbutoxy)methyl)piperidine-1-carboxylate

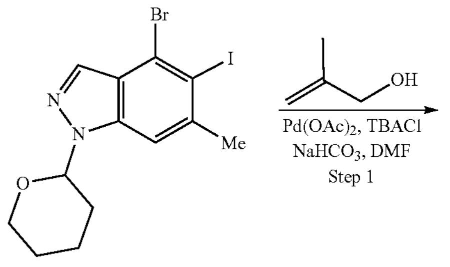

-continued

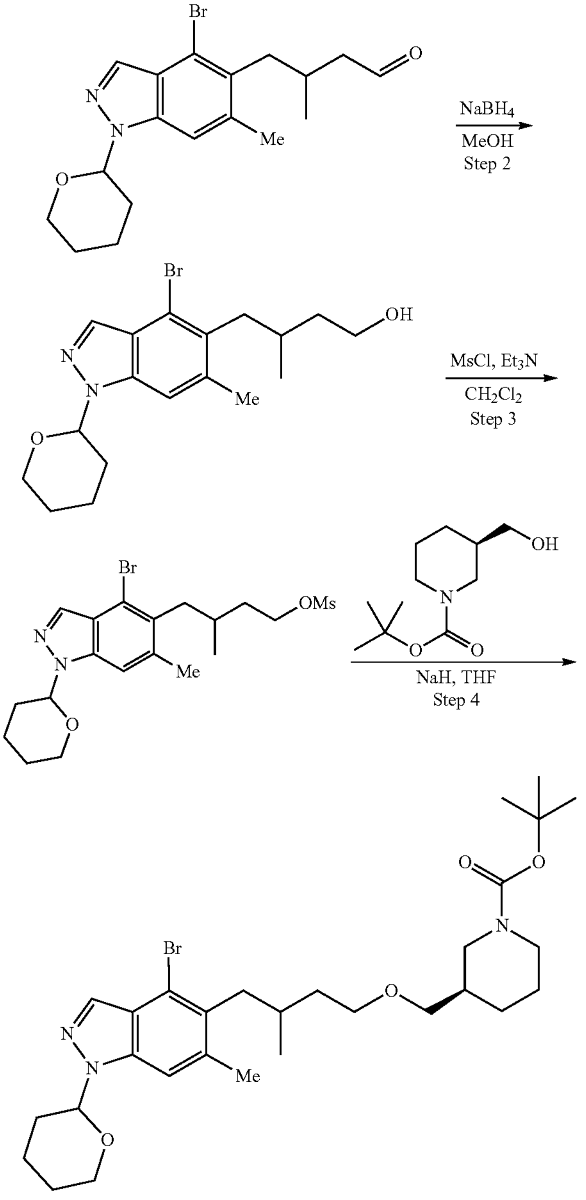

Intermediate CJ

Step 1. 4-(4-Bromo-6-methyl-1-(tetrahydro-2H-pyran-2-yl)-1H-indazol-5-yl)-3-methylbutanal. To a 40 mL vial was charged with 4-bromo-5-iodo-6-methyl-1-(tetrahydro-2H-pyran-2-yl)-1H-indazole (1.50 g, 3.56 mmol, Advanced ChemBlocks), sodium bicarbonate (0.75 g, 8.91 mmol), TBACl (0.99 g, 3.56 mmol), and palladium(II) acetate (40 mg, 0.18 mmol). The vial was purged with nitrogen and N,N-dimethylformamide (7 mL) and 3-methyl-3-buten-1-ol (0.55 mL, 5.34 mmol) were added and the reaction was stirred at 65° C. After stirring for 2 days, the reaction was cooled to rt and diluted with 10% aqueous LiCl and ethyl acetate. The layers were separated, and the organic layer was washed once more using 10% aqueous LiCl. The organic layer was dried with sodium sulfate, filtered, and concentrated. The crude material was purified by column chromatography on silica gel, eluting with 0-35% ethyl acetate in heptane, to give 4-(4-bromo-6-methyl-1-(tetrahydro-2H- pyran-2-yl)-1H-indazol-5-yl)-3-methylbutanal (0.96 g, 2.52 mmol, 71% yield) as clear oil. m/z (ESI): 379.0/381.0 $(M+H)^+$.

Step 2. 4-(4-Bromo-6-methyl-1-(tetrahydro-2H-pyran-2-yl)-1H-indazol-5-yl)-3-methylbutan-1-ol. A solution of 4-(4-bromo-6-methyl-1-(tetrahydro-2H-pyran-2-yl)-1H-indazol-5-yl)-3-methylbutanal (0.96 g, 2.52 mmol) in methanol (25 mL) was cooled to 0° C. and then sodium borohydride (0.12 g, 3.15 mmol) was added, and the reaction was stirred at 0° C. for 15 min. The reaction was quenched by the addition of saturated aqueous ammonium chloride and warmed to rt. The mixture was extracted with EtOAc, and the combined organic layers were dried with sodium sulfate, filtered, and concentrated under reduced pressure. The crude oil was purified by column chromatography on silica gel, eluting with a gradient of 0-40% EtOAc in heptane, to provide 4-(4-bromo-6-methyl-1-(tetrahydro-2H-pyran-2-yl)-1H-indazol-5-yl)-3-methylbutan-1-ol (0.82 g, 2.14 mmol, 85% yield) as colorless oil. m/z (ESI): 380.9/383.1 $(M+H)^+$.

Step 3. 4-(4-Bromo-6-methyl-1-(tetrahydro-2H-pyran-2-yl)-1H-indazol-5-yl)-3-methylbutyl methanesulfonate. To a 0° C. solution of 4-(4-bromo-6-methyl-1-(tetrahydro-2H-pyran-2-yl)-1H-indazol-5-yl)-3-methylbutan-1-ol (0.60 g, 1.58 mmol) in dichloromethane (8 mL) was added triethylamine (0.33 mL, 2.38 mmol) and methanesulfonyl chloride (0.15 mL, 1.9 mmol). The reaction mixture was allowed to slowly warm to rt with stirring over 4 h. The reaction was then recooled to 0° C. and quenched with saturated aqueous sodium bicarbonate. The layers were separated, the aqueous layer was extracted with DCM, and the combined organic layers were then dried with sodium sulfate, filtered, and concentrated. The oil was then purified by column chromatography on silica gel eluting with a gradient of 0-40% EtOAc in heptane, to provide 4-(4-bromo-6-methyl-1-(tetrahydro-2H-pyran-2-yl)-1H-indazol-5-yl)-3-methylbutyl methanesulfonate (0.71 g, 1.54 mmol, 97% yield) as colorless oil. m/z (ESI): 459.0/461.0 $(M+H)^+$.

Step 4. tert-Butyl (3R)-3-((4-(4-bromo-6-methyl-1-(tetrahydro-2H-pyran-2-yl)-1H-indazol-5-yl)-3-methylbutoxy)methyl)piperidine-1-carboxylate. To 0° C. solution of (R)-1-Boc-3-(hydroxymethyl)piperidine (0.47 g, 2.18 mmol, Combi-Blocks Inc.) in tetrahydrofuran (7.5 mL) was added sodium hydride (60% in mineral oil, 87 mg, 2.18 mmol). After stirring for 30 min, 4-(4-bromo-6-methyl-1-(tetrahydro-2H-pyran-2-yl)-1H-indazol-5-yl)-3-methylbutyl methanesulfonate (0.50 g, 1.09 mmol) as a solution in tetrahydrofuran (3.5 mL) was added and the reaction was stirred at 0° C. for 10 min, then warmed to 50° C. with stirring for 16 h. An additional 0.5 equiv of (R)-1-Boc-3-(hydroxymethyl)piperidine and 0.5 equiv of NaH was added and the reaction was continued to stir at 50° C. for another 5 h. The reaction was cooled to 0° C., and saturated aqueous ammonium chloride was added. The aqueous layer was extracted with EtOAc, and the combined organic layers were dried with sodium sulfate, filtered, and concentrated. The crude material was purified by column chromatography on silica gel, eluting with 0-40% ethyl acetate in heptane, to give tert-butyl (3R)-3-((4-(4-bromo-6-methyl-1-(tetrahydro-2H-pyran-2-yl)-1H-indazol-5-yl)-3-methylbutoxy)methyl)piperidine-1-carboxylate (0.41 g, 0.71 mmol, 65% yield) as clear oil. m/z (ESI): 599.9/601.9 $(M+Na)^+$.

Intermediate CK: tert-Butyl (2R)-2-((4-(4-bromo-6-chloro-1-(tetrahydro-2H-pyran-2-yl)-1H-indazol-5-yl)-3-methylbutoxy)methyl)morpholine-4-carboxylate

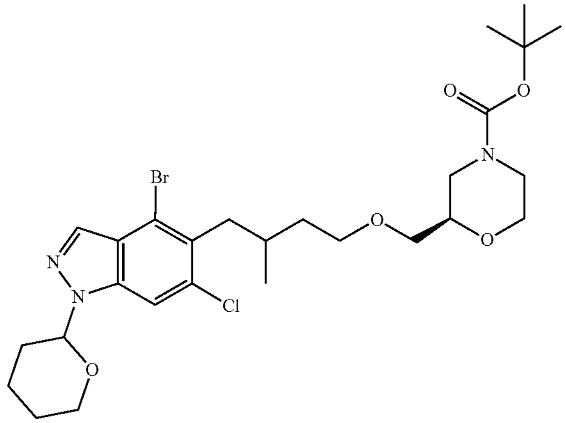 [SMILES: CC(CCOC[C@H]1CN(C(=O)OC(C)(C)C)CCO1)Cc1c(Cl)cc2c(cnn2C2CCCCO2)c1Br]

This compound was prepared in an analogous fashion to Intermediate CJ using 4-bromo-6-chloro-5-iodo-1-(tetrahydro-2H-pyran-2-yl)-1H-indazole (CAS #: 2791273-88-4, LabNetwork) in Step 1 and tert-butyl (R)-2-(hydroxymethyl)morpholine-4-carboxylate (CAS #: 135065-71-3, Combi-Blocks) in Step 4. m/z (ESI): 599.9/601.9 $(M+Na)^+$.

Intermediate CL: tert-Butyl 3-(2-(3-(4-bromo-6-chloro-1-(tetrahydro-2H-pyran-2-yl)-1H-indazol-5-yl)propyl)oxazol-5-yl)piperidine-1-carboxylate

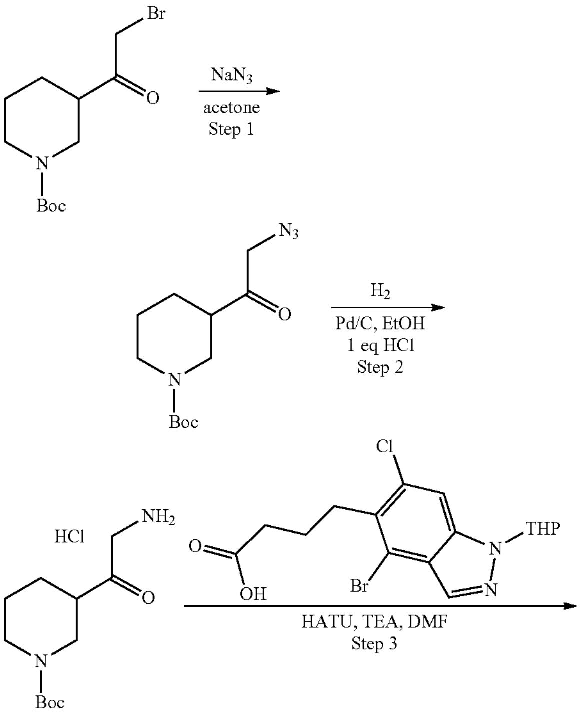

-continued

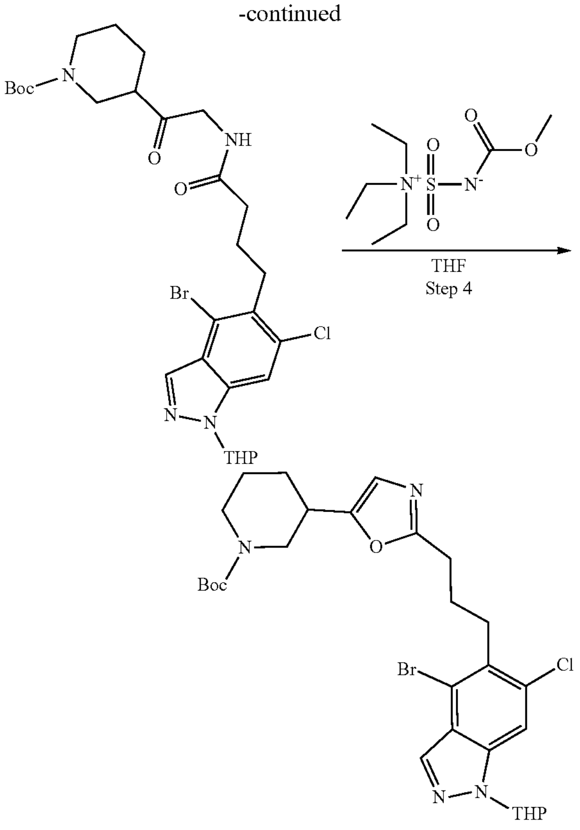

Intermediate CL

Step 1. tert-Butyl 3-(2-azidoacetyl)piperidine-1-carboxylate. To a 20-mL vial was charged with tert-butyl 3-(2-bromoacetyl)piperidine-1-carboxylate (0.50 g, 1.64 mmol, Enamine), acetone (7 mL) and sodium azide (0.14 g, 2.1 mmol). The mixture was stirred at rt for 16 h. The precipitate was filtered off and washed with acetone. The filtrate was concentrated in vacuo. The crude was purified by column chromatography on silica gel, eluting with a gradient of 0-100% EtOAc in heptane, to provide tert-butyl 3-(2-azidoacetyl)piperidine-1-carboxylate (0.35 g, 80% yield) as colorless oil. m/z (ESI): 291.1 $(M+Na)^+$. $^1H$ NMR (CHLOROFORM-d, 400 MHz) δ 4.0-4.1 (m, 3H), 3.82 (br s, 1H), 3.10 (dd, 1H, J=9.4, 13.6 Hz), 2.92 (br s, 1H), 2.5-2.6 (m, 1H), 1.9-2.0 (m, 1H), 1.6-1.8 (m, 2H), 1.5-1.5 (m, 1H), 1.46 (s, 9H).

Step 2. tert-Butyl 3-glycylpiperidine-1-carboxylate hydrochloride. A mixture of tert-butyl 3-(2-azidoacetyl)piperidine-1-carboxylate (0.33 g, 1.22 mmol), ethanol (30 mL), Pd/C, 10 wt % (0.37 g, 0.35 mmol) and HCl, 4 M solution in 1,4-dioxane (0.3 mL, 1.2 mmol) was hydrogenated under H2 (18 psi) at rt for 1 h. The reaction mixture was filtered through a pad of celite and washed with a mixed solution of EtOAc:EtOH (3:1). The filtrate was concentrated in vacuo to provide tert-butyl 3-glycylpiperidine-1-carboxylate hydrochloride (0.34 g, 100% yield) as off-white solid. m/z (ESI): 243.1 $(M+H)^+$. $^1H$ NMR (METHANOL-$d_4$, 400 MHz) δ 4.0-4.1 (m, 2H), 3.9-4.0 (m, 1H), 3.7-3.8 (m, 1H), 2.9-3.3 (m, 3H), 2.7-2.7 (m, 1H), 1.9-2.1 (m, 1H), 1.7-1.8 (m, 2H), 1.46 (s, 9H).

Step 3. tert-Butyl 3-((4-(4-bromo-6-chloro-1-(tetrahydro-2H-pyran-2-yl)-1H-indazol-5-yl)butanoyl)glycyl)piperidine-1-carboxylate. A mixture of 4-(4-bromo-6-chloro-1-(tetrahydro-2H-pyran-2-yl)-1H-indazol-5-yl)butanoic acid (0.58 g, 1.44 mmol, Step 1 in Intermediate CF), tert-butyl 3-glycylpiperidine-1-carboxylate hydrochloride (0.34 g, 1.22 mmol), DMF (10 mL), HATU (0.60 g, 1.58 mmol) and DIPEA (0.64 mL, 3.65 mmol) was stirred at rt for 13 h. The reaction mixture was diluted with EtOAc, the organic layer was separated, washed with water and brine, dried over $Na_2SO_4$, and concentrated. The crude product was purified by column chromatography on silica gel, eluting with a gradient of 0-100% EtOAc:EtOH (3:1) in heptane, to provide tert-butyl 3-((4-(4-bromo-6-chloro-1-(tetrahydro-2H-pyran-2-yl)-1H-indazol-5-yl)butanoyl)glycyl)piperidine-1-carboxylate (0.53 g, 70% yield) as white solid. m/z (ESI): 524.9/526.9 $(M+H)^+$. $^1H$ NMR (METHANOL-$d_4$, 400 MHz) δ 7.98 (s, 1H), 8.0-8.0 (m, 1H), 7.82 (s, 1H), 7.8-7.8 (m, 1H), 5.7-5.8 (m, 1H), 4.12 (d, 2H, J=7.9 Hz), 3.9-4.0 (m, 2H), 3.8-3.9 (m, 3H), 3.4-3.5 (m, 1H), 3.13 (br s, 1H), 3.1-3.2 (m, 3H), 2.96 (br d, 1H, J=8.2 Hz), 2.6-2.7 (m, 1H), 2.41 (s, 1H), 2.41 (br d, 3H, J=15.5 Hz), 1.9-2.0 (m, 2H), 1.6-1.7 (m, 3H), 1.44 (s, 9H).

Step 4. tert-Butyl 3-(2-(3-(4-bromo-6-chloro-1-(tetrahydro-2H-pyran-2-yl)-1H-indazol-5-yl)propyl)oxazol-5-yl)piperidine-1-carboxylate. A mixture of tert-butyl 3-((4-(4-bromo-6-chloro-1-(tetrahydro-2H-pyran-2-yl)-1H-indazol-5-yl)butanoyl)glycyl)piperidine-1-carboxylate (0.48 g, 0.77 mmol), Burgess reagent (0.55 g, 2.29 mmol, Combi-blocks) in 2-methyltetrahydrofuran (20 mL) in a 40 mL vial was purged with argon, then heated at 75° C. for 1.5 h. After cooling to rt, the mixture was concentrated and the crude was purified by column chromatography on silica gel, eluting with a gradient of 0-100% EtOAc in heptane, to provide tert-butyl 3-(2-(3-(4-bromo-6-chloro-1-(tetrahydro-2H-pyran-2-yl)-1H-indazol-5-yl)propyl)oxazol-5-yl)piperidine-1-carboxylate (0.34 g, 0.56 mmol, 73% yield) as white solid. m/z (ESI): 607.0/608.9 $(M+H)^+$. $^1H$ NMR (CHLOROFORM-d, 400 MHz) δ 7.95 (d, 1H, J=0.8 Hz), 7.63 (s, 1H), 6.68 (s, 1H), 5.63 (dd, 1H, J=2.7, 9.0 Hz), 3.99 (br d, 1H, J=10.2 Hz), 3.92 (br d, 1H, J=13.6 Hz), 3.7-3.8 (m, 1H), 3.1-3.1 (m, 2H), 2.8-3.0 (m, 5H), 2.4-2.5 (m, 1H), 2.0-2.2 (m, 6H), 1.6-1.8 (m, 5H), 1.46 (s, 10H).

Intermediate CM: tert-Butyl (3R)-3-(((3-(4-bromo-6-chloro-1-(tetrahydro-2H-pyran-2-yl)-1H-indazol-5-yl)propoxy)carbonyl)amino)azepane-1-carboxylate

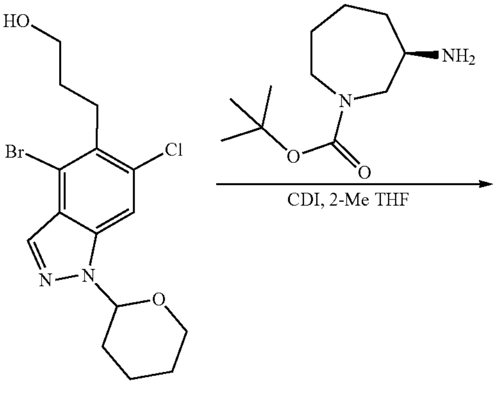

-continued

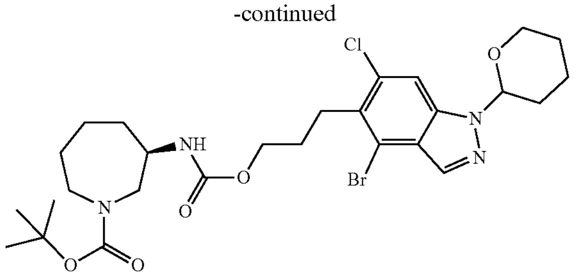

To a stirred solution of 3-(4-bromo-6-chloro-1-(tetrahydro-2H-pyran-2-yl)-1H-indazol-5-yl)propan-1-ol (0.42 g, 1.13 mmol, Intermediate FFF, Step 2) in 2-methyltetrahydrofuran (6 mL) was added 1,1'-carbonyldiimidazole (0.46 g, 2.83 mmol). The reaction mixture was stirred at rt for 20 min. Then tert-butyl (3R)-3-aminoazepane-1-carboxylate (0.49 g, 2.26 mmol, Synthonix Inc.) was added. The reaction mixture was stirred at 80° C. for 16 h. After cooling to rt, the mixture was treated with sat. aq. $NaHCO_3$ and diluted with EtOAc. The combined organic extracts were dried over $MgSO_4$, filtered, and concentrated in vacuo. The crude material was purified by column chromatography on silica gel, eluting with a gradient of 0-50% 3:1 EtOAc:EtOH (with 10% $NH_3$ in MeOH) in heptane, to provide tert-butyl (3R)-3-(((3-(4-bromo-6-chloro-1-(tetrahydro-2H-pyran-2-yl)-1H-indazol-5-yl)propoxy)carbonyl)amino)azepane-1-carboxylate (0.69 g, 1.12 mmol, 99% yield) as light-yellow oil. $^1H$ NMR (DMSO-$d_6$, 400 MHz) δ 8.07 (s, 1H), 8.02 (s, 1H), 7.07 (br s, 1H), 5.88 (dd, 1H, J=2.4, 9.7 Hz), 4.0-4.1 (m, 2H), 3.8-3.9 (m, 1H), 3.7-3.8 (m, 1H), 3.5-3.7 (m, 3H), 3.17 (d, 1H, J=5.4 Hz), 2.9-3.1 (m, 4H), 2.3-2.4 (m, 1H), 2.0-2.1 (m, 1H), 1.9-2.0 (m, 1H), 1.8-1.9 (m, 2H), 1.68 (br d, 4H, J=9.6 Hz), 1.6-1.6 (m, 2H), 1.4-1.4 (m, 9H), 1.2-1.3 (m, 2H). m/z (ESI): 613.3 $(M+H)^+$.

Intermediate CN: tert-Butyl (3R)-3-((4-(2-(4-bromo-6-chloro-1-(tetrahydro-2H-pyran-2-yl)-1H-indazol-5-yl)ethyl)pyrimidin-2-yl)oxy)piperidine-1-carboxylate

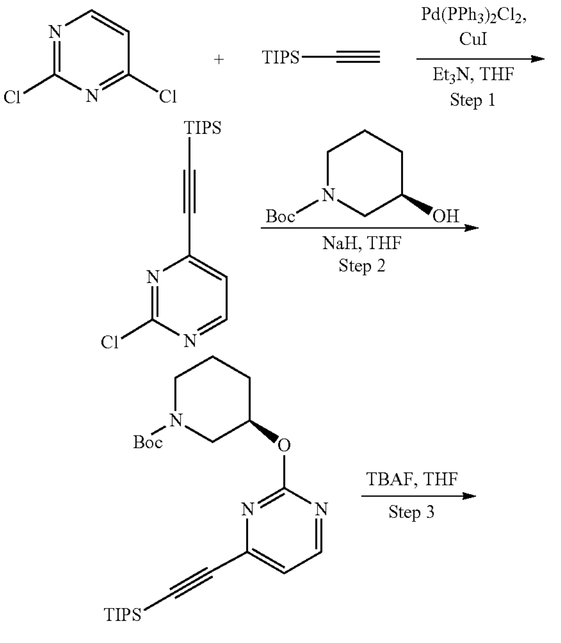

-continued

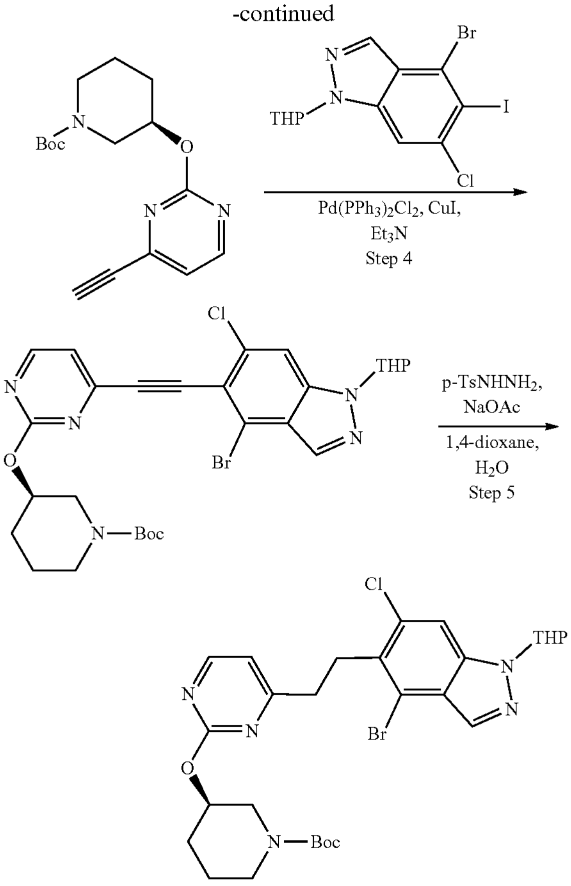

Intermediate CN

Step 1. 2-Chloro-4-((triisopropylsilyl)ethynyl)pyrimidine. To a 250-mL round-bottom flask was charged with 2,4-dichloropyrimidine (2.00 g, 13.4 mmol, Ambeed, Inc.), bis(triphenylphosphine)palladium(II) dichloride (0.71 g, 1.01 mmol), and copper(I) iodide (0.19 g, 1.01 mmol) in tetrahydrofuran (24 mL). The resulting mixture was purged with nitrogen for 5 min, then triethylamine (9.4 mL, 67 mmol) was added, followed by ethynyltriisopropylsilane (2.69 g, 14.8 mmol). The reaction mixture was heated for 3 h at 65° C. After cooling to rt, the mixture was filtered through celite and the filtrate was concentrated. The crude material was purified by column chromatography on silica gel, eluting with 0-20% EtOAc in heptane to provide 2-chloro-4-((triisopropylsilyl)ethynyl)pyrimidine (3.88 g, 13.2 mmol, 98% yield) as orange-yellow oil. m/z (ESI): 295.0 $(M+H)^+$ Step 2. tert-Butyl (R)-3-((4-((triisopropylsilyl)ethynyl)pyrimidin-2-yl)oxy)piperidine-1-carboxylate. To a 250-mL round-bottom flask was suspended sodium hydride (60% in mineral oil, 0.49 g, 12.2 mmol) in THF (12 mL) under nitrogen. The mixture was cooled to 0° C., and tert-butyl (R)-3-hydroxypiperidine-1-carboxylate (2.25 g, 11.2 mmol) in tetrahydrofuran (12 mL) was added, followed by the addition of 2-chloro-4-((triisopropylsilyl)ethynyl)pyrimidine (3.00 g, 10.2 mmol) in tetrahydrofuran (12 mL) at 0° C. The reaction mixture was stirred at rt for 1 h, and was quenched at 0° C. by sequential addition of isopropanol, MeOH, and saturated $NH_4Cl$ solution. Saturated NaCl solution was added, and the mixture was extracted with EtOAc. The combined organic layers were dried over $Na_2SO_4$, filtered, and concentrated. The crude material was purified by column chromatography on silica gel, eluting with a gradient of 0-50% EtOAc in heptane, to provide tert-butyl (R)-3-((4-((triisopropylsilyl)ethynyl)pyrimidin-2-yl)oxy)piperidine-1-carboxylate (4.47 g, 9.72 mmol, 96% yield) as pale yellow oil. m/z (ESI): 460.2 (M+H)+

Step 3. tert-Butyl (R)-3-((4-ethynylpyrimidin-2-yl)oxy)piperidine-1-carboxylate. To a solution of tert-butyl (R)-3-((4-((triisopropylsilyl)ethynyl)pyrimidin-2-yl)oxy)piperidine-1-carboxylate (4.47 g, 9.72 mmol) in THF (19 mL) was added tetrabutylammonium fluoride (1 M in THF, 10.7 mL, 10.7 mmol) dropwise at 0° C. The mixture was stirred at 0° C. for 15 min, then saturated NaCl solution was added, and the mixture was extracted with EtOAc. The combined organic layers were dried over $Na_2SO_4$, filtered, and concentrated. The crude material was purified by column chromatography on silica gel, eluting with 0-50% EtOAc in heptane, to provide tert-butyl (R)-3-((4-ethynylpyrimidin-2-yl)oxy)piperidine-1-carboxylate (1.02 g, 3.36 mmol, 35% yield) as white solid. m/z (ESI): 325.9 $(M+Na)^+$.

Step 4. tert-Butyl (3R)-3-((4-((4-bromo-6-chloro-1-(tetrahydro-2H-pyran-2-yl)-1H-indazol-5-yl)ethynyl)pyrimidin-2-yl)oxy)piperidine-1-carboxylate. To a microwave vial was charged with 4-bromo-6-chloro-5-iodo-1-(tetrahydro-2H-pyran-2-yl)-1H-indazole (0.73 g, 1.65 mmol, Pharmablock, Inc.), tert-butyl (R)-3-((4-ethynylpyrimidin-2-yl)oxy)piperidine-1-carboxylate (0.50 g, 1.65 mmol), bis(triphenylphosphine)palladium(II) dichloride (0.12 g, 0.17 mmol) and triethylamine (14.0 mL, 100 mmol). The resulting mixture was purged with nitrogen for 10 min then copper(I) iodide (16 mg, 0.082 mmol) was added. The vial was capped and irradiated with microwave at 65° C. for 15 h. After cooling to rt, the resulting mixture was concentrated and purified by column chromatography on silica gel, eluting with a gradient of 0-100% EtOAc in heptane, to provide tert-butyl (3R)-3-((4-((4-bromo-6-chloro-1-(tetrahydro-2H-pyran-2-yl)-1H-indazol-5-yl)ethynyl)pyrimidin-2-yl)oxy)piperidine-1-carboxylate (0.25 g, 0.40 mmol, 24% yield) as yellow oil. m/z (ESI): 615.6 $(M+H)^+$.

Step 5. tert-Butyl (3R)-3-((4-(2-(4-bromo-6-chloro-1-(tetrahydro-2H-pyran-2-yl)-1H-indazol-5-yl)ethyl)pyrimidin-2-yl)oxy)piperidine-1-carboxylate. To a 40-mL vial was charged with tert-butyl (3R)-3-((4-((4-bromo-6-chloro-1-(tetrahydro-2H-pyran-2-yl)-1H-indazol-5-yl)ethynyl)pyrimidin-2-yl)oxy)piperidine-1-carboxylate (0.25 g, 0.40 mmol) in 1,4-dioxane (4.0 mL). p-Toluenesulfonyl hydrazide (1.49 g, 8.01 mmol) was added and the mixture was degassed by $N_2$ for 10 min before heating to 85° C. Under inert atmosphere, sodium acetate (0.66 g, 8.01 mmol) in water was added via a syringe pump over 8 h. After cooling to rt, the reaction mixture was diluted with saturated NaCl solution and extracted with EtOAc. The combined organic layers were dried over $Na_2SO_4$, filtered, and concentrated. The crude material was purified by column chromatography on silica gel, eluting with 0-50% EtOAc in heptane, to provide tert-butyl (3R)-3-((4-(2-(4-bromo-6-chloro-1-(tetrahydro-2H-pyran-2-yl)-1H-indazol-5-yl)ethyl)pyrimidin-2-yl)oxy)piperidine-1-carboxylate (0.25 g, 0.40 mmol, 100% yield) as colorless oil. m/z (ESI): 619.6 $(M+H)^+$.

Intermediate CO: tert-Butyl (Z)-6-((4-(2-(4-bromo-6-chloro-1-(tetrahydro-2H-pyran-2-yl)-1H-indazol-5-yl)vinyl)-2H-1,2,3-triazol-2-yl)methyl)-1,4-oxazepane-4-carboxylate

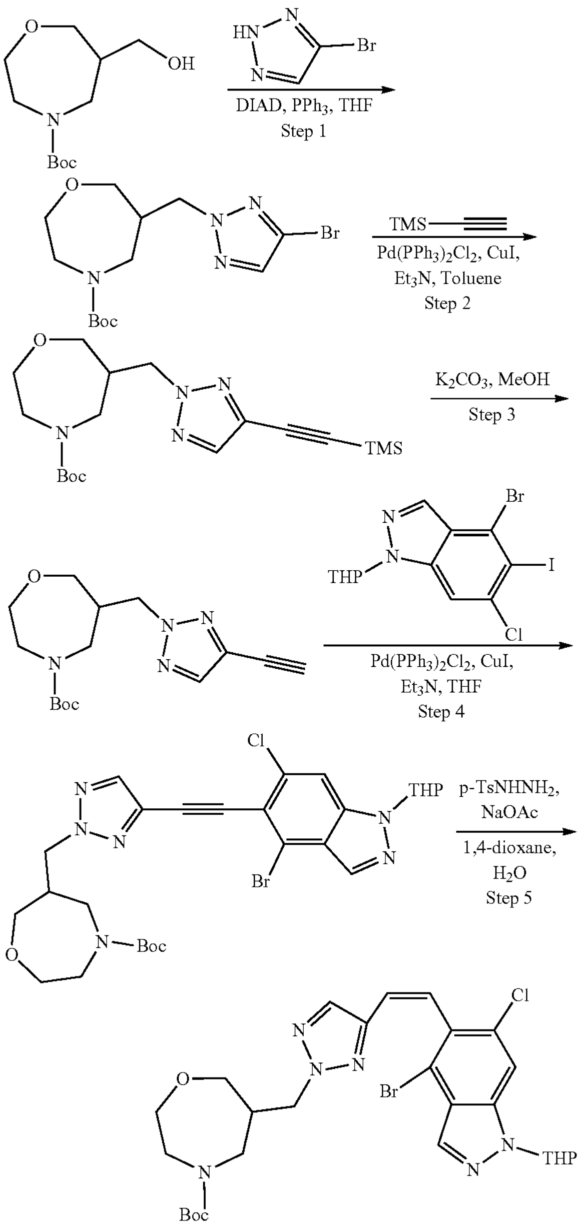

Intermediate CO

Step 1. tert-Butyl 6-((4-bromo-2H-1,2,3-triazol-2-yl)methyl)-1,4-oxazepane-4-carboxylate. To a 40-mL vial was charged with (E)-diisopropyl diazene-1,2-dicarboxylate (0.33 g, 1.65 mmol,) in tetrahydrofuran (6 mL). Triphenylphosphine (0.43 g, 1.65 mmol), tert-butyl 6-(hydroxymethyl)-1,4-oxazepane-4-carboxylate (0.35 g, 1.50 mmol, Chemspace Inc.) and 5-bromo-1H-1,2,3-triazole (0.22 g, 1.5 mmol, Ambeed, Inc.) was added sequentially. The reaction mixture was stirred at rt for 3 h. The resulting mixture was concentrated and purified by column chromatography on silica gel, eluting with 0-50% EtOAc in heptane, to provide tert-butyl 6-((4-bromo-2H-1,2,3-triazol-2-yl)methyl)-1,4-oxazepane-4-carboxylate (0.56 g, 1.56 mmol, 100% yield) as colorless oil. m/z (ESI): 382.8/384.8 $(M+Na)^+$ Step 2. tert-Butyl 6-((4-((trimethylsilyl)ethynyl)-2H-1,2,3-triazol-2-yl)methyl)-1,4-oxazepane-4-carboxylate. To a 5-mL microwave vial was charged with tert-butyl 6-((4-bromo-2H-1,2,3-triazol-2-yl)methyl)-1,4-oxazepane-4-carboxylate (0.54 g, 1.50 mmol), bis(triphenylphosphine)palladium(II) dichloride (79 mg, 0.11 mmol), and copper(I) iodide (21 mg, 0.11 mmol) in toluene (3 mL). The resulting mixture was purged with nitrogen for 5 min, then triethylamine (1.1 mL, 7.5 mmol) was added, followed by (trimethylsilyl)acetylene (0.32 mL, 2.3 mmol). The reaction mixture was irradiated at 85° C. for 4 h. After cooling to rt, the mixture was concentrated and the crude material was purified by column chromatography on silica gel, eluting with 0-50% EtOAc in hexane, to provide tert-butyl 6-((4-((trimethylsilyl)ethynyl)-2H-1,2,3-triazol-2-yl)methyl)-1,4-oxazepane-4-carboxylate (0.41 g, 1.09 mmol, 73% yield) as yellow oil. m/z (ESI): 378.9 $(M+H)^+$ Step 3. tert-Butyl 6-((4-ethynyl-2H-1,2,3-triazol-2-yl)methyl)-1,4-oxazepane-4-carboxylate. In a 40-mL vial was charged with a mixture of tert-butyl 6-((4-((trimethylsilyl)ethynyl)-2H-1,2,3-triazol-2-yl)methyl)-1,4-oxazepane-4-carboxylate (0.41 g, 1.09 mmol) and potassium carbonate (0.75 g, 5.46 mmol) in methanol (6 mL). The reaction mixture was stirred under nitrogen at rt for 30 min and was diluted with EtOAc and filtered through celite. The filtrate was concentrated, and the residue was diluted with EtOAc and washed with saturated $NH_4Cl$ solution. The organic layer was dried over $Na_2SO_4$, concentrated and the residue was purified by column chromatography on silica gel, eluting with a gradient of 0-100% EtOAc in heptane, to provide tert-butyl 6-((4-ethynyl-2H-1,2,3-triazol-2-yl)methyl)-1,4-oxazepane-4-carboxylate (0.25 g, 0.82 mmol, 75% yield) as colorless oil. m/z (ESI): 328.9 (M+Na)

Step 4. tert-Butyl 6-((4-((4-bromo-6-chloro-1-(tetrahydro-2H-pyran-2-yl)-1H-indazol-5-yl)ethynyl)-2H-1,2,3-triazol-2-yl)methyl)-1,4-oxazepane-4-carboxylate. To a 5-mL microwave vial was charged with 4-bromo-6-chloro-5-iodo-1-(oxan-2-yl)-1H-indazole (0.36 g, 0.82 mmol, Pharmablock, Inc.), tert-butyl 6-((4-ethynyl-2H-1,2,3-triazol-2-yl)methyl)-1,4-oxazepane-4-carboxylate (0.25 g, 0.82 mmol), bis(triphenylphosphine)palladium(II) dichloride (43 mg, 0.061 mmol) and copper(I) iodide (12 mg, 0.061 mmol). THF (1.6 mL) was added under nitrogen, followed by the addition of triethylamine (0.57 mL, 4.1 mmol). The resulting mixture was purged with nitrogen for 10 min and irradiated with microwave at 65° C. for 24 h. After cooling to rt, the mixture was concentrated and was purified by column chromatography on silica gel, eluting with a gradient of 0-100% EtOAc in heptane, to provide tert-butyl 6-((4-((4-bromo-6-chloro-1-(tetrahydro-2H-pyran-2-yl)-1H-indazol-5-yl)ethynyl)-2H-1,2,3-triazol-2-yl)methyl)-1,4-oxazepane-4-carboxylate (0.21 g, 0.33 mmol, 41% yield) as orange oil. m/z (ESI): 562.6, 564.6 $(M-{}^{t}Bu+H)^+$ Step 5. tert-Butyl (Z)-6-((4-(2-(4-bromo-6-chloro-1-(tetrahydro-2H-pyran-2-yl)-1H-indazol-5-yl)vinyl)-2H-1,2,3-triazol-2-yl)methyl)-1,4-oxazepane-4-carboxylate. To a 40-mL vial was charged with tert-butyl 6-((4-((4-bromo-6-chloro-1-(tetrahydro-2H-pyran-2-yl)-1H-indazol-5-yl)ethynyl)-2H-1,2,3-triazol-2-yl)methyl)-1,4-oxazepane-4-carboxylate (0.21 g, 0.33 mmol) in 1,4-dioxane (3 mL). p-Toluenesulfonyl hydrazide (1.24 g, 6.65 mmol) was added, and the mixture was degassed by $N_2$ for 10 min, then heated to 85° C. Sodium acetate (0.55 g, 6.65 mmol) in water (3 mL) was added via a syringe pump over 8 h. The mixture was stirred at 85° C. for an additional 7 h. After cooling to rt, the mixture was diluted with saturated NaCl solution and extracted with EtOAc. The combined organic layers were dried over $Na_2SO_4$, filtered, and concentrated. The crude was purified by column chromatography on silica gel, eluting with 0-50% EtOAc in heptane, to provide tert-butyl (Z)-6-((4-(2-(4-bromo-6-chloro-1-(tetrahydro-2H-pyran-2-yl)-1H-indazol-5-yl)vinyl)-2H-1,2,3-triazol-2-yl)methyl)-1,4-oxazepane-4-carboxylate (0.15 g, 0.24 mmol, 71% yield) as white foam. m/z (ESI): 620.9/622.9 $(M+H)^+$.

Intermediate CP: tert-Butyl (3R)-3-(2-(3-(4-bromo-6-chloro-1-(tetrahydro-2H-pyran-2-yl)-1H-indazol-5-yl)propyl)-2H-1,2,3-triazol-4-yl)piperidine-1-carboxylate

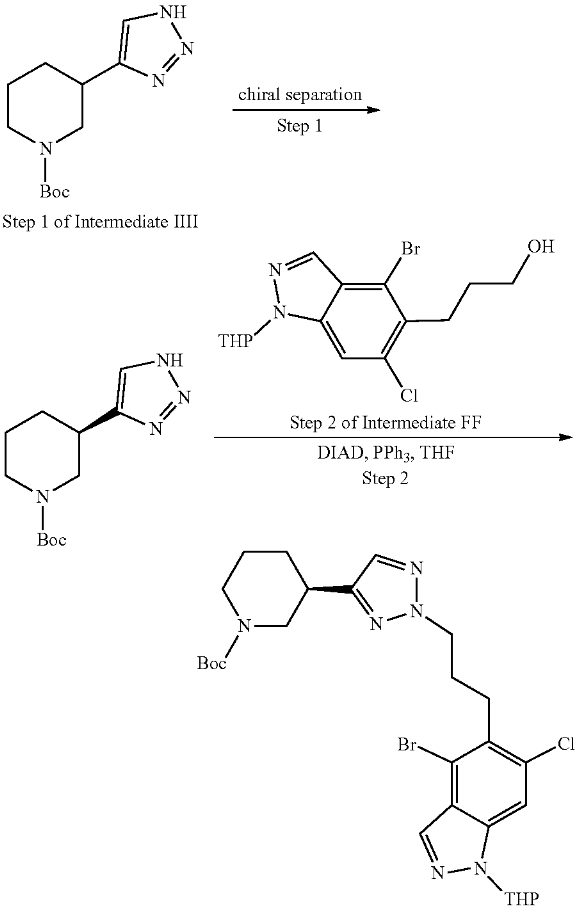

Intermediate CP

Step 1. tert-Butyl (R)-3-(1H-1,2,3-triazol-4-yl)piperidine-1-carboxylate. tert-Butyl-3-(1H-1,2,3-triazol-4-yl)piperidine-1-carboxylate (12.5 g, Step 1 of Intermediate IIII) was separated via SFC using a ChiralPak AD, 2×25 cm, 5 μm column with a mobile phase of 15% MeOH with 0.2% DEA, using a flowrate of 80 m/min, to provide tert-butyl (R)-3-(1H-1,2,3-triazol-4-yl)piperidine-1-carboxylate (4.97 g) with an ee of >99%. m/z (ESI): 253.1 $(M+H)^+$.

Step 2. tert-Butyl (3R)-3-(2-(3-(4-bromo-6-chloro-1-(tetrahydro-2H-pyran-2-yl)-1H-indazol-5-yl)propyl)-2H-1,2,3- triazol-4-yl)piperidine-1-carboxylate. To a 40-mL vial was charged with (E)-diisopropyl diazene-1,2-dicarboxylate (0.71 g, 3.50 mmol, Oakwood Products, Inc.) in tetrahydrofuran (8 mL). Triphenylphosphine (0.92 g, 3.50 mmol), 3-(4-bromo-6-chloro-1-(tetrahydro-2H-pyran-2-yl)-1H-indazol-5-yl)propan-1-ol (1.19 g, 3.18 mmol, Step 2 of Intermediate FF) in tetrahydrofuran (8 mL) were added, followed by tert-butyl (R)-3-(1H-1,2,3-triazol-4-yl)piperidine-1-carboxylate (0.84 g, 3.34 mmol) in tetrahydrofuran (8 mL). The reaction mixture was stirred at rt for 30 min, concentrated, and purified by column chromatography on silica gel, eluting with 0-50% EtOAc in heptane to provide tert-butyl (3R)-3-(2-(3-(4-bromo-6-chloro-1-(tetrahydro-2H-pyran-2-yl)-1H-indazol-5-yl)propyl)-2H-1,2,3-triazol-4-yl)piperidine-1-carboxylate (1.48 g, 2.43 mmol, 76% yield) as colorless oil. m/z (ESI): 629.2/631.2 $(M+Na)^+$.

Intermediate CQ: (S)-6-(7-chloro-8-fluoro-2-((1-methylpyrrolidin-2-yl)methoxy)pyrido[4,3-d]pyrimidin-4-yl)-6-azaspiro[3.5]nonan-2-ol

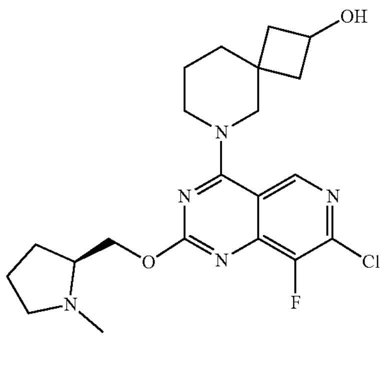 [SMILES: CN1CCC[C@H]1COc1nc(N2CCCC3(CC(O)C3)C2)c2cnc(Cl)c(F)c2n1]

This compound was prepared in an analogous fashion to Intermediate BE using (2S)-1-methyl-2-pyrrolidinemethanol (CAS #: 34381-71-0, Sigma-Aldrich Corporation) last in the procedure. m/z (ESI): 436.0 $(M+H)^+$.

Intermediate CR: (6S)-4-(7-Chloro-8-fluoro-2-(1-((S)-1-methylpyrrolidin-2-yl)ethoxy)pyrido[4,3-d]pyrimidin-4-yl)-1,4-oxazepan-6-ol

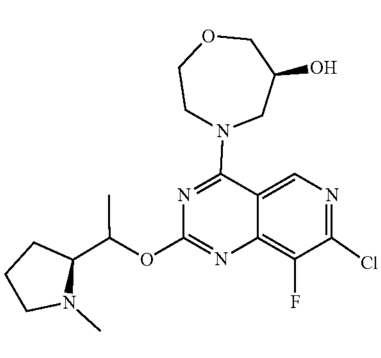 [SMILES: CC(Oc1nc(N2CCOC[C@@H](O)C2)c2cnc(Cl)c(F)c2n1)[C@@H]1CCCN1C]

The compound was prepared in an analogous fashion as Intermediate_BI adding 1-[(2S)-1-methylpyrrolidin-2-yl]ethan-1-ol (CAS #: 228857-49-6, Enamine) last in the procedure. m/z (ESI): 426.0 $(M+H)^+$.

Intermediate CS: Methyl 2-(3-(4-bromo-6-chloro-1-(tetrahydro-2H-pyran-2-yl)-1H-indazol-5-yl)propoxy)acetate

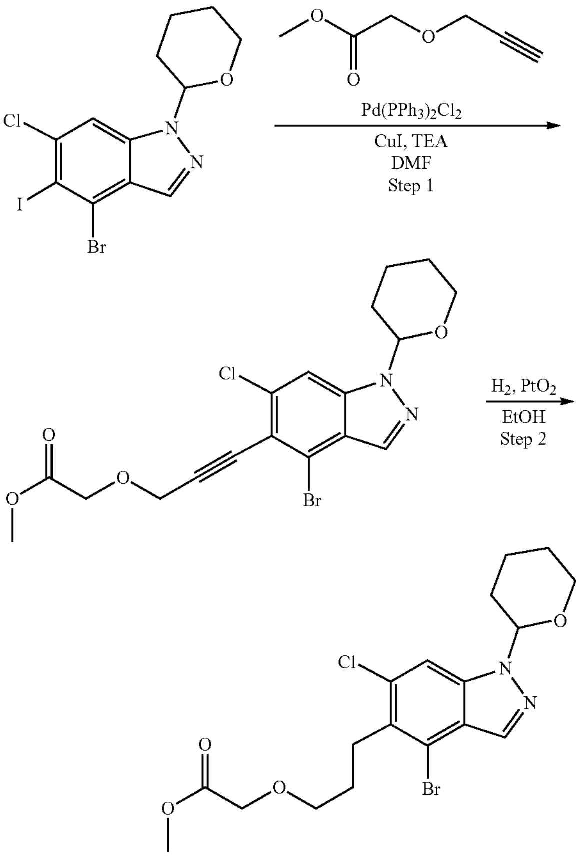

Intermediate CS

Step 1. Methyl 2-((3-(4-bromo-6-chloro-1-(tetrahydro-2H-pyran-2-yl)-1H-indazol-5-yl)prop-2-yn-1-yl)oxy)acetate. A vial was charged with 4-bromo-6-chloro-5-iodo-1-(tetrahydro-2H-pyran-2-yl)-1H-indazole (2.50 g, 5.66 mmol, Lab Network), methyl 2-(prop-2-yn-1-yloxy)acetate (1.67 g, 13.0 mmol, Enamine) and N,N-dimethylformamide (11 mL). The contents were degassed with nitrogen for 15 min, then bis(triphenylphosphine)palladium(II) dichloride (0.20 g, 0.28 mmol) and copper iodide (32 mg, 0.17 mmol) was added, then the mixture was heated to 50° C. for 6 h. After cooling to rt, the reaction was diluted with water and extracted with EtOAc. The combined organic phases were washed with 0.5 N HCl, water, brine, dried over anhydrous sodium sulfate, filtered, and concentrated under reduced pressure. The crude material was purified by column chromatography on silica gel, eluting with a gradient of 0-30% (3:1 EtOAc:EtOH) in heptane, to provide methyl 2-((3-(4-bromo-6-chloro-1-(tetrahydro-2H-pyran-2-yl)-1H-indazol-5-yl)prop-2-yn-1-yl)oxy)acetate (1.50 g, 3.40 mmol, 60% yield) as orange oil. m/z (ESI): 462.9/464.8 $(M+Na)^+$.

Step 2. Methyl 2-(3-(4-bromo-6-chloro-1-(tetrahydro-2H-pyran-2-yl)-1H-indazol-5-yl)propoxy)acetate. A 250-mL ChemGlass reactor tube was charged with methyl 2-((3-(4-bromo-6-chloro-1-(tetrahydro-2H-pyran-2-yl)-1H-indazol-5-yl)prop-2-yn-1-yl)oxy)acetate (0.53 g, 1.20 mmol) and platinum(IV) oxide (27 mg, 0.12 mmol). The vessel was purged with nitrogen, then charged with ethanol (6 mL). The vessel was pressurized with hydrogen to 25 psi, sealed and stirred at for 4 h. The reaction was filtered through a celite plug, washed with EtOAc and the organic phase was concentrated to provide methyl 2-(3-(4-bromo-6-chloro-1-(tetrahydro-2H-pyran-2-yl)-1H-indazol-5-yl) propoxy)acetate (0.51 g, 1.15 mmol, 96% yield) as orange oil, which was used without purification for the next step. m/z (ESI): 445.0/447.0 $(M+H)^+$.

Intermediate CT: tert-Butyl (R)-3-methyl-3-(methylamino)piperidine-1-carboxylate

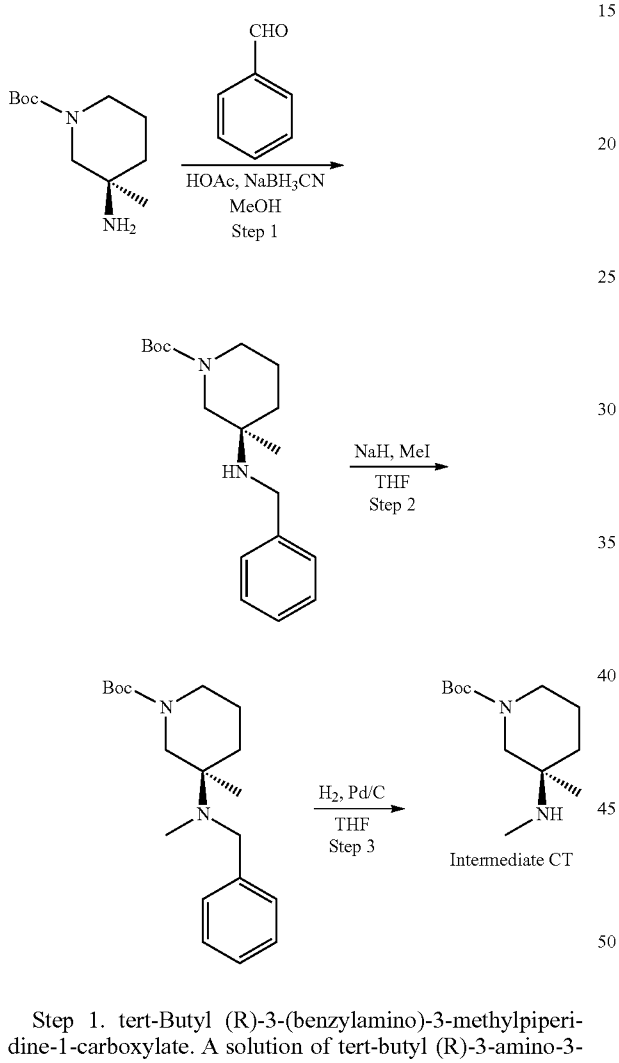

Step 1. tert-Butyl (R)-3-(benzylamino)-3-methylpiperidine-1-carboxylate. A solution of tert-butyl (R)-3-amino-3-methylpiperidine-1-carboxylate (1.00 g, 4.67 mmol) in methanol (20 mL) was treated with benzaldehyde (0.59 g, 5.60 mmol) and HOAc (28 mg, 0.47 mmol), stirred for 30 min, then treated with $NaBH_3CN$ (0.44 g, 7.0 mmol) in small portions. The resulting mixture was stirred for 2 h then treated with water and extracted with ethyl acetate. The combined organic layers were dried over $Na_2SO_4$, filtered, and concentrated. The residue was purified by column chromatography on silica gel, eluting with a gradient of 2-10% ethyl acetate in petroleum ether, to provide tert-butyl (R)-3-(benzylamino)-3-methylpiperidine-1-carboxylate (1.18 g, 3.88 mmol, 83% yield) as colorless oil. $^1H$ NMR (400 MHz, $CDCl_3$) δ 7.31-7.38 (m, 4H), 7.23-7.29 (m, 1H), 3.64-3.77 (m, 4H), 2.97-3.11 (m, 2H), 1.69-1.72 (m, 2H), 1.46-1.67 (m, 12H), 1.14 (s, 3H). m/z (ESI): 305.1 $(M+H)^+$.

Step 2. tert-Butyl (R)-3-(benzyl(methyl)amino)-3-methylpiperidine-1-carboxylate. To a solution of tert-butyl (R)-3-(benzylamino)-3-methylpiperidine-1-carboxylate (2.04 g, 6.69 mmol) in tetrahydrofuran (10 mL) at 0° C. was added NaH (0.48 g, 60 wt. % in mineral oil, 12.1 mmol). The mixture was stirred at 0° C. for 30 min then treated with Mel (1.7 mL, 26.8 mmol). The resulting mixture was stirred at 50° C. for 12 h, then cooled with an ice bath and then treated with saturated $NH_4Cl$ solution and extracted with ethyl acetate. The combined organic layers were dried over $Na_2SO_4$, filtered, and concentrated under reduced pressure. The residue was purified by column chromatography on silica gel, eluting with a gradient of 10-100% ethyl acetate in petroleum ether, to afford tert-butyl (R)-3-(benzyl (methyl)amino)-3-methylpiperidine-1-carboxylate (1.10 g) as colorless oil which was used as crude material. m/z (ESI): 319.1 $(M+H)^+$.

Step 3. tert-Butyl (R)-3-methyl-3-(methylamino)piperidine-1-carboxylate. To a solution of tert-butyl (R)-3-(benzyl (methyl)amino)-3-methylpiperidine-1-carboxylate (0.10 g, 0.31 mmol) in tetrahydrofuran (3 mL) was added Pd/C (0.10 mg, 10 wt %) under Ar atmosphere. The suspension was degassed and purged with H2 for 3 times. The mixture was stirred under H2 (15 psi) at rt for 12 h then filtered through a pad of celite, and the filtered cake was rinsed with ethyl acetate. The filtrate was concentrated under reduced pressure to give tert-butyl (R)-3-methyl-3-(methylamino)piperidine-1-carboxylate (80 mg) as a colorless oil which was used as crude material. m/z (ESI): 228.9 $(M+H)^+$.

Intermediate CU: 5-(2-((tert-Butyldimethylsilyl) oxy)ethyl)-6-chloro-1-(tetrahydro-2H-pyran-2-yl)-4-(4,4,5,5-tetramethyl-1,3,2-dioxaborolan-2-yl)-1H-indazole

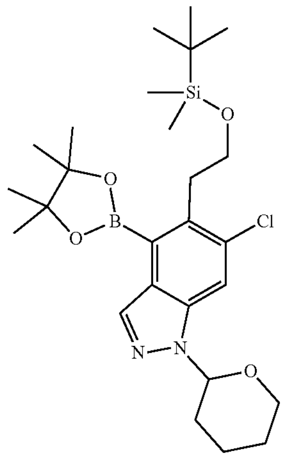 [SMILES: CC1(C)OB(c2c(CCO[Si](C)(C)C(C)(C)C)c(Cl)cc3c2cnn3C2CCCCO2)OC1(C)C]

The compound was prepared in an analogous fashion as Intermediate BN using 4-bromo-6-chloro-5-iodo-1-(tetrahydro-2H-pyran-2-yl)-1H-indazole (CAS #: 2791273-88-4, Lab Network) in Step 1 and osmium tetroxide solution in tert-butanol (CAS #: 20816-12-0, Thermo Fisher) in Step 2. m/z (ESI): 521.2 $(M+H)^+$.

Intermediate CV: (S)-7-Chloro-8-fluoro-2-((1-methylpyrrolidin-2-yl) methoxy)-4-(2,2,2-trifluoroethoxy)pyrido[4,3-d]pyrimidine

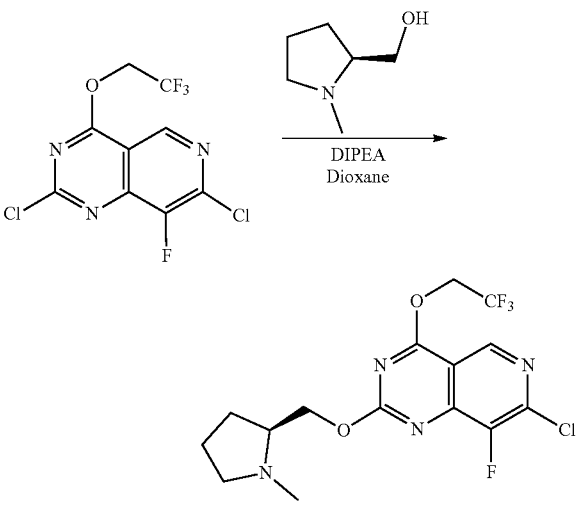

To a solution of 2,7-dichloro-8-fluoro-4-(2,2,2-trifluoroethoxy)pyrido[4,3-d]pyrimidine (30 g, 95 mmol, Step 1 in Intermediate AA) in 1,4-dioxane (600 mL) was added (R)-(1-methylpyrrolidin-2-yl)methanol (14.2 g, 123 mmol), followed by DIPEA (30.7 g, 237 mmol) dropwise under $N_2$. The mixture was stirred at rt for 3 h, then was diluted with $H_2O$ and extracted with EtOAc. The combined organic layers were washed with brine, dried over $Na_2SO_4$, filtered, and concentrated. The crude product was triturated with methyl tert-butyl ether for 1 h. The mixture was filtered, and the filter cake was washed with methyl tert-butyl ether, dried to give (S)-7-chloro-8-fluoro-2-((1-methylpyrrolidin-2-yl) methoxy)-4-(2,2,2-trifluoroethoxy)pyrido[4,3-d]pyrimidine (20.5 g, 52.0 mmol, 54% yield) as a yellow solid. $^1H$ NMR (400 MHz, CHLOROFORM-d) δ ppm 9.00 (s, 1H), 5.00-5.10 (m, 2H), 4.61-4.63 (m, 1H), 4.49-4.53 (m, 1H), 3.14-3.16 (m, 1H), 2.65-2.80 (s, 1H), 2.53 (s, 3H), 2.32-2.34 (m, 1H), 2.07-2.08 (m, 1H), 1.79-1.88 (m, 3H). $^{19}F$ NMR (376 MHz, CHLOROFORM-d) δ ppm −73.38 (s, 3 F), −133.74 (s, 1 F).

Intermediate CW: 1-(1-(((7-Chloro-8-fluoro-4-((3aR,7aR)-octahydro-6H-pyrrolo[2,3-c]pyridin-6-yl)pyrido[4,3-d]pyrimidin-2-yl)oxy)methyl)cyclopropyl)-N,N-dimethylmethanamine

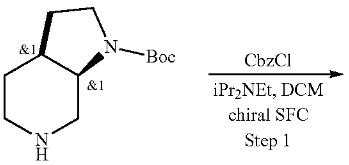

-continued

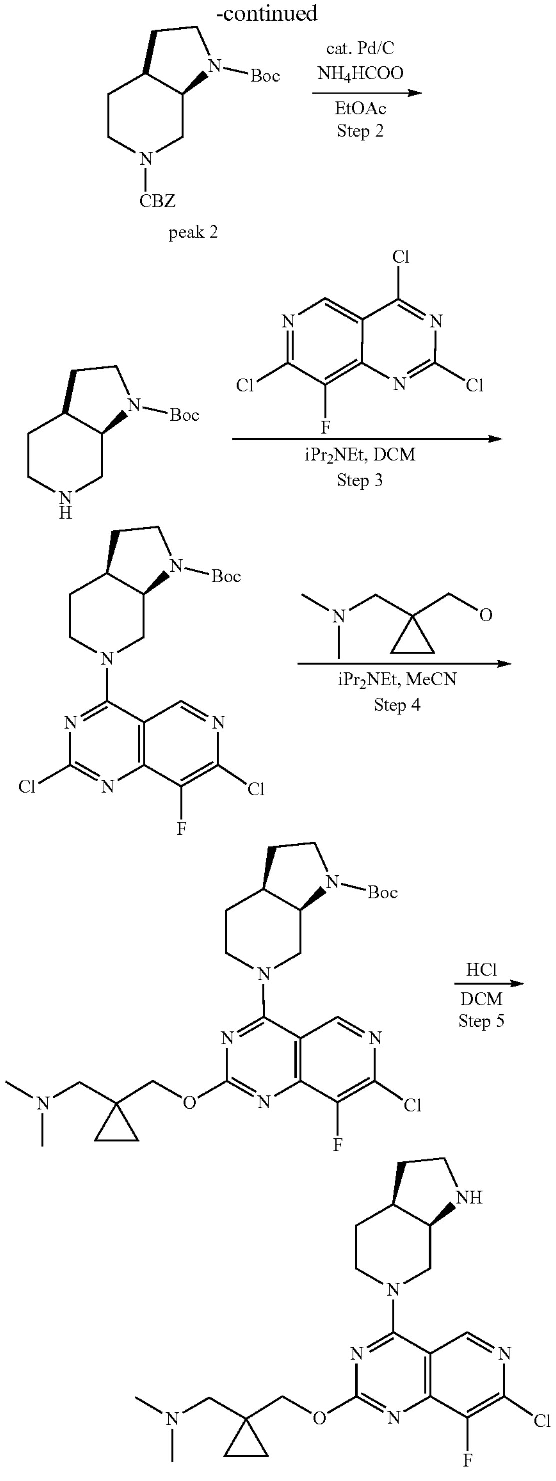

Intermediate CW

Step 1. 6-Benzyl 1-(tert-butyl) (3aS,7aR)-hexahydro-1H-pyrrolo[2,3-c]pyridine-1,6(2H)-dicarboxylate. A vial was charged with rac-tert-butyl (3aR,7aS)-octahydro-1H-pyrrolo [2,3-c]pyridine-1-carboxylate (10.0 g, 44.2 mmol, Aurum Pharmatech), TEA (9.3 mL, 66.3 mmol) and dichloromethane (88 mL). The content was cooled to 0° C., then Cbz-Cl (7.6 mL, 53.0 mmol) was added dropwise, then the reaction was stirred at 0° C. for 20 min, then at rt for 3 h. The crude material was purified by column chromatography on silica gel, eluting with a gradient of 0-50% (3:1 EtOAc/EtOH with 2% TEA) in heptane, to provide the crude product as light-yellow oil. The sample was purified via SFC using a ChiralPak IG, 3×25 cm 5 μm column with a mobile phase of 20% EtOH, using a flowyate of 160 nL/min to generate 7.05 g of peak 1 with an cc of 99% and 6.82 g of peak 2 with an cc of 99% as 6-benzyl 1-(tert-butyl) (3aS,7aR)-bexahydro-1H-pyrrolo[2,3-c]pyridine-1,6(2H)-dicarboxylate. Peak assignment determined by SF-C with ChiralPak IC column with 20% EtOH. m/z (ESI): 361.2 $(M+H)^+$.

Step 2. tert-Butyl (3aS,7aR)-octahydro-1H-pyrrolo[2,3-c]pyridine-1-carboxylate. A mixture of 6-benzyl-tert-butyl) (3aS,7aR)-hexahydro-1H-pyrrolo[2,3-c]pyridine-1,6(2H)-dicarboxylate (6.82 g, 18.9 mmol), ammonium formate (5.97 g, 95 mmol), and palladium 10% on activated carbon, 50% water wet paste (2.01 g, 1.89 mmol) in ethyl acetate (47 mL) was stirred at rt for 3 h. The reaction mixture was filtered through a pad of celite, washed with EtOAc/EtOH (3:1) and concentrated to provide tert-butyl (3aS,7aR)-octahydro-1H-pyrrolo[2,3-c]pyridine-1-carboxylate (4.1 g, 18 mmol, 96% yield) as light yellow oil. m/z (ESI): 227.2 $(M+H)^+$.

Step 3. tert-Butyl (3aS,7aR)-6-(2,7-dichloro-8-fluoro-pyrido[4,3-d]pyrimidin-5-yl)octahydro-1H-pyrrolo[2,3-c]pyridine-1-carboxylate. To a 20 ml vial was charged with 2,4,7-trichloro-8-fluoropyrido[4,3-d]pyrimidine (2.23 g, 8.84 mmol, Enamine), tert-butyl (3aS,7aR)-octahydro-1H-pyrrolo[2,3-c]pyridine-1-carboxylate (2.00 g, 8.84 mmol) in DCM (30 ml). The contents were cooled to −78° C. and 1,1'-dimethyltriethylamine (8.8 mL, 35 mmol) was added dropwise. The reaction mixture was stirred at −78° C. for 15 min, was then allowed to warm to rt and diluted with water and brine. The aqueous layer was extracted with $CH_2Cl_2$ and the combined organic layers were dried with sodium sulfate, filtered and concentrated. The crude was by column chromatography on silica gel, eluting with a gradient of 5-10% (3:1 EtOAc/EtOH with 2% TEA) in heptane, to provide tert-butyl (3aS,7aR)-6-(2,7-dichloro-8-fluoropyrido[4,3-d]pyrimidin-5-yl)octahydro-1H-pyrrolo[2,3-c]pyridine-1-carboxylate (3.4 g, 7.7 mmol, 87% yield) as white solid. m/z (ESI): 442.0 [M+H]*.

Step 4. tert-Butyl (3aS,7aR)-6-(7-chloro-2-((1-((dimethylamino)methyl)cyclopropyl)methoxy)-8-fluoropyrido[4,3-d]pyrimidin-4-yl)octahydro-1H-pyrrolo[2,3-c]pyridine-1-carboxylate. Lithium bis(trimethylsilyl)amide solution (1 M in tetrahydrofuran, 4.9 mL, 4.9 mmol) was added to a solution of (1-[(dimethylamino)methyl]cyclopropyl)methanol (0.42 mL, 3.3 mmol) in tetrahydrofuran (13 mL) cooled to 0° C. and the content was stirred at 0° C. for 5 min. A solution of tert-butyl (3aS,7aR)-6-(2,7-dichloro-8-fluoro-pyrido[4,3-d]pyrimidin-5-yl)octahydro-1H-pyrrolo[2,3-c]pyridine-1-carboxylate (1.20 g, 2.70 mmol in tetrahydrofuran (10 mL) was added and the reaction mixture was stirred at 0° C. for 10 min and was warmed to rt with stirring for 6 h. The reaction was quenched by the addition of water and extracted with EtOAc. The organic layer was dried over sodium sulfate, filtered, and concentrated. The crude material was purified by column chromatography on silica gel column, eluting with a gradient of 60-100% (3:1 EtOAc/EtOH with 2% $NH_{40}H$) in heptanes, to provide tert-butyl (3aS,7aR)-6-(7-chloro-2-((1-((dimethylamino)methyl)cyclopropyl)methoxy)-8-fluoropyrido[4,3-d]pyrimidin-4-yl)octahydro-1H-pyrrolo[2,3-c]pyridine-1-carboxylate (1.4 g, 2.7 mmol, 98% yield) as light-yellow solid. m/z (ESI): 535.0 $(M+H)^+$.

Step 5. 1-(1-(((7-Chloro-8-fluoro-4-((3aR,7aR)-octahydro-6H-pyrrolo[2,3-c]pyridin-6-yl)pyrido[4,3-d]pyrimidin-2-yl)oxy)methyl)cyclopropyl)-N,N-dimethylmethanamine. A round bottom flask was charged with tert-butyl (3aS,7aR)-6-(7-chloro-2-((1-((dimethylamino)methyl)cyclopropyl)methoxy)-8-fluoropyrido[4,3-d]pyrimidin-4-yl)octahydro-1H-pyrrolo[2,3-c]pyridine-1-carboxylate (1.4 g, 2.7 mmol) and dichloromethane (13 mL). Hydrogen chloride (4 M in dioxane, 6.7 mL, 26.8 mmol) was added dropwise. The reaction mixture was stirred at rt for 2 h, then was concentrated to dryness under reduced pressure. The residue was treated with saturated sodium bicarbonate and extracted with EtOAc. The organic layer was dried ($Na_2SO_4$), filtered and concentrated to provide 1-(1-(((7-chloro-8-fluoro-4-((3aR,7aR)-octahydro-6H-pyrrolo[2,3-c]pyridin-6-yl)pyrido[4,3-d]pyrimidin-2-yl)oxy)methyl)cyclopropyl)-N,N-dimethylmethanamine (0.24 g, 0.56 mmol, 21% yield) as a tan residue. m/z (ESI): 435.1 $(M+H)^+$.

Intermediate CX: 4-(2,7-Diazabicyclo[3.3.1]nonan-7-yl)-7-chloro-8-fluoro-2-(((2R,7aS)-2-fluorotetrahydro-1H-pyrrolizin-7a(5H)-yl)methoxy)pyrido[4,3-d]pyrimidine

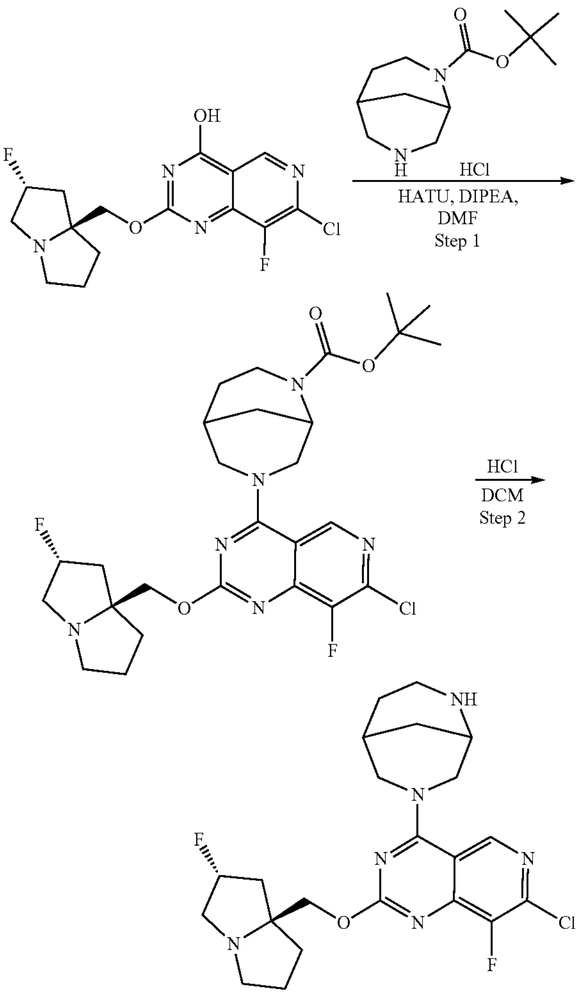

Intermediate CX

Step 1. tert-Butyl 7-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2,7-diazabicyclo[3.3.1]nonane-2- carboxylate. A 250 mL round bottom flask was charged with DIPEA (1.61 mL, 9.26 mmol), 7-chloro-8-fluoro-2-(((2R,7aS)-2-fluorotetrahydro-1H-pyrrolizin-7a(5H)-yl)methoxy)pyrido[4,3-d]pyrimidin-4-ol dihydrobromide (0.60 g, 1.16 mmol, Intermediate Z) and N,N-dimethylformamide (4 mL). The mixture was stirred at rt for 15 min, then HATU (0.53 g, 1.39 mmol) was added, and stirring was continued for 15 min. tert-Butyl 2,7-diazabicyclo[3.3.1]nonane-2-carboxylate hydrochloride (0.46 g, 1.74 mmol) was added and the reaction mixture was stirred at rt for 18 h. Water was added, and the mixture was extracted with EtOAc. The combined organic layers were washed with brine, dried over sodium sulfate, and concentrated in vacuo. The crude material was purified by column chromatography on silica gel, eluting with a gradient of 0-40% ethyl acetate in heptane, to provide tert-butyl 7-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2,7-diazabicyclo[3.3.1]nonane-2-carboxylate (0.65 g, 1.20 mmol, 99% yield) as a yellow solid. m/z (ESI): 565.0 $(M+H)^+$.

Step 2. 4-(2,7-Diazabicyclo[3.3.1]nonan-7-yl)-7-chloro-8-fluoro-2-(((2R,7aS)-2-fluorotetrahydro-1H-pyrrolizin-7a(5H)-yl)methoxy)pyrido[4,3-d]pyrimidine. tert-Butyl 7-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2,7-diazabicyclo[3.3.1]nonane-2-carboxylate (0.65 g, 1.20 mmol) dissolved in DCM (4 mL) was treated with 4 M HCl in dioxane (2.9 mL, 11.6 mmol) dropwise. The reaction mixture was stirred at rt for 18 h, then was neutralized with saturated $NaHCO_3$, and extracted with EtOAc. The combined organic layer was washed with brine, dried over sodium sulfate, and concentrated in vacuo to yield 4-(2,7-diazabicyclo[3.3.1]nonan-7-yl)-7-chloro-8-fluoro-2-(((2R,7aS)-2-fluorotetrahydro-1H-pyrrolizin-7a(5H)-yl)methoxy)pyrido[4,3-d]pyrimidine (0.37 g, 0.8 mmol, 69% yield) as yellow solid. m/z (ESI): 465.1 $(M+H)^+$.

Intermediate CY: 2-(2-(4-Bromo-6-chloro-1-(tetrahydro-2H-pyran-2-yl)-1H-indazol-5-yl)ethoxy)acetic acid

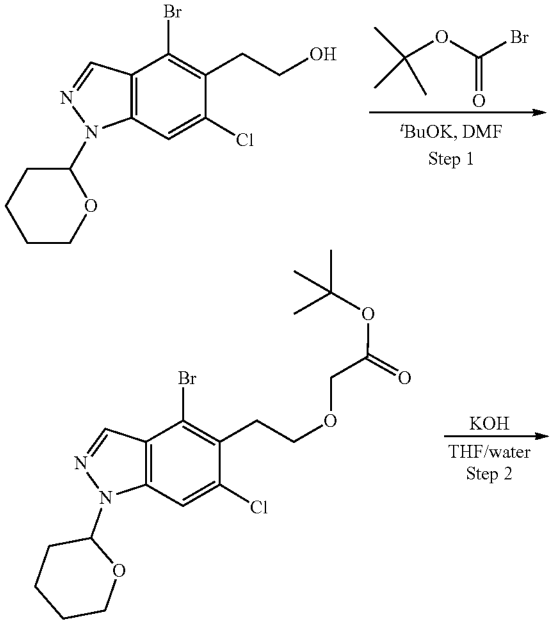

-continued

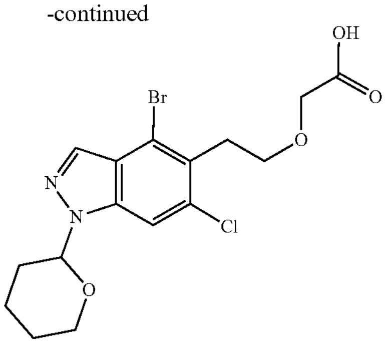

Intermediate CY

Step 1. tert-Butyl 2-(2-(4-bromo-6-chloro-1-(tetrahydro-2H-pyran-2-yl)-1H-indazol-5-yl)ethoxy)acetate. A vial was charged with 2-(4-bromo-6-chloro-1-(tetrahydro-2H-pyran-2-yl)-1H-indazol-5-yl)ethan-1-ol (3.00 g, 8.34 mmol, Step 1 of Intermediate XX) and N,N-dimethylformamide (20 mL) at 0° C. Then potassium tert-butoxide (1.87 g, 16.7 mmol) was added followed by tert-butyl bromoacetate (4.9 mL, 25 mmol) at 0° C. The ice bath was removed, and the reaction mixture was allowed to stir at rt for 15 min. The reaction was diluted with saturated $NH_4Cl$ and extracted with EtOAc. The combined organic layers were washed with brine, dried over $MgSO_4$, filtered, and concentrated. The crude material was purified by column chromatography on silica, eluting with a gradient of 0-45% 3:1 EtOAc/EtOH in heptane, to provide tert-butyl 2-(2-(4-bromo-6-chloro-1-(tetrahydro-2H-pyran-2-yl)-1H-indazol-5-yl)ethoxy)acetate (2.10 g, 4.40 mmol, 53% yield) as a colorless oil. m/z (ESI): 473.2 $(M+H)^+$.

Step 2. 2-(2-(4-Bromo-6-chloro-1-(tetrahydro-2H-pyran-2-yl)-1H-indazol-5-yl)ethoxy)acetic acid. To a 150-mL round-bottom flask was added tert-butyl 2-(2-(4-bromo-6-chloro-1-(tetrahydro-2H-pyran-2-yl)-1H-indazol-5-yl)ethoxy)acetate (2.1 g, 4.43 mmol) in ethanol (4.5 mL). A solution of potassium hydroxide (2.48 g, 44.3 mmol) in water (4.5 mL) was added and the reaction mixture was stirred at rt for 5 h. The reaction was diluted with water and extracted with EtOAc. The organic layer was discarded, and the aqueous layer was then acidified with 2 N HCl to pH 1, and extracted with EtOAc. The combined organic layers were washed with brine, dried over $MgSO_4$, filtered, and concentrated to give 2-(2-(4-bromo-6-chloro-1-(tetrahydro-2H-pyran-2-yl)-1H-indazol-5-yl)ethoxy)acetic acid (1.60 g, 3.80 mmol, 86% yield) as white solid. m/z (ESI): 417.0 $(M+H)^+$.

Intermediate CZ: 2-(3-(4-Bromo-6-chloro-1-(tetrahydro-2H-pyran-2-yl)-1H-indazol-5-yl)propoxy)acetic acid

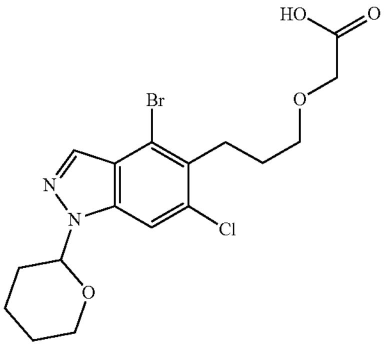 [SMILES: O=C(O)COCCCc1c(Cl)cc2c(cnn2C2CCCCO2)c1Br]

This compound was prepared in an analogous fashion as Intermediate CY using 3-(4-bromo-6-chloro-1-(tetrahydro-2H-pyran-2-yl)-1H-indazol-5-yl)propan-1-ol (Intermediate FFF, Step 2). m/z (ESI): 431.1 $(M+H)^+$.

Intermediate DA: 2-(2-(4-Bromo-1-(tetrahydro-2H-pyran-2-yl)-1,5,6,7-tetrahydrocyclopenta[f]indazol-5-yl)ethoxy)acetic acid

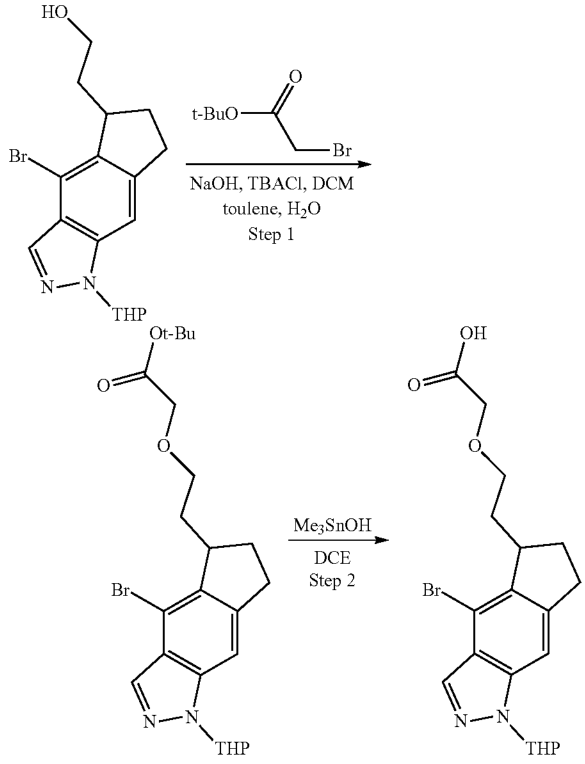

Intermediate DA

Step 1. tert-Butyl 2-(2-(4-bromo-1-(tetrahydro-2H-pyran-2-yl)-1,5,6,7-tetrahydrocyclopenta[f]indazol-5-yl)ethoxy) acetate. The mixture of 2-(4-bromo-1-(tetrahydro-2H-pyran-2-yl)-1,5,6,7-tetrahydrocyclopenta[f]indazol-5-yl) ethan-1-ol (1.00 g, 2.74 mmol) and TBACl (0.23 g, 0.82 mmol) in dichloromethane (5 mL) and toluene (5 mL) was stirred at 0° C. Then to the mixture was added NaOH (10 mL, 10 mmol) and tert-butyl 2-bromoacetate (1.60 g, 8.21 mmol) at 0° C. The reaction mixture was allowed to warm to rt with stirring for 6 h. The reaction mixture was diluted with $H_2O$ and extracted with EtOAc. The combined organic layers were washed with brine, dried over $Na_2SO_4$, filtered, and concentrated. The residue was purified by column chromatography on silica gel, eluting with a gradient of 0-20% EtOac in petroleum ether, to give tert-butyl 2-(2-(4-bromo-1-(tetrahydro-2H-pyran-2-yl)-1,5,6,7-tetrahydrocyclopenta[f]indazol-5-yl)ethoxy)acetate (1.20 g, 2.50 mmol, 91% yield).

Step 2. 2-(2-(4-Bromo-1-(tetrahydro-2H-pyran-2-yl)-1,5,6,7-tetrahydrocyclopenta[f]indazol-5-yl)ethoxy)acetic acid. A mixture of tert-butyl 2-(2-(4-bromo-1-(tetrahydro-2H-pyran-2-yl)-1,5,6,7-tetrahydrocyclopenta[f]indazol-5-yl) ethoxy)acetate (1.20 g, 2.50 mmol) and trimethylstannanol (3.60 g, 20 mmol) in DCE (12 mL) was stirred at 80° C. for 1 h. The reaction mixture was filtered, and the filtrate was concentrated under reduced pressure to give 2-(2-(4-bromo-1-(tetrahydro-2H-pyran-2-yl)-1,5,6,7-tetrahydrocyclopenta [f]indazol-5-yl)ethoxy)acetic acid (2 g crude product) which was used directly in the following step.

Intermediate DB: tert-Butyl (R)-3-amino-3-methylazepane-1-carboxylate

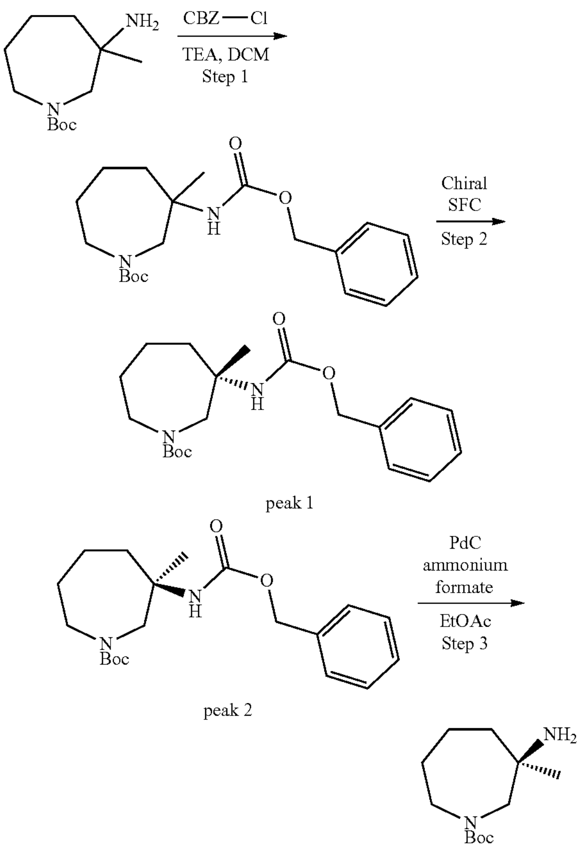

Intermediate DE

Step 1. tert-Butyl 3-(((benzyloxy)carbonyl)amino)-3-methylazepane-1-carboxylate. A vial was charged with tert-butyl 3-amino-3-methylazepane-1-carboxylate (5.00 g, 21.9 mmol, PharmaBlock), TEA (4.6 mL, 33 mmol) and dichloromethane (44 mL) and then cooled to 0° C. CBz-Cl (3.8 mL, 26 mmol) was added dropwise, and the reaction mixture was stirred at 0° C. for 20 min then was allowed to warm to rt for 3 h. The crude material was purified by column chromatography on silica gel, eluting with a gradient of 0-30% 3:1 EtOAc/EtOH in heptane, to provide tert-butyl 3-(((benzyloxy)carbonyl)amino)-3-methylazepane-1-carboxylate (5.39 g, 14.9 mmol, 68% yield) as colorless oil. m/z (ESI): 385.2 $(M+Na)^+$.

Step 2. tert-Butyl (R)-3-(((benzyloxy)carbonyl)amino)-3-methylazepane-1-carboxylate. tert-Butyl 3-(((benzyloxy) carbonyl)amino)-3-methylazepane-1-carboxylate (5.39 g) was purified via SFC using a ChiralPak IG, 3×25 cm 5 μm column with a mobile phase of 20% iPrOH with 0.2% DEA using a flowrate of 160 mL/min to generate 2.29 g of tert-butyl (S)-3-(((benzyloxy)carbonyl)amino)-3-methylazepane-1-carboxylate (Peak 1) with an ee of 99% and 2.27 g of tert-butyl (R)-3-(((benzyloxy)carbonyl)amino)-3-methylazepane-1-carboxylate (Peak 2) with an ee of 99%. Peak assignment determined by SFC with ChiralPak IG column with 15% iPrOH with 0.2% DEA. Chemical purity of Peak 1: >99%. Chemical purity of Peak 2: >99%. Peak 2 was carried forward.

Step 3. tert-Butyl (R)-3-amino-3-methylazepane-1-carboxylate. In a 250-mL round-bottom flask was charged with tert-butyl (R)-3-(((benzyloxy)carbonyl)amino)-3-methylazepane-1-carboxylate (2.13 g, 5.88 mmol), ammonium formate (1.85 g, 29.4 mmol), and palladium on carbon (0.94 g, 0.88 mmol) in ethyl acetate (20 mL). The reaction mixture was stirred at 40° C. for 1 h. After cooling to rt, the reaction was filtered through a plug of celite and washed with EtOAc. The filtrate was concentrated to afford tert-butyl (R)-3-amino-3-methylazepane-1-carboxylate (1.30 g, 5.70 mmol, 97% yield) as colorless oil. m/z (ESI): 229.3 $(M+H)^+$. $^1H$ NMR (CHLOROFORM-d, 400 MHz) δ 3.54 (br d, 2H, J=14.2 Hz), 3.0-3.4 (m, 3H), 1.78 (br s, 2H), 1.5-1.6 (m, 5H), 1.47 (s, 9H), 1.12 (br s, 3H).

Intermediate DC: Rac-tert-butyl (3R,5S)-3-hydroxy-5-(methylamino)piperidine-1-carboxylate

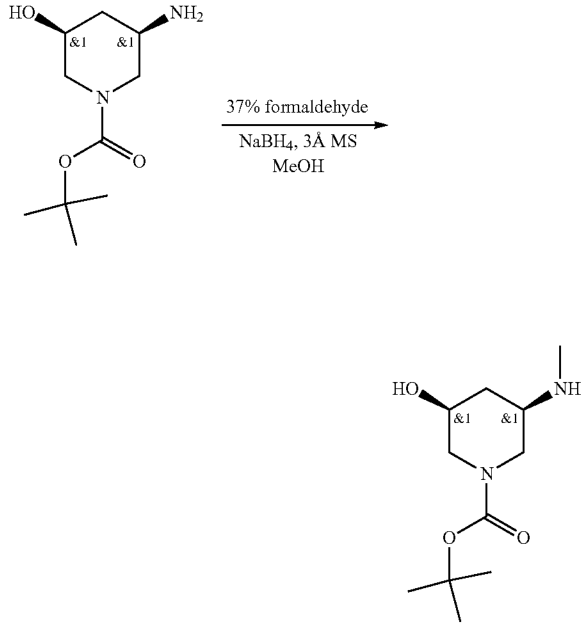

rac-cis-3-Amino-5-hydroxy-piperidine-1-carboxylic acid tert-butyl ester (1.00 g, 4.62 mmol, J & W Pharmlab, LLC) was added to a solution of formaldehyde, 37% solution (0.44 mL, 4.4 mmol) in methanol (23 mL) containing 3 Å MS. The mixture was stirred at rt for 72 h. Sodium borohydride (0.28 g, 7.4 mmol) was added and the mixture was stirred for 30 min. The reaction was quenched by the addition of 1N NaOH and extracted with DCM. The organic extract was washed with saturated NaCl and dried over $Na_2SO_4$, filtered, and concentrated to give rac-tert-butyl (3R,5S)-3-hydroxy-5-(methylamino)piperidine-1-carboxylate (1.02 g, 4.43 mmol, 96% yield). m/z (ESI): 231.1 $(M+H)^+$.

Intermediate DE: 3-(4-Bromo-6-chloro-1-(tetrahydro-2H-pyran-2-yl)-1H-indazol-5-yl)propan-1-amine

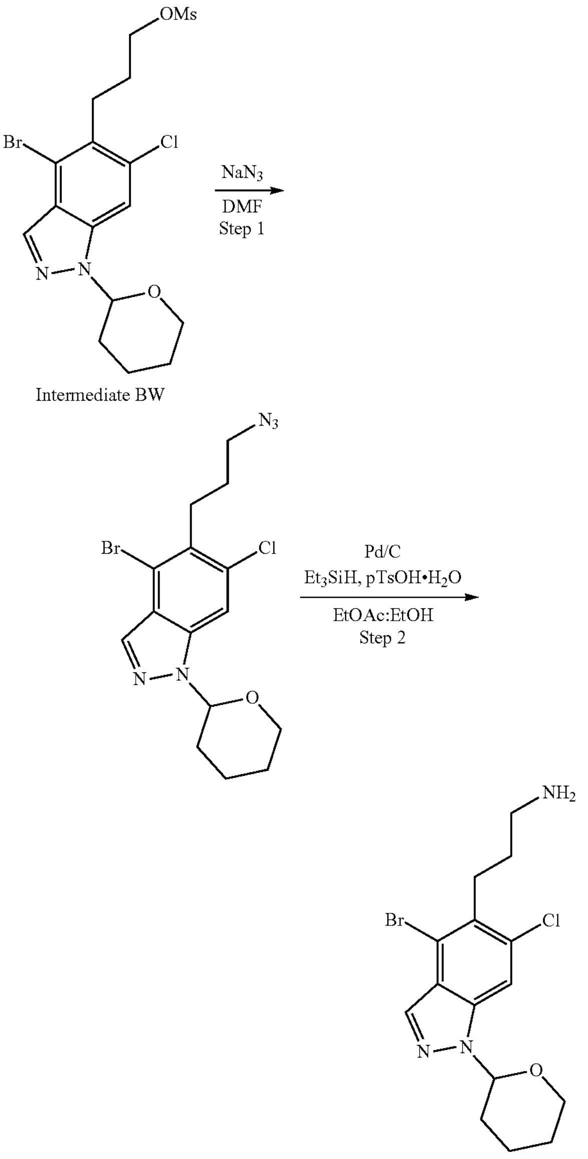

Intermediate DE

Step 1. 5-(3-Azidopropyl)-4-bromo-6-chloro-1-(tetrahydro-2H-pyran-2-yl)-1H-indazole. To a 40-mL vial was added 3-(4-bromo-6-chloro-1-(tetrahydro-2H-pyran-2-yl)-1H-indazol-5-yl)propyl methanesulfonate (0.49 g, 1.08 mmol, Intermediate BW) and sodium azide (0.18 g, 2.70 mmol) in N,N-dimethylformamide (2 mL). The resulting mixture was heated to 60° C. for 4 h. After cooling to rt, the reaction mixture was diluted with water and extracted with EtOAc. The combined organic layers were dried over $Na_2SO_4$, filtered, and concentrated under reduced pressure to give 5-(3-azidopropyl)-4-bromo-6-chloro-1-(tetrahydro-2H-pyran-2-yl)-1H-indazole (0.40 g, 1.01 mmol, 94% yield). m/z (ESI): 397.9 $(M+H)^+$.

Step 2. 3-(4-Bromo-6-chloro-1-(tetrahydro-2H-pyran-2-yl)-1H-indazol-5-yl)propan-1-amine. To a vial containing 5-(3-azidopropyl)-4-bromo-6-chloro-1-(tetrahydro-2H-pyran-2-yl)-1H-indazole (0.38 g, 0.96 mmol) in EtOAc (3.7 mL) and EtOH (3.77 mL) was added palladium on activated carbon (72 mg, 0.67 mmol). Under nitrogen atmosphere, 3-ethyl-3-silapentane (0.70 mL, 4.4 mmol) was added dropwise over 10 minutes. The mixture was stirred at rt for an additional 1.5 h. The mixture was filtered over Celite, and the volatiles were evaporated to afford 3-(4-bromo-6-chloro-1-(tetrahydro-2H-pyran-2-yl)-1H-indazol-5-yl)propan-1-amine (0.27 g, 0.73 mmol, 76% yield). m/z (ESI): 372.0 $(M+H)^+$.

Intermediate DF: tert-Butyl 2-(2H-1,2,3-triazol-4-yl)morpholine-4-carboxylate

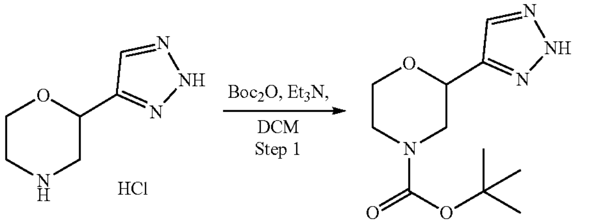

To a stirred suspension of 2-(2H-1,2,3-triazol-4-yl)morpholine hydrochloride (2.5 g, 13 mmol, Enamine) and triethylamine (9.2 mL, 66 mmol) in DCM (20 mL) was added di-tert-butyl dicarbonate (2.72 g, 12.5 mmol) at 0° C. The reaction mixture was stirred at 0° C. for 30 min and then at rt for 18 h. The resulting mixture was washed with water, dried over $Na_2SO_4$, filtered, concentrated. The residue was purified by column chromatography on silica gel, eluting with a gradient of 0-100% (3:1 EtOAc/EtOH with 2% $Et_3N$)/heptane, to provide tert-butyl 2-(2H-1,2,3-triazol-4-yl)morpholine-4-carboxylate (1.71 g, 6.72 mmol, 51% yield) as colorless oil. m/z (ESI): 255.1 $(M+H)^+$.

Intermediate DG: tert-Butyl 3-(2H-1,2,3-triazol-4-yl)azepane-1-carboxylate

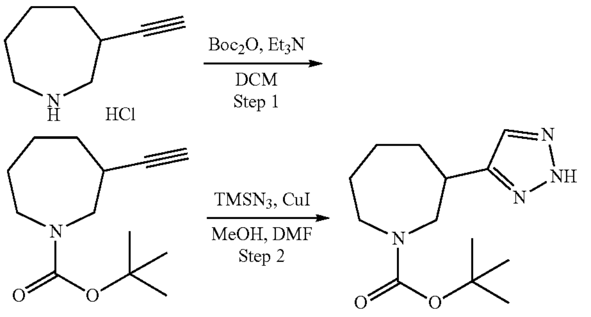

Intermediate DG

Step 1. tert-Butyl 3-ethynylazepane-1-carboxylate. To a stirred suspension of 3-ethynylazepane hydrochloride (2.50 g, 15.7 mmol, Enamine) and triethylamine (11 mL, 78 mmol) in DCM (20 mL) was added di-tert-butyl dicarbonate (3.76 g, 17.2 mmol) at 0° C. The reaction mixture was stirred at 0° C. for 30 min and then at rt for 4 h. The mixture was washed with water, dried over $Na_2SO_4$, filtered, and concentrated to provide tert-butyl 3-ethynylazepane-1-carboxylate (3.16 g, 14.2 mmol, 90% yield) as a brown oil. m/z (ESI): 168.1 $(M-{}^tBu+H)^+$. $^1H$ NMR (400 MHz, CHLOROFORM-d) δ ppm 3.66-4.08 (m, 2H), 2.98-3.12 (m, 2H), 2.70-2.90 (m, 1H), 2.06-2.14 (m, 1H), 1.72-1.89 (m, 3H), 1.61-1.72 (m, 2H), 1.47-1.52 (m, 10H).

Step 2. tert-Butyl 3-(2H-1,2,3-triazol-4-yl)azepane-1-carboxylate. To a 40-mL vial was added copper(I) iodide (43 mg, 0.22 mmol), tert-butyl 3-ethynylazepane-1-carboxylate (1.00 g, 4.50 mmol) and azidotrimethylsilane (0.77 g, 6.7 mmol, Enamine) in N,N-dimethylformamide (4 mL) and methanol (1 mL). The mixture was bubbled with $N_2$ for 10 min and then heated at 100° C. for 3 h. After cooling to rt, the mixture was quenched with water and extracted with EtOAc. The combined organic layers were dried over $Na_2SO_4$ and concentrated. The crude material was purified by column chromatography on silica gel, eluting with a gradient of 0-100% (3:1 EtOAc/EtOH with 2% $Et_3N$)/heptane, to provide tert-butyl 3-(2H-1,2,3-triazol-4-yl)azepane-1-carboxylate (1.03 g, 3.87 mmol, 86% yield) as brown oil. m/z (ESI): 267.2 $(M+H)^+$.

Intermediate DH: tert-Butyl 6-(2H-1,2,3-triazol-4-yl)-1,4-oxazepane-4-carboxylate

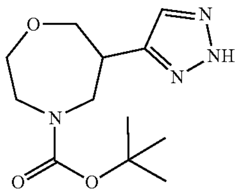 [SMILES: CC(C)(C)OC(=O)N1CCOCC(c2cn[nH]n2)C1]

The title compound was prepared using analogous manner to Intermediate DG using 6-ethynylhexahydro-1,4-oxazepine (CAS #: 2836742-97-1, Enamine) in Step 1. m/z (ESI): 269.2 $(M+H)^+$.

Intermediate DI: tert-Butyl 3-((tert-butyldiphenylsilyl)oxy)-5-(2H-1,2,3-triazol-4-yl)piperidine-1-carboxylate

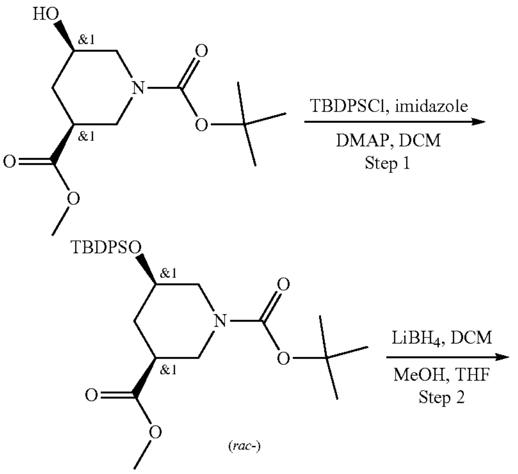

-continued

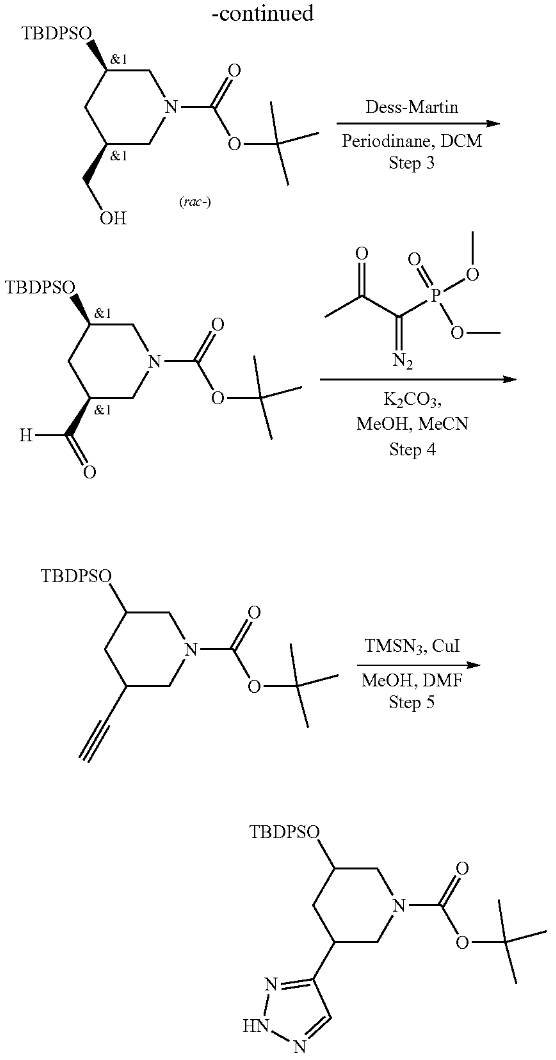

Intermediate DI

Step 1. rac-1-(tert-Butyl) 3-methyl (3R,5S)-5-((tert-butyldiphenylsilyl)oxy)piperidine-1,3-dicarboxylate. To a 250-mL round bottom flask was charged with 1-tert-butyl 3-methyl (3S,5R)-rel-5-hydroxypiperidine-1,3-dicarboxylate (1.00 g, 3.86 mmol, Pharmablock, Inc.), imidazole (0.656 g, 9.64 mmol), dichloromethane (40 mL), and 4-(N,N-dimethylamino)-pyridine (0.047 g, 0.39 mmol). To this mixture was added tert-butyl(chloro)diphenyl-silane (1.2 mL, 4.6 mmol) and the reaction mixture was stirred at rt for 18 h. The reaction was diluted with saturated aqueous sodium bicarbonate and extracted with DCM. The organic layer was dried over sodium sulfate, filtered, and concentrated The residue was purified by column chromatography on silica gel, eluting with a gradient of 0-50% ethyl acetate/heptane, to give rac-1-(tert-butyl) 3-methyl (3R,5S)-5-((tert-butyldiphenylsilyl)oxy)piperidine-1,3-dicarboxylate (1.86 g, 3.74 mmol, 97% yield) as colorless oil. m/z (ESI): 520.1 $(M+Na)^+$.

Step 2. rac-tert-Butyl (3R,5S)-3-((tert-butyldiphenylsilyl)oxy)-5-(hydroxymethyl)piperidine-1-carboxylate. To a 250-mL round-bottomed flask was added rac-1-(tert-butyl) 3-methyl (3R,5S)-5-((tert-butyldiphenylsilyl)oxy)piperidine-1,3-dicarboxylate (1.86 g, 3.74 mmol) in DCM (14 mL) and methanol (1.4 mL). The reaction mixture was cooled to 0° C. and lithium borohydride (2 M solution in tetrahydrofuran, 5.6 mL, 11.2 mmol) was added and the mixture was allowed to stir at 0° C. for 3 h. The reaction mixture was quenched with saturated $NH_4Cl$ solution and extracted with EtOAc. The combined organic layers were and dried over $Na_2SO_4$, filtered and concentrated. The crude material was purified by column chromatography on silica gel, eluting with a gradient of 0-100% ethyl acetate/heptane, to provide rac-tert-butyl (3R,5S)-3-((tert-butyldiphenylsilyl)oxy)-5-(hydroxymethyl)piperidine-1-carboxylate (1.74 g, 3.70 mmol, 99% yield) as a colorless oil. m/z (ESI): 492.1 $(M+Na)^+$.

Step 3. rac-tert-Butyl (3R,5S)-3-((tert-butyldiphenylsilyl)oxy)-5-formylpiperidine-1-carboxylate. To a 40-mL vial was added rac-tert-butyl (3R,5S)-3-((tert-butyldiphenylsilyl)oxy)-5-(hydroxymethyl)piperidine-1-carboxylate (1.74 g, 3.7 mmol) in dichloromethane (15 mL). The mixture was cooled to 0° C., and Dess-Martin periodinane (3.46 g, 8.14 mmol) was added. The reaction mixture was allowed to warm to rt with stirring for 4 h. The reaction mixture was concentrated, and the residue was partitioned between EtOAc and a mixture of saturated sodium bicarbonate solution and sodium thiosulfate solution. The aqueous phase was extracted with EtOAc and combined organic layers were and dried over $Na_2SO_4$, filtered, and concentrated. The crude material was purified by column chromatography on silica gel, eluting with a gradient of 0-50% ethyl acetate/heptane, to provide rac-tert-butyl (3R,5S)-3-((tert-butyldiphenylsilyl)oxy)-5-formylpiperidine-1-carboxylate (1.45 g, 3.10 mmol, 84% yield) as colorless viscous oil. m/z (ESI): 490.1 $(M+Na)^+$.

Step 4. tert-Butyl 3-((tert-butyldiphenylsilyl)oxy)-5-ethynylpiperidine-1-carboxylate. In a 40-mL vial was charged with dimethyl (1-azoacetonyl)phosphonate (10% in acetonitrile) (9.1 mL, 3.7 mmol), potassium carbonate (0.86 g, 6.20 mmol), rac-tert-butyl (3R,5S)-3-((tert-butyldiphenylsilyl)oxy)-5-formylpiperidine-1-carboxylate (1.45 g, 3.10 mmol) in methanol (16 mL) at 0° C. The reaction mixture was allowed to warm to rt with stirring for 4 h. The mixture was diluted with EtOAc, filtered through Celite, and concentrated. The residue was purified by column chromatography on silica gel, eluting with a gradient of 0-100% ethyl acetate/heptane, to provide tert-butyl 3-((tert-butyldiphenylsilyl)oxy)-5-ethynylpiperidine-1-carboxylate (1.14 g, 2.46 mmol, 79% yield) as colorless oil. m/z (ESI): 486.1 $(M+Na)^+$.

Step 5. tert-Butyl 3-((tert-butyldiphenylsilyl)oxy)-5-(2H-1,2,3-triazol-4-yl)piperidine-1-carboxylate. To a 40-mL vial was added copper(I) iodide (0.023 g, 0.12 mmol), tert-butyl 3-((tert-butyldiphenylsilyl)oxy)-5-ethynylpiperidine-1-carboxylate (1.14 g, 2.46 mmol) and azidotrimethylsilane (0.43 g, 3.7 mmol, Enamine) in N,N-dimethylformamide (4 mL) and methanol (1 mL). The mixture was bubbled with $N_2$ for 10 min and heated at 100° C. for 2 h. After cooling to rt, water was added, and the mixture was extracted with EtOAc. The combined organic layers were and dried over $Na_2SO_4$, filtered, and concentrated. The crude material was purified by column chromatography on silica gel, eluting with a gradient of 0-100% (3:1 EtOAc/EtOH with 2% $Et_3N$)/heptane, to provide tert-butyl 3-((tert-butyldiphenylsilyl)oxy)-5-(2H-1,2,3-triazol-4-yl)piperidine-1-carboxylate (0.97 g, 1.91 mmol, 78% yield) as yellow foam. m/z (ESI): 507.1 $(M+H)^+$.

Intermediate DJ: tert-Butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)-6-azaspiro[3.5]nonane-6-carboxylate

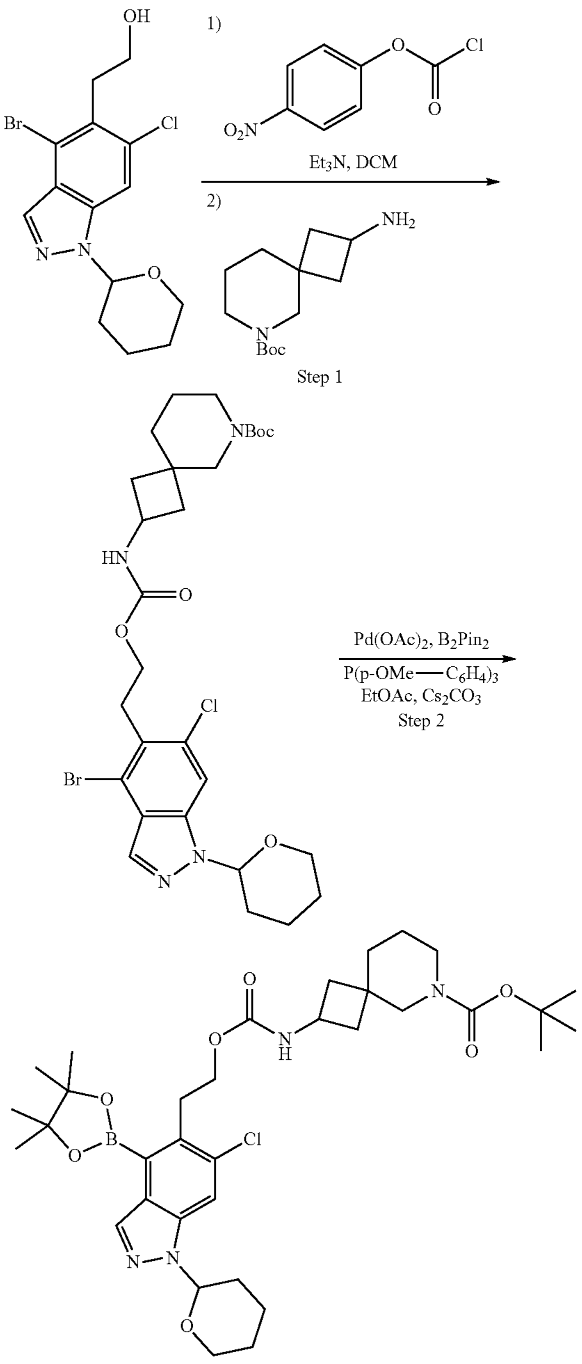

Intermediate DJ

Step 1. tert-Butyl 2-(((2-(4-bromo-6-chloro-1-(tetrahydro-2H-pyran-2-yl)-1H-indazol-5-yl)ethoxy)carbonyl)amino)-6-azaspiro[3.5]nonane-6-carboxylate. To a stirred solution of 2-(4-bromo-6-chloro-1-(tetrahydro-2H-pyran-2-yl)-1H-indazol-5-yl)ethan-1-ol (0.60 g, 1.67 mmol, Intermediate CH, Step 3) and triethylamine (1.2 mL, 8.3 mmol) in dichloromethane (9.5 mL) was added 4-nitrophenyl chloroformate (0.44 g, 2.17 mmol) at 0° C. The reaction mixture was allowed to warm to rt with stirring for 45 min. tert-Butyl 2-amino-6-azaspiro[3.5]nonane-6-carboxylate (0.80 g, 3.34 mmol) in DMF (2 mL) was then added, and the reaction was stirred at 40° C. for 1 h. After cooling to rt, the reaction mixture was diluted with water and extracted ethyl acetate. The combined organic layers were dried over $Na_2SO_4$, filtered, and concentrated under reduced pressure. The crude product was purified by column chromatography on silica gel, eluting with 0-60% (3:1 EtOAc: EtOH with 2% $Et_3N$) in heptane, to provide tert-butyl 2-(((2-(4-bromo-6-chloro-1-(tetrahydro-2H-pyran-2-yl)-1H-indazol-5-yl)ethoxy)carbonyl)amino)-6-azaspiro[3.5]nonane-6-carboxylate (1.00 g, 1.60 mmol, 96% yield). m/z (ESI): 525.0 $(M-Boc+H)^+$.

Step 2. tert-Butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)amino)-6-azaspiro[3.5]nonane-6-carboxylate. A 40 mL vial was charged with tris(4-methoxyphenyl)phosphine (66 mg, 0.19 mmol), palladium acetate (21 mg, 0.094 mmol), 4,4,4',4',5,5,5',5'-octamethyl-2,2'-bi(1,3,2-dioxaborolane) (0.57 g, 2.26 mmol), cesium carbonate (0.92 g, 2.83 mmol), tert-butyl 2-(((2-(4-bromo-6-chloro-1-(tetrahydro-2H-pyran-2-yl)-1H-indazol-5-yl)ethoxy)carbonyl)amino)-6-azaspiro[3.5]nonane-6-carboxylate (1.18 g, 1.89 mmol) and EtOAc (4 mL). The reaction mixture was sparged with nitrogen and then heated to 80° C. for 3 h. After cooling to rt, the reaction filtered and concentrated under reduced pressure. The crude residue was purified by column chromatography on silica gel, eluting with a gradient of 0-20% 3:1 (EtOAc/EtOH with 2% triethylamine) in heptane, to provide tert-butyl 2-(((2-(6-chloro-1-(tetrahydro-2H-pyran-2-yl)-4-(4,4,5,5-tetramethyl-1,3,2-dioxaborolan-2-yl)-1H-indazol-5-yl)ethoxy)carbonyl)amino)-6-azaspiro[3.5]nonane-6-carboxylate (1.07 g, 1.59 mmol, 84% yield) as yellow oil. m/z (ESI): 673.0 $(M+H)^+$.

Intermediate DK: tert-Butyl (3R)-3-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)amino)-3-methylazepane-1-carboxylate

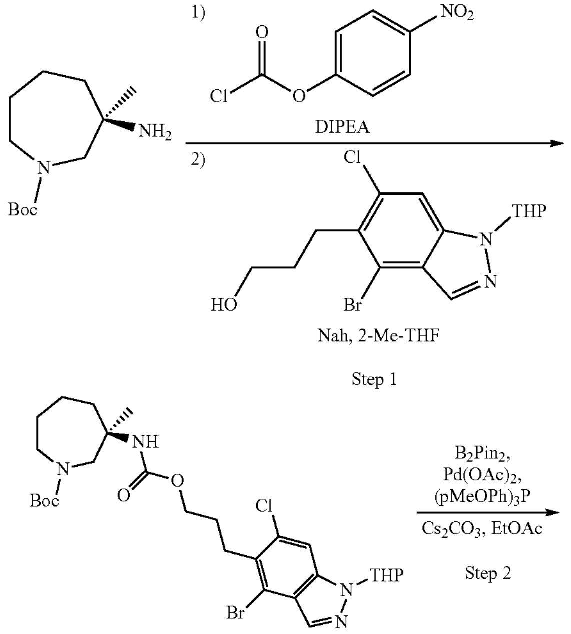

-continued

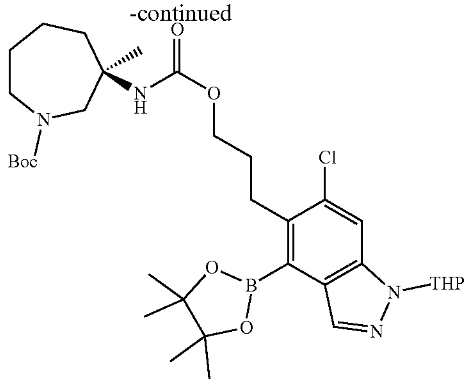

Intermediate DK

Step 1. tert-Butyl (3R)-3-(((3-(4-bromo-6-chloro-1-(tetrahydro-2H-pyran-2-yl)-1H-indazol-5-yl)propoxy)carbonyl)amino)-3-methylazepane-1-carboxylate. To a 100-mL round-bottom flask was added tert-butyl (R)-3-amino-3-methylazepane-1-carboxylate (0.32 g, 1.38 mmol, Intermediate DB) and N,N-diisopropylethylamine (0.2 mL, 1.4 mmol) in 1,2-dichloroethane (7 mL). The mixture was stirred at rt for 5 min, 4-nitrophenyl chloroformate (0.31 g, 1.5 mmol) was added slowly to the mixture. The reaction mixture was stirred at rt for 30 min. The crude material purified by column chromatography on silica gel column, eluting with a gradient of 0-40% EtOAc in heptane, to provide tert-butyl (R)-3-methyl-3-(((4-nitrophenoxy)carbonyl)amino)azepane-1-carboxylate as colorless oil. To a separate 100-mL round-bottom flask was charged with 3-(4-bromo-6-chloro-1-(tetrahydro-2H-pyran-2-yl)-1H-indazol-5-yl)propan-1-ol (0.567 g, 1.52 mmol, Intermediate FFF, Step 2) in 2-methyltetrahydrofuran (7 mL). The mixture was cooled to 0° C., and sodium hydride (60% dispersion in mineral oil, 83 mg, 2.1 mmol) was added. The resulting mixture was stirred at rt for 30 min. This mixture was transferred to a 20-mL resealable vial, then the previously prepared activated carbamate intermediate was added to the mixture slowly. The reaction mixture was stirred and heated at 80° C. for 16 h. After cooling to rt, the reaction mixture was diluted with EtOAc and saturated aqueous $NaHCO_3$. The aqueous layer was extracted with EtOAc, and the combined organic extracts were dried ($MgSO_4$), filtered and concentrated in vacuo. The crude material was purified by reverse-phase chromatography using a C18 column, eluting with a gradient of 5-95% MeCN in Water (0.1% formic acid as modifier), to provide tert-butyl (3R)-3-(((3-(4-bromo-6-chloro-1-(tetrahydro-2H-pyran-2-yl)-1H-indazol-5-yl)propoxy)carbonyl)amino)-3-methylazepane-1-carboxylate (0.40 g, 0.64 mmol, 46% yield) as off-white solid. m/z (ESI): 529.3 $(M+H-BOC)^+$.

Step 2. tert-Butyl (3R)-3-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)amino)-3-methylazepane-1-carboxylate. A vial was charged with tert-butyl (3R)-3-(((3-(4-bromo-6-chloro-1-(tetrahydro-2H-pyran-2-yl)-1H-indazol-5-yl)propoxy)carbonyl)amino)-3-methylazepane-1-carboxylate (0.39 g, 0.63 mmol), bis(pinacalato) diboron (0.47 g, 1.9 mmol), cesium carbonate (0.61 g, 1.9 mmol), palladium(II) acetate (28 mg, 0.12 mmol) and tris (4-methoxyphenyl)phosphine (88 mg, 0.25 mmol) in ethyl acetate (16 mL). The mixture was sparged with argon for 5 min, then the vial was sealed. The reaction mixture was stirred at 80° C. for 2 h. After cooling to rt, the reaction mixture was filtered through a pad of celite and concentrated in vacuo. The crude material was purified by column chromatography on silica gel, eluting with 0-60% (3:1 EtOAc:EtOH with 2% $Et_3N$) in heptane, to provide tert-butyl (3R)-3-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)amino)-3-methylazepane-1-carboxylate (0.4 g, 0.6 mmol, 95% yield) as colorless oil. m/z (ESI): 655.4 $(M+H)^+$.

Intermediate DL: tert-Butyl (3R)-3-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)amino)azepane-1-carboxylate

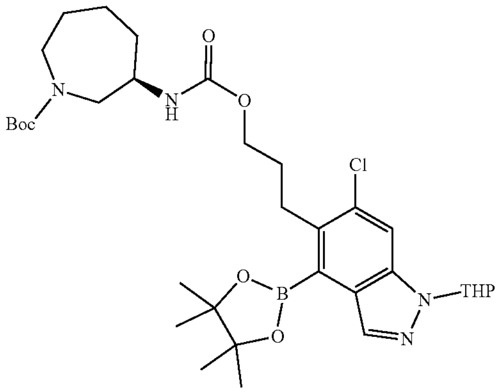

The title compound was prepared in an analogous manner to Intermediate Shon1 using (R)-tert-butyl 3-aminoazepane-1-carboxylate (CAS #: 1032684-85-7, Combi-Blocks) in Step 1. m/z (ESI): 649.7 $(M+Na)^+$.

Intermediate DM: tert-Butyl 3-(((3-(6-chloro-1-(tetrahydro-2H-pyran-2-yl)-4-(4,4,5,5-tetramethyl-1,3,2-dioxaborolan-2-yl)-1H-indazol-5-yl)propoxy)carbonyl)amino)-3-methylazepane-1-carboxylate

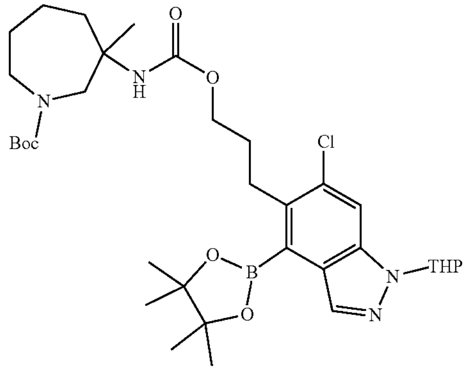

The title compound was prepared in an analogous manner to Intermediate DK using (R)-tert-butyl 3-aminoazepane-1-carboxylate (CAS #: 1032684-85-7, Combi-Blocks) in Step 1. m/z (ESI): 655.4 $(M+Na)^+$.

Intermediate DN: tert-Butyl(2-(2-fluoro-8-(4,4,5,5-tetramethyl-1,3,2-dioxaborolan-2-yl)naphthalen-1-yl)ethoxy)dimethylsilane

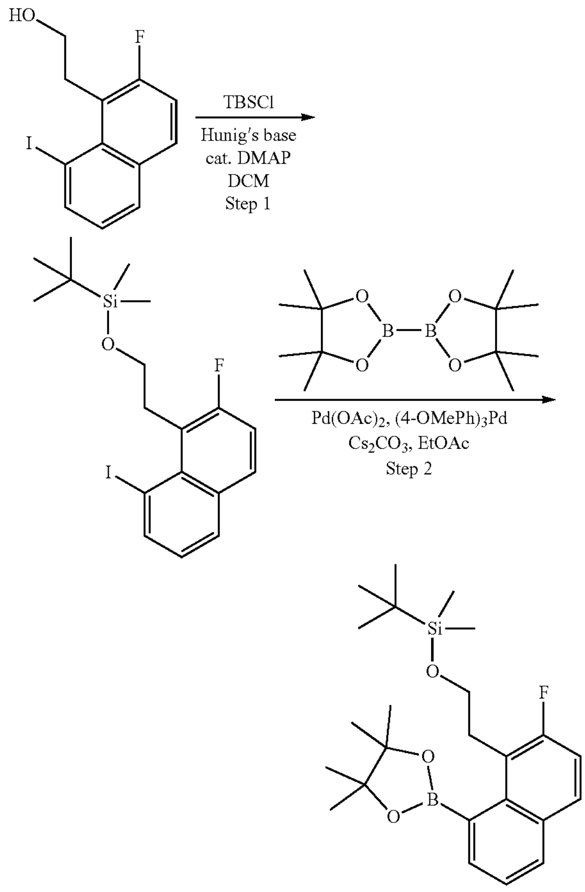

Intermediate DN

Step 1. tert-Butyl(2-(2-fluoro-8-iodonaphthalen-1-yl)ethoxy)dimethylsilane. To a stirred solution of 2-(2-fluoro-8-iodonaphthalen-1-yl)ethan-1-ol (0.50 g, 1.57 mmol, Step 3 in Intermediate QQ) and 1,1'-dimethyltriethylamine (0.30 mL, 1.7 mmol) in dichloromethane (2.5 mL) in a vial was added tert-butyldimethylsilyl chloride (0.26 g, 1.73 mmol) and 4-(dimethylamino)pyridine (9.6 mg, 0.079 mmol) at 0° C. The reaction mixture was allowed to warm to rt with stirring for 1.5 h. The reaction was concentrated under reduced pressure and the crude material was purified by column chromatography on silica gel, eluting with a gradient of 0-30% 3:1 EtOAc/EtOH in heptane, to provide tert-butyl(2-(2-fluoro-8-iodonaphthalen-1-yl)ethoxy)dimethylsilane (0.71 g, 1.66 mmol, 100% yield) as a orange oil.

Step 2. tert-Butyl(2-(2-fluoro-8-(4,4,5,5-tetramethyl-1,3,2-dioxaborolan-2-yl)naphthalen-1-yl)ethoxy)dimethylsilane. To a vial was added cesium carbonate (0.80 g, 2.44 mmol), 4,4,5,5-tetramethyl-1,3,2-dioxaborolane (0.83 g, 3.25 mmol,) and tert-butyl(2-(2-fluoro-8-iodonaphthalen-1-yl)ethoxy)dimethylsilane (0.70 g, 1.63 mmol) in ethyl acetate (2.5 mL). The reaction was flushed with $N_2$ for 5 minutes. To this was added $Pd(OAc)_2$ (37 mg, 0.16 mmol) and tris(4-methoxyphenyl)phosphine (63 mg, 0.18 mmol). The vial was sealed under $N_2$ and the reaction mixture was heated to 80° C. for 1 h. After cooling to rt, the reaction mixture was filtered through celite and washed with EtOAc. After concentrating the filtrate, the crude material was purified by column chromatography on silica gel column, eluting with a gradient of 0-50% 3:1 EtOAc/EtOH in heptane, to provide a mixture of tert-butyl(2-(2-fluoro-8-(4,4,5,5-tetramethyl-1,3,2-dioxaborolan-2-yl)naphthalen-1-yl)ethoxy)dimethylsilane (0.62 g, 1.43 mmol, 88% yield) and tert-butyl(2-(2-fluoronaphthalen-1-yl)ethoxy)dimethylsilane 1:1 as white solid. The inseparable mixture was used in the next step. m/z (ESI): 431.2 $(M+H)^+$.

Intermediate DO: (S)-4-(7-Chloro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol

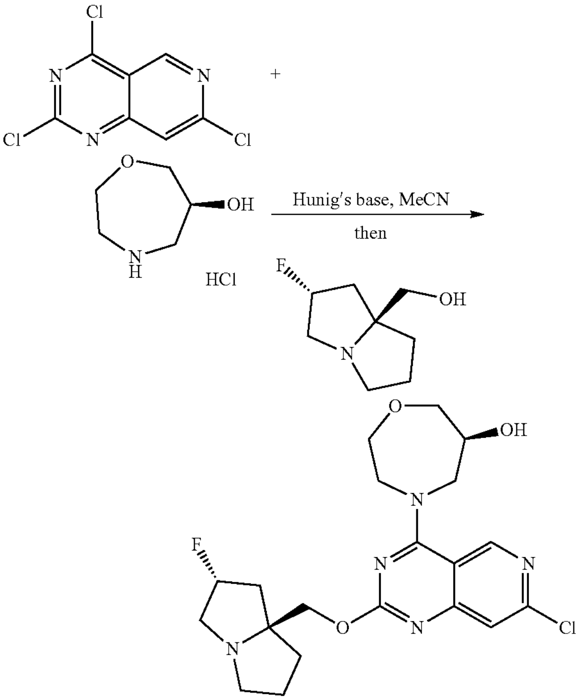

To a 40-mL vial was added 2,4,7-trichloropyrido[4,3-d]pyrimidine (1.02 g, 4.33 mmol, eNovation Chemicals LLC) and 1,1'-dimethyltriethylamine (3.4 mL, 19 mmol) in acetonitrile (11 mL). The mixture was cooled to 0° C. before (S)-1,4-oxazepan-6-ol hydrochloride (0.67 g, 4.3 mmol) was added. The reaction was stirred at 0° C. for 45 min, then ((2R,7aS)-2-fluorotetrahydro-1H-pyrrolizin-7a(5H)-yl)methanol (1.73 g, 10.8 mmol, Pharmablock, Inc.) was added and the reaction mixture was heated at 80° C. for 18 h. After cooling to rt, the solvent was removed under reduced pressure and the crude material was dissolved in DMSO (5 mL) and was purified by reverse-phase column chromatography using a C18 column, eluting with a gradient 0-25% 0.1% formic acid in $CH_3CN$/0.1% formic acid in $H_2O$, to provide (S)-4-(7-chloro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol (0.7 g, 1.6 mmol, 37% yield) as off-white solid. m/z (ESI): 438.2 $(M+H)^+$.

Intermediate DP: (S)-4-(7-Bromo-2-((1-((dimethylamino)methyl)cyclopropyl)methoxy)-6,8-difluoroquinazolin-4-yl)-1,4-oxazepan-6-ol

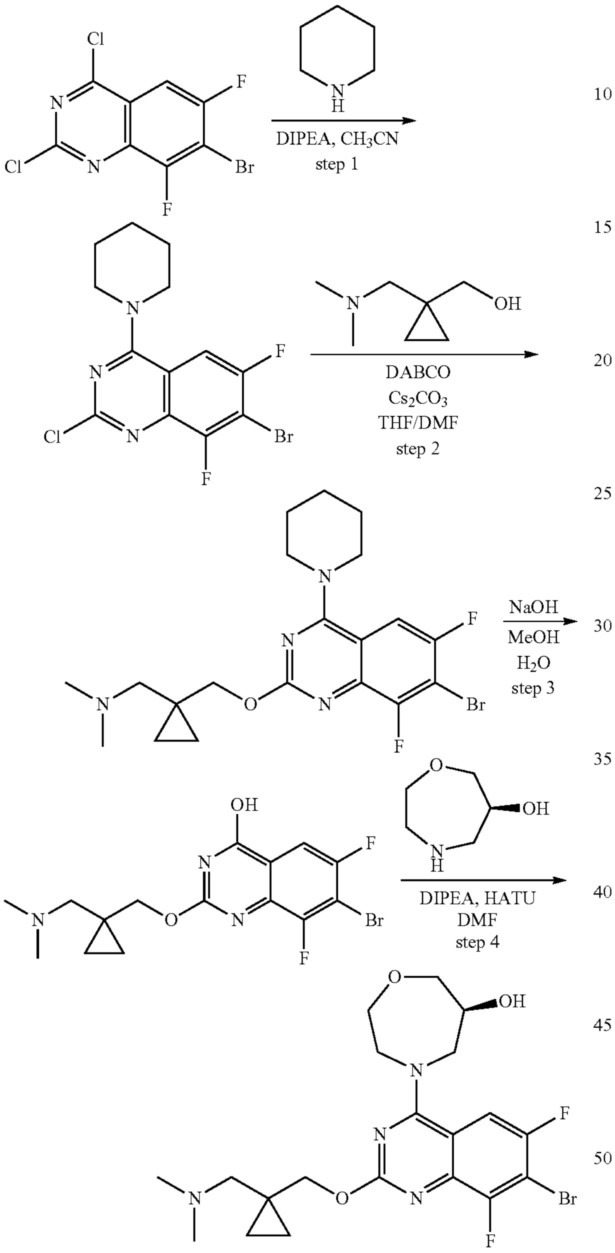

Intermediate DP

Step 1. 7-Bromo-2-chloro-6,8-difluoro-4-(piperidin-1-yl)quinazoline. To a solution of 7-bromo-2,4-dichloro-6,8-difluoroquinazoline (50.0 g, 159 mmol) in acetonitrile (800 mL) was added piperidine (15.8 mL, 159 mmol), followed by DIPEA (55.6 mL, 319 mmol) dropwise at 0° C. under $N_2$. The mixture was stirred at 0° C. for 0.5 h, then was diluted with $H_2O$ and extracted with ethyl acetate. The combined organic layers were washed with brine, dried over $Na_2SO_4$, filtered, and concentrated. The crude product was triturated with petroleum ether for 12 h. The suspension was filtered, and the filter cake was washed with petroleum ether, dried to give 7-bromo-2-chloro-6,8-difluoro-4-(piperidin-1-yl)quinazoline (53.0 g, 147 mmol, 92% yield) as white solid. m/z (ESI): 364.1/362.1 $(M+H)^+$.

Step 2. 1-(1-(((7-Bromo-6,8-difluoro-4-(piperidin-1-yl)quinazolin-2-yl) oxy)methyl)cyclopropyl)-N,N-dimethylmethanamine. To a solution of 7-bromo-2-chloro-6,8-difluoro-4-(piperidin-1-yl)quinazoline (30 g, 83 mmol) in tetrahydrofuran (300 mL) and N,N-dimethylformamide (300 mL) was added $Cs_2CO_3$ (32 g, 99 mmol), DABCO (2.78 g, 24.8 mmol) and (1-((dimethylamino)methyl)cyclopropyl)methanol (15.0 g, 116 mmol) in sequence under $N_2$. The reaction mixture was stirred at rt for 12 h, then diluted with $H_2O$ and extracted with EtOAc. The combined organic layers were washed with brine, dried over $Na_2SO_4$, filtered, and concentrated. The residue was purified by column chromatography on silica gel, eluting with a gradient of 0-100% EtOAc in petroleum, then triturated with the mixed solvent of EtOAc/MeOH (6:1) at rt for 12 h. The suspension was filtered, and the filter cake was washed with the mixed solvent of EtOAc/MeOH (6:1), dried to give 1-(1-(((7-bromo-6,8-difluoro-4-(piperidin-1-yl)quinazolin-2-yl) oxy) methyl)cyclopropyl)-N,N-dimethylmethanamine (20.0 g crude) as white solid. m/z (ESI): 457.1/455.1 $(M+H)^+$.

Step 3. 7-Bromo-2-((1-((dimethylamino)methyl)cyclopropyl)methoxy)-6,8-difluoroquinazolin-4-ol. To a solution of 1-(1-(((7-bromo-6,8-difluoro-4-(piperidin-1-yl)quinazolin-2-yl)oxy)methyl)cyclopropyl)-N,N-dimethylmethanamine (20.0 g, 43.9 mmol) in methanol (800 mL) and water (400 mL) was added NaOH (8.78 g, 220 mmol). The mixture was stirred at 100° C. for 12 h. After cooling to rt, the reaction mixture was filtered, and the filtrate was concentrated under reduced pressure. Then the residue was diluted with $H_2O$ and extracted with EtOAc. The combined organic layers were dried over $Na_2SO_4$, filtered and the filtrate was concentrated. The residue was purified triturated with the mixed solvent of DCM/MeOH/THF (10:1:1) at rt for 12 hr. The suspension was filtered, and the filter cake was washed with the with the mixed solvent of DCM/MeOH/THF (10:1:1), dried to give 7-bromo-2-((1-((dimethylamino)methyl)cyclopropyl)methoxy)-6,8-difluoroquinazolin-4-ol (10.4 g, 27.0 mmol, 32% yield over 2 steps) as white solid. $^1H$ NMR (400 MHz, DMSO-$d_6$, 25° C.) δ ppm 7.48 (d, J=7.6 Hz, 1H), 4.09 (s, 2H), 2.67 (s, 2H), 2.47 (s, 6H), 0.74 (s, 2H), 0.58 (s, 2H). $^{19}F$ NMR (376 MHz, DMSO-$d_6$) δ ppm −113.21 (s), −116.40 (s).

Step 4. (S)-4-(7-Bromo-2-((1-((dimethylamino)methyl)cyclopropyl)methoxy)-6,8-difluoroquinazolin-4-yl)-1,4-oxazepan-6-ol. HATU (1.76 g, 4.64 mmol) was added to a solution of (S)-[1,4]oxazepan-6-ol (0.543 g, 4.64 mmol), 7-bromo-2-((1-((dimethylamino)methyl)cyclopropyl)methoxy)-6,8-difluoroquinazolin-4-ol (1.50 g, 3.86 mmol), and N,N-diisopropylethylamine (2.7 mL, 15.5 mmol) in DMF (13 mL) at 0° C. The heterogeneous reaction was warmed to 80° C. and stirred for 16 h. After cooling to rt, the reaction mixture was filtered then diluted with water and EtOAc. The organic extract was washed with 1 M LiCl then saturated NaCl and dried over $Na_2SO_4$, filtered, and concentrated. The crude material was purified by column chromatography on silica gel, eluting with a gradient of 0-100% 3:1 EtOAc/EtOH with 2% $Et_3N$ in heptane, to provide (S)-4-(7-bromo-2-((1-((dimethylamino)methyl)cyclopropyl)methoxy)-6,8-difluoroquinazolin-4-yl)-1,4-oxazepan-6-ol (900 mg, 1.85 mmol, 48% yield) as off-white solid. m/z (ESI): 487.1 $(M+H)^+$.

Intermediate DQ: 6-(7-Chloro-8-fluoro-2-(((2S,4R)-4-methoxy-1-methylpyrrolidin-2-yl)methoxy)pyrido[4,3-d]pyrimidin-4-yl)-6-azaspiro[3.5]nonan-2-ol

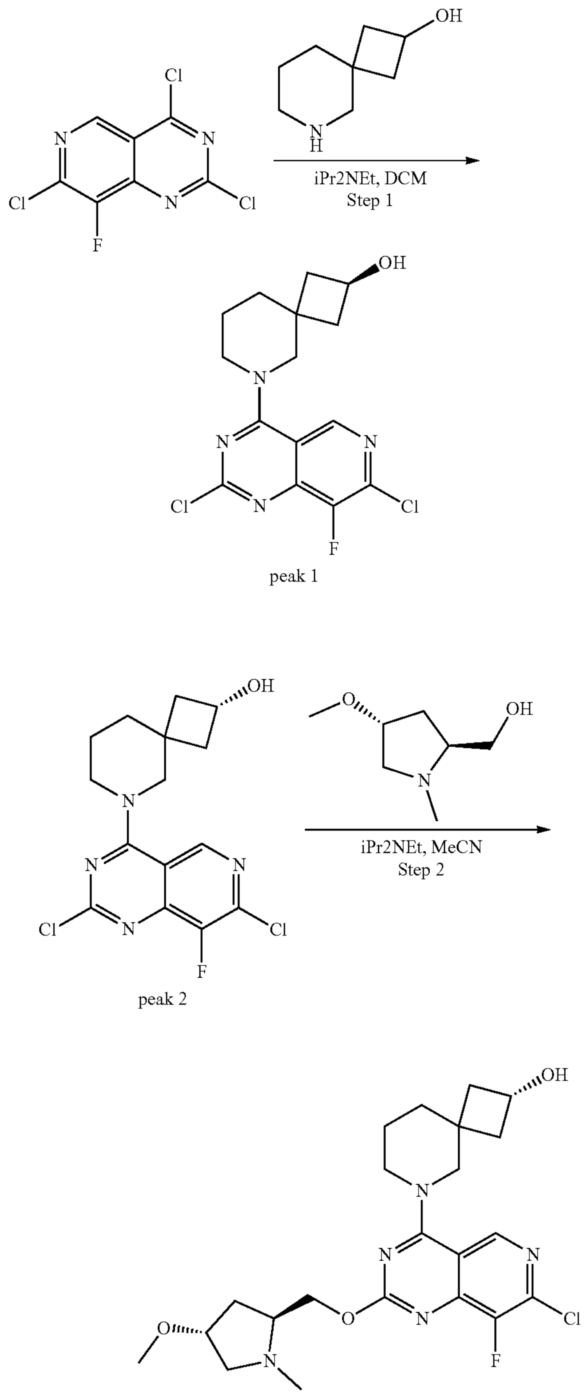

peak 1 peak 2

Intermediate DQ

Step 1: 6-(2,7-dichloro-8-fluoropyrido[4,3-d]pyrimidin-4-yl)-6-azaspiro[3.5]nonan-2-ol. To a 20 ml vial was charged with 2,4,7-trichloro-8-fluoropyrido[4,3-d]pyrimidine (9.48 g, 37.5 mmol, Enamine), 6-azaspiro[3.5]nonan-2-ol (5.30 g, 37.5 mmol) and 1,1'-dimethyltriethylamine (37.5 mL, 150 mmol) in DCM (125 ml) at −78° C. The reaction mixture was stirred at 78° C. for 15 min, then was allowed to warm to rt and diluted with water and brine, The aqueous layer was extracted with $CH_2Cl_2$ and the combined organic layers were dried with sodium sulfate, filtered and concentrated. The crude material was purified by column chromatography on silica gel, eluting with a gradient of 5-10% 3:1 EtOAc/EtOH in heptane, to afford 6-(2,7-dichloro-8-fluoropyrido[4,3-d]pyrimidin-4-yl)-6-azaspiro[3.5]nonan-2-ol (12.5 g, 34.9 mmol, 93% yield) as a white solid. The sample was purified via SFC using a Chiralcel OD, 3×25 cm 5 μm column with a mobile phase of 60% MeOH using a flowrate of 100 mL/min to generate 3.97 g of peak 1 with an ee of >99% and 4.44 g of peak 2 with an ee of 98.8%. Peak assignment determined by SFC with Chiralcel OD column with 60% MeOH. m/z (ESI): 357.0 $(M+H)^+$.

Step 2: 6-(7-Chloro-8-fluoro-2-(((2S,4R)-4-methoxy-1-methylpyrrolidin-2-yl)methoxy)pyrido[4,3-d]pyrimidin-4-yl)-6-azaspiro[3.5]nonan-2-ol. To a 20 mL vial was charged with 6-(2,7-dichloro-8-fluoropyrido[4,3-d]pyrimidin-4-yl)-6-azaspiro[3.5]nonan-2-ol (0.50 g, 1.4 mmol, peak 2), ((2S,4R)-4-methoxy-1-methylpyrrolidin-2-yl)methanol (0.24 g, 1.68 mmol, Enamine) and 1,1'-dimethyltriethylamine (0.73 mL, 4.2 mmol) in acetonitrile (14 mL). The reaction mixture was stirred at 80° C. for 1 h. After cooling to rt, the reaction was carefully quenched with water and extracted with EtOAc. The combined organic layers were dried over $Na_2SO_4$, filtered, and concentrated. The crude material was purified by flash column chromatography on silica gel, eluting with a gradient of 5-100% 3:1 EtOAc/EtOH (with 10% $Et_3N$) in heptane, to afford 6-(7-chloro-8-fluoro-2-(((2S,4R)-4-methoxy-1-methylpyrrolidin-2-yl)methoxy)pyrido[4,3-d]pyrimidin-4-yl)-6-azaspiro[3.5]nonan-2-ol as a yellow solid. m/z (ESI): 466.0 $(M+H)^+$.

Intermediate DR: (6S)-4-(7-Chloro-8-fluoro-2-((hexahydro-1H-pyrrolo[2,1-c][1,4]oxazin-6-yl)methoxy)pyrido[4,3-d]pyrimidin-4-yl)-6-methyl-1,4-oxazepan-6-ol

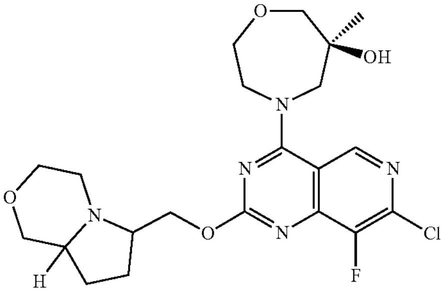 [SMILES: C[C@@]1(O)COCCN(c2nc(OCC3CCC4COCCN43)nc3c(F)c(Cl)ncc23)C1]

This compound was prepare in an analogous fashion as Intermediate BR using [cis-3,4,6,7,8,8a-hexahydro-1H-pyrrolo[2,1-c][1,4]oxazin-6-yl]methanol (Synnovator, Inc.) in Step 4. m/z (ESI): 468.1 $(M+H)^+$.

Intermediate DS: 4-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-(fluoromethyl)-1,4-oxazepan-6-ol

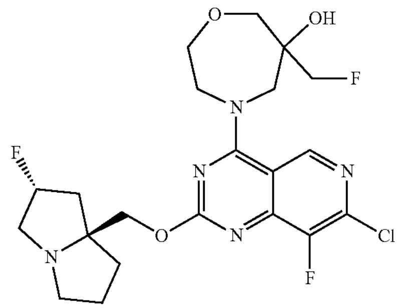 [SMILES: OC1(CF)COCCN(c2nc(OC[C@@]34CCCN3C[C@H](F)C4)nc3c(F)c(Cl)ncc23)C1]

The title compound was prepared in an analogous fashion to Intermediate EE using 6-(fluoromethyl)-1,4-oxazepan-6-ol hydrochloride (eNovation). m/z (ESI): 488.0 $(M+H)^+$.

Intermediate DT: 9-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-oxa-9-azaspiro[3.6]decan-2-ol

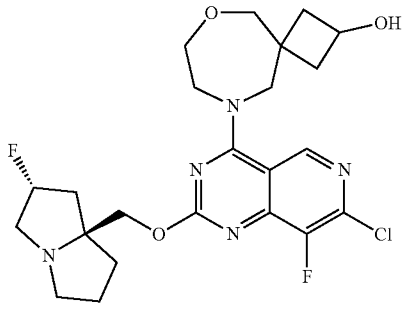 [SMILES: OC1CC2(COCCN(c3nc(OC[C@@]45CCCN4C[C@H](F)C5)nc4c(F)c(Cl)ncc34)C2)C1]

The title compound was prepared in an analogous fashion to Intermediate EE using 6-oxa-9-azaspiro[3.6]decan-2-ol hydrochloride (Enamine). m/z (ESI): 496.0 $(M+H)^+$.

Intermediate DU: 7-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-1-oxa-7-azaspiro[4.5]decan-3-ol

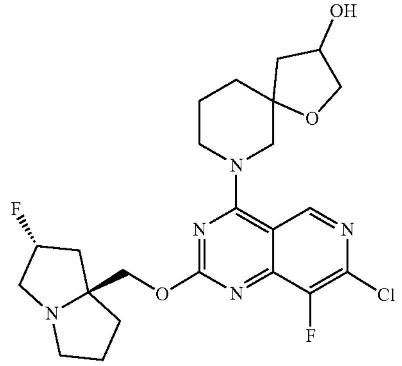 [SMILES: OC1COC2(CCCN(c3nc(OC[C@@]45CCCN4C[C@H](F)C5)nc4c(F)c(Cl)ncc34)C2)C1]

The title compound was prepared in an analogous fashion to Intermediate EE using 1-oxa-7-azaspiro[4.5]decan-3-ol hydrochloride (prepared via HCl mediated Boc-deprotection of tert-butyl 3-hydroxy-1-oxa-7-azaspiro[4.5]decane-7-carboxylate from AA Blocks). m/z (ESI): 496.0 $(M+H)^+$.

Intermediate DV: (S)-4-(7-Chloro-8-fluoro-2-(((2S,4R)-4-fluoro-1-methylpyrrolidin-2-yl)methoxy)pyrido[4,3-d]pyrimidin-4-yl)-6-methyl-1,4-oxazepan-6-ol

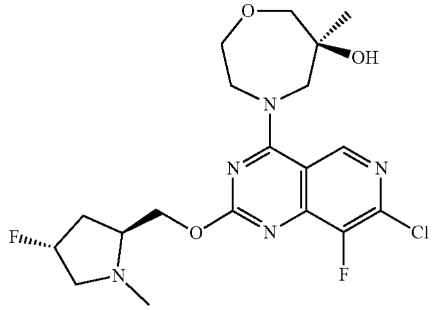 [SMILES: CN1C[C@H](F)C[C@H]1COc1nc(N2CCOC[C@@](C)(O)C2)c2cnc(Cl)c(F)c2n1]

This compound was prepare in an analogous manner as Intermediate BR using ((2S,4R)-4-fluoro-1-methylpyrrolidin-2-yl)methanol (CAS #2206737-78-0, AstaTech) in Step 4. m/z (ESI): 444.0 $(M+H)^+$.

Intermediate DW: (S)-4-(7-Chloro-8-fluoro-2-(((2S,4R)-4-methoxy-1-methylpyrrolidin-2-yl)methoxy)pyrido[4,3-d]pyrimidin-4-yl)-6-methyl-1,4-oxazepan-6-ol

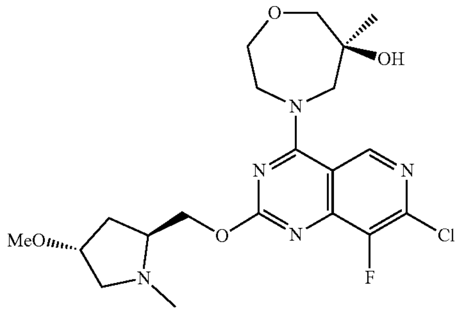 [SMILES: CO[C@@H]1C[C@@H](COc2nc(N3CCOC[C@@](C)(O)C3)c3cnc(Cl)c(F)c3n2)N(C)C1]

This compound was prepared in an analogous manner as Intermediate BR using ((2S,4R)-4-methoxy-1-methylpyrrolidin-2-yl)methanol (CAS #1842337-34-1, Advanced ChemBlocks) in Step 4. m/z (ESI): 456.0 $(M+H)^+$.

Intermediate DX: (2R,4S)-6-(2,7-Dichloro-8-fluoropyrido[4,3-d]pyrimidin-4-yl)-6-azaspiro[3.5]nonan-2-ol

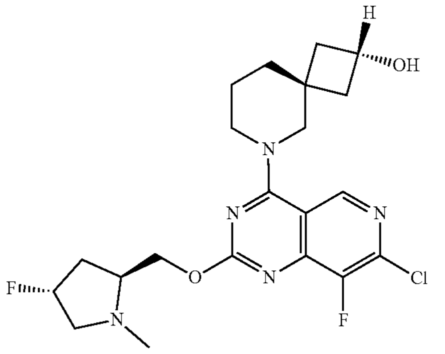 [SMILES: CN1C[C@H](F)C[C@H]1COc1nc(N2CCC[C@]3(C2)C[C@@H](O)C3)c2cnc(Cl)c(F)c2n1]

This compound was prepared in an analogous manner as Intermediate DQ using ((2S,4R)-4-fluoro-1-methylpyrrolidin-2-yl)methanol (CAS #2206737-78-0, AstaTech) in Step 4. m/z (ESI): 454.0 $(M+H)^+$.

Intermediate DY: (2S,4R)-8-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-2-methyl-5-oxa-8-azaspiro[3.5]nonan-2-ol

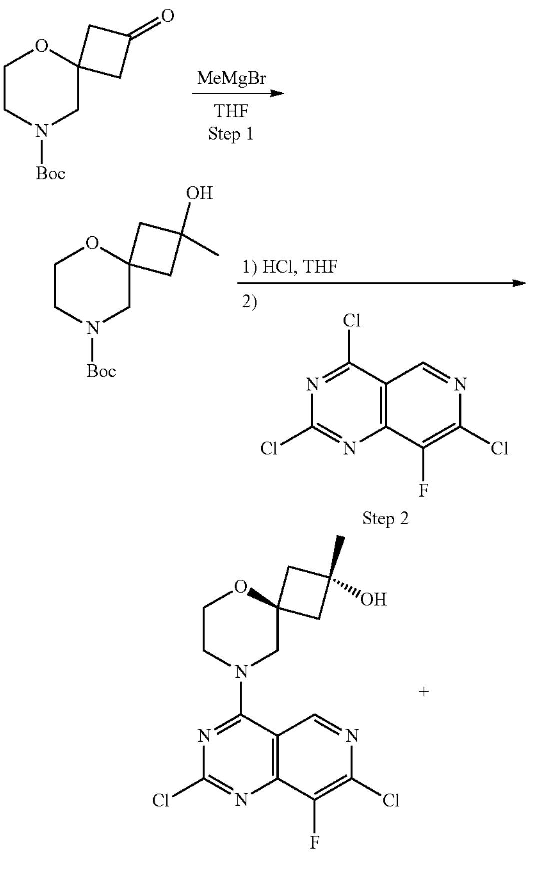

-continued

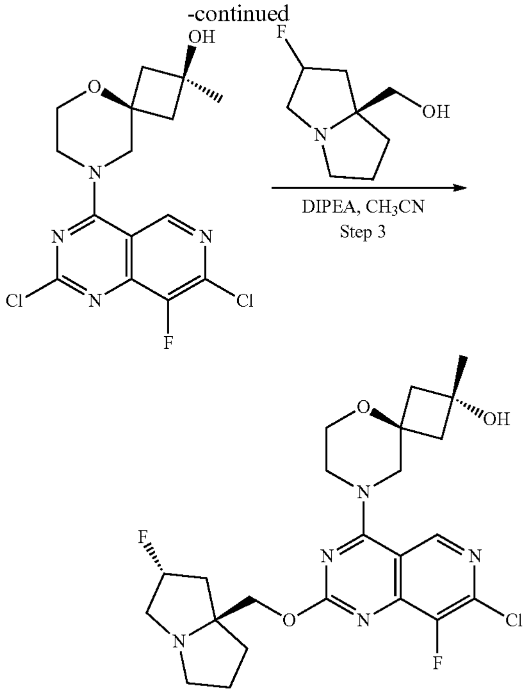

Intermediate DY

Step 1. tert-Butyl 2-hydroxy-2-methyl-5-oxa-8-azaspiro[3.5]nonane-8-carboxylate. To a −78° C. solution of tert-butyl 2-oxo-5-oxa-8-azaspiro[3.5]nonane-8-carboxylate (0.50 g, 2.07 mmol, Pharmablock) in THF (10 mL) was added a 1 M solution of methylmagnesium bromide in diethyl ether (3.1 mL, 3.1 mmol) dropwise. The reaction was stirred at −78° C. After 1 h, the reaction was quenched with saturated aqueous sodium bicarbonate and extracted with ethyl acetate. The organic layer was dried ($Na_2SO_4$), filtered and concentrated. The crude product was purified by column chromatography on silica gel, eluting with a gradient of 0-100% ethyl acetate in heptane, to provide tert-butyl 2-hydroxy-2-methyl-5-oxa-8-azaspiro[3.5]nonane-8-carboxylate (0.62 g, 2.4 mmol, >100% yield) as a colorless oil. m/z (ESI): 280.1 $(M+Na)^+$.

Step 2. (2R,4R)-8-(2,7-Dichloro-8-fluoropyrido[4,3-d]pyrimidin-4-yl)-2-methyl-5-oxa-8-azaspiro[3.5]nonan-2-ol and (2S,4S)-8-(2,7-dichloro-8-fluoropyrido[4,3-d]pyrimidin-4-yl)-2-methyl-5-oxa-8-azaspiro[3.5]nonan-2-ol. To a solution of tert-butyl 2-hydroxy-2-methyl-5-oxa-8-azaspiro[3.5]nonane-8-carboxylate (0.62 g, 2.4 mmol) in THF (12 mL) was added a 4 M solution of HCl in dioxane (3.0 mL, 12 mmol). The reaction mixture was stirred at rt for 30 minutes, then was concentrated. The residue was redissolved in acetonitrile (12 mL) and cooled to 0° C., then 2,4,7-trichloro-8-fluoropyrido[4,3-d]pyrimidine (0.67 g, 2.7 mmol, Enamine) and DIPEA (1.3 mL, 7.2 mmol) were added, and the reaction was stirred at 0° C. for 30 min. The reaction was partitioned between water and ethyl acetate and the organic layer was dried ($Na_2SO_4$), filtered and concentrated. The crude product was purified by column chromatography on silica gel, eluting with a gradient of 0-100% ethyl acetate in heptane to provide (2R,4R)-8-(2,7-dichloro-8-fluoropyrido[4,3-d]pyrimidin-4-yl)-2-methyl-5-oxa-8-azaspiro[3.5]nonan-2-ol (0.42 g, 1.1 mmol, 46% yield) and (2S,4S)-8-(2,7-dichloro-8-fluoropyrido[4,3-d]pyrimidin-4-yl)-2-methyl-5-oxa-8-azaspiro[3.5]nonan-2-ol (0.25 g, 0.66 mmol, 27% yield). m/z (ESI): 372.8 $(M+H)^+$, 373.0 $(M+H)^+$.

Step 3. (2S,4R)-8-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-2-methyl-5-oxa-8-azaspiro[3.5]nonan-2-ol. To a suspension of (2S,4S)-8-(2,7-dichloro-8-fluoropyrido[4,3-d]pyrimidin-4-yl)-2-methyl-5-oxa-8-azaspiro[3.5]nonan-2-ol (0.25 g, 0.66 mmol) and DIPEA (0.29 mL, 1.6 mmol) in acetonitrile (1.5 mL) was added ((2R,7aS)-2-fluorotetrahydro-1H-pyrrolizin-7a(5H)-yl)methanol (0.13 mg, 0.79 mmol). The reaction mixture was stirred at 80° C. for 16 h. After cooling to rt, the reaction mixture was concentrated and the crude product was purified by column chromatography on silica gel, eluting a gradient of with 0-100% (3:1 ethyl acetate/ethanol with 2% TEA) in heptane, to provide (2S,4R)-8-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2-methyl-5-oxa-8-azaspiro[3.5]nonan-2-ol (0.15 mg, 0.3 mmol, 46% yield) as off-white powder. m/z (ESI): 496.0 $(M+H)^+$.

Intermediate DZ: 5-(4-((tert-Butyldimethylsilyl)oxy)butyl)-6-chloro-1-(tetrahydro-2H-pyran-2-yl)-4-(4,4,5,5-tetramethyl-1,3,2-dioxaborolan-2-yl)-1H-indazole

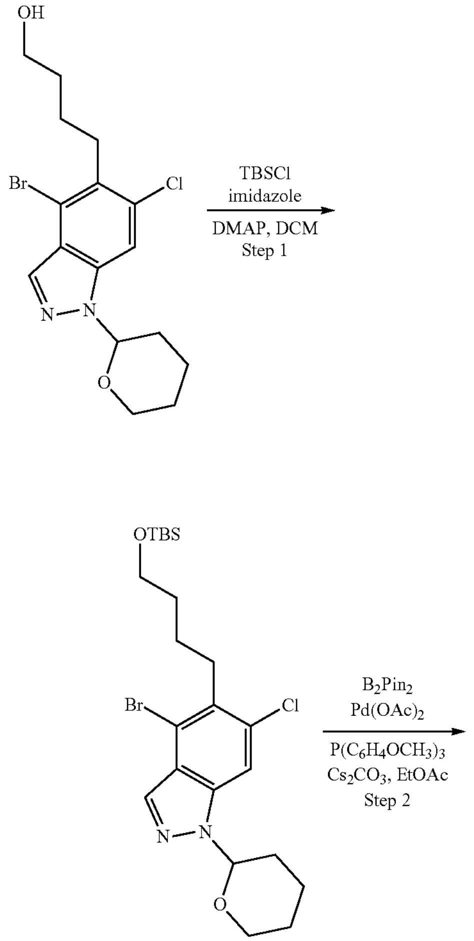

-continued

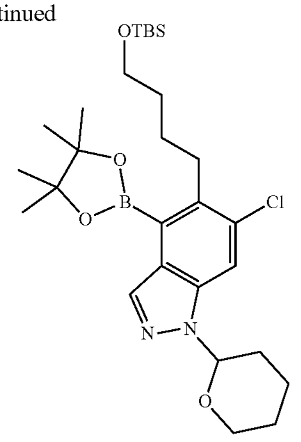

Intermediate DZ

Step 1. 4-bromo-5-(4-((tert-butyldimethylsilyl)oxy)butyl)-6-chloro-1-(tetrahydro-2H-pyran-2-yl)-1H-indazole. A round bottom flask was charged with 4-(4-bromo-6-chloro-1-(tetrahydro-2H-pyran-2-yl)-1H-indazol-5-yl)butan-1-ol (10.0 g, 25.8 mmol, Intermediate WWW), tert-butylchlorodimethylsilane (4.67 g, 31.0 mmol), imidazole (4.39 g, 64.5 mmol), N,N-dimethylpyridin-4-amine (0.32 g, 2.6 mmol) and dichloromethane (130 mL). The reaction mixture was stirred at rt for 6 h. The crude material was was purified by column chromatography on silica gel column, eluting with a gradient of 0-20% EtOAc/heptane, to provide 4-bromo-5-(4-((tert-butyldimethylsilyl)oxy)butyl)-6-chloro-1-(tetrahydro-2H-pyran-2-yl)-1H-indazole (12.1 g, 24.1 mmol, 93% yield) as white solid. m/z (ESI): 387.0/388.9 $(M+H)^+$. $^1H$ NMR (400 MHz, DMSO-$d_6$) δ ppm 0.85 (s, 9H) 1.18 (t, J=7.11 Hz, 1H) 1.25 (br s, 1H) 1.59 (br s, 6H) 1.71 (br d, J=7.32 Hz, 1H) 1.93-2.06 (m, 4H) 2.30-2.49 (m, 2H) 2.97-3.02 (m, 2H) 3.29 (s, 1H) 3.62-3.63 (m, 1H) 3.72-3.82 (m, 1H) 3.83-3.90 (m, 1H) 4.04 (q, J=7.25 Hz, 1H) 5.84-5.90 (m, 1H) 7.98-8.01 (m, 1H) 8.04-8.07 (m, 1H).

Step 2. 5-(4-((tert-Butyldimethylsilyl)oxy)butyl)-6-chloro-1-(tetrahydro-2H-pyran-2-yl)-4-(4,4,5,5-tetramethyl-1,3,2-dioxaborolan-2-yl)-1H-indazole. A vial was charged with tris(4-methoxyphenyl)phosphine (0.22 g, 0.57 mmol), palladium acetate (0.11 g, 0.48 mmol), 4,4,4',4',5,5,5',5'-octamethyl-2,2'-bi(1,3,2-dioxaborolane) (1.46 g, 5.74 mmol), cesium carbonate (2.34 g, 7.17 mmol), 4-bromo-5-(4-((tert-butyldimethylsilyl)oxy)butyl)-6-chloro-1-(tetrahydro-2H-pyran-2-yl)-1H-indazole (2.4 g, 4.8 mmol) and ethyl acetate (10 mL). The reaction mixture was sparged with $N_2$ and heated to 80° C. for 2 h. After cooling to rt, the mixture was filtered through celite, and concentrated under reduced pressure to afford 5-(4-((tert-butyldimethylsilyl)oxy)butyl)-6-chloro-1-(tetrahydro-2H-pyran-2-yl)-4-(4,4,5,5-tetramethyl-1,3,2-dioxaborolan-2-yl)-1H-indazole, which was directly used in the next step. m/z (ESI): 549.3 $(M+H)^+$.

Intermediate EA: (S)-4-(7-Chloro-2-(((2S,4R)-1,4-dimethylpyrrolidin-2-yl)methoxy)-8-fluoropyrido[4,3-d]pyrimidin-4-yl)-1,4-oxazepan-6-ol

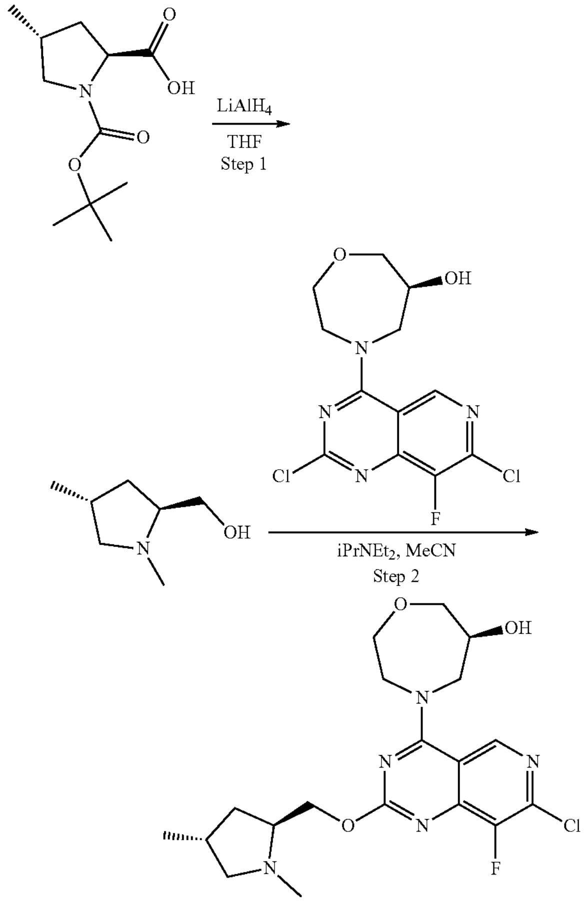

Intermediate EA

Step 1. ((2S,4R)-1,4-dimethylpyrrolidin-2-yl)methanol. To a stirring solution of (2S,4R)-1-[(tert-butoxy)carbonyl]-4-methylpyrrolidine-2-carboxylic acid (0.50 g, 2.20 mmol, Pharmablock, Inc.) in tetrahydrofuran (11 mL) was added lithium aluminum hydride solution (1 M in tetrahydrofuran, 11 mL, 11 mmol). The mixture was then heated to 70° C. for 16 h. After cooling to −10° C., sodium sulfate decahydrate (3.5 g, 11 mmol) was slowly added to the mixture. The reaction was stirred until a gel was formed, and then allowed to stir at rt for 15 min. The solution was then passed through a pad of celite and eluted with EtOAc. The filtrate was concentrated under reduced pressure to afford ((2S,4R)-1,4-dimethylpyrrolidin-2-yl)methanol (0.29 g, 2.3 mmol, 100% yield) as a light yellow oil. $^1$H NMR (METHANOL-d$_4$, 400 MHz) δ 3.5-3.6 (m, 1H), 3.4-3.5 (m, 1H), 3.0-3.2 (m, 1H), 2.4-2.5 (m, 1H), 2.39 (s, 3H), 2.1-2.3 (m, 1H), 1.8-2.0 (m, 2H), 1.5-1.6 (m, 1H), 1.03 (d, 3H, J=6.7 Hz).

Step 2. (S)-4-(7-Chloro-2-(((2S,4R)-1,4-dimethylpyrrolidin-2-yl)methoxy)-8-fluoropyrido[4,3-d]pyrimidin-4-yl)-1,4-oxazepan-6-ol. To a stirring solution of (S)-4-(2,7-dichloro-8-fluoropyrido[4,3-d]pyrimidin-4-yl)-1,4-oxazepan-6-ol (0.27 g, 0.80 mmol, Step 1 in Intermediate QQQ) and ((2S,4R)-1,4-dimethylpyrrolidin-2-yl)methanol (0.15 g, 1.19 mmol) in acetonitrile (4 mL) was added N,N-diisopropylethylamine (0.41 mL, 2.40 mmol). The reaction was then placed into a preheated aluminum block and heated at 80° C. for 3 h. After cooling to rt, the reaction mixture was concentrated and the residue was purified by column chromatography on silica gel, eluting with a gradient of 0-60% of a 3:1 EtOAc:EtOH mixture (containing 2% triethylamine) in heptane, to provide (S)-4-(7-chloro-2-(((2S,4R)-1,4-dimethylpyrrolidin-2-yl)methoxy)-8-fluoropyrido[4,3-d]pyrimidin-4-yl)-1,4-oxazepan-6-ol (0.19 g, 0.45 mmol, 57% yield) as light yellow solid. m/z (ESI): 426.0 (M+H)$^+$.

Intermediate EB: (S)-4-(7-Chloro-8-fluoro-2-(((1R,3S,5R)-2-methyl-2-azabicyclo[3.1.0]hexan-3-yl)methoxy)pyrido[4,3-d]pyrimidin-4-yl)-1,4-oxazepan-6-ol

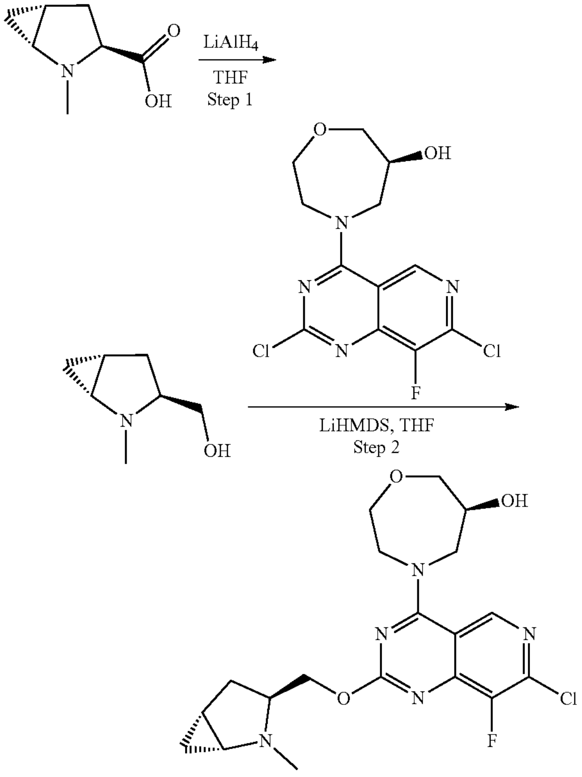

Intermediate EB

Step 1. ((1R,3S,5R)-2-Methyl-2-azabicyclo[3.1.0]hexan-3-yl)methanol. The compound was prepared in an analogous fashion as Step 1 in Intermediate EA using (1R,3S,5R)-2-(tert-butoxycarbonyl)-2-azabicyclo[3.1.0]hexane-3-carboxylic acid (Advanced ChemBlocks Inc., CAS #: 197142-34-0). $^1$H NMR (METHANOL-d$_4$, 400 MHz) δ 3.5-3.6 (m, 1H), 3.4-3.5 (m, 1H), 2.7-2.8 (m, 1H), 2.41 (s, 3H), 2.1-2.2 (m, 1H), 2.1-2.1 (m, 1H), 1.8-1.9 (m, 1H), 1.4-1.5 (m, 1H), 0.7-0.7 (m, 1H), 0.1-0.2 (m, 1H)

Step 2. (S)-4-(7-chloro-8-fluoro-2-(((1R,3S,5R)-2-methyl-2-azabicyclo[3.1.0]hexan-3-yl)methoxy)pyrido[4,3-d]pyrimidin-4-yl)-1,4-oxazepan-6-ol. A vial was charged with ((1R,3S,5R)-2-methyl-2-azabicyclo[3.1.0]hexan-3-yl)methanol (0.26 g, 2.01 mmol) and tetrahydrofuran (8 mL). The content was cooled to 0° C. and LiHMDS (1 M in THF, 2.4 mL, 2.4 mmol) was added dropwise. The reaction mixture was stirred at 0° C. for 15 min, then a solution of (S)-4-(2,7-dichloro-8-fluoropyrido[4,3-d]pyrimidin-4-yl)-1,4-oxazepan-6-ol (0.54 g, 1.61 mmol, Step 1 in Intermediate QQQ) in THF (4 mL) was added. After stirring at rt for 7 h, the reaction was carefully quenched with saturated aqueous ammonium chloride, and the aqueous layer was extracted with DCM. The combined organic layers were dried with sodium sulfate, filtered, and concentrated. The residue was purified by column chromatography on silica gel, eluting with a gradient of 0-60% of a 3:1 EtOAc:EtOH (containing 2% triethylamine) in heptane, to provide (S)-4-(7-chloro-8-fluoro-2-(((1R,3S,5R)-2-methyl-2-azabicyclo[3.1.0]hexan-3-yl)methoxy)pyrido[4,3-d]pyrimidin-4-yl)-1,4-oxazepan-6-ol (78 mg, 0.18 mmol, 11% yield) as yellow solid. m/z (ESI): 424.0 $(M+H)^+$.

Intermediate EC: (S)-4-(7-Chloro-8-fluoro-2-(((1S,3S,5S)-2-methyl-2-azabicyclo[3.1.0]hexan-3-yl)methoxy)pyrido[4,3-d]pyrimidin-4-yl)-1,4-oxazepan-6-ol

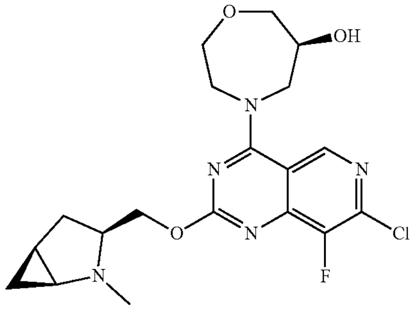 [SMILES: CN1[C@H](COc2nc(N3CCOC[C@@H](O)C3)c3cnc(Cl)c(F)c3n2)C[C@@H]2C[C@@H]21]

The compound was prepared in an analogous fashion as Intermediate EB using ((1S,3S,5S)-2-[(tert-butoxy)carbonyl]-2-azabicyclo[3.1.0]hexane-3-carboxylic acid (Pharmablock Inc., CAS #: 197142-36-2) in Step 1, then the resulting ((1S,3S,5S)-2-methyl-2-azabicyclo[3.1.0]hexan-3-yl)methanol in Step 2. m/z (ESI): 424.0 $(M+H)^+$.

Intermediate ED: 4-(2-Chloro-7-((1-((dimethylamino)methyl)cyclopropyl)methoxy)-8-fluoropyrido[4,3-d]pyrimidin-4-yl)-6-methyl-1,4-oxazepan-6-ol

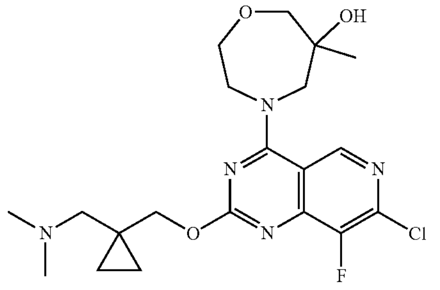 [SMILES: CN(C)CC1(COc2nc(N3CCOCC(C)(O)C3)c3cnc(Cl)c(F)c3n2)CC1]

The title compound was prepared in an analogous fashion to Step 1 in Intermediate W using 6-methyl-1,4-oxazepan-6-ol hydrochloride (CAS #: 1823315-50-9, Combi-Blocks), then (1-[(dimethylamino)methyl]cyclopropyl)methanol (CAS #: 39943-41-4, Ambeed). m/z (ESI): 444.0 $(M+H)^+$.

Intermediate EF: 1-(1-(((7-Chloro-8-fluoro-4-(trifluoromethoxy)pyrido[4,3-d]pyrimidin-2-yl)oxy)methyl)cyclopropyl)-N,N-dimethylmethanamine

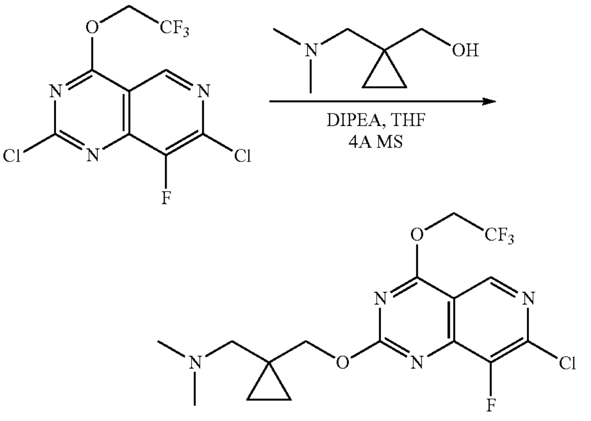

To a solution of 2,7-dichloro-8-fluoro-4-(trifluoromethoxy)pyrido[4,3-d]pyrimidine (30 g, 99 mmol) and 4 Å molecular sieves (4 g) in tetrahydrofuran (600 mL) was added (1-((dimethylamino) methyl)cyclopropyl) methanol (11.6 g, 89.0 mmol, Ambeed) and DIPEA (52.0 mL, 298 mmol) in sequence at −40° C. under $N_2$. Then the mixture was stirred at −40° C. for 2 h. The reaction mixture was diluted with $H_2O$ and extracted with EtOAc. The combined organic layers were washed with brine, dried over $Na_2SO_4$, filtered, and concentrated. The residue was purified by reversed-phase MPLC (0.1% $NH_4HCO_3$; 50-75% 35 min; 75-75% 35 min) to give 1-(1-(((7-chloro-8-fluoro-4-(trifluoromethoxy)pyrido[4,3-d]pyrimidin-2-yl)oxy)methyl)cyclopropyl)-N,N-dimethylmethanamine (17.4 g, 42.6 mmol, 47% yield) as yellow solid. $^1H$ NMR (400 MHz, DMSO-$d_6$) δ ppm 8.98 (s, 1H), 5.30-5.35 (m, 2H), 4.38 (s, 2H), 2.23 (s, 2H), 2.16 (s, 6H), 0.69 (s, 2H), 0.45 (s, 2H). $^{19}F$ NMR (376 MHz, DMSO-$d_6$) δ ppm −71.92 (s, 3F), −135.66 (s, 1F). m/z (ESI): 409.1, 411.1 $(M+H)^+$.

Intermediate EG: 4-(7-Chloro-8-fluoro-2-(((S)-1-methylpyrrolidin-2-yl)methoxy)pyrido[4,3-d]pyrimidin-4-yl)-6-(fluoromethyl)-1,4-oxazepan-6-ol

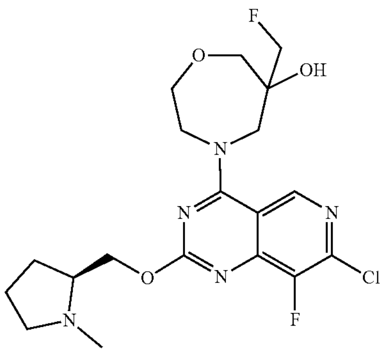 [SMILES: CN1CCC[C@H]1COc1nc(N2CCOCC(O)(CF)C2)c2cnc(Cl)c(F)c2n1]

The title compound was prepared in an analogous fashion to Step 1 in Intermediate W using 6-(fluoromethyl)-1,4-oxazepan-6-ol hydrochloride (eNovation), then (S)-(1-methylpyrrolidin-2-yl)methanol (CAS #: 34381-71-0, Ambeed). m/z (ESI): 444.0 $(M+H)^+$.

Intermediate EH: 1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-3-(fluoromethyl)azepan-3-ol

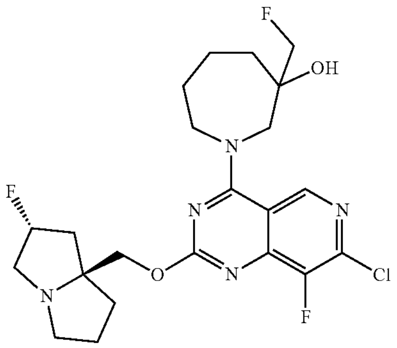 [SMILES: OC1(CF)CCCCN(c2nc(OC[C@@]34CCCN3C[C@H](F)C4)nc3c(F)c(Cl)ncc23)C1]

The title compound was prepared in an analogous fashion to Step 1 in Intermediate W using 6-(fluoromethyl)-1,4-oxazepan-6-ol hydrochloride (eNovation). m/z (ESI): 486.0 $(M+H)^+$.

Intermediate EI: 5-(3-((tert-Butyldiphenylsilyl)oxy)propyl)-6-chloro-1-(tetrahydro-2H-pyran-2-yl)-4-(4,4,5,5-tetramethyl-1,3,2-dioxaborolan-2-yl)-1H-indazole

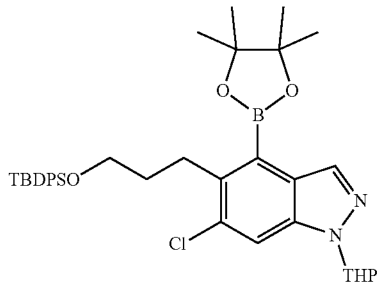

The title compound was prepared in an analogous fashion to Intermediate FFF using tert-butyl(chloro)diphenylsilane (CAS #: 58479-61-1, Aldrich) and imidazole in DCM and THF in Step 3. $^1$H NMR (400 MHz, CHLOROFORM-d) δ ppm 8.33 (s, 1H), 7.71-7.74 (m, 5H), 7.38-7.42 (m, 6H), 5.66 (dd, J=8.8, 2.4 Hz, 1H), 3.99-4.02 (m, 1H), 3.74-3.83 (m, 3H), 3.19-3.23 (m, 2H), 2.48-2.56 (m, 1H), 2.14-2.17 (m, 1H), 2.03-2.05 (m, 1H), 1.86-1.90 (m, 2H), 1.73-1.76 (m, 2H), 1.68 (s, 1H), 1.34 (s, 12H), 1.09 (s, 9H). m/z (ESI): 659.3/660.3/661.3 $(M+H)^+$.

Intermediate EJ: (6S)-4-(7-(5-(3-((tert-Butyldiphenylsilyl)oxy)propyl)-6-chloro-1-(tetrahydro-2H-pyran-2-yl)-1H-indazol-4-yl)-2-(((2R,7aS)-2-fluorotetrahydro-1H-pyrrolizin-7a(5H)-yl)methoxy)-8-methylpyrido[4,3-d]pyrimidin-4-yl)-1,4-oxazepan-6-ol

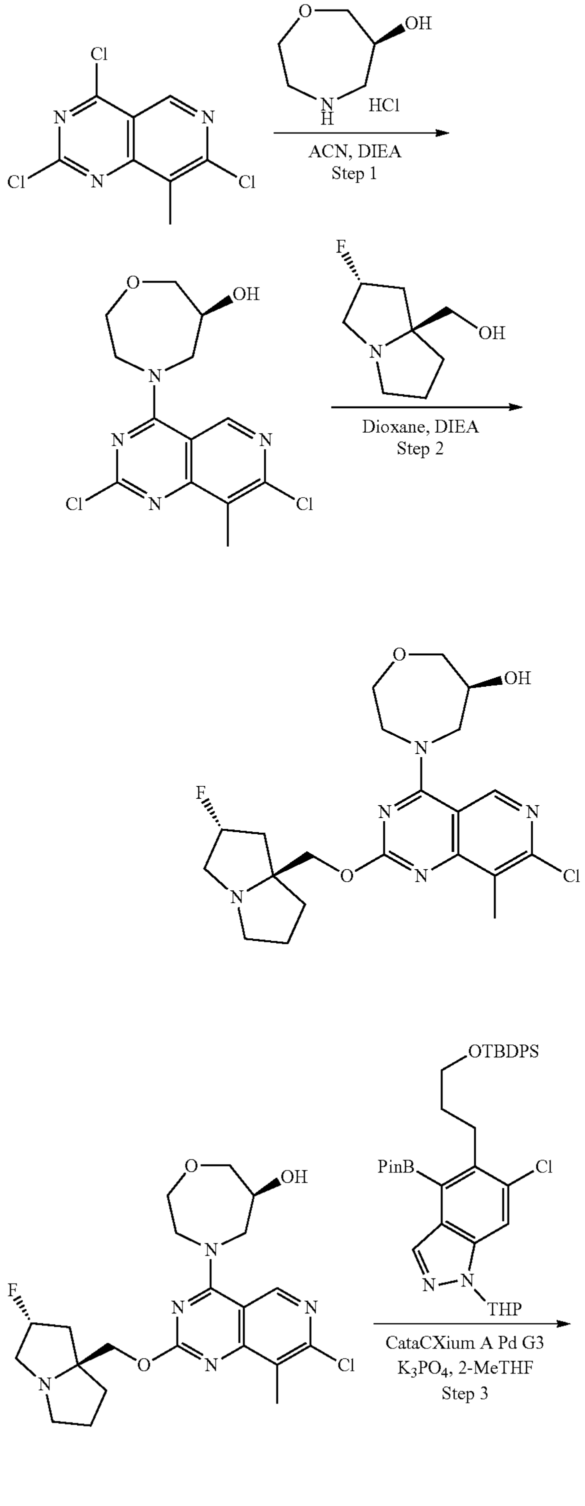

-continued

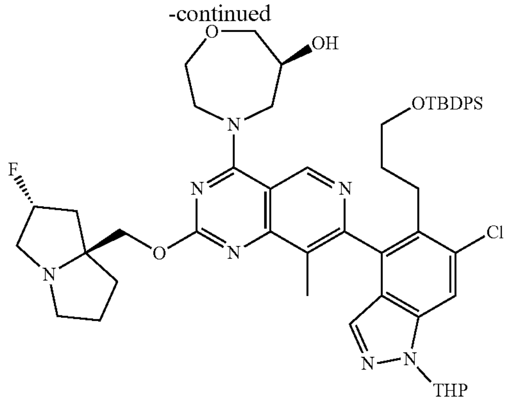

Intermediate EJ

Step 1: (S)-4-(2, 7-Dichloro-8-methylpyrido[4,3-d]pyrimidin-4-yl)-1, 4-oxazepan-6-ol. To a solution of 2,4,7-trichloro-8-methylpyrido[4,3-d]pyrimidine (1.00 g, 4.02 mmol, LabNetwork Inc., A WuXi AppTec Company) in acetonitrile (10 mL) was added (S)-1,4-oxazepan-6-ol hydrochloride (0.62 g, 4.02 mmol) and DIPEA (3.5 mL, 20 mmol) in acetonitrile (10 mL) at 0° C. Then the mixture was stirred at 0° C. for 2 h under $N_2$, then was diluted with water and extracted with ethyl acetate. The combined organic layers were washed with brine, dried over $Na_2SO_4$, filtered, and concentrated under reduced pressure. The residue was triturated with petroleum ether, filtered, and dried to provide (S)-4-(2, 7-dichloro-8-methylpyrido[4,3-d]pyrimidin-4-yl)-1, 4-oxazepan-6-ol (1.20 g, 3.70 mmol, 91% yield). m/z (ESI): 329.0 $(M+H)^+$. $^1H$ NMR (CHLOROFORM-d, 400 MHz) δ 9.14 (s, 1H), 4.41-4.51 (m, 1H), 4.24-4.39 (m, 2H), 3.91-4.11 (m, 4H), 3.82-3.94 (m, 1H), 3.86-3.89 (m, 1H), 3.73-3.76 (m, 1H), 2.63 (s, 3H).

Step 2: (S)-4-(7-Chloro-2-(((2R,7aS)-2-fluorotetrahydro-1H-pyrrolizin-7a(5H)-yl)methoxy)-8-methylpyrido[4,3-d]pyrimidin-4-yl)-1,4-oxazepan-6-ol. To a solution of (S)-4-(2,7-dichloro-8-methylpyrido[4,3-d]pyrimidin-4-yl)-1,4-oxazepan-6-ol (1.00 g, 3.04 mmol) in 1,4-dioxane (10 mL) was added DIPEA (10 mL, 57.3 mmol) and ((2R,7aS)-2-fluorotetrahydro-1H-pyrrolizin-7a(5H)-yl)methanol (1.45 g, 9.11 mmol) in sequence. The reaction mixture was stirred at 120° C. for 12 h under $N_2$ atmosphere. After cooling to rt, the reaction mixture was diluted with water and extracted with ethyl acetate. The combined organic layers were washed with brine, dried over $Na_2SO_4$, filtered, and concentrated. The residue was purified by prep-HPLC on a C18 column, eluting with a gradient of 25-55% $H_2O$ (0.05% $NH_3H_2O$+10 mM $NH_4HCO_3$) in $CH_3CN$ (0.05% $NH_3H_2O$+ 10 mM $NH_4HCO_3$), to provide (S)-4-(7-chloro-2-(((2R,7aS)-2-fluorotetrahydro-1H-pyrrolizin-7a(5H)-yl)methoxy)-8-methylpyrido[4,3-d]pyrimidin-4-yl)-1,4-oxazepan-6-ol (0.29 g, 0.64 mmol, 21% yield). m/z (ESI): 452.1 $(M+H)^+$. $^1H$ NMR (CHLOROFORM-d, 400 MHz) δ 8.95 (s, 1H), 5.18-5.39 (m, 1H), 4.24-4.41 (m, 4H), 4.17 (d, J=10.51 Hz, 1H), 3.87-3.97 (m, 4H), 3.77-3.86 (m, 1H), 3.51-3.61 (m, 1H), 3.23-3.34 (m, 2H), 3.17 (s, 1H), 2.93-3.03 (m, 1H), 2.58 (s, 3H), 2.18-2.29 (m, 2H), 2.07-2.16 (m, 2H), 1.82-2.00 (m, 4H). $^{19}F$ NMR (CHLOROFORM-d, 376 MHz) δ −172.94 (s, 1F).

Step 3: (6S)-4-(7-(5-(3-((tert-Butyldiphenylsilyl)oxy)propyl)-6-chloro-1-(tetrahydro-2H-pyran-2-yl)-1H-indazol-4-yl)-2-(((2R,7aS)-2-fluorotetrahydro-1H-pyrrolizin-7a(5H)-yl)methoxy)-8-methylpyrido[4,3-d]pyrimidin-4-yl)-1,4-oxazepan-6-ol. To a solution of (S)-4-(7-chloro-2-(((2R,7aS)-2-fluorotetrahydro-1H-pyrrolizin-7a(5H)-yl)methoxy)-8-methylpyrido[4,3-d]pyrimidin-4-yl)-1,4-oxazepan-6-ol (0.19 g, 0.42 mmol) in 2-methyltetrahydrofuran (5 mL) and water (0.5 mL) was added $K_3PO_4$ (0.29 g, 1.3 mmol), cataCXium Pd G3 (92 mg, 0.13 mmol) and 5-(3-((tert-butyldiphenylsilyl)oxy)propyl)-6-chloro-1-(tetrahydro-2H-pyran-2-yl)-4-(4,4,5,5-tetramethyl-1,3,2-dioxaborolan-2-yl)-1H-indazole (0.42 g, 0.63 mmol) in sequence. Then the mixture was stirred at 110° C. for 3 h under $N_2$ atmosphere. After cooling to rt, the reaction mixture was combined with another batch (0.1 g scale) and treated brine and extracted with ethyl acetate. The combined organic layers were dried over $Na_2SO_4$, filtered, and concentrated. The residue was purified by column chromatography on silica gel, eluting with a gradient of 0-50% ethyl acetate in petroleum ether, to provide (6S)-4-(7-(5-(3-((tert-butyldiphenylsilyl)oxy)propyl)-6-chloro-1-(tetrahydro-2H-pyran-2-yl)-1H-indazol-4-yl)-2-(((2R,7aS)-2-fluorotetrahydro-1H-pyrrolizin-7a(5H)-yl)methoxy)-8-methylpyrido[4,3-d]pyrimidin-4-yl)-1,4-oxazepan-6-ol (0.40 g, 0.42 mmol, 66% yield). m/z (ESI): 475.2 $(M/2+H)^+$. $^1H$ NMR (CHLOROFORM-d, 400 MHz) δ 9.18-9.22 (m, 1H), 7.70-7.80 (m, 1H), 7.50-7.59 (m, 4H), 7.27-7.41 (m, 8H), 5.61-5.78 (m, 1H), 5.18-5.43 (m, 1H), 4.32-4.45 (m, 2H), 4.17-4.30 (m, 3H), 4.12-4.15 (m, 1H), 3.96-4.05 (m, 1H), 3.87-3.95 (m, 3H), 3.70-3.82 (m, 2H), 3.51-3.64 (m, 3H), 3.19-3.40 (m, 3H), 2.99-3.09 (m, 1H), 2.79-2.94 (m, 1H), 2.63-2.73 (m, 1H), 2.44-2.56 (m, 1H), 2.22 (s, 4H), 2.11-2.21 (m, 3H), 1.93-2.04 (m, 5H), 1.66-1.69 (m, 1H), 0.92-1.00 (m, 2H), 0.80-0.91 (m, 9H), 0.62-0.72 (m, 1H). $^{19}F$ NMR (CHLOROFORM-d, 376 MHz) δ −172.96 (s, 1F).

Intermediate EK: tert-Butyl (2R,4S)-2-hydroxy-6-azaspiro[3.5]nonane-6-carboxylate

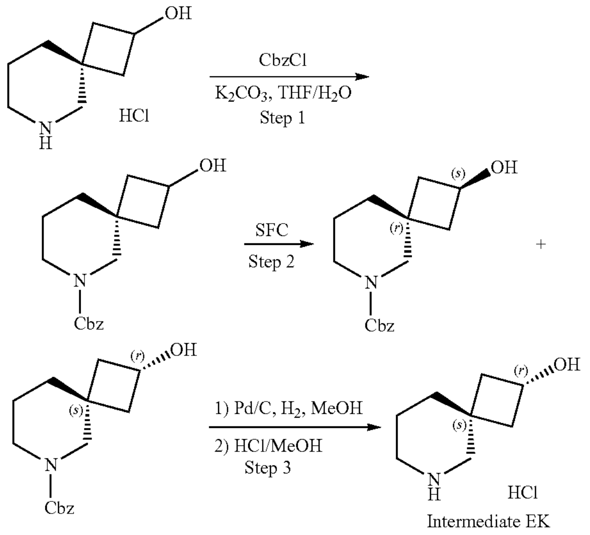

Intermediate EK

Step 1. Benzyl 2-hydroxy-6-azaspiro[3.5]nonane-6-carboxylate. To a solution of 6-azaspiro[3.5]nonan-2-ol hydrochloride (50.0 g, 281 mmol, LabNetwork) and $K_2CO_3$ (78.0 g, 563 mmol) in tetrahydrofuran (500 mL) and water (500 mL) was added Cbz-Cl (44.2 mL, 310 mmol) dropwise at 0° C. The reaction mixture was stirred at rt for 12 h. The reaction was combined with another 8 batches (50 g scale), diluted with $H_2O$, and extracted with EtOAc. The combined organic layers were washed with brine, dried over $Na_2SO_4$, filtered, and concentrated. The residue was purified by column chromatography on silica gel, eluting with a gradient of 5-30% EtOAc in petroleum ether, to provide benzyl 2-hydroxy-6-azaspiro[3.5]nonane-6-carboxylate (550 g, 2.00 mol, 79% yield) as yellow oil.

Step 2. Benzyl 2-hydroxy-6-azaspiro[3.5]nonane-6-carboxylate (550 g) was separated by SFC (Column: DAICEL CHIRALCEL OZ, 25 cm×5 cm, 10 μm; Mobile phase: 25% EtOH (0.1% $NH_3$ in $H_2O$); Flow rate: 200 g/min) to give peak 1 benzyl (2S,4R)-2-hydroxy-6-azaspiro[3.5]nonane-6-carboxylate (270 g, 981 mmol, 49% yield) as yellow oil and peak 2 benzyl (2R,4S)-2-hydroxy-6-azaspiro[3.5]nonane-6-carboxylate (92 g, 334 mmol, 167% yield) as yellow oil.

Step 3. (2R,4S)-6-Azaspiro[3.5]nonan-2-ol hydrochloride. To a solution benzyl (2R,4S)-2-hydroxy-6-azaspiro[3.5]nonane-6-carboxylate (45.0 g, 163 mmol) in MeOH under argon atmosphere was added Pd/C (10%, 5 g, 4.7 mmol). The mixture was stirred under H2 (45 psi) at 40° C. for 12 h. MeOH/HCl (100 mL, 400 mmol) was added to the reaction mixture and stirring was continued for 0.5 h. The reaction was combined another two batches (45 g scale, 2 g scale), filtered through a pad of celite. The filtrate was concentrated under reduced pressure to give (2R,4S)-6-azaspiro[3.5]nonan-2-ol hydrochloride (60.0 g, 33.8 mmol, 100% yield). $^1H$ NMR (DMSO-$d_6$, 400 MHz) δ ppm 9.00 (s, 2H), 4.00-4.15 (m, 1H), 2.81-2.93 (m, 4H), 2.00-2.11 (m, 2H), 1.49-1.76 (m, 6H).

Intermediate EL: (2S,4S)-6-(7-Chloro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol

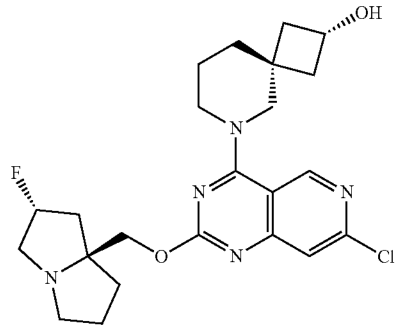 [SMILES: O[C@H]1C[C@]2(CCCN(c3nc(OC[C@@]45CCCN4C[C@H](F)C5)nc4cc(Cl)ncc34)C2)C1]

The title compound was prepared in an analogous manner as Intermediate DO using (2R,4S)-6-azaspiro[3.5]nonan-2-ol hydrochloride (Intermediate EK) in Step 1. $^1H$ NMR (400 MHz, CHLOROFORM-d) δ ppm 8.95 (s, 1H), 7.44 (s, 1H), 5.10-5.37 (m, 1H), 4.32 (t, J=6.4 Hz, 1H), 4.20-4.28 (m, 1H), 4.10-4.19 (m, 1H), 3.80-3.95 (m, 2H), 3.82 (s, 2H), 3.18-3.31 (m, 2H), 3.17 (s, 1H), 2.80-3.00 (m, 1H), 2.11-2.35 (m, 6H), 1.70-2.10 (m, 9H). m/z (ESI): 462.2 $(M+H)^+$.

Intermediate EM: 5-(2-((tert-Butyldiphenylsilyl)oxy)ethyl)-6-chloro-1-(tetrahydro-2H-pyran-2-yl)-4-(4,4,5,5-tetramethyl-1,3,2-dioxaborolan-2-yl)-1H-indazole

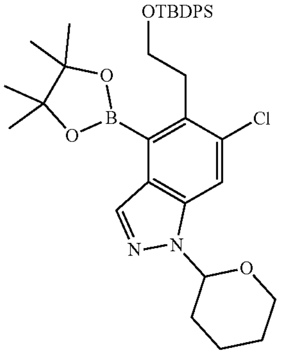

The title compound was prepared in an analogous fashion to Intermediate FFF using 2-(4-bromo-6-chloro-1-(tetrahydro-2H-pyran-2-yl)-1H-indazol-5-yl)ethan-1-ol (Step 1 of Intermediate XX) and tert-butyl(chloro)diphenylsilane (CAS #: 58479-61-1, Aldrich) and imidazole in DCM and THF in Step 3. $^1H$ NMR (400 MHz, $CDCl_3$) δ ppm 8.33 (s, 1H), 7.68 (s, 1H), 7.58-7.66 (m, 4H), 7.30-7.40 (m, 6H), 5.62-5.66 (m, 1H), 3.86-3.99 (m, 1H), 3.82-3.84 (m, 2H), 3.72-3.74 (m, 1H), 3.54-3.58 (m, 2H), 2.46-2.55 (m, 1H), 2.08-2.16 (m, 1H), 1.98-2.06 (m, 1H), 1.62-1.80 (m, 3H), 1.37 (s, 12H), 1.03 (s, 9H). m/z (ESI): 645.3/647.3 $(M+H)^+$.

Intermediate EN: (S)-4-(7-Chloro-8-fluoro-2-(((S)-1-methylpyrrolidin-2-yl)methoxy) pyrido[4,3-d]pyrimidin-4-yl)-6-methyl-1,4-oxazepan-6-ol

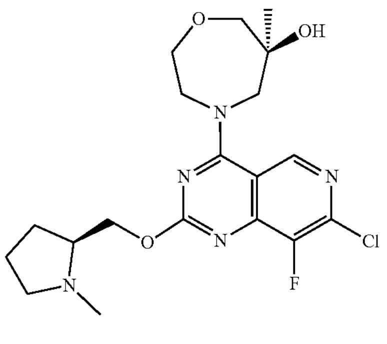 [SMILES: CN1CCC[C@H]1COc1nc(N2CCOC[C@@](C)(O)C2)c2cnc(Cl)c(F)c2n1]

The title compound was prepared in an analogous fashion to Intermediate EA using (S)-(1-methylpyrrolidin-2-yl)methanol in Step 2. $^1H$ NMR (400 MHz, CHLOROFORM-d) δ ppm 9.09 (s, 1H), 4.51-4.64 (m, 2H), 4.47 (s, 1H), 4.37-4.45 (m, 2H), 3.87-4.02 (m, 2H), 3.73-3.81 (m, 1H), 3.64-3.72 (m, 1H), 3.52-3.62 (m, 2H), 3.16 (t, J=7.2 Hz, 1H), 2.77 (s, 1H), 2.53 (s, 3H), 2.32-2.41 (m, 1H), 2.01-2.13 (m, 2H), 1.77-1.94 (m, 4H), 1.32 (s, 3H).

Intermediate EO: tert-Butyl(2-(2-fluoro-6-(methoxymethoxy)-8-(4,4,5,5-tetramethyl-1,3,2-dioxaborolan-2-yl)naphthalen-1-yl)ethoxy)dimethyl-silane

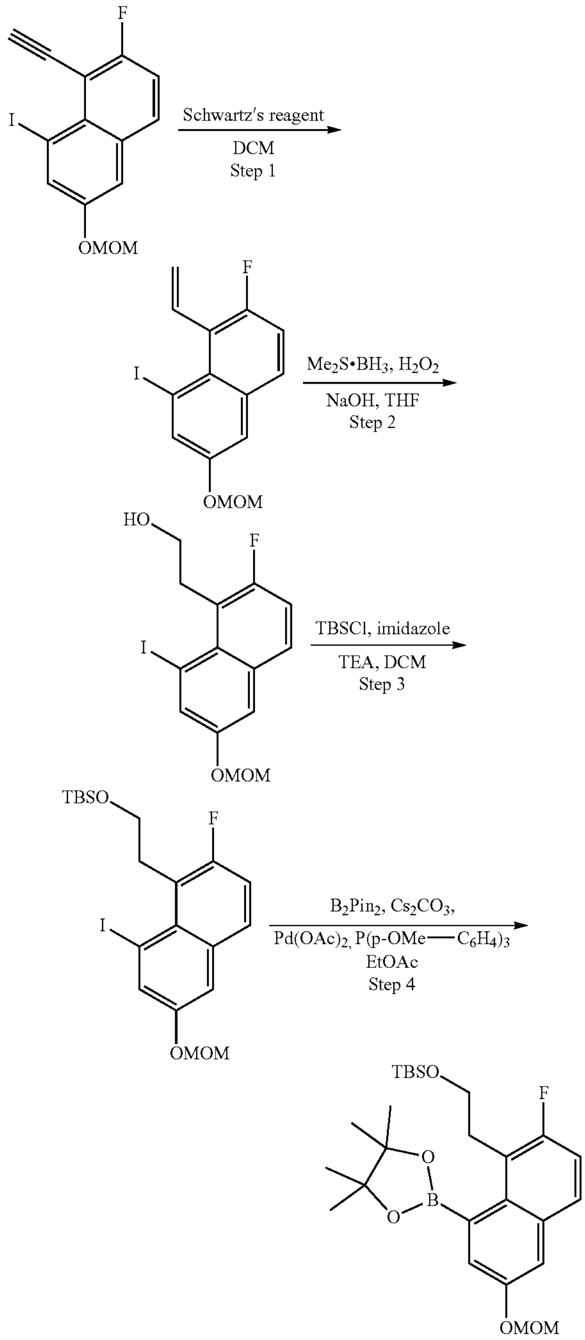

Intermediate EO

Step 1. 2-Fluoro-8-iodo-6-(methoxymethoxy)-1-vinylnaphthalene. To a solution of Schwartz's reagent (14.5 g, 56.2 mmol) in dichloromethane (100 mL) was added 1-ethynyl-2-fluoro-8-iodo-6-(methoxymethoxy)naphthalene (10 g, 28.1 mmol, Lab Network) at 0° C. in darkness. The reaction mixture was stirred at rt for 2 h in darkness, the was diluted with water and extracted with DCM. The combined organic layers were washed with brine, dried over $Na_2SO_4$, filtered, and concentrated. The residue was purified by column chromatography on silica gel, eluting with a gradient of 0-6% EtOAc in petroleum ether, to provide 2-fluoro-8-iodo-6-(methoxymethoxy)-1-vinylnaphthalene (4.5 g, 12.6 mmol, 45% yield) as yellow oil. $^1H$ NMR (400 MHz, $CDCl_3$), 7.89 (d, J=2.4 Hz, 1H), 7.42-7.48 (m, 1H), 7.32-7.38 (m, 1H), 7.23 (d, J=2.8 Hz, 1H), 7.10 (t, J=8.8 Hz, 1H), 5.55-5.58 (m, 1H), 5.33-5.38 (m, 1H), 5.08 (s, 2H), 3.35 (s, 3H).

Step 2. 2-(2-Fluoro-8-iodo-6-(methoxymethoxy)naphthalen-1-yl)ethan-1-ol. To a solution of 2-fluoro-8-iodo-6-(methoxymethoxy)-1-vinylnaphthalene (2.0 g, 5.58 mmol) in tetrahydrofuran (10 mL) was added $BH_3·Me_2S$ (2.8 mL, 28 mmol) at 0° C. The mixture was degassed and purged with $N_2$ three times, then was allowed to warm to rt with stirring for 12 h. The mixture was cooled to 0° C., 1N NaOH solution (28 mL, 28 mmol) was added, followed by $H_2O_2$ (3.15 mL, 30.8 mmol) dropwise. The reaction mixture was returned to rt with stirring for 6 h. The mixture was cooled to 0° C., treated with saturated $Na_2SO_3$ and extracted with EtOAc. The combined organic layers were dried over $Na_2SO_4$, filtered concentrated. The residue was purified by column chromatography on silica gel, eluting with a gradient of 30-100% EtOAc in petroleum ether, to provide 2-(2-fluoro-8-iodo-6-(methoxymethoxy)naphthalen-1-yl) ethan-1-ol (0.55 g, 1.46 mmol, 26% yield) as a white solid. $^1H$ NMR (400 MHz, CHLOROFORM-d) δ ppm 8.03 (d, J=2.4 Hz, 1H), 7.46-7.56 (m, 1H), 7.33 (d, J=2.4 Hz, 1H), 7.18 (t, J=9.6 Hz, 2H), 5.17 (s, 2H), 3.88-3.97 (m, 2H), 3.77-3.87 (m, 2H), 3.43 (s, 3H).

Step 3. tert-Butyl(2-(2-fluoro-6-(methoxymethoxy)naphthalen-1-yl)ethoxy) dimethylsilane. To a solution of 2-(2-fluoro-8-iodo-6-(methoxymethoxy)naphthalen-1-yl)ethan-1-ol (0.55 g, 1.46 mmol) and TEA (0.41 mL, 2.9 mmol) in dichloromethane (15 mL) was added imidazole (0.20 g, 2.9 mmol) and TBS-C1 (0.33 g, 2.2 mmol) at 0° C. under $N_2$. Then the mixture was stirred at rt for 3 h. The reaction was combined with another batch (3 g scale), diluted with $H_2O$ and extracted with DCM. The combined organic layers were washed with brine, dried over $Na_2SO_4$, filtered, and concentrated. The residue was purified by by column chromatography on silica gel, eluting with a gradient of 5-100% EtOAc in petroleum ether, to provide tert-butyl(2-(2-fluoro-6-(methoxymethoxy)naphthalen-1-yl)ethoxy) dimethylsilane (3.4 g, 6.9 mmol, 74% yield) as a yellow oil. $^1H$ NMR (400 MHz, CHLOROFORM-d) δ ppm 8.11 (d, J=2.8 Hz, 1H), 7.55-7.61 (m, 1H), 7.40 (d, J=2.8 Hz, 1H), 7.18-7.27 (m, 1H), 5.25 (s, 2H), 3.84-3.96 (m, 4H), 3.52 (s, 3H), 0.88 (s, 9H), 0.00 (s, 6H).

Step 4: tert-Butyl(2-(2-fluoro-6-(methoxymethoxy)-8-(4,4,5,5-tetramethyl-1,3,2-dioxaborolan-2-yl)naphthalen-1-yl) ethoxy)dimethylsilane. A mixture of tert-butyl(2-(2-fluoro-8-iodo-6-(methoxymethoxy)naphthalen-1-yl)ethoxy) dimethylsilane (0.50 g, 1.02 mmol), 4,4,4',4',5,5,5',5'-octamethyl-2,2'-bi(1,3,2-dioxaborolane) (0.39 g, 1.53 mmol), $Cs_2CO_3$ (0.66 g, 2.04 mmol) and P(4-OMe-C6H4)$_3$ (36 mg, 0.10 mmol) in ethyl acetate (5 mL) was degassed and purged with $N_2$. $Pd(OAc)_2$ (23 mg, 0.10 mmol) was added, and the reaction mixture was stirred at 80° C. for 2 h. The reaction was combined with another batch (2.5 g scale), diluted with $H_2O$ and extracted with DCM. The combined organic layers were washed with brine, dried over $Na_2SO_4$, filtered, and concentrated. The residue was purified by by column chromatography on silica gel, eluting with a gradient of 5-100% EtOAc in petroleum ether, to provide tert-butyl(2-(2-fluoro-6-(methoxymethoxy)-8-(4,4,5,5-tetramethyl-1,3,2-dioxaborolan-2-yl)naphthalen-1-yl)ethoxy)dimethylsilane (2.70 g, 5.50 mmol, 90% yield) as white solid. $^1$H NMR (400 MHz, CHLOROFORM-d) δ ppm 7.44-7.52 (m, 1H), 7.27 (s, 2H), 7.08 (t, J=9.2 Hz, 1H), 5.15 (s, 2H), 3.70 (t, J=7.6 Hz, 2H), 3.38 (s, 3H), 3.22-3.28 (m, 2H), 1.35 (s, 12H), 0.74 (s, 9H), −0.14 (s, 6H).

Intermediate EP: (S)-4-(7-chloro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol

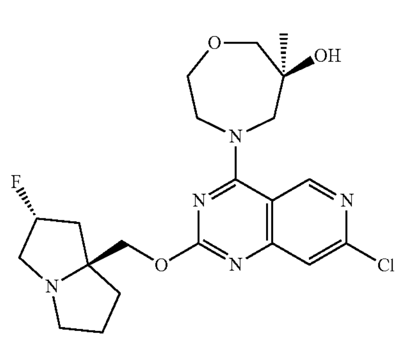 [SMILES: C[C@@]1(O)COCCN(c2nc(OC[C@@]34CCCN3C[C@H](F)C4)nc3cc(Cl)ncc23)C1]

The title compound was prepared in an analogous manner as Intermediate DO using (S)-6-methyl-1,4-oxazepan-6-ol (Step 2 in Intermediate BR) in Step 1. H NMR (400 MHz, CHLOROFORM-d) δ ppm 9.20 (s, 1H), 7.48 (s, 1H), 5.20-5.40 (m, 1H), 4.50-4.60 (m, 1H), 4.35-4.45 (m, 1H), 4.24 (s, 1H), 4.10-4.20 (m, 1H), 3.84-3.99 (m, 2H), 3.70-3.85 (m, 1H), 3.60-3.72 (m, 1H), 3.45-3.60 (m, 2H), 3.15-3.40 (m, 3H), 2.90-3.10 (m, 1H), 2.15-2.30 (m, 1H), 2.00-2.10 (m, 2H), 1.84-1.99 (m, 4H), 1.32 (s, 3H). m/z (ESI): 452.2 $(M+H)^+$.

Intermediate EQ: (S)-4-(7-Chloro-8-fluoro-2-(4-methylpiperazin-1-yl)pyrido[4,3-d]pyrimidin-4-yl)-1,4-oxazepan-6-ol

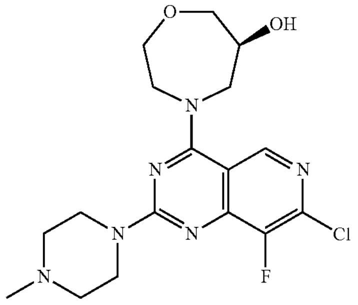 [SMILES: CN1CCN(c2nc(N3CCOC[C@@H](O)C3)c3cnc(Cl)c(F)c3n2)CC1]

The title compound was prepared in an analogous fashion to Intermediate BA using 1-methylpiperazine in Step 2. m/z (ESI): 397.2 $(M+H)^+$.

Intermediate ER: tert-Butyl (S)-4-(7-Chloro-8-fluoro-4-((S)-6-hydroxy-1,4-oxazepan-4-yl)pyrido[4,3-d]pyrimidin-2-yl)-2-methylpiperazine-1-carboxylate

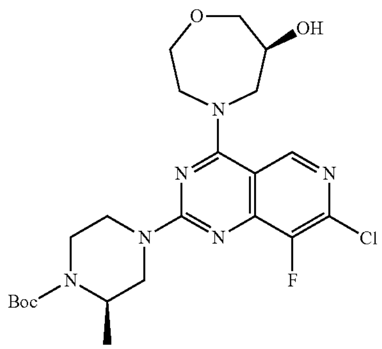 [SMILES: C[C@@H]1CN(c2nc(N3CCOC[C@@H](O)C3)c3cnc(Cl)c(F)c3n2)CCN1C(=O)OC(C)(C)C]

The title compound was prepared in an analogous fashion to Intermediate BA using tert-butyl (R)-2-methylpiperazine-1-carboxylate in Step 2. m/z (ESI): 497.2 $(M+H)^+$.

Intermediate ES: (2S,4S)-6-(7-Chloro-8-fluoro-2-(((2S,7aS)-2-fluorotetrahydro-1H-pyrrolizin-7a(5H)-yl)methoxy)pyrido[4,3-d]pyrimidin-4-yl)-6-azaspiro[3.5]nonan-2-ol

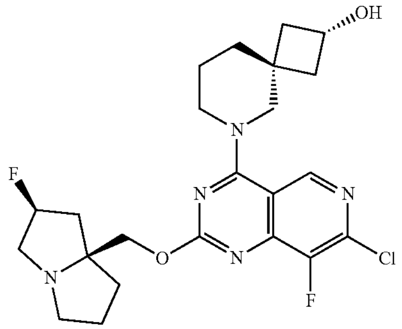 [SMILES: O[C@H]1C[C@]2(CCCN(c3nc(OC[C@@]45CCCN4C[C@@H](F)C5)nc4c(F)c(Cl)ncc34)C2)C1]

The title compound was prepared in an analogous fashion to Step 1 in Intermediate W using (2R,4S)-6-azaspiro[3.5]nonan-2-ol hydrochloride (Intermediate EK), then ((2S,7aS)-2-fluorotetrahydro-1H-pyrrolizin-7a(5H)-yl)methanol (Lab Network). m/z (ESI): 502.3 $(M+Na)^+$. $^1$H NMR (400 MHz, CHLOROFORM-d) δ 8.77 (s, 1H), 5.26-5.32 (m, 1H), 4.48 (d, J=10.27 Hz, 1H), 4.24-4.35 (m, 2H), 3.86 (s, 2H), 3.54 (m, J=19.56, 12.59 Hz, 1H), 3.12-3.22 (m, 1H), 2.74-2.91 (m, 1H), 2.60-2.71 (m, 2H), 2.11-2.24 (m, 4H), 1.83-2.00 (m, 6H), 1.71-1.82 (m, 6H).

Intermediate ET: 4-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-6-(methyl-d3)-1,4-oxazepan-6-ol

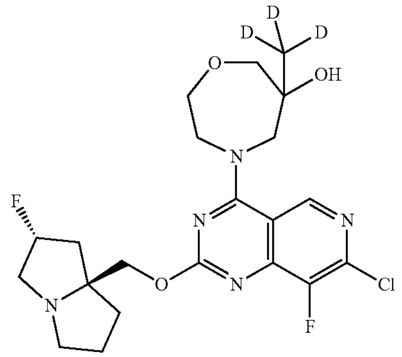 [SMILES: [2H]C([2H])([2H])C1(O)COCCN(c2nc(OC[C@@]34CCCN3C[C@H](F)C4)nc3c(F)c(Cl)ncc23)C1]

The title compound was prepared in an analogous fashion to Intermediate U using 6-(methyl-d3)-1,4-oxazepan-6-ol hydrochloride. $^1$H NMR (CHLOROFORM-d, 400 MHz) δ 9.08 (d, J=9.8 Hz, 1H), 5.23-5.38 (m, 1H), 4.50-4.65 (m, 1H), 4.38-4.49 (m, 1H), 4.23-4.39 (m, 2H), 3.90-3.97 (m, 2H), 3.72-3.82 (m, 1H), 3.63-3.70 (m, 1H), 3.52-3.62 (m, 2H), 3.31-3.40 (m, 1H), 3.15-3.30 (m, 2H), 2.97-3.06 (m, 1H), 2.23-2.31 (m, 1H), 2.16-2.23 (m, 1H), 2.08-2.16 (m, 1H), 1.89-2.02 (m, 3H).

Intermediate EU: tert-Butyl(3-(2-chloro-4-(methoxymethoxy)-6-(4,4,5,5-tetramethyl-1,3,2-dioxaborolan-2-yl)phenyl)propoxy)dimethylsilane

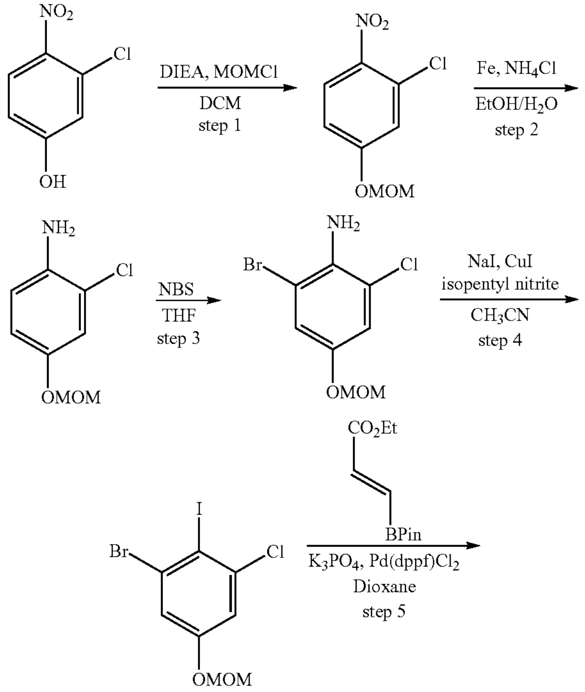

-continued

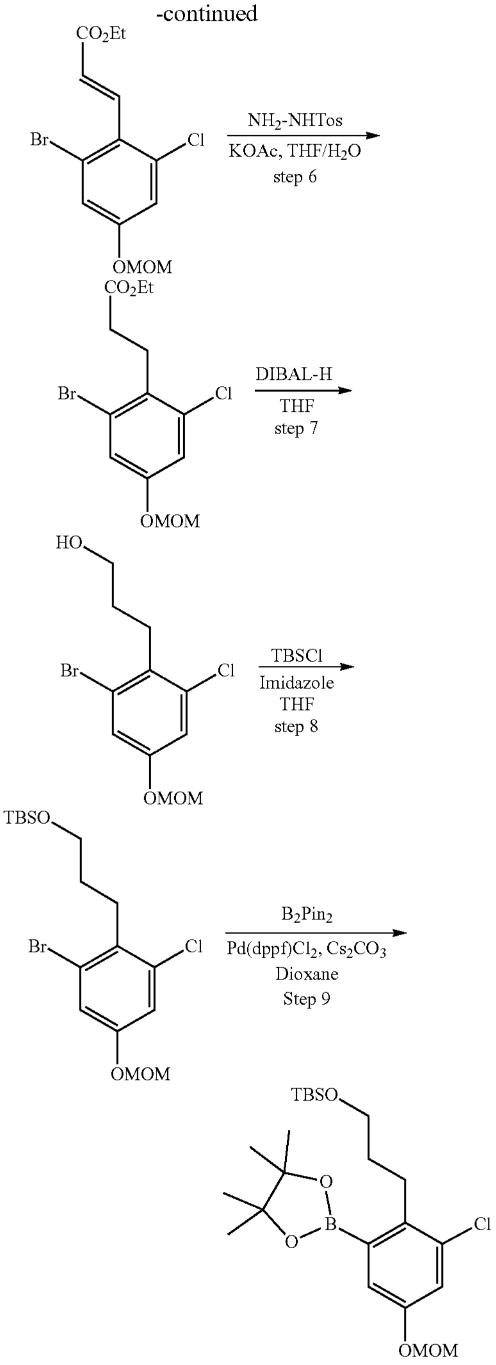

Intermediate EU

Step 1. 2-Chloro-4-(methoxymethoxy)-1-nitrobenzene. To a solution of 3-chloro-4-nitrophenol (40.0 g, 230 mmol) in dichloromethane (500 mL) was added DIPEA (81.0 mL, 461 mmol). The mixture was cooled to 0° C. then MOM-C1 (21.0 mL, 277 mmol) was added dropwise. The reaction mixture was stirred at rt for 1 h, combined with another batch (10 g), then was quenched by $H_2O$, and extracted with DCM. The combined organic layers were washed with brine, dried over $Na_2SO_4$, filtered, and concentrated to give 2-chloro-4-(methoxymethoxy)-1-nitrobenzene (57.8 g, 266 mmol, 92% yield) as yellow oil. $^1$H NMR (400 MHz, $CDCl_3$), 7.98 (d, J=9.2 Hz, 1H), 7.20 (d, J=2.8 Hz, 1H), 7.00-7.06 (m, 1H), 5.24 (s, 2H), 3.50 (s, 3H).

Step 2: 2-Chloro-4-(methoxymethoxy) aniline. To a solution of 2-chloro-4-(methoxymethoxy)-1-nitrobenzene (25.0 g, 115 mmol) in ethanol (200 mL) and water (100 mL) was added ammonium chloride (61.5 g, 1.15 mol). The reaction mixture heated to 50° C. and iron powder (32.1 g, 574 mmol) was added in portions. The mixture was stirred at 50° C. for 1 h. After cooling to rt, the reaction was combined with another batch (25 g), filtered, and concentrated under reduced pressure. The residue was diluted with $H_2O$ and extracted with EtOAc. The combined organic layers were washed with brine, dried over $Na_2SO_4$, filtered, and concentrated to give 2-chloro-4-(methoxymethoxy) aniline (40.0 g, 213 mmol, 93% yield) as a yellow oil. $^1$H NMR (400 MHz, $CDCl_3$), 7.03 (d, J=2.8 Hz, 1H), 6.80-6.85 (m, 1H), 6.72 (d, J=20.0 Hz, 1H), 5.07 (s, 2H), 3.89 (s, 2H), 3.48 (s, 3H).

Step 3: 2-Bromo-6-chloro-4-(methoxymethoxy) aniline. To a solution of 2-chloro-4-(methoxymethoxy)aniline (20.0 g, 107 mmol) in tetrahydrofuran (200 mL) was added NBS (20.9 g, 117 mmol) in portions. Then the mixture was stirred at 0° C. for 1 h. The reaction was combined with another batch (15 g), diluted with $H_2O$, and extracted with EtOAc. The combined organic layers were washed with brine, dried over $Na_2SO_4$, filtered, and concentrated. The residue was purified by column chromatography on silica gel, eluting with a gradient of 10-100% EtOAc in petroleum ether, to provide 2-bromo-6-chloro-4-(methoxymethoxy) aniline (27.0 g, 101 mmol, 54% yield) as yellow oil.

Step 4: 1-Bromo-3-chloro-2-iodo-5-(methoxymethoxy) benzene. The solution of CuI (53.6 g, 281 mmol), NaI (42.2 g, 281 mmol) and 2-bromo-6-chloro-4-(methoxymethoxy) aniline (25 g, 94 mmol) in acetonitrile (400 mL) was stirred at 50° C. for 30 min. To this solution was then added isoamyl nitrite (50.5 mL, 375 mmol) at 50° C. The resulting mixture was stirred at 50° C. for 1 h. After cooling to rt, the reaction mixture was filtered, and the filtrate was concentrated under reduced pressure. The residue was purified by column chromatography on silica gel, eluting with a gradient of 0-10% EtOAc in petroleum ether, to provide 1-bromo-3-chloro-2-iodo-5-(methoxymethoxy) benzene (28.0 g, 74.2 mmol, 79% yield) as a yellow oil. $^1$H NMR (400 MHz, CHLOROFORM-d) δ ppm 7.28 (d, J=2.8 Hz, 1H), 7.15 (d, J=2.8 Hz, 1H), 5.14 (s, 2H), 3.47 (s, 3H).

Step 5: Ethyl (E)-3-(2-bromo-6-chloro-4-(methoxymethoxy)phenyl)acrylate. To a solution of 1-bromo-3-chloro-2-iodo-5-(methoxymethoxy)benzene (9.00 g, 23.9 mmol) and ethyl (E)-3-(4,4,5,5-tetramethyl-1,3,2-dioxaborolan-2-yl)acrylate (5.93 g, 26.2 mmol) in 1,4-dioxane (270 mL) was added $K_3PO_4$ (10.1 g, 47.7 mmol) and Pd(dppf)$Cl_2$ (1.75 g, 2.39 mmol) under $N_2$. The mixture was stirred at 110° C. for 12 h. After cooling to rt, the reaction was combined with another 2 batches (total 30 g), diluted with $H_2O$ and extracted with EtOAc. The combined organic layers were washed with brine, dried over $Na_2SO_4$, filtered, and concentrated under reduced pressure to give ethyl (E)-3-(2-bromo-6-chloro-4-(methoxymethoxy)phenyl)acrylate (30.0 g, 22.3 mmol, 28% yield) as a yellow oil.

Step 6: Ethyl 3-(2-bromo-6-chloro-4-(methoxymethoxy) phenyl)propanoate. To a solution of ethyl (E)-3-(2-bromo-6-chloro-4-(methoxymethoxy)phenyl)acrylate (2.40 g, 6.86 mmol) in tetrahydrofuran (30 mL) and water (30 mL) was added KOAc (2.69 g, 27.5 mmol) and $NH_2$-NHTos (5.11 g, 27.5 mmol). The reaction mixture was stirred at 70° C. for 12 h. After cooling to rt, the reaction was combined with another 2 batches (2.4 g scale). The reaction mixture was diluted with $H_2O$ and extracted with EtOAc. The combined organic layers were washed with brine, dried over $Na_2SO_4$, filtered and concentrated under reduced pressure. The residue was purified by column chromatography on silica gel, eluting with a gradient of 0-100% EtOAc in petroleum ether, to provide ethyl 3-(2-bromo-6-chloro-4-(methoxymethoxy) phenyl)propanoate (4.60 g, 13.1 mmol, 64% yield) as yellow oil. $^1$H NMR (400 MHz, CHLOROFORM-d) δ ppm 7.20 (d, J=2.8 Hz, 1H), 7.06 (d, J=2.8 Hz, 1H), 5.13 (s, 2H), 4.15-4.22 (m, 2H), 3.47 (s, 3H), 3.20-3.26 (m, 2H), 2.52-2.57 (m, 2H), 1.28 (t, J=6.8 Hz, 3H).

Step 7: 3-(2-Bromo-6-chloro-4-(methoxymethoxy)phenyl)propan-1-ol. To a solution of ethyl 3-(2-bromo-6-chloro-4-(methoxymethoxy)phenyl)propanoate (2.00 g, 5.69 mmol) in tetrahydrofuran (20 mL) was added DIBAL-H (1 M in THF, 17.0 mL, 17.0 mmol) dropwise at −78° C. After addition, the mixture was stirred at rt for 1 h. The mixture was poured into ice water slowly and then extracted with EtOAc. The combined organic layers were washed with brine, dried over $Na_2SO_4$, filtered and concentrated to give 3-(2-bromo-6-chloro-4-(methoxymethoxy)phenyl)propan-1-ol (1.60 g, 5.00 mmol, 88% yield) as yellow oil. $^1$H NMR (400 MHz, CHLOROFORM-d) δ ppm 7.20 (d, J=2.4 Hz, 1H), 7.06 (d, J=2.8 Hz, 1H), 5.13 (s, 2H), 3.64 (t, J=6.4 Hz, 2H), 3.47 (s, 3H), 2.95-3.01 (m, 2H), 1.90-1.80 (m, 2H).

Step 8: (3-(2-Bromo-6-chloro-4-(methoxymethoxy)phenyl)propoxy)(tert-butyl)dimethylsilane. To a solution of 3-(2-bromo-6-chloro-4-(methoxymethoxy)phenyl)propan-1-ol (1.50 g, 4.85 mmol) in tetrahydrofuran (30 mL) was added imidazole (0.99 g, 14.5 mmol) and TBS-C1 (2.19 g, 14.5 mmol) under $N_2$. Then the mixture was stirred at rt for 1 h. The reaction mixture was diluted with $H_2O$ and extracted with EtOAc. The combined organic layers were washed with brine, dried over $Na_2SO_4$, filtered and concentrated to give (3-(2-bromo-6-chloro-4-(methoxymethoxy) phenyl)propoxy)(tert-butyl)dimethylsilane (1.70 g, 4.00 mmol, 83% yield) as colorless oil. $^1$H NMR (400 MHz, CHLOROFORM-d) δ ppm. 7.19 (d, J=2.4 Hz, 1H), 7.05 (d, J=2.4 Hz, 1H), 5.12 (s, 2H), 3.63 (t, J=6.4 Hz, 2H), 3.47 (s, 3H), 2.89-2.96 (m, 2H), 1.72-1.81 (m, 2H), 0.92 (s, 9H), 0.08 (s, 6H).

Step 9: tert-Butyl(3-(2-chloro-4-(methoxymethoxy)-6-(4,4,5,5-tetramethyl-1,3,2-dioxaborolan-2-yl)phenyl)propoxy) dimethylsilane. To a solution of (3-(2-bromo-6-chloro-4-(methoxymethoxy)phenyl)propoxy)(tert-butyl) dimethylsilane (0.90 g, 2.12 mmol) and $B_2Pin_2$ (0.81 g, 3.19 mmol) in 1,4-dioxane (10 mL) was added $Cs_2CO_3$ (1.38 g, 4.25 mmol) and Pd(dppf)$Cl_2$ (0.16 g, 0.21 mmol) under $N_2$. Then the mixture was stirred at 120° C. for 2 h. After cooling to rt, the reaction mixture was filtered, and the filtrate was concentrated under reduced pressure. The residue was purified by by column chromatography on silica gel, eluting with a gradient of 0-100% EtOAc in petroleum ether, to provide tert-butyl(3-(2-chloro-4-(methoxymethoxy)-6-(4,4,5,5-tetramethyl-1,3,2-dioxaborolan-2-yl)phenyl)propoxy)dimethylsilane (0.50 g, 1.06 mmol, 50% yield) as colorless oil.

Intermediate EV: 2-(4-Bromo-6-fluoro-1-(tetrahydro-2H-pyran-2-yl)-1H-indazol-5-yl)ethan-1-ol

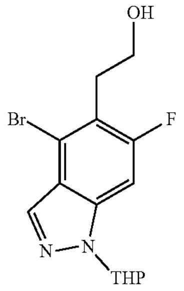

The title compound was prepared in an analogous manner as Intermediate CH using 4-bromo-6-fluoro-5-iodo-1-(tetrahydro-2H-pyran-2-yl)-1H-indazole in Step 1.

Intermediate EW: 5-(2-((tert-Butyldiphenylsilyl)oxy)ethyl)-6-fluoro-1-(tetrahydro-2H-pyran-2-yl)-4-(4,4,5,5-tetramethyl-1,3,2-dioxaborolan-2-yl)-1H-indazole

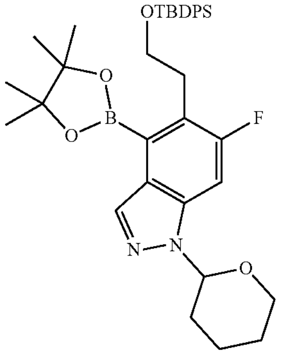

The title compound was prepared in an analogous manner as Intermediate FFF using 2-(4-bromo-6-fluoro-1-(tetrahydro-2H-pyran-2-yl)-1H-indazol-5-yl)ethan-1-ol (Intermediate EV) and tert-butyl(chloro)diphenylsilane (CAS #: 58479-61-1, Aldrich) and imidazole in DCM and THF in Step 3.

Intermediate EX: (2S,4S)-6-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol

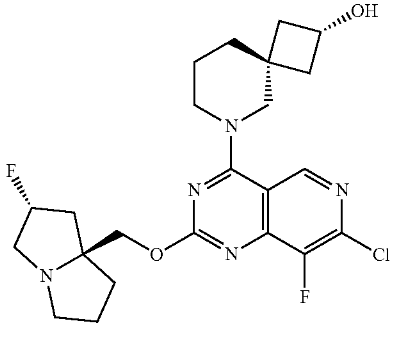 [SMILES: O[C@H]1C[C@]2(CCCN(c3nc(OC[C@@]45CCCN4C[C@H](F)C5)nc4c(F)c(Cl)ncc34)C2)C1]

The title compound was prepared in an analogous manner as Intermediate U using (2R,4S)-6-azaspiro[3.5]nonan-2-ol hydrochloride (Intermediate EK). $^1H$ NMR (400 MHz, DMSO-$d_6$) δ ppm 8.90 (s, 1H), 5.34 (d, J=54.0 Hz, 1H), 4.94 (s, 1H), 4.15-4.32 (m, 2H), 4.02-4.11 (m, 1H), 3.88 (s, 2H), 3.80 (s, 2H), 3.58-3.64 (m, 1H), 3.09-3.19 (m, 2H), 2.89 (s, 1H), 2.73 (s, 1H), 2.12-2.27 (m, 2H), 2.00-2.10 (m, 3H), 1.79-1.88 (m, 2H), 1.67 (s, 4H), 1.52-1.60 (m, 2H).

Intermediate EY: (2S,4s)-6-(3-Chloro-6-(((2R,7aS)-2-fluorotetrahydro-1H-pyrrolizin-7a(5H)-yl)methoxy)pyrimido[5,4-c]pyridazin-8-yl)-6-azaspiro[3.5]nonan-2-ol

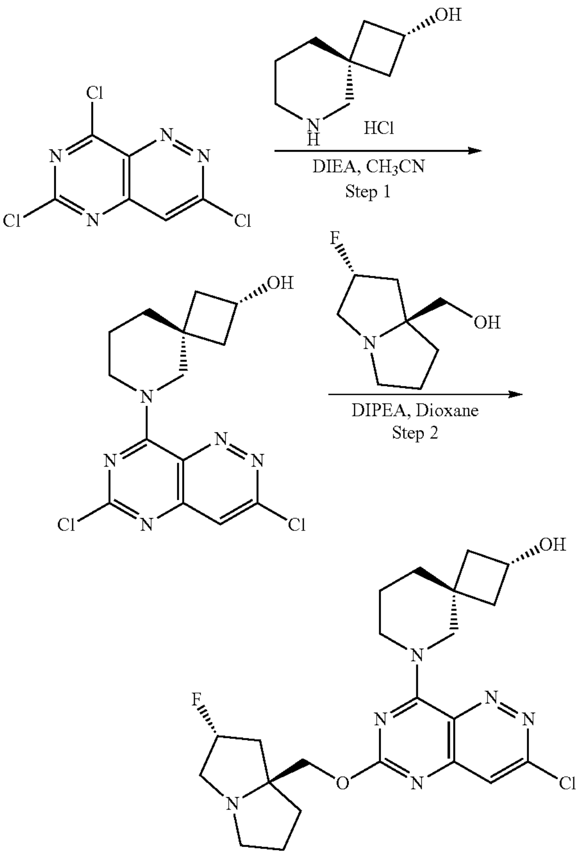

Intermediate EY

Step 1. (2R,4S)-6-(3,6-dichloropyrimido[5,4-c]pyridazin-8-yl)-6-azaspiro[3.5]nonan-2-ol. To a solution of 3,6,8-trichloropyrimido[5,4-c]pyridazine (2.00 g, 8.50 mmol, Intermediate OO) in acetonitrile (40 mL) was added (2R,4S)-6-azaspiro[3.5]nonan-2-ol hydrochloride (1.36 g, 7.64 mmol, Intermediate EK) and DIPEA (4.5 mL, 26 mmol)) in acetonitrile (12 mL). The mixture was stirred at −78° C. for 1 hr. After warming to rt, the reaction mixture was diluted with $H_2O$ and extracted with ethyl acetate. The combined organic layers were dried over $Na_2SO_4$, filtered, and concentrated to give 6-(3,6-dichloropyrimido[5,4-c]pyridazin-8-yl)-6-azaspiro[3.5]nonan-2-ol (1.6 g, crude) as a yellow solid. m/z (ESI): 340.1 $(M+H)^+$.

Step 2. (2S,4S)-6-(3-Chloro-6-(((2R,7aS)-2-fluorotetrahydro-1H-pyrrolizin-7a(5H)-yl)methoxy)pyrimido[5,4-c]pyridazin-8-yl)-6-azaspiro[3.5]nonan-2-ol. A mixture of (2R,4S)-6-(3,6-dichloropyrimido[5,4-c]pyridazin-8-yl)-6-azaspiro[3.5]nonan-2-ol (1.40 g, 4.12 mmol), ((2R,7aS)-2-fluorotetrahydro-1H-pyrrolizin-7a(5H)-yl)methanol (1.31 g, 8.23 mmol) and DIPEA (1.0 mL, 5.7 mmol) in 1,4-dioxane (1 mL) was degassed and purged with $N_2$. The reaction mixture was stirred at 110° C. for 12 hr. After cooling to rt, the residue was purified by column chromatography on silica gel, eluting with a gradient of 5-100% EtOAc in petroleum ether, to provide (2S,4S)-6-(3-chloro-6-(((2R,7aS)-2-fluorotetrahydro-1H-pyrrolizin-7a(5H)-yl)methoxy)pyrimido[5,4-c]pyridazin-8-yl)-6-azaspiro[3.5]nonan-2-ol (1.6 g, 3.5 mmol, 84% yield) as a yellow solid. $^1H$ NMR (400 MHz, DMSO-$d_6$) δ ppm 5.17-5.38 (m, 1H), 4.99 (s, 1H), 4.50-4.81 (m, 2H), 3.89-4.24 (m, 6H), 2.97-3.18 (m, 3H), 2.77-2.89 (m, 1H), 1.94-2.09 (m, 5H), 1.62-1.90 (m, 9H).

Intermediate EZ: (S)-4-(7-Chloro-8-fluoro-2-(((2S,7aS)-2-fluorotetrahydro-1H-pyrrolizin-7a(5H)-yl)methoxy)pyrido[4,3-d]pyrimidin-4-yl)-6-methyl-1,4-oxazepan-6-ol

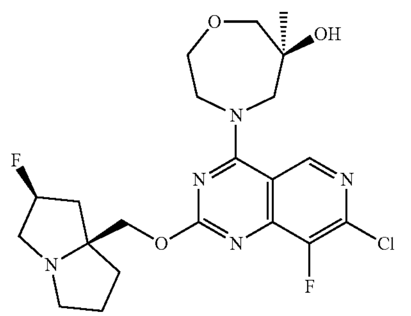 [SMILES: C[C@@]1(O)COCCN(c2nc(OC[C@@]34CCCN3C[C@@H](F)C4)nc3c(F)c(Cl)ncc23)C1]

The title compound was prepared in an analogous manner as Intermediate U using ((2S,7aS)-2-fluorotetrahydro-1H-pyrrolizin-7a(5H)-yl)methanol. $^1H$ NMR (CHLOROFORM-d, 400 MHz) δ 9.12 (s, 1H), 5.20-5.35 (m, 1H), 4.56-4.65 (m, 1H), 4.41-4.55 (m, 3H), 3.90-4.12 (m, 2H), 3.51-3.84 (m, 5H), 2.55-3.04 (m, 3H), 1.75-2.29 (m, 5H), 1.51-1.66 (m, 4H), 1.33-1.39 (m, 3H). m/z (ESI): 470.3 $(M+H)^+$.

Intermediate FA: 4-(3-Chloro-6-(((2R,7aS)-2-fluorotetrahydro-1H-pyrrolizin-7a(5H)-yl)methoxy)pyrimido[5,4-c]pyridazin-8-yl)-6-methyl-1,4-oxazepan-6-ol

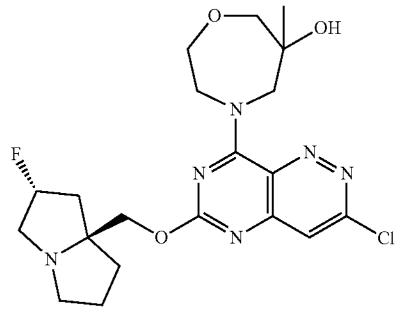 [SMILES: CC1(O)COCCN(c2nc(OC[C@@]34CCCN3C[C@H](F)C4)nc3cc(Cl)nnc23)C1]

The title compound was prepared in an analogous manner as Intermediate EY using 6-methyl-1,4-oxazepan-6-ol hydrochloride in Step 1.

Intermediate FB: 7-Bromo-5-chloro-6-iodo-1-methyl-1H-indazole

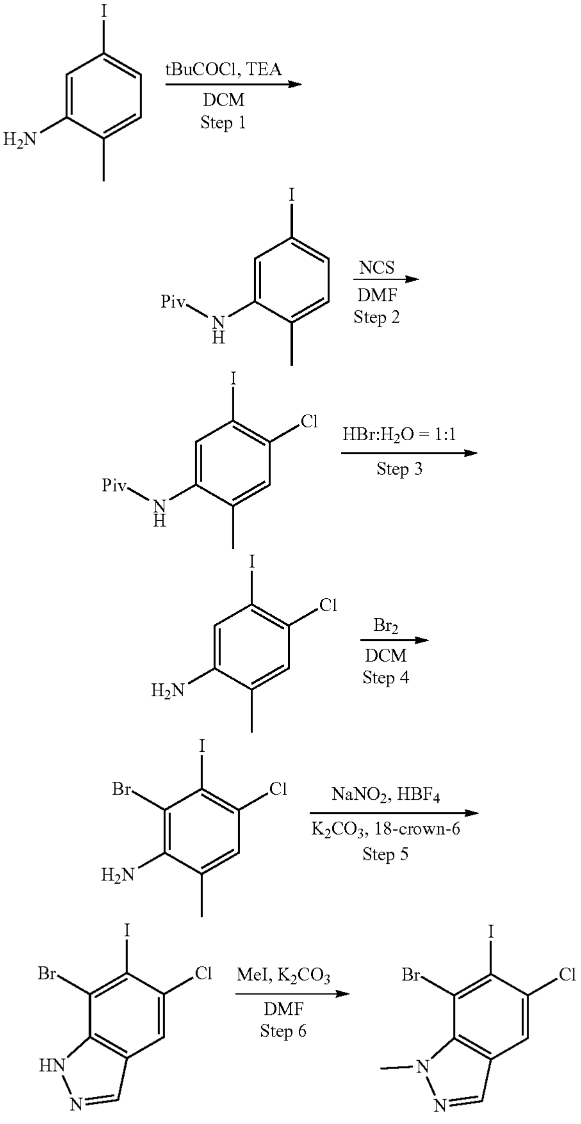

Intermediate FB

Step 1: N-(5-Iodo-2-methylphenyl) pivalamide. To a solution of 5-iodo-2-methylaniline (50.0 g, 215 mmol) in dichloromethane (600 mL) was added TEA (35.9 mL, 257 mmol) and pivaloyl chloride (28.9 mL, 236 mmol) in sequence. The reaction mixture was stirred at rt for 2 h, then diluted with $H_2O$ and extracted with DCM. The combined organic layers were dried over $Na_2SO_4$, filtered, and concentrated under reduced pressure to give N-(5-iodo-2-methylphenyl) pivalamide (200 g, 98% yield) as yellow solid.

Step 2. N-(4-Chloro-5-iodo-2-methylphenyl)pivalamide. To a solution of N-(5-iodo-2-methylphenyl)pivalamide (50.0 g, 158 mmol) in N,N-dimethylformamide (500 mL) was added NCS (27.4 g, 205 mmol). Then the mixture was stirred at 80° C. for 12 h. After cooling to rt, the reaction mixture was diluted with $H_2O$ and filtered. The filtrate was concentrated to give N-(4-chloro-5-iodo-2-methylphenyl) pivalamide (270 g, crude) as white solid.

Step 3: 4-Chloro-5-iodo-2-methylaniline. To a solution of N-(4-chloro-5-iodo-2-methylphenyl)pivalamide (25.0 g, 71.1 mmol) in 1,4-dioxane (300 mL) was added HBr (300 mL of 33% wt, 1.82 mol). The reaction mixture was stirred at 110° C. for 12 h. After cooling to rt, the reaction mixture was diluted with $H_2O$, adjusted to pH=7 by saturated $Na_2CO_3$, then extracted with. The combined organic layers were dried over $Na_2SO_4$, filtered, and concentrated. The residue was purified by MPLC to give 4-chloro-5-iodo-2-methylaniline (61.0 g, 228 mmol, 61% yield) as gray solid. $^1H$ NMR (CHLOROFORM-d, 400 MHz) δ 7.13 (d, J=8.0 Hz, 1H), 7.10 (s, 1H), 3.60 (s, 2H), 2.10 (s, 3H). m/z (ESI): 267.9 $(M+H)^+$.

Step 4: 2-Bromo-4-chloro-3-iodo-6-methylaniline. To a solution of 4-chloro-5-iodo-2-methylaniline (20.0 g, 74.8 mmol) in dichloromethane (200 mL) was added dropwise $Br_2$ (3.9 mL, 75 mmol) in dichloromethane (20 mL) at 0° C. The reaction mixture was stirred at 0° C. for 0.5 h, combined with another 2 batches (20 g scale), then diluted with $H_2O$ and extracted with EtOAc. The combined organics were dried over $Na_2SO_4$, filtered, and concentrated. The residue was purified by column chromatography on silica gel, eluting with a gradient of 1-10% EtOAc in petroleum ether, to provide 2-bromo-4-chloro-3-iodo-6-methylaniline (55.0 g, 159 mmol, 70% yield) as yellow solid. m/z (ESI): 347.8 $(M+H)^+$.

Step 5: 7-Bromo-5-chloro-6-iodo-1H-indazole. To a solution of 2-bromo-4-chloro-3-iodo-6-methylaniline (10.0 g, 28.9 mmol) in tetrafluoro-15-borane (63.4 g, 289 mmol) was added aqueous solution of sodium nitrite (2.99 g, 43.3 mmol) in water (5 mL) dropwise at 0° C. The resulting mixture was stirred at 0° C. for 1 h, then allowed to warm to rt with stirring for 1 h. The precipitate was collected by filtration, the solid was dissolved in chloroform (200 mL), then treated with 18-crown-6 (0.738 g, 2.79 mmol) and KOAc (8.22 g, 84 mmol) in sequence. Then the mixture was stirred at 35° C. for 1 h. The reaction was combined with four 10 g scale and one 5 g scale, diluted with water, and extracted with dichloromethane. The combined organic layers were dried over $Na_2SO_4$, filtered, and concentrated under reduced pressure to give 7-bromo-5-chloro-6-iodo-1H-indazole (50 g, 140 mmol, 88% yield) as yellow solid.

Step 6. 7-Bromo-5-chloro-6-iodo-1-methyl-1H-indazole. To a solution of 7-bromo-5-chloro-6-iodo-1H-indazole (10 g, 28 mmol) and $K_2CO_3$ (7.7 g, 56 mmol) in N,N-dimethylformamide (20 mL) was added MeI (7.0 mL, 0.11 mol). The reaction mixture was stirred at rt for 2 h, then diluted with water and extracted with EtOAc. The combined organic layers were washed with brine, dried over $Na_2SO_4$, filtered, and concentrated. The residue was purified by column chromatography on silica gel, eluting with a gradient of 1-5% EtOAc in petroleum ether, to provide 7-bromo-5-chloro-6-iodo-1-methyl-1H-indazole (21 g, 56 mmol, 40% yield) was obtained as yellow solid.

Intermediate FC: 6-(3-((tert-Butyldimethylsilyl)oxy) propyl)-5-chloro-1-methyl-7-(4,4,5,5-tetramethyl-1,3,2-dioxaborolan-2-yl)-1H-indazole

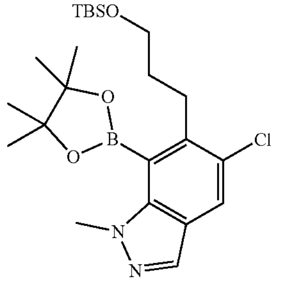 [SMILES: Cn1ncc2cc(Cl)c(CCCO[Si](C)(C)C(C)(C)C)c(B3OC(C)(C)C(C)(C)O3)c21]

The title compound was prepared in an analogous manner as Intermediate FFF using 7-bromo-5-chloro-6-iodo-1-methyl-1H-indazole in Step 1.

Intermediate FD: 5-(2-((tert-Butyldimethylsilyl)oxy) ethyl)-1-(tetrahydro-2H-pyran-2-yl)-4-(4,4,5,5-tetramethyl-1,3,2-dioxaborolan-2-yl)-1,5,6,7-tetrahydrocyclopenta[f]indazole

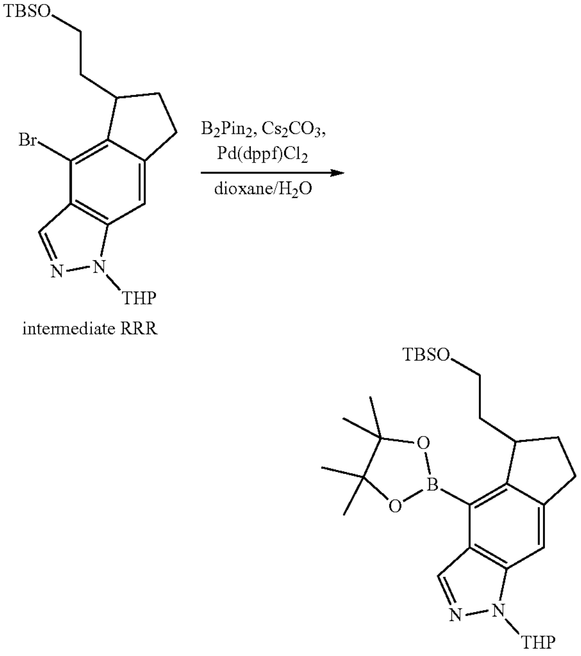

A mixture of 4-bromo-5-(2-((tert-butyldimethylsilyl)oxy) ethyl)-1-(tetrahydro-2H-pyran-2-yl)-1,5,6,7-tetrahydrocyclopenta[f]indazole (2.00 g, 4.20 mmol, Intermediate RRR), 4,4,4',4',5,5,5',5'-octamethyl-2,2'-bi(1,3,2-dioxaborolane) (5.30 g, 21 mmol), $Cs_2CO_3$ (3.40 g, 10 mmol) and Pd(dppf) C12 (0.31 g, 0.42 mmol) in 1,4-dioxane (8 mL) and water (1 mL) was degassed and purged with $N_2$. The reaction mixture was stirred at 120° C. for 1 h. After cooling to rt, the reaction was combined with another batch (2 g scale), diluted with $H_2O$, and extracted with EtOAc. The combined organic layers were washed with brine, dried over $Na_2SO_4$, filtered, and concentrated. The crude product was purified by reversed-phase MPLC to provide 5-(2-((tert-butyldimethylsilyl)oxy)ethyl)-1-(tetrahydro-2H-pyran-2-yl)-4-(4,4,5,5-tetramethyl-1,3,2-dioxaborolan-2-yl)-1,5,6,7-tetrahydrocyclopenta[f]indazole (2.70 g, 5.10 mmol, 61% yield) as yellow oil. $^1$H NMR (400 MHz, CHLOROFORM-d) δ ppm 8.36 (s, 1H), 7.48 (s, 1H), 5.67-5.74 (m, 1H), 3.98-4.06 (m, 1H), 3.68-3.80 (m, 3H), 3.56-3.62 (m, 1H), 3.06-3.17 (m, 1H), 2.86-2.92 (m, 1H), 2.52-2.62 (m, 1H), 2.10-2.20 (m, 3H), 1.60-1.85 (m, 7H), 1.39 (d, J=1.6 Hz, 12H), 0.91 (s, 9H), 0.07 (s, 6H).

Intermediate FE: (16S)-36-Chloro-28-fluoro-22-(methylsulfinyl)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one

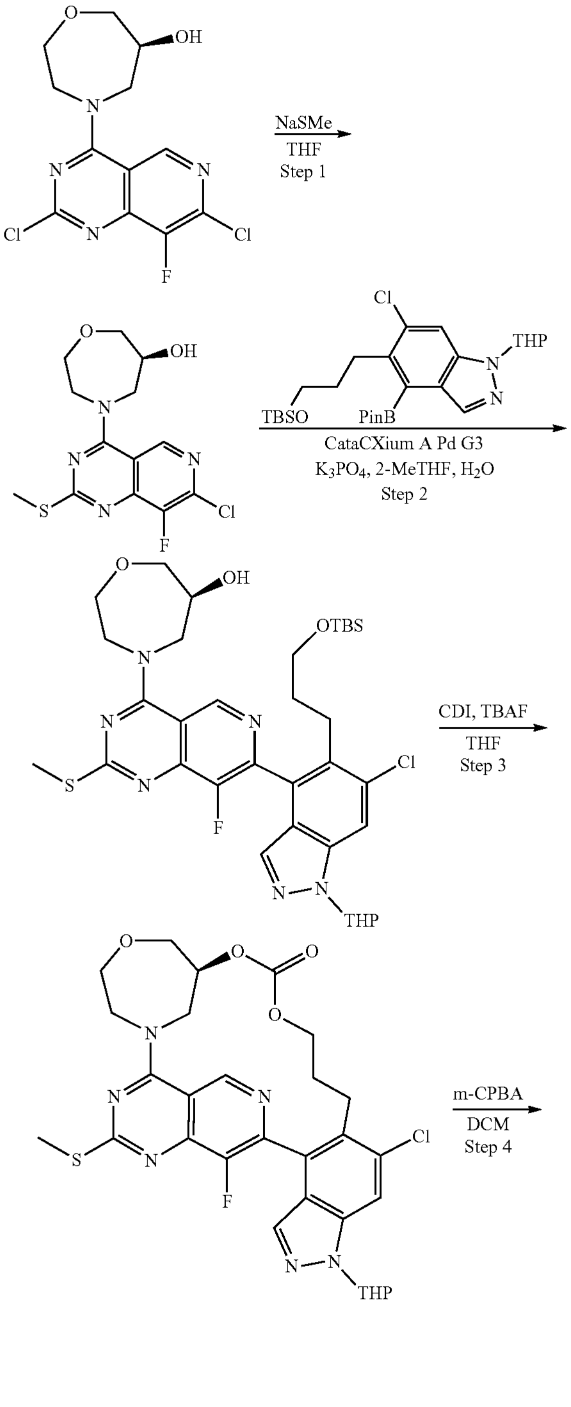

-continued

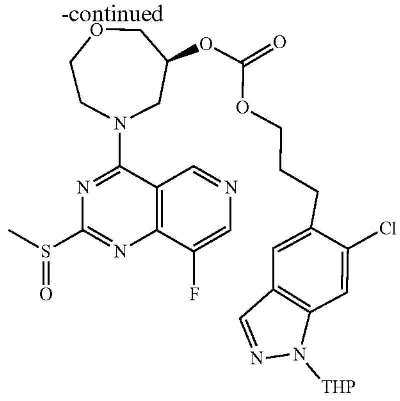

Intermediate FE

Step 1. (S)-4-(7-Chloro-8-fluoro-2-(methylthio)pyrido[4,3-d]pyrimidin-4-yl)-1,4-oxazepan-6-ol. To a solution of (S)-4-(2,7-dichloro-8-fluoropyrido[4,3-d]pyrimidin-4-yl)-1,4-oxazepan-6-ol (5.50 g, 16.5 mmol, Step 1 in Intermediate QQQ) in tetrahydrofuran (35 mL) was added NaSMe (6.65 g, 19.0 mmol) dropwise at 0° C. After addition, the mixture was stirred at 25° C. for 1 h The reaction mixture was quenched by addition of water and extracted with EtOAc. The combined organic layers were dried over $Na_2SO_4$, filtered, and concentrated under reduced pressure to give (S)-4-(7-chloro-8-fluoro-2-(methylthio)pyrido[4,3-d]pyrimidin-4-yl)-1,4-oxazepan-6-ol (5.3 g, 15.37 mmol, 93% yield) as yellow solid. m/z (ESI): 345.0 $(M+H)^+$.

Step 2. (6S)-4-(7-(5-(3-((tert-Butyldimethylsilyl)oxy)propyl)-6-chloro-1-(tetrahydro-2H-pyran-2-yl)-1H-indazol-4-yl)-8-fluoro-2-(methylthio)pyrido[4,3-d]pyrimidin-4-yl)-1,4-oxazepan-6-ol. A mixture of 5-(3-((tert-butyldimethylsilyl)oxy)propyl)-6-chloro-1-(tetrahydro-2H-pyran-2-yl)-4-(4,4,5,5-tetramethyl-1,3,2-dioxaborolan-2-yl)-1H-indazole (9.98 g, 18.7 mmol, Intermediate FFF), (S)-4-(7-chloro-8-fluoro-2-(methylthio)pyrido[4,3-d]pyrimidin-4-yl)-1,4-oxazepan-6-ol (5.30 g, 15.4 mmol), $K_3PO_4$ (9.90 g, 46.6 mmol) and cataCXiumA Pd G3 (2.26 g, 3.11 mmol) in 2-methyltetrahydrofuran (60 mL) and water (12 mL) was degassed and purged with $N_2$ for 3 times, and then the mixture was stirred at 110° C. for 5 h. The reaction mixture was combined with another batch (1 g scale), diluted with water, and extracted with EtOAc. The combined organic layers were dried over $Na_2SO_4$, filtered, and concentrated. The residue was purified by column chromatography on silica gel, eluting with a gradient of 10-100% methanol in DCM, to provide (6S)-4-(7-(5-(3-((tert-butyldimethylsilyl)oxy)propyl)-6-chloro-1-(tetrahydro-2H-pyran-2-yl)-1H-indazol-4-yl)-8-fluoro-2-(methylthio)pyrido[4,3-d]pyrimidin-4-yl)-1,4-oxazepan-6-ol (10.7 g, 82% yield) as yellow solid. m/z (ESI): 717.0 $(M+H)^+$.

Step 3. (16S)-36-Chloro-28-fluoro-22-(methylthio)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one. To solution of (6S)-4-(7-(5-(3-((tert-butyldimethylsilyl)oxy)propyl)-6-chloro-1-(tetrahydro-2H-pyran-2-yl)-1H-indazol-4-yl)-8-fluoro-2-(methylthio)pyrido[4,3-d]pyrimidin-4-yl)-1,4-oxazepan-6-ol (3.00 g, 4.18 mmol) in tetrahydrofuran (15 mL) was added CDI (3.39 g, 20.9 mmol) and purged with $N_2$ 3 times. Then the mixture was stirred at 45° C. for 5 h. After cooling to rt, TBAF (6.3 mL, 6.3 mmol, 1 M in THF) was added and the mixture was diluted with tetrahydrofuran (180 mL) and stirred at 45° C. for 5 h. The reaction was combined with other 2 batches (3 g scale) and concentrated under reduced pressure. The residue was purified by column chromatography on silica gel, eluting with a gradient of 1-100% EtOAc in petroleum ether, to provide (16S)-36-chloro-28-fluoro-22-(methylthio)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one (3.00 g, 4.80 mmol, 38% yield) as yellow solid. m/z (ESI): 629.0 $(M+H)^+$.

Step 4. (16S)-36-Chloro-28-fluoro-22-(methylsulfinyl)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one. To a solution of (16S)-36-chloro-28-fluoro-22-(methylthio)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one (1.50 g, 2.40 mmol) in dichloromethane (15 mL) was added m-CPBA (0.53 g, 2.6 mmol) at 0° C. The the mixture was stirred at 0° C. for 1 h, combined with another batch (1.5 g scale), and was concentrated under reduced pressure. The residue was purified by column chromatography on silica gel, eluting with a gradient of 30-100% EtOAc in petroleum ether, to provide (16S)-36-chloro-28-fluoro-22-(methylsulfinyl)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one (2.2 g, 72% yield) was obtained as a yellow solid. m/z (ESI): 645.2 $(M+H)^+$. $^1$H NMR (400 MHz, CHLOROFORM-d) δ 9.42 (d, J=3.6 Hz, 1H), 7.87 (d, J=10.0 Hz, 1H), 7.72 (t, J=5.2 Hz, 1H), 5.68-5.80 (m, 1H), 5.49 (d, J=16.8 Hz, 1H), 4.93-5.10 (m, 2H), 4.11-4.27 (m, 3H), 3.92-4.10 (m, 2H), 3.68-3.85 (m, 3H), 3.44-3.56 (m, 1H), 3.11-3.21 (m, 1H), 2.97-3.10 (m, 4H), 2.46-2.71 (m, 2H), 2.06-2.23 (m, 2H), 1.84-1.95 (m, 2H), 1.71-1.83 (m, 3H). $^{19}$F NMR (CHLOROFORM-d, 376 MHz) δ ppm −134.99 (s, 1F).

Intermediate FG: ((2S, 7aS)-2-(Prop-2-yn-1-yloxy)tetrahydro-1H-pyrrolizin-7a(5H)-yl)methanol

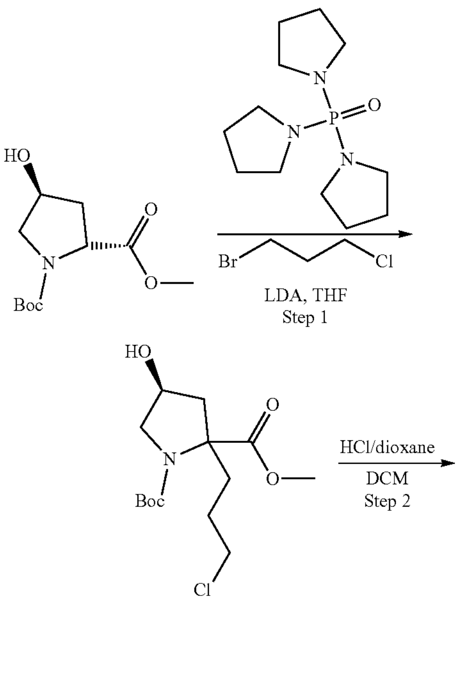

-continued

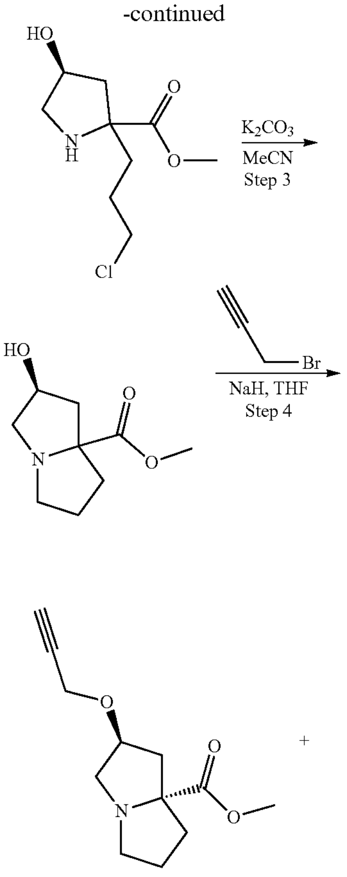

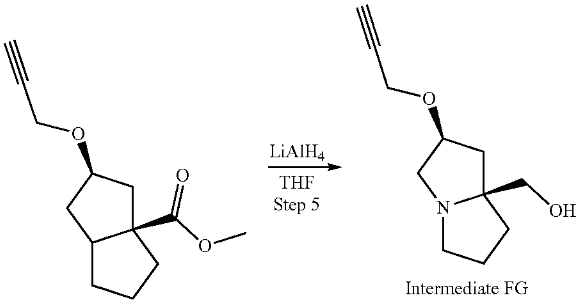

Intermediate FG

Step 1. 1-(tert-Butyl) 2-methyl (4S)-2-(3-chloropropyl)-4-hydroxypyrrolidine-1,2-dicarboxylate. To a solution of LDA (673 mL, 1.35 mol, 1 M in THF) in tetrahydrofuran (610 mL) was added tri(pyrrolidin-1-yl)phosphine oxide (219 g, 852 mmol) and 1-(tert-butyl) 2-methyl (2R,4S)-4-hydroxypyrrolidine-1,2-dicarboxylate (110 g, 448 mmol, AmBeed) in tetrahydrofuran (160 mL) at −65° C. The mixture was stirred at −65° C. for 10 min, then at 0° C. for 1 h. 1-Bromo-3-chloropropane (134 g, 852 mmol) was added the above mixture at −65° C. and the mixture was stirred at rt for 2 h. The reaction mixture was combined with another batch (90 g scale), quenched by addition of $NH_4Cl$ and extracted with EtOAc. The combined organic layers were washed with brine, dried over $Na_2SO_4$, filtered, and concentrated. The residue was purified by column chromatography on silica gel, eluting with a gradient of 50-100% EtOAc in petroleum ether, to provide 1-(tert-butyl) 2-methyl (4S)-2-(3-chloropropyl)-4-hydroxypyrrolidine-1,2-dicarboxylate (208 g, 647 mmol, 79% yield) as yellow oil.

Step 2. (4S)-2-(3-Chloropropyl)-4-hydroxypyrrolidine-2-carboxylate hydrochloride. To a solution of 1-(tert-butyl) 2-methyl (4S)-2-(3-chloropropyl)-4-hydroxypyrrolidine-1,2-dicarboxylate (50.0 g, 155 mmol) in dichloromethane (360 mL) was added hydrochloric acid in dioxane (4.0 M, 252 mL, 1.01 mol). Then the mixture was stirred at rt for 2 h, was then concentrated under reduced pressure to give methyl (4S)-2-(3-chloropropyl)-4-hydroxypyrrolidine-2-carboxylate hydrochloride (40.0 g, 180 mmol, 99% yield).

Step 3. (2S)-2-Hydroxytetrahydro-1H-pyrrolizine-7a(5H)-carboxylate. To a solution of methyl (4S)-2-(3-chloropropyl)-4-hydroxypyrrolidine-2-carboxylate hydrochloride (40.0 g, 180 mmol) in acetonitrile (280 mL) was added $K_2CO_3$ (100 g, 722 mmol). The reaction mixture was stirred at rt for 12 h, was then filtered. The filtrate was concentrated in vacuo to provide methyl (2S)-2-hydroxytetrahydro-1H-pyrrolizine-7a(5H)-carboxylate (22.0 g, 119 mmol, 66% yield) as a brown oil.

Step 4: Methyl (2S,7aR)-2-(prop-2-yn-1-yloxy)tetrahydro-1H-pyrrolizine-7a(5H)-carboxylate. To a solution of methyl (2S)-2-hydroxytetrahydro-1H-pyrrolizine-7a(5H)-carboxylate (22.0 g, 119 mmol) in tetrahydrofuran (130 mL) was added NaH (60% in oil, 6.18 g, 154 mmol) in portions at 0° C. The reaction mixture was stirred for 0.5 h at 0° C., then 3-bromoprop-1-yne (17.0 g, 143 mmol) was added, and then the mixture was allowed to warm to rt with stirring for 1 h. The reaction mixture was combined with other 3 batches (20 g scale) and was filtered and concentrated under reduced pressure. The residue was purified by column chromatography on silica gel, eluting with a gradient of 10-100% EtOAc in petroleum ether, to provide methyl (2S,7aR)-2-(prop-2-yn-1-yloxy)tetrahydro-1H-pyrrolizine-7a(5H)-carboxylate (10 g, 44 mmol, 13% yield) as a yellow oil, and methyl (2S,7aS)-2-(prop-2-yn-1-yloxy)tetrahydro-1H-pyrrolizine-7a(5H)-carboxylate (3.30 g, 14 mmol, 4% yield) as yellow oil.

Step 5. ((2S, 7aS)-2-(Prop-2-yn-1-yloxy)tetrahydro-1H-pyrrolizin-7a(5H)-yl)methanol. To a mixture of $LiAlH_4$ (3.1 mL, 7.8 mmol) in tetrahydrofuran (10 mL) was added methyl (2S,7aS)-2-(prop-2-yn-1-yloxy)tetrahydro-1H-pyrrolizine-7a(5H)-carboxylate (1.75 g, 7.84 mmol) in tetrahydrofuran (7 mL) dropwise at 0° C. The mixture was was allowed to warm to rt with stirring for 1 h. The reaction mixture was combined with other 3 batches (1.55 g scale), quenched with water and 15% NaOH solution. The mixture was filtered, and the filtrate was concentrated in vacuo to provide ((2S, 7aS)-2-(prop-2-yn-1-yloxy)tetrahydro-1H-pyrrolizin-7a(5H)-yl)methanol (2.5 g, 12 mmol, 87% yield) as yellow oil. $^1$H NMR (CHLOROFORM-d, 400 MHz) δ 4.29-4.33 (m, 1H), 4.14 (d, J=4.0 Hz, 2H), 3.41 (d, J=8.0 Hz, 1H), 3.28 (d, J=8.0 Hz, 1H), 3.07-3.28 (m, 1H), 2.95-3.05 (m, 1H), 2.75-2.91 (m, 1H), 2.61-2.71 (m, 1H), 2.35-2.45 (m, 1H), 1.95-2.10 (m, 1H), 1.65-1.85 (m, 5H), 1.51-1.64 (m, 1H).

Intermediate FH: tert-Butyl (3R)-3-(6-(4-bromo-6-chloro-1-(tetrahydro-2H-pyran-2-yl)-1H-indazol-5-yl)-2-oxohexyl)piperidine-1-carboxylate

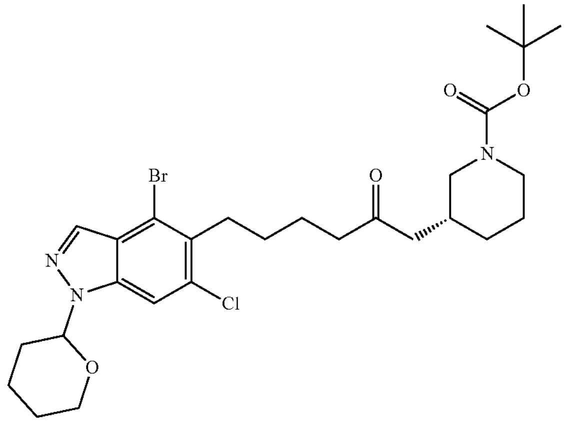 [SMILES: CC(C)(C)OC(=O)N1CCC[C@H](CC(=O)CCCCc2c(Cl)cc3c(cnn3C3CCCCO3)c2Br)C1]

This compound was prepared analogous to Intermediate BY using tert-butyl (S)-3-(2-hydroxyethyl)piperidine-1-carboxylate (CAS #: 143900-43-0, Aurum Pharmatech) in Step 1. m/z (ESI): 497.8 (M+H)$^+$.

Intermediate FI: 1-Azido-4-(4-bromo-6-methyl-1-(tetrahydro-2H-pyran-2-yl)-1H-indazol-5-yl)butan-2-one

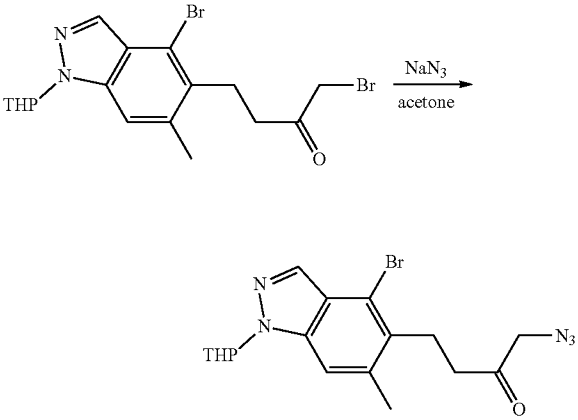

1-Bromo-4-(4-bromo-6-methyl-1-(tetrahydro-2H-pyran-2-yl)-1H-indazol-5-yl)butan-2-one was prepared in an analogous manner as Intermediate BX using 4-bromo-5-iodo-6-methyl-1-(tetrahydro-2H-pyran-2-yl)-1H-indazole in Step 1. $^1$H NMR (CHLOROFORM-d, 400 MHz) δ 7.94 (s, 1H), 7.36 (s, 1H), 5.64-5.67 (m, 1H), 4.00-4.03 (m, 1H), 3.94 (s, 2H), 3.65-3.75 (m, 1H), 3.16-3.23 (m, 2H), 2.87-2.91 (m, 2H), 2.51-2.52 (m, 3H), 1.95-2.30 (m, 3H), 1.65-1.78 (m, 3H). m/z (ESI): 445.0, 443.0, 447.0 (M+H)$^+$. Then the title compound was prepared in an analogous manner as Step 3 in Intermediate BX.

Intermediate FJ: tert-Butyl (3R)-3-((5-(2-(4-bromo-6-methyl-1-(tetrahydro-2H-pyran-2-yl)-1H-indazol-5-yl)ethyl)oxazol-2-yl)((tert-butyldimethylsilyl)oxy)methyl)piperidine-1-carboxylate

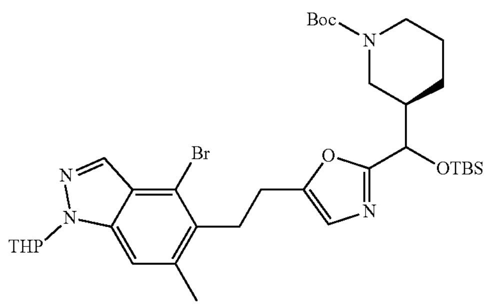

The title compound was prepared in an analogous manner as Intermediate CB using in Step 4 using 1-azido-4-(4-bromo-6-methyl-1-(tetrahydro-2H-pyran-2-yl)-1H-indazol-5-yl)butan-2-one.

Intermediate FK: tert-Butyl (3R)-3-((4-((1R,2S)-rel-2-(4-bromo-6-chloro-1-(tetrahydro-2H-pyran-2-yl)-1H-indazol-5-yl)cyclopropyl)-2H-1,2,3-triazol-2-yl)methyl)piperidine-1-carboxylate

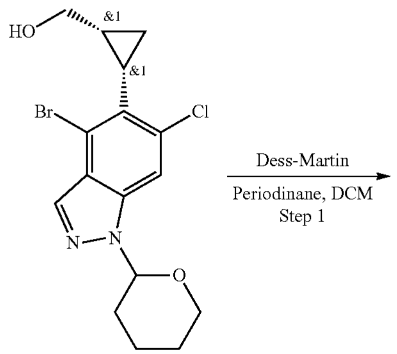

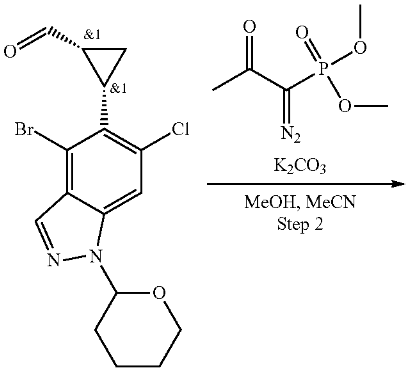

-continued

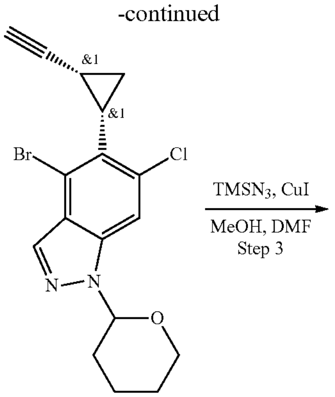

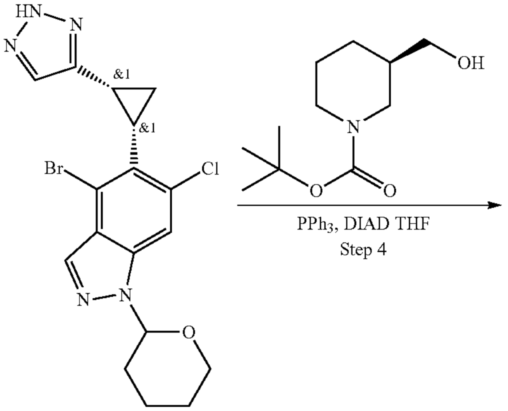

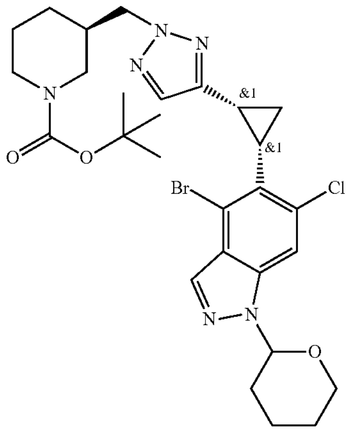

Intermediate FK

Step 1. rel-(1R,2S)-2-(4-Bromo-6-chloro-1-(tetrahydro-2H-pyran-2-yl)-1H-indazol-5-yl)cyclopropane-1-carbaldehyde. To a 250-mL round-bottom flask was charged with rac-((1R,2S)-2-(4-bromo-6-chloro-1-(tetrahydro-2H-pyran-2-yl)-1H-indazol-5-yl)cyclopropyl)methanol (1.12 g, 2.89 mmol, Step 2 in Example 46) in dichloromethane (30 mL). The mixture was cooled to 0° C., and Dess-Martin periodinane (1.41 g, 3.33 mmol) was added portionwise. The mixture was warmed to rt with stirring for 1 h. Solvent was removed, and the mixture was partitioned between EtOAc and a mixture of saturated sodium bicarbonate solution and sodium thiosulfate solution. The aqueous phase was extracted with EtOAc and the combined organic layers were dried ($Na_2SO_4$), filtered and and concentrated. The residue was purified by column chromatography on silica gel, eluting with a gradient of 0-50% EtOAc/heptane, to provide rel-(1R,2S)-2-(4-bromo-6-chloro-1-(tetrahydro-2H-pyran- 2-yl)-1H-indazol-5-yl)cyclopropane-1-carbaldehyde (1.10 g, 2.87 mmol, 99% yield) as a white solid. m/z (ESI): 382.9, 385.0 $(M+H)^+$.

Step 2. rel-4-Bromo-6-chloro-5-((1S,2R)-2-ethynylcyclopropyl)-1-(tetrahydro-2H-pyran-2-yl)-1H-indazole. In a 40-mL vial containing a suspension of potassium carbonate (0.79 g, 5.73 mmol) and rel-(1R,2S)-2-(4-bromo-6-chloro-1-(tetrahydro-2H-pyran-2-yl)-1H-indazol-5-yl)cyclopropane-1-carbaldehyde (1.10 g, 2.87 mmol) in methanol (20 mL) was charged with dimethyl (1-diazo-2-oxopropyl)phosphonate (10% in acetonitrile) (10.5 mL, 4.30 mmol). The reaction mixture was stirred at rt for 16 h. Solvent was evaporated, and the mixture was partitioned between EtOAc and brine (50 mL). The aqueous layer was extracted with EtOAc, and the combined organic layers were dried over $Na_2SO_4$, filtered, and concentrated. The crude material was purified by column chromatography on silica gel, eluting with a gradient of 0-50% EtOAc/heptane, to provide rel-4-bromo-6-chloro-5-((1S,2R)-2-ethynylcyclopropyl)-1-(tetrahydro-2H-pyran-2-yl)-1H-indazole (1.00 g, 2.64 mmol, 92% yield) as colorless oil. m/z (ESI): 379.1, 381.1 $(M+H)^+$.

Step 3. rel-5-((1S,2R)-2-(2H-1,2,3-Triazol-4-yl)cyclopropyl)-4-bromo-6-chloro-1-(tetrahydro-2H-pyran-2-yl)-1H-indazole. To a 40-mL vial was added copper(I) iodide (25 mg, 0.13 mmol), rel-4-bromo-6-chloro-5-((1S,2R)-2-ethynylcyclopropyl)-1-(tetrahydro-2H-pyran-2-yl)-1H-indazole (1.00 g, 2.64 mmol) and azidotrimethylsilane (0.52 mL, 4.0 mmol) in N,N-dimethylformamide (8 mL) and methanol (2 mL). The mixture was bubbled with $N_2$ for 10 min and then heated at 100° C. for 65 h. After cooling to rt, water was added, and the mixture was extracted with EtOAc. The combined organic layers were dried over $Na_2SO_4$, filtered, and concentrated. The crude material was purified column chromatography on silica gel, eluting with a gradient of 0-100% (3:1 EtOAc/EtOH with 2% $Et_3N$)/heptane, to provide rel-5-((1S,2R)-2-(2H-1,2,3-triazol-4-yl)cyclopropyl)-4-bromo-6-chloro-1-(tetrahydro-2H-pyran-2-yl)-1H-indazole (0.84 g, 1.98 mmol, 75% yield) as off-white foam. m/z (ESI): 422.0, 424.0 $(M+H)^+$.

Step 4. tert-Butyl (3R)-3-((4-((1R,2S)-rel-2-(4-bromo-6-chloro-1-(tetrahydro-2H-pyran-2-yl)-1H-indazol-5-yl)cyclopropyl)-2H-1,2,3-triazol-2-yl)methyl)piperidine-1-carboxylate. To a 40-mL vial was added rel-5-((1S,2R)-2-(2H-1,2,3-triazol-4-yl)cyclopropyl)-4-bromo-6-chloro-1-(tetrahydro-2H-pyran-2-yl)-1H-indazole (0.98 g, 2.31 mmol) in tetrahydrofuran (10 mL). Triphenylphosphine (0.67 g, 2.54 mmol) and tert-butyl (3R)-3-(hydroxymethyl)piperidine-1-carboxylate (0.55 g, 2.54 mmol) was then added. The mixture was cooled to 0° C., and diisopropyl azodicarboxylate (0.51 mL, 2.5 mmol) was added dropwise. The reaction mixture was stirred at rt for 16 h, then was concentrated, and directly purified by column chromatography on silica gel, eluting with a gradient of 0-50% EtOAc/heptane, to provide tert-butyl (3R)-3-((4-((1R,2S)-rel-2-(4-bromo-6-chloro-1-(tetrahydro-2H-pyran-2-yl)-1H-indazol-5-yl)cyclopropyl)-2H-1,2,3-triazol-2-yl)methyl)piperidine-1-carboxylate (1.31 g, 2.11 mmol, 91% yield) as colorless viscous oil. m/z (ESI): 619.1, 621.1 $(M+H)^+$.

Intermediate FL: (2S)-2-((5-(2-(4-Bromo-6-chloro-1-(tetrahydro-2H-pyran-2-yl)-1H-indazol-5-yl)ethyl)oxazol-2-yl)methyl)morpholine-4-carboxylate

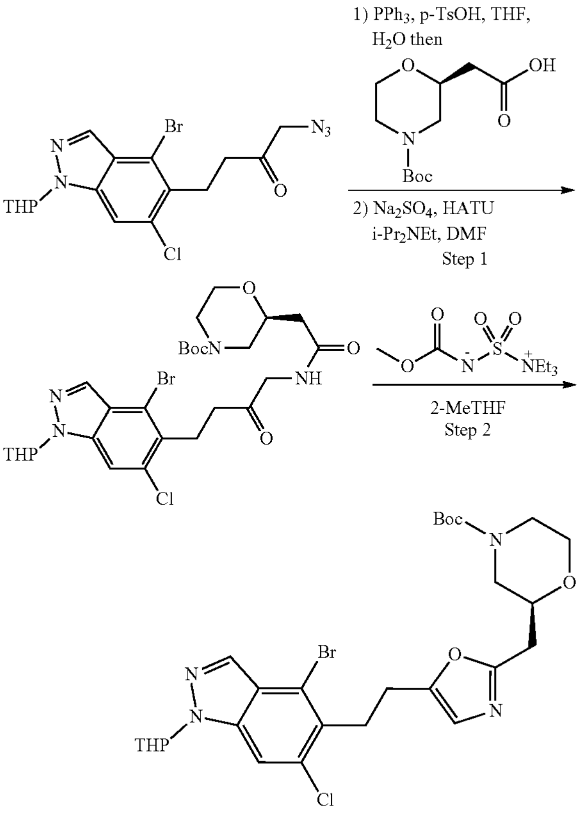

Intermediate FL

Step 1. tert-Butyl (5S)-5-(2-((4-(4-bromo-6-chloro-1-(tetrahydro-2H-pyran-2-yl)-1H-indazol-5-yl)-2-oxobutyl)amino)-2-oxoethyl)-1,3-oxazinane-3-carboxylate. To a 40-mL vial containing water (0.13 mL, 7.0 mmol) was added tetrahydrofuran (4 mL), 1-azido-4-(4-bromo-6-chloro-1-(tetrahydro-2H-pyran-2-yl)-1H-indazol-5-yl)butan-2-one (Step 3 in Intermediate BZ, 0.20 g, 0.469 mmol), triphenylphosphine (0.13 g, 0.49 mmol), and p-toluenesulfonic acid monohydrate (0.11 g, 0.56 mmol) sequentially. The mixture was stirred at rt for 7 h. Additional water (0.13 mL, 7.0 mmol) was added, and the mixture was stirred at rt for 17 h. Sodium sulfate, anhydrous (0.50 g, 3.52 mmol), N,N-dimethylformamide (1 mL), HATU (0.36 g, 0.94 mmol), (S)-2-(4-(tert-butoxycarbonyl)morpholin-2-yl)acetic acid (0.14 g, 0.56 mmol, Ambeed Inc.) and diisopropylethylamine (0.82 mL, 4.7 mmol) was added sequentially, and the mixture was stirred at rt for 3 h. The reaction mixture was concentrated and the residue was filtered and purified by reverse-phase chromatography using a C18 column, eluting with a gradient of 0-100% $CH_3CN$ with 0.1% formic acid/water with 0.1% formic acid, to provide tert-butyl (5S)-5-(2-((4-(4-bromo-6-chloro-1-(tetrahydro-2H-pyran-2-yl)-1H-indazol-5-yl)-2-oxobutyl)amino)-2-oxoethyl)-1,3-oxazinane-3-carboxylate (0.23 g, 0.36 mmol, 76% yield) as off-white solid. m/z (ESI): 627.1, 629.1 $(M+H)^+$.

Step 2. (2S)-2-((5-(2-(4-Bromo-6-chloro-1-(tetrahydro-2H-pyran-2-yl)-1H-indazol-5-yl)ethyl)oxazol-2-yl)methyl)

morpholine-4-carboxylate. In a 40-mL vial was added tert-butyl (5S)-5-(2-((4-(4-bromo-6-chloro-1-(tetrahydro-2H-pyran-2-yl)-1H-indazol-5-yl)-2-oxobutyl)amino)-2-oxoethyl)-1,3-oxazinane-3-carboxylate (0.23 g, 0.36 mmol) and Burgess reagent (0.26 g, 1.08 mmol) in 2-methyltetrahydrofuran (8 mL). The mixture was purged with $N_2$, then heated at 75° C. for 1 h. After cooling to rt, the reaction mixture was quenched with saturated NaCl solution and extracted with EtOAc. The organic combined layers were, dried ($Na_2SO_4$), filtered and concentrated. The residue was purified by column chromatography on silica gel, eluting with a gradient of 0-100% EtOAc/heptane, to provide tert-butyl (2S)-2-((5-(2-(4-bromo-6-chloro-1-(tetrahydro-2H-pyran-2-yl)-1H-indazol-5-yl)ethyl)oxazol-2-yl)methyl)morpholine-4-carboxylate (0.17 g, 0.27 mmol, 76% yield) as colorless oil. m/z (ESI): 609.2, 611.2 $(M+H)^+$.

Intermediate FM: tert-Butyl 6-((5-(2-(4-bromo-6-chloro-1-(tetrahydro-2H-pyran-2-yl)-1H-indazol-5-yl)ethyl)oxazol-2-yl)methyl)-1,4-oxazepane-4-carboxylate

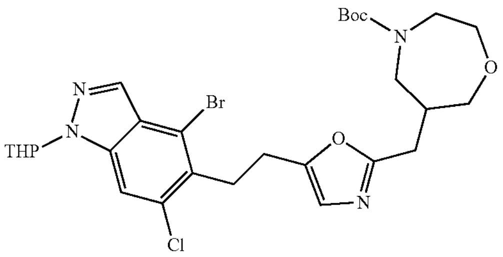

The title compound was prepared in an analogous manner to Intermediate FL using 2-(1-(tert-butoxycarbonyl)azepan-3-yl)acetic acid (CAS #: 79839-29-5, Enamine) in Step 1_2. m/z (ESI): 623.2, 625.2 $(M+H)^+$.

Intermediate FN: tert-Butyl (3R)-3-(((tert-butyldimethylsilyl)oxy)(5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)methyl)piperidine-1-carboxylate

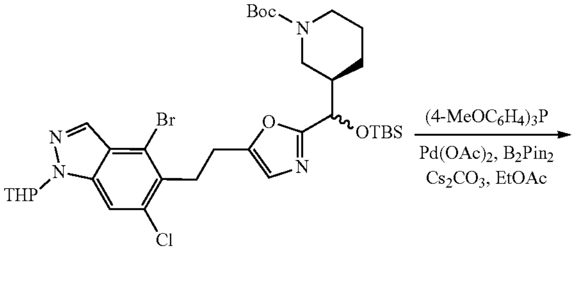

-continued

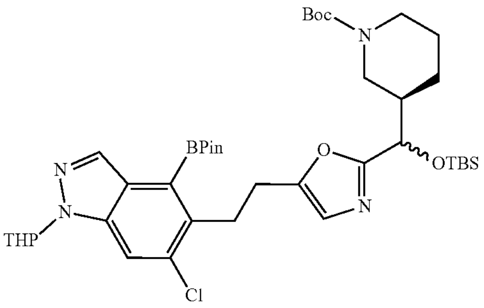

A 40-mL vial was charged with tris(4-methoxyphenyl)phosphine (0.11 g, 0.32 mmol), palladium acetate (60 mg, 0.27 mmol), 4,4,4',4',5,5,5',5'-octamethyl-2,2'-bi(1,3,2-dioxaborolane) (1.02 g, 4.02 mmol), cesium carbonate (1.75 g, 5.36 mmol), tert-butyl (3R)-3-((5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)piperidine-1-carboxylate (Intermediate CB, 1.98 g, 2.68 mmol) and EtOAc (8 mL). The contents were sparged with $N_2$ and heated to 80° C. for 1 h. After cooling to rt, the reaction mixture was filtered over Celite, and the filtrate was concentrated. The residue was purified by column chromatography on silica gel column, eluting with a gradient of 0-100% EtOAc/heptane to provide tert-butyl (3R)-3-(((tert-butyldimethylsilyl)oxy)(5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)methyl)piperidine-1-carboxylate (1.03 g, 1.31 mmol, 49% yield) as colorless viscous oil. m/z (ESI): 785.4 $(M+H)^+$.

Intermediate FO: tert-Butyl (2R)-2-((1R)-(5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)morpholine-4-carboxylate

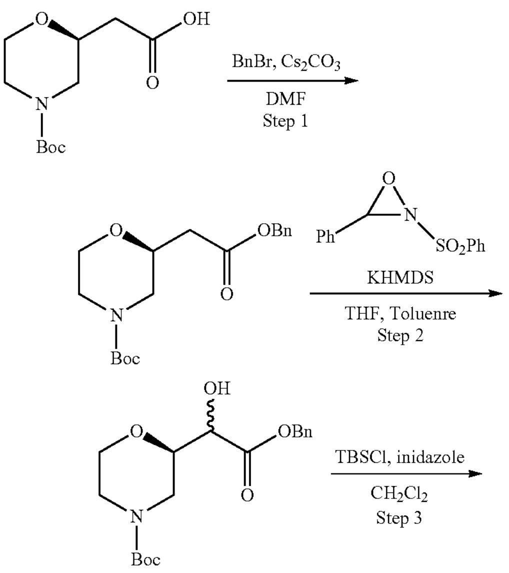

-continued

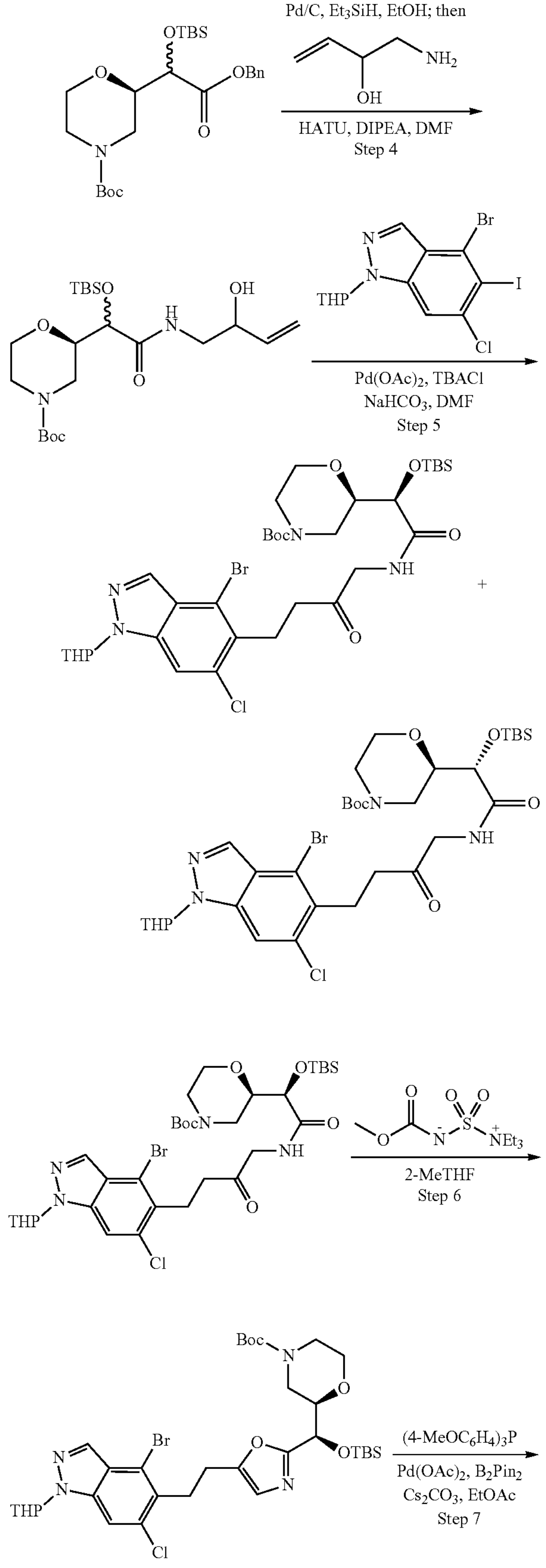

-continued

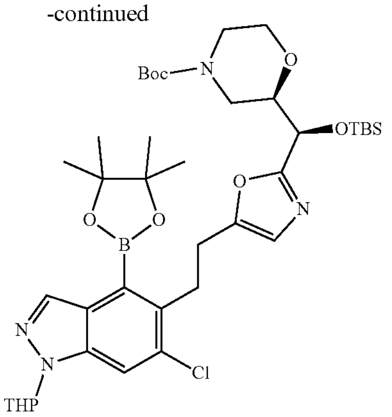

Intermediate FO

Step 1. tert-Butyl (S)-2-(2-(benzyloxy)-2-oxoethyl)morpholine-4-carboxylate. In a 40 mL vial was charged with (S)-2-(4-(tert-butoxycarbonyl)morpholin-2-yl)acetic acid (5.00 g, 20.4 mmol, Ambeed Inc.) and N,N-dimethylformamide (20 mL). The solution was cooled to 0° C. and cesium carbonate (6.97 g, 21.4 mmol) was added. The mixture was stirred at rt for 1 h, (bromomethyl)benzene (3.66 g, 21.4 mmol) was added and the mixture was stirred at 0° C. for another 30 minutes. The mixture was warmed to rt with stirring for 24 h, diluted with EtOAc and then filtered through Celite. The resulting mixture was washed sequentially with water and brine, dried over $Na_2SO_4$, filtered, and concentrated to provide tert-butyl (S)-2-(2-(benzyloxy)-2-oxoethyl)morpholine-4-carboxylate (7.00 g, 21.0 mmol, 100% yield) as a white solid. m/z (ESI): 358.1 $(M+Na)^+$.

Step 2. tert-Butyl (2R)-2-(2-(benzyloxy)-1-hydroxy-2-oxoethyl)morpholine-4-carboxylate. To a 250-mL round bottom flask was added tetrahydrofuran (8 mL) under nitrogen atmosphere. The vial was cooled to −78° C. and potassium bis(trimethylsilyl)amide (0.5 M solution in toluene, 25.3 mL, 12.6 mmol) was added. A solution of tert-butyl (S)-2-(2-(benzyloxy)-2-oxoethyl)morpholine-4-carboxylate (3.53 g, 10.5 mmol) in tetrahydrofuran (8 mL) was added dropwise at −78° C. and the mixture was stirred at −78° C. for 10 min. 3-Phenyl-2-(phenylsulfonyl)-1,2-oxaziridine (3.16 g, 12.1 mmol, Synthonix Inc.) in tetrahydrofuran (8 mL) was then added and the mixture was stirred at −78° C. for an additional 30 min. The mixture was quenched by the addition of saturated $NH_4Cl$ solution and warmed to rt. The mixture was partitioned between EtOAc and saturated NaCl solution. The organic layer was dried ($Na_2SO_4$), filtered and concentrated and the residue was purified by column chromatography on silica gel, eluting with a gradient of 0-50% EtOAc/heptane, to provide tert-butyl (2R)-2-(2-(benzyloxy)-1-hydroxy-2-oxoethyl)morpholine-4-carboxylate (3.16 g, 8.99 mmol, 85% yield) as colorless oil. m/z (ESI): 374.2 $(M+Na)^+$.

Step 3. tert-Butyl (2R)-2-(2-(benzyloxy)-1-((tert-butyldimethylsilyl)oxy)-2-oxoethyl)morpholine-4-carboxylate. To a 250-mL round-bottom flask was added tert-butyl (2R)-2-(2-(benzyloxy)-1-hydroxy-2-oxoethyl)morpholine-4-carboxylate (6.31 g, 18.0 mmol) in anhydrous dichloromethane (30 mL). Imidazole (1.83 g, 26.9 mmol) and tert-butyldimethylsilyl chloride (3.31 g, 21.6 mmol) was added sequentially at 0° C. The reaction mixture was stirred at rt for 16 h. The resulting mixture was filtered over Celite, concentrated, and directly purified by column chromatography on silica gel, eluting with a gradient of 0-50% EtOAc/heptane, to provide tert-butyl (2R)-2-(2-(benzyloxy)-1-((tert-butyldimethylsilyl)oxy)-2-oxoethyl)morpholine-4-carboxylate (6.21 g, 13.3 mmol, 74% yield) as colorless oil. m/z (ESI): 488.1 $(M+Na)^+$.

Step 4. tert-Butyl (2R)-2-(1-((tert-butyldimethylsilyl)oxy)-2-((2-hydroxybut-3-en-1-yl)amino)-2-oxoethyl)morpholine-4-carboxylate. In a 250-mL round-bottom flask was added palladium on activated carbon (0.58 g, 5.4 mmol). Under nitrogen, tert-butyl (2R)-2-(2-(benzyloxy)-1-((tert-butyldimethylsilyl)oxy)-2-oxoethyl)morpholine-4-carboxylate (3.60 g, 7.70 mmol) in ethanol (30 mL) was added. 3-Ethyl-3-silapentane (4.0 mL, 25 mmol) was then added via a syringe pump over 2 h. The resulting mixture was filtered over Celite and concentrated. The residue was dissolved in N,N-dimethylformamide (10 mL) and treated with HATU (3.23 g, 8.50 mmol), 1-amino-3-buten-2-ol (0.67 mL, 7.7 mmol), and N-ethyl-N-isopropylpropan-2-amine (3.0 g, 23 mmol) sequentially. The reaction mixture was stirred at rt for 30 min before it was quenched by the addition of water and extracted with EtOAc. The combined organic layers were dried over $Na_2SO_4$, filtered, and concentrated. The residue was purified by column chromatography on silica gel, eluting with a gradient of 0-100% EtOAc/heptane, to provide tert-butyl (2R)-2-(1-((tert-butyldimethylsilyl)oxy)-2-((2-hydroxybut-3-en-1-yl)amino)-2-oxoethyl)morpholine-4-carboxylate (2.34 g, 5.26 mmol, 68% yield) as colorless viscous oil. m/z (ESI): 445.3 $(M+H)^+$.

Step 5. tert-Butyl (2R)-2-((1R)-2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)morpholine-4-carboxylate. To a 40-mL vial was charged with 4-bromo-6-chloro-5-iodo-1-(tetrahydro-2H-pyran-2-yl)-1H-indazole (2.33 g, 5.28 mmol, Pharmablock Inc.), sodium bicarbonate (1.11 g, 13.2 mmol), TBACl (1.47 g, 5.28 mmol), palladium(II) acetate (59 mg, 0.26 mmol), tert-butyl (2R)-2-(1-((tert-butyldimethylsilyl)oxy)-2-((2-hydroxybut-3-en-1-yl)amino)-2-oxoethyl)morpholine-4-carboxylate (2.35 g, 5.28 mmol) and N,N-dimethylformamide (12 mL). The reaction mixture was heated at 65° C. for 24 h while open to the air. After cooling to rt, the mixture was diluted with water and extracted with ethyl acetate. The organic layer was washed with water, and then brine, dried over sodium sulfate, filtered, and concentrated. The crude material was purified by column chromatography on silica gel, eluting with a gradient of 0-80% EtOAc/heptane, to provide the less polar diastereomer tert-butyl (2R)-2-((1R)-2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)morpholine-4-carboxylate (1.17 g, 1.54 mmol, 29% yield) as white foam. m/z (ESI): 778.9, 780.9 $(M+Na)^+$.

Also isolated is the more polar diastereomer tert-butyl (2R)-2-((1S)-2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)morpholine-4-carboxylate (0.93 g, 1.23 mmol, 23% yield) as white foam. m/z (ESI): 778.9, 781.0 $(M+Na)^+$.

Step 6. tert-Butyl (2R)-2-((1R)-(5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)morpholine-4-carboxylate. In a 40-mL vial was added tert-butyl (2R)-2-((1S)-2-((4-(4-bromo-6-chloro-1-(tetrahydro-2H-pyran-2-yl)-1H-indazol-5-yl)-2-oxobutyl)amino)-1-((tert-butyldimethylsilyl)oxy)-2-oxoethyl)morpholine-4-carboxylate (1.17 g, 1.54 mmol) and Burgess reagent (1.47 g, 6.17 mmol) in 2-methyltetrahydrofuran (12 mL). The reaction mixture was purged with $N_2$, then heated at 75° C. for 3 h. After cooling to rt, the mixture was quenched with water and extracted with EtOAc. The combined organic layers were dried over sodium sulfate, filtered, and concentrated. The residue was purified by column chromatography on silica gel, eluting with a gradient of 0-50% EtOAc/heptane, to provide tert-butyl (2R)-2-((1R)-(5-(2-(4-bromo-6-chloro-1-(tetrahydro-2H-pyran-2-yl)-1H-indazol-5-yl)ethyl)oxazol-2-yl)((tert-butyldimethylsilyl)oxy)methyl)morpholine-4-carboxylate (0.80 g, 1.08 mmol, 70% yield) as white foam. m/z (ESI): 738.9, 740.9 $(M+H)^+$.

Intermediate FP: tert-Butyl 2-((tert-butyldimethylsilyl)oxy)-2-(5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)-6-azaspiro[3.5]nonane-6-carboxylate

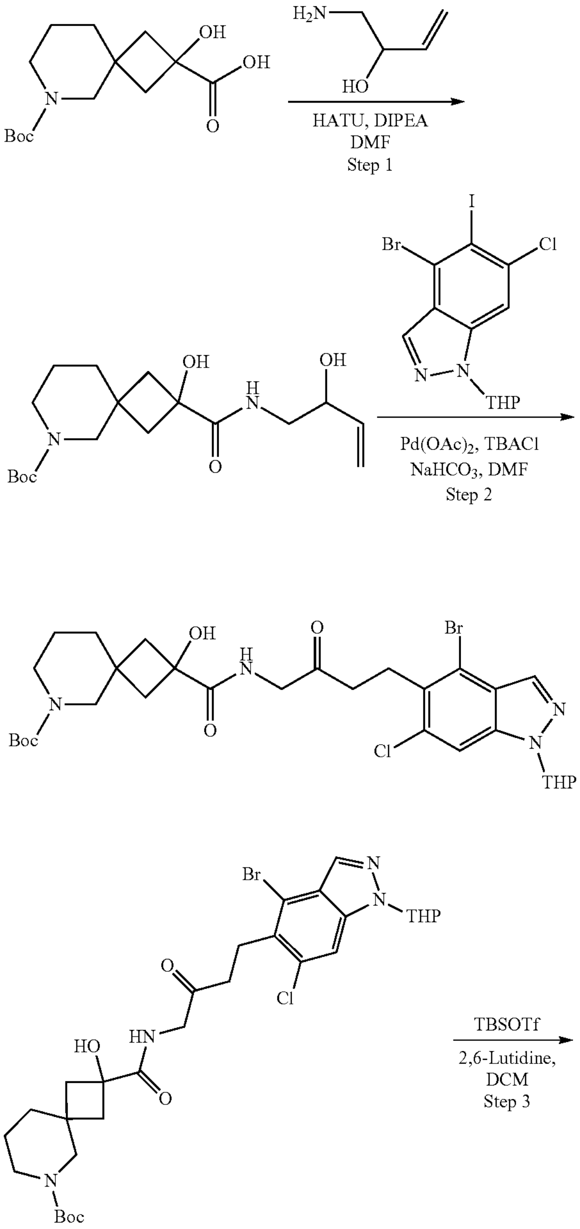

-continued

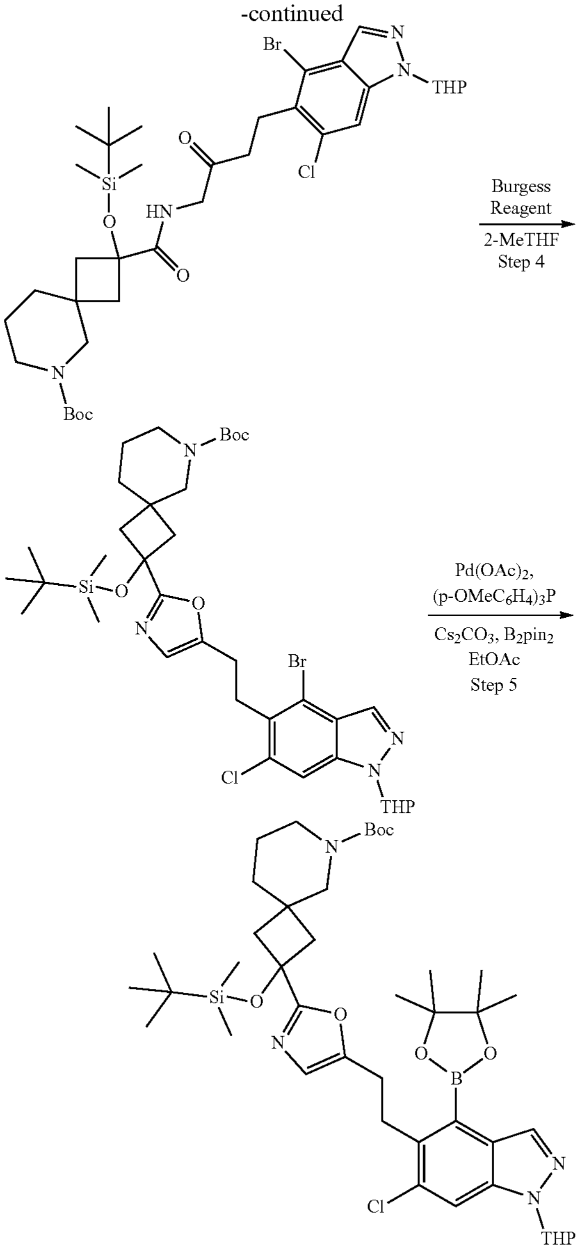

Intermediate FP

Step 1. tert-Butyl 2-hydroxy-2-((2-hydroxybut-3-en-1-yl)carbamoyl)-6-azaspiro[3.5]nonane-6-carboxylate. To a 20 mL vial was charged with 6-[(tert-butoxy)carbonyl]-2-hydroxy-6-azaspiro[3.5]nonane-2-carboxylic acid, mixture of diastereomers (1.50 g, 5.26 mmol, Enamine), N,N-dimethylformamide (11 mL), HATU (2.20 g, 5.80 mmol), 1-amino-3-buten-2-ol (0.48 mL, 5.5 mmol) and 1,1-dimethyltriethylamine (2.8 mL, 15.8 mmol) in this order. The mixture was stirred at rt for 16 h, then was quenched by the addition of saturated aqueous ammonium chloride and extracted with EtOAc. The organic layers were combined, dried over $Na_2SO_4$, filtered, and concentrated. The residue was purified by column chromatography on silica gel, eluting with a gradient of 25-100% 3:1 EtOAc/EtOH in heptane, to provide tert-butyl 2-hydroxy-2-((2-hydroxybut-3-en-1-yl)carbamoyl)-6-azaspiro[3.5]nonane-6-carboxylate (1.48 g, 4.17 mmol, 79% yield) as yellow viscous oil. $^1H$ NMR (400 MHz, CHLOROFORM-d) δ ppm 5.73-6.21 (m, 1H), 5.09-5.52 (m, 2H), 4.23-4.58 (m, 1H), 3.55-3.71 (m, 1H), 3.21-3.53 (m, 5H), 2.42-2.49 (m, 1H), 1.85-1.93 (m, 1H), 1.67-1.77 (m, 2H), 1.61-1.65 (m, 1H), 1.45-1.57 (m, 12H).

Step 2. tert-Butyl 2-((4-(4-bromo-6-chloro-1-(tetrahydro-2H-pyran-2-yl)-1H-indazol-5-yl)-2-oxobutyl)carbamoyl)-2-hydroxy-6-azaspiro[3.5]nonane-6-carboxylate. A 20 mL vial was charged with tert-butyl 2-hydroxy-2-((2-hydroxybut-3-en-1-yl)carbamoyl)-6-azaspiro[3.5]nonane-6-carboxylate (1.48 g, 4.17 mmol), 4-bromo-6-chloro-5-iodo-1-(tetrahydro-2H-pyran-2-yl)-1H-indazole (2.21 g, 5.00 mmol, Pharmablock, Inc.), sodium bicarbonate (0.88 g, 10.4 mmol), tetrabutylammonium chloride (1.2 mL, 4.2 mmol), and N,N-dimethylformamide (8.5 mL). The solution was degased for 3 min and then placed on a hot plate at 65° C., and palladium(II) acetate (47 mg, 0.21 mmol) was added. The reaction was heated at 65° C. for 17 h. After cooling to rt, the reaction was diluted with ethyl acetate and saturated aqueous ammonium chloride. The aqueous phase was extracted with ethyl acetate and the combined organic layers were dried over sodium sulfate, filtered, and concentrated The residue was purified by column chromatography on silica gel, eluting with a gradient of 0-100% ethyl acetate in heptane, to give tert-butyl 2-((4-(4-bromo-6-chloro-1-(tetrahydro-2H-pyran-2-yl)-1H-indazol-5-yl)-2-oxobutyl)carbamoyl)-2-hydroxy-6-azaspiro[3.5]nonane-6-carboxylate (1.19 g, 1.78 mmol, 43% yield). m/z (ESI): 688.2 $(M+Na)^+$.

Step 3. tert-Butyl 2-((4-(4-bromo-6-chloro-1-(tetrahydro-2H-pyran-2-yl)-1H-indazol-5-yl)-2-oxobutyl)carbamoyl)-2-((tert-butyldimethylsilyl)oxy)-6-azaspiro[3.5]nonane-6-carboxylate. In a 40 mL vial was charged with tert-butyl 2-((4-(4-bromo-6-chloro-1-(tetrahydro-2H-pyran-2-yl)-1H-indazol-5-yl)-2-oxobutyl)carbamoyl)-2-hydroxy-6-azaspiro[3.5]nonane-6-carboxylate (1.19 g, 1.78 mmol) in dichloromethane (9 mL) and 2,6-lutidine (0.42 mL, 3.6 mmol). The mixture was cooled to 0° C. and tert-butyldimethylsilyl trifluoromethanesulfonate (0.61 mL, 2.7 mmol) was added. The reaction mixture was allowed to warm to rt with stirring for 2 h. The mixture was quenched with saturated $NaHCO_3$ solution and extracted with DCM. The combined organic layers were dried over $Na_2SO_4$, filtered, and concentrated. The crude product was purified by column chromatography on silica gel, eluting with a gradient of 0-100% ethyl acetate in heptane, to provide tert-butyl 2-((4-(4-bromo-6-chloro-1-(tetrahydro-2H-pyran-2-yl)-1H-indazol-5-yl)-2-oxobutyl)carbamoyl)-2-((tert-butyldimethylsilyl)oxy)-6-azaspiro[3.5]nonane-6-carboxylate (0.934 g, 1.19 mmol, 67% yield) as yellow oil. m/z (ESI): 682.9 $(M+H)^+$.

Step 4. tert-Butyl 2-(5-(2-(4-bromo-6-chloro-1-(tetrahydro-2H-pyran-2-yl)-1H-indazol-5-yl)ethyl)oxazol-2-yl)-2-((tert-butyldimethylsilyl)oxy)-6-azaspiro[3.5]nonane-6-carboxylate. In a 40-mL vial was added tert-butyl 2-((4-(4-bromo-6-chloro-1-(tetrahydro-2H-pyran-2-yl)-1H-indazol-5-yl)-2-oxobutyl)carbamoyl)-2-((tert-butyldimethylsilyl)oxy)-6-azaspiro[3.5]nonane-6-carboxylate (0.934 g, 1.19 mmol) and Burgess reagent (1.14 g, 4.78 mmol) in 2-methyltetrahydrofuran (10 mL). The mixture was purged with $N_2$, then heated at 75° C. for 2 h. After cooling to rt, the mixture was quenched with water and extracted with EtOAc. The combined organic layers were dried over sodium sulfate, filtrated, and concentrated. The residue was purified by column chromatography on silica gel, eluting with a gradient of 0-100% ethyl acetate in heptane, to provide tert-butyl 2-(5-(2-(4-bromo-6-chloro-1-(tetrahydro-2H-pyran-2-yl)-1H-indazol-5-yl)ethyl)oxazol-2-yl)-2-((tert-butyldimethylsilyl)oxy)-6-azaspiro[3.5]nonane-6-carboxylate (0.70 g, 0.91 mmol, 76% yield) as yellow foam. m/z (ESI): 764.9 $(M+H)^+$.

Step 5. tert-Butyl 2-((tert-butyldimethylsilyl)oxy)-2-(5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)-6-azaspiro[3.5]nonane-6-carboxylate. A 40-mL vial was charged with tris(4-methoxyphenyl)phosphine (39 mg, 0.11 mmol), palladium acetate (20 mg, 0.091 mmol), 4,4,4',4',5,5,5',5'-octamethyl-2,2'-bi(1,3,2-dioxaborolane) (0.35 g, 1.37 mmol), cesium carbonate (0.59 g, 1.80 mmol), tert-butyl 2-(5-(2-(4-bromo-6-chloro-1-(tetrahydro-2H-pyran-2-yl)-1H-indazol-5-yl)ethyl)oxazol-2-yl)-2-((tert-butyldimethylsilyl)oxy)-6-azaspiro[3.5]nonane-6-carboxylate (0.70 g, 0.91 mmol,) and ethyl acetate (3.5 mL). The contents were sparged with nitrogen for 3 min and then heated to 80° C. for 1 h. After cooling to rt, the reaction mixture was filtered over celite, and the filtrate was concentrated. The residue was purified by column chromatography on silica gel, eluting with a gradient of 0-100% ethyl acetate in heptane, to provide tert-butyl 2-((tert-butyldimethylsilyl)oxy)-2-(5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)-6-azaspiro[3.5]nonane-6-carboxylate (0.35 g, 0.43 mmol, 47% yield) as white foam. m/z (ESI): 811.4 $(M+H)^+$.

Intermediate FQ: tert-Butyl 2-(2-(2-(6-chloro-1-(tetrahydro-2H-pyran-2-yl)-4-(4,4,5,5-tetramethyl-1,3,2-dioxaborolan-2-yl)-1H-indazol-5-yl)ethoxy)ethyl)-2-hydroxy-6-azaspiro[3,5]nonane-6-carboxylate

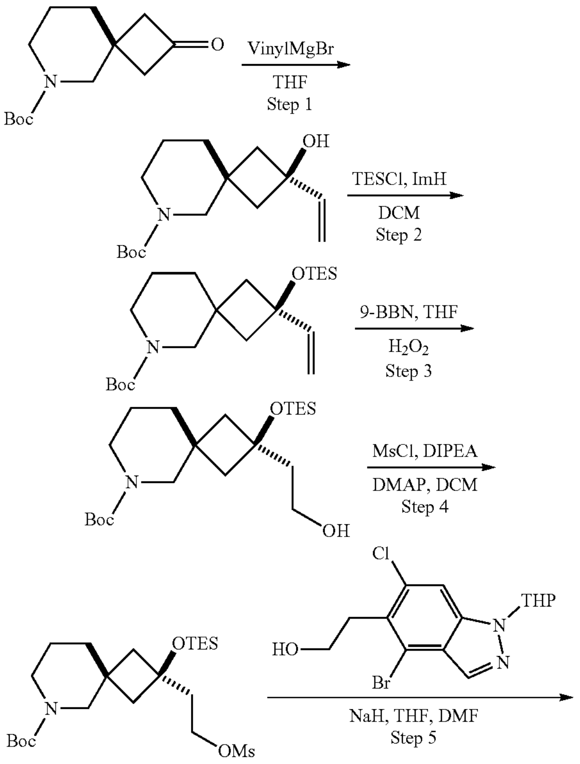

-continued

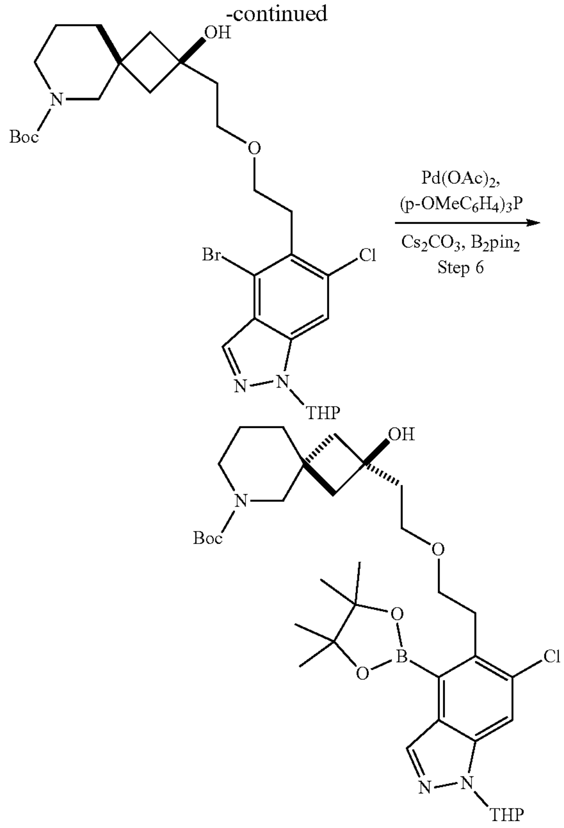

Intermediate FQ

Step 1. tert-Butyl (2S,4R)-2-hydroxy-2-vinyl-6-azaspiro[3.5]nonane-6-carboxylate. A 250 mL round-bottom flask was charged with tert-butyl 2-oxo-6-azaspiro[3.5]nonane-6-carboxylate (18.0 g, 75.0 mmol, Pharmablock Inc.) in tetrahydrofuran (350 mL) and cooled to 0° C. Vinylmagnesium bromide (0.7 M solution in THF, 114 mL, 80 mmol) was added and the reaction was stirred at rt for 1 h. The reaction was quenched with saturated aqueous ammonium chloride solution and extracted with EtOAc. The combined organic layers were dried over sodium sulfate, filtered, and concentrated. The crude was purified by column chromatography on silica gel, eluting with a gradient of 0-80% ethyl acetate in heptane, to yield tert-butyl (2R,4S)-2-hydroxy-2-vinyl-6-azaspiro[3.5]nonane-6-carboxylate (4.82 g, 18.0 mmol, 24% yield) as colorless oil, $^1H$ NMR (400 MHz, CHLOROFORM-d) δ ppm 5.99-6.20 (m, 1H), 4.94-5.34 (m, 2H), 3.47-3.58 (m, 2H), 3.29-3.40 (m, 2H), 2.01 (s, 4H), 1.55-1.57 (m, 1H), 1.45-1.52 (m, 13H) and tert-butyl (2S,4R)-2-hydroxy-2-vinyl-6-azaspiro[3.5]nonane-6-carboxylate (5.25 g, 19.7 mmol, 26% yield) as yellow oil, $^1H$ NMR (400 MHz, CHLOROFORM-d) δ ppm 6.14 (dd, J=17.2, 10.6 Hz, 1H), 5.07-5.39 (m, 2H), 3.20-3.39 (m, 4H), 2.14-2.32 (m, 2H), 1.84-1.94 (m, 2H), 1.65-1.80 (m, 3H), 1.45-1.52 (m, 11H). Diastereoisomers have been determined by NOESY NMR spectroscopy.

Step 2. tert-Butyl (2S,4R)-2-((triethylsilyl)oxy)-2-vinyl-6-azaspiro[3.5]nonane-6-carboxylate. In a 100 mL round-bottom flask was charged with tert-butyl (2s,4r)-2-hydroxy-2-vinyl-6-azaspiro[3.5]nonane-6-carboxylate (5.25 g, 19.7 mmol), imidazole (3.48 g, 51.1 mmol) in dichloromethane (100 mL). The mixture was cooled to 0° C. and chlorotriethylsilane (4.3 mL, 25.5 mmol) was added. The mixture was allowed to warm to rt with stirring for 30 minutes. Water was added and the aqueous phase was extracted with EtOAc. The combined organic layers were dried over sodium sulfate, filtered, and concentrated. The crude was purified by column chromatography on silica gel, eluting with a gradient of (0-50% ethyl acetate 0.1% $Et_3N$ as an additive) in heptane, to yield tert-butyl (2S,4R)-2-((triethylsilyl)oxy)-2-vinyl-6-azaspiro[3.5]nonane-6-carboxylate (7.40 g, 19.4 mmol, 99% yield) as colorless oil. $^1H$ NMR (400 MHz, CHLOROFORM-d) δ ppm 5.97-6.27 (m, 1H), 5.21-5.46 (m, 1H), 5.04-5.21 (m, 1H), 3.20-3.36 (m, 4H), 2.15-2.42 (m, 2H), 1.83-2.04 (m, 2H), 1.60-1.75 (m, 2H), 1.46-1.57 (m, 11H), 0.94-1.05 (m, 8H), 0.57-0.65 (m, 6H).

Step 3. tert-Butyl (2S,4R)-2-(2-hydroxyethyl)-2-((triethylsilyl)oxy)-6-azaspiro[3.5]nonane-6-carboxylate. In a 150 mL flask under nitrogen was charged with tert-butyl (2s,4r)-2-((triethylsilyl)oxy)-2-vinyl-6-azaspiro[3.5]nonane-6-carboxylate (7.40 g, 19.4 mmol) in tetrahydrofuran (100 mL). The content was cooled to 0° C. and 9-borabicyclo[3.3.1]nonane (80 mL, 40 mmol) was added slowly. The reaction mixture was allowed to warm to rt with stirring for 5 h. The mixture was cooled again to 0° C. and 3 N NaOH (42 mL, 14 mmol) and hydrogen peroxide (12.9 mL, 126 mmol) was added. The mixture was allowed to warm to rt with stirring for 3 h. The organic layer was separated, and the aqueous layer was extracted with EtOAc. The combined organic layers were dried over sodium sulfate, filtered, and concentrated. The crude was purified by column chromatography on silica gel, eluting with a gradient of 0-100% ethyl acetate in heptane, to give tert-butyl (2S,4R)-2-(2-hydroxyethyl)-2-((triethylsilyl)oxy)-6-azaspiro[3.5]nonane-6-carboxylate (6.23 g, 15.6 mmol, 80% yield) as colorless oil. $^1H$ NMR (400 MHz, CHLOROFORM-d) δ ppm 3.77-3.97 (m, 2H), 3.20-3.40 (m, 4H), 2.53-2.70 (m, 1H), 2.10-2.22 (m, 2H), 1.85-2.00 (m, 4H), 1.61-1.68 (m, 2H), 1.43-1.53 (m, 11H), 0.92-1.02 (m, 9H), 0.59-0.71 (m, 6H).

Step 4. tert-Butyl (2S,4R)-2-(2-((methylsulfonyl)oxy)ethyl)-2-((triethylsilyl)oxy)-5-azaspiro[3.5]nonane-5-carboxylate. To a 100-mL round bottom flask was charged with tert-butyl (2S,4R)-2-(2-hydroxyethyl)-2-((triethylsilyl)oxy)-6-azaspiro[3.5]nonane-6-carboxylate (6.23 g, 15.6 mmol) and triethylamine (6.5 mL, 47 mmol) in dichloromethane (80 mL). Methanesulfonyl chloride (2.4 mL, 31 mmol) and N,N-dimethylpyridin-4-amine (0.38 g, 3.11 mmol) was added sequentially. After 2 h of stirring at rt, the mixture was quenched with water and extracted with $CH_2Cl_2$. The combined organic layers were dried over $Na_2SO_4$, filtered, and concentrated. The crude material was purified by column chromatography on silica gel, eluting with a gradient of 0-100% ethyl acetate in heptane, to provide tert-butyl (2s,4r)-2-(2-((methylsulfonyl)oxy)ethyl)-2-((triethylsilyl)oxy)-5-azaspiro[3.5]nonane-5-carboxylate (6.66 g, 13.9 mmol, 90% yield) as yellow oil. $^1H$ NMR (400 MHz, CHLOROFORM-d) δ ppm 4.47-4.24 (m, 2H), 3.40-3.26 (m, 4H), 3.06-2.96 (m, 3H), 2.20-2.07 (m, 4H), 1.94-1.86 (m, 2H), 1.67-1.60 (m, 2H), 1.53-1.44 (m, 11H), 1.02-0.94 (m, 9H), 0.72-0.52 (m, 6H).

Step 5. tert-Butyl (2S,4R)-2-(2-(2-(4-bromo-6-chloro-1-(tetrahydro-2H-pyran-2-yl)-1H-indazol-5-yl)ethoxy)ethyl)-2-hydroxy-6-azaspiro[3.5]nonane-6-carboxylate. A 100 mL round-bottom flask was charged with 2-(4-bromo-6-chloro-1-(tetrahydro-2H-pyran-2-yl)-1H-indazol-5-yl)ethan-1-ol (5.08 g, 14.1 mmol, Step 1 of Intermediate XX), tetrahydrofuran (20 mL), and N,N-dimethylformamide (7 mL). Sodium hydride (60 wt % in mineral oil, 0.28 g, 7.08 mmol) was added, and the reaction mixture was stirred at rt for 30 min. tert-Butyl (2S,4R)-2-(2-((methylsulfonyl)oxy)ethyl)-2-((triethylsilyl)oxy)-5-azaspiro[3.5]nonane-5-carboxylate (1.69 g, 3.54 mmol) in THF (5 mL) was added and the reaction mixture was warmed to 50° C. for 72 h. The mixture was quenched carefully with water and extracted with EtOAc. The combined organic layer was dried over sodium sulfate, filtered, and concentrated. The crude material was purified by column chromatography on silica gel, eluting with a gradient of 0-100% ethyl acetate in heptane, to give tert-butyl (2S,4R)-2-(2-(2-(4-bromo-6-chloro-1-(tetrahydro-2H-pyran-2-yl)-1H-indazol-5-yl)ethoxy)ethyl)-2-hydroxy-6-azaspiro[3.5]nonane-6-carboxylate (0.68 g, 1.08 mmol, 31% yield) as yellow oil. m/z (ESI): 648.0 $(M+Na)^+$. $^1H$ NMR (400 MHz, CHLOROFORM-d) δ ppm 7.92-8.09 (m, 1H), 7.65-7.76 (m, 1H), 5.58-5.74 (m, 1H), 3.98-4.07 (m, 1H), 3.64-3.80 (m, 5H), 3.27-3.44 (m, 4H), 3.21-3.26 (m, 2H), 2.42-2.55 (m, 1H), 2.08-2.23 (m, 2H), 1.90-2.04 (m, 4H), 1.65-1.85 (m, 7H), 1.42-1.53 (m, 11H).

Step 6. tert-Butyl 2-(2-(2-(6-chloro-1-(tetrahydro-2H-pyran-2-yl)-4-(4,4,5,5-tetramethyl-1,3,2-dioxaborolan-2-yl)-1H-indazol-5-yl)ethoxy)ethyl)-2-hydroxy-6-azaspiro[3.5]nonane-6-carboxylate. A 40-mL vial was charged with tris(4-methoxyphenyl)phosphine (46 mg, 0.13 mmol), palladium acetate (24 mg, 0.11 mmol), bis(pinacolato)diboron (0.41 g, 1.62 mmol), cesium carbonate (0.71 g, 2.16 mmol), tert-butyl (2S,4R)-2-(2-(2-(4-bromo-6-chloro-1-(tetrahydro-2H-pyran-2-yl)-1H-indazol-5-yl)ethoxy)ethyl)-2-hydroxy-6-azaspiro[3.5]nonane-6-carboxylate (0.68 g, 1.08 mmol) and ethyl acetate (4 mL). The reaction mixture was then sparged with $N_2$ for 3 min and heated to 80° C. for 1 h. After cooling to rt, the mixture was filtered through a pad of celite and and the filtrate was purified by column chromatography on silica gel, eluting with a gradient of 0-100% ethyl acetate in heptane, to provide tert-butyl 2-(2-(2-(6-chloro-1-(tetrahydro-2H-pyran-2-yl)-4-(4,4,5,5-tetramethyl-1,3,2-dioxaborolan-2-yl)-1H-indazol-5-yl)ethoxy)ethyl)-2-hydroxy-6-azaspiro[3.5]nonane-6-carboxylate (0.49 g, 0.722 mmol, 67% yield, purity: 63%) as white foam. m/z (ESI): 674.4 $(M+H)^+$.

Intermediate FR: tert-Butyl 1-(5-(6-chloro-1-(tetrahydro-2H-pyran-2-yl)-4-(4,4,5,5-tetramethyl-1,3,2-dioxaborolan-2-yl)-1H-indazol-5-yl)pentanoyl)-3,3-difluorooctahydro-6H-pyrrolo[2,3-c]pyridine-6-carboxylate

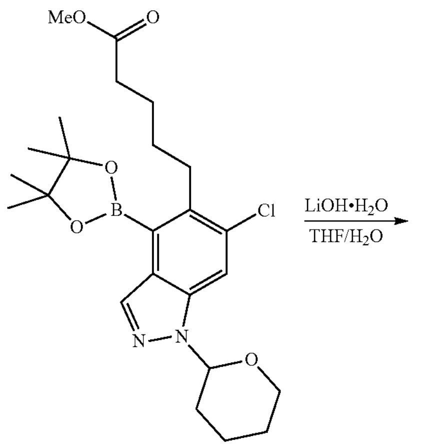

-continued

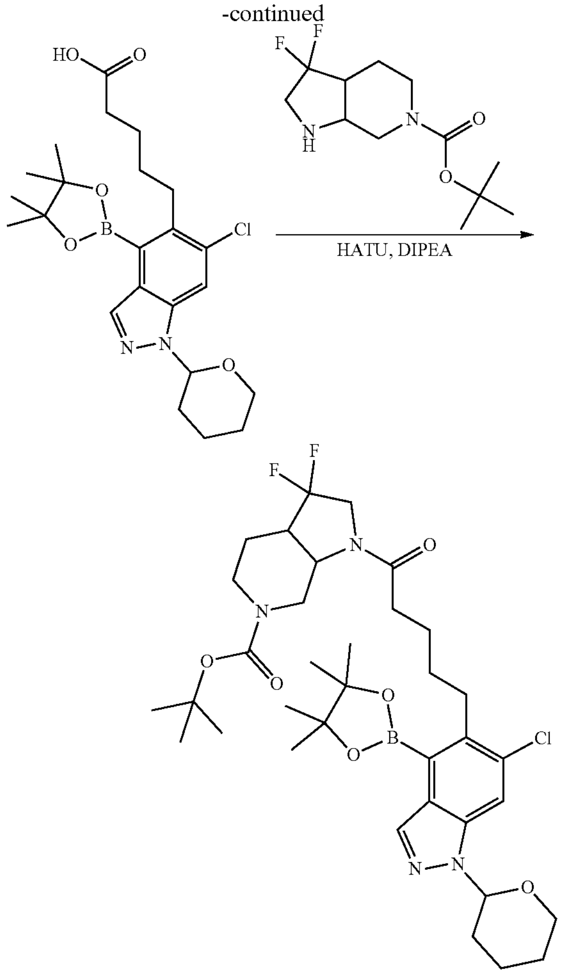

Intermediate FR

Step 1. 5-(6-Chloro-1-(tetrahydro-2H-pyran-2-yl)-4-(4,4,5,5-tetramethyl-1,3,2-dioxaborolan-2-yl)-1H-indazol-5-yl)pentanoic acid. To a 4 mL vial was added methyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate (0.53 g, 1.12 mmol, Intermediate LL) in tetrahydrofuran (1.9 mL) and water (1.9 mL). Lithium hydroxide, monohydrate (94 mg, 2.2 mmol) was added, and the reaction mixture was stirred at rt for 16 h. The reaction mixture was neutralized to pH 7 with 1 N HCl. The aqueous phase was extracted with EtOAc and the combined organic phases were washed with brine, dried over anhydrous sodium sulfate, filtered and concentrated under reduced pressure to provide 5-(6-chloro-1-(tetrahydro-2H-pyran-2-yl)-4-(4,4,5,5-tetramethyl-1,3,2-dioxaborolan-2-yl)-1H-indazol-5-yl)pentanoic acid (0.29 g, 0.64 mmol, 57% yield) as white foam. m/z (ESI): 463.0 $(M+H)^+$.

Step 2. tert-Butyl 1-(5-(6-chloro-1-(tetrahydro-2H-pyran-2-yl)-4-(4,4,5,5-tetramethyl-1,3,2-dioxaborolan-2-yl)-1H-indazol-5-yl)pentanoyl)-3,3-difluorooctahydro-6H-pyrrolo[2,3-c]pyridine-6-carboxylate. A vial was charged with 5-(6-chloro-1-(tetrahydro-2H-pyran-2-yl)-4-(4,4,5,5-tetramethyl-1,3,2-dioxaborolan-2-yl)-1H-indazol-5-yl)pentanoic acid (0.29 g, 0.64 mmol), tert-butyl 3,3-difluoro-octahydro-1H-pyrrolo[2,3-c]pyridine-6-carboxylate (0.17 g, 0.64 mmol, Synnovator, Inc.) and N,N-dimethylformamide (2.1 mL). HATU (0.27 g, 0.70 mmol) was added and the reaction mixture was stirred at rt for 10 min. Then 1,1'-dimethyltriethylamine (0.56 mL, 3.2 mmol) was added dropwise. The reaction was stirred at rt for 1 h, then was diluted with water and extracted with EtOAc. The combined organic phases were washed with aqueous LiCl, brine, dried ($Na_2SO_4$), filtered and concentrated. The crude material was purified by column chromatography on silica gel, eluting with a gradient of 0-60% EtOAc in hexane, to provide tert-butyl 1-(5-(6-chloro-1-(tetrahydro-2H-pyran-2-yl)-4-(4,4,5,5-tetramethyl-1,3,2-dioxaborolan-2-yl)-1H-indazol-5-yl)pentanoyl)-3,3-difluorooctahydro-6H-pyrrolo[2,3-c]pyridine-6-carboxylate (0.32 g, 0.45 mmol, 71% yield) as clear oil. m/z (ESI): 707.0 $(M+H)^+$.

Intermediate FS: tert-Butyl (3R)-3-(1-((tert-butyldimethylsilyl)oxy)-3-(2-(6-chloro-1-(tetrahydro-2H-pyran-2-yl)-4-(4,4,5,5-tetramethyl-1,3,2-dioxaborolan-2-yl)-1H-indazol-5-yl)ethoxy)propyl)piperidine-1-carboxylate

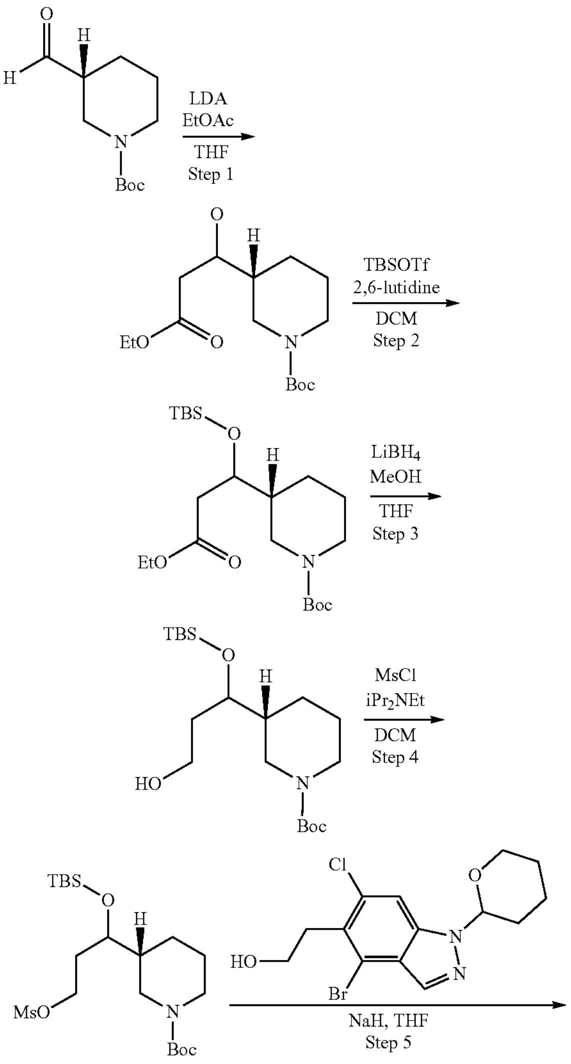

-continued

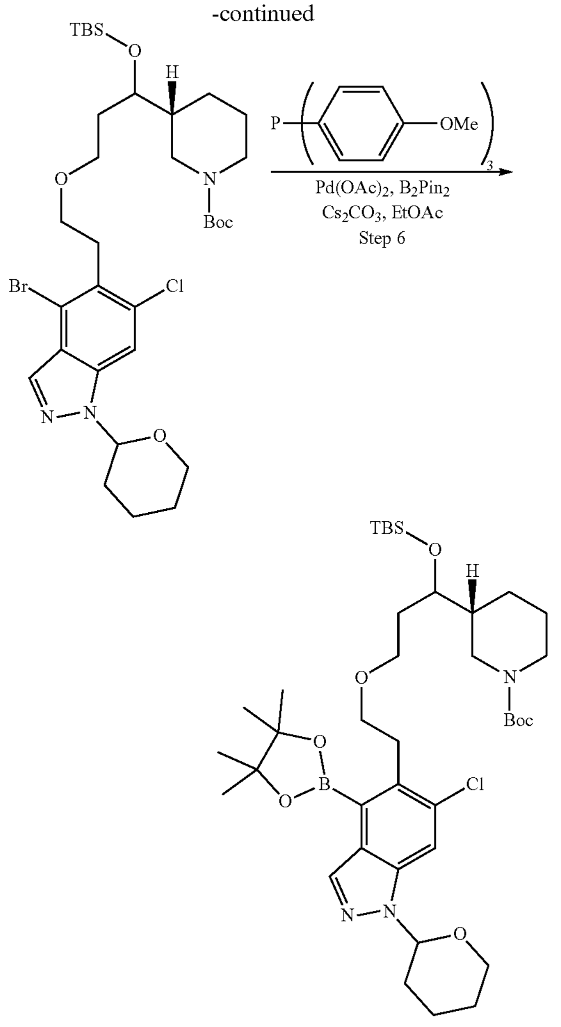

Intermediate FS

Step 1. tert-Butyl (3R)-3-(3-ethoxy-1-hydroxy-3-oxopropyl)piperidine-1-carboxylate. Ethyl acetate (2.0 mL, 20.6 mmol) was added dropwise to a solution of LDA (1.0 M in THF/hexanes, 18.8 mL, 18.8 mmo) in THF (26 mL) cooled to −78° C. The mixture was stirred for 30 minutes. A solution of (R)-tert-butyl 3-formylpiperidine-1-carboxylate (2.0 g, 9.38 mmol) in THF (5 mL) was added dropwise and stirred at −78° C. for 30 min. The reaction was slowly warmed to rt and the mixture was quenched by careful addition of saturated aqueous $NH_4Cl$ and extracted with EtOAc. The organic layer was dried over sodium sulfate, and concentrated and the crude material was purified by column chromatography on silica gel, eluting with a gradient of 0-100% EtOAc in heptanes, to provide tert-butyl (3R)-3-(3-ethoxy-1-hydroxy-3-oxopropyl)piperidine-1-carboxylate (2.40 g, 8.00 mmol, 85% yield) as light-yellow oil. m/z (ESI): 202.2 $(M+H-Boc)^+$.

Step 2. tert-Butyl (3R)-3-(1-((tert-butyldimethylsilyl)oxy)-3-ethoxy-3-oxopropyl)piperidine-1-carboxylate. tert-Butyldimethylsilyl trifluoromethanesulfonate (2.3 mL, 8.8 mmol) was added to a solution of tert-butyl (3R)-3-(3-ethoxy-1-hydroxy-3-oxopropyl)piperidine-1-carboxylate (2.4 g, 8.0 mmol) and 2,6-lutidine (1.1 mL, 9.6 mmol) in DCM (26 mL) cooled to 0° C. The reaction mixture was stirred for 1 h, then was diluted with saturated $NH_4Cl$ and extracted with DCM. The organic extract was washed with saturated NaCl, dried over $Na_2SO_4$, filtered, and concentrated in vacuo. The crude material was purified by chromatography on silica gel, eluting with a gradient of 0-75% EtOAc in heptane, to provide tert-butyl (3R)-3-(1-((tert-butyldimethylsilyl)oxy)-3-ethoxy-3-oxopropyl)piperidine-1-carboxylate (2.29 g, 5.51 mmol, 69% yield) as colorless oil. m/z (ESI): 416.3 $(M+H)^+$.

Step 3. tert-Butyl (3R)-3-(1-((tert-butyldimethylsilyl)oxy)-3-hydroxypropyl)piperidine-1-carboxylate. Lithium borohydride solution (2.0 M in THF, 7.7 mL, 15.4 mmol) was added slowly to a solution of tert-butyl (3R)-3-(1-((tert-butyldimethylsilyl)oxy)-3-ethoxy-3-oxopropyl)piperidine-1-carboxylate (3.20 g, 7.70 mmol) in THF (51 mL) cooled to 0° C. Methanol (3.1 mL, 77 mmol) was added and the mixture was allowed to warm to rt with stirring for 5 min, then heated to 50° C. for 2 h. An extra 1.0 equiv. of 2 M $LiBH_4$ in THF was added and the reaction was stirred for 1 h. The reaction was quenched by the careful addition of water and extracted with EtOAc. The organic extract was washed with saturated NaCl, dried over $Na_2SO_4$, filtered, and concentrated in vacuo. The crude material was purified by chromatography on silica gel, eluting with a gradient of 0-100% EtOAc in heptanes, to give tert-butyl (3R)-3-(1-((tert-butyldimethylsilyl)oxy)-3-hydroxypropyl)piperidine-1-carboxylate (1.20 g, 3.20 mmol, 42% yield) as colorless oil. $^1H$ NMR (400 MHz, CHLOROFORM-d) δ ppm 3.95-4.30 (m, 2H), 3.62-3.91 (m, 3H), 2.29-2.74 (m, 2H), 1.88-2.05 (m, 1H), 1.60-1.88 (m, 5H), 1.48 (s, 10H), 1.31-1.38 (m, 2H), 0.94 (s, 8H), 0.08-0.15 (m, 6H). m/z (ESI): 374.3 $(M+H)^+$.

Step 4. tert-Butyl (3R)-3-(1-((tert-butyldimethylsilyl)oxy)-3-((methylsulfonyl)oxy)propyl)piperidine-1-carboxylate. To a 40-mL vial was added tert-butyl (3R)-3-(1-((tert-butyldimethylsilyl)oxy)-3-hydroxypropyl)piperidine-1-carboxylate (0.21 g, 0.56 mmol) and N-ethyl-N-isopropylpropan-2-amine (0.13 mL, 0.73 mmol) in DCM (2 mL). Then, methanesulfonyl chloride (50 μL, 0.62 mmol) was added at 0° C. and the resulting mixture was allowed to warm to rt with stirring for 30 min. The reaction mixture was diluted with water and extracted with DCM. The organic layer was dried over $Na_2SO_4$, filtered, and concentrated. The crude residue was purified by column chromatography on silica gel, eluting with 0-100% EtOAc in heptane, to afford tert-butyl (3R)-3-(1-((tert-butyldimethylsilyl)oxy)-3-((methylsulfonyl)oxy)propyl)piperidine-1-carboxylate (0.24 g, 0.53 mmol, 95% yield) as a light-yellow oil. m/z (ESI): 396.2 $(M+H-tBu)^+$.

Step 5. tert-Butyl (3R)-3-(3-(2-(4-bromo-6-chloro-1-(tetrahydro-2H-pyran-2-yl)-1H-indazol-5-yl)ethoxy)-1-((tert-butyldimethylsilyl)oxy)propyl)piperidine-1-carboxylate. A 40-mL vial was charged with 2-(4-bromo-6-chloro-1-(tetrahydro-2H-pyran-2-yl)-1H-indazol-5-yl)ethan-1-ol (0.33 g, 0.90 mmol) and THF (1.5 mL) then cooled to 0° C. Sodium hydride (38 mg, 60% in mineral oil, 0.95 mmol) was added then the reaction was allowed to warm to rt with stirring for 30 min. A solution of tert-butyl (3R)-3-(1-((tert-butyldimethylsilyl)oxy)-3-((methylsulfonyl)oxy)propyl)piperidine-1-carboxylate (0.23 g, 0.52 mmol) in THF (1.0 mL) was added and the reaction was stirred at 50° C. for 16 h. After cooling, the reaction was carefully quenched with MeOH and the crude material was purified by column chromatography on silica gel, eluting with a gradient of 0-100% EtOAc in heptane, to afford tert-butyl (3R)-3-(3-(2-(4-bromo-6-chloro-1-(tetrahydro-2H-pyran-2-yl)-1H-indazol-5-yl)ethoxy)-1-((tert-butyldimethylsilyl)oxy)propyl)piperidine- 1-carboxylate (0.25 g, 0.35 mmol, 68% yield) as colorless oil. m/z (ESI): 714.3 $(M+H)^+$.

Step 6. tert-Butyl (3R)-3-(1-((tert-butyldimethylsilyl)oxy)-3-(2-(6-chloro-1-(tetrahydro-2H-pyran-2-yl)-4-(4,4,5,5-tetramethyl-1,3,2-dioxaborolan-2-yl)-1H-indazol-5-yl)ethoxy)propyl)piperidine-1-carboxylate. A screw-cap vial was charged with tris(4-methoxyphenyl)phosphine (18 mg, 0.050 mmol), palladium acetate (5.0 mg, 0.023 mmol), 4,4,4',4',5,5,5',5'-octamethyl-2,2'-bi(1,3,2-dioxaborolane) (98 mg, 0.39 mmol), cesium carbonate (0.16 g, 0.48 mmol), tert-butyl (3R)-3-(3-(2-(4-bromo-6-chloro-1-(tetrahydro-2H-pyran-2-yl)-1H-indazol-5-yl)ethoxy)-1-((tert-butyldimethylsilyl)oxy)propyl)piperidine-1-carboxylate (0.23 g, 0.32 mmol) and ethyl acetate (2 mL), then sparged with $N_2$ and heated to 80° C. for 1 h. The crude reaction was filtered through celite and washed with EtOAc. The filtrate was concentrated and used in the next step without further purification. m/z (ESI): 762.4 $(M+H)^+$.

Intermediate FU: rac-2-((1R,2R)-2-(4-Bromo-6-chloro-1-(tetrahydro-2H-pyran-2-yl)-1H-indazol-5-yl)cyclopropyl)ethyl methanesulfonate

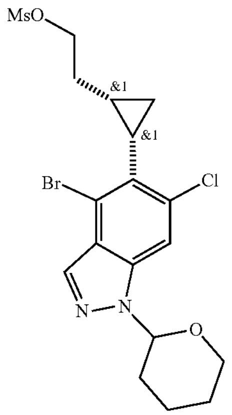 [SMILES: CS(=O)(=O)OCC[C@@H]1C[C@@H]1c1c(Cl)cc2c(cnn2C2CCCCO2)c1Br]

This compound was prepared in an analogous manner to Intermediate BT using rac-((1R,2S)-2-(4-bromo-6-chloro-1-(tetrahydro-2H-pyran-2-yl)-1H-indazol-5-yl)cyclopropyl)methanol (Example 46, Step 2) in Step 1. m/z (ESI): 476.8 $(M+H)^+$.

Intermediate FV: tert-Butyl (3R)-3-((4-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)methyl)piperidine-1-carboxylate

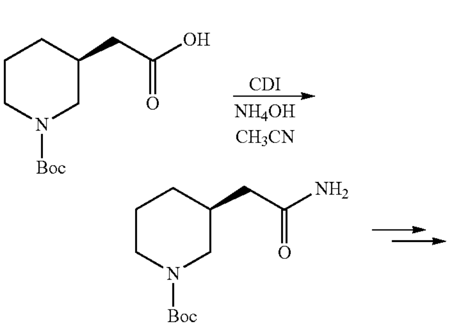

-continued

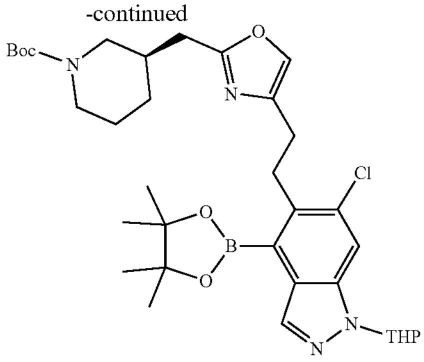

Intermediate FV

Step 1. tert-Butyl (R)-3-(2-amino-2-oxoethyl)piperidine-1-carboxylate. To a 100 mL round-bottom flask was added (S)-(1-Boc-piperidino)acetic acid (1.07 g, 4.39 mmol), CDI (1.42 g, 8.77 mmol) in acetonitrile (30 mL). The reaction mixture was stirred at rt for 16 h. Then ammonium hydroxide (16.7 mL, 132 mmol) was added dropwise. The reaction was stirred at rt for 3 h, diluted with EtOAc and saturated $NH_4Cl$. The aqueous layer was extracted with EtOAc, and the organic phase was washed with brine, dried over $Na_2SO_4$, filtered, and concentrated. The residue was purified by column chromatography on silica gel, eluting with a gradient of 0-100% 3:1 EtOAc/EtOH heptane, followed by reverse phase ISCO (10-100% water in MeCN with 0.1% TFA), then neutralized with $Na_2CO_3$ to provide tert-butyl (R)-3-(2-amino-2-oxoethyl)piperidine-1-carboxylate (0.86 g, 3.50 mmol, 81% yield) as colorless oil. MS: m/z (ESI): 243.25 $(M+H)^+$. $^1H$ NMR (METHANOL-$d_4$, 400 MHz) δ 3.8-4.0 (m, 2H), 2.8-2.9 (m, 1H), 2.5-2.7 (m, 1H), 2.12 (tt, 2H, J=7.1, 14.8 Hz), 1.8-1.9 (m, 2H), 1.6-1.7 (m, 1H), 1.45 (s, 11H).

Step 2&3. tert-Butyl (3R)-3-((4-(2-(6-chloro-1-(tetrahydro-2H-pyran-2-yl)-4-(4,4,5,5-tetramethyl-1,3,2-dioxaborolan-2-yl)-1H-indazol-5-yl)ethyl)oxazol-2-yl)methyl)piperidine-1-carboxylate. This compound was prepared in an analogous manner to Intermediate CF using tert-butyl (R)-3-(2-amino-2-oxoethyl)piperidine-1-carboxylate and 1-bromo-4-(4-bromo-6-chloro-1-(tetrahydro-2H-pyran-2-yl)-1H-indazol-5-yl)butan-2-one (Step 2 in Intermediate BZ) in Step 3. m/z (ESI): 655.2 $(M+H)^+$.

Intermediate FW: tert-Butyl 2-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)morpholine-4-carboxylate

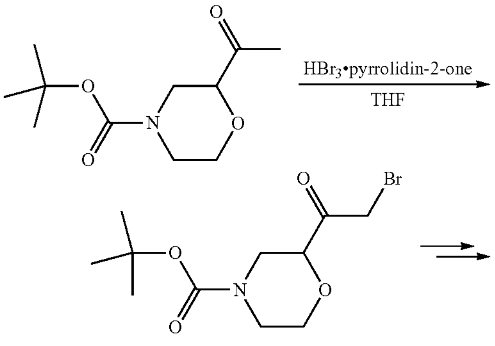

-continued

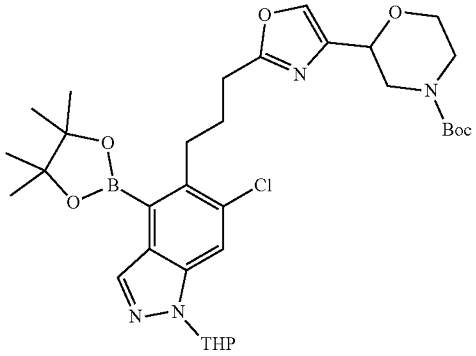

Intermediate FW

Step 1. tert-Butyl 2-(2-bromoacetyl)morpholine-4-carboxylate. To a 40-mL vial was charged with tert-butyl 2-acetylmorpholine-4-carboxylate (0.567 g, 2.47 mmol, Enamine), pyrrolidone hydrotribromide (1.23 g, 2.47 mmol, Combi-Blocks) in tetrahydrofuran (15 mL). This reaction mixture was stirred at rt, then was heated at 65° C. for 10 min. After cooling to rt, the reaction mixture was filtered and and the filtrate concentrated in vacuo. The crude was purified by silica gel chromatography on silica gel, eluting with a gradient of 0-50% ethyl acetate in heptane, to provide tert-butyl 2-(2-bromoacetyl)morpholine-4-carboxylate (0.48 g, 1.60 mmol, 63% yield) as colorless oil. m/z (ESI): 329.9/331.9 $(M+Na)^+$.

Steps 2&3. tert-Butyl 2-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)morpholine-4-carboxylate.

This compound was prepared in an analogous manner to Intermediate CF using tert-butyl 2-(2-bromoacetyl)morpholine-4-carboxylate in Step 3. m/z (ESI): 657.2 $(M+H)^+$.

Intermediate FX: tert-Butyl (3S)-3-((5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)-1,3,4-oxadiazol-2-yl)methyl)piperidine-1-carboxylate

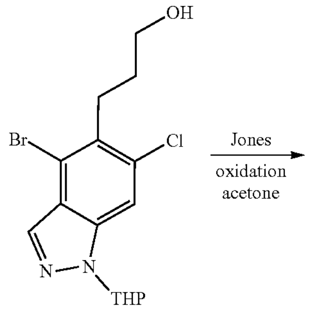

-continued

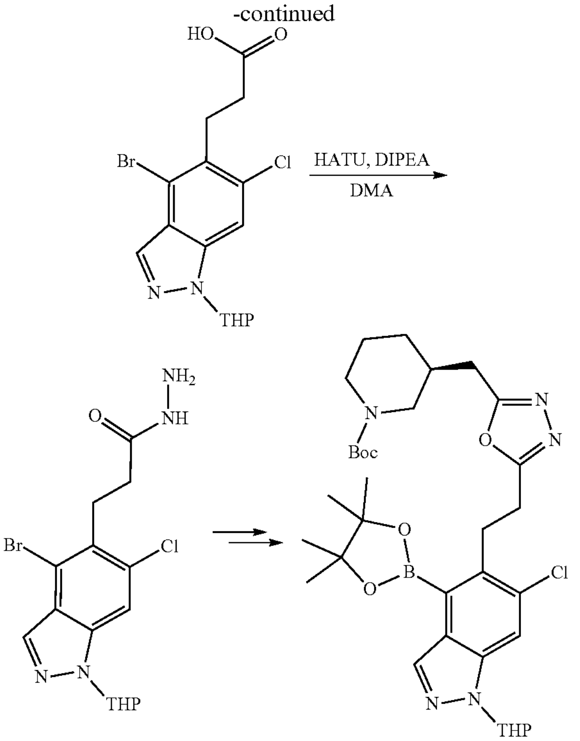

Intermediate FX

Step 1. 3-(4-Bromo-6-chloro-1-(tetrahydro-2H-pyran-2-yl)-1H-indazol-5-yl)propanoic acid. To a solution of 3-(4-bromo-6-chloro-1-(tetrahydro-2H-pyran-2-yl)-1H-indazol-5-yl)propan-1-ol (4.30 g, 11.5 mmol, Intermediate FFF, Step 2) at 0° C. in acetone (115 mL) was added chromium trioxide solution in sulfuric acid (7.0 mL, 15 mmol) dropwise. The reaction mixture was stirred at rt for 16 h. Solid sodium thiosulfate was added, and the solution was stirred for 10 min, filtered and the filtrate was concentrated in vacuo to provide 3-(4-bromo-6-chloro-1-(tetrahydro-2H-pyran-2-yl)-1H-indazol-5-yl)propanoic acid as off-white solid (4.40 g, 11.0 mmol, 99% yield). m/z (ESI): 387.0/389.0 $(M+H)^+$. $^1H$ NMR (DMSO-$d_6$, 400 MHz) δ ppm 12.1-12.5 (m, 1H), 8.0-8.1 (m, 1H), 8.02 (s, 1H), 5.88 (dd, 1H, J=2.4, 9.4 Hz), 3.8-3.9 (m, 1H), 3.7-3.8 (m, 1H), 3.2-3.3 (m, 2H), 2.4-2.5 (m, 2H), 2.3-2.4 (m, 1H), 1.9-2.1 (m, 2H), 1.6-1.8 (m, 1H), 1.5-1.6 (m, 2H).

Step 2. 3-(4-Bromo-6-chloro-1-(tetrahydro-2H-pyran-2-yl)-1H-indazol-5-yl)propanehydrazide. To solution of 3-(4-bromo-6-chloro-1-(tetrahydro-2H-pyran-2-yl)-1H-indazol-5-yl)propanoic acid (1.02 g, 2.63 mmol) in acetonitrile (8 mL) and N,N-dimethylacetamide (2 mL) was added DIPEA (0.5 mL) and HATU (1.26 g, 3.32 mmol). The mixture was stirred at rt for 20 min. Then the solution was added dropwise to the solution of hydrazine (0.19 mL, 6.1 mmol) and DIPEA (0.5 mL) in MeCN (10 mL) cooled in an ice bath. The reaction mixture was diluted with EtOAc and saturated $NH_4Cl$. The organic phase was washed with water and brine, dried over $Na_2SO_4$ and concentrated. The crude material was purified by column chromatography on silica gel, eluting with a gradient of 0-100% 3:1 EtOAc/EtOH in heptane, to provide 3-(4-bromo-6-chloro-1-(tetrahydro-2H-pyran-2-yl)-1H-indazol-5-yl)propanehydrazide (0.62 g, 1.50 mmol, 58%) as white solid. m/z (ESI): 423/425 $(M+Na)^+$. $^1H$ NMR (DMSO-$d_6$, 400 MHz) δ ppm 9.06 (br s, 1H), 8.06 (s, 1H), 8.01 (s, 1H), 5.9-5.9 (m, 1H), 4.19 (br s, 2H), 3.8-3.9 (m, 1H), 3.7-3.8 (m, 1H), 3.1-3.3 (m, 2H), 2.2-2.4 (m, 3H), 2.0-2.1 (m, 2H), 1.7-1.8 (m, 1H), 1.5-1.6 (m, 2H).

Step 3&4. tert-Butyl (3S)-3-((5-(2-(6-chloro-1-(tetrahydro-2H-pyran-2-yl)-4-(4,4,5,5-tetramethyl-1,3,2-dioxaborolan-2-yl)-1H-indazol-5-yl)ethyl)-1,3,4-oxadiazol-2-yl)methyl)piperidine-1-carboxylate. This compound was prepared in an analogous manner to Intermediate CL using 3-(4-bromo-6-chloro-1-(tetrahydro-2H-pyran-2-yl)-1H-indazol-5-yl)propanehydrazide in Step 3. m/z (ESI): 656.4 $(M+H)^+$.

Intermediate FY: (S)-4-(tert-Butoxy)-7-chloro-8-fluoro-2-((1-methylpyrrolidin-2-yl)methoxy)pyrido[4,3-d]pyrimidine

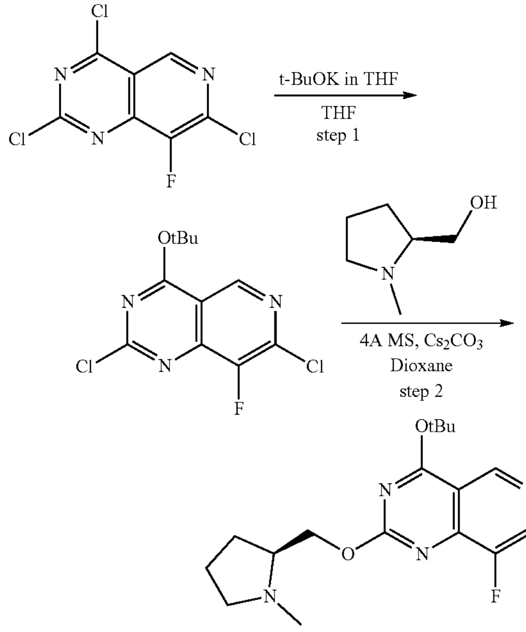

Intermediate FY

Step 1. 4-(tert-Butoxy)-2,7-dichloro-8-fluoropyrido[4,3-d]pyrimidine. To a solution of 2,4,7-trichloro-8-fluoropyrido[4,3-d]pyrimidine (50.0 g, 198 mmol, Enamine) in tetrahydrofuran (1.5 L) at −60° C. was added a solution of t-BuOK in THF (1 M, 190 mL, 190 mmol). The mixture was stirred at −60° C. for 2 h, then diluted with EtOAc and water slowly at 0° C. and extracted with EtOAc. The combined organic layers were washed with brine, dried over $Na_2SO_4$, filtered, and concentrated. The crude product was triturated with petroleum ether for 2 h. The solid was collected by filtration, dried to give 4-(tert-butoxy)-2,7-dichloro-8-fluoropyrido[4,3-d]pyrimidine (40.0 g, 138 mmol, 70% yield) as yellow solid.

Step 2. (S)-4-(tert-Butoxy)-7-chloro-8-fluoro-2-((1-methylpyrrolidin-2-yl)methoxy)pyrido[4,3-d]pyrimidine. To a solution of 4-(tert-butoxy)-2,7-dichloro-8-fluoropyrido[4,3-d]pyrimidine (14.0 g, 48.3 mmol) and 4 Å MS (2.5 g) in 1,4-dioxane (280 mL) was added (S)-(1-methylpyrrolidin-2-yl)methanol (8.34 g, 72.4 mmol) and $Cs_2CO_3$ (39.3 g, 121 mmol) in sequence. The reaction mixture was stirred at rt for 10 h, then diluted with EtOAc and water slowly at 0° C. and extracted with EtOAc. The combined organic layers were washed with brine, dried over $Na_2SO_4$, filtered, and concentrated. The crude product was triturated with MTBE for 2 h. The solid was collected by filtration, dried to (S)-4-(tert-butoxy)-7-chloro-8-fluoro-2-((1-methylpyrrolidin-2-yl)methoxy)pyrido[4,3-d]pyrimidine (7.89 g, 21.4 mmol, 44% yield) as white solid. m/z (ESI): 369.1, 371.1 $(M+H)^+$. $^1H$ NMR (400 MHz, $CDCl_3$) δ ppm 8.86 (s, 1H), 4.50-4.58 (m, 1H), 4.40-4.45 (m, 1H), 3.07-3.28 (m, 1H), 2.73-2.89 (m, 1H), 2.55 (s, 3H), 2.28-2.45 (m, 1H), 2.04-2.19 (m, 1H), 1.78-1.93 (m, 3H), 1.76 (s, 9H). $^{19}F$ NMR (376 MHz, $CDCl_3$) δ ppm −135.34 (s, 1 F).

Intermediate FZ: rac-tert-Butyl (3R,5S)-3-(5-(3-(4-bromo-6-chloro-1-(tetrahydro-2H-pyran-2-yl)-1H-indazol-5-yl)propyl)-1,2,4-oxadiazol-3-yl)-5-((tert-butyldiphenylsilyl)oxy)piperidine-1-carboxylate

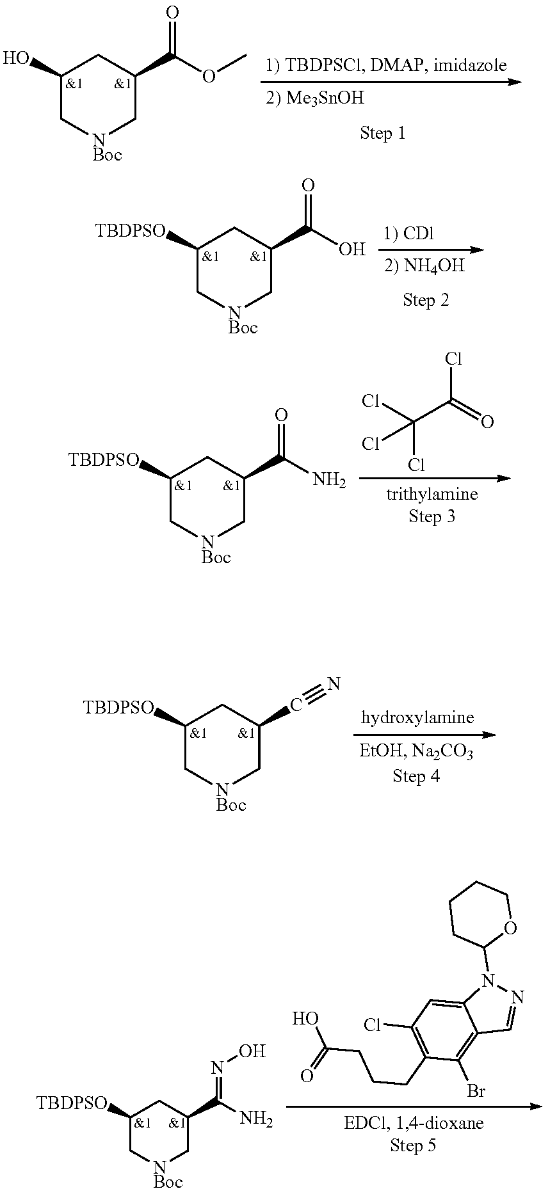

-continued

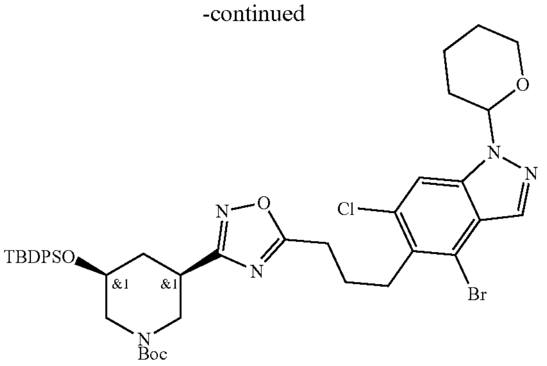

Intermediate FZ

Step 1. rac-(3R,5S)-1-(tert-Butoxycarbonyl)-5-((tert-butyldiphenylsilyl)oxy)piperidine-3-carboxylic acid. To a 500 mL round bottom flask was charged with 1-tert-butyl 3-methyl (3S,5R)-rel-5-hydroxypiperidine-1,3-dicarboxylate (4.00 g, 15.4 mmol), imidazole (2.63 g, 38.6 mmol), dichloromethane (155 mL), and 4-(N,N-dimethylamino)-pyridine (0.19 g, 1.54 mmol). tert-Butyl(chloro)diphenylsilane (4.75 mL, 18.5 mmol) was added, and the reaction was stirred at rt for 18 h. The reaction was diluted with saturated aqueous sodium bicarbonate and extracted with DCM. The DCM layer was dried over sodium sulfate, filtered, and concentrated. The residue was purified by column chromatography on silica gel, eluting with 0-50% ethyl acetate in heptane, to give rac-1-(tert-butyl) 3-methyl (3R,5S)-5-((tert-butyldiphenylsilyl)oxy)piperidine-1,3-dicarboxylate (7.00 g, 14.1 mmol, 91% yield) as colorless oil. m/z (ESI): 520.0 $(M+Na)^+$.

To a 500 mL round bottom flask was charged rac-1-(tert-butyl) 3-methyl (3R,5S)-5-((tert-butyldiphenylsilyl)oxy)piperidine-1,3-dicarboxylate (7.00 g, 14.1 mmol), trimethyltin hydroxide (10.2 g, 56.3 mmol), and 1,2-dichloroethane (140 mL). The reaction mixture was heated to 70° C. for 16 h. After cooling to rt, the reaction was filtered, and the filtrate was concentrated to give rac-(3R,5S)-1-(tert-butoxycarbonyl)-5-((tert-butyldiphenylsilyl)oxy)piperidine-3-carboxylic acid (6.80 g, 14.0 mol, 100% yield) as colorless semi-solid. m/z (ESI): 506.1 $(M+Na)^+$.

Step 2. rac-tert-Butyl (3R,5S)-3-((tert-butyldiphenylsilyl)oxy)-5-carbamoylpiperidine-1-carboxylate. To a 40 mL vial was added rac-(3R,5S)-1-(tert-butoxycarbonyl)-5-((tert-butyldiphenylsilyl)oxy)piperidine-3-carboxylic acid (1.00 g, 2.10 mmol), dichloromethane (8.5 mL), and CDI (0.67 g, 4.13 mmol). The reaction mixture was stirred for 1.5 h and then ammonium hydroxide (2.3 mL, 41 mmol) was added, and the reaction was stirred for an additional 1 h at rt. The precipitate was filtered, and the filtrate was concentrated. The residue was purified by reverse phase column chromatography using a C18 column, eluting with 5-100% acetonitrile with 0.1% formic acid/water with 0.1% formic acid, to give rac-tert-butyl (3R,5S)-3-((tert-butyldiphenylsilyl)oxy)-5-carbamoylpiperidine-1-carboxylate (0.41 g, 0.86 mmol, 42% yield) as white solid. m/z (ESI): 506.1 $(M+Na)^+$.

Step 3. (3R,5S)-3-((tert-Butyldiphenylsilyl)oxy)-5-cyanopiperidine-1-carboxylate. To a 250 mL round bottom flask was charged with rac-tert-butyl (3R,5S)-3-((tert-butyldiphenylsilyl)oxy)-5-carbamoylpiperidine-1-carboxylate (3.10 g, 6.40 mmol), dichloromethane (56 mL), and triethylamine (1.8 mL, 12.8 mmol). The contents were cooled to 0° C. and 2,2,2-trichloroacetyl chloride (1.4 mL, 12.8 mmol) was added dropwise. The reaction mixture was allowed to warm to rt with stirring for 1 h, then was diluted with water, and extracted with dichloromethane. The combined organics were dried by sodium sulfate, filtered, and concentrated. The residue was purified by column chromatography on silica gel, eluting with 0-50% ethyl acetate in heptane to give rac-tert-butyl (3R,5S)-3-((tert-butyldiphenylsilyl)oxy)-5-cyanopiperidine-1-carboxylate (2.90 g, 6.20 mmol, 97% yield) as colorless oil. m/z (ESI): 487.0 $(M+Na)^+$.

Step 4. rac-tert-Butyl (3R,5S)-3-((tert-butyldiphenylsilyl)oxy)-5-((Z)—N'-hydroxycarbamimidoyl)piperidine-1-carboxylate. To a 250 mL round bottom flask was charged with sodium carbonate (1.32 g, 12.5 mmol), rac-tert-butyl (3R,5S)-3-((tert-butyldiphenylsilyl)oxy)-5-cyanopiperidine-1-carboxylate (2.90 g, 6.20 mmol), hydroxylamine HCl (1.74 g, 25 mmol), ethanol (24 mL), and water (16 mL). The reaction mixture was heated to 80° C. for 10 h. After cooling to rt, the reaction was concentrated, diluted with saturated aqueous sodium chloride, and extracted with ethyl acetate and dichloromethane. The organics were dried over sodium sulfate, filtered, and concentrated to give rac-tert-butyl (3R,5S)-3-((tert-butyldiphenylsilyl)oxy)-5-((Z)—N-hydroxycarbamimidoyl)piperidine-1-carboxylate (3.00 g, 6.00 mmol, 97% yield) as white solid. m/z (ESI): 498.1 $(M+H)^+$.

Step 5. rac-tert-Butyl (3R,5S)-3-(5-(3-(4-bromo-6-chloro-1-(tetrahydro-2H-pyran-2-yl)-1H-indazol-5-yl)propyl)-1,2,4-oxadiazol-3-yl)-5-((tert-butyldiphenylsilyl)oxy)piperidine-1-carboxylate. To a 250 mL round bottom flask was charged with rac-tert-butyl (3R,5S)-3-((tert-butyldiphenylsilyl)oxy)-5-((Z)—N-hydroxycarbamimidoyl)piperidine-1-carboxylate (3.00 g, 6.00 mmol), 4-(4-bromo-6-chloro-1-(tetrahydro-2H-pyran-2-yl)-1H-indazol-5-yl)butanoic acid (2.42 g, 6.03 mmol, Step 1 in Intermediate CF), and 1,4-dioxane (40 mL). To this stirring solution was added 1-(3-dimethylaminopropyl)-3-ethylcarbodiimide hydrochloride (1.27 g, 6.63 mmol) and the reaction was sealed and heated to 100° C. for 20 h. After cooling to rt, the reaction mixture was concentrated and diluted with ethyl acetate. The solution was washed with aqueous 0.1 M acetic acid, followed by saturated aqueous sodium bicarbonate. The organics were dried ($Na_2SO_4$), filtered and concentrated and the residue was purified by reverse phase column chromatography using a C18 column, eluting with 5-100% acetonitrile with 0.1% formic acid/water with 0.1% formic acid, to give rac-tert-butyl (3R,5S)-3-(5-(3-(4-bromo-6-chloro-1-(tetrahydro-2H-pyran-2-yl)-1H-indazol-5-yl)propyl)-1,2,4-oxadiazol-3-yl)-5-((tert-butyldiphenylsilyl)oxy)piperidine-1-carboxylate (2.60 g, 3.10 mmol, 51% yield) as colorless semi-solid. m/z (ESI): 884.7 $(M+Na)^+$.

Intermediate GA: tert-Butyl 6-(5-(3-(4-bromo-6-chloro-1-(tetrahydro-2H-pyran-2-yl)-1H-indazol-5-yl)propyl)-1,2,4-oxadiazol-3-yl)-6-methyl-1,4-oxazepane-4-carboxylate

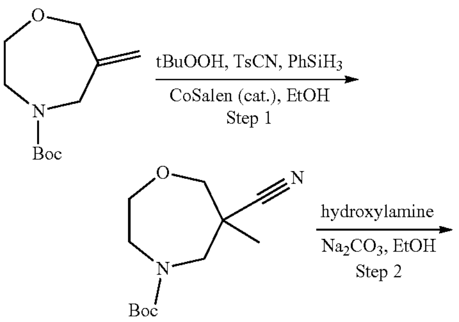

-continued

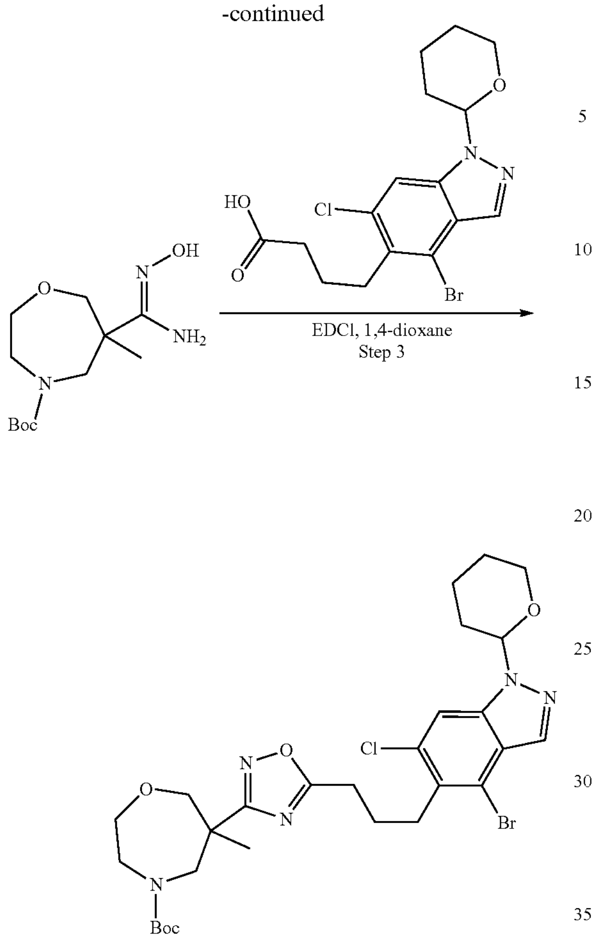

Intermediate GA

Step 1. tert-Butyl 6-cyano-6-methyl-1,4-oxazepane-4-carboxylate. To a 20 mL vial was charged with (S,S)-(+)-N,N'-bis(3,5-di-tert-butylsalicylidene)-1,2-cyclohexanediaminocobalt(II) (7.2 mg, 0.012 mmol), (R,R)-(−)-N,N'-bis(3,5-di-tert-butylsalicylidene)-1,2-cyclohexanediaminocobalt(II) (7.2 mg, 0.012 mmol), and ethanol (4 mL). The content was stirred for 2 minutes and then tert-butyl 6-methylene-1,4-oxazepane-4-carboxylate (0.25 g, 1.19 mmol) was added as a solution in ethanol (4 mL). To this was sequentially added tosyl cyanide (0.32 g, 1.79 mmol), 1,1-dimethylethyl hydroperoxide (65.0 μL, 0.36 mmol), and phenylsilane (0.15 μL, 1.2 mmol). The reaction was stirred at rt for 3 h. The reaction was repeated on 0.76 g, and the crude material was combined and purified by column chromatography on silica gel, eluting with a gradient of 0-60% ethyl acetate in heptane, to give tert-butyl 6-cyano-6-methyl-1,4-oxazepane-4-carboxylate (0.94 g, 3.9 mmol, 83% yield) as yellow oil. m/z (ESI): 263.2 $(M+Na)^+$.

Step 2. tert-Butyl (Z)-6-(N'-hydroxycarbamimidoyl)-6-methyl-1,4-oxazepane-4-carboxylate. The title compound was prepared in an analogous manner to Step 4 in Intermediate FZ. m/z (ESI): 274.2 $(M+H)^+$.

Step 3. tert-Butyl 6-(5-(3-(4-bromo-6-chloro-1-(tetrahydro-2H-pyran-2-yl)-1H-indazol-5-yl)propyl)-1,2,4-oxadiazol-3-yl)-6-methyl-1,4-oxazepane-4-carboxylate. The title compound was prepared in an analogous manner to Step 5 in Intermediate FZ. m/z (ESI): 639.8 $(M+H)^+$.

Intermediate GB: tert-Butyl 2-(2-(3-(6-chloro-1-(tetrahydro-2H-pyran-2-yl)-4-(4,4,5,5-tetramethyl-1,3,2-dioxaborolan-2-yl)-1H-indazol-5-yl)propyl)oxazol-4-yl)-2-methylmorpholine-4-carboxylate

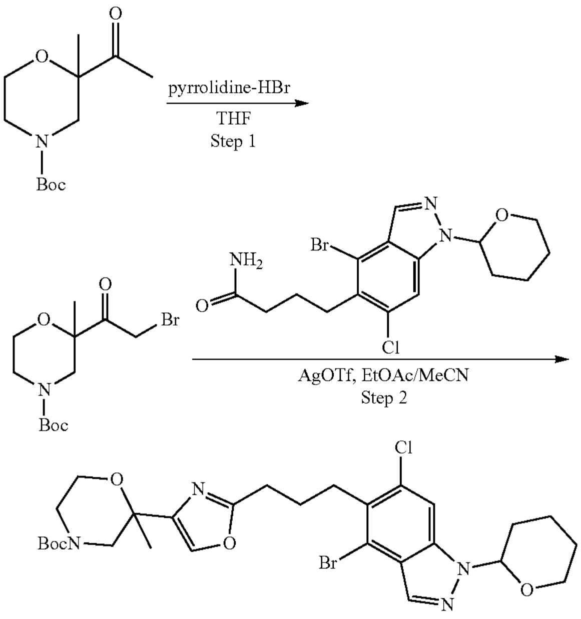

Intermediate GB

Step 1. tert-Butyl 2-(2-bromoacetyl)-2-methylmorpholine-4-carboxylate. To a 20 mL vial was charged with tert-butyl 2-acetyl-2-methylmorpholine-4-carboxylate (1.00 g, 4.11 mmol), tetrahydrofuran (20 mL), and pyrrolidone hydrotribromide (2.24 g, 4.52 mmol). The reaction mixture was stirred at 70° C. for 15 min. After cooling to rt, the precipitate was filtered off and the filtrate was concentrated. The crude was purified by column chromatography on silica gel, eluting with a gradient of 0-50% ethyl acetate in heptane, to give tert-butyl 2-(2-bromoacetyl)-2-methylmorpholine-4-carboxylate (0.46 g, 1.4 mmol, 35% yield) as colorless oil. m/z (ESI): 622.0 $(M-Boc+H)^+$.

Step 2. tert-Butyl 2-(2-(3-(4-bromo-6-chloro-1-(tetrahydro-2H-pyran-2-yl)-1H-indazol-5-yl)propyl)oxazol-4-yl)-2-methylmorpholine-4-carboxylate. The title compound was prepared in an analogous manner to Step 3 in Intermediate CF using 4-(4-bromo-6-chloro-1-(tetrahydro-2H-pyran-2-yl)-1H-indazol-5-yl)butanamide. m/z (ESI): 622.9 $(M+H)^+$.

Intermediate GC: tert-Butyl (6R)-(5-(3-(4-bromo-6-chloro-1-(tetrahydro-2H-pyran-2-yl)-1H-indazol-5-yl)propyl)-1,2,4-oxadiazol-3-yl)-1,4-oxazepane-4-carboxylate

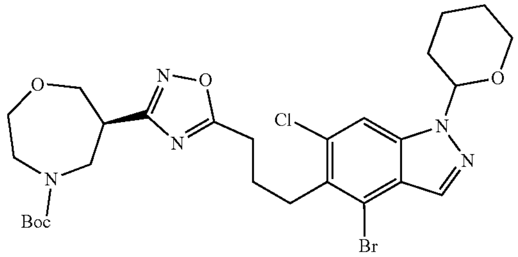 [SMILES: CC(C)(C)OC(=O)N1CCOC[C@@H](c2noc(CCCc3c(Cl)cc4c(cnn4C4CCCCO4)c3Br)n2)C1]

The title compound was prepared in an analogous manner to Step 4&5 in Intermediate FZ using tert-butyl 6-cyano-1,4 oxazepane-4-carboxylate (CAS #: 1823484-09-8, ChemSuttle). m/z (ESI): 624.0 $(M+H)^+$.

Intermediate GD: tert-Butyl 3-(5-(3-(4-bromo-6-chloro-1-(tetrahydro-2H-pyran-2-yl)-1H-indazol-5-yl)propyl)-1,2,4-oxadiazol-3-yl)azepane-1-carboxylate

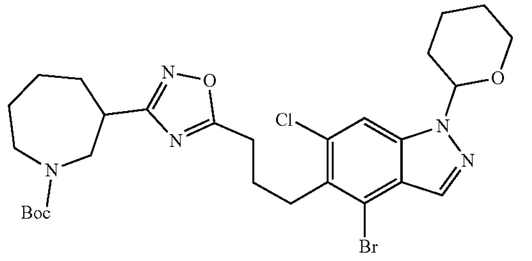 [SMILES: CC(C)(C)OC(=O)N1CCCCC(c2noc(CCCc3c(Cl)cc4c(cnn4C4CCCCO4)c3Br)n2)C1]

The title compound was prepared in an analogous manner to Steps 4&5 in Intermediate FZ using tert-butyl 3-cyano-azepane-1-carboxylate (CAS #: 1784386-41-9, Key Organics). m/z (ESI): 622.0 $(M+H)^+$.

Intermediate GE: tert-Butyl 6-(6-(4-bromo-6-chloro-1-(tetrahydro-2H-pyran-2-yl)-1H-indazol-5-yl)-1-((tert-butyldimethylsilyl)oxy)-2-oxohexyl)-1,4-oxazepane-4-carboxylate

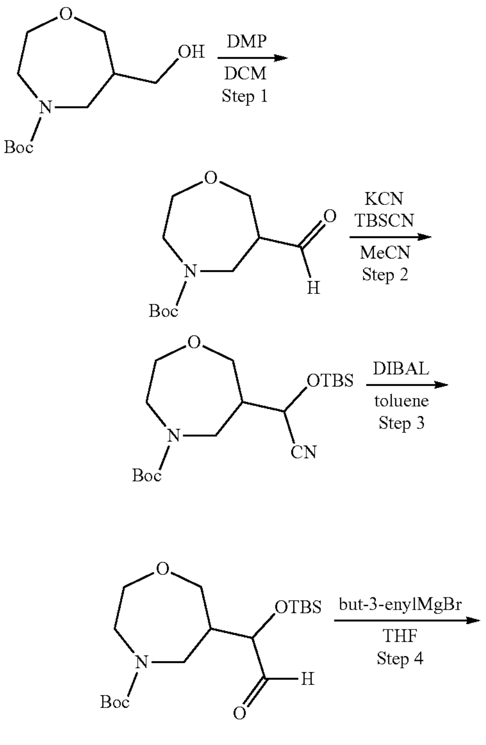

-continued

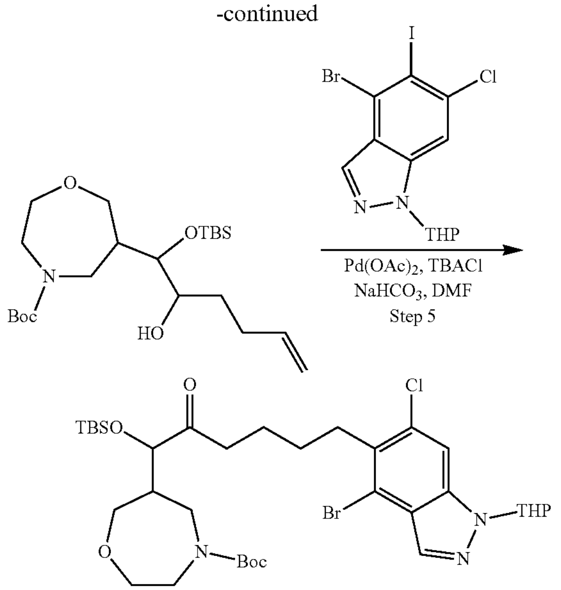

Intermediate GE

Step 1. tert-Butyl 6-formyl-1,4-oxazepane-4-carboxylate. A 150 mL flask was charged with tert-butyl 6-(hydroxymethyl)-1,4-oxazepane-4-carboxylate (1.50 g, 6.49 mmol, Pharmablock, Inc.) and Dess-Martin periodinane (3.58 g, 8.43 mmol) in dichloromethane (50 mL). The reaction mixture was stirred at rt for 2 h, was then quenched with sodium thiosulfate and extracted with DCM. The organic phase was dried over sodium sulfate, filtered, and concentrated. The crude was purified by column chromatography on silica gel, eluting with a gradient of 0-80% ethyl acetate in heptane, to give tert-butyl 6-formyl-1,4-oxazepane-4-carboxylate (1.00 g, 4.40 mmol, 67% yield) as colorless oil.

Step 2. tert-Butyl 6-(((tert-butyldimethylsilyl)oxy)(cyano)methyl)-1,4-oxazepane-4-carboxylate. To a solution of tert-butyldimethylsilanecarbonitrile (0.83 g, 5.89 mmol) and cyanopotassium (85 mg, 1.31 mmol) in acetonitrile (22 mL) was added tert-butyl 6-formyl-1,4-oxazepane-4-carboxylate (0.50 g, 2.18 mmol) under nitrogen. The reaction mixture was stirred at rt for 4 h. Saturated sodium bicarbonate solution was added, and the aqueous layer was extracted with ethyl acetate. The organic layer was dried over anhydrous sodium sulfate, filtered, and concentrated under reduced pressure. The residue was purified by column chromatography on silica gel, eluting with a gradient of 0-100% ethyl acetate in heptane, to yield tert-butyl 6-(((tert-butyldimethylsilyl)oxy)(cyano)methyl)-1,4-oxazepane-4-carboxylate (0.68 g, 1.80 mmol, 84% yield) as yellow oil. m/z (ESI): 393.3 $(M+Na)^+$ Step 3. tert-Butyl 6-(1-((tert-butyldimethylsilyl)oxy)-2-oxoethyl)-1,4-oxazepane-4-carboxylate. In a 150 mL round-bottom flask was charged with tert-butyl 6-(((tert-butyldimethylsilyl)oxy)(cyano)methyl)-1,4-oxazepane-4-carboxylate (0.68 g, 1.8 mmol) and toluene (46 mL). The content was cooled to −78° C. and diisobutylaluminum hydride (1 M in toluene, 2.3 mL, 2.3 mmol) was added dropwise and the mixture was stirred for 4 h at −78° C. The mixture was then slowly warmed up to −10° C. and quenched with methanol. The mixture was then warmed to rt and a saturated solution of Rochelle's salt was added and stirred vigorously until the phases separated. The aqueous phase was extracted with EtOAc, and the combined organic phase dried over sodium sulfate, filtered, and concentrated. The residue was purified by column chromatography on silica gel, eluting with a gradient of 0-100% ethyl acetate in heptane, to yield tert-butyl 6-(1-((tert-butyldimethylsilyl)oxy)-2-oxoethyl)-1,4-oxazepane-4-carboxylate (0.34 g, 0.91 mmol, 50% yield) as colorless oil containing 35% of the starting material (determined by NMR). m/z (ESI): 696.2 $(M+Na)^+$ Step 4. tert-Butyl 6-(1-((tert-butyldimethylsilyl)oxy)-2-hydroxyhex-5-en-1-yl)-1,4-oxazepane-4-carboxylate. In a 20 mL vial was charged with tert-butyl 6-(1-((tert-butyldimethylsilyl)oxy)-2-oxoethyl)-1,4-oxazepane-4-carboxylate (0.34 g, 0.59 mmol, crude) in tetrahydrofuran (2 mL) and cooled down to 0° C. But-3-en-1-ylmagnesium bromide (0.5 M in THF, 3.6 mL, 1.8 mmol) was added dropwise and the mixture was stirred for 30 min at 0° C. The reaction was quenched by the dropwise addition of saturated aqueous ammonium chloride solution and then extracted with EtOAc. The combined organic layers were dried over sodium sulfate, filtered, and concentrated. The crude material was purified by column chromatography on silica gel, eluting with a gradient of 0-100% ethyl acetate in heptane, to yield tert-butyl 6-(1-((tert-butyldimethylsilyl)oxy)-2-hydroxyhex-5-en-1-yl)-1,4-oxazepane-4-carboxylate (0.17 g, 0.40 mmol, 67% yield) as colorless oil. m/z (ESI): 452.2 $(M+Na)^+$.

Step 5. tert-Butyl 6-(6-(4-bromo-6-chloro-1-(tetrahydro-2H-pyran-2-yl)-1H-indazol-5-yl)-1-((tert-butyldimethylsilyl)oxy)-2-oxohexyl)-1,4-oxazepane-4-carboxylate. A 5 mL vial was charged with tert-butyl 6-(1-((tert-butyldimethylsilyl)oxy)-2-hydroxyhex-5-en-1-yl)-1,4-oxazepane-4-carboxylate (0.17 g, 0.40 mmol), 4-bromo-6-chloro-5-iodo-1-(tetrahydro-2H-pyran-2-yl)-1H-indazole (0.22 g, 0.49 mmol, Pharmablock, Inc.), sodium bicarbonate (86 mg, 1.0 mmol), tetrabutylammonium chloride (0.11 mL, 0.41 mmol), and N,N-dimethylformamide (0.8 mL). The solution was degased with $N_2$ for 3 min and then placed on a hot plate at 65° C. Palladium acetate (4.6 mg, 0.02 mmol) was added, and the reaction mixture was heated for 15 h at 65° C. After cooling to rt, the reaction mixture was diluted with ethyl acetate and saturated aqueous ammonium chloride. The aqueous layer was extracted with ethyl acetate and the combined organic layers were dried over sodium sulfate, filtered, and concentrated. The crude material was purified by column chromatography on silica gel, eluting with a gradient of 0-40% ethyl acetate in heptane, to give tert-butyl 6-(6-(4-bromo-6-chloro-1-(tetrahydro-2H-pyran-2-yl)-1H-indazol-5-yl)-1-((tert-butyldimethylsilyl)oxy)-2-oxohexyl)-1,4-oxazepane-4-carboxylate (0.13 g, 0.18 mmol, 44% yield) as yellow oil. m/z (ESI): 764.1 $(M+Na)^+$.

PREPARATION OF EXAMPLES

(15R)-31-Fluoro-8-(((2R,7aS)-2-fluorotetrahydro-1H-pyrrolo[1,2-a]pyrrol-7a(5H)-yl)methoxy)-27-hydroxy-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 1)

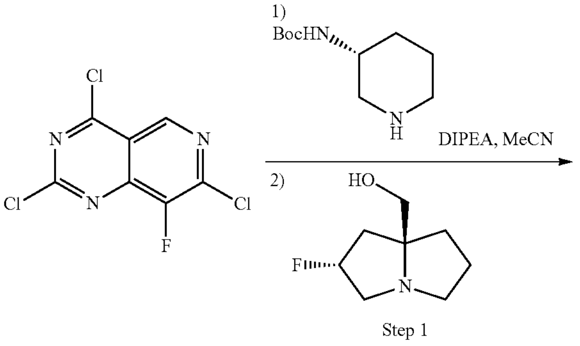

-continued

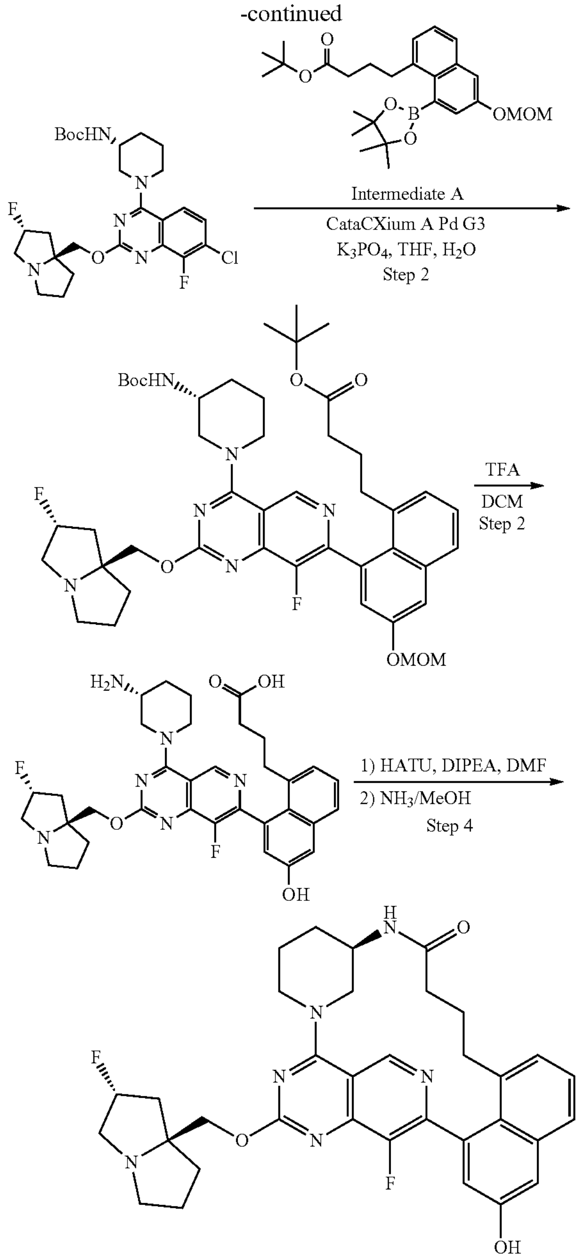

Example 1

Step 1: tert-Butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)carbamate. To a mixture of 2,4,7-trichloro-8-fluoropyrido[4,3-d]pyrimidine (1.00 g, 3.96 mmol, Enamine) and DIPEA (2.8 mL, 15.8 mmol) in acetonitrile (10 mL) at 0° C. was added (R)-tert-butyl piperidin-3-ylcarbamate (0.79 g, 3.96 mmol, Ambeed, Inc.). The reaction mixture was stirred at the same temperature for 1 h. Then, ((2R,7aS)-2-fluorotetrahydro-1H-pyrrolizin-7a(5H)-yl)methanol (0.63 g, 3.96 mmol, BLD Pharmatech) was added and the resulting mixture was stirred at 80° C. for 16 h. Saturated $NH_4Cl$ solution was then added to reaction mixture and the aqueous phases were extracted with EtOAc. The combined organic layers were dried over $Na_2SO_4$, filtered and volatiles were removed in vacuo. The crude product was purified by column chromatography on silica gel, eluting with a gradient of 0-100% EtOAc/EtOH (3:1) in heptane, to provide tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)carbamate (1.30 g, 2.41 mmol, 61% yield). m/z (ESI): 539.0 $(M+H)^+$.

Step 2: tert-Butyl 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl) butanoate. tert-Butyl 4-(6-(methoxymethoxy)-8-(4,4,5,5-tetramethyl-1,3,2-dioxaborolan-2-yl)naphthalen-1-yl) butanoate (76 mg, 0.17 mmol, Intermediate A), potassium phosphate, monohydrate (96 mg, 0.42 mmol), cataCXium A Pd G3 (20 mg, 0.03 mmol, Sigma-Aldrich Corporation) and tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)carbamate (75 mg, 0.14 mmol) were dissolved in tetrahydrofuran (1.2 mL) and water (0.12 mL) and degassed for 5 min. The mixture was then heated to 80° C. for 1 h. After cooling to rt, water was added to the reaction mixture and the aqueous layer was extracted with EtOAc. The combined organic layers were dried over $Na_2SO_4$, filtered and volatiles were removed in vacuo. The residue was purified by column chromatography on silica gel, eluting with a gradient of 0-100% EtOAc/EtOH (3:1) with 2% $Et_3N$ in heptane, to provide tert-butyl 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoate (0.11 g, 0.13 mmol, 92% yield). m/z (ESI): 833.4 $(M+H)^+$.

Step 3: 4-(8-(4-((R)-3-Aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-hydroxynaphthalen-1-yl)butanoic acid. To a solution of tert-butyl 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoate (0.10 g, 0.12 mmol) in dichloromethane (1.2 mL) was added trifluoroacetic acid (0.23 mL, 3.00 mmol) and the mixture was stirred at rt for 4 h. Volatiles were removed in vacuo and the mixture was purified via reverse phase column chromatography, eluting with a gradient of 5-100% MeCN with 0.1% TFA in $H_2O$, to provide the TFA salt of 4-(8-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-hydroxynaphthalen-1-yl)butanoic acid (63 mg, 0.10 mmol, 83% yield) as light-yellow oil. m/z (ESI): 633.2 $(M+H)^+$.

Step 4: (15R)-31-Fluoro-8-(((2R,7aS)-2-fluorotetrahydro-1H-pyrrolo[1,2-a]pyrrol-7a(5H)-yl)methoxy)-27-hydroxy-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate). The mixture of 4-(8-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-hydroxynaphthalen-1-yl)butanoic acid (51 mg, 0.08 mmol), HATU (61 mg, 0.16 mmol), and DIPEA (0.06 mL, 0.32 mmol) in N,N-dimethylformamide (9 mL) was stirred at rt for 1 h. 2 N ammonia in methanol (0.2 mL, 0.40 mmol) was added and reaction mixture was stirred for 10 min. Water was added and the resulting aqueous phase was extracted with EtOAc. The combined organic layers were dried over $Na_2SO_4$, filtered, and concentrated in vacuo. The mixture was purified by via reverse phase HPLC to provide (15R)-31-fluoro-8-(((2R,7aS)-2-fluorotetrahydro-1H-pyrrolo[1,2-a]pyrrol-7a(5H)-yl)methoxy)-27-hydroxy-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) as off-white solid (5 mg, 5.93 μmol, 7% yield). m/z (ESI): 615.2 $(M+H)^+$. $^1H$ NMR (400 MHz, METHANOL-$d_4$) δ ppm 9.15 (s, 1H), 7.75 (br d, J=5.4 Hz, 1H), 7.65 (d, J=8.3 Hz, 1H), 7.37 (t, J=7.7 Hz, 1H), 7.33 (d, J=2.7 Hz, 1H), 7.20 (d, J=2.7 Hz, 2H), 5.53-5.71 (m, 1H), 5.17-5.26 (m, 1H), 5.07 (br d, J=12.4 Hz, 1H), 4.74-4.81 (m, 1H), 4.61-4.68 (m, 1H), 3.99-4.13 (m, 1H), 3.90-3.99 (m, 4H), 3.46-3.54 (m, 1H), 2.69-2.82 (m, 1H), 2.63-2.69 (m, 1H), 2.34-2.49 (m, 4H), 2.15 (br s, 3H), 1.90-2.03 (m, 2H), 1.74-1.83 (m, 3H), 1.62-1.73 (m, 2H). Stereochemistry of Example 1 was confirmed by X-Ray crystallography analysis.

(15R)-31-Fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 3)

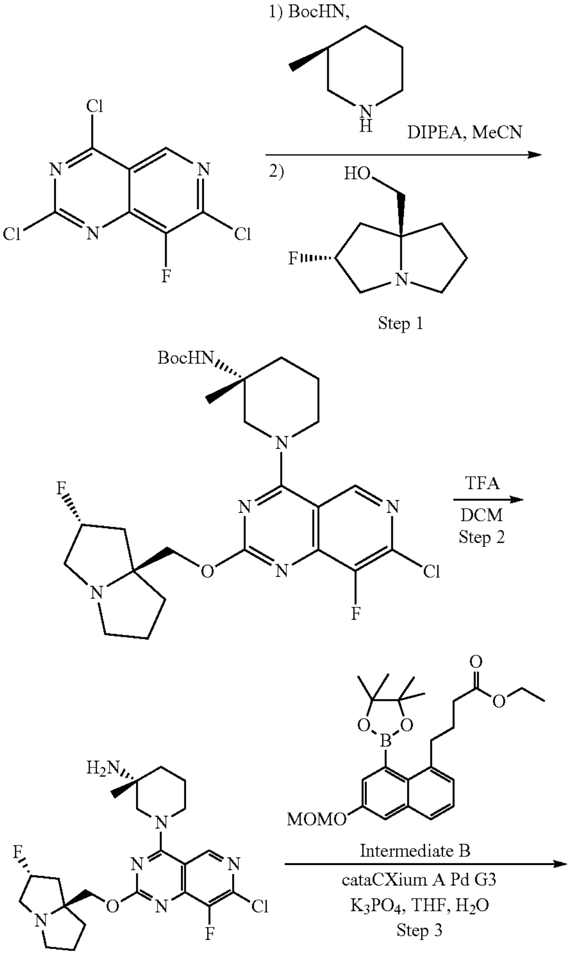

-continued

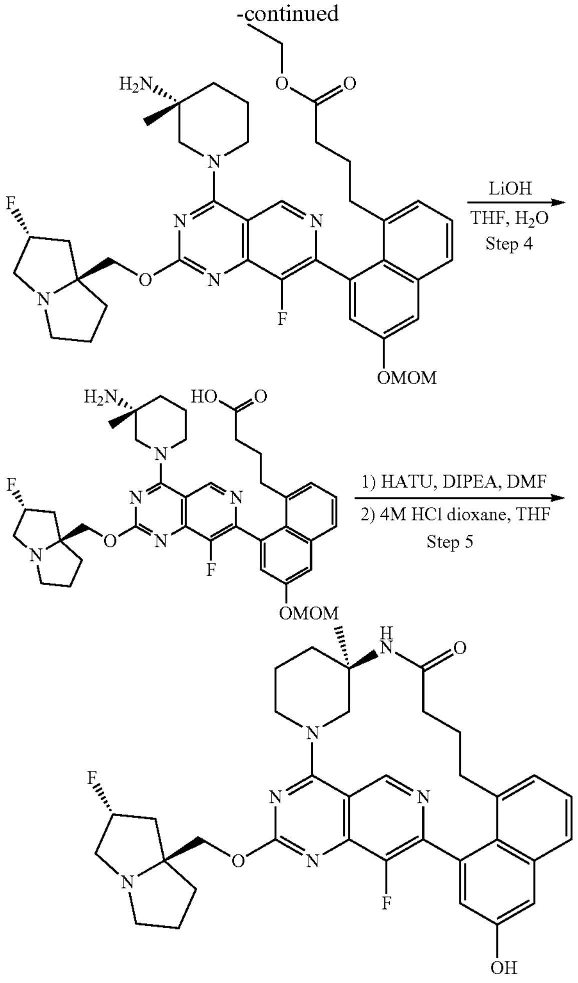

Example 3

Step 1. tert-Butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-yl)carbamate. To a mixture of 2,4,7-trichloro-8-fluoropyrido[4,3-d]pyrimidine (1.00 g, 3.96 mmol, Enamine) and DIPEA (2.8 mL, 15.8 mmol) in acetonitrile (10 mL) at 0° C. was added tert-butyl N-[(3R)-3-methylpiperidin-3-yl]carbamate (0.85 g, 3.96 mmol, Pharmablock, Inc.) and the reaction mixture was stirred at the same temperature for 1 h. ((2R,7aS)-2-fluorotetrahydro-1H-pyrrolizin-7a(5H)-yl)methanol (0.63 g, 3.96 mmol, BLD Pharmatech) was added and the resulting mixture was stirred at 80° C. for 16 h. Saturated $NH_4Cl$ solution was then added and the aqueous phases were extracted with EtOAc. The combined organic layers were dried over $Na_2SO_4$, filtered and volatiles were removed in vacuo. The crude product was purified by column chromatography on silica gel, eluting with a gradient of 0-100% EtOAc/EtOH (3:1) in heptane, to provide tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-yl)carbamate (1.30 g, 2.35 mmol, 59% yield) as off-white solid. m/z (ESI): 553.0 $(M+H)^+$.

Step 2. (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-amine. To a solution of tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-yl)carbamate (0.50 g, 0.90 mmol) in DCM (1.5 mL) at 0° C. was added TFA (1.7 mL, 22.6 mmol). The reaction mixture was stirred at 0° C. for 1 h. The volatiles were removed in vacuo to provide crude (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-amine as oil. m/z (ESI): 453.2 $(M+H)^+$.

Step 3. Ethyl 4-(8-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoate. (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-amine (0.10 g, 0.22 mmol) was dissolved in tetrahydrofuran (2.0 mL), cataCXium A Pd G3 (32 mg, 0.044 mmol, Sigma-Aldrich Corporation), potassium phosphate (0.14 g, 0.66 mmol, Sigma Aldrich) and ethyl 4-(6-(methoxymethoxy)-8-(4,4,5,5-tetramethyl-1,3,2-dioxaborolan-2-yl)naphthalen-1-yl)butanoate (0.11 g, 0.27 mmol, Intermediate B) were added, followed by water (0.20 mL) and the mixture was degassed for 10 minutes. The mixture was then heated to 80° C. for 2 h. After cooling to rt, the volatiles were removed in vacuo and the residue was purified via column chromatography (0-100% EtOAc:EtOH (3:1) with 2% $NEt_3$ in heptane to 100% MeOH) to yield ethyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoate (0.13 g, 0.18 mmol, 79% yield). m/z (ESI): 719.2 $(M+H)^+$.

Step 4. 4-(8-(4-((R)-3-Amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoic acid. Ethyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoate (0.13 g, 0.18 mmol) was dissolved in tetrahydrofuran (1.2 mL) and water (0.4 mL), lithium hydroxide monohydrate (22 mg, 0.53 mmol) was added. The mixture was heated to 40° C. for 4 h. After cooling to rt, the mixture was purified by reverse phase chromatography to yield the TFA salt of 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoic acid (79 mg, 0.11 mmol, 65% yield) as oil. m/z (ESI): 691.3 $(M+H)^+$.

Step 5. (15R)-31-Fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate). To 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(methoxymethoxy)naphthalen-1-yl)butanoic acid (79 mg, 0.11 mmol) dissolved in N,N-dimethylformamide (13 mL) was added HATU (87 mg, 0.23 mmol) and DIPEA (0.08 mL, 0.46 mmol). The mixture was stirred at rt for 30 min. Water was added and the aqueous phase was extracted with EtOAc. The combined organic phases were dried over $Na_2SO_4$, filtered and volatiles were removed in vacuo. The residue was redissolved in THF (2 mL) and 4 M HCl/dioxane (3 mL) was added. The resulting mixture was stirred for 3 h. Volatiles were removed in vacuo and the crude residue was purified by reverse phase HPLC, to provide (15R)-31-fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (24 mg, 0.03 mmol, 25% yield). m/z (ESI): 629.2 $(M+H)^+$. $^1H$ NMR (500 MHz, METHANOL-$d_4$) δ ppm 9.23-9.24 (m, 1H), 9.23 (s, 1H), 7.62-7.66 (m, 1H), 7.15 (d, J=7.1 Hz, 1H), 5.80 (br d, J=13.5 Hz, 1H), 5.53-5.67 (m, 1H), 5.13 (br d, J=13.2 Hz, 1H), 4.71-4.75 (m, 1H), 4.62-4.67 (m, 1H), 3.98-4.09 (m, 1H), 3.90 (br s, 3H), 3.69 (d, J=13.9 Hz, 1H), 3.45-3.53 (m, 1H), 3.15-3.21 (m, 1H), 2.74 (s, 1H), 2.66 (s, 1H), 2.29-2.48 (m, 5H), 2.15-2.23 (m, 1H), 2.03-2.11 (m, 2H), 1.82-1.92 (m, 2H), 1.69 (br s, 5H), 1.54-1.61 (m, 1H), 1.43 (s, 3H). $^{19}F$ NMR (471 MHz, METHANOL-$d_4$) δ ppm −77.32 (br s), −142.09-−141.96 (m), −174.19-−174.04 (m).

(15R)-22,31-Difluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 4)

Example 4

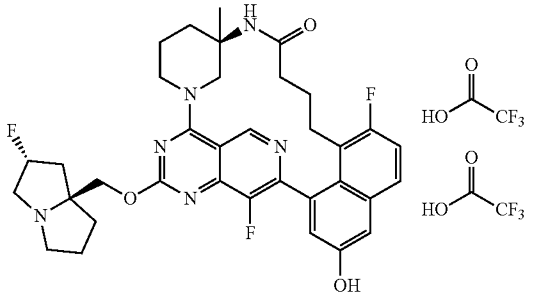

The title compound was prepare in an analogous manner to Example using tert-butyl N-[(3R)-3-methylpiperidin-3-yl]carbamate (CAS #: 1169762-18-8, Pharmablock, Inc.) as amine in step 1, Intermediate D as the boronic ester in the Suzuki coupling reaction in step 3.

m/z (ESI): 647.0 $(M+H)^+$. $^1H$ NMR (400 MHz, METHANOL-$d_4$) δ ppm 9.34 (s, 1H), 7.69 (dd, J=9.1, 5.7 Hz, 1H), 7.31 (s, 2H), 7.21-7.26 (m, 2H), 5.87-5.94 (m, 1H), 5.51-5.66 (m, 1H), 5.12 (br d, J=11.7 Hz, 1H), 4.60-4.73 (m, 2H), 3.92-4.05 (m, 1H), 3.83-3.92 (m, 2H), 3.67 (d, J=14.0 Hz, 1H), 3.43-3.50 (m, 1H), 3.19 (td, J=12.4, 2.0 Hz, 1H), 2.69-2.77 (m, 1H), 2.65 (s, 2H), 2.31-2.45 (m, 3H), 2.21-2.29 (m, 1H), 2.10-2.19 (m, 1H), 1.98-2.08 (m, 2H), 1.81-1.90 (m, 2H), 1.76-1.81 (m, 1H), 1.68-1.74 (m, 1H), 1.59-1.67 (m, 1H), 1.38 (s, 3H).

(15R)-22,31-Difluoro-8-(((2S,4R)-4-fluoro-1-methyl-2-pyrrolidinyl)methoxy)-27-hydroxy-15-methyl-3,7,9,11,16-pentaazahexacyclo[19.7.1.1~2,6~.1~11,15~0.0~5,10~.0~25,29~]hentriaconta-1(28),2(31),3,5,7,9,21,23,25(29),26-decaen-17-one bis(2,2,2-trifluoroacetate) (Example 5)

Example 5

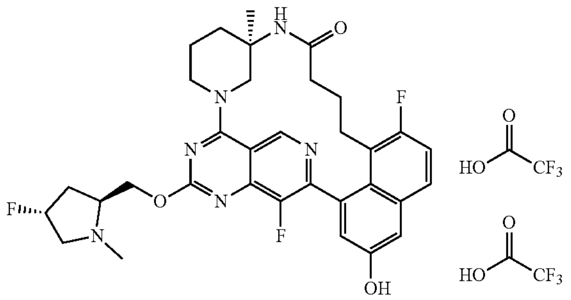

The title compound was synthesized in an analogous fashion to Example 3, using tert-butyl N-[(3R)-3-methylpiperidin-3-yl]carbamate (CAS #: 1169762-18-8, Pharmablock, Inc.) as the amine and [(2S,4R)-4-fluoro-1-methyl-pyrrolidin-2-yl]methanol for ((2R,7aS)-2-florohexahydro-1H-pyrro-7a-yl)methanol in Step 1 and Intermediate D as the boronic ester in the Suzuki coupling reaction in Step 3. m/z (ESI): 620.9 $(M+H)^+$. $^1H$ NMR (400 MHz, METHANOL-$d_4$) δ ppm 9.34 (s, 1H), 7.69 (dd, J=8.99, 5.64 Hz, 1H), 7.31 (s, 2H), 7.23 (s, 2H), 5.90 (br d, J=14.00 Hz, 1H), 5.38-5.63 (m, 1H), 5.11 (br d, J=11.91 Hz, 1H), 4.93 (dd, J=12.96, 2.09 Hz, 1H), 4.75 (br dd, J=13.17, 5.64 Hz, 2H), 4.27 (br s, 1H), 3.64-3.73 (m, 2H), 3.14-3.20 (m, 3H), 3.11-3.26 (m, 1H), 2.64-2.74 (m, 2H), 2.32-2.56 (m, 1H), 2.25 (br t, J=13.90 Hz, 1H), 1.99-2.08 (m, 2H), 1.75-1.90 (m, 4H), 1.59-1.72 (m, 3H), 1.39 (s, 3H), 1.23-1.31 (m, 1H). $^{19}F$ NMR (376 MHz, METHANOL-$d_4$) δ ppm −77.40 (s), −118.82 (s), −141.23 (br s), −174.56-−173.89 (m).

(15R)-22,31-Difluoro-27-hydroxy-8-methoxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 6)

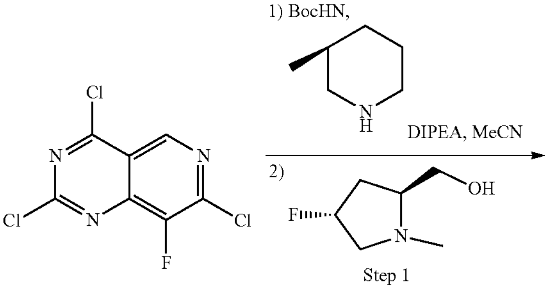

-continued

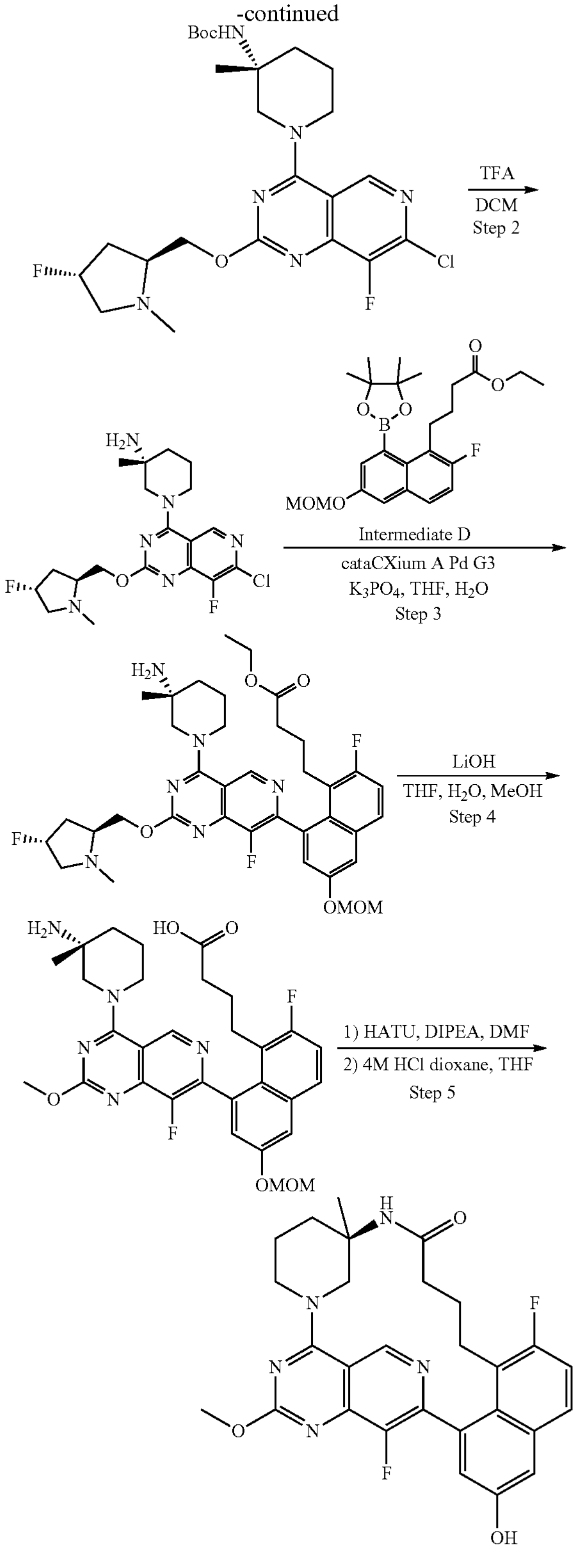

Example 6

Step 1: tert-Butyl ((R)-1-(7-chloro-8-fluoro-2-(((2S,4R)-4-fluoro-1-methylpyrrolidin-2-yl)methoxy)pyrido[4,3-d]pyrimidin-4-yl)-3-methylpiperidin-3-yl)carbamate. To a mixture of 2,4,7-trichloro-8-fluoropyrido[4,3-d]pyrimidine (0.50 g, 1.98 mmol, Enamine) and DIEA (1.0 mL, 5.94 mmol) in acetonitrile (6.5 mL) at 0° C. was added tert-butyl N-[(3R)-3-methylpiperidin-3-yl]carbamate (0.42 g, 1.98 mmol, Pharmablock, Inc.). The reaction mixture was stirred at 0° C. for 1 h. Then, [(2S,4R)-4-fluoro-1-methyl-pyrrolidin-2-yl]methanol (0.32 g, 2.38 mmol, Synnovator, Inc.) was added and the resulting mixture was stirred at 80° C. for 16 h. The reaction mixture was concentrated, and the crude product was purified by column chromatography on silica gel, eluting with a gradient of 0-100% (3:1 EtOAc/EtOH+2% TEA) in heptane to yield tert-butyl ((R)-1-(7-chloro-8-fluoro-2-(((2S,4R)-4-fluoro-1-methylpyrrolidin-2-yl)methoxy)pyrido[4,3-d]pyrimidin-4-yl)-3-methylpiperidin-3-yl)carbamate (0.69 g, 1.32 mmol, 67% yield) as off-white solid. m/z (ESI): 527.2 $(M+H)^+$.

Step 2: (R)-1-(7-Chloro-8-fluoro-2-(((2S,4R)-4-fluoro-1-methylpyrrolidin-2-yl)methoxy)pyrido[4,3-d]pyrimidin-4-yl)-3-methylpiperidin-3-amine. To a solution of tert-butyl ((R)-1-(7-chloro-8-fluoro-2-(((2S,4R)-4-fluoro-1-methylpyrrolidin-2-yl)methoxy)pyrido[4,3-d]pyrimidin-4-yl)-3-methylpiperidin-3-yl)carbamate (0.20 g, 0.38 mmol) in DCM (2.0 mL) at 0° C. was added TFA (0.59 mL, 7.59 mmol) and the reaction mixture was stirred at rt for 30 minutes. The mixture was neutralized with saturated aqueous sodium bicarbonate solution and extracted with DCM. The organic layer was concentrated in vacuo to give (R)-1-(7-chloro-8-fluoro-2-(((2S,4R)-4-fluoro-1-methylpyrrolidin-2-yl)methoxy)pyrido[4,3-d]pyrimidin-4-yl)-3-methylpiperidin-3-amine which was used directly in the following step. m/z (ESI): 427.0 $(M+H)^+$.

Step 3: Ethyl 4-(8-(4-((R)-3-amino-3-methylpiperidin-1-yl)-8-fluoro-2-(((2S,4R)-4-fluoro-1-methylpyrrolidin-2-yl)methoxy)pyrido[4,3-d]pyrimidin-7-yl)-2-fluoro-6-(methoxymethoxy)naphthalen-1-yl)butanoate. To a suspension of (R)-1-(7-chloro-8-fluoro-2-(((2S,4R)-4-fluoro-1-methylpyrrolidin-2-yl)methoxy)pyrido[4,3-d]pyrimidin-4-yl)-3-methylpiperidin-3-amine (0.16 g, 0.38 mmol) and ethyl 4-(2-fluoro-6-(methoxymethoxy)-8-(4,4,5,5-tetramethyl-1,3,2-dioxaborolan-2-yl)naphthalen-1-yl)butanoate (0.19 g, 0.42 mmol, Intermediate D) in tetrahydrofuran (1.7 mL) and water (0.17 mL) were added potassium phosphate (0.32 g, 1.52 mmol) and cataCXium A Pd G3 (28 mg, 0.038 mmol). The reaction mixture was sparged with argon and stirred at 70° C. for 2 h. The reaction mixture was partitioned between water and ethyl acetate, the organic layer was concentrated and the crude product was purified by column chromatography on silica gel, eluting with 0-100% (3:1 ethyl acetate/ethanol with 2% TEA) in heptane, to provide ethyl 4-(8-(4-((R)-3-amino-3-methylpiperidin-1-yl)-8-fluoro-2-(((2S,4R)-4-fluoro-1-methylpyrrolidin-2-yl)methoxy)pyrido[4,3-d]pyrimidin-7-yl)-2-fluoro-6-(methoxymethoxy)naphthalen-1-yl)butanoate (0.18 g, 0.25 mmol, 65% yield over two steps). m/z (ESI): 711.2 $(M+H)^+$.

Step 4: (R)-4-(8-(4-(3-Amino-3-methylpiperidin-1-yl)-8-fluoro-2-methoxypyrido[4,3-d]pyrimidin-7-yl)-2-fluoro-6-(methoxymethoxy)naphthalen-1-yl)butanoic acid. To a solution of ethyl 4-(8-(4-((R)-3-amino-3-methylpiperidin-1-yl)-8-fluoro-2-(((2S,4R)-4-fluoro-1-methylpyrrolidin-2-yl)methoxy)pyrido[4,3-d]pyrimidin-7-yl)-2-fluoro-6-(methoxymethoxy)naphthalen-1-yl)butanoate (0.18 g, 0.25 mmol) in a mixture of solvents of tetrahydrofuran (1.2 mL), methanol (1 mL) and water (0.4 mL) was added lithium hydroxide monohydrate (31 mg, 0.74 mmol). The reaction mixture was stirred at rt for 2 h. The reaction was then quenched with 4 N HCl in dioxane (0.18 mL, 0.72 mmol) and concentrated to dryness to yield (R)-4-(8-(4-(3-amino-3-methylpiperidin-1-yl)-8-fluoro-2-methoxypyrido[4,3-d]pyrimidin-7-yl)-2-fluoro-6-(methoxymethoxy)naphthalen- 1-yl)butanoic acid which was used directly in the following step. m/z (ESI): 582.2 $(M+H)^+$.

Step 5: (15R)-22,31-Difluoro-27-hydroxy-8-methoxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate). To a solution of (R)-4-(8-(4-(3-amino-3-methylpiperidin-1-yl)-8-fluoro-2-methoxypyrido[4,3-d]pyrimidin-7-yl)-2-fluoro-6-(methoxymethoxy)naphthalen-1-yl)butanoic acid (0.17 g, 0.25 mmol) in N,N-dimethylformamide (30 mL) were added HATU (0.19 g, 0.49 mmol), followed by DIPEA (0.22 mL, 1.23 mmol) dropwise. The reaction was stirred at rt for 30 min. Water was added and the aqueous phase was extracted with EtOAc, and the organic phase was concentrated. The residue was redissolved in acetonitrile (2 mL) and 4 N HCl in dioxane (2 mL) was added. After 30 min, the volatiles were removed in vacuo and the crude was purified by reverse phase HPLC to provide (15R)-22,31-difluoro-27-hydroxy-8-methoxy-15-methyl-3,7,9,11,16 pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (9 mg, 0.012 mmol, 5% yield) as white solid. m/z (ESI): 520.2 $(M+H)^+$. $^1H$ NMR (400 MHz, METHANOL-$d_4$) δ ppm 9.41 (s, 1H), 7.71 (dd, J=8.88, 5.75 Hz, 1H), 7.34 (s, 2H), 7.23-7.33 (m, 2H), 5.92 (br d, J=13.59 Hz, 1H), 5.21 (br d, J=11.71 Hz, 1H), 4.19 (s, 3H), 3.78 (d, J=13.80 Hz, 1H), 3.10-3.25 (m, 1H), 2.66-2.70 (m, 1H), 2.19-2.28 (m, 1H), 2.02-2.11 (m, 2H), 1.77-1.96 (m, 6H), 1.65-1.72 (m, 2H), 1.40 (s, 3H), 1.29 (br d, J=13.38 Hz, 1H). $^{19}F$ NMR (376 MHz, METHANOL-$d_4$) δ ppm −77.38 (s, 18 F), −118.26 (s, 1 F), −140.41 (s, 1 F).

(15R)-22,31-Difluoro-8-(((2R,7aS)-2-fluorotetrahydro-1H-pyrrolo[1,2-a]pyrrol-7a(5H)-yl)methoxy)-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 7)

Example 7

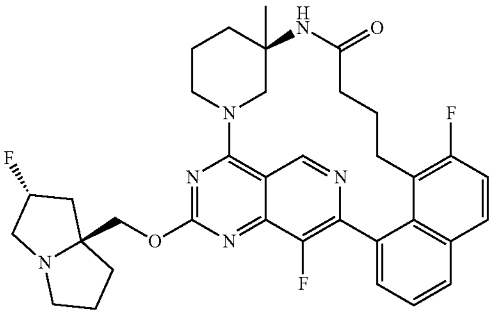

The title compound was prepared in an analogous manner to Example 1 using tert-butyl N-[(3R)-3-methylpiperidin-3-yl]carbamate (CAS #: 1169762-18-8, Pharmablock, Inc.) as the amine in step 1, and Intermediate C as the boronic ester in the Suzuki coupling reaction in step 2. m/z (ESI): (M+H)+ 631.2. $^1H$ NMR (500 MHz, METHANOL-$d_4$) δ ppm 9.26 (s, 1H), 8.04 (dd, J=8.2, 1.2 Hz, 1H), 7.92 (dd, J=8.9, 5.8 Hz, 1H), 7.70 (d, J=6.4 Hz, 1H), 7.60 (dd, J=8.0, 7.1 Hz, 1H), 7.29-7.36 (m, 2H), 5.86 (br d, J=13.9 Hz, 1H), 5.27-5.42 (m, 1H), 5.06 (br d, J=12.2 Hz, 1H), 4.37 (d, J=10.6 Hz, 1H), 4.24 (d, J=10.8 Hz, 1H), 3.63 (d, J=14.0 Hz, 1H), 3.35-3.40 (m, 1H), 3.24-3.30 (m, 1H), 3.15 (td, J=12.6, 2.1 Hz, 1H), 3.08 (br d, J=5.3 Hz, 1H), 2.74-2.82 (m, 1H), 2.35 (br s, 3 H), 2.18 (br s, 1H), 2.05 (s, 4H), 1.86-1.99 (m, 2H), 1.77-1.86 (m, 3H), 1.64-1.71 (m, 2H), 1.36-1.40 (m, 3H). $^{19}F$ NMR (471 MHz, METHANOL-$d_4$) δ ppm −77.35−−77.29 (m), −114.25−−114.20 (m), −141.67 (br s), −174.16−−174.09 (m). Stereochemistry of Example 7 was confirmed by X-Ray crystallography analysis.

(15R)-32-Fluoro-8-(((2R,7aS)-2-fluorotetrahydro-1H-pyrrolo[1,2-a]pyrrol-7a(5H)-yl)methoxy)-28-hydroxy-15-methyl-3,7,9,11,16-pentaazahexacyclo[20.7.1.1~2,6~.1~11,15~.0~5,10~.0~26,30~]dotriaconta-1(29),2(32),3,5,7,9,22,24,26(30),27-decaen-17-one (2,2,2-trifluoroacetate) salt (Example 8)

Example 8

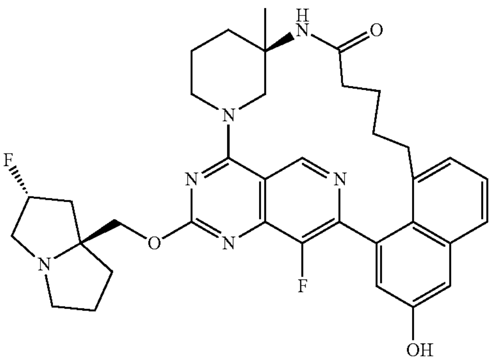

The title compound was prepared in an analogous manner to Example 3 using tert-butyl N-[(3R)-3-methylpiperidin-3-yl]carbamate (CAS #: 1169762-18-8, Pharmablock, Inc.) as the amine in step 1, and Intermediate E as the boronic ester in the Suzuki coupling reaction in step 3. m/z (ESI): 643.2 $(M+H)^+$. $^1H$ NMR (400 MHz, METHANOL-$d_4$) δ ppm 9.20-9.38 (m, 1H), 7.61-7.76 (m, 1H), 7.34-7.39 (m, 1H), 7.31-7.33 (m, 1H), 7.25-7.29 (m, 1H), 7.18-7.22 (m, 1H), 7.13-7.16 (m, 1H), 5.82-5.92 (m, 1H), 5.53-5.72 (m, 1H), 5.03-5.17 (m, 2H), 4.60-4.75 (m, 1H), 3.85-4.16 (m, 3H), 3.62-3.73 (m, 1H), 3.42-3.56 (m, 1H), 3.11-3.25 (m, 1H), 2.61-2.76 (m, 3H), 2.29-2.51 (m, 4H), 2.04-2.27 (m, 2H), 1.67-1.99 (m, 5H), 1.54-1.67 (m, 2H), 1.34-1.52 (m, 4H), 1.08-1.31 (m, 1H), 0.68-0.97 (m, 1H). $^{19}F$ NMR (376 MHz, METHANOL-$d_4$) δ ppm −77.18 (br s), −138.83 (s), −174.15 (s).

32-Fluoro-4-(((2R,7aS)-2-fluorotetrahydro-1H-pyrrolo[1,2-a]pyrrol-7a(5H)-yl)methoxy)-13-hydroxy-1,3,5,9,25-pentaazahexacyclo[23.3.2.1~6,10~.1~11,15~.0~2,7~.0~19,31~]dotriaconta-2,4,6(32),7,9,11(31),12,14,16,18-decaen-24-one bis(2,2,2-trifluoroacetate) (Example 9)

Example 9

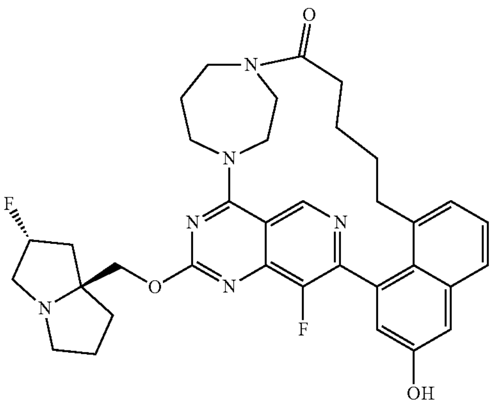

The title compound was synthesized in an analogous fashion to Example 3, using tert-butyl 1,4-diazepane-1-carboxylate (CAS #: 112275-50-0, Oakwood Chemical) in Step 1 and using Intermediate E as the boronic ester in the Suzuki coupling reaction in step 3. m/z (ESI): 629.0 $(M+H)^+$. $^1H$ NMR (400 MHz, METHANOL-$d_4$) δ ppm 9.32 (s, 1H), 7.65 (d, J=8.15 Hz, 1H), 7.29-7.39 (m, 2H), 7.12-7.25 (m, 2H), 6.58-6.59 (m, 1H), 5.47-5.72 (m, 1H), 5.09 (br d, J=13.38 Hz, 1H), 4.84-4.96 (m, 1H), 4.61-4.76 (m, 2H), 4.47 (br d, J=13.59 Hz, 1H), 4.07-4.26 (m, 3H), 3.98-4.05 (m, 1H), 3.84-3.96 (m, 2H), 3.61-3.76 (m, 1H), 3.42-3.59 (m, 2H), 2.90-2.99 (m, 1H), 2.56-2.82 (m, 2H), 2.26-2.52 (m, 4H), 1.95-2.22 (m, 7H), 1.76 (br d, J=14.21 Hz, 1H), 1.51-1.67 (m, 2H), 1.27-1.45 (m, 1H). $^{19}F$ NMR (376 MHz, METHANOL-$d_4$) 6 ppm −77.26 (br s), −139.92 (d, J=9.54 Hz), −174.01 (s).

(14R)-21,30-Difluoro-8-(((2R,7aS)-2-fluorotetrahydro-1H-pyrrolo[1,2-a]pyrrol-7a(5H)-yl)methoxy)-26-hydroxy-14-methyl-3,7,9,11,15-pentaazahexacyclo[18.7.1.1~2,6~.1~11,14~.0~5,10~.0~24,28~]triaconta-1(27),2(30),3,5,7,9,20,22,24(28),25-decaen-16-one 2,2,2-trifluoroacetate salt (Example 10)

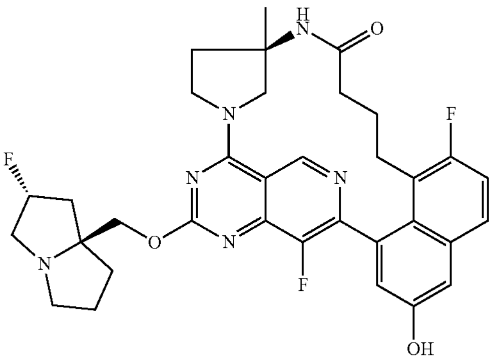 [SMILES: C[C@@]12CCN(C1)c1nc(OC[C@@]34CCCN3C[C@H](F)C4)nc3c(F)c(ncc13)-c1cc(O)cc3ccc(F)c(c13)CCCC(=O)N2]

The title compound was synthesized in an analogous fashion to Example 3, using tert-butyl (R)-(3-methylpyrrolidin-3-yl) carbamate (CAS #: 167888-15-5, Ambeed) in Step 1 and Intermediate D as the boronic ester in the Suzuki coupling reaction in step 3. m/z (ESI): (M+H)+633.0. $^1H$ NMR (400 MHz, METHANOL-$d_4$) δ ppm 9.21 (s, 1H), 7.70 (dd, J=9.0, 5.9 Hz, 1H), 7.31-7.35 (m, 2H), 7.23 (t, J=9.7 Hz, 1H), 5.51-5.67 (m, 1H), 5.40-5.48 (m, 1H), 4.96-5.04 (m, 1H), 4.72-4.77 (m, 1H), 4.63-4.69 (m, 1H), 3.96-4.09 (m, 1H), 3.88-3.95 (m, 2H), 3.55-3.64 (m, 2H), 3.46-3.54 (m, 1H), 2.66-2.81 (m, 1H), 2.57-2.65 (m, 1H), 2.34-2.44 (m, 3H), 1.92-2.22 (m, 7H), 1.71-1.79 (m, 1H), 1.53-1.56 (m, 3H). $^{19}F$ NMR (376 MHz, METHANOL-$d_4$) δ ppm −77.25 (s), −117.52-−117.12 (m), −142.80-−142.49 (m), −174.13 (s).

(15R,18R)-18,22,31-Trifluoro-8-(((2R,7aS)-2-fluorotetrahydro-1H-pyrrolo[1,2-a]pyrrol-7a(5H)-yl)methoxy)-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one and (15R,18S)-18,22,31-trifluoro-8-(((2R,7aS)-2-fluorotetrahydro-1H-pyrrolo[1,2-a]pyrrol-7a(5H)-yl)methoxy)-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 11)

Example 11

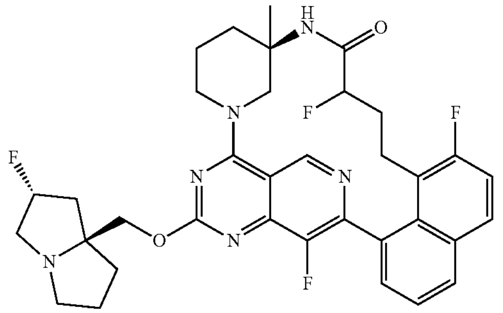

The title compound was prepared in an analogous manner to Example using tert-butyl N-[(3R)-3-methylpiperidin-3-yl] carbamate (CAS #: 1169762-18-8, Pharmablock, Inc.) as the amine in step 1, and Intermediate H as the boronic ester in the Suzuki coupling reaction in step 3. m/z (ESI): (M+H)+ 648.8. $^1H$ NMR (400 MHz, METHANOL-$d_4$) δ ppm 9.34 (d, J=10.9 Hz, 1H), 8.01-8.21 (m, 2H), 7.94-8.00 (m, 1H), 7.55-7.84 (m, 3H), 7.33-7.54 (m, 2H), 5.72-5.92 (m, 1H), 5.49-5.67 (m, 1H), 5.04-5.13 (m, 1H), 4.57-4.74 (m, 3H), 4.30-4.48 (m, 1H), 3.84-4.07 (m, 4H), 3.70-3.76 (m, 1H), 3.43-3.52 (m, 1H), 3.17-3.26 (m, 1H), 2.70-2.80 (m, 1H), 2.59-2.65 (m, 2H), 2.33-2.46 (m, 3H), 2.10-2.22 (m, 2H), 2.01-2.07 (m, 1H), 1.84-1.95 (m, 2H), 1.67-1.78 (m, 2H), 1.41-1.45 (m, 3H). $^{19}F$ NMR (376 MHz, METHANOL-$d_4$) δ ppm −77.25 (s), −115.06 (s), −141.40 (s), −174.11 (s), −183.56 (s).

(15R,18R)-18,22,31-trifluoro-8-(((2R,7aS)-2-fluoro-tetrahydro-1H-pyrrolo[1,2-a]pyrrol-7a(5H)-yl) methoxy)-15-methyl-3,7,9,11,16-pentaazahexacyclo [19.7.1.1~2,6~.1~11,15~.0~5,10~.0~25,29~] hentriaconta-1(28),2(31),3,5,7,9,21,23,25(29),26-decaen-17-one (Example 2) and (15R,18S)-18,22,31-trifluoro-8-(((2R,7aS)-2-fluorotetrahydro-1H-pyrrolo[1,2-a]pyrrol-7a(5H)-yl)methoxy)-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (Example 12)

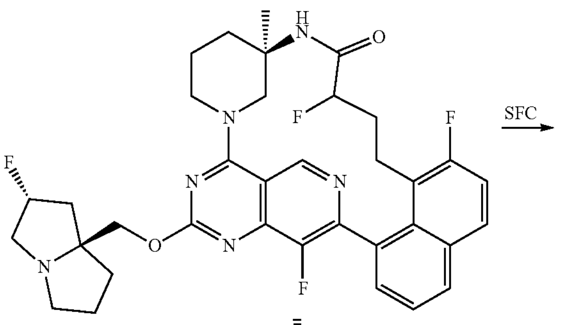

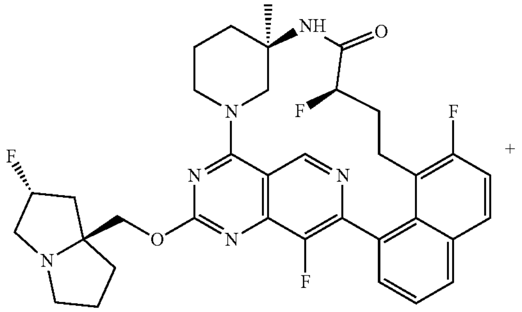

+

Example 2

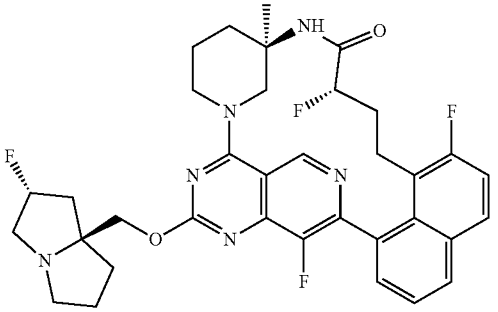

Example 12

Material from Example 11 (55 mg) was separated by SFC using Daicel Chiralpak IG column (250 mm×30 mm, 10 mm), with mobile phase (A for C02 and B for EtOH (0.1% $NH_{40}H$), gradient 50% B isocratic elution mode), flow rate of 65 m/min, monitor wavelength of 220 nm & 254 nm, column temperature at 40° C., system back pressure at 100 bar. The $1^{st}$ eluent was Example 2 (8.2 mg, 0.013 mmol) obtained as off-white solid. $^1H$ NMR (400 MHz, METHANOL-$d_4$) δ ppm 9.24 (s, 1H), 8.03 (d, J=7.2 Hz, 1H), 7.91-7.93 (m, 1H), 7.68 (d, J=6.8 Hz, 1H), 7.59-7.61 (t, 1H), 7.31-7.35 (t, 1H), 5.71 (d, J=14.4 Hz, 1H), 5.27 (d, J=53.2 Hz, 1H), 5.01 (d, J=28 Hz, 1H), 4.34-4.44 (m, 1H), 4.15-4.30 (m, 2H), 3.68 (d, J=14.4 Hz, 1H), 3.19-3.22 (m, 4H), 2.90-3.00 (m, 1H), 2.60-2.80 (m, 2H), 2.05-2.30 (m, 5H), 1.80-2.00 (m, 5H), 1.65 (d, J=20 Hz, 1H), 1.41 (s, 3H), 1.29-1.32 (m, 1H). The $2^{nd}$ eluent was Example 12 (39 mg, 0.061 mmol) obtained as off-white solid. $^1H$ NMR (400 MHz, METHANOL-$d_4$) δ ppm 9.25 (s, 1H), 8.01 (d, J=6.8 Hz, 1H), 7.92-7.93 (m, 1H), 7.66 (d, J=6.4 Hz, 1H), 7.58-7.60 (t, 1H), 7.31-7.36 (t, 1H), 5.81 (d, J=14.0 Hz, 1H), 5.26 (d, J=56.0 Hz, 1H), 5.00 (d, J=12 Hz, 1H), 4.55-4.70 (m, 1H), 4.15-4.31 (m, 2H), 3.67 (d, J=14.0 Hz, 1H), 3.19-3.22 (m, 4H), 2.90-3.00 (m, 1H), 2.50-2.70 (m, 2H), 1.82-2.16 (m, 10H), 1.65 (d, J=20 Hz, 1H), 1.39 (s, 3H), 1.21-1.23 (m, 1H). m/z (ESI): 649.3 $(M+H)^+$.

(15R)-31-Fluoro-8-(((2R,7aS)-2-fluorotetrahydro-1H-pyrrolo[1,2-a]pyrrol-7a(5H)-yl)methoxy)-15-methyl-3,7,9,11,16,21-hexaazahexacyclo[19.7.1.1~2,6~.1~11,15~.0~5,10~.0~25,29~]hentriaconta-1(29),2(31),3,5,7,9,25,27-octaen-17-one bis(2,2,2-trifluoroacetate) (Example 13)

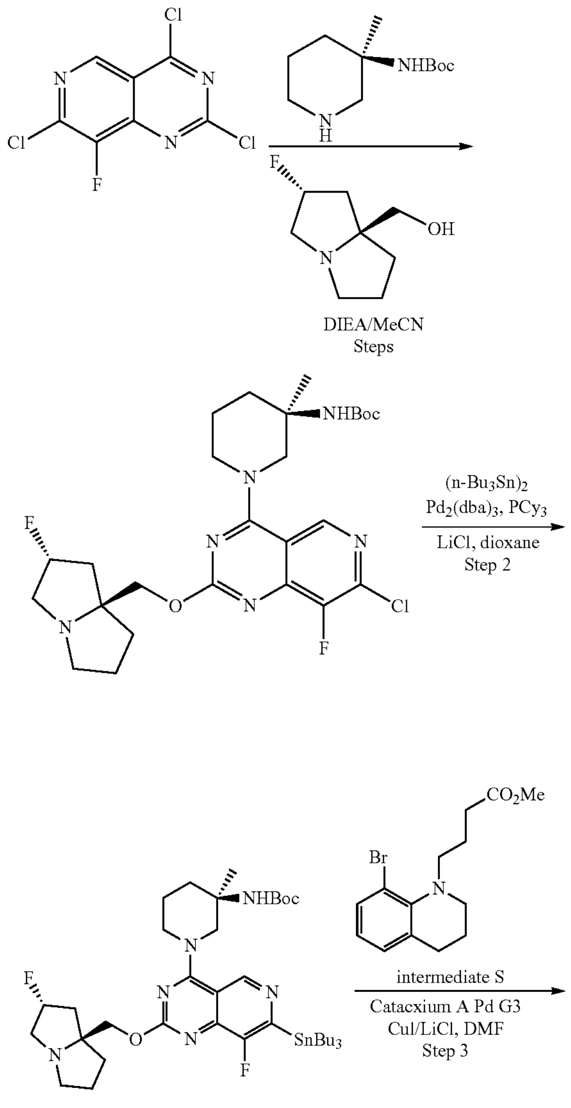

-continued

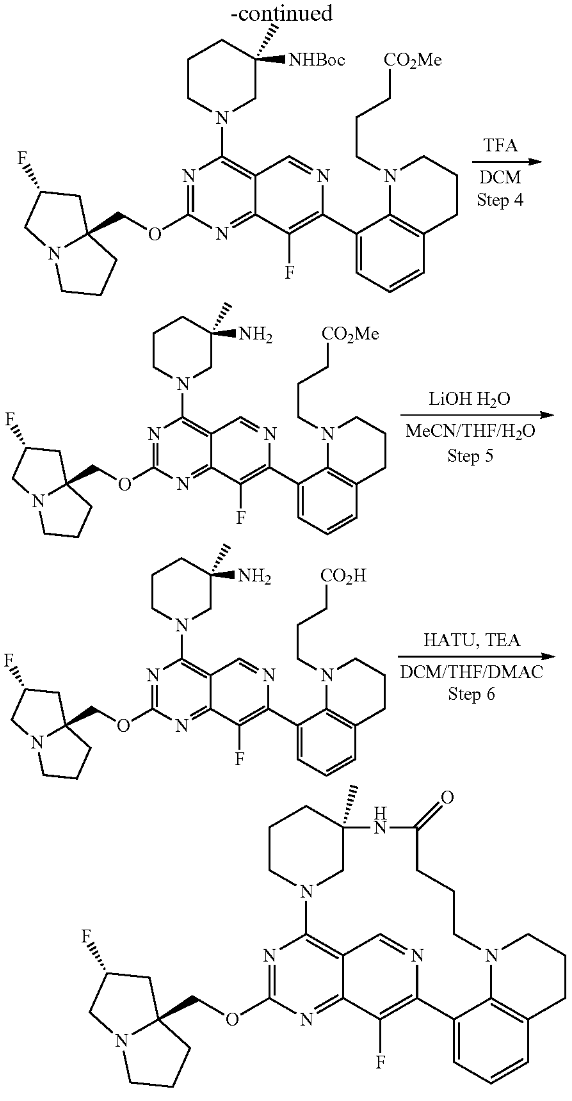

Example 13

Steps 1. tert-Butyl ((R)-1-(7-chloro-8-fluoro-2-(((2R,7aS)-2-fluorotetrahydro-1H-pyrrolizin-7a(5H1)-yl)methoxy)pyrido[4,3-d]pyrimidin-4-yl)-3-methylpiperidin-3-yl)carbamate. To a stirred solution of 2,4,7-trichloro-8-fluoropyrido[4,3-d]pyrimidine (2.00 g, 7.92 mmol, Enamine Inc.) and DIEA (4.10 g, 5.53 mL, 31.7 mmol) in acetonitrile (25 mL) cooled to 0° C. was added tert-butyl N-[(3R)-3-methylpiperidin-3-yl]carbamate (1.70 g, 7.92 mmol, Pharmablock, Inc.). The reaction was stirred at 0° C. for 20 min before ((2R,7aS)-2-fluorotetrahydro-1H-pyrrolizin-7a(5H)-yl)methanol (2.48 g, 12.7 mmol, Pharmablock, Inc.) was added. The resulting mixture was heated at 75° C. for 16 h. The volatiles were removed and the residue was purified by column chromatography on silica gel, eluting with 0-60% (20% MeOH/DCM with 1% TEA) in DCM, to provide tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-yl)carbamate (3.11 g, 5.62 mmol, 71% yield) as off-white solid. $^{1}$H NMR (CHLOROFORM-d, 400 MHz) δ ppm 8.78 (s, 1H), 5.1-5.5 (m, 2H), 4.63 (br d, 1H, J=13.2 Hz), 4.2-4.4 (m, 2H), 3.5-3.6 (m, 1H), 3.2-3.4 (m, 3H), 3.0-3.1 (m, 1H), 2.2-2.5 (m, 4H), 1.8-2.1 (m, 4H), 1.71 (qd, 1H, J=3.8, 17.9 Hz), 1.4-1.6 (m, 3H), 1.39 (s, 3H), 1.33 (s, 9H). $^{19}$F NMR (CHLOROFORM-d, 376 MHz) δ ppm −134.76 (br s), −174.1-−174.0 (in), −173.04 (br d, J=7.8 Hz). m/7 (ESI): 553.0 $(M+1)^+$.

Step 2. tert-Butyl ((R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-3-methylpiperidin-3-yl)carbamate. A mixture of tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-yl)carbamate (0.90 g, 1.63 mmol), tris(dibenzylideneacetone)-dipalladium(0) (0.22 g, 0.24 mmol), tricyclohexylphosphine (0.14 g, 0.49 mmol), and lithium chloride (0.35 g, 8.14 mmol) in 1,4-dioxane (12 mL) in a 10-mL microwave vessel was purged with nitrogen for 10 min before bis(tributyltin) (2.5 mL, 4.9 mmol) was introduced via a syringe. The vessel was sealed and subjected to microwave irradiation (4.5 h at 120° C.). After cooling to rt, the crude mixture was purified by column chromatography on silica gel, eluting with 0-20% (20% MeOH/DCM with 1% TEA) in DCM, to provide tert-butyl ((R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-3-methylpiperidin-3-yl)carbamate (1.00 g, 1.24 mmol, 76% yield) as colorless film. m/z (ESI): 809.4 $(M+H)^+$.

Step 3. Methyl 4-(8-(4-((R)-3-((tert-butoxycarbonyl)amino)-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoate. Into a 20-mL microwave reaction vessel were placed cataCXium A Pd G3 (0.16 g, 0.22 mmol), copper(I) iodide (0.11 g, 0.56 mmol), and lithium chloride (95 mg, 2.24 mmol), followed by a solution of tert-butyl ((R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)-3-methylpiperidin-3-yl)carbamate (1.04 g, 1.29 mmol) and methyl 4-(8-bromo-3,4-dihydroquinolin-1(2H)-yl)butanoate (0.35 g, 1.12 mmol, Intermediate S) in DMF (12 mL). The mixture was purged with nitrogen for 10 min before the vessel was sealed and subjected to microwave irradiation (16 h at 84° C.). The crude was purified by column chromatography on silica gel, eluting with 0-20% (20% MeOH/DCM with 1% TEA) in DCM, to provide methyl 4-(8-(4-((R)-3-((tert-butoxycarbonyl)amino)-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoate, which was taken onto the next step without further purification. m/z (ESI): 750.0 $(M+H)^+$.

Step 4. Methyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoate. To a stirred solution of methyl 4-(8-(4-((R)-3-((tert-butoxycarbonyl)amino)-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoate (0.50 g, 0.67 mmol) in DCM (10 mL) was added 2,2,2-trifluoroacetic acid (8.0 mL, 0.67 mmol). The resulting mixture was stirred at rt for 1 h. The volatiles were removed and the residue was dissolved in DCM and passed through a silica gel precolumn covered with a layer of sodium carbonate, and purified by column chromatography on silica gel, eluting with 0-20% (20% MeOH/DCM with 1% TEA) in DCM, to give methyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3, 4-dihydroquinolin-1(2H)-yl)butanoate as colorless film, which was taken onto the next step without further purification. m/z (ESI): 650.2 (M+H)+.

Step 5. 4-(8-(4-((R)-3-Amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoic acid. A mixture of methyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoate (0.35 g, 0.54 mmol) and excess lithium hydroxide monohydrate in acetonitrile (10 mL), THF (5 mL), and water (5 mL) was stirred at 50° C. for 40 min. After cooling to rt, the volatiles were removed in vacuo and the residue was azetroped with toluene to give crude 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoic acid as off-white solid, which was used in the next step without purification. m/z (ESI): 636.0 (M+H)+.

Step 6. (15R)-31-Fluoro-8-(((2R,7aS)-2-fluorotetrahydro-1H-pyrrolo[1,2-a]pyrrol-7a(5H)-yl)methoxy)-15-methyl-3,7,9,11,16,21-hexaazahexacyclo[19.7.1.1~2,6~.1~11,15~.0~5,10~.0~25,29~]hentriaconta-1(29),2(31),3,5,7,9,25,27-octaen-17-one bis(2,2,2-trifluoroacetate). To a stirred suspension/solution of 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-3,4-dihydroquinolin-1(2H)-yl)butanoic acid (75 mg, 0.12 mmol) in a mixed solvent of DCM (100 mL), THF (20 mL), and N,N-dimethylacetamide (2 mL) was added excess HATU, followed by TEA (3 mL, 22 mmol). The resulting mixture was stirred at rt for 0.5 h. The volatiles were removed and the crude residue was purified by column chromatography on silica gel, eluting with 0-20% (20% MeOH/DCM with 1% TEA) in DCM, followed by reverse phase HPLC, to provide (15R)-31-fluoro-8-(((2R,7aS)-2-fluorotetrahydro-1H-pyrrolo[1,2-a]pyrrol-7a(5H)-yl)methoxy)-15-methyl-3,7,9,11,16,21-hexaazahexacyclo[19.7.1.1~2,6~.1~11,15~.0~5,10~.0~25,29~]hentriaconta-1(29),2(31),3,5,7,9,25,27-octaen-17-one bis(2,2,2-trifluoroacetate) (24 mg, 0.039 mmol, 33% yield) as light-yellow solid. $^1$H NMR (METHANOL-$d_4$, 400 MHz) δ 9.31 (s, 1H), 7.43 (d, 1H, J=7.5 Hz), 7.2-7.4 (m, 2H), 7.1-7.2 (m, 1H), 5.81 (br d, 1H, J=14.0 Hz), 5.5-5.7 (m, 1H), 5.07 (br d, 1H, J=12.3 Hz), 4.7-4.7 (m, 1H), 4.6-4.7 (m, 1H), 3.8-4.1 (m, 3H), 3.62 (d, 1H, J=14.0 Hz), 3.47 (dt, 1H, J=5.7, 10.7 Hz), 3.1-3.3 (m, 3H), 2.93 (br t, 2H, J=6.6 Hz), 2.5-2.8 (m, 3H), 2.3-2.5 (m, 3H), 2.1-2.2 (m, 1H), 1.6-2.0 (m, 9H), 1.30 (s, 3H), 0.87 (br d, 1H, J=3.3 Hz). $^{19}$F NMR (METHANOL-$d_4$, 376 MHz) δ −139.32 (br s, 1F), −174.12 (s, 1F). m/z (ESI): 618.0 (M+H)+.

(15R)-22,31-Difluoro-27-hydroxy-8,15-dimethyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate (Example 14)

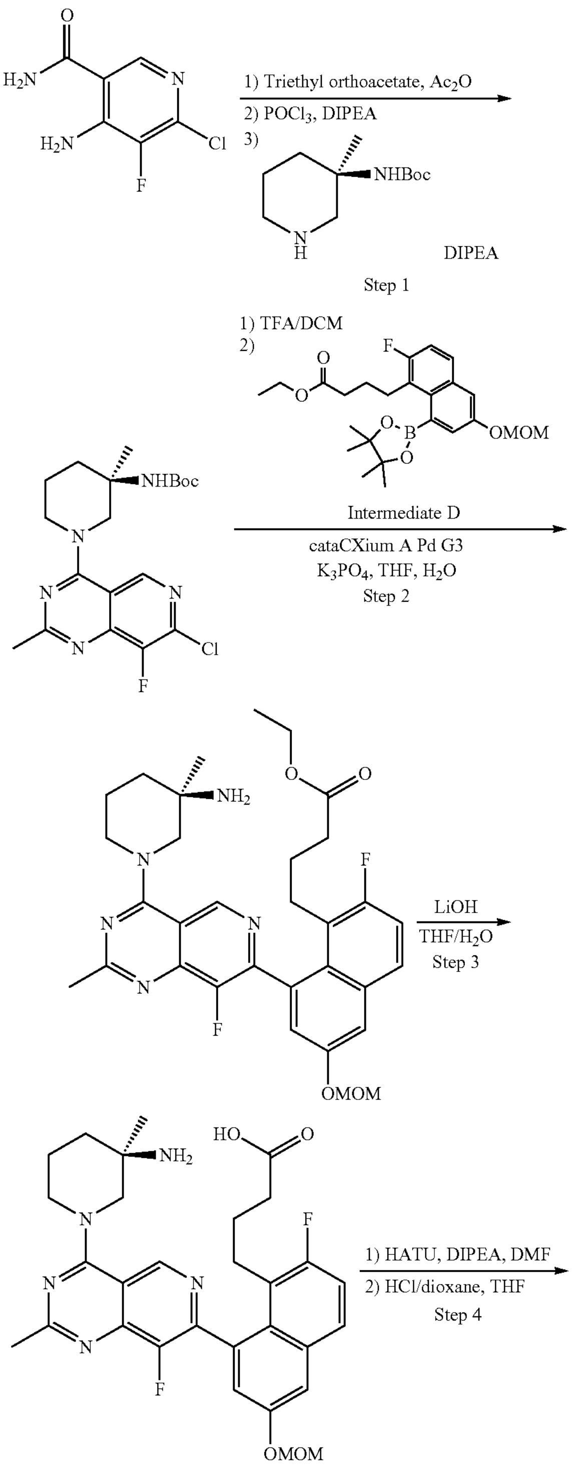

-continued

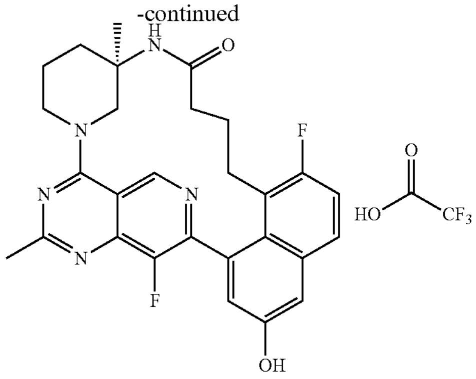

Example 14

Step 1. tert-Butyl (R)-(1-(7-chloro-8-fluoro-2-methylpyrido[4,3-d]pyrimidin-4-yl)-3-methylpiperidin-3-yl)carbamate. 4-Amino-6-chloro-5-fluoronicotinamide (0.10 g, 0.53 mmol) was suspended in acetic anhydride (1.0 mL), triethyl orthoacetate (1.9 mL, 10.6 mmol) was added and the mixture was stirred in a microwave reactor at 135° C. for 10 h. After cooling to rt, the mixture was purified by reverse phase HPLC to provide 7-chloro-8-fluoro-2-methylpyrido[4,3-d]pyrimidin-4(3H)-one (33 mg, 0.15 mmol, 29% yield), which was resuspended in MeCN (1.0 mL) and DIPEA (0.1 mL, 0.58 mmol) was added. The reaction mixture was cooled to 0° C., phosphorous oxychloride (0.05 mL, 0.48 mmol) was added dropwise, and the mixture was heated to 80° C. for 1 h. Volatiles were removed in vacuo, the residue was coevaporated with toluene and resuspended in MeCN (1.0 mL). DIPEA (0.1 mL, 0.58 mmol) and tert-butyl N-[(3R)-3-methylpiperidin-3-yl]carbamate (0.11 g, 0.53 mmol) was added and the mixture was stirred at rt for 1 h. Volatiles were removed in vacuo and the residue was purified via column chromatography on silica gel, eluting with a gradient of 0-100% (EtOAc:EtOH 3:1+2% $NEt_3$) in heptane, to provide tert-butyl (R)-(1-(7-chloro-8-fluoro-2-methylpyrido[4,3-d]pyrimidin-4-yl)-3-methylpiperidin-3-yl)carbamate (50 mg, 0.12 mmol, 23% yield). m/z (ESI): $(M+H)^+$ 410.0.

Step 2. Ethyl (R)-4-(8-(4-(3-amino-3-methylpiperidin-1-yl)-8-fluoro-2-methylpyrido[4,3-d]pyrimidin-7-yl)-2-fluoro-6-(methoxymethoxy)naphthalen-1-yl)butanoate. tert-Butyl (R)-(1-(7-chloro-8-fluoro-2-methylpyrido[4,3-d]pyrimidin-4-yl)-3-methylpiperidin-3-yl)carbamate (50 mg, 0.12 mmol) was dissolved in DCM (1 mL) and TFA (0.3 mL) was added. The mixture was stirred at rt for 3h, saturated $NaHCO_3$(20 mL) was added, and the aqueous phase was extracted with DCM (2×20 mL). combined organic layers were dried over $Na_2SO_4$, filtered and volatiles were removed in vacuo. Resulting (R)-1-(7-chloro-8-fluoro-2-methylpyrido[4,3-d]pyrimidin-4-yl)-3-methylpiperidin-3-amine, cataCXium A Pd G3 (18 mg, 0.024 mmol, Sigma-Aldrich Corporation), phosphoric acid (potassium) (78 mg, 0.37 mmol, Combi-Blocks Inc.) and ethyl 4-(2-fluoro-6-(methoxymethoxy)-8-(4,4,5,5-tetramethyl-1,3,2-dioxaborolan-2-yl)naphthalen-1-yl)butanoate (82 mg, 0.18 mmol, Intermediate D) were dissolved in water (0.12 mL)/THF (1.2 mL) and degassed for 10 minutes. The mixture was then heated to 80° C. for 1.5 h. Volatiles were removed in vacuo and the crude material was purified via reverse phase column chromatography (10-100% $MeCN/H_2O$+0.1% TFA) to yield ethyl (R)-4-(8-(4-(3-amino-3-methylpiperidin-1-yl)-8-fluoro-2-methylpyrido[4,3-d]pyrimidin-7-yl)-2-fluoro-6-(methoxymethoxy)naphthalen-1-yl)butanoate (70 mg, 0.12 mmol, 97% yield). m/z (ESI): $(M+H)^+$ 594.0.

Step 3. (R)-4-(8-(4-(3-Amino-3-methylpiperidin-1-yl)-8-fluoro-2-methylpyrido[4,3-d]pyrimidin-7-yl)-2-fluoro-6-(methoxymethoxy)naphthalen-1-yl)butanoic acid. Ethyl (R)-4-(8-(4-(3-amino-3-methylpiperidin-1-yl)-8-fluoro-2-methylpyrido[4,3-d]pyrimidin-7-yl)-2-fluoro-6-(methoxymethoxy)naphthalen-1-yl)butanoate (60 mg, 0.10 mmol) was dissolved in water (0.3 mL)/THF (0.8 mL) and stirred at 40° C. for 3 h. 1 M aqueous hydrochloric acid (0.5 mL, 0.5 mmol) was added to adjust the pH of the solution to 3-4. The mixture was purified via reverse phase column chromatography to yield (R)-4-(8-(4-(3-amino-3-methylpiperidin-1-yl)-8-fluoro-2-methylpyrido[4,3-d]pyrimidin-7-yl)-2-fluoro-6-(methoxymethoxy)naphthalen-1-yl)butanoic acid (18 mg, 0.03 mmol, 32% yield). m/z (ESI): $(M+H)^+$ 566.0.

Step 4. (15R)-22,31-Difluoro-27-hydroxy-8,15-dimethyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate salt. (R)-4-(8-(4-(3-amino-3-methylpiperidin-1-yl)-8-fluoro-2-methylpyrido[4,3-d]pyrimidin-7-yl)-2-fluoro-6-(methoxymethoxy)naphthalen-1-yl)butanoic acid (18 mg, 0.03 mmol) and HATU (24 mg, 0.06 mmol) were dissolved in DMF (8 mL) and stirred for 10 min. DIPEA (0.03 mL, 0.16 mmol) was added dropwise and the mixture was stirred at rt for 1 h. The reaction was quenched with the addition of water and saturated aqueous NaCl solution and the aqueous phase was extracted with EtOAc. The combined organic layers were dried over $Na_2SO_4$, filtered and volatiles were removed in vacuo. The residue was purified via reverse phase HPLC to provide (13R)-28,37-difluoro-33-(methoxymethoxy)-13,22-dimethyl-8-aza-2(4,7)-pyrido[4,3-d]pyrimidina-1(1,3)-piperidina-3(1,8)-naphthalenacyclooctaphan-7-one, which was dissolved in THF (1 mL) and treated with 4 M HCl/dioxane (1 mL). The mixture was stirred at rt for 3 h, volatiles were removed in vacuo and the residue was purified by reverse phase HPLC to provide (15R)-22,31-difluoro-27-hydroxy-8,15-dimethyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate (5.5 mg, 0.008 mmol, 28% yield). m/z (ESI): (M+H)+503.8. $^1H$ NMR (400 MHz, METHANOL-$d_4$) δ ppm 9.49 (s, 1H), 7.72 (dd, J=9.0, 5.6 Hz, 1H), 7.36 (br d, J=6.5 Hz, 4H), 5.94-6.05 (m, 1H), 5.42 (br d, J=12.1 Hz, 1H), 3.84 (d, J=13.8 Hz, 1H), 2.69 (s, 2H), 2.59-2.86 (m, 1H), 2.13-2.24 (m, 1H), 2.04-2.12 (m, 1H), 1.84-1.98 (m, 5H), 1.66-1.76 (m, 1H), 1.41 (s, 3H), 1.26-1.35 (m, 1H). $^{19}F$ NMR (376 MHz, METHANOL-$d_4$) δ ppm −77.09 (br s), −118.15 (s), −141.01 (s).

(15R)-3,22,31-Trifluoro-8-(((2R,7aS)-2-fluorotetrahydro-1H-pyrrolo[1,2-a]pyrrol-7a(5H)-yl)methoxy)-27-hydroxy-15-methyl-7,9,11,16-tetraazahexacyclo [19.7.1.1~2,6~.1~11,15~.0~5,10~.0~25,29~] hentriaconta-1(28),2(31),3,5,7,9,21,23,25(29),26-decaen-17-one bis(2,2,2-trifluoroacetate) (Example 15)

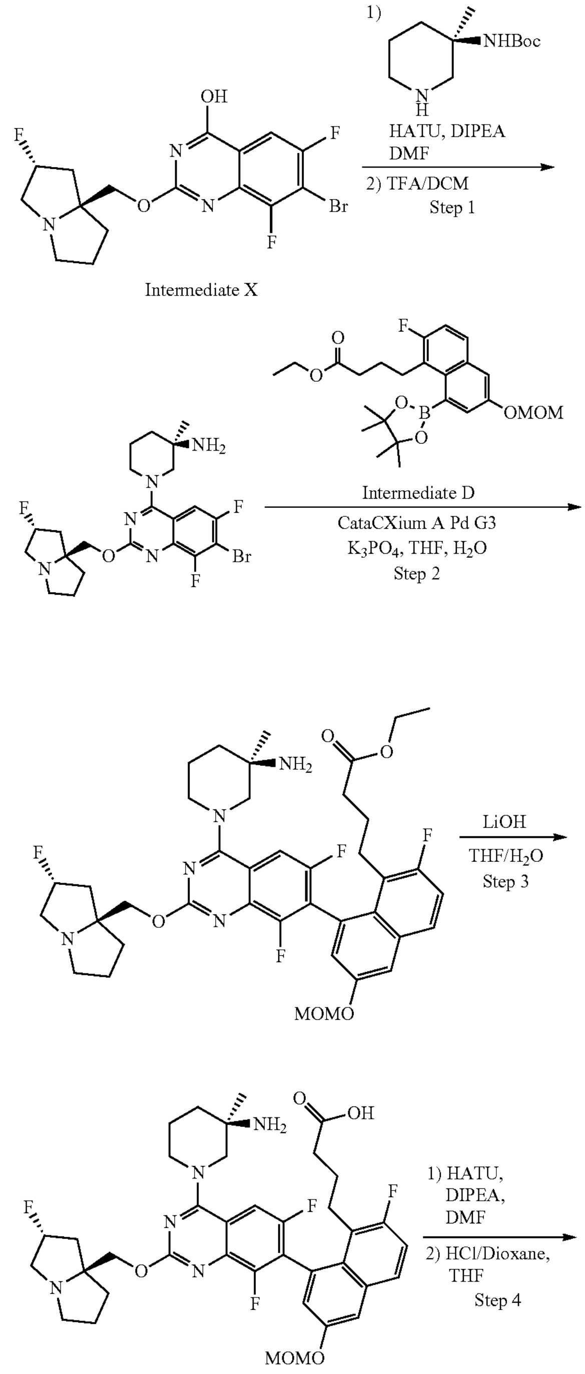

-continued

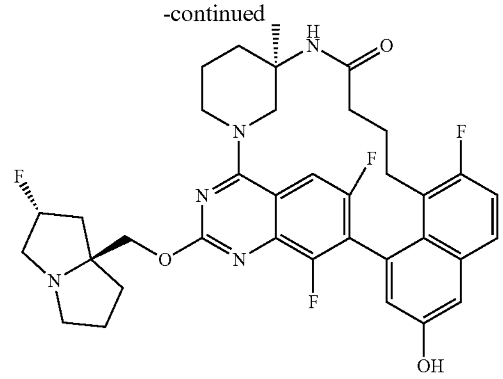

Example 15

Step 1. (R)-1-(7-Bromo-6,8-difluoro-2-(((2R,7aS)-2-fluorotetrahydro-1H-pyrrolizin-7a(5H)-yl)methoxy)quinazolin-4-yl)-3-methylpiperidin-3-amine. 7-Bromo-6,8-difluoro-2-(((2R,7aS)-2-fluorotetrahydro-1H-pyrrolizin-7a(5H)-yl)methoxy)quinazolin-4-ol (0.25 g, 0.60 mmol, Intermediate X) was dissolved in DMF (3 mL) and HATU (0.27 g, 0.72 mmol) and DIPEA (0.31 mL, 1.79 mmol) were added. The mixture was stirred at rt for 10 min and tert-butyl N-[(3R)-3-methylpiperidin-3-yl]carbamate (0.19 g, 0.90 mmol) was added. After stirring for 4 h at rt, water was added, and the aqueous layer was extracted with EtOAc. The combined organic layers were dried over $Na_2SO_4$, filtered and volatiles were removed in vacuo. The crude residue was purified via column chromatography on silica gel, eluting with a gradient of 0-100% (EtOAc:EtOH 3:1+2% $NEt_3$) in heptane to provide tert-butyl ((R)-1-(7-bromo-6,8-difluoro-2-(((2R,7aS)-2-fluorotetrahydro-1H-pyrrolizin-7a(5H)-yl)methoxy)quinazolin-4-yl)-3-methylpiperidin-3-yl)carbamate (0.24 g, 0.40 mmol, 65% yield), which was redissolved in DCM (5 mL) and treated with TFA (2.0 mL). The mixture was stirred at rt for 2 h, neutralized with saturated $NaHCO_3$ solution and extracted with DCM. The volatiles were removed in vacuo to provide (R)-1-(7-bromo-6,8-difluoro-2-(((2R,7aS)-2-fluorotetrahydro-1H-pyrrolizin-7a(5H)-yl)methoxy)quinazolin-4-yl)-3-methylpiperidin-3-amine (0.20 g, 0.39 mmol, 65% yield). m/z (ESI): $(M+H)^+$ 514.0.

Step 2: Ethyl 4-(8-(4-((R)-3-amino-3-methylpiperidin-1-yl)-6,8-difluoro-2-(((2R,7aS)-2-fluorotetrahydro-1H-pyrrolizin-7a(5H)-yl)methoxy)quinazolin-7-yl)-2-fluoro-6-(methoxymethoxy)naphthalen-1-yl)butanoate. Ethyl 4-(2-fluoro-6-(methoxymethoxy)-8-(4,4,5,5-tetramethyl-1,3,2-dioxaborolan-2-yl)naphthalen-1-yl)butanoate (0.19 g, 0.43 mmol, Intermediate D), (R)-1-(7-bromo-6,8-difluoro-2-(((2R,7aS)-2-fluorotetrahydro-1H-pyrrolizin-7a(5H)-yl)methoxy)quinazolin-4-yl)-3-methylpiperidin-3-amine (0.20 g, 0.39 mmol), potassium phosphate (0.25 g, 1.17 mmol) and cataCXium A Pd G3 (57 mg, 0.08 mmol) were dissolved in water (0.2 mL)/tetrahydrofuran (2.0 mL) and degassed for 10 min. The mixture was then stirred at 80° C. for 6 h. Volatiles were then removed in vacuo and the residue was purified via reverse phase column chromatography to provide ethyl 4-(8-(4-((R)-3-amino-3-methylpiperidin-1-yl)-6,8-difluoro-2-(((2R,7aS)-2-fluorotetrahydro-1H-pyrrolizin-7a(5H)-yl)methoxy)quinazolin-7-yl)-2-fluoro-6-(methoxymethoxy)naphthalen-1-yl)butanoate (0.11 g, 0.15 mmol, 38% yield). m/z (ESI): $(M+H)^+$ 754.2.

Step 3: 4-(8-(4-((R)-3-Amino-3-methylpiperidin-1-yl)-6,8-difluoro-2-(((2R,7aS)-2-fluorotetrahydro-1H-pyrrolizin-7a(5H)-yl)methoxy)quinazolin-7-yl)-2-fluoro-6-

(methoxymethoxy)naphthalen-1-yl)butanoic acid. Ethyl 4-(8-(4-((R)-3-amino-3-methylpiperidin-1-yl)-6,8-difluoro-2-(((2R,7aS)-2-fluorotetrahydro-1H-pyrrolizin-7a(5H)-yl) methoxy)quinazolin-7-yl)-2-fluoro-6-(methoxymethoxy) naphthalen-1-yl)butanoate (0.11 g, 0.15 mmol) was dissolved in water (0.3 mL), methanol (0.3 mL) and tetrahydrofuran (0.9 mL). Lithium hydroxide monohydrate (37 mg, 0.88 mmol) was added. The mixture was stirred at 40° C. for 3 h, then 1 N hydrochloric acid (0.88 mL, 0.88 mmol) was added, and volatiles were removed in vacuo. The mixture was purified via reverse phase HPLC to provide 4-(8-(4-((R)-3-amino-3-methylpiperidin-1-yl)-6,8-difluoro-2-(((2R,7aS)-2-fluorotetrahydro-1H-pyrrolizin-7a(5H)-yl) methoxy)quinazolin-7-yl)-2-fluoro-6-(methoxymethoxy) naphthalen-1-yl)butanoic acid (74 mg, 0.10 mmol, 69% yield). m/z (ESI): $(M+H)^+$726.2.

Step 4. (15R)-3,22,31-Trifluoro-8-(((2R,7aS)-2-fluorotetrahydro-1H-pyrrolo[1,2-a]pyrrol-7a(5H)-yl)methoxy)-27-hydroxy-15-methyl-7,9,11,16-tetraazahexacyclo [19.7.1.1~2,6~.1~11,15~.0~5,10~.0~25,29~]hentriaconta-1 (28),2(31),3,5,7,9,21,23,25(29),26-decaen-17-one bis(2,2,2-trifluoroacetate). 4-(8-(4-((R)-3-Amino-3-methylpiperidin-1-yl)-6,8-difluoro-2-(((2R,7aS)-2-fluorotetrahydro-1H-pyrrolizin-7a(5H)-yl)methoxy)quinazolin-7-yl)-2-fluoro-6-(methoxymethoxy)naphthalen-1-yl)butanoic acid (71 mg, 0.10 mmol) and HATU (74 mg, 0.2 mmol) were dissolved in DMF (20 mL). DIPEA (0.09 mL, 0.50 mmol) was added dropwise, and the mixture was stirred at rt for 90 min. Water and brine were added and the aqueous phase was extracted with EtOAc. The combined organic phases were dried over $Na_2SO_4$, filtered and volatiles were removed in vacuo. The residue was purified via column chromatography on silica gel, eluting with a gradient of 0-100% (20% MeOH/DCM+ 2% $NEt_3$) in DCM to provide (13R)-26,28,37-trifluoro-22-(((2R,7aS)-2-fluorotetrahydro-1H-pyrrolizin-7a(5H)-yl) methoxy)-33-(methoxymethoxy)-13-methyl-8-aza-2(4,7)-quinazolina-1(1,3)-piperidina-3(1,8)-naphthalenacyclooctaphan-7-one, which was redissolved in THF (1 mL) and treated with 4 M HCl/dioxane (1 mL). The mixture was stirred at rt for 4 h, volatiles were removed in vacuo and the residue was purified by reverse phase HPLC to provide (15R)-3,22,31-trifluoro-8-(((2R,7aS)-2-fluorotetrahydro-1H-pyrrolo[1,2-a]pyrrol-7a(5H)-yl)methoxy)-27-hydroxy-15-methyl-7,9,11,16-tetraazahexacyclo [19.7.1.1~2,6~.1~11,15~.0~5,10~.0~25,29~]hentriaconta-1 (28),2(31),3,5,7,9,21,23,25(29),26-decaen-17-one bis(2,2,2-trifluoroacetate) (12 mg, 0.013 mmol, 14% yield). m/z (ESI): (M+H)+664.2. $^1$H NMR (500 MHz, METHANOL-$d_4$) δ ppm 7.89-7.94 (m, 1H), 7.69 (dd, J=9.0, 5.8 Hz, 1H), 7.29 (d, J=2.6 Hz, 1H), 7.20-7.26 (m, 2H), 7.11 (d, J=2.6 Hz, 1H), 5.81 (br d, J=14.0 Hz, 1H), 5.50-5.63 (m, 1H), 5.04 (br d, J=12.5 Hz, 1H), 4.59-4.70 (m, 2H), 3.87 (br dd, J=16.7, 2.5 Hz, 3H), 3.57 (d, J=14.0 Hz, 1H), 3.41-3.48 (m, 1H), 3.14 (br d, J=2.2 Hz, 1H), 2.82-2.91 (m, 1H), 2.64-2.75 (m, 1H), 2.57-2.63 (m, 1H), 2.43-2.52 (m, 1H), 2.34 (br s, 3H), 1.97-2.17 (m, 3H), 1.74-1.89 (m, 3H), 1.59-1.70 (m, 2H), 1.38-1.41 (m, 3H). $^{19}$F NMR (471 MHz, METHANOL-$d_4$) δ ppm −77.33 (br s), −119.46--119.25 (m), −127.64--127.48 (m), −174.36--174.18 (m). Stereochemistry of Example 15 was confirmed by X-Ray crystallography analysis.

(15R)-22,31-Difluoro-8-(((2R,7aS)-2-fluorotetrahydro-1H-pyrrolo[1,2-a]pyrrol-7a(5H)-yl)methoxy)-27-hydroxy-15-methyl-7,9,11,16-tetraazahexacyclo [19.7.1.1~2,6~.1~11,15~.0~5,10~.0~25,29~] hentriaconta-1(28),2(31),3,5,7,9,21,23,25(29),26-decaen-17-one bis(2,2,2-trifluoroacetate) (Example 16)

Example 16

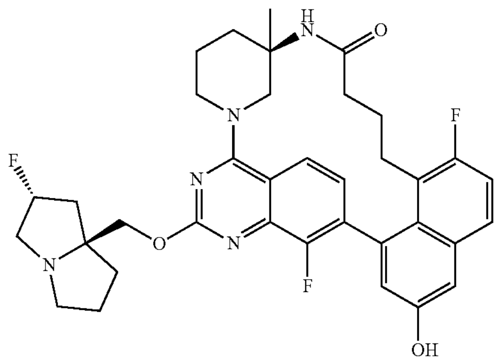

The title compound was synthesized in an analogous fashion to Example 15, using Intermediate Y and tert-butyl N-[(3R)-3-methylpiperidin-3-yl]carbamate (CAS #: 1169762-18-8, Pharmablock, Inc.) as the amine in Step 1 and Intermediate D as the boronic ester in the Suzuki coupling in Step 2.

m/z (ESI): (M+H)+646.3. $^1$H NMR (400 MHz, METHANOL-$d_4$) δ ppm 8.08 (d, J=8.9 Hz, 1H), 7.67 (dd, J=9.0, 5.7 Hz, 1H), 7.56-7.62 (m, 1H), 7.26 (s, 3H), 7.12 (d, J=2.5 Hz, 1H), 5.81-5.89 (m, 1H), 5.48-5.65 (m, 1H), 5.03-5.10 (m, 1H), 4.61-4.74 (m, 2H), 3.86 (br d, J=6.0 Hz, 3H), 3.61 (d, J=14.1 Hz, 1H), 3.40-3.49 (m, 1H), 3.14-3.23 (m, 1H), 2.59-2.82 (m, 3H), 2.30-2.44 (m, 4H), 1.96-2.17 (m, 3H), 1.79-1.89 (m, 2H), 1.67-1.78 (m, 2H), 1.57-1.66 (m, 1H), 1.37-1.41 (m, 3H). $^{19}$F NMR (376 MHz, METHANOL-$d_4$) δ ppm −77.24 (s), −119.39 (br d, J=6.9 Hz), −132.06--131.84 (m), −174.34 (s).

(15R,18R)-18,22,31-trifluoro-8-(((2R,7aS)-2-fluorotetrahydro-1H-pyrrolo[1,2-a]pyrrol-7a(5H)-yl) methoxy)-27-hydroxy-15-methyl-7,9,11,16-tetraazahexacyclo[19.7.1.1~2,6~.1~11,15~.0~5,10~.0~25, 29~]hentriaconta-1(28),2(31),3,5,7,9,21,23,25(29), 26-decaen-17-one and (15R,18S)-18,22,31-trifluoro-8-(((2R,7aS)-2-fluorotetrahydro-1H-pyrrolo[1,2-a] pyrrol-7a(5H)-yl)methoxy)-27-hydroxy-15-methyl-7,9,11,16-tetraazahexacyclo[19.7.1.1~2,6~.1~11, 15~.0~5,10~.0~25,29~]hentriaconta-1(28),2(31),3,5, 7,9,21,23,25(29),26-decaen-17-one 2,2,2-trifluoroacetate salt (Example 17)

Example 17

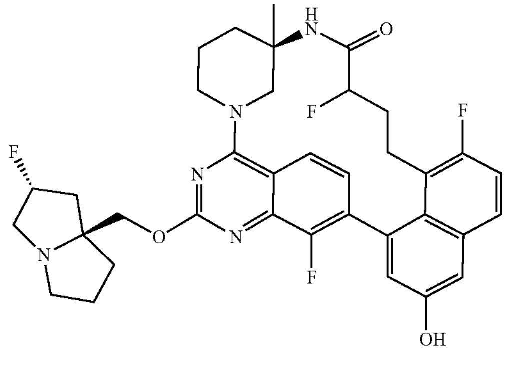

The title compound was synthesized in an analogous fashion to Example 15, using Intermediate Y and tert-butyl N-[(3R)-3-methylpiperidin-3-yl]carbamate (CAS #: 1169762-18-8, Pharmablock, Inc.) as the amine in Step 1 and Intermediate F as the boronic ester in the Suzuki coupling reaction in Step 2. m/z (ESI): $(M+H)^+$ 664.2. $^1H$ NMR (400 MHz, METHANOL-$d_4$) δ ppm 8.08 (t, J=8.4 Hz, 1H), 7.63-7.73 (m, 2H), 7.20-7.28 (m, 2H), 7.13 (dd, J=4.3, 2.6 Hz, 1H), 5.67-5.84 (m, 1H), 5.48-5.65 (m, 1H), 4.97-5.05 (m, 1H), 4.64-4.71 (m, 2H), 3.87-4.01 (m, 2H), 3.82-3.87 (m, 2H), 3.63-3.70 (m, 1H), 3.39-3.62 (m, 2H), 3.13-3.29 (m, 2H), 2.70-2.80 (m, 1H), 2.51-2.69 (m, 5H), 2.31-2.42 (m, 4H), 2.02-2.17 (m, 5H), 1.41-1.44 (m, 3H). $^{19}F$ NMR (376 MHz, METHANOL-$d_4$) δ ppm −77.24 (br s, 1 F), −120.09-−118.59 (m, 1 F), −132.48-−131.85 (m), −174.61-−174.13 (m), −182.49-−182.17 (m), −187.10-−186.75 (m).

(15R)-22-Fluoro-8-(((2R,7aS)-2-fluorotetrahydro-1H-pyrrolo[1,2-a]pyrrol-7a(5H)-yl)methoxy)-27-hydroxy-15,31-dimethyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (Example 18)

Example 18

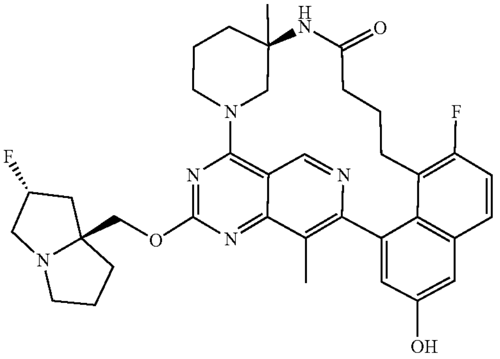

The title compound was synthesized in an analogous fashion to Example 3, using 2,4,7-trichloro-8-methyl-pyrido[4,3-d]pyrimidine (CAS #: 2454396-72-4, Pharmablock) and tert-butyl N-[(3R)-3-methylpiperidin-3-yl]carbamate (CAS #: 1169762-18-8, Pharmablock, Inc.) as the amine in Step 1 and Intermediate D as the boronic ester in the Suzuki coupling reaction in Step 3. m/z (ESI): 643.0 $(M+1)^+$. $^1H$ NMR (METHANOL-$d_4$, 400 MHz) δ 9.57 (s, 1H), 7.74 (dd, 1H, J=5.7, 8.9 Hz), 7.38 (s, 1H), 7.2-7.3 (m, 3H), 5.91 (br d, 1H, J=14.4 Hz), 5.5-5.7 (m, 1H), 5.24 (br d, 1H, J=12.3 Hz), 4.6-4.7 (m, 2H), 3.8-4.0 (m, 3H), 3.67 (d, 1H, J=14.0 Hz), 3.47 (dt, 1H, J=6.2, 10.6 Hz), 3.17 (br t, 1H, J=12.2 Hz), 2.5-2.8 (m, 3H), 2.3-2.5 (m, 3H), 2.0-2.3 (m, 3H), 1.7-2.0 (m, 8H), 1.6-1.6 (m, 1H), 1.2-1.4 (m, 4H). $^{19}F$ NMR (METHANOL-$d_4$, 376 MHz) δ −117.25 (s), −174.27 (s).

(15R)-22-Fluoro-8-(((2R,7aS)-2-fluorotetrahydro-1H-pyrrolo[1,2-a]pyrrol-7a(5H)-yl)methoxy)-27-hydroxy-31-methoxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (Example 19)

Example 19

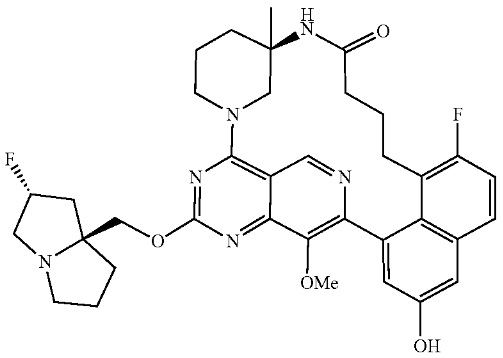

The title compound was synthesized in an analogous fashion to Example 3, using 2,4,7-trichloro-8-methoxy-pyrido[4,3-d]pyrimidine (CAS #: 2454491-03-1, Pharmablock) and tert-butyl N-[(3R)-3-methylpiperidin-3-yl]carbamate (CAS #: 1169762-18-8, Pharmablock, Inc.) as the amine in Step 1 and Intermediate D as the boronic ester in the Suzuki coupling reaction in Step 3. m/z (ESI): 659.0 $(M+1)^+$. $^1H$ NMR (METHANOL-$d_4$, 400 MHz) δ 9.37 (s, 1H), 7.70 (dd, 1H, J=5.7, 8.9 Hz), 7.36 (dd, 2H, J=2.5, 16.1 Hz), 7.2-7.3 (m, 2H), 5.91 (br d, 1H, J=14.0 Hz), 5.5-5.7 (m, 1H), 5.18 (br d, 1H, J=12.8 Hz), 4.6-4.7 (m, 3H), 3.8-4.0 (m, 3H), 3.68 (d, 1H, J=14.0 Hz), 3.4-3.5 (m, 1H), 3.32 (br s, 1H), 3.1-3.2 (m, 1H), 2.5-2.8 (m, 3H), 2.3-2.5 (m, 3H), 1.7-2.2 (m, 8H), 1.5-1.6 (m, 1H), 1.37 (s, 4H). $^{19}F$ NMR (METHANOL-$d_4$, 377 MHz) δ −118.05 (s), −174.37 (s).

(17R)-30-Fluoro-24-(((2R,7aS)-2-fluorotetrahydro-1H-pyrrolo[1,2-a]pyrrol-7a(5H)-yl)methoxy)-9,17-dimethyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one bis(2,2,2-trifluoroacetate) (Example 20)

Example 20

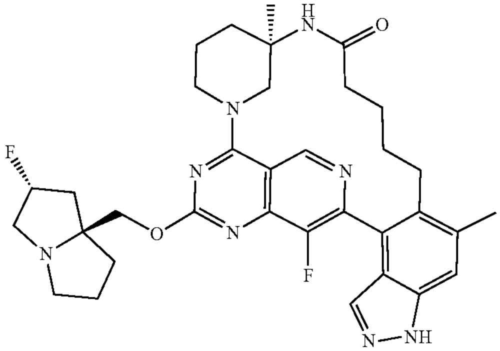

The title compound was synthesized in an analogous fashion to Example 3, using tert-butyl N-[(3R)-3-methylpiperidin-3-yl]carbamate (CAS #: 1169762-18-8, Pharmablock, Inc.) as amine in Step 1 and Intermediate J as the boronic ester in the Suzuki coupling reaction in Step 3. m/z (ESI): 631.2 $(M+H)^+$. $^1H$ NMR (400 MHz, METHANOL-$d_4$) δ ppm 9.30 (s, 1H), 7.81 (s, 1H), 7.53 (s, 1H), 5.63-5.71 (m, 1H), 5.52 (br s, 1H), 5.13 (br d, J=12.12 Hz, 1H), 4.66-4.78 (m, 2H), 3.80-4.11 (m, 4H), 3.65 (d, J=14.00 Hz, 1H), 3.44-3.52 (m, 1H), 3.14-3.23 (m, 1H), 2.59-2.74 (m, 4H), 2.56 (s, 3H), 2.33-2.52 (m, 5H), 2.16-2.27 (m, 1H), 1.98-2.10 (m, 1H), 1.67-1.95 (m, 4H), 1.42-1.64 (m, 3H), 1.41 (s, 3H), 1.28-1.35 (m, 1H), 1.19 (br dd, J=15.89, 10.87 Hz, 1H), 1.03-1.11 (m, 1H). $^{19}F$ NMR (376 MHz, METHANOL-$d_4$) δ ppm −77.21 (s), −141.35 (s), −174.05 (s). Stereochemistry of Example 20 was confirmed by X-Ray crystallography analysis.

(18R)-31-Fluoro-25-(((2R,7aS)-2-fluorotetrahydro-1H-pyrrolo[1,2-a]pyrrol-7a(5H)-yl)methoxy)-9,18-dimethyl-5,6,17,22,24,26,30-heptaazahexacyclo [25.3.1.1~18,22~0.0~2,10~0.0~3,7~0.0~23,28~] dotriaconta-1(31),2,4,7,9,23,25,27,29-nonaen-16-one (Example 21)

Example 21

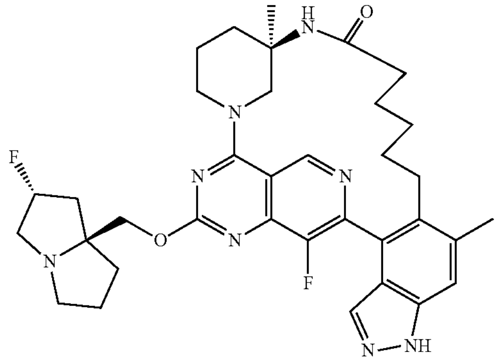

The title compound was synthesized in an analogous fashion to Example 1, using tert-butyl N-[(3R)-3-methylpiperidin-3-yl]carbamate (CAS #: 1169762-18-8, Pharmablock, Inc.) as the amine in Step 1. Intermediate I as the boronic ester in the Suzuki coupling reaction in Step 2. m/z (ESI): 645.2 $(M+H)^+$. $^1H$ NMR (400 MHz, METHANOL-$d_4$) δ ppm 9.20-9.38 (m, 1H), 7.61-7.76 (m, 1H), 7.34-7.39 (m, 1H), 7.31-7.33 (m, 1H), 7.25-7.29 (m, 1H), 7.18-7.22 (m, 1H), 7.13-7.16 (m, 1H), 5.82-5.92 (m, 1H), 5.53-5.72 (m, 1H), 5.03-5.17 (m, 2H), 4.60-4.75 (m, 1H), 3.85-4.16 (m, 3H), 3.62-3.73 (m, 1H), 3.42-3.56 (m, 1H), 3.11-3.25 (m, 1H), 2.61-2.76 (m, 3H), 2.29-2.51 (m, 4H), 2.04-2.27 (m, 2H), 1.67-1.99 (m, 5H), 1.54-1.67 (m, 2H), 1.34-1.52 (m, 4H), 1.08-1.31 (m, 1H), 0.68-0.97 (m, 1H). $^{19}F$ NMR (376 MHz, METHANOL-$d_4$) δ ppm −77.18 (br s), −139.11 (s), −173.96 (s).

(15R)-8-((1-((Dimethylamino)methyl)cyclopropyl)methoxy)-22,31-difluoro-27-hydroxy-15-methyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 22)

Example 22

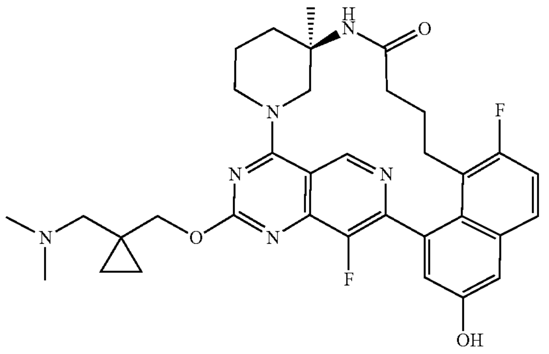

The title compound was synthesized in an analogous fashion to Example 3, tert-butyl N-[(3R)-3-methylpiperidin-3-yl] carbamate (CAS #: 1169762-18-8, Pharmablock, Inc.) as the amine and (1-[(dimethylamino)methyl]cyclopropyl)methanol (CAS #39943-41-4, Advanced ChemBlock) in Step 1 and Intermediate D as the boronic ester in the Suzuki coupling reaction in Step 3. m/z (ESI): $(M+H)^+$616.9. $^1H$ NMR (400 MHz, METHANOL-$d_4$) δ ppm 9.31 (s, 1H), 7.70 (dd, J=8.9, 5.8 Hz, 1H), 7.31-7.33 (m, 2H), 7.21-7.27 (m, 1H), 5.85-5.92 (m, 1H), 5.03-5.09 (m, 1H), 4.37-4.50 (m, 2H), 3.67 (d, J=13.9 Hz, 1H), 3.36-3.40 (m, 1H), 3.24-3.29 (m, 1H), 3.14-3.22 (m, 1H), 2.96 (s, 6H), 2.65-2.76 (m, 1H), 2.21-2.31 (m, 1H), 1.99-2.09 (m, 2H), 1.78-1.91 (m, 3H), 1.59-1.74 (m, 2H), 1.38 (s, 3H), 1.19-1.30 (m, 1H), 0.88-1.00 (m, 4H). $^{19}F$ NMR (376 MHz, METHANOL-$d_4$) 6 ppm −77.15 (s), −118.99--118.71 (m), −141.86--141.83 (m).

(15R)-23,32-Difluoro-8-(((2R,7aS)-2-fluorotetrahydro-1H-pyrrolo[1,2-a]pyrrol-7a(5H)-yl)methoxy)-28-hydroxy-15-methyl-3,7,9,11,16-pentaazahexacyclo[20.7.1.1~2,6~.1~11,15~.0~5,10~.0~26,30~] dotriaconta-1(30),2(32),3,5,7,9,22,24,26,28-decaen-17-one (Example 47)

Example 47

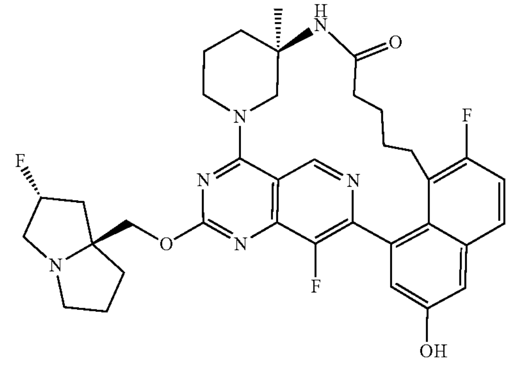

The title compound was synthesized in an analogous fashion to Example 15, using Intermediate CC as the boronic acid in Step 2. m/z (ESI): (M+H)+661.1. $^1$H NMR (400 MHz, DMSO-$d_6$) δ ppm 9.89 (s, 1H), 9.16 (s, 1H), 7.75 (dd, J=6.0, 9.1 Hz, 1H), 7.20-7.39 (m, 3H), 7.06 (d, J=2.6 Hz, 1H), 5.52 (d, J=13.8 Hz, 1H), 5.13-5.41 (m, 1H), 4.78 (d, J=11.8 Hz, 1H), 4.11-4.18 (m, 1H), 4.04 (d, J=10.4 Hz, 1H), 3.52 (d, J=13.8 Hz, 1H), 3.00-3.15 (m, 4H), 2.78-2.89 (m, 1H), 2.42 (d, J=6.1 Hz, 2H), 2.08-2.18 (m, 2H), 2.98-2.07 (m, 2H), 1.81-1.89 (m, 2H), 1.75-1.81 (m, 2H), 1.64-1.73 (m, 2H), 1.52-1.59 (m, 1H), 1.40-1.49 (m, 1H), 1.31-1.37 (m, 1H), 1.30 (s, 3H), 1.19-1.27 (m, 1H), 0.90-1.05 (m, 1H), 0.68-0.82 (m, 1H).

(15R)-22-Fluoro-27-hydroxy-15,31-dimethyl-8-((1r, 4r)-7-oxabicyclo[2.2.1]heptan-1-ylmethoxy)-3,7,9, 11,16-pentaazahexacyclo[19.7.1.1~2,6~.1~11, 15~.0~5,10~.0~25,29~]hentriaconta-1(28),2(31),3,5, 7,9,21,23,25(29),26-decaen-17-one (Example 23)

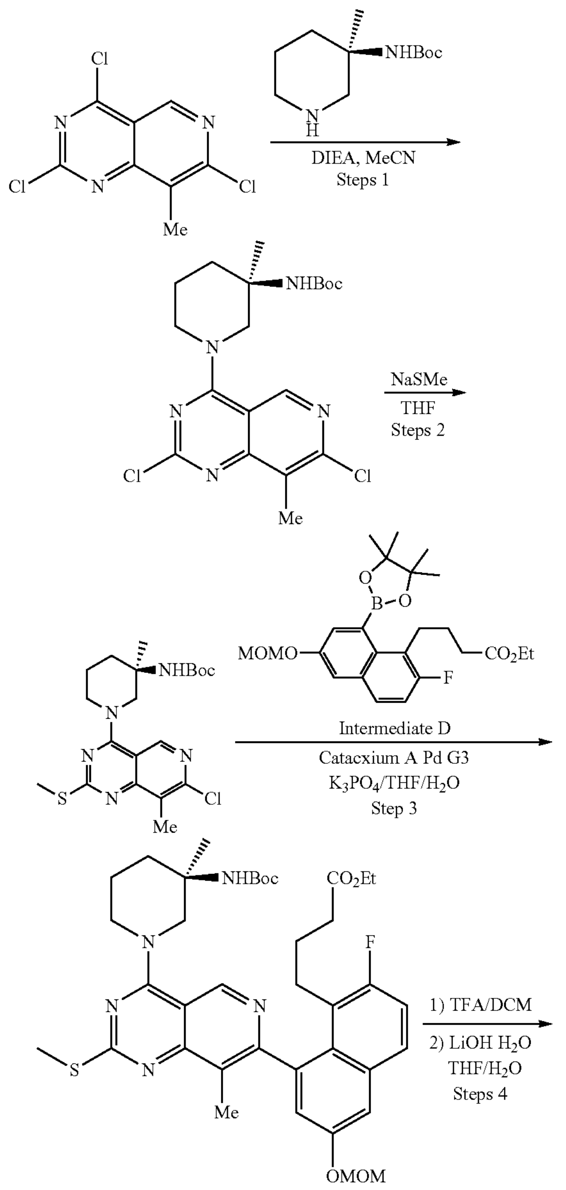

-continued

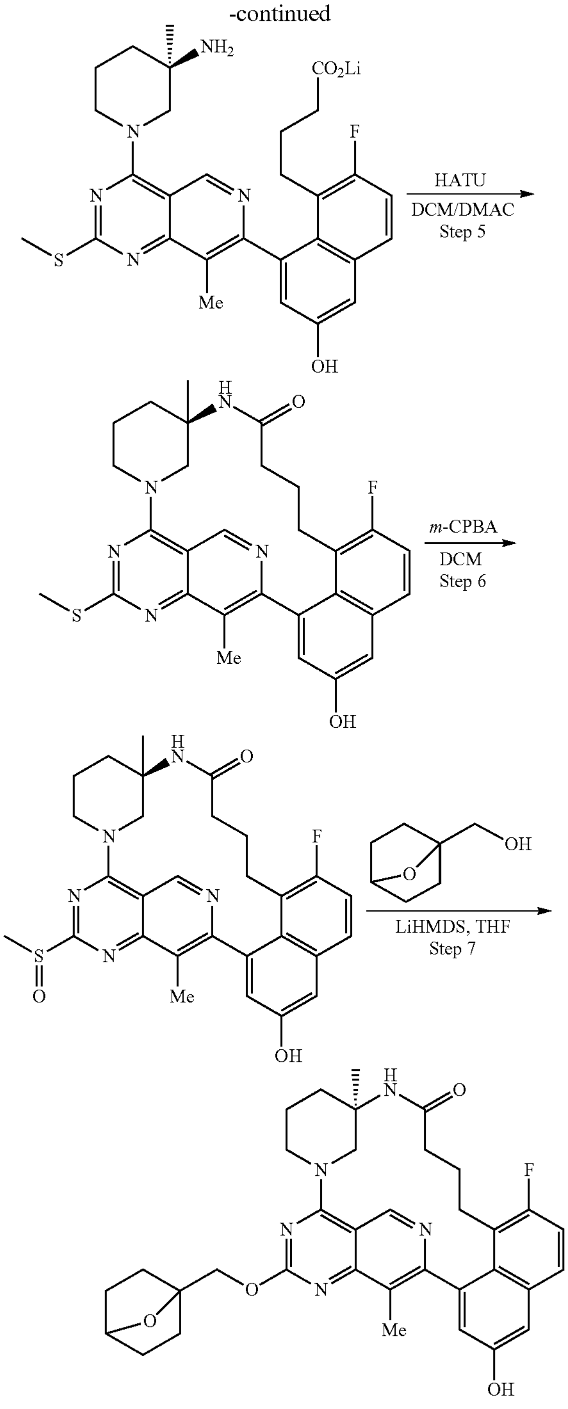

Example 23

Step 1. tert-Butyl (R)-(1-(2,7-dichloro-8-methylpyrido[4, 3-d]pyrimidin-4-yl)-3-methylpiperidin-3-yl)carbamate. To a stirred, ice-cooled solution of 2,4,7-trichloro-8-methyl-pyrido[4,3-d]pyrimidine (3.00 g, 12.1 mmol, Pharmablock, Inc.) and DIEA (8.4 mL, 48.3 mmol) in acetonitrile (40 mL) was added tert-butyl N-[(3R)-3-methylpiperidin-3-yl]carbamate (2.59 g, 12.1 mmol, Pharmablock, Inc.) in one portion. The reaction was stirred at 0° C. for 20 min. The volatiles were removed in vacuo and the crude residue was purified by column chromatography silica gel, eluting with MeOH/DCM to give tert-butyl (R)-(1-(2,7-dichloro-8-methylpyrido[4,3-d]pyrimidin-4-yl)-3-methylpiperidin-3-yl)carbamate (4.50 g, 10 mmol, 87% yield) as off-white solid. $^1$H NMR (CHLOROFORM-d, 400 MHz) δ 8.94 (s, 1H), 5.34 (br s, 1H), 4.70 (br d, 1H, J=13.4 Hz), 4.29 (br d, 1H, J=12.8 Hz), 3.6-3.7 (m, 1H), 3.35 (d, 1H, J=13.4 Hz), 2.64 (s, 3H), 2.46 (br d, 1H, J=13.6 Hz), 1.8-2.0 (m, 1H), 1.6-1.8 (m, 1H), 1.5-1.6 (m, 1H), 1.39 (s, 3H), 1.32 (s, 9H).

Step 2. tert-Butyl (R)-(1-(7-chloro-8-methyl-2-(methylthio)pyrido[4,3-d]pyrimidin-4-yl)-3-methylpiperidin-3-yl) carbamate. To a stirred solution of tert-butyl (R)-(1-(2,7-dichloro-8-methylpyrido[4,3-d]pyrimidin-4-yl)-3-methylpiperidin-3-yl)carbamate (1.80 g, 4.22 mmol) in THF (12 mL) was added sodium methanethiolate (0.39 g, 5.49 mmol) in one portion. The resulting mixture was stirred at rt for 20 h. The volatiles were removed in vacuo and the crude residue was purified by column chromatography on silica gel, eluting with EtOAc/heptane to give tert-butyl (R)-(1-(7-chloro-8-methyl-2-(methylthio)pyrido[4,3-d]pyrimidin-4-yl)-3-methylpiperidin-3-yl)carbamate as off-white solid in nearly quantitative yield. m/z (ESI): 438.0 $(M+H)^+$. $^1$H NMR (CHLOROFORM-d, 400 MHz) δ 8.83 (s, 1H), 5.79 (br s, 1H), 4.53 (br d, 1H, J=13.4 Hz), 4.20 (br d, 1H, J=12.8 Hz), 3.58 (ddd, 1H, J=3.1, 11.3, 12.9 Hz), 3.20 (d, 1H, J=13.6 Hz), 2.5-2.6 (m, 7H), 1.8-1.9 (m, 1H), 1.6-1.7 (m, 1H), 1.48 (dt, 1H, J=4.1, 12.9 Hz), 1.41 (s, 3H), 1.37 (s, 9H).

Step 3. Ethyl (R)-4-(8-(4-(3-((tert-butoxycarbonyl)amino)-3-methylpiperidin-1-yl)-8-methyl-2-(methylthio)pyrido[4,3-d]pyrimidin-7-yl)-2-fluoro-6-(methoxymethoxy)naphthalen-1-yl)butanoate. In a 20-mL microwave reaction vessel were charged with tert-butyl (R)-(1-(7-chloro-8-methyl-2-(methylthio)pyrido[4,3-d]pyrimidin-4-yl)-3-methylpiperidin-3-yl)carbamate (0.65 g, 1.48 mmol), ethyl 4-(2-fluoro-6-(methoxymethoxy)-8-(4,4,5,5-tetramethyl-1,3,2-dioxaborolan-2-yl)naphthalen-1-yl)butanoate (0.73 g, 1.63 mmol, Intermediate D), cataCXium A Pd G3 (0.22 g, 0.30 mmol), and potassium phosphate tribasic (0.95 g, 4.45 mmol), followed by THF (15 mL) and water (1.5 mL). The resulting mixture was purged with nitrogen for 10 min before sealed and irradiated under microwave at 80° C. for 2.5 h. The volatiles were removed and the crude residue was purified by column chromatography on silica gel, eluting with EtOAc/heptane to give ethyl (R)-4-(8-(4-(3-((tert-butoxycarbonyl)amino)-3-methylpiperidin-1-yl)-8-methyl-2-(methylthio)pyrido[4,3-d]pyrimidin-7-yl)-2-fluoro-6-(methoxymethoxy)naphthalen-1-yl)butanoate (0.82 g, 1.14 mmol, 77% yield) as red oil. m/z (ESI): 722.0 $(M+H)^+$.

Step 4. (R)-4-(8-(4-(3-Amino-3-methylpiperidin-1-yl)-8-methyl-2-(methylthio)pyrido[4,3-d]pyrimidin-7-yl)-2-fluoro-6-hydroxynaphthalen-1-yl)butanoic acid. To a stirred solution of ethyl (R)-4-(8-(4-(3-((tert-butoxycarbonyl)amino)-3-methylpiperidin-1-yl)-8-methyl-2-(methylthio)pyrido[4,3-d]pyrimidin-7-yl)-2-fluoro-6-(methoxymethoxy)naphthalen-1-yl)butanoate (1.64 g, 2.27 mmol) in DCM (15 mL) was added hydrogen chloride (4 N solution in dioxane, 5.7 mL, 22.8 mmol). The reaction mixture was stirred at rt for 1 h. The volatiles were removed in vacuo to give crude ethyl (R)-4-(8-(4-(3-amino-3-methylpiperidin-1-yl)-8-methyl-2-(methylthio)pyrido[4,3-d]pyrimidin-7-yl)-2-fluoro-6-hydroxynaphthalen-1-yl)butanoate as a HCl salt. m/z (ESI): 577.8 $(M+H)^+$.

A mixture of the (1.31 g, 2.27 mmol) (an HCl salt, assumed quantitative yield in the last step) and lithium hydroxide monohydrate (0.48 g, 11.4 mmol) in THF (30 mL) and water (20 mL) was stirred at rt for 16 h. THF was removed in vacuo and the residue was lyophilized to give crude (R)-4-(8-(4-(3-amino-3-methylpiperidin-1-yl)-8-methyl-2-(methylthio)pyrido[4,3-d]pyrimidin-7-yl)-2-fluoro-6-hydroxynaphthalen-1-yl)butanoic acid as off-white solid. m/z (ESI): 550.0 $(M+H)^+$.

Step 5. (15R)-22-Fluoro-27-hydroxy-15,31-dimethyl-8-(methylthio)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one. To a stirred mixture of (R)-4-(8-(4-(3-amino-3-methylpiperidin-1-yl)-8-methyl-2-(methylthio)pyrido[4,3-d]pyrimidin-7-yl)-2-fluoro-6-hydroxynaphthalen-1-yl)butanoic acid (0.64 g, 1.16 mmol) in DCM (200 mL), N,N-dimethylacetamide (4 mL) and DMF (2 mL) was added HATU (0.70 g, 1.86 mmol). The reaction mixture was stirred at rt for 4 h. Dimethylamine (2.0 M in THF, 3.8 mL, 7.6 mmol) was added and the reaction mixture was stirred at rt for 5 h. The volatiles were removed and the residue was purified by column chromatography on silica gel, eluting with MeOH/DCM, followed by preparative reverse-phase HPLC to provide, after lyophilization, (15R)-22-fluoro-27-hydroxy-15,31-dimethyl-8-(methylthio)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (0.19 g, 0.37 mmol, 32% yield) as off-white solid as a TFA salt. $^1$H NMR (METHANOL-$d_4$, 400 MHz) δ 9.54 (s, 1H), 7.75 (dd, 1H, J=5.6, 9.0 Hz), 7.4-7.5 (m, 2H), 7.3-7.3 (m, 2H), 5.82 (br d, 1H, J=13.8 Hz), 5.29 (br d, 1H, J=11.7 Hz), 3.67 (d, 1H, J=14.2 Hz), 3.1-3.2 (m, 1H), 2.6-2.7 (m, 4H), 2.2-2.3 (m, 1H), 2.0-2.1 (m, 1H), 1.6-2.0 (m, 9H), 1.35 (s, 3H). $^{19}$F NMR (METHANOL-$d_4$, 376 MHz) δ −117.14 (s, 1F). m/z (ESI): 532.0 $(M+H)^+$.

Step 6. (15R)-22-Fluoro-27-hydroxy-15,31-dimethyl-8-(methylsulfinyl)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one. To a stirred ice-cooled solution of (15R)-22-fluoro-27-hydroxy-15,31-dimethyl-8-(methylthio)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (32 mg, 0.06 mmol) in DCM (3 mL) was added 3-chloroperoxybenzoic acid (14 mg, 0.06 mmol) in one portion. The resulting mixture was stirred at 0° C. for 1.5 h. The crude mixture was purified by column chromatography, eluting with MeOH/DCM to give crude (15R)-22-Fluoro-27-hydroxy-15,31-dimethyl-8-(methylsulfinyl)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (23 mg) as white solid, contaminated with its corresponding sulfone. m/z (ESI): 548.0 $(M+H)^+$.

Step 7. (15R)-22-Fluoro-27-hydroxy-15,31-dimethyl-8-((1r,4r)-7-oxabicyclo[2.2.1]heptan-1-ylmethoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one. To a stirred ice-cooled solution of (7-oxabicyclo[2.2.1]heptan-1-yl)methanol (23 mL, 0.18 mmol, Enamine) in THF (3 mL) was added 1,1,1,3,3,3-hexamethyldisilazane lithium salt (1 M solution in THF, 0.18 mL, 0.18 mmol) under nitrogen. The resulting mixture was stirred at 0° C. for 10 min before a solution of impure (15R)-22-Fluoro-27-hydroxy-15,31-dimethyl-8-(methylsulfinyl)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (20 mg, 0.037 mmol) in THF (3 mL) was added. The resulting mixture was stirred at 0° C. for 30 min. The crude mixture was purified by column chromatography, eluting with MeOH/DCM to give crude product, which was purified by reverse-phase HPLC to provide (15R)-22-fluoro-27-hydroxy-15,31-dimethyl-8-((1r,4r)-7-oxabicyclo[2.2.1]heptan-1-ylmethoxy)-3,7,9,11, 16-pentaazahexacyclo[19.7.1.1~2,6~.1~11,15~.0~5,10~.0~25,29~]hentriaconta-1(28),2(31),3,5,7,9,21,23,25(29),26-decaen-17-one (12 mg, 0.02 mmol, 54% yield) as white solid. $^1$H NMR (METHANOL-$d_4$, 400 MHz) δ 9.53 (s, 1H), 7.75 (dd, 1H, J=5.6, 9.0 Hz), 7.4-7.4 (m, 2H), 7.2-7.3 (m, 2H), 5.86 (br d, 1H, J=14.0 Hz), 5.24 (br d, 1H, J=12.1 Hz), 4.8-4.9 (m, 1H), 4.58 (t, 1H, J=4.9 Hz), 3.67 (d, 1H, J=14.2 Hz), 3.1-3.2 (m, 1H), 2.6-2.7 (m, 1H), 1.9-2.2 (m, 3H), 1.6-1.9 (m, 16H), 1.36 (s, 3H), 1.2-1.3 (m, 1H). $^{19}$F NMR (METHANOL-$d_4$, 376 MHz) δ −117.22 (s). m/z (ESI): 612.0 $(M+H)^+$.

(15R)-22-Fluoro-27-hydroxy-15,31-dimethyl-8-(((2R)-4-methyl-2-morpholinyl)methoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one and (15R)-22-fluoro-27-hydroxy-15,31-dimethyl-8-(((2S)-4-methyl-2-morpholinyl)methoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (Example 24)

Example 24

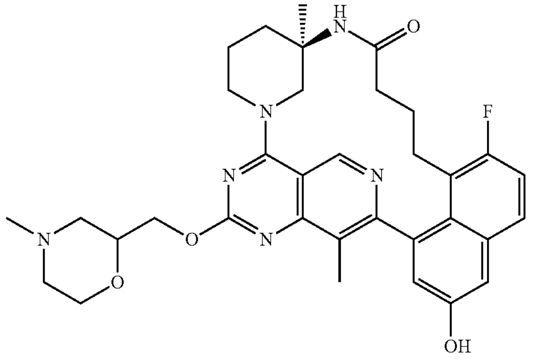

The title compound was synthesized in an analogous fashion to Example 3, using tert-butyl N-[(3R)-3-methylpiperidin-3-yl]carbamate (CAS #: 1169762-18-8, Pharmablock, Inc.) as the amine and 4-methyl-2-morpholinemethanol (CAS #: 40987-46-0, AmBeed) in Step 1, and Intermediate D as the boronic ester in the Suzuki coupling reaction in Step 3. m/z (ESI): 615.0 $(M+H)^+$. $^1$H NMR (METHANOL-$d_4$, 400 MHz) δ 9.59 (s, 1H), 7.76 (dd, 1H, J=5.6, 9.1 Hz), 7.40 (d, 2H, J=2.5 Hz), 7.2-7.3 (m, 2H), 5.86 (br d, 1H, J=14.3 Hz), 5.21 (br d, 1H, J=12.4 Hz), 4.5-4.7 (m, 2H), 4.1-4.3 (m, 2H), 3.87 (br t, 1H, J=12.4 Hz), 3.6-3.7 (m, 2H), 3.4-3.5 (m, 1H), 3.1-3.3 (m, 3H), 2.97 (s, 3H), 2.6-2.7 (m, 1H), 2.0-2.2 (m, 2H), 1.8-2.0 (m, 7H), 1.6-1.8 (m, 2H), 1.36 (s, 3H), 1.2-1.3 (m, 1H). $^{19}$F NMR (METHANOL-$d_4$, 376 MHz) δ −117.16 (br s).

(15R)-22-Fluoro-27-hydroxy-15,31-dimethyl-8-(((1s,4s)-3-oxo-2-azabicyclo[2.2.2]octan-1-yl)methoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (Example 25)

Example 25

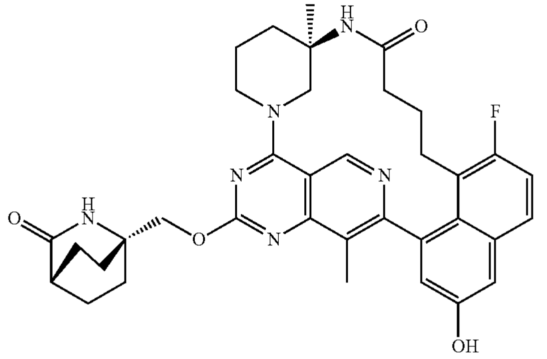

The title compound was synthesized in an analogous fashion to Example 3, using tert-butyl N-[(3R)-3-methylpiperidin-3-yl]carbamate (CAS #: 1169762-18-8, Pharmablock, Inc.) as the amine and 1-(hydroxymethyl)-2-azabicyclo[2.2.2]octan-3-one (CAS #: 1334412-35-9, AmBeed) in Step 1, and Intermediate D as the boronic ester in the Suzuki coupling reaction in Step 3. m/z (ESI): 639.0 $(M+H)^+$. $^1$H NMR (METHANOL-$d_4$, 400 MHz) δ 9.59 (s, 1H), 7.76 (dd, 1H, J=5.7, 9.0 Hz), 7.4-7.4 (m, 2H), 7.2-7.3 (m, 2H), 5.87 (br d, 1H, J=14.7 Hz), 5.25 (br d, 1H, J=13.1 Hz), 4.5-4.6 (m, 3H), 3.68 (d, 1H, J=14.1 Hz), 3.2-3.2 (m, 1H), 2.6-2.7 (m, 1H), 2.49 (br s, 1H), 2.0-2.2 (m, 2H), 1.91 (s, 3H), 1.8-1.9 (m, 11H), 1.6-1.7 (m, 1H), 1.2-1.4 (m, 6H). $^{19}$F NMR (METHANOL-$d_4$, 377 MHz) δ −117.03 (s).

(15R)-22-Fluoro-27-hydroxy-8-(2-hydroxy-2-methylpropoxy)-15,31-dimethyl-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one (Example 26)

Example 26

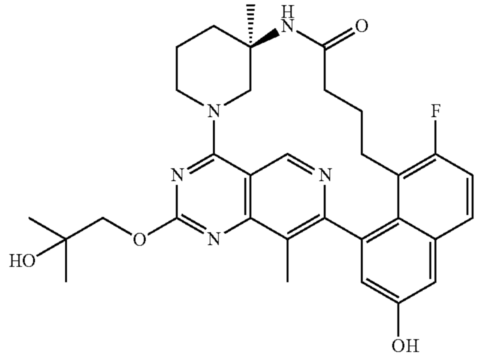

The title compound was synthesized in an analogous fashion to Example 3, using tert-butyl N-[(3R)-3-methylpiperidin- 3-yl]carbamate (CAS #: 558-43-0, Pharmablock, Inc.) as the amine and 2-methylpropane-1,2-diol (CAS #: 1334412-35-9, AmBeed) in Step 1, and Intermediate D as the boronic ester in the Suzuki coupling reaction in Step 3. $^1H$ NMR (METHANOL-$d_4$, 400 MHz) δ 9.57 (s, 1H), 7.76 (dd, 1H, J=5.6, 9.1 Hz), 7.4-7.5 (m, 2H), 7.2-7.4 (m, 2H), 5.85 (br d, 1H, J=14.1 Hz), 5.24 (br d, 1H, J=12.0 Hz), 4.3-4.4 (m, 2H), 3.68 (d, 1H, J=14.3 Hz), 3.1-3.2 (m, 1H), 2.6-2.7 (m, 1H), 2.0-2.3 (m, 2H), 1.9-2.0 (m, 1H), 1.89 (s, 3H), 1.8-1.9 (m, 3H), 1.7-1.8 (m, 1H), 1.6-1.7 (m, 1H), 1.2-1.4 (m, 9H). $^{19}F$ NMR (METHANOL-$d_4$, 376 MHz) δ −117.17 (s, 1F). m/z (ESI): 574.0 $(M+H)^+$.

(15R,21R)-31-Fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(29),2(31),3,5,7,9,25,27-octaen-17-one 2,2,2-trifluoroacetate salt (Example 27) and (15R,21S)-31-fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(29),2(31),3,5,7,9,25,27-octaen-17-one 2,2,2-trifluoroacetate salt (Example 28)

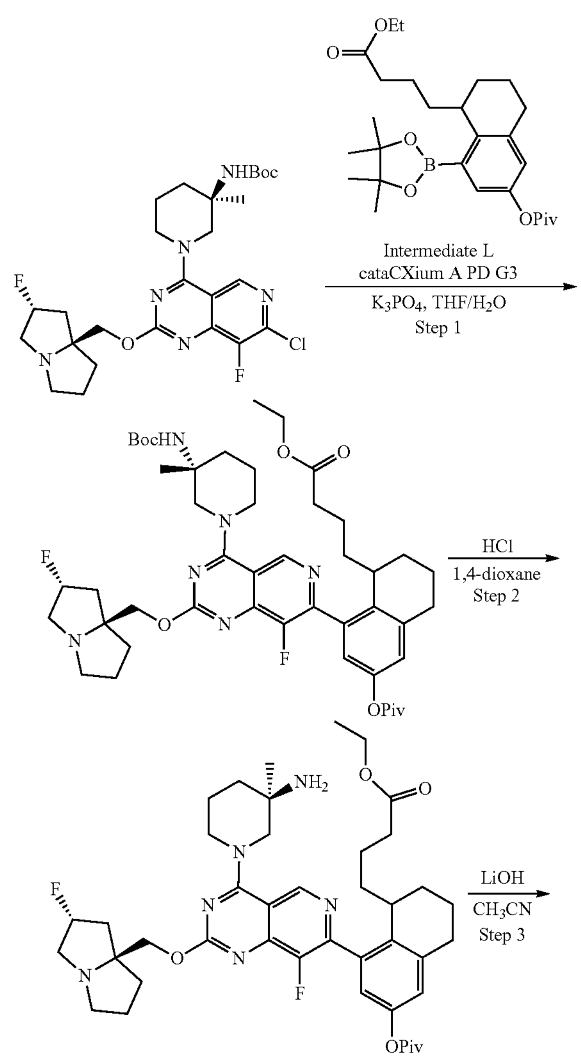

-continued

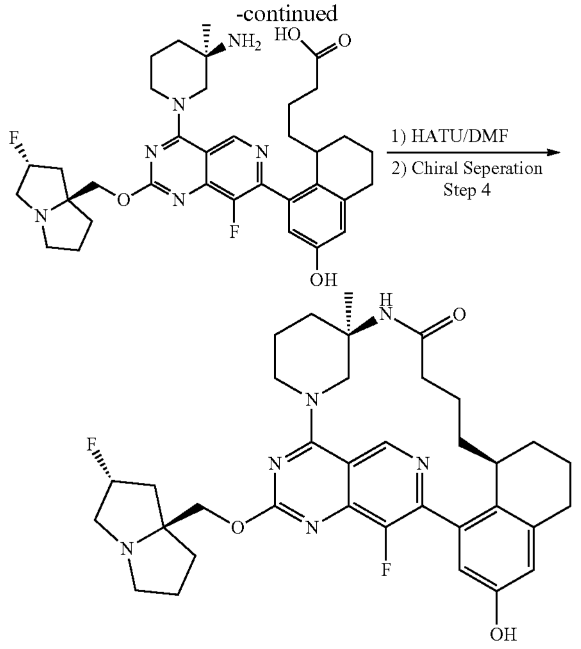

Example 27

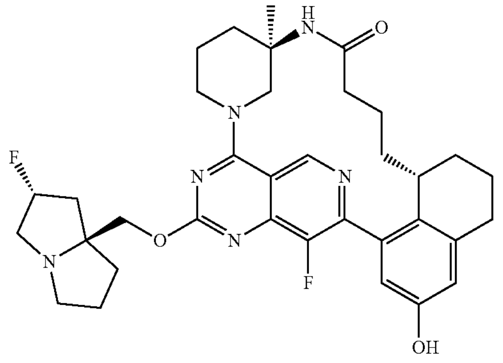

Example 28

Step 1. Ethyl 4-(8-(4-((R)-3-((tert-butoxycarbonyl)amino)-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(pivaloyloxy)-1,2,3,4-tetrahydronaphthalen-1-yl)butanoate. To a 20-mL vial was added tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-yl)carbamate (0.19 g, 0.34 mmol), ethyl 4-(6-(pivaloyloxy)-8-(4,4,5,5-tetramethyl-1,3,2-dioxaborolan-2-yl)-1,2,3,4-tetrahydronaphthalen-1-yl)butanoate (0.16 g, 0.34 mmol, Intermediate L), potassium phosphate (0.21 g, 1.10 mmol) and cataCXium A Pd G3 (25 mg, 0.034 mmol) in tetrahydrofuran (2.0 mL) and water (0.2 mL). The reaction mixture was stirred at 75° C. for 3 h, cooled to rt and concentrated. The crude material was purified by column chromatography on silica gel, eluting with a gradient of 0-100% (3:1 EtOAc/EtOH with 1% TEA) in heptane, to provide ethyl 4-(8-(4-((R)-3-((tert-butoxycarbonyl)amino)-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(pivaloyloxy)-1,2,3,4-tetrahydronaphthalen-1-yl)butanoate (0.20 g, 0.23 mmol, 69% yield) as off-white solid. m/z (ESI): 862.9 $(M+H)^+$.

Step 2. Ethyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(pivaloyloxy)-1,2,3,4-tetrahydronaphthalen-1-yl)butanoate. To a 50-mL round-bottom flask was added ethyl 4-(8-(4-((R)-3-((tert-butoxycarbonyl)amino)-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(pivaloyloxy)-1,2,3,4-tetrahydronaphthalen-1-yl)butanoate (0.20 g, 0.23 mmol) in 1,4-dioxane (1.2 mL). HCl in 1,4-dioxane, (4 M, 1.1 mL, 4.4 mmol) was added and the reaction mixture was stirred at rt for 3 h. The mixture was diluted with sat'd $NaHCO_3$ solution and extracted with EtOAc. The organic extract was washed with brine, dried over $MgSO_4$, filtered and concentrated in vacuo to give the crude ethyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(pivaloyloxy)-1,2,3,4-tetrahydronaphthalen-1-yl)butanoate as off-white solid. m/z (ESI): 763.0 $(M+H)^+$.

Step 3. 4-(8-(4-((R)-3-Amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-hydroxy-1,2,3,4-tetrahydronaphthalen-1-yl)butanoic acid dihydrochloride. To a 20-mL vial was added ethyl 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-(pivaloyloxy)-1,2,3,4-tetrahydronaphthalen-1-yl)butanoate (90 mg, 0.12 mmol) and lithium hydroxide (14 mg, 0.59 mmol) in acetonitrile (0.9 mL) and water (0.3 mL). The reaction mixture was stirred at 40° C. for 2 h. After cooling to rt, the reaction mixture was quenched with acetic acid (34 μL, 0.59 mmol) and concentrated. The crude material was purified by reverse phrase column chromatography, then treated with 1 N HCl and lyophilized to give 4-(8-(4-((R)-3-amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-hydroxy-1,2,3,4-tetrahydronaphthalen-1-yl)butanoic acid dihydrochloride as yellow solid (60 mg, 0.083 mmol, 70% yield). m/z (ESI): 651.0 $(M+H)^+$.

Step 4. (15R,21R)-31-Fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(29),2(31),3,5,7,9,25,27-octaen-17-one 2,2,2-trifluoroacetate salt (Example 27) and (15R,21S)-31-fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(29),2(31),3,5,7,9,25,27-octaen-17-one 2,2,2-trifluoroacetate salt. 4-(8-(4-((R)-3-Amino-3-methylpiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-hydroxy-1,2,3,4-tetrahydronaphthalen-1-yl)butanoic acid hydrochloride (53 mg, 0.077 mmol) was dissolved in DMF (22 mL) and HATU (44 mg, 0.12 mmol) added. The reaction mixture was stirred for 10 min then DIPEA (0.51 mL, 0.54 mmol) was added dropwise. The reaction mixture was stirred at rt for 1 h, and then treated with 1 mL of 2 M ammonia in MeOH and stirred for 1 h. Water and saturated aqueous NaCl were added and the aqueous phase was extracted with EtOAc. The combined organic layers were dried over $Na_2SO_4$, filtered and volatiles were removed in vacuo. The residue was purified by preparative HPLC to give (15R,21R)-31-fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(29),2(31),3,5,7,9,25,27-octaen-17-one 2,2,2-trifluoroacetate (12 mg, Example 27) as the first eluting peak. m/z (ESI): 633.0. $^1H$ NMR (400 MHz, METHANOL-$d_4$) δ ppm 9.24 (s, 1H), 7.16 (s, 1H), 6.85-6.90 (m, 1H), 6.65-6.69 (m, 1H), 5.73-5.84 (m, 1H), 5.51-5.68 (m, 1H), 5.07-5.21 (m, 1H), 4.58-4.77 (m, 3H), 3.79-4.15 (m, 4H), 3.56-3.68 (m, 1H), 3.40-3.53 (m, 1H), 3.05-3.20 (m, 1H), 2.72-2.82 (m, 3H), 2.54-2.68 (m, 2H), 2.31-2.51 (m, 4H), 2.13-2.25 (m, 1H), 1.94-2.06 (m, 1H), 1.61-1.92 (m, 8H), 1.45-1.57 (m, 1H), 1.20-1.42 (m, 4H).

Also isolated was (15R,21S)-31-fluoro-8-(((2R,7aS)-2-fluorotetrahydro-1H-pyrrolo[1,2-a]pyrrol-7a(5H)-yl)methoxy)-27-hydroxy-15-methyl-3,7,9,11,16-pentaazahexacyclo[19.7.1.1~2,6~.1~11,15~.0~5,10~.0~25,29~]hentriaconta-1(29),2(31),3,5,7,9,25,27-octaen-17-one 2,2,2-trifluoroacetate (15 mg, Example 28) as the second eluting peak. m/z (ESI): 633.0 $(M+H)^+$. $^1H$ NMR (400 MHz, METHANOL-$d_4$) δ ppm 9.14-9.21 (m, 1H), 6.96 (s, 1H), 6.73-6.79 (m, 1H), 6.65-6.71 (m, 1H), 5.50-5.68 (m, 2H), 4.96-5.06 (m, 1H), 4.60-4.74 (m, 3H), 3.79-4.02 (m, 4H), 3.57-3.68 (m, 1H), 3.43-3.54 (m, 1H), 3.13-3.30 (m, 1H), 2.71-2.86 (m, 3H), 2.57-2.69 (m, 2H), 2.32-2.50 (m, 4H), 1.97-2.28 (m, 4H), 1.62-1.96 (m, 8H), 1.36 (s, 4H).

(17R)-30-fluoro-24-(((2R,7aS)-2-fluorotetrahydro-1H-pyrrolo[1,2-a]pyrrol-7a(5H)-yl)methoxy)-9-methyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one 2,2,2-trifluoroacetate (Example 48)

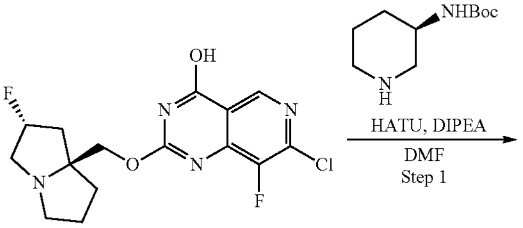

Intermediate Z

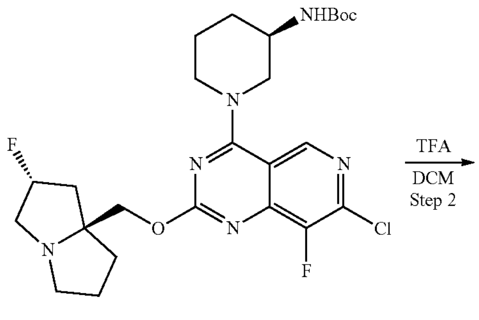

-continued

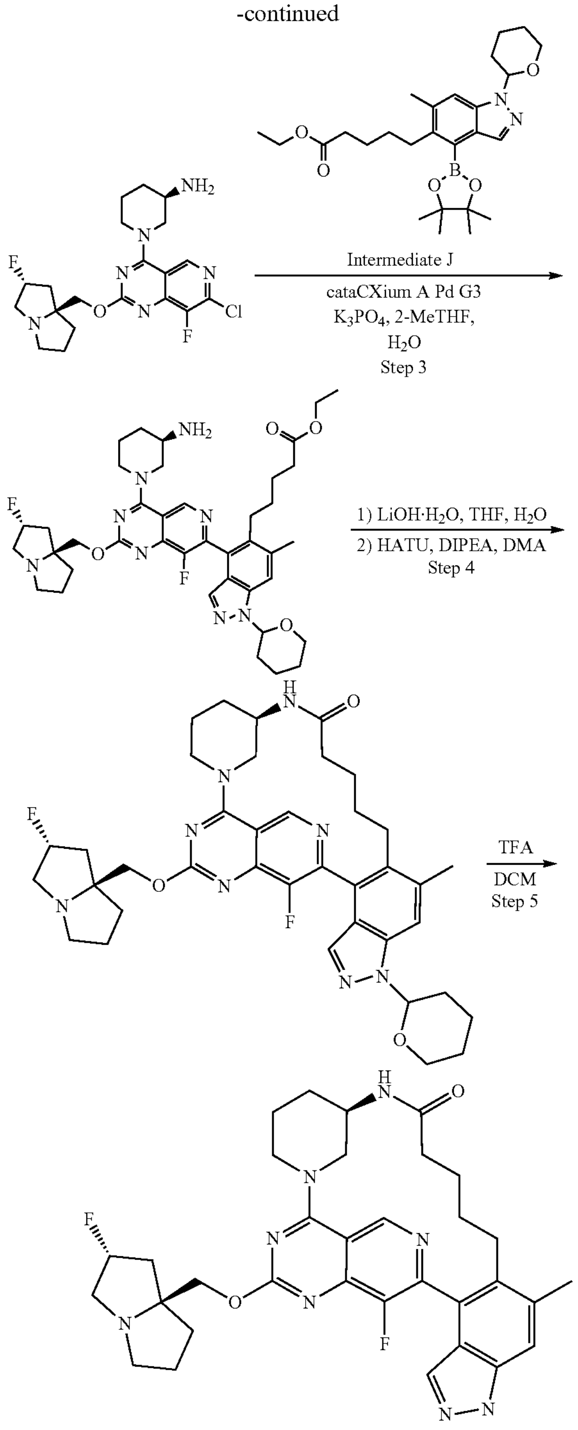

Example 48

Step 1. tert-Butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)carbamate. A round-bottom flask was charged with HATU (3.20 g, 8.41 mmol), 7-chloro-8-fluoro-2-(((2R,7aS)-2-fluorotetrahydro-1H-pyrrolizin-7a(5H)-yl)methoxy)pyrido[4,3-d]pyrimidin-4-ol (2.00 g, 5.61 mmol, Intermediate Z) and DIPEA (4.9 mL, 28 mmol). The contents were dissolved in N,N-dimethylformamide (28 mL) and stirred at rt for 10 min. (R)-3-Boc-amino piperidine (1.35 g, 6.73 mmol) was added and the mixture was stirred at rt overnight. The reaction was diluted with EtOAc and washed with water. The organic layer was separated and washed with brine, dried with $MgSO_4$, and concentrated. The mixture was purified via column chromatography on silica gel, eluting with a gradient of 0-100% 3:1 EtOAc:EtOH (with 2% triethylamine) in heptane to yield tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)carbamate (2.40 g, 4.50 mmol, 79% yield). m/z (ESI): $(M+H)^+$ 539.0.

Step 2. (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-amine. To a solution of tert-butyl ((R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)carbamate (2.40 g, 4.50 mmol) in DCM (14 mL) was added TFA (4.0 mL, 53 mmol) at 0° C. and the mixture was stirred at rt for 4 h. A saturated solution of $NaHCO_3$ was added to neutralize the solution and the aqueous layer was extracted twice with DCM. The combined organic layers were dried over $Na_2SO_4$, filtered and volatiles were removed in vacuo to yield (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-amine (0.83 g, 1.90 mmol, 42% yield) as yellowish foam. m/z (ESI): $(M+H)^+$ 439.0.

Step 3. Ethyl 5-(4-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)pentanoate. A vial was charged with (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-amine (0.61 g, 1.40 mmol), potassium phosphate (0.89 mg, 4.10 mmol), cataCXium A Pd G3 (0.20 g, 0.28 mmol), ethyl 5-(6-methyl-1-(tetrahydro-2H-pyran-2-yl)-4-(4,4,5,5-tetramethyl-1,3,2-dioxaborolan-2-yl)-1H-indazol-5-yl)pentanoate (0.85 g, 1.80 mmol, Intermediate J). Water (0.6 mL) and 2-methyltetrahydrofuran (6.5 mL) were added and the reaction mixture was heated to 80° C. for 3 h. The volatiles were removed in vacuo and the crude material was purified via reverse phase column chromatography (10-100% MeCN/$H_2O$+0.1% TFA). The product containing fractions were neutralized with aqueous sodium bicarbonate, extracted with DCM to afford ethyl 5-(4-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)pentanoate (0.66 g, 0.88 mmol, 63% yield). m/z (ESI): $(M+H)^+$ 747.2.

Step 4. (17R)-30-Fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one. A 40 mL vial was charged with ethyl 5-(4-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)pentanoate (0.66 g, 0.88 mmol) in tetrahydrofuran (3.5 mL) and water (3.5 mL). Then lithium hydroxide, monohydrate (74 mg, 1.8 mmol) was added, and the mixture was heated to 45° C. for 90 min. Upon completion, the reaction was cooled to rt and quenched by addition of 2 M hydrochloric acid (0.9 mL, 1.8 mmol) dropwise. The volatiles were removed in vacuo and the crude material was purified via reverse phase column chromatography (10-100%

$MeCN/H_2O$+0.1% formic acid). The desired fraction was were concentrated and azeotroped with toluene three times to afford 5-(4-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)pentanoic acid (0.42 g, 0.59 mmol, 67% yield) as light yellow solid. m/z (ESI): $(M+H)^+$ 719.2.

To a solution of 5-(4-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)pentanoic acid (0.42 g, 0.59 mmol) in DMA (125 mL) was added HATU (0.33 g, 0.88 mmol). The mixture was stirred for 5 min and then DIPEA (0.41 mL, 2.3 mmol) was added dropwise. The mixture was stirred at rt for 90 min, then water and brine were added. The aqueous layer was extracted with EtOAc, and the combined organic layers were dried over $Na_2SO_4$, filtered and volatiles removed in vacuo. The mixture was purified via reverse phase column chromatography (10-90% $MeCN/H_2O$+0.1% TFA) to yield (17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one (91 mg, 0.13 mmol, 22% yield). m/z (ESI): $(M+H)^+$ 701.2.

Step 5. (17R)-30-Fluoro-24-(((2R,7aS)-2-fluorotetrahydro-1H-pyrrolo[1,2-a]pyrrol-7a(5H)-yl)methoxy)-9-methyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one 2,2,2-trifluoroacetate. To a solution of (17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one (30 mg, 0.043 mmol) in DCM (0.5 mL) was added TFA (0.1 mL, 1.3 mmol). The reaction mixture was stirred at rt for 2 h and then was quenched with saturated sodium bicarbonate solution at 0° C. and extracted with EtOAc. The combined organic layers were concentrated and the crude product was purified by reverse phase preparative HPLC to provide (17R)-30-fluoro-24-(((2R,7aS)-2-fluorotetrahydro-1H-pyrrolo[1,2-a]pyrrol-7a(5H)-yl)methoxy)-9-methyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one 2,2,2-trifluoroacetate (5.6 mg, 7.7 μmol, 18% yield) as white powder. m/z (ESI): (M+H)+617.2. $^1H$ NMR (400 MHz, METHANOL-$d_4$) δ ppm 9.19-9.27 (m, 1H), 7.72 (d, J=0.8 Hz, 1H), 7.50-7.60 (m, 1H), 5.52-5.74 (m, 1H), 5.05-5.23 (m, 2H), 4.57-4.71 (m, 2H), 3.98-4.15 (m, 1H), 3.91 (br s, 4H), 3.45-3.54 (m, 1H), 3.22-3.29 (m, 1H), 2.63-2.85 (m, 2H), 2.56 (s, 8H), 1.94-2.24 (m, 5H), 1.57-1.81 (m, 4H), 0.85-1.54 (m, 7H). $^{19}F$ NMR (376 MHz, METHANOL-$d_4$) δ ppm −78.51−−76.05 (m), −142.98−−141.85 (m), −174.04−−173.96 (m).

TABLE 8

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 49 | 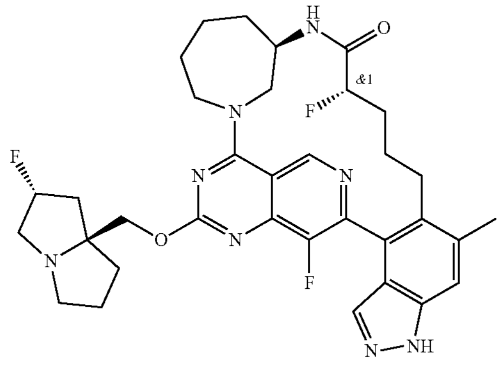 [SMILES: Cc1cc2[nH]ncc2c2c1CCC[C@H](F)C(=O)N[C@@H]1CCCCN(C1)c1nc(OC[C@@]34CCCN3C[C@H](F)C4)nc3c(F)c-2ncc13] (17R)-14,30-difluoro-24-(((2R,7aS)-2-fluorotetrahydro-1H-pyrrolo[1,2-a]pyrrol-7a(5H)-yl)methoxy)-9-methyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | 2,2,2-trifluoro-aceate | Step 3. Intermediate DD | |

TABLE 8-continued

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 50 | 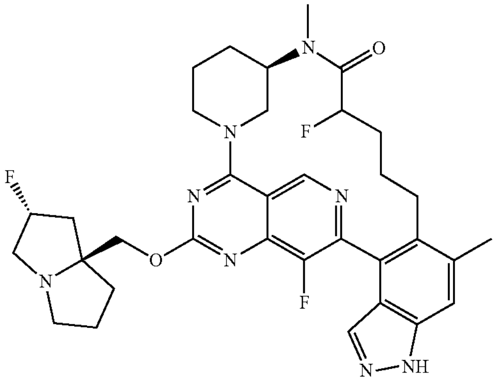 [SMILES: Cc1cc2[nH]ncc2c2c1CCCC(F)C(=O)N(C)[C@@H]1CCCN(C1)c1nc(OC[C@@]34CCCN3C[C@H](F)C4)nc3c(F)c-2ncc13] (17R)-30-fluoro-24-(((2R,7aS)-2-fluorotetrahydro-1H-pyrrolo[1,2-a]pyrrol-7a(5H)-yl)methoxy)-9,16-dimethyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | 2,2,2-trifluoro-acetate | Step 1. tert-butyl (R)-methyl(piper-idin-3-yl)carbamate (CAS#: 309962-67-2, Combi-Blocks Inc.) | The reaction was heated to 30° C. in Step 5. |
| 51 | 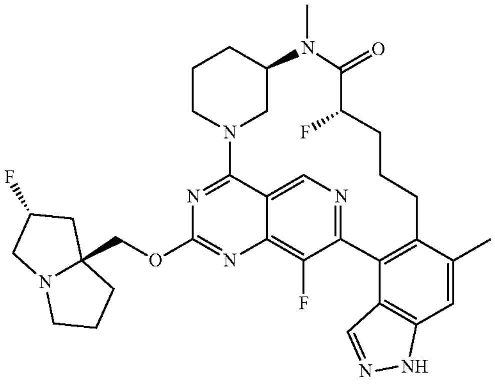 [SMILES: Cc1cc2[nH]ncc2c2c1CCC[C@H](F)C(=O)N(C)[C@@H]1CCCN(C1)c1nc(OC[C@@]34CCCN3C[C@H](F)C4)nc3c(F)c-2ncc13] (14S,17R)-14,30-difluoro-24-(((2R,7aS)-2-fluorotetrahydro-1H-pyrrolo[1,2-a]pyrrol-7a(5H)-yl)methoxy)-9,16-dimethyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 1. tert-Butyl (R)-methyl(piper-idin-3-yl)carbamate (CAS#: 309962-67-2, Combi-Blocks Inc.) Step 3: Intermediate DD | Chiral separation by SFC after Step 5. Details included below. |

TABLE 8-continued

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 52 | 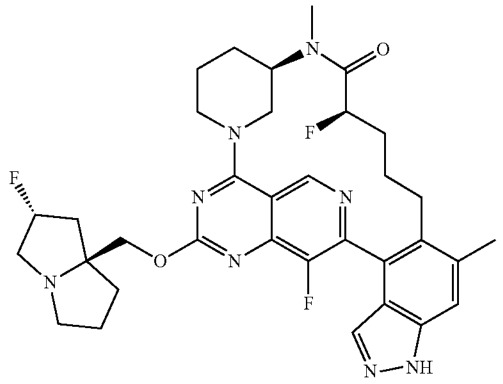 [SMILES: Cc1cc2[nH]ncc2c2c1CCC[C@@H](F)C(=O)N(C)[C@@H]1CCCN(C1)c1nc(OC[C@@]34CCCN3C[C@H](F)C4)nc3c(F)c-2ncc13]<br>(14R,17R)-14,30-difluoro-24-(((2R,7aS)-2-fluorotetrahydro-1H-pyrrolo[1,2-a]pyrrol-7a(5H)-yl)methoxy)-9,16-dimethyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 1. tert-butyl (R)-methyl(piper-idin-3-yl)carbamate (CAS#: 309962-67-2, Combi-Blocks Inc.)<br>Step 3: Intermediate DD | Chiral separation by SFC after Step 5. Details included below. |
| 53 | 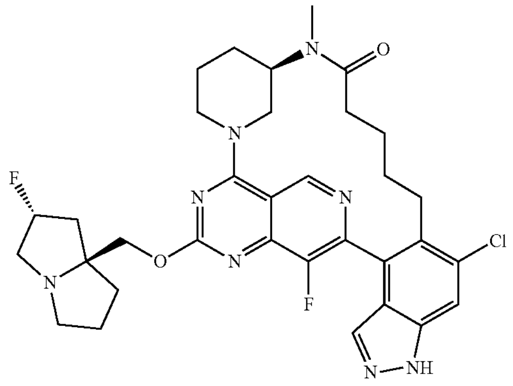 [SMILES: CN1C(=O)CCCCc2c(Cl)cc3[nH]ncc3c2-c2ncc3c(nc(OC[C@@]45CCCN4C[C@H](F)C5)nc3c2F)N2CCC[C@@H]1C2]<br>(17R)-9-chloro-30-fluoro-24-(((2R,7aS)-2-fluorotetrahydro-1H-pyrrolo[1,2-a]pyrrol-7a(5H)-yl)methoxy)-16-methyl-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | N/A | Step 1. tert-butyl (R)-methyl (piper-idin-3-yl)carbamate (CAS#: 309962-67-2, Combi-Blocks Inc.)<br>Step 3: Intermediate P | |

TABLE 8-continued

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 54 | 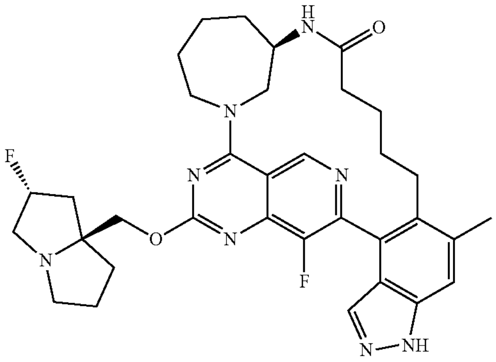 (26R)-32-fluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one | Free base | Step 2. Intermediate FF | Step 1: not performed. |
| 55 | 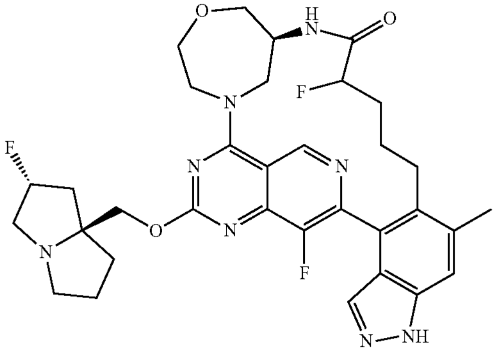 [SMILES: Cc1cc2[nH]ncc2c2c1CCCC(F)C(=O)N[C@@H]1COCCN(C1)c1nc(OC[C@@]34CCCN3C[C@H](F)C4)nc3c(F)c-2ncc13] (23R,26S)-23,32-difluoro-4-(((2R,7aS)-2-fluorotetrahydro-1H-pyrrolo[1,2-a]pyrrol-7a(5H)-yl)methoxy)-18-methyl-28-oxa-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one, and (23S,26S)-23,32-difluoro-4-(((2R,7aS)-2-fluorotetrahydro-1H-pyrrolo[1,2-a]pyrrol-7a(5H)-yl)methoxy)-18-methyl-28-oxa-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-aceate) | Step 1. Intermediate Z, tert-butyl N-[(6S)-1,4-oxazepan-6-yl]carbamate (CAS#: 2306247-11-8, Aurum Pharmatech). Step 3. Intermediate DD | Step 4 (2): ((1H-benzo[d][1,2,3]triazol-1-yl)oxy)tris(dimethylamino)phosphonium hexafluorophosphate(v) (CAS: 56602-33-6, Ambeed) instead of HATU |

TABLE 8-continued

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 56 | 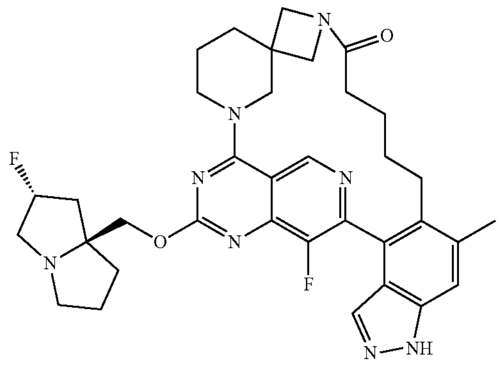 [SMILES: Cc1cc2[nH]ncc2c2c1CCCCC(=O)N1CC3(CCCN(C3)c3nc(OC[C@@]45CCCN4C[C@H](F)C5)nc4c(F)c-2ncc34)C1] 32-fluoro-24-(((2R,7aS)-2-fluorotetrahydro-1H-pyrrolo[1,2-a]pyrrol-7a(5H)-yl)methoxy)-10-methyl-3,13,14,19,23,25,27-heptaazaheptacyclo[25.3.1.1~1,3~.1~18,22~.0~9,17~.0~12,16~.0~21,26~]tritriaconta-9,11,14,16,18(32),19,21,23,25-nonaen-4-one | Free base | Step 2. Intermediate GG | Step 1: not performed. |
| 57 | 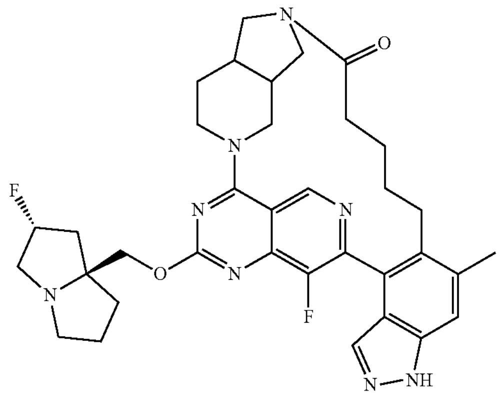 [SMILES: Cc1cc2[nH]ncc2c2c1CCCCC(=O)N1CC3CCN(CC3C1)c1nc(OC[C@@]34CCCN3C[C@H](F)C4)nc3c(F)c-2ncc13] (18R,19R)-31-fluoro-25-(((2R,7aS)-2-fluorotetrahydro-1H-pyrrolo[1,2-a]pyrrol-7a(5H)-yl)methoxy)-9-methyl-5,6,16,22,24,26,30-heptaazaheptacyclo[25.3.1.1~16,19~.1~18,22~.0~2,10~.0~3,7~.0~23,28~]tritriaconta-1(31),2,4,7,9,23,25,27,29-nonaen-15-one and (18S,19S)-31-fluoro-25-(((2R,7aS)-2-fluorotetrahydro-1H-pyrrolo[1,2-a]pyrrol-7a(5H)-yl)methoxy)-9-methyl-5,6,16,22,24,26,30-heptaazaheptacyclo[25.3.1.1~16,19~.1~18,22~.0~2,10~.0~3,7~.0~23,28~]tritriaconta-1(31),2,4,7,9,23,25,27,29-nonaen-15-one | Bis (2,2,2-trifluoro-acetate) | Step 2. Intermediate HH | Step 1: not performed. |

TABLE 8-continued

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 59 | 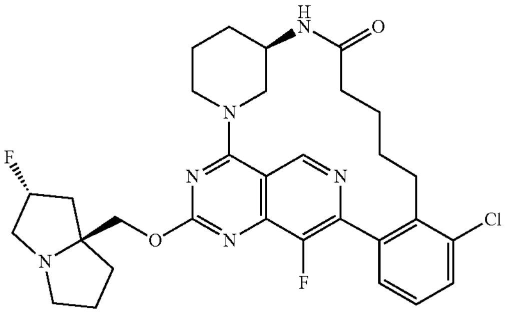 [SMILES: O=C1CCCCc2c(Cl)cccc2-c2ncc3c(nc(OC[C@@]45CCCN4C[C@H](F)C5)nc3c2F)N2CCC[C@H](C2)N1] (23R)-15-chloro-28-fluoro-4-(((2R,7aS)-2-fluorotetrahydro-1H-pyrrolo[1,2-a]pyrrol-7a(5H)-yl)methoxy)-1,3,5,9,22-pentaazapentacyclo[21.3.1.1~6,10~.0~2,7~.0~11,16~]octacosa-2,4,6,8,10(28),11,13,15-octaen-21-one | 2,2,2-trifluoro-aceate | Step 3. Intermediate II | Step 5. Not performed |
| 159 | 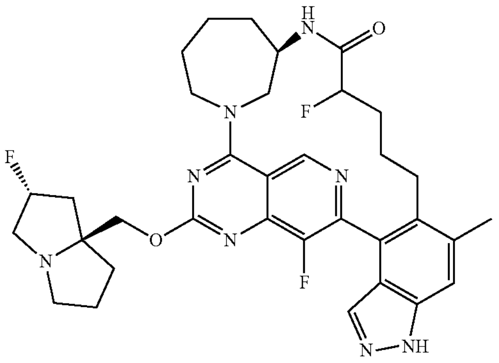 [SMILES: Cc1cc2[nH]ncc2c2c1CCCC(F)C(=O)N[C@@H]1CCCCN(C1)c1nc(OC[C@@]34CCCN3C[C@H](F)C4)nc3c(F)c-2ncc13] (26R)-23,32-difluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one Isomer 1 | | Step 1. Hexameth-yleneimine (CAS#: 111-49-9, Sigma-Aldrich) Step 3. Intermediate DD | Chiral separation by SFC after Step 5. Details included below. |
| 160 | 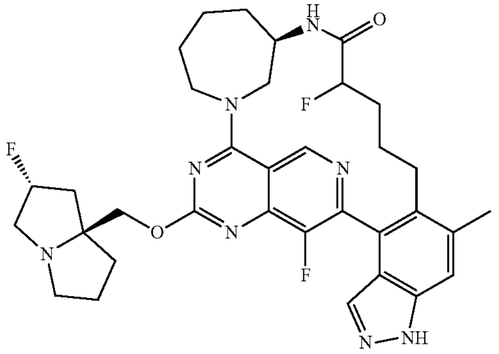 [SMILES: Cc1cc2[nH]ncc2c2c1CCCC(F)C(=O)N[C@@H]1CCCCN(C1)c1nc(OC[C@@]34CCCN3C[C@H](F)C4)nc3c(F)c-2ncc13] (26R)-23,32-difluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one Isomer 2 | | Step 1. Hexameth-yleneimine (CAS#: 111-49-9, Sigma-Aldrich) Step 3. Intermediate DD | Chiral separation by SFC after Step 5. Details included below. |

TABLE 8-continued

Additional Examples 49 to 59, 159 to 161 and 267 to 269. Prepared in an Analogous Manner to Example 48.

| Ex. # | Structure & Name | Salt Form | Reagent | Method Change |
|---|---|---|---|---|
| 161 | 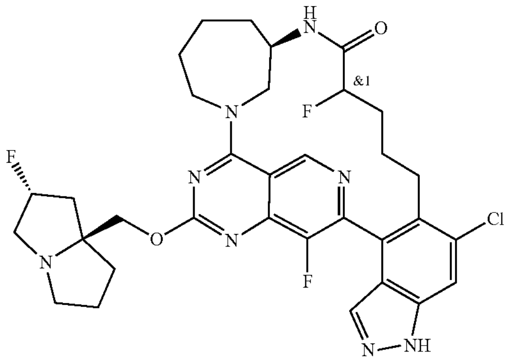 [SMILES: O=C1N[C@@H]2CCCCN(C2)c2nc(OC[C@@]34CCCN3C[C@H](F)C4)nc3c(F)c(ncc23)-c2c(c(Cl)cc3[nH]ncc23)CCCC1F] (23R,26R)-18-chloro-23,32-difluoro-4-(((2R,7aS)-2-fluorotetrahydro-1H-pyrrolo[1,2-a]pyrrol-7a(5H)-yl)methoxy)-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one and (23S,26R)-18-chloro-23,32-difluoro-4-(((2R,7aS)-2-fluorotetrahydro-1H-pyrrolo[1,2-a]pyrrol-7a(5H)-yl)methoxy)-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one | | Step 1. Hexamethyleneimine (CAS#: 111-49-9, Sigma-Aldrich) Step 3. Intermediate UUUU | |
| 267 | 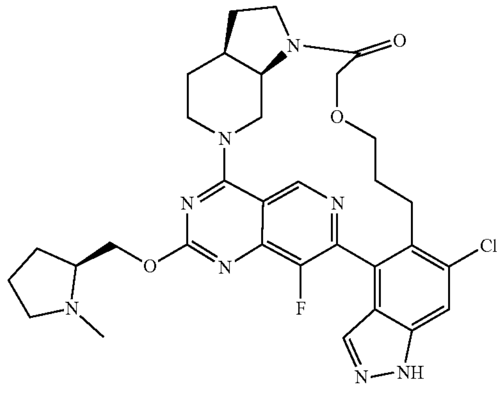 [SMILES: CN1CCC[C@H]1COc1nc2c3cnc(c(F)c3n1)-c1c(c(Cl)cc3[nH]ncc13)CCCOCC(=O)N1CC[C@@H]3CCN2C[C@@H]31] (29S,33R)-18-chloro-34-fluoro-4-(((2S)-1-methyl-2-pyrrolidinyl)methoxy)-23-oxa-1,3,5,9,14,15,26-heptaazaheptacyclo[24.5.2.1~6,10~.0~2,7~.0~11,19~.0~12,16~.0~29,33~]tetratriaconta-2,4,6(34),7,9,11,13,16,18-nonaen-25-one | trifluoroacetate | Step 1. Intermediate CV and tert-butyl (3aS,7aR)-octahydro-1H-pyrrolo[2,3-c]pyridine-1-carboxylate (CAS#: 949559-11-9, PharmaBlock) | |

TABLE 8-continued

| Additional Examples 49 to 59, 159 to 161 and 267 to 269. Prepared in an Analogous Manner to Example 48. | | | | |
|---|---|---|---|---|
| Ex. # | Structure & Name | Salt Form | Reagent | Method Change |
| 268 | 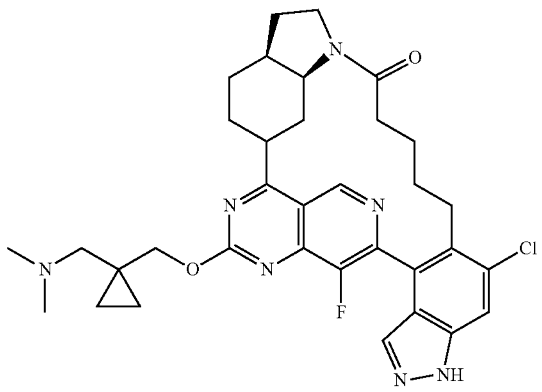 [SMILES: CN(C)CC1(COc2nc3c4cnc(c(F)c4n2)-c2c(c(Cl)cc4[nH]ncc24)CCCCC(=O)N2CC[C@@H]4CCC3C[C@@H]42)CC1] (28S,32R)-18-chloro-4-((1-((dimethylamino)methyl)cyclopropyl)methoxy)-33-fluoro-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | Bis (2,2,2-trifluoro-acetate) | Step 3: Intermediate CW and Intermediate LL | |
| 269 | 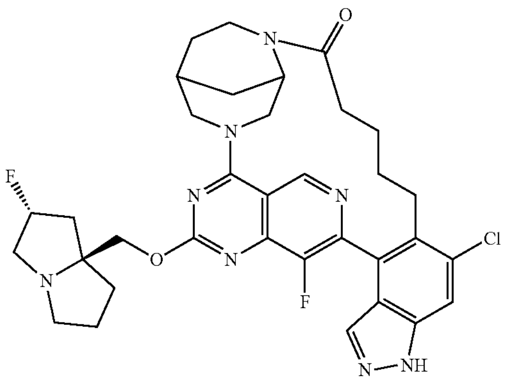 [SMILES: O=C1CCCCc2c(Cl)cc3[nH]ncc3c2-c2ncc3c(nc(OC[C@@]45CCCN4C[C@H](F)C5)nc3c2F)N2CC3CCN1C(C3)C2] (19R,21S)-9-chloro-32-fluoro-26-(((2R,7aS)-2-fluorotetrahydro-1H-pyrrolo[1,2-a]pyrrol-7a(5H)-yl)methoxy)-5,6,16,23,25,27,31-heptaazaheptacyclo[26.3.1.1~19,23~.0~2,10~.0~3,7~.0~16,21~.0~24,29~]tritriaconta-1(32),2,4,7,9,24,26,28,30-nonaen-15-one, (19S,21R)-9-chloro-32-fluoro-26-(((2R,7aS)-2-fluorotetrahydro-1H-pyrrolo[1,2-a]pyrrol-7a(5H)-yl)methoxy)-5,6,16,23,25,27,31-heptaazaheptacyclo[26.3.1.1~19,23~.0~2,10~.0~3,7~.0~16,21~.0~24,29~]tritriaconta-1(32),2,4,7,9,24,26,28,30-nonaen-15-one | 2,2,2-trifluoro-acetate | Step 3: Intermediate CX and Intermediate LL | |

TABLE 9

| Conditions for Chiral SFC Separation. | | |
|---|---|---|
| Separation | SFC Conditions | Peak to Ex # |
| 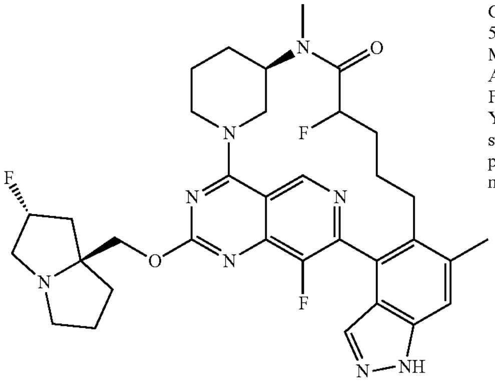 | Column: ChiralPak IC (2 × 25 cm, 5 μm)<br>Mobile phase: 70% 1:1 ACN:MeOH with 0.2% TEA<br>Flowrate: 80 mL/min.<br>Yield: 90 mg sample was submitted to generate 16.6 mg of peak 1 with an ee of 99% and 37.8 mg of peak 2 with an ee of 95%. | Peak 1: Example 51<br>Peak 2: Example 52 |
| 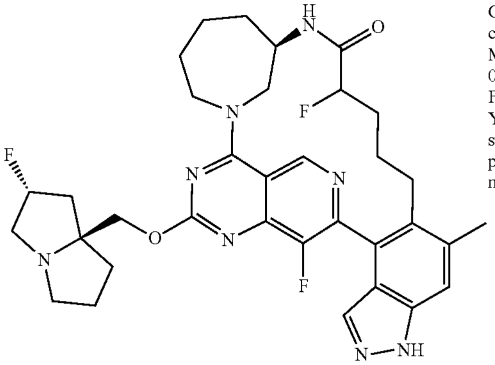 | Column: (S.S) Whelk-0 (2 × 15 cm, 5 μm)<br>Mobile phase: 50% MeOH with 0.2% DEA<br>Flowrate: 80 mL/min.<br>Yield: 50 mg sample was submitted to generate 23 mg of peak 1 with an ee of 99% and 20 mg of peak 2 with an ee of 99%. | Peak 1: Example 159<br>Peak 2: Example 160 |

TABLE 10

| Analytical Data for Examples 49 to 59, 159 to 161 and 267 to 269. | | |
|---|---|---|
| Ex. # | MS m/z (ESI): $(M + H)^+$ | $^1H$ NMR and $^{19}F$ NMR |
| 49 | 635.2 | $^1H$ NMR (400 MHz, METHANOL-$d_4$) δ ppm 9.17-9.28 (m, 1 H), 7.74-7.96 (m, 1 H), 7.49-7.63 (m, 2 H), 5.53-5.72 (m, 1 H), 5.10-5.27 (m, 2 H), 4.52-4.76 (m, 3 H), 4.09 (dt, J = 13.8, 3.6 Hz, 1 H), 3.84-4.05 (m, 5 H), 3.43-3.57 (m, 1 H), 3.22-3.31 (m, 1 H), 2.72-2.91 (m, 2 H), 2.32-2.70 (m, 9 H), 2.07-2.24 (m, 3 H), 1.72-1.92 (m, 3 H), 0.78-1.67 (m, 4 H). $^{19}F$ NMR (376 MHz, METHANOL-$d_4$) δ ppm −77.35 (s), −142.64--141.83 (m), −174.14--173.79 (m), −186.10--185.54 (m), −186.91--186.35 (m). Stereochemistry of Example 49 was confirmed by X-Ray crystallography analysis. |
| 50 | 631.2 | $^1H$ NMR (400 MHz, METHANOL-$d_4$) δ ppm 9.39 (s, 1 H), 9.17 (s, 1 H), 7.75 (s, 1 H), 7.67 (s, 1 H), 7.53 (s, 1 H), 5.51-5.72 (m, 1 H), 5.21 (br d, J = 14.2 Hz, 1 H), 4.94 (br d, J = 13.4 Hz, 2 H), 4.67-4.78 (m, 3 H), 4.18 (br s, 1 H), 4.03-4.24 (m, 1 H), 3.84-4.01 (m, 3 H), 3.44--3.55 (m, 1 H), 3.35-3.43 (m, 1 H), 2.97-3.27 (m, 1 H), 2.92 (s, 1 H), 2.60-2.83 (m, 3 H), 2.34-2.60 (m, 9 H), 2.13-2.27 (m, 2 H), 1.91-2.11 (m, 2 H), 1.82 (br d, J = 13.6 Hz, 1 H), 1.67-1.76 (m, 1 H), 1.58 (br s, 1 H), 1.38-1.53 (m, 2 H), 1.23 (br d, J = 7.9 Hz, 1 H). $^{19}F$ NMR (376 MHz, METHANOL-$d_4$) δ ppm −77.56--76.95 (m), −140.63 (s), −142.60 (s), −174.78--173.58 (m). Stereochemistry of Example 50 was confirmed by X-Ray crystallography analysis. |
| 51 | 649.2 | $^1H$ NMR (400 MHz, METHANOL-$d_4$) δ ppm 9.04-9.27 (m, 1 H), 7.71-7.87 (m, 1 H), 7.51 (d, J = 6.1 Hz, 1 H), 5.24-5.44 (m, 1 H), 5.12 (br d, J = 14.4 Hz, 1 H), 4.85-4.96 (m, 2 H), 4.51-4.70 (m, 1 H), 4.27-4.44 (m, 2 H), 3.82-4.03 (m, 1 H), 3.65-3.78 (m, 1 H), 3.35-3.39 (m, 2 H), 3.12-3.29 (m, 4 H), 3.01-3.10 (m, 1 H), 2.94 (s, 1 H), 2.64-2.82 (m, 3 H), 2.56 (d, J = 7.7 Hz, 3 H), 2.12- |

TABLE 10-continued

Analytical Data for Examples 49 to 59, 159 to 161 and 267 to 269.

| Ex. # | MS m/z (ESI): $(M + H)^+$ | $^1$H NMR and $^{19}$F NMR |
|---|---|---|
| | | 2.44 (m, 5 H), 1.99-2.07 (m, 3 H), 1.88-1.99 (m, 2 H), 1.68-1.86 (m, 2 H), 1.44-1.66 (m, 2 H), 1.28-1.34 (m, 2 H), 0.63-1.19 (m, 1 H). $^{19}$F NMR (376 MHz, METHANOL-$d_4$) δ ppm −76.93 (s), −139.67 (s), −142.52 (s), −173.69 (d, J = 32.1 Hz), −185.47 (s). Stereochemistry of Example 51 was confirmed by X-Ray crystallography analysis. |
| 52 | 649.2 | $^1$H NMR (400 MHz, METHANOL-$d_4$) δ ppm 9.07-9.19 (m, 1 H), 7.74 (s, 1 H), 7.53 (s, 1 H), 5.22-5.45 (m, 2 H), 5.14 (br d, J = 14.0 Hz, 1 H), 4.96 (br dd, J = 11.3, 1.9 Hz, 2 H), 4.53-4.71 (m, 1 H), 4.14-4.45 (m, 3 H), 3.86-4.00 (m, 1 H), 3.49-3.69 (m, 1 H), 3.37 (s, 2 H), 3.17-3.27 (m, 3 H), 2.99-3.10 (m, 1 H), 2.74-2.87 (m, 1 H), 2.67 (s, 3 H), 2.49-2.62 (m, 5 H), 2.26-2.41 (m, 1 H), 2.20-2.40 (m, 6 H), 1.97-2.19 (m, 6 H), 1.77-1.97 (m, 4 H), 1.51-1.67 (m, 4 H), 1.31 (br s, 6 H). $^{19}$F NMR (376 MHz, METHANOL-$d_4$) δ ppm −76.94 (s), −141.69 (s), −173.76 (s), −173.82 (s), −173.85 (s). Stereochemistry of Example 52 was confirmed by X-Ray crystallography analysis. |
| 53 | 651.0 | $^1$H NMR (400 MHz, METHANOL-$d_4$) δ ppm 9.15 (s, 1 H) 7.80 (s, 2 H) 5.32-5.61 (m, 1 H) 4.91-5.23 (m, 1 H) 4.47-4.63 (m, 2 H) 4.11-4.21 (m, 1 H) 3.37-3.91 (m, 5 H) 2.91 (s, 3 H) 2.53 (s, 5 H) 1.96-2.36 (m, 8 H) 1.19-1.83 (m, 6 H) 0.79-0.96 (m, 1 H). $^{19}$F NMR (376 MHz, METHANOL-$d_4$) δ ppm −73.92 (s) −75.80 (s) −140.55 (s) −142.19 (s) −173.89 (s) −173.94 (s). |
| 54 | 631.0 | $^1$H NMR (400 MHz, METHANOL-$d_4$) δ ppm 9.12-9.35 (m, 1 H), 7.65-7.76 (m, 1 H), 7.45-7.58 (m, 1 H), 7.10-7.21 (m, 1 H), 5.12-5.44 (m, 2 H), 4.59-4.71 (m, 1 H), 4.35 (br d, J = 12.5 Hz, 2 H), 3.89-4.02 (m, 1 H), 3.65-3.79 (m, 1 H), 3.35-3.40 (m, 2 H), 3.24-3.28 (m, 1 H), 3.00-3.12 (m, 1 H), 2.55 (s, 4 H), 2.40-2.50 (m, 1 H), 2.20-2.39 (m, 3 H), 2.09-2.18 (m, 1 H), 1.85-2.08 (m, 6 H), 1.74-1.84 (m, 1 H), 1.49-1.71 (m, 4 H), 1.23-1.48 (m, 3 H). |
| 55 | 651.2 | $^1$H NMR (400 MHz, METHANOL-$d_4$) δ ppm 9.39 (d, J = 6.9 Hz, 1 H), 7.68-7.85 (m, 1 H), 7.55 (s, 1 H), 6.92-7.11 (m, 1 H), 5.51-5.70 (m, 1 H), 5.30-5.46 (m, 1 H), 4.63-4.77 (m, 3 H), 4.38-4.50 (m, 1 H), 3.87-4.11 (m, 7 H), 3.69-3.82 (m, 2 H), 3.45-3.54 (m, 1 H), 2.72-2.92 (m, 3 H), 2.55-2.60 (m, 3 H), 2.34-2.53 (m, 4 H), 2.12-2.26 (m, 1 H), 1.56-1.73 (m, 1 H), 1.27-1.53 (m, 4 H). $^{19}$F NMR (376 MHz, METHANOL-$d_4$) δ ppm −77.45 (s), −141.95 (s), −174.18-−173.91 (m), −192.37-−186.40 (m). |
| 56 | 642.9 | $^1$H NMR (400 MHz, METHANOL-$d_4$) δ ppm 9.34 (s, 1 H), 7.61-7.77 (m, 1 H), 7.44-7.59 (m, 1 H), 5.31-5.64 (m, 1 H), 5.00-5.15 (m, 1 H), 4.86-4.98 (m, 1 H), 4.43-4.63 (m, 2 H), 3.86-3.98 (m, 1 H), 3.47-3.75 (m, 6 H), 3.15-3.28 (m, 2 H), 2.86-2.97 (m, 1 H), 2.56 (s, 7 H), 2.27-2.35 (m, 1 H), 2.12-2.25 (m, 2 H), 1.97-2.12 (m, 2 H), 1.74-1.94 (m, 3 H), 1.42-1.74 (m, 4 H), 1.19-1.32 (m, 1 H), 1.04-1.18 (m, 1 H). |
| 57 | 643.2 | $^1$H NMR (400 MHz, METHANOL-$d_4$) δ ppm 9.14-9.40 (m, 1 H), 7.65-7.87 (m, 1 H), 7.48-7.59 (m, 1 H), 5.44-5.72 (m, 2 H), 4.85-5.08 (m, 3 H), 4.24-4.75 (m, 1 H), 3.37 (br s, 10 H), 2.53 (s, 10 H), 2.29-2.44 (m, 3 H), 1.85-2.25 (m, 5 H), 1.11-1.51 (m, 4 H). |
| 58 | 617.2 | $^1$H NMR (400 MHz, METHANOL-$d_4$) δ ppm 9.37-9.44 (m, 1 H), 7.73-7.83 (m, 1 H), 7.62-7.70 (m, 1 H), 7.50-7.56 (m, 1 H), 5.73-5.81 (m, 1 H), 5.48-5.70 (m, 1 H), 4.64-4.78 (m, 2 H), 3.87-4.15 (m, 3 H), 3.51 (d, J = 5.6 Hz, 4 H), 3.09-3.24 (m, 2 H), 2.57-2.79 (m, 5 H), 2.33-2.52 (m, 4 H), 2.12-2.31 (m, 1 H), 1.72-1.86 (m, 1 H), 1.45-1.58 (m, 3 H), 1.06-1.17 (m, 3 H), 0.87-0.95 (m, 1 H), 0.64-0.79 (m, 2 H). |
| 59 | 597.3 | $^1$H NMR (400 MHz, $CDCl_3$) δ ppm 9.02 (s, 1 H), 7.46 (d, J = 8.0 Hz, 2 H), 7.28-7.35 (m, 1 H), 5.36 (d, J = 21.60 Hz, 1 H), 4.95-5.10 (m, 3 H), 4.25-4.35 (m, 1 H), 4.15-4.20 (m, 1 H), 4.02 (s, 1 H), 3.65-3.75 (m, 1 H), 3.25-3.30 (m, 3 H), 2.95-3.10 (m, 2 H), 2.65-2.75 (m, 1 H), 2.35-2.45 (m, 1 H), 2.15-2.30 (m, 3 H), 1.80-2.05 (m, 6 H), 1.60-1.75 (m, 2 H), 1.40-1.50 (m, 1 H), 1.00-1.30 (m, 4 H). |
| 159 | 649.4 | 1H NMR (600 MHz, DMSO-$d_6$) δ ppm 9.28 (s, 1 H), 7.79 (br d, J = 7.2 Hz, 1 H), 7.55 (s, 1 H), 7.49 (s, 1 H), 5.34 (br s, 1 H), 5.25 (br s, 1 H), 5.15 (br d, J = 16.3 Hz, 1 H), 4.53-4.57 (m, 1 H), 4.02-4.19 (m, 3 H), 3.92-3.99 (m, 1 H), 3.77 (br dd, J = 16.5, 3.9 Hz, 1 H), 3.19-3.25 (m, 1 H), 3.06-3.13 (m, 1 H), 3.04 (br s, 1 H), 2.76-2.87 (m, 1 H), 2.29 (br t, J = 7.2 Hz, 1 H), 2.07-2.19 (m, 3 H), 1.96-2.05 (m, 2 H), 1.71-1.90 (m, 6 H), 1.45-1.62 (m, 3 H), 1.21-1.40 (m, 7 H). |
| 160 | 649.4 | 1H NMR (600 MHz, DMSO-$d_6$) δ ppm 9.26 (s, 1 H), 7.61 (s, 1 H), 7.57 (br d, J = 6.2 Hz, 1 H), 7.47 (s, 1 H), 5.34 (br s, 1 H), 5.25 (br s, 1 H), 5.10 (br d, J = 16.6 Hz, 1 H), 4.61 (br d, J = 5.0 Hz, 1 H), 4.48- |

TABLE 10-continued

Analytical Data for Examples 49 to 59, 159 to 161 and 267 to 269.

| Ex. # | MS m/z (ESI): $(M + H)^+$ | $^1H$ NMR and $^{19}F$ NMR |
|---|---|---|
| | | 4.54 (m, 1 H), 4.16 (d, J = 10.4 Hz, 1 H), 4.06 (d, J = 10.3 Hz, 1 H), 3.80 (br d, J = 12.9 Hz, 1 H), 3.31-3.34 (m, 1 H), 3.06-3.13 (m, 2 H), 3.04 (br s, 1 H), 2.78-2.87 (m, 1 H), 1.99-2.18 (m, 5 H), 1.73-1.91 (m, 7 H), 1.50-1.58 (m, 4 H), 1.30-1.47 (m, 2 H), 0.98-1.06 (m, 1 H). |
| 161 | 669.2 | $^1H$ NMR (400 MHz, METHANOL-$d_4$) δ ppm 9.20-9.42 (m, 1 H), 7.80-7.90 (m, 1 H), 7.70-7.79 (m, 1 H), 5.22-5.46 (m, 2 H), 4.61-4.81 (m, 1 H), 4.38-4.45 (m, 1 H), 4.27-4.38 (m, 1 H), 4.00-4.16 (m, 1 H), 3.78-3.96 (m, 1 H), 3.37-3.43 (m, 1 H), 3.24-3.30 (m, 1 H), 3.04-3.20 (m, 2 H), 2.46-2.75 (m, 1 H), 2.24-2.45 (m, 3 H), 2.13-2.23 (m, 1 H), 2.05 (s, 7 H), 1.61-1.81 (m, 4 H), 1.15-1.56 (m, 3 H). |
| 267 | 635.05 | $^1H$ NMR (METHANOL-$d_4$, 400 MHz) δ 9.19 (s, 1H), 7.77 (s, 2H), 5.89 (br d, 1H, J = 14.7 Hz), 4.7-4.8 (m, 2H), 4.6-4.7 (m, 1H), 3.94 (br dd, 1H, J = 2.3, 14.7 Hz), 3.79 (br d, 1H, J = 5.4 Hz), 3.70 (d, 1H, J = 15.1 Hz), 3.55 (br s, 1H), 3.4-3.5 (m, 1H), 3.38 (d, 1H, J = 15.1 Hz), 3.3-3.4 (m, 1H), 3.2-3.3 (m, 3H), 2.9-3.1 (m, 3H), 2.91 (s, 4H), 2.6-2.7 (m, 2H), 2.2-2.3 (m, 1H), 2.0-2.1 (m, 1H), 1.8-2.0 (m, 6H), 1.62 (br dd, 1H, J = 5.8, 12.4 Hz), 1.40 (br dd, 1H, J = 4.1, 8.9 Hz). $^{19}F$ NMR (METHANOL-$d_4$, 377 MHz) δ −76.83 (s), −140.77 (s). |
| 268 | 633.1 | $^1H$ NMR (METHANOL-$d_4$, 400 MHz) δ 9.2-9.3 (m, 1H), 7.8-7.8 (m, 2H), 5.5-5.6 (m, 1H), 4.9-5.0 (m, 1H), 4.4-4.5 (m, 2H), 3.8-4.0 (m, 2H), 3.4-3.4 (m, 2H), 3.0-3.0 (m, 6H), 2.8-2.9 (m, 2H), 2.4-2.5 (m, 1H), 2.2-2.3 (m, 2H), 1.9-2.0 (m, 2H), 1.8-1.9 (m, 2H), 1.5-1.7 (m, 3H), 1.4-1.5 (m, 3H), 1.2-1.3 (m, 1H), 1.0-1.0 (m, 2H), 0.9-0.9 (m, 2H). $^{19}F$ NMR (METHANOL-$d_4$, 376 MHz) δ −77.3 (m), −143.03 (s). |
| 269 | 663.0 | $^1H$ NMR (METHANOL-$d_4$, 400 MHz) δ 9.21 (s, 1H), 7.82 (s, 1H), 7.8-7.8 (m, 1H), 5.5-5.7 (m, 2H), 5.15 (br d, 1H, J = 14.0 Hz), 4.6-4.8 (m, 4H), 4.39 (br s, 1H), 4.0-4.1 (m, 1H), 3.8-4.0 (m, 4H), 3.4-3.5 (m, 2H), 2.7-2.8 (m, 1H), 2.6-2.7 (m, 3H), 2.36 (br dd, 4H, J = 6.0, 11.0 Hz), 2.1-2.2 (m, 2H), 1.9-2.0 (m, 2H), 1.8-1.9 (m, 1H), 1.6-1.7 (m, 1H), 1.5-1.5 (m, 1H), 1.4-1.5 (m, 1H), 1.1-1.2 (m, 1H), 1.14 (br d, 1H, J = 2.9 Hz).$^{19}F$ NMR (METHANOL-$d_4$, 376 MHz) δ −78.50 (s, 9F), −143.88 (d, 1F, J = 13.0 Hz), −175.3 (m, 1F). |

(28R,32S)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one and (28S,32R)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one (Example 60)

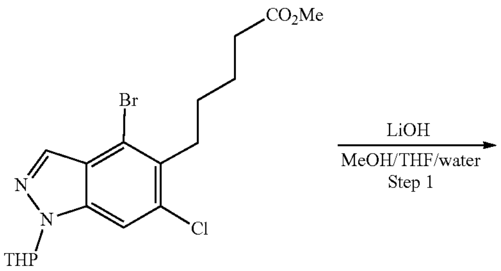

intermediate P

-continued

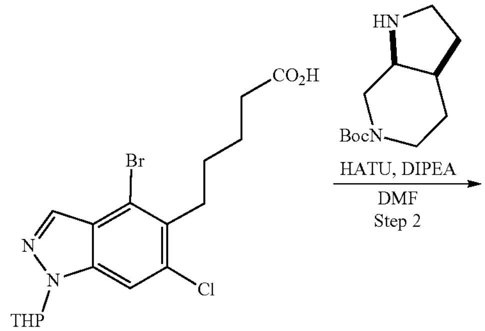

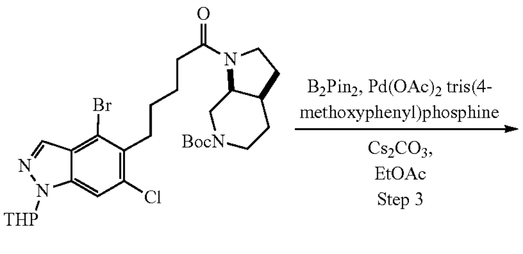

-continued

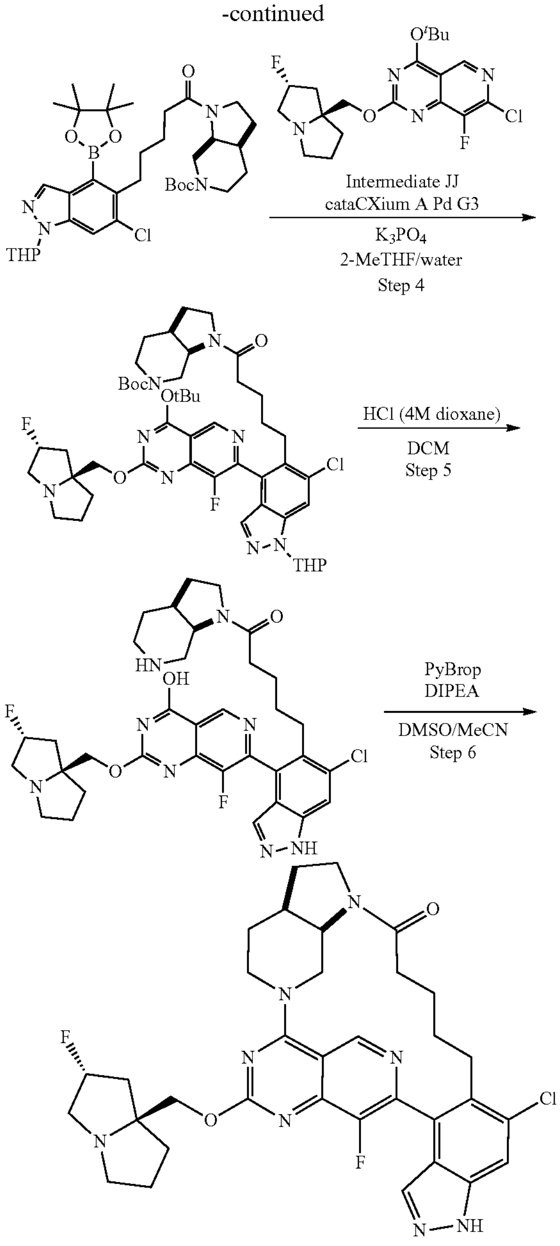

Example 60

Step 1. Methyl 5-(4-bromo-6-chloro-1-(tetrahydro-2H-pyran-2-yl)-1H-indazol-5-yl)pentanoate. A vial was charged with methyl 5-(4-bromo-6-chloro-1-(tetrahydro-2H-pyran-2-yl)-1H-indazol-5-yl)pentanoate (2.25 g, 5.24 mmol, Intermediate P), methanol (4.0 mL), tetrahydrofuran (8.5 mL) and water (8.5 mL). Lithium hydroxide hydrate (0.88 g, 21 mmol) was added, and the reaction mixture was stirred at rt for 30 min. The reaction mixture was neutralized to pH=7 with 1 N HCl and saturated aqueous sodium bicarbonate. The aqueous phase was extracted with EtOAc, and the combined organic phases were washed with brine, dried over sodium sulfate, filtered and concentrated under reduced pressure to provide 5-(4-bromo-6-chloro-1-(tetrahydro-2H-pyran-2-yl)-1H-indazol-5-yl)pentanoic acid (2.2 g, 5.3 mmol, 100% yield) as clear light-yellow oil, which was directly used for the next step. m/z (ESI): 414.9/416.8 $(M+H)^+$.

Step 2. rac-tert-Butyl (3aR,7aR)-1-(5-(4-bromo-6-chloro-1-(tetrahydro-2H-pyran-2-yl)-1H-indazol-5-yl)pentanoyl) octahydro-6H-pyrrolo[2,3-c]pyridine-6-carboxylate. A vial was charged with rac-tert-butyl (3aR,7aR)-octahydro-6H-pyrrolo[2,3-c]pyridine-6-carboxylate (1.14 g, 5.05 mmol, Angel Pharmatech), 5-(4-bromo-6-chloro-1-(tetrahydro-2H-pyran-2-yl)-1H-indazol-5-yl)pentanoic acid (2.10 g, 5.05 mmol), HATU (2.11 g, 5.56 mmol) and N,N-dimethylformamide (15 mL). The reaction mixture was stirred at rt for 10 min, then N-ethyl-N-isopropylpropan-2-amine (4.4 mL, 25 mmol) was added dropwise. The reaction was stirred at rt for 5 min, then was diluted with water and extracted with EtOAc. The combined organic phases were washed with aqueous LiCl, brine, dried ($Na_2SO_4$), filtered and concentrated. The crude material was dissolved in DMSO (2.0 mL) and injected into C18 column (100 g), eluting with a gradient of 5-100% (0.1% formic acid MeCN)/(0.1% formic acid water) over 20 min. The desired fractions were basified using aqueous sodium bicarbonate, extracted with EtOAc. The organic layer was dried ($Na_2SO_4$) and concentrated under reduced pressure to provide rac-tert-butyl (3aR,7aR)-1-(5-(4-bromo-6-chloro-1-(tetrahydro-2H-pyran-2-yl)-1H-indazol-5-yl)pentanoyl)octahydro-6H-pyrrolo[2,3-c]pyridine-6-carboxylate (2.35 g, 3.77 mmol, 75% yield) as white foam. m/z (ESI): 644.8/646.8 $(M+Na)^+$.

Step 3. rac-tert-Butyl (3aR,7aR)-1-(5-(6-chloro-1-(tetrahydro-2H-pyran-2-yl)-4-(4,4,5,5-tetramethyl-1,3,2-dioxaborolan-2-yl)-1H-indazol-5-yl)pentanoyl)octahydro-6H-pyrrolo[2,3-c]pyridine-6-carboxylate. A vial was charged with rac-tert-butyl (3aR,7aR)-1-(5-(4-bromo-6-chloro-1-(tetrahydro-2H-pyran-2-yl)-1H-indazol-5-yl)pentanoyl)octahydro-6H-pyrrolo [2,3-c]pyridine-6-carboxylate (0.15 g, 0.24 mmol), tris(4-methoxyphenyl)phosphine (8.5 mg, 0.024 mmol, Ambeed, Inc.), palladium acetate (2.7 mg, 0.012 mmol), 4,4,4',4',5,5,5',5'-octamethyl-2,2'-bi(1,3,2-dioxaborolane) (73 mg, 0.29 mmol), cesium carbonate (0.12 g, 0.36 mmol), and ethyl acetate (0.5 mL). The reaction mixture was sparged with $N_2$ and heated to 80° C. for 3 h. After cooling to rt, the reaction mixture was passed through a syringe filter and washed with EtOAc. The filtrate was concentrated and used directly for the next step. m/z (ESI): 571.0 $(M-Boc+H)^+$.

Step 4. tert-Butyl (3aR,7aR)-1-(5-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)pentanoyl) octahydro-6H-pyrrolo[2,3-c]pyridine-6-carboxylate and tert-butyl (3aS,7aS)-1-(5-(4-(4-(tert-butoxy)-8-fluoro-2-(((2R,7aS)-2-fluorotetrahydro-1H-pyrrolizin-7a(5H)-yl) methoxy)pyrido[4,3-d]pyrimidin-7-yl)-6-chloro-1-(tetrahydro-2H-pyran-2-yl)-1H-indazol-5-yl)pentanoyl) octahydro-6H-pyrrolo[2,3-c]pyridine-6-carboxylate. A vial was charged with rac-tert-butyl (3aR,7aR)-1-(5-(6-chloro- 1-(tetrahydro-2H-pyran-2-yl)-4-(4,4,5,5-tetramethyl-1,3,2-dioxaborolan-2-yl)-1H-indazol-5-yl)pentanoyl)octahydro-6H-pyrrolo[2,3-c]pyridine-6-carboxylate (0.60 g, 1.45 mmol), 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (0.95 g, 1.45 mmol, Intermediate JJ), potassium phosphate tribasic (0.92 g, 4.3 mmol), cataCXium A Pd G3 (0.11 g, 0.15 mmol), water (0.2 mL) and 2-methyltetrahydrofuran (2.2 mL). The reaction mixture was heated to 80° C. for 1 h. After cooling to rt, the reaction was diluted with water and extracted with EtOAc. The combined organic phases were washed with brine, dried ($Na_2SO_4$), filtered, and concentrated. The crude material was purified by column chromatography on silica gel, eluting with a gradient of 0-60% 3:1 EtOAc/EtOH with 2% triethylamine/heptane, to provide tert-butyl (3aR,7aR)-1-(5-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)pentanoyl)octahydro-6H-pyrrolo[2,3-c]pyridine-6-carboxylate and tert-butyl (3aS,7aS)-1-(5-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)pentanoyl)octahydro-6H-pyrrolo [2,3-c]pyridine-6-carboxylate (0.50 g, 0.54 mmol, 37% yield) as off-white solid. m/z (ESI): 920.8 $(M+H)^+$.

Step 5. 5-(6-Chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-((3aS,7aR)-octahydro-1H-pyrrolo[2,3-c]pyridin-1-yl)pentan-1-one and 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-((3aR,7aS)-octahydro-1H-pyrrolo[2,3-c]pyridin-1-yl)pentan-1-one. A vial was charged with tert-butyl (3aR,7aR)-1-(5-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)pentanoyl)octahydro-6H-pyrrolo[2,3-c]pyridine-6-carboxylate and tert-butyl (3aS,7aS)-1-(5-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)pentanoyl)octahydro-6H-pyrrolo[2,3-c]pyridine-6-carboxylate (0.50 g, 0.54 mmol) and dichloromethane (5.5 mL). Hydrogen chloride, 4 N solution in 1,4-dioxane (6.8 mL, 27 mmol) was added and the reaction mixture was stirred vigorously at rt for 30 min, then was concentrated under reduced pressure. The crude product was dissolved in MeOH and eluted through a 5 g SCX column with additional MeOH wash. The SCX column was dried, then eluted with 2.0 M ammonia MeOH to provide 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-((3aS,7aR)-octahydro-1H-pyrrolo[2,3-c]pyridin-1-yl)pentan-1-one and 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-((3aR,7aS)-octahydro-1H-pyrrolo[2,3-c]pyridin-1-yl)pentan-1-one as white solid, which was used directly in the next step. m/z (ESI): 681.0 $(M+H)^+$.

Step 6. (28R,32S)-18-Chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one and (28S,32R)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one. A vial was charged with bromotripyrrolidinophosphonium hexafluorophosphate (0.30 g, 0.65 mmol), acetonitrile (100 mL) and Hunig's base (0.5 mL, 2.7 mmol). A solution of 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-((3aS,7aR)-octahydro-1H-pyrrolo[2,3-c]pyridin-1-yl)pentan-1-one and 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-((3aR,7aS)-octahydro-1H-pyrrolo[2,3-c]pyridin-1-yl)pentan-1-one in dimethyl sulfoxide (6.8 mL) was added dropwise over 15 min, then the reaction was stirred at rt for additional 3.5 h. The reaction was diluted with water and MeCN was removed under reduced pressure. The aqueous layer was extracted with EtOAc, and the combined organic phases were washed with water, brine, dried ($Na_2SO_4$), filtered and concentrated. The crude material was purified by column chromatography on silica gel, eluting with a gradient of 3:1 EtOAc/EtOH with 2% triethylamine/heptane, to provide (28R,32S)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one and (28S,32R)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one (0.15 g, 0.23 mmol, 42% yield) as tan solid. m/z (ESI): 662.8 $(M+H)^+$. $^1H$ NMR (400 MHz, METHANOL-$d_4$) δ ppm 7.73-9.48 (m, 3H) 5.27-5.58 (m, 2H) 4.90-5.01 (m, 1H) 4.34-4.48 (m, 1H) 3.82-3.97 (m, 1H) 3.43-3.65 (m, 1H) 3.38-3.42 (m, 1H) 3.08-3.20 (m, 1H) 2.80-2.87 (m, 1H) 2.42-2.52 (m, 1H) 2.23-2.38 (m, 2H) 2.16-2.20 (m, 1H) 2.04-2.13 (m, 2H) 1.82-2.01 (m, 4H) 1.55-1.67 (m, 2H) 1.41-1.54 (m, 4H) 1.34-1.38 (in, 2H) 1.10-1.29 (m, 5H) 0.89-0.94 (in, 1H) 1H not observed; $^{19}F$ NMR (376 MHz, METHANOL-$d_4$) δ ppm −142.27 (s) −142.29 (s) −173.70 (s) −173.80 (s).

TABLE 11

| Analytical Data for Examples 61 to 64, 75, 162 to 168 and 270 to 279. | | | | |
|---|---|---|---|---|
| Ex. # | Structure & Name | Salt Form | Reagent | Method Change |
| 61 | 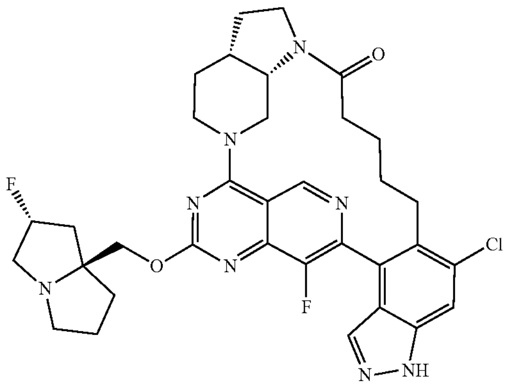 [SMILES: O=C1CCCCc2c(Cl)cc3[nH]ncc3c2-c2ncc3c(nc(OC[C@@]45CCCN4C[C@H](F)C5)nc3c2F)N2CC[C@@H]3CCN1[C@@H]3C2] (28R,32S)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | | | Chiral separation after Step 6. Details included below. |
| 62 | 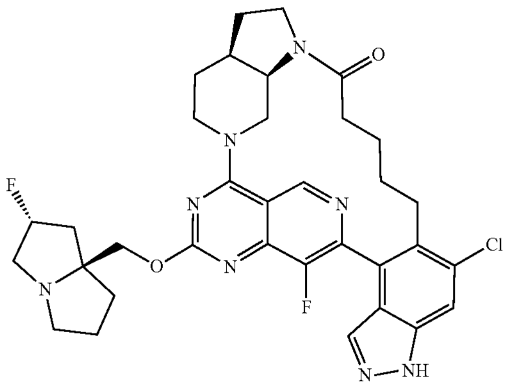 [SMILES: O=C1CCCCc2c(Cl)cc3[nH]ncc3c2-c2ncc3c(nc(OC[C@@]45CCCN4C[C@H](F)C5)nc3c2F)N2CC[C@H]3CCN1[C@H]3C2] (28S,32R)-18-chloro-33-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | | | Chiral separation after Step 6. Details included below. |

TABLE 11-continued

Analytical Data for Examples 61 to 64, 75, 162 to 168 and 270 to 279.

| Ex. # | Structure & Name | Salt Form | Reagent | Method Change |
|---|---|---|---|---|
| 63 | 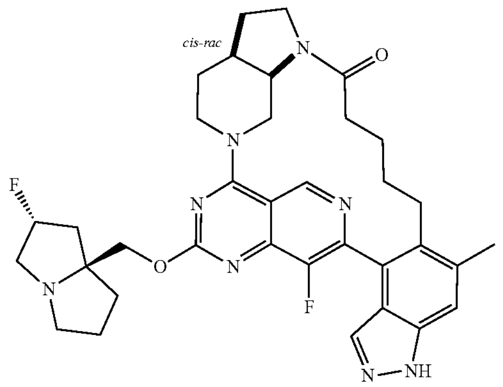 (28R,32S)-33-fluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one and (28S,32R)-33-fluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | TFA | Step 1. Intermediate J | |
| 64 | 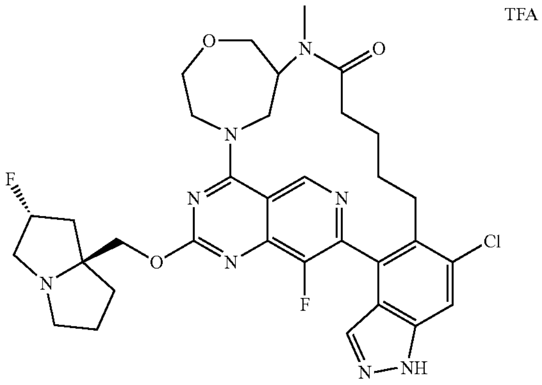 (26R)-18-chloro-32-fluoro-4-(((2R,7aS)-2-fluorotetrahydro-1H-pyrrolo[1,2-a]pyrrol-7a(5H)-yl)methoxy)-25-methyl-28-oxa-1,3,5,9,14,15,25-heptaazahexacyclo [24.4.1.1~6,10~.0~2,7~.0~11,19~.0~12,16~]dotriaconta-2,4,6(32),7,9,11,13,16,18-nonaen-24-one and (26S)-18-chloro-32-fluoro-4-(((2R,7aS)-2-fluorotetrahydro-1H-pyrrolo[1,2-a]pyrrol-7a(5H)-yl)methoxy)-25-methyl-28-oxa-1,3,5,9,14,15,25-heptaazahexacyclo[24.4.1.1~6,10~.0~2,7~.0~11,19~.0~12,16~]dotriaconta-2,4,6(32),7,9,11,13,16,18-nonaen-24-one | TFA | Step 2. tert-butyl 6-(methylamino)-1,4-oxazepane-4-carboxylate (CAS#: 1374243-36-3, Enamine) Step 4. Intermediate KK | Step 3: not performed. Step 4: used CuI, LiCl in DMF instead of $K_3PO_4$ |

TABLE 11-continued

| Analytical Data for Examples 61 to 64, 75, 162 to 168 and 270 to 279. | | | | |
|---|---|---|---|---|
| Ex. # | Structure & Name | Salt Form | Reagent | Method Change |
| 75 | 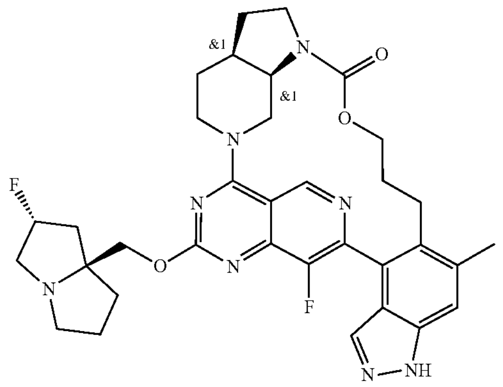 [SMILES: Cc1cc2[nH]ncc2c2c1CCCOC(=O)N1CC[C@@H]3CCN(C[C@@H]31)c1nc(OC[C@@]34CCCN3C[C@H](F)C4)nc3c(F)c-2ncc13] (28S,32R)-33-fluoro-4-(((2R,7aS)-2-fluorotetrahydro-1H-pyrrolo[1,2-a]pyrrol-7a(5H)-yl)methoxy)-18-methyl-23-oxa-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | 2,2,2-trifluoroacetate | Step 3. Intermediate PP | Step 1 & 2 not performed. |
| 162 | 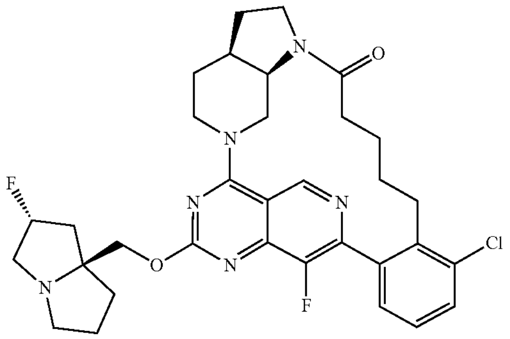 [SMILES: O=C1CCCCc2c(Cl)cccc2-c2ncc3c(nc(OC[C@@]45CCCN4C[C@H](F)C5)nc3c2F)N2CC[C@H]3CCN1[C@H]3C2] (25S,29R)-15-chloro-30-fluoro-4-(((2R,7aS)-2-fluorotetrahydro-1H-pyrrolo[1,2-a]pyrrol-7a(5H)-yl)methoxy)-1,3,5,9,22-pentaazahexacyclo[20.5.2.1~6,10~.0~2,7~.0~11,16~.0~25,29~]triaconta-2,4,6,8,10(30),11,13,15-octaen-21-one | | Step 1. Intermediate SSSS | Chiral separation after Step 6. Details included below. |
| 163 | 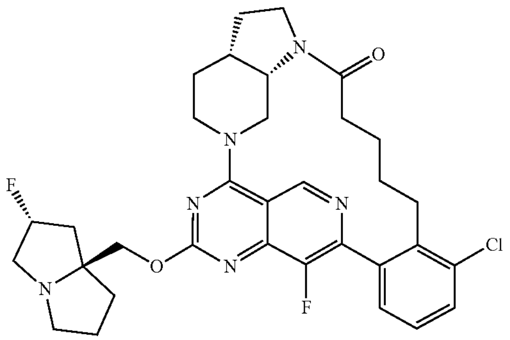 [SMILES: O=C1CCCCc2c(Cl)cccc2-c2ncc3c(nc(OC[C@@]45CCCN4C[C@H](F)C5)nc3c2F)N2CC[C@@H]3CCN1[C@@H]3C2] 2-fluorotetrahydro-1H-pyrrolo[1,2-a]pyrrol-7a(5H)-yl)methoxy)-1,3,5,9,22-pentaazahexacyclo[20.5.2.1~6,10~.0~2,7~.0~11,16~.0~25,29~]triaconta-2,4,6,8,10(30),11,13,15-octaen-21-one | | Step 1. Intermediate SSSS | Chiral separation after Step 6. Details included below. |

TABLE 11-continued

Analytical Data for Examples 61 to 64, 75, 162 to 168 and 270 to 279.

| Ex. # | Structure & Name | Salt Form | Reagent | Method Change |
|---|---|---|---|---|
| 164 | 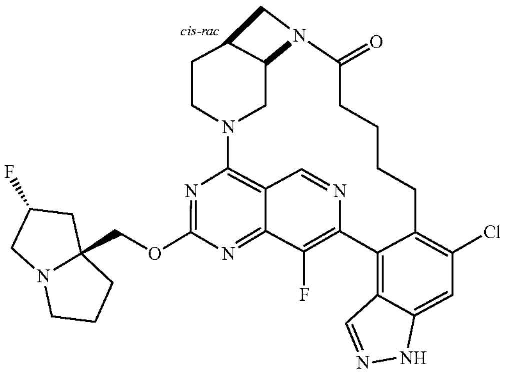 (27R,31S)-18-chloro-32-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.4.2.1~6,10~.0~2,7~.0~11,19~.0~12,16~.0~27,31~]dotriaconta-2,4,6,8,10(32), 11,13,16,18-nonaen-24-one, (27S,31R)-18-chloro-32-fluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.4.2.1~6,10~.0~2,7~.0~11,19~.0~12,16~.0~27,31~]dotriaconta-2,4,6,8,10(32),11,13,16,18-nonaen-24-one | | Step 2. rac-tert-butyl (1R,6S)-3,8-diazabicyclo [4.2.0]octane-3-carboxylate (CAS#: 2007925-05-3, Enamine) | |
| 165 | 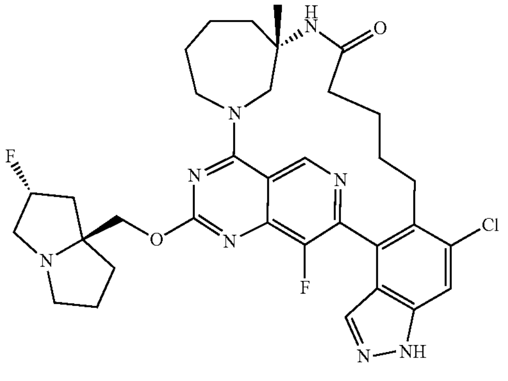 [SMILES: C[C@]12CCCCN(C1)c1nc(OC[C@@]34CCCN3C[C@H](F)C4)nc3c(F)c(ncc13)-c1c(c(Cl)cc3[nH]ncc13)CCCCC(=O)N2] (26S)-18-chloro-32-fluoro-4-(((2R,7aS)-2-fluorotetrahydro-1H-pyrrolo[1,2-a]pyrrol-7a(5H)-yl)methoxy)-26-methyl-1,3,5,9,14,15,25-heptaazahexacyclo [24.4.1.1~6,10~.0~2,7~.0~11,19~.0~12,16~]dotriaconta-2,4,6,8,10(32),11,13,16,18-nonaen-24-one | | Step 2: tert-butyl 3-amino-3-methyl-azepane-1-carboxylate (CAS#: 1513512-18-9, Angel Pharmatech Ltd.) | Step 1 was not performed. Step 5. TFA/DCM was used. Step 6. Bromotris (dimethylamino) phosphonium Hexafluorophosphate was used. Chiral separation after synthesis. Details included below. |

TABLE 11-continued

| Analytical Data for Examples 61 to 64, 75, 162 to 168 and 270 to 279. | | | | |
|---|---|---|---|---|
| Ex. # | Structure & Name | Salt Form | Reagent | Method Change |
| 166 | 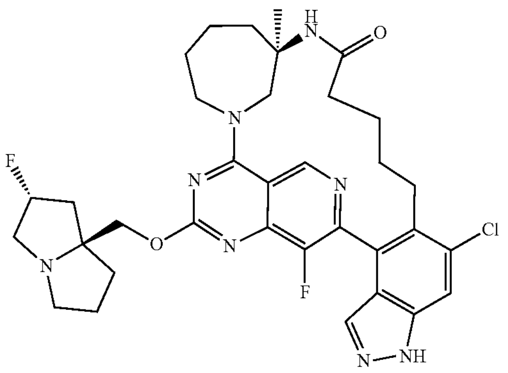 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCCC(=O)N2] (26R)-18-chloro-32-fluoro-4-(((2R,7aS)-2-fluorotetrahydro-1H-pyrrolo[1,2-a]pyrrol-7a(5H)-yl)methoxy)-26-methyl-1,3,5,9,14,15,25-heptaazahexacyclo [24.4.1.1~6,10~.0~2,7~.0~11,19~.0~12,16~]dotriaconta-2,4,6,8,10(32),11,13,16,18-nonaen-24-one | | Step 2: tert-butyl 3-amino-3-methyl-azepane-1-carboxylate (CAS#: 1513512-18-9, Angel Pharmatech Ltd.) | Step 1 was not performed. Step 5. TFA/DCM was used. Step 6. Bromotris (dimethylamino) phosphonium Hexafluorophos phate was used. Chiral separation after synthesis. Details included below. |
| 167 | 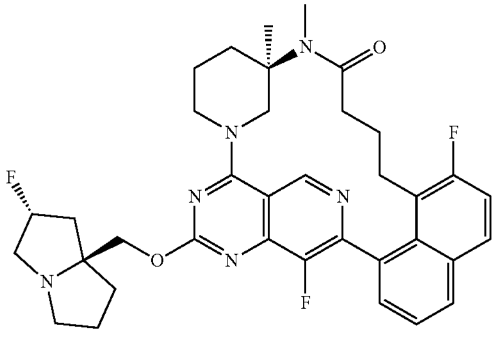 [SMILES: CN1C(=O)CCCc2c(F)ccc3cccc(c23)-c2ncc3c(nc(OC[C@@]45CCCN4C[C@H](F)C5)nc3c2F)N2CCC[C@]1(C)C2] (15R)-22,31-difluoro-8-(((2R,7aS)-2-fluorotetrahydro-1H-pyrrolo[1,2-a]pyrrol-7a(5H)-yl)methoxy)-15,16-dimethyl-3,7,9,11,16-pentaazahexacyclo [19.7.1.1~2,6~. 1~11,15~.0~5,10~.0~25,29~]hentriaconta-1(29),2(31),3,5,7,9,21,23,25,27-decaen-17-one | | Step 2. Intermediate G and Intermediate CT | Step 3 were not performed. |

TABLE 11-continued

Analytical Data for Examples 61 to 64, 75, 162 to 168 and 270 to 279.

| Ex. # | Structure & Name | Salt Form | Reagent | Method Change |
|---|---|---|---|---|
| 168 | 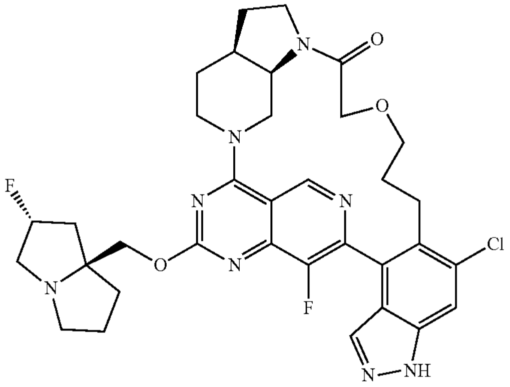 [SMILES: O=C1COCCCc2c(Cl)cc3[nH]ncc3c2-c2ncc3c(nc(OC[C@@]45CCCN4C[C@H](F)C5)nc3c2F)N2CC[C@H]3CCN1[C@H]3C2] (29S,33R)-18-chloro-34-fluoro-4-(((2R,7aS)-2-fluorotetrahydro-1H-pyrrolo[1,2-a]pyrrol-7a(5H)-yl)methoxy)-23-oxa-1,3,5,9,14,15,26-heptaazaheptacyclo[24.5.2.1~6,10~.0~2,7~.0~11,19~.0~12,16~.0~29,33~]tetratriaconta-2,4,6,8,10(34),11,13,16,18-nonaen-25-one | | Step 1. Intermediate CS | |
| 270 | 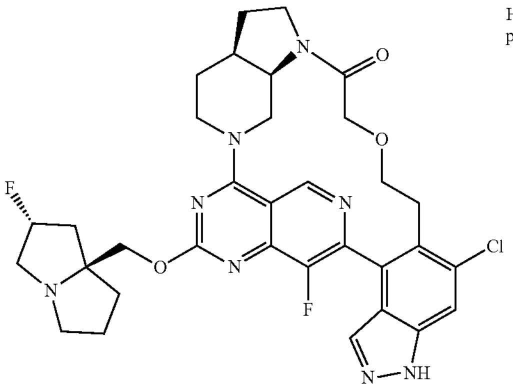 (28S,32R)-18-chloro-33-fluoro-4-(((2R,7aS)-2-fluorotetrahydro-1H-pyrrolo[1,2-a]pyrrol-7a(5H)-yl)methoxy)-22-oxa-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | Hexafluoro phosphate | Step 2. Intermediate CY and tert-butyl (3aR,7aR)-octahydro-6H-pyrrolo[2,3-c]pyridine-6-carboxylate (CAS#: 1821737-93-2) | Step 6. HATU followed by dimethylamine in MeOH was used instead of PyBrOP. |

TABLE 11-continued

| Analytical Data for Examples 61 to 64, 75, 162 to 168 and 270 to 279. | | | | |
|---|---|---|---|---|
| Ex. # | Structure & Name | Salt Form | Reagent | Method Change |
| 271 | 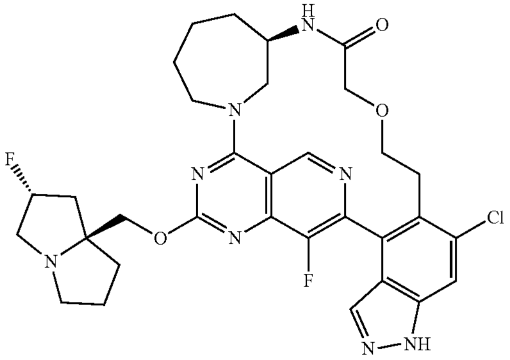 [SMILES: O=C1COCCc2c(Cl)cc3[nH]ncc3c2-c2ncc3c(nc(OC[C@@]45CCCN4C[C@H](F)C5)nc3c2F)N2CCCC[C@H](C2)N1] (26R)-18-chloro-32-fluoro-4-(((2R,7aS)-2-fluorotetrahydro-1H-pyrrolo[1,2-a]pyrrol-7a(5H)-yl)methoxy)-22-oxa-1,3,5,9,14,15,25-heptaazahexacyclo [24.4.1.1~6,10~.0~2,7~.0~11,19~.0~12,16~]dotriaconta-2,4,6,8,10(32),11,13,16,18-nonaen-24-one | | Step 2. Intermediate CY and tert-butyl (3R)-3-aminoazepane-1-carboxylate (CAS#: 1032684-85-7, Synthonix Inc.) | |
| 272 | 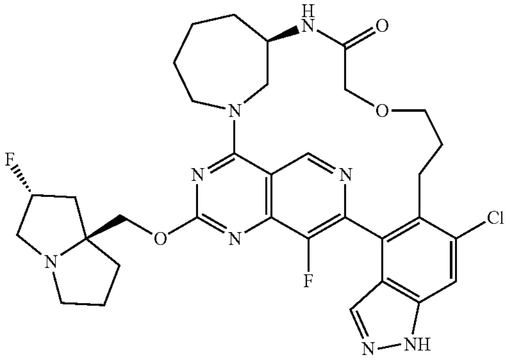 [SMILES: O=C1COCCCc2c(Cl)cc3[nH]ncc3c2-c2ncc3c(nc(OC[C@@]45CCCN4C[C@H](F)C5)nc3c2F)N2CCCC[C@H](C2)N1] (27R)-18-chloro-33-fluoro-4-(((2R,7aS)-2-fluorotetrahydro-1H-pyrrolo[1,2-a]pyrrol-7a(5H)-yl)methoxy)-23-oxa-1,3,5,9,14,15,26-heptaazahexacyclo [25.4.1.1~6,10~.0~2,7~.0~11,19~.0~12,16~]tritriaconta-2,4,6,8,10(33),11,13,16,18-nonaen-25-one | | Step 2. Intermediate CZ and tert-butyl (3R)-3-aminoazepane-1-carboxylate (CAS#: 1032684-85-7, Synthonix Inc.) | Step 6. HATU followed by dimethylamine in MeOH was used instead of PyBrOP. |
| 273 | 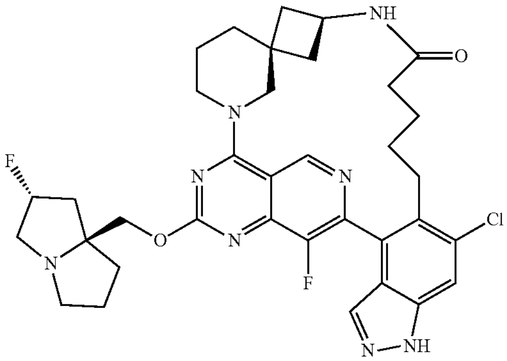 [SMILES: O=C1CCCCc2c(Cl)cc3[nH]ncc3c2-c2ncc3c(nc(OC[C@@]45CCCN4C[C@H](F)C5)nc3c2F)N2CCC[C@]3(C2)C[C@H](C3)N1] (1S,3R)-11-chloro-33-fluoro-25-(((2R,7aS)-2-fluorotetrahydro-1H-pyrrolo[1,2-a]pyrrol-7a(5H)-yl)methoxy)-4,14,15,20,24,26,28-heptaazaheptacyclo[26.3.1.1~1,3~. 1~19,23~.0~10,18~.0~13,17~.0~22,27~]tetratriaconta-10,12,15,17,19(33),20,22,24,26-nonaen-5-one | | Step 2. tert-butyl 2-amino-6-azaspiro[3.5]nonane-6-carboxylate (CAS#: 1363381-69-4, eNovation) | |

TABLE 11-continued

| Analytical Data for Examples 61 to 64, 75, 162 to 168 and 270 to 279. | | | | |
|---|---|---|---|---|
| Ex. # | Structure & Name | Salt Form | Reagent | Method Change |
| 274 | 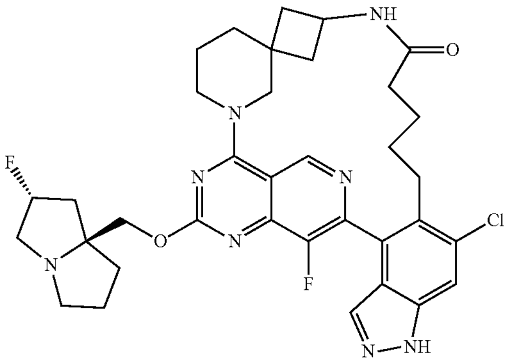 [SMILES: O=C1CCCCc2c(Cl)cc3[nH]ncc3c2-c2ncc3c(nc(OC[C@@]45CCCN4C[C@H](F)C5)nc3c2F)N2CCCC3(CC(C3)N1)C2] (1R,3S)-10-chloro-32-fluoro-24-(((2R,7aS)-2-fluorotetrahydro-1H-pyrrolo[1,2-a]pyrrol-7a(5H)-yl)methoxy)-4,13,14,19,23,25,27-heptaazaheptacyclo[25.3.1.1~1,3~. 1~18,22~.0~9,17~.0~12,16~.0~21,26~]tritriaconta-9,11,14,16,18(32),19,21,23,25-nonaen-5-one, (1S,3R)-10-chloro-32-fluoro-24-(((2R,7aS)-2-fluorotetrahydro-1H-pyrrolo[1,2-a]pyrrol-7a(5H)-yl)methoxy)-4,13,14,19,23,25,27-heptaazaheptacyclo[25.3.1.1~1,3~. 1~18,22~.0~9,17~.0~12,16~.0~21,26~]tritriaconta-9,11,14,16,18(32),19,21,23,25-nonaen-5-one | | Step 2. tert-butyl 2-amino-6-azaspiro[3.5]nonane-6-carboxylate (CAS#: 1363381-69.4, eNovation) and Intermediate CF (Step 1) | |
| 275 | 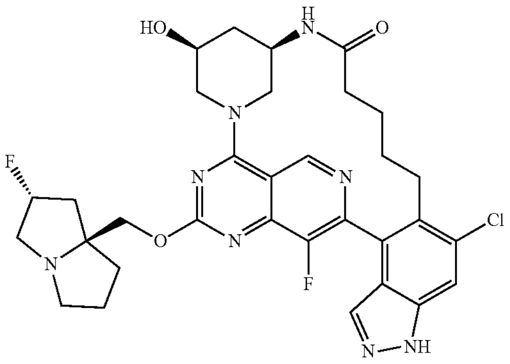 [SMILES: O=C1CCCCc2c(Cl)cc3[nH]ncc3c2-c2ncc3c(nc(OC[C@@]45CCCN4C[C@H](F)C5)nc3c2F)N2C[C@@H](O)C[C@H](C2)N1] (17R,19S)-9-chloro-30-fluoro-24-(((2R,7aS)-2-fluorotetrahydro-1H-pyrrolo[1,2-a]pyrrol-7a(5H)-yl)methoxy)-19-hydroxy-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 2. rac-cis-3-amino-5-hydroxy-piperidine-1-carboxylic acid tert-butyl ester (CAS#: 1923165-22-3, J&W Pharmalab) | Step 6. BroP was used instead of PyBrop. Chiral separation after Step 6. Details included below. |

TABLE 11-continued

Analytical Data for Examples 61 to 64, 75, 162 to 168 and 270 to 279.

| Ex. # | Structure & Name | Salt Form | Reagent | Method Change |
|---|---|---|---|---|
| 276 | 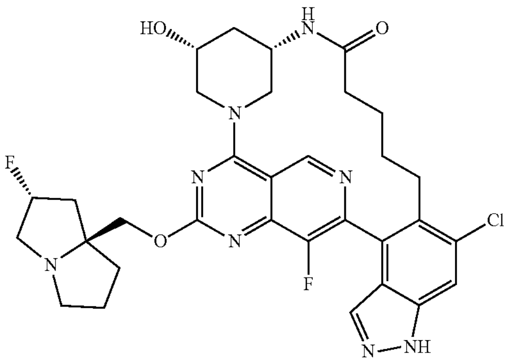 [SMILES: O=C1CCCCc2c(Cl)cc3[nH]ncc3c2-c2ncc3c(nc(OC[C@@]45CCCN4C[C@H](F)C5)nc3c2F)N2C[C@H](O)C[C@@H](C2)N1] (17S,19R)-9-chloro-30-fluoro-24-(((2R,7aS)-2-fluorotetrahydro-1H-pyrrolo[1,2-a]pyrrol-7a(5H)-yl)methoxy)-19-hydroxy-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 2. rac-cis-3-amino-5-hydroxy-piperidine-1-carboxylic acid tert-butyl ester (CAS#: 1923165-22-3) | Step 6. BroP was used instead of PyBrop. Chiral separation after Step 6. Details included below. |
| 277 | 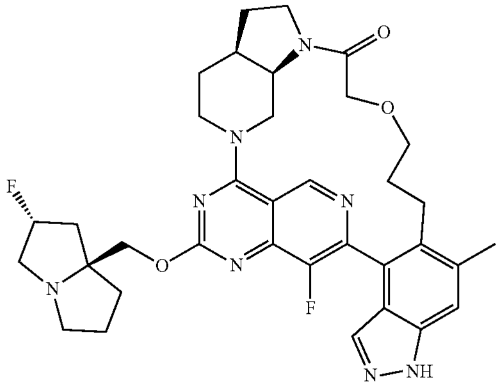 [SMILES: Cc1cc2[nH]ncc2c2c1CCCOCC(=O)N1CC[C@@H]3CCN(C[C@@H]31)c1nc(OC[C@@]34CCCN3C[C@H](F)C4)nc3c(F)c-2ncc13] (29S,33R)-34-fluoro-4-(((2R,7aS)-2-fluorotetrahydro-1H-pyrrolo[1,2-a]pyrrol-7a(5H)-yl)methoxy)-18-methyl-23-oxa-1,3,5,9,14,15,26-heptaazaheptacyclo[24.5.2.1~6,10~.0~2,7~.0~11,19~.0~12,16~.0~29,33~]tetratriaconta-2,4,6,8,10(34),11,13,16,18-nonaen-25-one | | Step 2. Intermediate CS and tert-butyl (3aR,7aR)-octahydro-6H-pyrrolo[2,3-c]pyridine-6-carboxylate (CAS#: 1821737-93-2) | Step 6. BroP was used instead of PyBrop. |

TABLE 11-continued

| Analytical Data for Examples 61 to 64, 75, 162 to 168 and 270 to 279. | | | | |
|---|---|---|---|---|
| Ex. # | Structure & Name | Salt Form | Reagent | Method Change |
| 278 | 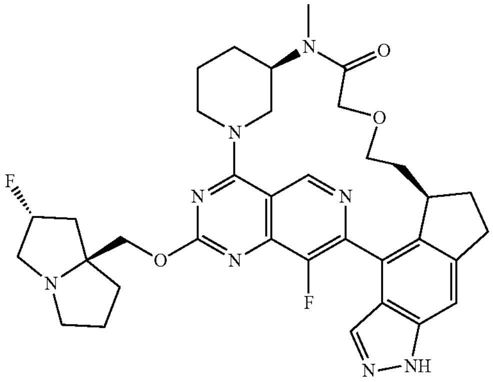 [SMILES: CN1C(=O)COCC[C@H]2CCc3cc4[nH]ncc4c(c32)-c2ncc3c(nc(OC[C@@]45CCCN4C[C@H](F)C5)nc3c2F)N2CCC[C@@H]1C2] (15R,22R)-34-fluoro-8-(((2R,7aS)-2-fluorotetrahydro-1H-pyrrolo[1,2-a]pyrrol-7a(5H)-yl)methoxy)-16-methyl-19-oxa-3,7,9,11,16,28,29-heptaazaheptacyclo[20.9.1.1~2,6~. 1~11,15~.0~5,10~.0~25,32~.0~27,31~]tetratriaconta-1(31),2(34),3,5,7,9,25(32),26,29-nonaen-17-one | | Step 2. Intermediate DA and tert-butyl (R)-3-(methylamino) piperidine-1-carboxylate (CAS#: 203941-94-0) | Chiral separation after Step 6. Details included below. |
| 279 | 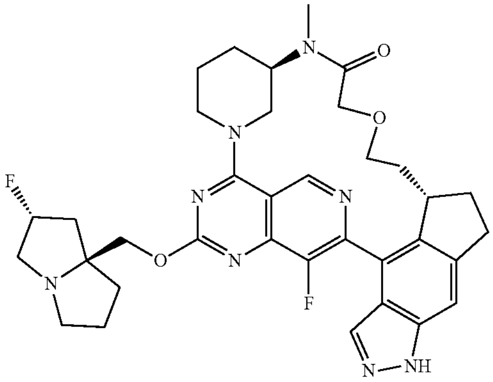 [SMILES: CN1C(=O)COCC[C@@H]2CCc3cc4[nH]ncc4c(c32)-c2ncc3c(nc(OC[C@@]45CCCN4C[C@H](F)C5)nc3c2F)N2CCC[C@@H]1C2] (15R,22S)-34-fluoro-8-(((2R,7aS)-2-fluorotetrahydro-1H-pyrrolo[1,2-a]pyrrol-7a(5H)-yl)methoxy)-16-methyl-19-oxa-3,7,9,11,16,28,29-heptaazaheptacyclo[20.9.1.1~2,6~. 1~11,15~.0~5,10~.0~25,32~.0~27,31~]tetratriaconta-1(31),2(34),3,5,7,9,25(32),26,29-nonaen-17-one | | Step 2. Intermediate DA and tert-butyl (R)-3-(methylamino) piperidine-1-carboxylate (CAS#: 203941-94-0,) | Chiral separation after Step 6. Details included below. |

TABLE 12

Conditions for Chiral SFC Separation.

| Separation | SFC Conditions | Peak to Ex# |
|---|---|---|
| 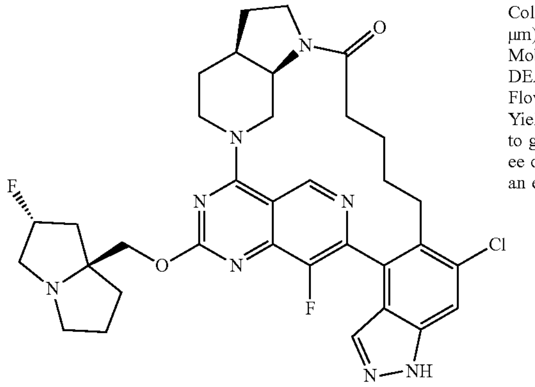 | Column: ChiralPak AD (2 × 25 cm, 5 μm)<br>Mobile phase: 45% iPrOH with 0.2% DEA<br>Flowrate: 80 mL/min.<br>Yield: 150 mg sample was submitted to generate 71 mg of peak 1 with an ee of 99% and 55 mg of peak 2 with an ee of 99%. | Peak 1: Ex. 61<br>Peak 2: Ex. 62 |
| 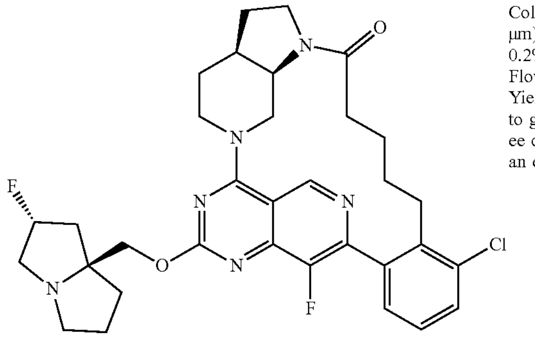 | Column: Chiralcel OD (2 × 25 cm, 5 μm) Mobile phase: 35% MeOH with 0.2% DEA<br>Flowrate: 80 mL/min.<br>Yield: 50 mg of sample was submitted to generate 20 mg of peak 1 with an ee of 95% and 15 mg of peak 2 with an ee of 98%. | Peak 1: Example 162<br>Peak 2: Example 163 |
| 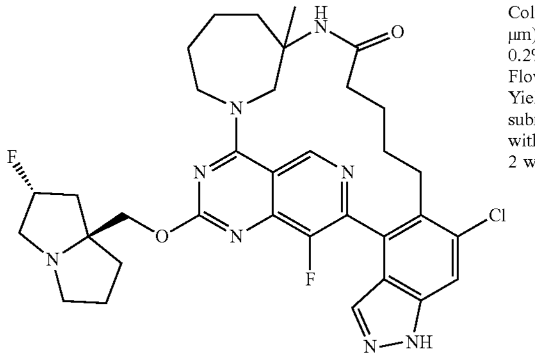 | Column: (S,S) Whelk-0 (2 × 15 cm, 5 μm) Mobile phase: 45% MeOH with 0.2% DEA<br>Flowrate: 100 mL/min.<br>Yield: 200 mg of sample was submitted to generate 84 mg of peak 1 with an ee of 99% and 86 mg of peak 2 with an ee of 99%. | Peak 1: Example 165<br>Peak 2: Example 166 |
| 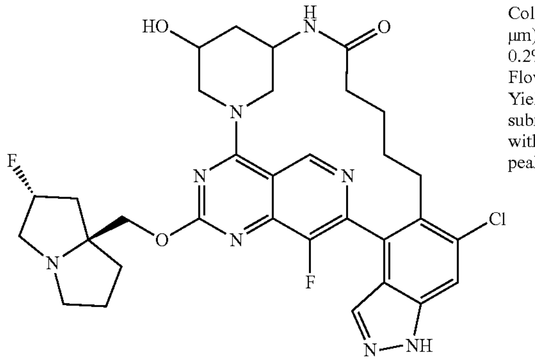 | Column: Chiralcel OD (2 × 15 cm, 5 μm) Mobile phase: 15% MeOH with 0.2% DEA<br>Flowrate: 110 mL/min.<br>Yield: 200 mg of sample was submitted to generate 80 mg of peak 1 with an ee of 99.5% and 73 mg of peak 2 with an ee of 98.7%. | Peak 1: Example 276<br>Peak 2: Example 275 |

TABLE 12-continued

| Conditions for Chiral SFC Separation. | | |
|---|---|---|
| Separation | SFC Conditions | Peak to Ex# |
| 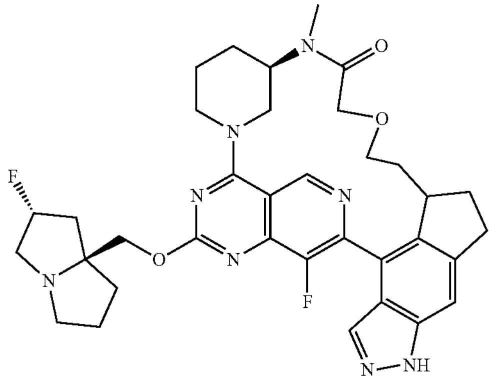 [SMILES: CN1C(=O)COCCC2CCc3cc4[nH]ncc4c(c32)-c2ncc3c(nc(OC[C@@]45CCCN4C[C@H](F)C5)nc3c2F)N2CCC[C@@H]1C2] | Column: Daicel Chiralpak AD (3 × 15 cm, 10 μm)<br>Mobile phase: 54% IPA<br>Yield: 100 mg sample was submitted to generate 21 mg of peak 1 with an ee of 99% and 22 mg of peak 2 with an ee of 99.9%. | Peak 1: Example 279<br>Peak 2: Example 278 |

TABLE 13

Analytical Data for Examples 61 to 64, 75, 162 to 168 and 270 to 279.

| Ex. # | MS m/z (ESI): $(M + H)^+$ | $^1$ NMR |
|---|---|---|
| 61 | 663.2 | $^1$H NMR (600 MHz, DMSO-$d_6$) δ ppm 9.11-9.59 (m, 1 H) 7.68-7.90 (m, 2 H) 5.17-5.37 (m, 2 H) 4.46-4.82 (m, 1 H) 4.05-4.22 (m, 2 H) 3.74-3.97 (m, 3 H) 3.07-3.23 (m, 2 H) 2.79-2.88 (m, 1 H) 2.60-2.75 (m, 1 H) 1.97-2.35 (m, 6 H) 1.78 (br d, J = 5.14 Hz, 7 H) 1.41 (br d, J = 3.23 Hz, 6 H) 1.18-1.33 (m, 3 H). |
| 62 | 663.2 | $^1$H NMR (400 MHz, METHANOL-$d_4$) δ ppm 9.12-9.55 (m, 1 H) 7.64-7.93 (m, 2 H) 5.23-5.62 (m, 2 H) 4.30-4.61 (m, 2 H) 3.81-4.02 (m, 2 H) 3.40-3.61 (m, 4 H) 3.11-3.23 (m, 1 H) 2.62-2.92 (m, 3 H) 2.19-2.53 (m, 6 H) 1.82-2.16 (m, 7 H) 1.10-1.63 (m, 7 H); $^{19}$F NMR (376 MHz, METHANOL-$d_4$) δ ppm −144.57-−140.22 (m) −173.82 (s). Stereochemistry of Example 62 was confirmed by X-Ray crystallography analysis. |
| 63 | 643.0 | $^1$H NMR (400 MHz, METHANOL-$d_4$) δ ppm 9.25 (s, 1 H) 7.63-7.73 (m, 1 H) 7.53 (s, 2 H) 5.52-5.71 (m, 2 H) 4.92-5.02 (m, 1 H) 4.64-4.72 (m, 2 H) 3.89-3.99 (m, 5 H) 3.46-3.55 (m, 2 H) 3.39-3.44 (m, 1 H) 2.81-2.90 (m, 1 H) 2.65-2.79 (m, 3 H) 2.32-2.50 (m, 6 H) 2.16-2.26 (m, 3 H) 1.98-2.04 (m, 1 H) 1.81-1.92 (m, 2 H) 1.56-1.68 (m, 2 H) 1.45 (br s, 3 H) 1.13-1.27 (m, 1 H). $^{19}$F NMR (376 MHz, METHANOL-$d_4$) δ ppm −77.37 (s) −144.68-−141.41 (m) −174.11 (s). |
| 64 | 667.0 | $^1$H NMR (500 MHz, METHANOL-$d_4$) δ ppm 9.67-9.82 (m, 1 H), 7.69-7.87 (m, 2 H), 5.47-5.74 (m, 1 H), 4.92-5.06 (m, 1 H), 4.74 (br s, 2 H), 4.16-4.29 (m, 1 H), 3.96 (br s, 6 H), 3.65-3.77 (m, 1 H), 3.41-3.62 (m, 2 H), 2.93 (s, 2 H), 2.57-2.85 (m, 3 H), 2.30-2.54 (m, 4 H), 2.12-2.29 (m, 2 H), 1.84-2.11 (m, 2 H), 1.69-1.83 (m, 1 H), 1.21-1.58 (m, 2 H). $^{19}$F NMR (471 MHz, METHANOL-$d_4$) δ ppm −77.37 (s), −140.96 (s), −174.24-−173.94 (m). |
| 75 | 644.7 | $^1$H NMR (400 MHz, METHANOL-$d_4$) δ ppm 1.41-1.53 (m, 1 H) 1.61 (br d, J = 11.20 Hz, 1 H) 1.76-2.05 (m, 7 H) 2.20 (br d, J = 14.72 Hz, 1 H) 2.25-2.49 (m, 5 H) 2.55 (s, 3 H) 2.57-2.85 (m, 5 H) 3.21-3.28 (m, 1 H) 3.37-3.54 (m, 3 H) 3.54-3.74 (m, 1 H) 3.80-3.98 (m, 5 H) 4.02-4.16 (m, 1 H) 4.62-4.76 (m, 2 H) 5.42 (br d, J = 13.68 Hz, 1 H) 5.64 (br d, J = 3.94 Hz, 1 H) 7.52 (s, 1 H) 7.75 (br s, 1 H) 9.32 (s, 1 H). $^{19}$F NMR (376 MHz, METHANOL-$d_4$) δ ppm −174.11 (d, J = 16.48 Hz) −144.35 (d, J = 7.80 Hz) −142.29 (br d, J = 23.40 Hz). |
| 162 | 623.0 | $^1$H NMR (600 MHz, DMSO-$d_6$) δ ppm 8.98-9.51 (m, 1 H) 7.18-7.65 (m, 4 H) 4.97-5.46 (m, 2 H) 4.42-4.77 (m, 1 H) 3.95-4.29 (m, 2 H) 3.72-3.85 (m, 1 H) 3.33 (br dd, J = 10.12, 4.40 Hz, 4 H) 3.01-3.21 (m, 1 H) 2.79-2.97 (m, 1 H) 2.58-2.69 (m, 1 H) 1.96-2.30 (m, 4 H) 1.60-1.91 (m, 7 H) 1.24 (br s, 7 H) 0.82-1.10 (m, 1 H). |
| 163 | 623.2 | $^1$H NMR (600 MHz, DMSO-$d_6$) δ ppm 9.01-9.54 (m, 1 H) 7.34-7.61 (m, 4 H) 4.94-5.43 (m, 3 H) 4.63-4.83 (m, 1 H) 3.89-4.30 (m, 3 H) 3.73-3.84 (m, 1 H) 3.36 (br s, 3 H) 2.52-2.70 |

TABLE 13-continued

| Analytical Data for Examples 61 to 64, 75, 162 to 168 and 270 to 279. | | |
|---|---|---|
| Ex. # | MS m/z (ESI): $(M + H)^+$ | $^1$ NMR |
| | | (m, 1 H) 2.05-2.36 (m, 3 H) 1.63-1.91 (m, 7 H) 1.33-1.60 (m, 7 H) 0.81-1.20 (m, 3 H). |
| 164 | 649.2 | $^1$H NMR (400 MHz, METHANOL-$d_4$) δ ppm 9.21-9.35 (m, 1 H) 7.70-7.96 (m, 2 H) 5.29-5.50 (m, 1 H) 4.90-5.11 (m, 1 H) 4.37-4.66 (m, 3 H) 3.50 (br s, 6 H) 2.69-3.25 (m, 4 H) 1.78-2.56 (m, 11 H) 0.79-1.67 (m, 6 H). $^{19}$F NMR (376 MHz, METHANOL-$d_4$) δ ppm −142.61--140.80 (m) −174.41--173.31 (m). |
| 165 | 665.2 | 1H NMR (600 MHz, DMSO-$d_6$) δ ppm 9.19 (s, 1 H), 7.80 (s, 1 H), 7.64 (s, 1 H), 6.84 (s, 1 H), 5.55 (br d, J = 16.1 Hz, 1 H), 5.33 (br s, 1 H), 5.23 (br s, 1 H), 4.47 (br dd, J = 12.7, 3.9 Hz, 1 H), 4.15 (d, J = 10.3 Hz, 1 H), 4.05 (d, J = 10.3 Hz, 1 H), 3.28-3.37 (m, 1 H), 3.16-3.26 (m, 1 H), 3.01-3.13 (m, 2 H), 2.83 (td, J = 9.3, 5.4 Hz, 2 H), 2.36-2.40 (m, 1 H), 2.14-2.20 (m, 1 H), 2.11-2.13 (m, 1 H), 1.96-2.08 (m, 2 H), 1.73-1.90 (m, 4 H), 1.67-1.72 (m, 1 H), 1.49-1.64 (m, 4 H), 1.31-1.40 (m, 2 H), 1.29 (s, 4 H), 1.09-1.20 (m, 1 H), 0.94-1.05 (m, 2 H). |
| 166 | 665.2 | 1H NMR (600 MHz, DMSO-$d_6$) δ ppm 9.20 (s, 1 H), 7.80 (s, 1 H), 7.65 (s, 1 H), 6.84 (s, 1 H), 5.55 (br d, J = 16.1 Hz, 1 H), 5.33 (br s, 1 H), 5.24 (br s, 1 H), 4.46 (br dd, J = 12.6, 4.1 Hz, 1 H), 4.15 (d, J = 10.4 Hz, 1 H), 4.06 (d, J = 10.3 Hz, 1 H), 3.32-3.40 (m, 1 H), 3.16-3.26 (m, 1 H), 3.03-3.12 (m, 3 H), 2.81-2.87 (m, 2 H), 2.34-2.41 (m, 1 H), 2.05-2.22 (m, 3 H), 1.96-2.03 (m, 1 H), 1.68-1.91 (m, 6 H), 1.50-1.63 (m, 4 H), 1.30-1.39 (2 H, 1.29 (s, 3 H), 1.05-1.19 (m, 1 H), 0.94-1.04 (m, 2 H). |
| 167 | 645.3 | $^1$H NMR (400 MHz, METHANOL-$d_4$) δ ppm, 9.10 (s, 1 H), 7.94-7.96 (m, 1 H), 7.81-7.82 (m, 1 H), 7.79-7.80 (m, 1 H), 7.53-7.55 (m, 1 H), 7.26-7.27 (m, 1 H), 6.20 (d, J = 14.4 Hz, 1 H), 5.29 (d, J = 53.6 Hz, 1 H), 5.03 (d, J = 11.2 Hz, 1 H), 4.17-4.33 (m, 2 H), 3.20-3.34 (m, 3 H), 3.02-3.03 (m, 2 H), 2.75-2.91 (m, 1 H), 2.59 (s, 3 H), 2.22-2.30 (m, 6 H), 1.76-2.21 (m, 4 H), 1.55-1.72 (m, 4 H), 1.49-1.55 (m, 1 H), 1.45-1.46 (m, 3 H), 1.09-1.10 (m, 1 H). |
| 168 | 679.2 | $^1$H NMR (400 MHz, METHANOL-$d_4$) δ ppm 9.08-9.30 (m, 1 H) 7.65-7.84 (m, 2 H) 5.81-5.97 (m, 1 H) 5.24-5.54 (m, 1 H) 4.46 (s, 2 H) 3.70-3.99 (m, 3 H) 3.36-3.57 (m, 5 H) 3.01-3.28 (m, 5 H) 2.84-2.96 (m, 1 H) 2.59-2.73 (m, 1 H) 1.82-2.50 (m, 12 H) 1.60-1.72 (m, 1 H) 1.38-1.51 (m, 1 H) 1H not observed; $^{19}$F NMR (376 MHz, METHANOL-$d_4$) δ ppm −141.34--140.35 (m) −174.42--173.25 (m). Stereochemistry of Example 168 was confirmed by X-Ray crystallography analysis. |
| 270 | 665.2 | $^1$H NMR (METHANOL-$d_4$, 400 MHz) δ ppm, 9.24 (s, 1H), 7.8-7.8 (m, 2H), 5.61 (br d, 1H, J = 14.6 Hz), 5.3-5.5 (m, 1H), 4.8-5.0 (m, 1H), 4.53 (d, 1H, J = 11.3 Hz), 4.4-4.5 (m, 1H), 4.03 (d, 1H, J = 16.5 Hz), 3.9-3.9 (m, 3H), 3.4-3.7 (m, 6H), 3.00 (ddd, 1H, J = 5.9, 9.9, 13.3 Hz), 2.77 (dt, 1H, J = 6.3, 10.2 Hz), 2.6-2.7 (m, 2H), 2.4-2.6 (m, 1H), 2.3-2.4 (m, 2H), 2.2-2.3 (m, 2H), 2.1-2.2 (m, 3H), 2.0-2.1 (m, 1H), 1.93 (ddd, 1H, J = 3.7, 7.1, 14.3 Hz), 1.8-1.9 (m, 2H), 1.5-1.6 (m, 1H). $^{19}$F NMR (METHANOL-d4, 376 MHz) δ −73.84 (s), −75.72 (s), −142.31 (s), −173.89 (s). |
| 271 | 653.2 | $^1$H NMR (METHANOL-$d_4$, 400 MHz) δ ppm 9.35 (s, 1H), 8.47 (s, 1H), 7.81 (d, 1H, J = 0.8 Hz), 7.79 (d, 1H, J = 0.8 Hz), 5.3-5.5 (m, 2H), 4.86 (br dd, 1H, J = 4.6, 13.4 Hz), 4.47 (d, 1H, J = 11.1 Hz), 4.4-4.4 (m, 1H), 4.17 (td, 1H, J = 5.5, 10.7 Hz), 3.90 (br d, 1H, J = 16.9 Hz), 3.7-3.8 (m, 1H), 3.60 (d, 1H, J = 14.6 Hz), 3.5-3.6 (m, 1H), 3.4-3.5 (m, 3H), 3.3-3.4 (m, 2H), 3.2-3.3 (m, 2H), 3.16 (dt, 1H, J = 5.9, 9.7 Hz), 2.9-3.0 (m, 1H), 2.4-2.5 (m, 1H), 2.3-2.4 (m, 1H), 2.2-2.3 (m, 2H), 2.1-2.2 (m, 2H), 1.8-2.0 (m, 4H), 1.5-1.7 (m, 1H), 1.22 (br d, 1H, J = 13.2 Hz). $^{19}$F NMR (METHANOL-d4, 376 MHz) δ −142.78 (s), −173.80 (s). |
| 272 | 667.15 | $^1$H NMR (METHANOL-$d_4$, 400 MHz) δ ppm 9.43 (s, 1H), 8.49 (s, 1H), 7.78 (s, 1H), 7.7-7.8 (m, 1H), 5.36 (br d, 2H, J = 16.9 Hz), 4.88 (br dd, 1H, J = 3.7, 13.3 Hz), 4.4-4.5 (m, 1H), 4.3-4.4 (m, 1H), 4.20 (td, 1H, J = 5.4, 10.9 Hz), 4.00 (br dd, 1H, J = 5.6, 16.9 Hz), 3.79 (d, 1H, J = 14.4 Hz), 3.5-3.6 (m, 2H), 3.3-3.5 (m, 4H), 3.1-3.3 (m, 4H), 2.8-2.9 (m, 1H), 2.4-2.5 (m, 1H), 2.2-2.4 (m, 3H), 2.10 (br dd, 2H, J = 6.3, 10.9 Hz), 1.9-2.0 (m, 2H), 1.8-1.9 (m, 3H), 1.7-1.8 (m, 1H), 1.61 (q, 1H, J = 11.4 Hz), 1.33 (s, 1H). $^{19}$F NMR (METHANOL-d4, 376 MHz) δ −139.60 (s), −173.77 (s). |

TABLE 13-continued

| Analytical Data for Examples 61 to 64, 75, 162 to 168 and 270 to 279. | | |
|---|---|---|
| Ex. # | MS m/z (ESI): $(M + H)^+$ | $^1$ NMR |
| 273 | 676.9 | $^1$H NMR (400 MHz, METHANOL-$d_4$) δ ppm 9.24 (s, 1 H) 7.81 (s, 2 H) 5.24-5.47 (m, 1 H) 4.85-4.97 (m, 1 H) 4.24-4.49 (m, 2 H) 3.75-3.91 (m, 2 H) 3.35 (br s, 2 H) 3.04-3.24 (m, 3 H) 2.52-2.71 (m, 1 H) 1.07-1.53 (m, 1 H) 1.01-2.48 (m, 21 H). $^{19}$F NMR (376 MHz, METHANOL-$d_4$) δ ppm −140.41 (s) −173.77 (s). |
| 274 | 663.0 | $^1$H NMR (400 MHz, METHANOL-$d_4$) δ ppm 9.04-9.39 (m, 1 H) 7.56-7.88 (m, 2 H) 5.48-5.70 (m, 1 H) 4.89-5.23 (m, 1 H) 3.68-4.10 (m, 5 H) 3.45-3.56 (m, 1 H) 3.02-3.31 (m, 2 H) 2.55-2.79 (m, 2 H) 2.27-2.51 (m, 4 H) 1.55-2.25 (m, 14 H) 1.25-1.36 (m, 1 H) 1.01-1.17 (m, 1 H). $^{19}$F NMR (376 MHz, METHANOL-$d_4$) δ ppm −76.48--72.93 (m) −142.64--141.32 (m) −174.13 (d, J = 44.21 Hz). |
| 275 | 653.2 | $^1$H NMR (400 MHz, METHANOL-$d_4$) δ ppm 9.15-9.27 (m, 1 H) 7.74-7.86 (m, 2 H) 5.53-5.62 (m, 1 H) 5.22-5.42 (m, 1 H) 5.10-5.18 (m, 1 H) 4.44-4.54 (m, 1 H) 4.16-4.30 (m, 2 H) 4.02-4.12 (m, 1 H) 3.79-3.89 (m, 1 H) 3.18-3.27 (m, 2 H) 2.96-3.05 (m, 1 H) 2.75-2.87 (m, 1 H) 2.43-2.54 (m, 1 H) 2.13-2.38 (m, 4 H) 1.84-2.03 (m, 5 H) 1.47-1.64 (m, 2 H) 1.22-1.37 (m, 4 H) 1.07-1.19 (m, 1 H). $^{19}$F NMR (376 MHz, METHANOL-$d_4$) δ ppm −143.71--140.25 (m) −177.96--171.24 (m). |
| 276 | 653.2 | $^1$H NMR (400 MHz, METHANOL-$d_4$) δ ppm 9.13-9.31 (m, 1 H) 7.73-7.86 (m, 2 H) 5.51-5.67 (m, 1 H) 5.22-5.45 (m, 1 H) 5.08-5.19 (m, 1 H) 4.45-4.55 (m, 1 H) 4.18-4.33 (m, 2 H) 4.06-4.15 (m, 1 H) 3.81-3.90 (m, 1 H) 3.28 (br s, 1 H) 3.15-3.21 (m, 1 H) 3.01-3.08 (m, 1 H) 2.78-2.87 (m, 1 H) 2.32-2.54 (m, 2 H) 2.10-2.27 (m, 3 H) 1.98-2.07 (m, 3 H) 1.85-1.96 (m, 2 H) 1.59-1.68 (m, 1 H) 1.45-1.56 (m, 1 H) 1.25-1.37 (m, 4 H) 1.06-1.18 (m, 1 H). $^{19}$F NMR (376 MHz, METHANOL-$d_4$) δ ppm −141.87 (s) −173.13 (s). |
| 277 | 659.2 | $^1$H NMR (400 MHz, METHANOL-$d_4$) δ ppm 9.16-9.29 (m, 1 H) 7.43-7.67 (m, 2 H) 5.88-6.03 (m, 1 H) 5.42-5.61 (m, 1 H) 4.52-4.68 (m, 4 H) 3.95-4.03 (m, 1 H) 3.80-3.85 (m, 1 H) 3.68-3.78 (m, 4 H) 3.40-3.46 (m, 1 H) 3.36-3.39 (m, 2 H) 3.23-3.30 (m, 1 H) 3.06-3.17 (m, 2 H) 2.87-3.00 (m, 1 H) 2.71-2.79 (m, 1 H) 2.62-2.66 (m, 1 H) 2.57 (d, J = 0.63 Hz, 4 H) 2.45-2.51 (m, 1 H) 2.24-2.42 (m, 4 H) 2.07-2.17 (m, 1 H) 1.84-1.94 (m, 3 H) 1.59-1.74 (m, 1 H) 1.37-1.50 (m, 1 H). $^{19}$F NMR (376 MHz, METHANOL-$d_4$) δ ppm −75.94--73.62 (m) −141.34--140.93 (m) −174.10--173.98 (m). |
| 278 | 659.3 | $^1$H NMR (METHANOL-$d_4$, 400 MHz) δ ppm 9.10-9.21 (m, 1H), 7.65-8.01 (m, 1H), 7.49 (s, 1H), 5.31 (d, J = 54.4 Hz, 1H), 4.48-4.60 (m, 2H), 4.33-4.45 ( m, 1H), 4.26-4.31 (m, 1H), 3.89-4.01 (m, 1H), 3.65-3.85 (m, 2H), 3.37-3.61 (m, 2H), 3.10-3.29 (m, 7H), 3.00-3.08 (m, 3H), 2.86-2.89 (m, 2H), 2.21-2.39 (m, 4H), 2.09-2.20 (m, 2H), 1.98-2.07 (m, 3H), 1.86-1.96 (m, 3H), 1.31-1.41 (m, 2H). $^{19}$F NMR (METHANOL-$d_4$, 400 MHz-$d_4$) δ ppm −143.10(s), −173.77 (s). |
| 279 | 659.3 | $^1$H NMR (400 MHz, METHANOL-$d_4$) δ ppm 9.16 (s, 1H), 7.79 (d, J = 2.4 Hz, 1H), 7.39 (s, 1H), 5.58-5.64 (m, 1H), 5.42-5.61 (m, 1H), 4.96 (d, J = 12.8 Hz, 1H), 4.52-4.66 (m, 3H), 3.94-4.03 (m, 2H), 3.78-3.87 (m, 2H), 3.60-3.66 (m, 2H), 3.31-3.56 (m, 4H), 3.11-3.17 (m, 1H), 3.02-3.10 (m, 1H), 2.91-2.98 (m, 1H), 2.87 (s, 3H), 2.57-2.73 (m, 1H), 2.48-2.54 (m, 2H), 2.33-2.43 (m, 1H), 2.23-2.32 (m, 3H), 2.01-2.16 (m, 2H), 1.60-1.84 (m, 5H). |

(26R)-18-Chloro-32-fluoro-4-(((2R,7aS)-2-fluorotetrahydro-1H-pyrrolo[1,2-a]pyrrol-7a(511)-yl)methoxy)-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one bis(2,2,2-trifluoroacetate) (Example 65)

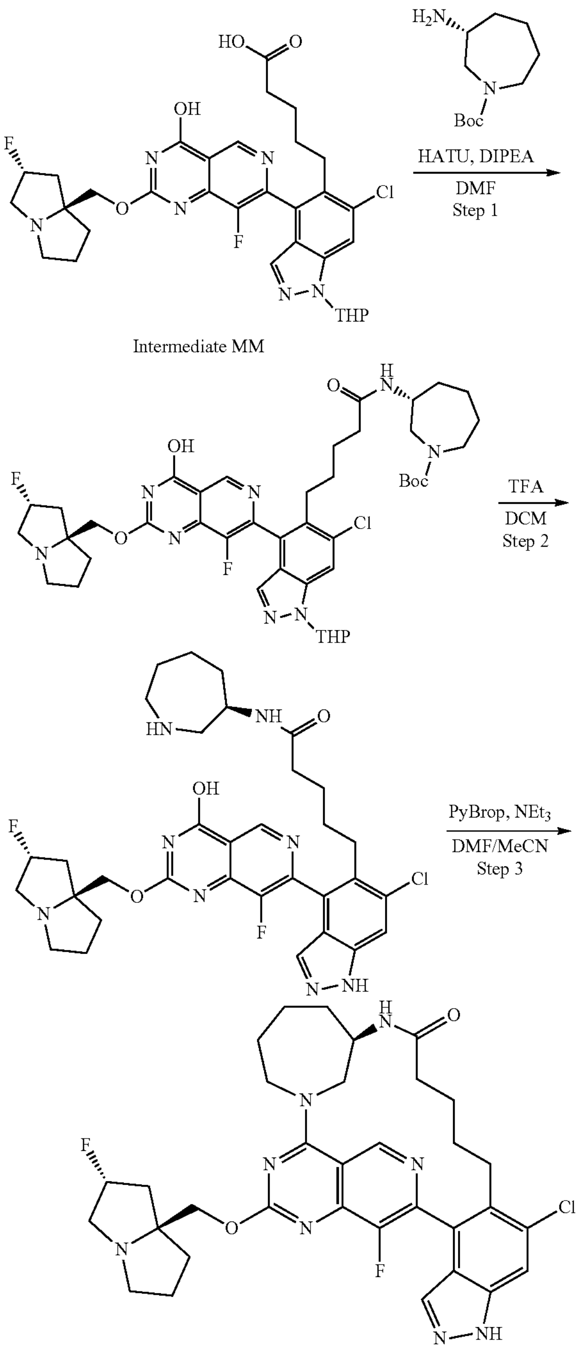

Example 65

Step 1. tert-Butyl (3R)-3-(5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1-(tetrahydro-2H-pyran-2-yl)-1H-indazol-5-yl)pentanamido)azepane-1-carboxylate. A 40-mL vial was charged with HATU (99 mg, 0.26 mmol), 1,1-dimethyltriethylamine (0.13 mL, 0.74 mmol), tert-butyl (3R)-3-aminoazepane-1-carboxylate (53 mg, 0.25 mmol, Synthonix Inc.), 5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1-(tetrahydro-2H-pyran-2-yl)-1H-indazol-5-yl)pentanoic acid (0.16 g, 0.25 mmol, Intermediate MM) and N,N-dimethylformamide (1.2 mL). The reaction mixture was stirred at rt for 1 h and was quenched with water. The mixture was extracted with DCM and the organic layer was dried ($Na_2SO_4$), concentrated under reduced pressure. The crude material was purified by column chromatography on silica gel, eluting with first a gradient of 0-85% 3:1 EtOAc/EtOH (with 2% triethylamine) in heptane (no product eluted), then with methanol to yield tert-butyl (3R)-3-(5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1-(tetrahydro-2H-pyran-2-yl)-1H-indazol-5-yl)pentanamido)azepane-1-carboxylate, which was used directly in the following step. m/z (ESI): 853.2 $(M+H)^+$.

Step 2. N—((R)-Azepan-3-yl)-5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)pentanamide. tert-Butyl (3R)-3-(5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1-(tetrahydro-2H-pyran-2-yl)-1H-indazol-5-yl)pentanamido)azepane-1-carboxylate was dissolved in DCM (1.5 mL) and treated with trifluoroacetic acid (1.2 mL). The reaction mixture was stirred at rt for 1 h, concentrated and the crude mixture was purified by reverse phase chromatography. The fractions were collected and passed through an SCX column, eluting with 2% ammonia in methanol to yield N—((R)-azepan-3-yl)-5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)pentanamide (0.13 g, 0.20 mmol, 79% yield, over two steps). m/z (ESI): 669.2 $(M+H)^+$.

Step 3. (26R)-18-Chloro-32-fluoro-4-(((2R,7aS)-2-fluorotetrahydro-1H-pyrrolo[1,2-a]pyrrol-7a(5H)-yl)methoxy)-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one bis(2,2,2-trifluoroacetate). To a 100 mL RBF was charged with bromotripyrrolidinophosphonium hexafluorophosphate (0.24 g, 0.52 mmol), acetonitrile (18 mL), N,N-diisopropylethylamine (0.13 mL, 1.04 mmol), and N,N-dimethylformamide (3.5 mL). To this was charged a solution of N—((R)-azepan-3-yl)-5-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)pentanamide (0.23 g, 0.35 mmol) in DMF (25 mL). This reaction mixture was stirred at rt for 1 h. The volatiles were removed under reduced pressure and the crude product was purified by reverse phase HPLC to yield (26R)-18-chloro-32-fluoro-4-(((2R,7aS)-2-fluorotetrahydro-1H-pyrrolo[1,2-a]pyrrol-7a(5H)-yl)methoxy)-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one bis(2,2,2-trifluoroacetate) (32 mg, 0.036 mmol, 11% yield) as white solid after lyophilization. m/z (ESI): 651.0 $(M+H)^+$. $^1H$ NMR (400 MHz, METHANOL-$d_4$) δ ppm 9.28-9.41 (m, 1H), 7.66-7.73 (m, 1H), 7.51-7.59 (m, 1H), 5.46-5.70 (m, 1H), 5.31-5.44 (m, 1H), 4.71 (s, 2H), 4.35-4.47 (m, 1H), 3.82-4.08 (m, 7H), 3.59-3.77 (m, 2H), 3.42-3.54 (m, 1H), 2.31-2.81 (m, 11H), 2.13-2.26 (m, 1H), 1.95 (br d, J=17.3 Hz, 1H), 1.30-1.64 (m, 4H), 1.15-1.28 (m, 1H).

TABLE 14

| Additional Examples 66 to 67, 169 to 171 and 280. Prepared in an Analogous Manner to Example 65. | | | | |
|---|---|---|---|---|
| Ex.# | Structure & Name | Salt Form | Reagent | Method Change |
| 66 | 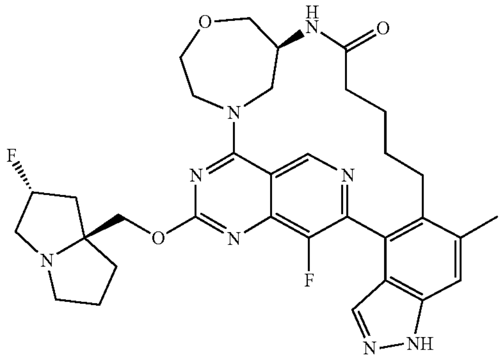 [SMILES: Cc1cc2[nH]ncc2c2c1CCCCC(=O)N[C@@H]1COCCN(C1)c1nc(OC[C@@]34CCCN3C[C@H](F)C4)nc3c(F)c-2ncc13] (26S)-32-fluoro-4-(((2R,7aS)-2-fluorotetrahydro-1H-pyrrolo[1,2-a]pyrrol-7a(5H)-yl)methoxy)-18-methyl-28-oxa-1,3,5,9,14,15,25-heptaazahexacyclo [24.4.1.1~6,10~.0~2,7~.0~11,19~.0~12,16~]dotriaconta-2,4,6,8,10(32), 11,13,16,18-nonaen-24-one | Bis (2,2,2-trifluoroaceate) | Step 1. Intermediate NN & (S)-4-Boc-6-amino-[1,4]oxazepane (CAS#: 1932377-93-9, J & W Pharmlab, LLC) | |
| 67 | 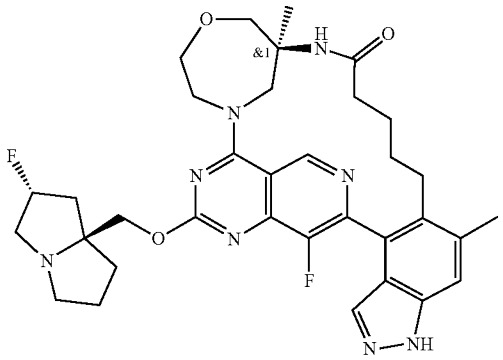 [SMILES: Cc1cc2[nH]ncc2c2c1CCCCC(=O)N[C@]1(C)COCCN(C1)c1nc(OC[C@@]34CCCN3C[C@H](F)C4)nc3c(F)c-2ncc13] (26R)-32-fluoro-4-(((2R,7aS)-2-fluorotetrahydro-1H-pyrrolo[1,2-a]pyrrol-7a(5H)-yl)methoxy)-18,26-dimethyl-28-oxa-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one and (26S)-32-fluoro-4-(((2R,7aS)-2-fluorotetrahydro-1H-pyrrolo[1,2-a]pyrrol-7a(5H)-yl)methoxy)-18,26-dimethyl-28-oxa-1,3,5,9,14,15,25-heptaazahexacyclo [24.4.1.1~6,10~.0~2,7~.0~11,19~.0~12,16~]dotriaconta-2,4,6,8,10(32), 11,13,16,18-nonaen-24-one | Bis (2,2,2-trifluoroaceate) | Step 1. Intermediate NN and tert-Butyl-6-amino-6-methyl-1,4-oxazepane-4-carboxylate (CAS#: 2306265-25-6, Pharmablock, Inc.) | |

TABLE 14-continued

| Additional Examples 66 to 67, 169 to 171 and 280. Prepared in an Analogous Manner to Example 65. | | | | |
|---|---|---|---|---|
| Ex.# | Structure & Name | Salt Form | Reagent | Method Change |
| 169 | 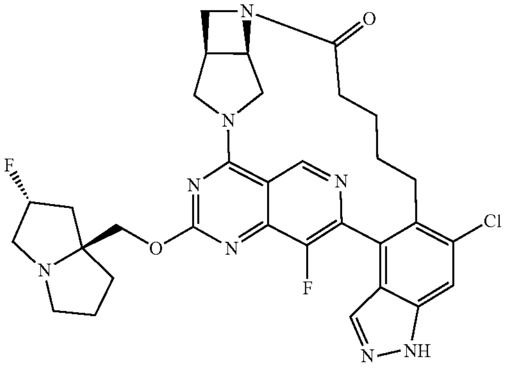 [SMILES: O=C1CCCCc2c(Cl)cc3[nH]ncc3c2-c2ncc3c(nc(OC[C@@]45CCCN4C[C@H](F)C5)nc3c2F)N2C[C@H]3CN1[C@H]3C2] (18S,19R)-9-chloro-30-fluoro-24-(((2R,7aS)-2-fluorotetrahydro-1H-pyrrolo[1,2-a]pyrrol-7a(5H)-yl)methoxy)-5,6,16,21,23,25,29-heptaazaheptacyclo[24.3.1.1~18,21~.0~2,10~.0~3,7~.0~16,19~.0~22,27~]hentriaconta-1(30),2,4,7,9,22,24,26,28-nonaen-15-one | | Step 1. tert-butyl (1R,5R)-3,6-diazabicyclo[3.2.0]heptane-3-carboxylate hydrochloride (CAS#: 2306246-64-8, eNovation) | Chiral separation after Step 3. Details included below. |
| 170 | 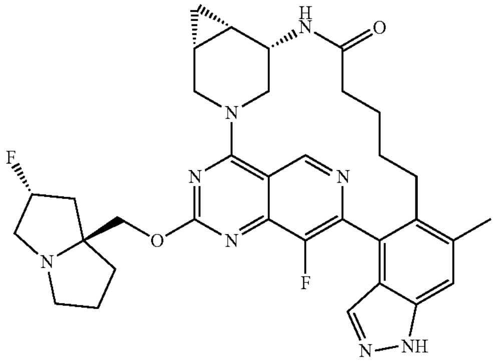 [SMILES: Cc1cc2[nH]ncc2c2c1CCCCC(=O)N[C@@H]1CN(C[C@@H]3C[C@@H]31)c1nc(OC[C@@]34CCCN3C[C@H](F)C4)nc3c(F)c-2ncc13] (26S,27S,29R)-32-fluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazaheptacyclo[24.4.1.1~6,10~.0~2,7~.0~11,19~.0~12,16~.0~27,29~]dotriaconta-2,4,6,8,10(32),11,13,16,18-nonaen-24-one | | Step 1. Intermediate NN | Chiral separation after Step 3. Details included below. |

TABLE 14-continued

| Additional Examples 66 to 67, 169 to 171 and 280. Prepared in an Analogous Manner to Example 65. | | | | |
|---|---|---|---|---|
| Ex.# | Structure & Name | Salt Form | Reagent | Method Change |
| 171 | 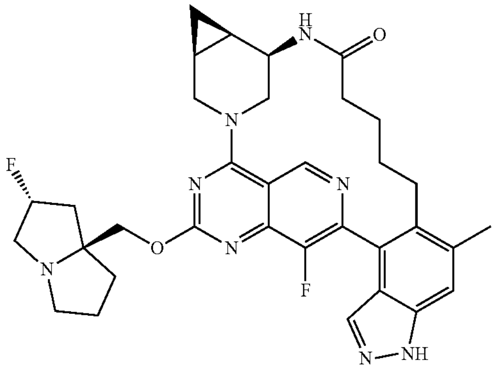 [SMILES: Cc1cc2[nH]ncc2c2c1CCCCC(=O)N[C@H]1CN(C[C@H]3C[C@H]31)c1nc(OC[C@@]34CCCN3C[C@H](F)C4)nc3c(F)c-2ncc13] (26R,27R,29S)-32-fluoro-4-(((2R,7aS)-2-fluorotetrahydro-1H-pyrrolo[1,2-a]pyrrol-7a(5H)-yl)methoxy)-18-methyl-1,3,5,9,14,15,25-heptaazaheptacyclo[24.4.1.1~6,10~.0~2,7~.0~11,19~.0~12,16~.0~27,29~]dotriaconta-2,4,6,8,10(32), 11,13,16,18-nonaen-24-one | | Step 1. Intermediate NN | Chiral separation after Step 3. Details included below. |
| 280 | 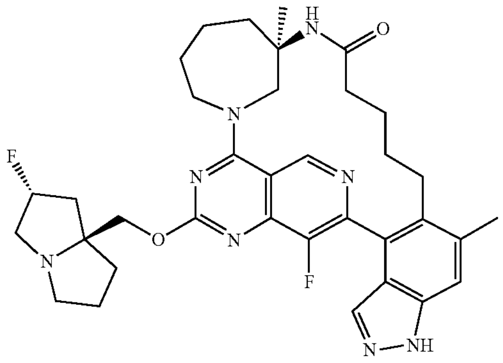 [SMILES: Cc1cc2[nH]ncc2c2c1CCCCC(=O)N[C@]1(C)CCCCN(C1)c1nc(OC[C@@]34CCCN3C[C@H](F)C4)nc3c(F)c-2ncc13] (26R)-32-fluoro-4-(((2R,7aS)-2-fluorotetrahydro-1H-pyrrolo[1,2-a]pyrrol-7a(5H)-yl)methoxy)-18,26-dimethyl-1,3,5,9,14,15,25-heptaazahexacyclo [24.4.1.1~6, 10~.0~2,7~.0~11,19~.0~12,16~]dotriaconta-2,4,6,8,10(32), 11,13,16,18-nonaen-24-one | Hexafluoro-phosphate | Step 1. Intermediate NN and Intermediate DB | |

TABLE 15

Conditions for Chiral SFC Separation.

| Separation | SFC Conditions | Peak to Ex# |
|---|---|---|
| 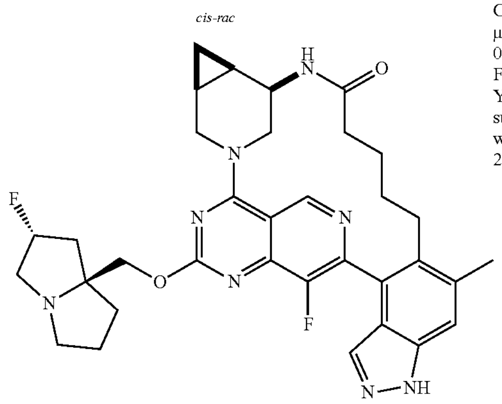 | Column: Chiralcel OV (2 × 25, cm 5 μm) Mobile phase: 55% MeOH with 0.2% DEA<br>Flowrate: 70 mL/min.<br>Yield: 15 mg of sample was submitted to generate 6 mg of peak 1 with an ee of 98.8% and 6 mg of peak 2 with an ee of 98%. | Peak 1: Example 170<br>Peak 2: Example 171 |

TABLE 16

Analytical Data for Examples 66 to 67, 169 to 171 and 280.

| Cmpd. # | MS m/z (ESI): $(M + H)^+$ | $^1H$ NMR |
|---|---|---|
| 66 | 633.0 | $^1H$ NMR (400 MHz, METHANOL-$d_4$) δ ppm 9.28-9.41 (m, 1 H), 7.66-7.73 (m, 1 H), 7.51-7.59 (m, 1 H), 5.46-5.70 (m, 1 H), 5.31-5.44 (m, 1 H), 4.71 (s, 2 H), 4.35-4.47 (m, 1 H), 3.82-4.08 (m, 7 H), 3.59-3.77 (m, 2 H), 3.42-3.54 (m, 1 H), 2.31-2.81 (m, 11 H), 2.13-2.26 (m, 1 H), 1.95 (br d, J = 17.3 Hz, 1 H), 1.30-1.64 (m, 4 H), 1.15-1.28 (m, 1 H). |
| 67 | 647.1 | $^1H$ NMR (400 MHz, METHANOL-$d_4$) δ ppm 9.24-9.40 (m, 1 H), 7.61-7.68 (m, 1 H), 7.48-7.58 (m, 1 H), 5.68-5.75 (m, 1 H), 5.47-5.67 (m, 1 H), 4.70 (s, 3 H), 4.29-4.41 (m, 1 H), 3.82-4.11 (m, 5 H), 3.58-3.75 (m, 3 H), 3.42-3.53 (m, 2 H), 3.17 (br d, J = 3.6 Hz, 1 H), 2.53-2.81 (m, 7 H), 2.32-2.50 (m, 4 H), 2.01-2.29 (m, 2 H), 1.79-1.91 (m, 1 H), 1.43-1.57 (m, 3 H), 1.41 (s, 3 H), 1.10-1.33 (m, 2 H). |
| 169 | 635.0 | $^1H$ NMR (400 MHz, DMSO-$d_6$) δ ppm 9.30-9.49 (m, 1 H), 7.69-8.01 (m, 2 H), 5.44-5.69 (m, 1 H), 5.22-5.38 (m, 1 H), 4.71-5.03 (m, 2 H), 4.53-4.70 (m, 2 H), 4.04-4.09 (m, 1 H), 3.79-3.87 (m, 1 H), 3.65-3.72 (m, 2 H), 2.89-3.13 (m, 3 H), 2.55-2.65 (m, 1 H), 2.40-2.48 (m, 1 H), 2.26-2.39 (m, 2 H), 2.12-2.24 (m, 2 H), 1.95 (s, 6 H), 1.24-1.41 (m, 2 H), 1.01-1.17 (m, 2 H), 0.50-0.85 (m, 1 H); $^{19}F$ NMR (376 MHz, DMSO-$d_6$) δ ppm −77.18-−65.45 (m) −142.54-−140.59 (m) −174.03-−171.68 (m). |
| 170 | 629.4 | $^1H$ NMR (600 MHz, DMSO-$d_6$) δ ppm 9.10 (s, 1 H) 7.36-7.66 (m, 2 H) 6.94-7.17 (m, 1 H) 5.15-5.39 (m, 2 H) 4.74-4.86 (m, 1 H) 4.02-4.17 (m, 3 H) 3.36-3.62 (m, 2 H) 3.31-3.35 (m, 1 H) 3.01-3.14 (m, 2 H) 2.80-2.88 (m, 1 H) 2.46 (s, 1 H) 2.17-2.26 (m, 1 H) 2.07-2.15 (m, 2 H) 1.99-2.05 (m, 1 H) 1.73-1.92 (m, 4 H) 1.49-1.58 (m, 1 H) 1.34-1.43 (m, 1 H) 1.15 (br s, 5 H) 0.96-1.08 (m, 2 H) 0.42-0.53 (m, 2 H). |
| 171 | 629.2 | $^1H$ NMR (600 MHz, DMSO-$d_6$) δ ppm 9.10 (s, 1 H) 7.45 (s, 3 H) 5.25 (s, 3 H) 3.90-4.30 (m, 3 H) 3.38-3.61 (m, 2 H) 3.30-3.36 (m, 1 H) 2.99-3.16 (m, 2 H) 2.80-2.91 (m, 1 H) 2.46 (s, 1 H) 2.18-2.26 (m, 1 H) 1.99-2.16 (m, 3 H) 1.84-1.91 (m, 1 H) 1.71-1.83 (m, 3 H) 1.50-1.58 (m, 1 H) 1.33-1.42 (m, 1 H) 0.98-1.30 (m, 7 H) 0.43-0.52 (m, 2 H). |
| 280 | 645.4 | $^1H$ NMR (METHANOL-$d_4$, 400 MHz) δ 9.27 (s, 1H), 7.63 (d, 1H, J = 1.0 Hz), 7.51 (s, 1H), 6.72 (s, 1H), 5.78 (br d, 1H, J = 16.1 Hz), 5.4-5.6 (m, 1H), 4.7-4.7 (m, 3H), 4.6-4.6 (m, 1H), 3.8-4.0 (m, 3H), 3.4-3.5 (m, 2H), 3.3-3.4 (m, 1H), 2.8-2.9 (m, 1H), 2.7-2.8 (m, 1H), 2.6-2.6 (m, 1H), 2.55 (s, 3H), 2.46 (br dd, 1H, J = 6.8, 14.3 Hz), 2.3-2.4 (m, 4H), 2.1-2.2 (m, 1H), 1.9-2.0 (m, 1H), 1.7-1.8 (m, 3H), 1.6-1.7 (m, 2H), 1.4-1.5 (m, 3H), 1.40 (s, 3H), 1.1-1.3 (m, 2H). $^{19}F$ NMR (METHANOL-d4, 376 MHz) δ −73.61 (s), −75.49 (s), −142.73 (s), −174.10 (s). |

(15R)-22,31-Difluoro-8-(((2R,7aS)-2-fluorotetrahydro-1H-pyrrolo[1,2-a]pyrrol-7a(5H)-yl)methoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate. (Example 68)

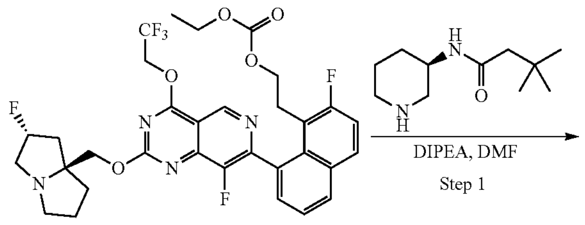

Intermediate BB

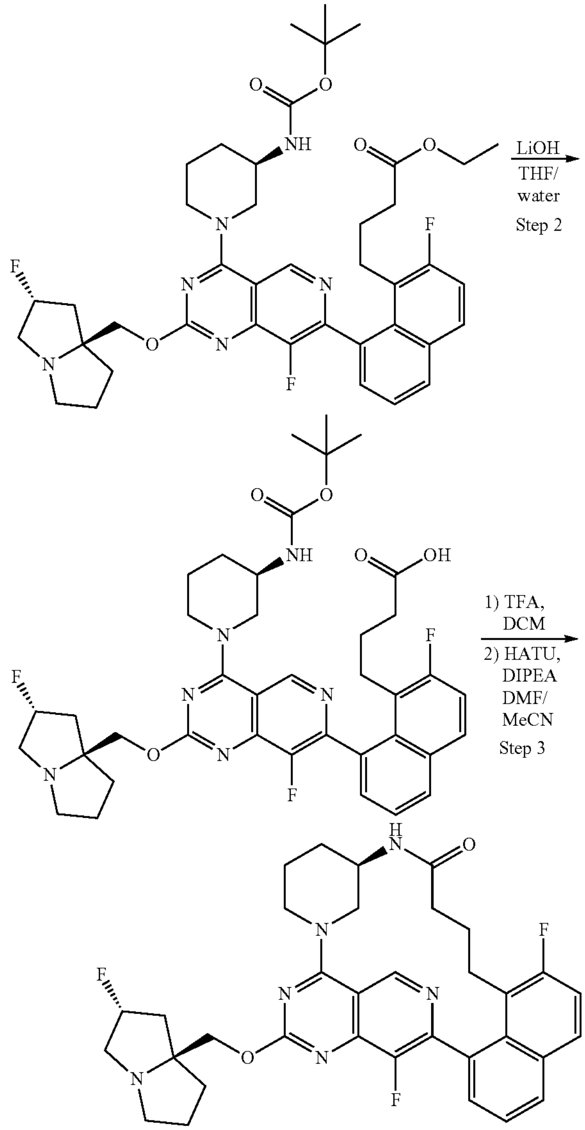

Example 68

Step 1. Ethyl 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoate. In a 20-mL vial was charged with ethyl 4-(2-fluoro-8-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-1-yl)butanoate (0.35 g, 0.53 mmol, Intermediate BB), (R)-3-Boc-amino piperidine (0.16 g, 0.80 mmol) and DMF (2.5 mL). 1,1-Dimethyltriethylamine (0.28 mL, 1.6 mmol) was added, and the reaction mixture was stirred at 60° C. for 1 h. After cooling to rt, the reaction mixture was treated with water and saturated aqueous $NH_4Cl$. The aqueous layer was extracted with EtOAc, and the combined organic layers were dried over $Na_2SO_4$, filtered and volatiles were removed in vacuo. The mixture was purified via column chromatography on silica gel, eluting with 0-60% (3:1 EtOAc/EtOH with 1.5% $Et_3N$) in heptane, to provide ethyl 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoate (0.31 g, 0.40 mmol, 76% yield) as off-white solid. m/z (ESI): 763.3 $(M+H)^+$.

Step 2. 4-(8-(4-((R)-3-((tert-Butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoic acid. A 50-mL RBF was charged with ethyl 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoate (0.31 g, 0.40 mmol) in acetonitrile (3 mL) and water (1 mL). Lithium hydroxide, monohydrate (59 mg, 1.40 mmol) was added, and the reaction mixture was stirred at rt for 16 h. The reaction was neutralized with glacial acetic acid (82 µL, 1.4 mmol) and fully concentrated. The residue was purified by C18 column, eluting with a gradient of 5-100% (0.1% formic acid MeCN)/(0.1% formic acid water) over 15 min. The desired fractions were lyophilized to provide 4-(8-(4-((R)-3-((tert-butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoic acid (0.15 g, 0.20 mmol, 50% yield) as off-white solid. m/z (ESI): 735.2 $(M+H)^+$.

Step 3. (15R)-22,31-Difluoro-8-(((2R,7aS)-2-fluorotetrahydro-1H-pyrrolo[1,2-a]pyrrol-7a(5H)-yl)methoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate. 4-(8-(4-((R)-3-((tert-Butoxycarbonyl)amino)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoic acid (0.15 g, 0.20 mmol) was dissolved in 1 mL of DCM. TFA (0.5 mL) was added, and the reaction mixture was stirred at rt for 2 h. The mixture was fully concentrated, dissolved in $CH_3CN$ (0.5 mL) and treated with hydrogen chloride solution, 4.0 M in dioxane (0.05 mL, 0.2 mmol). The contents were concentrated, and the residue was dissolved in water (0.5 mL) and treated with 1 N HCl (0.2 mL). The solution was lyophilized to give 4-(8-(4-((R)-3-aminopiperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoic acid dihydrochloride as tan solid.

The above solid was dissolved in DMF (34 mL) and HATU (48 mg, 0.13 mmol) was added. The reaction mixture was stirred for 10 min, 1,1-dimethyltriethylamine (0.1 mL, 0.59 mmol) was added dropwise and the mixture was stirred for 30 min. The reaction mixture was treated with brine. The aqueous phase was extracted with EtOAc, and the combined organic layers were dried ($Na_2SO_4$) concentrated. The residue was purified by reverse-phase preparative HPLC using a Phenomenex Gemini column, 10 micron, C18, 110 Å, 150×30 mm, 0.1% TFA in $CH_3CN/H_2O$, gradient 5-95% over 15 min to provide (15R)-22,31-difluoro-8-(((2R,7aS)-2-fluorotetrahydro-1H-pyrrolo[1,2-a]pyrrol-7a(5H)-yl)methoxy)-3,7,9,11,16-pentaazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate (43 mg, 0.059 mmol, 30% yield) as off-white solid. m/z (ESI): 617.0 $(M+H)^+$. $^1H$ NMR (400 MHz, METHANOL-$d_4$) δ ppm 9.26 (s, 1H), 8.08 (d, J=7.73 Hz, 1H), 7.96 (dd, J=8.88, 6.17 Hz, 1H), 7.56-7.71 (m, 3H), 7.37 (t, J=9.62 Hz, 1H), 5.50-5.71 (m, 1H), 5.31 (br d, J=14.00 Hz, 1H), 5.08 (br d, J=13.59 Hz, 1H), 4.60-4.77 (m, 2H), 3.84-4.11 (m, 6H), 3.43-3.54 (m, 1H), 2.57-2.72 (m, 2H), 2.29-2.53 (m, 5H), 2.06-2.23 (m, 4H), 1.70-1.85 (m, 3H), 1.53-1.68 (m, 1H), 1.20-1.44 (in, 1H).

TABLE 17

Additional Examples 69 to 70. Prepared in an Analogous Manner to Example 68.

| Ex.# | Structure & Name | Salt Form | Reagent | Method Change |
|---|---|---|---|---|
| 69 | 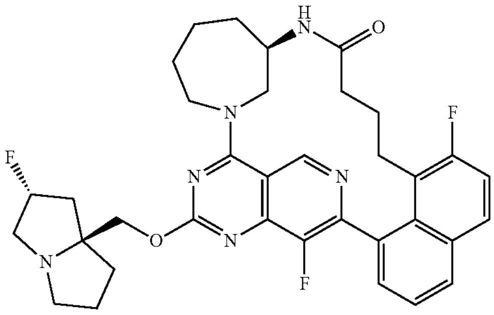 [SMILES: O=C1CCCc2c(F)ccc3cccc(c23)-c2ncc3c(nc(OC[C@@]45CCCN4C[C@H](F)C5)nc3c2F)N2CCCC[C@H](C2)N1] (16R)-23,32-difluoro-8-(((2R,7aS)-2-fluorotetrahydro-1H-pyrrolo[1,2-a]pyrrol-7a(5H)-yl)methoxy)-3,7,9,11,17-pentaazahexacyclo[20.7.1.1~2,6~. 1~11,16~.0~5,10~.0~26,30~]dotriaconta-1(29),2(32),3,5,7,9,22,24,26(30),27-decaen-18-one | 2,2,2-trifluoroaceate | Step 1. (R)-tert-butyl azepan-3-ylcarbamate (CAS#: 1354351-56-6, Combi-Blocks Inc.) | |
| 70 | 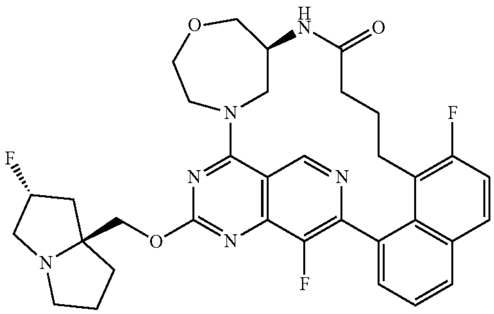 [SMILES: O=C1CCCc2c(F)ccc3cccc(c23)-c2ncc3c(nc(OC[C@@]45CCCN4C[C@H](F)C5)nc3c2F)N2CCOC[C@H](C2)N1] (16S)-23,32-difluoro-8-(((2R,7aS)-2-fluorotetrahydro-1H-pyrrolo[1,2-a]pyrrol-7a(5H)-yl)methoxy)-14-oxa-3,7,9,11,17-pentaazahexacyclo[20.7.1.1~2,6~. 1~11,16~.0~5,10~.0~26,30~]dotriaconta-1(29),2(32),3,5,7,9,22,24,26(30),27-decaen-18-one | 2,2,2-trifluoroaceate | Step 1. tert-butyl N-[(6S)-1,4-oxazepan-6-yl]carbamate (CAS#: 2306247-11-8, Aurum Pharmatech) | |

TABLE 18

Analytical Data for Examples 69 to 70.

| Cmpd. # | MS m/z (ESI): $(M + H)^+$ | $^1H$ NMR |
|---|---|---|
| 69 | 631.0 | $^1H$ NMR (400 MHz, METHANOL-$d_4$) δ ppm 9.35 (s, 1 H), 8.08 (dd, J = 8.15, 1.05 Hz, 1 H), 7.97 (dd, J = 8.99, 6.06 Hz, 1 H), 7.52-7.64 (m, 1 H), 7.48 (d, J = 6.90 Hz, 1 H), 7.34-7.44 (m, 1 H), 5.56-5.71 (m, 1 H), 5.54 (s, 1 H), 4.63-4.77 (m, 3 H), 3.77-4.13 (m, 5 H), 3.34-3.55 (m, 3 H), 3.05-3.06 (m, 1 H), 2.56-2.85 (m, 3 H), 2.12-2.50 (m, 8 H), 1.91-2.12 (m, 3 H), 1.57-1.90 (m, 5 H), 1.39-1.57 (m, 2 H). |
| 70 | 633.1 | $^1H$ NMR (400 MHz, METHANOL-$d_4$) δ ppm 9.35 (s, 1 H), 8.05-8.13 (m, 1 H), 7.98 (dd, J = 9.02, 6.12 Hz, 1 H), 7.68 (br d, J = 5.80 Hz, 1 H), 7.55-7.63 (m, 1 H), 7.48-7.54 (m, 1 H), 7.39 (t, J = 9.54 Hz, 1 H), 5.52-5.70 (m, 1 H), 5.45 (br d, J = 14.72 Hz, 1 H), 4.64-4.78 (m, 3 H), 4.48 (td, J = 11.09, 5.39 Hz, 1 H), 3.82-4.10 (m, 7 H), 3.66-3.81 (m, 2 H), 3.45-3.54 (m, 1 H), 2.71-2.82 (m, 1 H), 2.58-2.68 (m, 1 H), 2.10-2.50 (m, 6 H), 1.50-1.75 (m, 2 H), 1.38-1.49 (m, 1 H). $^{19}F$ NMR (376 MHz, METHANOL-$d_4$) δ ppm −74.03 (s), −75.91 (s), −76.94 (s), −115.02 (s), −139.93 (s), −174.09 (s). |

(27R,31S)-18,33-Difluoro-4-(((2R,7aS)-2-fluorotetrahydro-1H-pyrrolo[1,2-a]pyrrol-7a(5H)-yl)methoxy)-1,3,5,9,24 pentaazaheptacyclo[22.5.2.1~6,10~.1~11,15~.0~2,7~.0~19,32~.0~27,31~]tritriaconta-2,4,6,8,10(33),11,13,15(32),16,18-decaen-23-one (Example 71) and (27S,31R)-18,33-difluoro-4-(((2R,7aS)-2-fluorotetrahydro-1H-pyrrolo[1,2-a]pyrrol-7a(5H)-yl)methoxy)-1,3,5,9,24-pentaazaheptacyclo[22.5.2.1~6,10~.1~11,15~.0~2,7~.0~19,32~.0~27,31~]tritriaconta-2,4,6,8,10(33),11,13,15(32),16,18-decaen-23-one (Example 72)

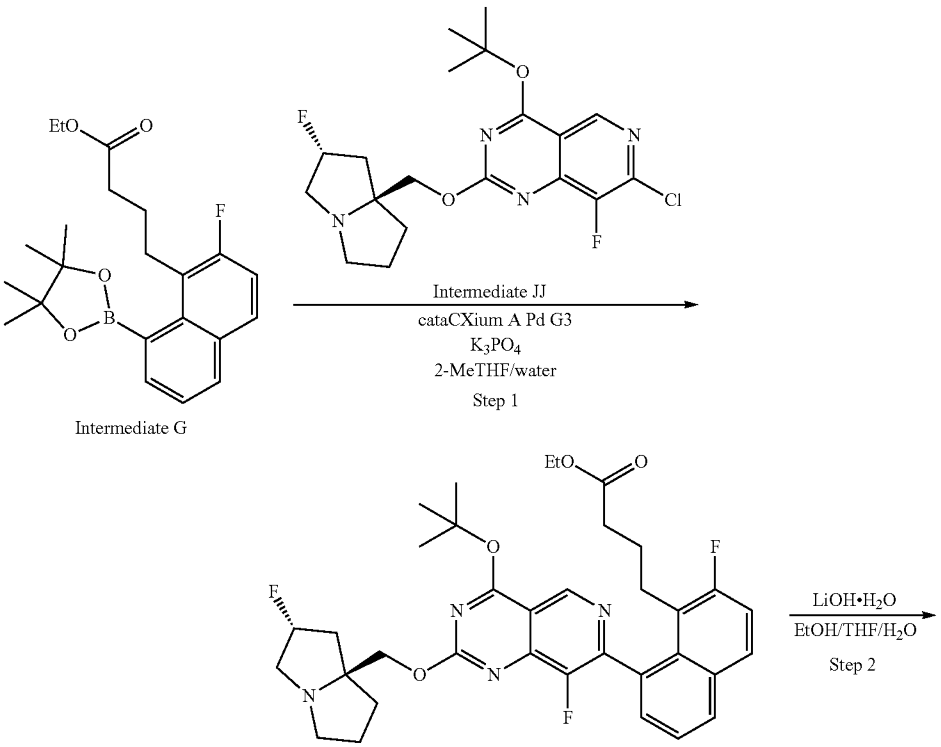

-continued

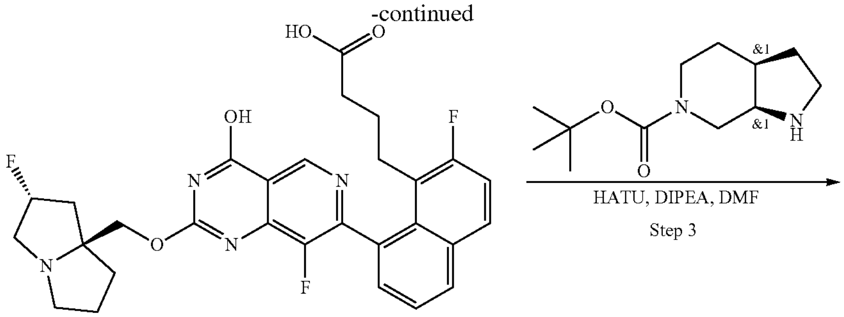

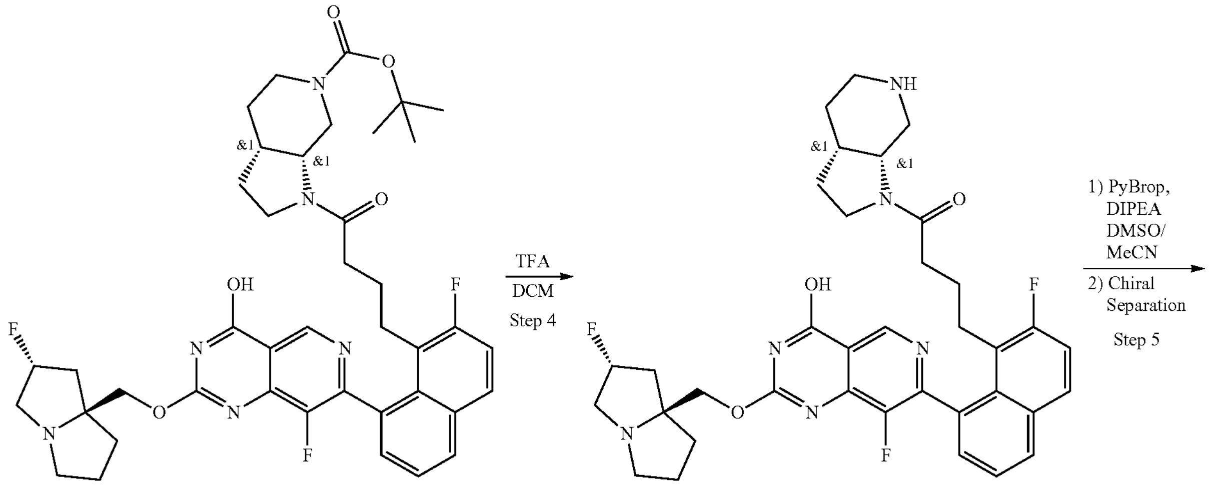

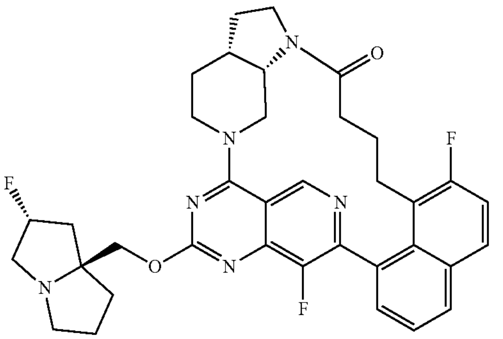

Example 71

+

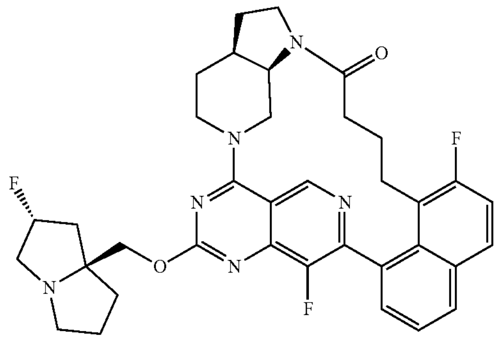

Example 72

Step 1. Ethyl 4-(8-(4-(tert-Butoxy)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoate. A vial was charged with ethyl 4-(2-fluoro-8-(4,4,5,5-tetramethyl-1,3,2-dioxaborolan-2-yl)naphthalen-1-yl)butanoate (1.68 g, 4.36 mmol, Intermediate G), 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (1.50 g, 3.63 mmol, Intermediate JJ), potassium phosphate (2.31 g, 10.9 mmol), cataCXium A Pd G3 (0.27 g, 0.36 mmol), water (1.7 mL) and 2-methyltetrahydrofuran (17 mL). The reaction mixture was heated to 80° C. for 1 h. After cooling to rt, the reaction mixture was concentrated and purified by column chromatography on silica gel, eluting with a gradient of 0-85% EtOAc/EtOH (3:1) with 2% $Et_3N$ in heptane, to provide ethyl 4-(8-(4-(tert-butoxy)-8-fluoro-2-(((2R,7aS)-2-fluorotetrahydro-1H-pyrrolizin-7a(5H)-yl)

methoxy)pyrido[4,3-d]pyrimidin-7-yl)-2-fluoronaphthalen-1-yl)butanoate (2.30 g, 3.60 mmol, 99% yield). m/z (ESI): 637.2 $(M+H)^+$.

Step 2. 4-(2-Fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)butanoic acid. A vial was charged with ethyl 4-(8-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-2-fluoronaphthalen-1-yl)butanoate (2.30 g, 3.60 mmol) in tetrahydrofuran (5.8 mL) and water (5.8 mL). Lithium hydroxide, monohydrate (0.76 g, 18.1 mmol) was added, and the mixture was stirred at rt for 2 h. The volatiles were removed in vacuo and the crude material was purified by reverse phase column chromatography, eluting with a gradient of 10-100% acetonitrile with 0.1% formic acid/water with 0.1% formic acid to afford 4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)butanoic acid (0.92 g, 1.70 mmol, 46% yield). m/z (ESI): 553.0 $(M+H)^+$.

Step 3. tert-Butyl 1-(4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)butanoyl)octahydro-6H-pyrrolo[2,3-c]pyridine-6-carboxylate. A vial was charged with 4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)butanoic acid (0.92 g, 1.66 mmol), rac-tert-butyl cis-1,2,3,3a,4,5,7,7a-octahydropyrrolo[2,3-c]pyridine-6-carboxylate (0.45 g, 1.99 mmol, Angel Pharmatech), HATU (0.92 g, 2.41 mmol), DIPEA (0.87 mL, 4.98 mmol), and N,N-dimethylformamide (8.5 mL). The reaction was stirred at rt for 1.5 h. The crude material was purified by reverse phase column chromatography, eluting with a gradient of 10-100% acetonitrile with 0.1% formic acid/water with 0.1% formic acid, to yield tert-butyl 1-(4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)butanoyl)octahydro-6H-pyrrolo[2,3-c]pyridine-6-carboxylate (1.20 g, 1.60 mmol, 95% yield). m/z (ESI): 761.2 $(M+H)^+$.

Step 4. 4-(2-Fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)-1-(octahydro-1H-pyrrolo[2,3-c]pyridin-1-yl)butan-1-one. A vial was charged with tert-butyl 1-(4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)butanoyl)octahydro-6H-pyrrolo[2,3-c]pyridine-6-carboxylate (1.20 g, 1.60 mmol) in dichloromethane (5 mL). Trifluoroacetic acid (3.7 mL, 48 mmol) was added, and the reaction mixture was stirred at rt for 30 min, and then concentrated. The crude material was purified by reverse phase column chromatography, eluting with a gradient of 5-80% acetonitrile with 0.1% formic acid/water with 0.1% formic acid. The crude product was dissolved in MeOH and eluted through a 10 g SCX column with additional MeOH wash. The SCX column was dried, then eluted with 2.0 M ammonia MeOH to give 4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)-1-(octahydro-1H-pyrrolo[2,3-c]pyridin-1-yl)butan-1-one (0.65 g, 0.99 mmol, 63% yield). m/z (ESI): 661.0 $(M+H)^+$.

Step 5. (27R,31S)-18,33-Difluoro-4-(((2R,7aS)-2-fluorotetrahydro-1H-pyrrolo[1,2-a]pyrrol-7a(5H)-yl)methoxy)-1,3,5,9,24 pentaazaheptacyclo[22.5.2.1~6,10~.1~11,15~.0~2,7~.0~19,32~.0~27,31~]tritriaconta-2,4,6,8,10(33),11,13,15(32),16,18-decaen-23-one (Example 71) and (27S,31R)-18,33-difluoro-4-(((2R,7aS)-2-fluorotetrahydro-1H-pyrrolo[1,2-a]pyrrol-7a(5H)-yl)methoxy)-1,3,5,9,24-pentaazaheptacyclo[22.5.2.1~6,10~.1~11,15~.0~2,7~.0~19,32~.0~27,31~]tritriaconta-2,4,6,8,10(33),11,13,15(32),16,18-decaen-23-one (Example 72). A vial was charged with bromotripyrrolidinophosphonium hexafluorophosphate (0.69 g, 1.48 mmol) and DIPEA (0.86 mL, 4.9 mmol) in acetonitrile (185 mL). A solution of 4-(2-fluoro-8-(8-fluoro-2-(((2R,7aS)-2-fluorotetrahydro-1H-pyrrolizin-7a(5H)-yl)methoxy)-4-hydroxypyrido[4,3-d]pyrimidin-7-yl)naphthalen-1-yl)-1-(octahydro-1H-pyrrolo[2,3-c]pyridin-1-yl)butan-1-one (0.65 g, 0.98 mmol) in dimethyl sulfoxide (12 mL) was added via syringe pump over 50 min, then the reaction was stirred at rt for 24 h. The reaction was concentrated and purified by reverse phase column chromatography, eluting with a gradient of 10-100% acetonitrile with 0.1% trifluoroacetic acid/water with 0.1% trifluoroacetic acid. Then chiral SFC separation was performed using Chiralcel OJ (2×25 cm, 5 μm) column with 25% MeOH with 0.2% diethylamine as mobile phase and a flowrate of 90 mL/min. 200 mg of sample was submitted to generate 48 mg of peak 1 with an ee of 98.4% as (27R,31S)-18,33-difluoro-4-(((2R,7aS)-2-fluorotetrahydro-1H-pyrrolo[1,2-a]pyrrol-7a(5H)-yl)methoxy)-1,3,5,9,24 pentaazaheptacyclo[22.5.2.1~6,10~.1~11,15~.0~2,7~.0~19,32~.0~27,31~]tritriaconta-2,4,6,8,10(33),11,13,15(32),16,18-decaen-23-one (Example 71): m/z (ESI): 643.2 $(M+H)^+$. $^1H$ NMR (600 MHz, DMSO-$d_6$) δ ppm 9.16 (s, 1H), 8.09-8.15 (m, 1H), 7.99-8.06 (m, 1H), 7.58-7.67 (m, 2H), 7.43-7.58 (m, 1H), 5.61 (br d, J=15.1 Hz, 1H), 5.18-5.40 (m, 1H), 4.68 (br d, J=12.2 Hz, 1H), 4.05-4.26 (m, 2H), 3.83 (br dd, J=15.0, 2.1 Hz, 1H), 3.70 (br d, J=5.9 Hz, 1H), 3.00-3.19 (m, 3H), 2.79-2.88 (m, 2H), 2.22-2.31 (m, 1H), 1.96-2.15 (m, 4H), 1.36-1.92 (m, 12H). $^{19}F$ NMR (376 MHz, METHANOL-$d_4$) δ ppm −173.62 (s), −140.77 (s), −113.80 (s) and 47 mg of peak 2 with an ee of 99% as (27S,31R)-18,33-difluoro-4-(((2R,7aS)-2-fluorotetrahydro-1H-pyrrolo[1,2-a]pyrrol-7a(5H)-yl)methoxy)-1,3,5,9,24-pentaazaheptacyclo[22.5.2.1~6,10~.1~11,15~.0~2,7~.0~19,32~.0~27,31~]tritriaconta-2,4,6,8,10(33),11,13,15(32),16,18-decaen-23-one (Example 72): m/z (ESI): 643.2 $(M+H)^+$. $^1H$ NMR (600 MHz, DMSO-$d_6$) δ ppm 9.16 (s, 1H), 8.09-8.15 (m, 1H), 8.00-8.06 (m, 1H), 7.58-7.67 (m, 2H), 7.43-7.58 (m, 1H), 5.61 (br d, J=15.1 Hz, 1H), 5.18-5.38 (m, 1H), 4.68 (br d, J=12.0 Hz, 1H), 4.04-4.23 (m, 2H), 3.77-3.89 (m, 1H), 3.71 (br d, J=5.7 Hz, 1H), 2.98-3.20 (m, 3H), 2.78-2.88 (m, 2H), 2.16-2.31 (m, 1H), 2.01-2.16 (m, 3H), 1.91-2.01 (m, 1H), 1.36-1.91 (in, 12H). $^{19}F$ NMR (376 MHz, METHANOL-$d_4$) δ ppm −173.72 (s), −140.79 (s), −113.78 (s).

TABLE 19

| Additional Examples 172 to 175 and 281. Prepared in an Analogous Manner to Example 71 & 72. | | | | |
|---|---|---|---|---|
| Ex.# | Structure & Name | Salt Form | Reagent | Method Change |
| 172 | 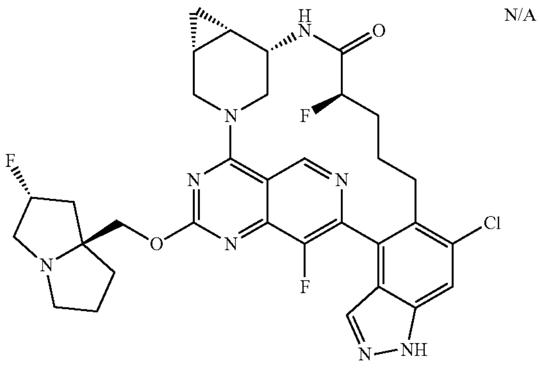 (23R,26S,27S,29R)-18-chloro-23,32-difluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[24.4.1.1~6,10~.0~2,7~.0~11,19~.0~12,16~.0~27,29~]dotriaconta-2,4,6,8,10(32), 11,13,16,18-nonaen-24-one | N/A | Step 1. Intermediate UUUU | Step 4. 4N HCl in dioxane was used instead of TFA/DCM. Chiral separation after Step 5. Details included below. |
| 173 | 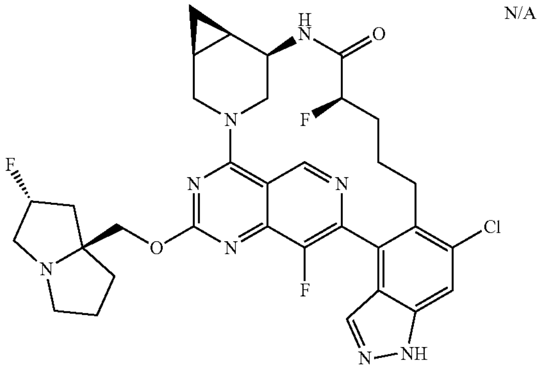 (23R,26R,27R,29S)-18-chloro-23,32-difluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[24.4.1.1~6,10~.0~2,7~.0~11,19~.0~12,16~.0~27,29~]dotriaconta-2,4,6,8,10(32), 11,13,16,18-nonaen-24-one | N/A | Step 1. Intermediate UUUU | Step 4. 4N HCI in dioxane was used instead of TFA/DCM. Chiral separation after Step 5. Details included below. |

TABLE 19-continued

| Additional Examples 172 to 175 and 281. Prepared in an Analogous Manner to Example 71 & 72. | | | | |
|---|---|---|---|---|
| Ex.# | Structure & Name | Salt Form | Reagent | Method Change |
| 174 | 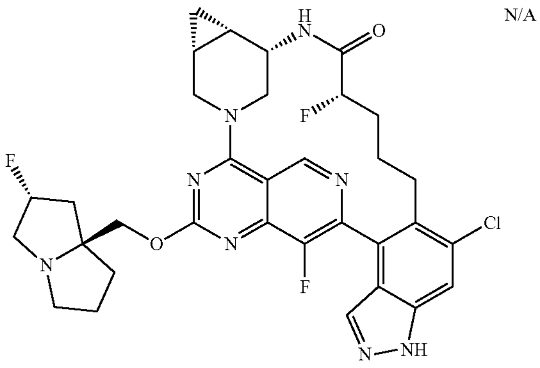 (23S,26S,27S,29R)-18-chloro-23,32-difluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[24.4.1.1~6,10~.0~2,7~.0~11,19~.0~12,16~.0~27,29~]dotriaconta-2,4,6,8,10(32), 11,13,16,18-nonaen-24-one | N/A | Step 1. Intermediate UUUU | Step 4. 4N HCl in dioxane was used instead of TFA/DCM. Chiral separation after Step 5. Details included below. |
| 175 | 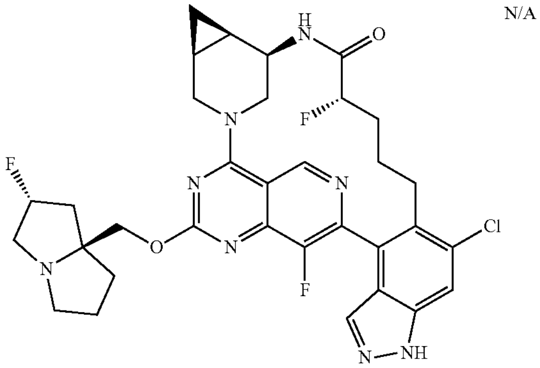 (23S,26R,27R,29S)-18-chloro-23,32-difluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[24.4.1.1~6,10~.0~2,7~.0~11,19~.0~12,16~.0~27,29~]dotriaconta-2,4,6,8,10(32), 11,13,16,18-nonaen-24-one | N/A | Step 1. Intermediate UUUU | Step 4. 4N HCl in dioxane was used instead of TFA/DCM. Chiral separation after Step 5. Details included below. |

TABLE 19-continued

Additional Examples 172 to 175 and 281. Prepared in an Analogous Manner to Example 71 & 72.

| Ex.# | Structure & Name | Salt Form | Reagent | Method Change |
|---|---|---|---|---|
| 281 | 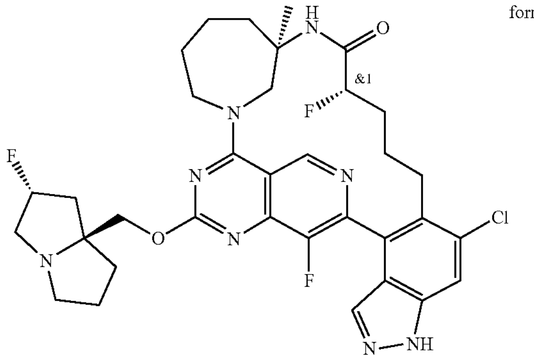 (23RS,26R)-18-chloro-23,32-difluoro-4-(((2R,7aS)-2-fluorotetrahydro-1H-pyrrolo[1,2-a]pyrrol-7a(5H)-yl)methoxy)-26-methyl-1,3,5,9,14,15,25-heptaazahexacyclo [24.4.1.1~6,10~.0~2,7~.0~11,19~.0~12,16~]dotriaconta-2,4,6,8,10(32), 11,13,16,18-nonaen-24-one | formate | Step 1. Intermediate UUUU Step 3. Intermediate DB | Step 5. 4N HCl in dioxane was used instead of TFA/DCM |

TABLE 20

Conditions for Chiral SFC Separation.

| Separation | SFC Conditions | Peak to Ex# |
|---|---|---|
| 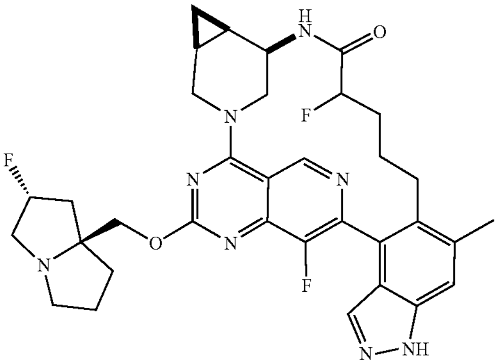 [SMILES: Cc1cc2[nH]ncc2c2c1CCCC(F)C(=O)N[C@H]1CN(C[C@H]3C[C@H]31)c1nc(OC[C@@]34CCCN3C[C@H](F)C4)nc3c(F)c-2ncc13] | Column: Chiralcel OD (2 × 25 cm, 5 μm) Mobile phase: 40% MeOH with 0.2% DEA Flowrate: 80 mL/min. Yield: 115 mg of sample was submitted to to generate 22 mg of peak 1 with an ee of 99%, 22 mg of peak 2 with an ce of 98%, 19 mg of peak. 3 with an ce of 98%, and 22 mg of peak 4 with an ec of 98%. | Peak 1: Example 172 Peak 2: Example 173 Peak 3: Example 174 Peak 4: Example 175 |

TABLE 21

Analytical Data for Examples 172 to 175 and 281.

| Cmpd. # | MS m/z (ESI): $(M + H)^+$ | $^1H$ NMR |
|---|---|---|
| 172 | 667.2 | $^1H$ NMR (600 MHz, DMSO-$d_6$) δ ppm 9.17 (s, 1 H) 7.45-7.84 (m, 3 H) 5.23-5.42 (m, 2 H) 4.64-4.75 (m, 1 H) 4.34-4.51 (m, 1 H) 4.15-4.29 (m, 2 H) 3.62-3.72 (m, 1 H) 3.36-3.50 (m, 1 H) 2.89-3.07 (m, 3 H) 2.27-2.40 (m, 1 H) 1.97-2.05 (m, 1 H) 1.42-1.57 (m, 2 H) 1.27 (br s, 5 H) 1.16 (t, J = 7.34 Hz, 4 H) 0.74-0.90 (m, 2 H) 0.35-0.59 (m, 2 H). |
| 173 | 667.2 | $^1H$ NMR (600 MHz, DMSO-$d_6$) δ ppm 9.12 (s, 1 H) 7.69-7.95 (m, 2 H) 7.05-7.25 (m, 1 H) 5.17-5.38 (m, 2 H) 4.66-4.84 (m, 1 H) |

TABLE 21-continued

| Analytical Data for Examples 172 to 175 and 281. | | |
|---|---|---|
| Cmpd. # | MS m/z (ESI): $(M + H)^+$ | $^1H$ NMR |
| | | 4.38-4.60 (m, 1 H) 3.99-4.25 (m, 3 H) 3.35-3.73 (m, 2 H) 2.87-3.20 (m, 2 H) 2.34-2.45 (m, 1 H) 1.74-2.20 (m, 6 H) 1.45-1.54 (m, 1 H) 1.23-1.35 (m, 3 H) 0.97-1.19 (m, 3 H) 0.35-0.77 (m, 3 H). |
| 174 | 667.2 | $^1H$ NMR (600 MHz, DMSO-$d_6$) δ ppm 9.04-9.25 (m, 1 H) 7.34-8.00 (m, 3 H) 5.15-5.43 (m, 2 H) 3.88-4.78 (m, 5 H) 3.37-3.71 (m, 2 H) 2.82-3.16 (m, 2 H) 2.28-2.45 (m, 1 H) 1.73-2.21 (m, 6 H) 1.42-1.55 (m, 2 H) 1.20-1.35 (m, 4 H) 1.02-1.15 (m, 1 H) 0.71-0.83 (m, 1 H) 0.40 (br d, J = 5.58 Hz, 2 H). |
| 175 | 667.2 | $^1H$ NMR (600 MHz, DMSO-$d_6$) δ ppm 9.12 (s, 1 H) 6.85-7.96 (m, 3 H) 5.17-5.43 (m, 2 H) 4.41-4.79 (m, 2 H) 3.98-4.29 (m, 3 H) 3.62-3.73 (m, 1 H) 3.33-3.50 (m, 1 H) 2.81-3.20 (m, 2 H) 2.37-2.46 (m, 1 H) 1.97-2.19 (m, 3 H) 1.73-1.93 (m, 3 H) 1.45-1.56 (m, 1 H) 1.30 (br d, J = 2.05 Hz, 3 H) 0.96-1.20 (m, 3 H) 0.42-0.78 (m, 3 H). |
| 281 | 682.9 | $^1H$ NMR (400 MHz, METHANOL-d4) δ ppm 9.27-9.35 (m, 1 H), 7.63-7.86 (m, 2 H), 5.73-5.89 (m, 1 H), 5.25-5.52 (m, 1 H), 4.63-4.75 (m, 1 H), 4.37-4.60 (m, 2 H), 3.38-3.78 (m, 5 H), 3.05-3.29 (m, 3 H), 2.51-2.67 (m, 1 H), 2.28-2.50 (m, 3 H), 1.27-2.28 (m, 20 H). $^{19}F$ NMR (376 MHz, METHANOL-d4) δ ppm −142.49−−141.36 (m, 1 F), −174.57−−173.44 (m, 1 F), −188.99−−185.43 (m, 1 F). |

(17R)-9-Chloro-24-(((2R,7aS)-2-fluorotetrahydro-1H-pyrrolo[1,2-a]pyrrol-7a(5H)-yl)methoxy)-16-methyl-5,6,16,21,23,25,28,29-octaazahexacyclo [24.3.1.1~17,21~.0~2,10~.0~3,7~.0~22,27~] hentriaconta-1(30),2,4,7,9,22,24,26,28-nonaen-15-one (Example 73)

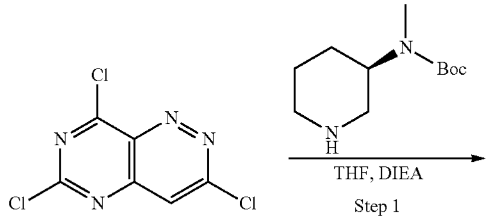

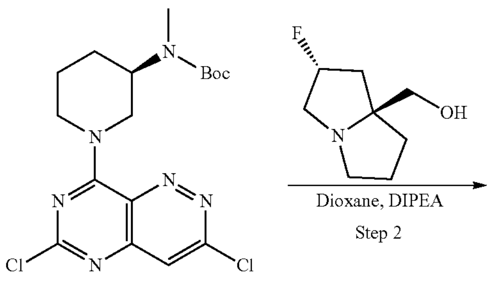

-continued

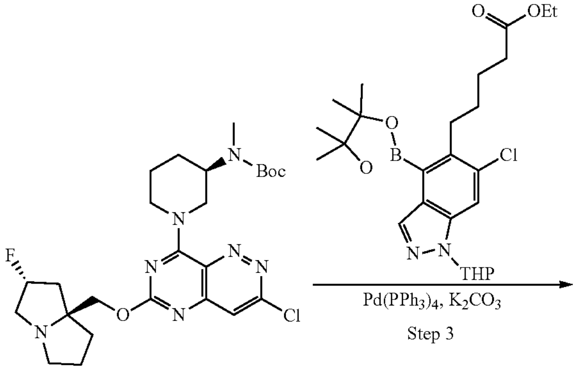

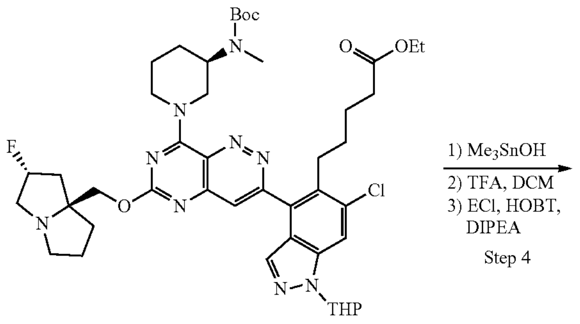

-continued

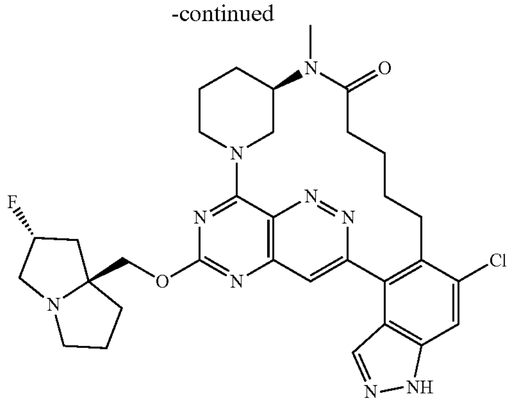

Example 73

Step 1. tert-Butyl (R)-(1-(3,6-dichloropyrimido[5,4-c]pyridazin-8-yl)piperidin-3-yl)(methyl)carbamate. To a solution of 3,6,8-trichloropyrimido[5,4-c]pyridazine (3.20 g, 13.6 mmol, Intermediate 00) in THF (40 mL) at −78° C. was added DIPEA (7.1 mL, 41 mmol) followed by tert-butyl (R)-methyl(piperidin-3-yl)carbamate (2.00 g, 9.50 mmol). The mixture was stirred at −78° C. for 1 h then diluted with $H_2O$ and extracted with EtOAc. The combined organic layers were washed with brine, dried over $Na_2SO_4$, filtered, and concentrated. The residue was purified by column chromatography on silica gel, eluting with 30-50% EtOAc in petroleum ether to give tert-butyl (R)-(1-(3,6-dichloropyrimido[5,4-c]pyridazin-8-yl)piperidin-3-yl)(methyl)carbamate (4.00 g, 9.70 mmol, 100% yield) as brown solid. m/z (ESI): 414.0 $(M+H)^+$.

Step 2. tert-Butyl ((R)-1-(3-chloro-6-(((2R,7aS)-2-fluorotetrahydro-1H-pyrrolizin-7a(5H)-yl)methoxy)pyrimido[5,4-c]pyridazin-8-yl)piperidin-3-yl)(methyl)carbamate. To a solution of tert-butyl (R)-(1-(3,6-dichloropyrimido[5,4-c]pyridazin-8-yl)piperidin-3-yl)(methyl)carbamate (4.00 g, 9.70 mmol) in 1,4-dioxane (20 mL) was added DIPEA (6.7 mL, 39 mmol) followed by ((2R,7aS)-2-fluorotetrahydro-1H-pyrrolizin-7a(5H)-yl)methanol (2.20 g, 13.6 mmol, Pharmacore). The mixture was stirred at 120° C. for 12 h, then cooled to rt, diluted with $H_2O$, and extracted with EtOAc. The combined organic layers were washed with brine, dried over $Na_2SO_4$, filtered, and concentrated. The residue was purified by column chromatography on silica gel, eluting with 30-50% EtOAc in petroleum ether to afford tert-butyl ((R)-1-(3-chloro-6-(((2R,7aS)-2-fluorotetrahydro-1H-pyrrolizin-7a(5H)-yl)methoxy)pyrimido[5,4-c]pyridazin-8-yl)piperidin-3-yl)(methyl)carbamate (3.20 g, 6.00 mmol, 62% yield) as brown solid. $^1H$ NMR (400 MHz, DMSO-$d_6$) δ ppm 7.85 (s, 1H), 5.87-6.21 (m, 1H), 5.26 (d, J=56.00 Hz, 1H), 4.85-5.14 (m, 1H), 3.78-4.24 (m, 4H), 2.93-3.14 (m, 4H), 2.74-2.87 (m, 5H), 1.59-2.07 (m, 9H), 1.30-1.50 (m, 9H). m/z (ESI): 536.5 $(M+H)^+$.

Step 3. Ethyl 5-(4-(8-((R)-3-((tert-butoxycarbonyl)(methyl)amino)piperidin-1-yl)-6-(((2R,7aS)-2-fluorotetrahydro-1H-pyrrolizin-7a(5H)-yl)methoxy)pyrimido[5,4-c]pyridazin-3-yl)-6-chloro-1-(tetrahydro-2H-pyran-2-yl)-1H-indazol-5-yl)pentanoate. A mixture of ethyl 5-(6-chloro-1-(tetrahydro-2H-pyran-2-yl)-4-(4,4,5,5-tetramethyl-1,3,2-dioxaborolan-2-yl)-1H-indazol-5-yl)pentanoate (0.23 g, 0.47 mmol, Intermediate LL), tert-butyl ((R)-1-(3-chloro-6-(((2R,7aS)-2-fluorotetrahydro-1H-pyrrolizin-7a(5H)-yl)methoxy)pyrimido[5,4-c]pyridazin-8-yl)piperidin-3-yl)(methyl)carbamate (0.21 g, 0.39 mmol), $Pd(PPh_3)_4$ (45 mg, 0.04 mmol) and $K_2CO_3$ (0.11 g, 0.78 mmol) in toluene (2 mL), water (0.3 mL) and EtOH (1 mL) was degassed and purged with $N_2$. The reaction mixture was heated at 100° C. for 12 h under nitrogen. After cooling to rt, the mixture was diluted with $H_2O$ and extracted with EtOAc. The combined organic layers were washed with brine, dried over $Na_2SO_4$, filtered, and concentrated. The residue was purified by column chromatography on silica gel, eluting with 5-10% EtOH in EtOAc to give ethyl 5-(4-(8-((R)-3-((tert-butoxycarbonyl)(methyl)amino)piperidin-1-yl)-6-(((2R,7aS)-2-fluorotetrahydro-1H-pyrrolizin-7a(5H)-yl)methoxy)pyrimido[5,4-c]pyridazin-3-yl)-6-chloro-1-(tetrahydro-2H-pyran-2-yl)-1H-indazol-5-yl)pentanoate (0.22 g, 0.23 mmol, 58% yield) as yellow solid. m/z (ESI): 864.5 $(M+H)^+$.

Step 4. (17R)-9-Chloro-24-(((2R,7aS)-2-fluorotetrahydro-1H-pyrrolo[1,2-a]pyrrol-7a(5H)-yl)methoxy)-16-methyl-5,6,16,21,23,25,28,29-octaazahexacyclo[24.3.1.1~17,21~.0~2,10~.0~3,7~.0~22,27~]hentriaconta-1(30),2,4,7,9,22,24,26,28-nonaen-15-one. To a solution of ethyl 5-(4-(8-((R)-3-((tert-butoxycarbonyl)(methyl)amino)piperidin-1-yl)-6-(((2R,7aS)-2-fluorotetrahydro-1H-pyrrolizin-7a(5H)-yl)methoxy)pyrimido[5,4-c]pyridazin-3-yl)-6-chloro-1-(tetrahydro-2H-pyran-2-yl)-1H-indazol-5-yl)pentanoate (0.22 g, 0.23 mmol) in 1,2-dichloroethane (2 mL) was added trimethylstannanol (0.30 g, 1.65 mmol). The mixture was stirred at 100° C. for 18 h then concentrated under reduced pressure to give 5-(4-(8-((R)-3-((tert-butoxycarbonyl)(methyl)amino)piperidin-1-yl)-6-(((2R,7aS)-2-fluorotetrahydro-1H-pyrrolizin-7a(5H)-yl)methoxy)pyrimido[5,4-c]pyridazin-3-yl)-6-chloro-1-(tetrahydro-2H-pyran-2-yl)-1H-indazol-5-yl)pentanoic acid as yellow solid which was used in the next step without purification. m/z (ESI): 836.5 $(M+H)^+$.

The above crude acid (0.30 g, 0.31 mmol) was dissolved in DCM (2 mL) and treated with TFA (0.5 mL, 6.5 mmol). After stirring at rt for 5 h, the reaction mixture was concentrated and the residue was co-evaporated with toluene to give 5-(6-chloro-4-(6-(((2R,7aS)-2-fluorotetrahydro-1H-pyrrolizin-7a(5H)-yl)methoxy)-8-((R)-3-(methylamino)piperidin-1-yl)pyrimido[5,4-c]pyridazin-3-yl)-1H-indazol-5-yl)pentanoic acid as yellow solid which was used in the next step without purification. m/z (ESI): 652.3 $(M+H)^+$.

The above crude acid was dissolved in DCM (30 mL) then treated with HOBt (0.16 g, 1.20 mmol), EDCI (0.22 g, 1.20 mmol), and DIPEA (0.54 mL, 3.1 mmol). After stirring at rt for 36 h, the reaction mixture was concentrated, and the residue was treated with water and extracted with ethyl acetate. The combined organic layers were dried over $Na_2SO_4$, filtered, and concentrated. The residue was purified by preparative HPLC using C18 100×30 mm×10 mm column, eluting with water (10 mM $NH_4HCO_3$)/$CH_3CN$ to afford (17R)-9-chloro-24-(((2R,7aS)-2-fluorotetrahydro-1H-pyrrolo[1,2-a]pyrrol-7a(5H)-yl)methoxy)-16-methyl-5,6,16,21,23,25,28,29-octaazahexacyclo[24.3.1.1~17,21~.0~2,10~.0~3,7~.0~22,27~]hentriaconta-1(30),2,4,7,9,22,24,26,28-nonaen-15-one (37 mg, 0.046 mmol, 20% yield) as off-white solid. $^1H$ NMR (400 MHz, DMSO-$d_6$) δ ppm 13.37 (s, 1H), 7.98 (s, 1H), 7.82 (s, 1H), 7.75 (s, 1H), 6.37 (d, J=12.00 Hz, 1H), 5.29 (d, J=54.00 Hz, 1H), 5.00-5.05 (m, 1H), 4.10-4.15 (m, 2H), 3.80-3.92 (m, 1H), 3.61-3.72 (m, 1H), 3.00-3.20 (m, 4H), 2.72-2.92 (m, 4H), 2.18-2.30 (m, 1H), 1.94-2.18 (m, 7H), 1.52-1.89 (m, 9H), 1.02-1.29 (m, 1H). m/z (ESI): 634.3 $(M+H)^+$.

(17R)-9-Chloro-30-fluoro-24-(((2R,7aS)-2-fluorotetrahydro-1H-pyrrolo[1,2-a]pyrrol-7a(5H)-yl)methoxy)-16-methyl-14-oxa-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one (Example 74)
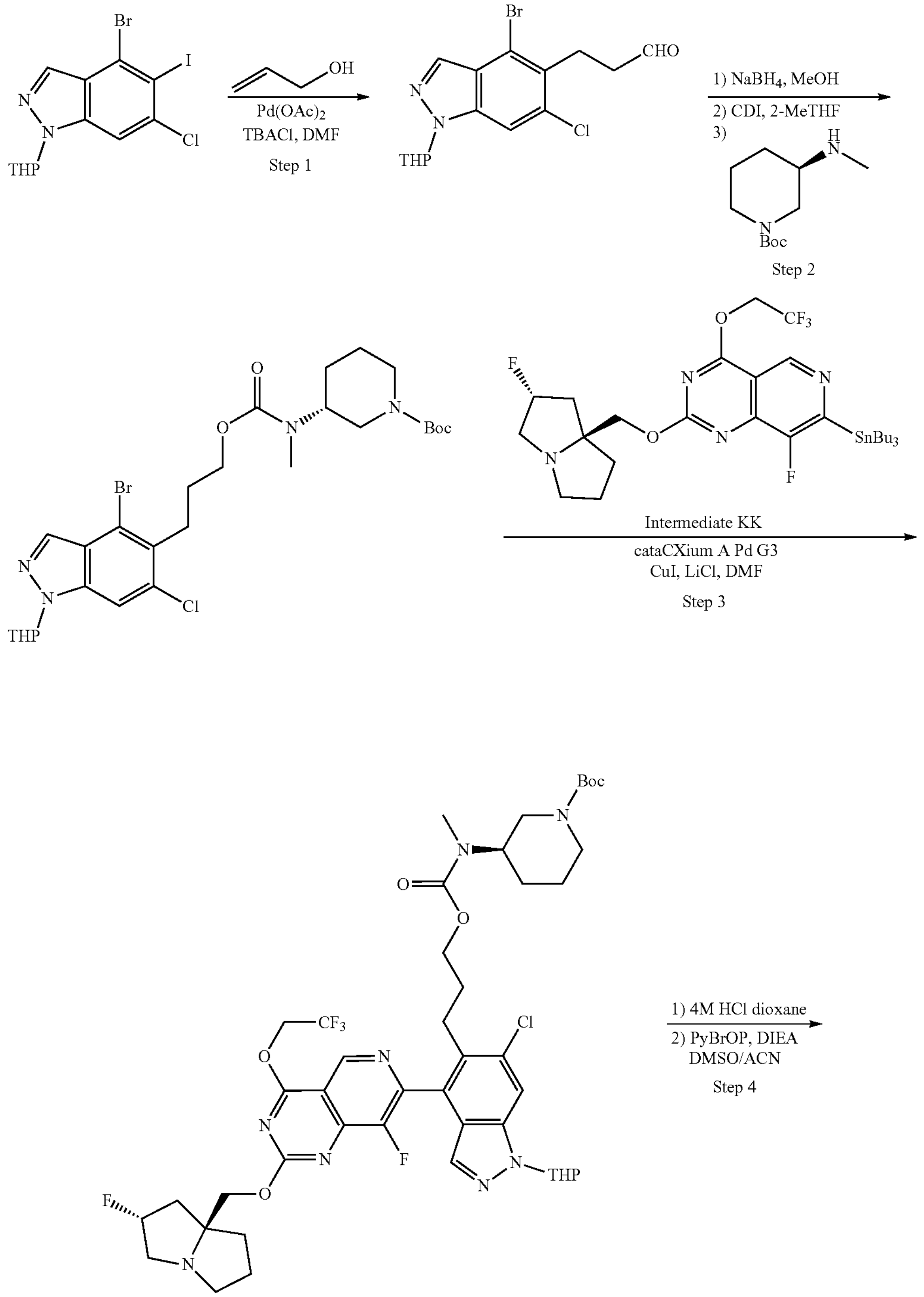

-continued

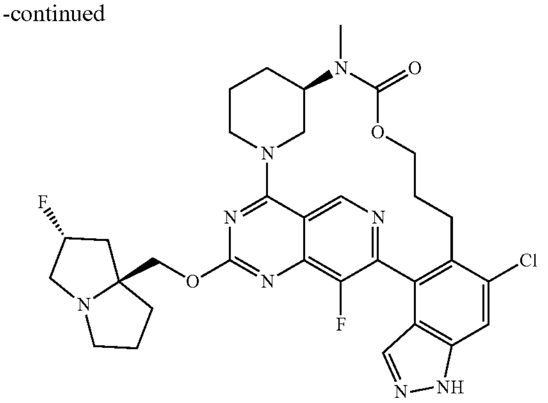

Example 74

Step 1. 3-(4-Bromo-6-chloro-1-(tetrahydro-2H-pyran-2-yl)-1H-indazol-5-yl)propanal. A suspension of 4-bromo-6-chloro-5-iodo-1-(tetrahydro-2H-pyran-2-yl)-1H-indazole (3.00 g, 6.80 mmol, Lab Network), sodium bicarbonate (1.43 g, 17 mmol), and tetrabutylammonium chloride (1.89 g, 6.80 mmol) in DMF (14 mL) was degassed with nitrogen for 10 min. To this was added palladium(II) acetate (76 mg, 0.34 mmol) and allyl alcohol (0.69 mL, 10 mmol). The reaction mixture was stirred at 50° C. for 16 h, cooled and diluted with saturated aqueous ammonium chloride and extracted with EtOAc. The aqueous layer was extracted with EtOAc, and the organic layer was washed with saturated aqueous sodium chloride, dried ($Na_2SO_4$) and concentrated. The crude material was purified by column chromatography on silica gel, eluting with 0-35% EtOAc in heptane, to provide 3-(4-bromo-6-chloro-1-(tetrahydro-2H-pyran-2-yl)-1H-indazol-5-yl)propanal (2.10 g, 5.60 mmol, 83% yield) as yellow solid. m/z (ESI): 371.0 $(M+H)^+$.

Step 2. tert-Butyl (3R)-3-(((3-(4-bromo-6-chloro-1-(tetrahydro-2H-pyran-2-yl)-1H-indazol-5-yl)propoxy)carbonyl)(methyl)amino)piperidine-1-carboxylate. To a solution of 3-(4-bromo-6-chloro-1-(tetrahydro-2H-pyran-2-yl)-1H-indazol-5-yl)propanal (2.10 g, 5.70 mmol) in methanol (56 mL) and dichloromethane (5 mL) was added sodium borohydride (0.24 g, 6.20 mmol). The reaction mixture was stirred at rt for 10 min, then carefully quenched by addition of saturated aqueous ammonium chloride. The mixture was concentrated, diluted with dichloromethane, and filtered through a plug of sodium sulfate. The filtrate was concentrated to yield white solid.

The above intermediate (0.20 g, 0.54 mmol) was dissolved in 2-methyltetrahydrofuran (3 mL), and 1,1'-carbonyldiimidazole (0.10 g, 0.64 mmol) was added. The reaction mixture was stirred at rt. After 1 h, the reaction was ~70% complete, another portion of 1,1'-carbonyldiimidazole (52 mg, 0.32 mmol) was added, and the reaction was stirred for another hour, (R)-1-N-Boc-3-methylaminopiperidine (0.57 g, 2.68 mmol, Combi-Blocks Inc.) was added, and the reaction was stirred at 80° C. for 16 h. After cooling to rt, the reaction mixture was partitioned between water and EtOAc. The organic layer was dried ($Na_2SO_4$) and concentrated. The crude product was purified by column chromatography on silica gel, eluting with 0-100% (3:1 ethyl acetate/ethanol with 2% TEA) in heptane, to provide tert-butyl (3R)-3-(((3-(4-bromo-6-chloro-1-(tetrahydro-2H-pyran-2-yl)-1H-indazol-5-yl)propoxy)carbonyl)(methyl)amino)piperidine-1-carboxylate (0.37 g, 0.60 mmol, quantitative yield) as off-white solid. m/z (ESI): 512.8 $(M\text{-}Boc)^+$.

Step 3. tert-Butyl (3R)-3-(((3-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)propoxy)carbonyl)(methyl)amino)piperidine-1-carboxylate. To a solution of tert-butyl (3R)-3-(((3-(4-bromo-6-chloro-1-(tetrahydro-2H-pyran-2-yl)-1H-indazol-5-yl)propoxy)carbonyl)(methyl)amino)piperidine-1-carboxylate (0.33 g, 0.54 mmol) and 8-fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d]pyrimidine (0.74 g, 1.10 mmol, Intermediate KK) in DMF (3.5 mL) was added lithium chloride (45 mg, 1.10 mmol), copper(I) iodide (51 mg, 0.27 mmol), and cataCXium A Pd G3 (78 mg, 0.11 mmol). The reaction was sparged with argon, capped, and stirred at 100° C. for 1 h. After cooling to rt, the reaction mixture was partitioned between water and EtOAc. The organic layer was dried ($Na_2SO_4$) and concentrated. The crude product was purified by column chromatography on silica gel, eluting with 0-100% (3:1 ethyl acetate/ethanol+2% TEA) in heptane, to provide tert-butyl (3R)-3-(((3-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)propoxy)carbonyl)(methyl)amino)piperidine-1-carboxylate (0.22 g, 0.24 mmol, 44% yield) as light-yellow powder. m/z (ESI): 937.2 $(M+H)^+$.

Step 4. (17R)-9-Chloro-30-fluoro-24-(((2R,7aS)-2-fluorotetrahydro-1H-pyrrolo[1,2-a]pyrrol-7a(5H)-yl)methoxy)-16-methyl-14-oxa-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one. To a suspension of tert-butyl (3R)-3-(((3-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)propoxy)carbonyl)(methyl)amino)piperidine-1-carboxylate (0.22 g, 0.24 mmol) in 1,4-dioxane (1.5 mL) was added a 4 M solution of HCl in dioxane (3 mL, 12 mmol). The reaction was stirred at rt for 2 h, concentrated, and the residue was redissolved in methanol and loaded onto a SCX column. The column was washed with methanol, and the desired intermediate was eluted with 1 M DIEA in methanol. The eluent was concentrated to off-white solid.

The above solid was redissolved in dimethyl sulfoxide (3.5 mL) and was added dropwise to a solution of bromotripyrrolidinophosphonium hexafluorophosphate (0.15 g, 0.31 mmol) and DIEA (0.11 mL, 0.63 mmol) in acetonitrile (17 mL). The reaction mixture was stirred at rt for 16 h, then concentrated to ~5 mL, and loaded onto a SCX column. The column was washed with methanol, and the crude product was eluted with 2 M ammonia in methanol. The eluent was concentrated, and the residue was purified by reverse phase HPLC, eluting with 10-60% (ACN/0.1% TFA) in (water/0.1% TFA). The product-containing fractions were combined, and lyophilized to provide (17R)-9-chloro-30-fluoro-24-(((2R,7aS)-2-fluorotetrahydro-1H-pyrrolo[1,2-a]pyrrol-7a(5H)-yl)methoxy)-16-methyl-14-oxa-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one (26 mg, 0.03 mmol, 14% yield) as white powder. m/z (ESI): 653.0 $(M+H)^+$. $^1H$ NMR (500 MHz, METHANOL-$d_4$) δ ppm 9.30 (s, 1H), 7.83 (dd, J=9.0, 1.0 Hz, 2H), 5.53-5.70 (m, 1H), 5.21-5.31 (m, 1H), 5.00-5.10 (m, 1H), 4.65-4.80 (m, 3H), 3.85-4.08 (m, 6H), 3.59-3.64 (m, 1H), 3.47-3.56 (m, 2H), 3.34-3.38 (m, 1H), 2.98 (ddd, J=13.7, 8.2, 5.3 Hz, 1H), 2.90 (s, 1H), 2.52-2.82 (m, 4H), 2.42-2.47 (m, 1H), 2.34-2.41 (m, 4H), 2.18-2.26 (m, 2H), 2.03 (br d, J=10.4 Hz, 1H), 1.74-1.90 (m, 3H). $^{19}F$ NMR (471 MHz, METHANOL-$d_4$) δ ppm −77.32 (s), −142.26 (s), −174.14 (s).

TABLE 22

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| 76 | 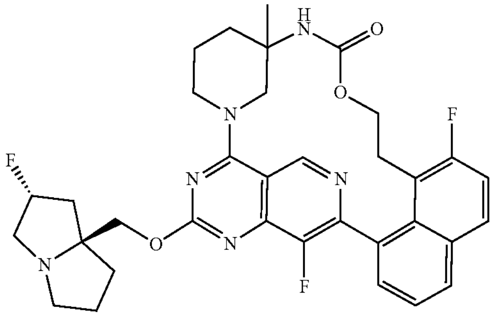 [SMILES: CC12CCCN(C1)c1nc(OC[C@@]34CCCN3C[C@H](F)C4)nc3c(F)c(ncc13)-c1cccc3ccc(F)c(c13)CCOC(=O)N2] (15R)-22,31-difluoro-8-(((2R,7aS)-2-fluorotetrahydro-1H-pyrrolo[1,2-a]pyrrol-7a(5H)-yl)methoxy)-15-methyl-18-oxa-3,7,9,11,16-pentaazahexacyclo[19.7.1.1~2,6~.1~11,15~.0~5,10~.0~25,29~]hentriaconta-1(29),2(31),3,5,7,9,21,23,25,27-decaen-17-one and (15S)-22,31-difluoro-8-(((2R,7aS)-2-fluorotetrahydro-1H-pyrrolo[1,2-a]pyrrol-7a(5H)-yl)methoxy)-15-methyl-18-oxa-3,7,9,11,16-pentaazahexacyclo[19.7.1.1~2,6~.1~11,15~.0~5,10~.0~25,29~]hentriaconta-1(29),2(31),3,5,7,9,21,23,25,27-decaen-17-one | | Step 3. Intermediate QQ | Step 1 & 2 not performed |
| 77 | 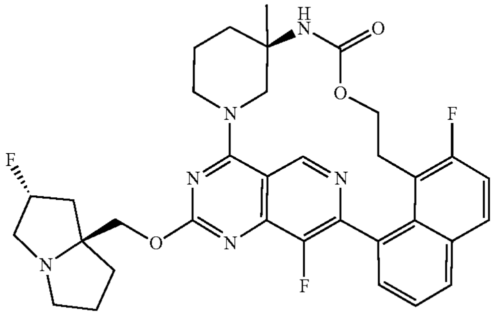 [SMILES: C[C@@]12CCCN(C1)c1nc(OC[C@@]34CCCN3C[C@H](F)C4)nc3c(F)c(ncc13)-c1cccc3ccc(F)c(c13)CCOC(=O)N2] (15R)-22,31-difluoro-8-(((2R,7aS)-2-fluorotetrahydro-1H-pyrrolo[1,2-a]pyrrol-7a(5H)-yl)methoxy)-15-methyl-18-oxa-3,7,9,11,16-pentaazahexacyclo[19.7.1.1~2,6~.1~11,15~.0~5,10~.0~25,29~]hentriaconta-1(29),2(31),3,5,7,9,21,23,25,27-decaen-17-one | | Step 3. Intermediate QQ | Step 1 & 2 not performed Chiral separation performed after Step 4. Details included below. |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| 78 | 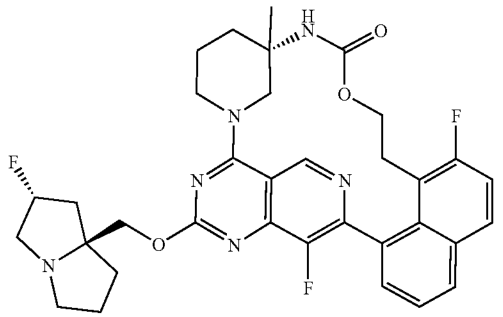 [SMILES: C[C@]12CCCN(C1)c1nc(OC[C@@]34CCCN3C[C@H](F)C4)nc3c(F)c(ncc13)-c1cccc3ccc(F)c(c13)CCOC(=O)N2] (15S)-22,31-difluoro-8-(((2R,7aS)-2-fluorotetrahydro-1H-pyrrolo[1,2-a]pyrrol-7a(5H)-yl)methoxy)-15-methyl-18-oxa-3,7,9,11,16-pentaazahexacyclo[19.7.1.1~2,6~.1~11,15~.0~5,10~.0~25,29~]hentriaconta-1(29),2(31),3,5,7,9,21,23,25,27-decaen-17-one | | Step 3. Intermediate QQ | Step 1 & 2: not performed Chiral separation performed after Step 4. Details included below. |
| 79 | 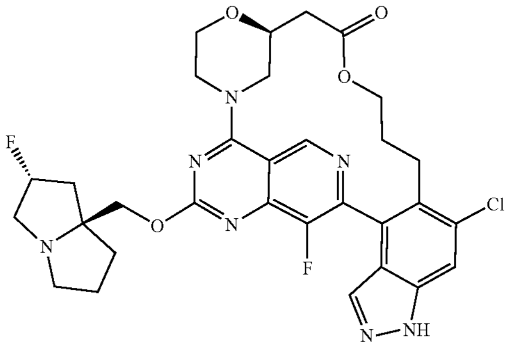 [SMILES: O=C1C[C@H]2CN(CCO2)c2nc(OC[C@@]34CCCN3C[C@H](F)C4)nc3c(F)c(ncc23)-c2c(c(Cl)cc3[nH]ncc23)CCCO1] (17S)-9-chloro-30-fluoro-24-(((2R,7aS)-2-fluorotetrahydro-1H-pyrrolo[1,2-a]pyrrol-7a(5H)-yl)methoxy)-14,18-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | | Step 2. (S)-2-(4-(tert-butoxy-carbonyl) morpholin-2-yl)acetic acid (CAS#: 1257850-82-0, Ambeed, Inc.) | Step 2. DCC, DMAP, DCM was used. |
| 176 | 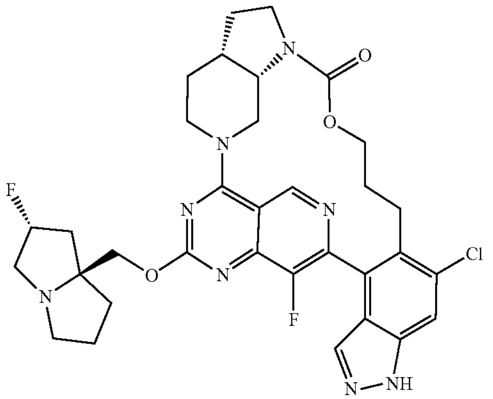 [SMILES: O=C1OCCCc2c(Cl)cc3[nH]ncc3c2-c2ncc3c(nc(OC[C@@]45CCCN4C[C@H](F)C5)nc3c2F)N2CC[C@@H]3CCN1[C@@H]3C2] (28R,32S)-18-chloro-33-fluoro-4-(((2R,7aS)-2-fluorotetrahydro-1H-pyrrolo[1,2-a]pyrrol-7a(5H)-yl)methoxy)-23-oxa-1,3,5,9,14,15,25- | bis(2, 2,2-trifluoro-acetate) | Step 2. Intermediate VVVV Step 2_3. tert-butyl cis-1,2,3,3a,4,5,7,7a-octahydro-pyrrolo[2,3-c]pyridine -6-carboxylate (CAS#: 1286755-20-1) | Step 2_1 was not performed. Step 2_2. Triethylamine and 4-nitrophenyl chloroformate (CAS#: 7693-46-1) was used. Step 3 was not performed. |

TABLE 22-continued

| Additional Examples 76 to 79, 176 to 178 and 282 to 302. Prepared in an Analogous Manner to Example 74. | | | | |
|---|---|---|---|---|
| Ex. # | Structure & Name | Salt Form | Reagent | Method Change |
| | heptaazaheptacyclo[23.5.2.1~6,10~.0~2,7~.0~11,19~.0~12,16~.0~28,32~]tritriaconta-2,4,6,8,10(33),11,13,16,18-nonaen-24-one | | | |
| 177 | 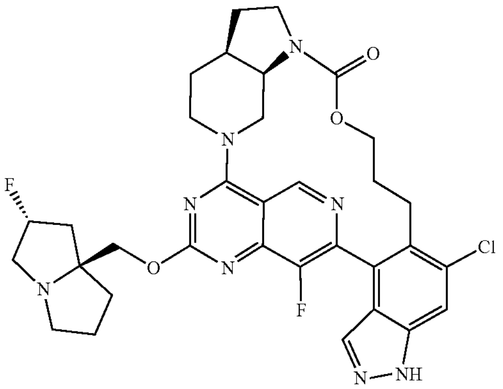 [SMILES: O=C1OCCCc2c(Cl)cc3[nH]ncc3c2-c2ncc3c(nc(OC[C@@]45CCCN4C[C@H](F)C5)nc3c2F)N2CC[C@H]3CCN1[C@H]3C2] (28S,32R)-18-chloro-33-fluoro-4-(((2R,7aS)-2-fluorotetrahydro-1H-pyrrolo[1,2-a]pyrrol-7a(5H)-yl)methoxy)-23-oxa-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | bis(2,2,2-trifluoro-acetate) | Step 2. Intermediate VVVV Step 2_3. tert-butyl cis-1,2,3,3a,4,5,7,7a-octahydro-pyrrolo[2,3-c]pyridine -6-carboxylate (CAS#: 1286755-20-1) | Step 2_1 was not performed. Step 2_2. Triethylamine and 4-nitrophenyl chloroformate (CAS#: 7693-46-1, Acros Organics) was used. Step 3 was not performed. |
| 178 | 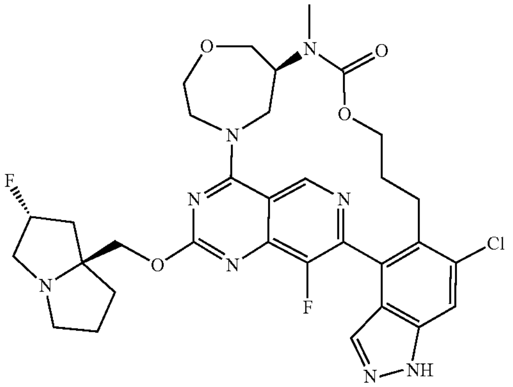 [SMILES: CN1C(=O)OCCCc2c(Cl)cc3[nH]ncc3c2-c2ncc3c(nc(OC[C@@]45CCCN4C[C@H](F)C5)nc3c2F)N2CCOC[C@@H]1C2] (26S)-18-chloro-32-fluoro-4-(((2R,7aS)-2-fluorotetrahydro-1H-pyrrolo[1,2-a]pyrrol-7a(5H)-yl)methoxy)-25-methyl-23,28-dioxa-1,3,5,9,14,15,25-heptaazahexacyclo[24.4.1.1~6,10~.0~2,7~.0~11,19~.0~12,16~]dotriaconta-2,4,6,8,10(32),11,13,16,18-nonaen-24-one | | Step 4. Intermediate WWWW | Steps 1-3 not performed |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
| --- | --- | --- | --- | --- |
| 282 | 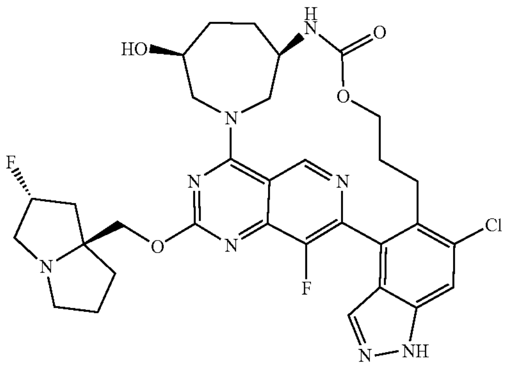 [SMILES: O=C1N[C@@H]2CC[C@H](O)CN(C2)c2nc(OC[C@@]34CCCN3C[C@H](F)C4)nc3c(F)c(ncc23)-c2c(c(Cl)cc3[nH]ncc23)CCCO1] (26R,29S)-18-chloro-32-fluoro-4-(((2R,7aS)-2-fluorotetrahydro-1H-pyrrolo[1,2-a]pyrrol-7a(5H)-yl)methoxy)-29-hydroxy-23-oxa-1,3,5,9,14,15,25-heptaazahexacyclo[24.4.1.1~6,10~.0~2,7~.0~11,19~.0~12,16~]dotriaconta-2,4,6(32),7,9,11,13,16,18-nonaen-24-one | | Step 2. Intermediate VVVV Step 2_3. rac tert-butyl (3S,6R)-3-amino-6-hydroxyazepane-1-carboxylate hydrochloride (CAS#: 2247101-92-2, Enamine) | Step 2_1 was not performed. Step 2_2. Triethylamine and 4-nitrophenyl chloroformate (CAS#: 7693-46-1, Acros Organics) was used. Step 3 was not performed. Step 4_2. BroP was used. Chiral separation performed after Step 4. Details included below. |
| 283 | 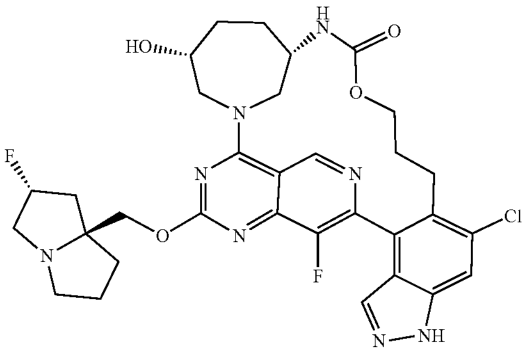 [SMILES: O=C1N[C@H]2CC[C@@H](O)CN(C2)c2nc(OC[C@@]34CCCN3C[C@H](F)C4)nc3c(F)c(ncc23)-c2c(c(Cl)cc3[nH]ncc23)CCCO1] (26S,29R)-18-chloro-32-fluoro-4-(((2R,7aS)-2-fluorotetrahydro-1H-pyrrolo[1,2-a]pyrrol-7a(5H)-yl)methoxy)-29-hydroxy-23-oxa-1,3,5,9,14,15,25-heptaazahexacyclo[24.4.1.1~6,10~.0~2,7~.0~11,19~.0~12,16~]dotriaconta-2,4,6(32),7,9,11,13,16,18-nonaen-24-one | | Step 2. Intermediate VVVV Step 2_3. rac tert-butyl (3S,6R)-3-amino-6-hydroxy-azepane-1-carboxylate hydrochloride (CAS#: 2247101-92-2) | Step 2_1 was not performed. Step 2_2. Triethylamine and 4-nitrophenyl chloroformate (CAS#: 7693-46-1) was used. Step 3 was not performed. Step 4_2. BroP was used. Chiral separation performed after Step 4. Details included below. |
| 284 | 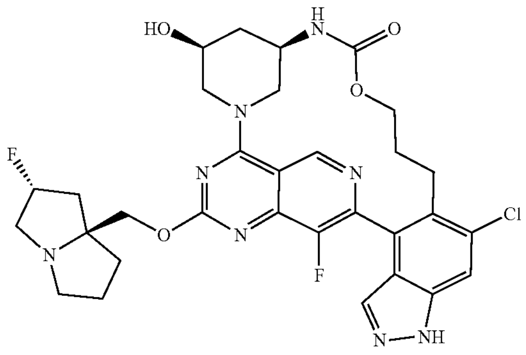 [SMILES: O=C1N[C@@H]2C[C@H](O)CN(C2)c2nc(OC[C@@]34CCCN3C[C@H](F)C4)nc3c(F)c(ncc23)-c2c(c(Cl)cc3[nH]ncc23)CCCO1] (17R,19S)-9-chloro-30-fluoro-24-(((2R,7aS)-2-fluorotetrahydro-1H-pyrrolo[1,2-a]pyrrol-7a(5H)-yl)methoxy)-19-hydroxy-14-oxa-5,6,16,21,23,25,29- | | Step 2. Intermediate VVVV Step 2_3. cis-3-amino-5-hydroxy-piperidine-1-carboxylic acid tert-butyl ester (CAS#: 1923165-22-3) | Step 2_1 was not performed. Step 2_2. Triethylamine and 4-nitrophenyl chloroformate (CAS#: 7693-46-1) was used. Step 3 was not performed. Step 4_2. BroP was used. Chiral separation performed after Step 4. Details included below. |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| | heptaazahexacyclo[24.3.1.1~17,21~.0~2,10~.0~3,7~.0~22,27~]hentriaconta-1(30),2,4,7,9,22,24,26,28-nonaen-15-one | | | |
| 285 | 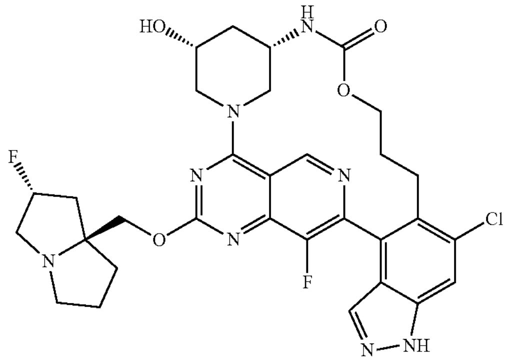 [SMILES: O=C1N[C@H]2C[C@@H](O)CN(C2)c2nc(OC[C@@]34CCCN3C[C@H](F)C4)nc3c(F)c(ncc23)-c2c(c(Cl)cc3[nH]ncc23)CCCO1] (17S,19R)-9-chloro-30-fluoro-24-(((2R,7aS)-2-fluorotetrahydro-1H-pyrrolo[1,2-a]pyrrol-7a(5H)-yl)methoxy)-19-hydroxy-14-oxa-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 2. Intermediate VVVV Step 2_3. cis-3-amino-5-hydroxy-piperidine-1-carboxylic acid tert-butyl ester (CAS#: 1923165-22-3) | Step 2_1 was not performed. Step 2_2. Triethylamine and 4-nitrophenyl chloroformate (CAS#: 7693-46-1) was used. Step 3 was not performed. Step 4_2. BroP was used. Chiral separation performed after Step 4. Details included below. |
| 286 | 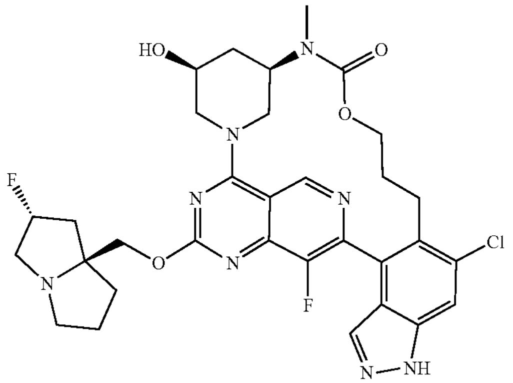 [SMILES: CN1C(=O)OCCCc2c(Cl)cc3[nH]ncc3c2-c2ncc3c(nc(OC[C@@]45CCCN4C[C@H](F)C5)nc3c2F)N2C[C@@H](O)C[C@@H]1C2] (17R,19S)-9-chloro-30-fluoro-24-(((2R,7aS)-2-fluorotetrahydro-1H-pyrrolo[1,2-a]pyrrol-7a(5H)-yl)methoxy)-19-hydroxy-16-methyl-14-oxa-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 2. Intermediate VVVV Step 2_3. Intermediate DC | Step 2_1 was not performed. Step 2_2. Triethylamine and 4-nitrophenyl chloroformate (CAS#: 7693-46-1) was used. Step 3 was not performed. Step 4_2. BroP was used. Chiral separation performed after Step 4. Details included below. |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| 287 | 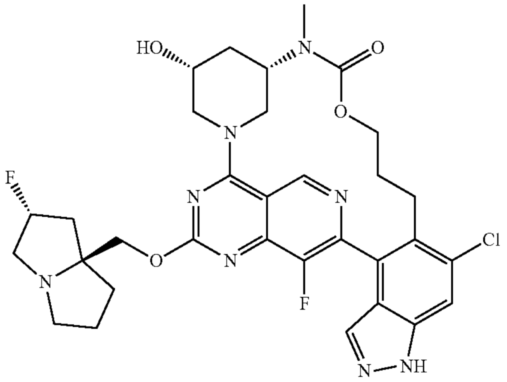 [SMILES: CN1C(=O)OCCCc2c(Cl)cc3[nH]ncc3c2-c2ncc3c(nc(OC[C@@]45CCCN4C[C@H](F)C5)nc3c2F)N2C[C@H](O)C[C@H]1C2] (17S,19R)-9-chloro-30-fluoro-24-(((2R,7aS)-2-fluorotetrahydro-1H-pyrrolo[1,2-a]pyrrol-7a(5H)-yl)methoxy)-19-hydroxy-16-methyl-14-oxa-5,6,16,21,23,25,29-heptaazahexacyclo[24.3.1.1~17,21~.0~2,10~.0~3,7~.0~22,27~]hentriaconta-1(30),2,4,7,9,22,24,26,28-nonaen-15-one | | Step 2. Intermediate VVVV Step 2_3. Intermediate DC | Step 2_1 was not performed. Step 2_2. Triethylamine and 4-nitrophenyl chloroformate (CAS#: 7693-46-1, Acros Organics) was used. Step 3 was not performed. Step 4_2. BroP was used. Chiral separation performed after Step 4. Details included below. |
| 288 | 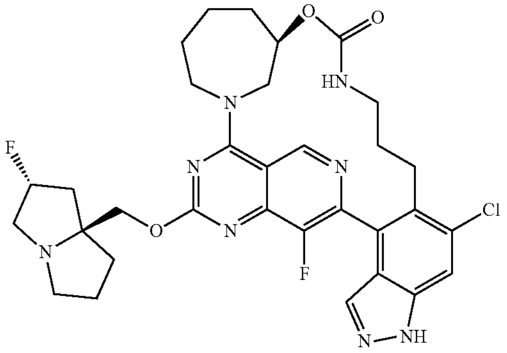 [SMILES: O=C1NCCCc2c(Cl)cc3[nH]ncc3c2-c2ncc3c(nc(OC[C@@]45CCCN4C[C@H](F)C5)nc3c2F)N2CCCC[C@H](C2)O1] (26R)-18-chloro-32-fluoro-4-(((2R,7aS)-2-fluorotetrahydro-1H-pyrrolo[1,2-a]pyrrol-7a(5H)-yl)methoxy)-25-oxa-1,3,5,9,14,15,23-heptaazahexacyclo[24.4.1.1~6,10~.0~2,7~.0~11,19~.0~12,16~]dotriaconta-2,4,6(32),7,9,11,13,16,18-nonaen-24-one | | Step 2. tert-butyl-(3R)-3-hydroxy-azepane-1-carboxylate (CAS#: 1493733-00-8) Step 2_3. Intermediate DE Step 3. Intermediate BX | Step 2_1 was not performed. Step 2_2. Triethylamine and 4-nitrophenyl chloroformate (CAS#: 7693-46-1, Acros Organics) was used. Step 4_2. BroP was used. |
| 289 | 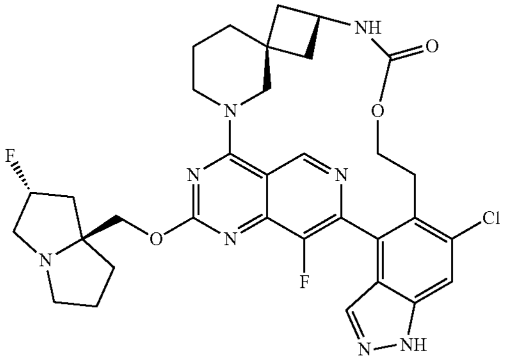 [SMILES: O=C1N[C@H]2C[C@@]3(CCCN(C3)c3nc(OC[C@@]45CCCN4C[C@H](F)C5)nc4c(F)c(ncc34)-c3c(c(Cl)cc4[nH]ncc34)CCO1)C2] 10-chloro-32-fluoro-24-(((2R,7aS)-2-fluorotetrahydro-1H-pyrrolo[1,2-a]pyrrol-7a(5H)-yl)methoxy)-6-oxa-4,13,14,19,23,25,27- | Bis (2,2,2-trifluoro-aceate) | Step 3. Intermediate DJ | Steps 1-2 were not performed. Step 4. BroP was used instead of PyBrOP. |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| | heptaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 290 | 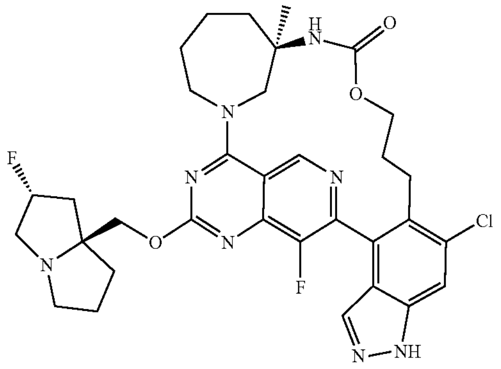 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCOC(=O)N2] (26R)-18-chloro-32-fluoro-4-(((2R,7aS)-2-fluorotetrahydro-1H-pyrrolo[1,2-a]pyrrol-7a(5H)-yl)methoxy)-26-methyl-23-oxa-1,3,5,9,14,15,25-heptaazahexacyclo[24.4.1.1~6,10~.0~2,7~.0~11,19~.0~12,16~]dotriaconta-2,4,6(32),7,9,11,13,16,18-nonaen-24-one | | Step 3. Intermediate DK and Intermediate JJ | Steps 1-2 were not performed. Step 4. BroP was used instead of PyBrOP. |
| 291 | 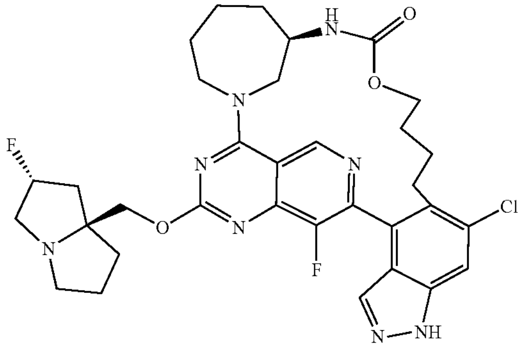 [SMILES: O=C1N[C@@H]2CCCCN(C2)c2nc(OC[C@@]34CCCN3C[C@H](F)C4)nc3c(F)c(ncc23)-c2c(c(Cl)cc3[nH]ncc23)CCCCO1] (27R)-18-chloro-33-fluoro-4-(((2R,7aS)-2-fluorotetrahydro-1H-pyrrolo[1,2-a]pyrrol-7a(5H)-yl)methoxy)-24-oxa-1,3,5,9,14,15,26-heptaazahexacyclo[25.4.1.1~6,10~.0~2,7~.0~11,19~.0~12,16~]tritriaconta-2,4,6(33),7,9,11,13,16,18-nonaen-25-one | | Step 3. Intermediate DL and Intermediate JJ | Steps 1-2 were not performed. Step 4. BroP was used instead of PyBrOP. |
| 292 | 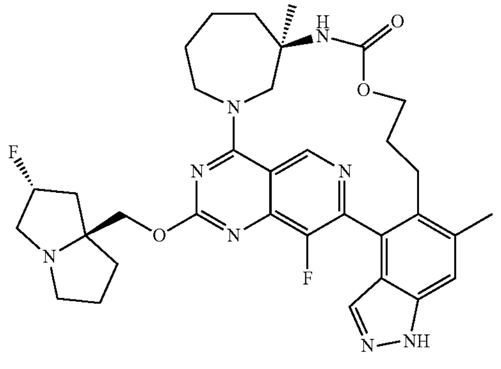 [SMILES: Cc1cc2[nH]ncc2c2c1CCCOC(=O)N[C@]1(C)CCCCN(C1)c1nc(OC[C@@]34CCCN3C[C@H](F)C4)nc3c(F)c-2ncc13] (26R)-32-fluoro-4-(((2R,7aS)-2-fluorotetrahydro-1H-pyrrolo[1,2-a]pyrrol- | | Step 3. Intermediate DM and Intermediate JJ | Steps 1-2 were not performed. Step 4. BroP was used instead of PyBrOP. Chiral separation performed after Step 4. Details included below. |

TABLE 22-continued

| Additional Examples 76 to 79, 176 to 178 and 282 to 302. Prepared in an Analogous Manner to Example 74. | | | | |
|---|---|---|---|---|
| Ex. # | Structure & Name | Salt Form | Reagent | Method Change |
| | 7a(5H)-yl)methoxy)-18,26-dimethyl-23-oxa-1,3,5,9,14,15,25-heptaazahexacyclo[24.4.1.1~6,10~.0~2,7~.0~11,19~.0~12,16~]dotriaconta-2,4,6(32),7,9,11,13,16,18-nonaen-24-one | | | |
| 293 | 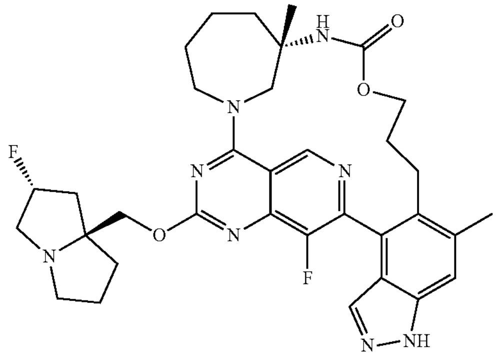 [SMILES: Cc1cc2[nH]ncc2c2c1CCCOC(=O)N[C@@]1(C)CCCCN(C1)c1nc(OC[C@@]34CCCN3C[C@H](F)C4)nc3c(F)c-2ncc13] (26S)-32-fluoro-4-(((2R,7aS)-2-fluorotetrahydro-1H-pyrrolo[1,2-a]pyrrol-7a(5H)-yl)methoxy)-18,26-dimethyl-23-oxa-1,3,5,9,14,15,25-heptaazahexacyclo[24.4.1.1~6,10~.0~2,7~.0~11,19~.0~12,16~]dotriaconta-2,4,6(32),7,9,11,13,16,18-nonaen-24-one | | Step 3. Intermediate DM and Intermediate JJ | Steps 1-2 were not performed. Step 4. BroP was used instead of PyBrOP. Chiral separation performed after Step 4. Details included below. |
| 294 | 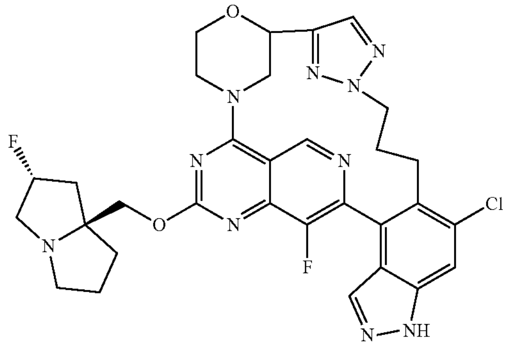 [SMILES: Fc1c2ncc3c(nc(OC[C@@]45CCCN4C[C@H](F)C5)nc13)N1CCOC(C1)c1cnn(n1)CCCc1c(Cl)cc3[nH]ncc3c1-2] 9-chloro-31-fluoro-25-(((2R,7aS)-2-fluorotetrahydro-1H-pyrrolo[1,2-a]pyrrol-7a(5H)-yl)methoxy)-19-oxa-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene | bis(2,2,2-trifluoro-acetate) | Step 2_2. Intermediate VVVV and Intermediate DF | Step 2_1 was not performed. Step 2_2. $PPh_3$, DIAD in THF were used instead of CDI in DCM:DMF (5:1). |
| 295 | 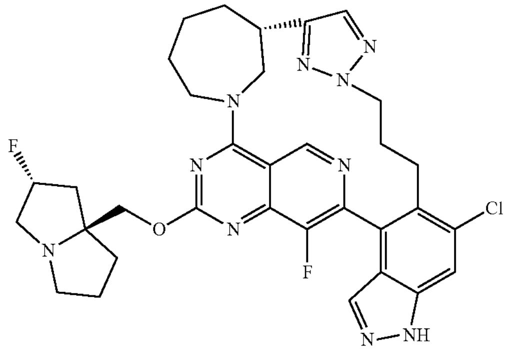 [SMILES: Fc1c2ncc3c(nc(OC[C@@]45CCCN4C[C@H](F)C5)nc13)N1CCCC[C@@H](C1)c1cnn(n1)CCCc1c(Cl)cc3[nH]ncc3c1-2] | bis(2,2,2-trifluoro-acetate) | Step 2_2. Intermediate VVVV and Intermediate DG | Step 2_1 was not performed. Step 2_2. $PPh_3$, DIAD in THF were used instead of CDI in DCM:DMF (5:1). |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| | (1S)-10-chloro-33-fluoro-24-(((2R,7aS)-2-fluorotetrahydro-1H-pyrrolo[1,2-a]pyrrol-7a(5H)-yl)methoxy)-4,5,13,14,19,23,25,27,34-nonaazaheptacyclo[25.4.1.1~2,5~.1~18,22~.0~9,17~.0~12,16~.0~21,26~]tetratriaconta-2(34),3,9,11,14,16,18(33),19,21,23,25-undecaene | | | |
| 296 | 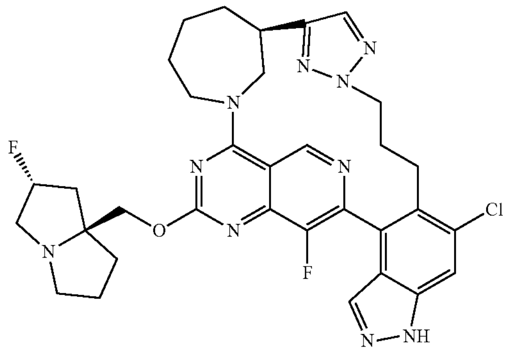 [SMILES: Fc1c2ncc3c(nc(OC[C@@]45CCCN4C[C@H](F)C5)nc13)N1CCCC[C@H](C1)c1cnn(n1)CCCc1c(Cl)cc3[nH]ncc3c1-2] (1R)-10-chloro-33-fluoro-24-(((2R,7aS)-2-fluorotetrahydro-1H-pyrrolo[1,2-a]pyrrol-7a(5H)-yl)methoxy)-4,5,13,14,19,23,25,27,34-nonaazaheptacyclo[25.4.1.1~2,5~.1~18,22~.0~9,17~.0~12,16~.0~21,26~]tetratriaconta-2(34),3,9,11,14,16,18(33),19,21,23,25-undecaene | bis(2, 2,2 trifluoro-acetate) | Step 2_2. Intermediate VVVV and Intermediate DG | Step 2_1 was not performed. Step 2_2. $PPh_3$, DIAD in THF were used instead of CDI in DCM:DMF (5:1). |
| 297 | 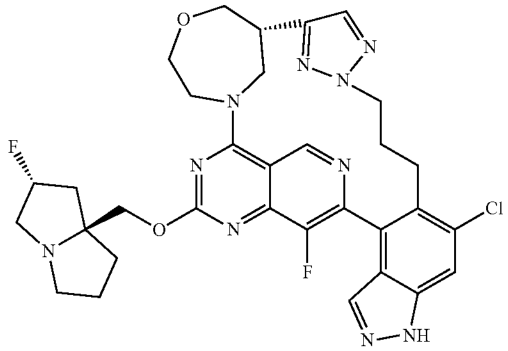 [SMILES: Fc1c2ncc3c(nc(OC[C@@]45CCCN4C[C@H](F)C5)nc13)N1CCOC[C@@H](C1)c1cnn(n1)CCCc1c(Cl)cc3[nH]ncc3c1-2] (1S)-10-chloro-33-fluoro-24-(((2R,7aS)-2-fluorotetrahydro-1H-pyrrolo[1,2-a]pyrrol-7a(5H)-yl)methoxy)-30-oxa-4,5,13,14,19,23,25,27,34-nonaazaheptacyclo[25.4.1.1~2,5~.1~18,22~.0~9,17~.0~12,16~.0~21,26~]tetratriaconta-2(34),3,9,11,14,16,18(33),19,21,23,25-undecaene | | Step 2_2. Intermediate VVVV and Intermediate DH | Step 2_1 was not performed. Step 2_2. $PPh_3$, DIAD in THF were used instead of CDI in DCM:DMF (5:1). |

TABLE 22-continued

Additional Examples 76 to 79, 176 to 178 and 282 to 302. Prepared in an Analogous Manner to Example 74.

| Ex. # | Structure & Name | Salt Form | Reagent | Method Change |
|---|---|---|---|---|
| 298 | 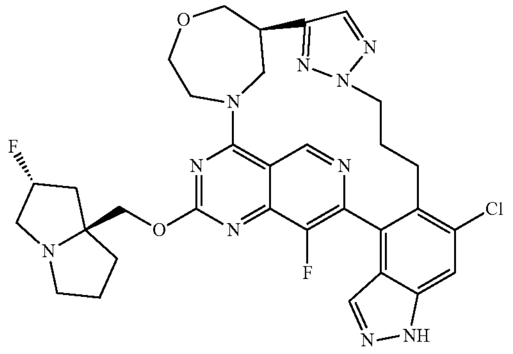 [SMILES: Fc1c2ncc3c(nc(OC[C@@]45CCCN4C[C@H](F)C5)nc13)N1CCOC[C@H](C1)c1cnn(n1)CCCc1c(Cl)cc3[nH]ncc3c1-2] (1R)-10-chloro-33-fluoro-24-(((2R,7aS)-2-fluorotetrahydro-1H-pyrrolo[1,2-a]pyrrol-7a(5H)-yl)methoxy)-30-oxa-4,5,13,14,19,23,25,27,34-nonaazaheptacyclo[25.4.1.1~2,5~.1~18,22~.0~9,17~.0~12,16~.0~21,26~]tetratriaconta-2(34),3,9,11,14,16,18(33),19,21,23,25-undecaene | | Step 2_2. Intermediate VVVV and Intermediate DH | Step 2_1 was not performed. Step 2_2. $PPh_3$, DIAD in THF were used instead of CDI in DCM:DMF (5:1). |
| 299 | 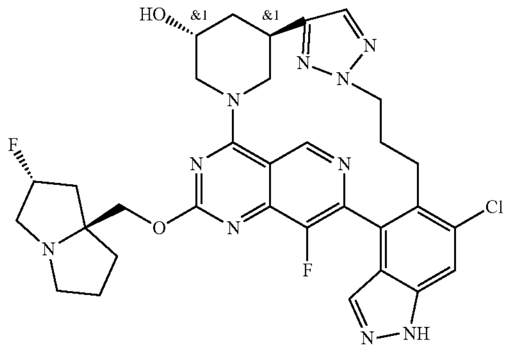 [SMILES: O[C@@H]1C[C@@H]2CN(C1)c1nc(OC[C@@]34CCCN3C[C@H](F)C4)nc3c(F)c(ncc13)-c1c(c(Cl)cc3[nH]ncc13)CCCn1ncc2n1] (18R,20R)-rel-9-chloro-31-fluoro-25-(((2R,7aS)-2-fluorotetrahydro-1H-pyrrolo[1,2-a]pyrrol-7a(5H)-yl)methoxy)-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaen-20-ol | | Step 2_2. Intermediate VVVV and Intermediate DI | Step 2_1 was not performed. Step 2_2. $PPh_3$, DIAD in THF were used instead of CDI in DCM:DMF (5:1). Step 5. TMAF in THF and $CH_3CN$ was used, |
| 300 | 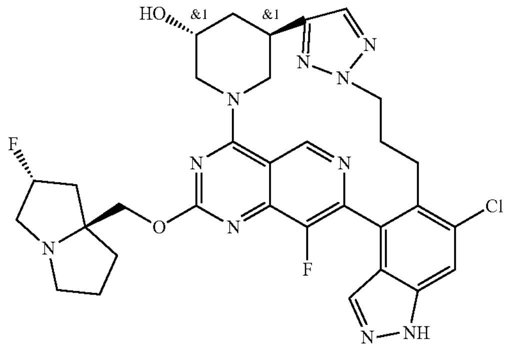 [SMILES: O[C@@H]1C[C@@H]2CN(C1)c1nc(OC[C@@]34CCCN3C[C@H](F)C4)nc3c(F)c(ncc13)-c1c(c(Cl)cc3[nH]ncc13)CCCn1ncc2n1] (18R,20S)-rel-9-chloro-31-fluoro-25-(((2R,7aS)-2-fluorotetrahydro-1H-pyrrolo[1,2-a]pyrrol-7a(5H)-yl)methoxy)- | | Step 2_2. Intermediate VVVV and Intermediate DI | Step 2_1 was not performed. Step 2_2. $PPh_3$, DIAD in THF were used instead of CDI in DCM:DMF (5:1). Step 5. TMAF in THF and $CH_3CN$ was used, |

TABLE 22-continued

| Additional Examples 76 to 79, 176 to 178 and 282 to 302. Prepared in an Analogous Manner to Example 74. | | | | |
|---|---|---|---|---|
| Ex. # | Structure & Name | Salt Form | Reagent | Method Change |
| | 5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaen-20-ol | | | |
| 301 | 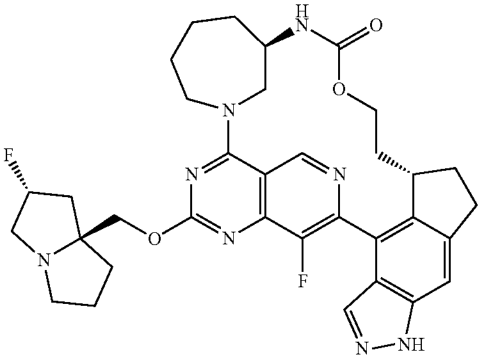 [SMILES: O=C1N[C@@H]2CCCCN(C2)c2nc(OC[C@@]34CCCN3C[C@H](F)C4)nc3c(F)c(ncc23)-c2c3c(cc4[nH]ncc24)CC[C@H]3CCO1] (16R,22S)-34-fluoro-8-(((2R,7aS)-2-fluorotetrahydro-1H-pyrrolo[1,2-a]pyrrol-7a(5H)-yl)methoxy)-19-oxa-3,7,9,11,17,28,29-heptaazaheptacyclo[20.9.1.1~2,6~.1~11,16~.0~5,10~.0~25,32~.0~27,31~]tetratriaconta-1(31),2(34),3,5,7,9,25(32),26,29-nonaen-18-one | | Step 2_2. 2-(7-bromo-5-fluoro-2,3-dihydro-1H-inden-1-yl)ethan-1-ol (Step 3_1 of Intermediate RRR) Step 2_3. tert-butyl (R)-3-aminoazepane-1-carboxylate (CAS#: 1032684-85-7, Combi-Blocks) was used | Chiral separation after Step 4. Details included below. |
| 302 | 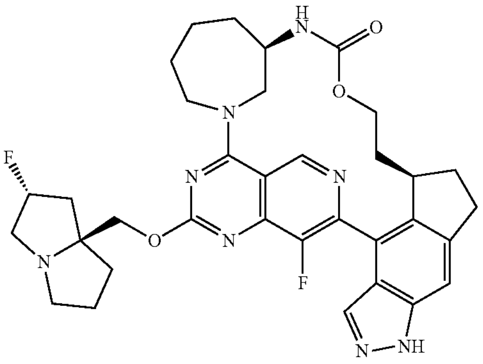 [SMILES: O=C1N[C@@H]2CCCCN(C2)c2nc(OC[C@@]34CCCN3C[C@H](F)C4)nc3c(F)c(ncc23)-c2c3c(cc4[nH]ncc24)CC[C@@H]3CCO1] (16R,22R)-34-fluoro-8-(((2R,7aS)-2-fluorotetrahydro-1H-pyrrolo[1,2-a]pyrrol-7a(5H)-yl)methoxy)-19-oxa-3,7,9,11,17,28,29-heptaazaheptacyclo[20.9.1.1~2,6~.1~11,16~.0~5,10~.0~25,32~.0~27,31~]tetratriaconta-1(31),2(34),3,5,7,9,25(32),26,29-nonaen-18-one | | Step 2_2. 2-(7-bromo-5-fluoro-2,3-dihydro-1H-inden-1-yl)ethan-1-ol (Step 3_1 of Intermediate RRR) Step 2_3. tert-butyl (R)-3-aminoazepane-1-carboxylate (CAS#: 1032684-85-7, Combi-Blocks) was used | Chiral separation after Step 4. Details included below. |

TABLE 23

Conditions for Chiral SFC Separation.

| Separation | SFC Conditions | Peak to Ex# |
|---|---|---|
| 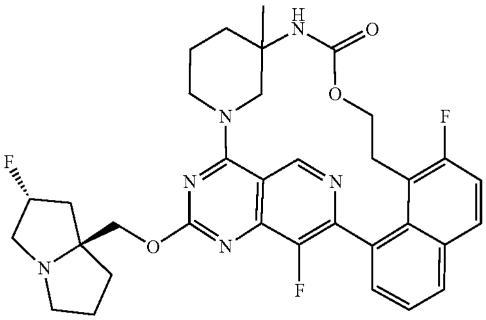 [SMILES: CC12CCCN(C1)c1nc(OC[C@@]34CCCN3C[C@H](F)C4)nc3c(F)c(ncc13)-c1cccc3ccc(F)c(c13)CCOC(=O)N2] | Column: ChiralPak IG-3 (4.6 x 50 cm, 3 μm)<br>Mobile phase: EtOH with 0.2% (7 M) $NH_3$ in MeOH<br>Flowrate: 4 mL/min.<br>Yield: 50 mg sample was submitted to generate 23 mg of peak 1 with an ee of 99% and 14 mg of peak 2 with an ee of 99%. | Peak 1:<br>Ex. 77<br>Peak 2:<br>Ex. 78 |
| 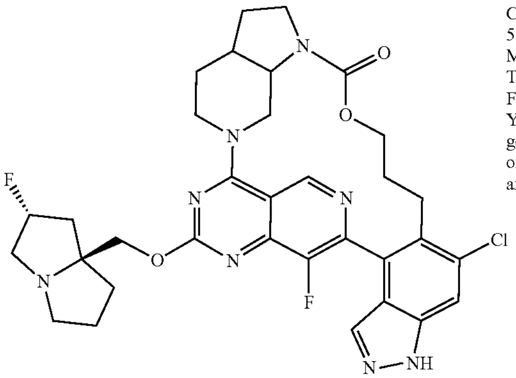 | Column: Chiralcel OX, (21 x 250 mm, 5 μm)<br>Mobile phase: 50% MeOH with 0.2% TEA<br>Flowrate: 80 mL/min<br>Yield: 63 mg sample was submitted to generate 11.1 mg of peak 1 with an ee of >96% and 12.2 mg of peak 2 with an ee of >96%. | Peak 1:<br>Example 177<br>Peak 2:<br>Example 176 |
| 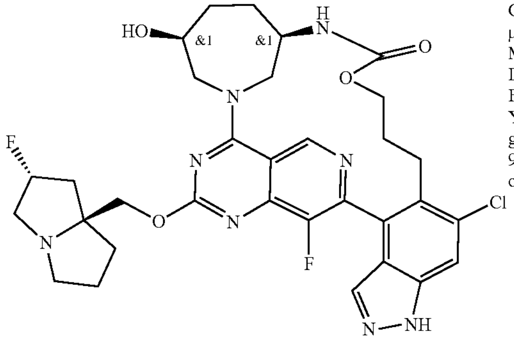 | Column: (S,S) Whelk-0 (2 x 15 cm, 5 μm)<br>Mobile phase: 50% MeOH w/ 0.2% DEA<br>Flowrate: 80 mL/min.<br>Yield: 90 mg sample was submitted to generate 27 mg of peak 1 with an ee of 99% and 26.3 mg of peak 2 with an ee of 98%. | Peak 1:<br>Example<br>283<br>Peak 1:<br>Example<br>282 |
| 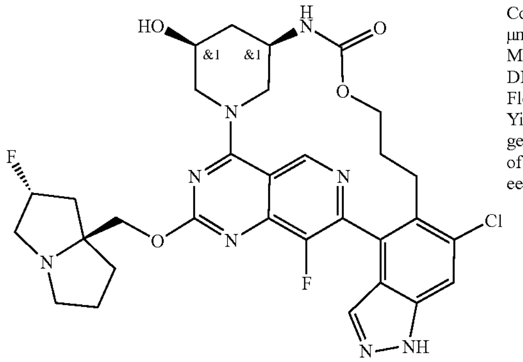 | Column: ChiralPak IC (2 x 25 cm, 5 μm)<br>Mobile phase: 55% MeOH w/ 0.2% DEA<br>Flowrate: 80 mL/min.<br>Yield: 99 mg sample was submitted to generate 27.3 mg of peak 1 with an ee of 99% and 20.5 mg of peak 2 with an ee of 99%. | Peak 1:<br>Example<br>285<br>Peak 1:<br>Example<br>284 |

TABLE 23-continued

Conditions for Chiral SFC Separation.

| Separation | SFC Conditions | Peak to Ex# |
|---|---|---|
| 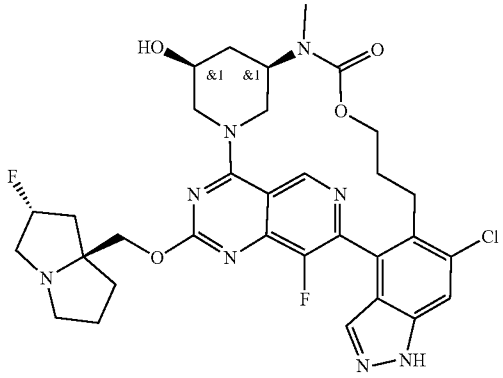 [SMILES: CN1C(=O)OCCCc2c(Cl)cc3[nH]ncc3c2-c2ncc3c(nc(OC[C@@]45CCCN4C[C@H](F)C5)nc3c2F)N2C[C@@H](O)C[C@@H]1C2] | Column: (S,S) Whelk-0 (2 x 25 cm, 5 μm)<br>Mobile phase: 50% MeOH w/ 0.2% DEA<br>Flowrate: 80 mL/min.<br>Yield: 55 mg sample was submitted to generate 9.9 mg of peak 1 with an ee of 99% and 9.2 mg of peak 2 with an ee of 98%. | Peak 1:<br>Example 286<br>Peak 1:<br>Example 287 |
| 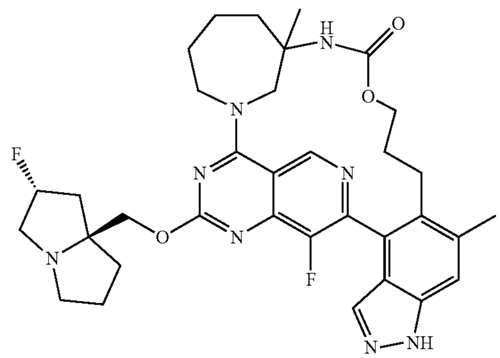 [SMILES: Cc1cc2[nH]ncc2c2c1CCCOC(=O)NC1(C)CCCCN(C1)c1nc(OC[C@@]34CCCN3C[C@H](F)C4)nc3c(F)c-2ncc13] | Column: (S,S) Whelk-0,2 x 15 cm 5 μm column Mobile phase: 50% MeOH with 0.2% DEA<br>Flowrate: 120 mL/min.<br>Yield: 11 mg sample was submitted to generate 4 mg of peak 1 with an ee of >99% and 4 mg of peak 2 with an ee of 99%. | Peak 1/2:<br>Example 292<br>Peak 2:<br>Example 293 |
| 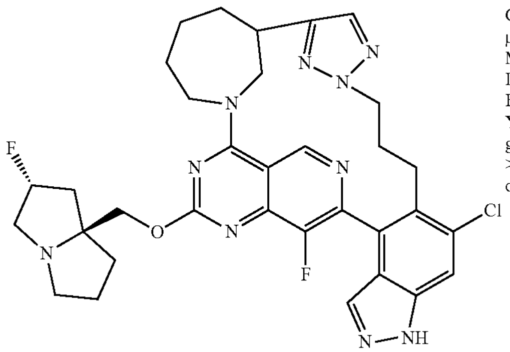 | Column: Chiralcel OD (2 x 15 cm, 5 μm)<br>Mobile phase: 40% MeOH with 0.2% DEA<br>Flowrate: 80 mL/min.<br>Yield: 15 mg sample was submitted to generate 3 mg of peak 1 with an ee of >99% and 4 mg of peak 2 with an ee of 99%. | Peak 1:<br>Example 295<br>Peak 2:<br>Example 296 |
| 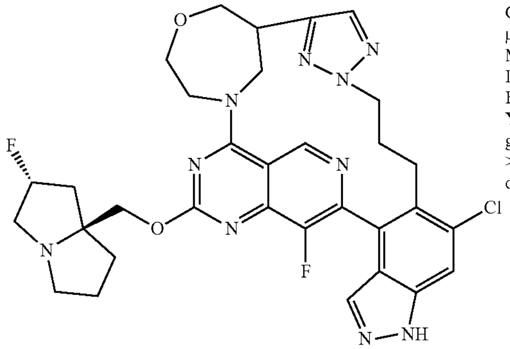 | Column: Chiralcel OD (2 x 15 cm, 5 μm)<br>Mobile phase: 40% MeOH with 0.2% DEA<br>Flowrate: 120 mL/min.<br>Yield: 72 mg sample was submitted to generate 31 mg of peak 1 with an ee of >99% and 31 mg of peak 2 with an ee of 98.9%. | Peak 1:<br>Example 297<br>Peak 2:<br>Example 298 |

TABLE 23-continued

Conditions for Chiral SFC Separation.

| Separation | SFC Conditions | Peak to Ex# |
|---|---|---|
| 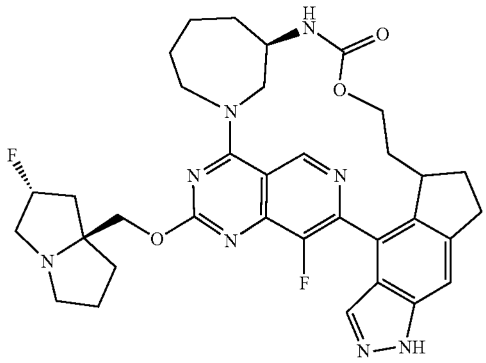 [SMILES: O=C1N[C@@H]2CCCCN(C2)c2nc(OC[C@@]34CCCN3C[C@H](F)C4)nc3c(F)c(ncc23)-c2c3c(cc4[nH]ncc24)CCC3CCO1] | Column: Daicel Chiralcel OD (3 x 25 cm, 10 μm) Mobile phase: EtOH (0.1% $NH_3$•$H_2O$) Yield: 19 mg peak 1 with an ee of 100% and 18 mg peak 2 with an ee of 100%. | Peak 1: Example 302 Peak 2: Example 301 |

TABLE 24

Analytical Data for Examples 76 to 79, 176 to 178 and 282 to 302.

| Cmpd. # | MS m/z (ESI): $(M + H)^+$ | $^1H$ NMR |
|---|---|---|
| 76 | 633.2 | $^1H$ NMR (400 MHz, DMSO-$d_6$) δ ppm 9.19 (s, 1 H), 7.99-8.20 (m, 2 H), 7.57-7.84 (m, 2 H), 7.48 (t, J = 9.6 Hz, 1 H), 6.40-6.71 (m, 1 H), 5.07-5.42 (m, 2 H), 4.79-5.00 (m, 1 H), 4.03-4.23 (m, 2 H), 3.80-3.86 (m, 1 H), 3.46-3.61 (m, 2 H), 3.09-3.22 (m, 2 H), 2.96-3.03 (m, 2 H), 2.82-2.89 (m, 1 H), 2.16-2.36 (m, 2 H), 1.95-2.15 (m, 4 H), 1.76-1.92 (m, 4 H), 1.55-1.72 (m, 1 H), 1.53 (d, J = 13.9 Hz, 1 H), 1.26 (s, 3 H). |
| 77 | 633.2 | $^1H$ NMR (400 MHz, DMSO-$d_6$) δ ppm 9.19 (s, 1 H), 8.15 (d, J = 7.9 Hz, 1 H), 8.07 (dd, J = 6.4, 8.9 Hz, 1 H), 7.75 (d, J = 6.6 Hz, 1 H), 7.63-7.69 (m, 1 H), 7.45 (t, J = 9.5 Hz, 1H), 6.47-6.72 (m, 1 H), 5.15-5.39 (m, 2 H), 4.85-4.90 (m, 1 H), 4.20 (d, J = 10.4 Hz, 1 H), 4.06 (d, J = 10.5 Hz, 1 H), 3.78-3.93 (m, 1 H), 3.49-3.60 (m, 2 H), 3.09-3.21 (m, 2 H), 2.95-3.04 (m, 2 H), 2.82-2.89 (m, 1 H), 2.11-2.28 (m, 2 H), 1.98-2.10 (m, 4 H), 1.76-1.92 (m, 4 H), 1.65-1.75 (m, 1 H), 1.45-i 1.55 (m, 1 H), 1.26 (s, 3 H). |
| 78 | 633.2 | $^1H$ NMR (400 MHz, DMSO-$d_6$) δ ppm 9.20 (s, 1 H), 8.16 (d, J = 8.10 Hz, 1 H), 8.08 (dd, J = 6.4, 8.8 Hz, 1 H), 7.63-7.80 (m, 2 H), 7.46 (t, J = 9.40 Hz, 1 H), 6.42-6.62 (s, 1 H), 5.14-5.41 (m, 2 H), 4.83-5.01 (m, 1 H), 4.04-4.23 (m, 2 H), 3.78-3.96 (m, 1 H), 3.48-3.63 (m, 2 H), 3.09-3.22 (m, 2 H), 2.92-3.06 (m, 2 H), 2.82-2.91 (m, 1 H), 2.11-2.30 (m, 2 H), 2.00-2.10 (m, 4 H), 1.76-1.92 (m, 4 H), 1.66-1.74 (m, 1 H), 1.45-1.55 (m, 1 H), 1.27 (s, 3 H). |
| 79 | 640.2 | $^1H$ NMR (400 MHz, METHANOL-$d_4$) δ ppm 9.24 (s, 1 H), 7.84 (s, 1 H), 7.79-7.83 (m, 1 H), 5.45-5.66 (m, 1 H), 4.88-5.15 (m, 2 H), 4.72 (br d, J = 12.1 Hz, 2 H), 4.59-4.68 (m, 1 H), 4.20-4.38 (m, 2 H), 4.06-4.17 (m, 1 H), 3.94-4.04 (m, 1 H), 3.77-3.93 (m, 5 H), 3.70 (br s, 1 H), 3.52 (br d, J = 3.8 Hz, 1 H), 2.83 (s, 1 H), 2.65 (s, 1 H), 2.51-2.61 (m, 1 H), 2.27-2.46 (m, 5 H), 2.21 (br dd, J = 16.4, 11.6 Hz, 2 H), 1.67-1.81 (m, 2 H). $^{19}F$ NMR (376 MHz, METHANOL-$d_4$) δ ppm −142.22 (s), −174.02 (s). |
| 176 | 665.2 | $^1H$ NMR (400 MHz, DMSO-$d_6$) δ ppm 8.35-8.60 (m, 1 H), 6.86-7.23 (m, 2 H), 4.36-4.66 (m, 2 H), 4.03-4.27 (m, 1 H), 3.43-3.63 (m, 2 H), 3.30 (br d, J = 2.3 Hz, 1 H), 2.92-3.12 (m, 2 H), 2.77-2.89 (m, 1 H), 2.64-2.76 (m, 1 H), 2.36-2.49 (m, 4 H), 2.18-2.35 (m, 2 H), 2.04-2.17 (m, 1 H), 1.86 (br d, J = 7.1 Hz, 2 H), 1.63-1.77 (m, 1 H), 1.29-1.61 (m, 4 H), 1.17-1.26 (m, 2 H), 1.09-1.17 (m, 3 H), 0.96-1.04 (m, 1 H), 0.80-0.92 (m, 1 H), 0.68 (br d, J = 3.6 Hz, 1 H). $^{19}F$ NMR (DMSO-$d_6$, 376 MHz) δ −144.75, −174.42. |
| 177 | 665.2 | $^1H$ NMR (400 MHz, METHANOL-$d_4$) δ ppm 9.16-9.36 (m, 1 H), 7.75-8.01 (m, 2 H), 5.23-5.46 (m, 2 H), 4.92-5.07 (m, 1 H), 4.25-4.40 (m, 2 H), 4.05-4.15 (m, 1 H), 3.77-3.93 (m, 2 H), 3.56-3.69 (m, 1 H), 3.46-3.54 (m, 1 H), 3.20-3.27 (m, 2 H), 3.00-3.13 (m, 2 H), 2.87-2.99 (m, 1 H), 2.61-2.75 (m, 2 H), 2.52 (br dd, J = 6.9, 2.7 Hz, 1 H), 2.32-2.41 (m, 1 H), 2.21-2.30 (m, 2 H), 2.11-2.19 (m, 1 H), 1.94-2.07 (m, 4 H), 1.89-1.92 (m, 1 H), 1.75-1.89 (m, 2 H), 1.60-1.74 (m, 1 H), 1.43-1.53 (m, 1 H), 1.30-1.38 (m, 1 H). $^{19}F$ NMR (376 MHz, METHANOL-$d_4$) δ ppm −143.95, −173.71. |
| 178 | 669.2 | $^1H$ NMR (400 MHz, DMSO-$d_6$) δ ppm 13.31 (br s, 1 H), 9.33-9.74 (m, 1 H), 7.67-7.98 (m, 2 H), 5.14-5.42 (m, 1 H), 4.90 (br dd, J = 15.6, 5.5 Hz, 1 H), 4.57-4.71 (m, 1 H), 4.28-4.42 (m, 1 H), 3.99-4.25 (m, 4 H), |

TABLE 24-continued

Analytical Data for Examples 76 to 79, 176 to 178 and 282 to 302.

| Cmpd. # | MS m/z (ESI): $(M + H)^+$ | $^1H$ NMR |
|---|---|---|
| | | 3.72-3.99 (m, 4 H), 3.44-3.66 (m, 2 H), 3.04-3.19 (m, 3 H), 2.76-2.93 (m, 4 H), 2.60-2.72 (m, 1 H), 2.25-2.39 (m, 1 H), 2.08-2.19 (m, 2 H), 1.98-2.06 (m, 1 H), 1.65-1.95 (m, 5 H). $^{19}F$ NMR (376 MHz, DMSO-$d_6$) δ ppm −141.73, −172.14. |
| 282 | 669.0 | 1H NMR (400 MHz, METHANOL-d4) δ ppm 9.37 (s, 1 H), 7.81 (s, 1 H), 7.77 (s, 1 H), 5.23-5.45 (m, 2 H), 4.59 (br d, J = 15.0 Hz, 1 H), 4.40 (d, J = 10.9 Hz, 1 H), 4.29 (d, J = 10.7 Hz, 1 H), 4.18 (br d, J = 3.8 Hz, 1 H), 3.89-3.97 (m, 1 H), 3.73-3.81 (m, 1 H), 3.63-3.72 (m, 2 H), 3.54-3.63 (m, 1 H), 3.19-3.30 (m, 2 H), 3.03-3.12 (m, 1 H), 2.89-3.01 (m, 1 H), 2.58-2.69 (m, 1 H), 2.28-2.45 (m, 1 H), 2.07-2.26 (m, 2 H), 1.97-2.06 (m, 2 H), 1.89-1.97 (m, 1 H), 1.78-1.88 (m, 4 H), 1.65-1.76 (m, 2 H), 1.31 (br s, 3 H), 0.85-0.97 (m, 1 H). $^{19}F$ NMR (376 MHz, METHANOL-d4) δ ppm −141.52 (s), −173.33 (s). |
| 283 | 669.0 | $^1H$ NMR (400 MHz, METHANOL-$d_4$) δ 9.38 (s, 1H), 7.81 (s, 1H), 7.77 (s, 1H), 5.47-5.22 (m, 2H), 4.61 (br d, J = 15.0 Hz, 1H), 4.49-4.24 (m, 2H), 4.18 (br d, J = 3.8 Hz, 1H), 3.93 (dt, J = 11.0, 5.3 Hz, 1H), 3.82-3.73 (m, 1H), 3.71-3.61 (m, 2H), 3.61-3.52 (m, 1H), 3.30-3.18 (m, 2H), 3.12-3.00 (m, 1H), 2.98-2.88 (m, 1H), 2.71-2.57 (m, 1H), 2.37-2.12 (m, 3H), 2.02 (br dd, J = 11.0, 5.5 Hz, 4H), 1.88-1.79 (m, 5H), 1.79-1.62 (m, 4H). $^{19}F$ NMR (376 MHz, METHANOL-d4) δ ppm −141.52 (s), −173.54 (s). |
| 284 | 655.0 | $^1H$ NMR (400 MHz, METHANOL-$d_4$) δ 9.34 (s, 1H), 7.84 (s, 1H), 7.80 (s, 1H), 5.63 (br d, J = 14.0 Hz, 1H), 5.46-5.29 (m, 2H), 5.23-5.13 (m, 2H), 4.60-4.51 (m, 5H), 4.23 (br s, 2H), 4.08-3.80 (m, 2H), 3.19-3.05 (m, 2H), 2.92-2.74 (m, 1H), 2.58-2.06 (m, 9H), 1.99-1.82 (m, 4H). $^{19}F$ NMR (376 MHz, METHANOL-d4) δ ppm −141.94 (br s), −173.82 (s). |
| 285 | 655.2 | $^1H$ NMR (400 MHz, METHANOL-$d_4$) δ 9.33 (s, 1H), 7.84 (s, 1H), 7.79 (s, 1H), 5.74-5.59 (m, 1H), 5.46-5.26 (m, 2H), 5.16 (br d, J = 14.2 Hz, 1H), 4.59 (br d, J = 10.9 Hz, 1H), 4.28-4.18 (m, 3H), 3.99-3.78 (m, 2H), 3.63-3.46 (m, 2H), 3.18-3.00 (m, 2H), 2.85-2.71 (m, 1H), 2.61-2.48 (m, 1H), 2.45-1.80 (m, 12H), 1.67 (br dd, J = 6.5, 2.7 Hz, 2H). $^{19}F$ NMR (376 MHz, METHANOL-d4) δ ppm −141.90 (s), −173.12 (s). |
| 286 | 668.8 | $^1H$ NMR (600 MHz, DMSO-$d_6$) δ 9.33 (s, 1H), 7.98 (s, 1H), 7.81 (s, 1H), 5.40-5.19 (m, 2H), 4.81-4.68 (m, 1H), 4.54-4.42 (m, 2H), 4.20-4.07 (m, 3H), 3.73-3.62 (m, 2H), 3.43-3.35 (m, 4H), 3.15-3.02 (m, 3H), 2.96-2.81 (m, 3H), 2.78 (s, 2H), 2.51-2.48 (m, 1H), 2.16-2.00 (m, 4H), 1.87-1.71 (m, 5H). |
| 287 | 668.8 | $^1H$ NMR (600 MHz, DMSO-$d_6$) δ 9.33 (s, 1H), 7.99 (s, 1H), 7.80 (s, 1H), 5.42-5.21 (m, 2H), 4.81-4.69 (m, 1H), 4.54-4.42 (m, 2H), 4.31-4.03 (m, 3H), 3.75-3.62 (m, 2H), 3.51-3.42 (m, 1H), 3.15-3.02 (m, 2H), 2.98-2.82 (m, 4H), 2.78 (s, 2H), 2.23-1.71 (m, 11H), 1.44-1.37 (m, 2H). |
| 288 | 653.2 | $^1H$ NMR (400 MHz, METHANOL-$d_4$) δ 9.42 (s, 1H), 7.80 (s, 1H), 7.70 (s, 1H), 5.73-5.50 (m, 2H), 4.98-4.89 (m, 1H), 4.72 (d, J = 3.1 Hz, 2H), 4.14-3.81 (m, 4H), 3.67-3.39 (m, 2H), 3.29-3.20 (m, 1H), 2.92-2.74 (m, 2H), 2.72-2.57 (m, 3H), 2.52-2.32 (m, 6H), 2.28-2.11 (m, 1H), 2.08-1.99 (m, 1H), 1.94-1.87 (m, 1H), 1.84-1.54 (m, 6H). $^{19}F$ NMR (376 MHz, METHANOL-$d_4$) δ ppm −77.35 (br s), −141.97 (s), −174.07 (s). |
| 289 | 665.2 | $^1H$ NMR (400 MHz, METHANOL-$d_4$) δ 9.28 (s, 1H), 7.88 (s, 1H), 7.81 (s, 1H), 5.71-5.50 (m, 1H), 5.25 (br d, J = 13.6 Hz, 1H), 4.93 (br d, J = 12.3 Hz, 1H), 4.75-4.65 (m, 3H), 4.57 (dt, J = 10.9, 5.0 Hz, 1H), 4.11-3.79 (m, 5H), 3.73 (br d, J = 13.2 Hz, 1H), 3.59 (br t, J = 8.2 Hz, 1H), 3.54-3.44 (m, 1H), 3.29-3.12 (m, 2H), 2.75 (br dd, J = 19.8, 4.5 Hz, 2H), 2.69-2.57 (m, 2H), 2.52-2.32 (m, 4H), 2.27-2.17 (m, 1H), 2.17-2.03 (m, 2H), 1.91-1.75 (m, 4H). $^{19}F$ NMR (376 MHz, METHANOL-d4) δ ppm −77.43 (s), −142.97 (br d, J = 19.9 Hz), −174.15–−173.98 (m). |
| 290 | 667.2 | $^1H$ NMR (METHANOL-$d_4$, 500 MHz) δ 9.32 (s, 1H), 7.82 (d, 2H, J = 2.6 Hz), 5.66 (br d, 1H, J = 16.5 Hz), 5.2-5.4 (m, 1H), 4.7-4.8 (m, 1H), 4.3-4.4 (m, 2H), 3.6-3.7 (m, 1H), 3.5-3.5 (m, 1H), 3.4-3.4 (m, 1H), 3.2-3.3 (m, 2H), 2.9-3.1 (m, 2H), 2.6-2.7 (m, 1H), 2.1-2.4 (m, 4H), 1.8-2.1 (m, 8H), 1.6-1.7 (m, 2H), 1.2-1.4 (m, 5H). 2H not observed. |
| 291 | 667.2 | $^1H$ NMR (METHANOL-$d_4$, 400 MHz) δ 9.43 (s, 1H), 7.80 (s, 1H), 7.63 (s, 1H), 5.4-5.6 (m, 1H), 5.3-5.4 (m, 1H), 4.50 (br d, 4H, J = 11.5 Hz), 3.8-3.9 (m, 2H), 3.5-3.7 (m, 2H), 3.50 (br s, 2H), 3.1-3.2 (m, 2H), 2.7-2.8 (m, 1H), 2.5-2.7 (m, 1H), 2.35 (br d, 2H, J = 14.2 Hz), 2.2-2.3 (m, 1H), 2.1-2.2 (m, 2H), 2.0-2.1 (m, 2H), 1.8-2.0 (m, 2H), 1.73 (br d, 2H, J = 9.8 Hz), 1.6-1.7 (m, 2H), 1.3-1.4 (m, 4H). |

TABLE 24-continued

Analytical Data for Examples 76 to 79, 176 to 178 and 282 to 302.

| Cmpd. # | MS m/z (ESI): $(M + H)^+$ | $^1H$ NMR |
|---|---|---|
| 292 | 647.3 | $^1H$ NMR (400 MHz, DMSO-$d_6$) δ ppm 12.97 (br s, 1H), 9.28 (s, 1H), 7.56 (s, 1H), 7.48 (s, 1H), 6.57 (s, 1H), 5.52 (br d, J = 16.5 Hz, 1H), 4.52 (br d, J = 8.6 Hz, 1H), 4.22-4.15 (m, 1H), 4.10-4.03 (m, 1H), 3.75-3.64 (m, 1H), 3.41-3.35 (m, 2H), 3.24-3.08 (m, 4H), 3.04 (br s, 1H), 2.92-2.79 (m, 1H), 2.68-2.59 (m, 1H), 2.22-1.96 (m, 5H), 1.92-1.66 (m, 8H), 1.45 (br s, 3H), 1.27 (s, 5H). $^{19}F$ NMR (376 MHz, DMSO-$d_6$) δ ppm −142.53 (s, 1F), −172.10-−172.41 (m, 1F). |
| 293 | 647.3 | $^1H$ NMR (400 MHz, DMSO-$d_6$) δ ppm 12.97 (br s, 1H), 9.28 (s, 1H), 7.56 (s, 1H), 7.48 (s, 1H), 6.57 (s, 1H), 5.52 (br d, J = 16.3 Hz, 1H), 4.53 (br d, J = 9.8 Hz, 1H), 4.22-4.03 (m, 2H), 3.70 (dt, J = 11.0, 5.3 Hz, 1H), 3.42-3.36 (m, 2H), 3.25-3.04 (m, 6H), 2.87 (br d, J = 4.8 Hz, 1H), 2.68-2.58 (m, 1H), 2.26-1.99 (m, 5H), 1.92-1.79 (m, 3H), 1.78-1.67 (m, 5H), 1.60-1.52 (m, 1H), 1.50-1.41 (m, 1H), 1.34-1.16 (m, 5H). $^{19}F$ NMR (376 MHz, DMSO-$d_6$) δ ppm −142.46-−142.54 (m, 1F), −172.10 (br s, 1F). |
| 294 | 649.3 | $^1H$ NMR (400 MHz, METHANOL-$d_4$) δ ppm 9.24 (s, 1 H), 7.84 (s, 1 H), 7.82 (s, 1 H), 7.19-7.24 (m, 1 H), 5.48-5.72 (m, 1 H), 5.17-5.22 (m, 1 H), 5.15 (br d, J = 4.35 Hz, 1 H), 5.06 (br d, J = 14.31 Hz, 1 H), 4.64-4.76 (m, 2 H), 4.55 (dd, J = 14.62, 4.46 Hz, 1 H), 4.14-4.34 (m, 3 H), 3.99-4.10 (m, 2 H), 3.94 (br d, J = 17.62 Hz, 3 H), 3.68 (br s, 1 H), 3.50 (br s, 1 H), 2.83 (s, 1 H), 2.58-2.72 (m, 3 H), 2.32-2.54 (m, 2 H), 2.12-2.30 (m, 2 H), 1.74-1.91 (m, 2 H). $^{19}F$ NMR (376 MHz, METHANOL-$d_4$) δ ppm −143.86-−143.69 (m), −175.54-−175.46 (m). |
| 295 | 661.3 | $^1H$ NMR (400 MHz, METHANOL-$d_4$) δ ppm 9.14 (s, 1 H), 7.80 (s, 1 H), 7.66 (s, 1 H), 6.94 (s, 1 H), 5.23-5.53 (m, 1 H), 4.76 (br dd, J = 13.4, 5.1 Hz, 1 H), 4.29-4.43 (m, 3 H), 4.16-4.25 (m, 2 H), 3.36-3.42 (m, 1 H), 3.21-3.30 (m, 3 H), 2.94-3.08 (m, 2 H), 2.35-2.53 (m, 3 H), 2.27-2.34 (m, 1 H), 1.96-2.25 (m, 10 H), 1.86-1.94 (m, 1 H), 1.82 (br d, J = 11.8 Hz, 1 H), 1.59-1.70 (m, 1 H), 1.22-1.38 (m, 1 H). $^{19}F$ NMR (376 MHz, METHANOL-$d_4$) δ ppm −141.89 (s), −173.60 (s). |
| 296 | 661.3 | $^1H$ NMR (400 MHz, METHANOL-$d_4$) δ ppm 9.14 (s, 1 H), 7.80 (s, 1 H), 7.68 (s, 1 H), 6.94 (s, 1 H), 5.20-5.53 (m, 3 H), 4.75 (br dd, J = 12.4, 3.5 Hz, 1 H), 4.27-4.44 (m, 3 H), 4.17-4.26 (m, 2 H), 3.36-3.41 (m, 1 H), 3.19-3.28 (m, 2 H), 2.96-3.08 (m, 2 H), 2.33-2.52 (m, 3 H), 2.11-2.31 (m, 6 H), 1.89-2.09 (m, 5 H), 1.77 (s, 1 H), 1.58-1.70 (m, 1 H), 1.31 (br s, 1 H). $^{19}F$ NMR (376 MHz, METHANOL-$d_4$) δ ppm −141.89 (s), −173.60 (s). |
| 297 | 663.2 | $^1H$ NMR (600 MHz, DMSO-$d_6$) δ ppm 9.16 (s, 1 H), 7.80 (s, 1 H), 7.71 (s, 1 H), 6.92 (s, 1 H), 5.34 (br s, 1 H), 5.21-5.27 (m, 2 H), 4.59 (br dd, J = 13.8, 4.3 Hz, 1 H), 4.26-4.35 (m, 2 H), 4.07-4.20 (m, 5 H), 4.00 (dd, J = 11.4, 5.0 Hz, 1 H), 3.62-3.75 (m, 2 H), 3.44 (q, J = 5.0 Hz, 1 H), 3.31-3.36 (m, 1 H), 3.01-3.18 (m, 3 H), 2.81-2.88 (m, 1 H), 2.71-2.77 (m, 1 H), 2.13-2.20 (m, 1 H), 1.99-2.13 (m, 3 H), 1.77-1.96 (m, 5 H). |
| 298 | 663.2 | $^1H$ NMR (600 MHz, DMSO-$d_6$) δ ppm 9.16 (s, 1 H), 7.80 (s, 1 H), 7.72 (s, 1 H), 6.92 (s, 1 H), 5.34 (br s, 1 H), 5.21-5.27 (m, 2 H), 4.59 (br dd, J = 13.7, 4.2 Hz, 1 H), 4.25-4.35 (m, 2 H), 4.10-4.20 (m, 5 H), 3.99 (dd, J = 11.5, 4.9 Hz, 1 H), 3.62-3.75 (m, 2 H), 3.42-3.46 (m, 1 H), 3.33-3.36 (m, 2 H), 3.01-3.14 (m, 2 H), 2.81-2.87 (m, 1 H), 2.71-2.77 (m, 1 H), 2.33-2.40 (m, 1 H), 2.15-2.19 (m, 1 H), 2.07-2.13 (m, 1 H), 1.98-2.05 (m, 1 H), 1.77-1.96 (m, 5 H). |
| 299 | 663.2 | $^1H$ NMR (400 MHz, DMSO-$d_6$) δ ppm 9.14 (d, J = 2.09 Hz, 1 H), 7.81 (s, 1 H), 7.77 (s, 1 H), 6.91 (d, J = 17.14 Hz, 1 H), 5.49-5.73 (m, 1 H), 5.11-5.20 (m, 1 H), 4.93 (br d, J = 14.63 Hz, 1 H), 4.75-4.80 (m, 1 H), 4.65-4.74 (m, 2 H), 4.24 (br d, J = 5.23 Hz, 2 H), 4.13 (br dd, J = 14.21, 3.14 Hz, 1 H), 3.89-3.99 (m, 3 H), 3.45-3.60 (m, 3 H), 3.05-3.16 (m, 1 H), 2.58-2.88 (m, 5 H), 2.27-2.56 (m, 5 H), 2.01-2.26 (m, 3 H), 1.66-1.96 (m, 3 H). $^{19}F$ NMR (376 MHz, DMSO-$d_6$) δ ppm −144.18 (s), −144.34 (s), −175.63 (s), −175.70 (s). |
| 300 | 663.2 | $^1H$ NMR (400 MHz, METHANOL-$d_4$) δ ppm 9.12 (s, 1 H), 7.82 (s, 1 H), 7.75 (s, 1 H), 7.54 (d, J = 4.81 Hz, 1 H), 5.52-5.74 (m, 1 H), 5.49 (br d, J = 14.63 Hz, 1 H), 5.08 (br dd, J = 13.38, 5.43 Hz, 1 H), 4.74 (d, J = 1.46 Hz, 1 H), 4.58-4.72 (m, 1 H), 4.29-4.38 (m, 2 H), 4.07-4.29 (m, 3 H), 3.87-4.05 (m, 3 H), 3.42-3.63 (m, 4 H), 2.65-2.85 (m, 2 H), 2.51-2.63 (m, 2 H), 2.34-2.47 (m, 4 H), 2.08-2.27 (m, 2 H), 2.03 (br d, J = 14.00 Hz, 1 H), 1.88-1.98 (m, 2 H), 1.04 (s, 1 H). $^{19}F$ NMR (376 MHz, METHANOL-$d_4$) δ ppm −142.84-−142.79 (m), −143.11 (s), −174.07 (s), −174.26 (s). |
| 301 | 645.4 | $^1H$ NMR (400 MHz, METHANOL-$d_4$) δ ppm 9.28 (s, 1H), 7.80 (s, 1H), 7.50 (s, 1H), 5.15-5.48 (m, 2H), 4.70 (d, J = 14.4 Hz, 1H), 4.25-4.41 (m, 2H), 4.08-4.18 (m, 1H), 3.60-3.80 (m, 4H), 3.23 (s, 2H), 2.94-3.09 (m, 2H), 2.09-2.43 (m, 6H), 1.88-2.07 (m, 7H), 1.51-1.84 (m, 4H), 1.09-1.39 (m, 3H). |
| 302 | 645.4 | $^1H$ NMR (400 MHz, METHANOL-$d_4$) δ ppm 9.36 (s, 1H), 7.83 (s, 1H), 7.48 (s, 1H), 5.35-5.50 (m, 2H), 4.55-4.70 (m, 1H), 4.38-4.51 (m, 3H), |

TABLE 24-continued

| Analytical Data for Examples 76 to 79, 176 to 178 and 282 to 302. | | |
|---|---|---|
| Cmpd. # | MS m/z (ESI): $(M + H)^+$ | $^1H$ NMR |
| | | 3.66-3.83 (m, 3H), 3.41-3.60 (m, 4H), 3.13-3.25 (m, 2H), 2.98-3.08 (m, 1H), 2.38-2.57 (m, 4H), 2.22-2.37 (m, 1H), 2.12-2.20 (m, 2H), 2.00-2.10 (m, 2H), 1.86-1.98 (m, 2H), 1.60-1.75 (m, 3H), 1.40-4.50 (m, 1H), 1.15 (d, J = 6.4 Hz, 2H), 0.86-0.98 (m, 1H). |

(15R)-31-Fluoro-8-(((2R,7aS)-2-fluorotetrahydro-1H-pyrrolo[1,2-a]pyrrol-7a(5H)-yl)methoxy)-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 29)

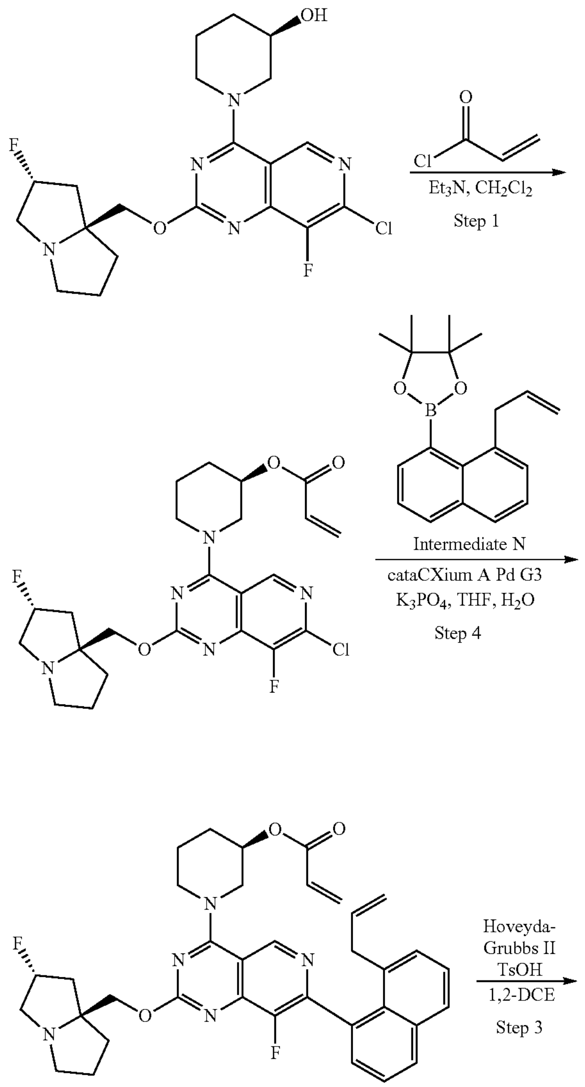

-continued

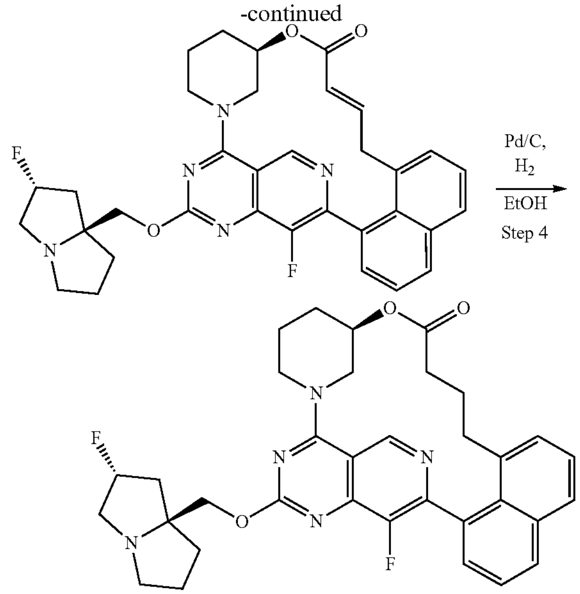

Example 29

Step 1. (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl acrylate. A mixture of (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.10 g, 0.23 mmol, Intermediate W, step 1) and triethylamine (48 μL, 0.34 mmol) in dichloromethane (1.0 mL) at 0° C. was treated with 2-propenoyl chloride (22 μL, 0.27 mmol). The reaction mixture was allowed to warm to rt and stirred for 4.5 h. The mixture was purified by column chromatography on silica gel, eluting with a gradient of 0-75% (3:1 EtOAc:EtOH with 2% triethylamine) in heptane, to provide (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl acrylate (71 mg, 0.14 mmol, 63% yield) as yellow solid. m/z (ESI): 494.0 $(M+H)^+$.

Step 2. (R)-1-(7-(8-Allylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl acrylate. A vial was charged with (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl acrylate (60 mg, 0.12 mmol), 2-(8-allylnaphthalen-1-yl)-4,4,5,5-tetramethyl-1,3,2-dioxaborolane (72 mg, 0.24 mmol, Intermediate N), potassium phosphate (52 mg, 0.24 mmol), and cataCXium A Pd G3 (14 mg, 0.02 mmol). The vial was purged with nitrogen and then the reactants were suspended in degassed tetrahydrofuran (1.1 mL) and water (0.11 mL).

The reaction mixture was then sealed and heated to 75° C. for 3 h. After cooling to rt, the reaction mixture was and concentrated in vacuo. The crude material was purified via reverse phase column chromatography, to provide (R)-1-(7-(8-allylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl acrylate (18.5 mg, 0.03 mmol, 24% yield) as off white solid. m/z (ESI): 626.4 $(M+H)^+$.

Step 3. (13R,E)-28-Fluoro-22-(((2R,7aS)-2-fluorotetrahydro-1H-pyrrolizin-7a(5H)-yl)methoxy)-8-oxa-2(4,7)-pyrido[4,3-d]pyrimidina-1(1,3)-piperidina-3(1,8)-naphthalenacyclooctaphan-5-en-7-one. (R)-1-(7-(8-Allylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl acrylate (18.5 mg, 0.03 mmol) and PTSA (11 mg, 0.06 mmol, Sigma Aldrich) were dissolved in 1,2-dichloroethane (14.8 mL) and degassed for 10 min. (1,3-Bis-(2,4,6-trimethylphenyl)-2-imidazolidinylidene)dichloro(o-isopropoxyphenylmethylene)ruthenium (5.6 mg, 8.87 μmol, Sigma-Aldrich) was added and the mixture was heated at 80° C. for 5 h. Volatiles were removed in vacuo and the residue was purified by column chromatography on silica gel, eluting with a gradient of 0-60% 3:1 (EtOAc:EtOH mixture with 2% triethylamine) in heptane, to provide (13R,E)-28-fluoro-22-(((2R,7aS)-2-fluorotetrahydro-1H-pyrrolizin-7a(5H)-yl)methoxy)-8-oxa-2(4,7)-pyrido[4,3-d]pyrimidina-1(1,3)-piperidina-3(1,8)-naphthalenacyclooctaphan-5-en-7-one (6.8 mg, 0.01 mmol, 38% yield, contaminated with Z isomer) as off-white solid. m/z (ESI): 598.0 $(M+H)^+$.

Step 4. (15R)-31-Fluoro-8-(((2R,7aS)-2-fluorotetrahydro-1H-pyrrolo[1,2-a]pyrrol-7a(5H)-yl)methoxy)-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate). A mixture of (13R,E)-28-fluoro-22-(((2R,7aS)-2-fluorotetrahydro-1H-pyrrolizin-7a(5H)-yl)methoxy)-8-oxa-2(4,7)-pyrido[4,3-d]pyrimidina-1(1,3)-piperidina-3(1,8)-naphthalenacyclooctaphan-5-en-7-one (6.8 mg, 0.01 mmol) and 5% Pd/C (7.3 mg, 3.41 μmol) in ethanol (0.23 mL) was purged three times with hydrogen and the stirred under a 45 psi atmosphere of hydrogen at rt for 16 h. The reaction mixture was filtered through a plug of celite, and the plug was washed with EtOAc. The filtrate was concentrated under reduced pressure and the residue was purified by reverse phase HPLC to provide (15R)-31-fluoro-8-(((2R,7aS)-2-fluorotetrahydro-1H-pyrrolo[1,2-a]pyrrol-7a(5H)-yl)methoxy)-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (1.7 mg, 2.02 μmol, 18% yield) as white solid. m/z (ESI): 600.0 $(M+H)^+$. $^1$H NMR (400 MHz, METHANOL-$d_4$) δ ppm 9.17 (s, 1H) 8.05-8.13 (m, 1H) 7.85-7.94 (m, 1H) 7.60-7.71 (m, 2H) 7.42-7.53 (m, 1H) 7.31-7.40 (m, 1H) 5.51-5.71 (m, 1H) 5.08-5.28 (m, 2H) 4.91-4.99 (m, 1H) 4.62-4.78 (m, 2H) 3.81-4.16 (m, 4H) 3.44-3.56 (m, 1H) 2.32-2.86 (m, 6H) 2.03-2.26 (m, 3H) 1.95 (s, 7H) 1.45-1.58 (m, 1H). $^{19}$F NMR (376 MHz, METHANOL-$d_4$) δ ppm −77.33 (br s), −140.92 (s), −174.14 (s).

(17R)-30-Fluoro-24-(((2R,7aS)-2-fluorotetrahydro-1H-pyrrolo[1,2-a]pyrrol-7a(5H)-yl)methoxy)-11,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (Example 30)

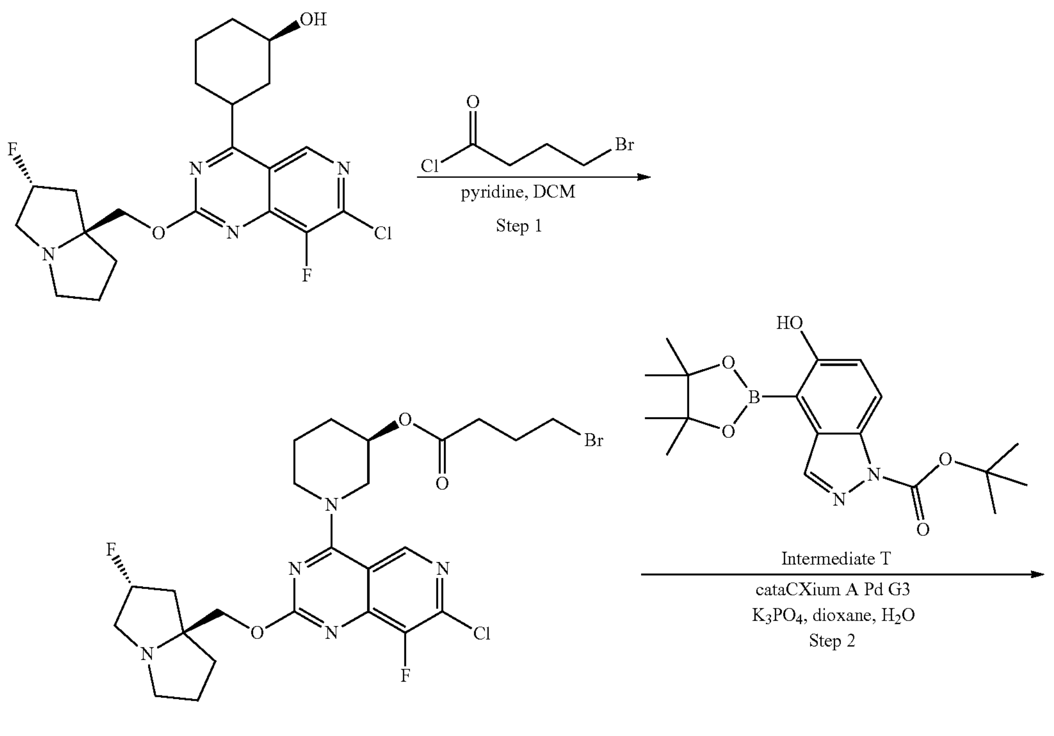

-continued

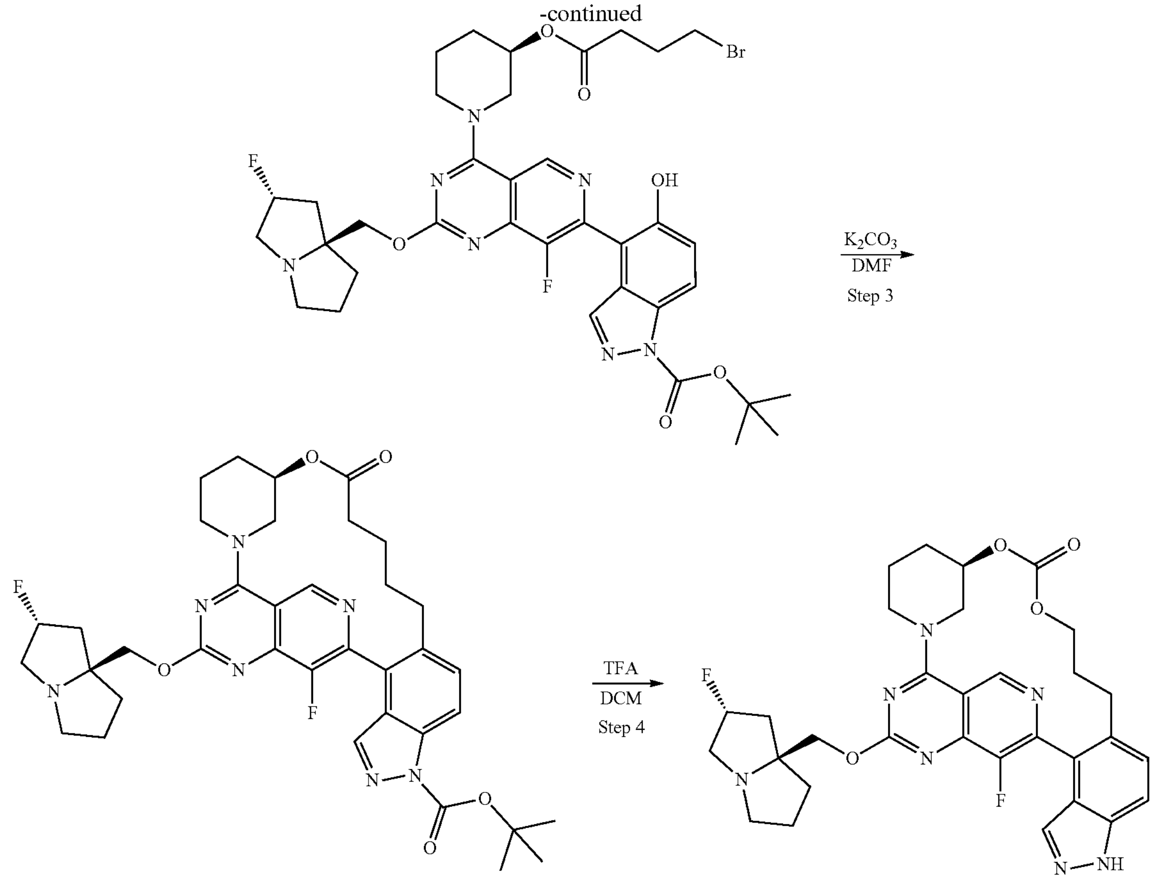

Example 30

Step 1. (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl 4-bromobutanoate. A mixture of (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.60 g, 1.36 mmol, Intermediate W, step 1) and pyridine (0.17 mL, 2.05 mmol) in dichloromethane (5 mL) at 0° C. under $N_2$ was added 4-bromobutyryl chloride (0.28 mL, 1.5 mmol). The reaction mixture was allowed to slowly warm to rt for 15 min. The resulting mixture was diluted with water and extracted with DCM. The combined organic layers were washed with brine, dried over $MgSO_4$, filtered, and concentrated under reduced pressure. The crude material was directly used in the next step without further purification.

Step 2. tert-Butyl 4-(4-((R)-3-((4-bromobutanoyl)oxy)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-5-hydroxy-1H-indazole-1-carboxylate. A 20-mL vial was charged with (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl 4-bromobutanoate (1.32 g, 2.24 mmol), (1-(tert-butoxycarbonyl)-5-hydroxy-1H-indazol-4-yl)boronic ester (0.93 g, 3.36 mmol, Intermediate T) and potassium phosphate tribasic (1.43 g, 6.72 mmol) in 1,4-dioxane (8.0 mL)/water (0.8 mL). Then the vial was sparged with argon and cataCXium A Pd G3 (0.16 g, 0.22 mmol) was added. The vial was sealed, and the reaction mixture was heated at 80° C. for 1 h. After cooling to rt, the reaction mixture diluted with water and extracted with EtOAc. The combined organic layers were washed with brine, dried over $MgSO_4$, filtered, and concentrated. The crude material was purified by column chromatography on silica gel, eluting with a gradient of 0-100% (3:1 EtOAc: EtOH with 2% $Et_3N$) in heptane, to provide tert-butyl 4-(4-((R)-3-((4-bromobutanoyl)oxy)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-5-hydroxy-1H-indazole-1-carboxylate (0.28 g, 0.35 mmol, 16% yield) as impure brown solid. m/z (ESI): 787.2 $(M+H)^+$.

Step 3. N-(tert-butoxy-carbonyl)-(17R)-30-Fluoro-24-(((2R,7aS)-2-fluorotetrahydro-1H-pyrrolo[1,2-a]pyrrol-7a(5H)-yl)methoxy)-11,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one. To a 100-mL round-bottom flask was added tert-butyl 4-(4-((R)-3-((4-bromobutanoyl)oxy)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-5-hydroxy-1H-indazole-1-carboxylate (0.28 g, 0.35 mmol), potassium carbonate (0.19 g, 1.40 mmol) in DMF (20 mL). The vial was sealed, and the content stirred at rt for 3 h. The reaction mixture was diluted with water and extracted with EtOAc. The combined organic layers were washed with brine, dried over $MgSO_4$, filtered, and concentrated under reduced pressure. The crude material was purified by reverse-phase column chromatography, to provide N-(tert-butoxy-carbonyl)-(17R)-30-fluoro-24-(((2R,7aS)-2-fluorotetrahydro-1H-pyrrolo[1,2-a]pyrrol-7a(5H)-yl)methoxy)-11,16-dioxa-5,6,21,23,25,29-hexaaza-hexacyclo[24.3.1.1~17,21~.0~2,10~.0~3,7~.0~22,27~]

hentriaconta-1(30),2,4,7,9,22,24,26,28-nonaen-15-one (60 mg, 0.085 mmol, 24% yield) as light-yellow solid. m/z (ESI): 706.3 $(M+H)^+$. $^1H$ NMR (400 MHz, DMSO-$d_6$) δ ppm 9.23 (s, 1H), 8.28 (s, 1H), 8.20 (d, J=9.0 Hz, 1H), 7.60 (d, J=9.0 Hz, 1H), 5.21-5.25 (m, 1H), 5.37 (br s, 1H), 4.74-4.87 (m, 3H), 4.19 (d, J=10.5 Hz, 1H), 4.11 (d, J=10.5 Hz, 1H), 3.88-4.01 (m, 2H), 3.63 (br t, J=7.9 Hz, 1H), 3.17-3.24 (m, 1H), 3.11 (br d, J=13.0 Hz, 2H), 3.04 (br s, 1H), 2.79-2.90 (m, 1H), 2.12-2.23 (m, 1H), 2.09 (br d, J=4.8 Hz, 1H), 1.95-2.05 (m, 3H), 1.83-1.91 (m, 2H), 1.75-1.83 (m, 2H), 1.68 (s, 9H), 1.56-1.64 (m, 1H), 1.32-1.49 (m, 2H), 0.98 (dt, J=18.6, 7.6 Hz, 1H. $^{19}F$ NMR (376 MHz, DMSO-$d_6$) δ ppm −139.20 (s), −172.05 (s).

Step 4. (17R)-30-Fluoro-24-(((2R,7aS)-2-fluorotetrahydro-1H-pyrrolo[1,2-a]pyrrol-7a(5H)-yl)methoxy)-11,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one. To a 100-mL round-bottom flask charged with N-(tert-butoxy-carbonyl)-(17R)-30-fluoro-24-(((2R,7aS)-2-fluorotetrahydro-1H-pyrrolo[1,2-a]pyrrol-7a(5H)-yl)methoxy)-11,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (60 mg, 0.085 mmol) was added dichloromethane (2 mL) and the reaction mixture was cooled down to 0° C. Trifluoroacetic acid (1 mL) was added dropwise and the reaction mixture was allowed to rt with stirring. After 1 h, the reaction mixture was quenched with saturated $NaHCO_3$ solution and extracted with DCM. The combined organic layers were washed with brine, dried over $MgSO_4$, filtered, and concentrated. The crude material was purified by reverse-phase column chromatography to provide (17R)-30-fluoro-24-(((2R,7aS)-2-fluorotetrahydro-1H-pyrrolo[1,2-a]pyrrol-7a(5H)-yl)methoxy)-11,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (31 mg, 0.051 mmol, 60% yield) as white solid. m/z (ESI, +ve ion): 606.2 $(M+H)^+$. $^1H$ NMR (400 MHz, DMSO-$d_6$) δ ppm 13.21 (br s, 1H), 9.21 (s, 1H), 7.92 (s, 1H), 7.68 (d, J=8.8 Hz, 1H), 7.33 (d, J=9.0 Hz, 1H), 5.41 (br s, 1H), 4.75-4.88 (m, 3H), 4.11-4.31 (m, 2H), 3.86-3.99 (m, 2H), 3.47-3.58 (m, 1H), 3.14-3.25 (m, 4H), 2.92 (br s, 1H), 2.18-2.34 (m, 1H), 2.15 (br s, 1H), 1.81-2.09 (m, 7H), 1.70 (br d, J=12.8 Hz, 1H), 1.59 (br d, J=11.9 Hz, 1H), 1.40 (br s, 2H), 0.93-1.05 (m, 1H). $^{19}F$ NMR (376 MHz, DMSO-$d_6$) δ ppm −139.62 (s), −172.17 (s).

(17R)-30-Fluoro-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaazahexacyclo[24.3.1.1~17,21~0.0~2,10~.0~3,7~.0~22,27~]hentriaconta-1(30),2,4,7,9,22,24,26,28-nonaen-15-one bis(2,2,2-trifluoroacetate) (Example 31)

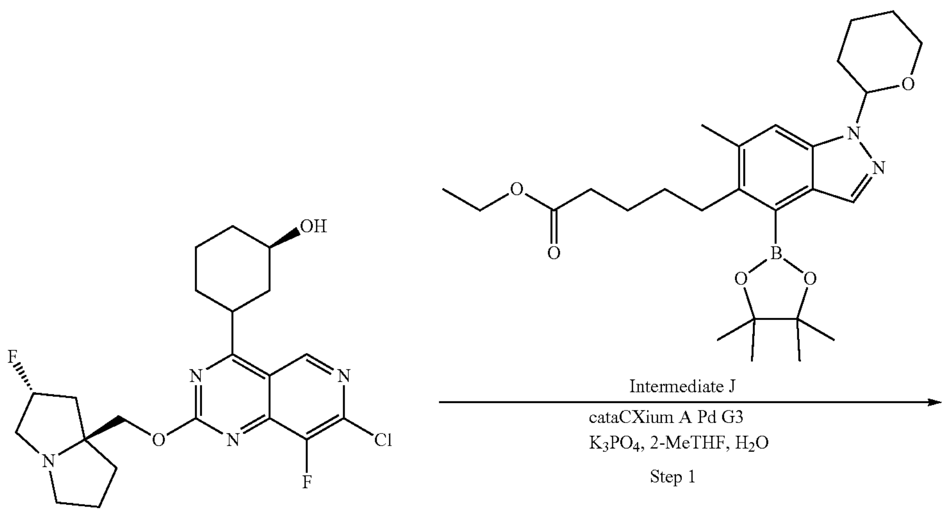

-continued

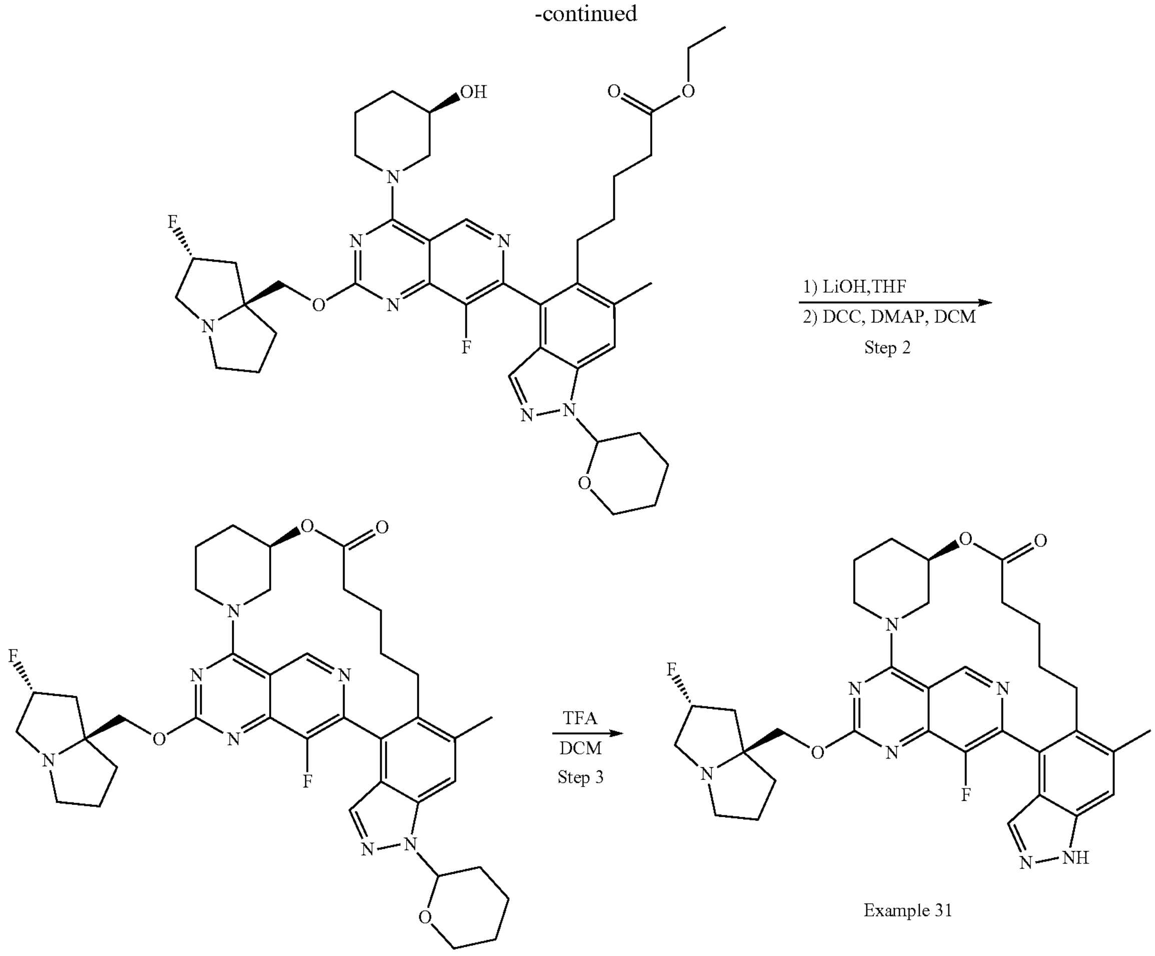

Example 31

Step 1. Ethyl 5-(4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-methyl-1-(tetrahydro-2H-pyran-2-yl)-1H-indazol-5-yl) pentanoate. To a 20 mL vial was charged with (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl) piperidin-3-ol (0.15 g, 0.34 mmol, Intermediate W, step 1), ethyl 5-(6-methyl-1-(tetrahydro-2H-pyran-2-yl)-4-(4,4,5,5-tetramethyl-1,3,2-dioxaborolan-2-yl)-1H-indazol-5-yl)pentanoate (0.24 g, 0.51 mmol, Intermediate J), $K_3PO_4$ (0.29 g, 1.36 mmol), 2-methyltetrahydrofuran (1.5 mL), and water (0.15 mL). The solution was sparged with nitrogen for 10 min, and then palladium acetate (15 mg, 0.068 mmol), (S)-(−)-2-(diphenylphosphino)-2-methoxy-1-,1-binaphthyl (32 mg, 0.068 mmol), and (R)-(+)-2-(diphenylphosphino)-2'-methoxy-1,1'-binaphthyl (32 mg, 0.068 mmol) were added. The reaction was capped and heated at 80° C. for 16 h. After cooling to rt, the reaction mixture was concentrated, and the crude material was purified by column chromatography on silica gel, eluting with 0-100% (3:1 EtOAc:EtOH with 2% triethylamine) in heptane, to provide ethyl 5-(4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-methyl-1-(tetrahydro-2H-pyran-2-yl)-1H-indazol-5-yl)pentanoate (0.20 g, 0.27 mmol, 80% yield) as yellow oil. m/z (ESI): 748.2 $(M+H)^+$.

Step 2. N-(tetrahydro-2H-pyran-2-yl)-(17R)-30-Fluoro-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaazahexacyclo[24.3.1.1~17,21~.0~2,10~.0~3,7~.0~22, 27~]hentriaconta-1(30),2,4,7,9,22,24,26,28-nonaen-15-one. To a 20 mL vial was charged with ethyl 5-(4-(8-fluoro-2-(((2R,7aS)-2-fluorotetrahydro-1H-pyrrolizin-7a(5H)-yl) methoxy)-4-((R)-3-hydroxypiperidin-1-yl)pyrido[4,3-d]pyrimidin-7-yl)-6-methyl-1-(tetrahydro-2H-pyran-2-yl)-1H-indazol-5-yl)pentanoate (0.20 g, 0.27 mmol), tetrahydrofuran (2.0 mL), acetonitrile (67 μL), and water (0.67 mL). Lithium hydroxide, monohydrate (23 mg, 0.55 mmol) was added and the reaction mixture was heated to 40° C. with vigorous stirring for 3.5 h. This solution was then concentrated and taken into DCM (11 mL). Diisopropylethylamine (0.22 mL, 1.25 mmol) and 4-(dimethylamino)pyridine (18 mg, 0.15 mmol) were added. The reaction mixture was stirred at rt for 16 h. Upon completion the reaction was filtered, concentrated, and the crude material was purified by reverse phase chromatography, to provide N-(tetrahydro-2H-pyran-2-yl)-(17R)-30-fluoro-24-(((2R,7aS)-2-fluorotetrahydro-1H-pyrrolo [1,2-a]pyrrol-7a(5H)-yl)methoxy)-9-methyl-16-oxa-5,6,21,23,25,29-hexaazahexacyclo [24.3.1.1~17,21~.0~2,10~.0~3,7~.0~22,27~]hentriaconta-1 (30),2,4,7,9,22,24,26,28-nonaen-15-one (36 mg, 0.051 mmol, 18% yield) as yellow oil. m/z (ESI): 702.6 $(M+H)^+$.

Step 3. (17R)-30-Fluoro-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaazahexacyclo [24.3.1.1~17,21~.0~2,10~.0~3,7~.0~22,27~]hentriaconta-1

(30),2,4,7,9,22,24,26,28-nonaen-15-one bis(2,2,2-trifluoroacetate). To a 20 mL vial was charged with N-(tetrahydro-2H-pyran-2-yl)-(17R)-30-fluoro-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaaza-hexacyclo[24.3.1.1~17,21~.0~2,10~.0~3,7~.0~22,27~]hentriaconta-1(30),2,4,7,9,22,24,26,28-nonaen-15-one (38 mg, 0.054 mmol), in dichloromethane (0.5 mL). Trifluoroacetic acid (83 μL, 1.08 mmol) was added and the reaction was stirred at rt for 1.5 h. The mixture was concentrated and the crude material was purified by reverse phase preparative HPLC to provide (17R)-30-fluoro-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one bis(2,2,2-trifluoroacetate) (9.1 mg, 10.8 μmol, 20% yield) as white solid. m/z (ESI): 618.0 $(M+H)^+$. $^1H$ NMR (400 MHz, METHANOL-$d_4$) δ ppm 9.24 (s, 1H), 7.75 (s, 1H), 7.53 (s, 1H), 5.56-5.70 (m, 1H), 5.05-5.15 (m, 2H), 4.84-5.00 (m, 1H), 4.64-4.73 (m, 2H), 3.86-4.12 (m, 4H), 3.46-3.55 (m, 1H), 3.22-3.31 (m, 1H), 2.61-2.85 (m, 2H), 2.35-2.60 (m, 8H), 2.14-2.27 (m, 1H), 1.99-2.14 (m, 3H), 1.81-1.98 (m, 1H), 1.61-1.80 (m, 1H), 1.41-1.58 (m, 1H), 1.25-1.41 (m, 2H), 0.98-1.21 (m, 2H). $^{19}F$ NMR (376 MHz, METHANOL-$d_4$) δ ppm −77.41 (s), −141.92 (s), −174.1−−173.9 (m). Stereochemistry of Example 31 was confirmed by X-Ray crystallography analysis.

TABLE 25

Additional Examples 32 to 34 and 80 to 87. Prepared in an Analogous Manner to Example 31.

| Ex.# | Structure & Name | Salt Form | Reagent | Method Change |
|---|---|---|---|---|
| 32 | 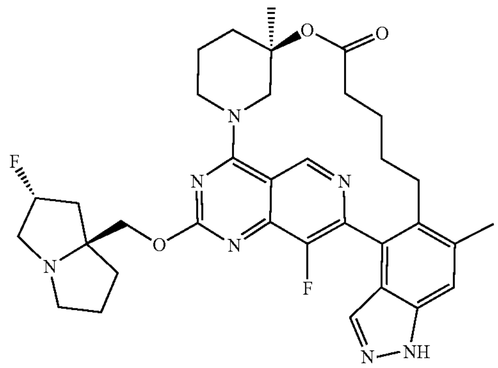 [SMILES: Cc1cc2[nH]ncc2c2c1CCCCC(=O)O[C@]1(C)CCCN(C1)c1nc(OC[C@@]34CCCN3C[C@H](F)C4)nc3c(F)c-2ncc13] (17R)-30-fluoro-24-(((2R,7aS)-2-fluorotetrahydro-1H-pyrrolo[1,2-a]pyrrol-7a(5H)-yl)methoxy)-9,17-dimethyl-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | bis(2,2,2-trifluoro-acetate) | Step 1. Intermediate U | |
| 33 | 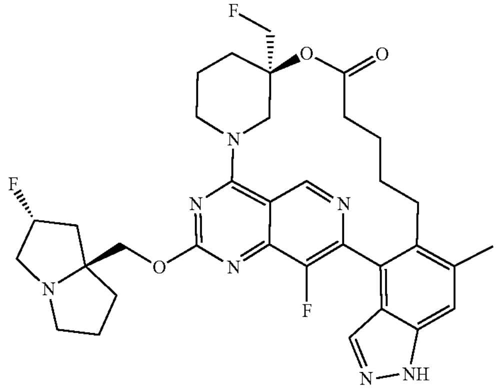 [SMILES: Cc1cc2[nH]ncc2c2c1CCCCC(=O)O[C@]1(CF)CCCN(C1)c1nc(OC[C@@]34CCCN3C[C@H](F)C4)nc3c(F)c-2ncc13] (17R)-30-fluoro-17-(fluoromethyl)-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | bis(2,2,2-trifluoro-acetate) | Step 1. Intermediate V | |

TABLE 25-continued

| Additional Examples 32 to 34 and 80 to 87. Prepared in an Analogous Manner to Example 31. | | | | |
|---|---|---|---|---|
| Ex.# | Structure & Name | Salt Form | Reagent | Method Change |
| 34 | 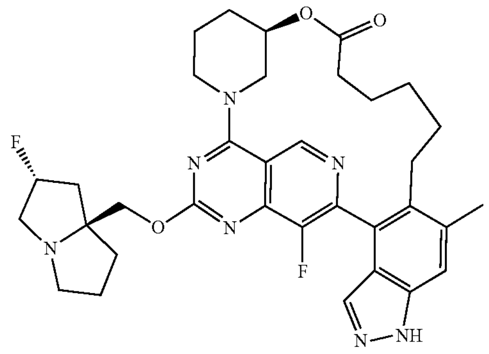 [SMILES: Cc1cc2[nH]ncc2c2c1CCCCCC(=O)O[C@@H]1CCCN(C1)c1nc(OC[C@@]34CCCN3C[C@H](F)C4)nc3c(F)c-2ncc13] (18R)-31-fluoro-25-(((2R,7aS)-2-fluorotetrahydro-1H-pyrrolo[1,2-a]pyrrol-7a(5H)-yl)methoxy)-9-methyl-17-oxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one | 2,2,2-trifluoro-acetate | Step 1. Intermediate I | Step 2. Used TFA/DCM |
| 80 | 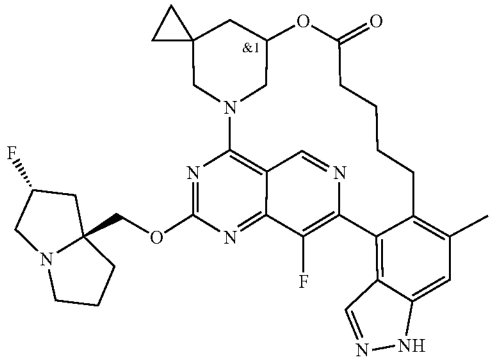 [SMILES: Cc1cc2[nH]ncc2c2c1CCCCC(=O)OC1CN(CC3(CC3)C1)c1nc(OC[C@@]34CCCN3C[C@H](F)C4)nc3c(F)c-2ncc13] (17'R)-30'-fluoro-24'-(((2R,7aS)-2-fluorotetrahydro-1H-pyrrolo[1,2-a]pyrrol-7a(5H)-yl)methoxy)-9'-methyl-16'-oxa-5',6',21',23',25',29'-hexaazaspiro[cyclopropane-1,19'-hexacyclo[24.3.1.1~17,21~.0~2,10~.0~3,7~.0~22,27~]hentriacontane]-1'(30'),2',4',7',9',22',24',26',28'-nonaen-15'-one | | Pre-Step 1: Intermediate Z, (3R)-5-azaspiro[2.5] octan-7-ol hydrochloride (CAS#: 2248351-69-9, Enamine) | |
| 81 | 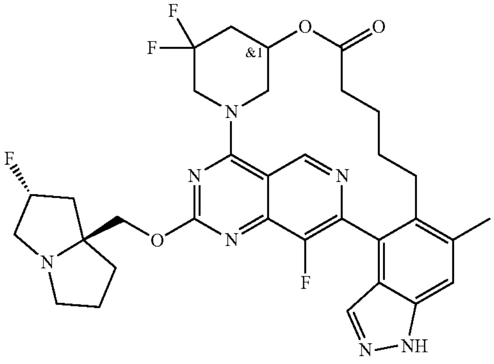 [SMILES: Cc1cc2[nH]ncc2c2c1CCCCC(=O)OC1CN(CC(F)(F)C1)c1nc(OC[C@@]34CCCN3C[C@H](F)C4)nc3c(F)c-2ncc13] (17S)-19,19,30-trifluoro-24-(((2R,7aS)-2-fluorotetrahydro-1H-pyrrolo[1,2-a]pyrrol-7a(5H)-yl)methoxy)-9-methyl-16-oxa-5,6,21,23,25,29- | | Pre-Step 1: Intermediate Z, tert-butyl 3,3-difluoro-5-hydroxypiperi-dine-1-carboxylate (CAS#: 1258638-32-2, Enamine) | |

TABLE 25-continued

| Ex.# | Structure & Name | Salt Form | Reagent | Method Change |
|---|---|---|---|---|
| | Additional Examples 32 to 34 and 80 to 87. Prepared in an Analogous Manner to Example 31. | | | |
| | hexaazahexacyclo[24.3.1.1~17,21~.0~2,10~.0~3,7~.0~22,27~]hentriaconta-1(30),2,4,7,9,22,24,26,28-nonaen-15-one and (17R)-19,19,30-trifluoro-24-(((2R,7aS)-2-fluorotetrahydro-1H-pyrrolo[1,2-a]pyrrol-7a(5H)-yl)methoxy)-9-methyl-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | | | |
| 82 | 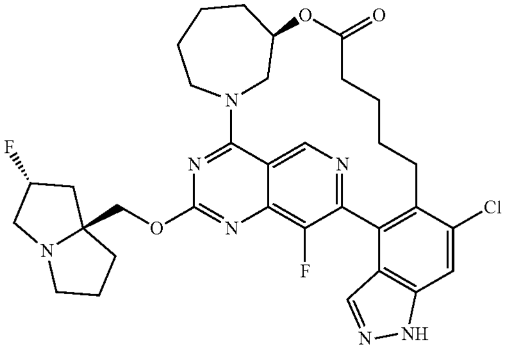 [SMILES: O=C1CCCCc2c(Cl)cc3[nH]ncc3c2-c2ncc3c(nc(OC[C@@]45CCCN4C[C@H](F)C5)nc3c2F)N2CCCC[C@H](C2)O1] (26R)-18-chloro-32-fluoro-4-(((2R,7aS)-2-fluorotetrahydro-1H-pyrrolo[1,2-a]pyrrol-7a(5H)-yl)methoxy)-25-oxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-aceate) | Step 1. Intermediate UU and Intermediate LL | |
| 83 | 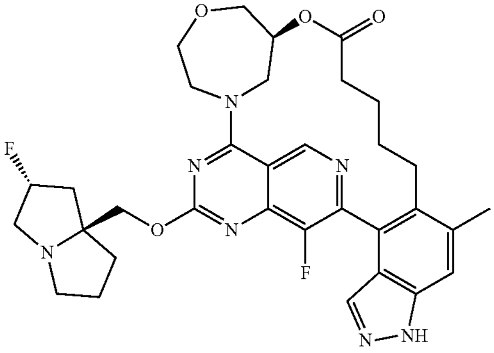 [SMILES: Cc1cc2[nH]ncc2c2c1CCCCC(=O)O[C@@H]1COCCN(C1)c1nc(OC[C@@]34CCCN3C[C@H](F)C4)nc3c(F)c-2ncc13] (26S)-32-fluoro-4-(((2R,7aS)-2-fluorotetrahydro-1H-pyrrolo[1,2-a]pyrrol-7a(5H)-yl)methoxy)-18-methyl-25,28-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-aceate) | Step 1. Intermediate VV | |

TABLE 25-continued

Additional Examples 32 to 34 and 80 to 87. Prepared in an Analogous Manner to Example 31.

| Ex.# | Structure & Name | Salt Form | Reagent | Method Change |
|---|---|---|---|---|
| 84 | 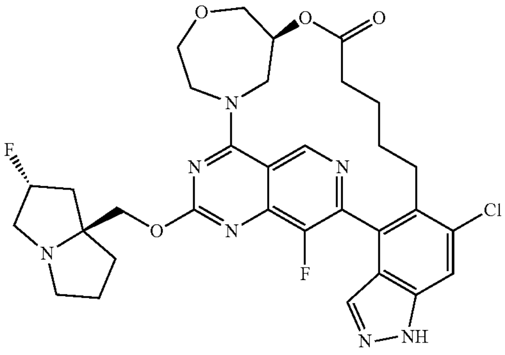 [SMILES: O=C1CCCCc2c(Cl)cc3[nH]ncc3c2-c2ncc3c(nc(OC[C@@]45CCCN4C[C@H](F)C5)nc3c2F)N2CCOC[C@H](C2)O1] (26S)-18-chloro-32-fluoro-4-(((2R,7aS)-2-fluorotetrahydro-1H-pyrrolo[1,2-a]pyrrol-7a(5H)-yl)methoxy)-25,28-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-aceate) | Step 1. Intermediate LL and Intermediate VV | |
| 85 | 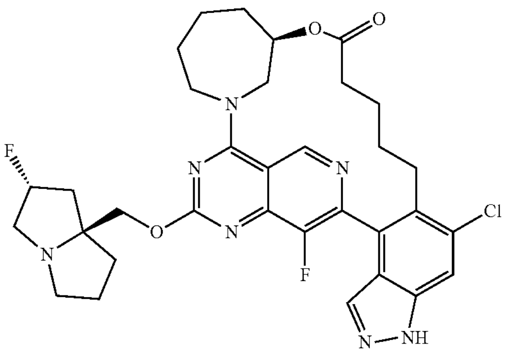 [SMILES: O=C1CCCCc2c(Cl)cc3[nH]ncc3c2-c2ncc3c(nc(OC[C@@]45CCCN4C[C@H](F)C5)nc3c2F)N2CCCC[C@H](C2)O1] (26R)-18-chloro-32-fluoro-4-(((2S,4R)-4-fluoro-1-methyl-2-pyrrolidinyl)methoxy)-25-oxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis(2,2,2-trifluoro-acetate) | Step 1. Intermediate RR and Intermediate LL | Step 2 (2): 2-chloro-1-methyl-pyridinium iodide (CAS#: 14338-32-0, Ambeed Inc.), TEA in DCE |
| 86 | 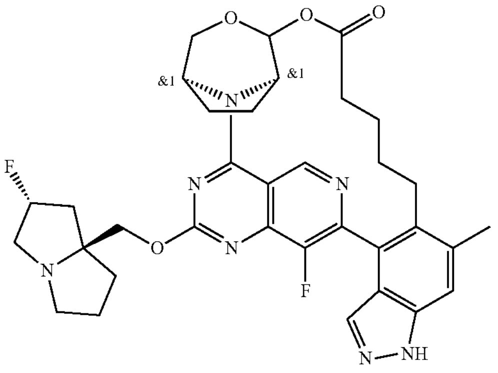 [SMILES: Cc1cc2[nH]ncc2c2c1CCCCC(=O)OC1OC[C@@H]3CC[C@H]1N3c1nc(OC[C@@]34CCCN3C[C@H](F)C4)nc3c(F)c-2ncc13] (17R,20R,23S)-33-fluoro-27-(((2R,7aS)-2-fluorotetrahydro-1H-pyrrolo[1,2-a]pyrrol-7a(5H)-yl)methoxy)-9-methyl-16-oxa-5,6,24,26,28,32-hexaazaheptacyclo[27.3.1.0~2,10~.0~3,7~.0~17,23~.0~20,24~.0~25,30~]tritriaconta- | 2,2,2-trifluoro-acetate | Step 1. (1R,2S,5S)-8-(7-Chloro-8-fluoro-2-(((2R,7aS)-2-fluorotetra-hydro-1H-pyrrolizin-7a(5H)-yl)methoxy) pyrido[4,3-d]pyrimidin-4-yl)-8-azabicyclo[3.2.1]octan-2-ol and Intermediate SS | |

TABLE 25-continued

| Ex.# | Structure & Name | Salt Form | Reagent | Method Change |
|---|---|---|---|---|
| | Additional Examples 32 to 34 and 80 to 87. Prepared in an Analogous Manner to Example 31. | | | |
| | 1(33),2,4,7,9,25,27,29,31-nonaen-15-one and (17S,20S,23R)-33-fluoro-27-(((2R,7aS)-2-fluorotetrahydro-1H-pyrrolo[1,2-a]pyrrol-7a(5H)-yl)methoxy)-9-methyl-16-oxa-5,6,24,26,28,32-hexaazaheptacyclo[27.3.1.0~2,10~.0~3,7~.0~17,23~.0~20,24~.0~25,30~]tritriaconta-1(33),2,4,7,9,25,27,29,31-nonaen-15-one (racemic) | | | |
| 87 | 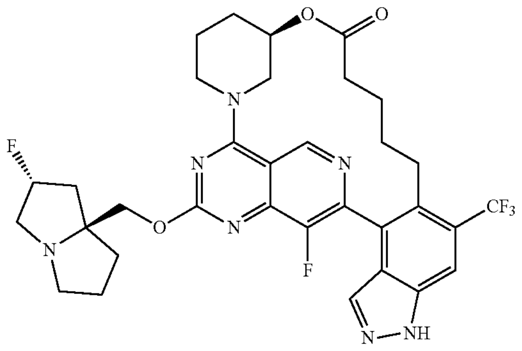 [SMILES: O=C1CCCCc2c(C(F)(F)F)cc3[nH]ncc3c2-c2ncc3c(nc(OC[C@@]45CCCN4C[C@H](F)C5)nc3c2F)N2CCC[C@H](C2)O1] (17R)-30-fluoro-24-(((2R,7aS)-2-fluorotetrahydro-1H-pyrrolo[1,2-a]pyrrol-7a(5H)-yl)methoxy)-9-(trifluoromethyl)-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | | Step 1. Intermediate TT | Step 2. $C_6F_5COCl$, $Et_3N$, toluene |

TABLE 26

| Cmpd. # | MS m/z (ESI): $(M + H)^+$ | $^1H$ and $^{19}F$ NMR |
|---|---|---|
| | Analytical Data for Examples 32 to 34 and 80 to 87. | |
| 32 | 632.2 | $^1H$ NMR (400 MHz, METHANOL-$d_4$) δ ppm 9.33 (s, 1 H), 7.78 (s, 1 H), 7.53 (s, 1 H), 5.61-5.55 (m, 2 H), 5.19 (br d, J = 12.3 Hz, 1 H), 4.75-4.66 (m, 2 H), 4.04-4.11 (m, 1 H), 3.82-4.01 (m, 3H), 3.45-3.54 (m, 1 H), 3.22-3.15 (m, 1H), 2.80-2.57 (m, 3H), 2.56 (s, 3H), 2.30-2.52 (m, 5 H), 2.14-2.27 (m, 1 H), 1.89-2.13 (m, 2 H), 1.76-1.89 (m, 2 H), 1.70 (br d, J = 11.3 Hz, 2 H), 1.55 (s, 3 H), 1.26-1.53 (m, 4 H), 0.98-1.24 (m, 2 H). $^{19}F$ NMR (376 MHz, METHANOL-$d_4$) δ ppm −77.47 (s), −141.59 (s), −174.10-−173.90 (m). |
| 33 | 650.2 | $^1H$ NMR (400 MHz, METHANOL-$d_4$) δ ppm 9.34 (s, 1 H), 7.79 (s, 1 H), 7.53 (s, 1 H), 5.67 (br s, 1 H), 5.50-5.60 (m, 2 H), 5.19 (br d, J = 12.1 Hz, 1 H), 4.85-4.93 (m, 1 H), 4.67-4.80 (m, 3 H), 3.86-4.11 (m, 4 H), 3.43-3.60 (m, 1 H), 3.17-3.31 (m, 1 H), 2.54-2.74 (m, 6 H), 2.32-2.53 (m, 4 H), 2.21 (br d, J = 3.8 Hz, 1 H), 1.92-2.13 (m, 4 H), 1.71-1.83 (m, 1 H), 1.46 (br dd, J = 14.0, 10.0 Hz, 2 H), 1.37 (br s, 2 H), 1.31 (br s, 1 H), 1.07-1.26 (m, 2 H). $^{19}F$ NMR (376 MHz, METHANOL-$d_4$) δ ppm −77.41 (s), −141.43 (s), −174.08 (td, J = 35.8, 18.6 Hz), −232.37 (s). |
| 34 | 632.4 | $^1H$ NMR (400 MHz, METHANOL-$d_4$) δ ppm 9.31 (s, 1 H), 7.51-7.67 (m, 2 H), 5.51-5.73 (m, 1 H), 5.06-5.14 (m, 2 H), 4.84-5.00 (m, 1 H), 4.64-4.73 (m, 2 H), 4.05-4.20 (m, 1 H) 3.85-4.00 (m, 3 H), 3.50 (s, 1 H), 3.22-3.31 (m, 1 H), 2.32-2.93 (m, 10 H), 1.69-2.15 (m, 6 H), 1.11-1.64 (m, 7 H). $^{19}F$ NMR (376 MHz, METHANOL-$d_4$) δ ppm −77.04 (s), −139.81 (s), −174.11 (s, 1 F). |
| 80 | 644.2 | $^1H$ NMR (400 MHz, METHANOL-$d_4$) δ ppm 9.16-9.28 (m, 1 H), 7.65-7.79 (m, 1 H), 7.46-7.60 (m, 1 H), 5.16-5.41 (m, 2 H), 5.02-5.08 (m, 1 H), 4.66-4.73 (m, 1 H), 4.66-4.73 (m, 1H), 4.18-4.37 (m, 2 H), 4.07-4.17 (m, 1 H), 3.92-4.01 (m, 1 H), 3.53-3.61 (m, 1 H), 3.15-3.25 (m, 2 H), 2.99-3.08 (m, 1 H), 2.44-2.60 (m, |

TABLE 26-continued

| Analytical Data for Examples 32 to 34 and 80 to 87. | | |
|---|---|---|
| Cmpd. # | MS m/z (ESI): $(M + H)^+$ | $^1H$ and $^{19}F$ NMR |
| | | 6 H), 2.24-2.34 (m, 1 H), 2.07-2.13 (m, 1 H), 1.87-2.03 (m, 4 H), 1.58-1.70 (m, 1 H), 1.48-1.55 (m, 1 H), 1.08-1.25 (m, 5 H), 0.93-0.91 (m, 1 H), 0.53-0.61 (m, 1 H), 0.44-0.51 (m, 1 H), 0.24-0.33 (m, 1H). $^{19}F$ NMR (376 MHz, METHANOL-$d_4$) δ ppm −80.13−−75.45 (m), −141.68 (s). |
| 81 | 654.2 | $^1H$ NMR (400 MHz, METHANOL-$d_4$) δ ppm 9.19-9.36 (m, 1 H), 7.67-7.77 (m, 1 H), 7.46-7.57 (m, 1 H), 5.66-5.82 (m, 1 H), 5.33-5.58 (m, 1 H), 5.11-5.27 (m, 2 H), 4.34-4.61 (m, 2 H), 3.99-4.07 (m, 1 H), 3.47-3.67 (m, 4 H), 3.15-3.26 (m, 1 H), 2.48-2.63 (m, 5 H), 2.00-2.49 (m, 10 H), 1.48-1.72 (m, 2 H), 1.31-1.44 (m, 1 H), 1.12-1.21 (m, 2 H). $^{19}F$ NMR (376 MHz, METHANOL-$d_4$) δ ppm −101.93−−95.56 (m), −142.27−−141.05 (m), −174.72−−173.20 (m). |
| 82 | 651.9 | $^1H$ NMR (400 MHz, METHANOL-$d_4$) δ ppm 9.26-9.43 (m, 1 H), 7.67-7.92 (m, 2 H), 5.36-5.67 (m, 2 H), 5.01-5.12 (m, 1 H), 4.73 (br d, J = 6.7 Hz, 3 H), 3.76-4.10 (m, 4 H), 3.44-3.55 (m, 1 H), 3.29-3.34 (m, 1 H), 2.92-3.06 (m, 1 H), 2.54-2.84 (m, 2 H), 2.36 (br s, 5 H), 2.11-2.27 (m, 1 H), 1.79-2.03 (m, 3 H), 1.51-1.73 (m, 5 H), 1.25-1.47 (m, 2 H), 1.01-1.23 (m, 1 H). |
| 83 | 634.0 | $^1H$ NMR (400 MHz, METHANOL-$d_4$) δ ppm 9.38 (s, 1 H), 7.60-7.70 (m, 1 H), 7.55 (s, 1 H), 5.52-5.73 (m, 1 H), 5.35-5.47 (m, 1 H), 4.97-5.09 (m, 1 H), 4.72 (d, J = 2.7 Hz, 3 H), 4.32-4.43 (m, 1 H), 3.85-4.11 (m, 6 H), 3.57-3.72 (m, 2 H), 3.45-3.56 (m, 1 H), 2.61-2.86 (m, 3 H), 2.58 (s, 3 H), 2.30-2.53 (m, 4 H), 2.14-2.26 (m, 1 H), 1.91-2.07 (m, 1 H), 1.09-1.63 (m, 5 H). |
| 84 | 654.0 | $^1H$ NMR (400 MHz, METHANOL-$d_4$) δ ppm 9.35-9.45 (m, 1 H), 7.80-7.89 (m, 1 H), 7.68-7.78 (m, 1 H), 5.52-5.72 (m, 1 H), 5.37-5.49 (m, 1 H), 4.99-5.09 (m, 1 H), 4.69-4.75 (m, 2 H), 4.30-4.42 (m, 1 H), 3.90-4.08 (m, 6 H), 3.56-3.69 (m, 2 H), 3.45-3.55 (m, 1 H), 2.94-3.03 (m, 1 H), 2.59-2.85 (m, 2 H), 2.35-2.53 (m, 4 H), 2.16-2.29 (m, 1 H), 1.92-2.03 (m, 1 H), 1.47-1.66 (m, 3 H), 1.36-1.45 (m, 1 H), 1.25-1.35 (m, 1 H), 1.05-1.17 (m, 1 H). |
| 85 | 625.9 | $^1H$ NMR (400 MHz, METHANOL-$d_4$) δ ppm 9.38 (s, 1 H) 7.79-7.86 (m, 1 H) 7.68-7.76 (m, 1 H) 5.40-5.63 (m, 2 H) 4.96-5.13 (m, 2 H) 4.72-4.76 (m, 1 H) 3.98-4.40 (m, 2 H) 3.80-3.91 (m, 1 H) 3.63-3.78 (m, 1 H) 3.36-3.52 (m, 2 H) 3.21 (s, 3 H) 2.91-3.03 (m, 1 H) 2.64-2.81 (m, 1 H) 2.35-2.60 (m, 3 H) 1.84-2.04 (m, 3 H) 1.53-1.72 (m, 5 H) 1.24-1.45 (m, 2 H) 1.05-1.20 (m, 1 H). |
| 86 | 644.0 | $^1H$ NMR (400 MHz, METHANOL-$d_4$) δ ppm 9.24-9.31 (m, 1 H), 7.67-7.76 (m, 1 H), 7.47-7.59 (m, 1 H), 5.52-5.73 (m, 1 H), 5.20-5.52 (m, 2 H), 4.64-4.76 (m, 2 H), 3.84-4.15 (m, 3 H), 3.45-3.56 (m, 1 H), 2.48-2.89 (m, 8 H), 2.33-2.47 (m, 5 H), 1.88-2.32 (m, 6 H), 1.46-1.68 (m, 4 H), 1.12-1.29 (m, 2 H), 0.86-1.02 (m, 1 H). $^{19}F$ NMR (376 MHz, METHANOL-$d_4$) δ ppm −77.38 (s), −141.82 (d, J = 12.1 Hz), −174.10−−173.94 (m). |
| 87 | 671.8 | $^1H$ NMR (400 MHz, METHANOL-$d_4$) δ ppm 9.23 (s, 1 H) 8.11 (s, 1 H) 7.87-7.98 (m, 1 H) 5.26-5.46 (m, 1 H) 4.90-5.12 (m, 3 H) 4.27-4.46 (m, 2 H) 3.95-4.07 (m, 1 H) 3.62-3.69 (m, 1 H) 3.27 (br s, 2 H) 3.03-3.13 (m, 1 H) 2.61-2.70 (m, 2 H) 2.10 (br s, 5 H) 1.83-2.06 (m, 5 H) 1.64-1.76 (m, 2 H) 1.50-1.62 (m, 2 H) 1.03-1.19 (m, 3 H). $^{19}F$ NMR (376 MHz, METHANOL-$d_4$) δ ppm −60.29 (s) −141.40 (s) −174.17−−173.32 (m). |

(15R)-31-Fluoro-8-(((2R,7aS)-2-fluorotetrahydro-1H-pyrrolo[1,2-a]pyrrol-7a(51)-yl)methoxy)-18-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one, (15S)-31-fluoro-8-(((2R,7aS)-2-fluorotetrahydro-1H-pyrrolo[1,2-a]pyrrol-7a(5H)-yl)methoxy)-18-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one (Example 88)

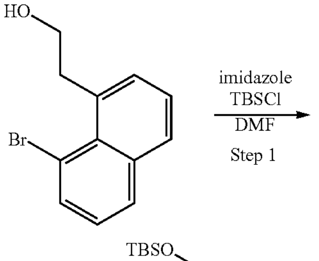

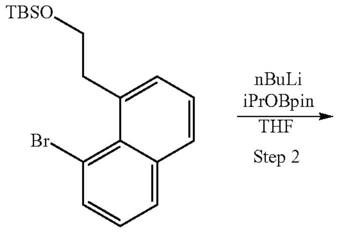

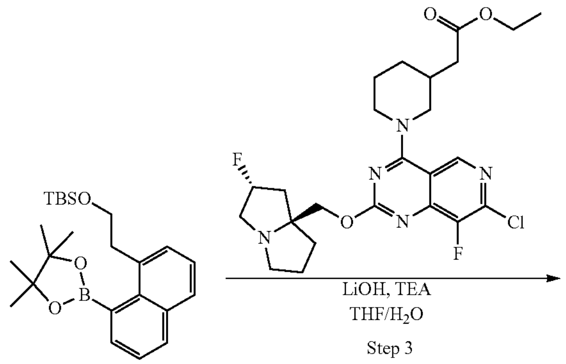

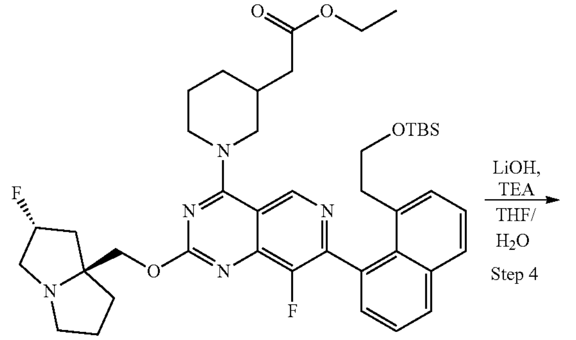

-continued

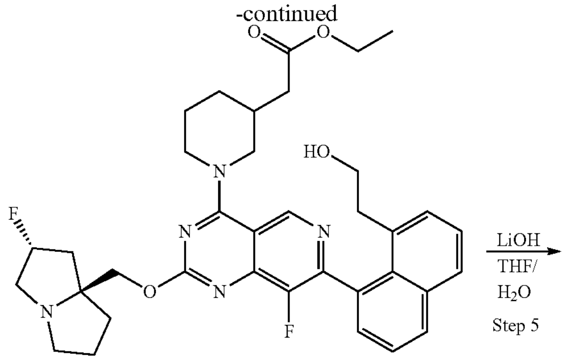

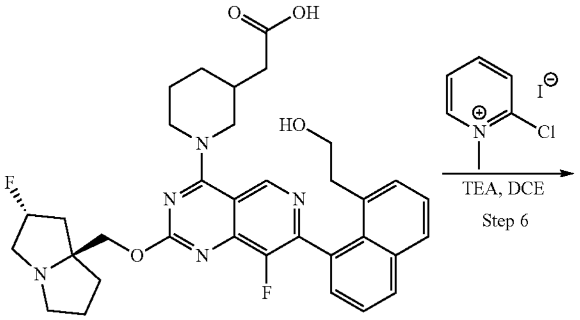

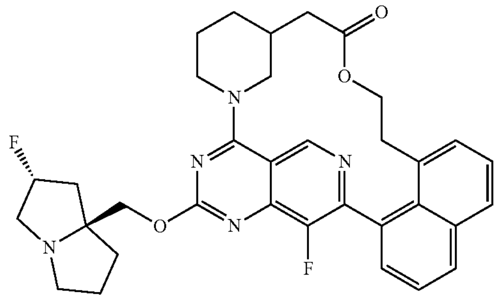

Example 88

Step 1. (2-(8-Bromonaphthalen-1-yl)ethoxy)(tert-butyl)dimethylsilane. A 40-mL vial was charged with imidazole (1.38 g, 20.3 mmol), (1,1-dimethylethyl)dimethylsilyl chloride (1.22 g, 8.12 mmol), 2-(8-bromonaphthalen-1-yl)ethanol (1.7 g, 6.8 mmol, WuXi App Tec Co. Ltd.) and N,N-dimethylformamide (7.5 mL). The reaction mixture was stirred at rt for 16 h. Water and DCM were added to the mixture and the organic layer was separated, dried ($Na_2SO_4$) and concentrated. The crude product was purified by column chromatography on silica gel, eluting with a gradient of 0-85% 3:1 EtOAc/EtOH (with 2% triethylamine additive) in heptane to yield (2-(8-bromonaphthalen-1-yl)ethoxy)(tert-butyl)dimethylsilane (1.12 g, 3.07 mmol, 45% yield).

Step 2. tert-Butyldimethyl(2-(8-(4,4,5,5-tetramethyl-1,3,2-dioxaborolan-2-yl)naphthalen-1-yl)ethoxy)silane. (2-(8-bromonaphthalen-1-yl)ethoxy)(tert-butyl)dimethylsilane (0.74 g, 2.0 mmol) was dissolved in tetrahydrofuran (13.5 mL) and cooled to −78° C. n-Butyl lithium (1.6 M in hexanes, 1.2 mL, 3.1 mmol) was added dropwise and the mixture was stirred at −78° C. for 10 min. 2-Isopropoxy-4,4,5,5-tetramethyl-1,3,2-dioxaborolane (0.75 mL, 3.7 mmol) was then added dropwise and the mixture was stirred at −78° C. for 10 min. Saturated aq. $NH_4Cl$ was added, the mixture was allowed to warm to rt and the aqueous layer was extracted with EtOAc. The combined organic layers were dried over $Na_2SO_4$, filtered and volatiles were removed in vacuo. The residue was purified via column chromatography (0-5% EtOAc in heptane) to yield tert-butyldimethyl(2-(8-(4,4,5,5-tetramethyl-1,3,2-dioxaborolan-2-yl)naphthalen-1-yl)ethoxy)silane (0.61 g, 1.50 mmol, 73% yield) as white solid. m/z (ESI): 413.2 $(M+H)^+$.

Step 3. Ethyl 2-(1-(7-(8-(2-((tert-butyldimethylsilyl)oxy)ethyl)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate. An 8-mL vial was charged with tert-butyldimethyl(2-(8-(4,4,5,5-tetramethyl-1,3,2-dioxaborolan-2-yl)naphthalen-1-yl)ethoxy)silane (0.18 g, 0.44 mmol), ethyl 2-(1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (0.15 g, 0.29 mmol, Step 1 of Example 39), phosphoric acid (potassium) (0.25 g, 1.12 mmol,), cataCXium A Pd G3 (43 mg, 0.059 mmol), tetrahydrofuran (1.4 mL) and water (140 μL). The reaction was stirred at 80° C. for 1 h. After cooling to rt, the crude mixture was purified by column chromatography on silica gel, eluting with a gradient of 0-85% 3:1 EtOAc/EtOH (with 2% triethylamine additive) in heptane, to yield ethyl 2-(1-(7-(8-(2-((tert-butyldimethylsilyl)oxy)ethyl)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (0.15 g, 0.20 mmol, 69% yield). m/z (ESI): 760.2 $(M+H)^+$.

Step 4. Ethyl 2-(1-(8-fluoro-2-(((2R,7aS)-2-fluorotetrahydro-1H-pyrrolizin-7a(5H)-yl)methoxy)-7-(8-(2-hydroxyethyl)naphthalen-1-yl)pyrido[4,3-d]pyrimidin-4-yl)piperidin-3-yl)acetate. A 40 mL vial was charged with tetrabutylammonium fluoride (1 N in THF, 0.51 mL, 0.51 mmol) and ethyl 2-(1-(7-(8-(2-((tert-butyldimethylsilyl)oxy)ethyl)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (154 mg, 0.20 mmol). The solids were then dissolved with tetrahydrofuran (2 mL) and the reaction was allowed to stir at 40° C. for 2 h. The crude mixture was purified by column chromatography on silica gel, eluting with a gradient of 0-85% 3:1 EtOAc/EtOH (with 2% triethylamine) in heptane to yield ethyl 2-(1-(8-fluoro-2-(((2R,7aS)-2-fluorotetrahydro-1H-pyrrolizin-7a(5H)-yl)methoxy)-7-(8-(2-hydroxyethyl)naphthalen-1-yl)pyrido[4,3-d]pyrimidin-4-yl)piperidin-3-yl)acetate (93 mg, 0.14 mmol, 71% yield). m/z (ESI): 646.0 $(M+H)^+$.

Step 5. 2-(1-(8-Fluoro-2-(((2R,7aS)-2-fluorotetrahydro-1H-pyrrolizin-7a(5H)-yl)methoxy)-7-(8-(2-hydroxyethyl)naphthalen-1-yl)pyrido[4,3-d]pyrimidin-4-yl)piperidin-3-yl)acetic acid. Ethyl 2-(1-(8-fluoro-2-(((2R,7aS)-2-fluorotetrahydro-1H-pyrrolizin-7a(5H)-yl)methoxy)-7-(8-(2-hydroxyethyl)naphthalen-1-yl)pyrido[4,3-d]pyrimidin-4-yl)piperidin-3-yl)acetate (93 mg, 0.14 mmol) was stirred in the presence of lithium hydroxide, monohydrate (60 mg, 1.4 mmol) in a mixture of water (0.35 mL) and THF (0.35 mL) at 40° C. for 1 h. N,N-diethyl-ethanamine hydrochloride (0.20 g, 1.44 mmol) was added to quench the reaction. The crude product was purified by reverse phase chromatography using formic acid as modifier to yield 2-(1-(8-fluoro-2-(((2R,7aS)-2-fluorotetrahydro-1H-pyrrolizin-7a(5H)-yl)methoxy)-7-(8-(2-hydroxyethyl)naphthalen-1-yl)pyrido[4,3-d]pyrimidin-4-yl)piperidin-3-yl)acetic acid (32 mg, 0.052 mmol, 36% yield) as off-white solid. m/z (ESI): 618.2 $(M+H)^+$.

Step 6. (15R)-31-Fluoro-8-(((2R,7aS)-2-fluorotetrahydro-1H-pyrrolo[1,2-a]pyrrol-7a(5H)-yl)methoxy)-18-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one, (15S)-31-fluoro-8-(((2R,7aS)-2-fluorotetrahydro-1H-pyrrolo[1,2-a]pyrrol-7a(5H)-yl)methoxy)-18-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one. 2-(1-(8-Fluoro-2-(((2R,7aS)-2-fluorotetrahydro-1H-pyrrolizin-7a(5H)-yl)methoxy)-7-(8-(2-hydroxyethyl)naphthalen-1-yl)pyrido[4,3-d]pyrimidin-4-yl)piperidin-3-yl)acetic acid (32 mg, 0.052 mmol) was dissolved in DCE (15 mL), 2-chloro-1-methylpyridinium iodide (79 mg, 0.31 mmol, Ambeed, Inc.) and triethylamine (0.073 mL, 0.52 mmol) were added and the mixture was stirred at 50° C. for 1 h. The volatiles were removed in vacuo and the crude product was purified via reverse phase HPLC (10-90% $MeCN/H_2O$+0.1% TFA) to yield (15R)-31-fluoro-8-(((2R,7aS)-2-fluorotetrahydro-1H-pyrrolo[1,2-a]pyrrol-7a(5H)-yl)methoxy)-18-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one, (15S)-31-fluoro-8-(((2R,7aS)-2-fluorotetrahydro-1H-pyrrolo[1,2-a]pyrrol-7a(5H)-yl)methoxy)-18-oxa-3,7,9,11-tetraazahexacyclo[19.7.1.1~2,6~.1~11,15~.0~5,10~.0~25,29]hentriaconta-1(28),2(31),3,5,7,9,21,23,25(29),26-decaen-17-one 2,2,2-trifluoroacetate (31 mg, 0.043 mmol, 84% yield) as white solid. m/z (ESI): 600.2 $(M+H)^+$. $^1H$ NMR (400 MHz, METHANOL-$d_4$) δ ppm 9.15-9.27 (m, 1H), 8.08-8.15 (m, 1H), 7.93-7.99 (m, 1H), 7.66 (s, 2H), 7.46-7.55 (m, 1H), 7.29-7.45 (m, 1H), 5.48-5.72 (m, 1H), 4.86-5.24 (m, 2H), 4.64-4.79 (m, 2H), 3.84-4.34 (m, 5H), 3.41-3.54 (m, 1H), 3.20-3.31 (m, 1H), 2.32-2.87 (m, 7H), 2.17-2.28 (m, 1H), 2.08 (br d, J=15.7 Hz, 1H), 1.46-2.04 (m, 5H).

(11Z,17S)-9-Chloro-30-fluoro-24-(((2R,7aS)-2-fluorotetrahydro-1H-pyrrolo[1,2-a]pyrrol-7a(5H)-yl)methoxy)-16-oxa-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one bis(2,2,2-trifluoroacetate) (Example 35)
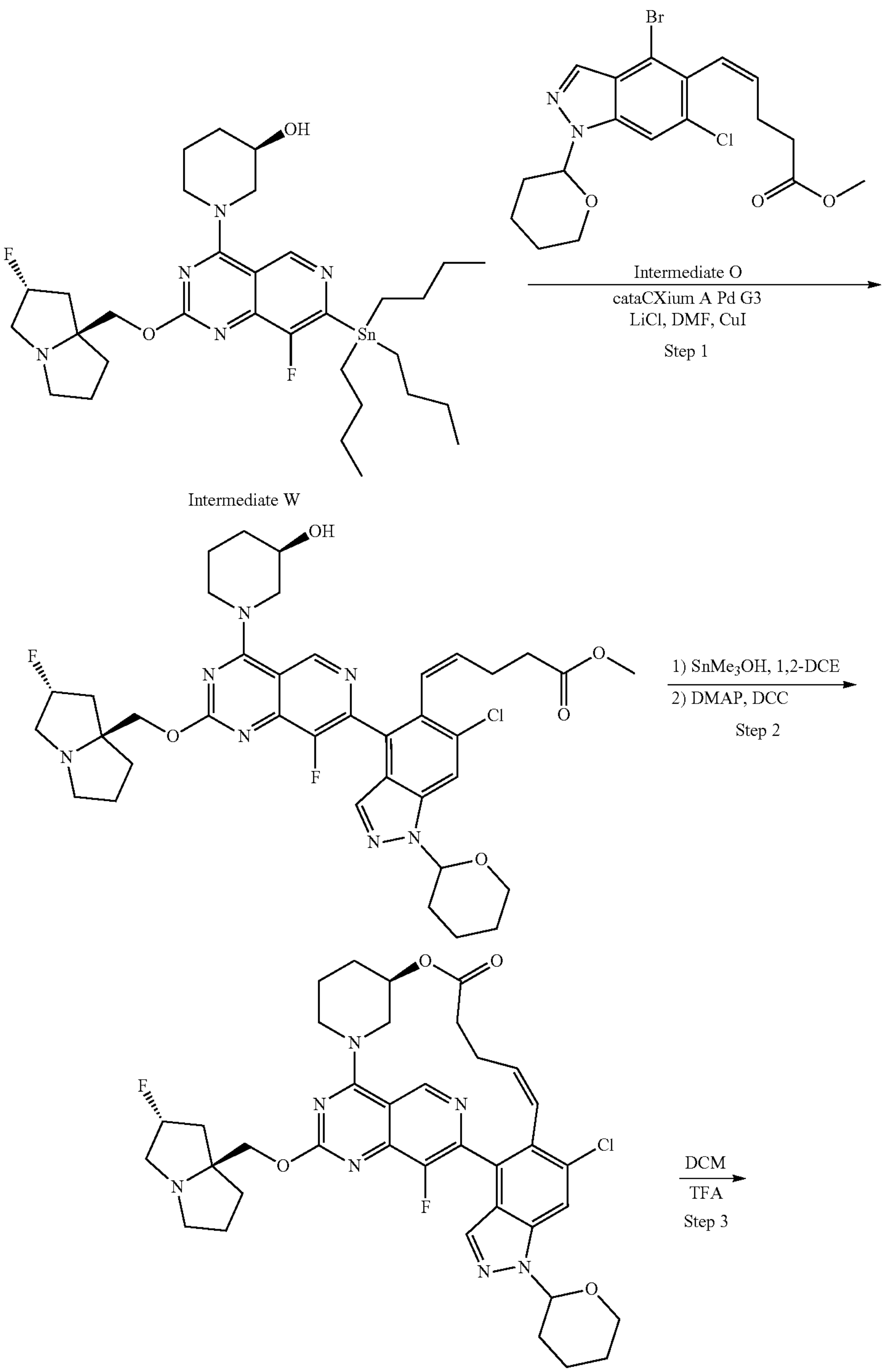

-continued

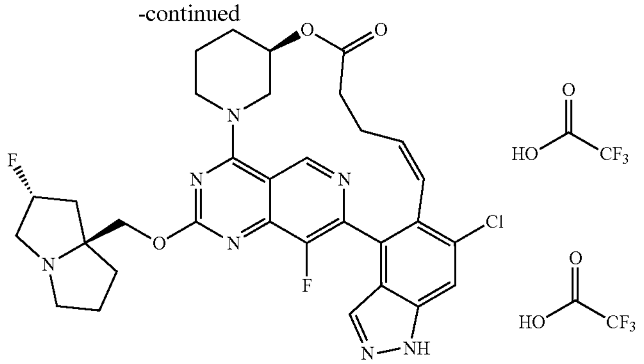

Example 35

Step 1. Methyl (Z)-5-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)pent-4-enoate. A vial was charged with methyl (Z)-5-(4-bromo-6-chloro-1-(tetrahydro-2H-pyran-2-yl)-1H-indazol-5-yl)pent-4-enoate (0.22 g, 0.51 mmol, Intermediate O), (R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-ol (0.53 g, 0.76 mmol, Intermediate W), cataCXium A Pd G3 (37 mg, 0.05 mmol), copper(I) iodide (48 mg, 0.25 mmol), lithium chloride (43 mg, 1.01 mmol) and degassed DMF (3.4 mL). The reaction mixture was heated to 100° C. for 7 h. After cooling to rt, the reaction mixture was purified by reverse phase column chromatography. The desired fractions were basified with saturated aqueous sodium bicarbonate and extracted with EtOAc. The combined organic phases were concentrated under reduced pressure to provide methyl (Z)-5-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)pent-4-enoate (0.18 g, 0.24 mmol, 47% yield) as tan solid (mixture of isomers). m/z (ESI): 752.0 $(M+H)^+$.

Step 2. N-(tetrahydro-2H-pyran-2-yl)-(11Z,17R)-9-chloro-30-fluoro-24-(((2R,7aS)-2-fluorotetrahydro-1H-pyrrolo[1,2-a]pyrrol-7a(5H)-yl)methoxy)-16-oxa-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one. To a 20 mL vial was charged with methyl (Z)-5-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)pent-4-enoate (0.18 g, 0.24 mmol), trimethyltin hydroxide (0.43 g, 2.39 mmol), and 1,2-dichloroethane (1.2 mL). The solution was heated to 70° C. for 18 h. After cooling to rt, the reaction mixture was filtered and rinsed with DCM. The crude material was purified by reverse phase column chromatography, eluting with 5-50% acetonitrile in water with 0.1% formic acid, to provide (Z)-5-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)pent-4-enoic acid formate salt (84 mg, 0.11 mmol, 45% yield) as white solid. m/z (ESI): 738.2 $(M+H)^+$.

To a 40 mL vial was charged with (Z)-5-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)pent-4-enoic acid (80 mg, 0.11 mmol), N,N'-dicyclohexylcarbodiimide (0.10 g, 0.49 mmol), DMAP (60 mg, 0.49 mmol), and dichloromethane (11 mL). The reaction mixture was stirred at rt for 4.5 h. The mixture was concentrated in vacuo and the crude material was purified by reverse phase column chromatography, to provide N-(tetrahydro-2H-pyran-2-yl)-(11Z,17R)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one (63 mg, 0.087 mmol, 80% yield) as yellow solid as a mixture of the desired product and dimer. m/z (ESI): 720.2 $(M+H)^+$.

Step 3. (11Z,17R)-9-chloro-30-fluoro-24-(((2R,7aS)-2-fluorotetrahydro-1H-pyrrolo[1,2-a]pyrrol-7a(5H)-yl)methoxy)-16-oxa-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one bis(2,2,2-trifluoroacetate). To a 20 mL vial was charged with N-(tetrahydro-2H-pyran-2-yl)-(11Z,17R)-9-chloro-30-fluoro-24-(((2R,7aS)-2-fluorotetrahydro-1H-pyrrolo[1,2-a]pyrrol-7a(5H)-yl)methoxy)-16-oxa-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one (63 mg, 0.087 mmol) and DCM (0.8 mL). Trifluoroacetic acid (0.13 mL, 1.74 mmol) was added, and the reaction mixture was stirred at rt for 90 min. The reaction was cooled to 0° C. and diluted with triethylamine (3 mL). The mixture was concentrated and the crude material was purified by reverse-phase preparative HPLC to provide (11Z,17R)-9-chloro-30-fluoro-24-(((2R,7aS)-2-fluorotetrahydro-1H-pyrrolo[1,2-a]pyrrol-7a(5H)-yl)methoxy)-16-oxa-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one (15 mg, 0.017 mmol, 19% yield) as light-yellow solid. m/z (ESI): 635.8 $(M+H)^+$. $^1H$ NMR (400 MHz, METHANOL-$d_4$) δ ppm 9.33 (s, 1H), 8.13 (d, J=0.8 Hz, 1H), 7.86 (s, 1H), 6.56 (br d, J=11.9 Hz, 1H), 5.69-5.56 (m, 1H), 5.38 (td, J=12.1, 2.5 Hz, 1H), 5.06-5.19 (m, 2H), 4.95 (br s, 1H), 4.76 (br d, J=12.1 Hz, 1H), 4.66 (d, J=12.1 Hz, 1H), 3.87-4.11 (m, 5H), 3.43-3.58 (m, 1H), 3.20-3.31 (m, 1H), 2.55-2.76 (m, 2H), 2.33-2.48 (m, 3H), 2.17-2.31 (m, 2H), 2.01-2.15 (m, 2H), 1.68-1.92 (m, 4H), 1.59 (q, J=12.8 Hz, 1H), 1.22-1.45 (m, 1H), 0.45-0.55 (m, 1H). $^{19}F$ NMR (376 MHz, METHANOL-$d_4$) δ ppm −77.31 (s), −137.90 (s), −173.90–−174.10 (m).

(17R)-9-Chloro-30-fluoro-24-(((2R,7aS)-2-fluorotetrahydro-1H-pyrrolo[1,2-a]pyrrol-7a(5H)-yl)methoxy)-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one bis(2,2,2-trifluoroacetate) (Example 36)

Example 36

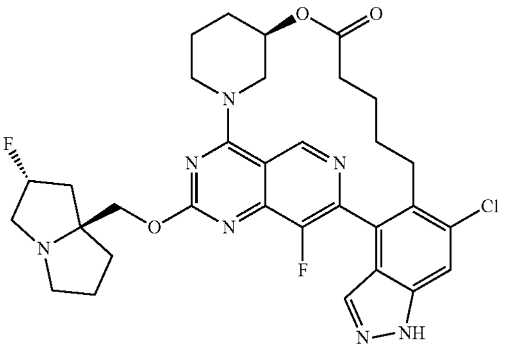

The title compound was synthesized in an analogous fashion to Example 35, using 5-(4-bromo-6-chloro-1-(tetrahydro-2H-pyran-2-yl)-1H-indazol-5-yl)pentanoate (Intermediate P) in Step 1. m/z (ESI): 638.0 $(M+H)^+$. $^1H$ NMR (400 MHz, METHANOL-$d_4$) δ ppm 9.26 (s, 1H), 7.84 (s, 1H), 7.81 (s, 1H), 5.56-5.69 (m, 1H), 5.10 (br t, J=13.4 Hz, 2H), 4.98 (s, 1H), 4.76 (s, 1H), 4.66-4.73 (m, 1H), 3.88-4.11 (m, 4H), 3.51 (td, J=10.7, 6.0 Hz, 1H), 3.23-3.31 (m, 1H), 2.59-2.85 (m, 3H), 2.32-2.52 (m, 4H), 2.21 (br d, J=6.5 Hz, 1H), 2.00-2.13 (m, 3H), 1.88 (br d, J=10.5 Hz, 1H), 1.69-1.80 (m, 1H), 1.46-1.69 (m, 2H), 1.31 (s, 1H), 1.02-1.24 (m, 3H). $^{19}F$ NMR (376 MHz, METHANOL-$d_4$) δ ppm −77.29 (s, 6 F), −141.76 (s, 1 F), −175.71-−172.59 (m, 1 F).

(18R)-9-Chloro-31-fluoro-25-(((2R,7aS)-2-fluorotetrahydro-1H-pyrrolo[1,2-a]pyrrol-7a(5H)-yl)methoxy)-14,17-dioxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one bis(2,2,2-trifluoroacetate) (Example 37)

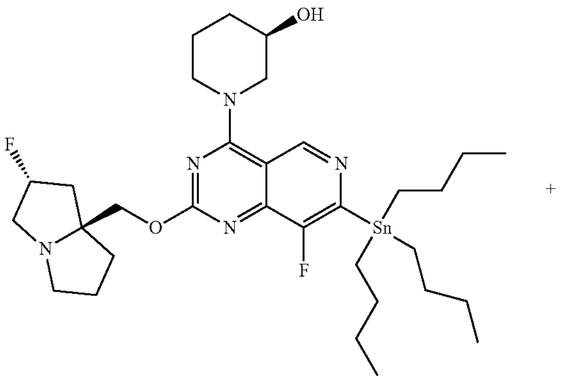

Intermediate W

-continued

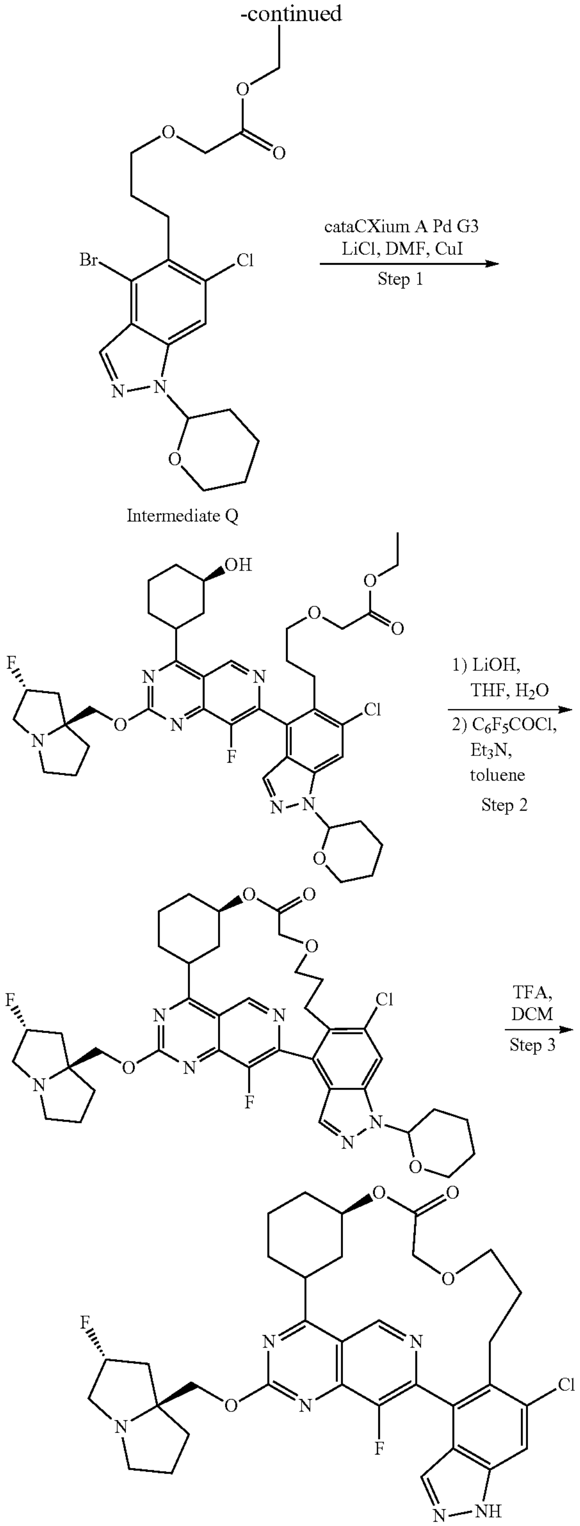

Intermediate Q

Example 37

Step 1. Ethyl 2-(3-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)propoxy) acetate. A vial was charged with (R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)

piperidin-3-ol (0.59 g, 0.85 mmol, Intermediate W), ethyl 2-(3-(4-bromo-6-chloro-1-(tetrahydro-2H-pyran-2-yl)-1H-indazol-5-yl)propoxy)acetate (0.26 g, 0.57 mmol, Intermediate Q), cataCXium A Pd G3 (83 mg, 0.11 mmol), copper(I) iodide (54 mg, 0.28 mmol), and degassed N,N-dimethylformamide (3.8 mL). The reaction mixture was heated to 100° C. for 16 h. After cooling to rt, the mixture was purified by reverse phase column chromatography, eluting with a gradient of 5-80% (0.1% formic acid MeCN)/(0.1% formic acid water) over 10 min. The desired fractions were basified with saturated aqueous sodium bicarbonate and extracted with EtOAc. The combined organics were concentrated under reduced pressure to provide ethyl 2-(3-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)propoxy)acetate (0.18 g, 0.24 mmol, 41% yield) as tan solid. m/z (ESI): 784.2 $(M+H)^+$.

Step 2. N-(tetrahydro-2H-pyran-2-yl)-(18R)-9-Chloro-31-fluoro-25-(((2R,7aS)-2-fluorotetrahydro-1H-pyrrolo[1,2-a]pyrrol-7a(5H)-yl)methoxy)-14,17-dioxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one. A 40 mL vial was charged with ethyl 2-(3-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)propoxy)acetate (0.43 g, 0.55 mmol) in THF (2.1 mL) and water (2.1 mL). Then lithium hydroxide, monohydrate (46 mg, 1.1 mmol) was added, and the mixture was heated to 45° C. for 25 min. After cooling to rt, the reaction mixture was quenched by addition of 2 N aqueous hydrochloric acid (0.55 mL, 1.1 mmol) dropwise. This solution was then extracted with dichloromethane. The combined organic layers were then dried over $MgSO_4$, filtered, and concentrated to afford 2-(3-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)propoxy)acetic acid as yellow solid (0.38 g, 0.5 mmol, 91% yield). m/z (ESI): 756.2 $(M+H)^+$.

A 250 mL round bottom flask was charged with 2-(3-(6-chloro-4-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)propoxy)acetic acid (0.13 g, 0.18 mmol), toluene (35 mL), and triethylamine (50 μL, 0.35 mmol). The reaction mixture was heated to 90° C. and pentafluorobenzoylchloride (49 μL, 0.21 mmol, Ambeed, Inc.) was added. The reaction was heated at 90° C. for 16 h. After cooling to rt, the reaction mixture was concentrated and the residue was purified by reverse phase chromatography, eluting with 0-100% acetonitrile with 0.1% TFA in water with 0.1% TFA to provide N-(tetrahydro-2H-pyran-2-yl)-(18R)-9-chloro-31-fluoro-25-(((2R,7aS)-2-fluorotetrahydro-1H-pyrrolo[1,2-a]pyrrol-7a(5H)-yl)methoxy)-14,17-dioxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one (55 mg, 0.075 mmol, 42% yield) as yellow solid. m/z (ESI): 738.2 $(M+H)^+$.

Step 3. (18R)-9-Chloro-31-fluoro-25-(((2R,7aS)-2-fluorotetrahydro-1H-pyrrolo[1,2-a]pyrrol-7a(5H)-yl)methoxy)-14,17-dioxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one bis(2,2,2-trifluoroacetate). To a 20 mL vial was charged with N-(tetrahydro-2H-pyran-2-yl)-(18R)-9-chloro-31-fluoro-25-(((2R,7aS)-2-fluorotetrahydro-1H-pyrrolo[1,2-a]pyrrol-7a(5H)-yl)methoxy)-14,17-dioxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one (55 mg, 0.075 mmol) and DCM (0.75 mL). Trifluoroacetic acid (0.12 mL, 1.49 mmol) was added the reaction mixture was stirred at rt for 2 h, and then warmed to 30° C. for 45 min. After cooling to rt, the mixture was concentrated and purified by reverse phase HPLC to provide (18R)-9-chloro-31-fluoro-25-(((2R,7aS)-2-fluorotetrahydro-1H-pyrrolo[1,2-a]pyrrol-7a(5H)-yl)methoxy)-14,17-dioxa-5,6,22,24,26,30-hexaazahexacyclo[25.3.1.1~18,22~.0~2,10~.0~3,7~.0~23,28~]dotriaconta-1(31),2,4,7,9,23,25,27,29-nonaen-16-one bis(2,2,2-trifluoroacetate) (27 mg, 0.031 mmol, 41% yield) as white solid. m/z (ESI): 654.0 $(M+H)^+$. $^1H$ NMR (400 MHz, METHANOL-$d_4$) δ ppm 9.24 (s, 1H), 7.81 (s, 1H), 7.72 (s, 1H), 5.67-5.54 (m, 1H), 5.24 (br d, J=13.6 Hz, 1H), 5.00 (br d, J=13.2 Hz, 1H), 4.85-4.94 (m, 1H), 4.69-4.79 (m, 3H), 4.07 (d, J=14.4 Hz, 2H), 3.86-4.02 (m, 3H), 3.63 (d, J=15.3 Hz, 1H), 3.45-3.56 (m, 2H), 3.35-3.41 (m, 2H), 3.16 (d, J=15.5 Hz, 1H), 2.87-2.96 (m, 1H), 2.58-2.83 (m, 3H), 2.33-2.50 (m, 3H), 2.03-2.26 (m, 3H), 1.97 (br d, J=11.3 Hz, 1H), 1.79-1.90 (m, 1H), 1.72 (br d, J=11.5 Hz, 1H), 1.43 (dt, J=13.8, 10.0 Hz, 1H), 1.31 (s, 1H). $^{19}F$ NMR (376 MHz, METHANOL-$d_4$) δ ppm −80.56-76.05 (m), −141.86−−139.09 (m), −174.12 (br s).

TABLE 27

Additional Examples 89 to 91. Prepared in an Analogous Manner to Example 37.

| Ex.# | Structure & Name | Salt Form | Reagent | Method Change |
|---|---|---|---|---|
| 89 | 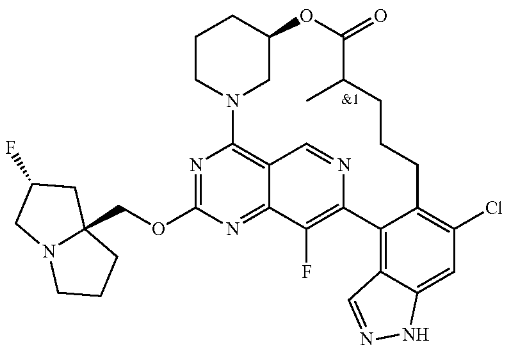 [SMILES: CC1CCCc2c(Cl)cc3[nH]ncc3c2-c2ncc3c(nc(OC[C@@]45CCCN4C[C@H](F)C5)nc3c2F)N2CCC[C@H](C2)OC1=O] | bis(2, 2,2-trifluoro-acetate) | Step 1. Intermediate WW | |

TABLE 27-continued

| Additional Examples 89 to 91. Prepared in an Analogous Manner to Example 37. | | | | |
|---|---|---|---|---|
| Ex.# | Structure & Name | Salt Form | Reagent | Method Change |
| | (14R,17R)-9-chloro-30-fluoro-24-(((2R,7aS)-2-fluorotetrahydro-1H-pyrrolo[1,2-a]pyrrol-7a(5H)-yl)methoxy)-14-methyl-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and (14S,17R)-9-chloro-30-fluoro-24-(((2R,7aS)-2-fluorotetrahydro-1H-pyrrolo[1,2-a]pyrrol-7a(5H)-yl)methoxy)-14-methyl-16-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | | | |
| 90 | 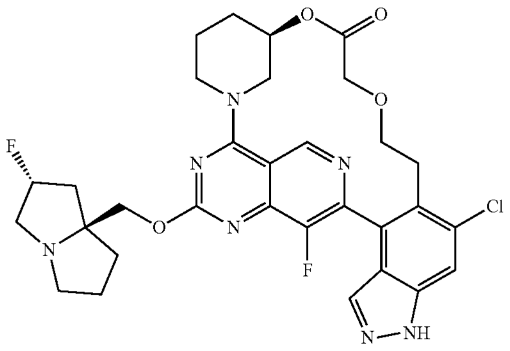 [SMILES: O=C1COCCc2c(Cl)cc3[nH]ncc3c2-c2ncc3c(nc(OC[C@@]45CCCN4C[C@H](F)C5)nc3c2F)N2CCC[C@H](C2)O1] (17R)-9-chloro-30-fluoro-24-(((2R,7aS)-2-fluorotetrahydro-1H-pyrrolo[1,2-a]pyrrol-7a(5H)-yl)methoxy)-13,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | Bis (2,2,2-trifluoro-aceate) | Step 1. Intermediate XX | |
| 91 | 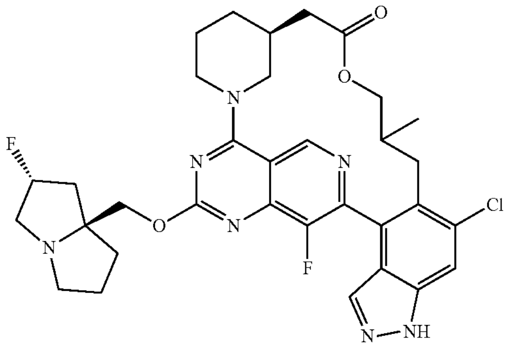 [SMILES: CC1COC(=O)C[C@@H]2CCCN(C2)c2nc(OC[C@@]34CCCN3C[C@H](F)C4)nc3c(F)c(ncc23)-c2c(c(Cl)cc3[nH]ncc23)C1] (12R,17S)-9-chloro-30-fluoro-24-(((2R,7aS)-2-fluorotetrahydro-1H-pyrrolo[1,2-a]pyrrol-7a(5H)-yl)methoxy)-12-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one, and (12S,17S)-9-chloro-30-fluoro-24-(((2R,7aS)-2-fluorotetrahydro-1H-pyrrolo[1,2-a]pyrrol-7a(5H)-yl)methoxy)-12-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | Bis(2,2,2-trifluoro-acetate) | Step 1. Intermediate YY and Intermediate AAA | |

TABLE 28

Analytical Data for Examples 89 to 91.

| Cmpd. # | MS m/z (ESI): $(M + H)^+$ | $^1H$ and $^{19}F$ NMR |
|---|---|---|
| 89 | 640.0 | $^1H$ NMR (400 MHz, METHANOL-$d_4$) δ ppm 9.26-9.38 (m, 1 H), 7.77-7.93 (m, 2 H), 5.53-5.73 (m, 1 H), 5.03-5.15 (m, 3 H), 4.63-4.78 (m, 2 H), 4.00-4.13 (m, 2 H), 3.88-3.97 (m, 3 H), 3.37-3.56 (m, 3 H), 3.06-3.17 (m, 2 H), 3.02-3.21 (m, 2 H), 2.83-2.97 (m, 1 H), 2.64-2.78 (m, 2 H), 2.34-2.52 (m, 3 H), 2.17-2.27 (m, 1 H), 1.99-2.12 (m, 2 H), 1.83-1.91 (m, 1 H), 1.69-1.78 (m, 1 H), 1.25-1.42 (m, 2 H). $^{19}F$ NMR (376 MHz, METHANOL-$d_4$) δ ppm −78.46−−76.91 (m), −142.61−−141.26 (m), −174.29−−175.41 (m). |
| 90 | 640.0 | $^1H$ NMR (400 MHz, METHANOL-$d_4$) δ ppm 9.26-9.38 (m, 1 H), 7.77-7.93 (m, 2 H), 5.53-5.73 (m, 1 H), 5.03-5.15 (m, 3 H), 4.63-4.78 (m, 2 H), 4.00-4.13 (m, 2 H), 3.88-3.97 (m, 3 H), 3.37-3.56 (m, 3 H), 3.06-3.17 (m, 2 H), 3.02-3.21 (m, 2 H), 2.83-2.97 (m, 1 H), 2.64-2.78 (m, 2 H), 2.34-2.52 (m, 3 H), 2.17-2.27 (m, 1 H), 1.99-2.12 (m, 2 H), 1.83-1.91 (m, 1 H), 1.69-1.78 (m, 1 H), 1.25-1.42 (m, 2 H). $^{19}F$ NMR (376 MHz, METHANOL-$d_4$) δ ppm −78.46−−76.91 (m, 6 F), −142.61−−141.26 (m, 1 F), −174.29−−175.41 (m, 1 F). |
| 91 | 651.8 | $^1H$ NMR (400 MHz, METHANOL-$d_4$) δ ppm 9.12-9.34 (m, 1 H), 7.76-7.99 (m, 2 H), 5.51-5.79 (m, 1 H), 5.13-5.29 (m, 1 H), 4.85-4.95 (m, 1 H), 4.60-4.72 (m, 2 H), 3.82-4.16 (m, 4H), 3.61-3.73 (m, 1 H), 3.42-3.56 (m, 1 H), 3.13-3.29 (m, 2 H), 2.53-2.85 (m, 4 H), 2.29-2.51 (m, 4 H), 2.01-2.25 (m, 4 H), 1.59-1.90 (m, 4 H), 0.94 (br d, J = 7.1 Hz, 3 H). |

(17R)-30-Fluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one bis(2,2,2-trifluoroacetate) (Example 38)

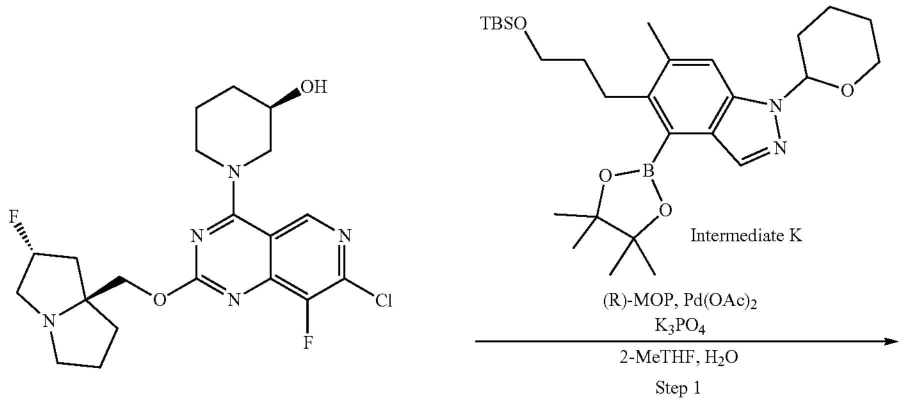

-continued

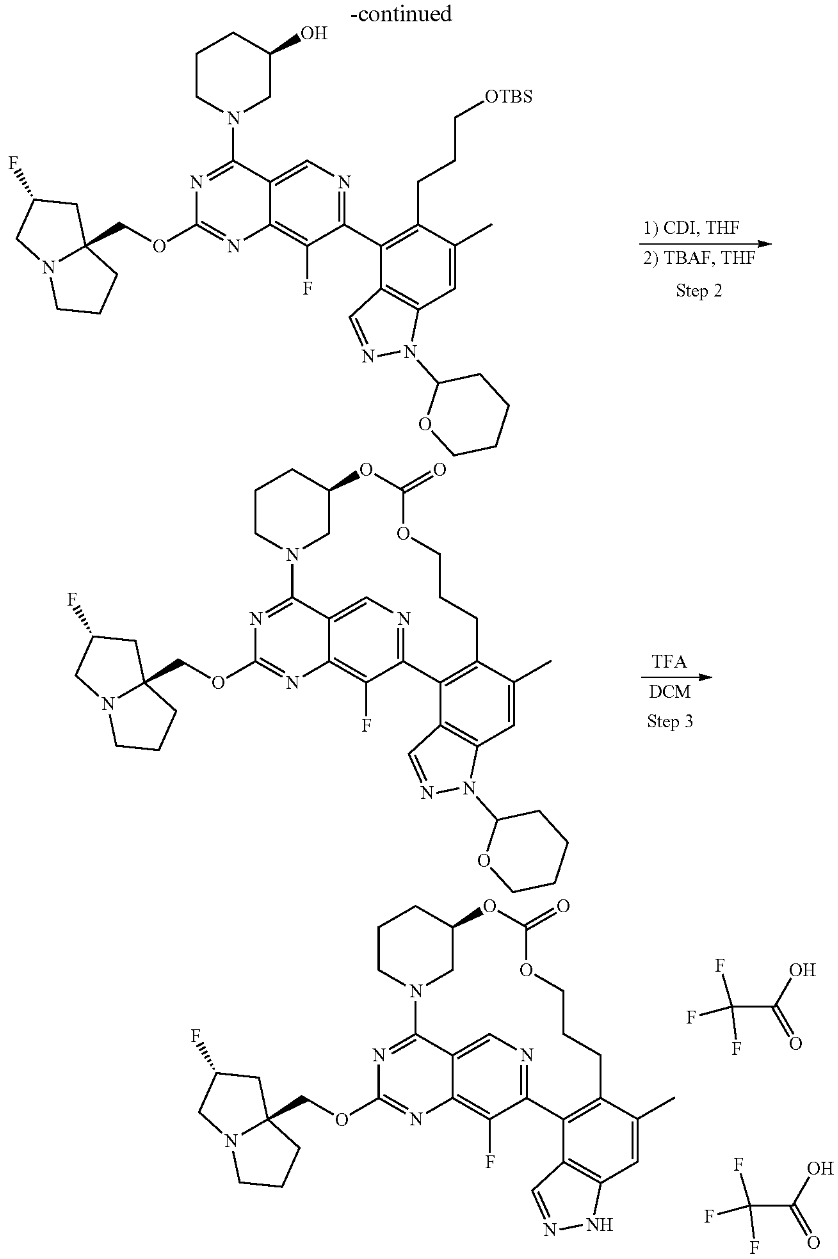

Example 38

Step 1. (3R)-1-(7-(5-(3-((tert-Butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. A 20 mL vial was charged with (R)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.15 g, 0.34 mmol), 5-(3-((tert-butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole (0.26 g, 0.51 mmol, Intermediate K), potassium phosphate (0.18 g, 0.85 mmol), (R)-(+)-2-(diphenylphosphino)-2'-methoxy-1,1'-binaphthyl (64 mg, 0.14 mmol), and palladium (II) acetate (15 mg, 0.068 mmol). The vial was purged with nitrogen and then the reactants were suspended in degassed 2-methyltetrahydrofuran (2.7 mL) and water (0.7 mL). The reaction was then sealed and heated to 80° C. for 3.5 h. After cooling to rt, the reaction was concentrated and the residue was purified by column chromatography on silica gel, eluting with a gradient of 0-70% of a 3:1 EtOAc:EtOH mixture (with 2% triethylamine) in heptane to provide (3R)-1-(7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.24 g, 0.3 mmol, 89% yield) as light yellow solid. m/z (ESI): 792.2 $(M+H)^+$.

Step 2. N-(tetrahydro-2H-pyran-2-yl)-(17R)-30-Fluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28- nonaen-15-one. A 40 mL vial was charged with (3R)-1-(7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.10 g, 0.13 mmol) and 1,1'-carbonyldiimidazole (51 mg, 0.32 mmol). The solids were dissolved with tetrahydrofuran (1.3 mL) and the reaction was stirred at rt for 16 h. The reaction mixture was diluted with THF (15 mL) and tetrabutylammonium fluoride (1 M in THF, 0.32 mL, 0.32 mmol) was added. The reaction mixture was stirred at rt for 6 h, concentrated and the residue was purified by column chromatography on silica gel, eluting with a gradient of 0-80% of a 3:1 EtOAc:EtOH (with 2% triethylamine) in heptane, to provide N-(tetrahydro-2H-pyran-2-yl)-(17R)-30-Fluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (51 mg, 0.072 mmol, 57% yield). m/z (ESI): 704.2 $(M+H)^+$.

Step 3. (17R)-30-Fluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one bis(2,2,2-trifluoroacetate). N-(tetrahydro-2H-pyran-2-yl)-(17R)-30-fluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (51 mg, 0.072 mmol) was dissolved in DCM (3 mL) and 1,1,1-trifluoroacetic acid (0.43 mL, 3.8 mmol) was added. After stirring for 1.5 h at rt, the reaction was concentrated and the residue that was purified via reverse phase HPLC to provide (17R)-30-fluoro-24-(((2R,7aS)-2-fluorotetrahydro-1H-pyrrolo [1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one bis(2,2,2-trifluoroacetate) (35 mg, 0.042 mmol, 33% yield) as white solid. m/z (ESI): 620.2 $(M+H)^+$. $^1H$ NMR (400 MHz, METHANOL-$d_4$) δ ppm 1.52-1.65 (m, 2H) 1.67-1.75 (m, 1H) 1.89-1.99 (m, 1H) 1.99-2.14 (m, 2H) 2.16-2.27 (m, 1H) 2.33-2.50 (m, 3H) 2.56 (s, 5H) 2.61-2.90 (m, 2H) 3.24-3.32 (m, 1H) 3.45-3.57 (m, 1H) 3.63-3.71 (m, 1H) 3.85-4.15 (m, 4H) 4.20-4.30 (m, 1H) 4.65-4.78 (m, 2H) 4.90-4.97 (m, 1H) 5.06-5.18 (m, 2H) 5.50-5.69 (m, 1H) 7.50-7.60 (m, 1H) 7.75-7.82 (m, 1H) 9.30 (s, 1H). $^{19}F$ NMR (376 MHz, METHANOL-$d_4$) δ ppm −77.43 (s), −142.00 (s), −174.08 (s).

TABLE 29

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 92 | 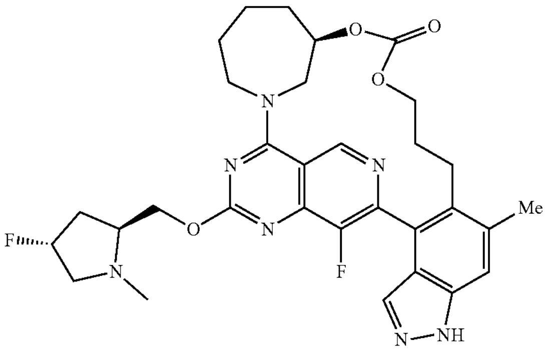 [SMILES: Cc1cc2[nH]ncc2c2c1CCCOC(=O)O[C@@H]1CCCCN(C1)c1nc(OC[C@@H]3C[C@@H](F)CN3C)nc3c(F)c-2ncc13] (26R)-32-fluoro-4-(((2S,4R)-4-fluoro-1-methyl-2-pyrrolidinyl)methoxy)-18-methyl-23,25-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate) | Step 1. Intermediate RR | Step 1: (S)-(-)-2-(diphenyl-phosphino)-2-methoxy-1-,1-binaphthyl (s)-mop was used instead of (R)-MOP |
| 93 | 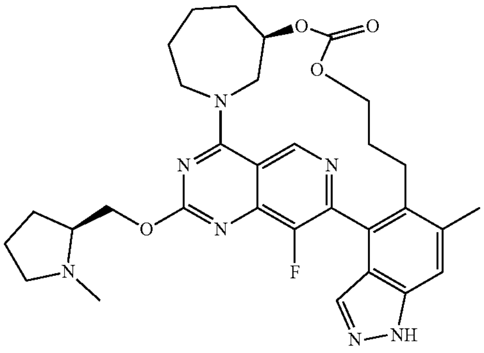 [SMILES: Cc1cc2[nH]ncc2c2c1CCCOC(=O)O[C@@H]1CCCCN(C1)c1nc(OC[C@@H]3CCCN3C)nc3c(F)c-2ncc13] | (2,2,2-trifluoro-acetate) | Step 1. Intermediate BBB | |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| | (17R,18S)-18,30-difluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and (17S,18R)-18,30-difluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (racemic) | | | |
| 94 | 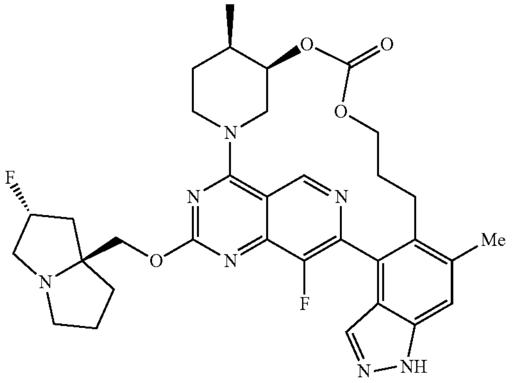 [SMILES: Cc1cc2[nH]ncc2c2c1CCCOC(=O)O[C@H]1CN(CC[C@H]1C)c1nc(OC[C@@]34CCCN3C[C@H](F)C4)nc3c(F)c-2ncc13] (17R,18R)-30-fluoro-24-(((2R,7aS)-2-fluorotetrahydro-1H-pyrrolo[1,2-a]pyrrol-7a(5H)-yl)methoxy)-9,18-dimethyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | bis(2,2,2-trifluoro-acetate) | Step 1. Intermediate CCC | |
| 95 | 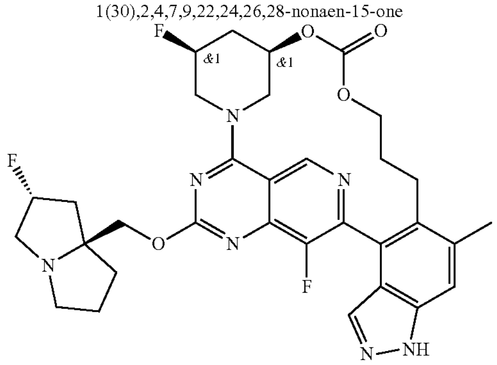 (17R,19S)-19,30-difluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and (17S,19R)-19,30-difluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (racemic) | bis(2,2,2-trifluoro-acetate) | Step 1: Intermediate DDD | |

TABLE 29-continued

| Ex.# | Structure & Name | Salt Form | Reagent | Method Change |
|---|---|---|---|---|
| | Additional Examples 92 to 98, 100 to 102, 179 to 212 and 303 to 368. Prepared in an Analogous Manner to Example 38. | | | |
| 96 | 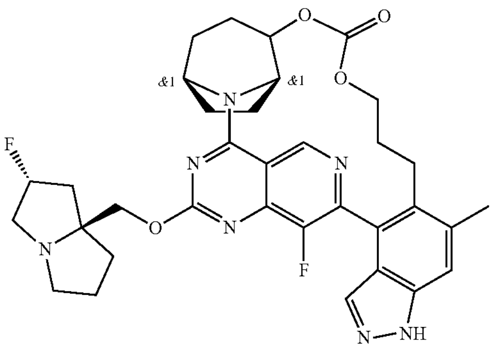 [SMILES: Cc1cc2[nH]ncc2c2c1CCCOC(=O)OC1CC[C@@H]3CC[C@H]1N3c1nc(OC[C@@]34CCCN3C[C@H](F)C4)nc3c(F)c-2ncc13] (17R,20R,23S)-33-fluoro-27-(((2R,7aS)-2-fluorotetrahydro-1H-pyrrolo[1,2-a]pyrrol-7a(5H)-yl)methoxy)-9-methyl-14,16-dioxa-5,6,24,26,28,32-hexaazaheptacyclo[27.3.1.0~2,10~.0~3,7~.0~17,23~.0~20,24~.0~25,30~]tritriaconta-1(33),2,4,7,9,25,27,29,31-nonaen-15-one, and (17S,20S,23R)-33-fluoro-27-(((2R,7aS)-2-fluorotetrahydro-1H-pyrrolo[1,2-a]pyrrol-7a(5H)-yl)methoxy)-9-methyl-14,16-dioxa-5,6,24,26,28,32-hexaazaheptacyclo[27.3.1.0~2,10~.0~3,7~.0~17,23~.0~20,24~.0~25,30~]tritriaconta-1(33),2,4,7,9,25,27,29,31-nonaen-15-one (racemic) | bis(2,2,2-trifluoro-acetate) | Step 1. (1R,2S,5S)-8-(7-chloro-8-fluoro-2-(((2R,7aS)-2-fluorotetra-hydro-1H-pyrrolizin-7a(5H)-yl)methoxy) pyrido[4,3-d]pyrimidin-4-yl)-8-azabicyclo[3.2.1]octan-2-ol and Intermediate SS | |
| 97 | 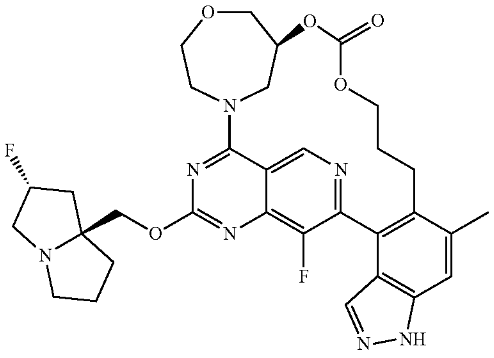 [SMILES: Cc1cc2[nH]ncc2c2c1CCCOC(=O)O[C@@H]1COCCN(C1)c1nc(OC[C@@]34CCCN3C[C@H](F)C4)nc3c(F)c-2ncc13] (26S)-32-fluoro-4-(((2R,7aS)-2-fluorotetrahydro-1H-pyrrolo[1,2-a]pyrrol-7a(5H)-yl)methoxy)-18-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32), 11,13,16,18-nonaen-24-one | Bis (2,2,2-trifluoro-aceate) | Step 1. Intermediate VV | Step 1. cataCXium A Pd G3 was used instead of (R)-MOP/ $Pd(OAc)_2$. Solvent was THF instead of 2-MeTHF. |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 98 | 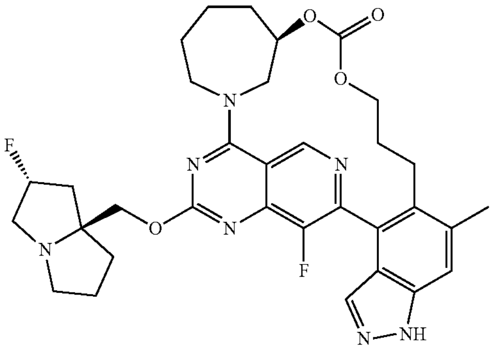 [SMILES: Cc1cc2[nH]ncc2c2c1CCCOC(=O)O[C@@H]1CCCCN(C1)c1nc(OC[C@@]34CCCN3C[C@H](F)C4)nc3c(F)c-2ncc13] (26R)-32-fluoro-4-(((2R,7aS)-2-fluorotetrahydro-1H-pyrrolo[1,2-a]pyrrol-7a(5H)-yl)methoxy)-18-methyl-23,25-dioxa-1,3,5,9,14,15-hexaazahexacyclo[24.4.1.1~6,10~.0~2,7~.0~11,19~.0~12,16~]dotriaconta-2,4,6,8,10(32), 11,13,16,18-nonaen-24-one | Bis (2,2,2-trifluoro-aceate) | Step 1. Intermediate UU | Step 1. cataCXium A Pd G3 was used instead of (R)-MOP/ $Pd(OAc)_2$. Solvent was THF instead of 2-MeTHF. |
| 100 | 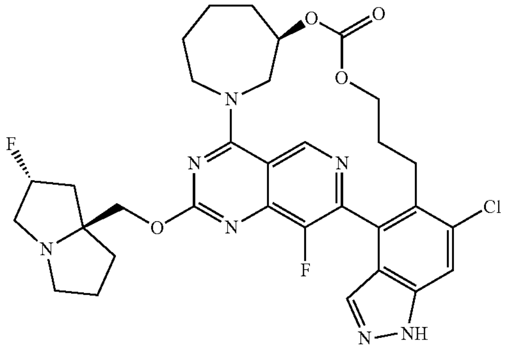 [SMILES: O=C1OCCCc2c(Cl)cc3[nH]ncc3c2-c2ncc3c(nc(OC[C@@]45CCCN4C[C@H](F)C5)nc3c2F)N2CCCC[C@H](C2)O1] (26R)-18-chloro-32-fluoro-4-(((2R,7aS)-2-fluorotetrahydro-1H-pyrrolo[1,2-a]pyrrol-7a(5H)-yl)methoxy)-23,25-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-aceate) | Step 1. Intermediate UU and Intermediate FFF | Step 1. cataCXium A Pd G3 was used instead of (R)-MOP/ $Pd(OAc)_2$. Solvent was THF instead of 2-MeTHF. |
| 101 | 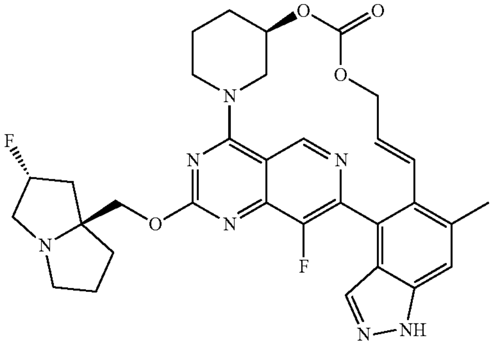 [SMILES: Cc1cc2[nH]ncc2c2c1/C=C/COC(=O)O[C@@H]1CCCN(C1)c1nc(OC[C@@]34CCCN3C[C@H](F)C4)nc3c(F)c-2ncc13] (11E,17R)-30-fluoro-24-(((2R,7aS)-2-fluorotetrahydro-1H-pyrrolo[1,2-a]pyrrol-7a(5H)-yl)methoxy)-9-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,11,22,24,26,28-decaen-15-one | | Step 2. Intermediate EEE | Step 1 was not performed. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 102 | 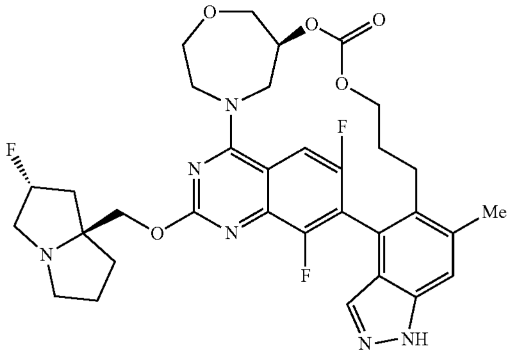 [SMILES: Cc1cc2[nH]ncc2c2c1CCCOC(=O)O[C@@H]1COCCN(C1)c1nc(OC[C@@]34CCCN3C[C@H](F)C4)nc3c(F)c-2c(F)cc13] (26S)-9,32-difluoro-4-(((2R,7aS)-2-fluorotetrahydro-1H-pyrrolo[1,2-a]pyrrol-7a(5H)-yl)methoxy)-18-methyl-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-acetate | Step 1. Intermediate GGG | |
| 179 | 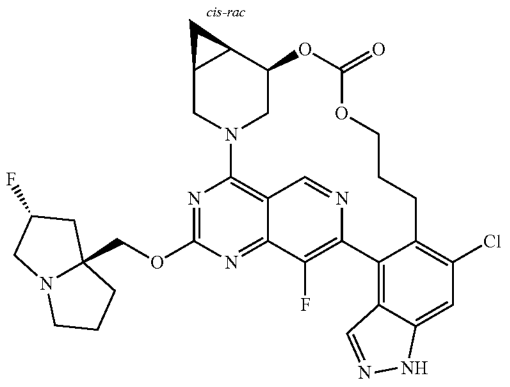 [SMILES: O=C1OCCCc2c(Cl)cc3[nH]ncc3c2-c2ncc3c(nc(OC[C@@]45CCCN4C[C@H](F)C5)nc3c2F)N2C[C@H]3C[C@H]3[C@H](C2)O1] (26R,27R,29S)-18-chloro-32-fluoro-4-(((2R,7aS)-2-fluorotetrahydro-1H-pyrrolo[1,2-a]pyrrol-7a(5H)-yl)methoxy)-23,25-dioxa-1,3,5,9,14,15-hexaazaheptacyclo[24.4.1.1~6,10~.0~2,7~.0~11,19~.0~12,16~.0~27,29~]dotriaconta-2,4,6(32),7,9,11,13,16,18-nonaen-24-one, (26S,27S,29R)-18-chloro-32-fluoro-4-(((2R,7aS)-2-fluorotetrahydro-1H-pyrrolo[1,2-a]pyrrol-7a(5H)-yl)methoxy)-23,25-dioxa-1,3,5,9,14,15-hexaazaheptacyclo[24.4.1.1~6,10~.0~2,7~.0~11,19~.0~12,16~.0~27,29~]dotriaconta-2,4,6(32),7,9,11,13,16,18-nonaen-24-one | | Step 1. Starting material prepared via HCl deprotection of tert-butyl 5-hydroxy-3-azabicyclo[4.1.0]heptane-3-carboxylate (CAS#: 1412905-37-3, J & W Pharmalab), followed by SNAr with Step 2 of Intermediate AA | |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 180 | 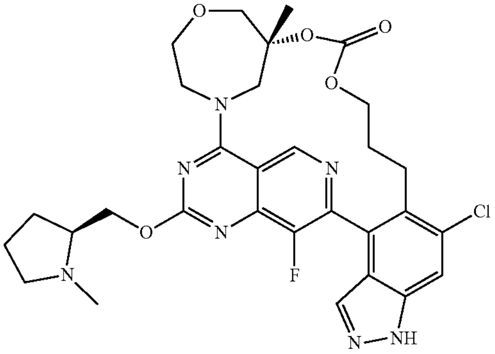 [SMILES: CN1CCC[C@H]1COc1nc2c3cnc(c(F)c3n1)-c1c(c(Cl)cc3[nH]ncc13)CCCOC(=O)O[C@@]1(C)COCCN2C1] (26R)-18-chloro-32-fluoro-26-methyl-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | | Step 1: Intermediate XXXX and Intermediate FFF | Step 1: cataCXium A Pd G3 was used instead of $Pd(OAc)_2$/(R)-MOP. Chiral separation after Step 3. Details included below. |
| 181 | 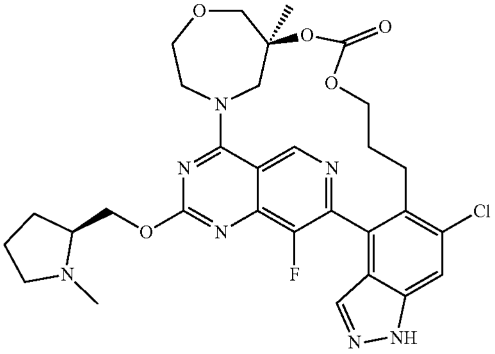 [SMILES: CN1CCC[C@H]1COc1nc2c3cnc(c(F)c3n1)-c1c(c(Cl)cc3[nH]ncc13)CCCOC(=O)O[C@]1(C)COCCN2C1] (26S)-18-chloro-32-fluoro-26-methyl-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32), 11,13,16,18-nonaen-24-one | | Step 1: Intermediate XXXX and Intermediate FFF | Step 1: cataCXium A Pd G3 was used instead of $Pd(OAc)_2$/(R)-MOP. Chiral separation after Step 3. Details included below. |
| 182 | 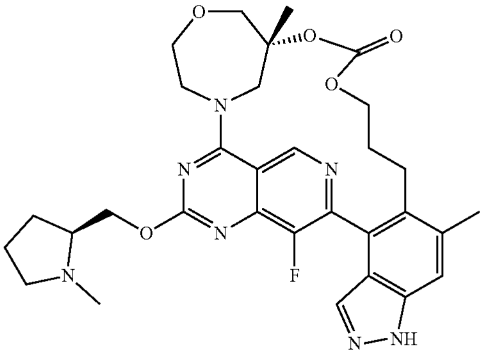 [SMILES: Cc1cc2[nH]ncc2c2c1CCCOC(=O)O[C@@]1(C)COCCN(C1)c1nc(OC[C@@H]3CCCN3C)nc3c(F)c-2ncc13] (26R)-32-fluoro-18,26-dimethyl-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | | Step 1: Intermediate XXXX and Intermediate K | Step 1: cataCXium A Pd G3 was used instead of $Pd(OAc)_2$/(R)-MOP. Chiral separation after Step 3. Details included below. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 183 | 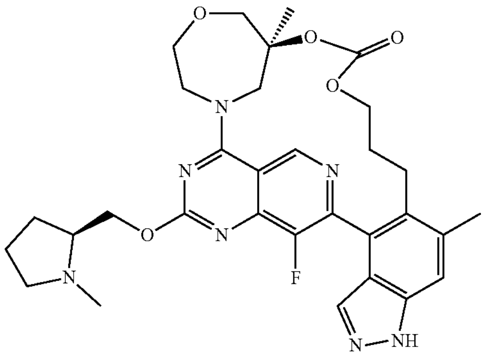 [SMILES: Cc1cc2[nH]ncc2c2c1CCCOC(=O)O[C@]1(C)COCCN(C1)c1nc(OC[C@@H]3CCCN3C)nc3c(F)c-2ncc13] (26S)-32-fluoro-18,26-dimethyl-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | | Step 1: Intermediate XXXX and Intermediate K | Step 1: cataCXium A Pd G3 was used instead of $Pd(OAc)_2$/(R)-MOP. Chiral separation after Step 3. Details included below. |
| 184 | 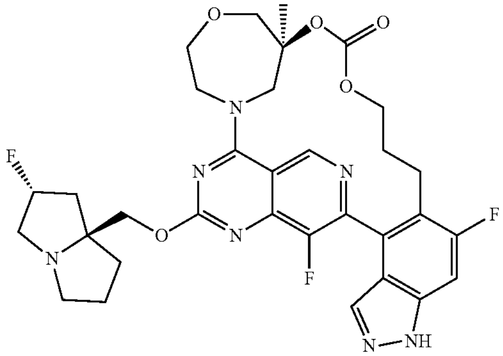 [SMILES: C[C@@]12COCCN(C1)c1nc(OC[C@@]34CCCN3C[C@H](F)C4)nc3c(F)c(ncc13)-c1c(c(F)cc3[nH]ncc13)CCCOC(=O)O2] (26S)-18,32-difluoro-4-(((2R,7aS)-2-fluorotetrahydro-1H-pyrrolo[1,2-a]pyrrol-7a(5H)-yl)methoxy)-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis(2,2-trifluoro-acetate) | Step 1: Intermediate YYYY and Intermediate ZZZZ | Step 1: cataCXium A Pd G3 was used instead of $Pd(OAc)_2$/(R)-MOP. Chiral separation after Step 3. Details included below. |
| 185 | 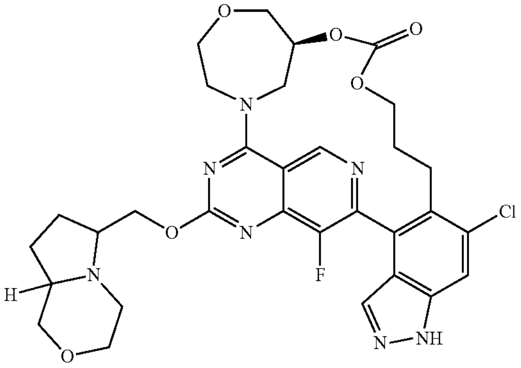 [SMILES: O=C1OCCCc2c(Cl)cc3[nH]ncc3c2-c2ncc3c(nc(OCC4CCC5COCCN54)nc3c2F)N2CCOC[C@H](C2)O1] (26S)-18-chloro-32-fluoro-4-((6R,8aR)-hexahydro-1H-pyrrolo[2,1-c][1,4]oxazin-6-ylmethoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis(2,2-trifluoro-acetate) | Step 1: Intermediate BA and Intermediate FFF | Step 1: cataCXium A Pd G3 was used instead of $Pd(OAc)_2$/(R)-MOP. |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 186 | 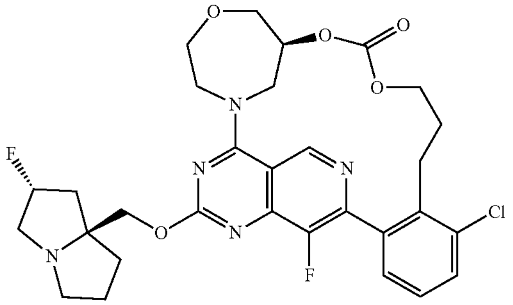 [SMILES: O=C1OCCCc2c(Cl)cccc2-c2ncc3c(nc(OC[C@@]45CCCN4C[C@H](F)C5)nc3c2F)N2CCOC[C@H](C2)O1] (23S)-15-chloro-29-fluoro-4-(((2R,7aS)-2-fluorotetrahydro-1H-pyrrolo[1,2-a]pyrrol-7a(5H)-yl)methoxy)-20,22,25-trioxa-1,3,5,9-tetraazapentacyclo[21.4.1.1~6,10~.0~2,7~.0~11,16~]nonacosa-2,4,6,8,10(29),11,13,15-octaen-21-one | | Step 1. Intermediate VV and Intermediate BC | Step 1: cataCXium A Pd G3 was used instead of $Pd(OAc)_2$/(R)-MOP. Step 3 was not performed. |
| 187 | 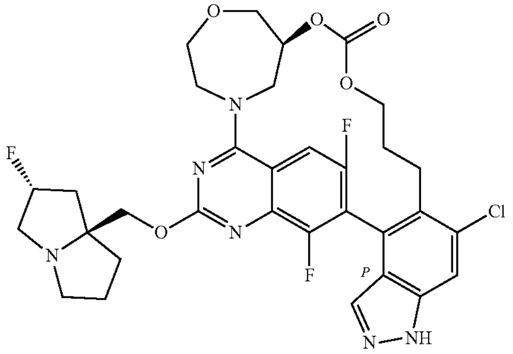 p-(26S)-18-chloro-9,32-difluoro-4-(((2R,7aS)-2-fluorotetrahydro-1H-pyrrolo[1,2-a]pyrrol-7a(5H)-yl)methoxy)-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate) | Step 1. Intermediate GGG and Intermediate FFF | Step 1: a 1:1 mixture of (S)-(-)-2-(diphenyl-phosphino)-2-methoxy-1-,1-binaphthyl (S)-MOP and (R)-MOP was used. |
| 188 | 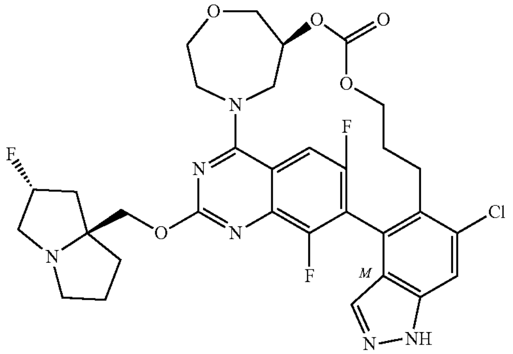 m-(26S)-18-chloro-9,32-difluoro-4-(((2R,7aS)-2-fluorotetrahydro-1H-pyrrolo[1,2-a]pyrrol-7a(5H)-yl)methoxy)-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate) | Step 1. Intermediate GGG and Intermediate FFF | Step 1: a 1:1 mixture of (S)-(-)-2-(diphenyl-phosphino)-2-methoxy-1-,1-binaphthyl (S)-MOP and (R)-MOP was used. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 189 | 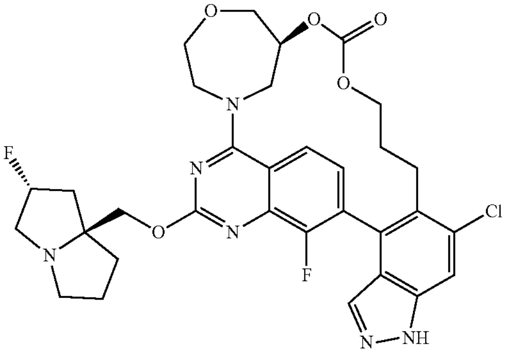 [SMILES: O=C1OCCCc2c(Cl)cc3[nH]ncc3c2-c2ccc3c(nc(OC[C@@]45CCCN4C[C@H](F)C5)nc3c2F)N2CCOC[C@H](C2)O1] (26S)-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate | Step 1. Intermediate BD and Intermediate FFF | Step 1. cataCXium A Pd G3 was used instead of (R)-MOP/ $Pd(OAc)_2$. Step 2_1. Temperature was 40° C. instead of rt |
| 190 | 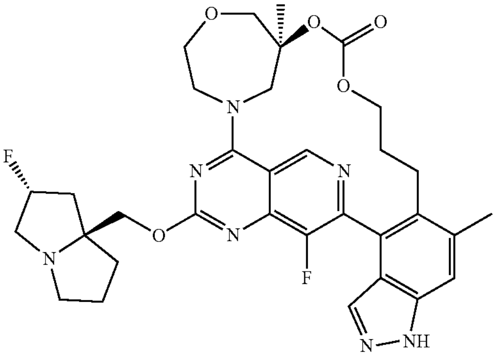 [SMILES: Cc1cc2[nH]ncc2c2c1CCCOC(=O)O[C@]1(C)COCCN(C1)c1nc(OC[C@@]34CCCN3C[C@H](F)C4)nc3c(F)c-2ncc13] (26S)-32-fluoro-4-(((2R,7aS)-2-fluorotetrahydro-1H-pyrrolo[1,2-a]pyrrol-7a(5H)-yl)methoxy)-18,26-dimethyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | formate | Step 1. Intermediate YYYY | Step 1. cataCXium A Pd G3 was used instead of (R)-MOP/ $Pd(OAc)_2$. Step 2_1. Solvent was MeTHF instead of THF, temperature was 50° C. |
| 191 | 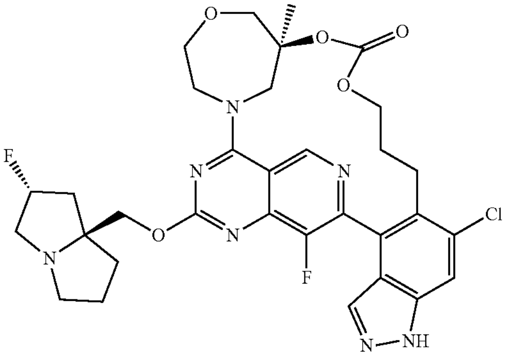 [SMILES: C[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2] (26S)-18-chloro-32-fluoro-4-(((2R,7aS)-2-fluorotetrahydro-1H-pyrrolo[1,2-a]pyrrol-7a(5H)-yl)methoxy)-26-methyl-23,25,28-trioxa-1,3,5,9,14,15-hexaazahexacyclo[24.4.1.1~6,10~.0~2,7~.0~11, | bis (2,2,2-trifluoro-aceate) | Step 1. Intermediate YYYY and Intermediate FFF | Step 1. cataCXium A Pd G3 was used instead of (R)-MOP/ $Pd(OAc)_2$. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | 19~.0~12,16~]dotriaconta-2,4,6,8,10(32),11,13,16,18-nonaen-24-one | | | |
| 192 | 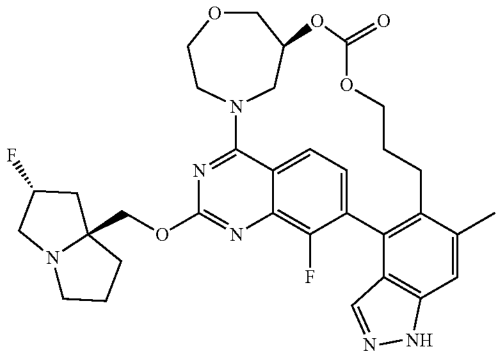 [SMILES: Cc1cc2[nH]ncc2c2c1CCCOC(=O)O[C@@H]1COCCN(C1)c1nc(OC[C@@]34CCCN3C[C@H](F)C4)nc3c(F)c-2ccc13]<br>(26S)-32-fluoro-4-(((2R,7aS)-2-fluorotetrahydro-1H-pyrrolo[1,2-a]pyrrol-7a(5H)-yl)methoxy)-18-methyl-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate) | Step 1. Intermediate BD | Step 1. cataCXium A Pd G3 was used instead of (R)-MOP/Pd(OAc)$_2$. Step 2_1. Temperature was 40° C. instead of RT |
| 193 | 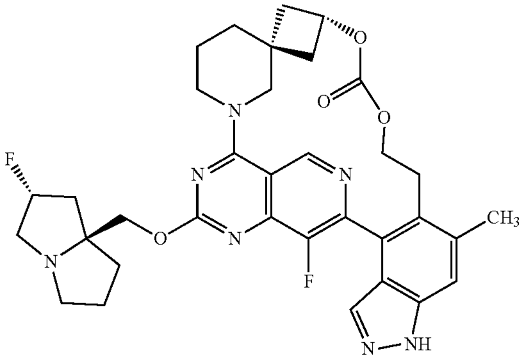 [SMILES: Cc1cc2[nH]ncc2c2c1CCOC(=O)O[C@H]1C[C@]3(CCCN(C3)c3nc(OC[C@@]45CCCN4C[C@H](F)C5)nc4c(F)c-2ncc34)C1]<br>(1R,3S)-32-fluoro-24-(((2R,7aS)-2-fluorotetrahydro-1H-pyrrolo[1,2-a]pyrrol-7a(5H)-yl)methoxy)-10-methyl-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1. Intermediate BE and Intermediate BN | Step 1. cataCXium A Pd G3 was used instead of (R)-MOP/Pd(OAc)$_2$. |
| 194 | 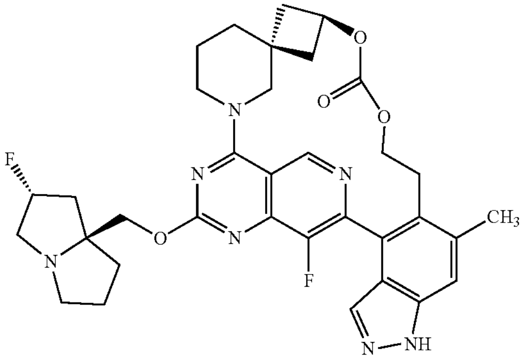 [SMILES: Cc1cc2[nH]ncc2c2c1CCOC(=O)O[C@H]1C[C@@]3(CCCN(C3)c3nc(OC[C@@]45CCCN4C[C@H](F)C5)nc4c(F)c-2ncc34)C1] | NA | Step 1. Intermediate BE and Intermediate BN | Step 1. cataCXium A Pd G3 was used instead of (R)-MOP/Pd(OAc)$_2$. |

TABLE 29-continued

| Ex.# | Structure & Name | Salt Form | Reagent | Method Change |
|---|---|---|---|---|
| | Additional Examples 92 to 98, 100 to 102, 179 to 212 and 303 to 368. Prepared in an Analogous Manner to Example 38. | | | |
| | (1S,3R)-32-fluoro-24-(((2R,7aS)-2-fluorotetrahydro-1H-pyrrolo[1,2-a]pyrrol-7a(5H)-yl)methoxy)-10-methyl-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 195 | 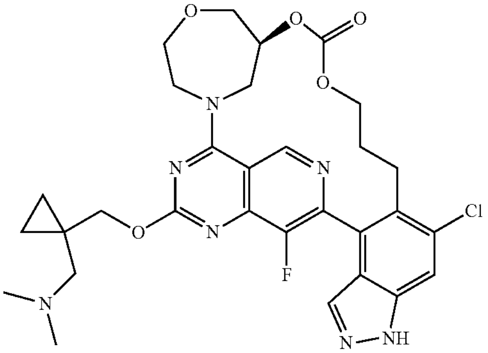 [SMILES: CN(C)CC1(COc2nc3c4cnc(c(F)c4n2)-c2c(c(Cl)cc4[nH]ncc24)CCCOC(=O)O[C@@H]2COCCN3C2)CC1]<br>(26S)-18-chloro-4-((1-((dimethylamino)methyl)cyclopropyl)methoxy)-32-fluoro-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1. Intermediate FFF and Intermediate BF | Step 1. cataCXium A Pd G3 was used instead of (R)-MOP/ $Pd(OAc)_2$. |
| 196 | 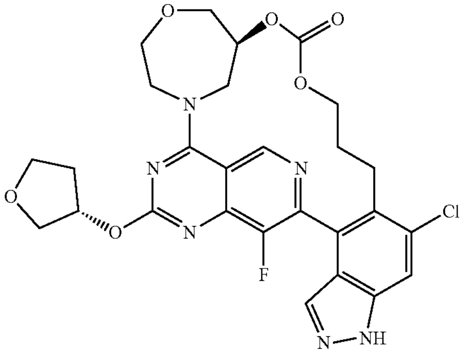 [SMILES: O=C1OCCCc2c(Cl)cc3[nH]ncc3c2-c2ncc3c(nc(O[C@H]4CCOC4)nc3c2F)N2CCOC[C@H](C2)O1]<br>(26S)-18-chloro-32-fluoro-4-((3S)-tetrahydro-3-furanyloxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-aceate | Step 1. Intermediate BG and Intermediate FFF | Step 1. cataCXium A Pd G3 was used instead of (R)-MOP/ $Pd(OAc)_2$. |
| 197 | 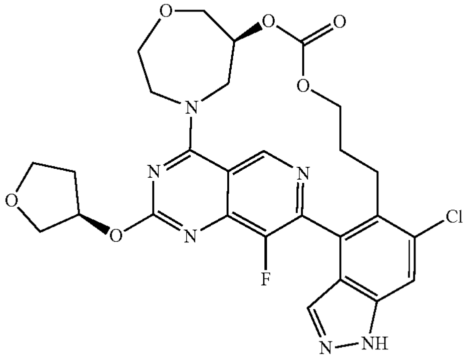 [SMILES: O=C1OCCCc2c(Cl)cc3[nH]ncc3c2-c2ncc3c(nc(O[C@@H]4CCOC4)nc3c2F)N2CCOC[C@H](C2)O1] | 2,2,2-trifluoro-aceate | Step 1. Intermediate BH and Intermediate FFF | Step 1. cataCXium A Pd G3 was used instead of (R)-MOP/ $Pd(OAc)_2$. |

TABLE 29-continued

| Ex.# | Structure & Name | Salt Form | Reagent | Method Change |
|---|---|---|---|---|
| Additional Examples 92 to 98, 100 to 102, 179 to 212 and 303 to 368. Prepared in an Analogous Manner to Example 38. | | | | |
| | (26S)-18-chloro-32-fluoro-4-((3R)-tetrahydro-3-furanyloxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | | | |
| 198 | 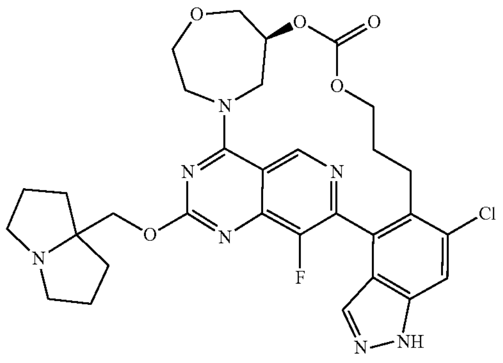 [SMILES: O=C1OCCCc2c(Cl)cc3[nH]ncc3c2-c2ncc3c(nc(OCC45CCCN4CCC5)nc3c2F)N2CCOC[C@H](C2)O1] (26S)-18-chloro-32-fluoro-4-(tetrahydro-1H-pyrrolo[1,2-a]pyrrol-7a(5H)-ylmethoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-aceate | Step 1. Intermediate BI and Intermediate FFF | Step 1. cataCXium A Pd G3 was used instead of (R).MOP/ $Pd(OAc)_2$. |
| 199 | 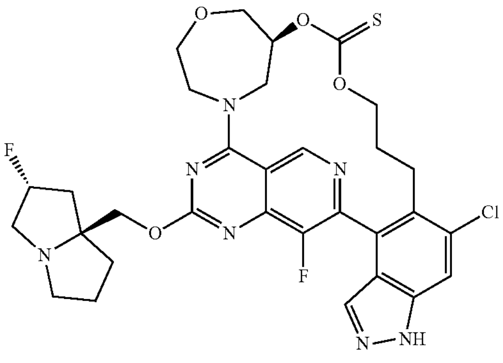 [SMILES: Fc1c2ncc3c(nc(OC[C@@]45CCCN4C[C@H](F)C5)nc13)N1CCOC[C@H](C1)OC(=S)OCCCc1c(Cl)cc3[nH]ncc3c1-2] (26S)-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaene-24-thione | NA | Step 1. Intermediate VV and Intermediate FFF | Step 1. cataCXium A Pd G3 was used. Step 2. Use 1,1'-thiocarbonyl-diimidazole Reaction heated to 40° C. prior to TBAF addition. |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 200 | 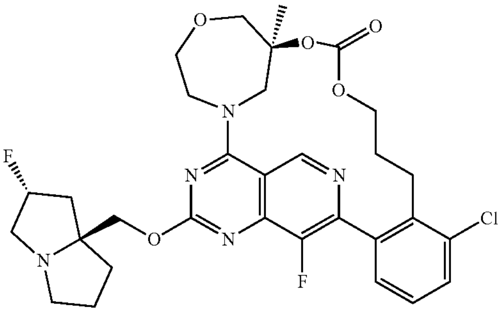 [SMILES: C[C@@]12COCCN(C1)c1nc(OC[C@@]34CCCN3C[C@H](F)C4)nc3c(F)c(ncc13)-c1cccc(Cl)c1CCCOC(=O)O2]<br>(23S)-15-chloro-29-fluoro-4-(((2R,7aS)-2-fluorotetrahydro-1H-pyrrolo[1,2-a]pyrrol-7a(5H)-yl)methoxy)-23-methyl-20,22,25-trioxa-1,3,5,9-tetraazapentacyclo[21.4.1.1~6,10~.0~2,7~.0~11,16~]nonacosa-2,4,6,8,10(29),11,13,15-octaen-21-one | NA | Step 1. Intermediate YYYY and Intermediate BM | Step 3 was not performed. |
| 201 | 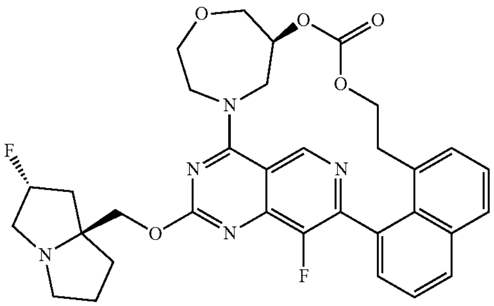 [SMILES: O=C1OCCc2cccc3cccc(c23)-c2ncc3c(nc(OC[C@@]45CCCN4C[C@H](F)C5)nc3c2F)N2CCOC[C@H](C2)O1]<br>(16S)-32-fluoro-8-(((2R,7aS)-2-fluorotetrahydro-1H-pyrrolo[1,2-a]pyrrol-7a(5H)-yl)methoxy)-14,17,19-trioxa-3,7,9,11-tetraazahexacyclo[20.7.1.1~2,6~.1~11,16~.0~5,10~.0~26,30~]dotriaconta-1(29),2(32),3,5,7,9,22,24,26(30),27-decaen-18-one | NA | Step 1. Intermediate BO and Intermediate VV | Step 3 was not performed. |
| 202 | 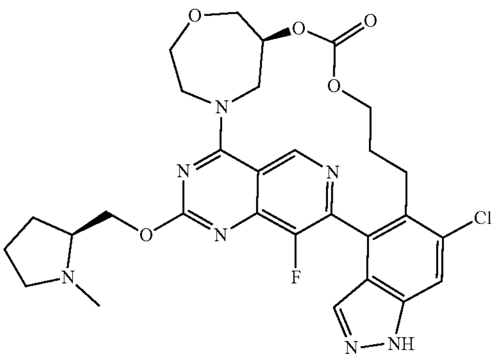 [SMILES: CN1CCC[C@H]1COc1nc2c3cnc(c(F)c3n1)-c1c(c(Cl)cc3[nH]ncc13)CCCOC(=O)O[C@@H]1COCCN2C1]<br>(26R)-18-chloro-32-fluoro-4-(((2S)-1-methyl-2-pyrrolidinyl)methoxy)-23,25-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-acetate | Step 1: Intermediate BP and Intermediate FFF | Step 1. (S)-MOP was used in place of (R)-MOP. |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 203 | 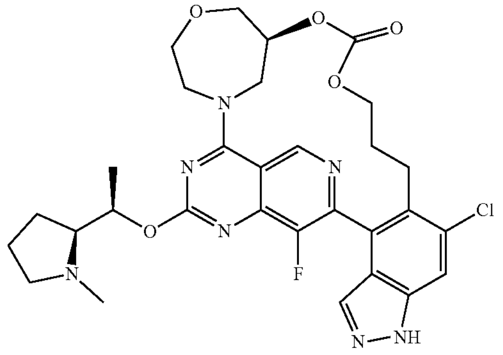 [SMILES: C[C@@H](Oc1nc2c3cnc(c(F)c3n1)-c1c(c(Cl)cc3[nH]ncc13)CCCOC(=O)O[C@@H]1COCCN2C1)[C@@H]1CCCN1C] (26S)-18-chloro-32-fluoro-4-((1R)-1-((2S)-1-methyl-2-pyrrolidinyl)ethoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate) | Step 1: Intermediate CR and Intermediate FFF | Step 1. (S)-MOP was used in place of (R)-MOP. Chiral separation after Step 4. Details included below. |
| 204 | 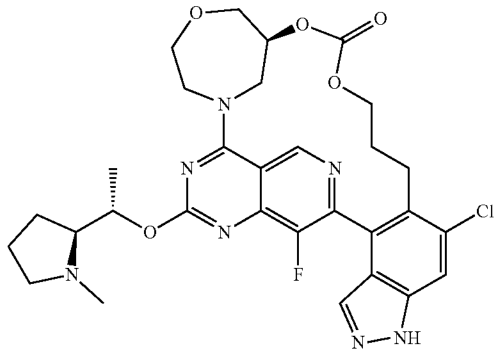 (26S)-18-chloro-32-fluoro-4-((1S)-1-((2S)-1-methyl-2-pyrrolidinyl)ethoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-acetate | Step 1: Intermediate CR and Intermediate FFF | Step 1. (S)-MOP was used in place of (R)-MOP. Chiral separation after Step 4. Details included below. |
| 205 | 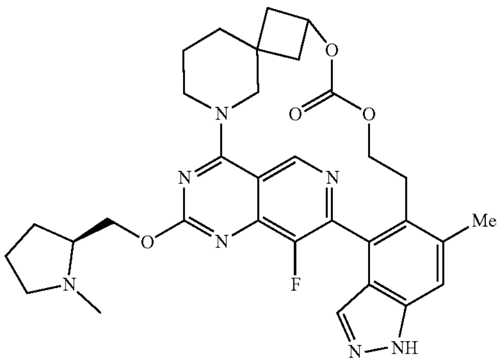 [SMILES: Cc1cc2[nH]ncc2c2c1CCOC(=O)OC1CC3(CCCN(C3)c3nc(OC[C@@H]4CCCN4C)nc4c(F)c-2ncc34)C1] (1R,3S)-32-fluoro-10-methyl-24-(((2S)-1-methyl-2-pyrrolidinyl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | bis(2,2,2-trifluoro-acetate) | Step 1: Intermediate BN and Intermediate CQ | Step 1. (S)-MOP was used in place of (R)-MOP. |

TABLE 29-continued

| Ex.# | Structure & Name | Salt Form | Reagent | Method Change |
|---|---|---|---|---|
| | Additional Examples 92 to 98, 100 to 102, 179 to 212 and 303 to 368. Prepared in an Analogous Manner to Example 38. | | | |
| 206 | 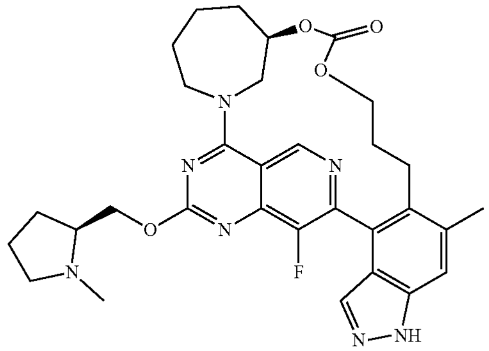 [SMILES: Cc1cc2[nH]ncc2c2c1CCCOC(=O)O[C@@H]1CCCCN(C1)c1nc(OC[C@@H]3CCCN3C)nc3c(F)c-2ncc13] (26R)-32-fluoro-18-methyl-4-(((2S)-1-methyl-2-pyrrolidinyl)methoxy)-23,25-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | bis(2,2,2-trifluoro-acetate) | Step 1: Intermediate BP and Intermediate K | Step 1. (S)-MOP was used in place of (R)-MOP. |
| 207 | 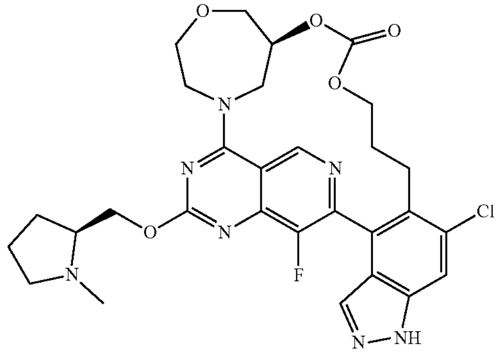 [SMILES: CN1CCC[C@H]1COc1nc2c3cnc(c(F)c3n1)-c1c(c(Cl)cc3[nH]ncc13)CCCOC(=O)O[C@@H]1COCCN2C1] (26S)-18-chloro-32-fluoro-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis(2,2,2-trifluoro-acetate) | Step 1: Intermediate BQ and Intermediate FFF | Step 1. (S)-MOP was used in place of (R)-MOP. |
| 208 | 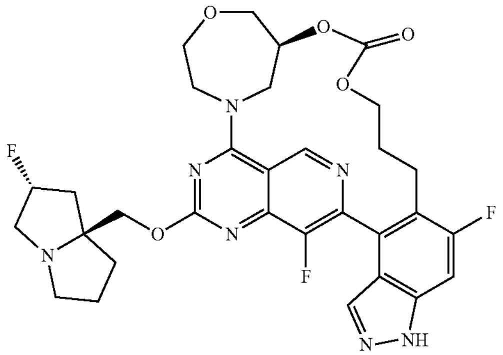 [SMILES: O=C1OCCCc2c(F)cc3[nH]ncc3c2-c2ncc3c(nc(OC[C@@]45CCCN4C[C@H](F)C5)nc3c2F)N2CCOC[C@H](C2)O1] (26S)-18,32-difluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1. Intermediate ZZZZ and Intermediate VV | Step 1. cataCXium A Pd G3 was used instead of (R)-MOP/$Pd(OAc)_2$. |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 209 | 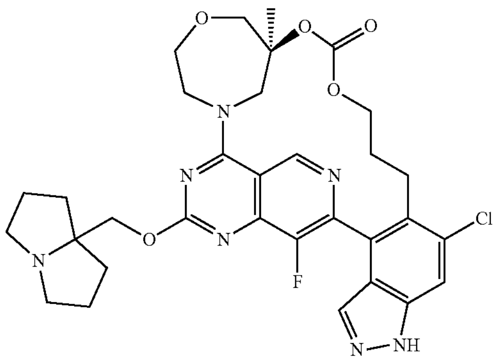 [SMILES: C[C@@]12COCCN(C1)c1nc(OCC34CCCN3CCC4)nc3c(F)c(ncc13)-c1c(c(Cl)cc3[nH]ncc13)CCCOC(=O)O2] (26S)-18-chloro-32-fluoro-26-methyl-4-(tetrahydro-1H-pyrrolo[1,2-a]pyrrol-7a(5H)-ylmethoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-aceate) | Step 1: Intermediate BR and Intermediate FFF | Step 1. cataCXium A Pd G3 was used instead of (R)-MOP/ $Pd(OAc)_2$. |
| 210 | 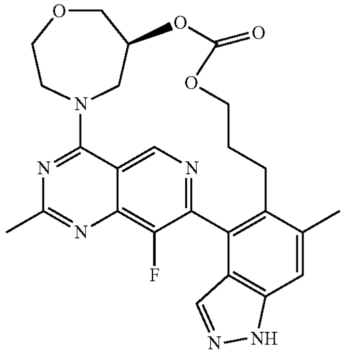 (26S)-32-fluoro-4,18-dimethyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-acetate | Step 1. Intermediate BS | Step 1: cataCXium A Pd G3, $K_3PO_4$ in THF/Water was used instead of (R)-MOP, $Pd(OAc)_2$, $K_3PO_4$ in 2-MeTHF/ Water |
| 211 | 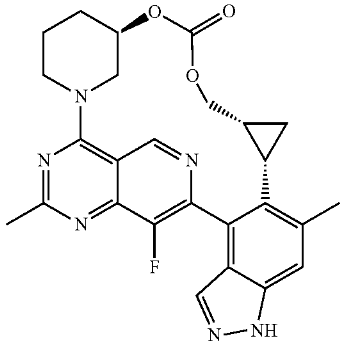 (11S,13R,18R)-31-fluoro-9,25-dimethyl-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one | 2,2,2-trifluoro-acetate | Step 1. Intermediate BS and Intermediate BU | Step 1: cataCXium A Pd G3, $K_3PO_4$ in THF/Water was used instead of (R)-MOP, $Pd(OAc)_2$, $K_3PO_4$ in 2-MeTHF/ Water |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 212 | 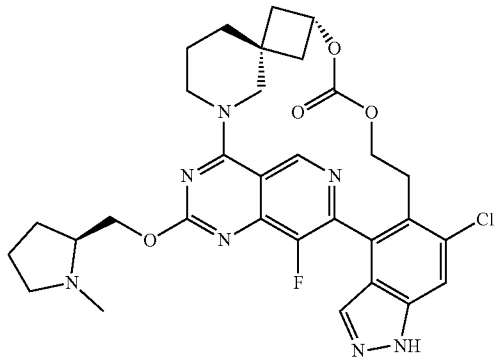 [SMILES: CN1CCC[C@H]1COc1nc2c3cnc(c(F)c3n1)-c1c(c(Cl)cc3[nH]ncc13)CCOC(=O)O[C@H]1C[C@]3(CCCN2C3)C1] (1S,3R)-10-chloro-32-fluoro-24-(((2S)-1-methyl-2-pyrrolidinyl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | bis(2,2,2-trifluoro-acetate) | Step 1: Intermediate CU and Intermediate CQ, peak 2 | |
| 303 | 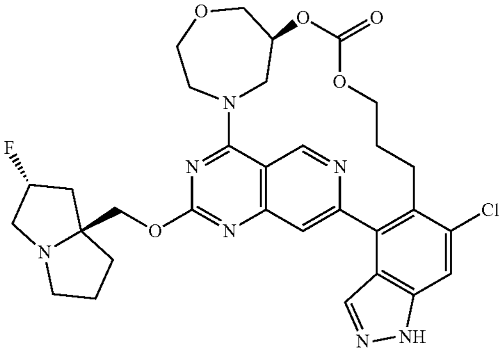 [SMILES: O=C1OCCCc2c(Cl)cc3[nH]ncc3c2-c2cc3nc(OC[C@@]45CCCN4C[C@H](F)C5)nc(c3cn2)N2CCOC[C@H](C2)O1] (26S)-18-chloro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | 2,2,2-trifluoro-acetate | Step 1. Intermediate DO | Step 1. cataCXium A Pd G3 was used instead of (R)-MOP/ $Pd(OAc)_2$. Solvent was THF instead of 2-MeTHF. |
| 304 | 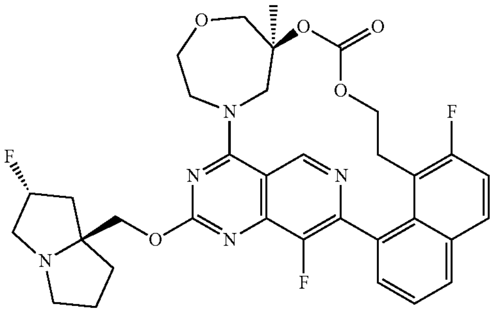 [SMILES: C[C@@]12COCCN(C1)c1nc(OC[C@@]34CCCN3C[C@H](F)C4)nc3c(F)c(ncc13)-c1cccc3ccc(F)c(c13)CCOC(=O)O2] (16S)-23,32-difluoro-8-(((2R,7aS)-2-fluorotetrahydro-1H-pyrrolo[1,2-a]pyrrol-7a(5H)-yl)methoxy)-16-methyl-14,17,19-trioxa-3,7,9,11-tetraazahexacyclo[20.7.1.1~2,6~.1~11,16~.0~5,10~.0~26,30~]dotriaconta-1(30),2(32),3,5,7,9,22,24,26,28-decaen-18-one | NA | Step 1. Intermediate YYYY and Intermediate DN | Step 1. cataCXium A Pd G3 was used instead of (R)-MOP/ $Pd(OAc)_2$. Solvent was THF instead of 2-MeTHF. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 305 | 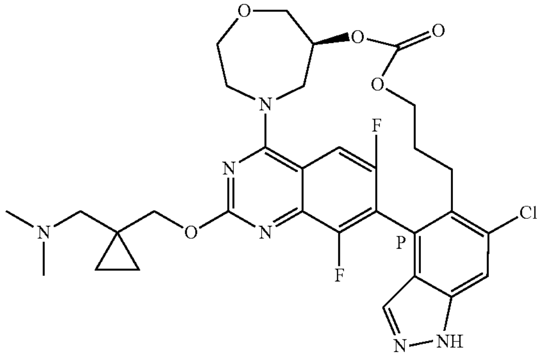 p-(26S)-18-chloro-4-((1-((dimethylamino)methyl)cyclopropyl)methoxy)-9,32-difluoro-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | bis (2,2,2-trifluoro-aceate) | Step 1. Intermediate DP and Intermediate FFF | Step 1: a 1:1 mixture of (S)-(-)-2-(diphenyl-phosphino)-2-methoxy-1-,1-binaphthyl (S)-MOP and (R)-MOP was used. |
| 306 | 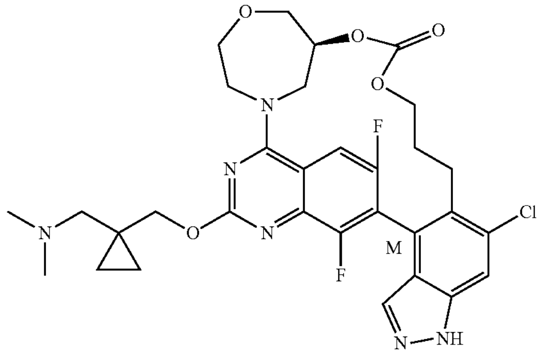 m-(26S)-18-chloro-4-((1-((dimethylamino)methyl)cyclopropyl)methoxy)-9,32-difluoro-23,25,28-trioxa-1,3,5,14,15-pentaazahexacyclo[24.4.1.1~6,10~.0~2,7~.0~11,19~.0~12,16~]dotriaconta-2,4,6,8,10(32),11,13,16,18-nonaen-24-one | bis (2,2,2-trifluoro-aceate | Step 1. Intermediate DP and Intermediate FFF | Step 1: a 1:1 mixture of (S)-(-)-2-(diphenyl-phosphino)-2-methoxy-1-,1-binaphthyl (S)-MOP and (R)-MOP was used. |
| 307 | 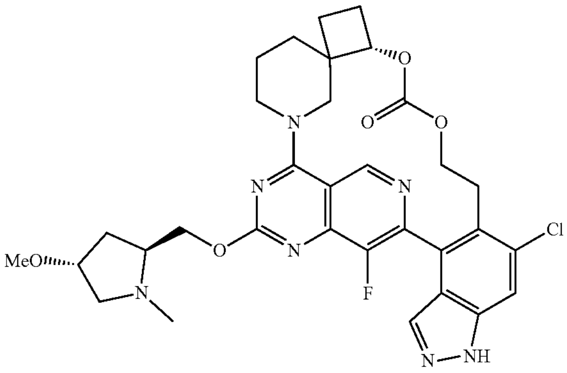 [SMILES: CO[C@@H]1C[C@@H](COc2nc3c4cnc(c(F)c4n2)-c2c(c(Cl)cc4[nH]ncc24)CCOC(=O)O[C@H]2CCC24CCCN3C4)N(C)C1] (1R,3S)-10-chloro-32-fluoro-24-(((25,4R)-4-methoxy-1-methyl-2-pyrrolidinyl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one, | Tris 2,2,2-trifluoro-acetate | Step 1: Intermediate CU and Intermediate DQ | |

TABLE 29-continued

| Ex.# | Structure & Name | Salt Form | Reagent | Method Change |
|---|---|---|---|---|
| | Additional Examples 92 to 98, 100 to 102, 179 to 212 and 303 to 368. Prepared in an Analogous Manner to Example 38. | | | |
| | (1S,3R)-10-chloro-32-fluoro-24-(((2S,4R)-4-methoxy-1-methyl-2-pyrrolidinyl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 308 | 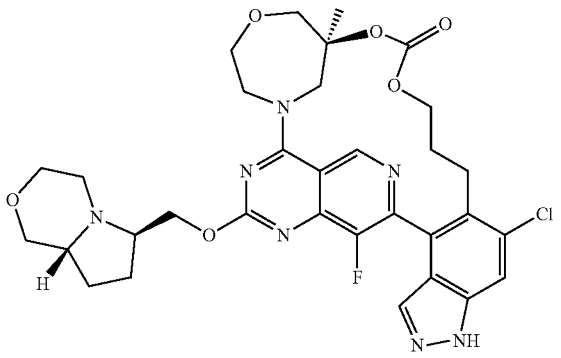 [SMILES: C[C@@]12COCCN(C1)c1nc(OC[C@H]3CC[C@@H]4COCCN43)nc3c(F)c(ncc13)-c1c(c(Cl)cc3[nH]ncc13)CCCOC(=O)O2] (26S)-18-chloro-32-fluoro-4-((6R,8aR)-hexahydro-1H-pyrrolo[2,1-c][1,4]oxazin-6-ylmethoxy)-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate FFF and Intermediate DR | Step 1. (S)-MOP was used in place of (R)-MOP. |
| 309 | 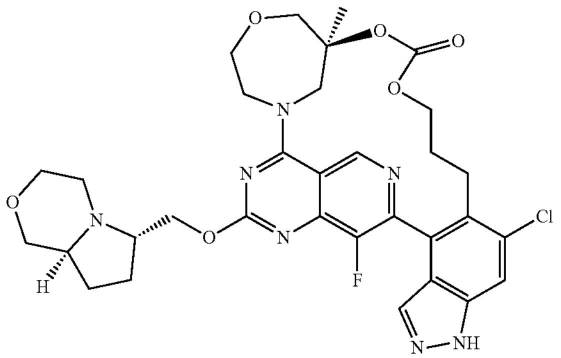 (26S)-18-chloro-32-fluoro-4-((6S,8aS)-hexahydro-1H-pyrrolo[2,1-c][1,4]oxazin-6-ylmethoxy)-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate FFF and Intermediate DR | |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 310 | 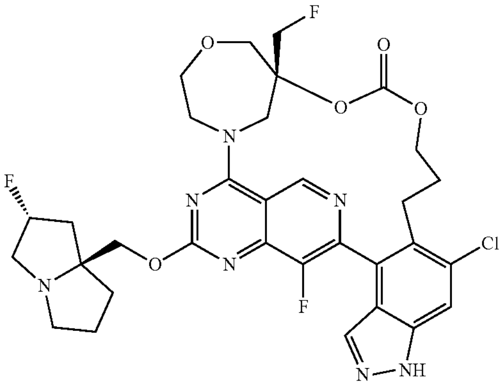 [SMILES: O=C1OCCCc2c(Cl)cc3[nH]ncc3c2-c2ncc3c(nc(OC[C@@]45CCCN4C[C@H](F)C5)nc3c2F)N2CCOC[C@@](CF)(C2)O1] (26R)-18-chloro-32-fluoro-26-(fluoromethyl)-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate FFF and Intermediate DS | Chiral separation after Step 3. Details included below. |
| 311 | 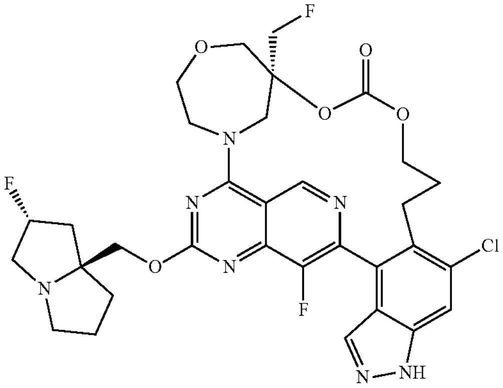 [SMILES: O=C1OCCCc2c(Cl)cc3[nH]ncc3c2-c2ncc3c(nc(OC[C@@]45CCCN4C[C@H](F)C5)nc3c2F)N2CCOC[C@](CF)(C2)O1] (26S)-18-chloro-32-fluoro-26-(fluoromethyl)-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate FFF and Intermediate DS | Chiral separation after Step 3. Details included below. |
| 312 | 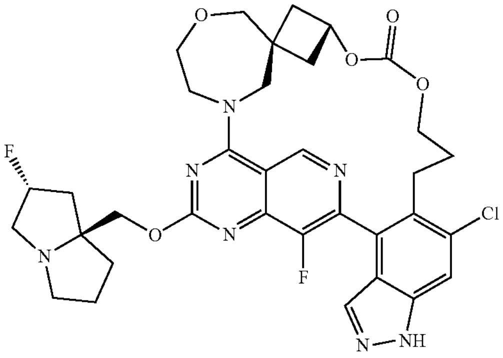 [SMILES: O=C1OCCCc2c(Cl)cc3[nH]ncc3c2-c2ncc3c(nc(OC[C@@]45CCCN4C[C@H](F)C5)nc3c2F)N2CCOC[C@]3(C2)C[C@@H](C3)O1] (1S,3S)-11-chloro-34-fluoro-25-(((2R,7aS)-2-fluorotetrahydro-1H-pyrrolo[1,2-a]pyrrol- | NA | Step 1: Intermediate FFF and Intermediate DT | Step 1: cataXCium A Pd G3 used instead of $Pd(OAc)_2$/MOP Step 3: formic acid modifier used for FCC |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
| --- | --- | --- | --- | --- |
| | 7a(5H)-yl)methoxy)-4,6,31-trioxa-14,15,20,24,26,28-hexaazaheptacyclo[26.4.1.1~1,3~.1~19,23~.0~10,18~.0~13,17~.0~22,27~]pentatriaconta-10,12,15,17,19(34),20,22,24,26-nonaen-5-one | | | |
| 313 | 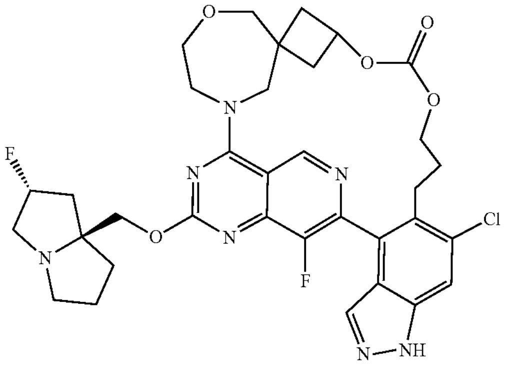 [SMILES: O=C1OCCCc2c(Cl)cc3[nH]ncc3c2-c2ncc3c(nc(OC[C@@]45CCCN4C[C@H](F)C5)nc3c2F)N2CCOCC3(CC(C3)O1)C2] (1S,3S)-11-chloro-34-fluoro-25-(((2R,7aS)-2-fluorotetrahydro-1H-pyrrolo[1,2-a]pyrrol-7a(5H)-yl)methoxy)-4,6,31-trioxa-14,15,20,24,26,28-hexaazaheptacyclo[26.4.1.1~1,3~.1~19,23~.0~10,18~.0~13,17~.0~22,27~]pentatriaconta-10,12,15,17,19(34),20,22,24,26-nonaen-5-one and (1R,3R)-11-chloro-34-fluoro-25-(((2R,7aS)-2-fluorotetrahydro-1H-pyrrolo[1,2-a]pyrrol-7a(5H)-yl)methoxy)-4,6,31-trioxa-14,15,20,24,26,28-hexaazaheptacyclo[26.4.1.1~1,3~.1~19,23~.0~10,18~.0~13,17~.0~22,27~]pentatriaconta-10,12,15,17,19(34),20,22,24,26-nonaen-5-one | NA | Step 1: Intermediate FFF and Intermediate DT | Step 1: cataXCium A Pd G3 used instead of $Pd(OAc)_2$/MOP Step 3: formic acid modifier used for FCC |
| 314 | 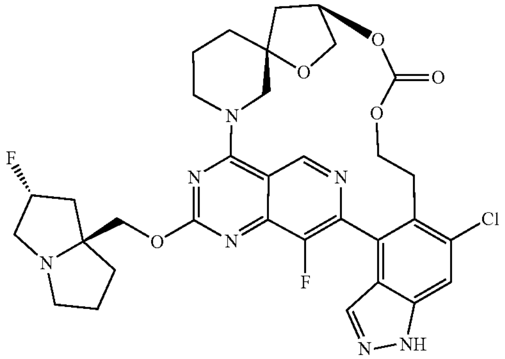 [SMILES: O=C1OCCc2c(Cl)cc3[nH]ncc3c2-c2ncc3c(nc(OC[C@@]45CCCN4C[C@H](F)C5)nc3c2F)N2CCC[C@@]3(C[C@H](CO3)O1)C2] (1R,4R)-11-chloro-33-fluoro-25-(((2R,7aS)-2-fluorotetrahydro-1H-pyrrolo[1,2-a]pyrrol-7a(5H)-yl)methoxy)-2,5,7-trioxa-14,15,20,24,26,28-hexaazaheptacyclo[26.3.1.1~1,4~.1~19,23~.0~10,18~.0~13,17~.0~22,27~]tetratriaconta-10,12,15,17,19(33),20,22,24,26-nonaen-6-one | NA | Step 1. Intermediate DU and Intermediate CU | Step 1: cataXCium A Pd G3 used instead of $Pd(OAc)_2$/MOP Chiral separation after Step 3. Details included below. |

TABLE 29-continued

| Ex.# | Structure & Name | Salt Form | Reagent | Method Change |
|---|---|---|---|---|
| | Additional Examples 92 to 98, 100 to 102, 179 to 212 and 303 to 368. Prepared in an Analogous Manner to Example 38. | | | |
| 315 | 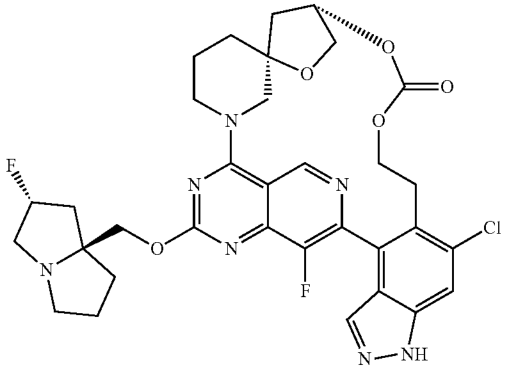 [SMILES: O=C1OCCc2c(Cl)cc3[nH]ncc3c2-c2ncc3c(nc(OC[C@@]45CCCN4C[C@H](F)C5)nc3c2F)N2CCC[C@]3(C[C@@H](CO3)O1)C2] (1S,4S)-11-chloro-33-fluoro-25-(((2R,7aS)-2-fluorotetrahydro-1H-pyrrolo[1,2-a]pyrrol-7a(5H)-yl)methoxy)-2,5,7-trioxa-14,15,20,24,26,28-hexaazaheptacyclo[26.3.1.1~1,4~.1~19,23~.0~10,18~.0~13,17~.0~22,27~]tetratriaconta-10,12,15,17,19(33),20,22,24,26-nonaen-6-one | NA | Step 1. Intermediate DU and Intermediate CU | Step 1: cataXCium A Pd G3 used instead of $Pd(OAc)_2$/MOP Chiral separation after Step 3. Details included below. |
| 316 | 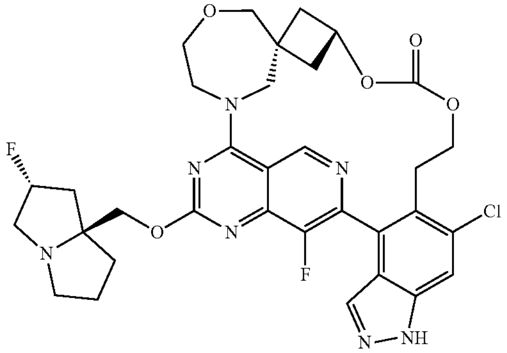 [SMILES: O=C1OCCc2c(Cl)cc3[nH]ncc3c2-c2ncc3c(nc(OC[C@@]45CCCN4C[C@H](F)C5)nc3c2F)N2CCOC[C@]3(C2)C[C@H](C3)O1] (1R,3R)-10-chloro-33-fluoro-24-(((2R,7aS)-2-fluorotetrahydro-1H-pyrrolo[1,2-a]pyrrol-7a(5H)-yl)methoxy)-4,6,30-trioxa-13,14,19,23,25,27-hexaazaheptacyclo[25.4.1.1~1,3~.1~18,22~.0~9,17~.0~12,16~.0~21,26~]tetratriaconta-9,11,14,16,18(33),19,21,23,25-nonaen-5-one | NA | Step 1. Intermediate DT and Intermediate CU | Step 1: cataXCium A Pd G3 used instead of $Pd(OAc)_2$/MOP Step 3: formic acid modifier used for FCC |
| 317 | 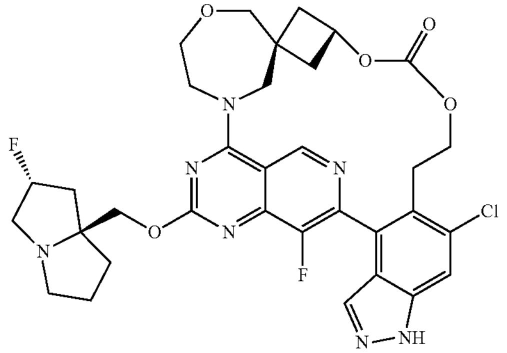 [SMILES: O=C1OCCc2c(Cl)cc3[nH]ncc3c2-c2ncc3c(nc(OC[C@@]45CCCN4C[C@H](F)C5)nc3c2F)N2CCOC[C@]3(C2)C[C@@H](C3)O1] (1S,3S)-10-chloro-33-fluoro-24-(((2R,7aS)-2-fluorotetrahydro-1H-pyrrolo[1,2-a]pyrrol-7a(5H)-yl)methoxy)-4,6,30-trioxa-13,14,19,23,25,27- | NA | Step 1. Intermediate DT and Intermediate CU | Step 1: cataXCium A Pd G3 used instead of $Pd(OAc)_2$/MOP Step 3: formic acid modifier used for FCC |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | hexaazaheptacyclo[25.4.1.1~1,3~.1~18,22~.0~9,17~.0~12,16~.0~21,26~]tetratriaconta-9,11,14,16,18(33),19,21,23,25-nonaen-5-one | | | |
| 318 | 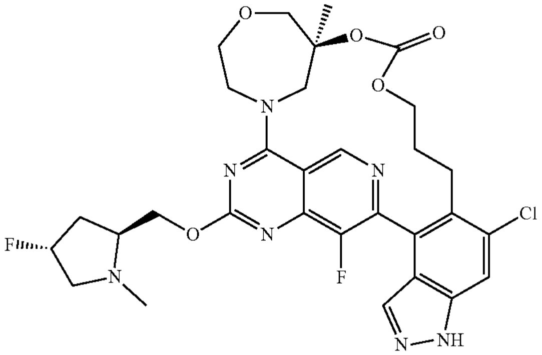 [SMILES: CN1C[C@H](F)C[C@H]1COc1nc2c3cnc(c(F)c3n1)-c1c(c(Cl)cc3[nH]ncc13)CCCOC(=O)O[C@]1(C)COCCN2C1] (26S)-18-chloro-32-fluoro-4-(((2S,4R)-4-fluoro-1-methyl-2-pyrrolidinyl)methoxy)-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1. Intermediate DV and Intermediate FFF | Step 1. cataCXium A Pd G3 was used instead of (R)-MOP/ Pd(OAc)$_2$ |
| 319 | 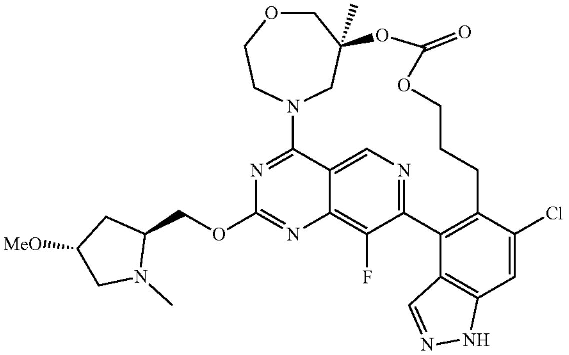 [SMILES: CO[C@@H]1C[C@@H](COc2nc3c4cnc(c(F)c4n2)-c2c(c(Cl)cc4[nH]ncc24)CCCOC(=O)O[C@]2(C)COCCN3C2)N(C)C1] (26S)-18-chloro-32-fluoro-4-(((2S,4R)-4-methoxy-1-methyl-2-pyrrolidinyl)methoxy)-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1. Intermediate DW and Intermediate FFF | Step 1. cataCXium A Pd G3 was used instead of (R)-MOP/ Pd(OAc)$_2$ |
| 320 | 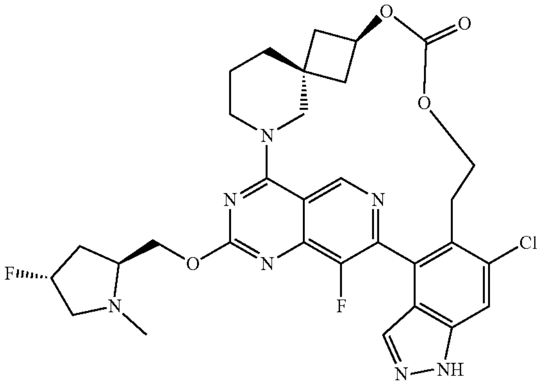 [SMILES: CN1C[C@H](F)C[C@H]1COc1nc2c3cnc(c(F)c3n1)-c1c(c(Cl)cc3[nH]ncc13)CCOC(=O)O[C@H]1C[C@@]3(CCCN2C3)C1] | NA | Step 1: Intermediate CU and Intermediate DX | Step 1. cataCXium A Pd G3 was used instead of (R)-MOP/ Pd(OAc)$_2$ |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| | (1S,3R)-10-chloro-32-fluoro-24-(((2S,4R)-4-fluoro-1-methyl-2-pyrrolidinyl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 321 | 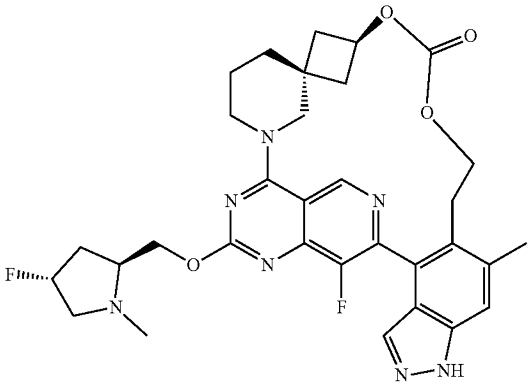 [SMILES: Cc1cc2[nH]ncc2c2c1CCOC(=O)O[C@H]1C[C@@]3(CCCN(C3)c3nc(OC[C@@H]4C[C@@H](F)CN4C)nc4c(F)c-2ncc34)C1] (1S,3R)-32-fluoro-24-(((2S,4R)-4-fluoro-1-methyl-2-pyrrolidinyl)methoxy)-10-methyl-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate BN and Intermediate DX | Step 1. cataCXium A Pd G3 was used instead of (R)-MOP/ $Pd(OAc)_2$ |
| 322 | 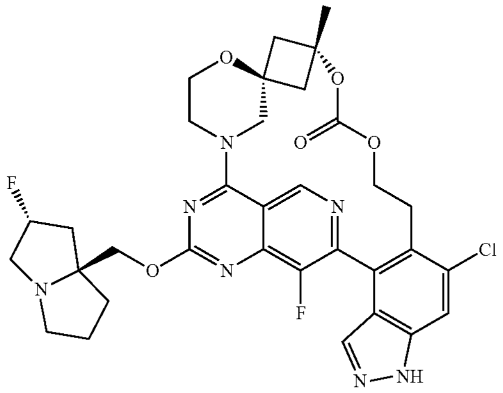 [SMILES: C[C@]12C[C@]3(CN(CCO3)c3nc(OC[C@@]45CCCN4C[C@H](F)C5)nc4c(F)c(ncc34)-c3c(c(Cl)cc4[nH]ncc34)CCOC(=O)O1)C2] (1S,3S)-10-chloro-32-fluoro-24-(((2R,7aS)-2-fluorotetrahydro-1H-pyrrolo[1,2-a]pyrrol-7a(5H)-yl)methoxy)-3-methyl-4,6,30-trioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate CU and Intermediate DY | Step 1. cataCXium A Pd G3 was used instead of (R)-MOP/ $Pd(OAc)_2$ |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 323 | 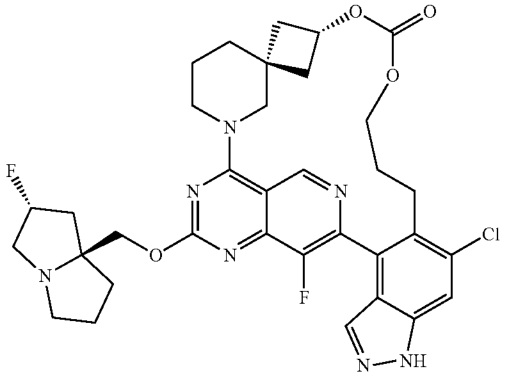 [SMILES: O=C1OCCCc2c(Cl)cc3[nH]ncc3c2-c2ncc3c(nc(OC[C@@]45CCCN4C[C@H](F)C5)nc3c2F)N2CCC[C@]3(C2)C[C@H](C3)O1] (1R,3S)-11-chloro-33-fluoro-25-(((2R,7aS)-2-fluorotetrahydro-1H-pyrrolo[1,2-a]pyrrol-7a(5H)-yl)methoxy)-4,6-dioxa-14,15,20,24,26,28-hexaazaheptacyclo[26.3.1.1~1,3~.1~19,23~.0~10,18~.0~13,17~.0~22,27~]tetratriaconta-10,12,15,17,19(33),20,22,24,26-nonaen-5-one | NA | Step 1. Intermediate DQ and Intermediate FFF | Step 1. cataCXium A Pd G3 was used instead of (R)-MOP/ $Pd(OAc)_2$ |
| 324 | 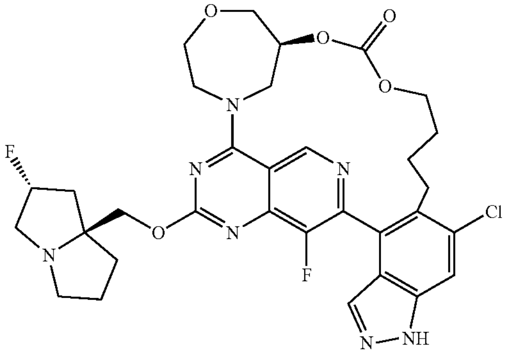 [SMILES: O=C1OCCCCc2c(Cl)cc3[nH]ncc3c2-c2ncc3c(nc(OC[C@@]45CCCN4C[C@H](F)C5)nc3c2F)N2CCOC[C@H](C2)O1] (27S)-18-chloro-33-fluoro-4-(((2R,7aS)-2-fluorotetrahydro-1H-pyrrolo[1,2-a]pyrrol-7a(5H)-yl)methoxy)-24,26,29-trioxa-1,3,5,9,14,15-hexaazahexacyclo[25.4.1.1~6,10~.0~2,7~.0~11,19~.0~12,16~]tritriaconta-2,4,6,8,10(33),11,13,16,18-nonaen-25-one | NA | Step 1. Intermediate VV and Intermediate DZ | Step 1. cataCXium A Pd G3 was used instead of (R)-MOP/ $Pd(OAc)_2$ |
| 325 | 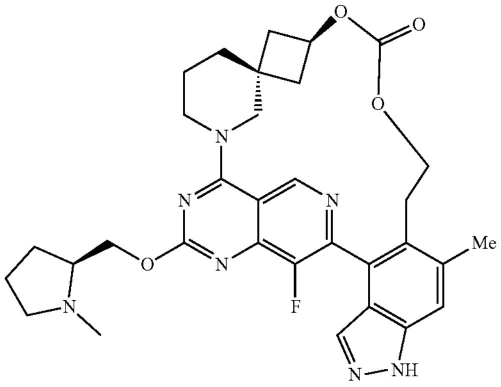 [SMILES: Cc1cc2[nH]ncc2c2c1CCOC(=O)O[C@H]1C[C@@]3(CCCN(C3)c3nc(OC[C@@H]4CCCN4C)nc4c(F)c-2ncc34)C1] (1R,3S)-32-fluoro-10-methyl-24-(((2S)-1-methyl-2-pyrrolidinyl)methoxy)-4,6-dioxa-13,14,19,23,25,27- | NA | Step 1: Intermediate BN and Intermediate CQ | |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | hexaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 326 | 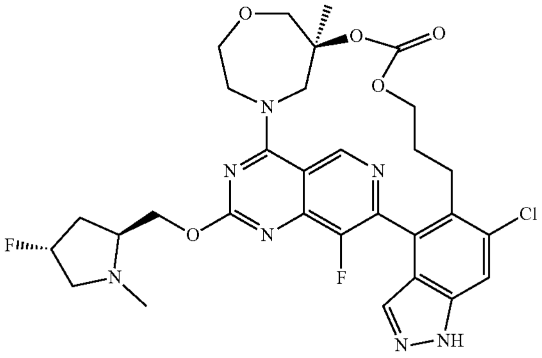 [SMILES: CN1C[C@H](F)C[C@H]1COc1nc2c3cnc(c(F)c3n1)-c1c(c(Cl)cc3[nH]ncc13)CCCOC(=O)O[C@]1(C)COCCN2C1] (1S,3R)-32-fluoro-10-methyl-24-(((2S)-1-methyl-2-pyrrolidinyl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate BN and Intermediate CQ | |
| 327 | 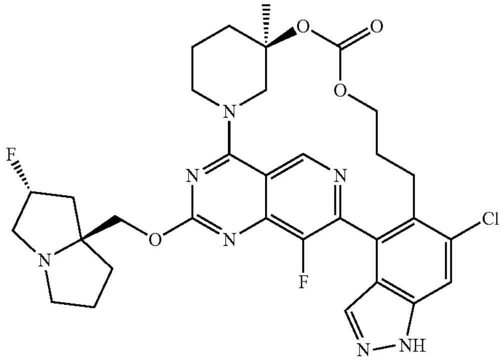 [SMILES: C[C@@]12CCCN(C1)c1nc(OC[C@@]34CCCN3C[C@H](F)C4)nc3c(F)c(ncc13)-c1c(c(Cl)cc3[nH]ncc13)CCCOC(=O)O2] (17R)-9-chloro-30-fluoro-24-(((2R,7aS)-2-fluorotetrahydro-1H-pyrrolo[1,2-a]pyrrol-7a(5H)-yl)methoxy)-17-methyl-14,16-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one | NA | Step 1: Intermediate FFF and Intermediate U | Step 1: (S)-(-)-2-(diphenyl-phosphino)-2-methoxy-1-,1-binaphthyl (S)-mop, was used |
| 328 | 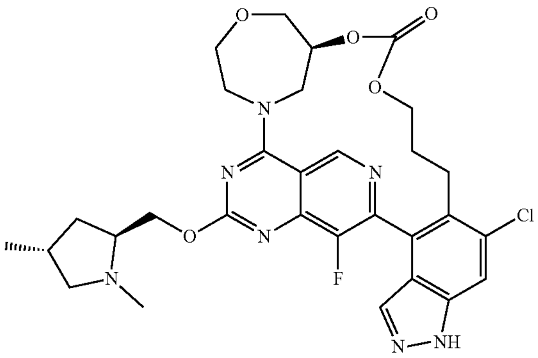 [SMILES: C[C@@H]1C[C@@H](COc2nc3c4cnc(c(F)c4n2)-c2c(c(Cl)cc4[nH]ncc24)CCCOC(=O)O[C@@H]2COCCN3C2)N(C)C1] (26S)-18-chloro-4-(((2S,4R)-1,4-dimethyl-2-pyrrolidinyl)methoxy)-32-fluoro-23,25,28- | 2,2,2-trifluoro-acetate | Step 1: Intermediate FFF and Intermediate EA | Step 1: (S)-(-)-2-(diphenyl-phosphino)-2-methoxy-1-,1-binaphthyl (S)-mop, was used |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| | trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | | | |
| 329 | 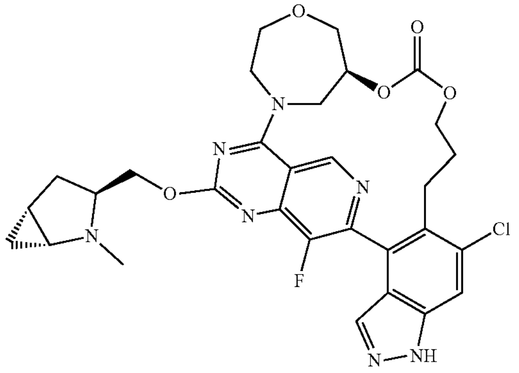 [SMILES: CN1[C@H](COc2nc3c4cnc(c(F)c4n2)-c2c(c(Cl)cc4[nH]ncc24)CCCOC(=O)O[C@@H]2COCCN3C2)C[C@H]2C[C@H]21] (26S)-18-chloro-32-fluoro-4-(((1R,3S,5R)-2-methyl-2-azabicyclo[3.1.0]hexan-3-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-acetate) | Step 1: Intermediate FFF and Intermediate EB | Step 1: methane-sulfonato (diadamantyl-n-butyl-phosphino)-2'-amino-1,1'-biphenyl-2-yl)palladium (ii) was used |
| 330 | 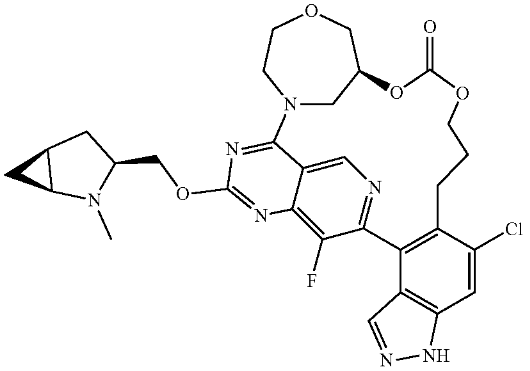 [SMILES: CN1[C@H](COc2nc3c4cnc(c(F)c4n2)-c2c(c(Cl)cc4[nH]ncc24)CCCOC(=O)O[C@@H]2COCCN3C2)C[C@@H]2C[C@@H]21] (26S)-18-chloro-32-fluoro-4-(((1S,3S,5S)-2-methyl-2-azabicyclo[3.1.0]hexan-3-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | Bis (2,2,2-trifluoro-acetate) | Step 1: Intermediate FFF and Intermediate EC | Step 1: methane-sulfonato (diadamantyl-n-butyl-phosphino)-2'-amino-1,1'-biphenyl-2-yl)palladium (ii) wasused |
| 331 | 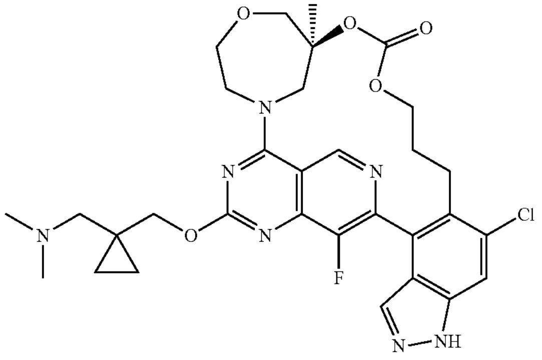 [SMILES: CN(C)CC1(COc2nc3c4cnc(c(F)c4n2)-c2c(c(Cl)cc4[nH]ncc24)CCCOC(=O)O[C@]2(C)COCCN3C2)CC1] | NA | Step 1. Intermediate ED and Intermediate FFF | Step 1. cataCXium A Pd G3 was used. Chiral separation after was performed Step 3. Details included below. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | (26S)-18-chloro-4-((1-((dimethylamino)methyl)cyclopropyl)methoxy)-32-fluoro-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | | | |
| 332 | 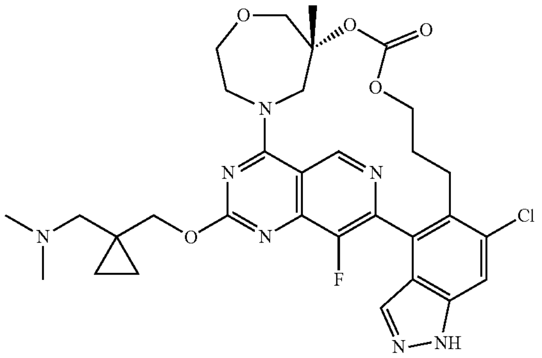 [SMILES: CN(C)CC1(COc2nc3c4cnc(c(F)c4n2)-c2c(c(Cl)cc4[nH]ncc24)CCCOC(=O)O[C@@]2(C)COCCN3C2)CC1] (26R)-18-chloro-4-((1-((dimethylamino)methyl)cyclopropyl)methoxy)-32-fluoro-26-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1. Intermediate ED and Intermediate FFF | cataCXium A Pd G3 was used. Chiral separation after was performed Step 3. Details included below. |
| 333 | 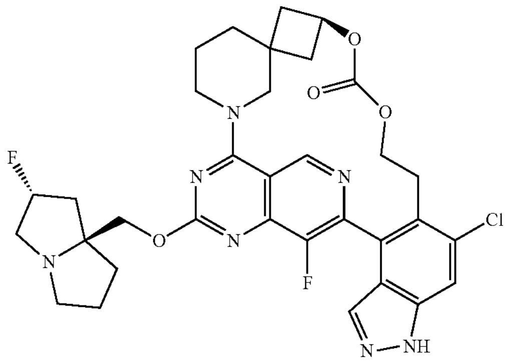 (1R,3S)-10-chloro-32-fluoro-24-(((2R,7aS)-2-fluorotetrahydro-1H-pyrrolo[1,2-a]pyrrol-7a(5H)-yl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | bis (tri-fluoro-acetate) | Step 1. Intermediate BE and Intermediate CU | Step 1. cataCXium A Pd G3 was used instead of (R)-MOP/ $Pd(OAc)_2$. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 334 | 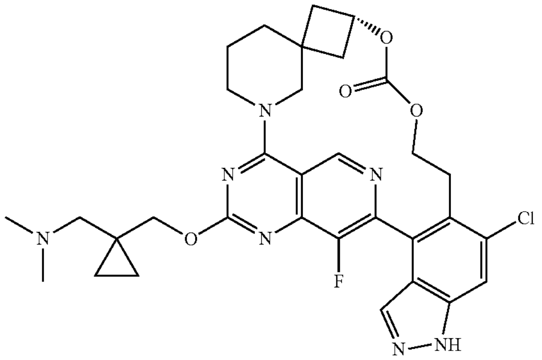 (1S,3R)-10-chloro-24-((1-((dimethylamino)methyl)cyclopropyl)methoxy)-32-fluoro-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | trifluoro-acetate | Step 1. Intermediate EF and Intermediate CU | Step 1. cataCXium A Pd G3 was used instead of (R)-MOP/ $Pd(OAc)_2$. |
| 335 | 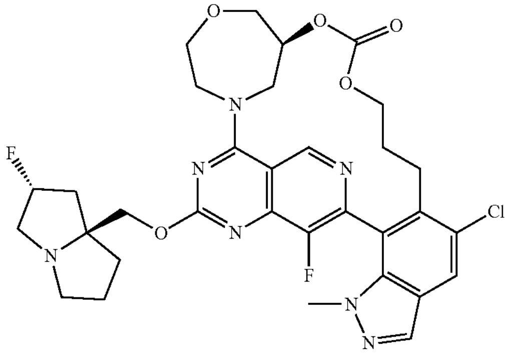 [SMILES: Cn1ncc2cc(Cl)c3c(c21)-c1ncc2c(nc(OC[C@@]45CCCN4C[C@H](F)C5)nc2c1F)N1CCOC[C@H](C1)OC(=O)OCCC3] (26S)-18-chloro-32-fluoro-4-(((2R,7aS)-2-fluorotetrahydro-1H-pyrrolo[1,2-a]pyrrol-7a(5H)-yl)methoxy)-13-methyl-23,25,28-trioxa-1,3,5,9,13,14-hexaazahexacyclo[24.4.1.1~6,10~.0~2,7~.0~11,19~.0~12,16~]dotriaconta-2,4,6,8,10(32),11,14,16,18-nonaen-24-one | Formate | Step 1. Intermediate FC and Intermediate VV | |
| 336 | 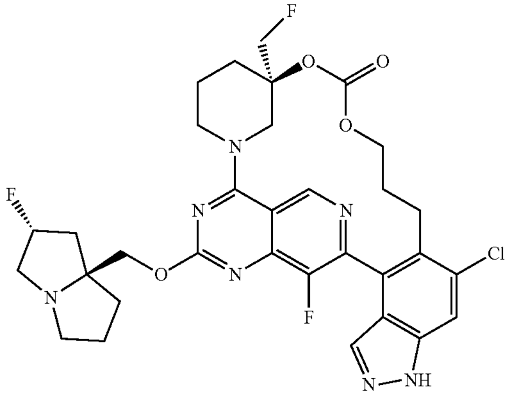 [SMILES: O=C1OCCCc2c(Cl)cc3[nH]ncc3c2-c2ncc3c(nc(OC[C@@]45CCCN4C[C@H](F)C5)nc3c2F)N2CCC[C@](CF)(C2)O1] (17R)-9-chloro-30-fluoro-17-(fluoromethyl)-24-(((2R,7aS)-2-fluorotetrahydro-1H-pyrrolo[1,2-a]pyrrol-7a(5H)-yl)methoxy)-14,16-dioxa-5,6,21,23,25,29- | NA | Step 1: Intermediate V and Intermediate FFF | Sample went through additional SFC purification . using a HILIC, 21.2 x 100 mm, 5 um column, a mobile phase of methanol with 0.2% DEA and a flowrate of 80 mL/min. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | hexaazahexacyclo[24.3.1.1~17,21~.0~2,10~.0~3,7~.0~22,27~]hentriaconta-1(30),2,4,7,9,22,24,26,28-nonaen-15-one | | | |
| 337 | 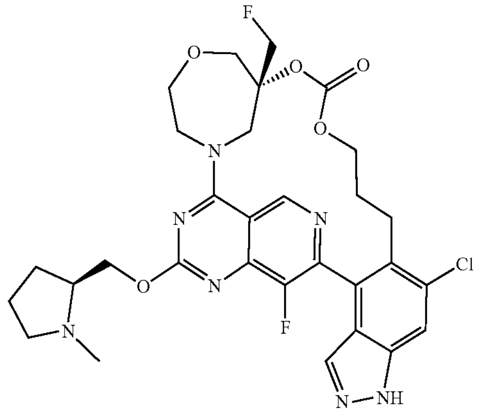 [SMILES: CN1CCC[C@H]1COc1nc2c3cnc(c(F)c3n1)-c1c(c(Cl)cc3[nH]ncc13)CCCOC(=O)O[C@@]1(CF)COCCN2C1] (26R)-18-chloro-32-fluoro-26-(fluoromethyl)-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate EG and Intermediate FFF | Chiral separation after Step 3. Details included below. |
| 338 | 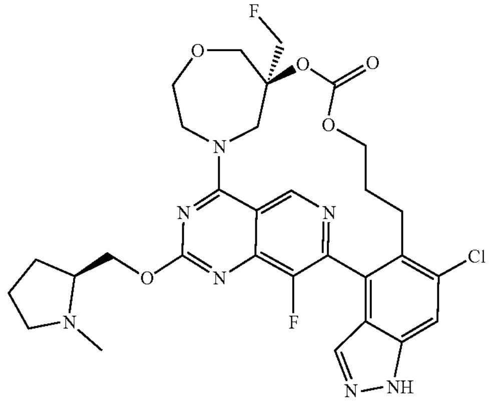 [SMILES: CN1CCC[C@H]1COc1nc2c3cnc(c(F)c3n1)-c1c(c(Cl)cc3[nH]ncc13)CCCOC(=O)O[C@]1(CF)COCCN2C1] (26S)-18-chloro-32-fluoro-26-(fluoromethyl)-4-(((2S)-1-methyl-2-pyrrolidinyl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate EG and Intermediate FFF | Chiral separation after Step 3. Details included below. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 339 | 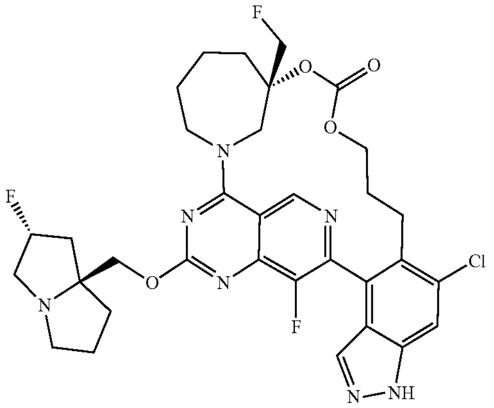 [SMILES: O=C1OCCCc2c(Cl)cc3[nH]ncc3c2-c2ncc3c(nc(OC[C@@]45CCCN4C[C@H](F)C5)nc3c2F)N2CCCC[C@@](CF)(C2)O1] (26S)-18-chloro-32-fluoro-26-(fluoromethyl)-4-(((2R,7aS)-2-fluorotetrahydro-1H-pyrrolo[1,2-a]pyrrol-7a(5H)-yl)methoxy)-23,25-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate EH and Intermediate FFF | Chiral separation after Step 3. Details included below. |
| 340 | 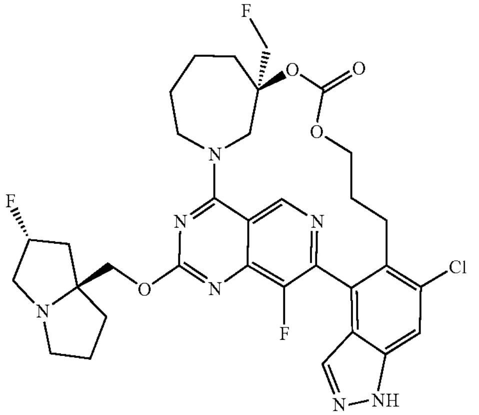 [SMILES: O=C1OCCCc2c(Cl)cc3[nH]ncc3c2-c2ncc3c(nc(OC[C@@]45CCCN4C[C@H](F)C5)nc3c2F)N2CCCC[C@](CF)(C2)O1] (26R)-18-chloro-32-fluoro-26-(fluoromethyl)-4-(((2R,7aS)-2-fluorotetrahydro-1H-pyrrolo[1,2-a]pyrrol-7a(5H)-yl)methoxy)-23,25-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate EH and Intermediate FFF | Chiral separation after Step 3. Details included below. |
| 341 | 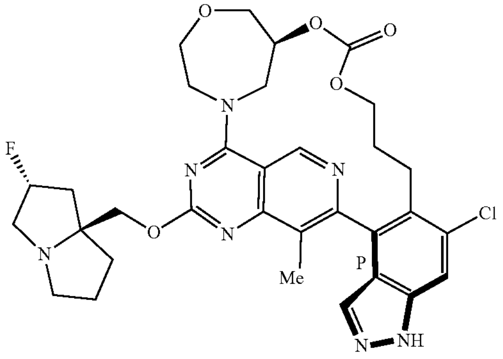 | NA | Step 2: Intermediate EJ | Step 1 was not preformed. Pre-TLC separation after Step 3. |

TABLE 29-continued

| Ex.# | Structure & Name | Salt Form | Reagent | Method Change |
|---|---|---|---|---|
| | Additional Examples 92 to 98, 100 to 102, 179 to 212 and 303 to 368. Prepared in an Analogous Manner to Example 38. | | | |
| | (26S)-18-chloro-4-(((2R,7aS)-2-fluorotetrahydro-1H-pyrrolo[1,2-a]pyrrol-7a(5H)-yl)methoxy)-32-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | | | |
| 342 | 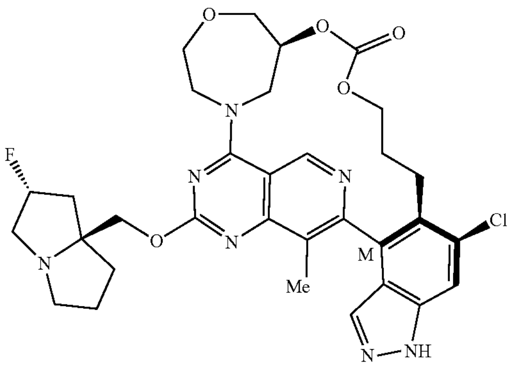 (26S)-18-chloro-4-(((2R,7aS)-2-fluorotetrahydro-1H-pyrrolo[1,2-a]pyrrol-7a(5H)-yl)methoxy)-32-methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 2: Intermediate EJ | Step 1 was not preformed. Pre-TLC separation after Step 3. |
| 343 | 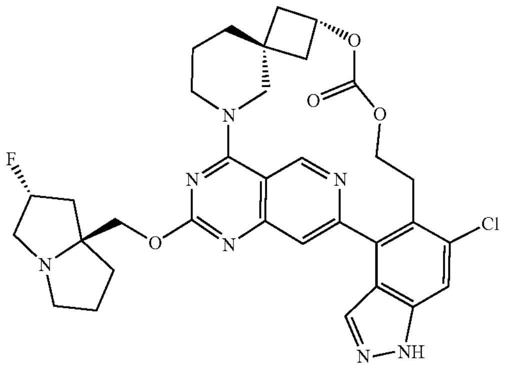 [SMILES: O=C1OCCc2c(Cl)cc3[nH]ncc3c2-c2cc3nc(OC[C@@]45CCCN4C[C@H](F)C5)nc(c3cn2)N2CCC[C@]3(C2)C[C@H](C3)O1] (1R,3S)-10-chloro-24-(((2R,7aS)-2-fluorotetrahydro-1H-pyrrolo[1,2-a]pyrrol-7a(5H)-yl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate EL and Intermediate EM | Step 1: $Pd(Ph_3P)_4$ was used instead of $Pd(OAc)_2$/(R)-MOP. |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| 344 | 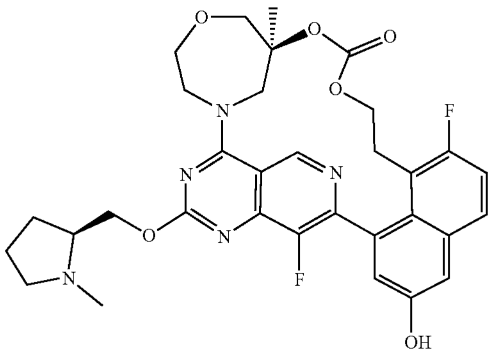 [SMILES: CN1CCC[C@H]1COc1nc2c3cnc(c(F)c3n1)-c1cc(O)cc3ccc(F)c(c13)CCOC(=O)O[C@]1(C)COCCN2C1] (16S)-23,32-difluoro-28-hydroxy-16-methyl-8-(((2S)-1-methyl-2-pyrrolidinyl)methoxy)-14,17,19-trioxa-3,7,9,11-tetraazahexacyclo[20.7.1.1~2,6~.1~11,16~.0~5,10~.0~26,30~]dotriaconta-1(30),2(32),3,5,7,9,22,24,26,28-decaen-18-one | NA | Step 1: Intermediate EN and Intermediate EO | Step 1: cataCXium A Pd G3 was used instead of $Pd(OAc)_2$/(R)-MOP. Step 2 Temperature was 80° C. instead of rt. |
| 345 | 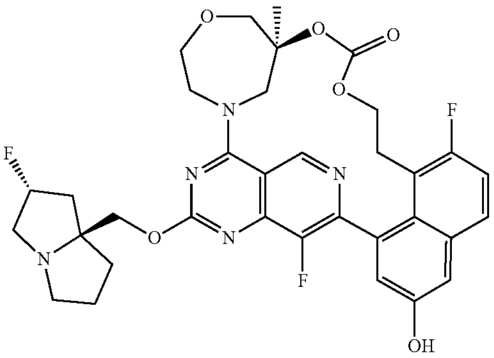 [SMILES: C[C@@]12COCCN(C1)c1nc(OC[C@@]34CCCN3C[C@H](F)C4)nc3c(F)c(ncc13)-c1cc(O)cc3ccc(F)c(c13)CCOC(=O)O2] (16S)-23,32-difluoro-8-(((2R,7aS)-2-fluorotetrahydro-1H-pyrrolo[1,2-a]pyrrol-7a(5H)-yl)methoxy)-28-hydroxy-16-methyl-14,17,19-trioxa-3,7,9,11-tetraazahexacyclo[20.7.1.1~2,6~.1~11,16~.0~5,10~.0~26,30~]dotriaconta-1(30),2(32),3,5,7,9,22,24,26,28-decaen-18-one | | Step 1: Intermediate YYYY and Intermediate EO | Step 1: cataCXium A Pd G3 was used instead of $Pd(OAc)_2$/(R)-MOP. Step 2 Temperature was 45° C. instead of rt |
| 346 | 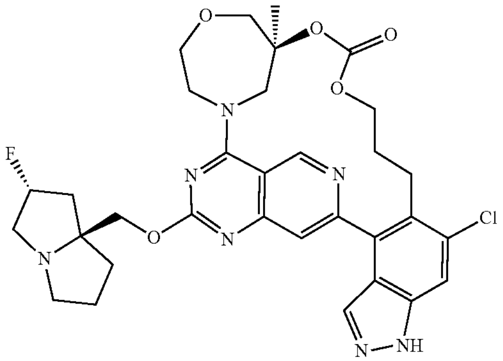 [SMILES: C[C@@]12COCCN(C1)c1nc(OC[C@@]34CCCN3C[C@H](F)C4)nc3cc(ncc13)-c1c(c(Cl)cc3[nH]ncc13)CCCOC(=O)O2] (26S)-18-chloro-4-(((2R,7aS)-2-fluorotetrahydro-1H-pyrrolo[1,2-a]pyrrol-7a(5H)-yl)methoxy)-26-methyl-23,25,28-trioxa-1,3,5,9,14,15- | NA | Step 1: Intermediate EP and Intermediate FFF | Step 1: cataCXium A Pd G3 was used instead of $Pd(OAc)_2$/(R)-MOP. Step 2 Temperature was 60~70° C. instead of rt |

TABLE 29-continued

Additional Examples 92 to 98, 100 to 102, 179 to 212 and 303 to 368. Prepared in an Analogous Manner to Example 38.

| Ex.# | Structure & Name | Salt Form | Reagent | Method Change |
|---|---|---|---|---|
| | hexaazahexacyclo[24.4.1.1~6,10~.0~2,7~.0~11,19~.0~12,16~]dotriaconta-2,4,6(32),7,9,11,13,16,18-nonaen-24-one | | | |
| 347 | 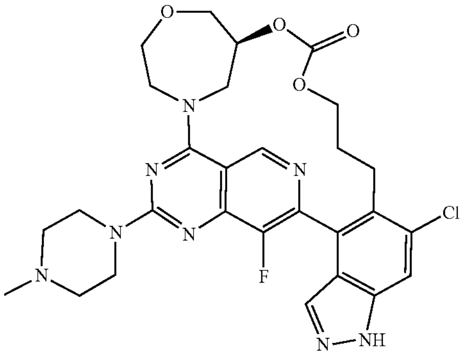 [SMILES: CN1CCN(c2nc3c4cnc(c(F)c4n2)-c2c(c(Cl)cc4[nH]ncc24)CCCOC(=O)O[C@@H]2COCCN3C2)CC1] (26S)-18-chloro-32-fluoro-4-(4-methyl-1-piperazinyl)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate EQ and Intermediate FFF | Step 1: cataCXium A Pd G3 was used instead of $Pd(OAc)_2$/(R)-MOP. Step 2 Temperature was 45° C. instead of rt |
| 348 | 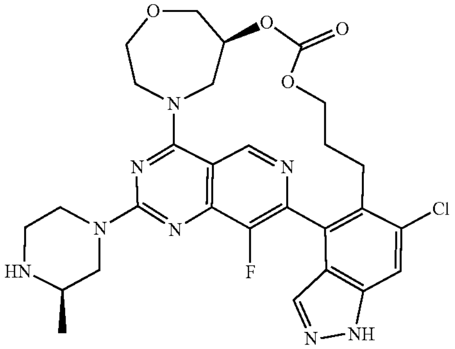 [SMILES: C[C@@H]1CN(c2nc3c4cnc(c(F)c4n2)-c2c(c(Cl)cc4[nH]ncc24)CCCOC(=O)O[C@@H]2COCCN3C2)CCN1] (26S)-18-chloro-32-fluoro-4-((3R)-3-methyl-1-piperazinyl)-23,25,28-trioxa-1,3,5,9,14,15-hexaazahexacyclo[4.4.1.1~6,10~.0~2,7~.0~11,19~.0~12,16~]dotriaconta-2,4,6,8,10(32),11,13,16,18-nonaen-24-one | NA | Step 1: Intermediate ER and Intermediate FFF | Step 1: cataCXium A Pd G3 was used instead of $Pd(OAc)_2$/(R)-MOP. Step 2 Temperature was 45° C. instead of rt |
| 349 | 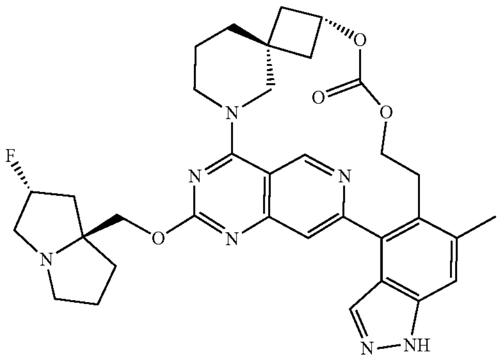 [SMILES: Cc1cc2[nH]ncc2c2c1CCOC(=O)O[C@H]1C[C@]3(CCCN(C3)c3nc(OC[C@@]45CCCN4C[C@H](F)C5)nc4cc-2ncc34)C1] (1R,3S)-24-(((2R,7aS)-2-fluorotetrahydro-1H-pyrrolo[1,2-a]pyrrol-7a(5H)-yl)methoxy)-10-methyl-4,6-dioxa-13,14,19,23,25,27- | NA | Step 1: Intermediate EL and Intermediate BN | Step 1: cataCXium A Pd G3 was used instead of $Pd(OAc)_2$/(R)-MOP. Step 2 Temperature was 20-40° C. instead of rt |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | hexaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 350 | 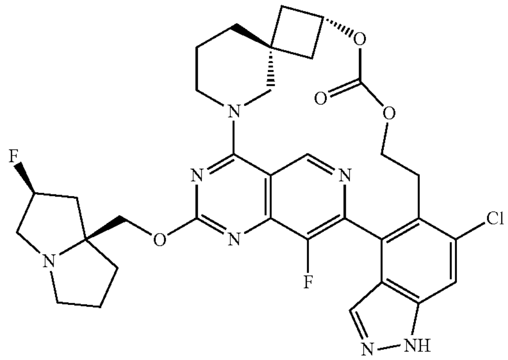 [SMILES: O=C1OCCc2c(Cl)cc3[nH]ncc3c2-c2ncc3c(nc(OC[C@@]45CCCN4C[C@@H](F)C5)nc3c2F)N2CCC[C@]3(C2)C[C@H](C3)O1] (1R,3S)-10-chloro-32-fluoro-24-(((2S,7aS)-2-fluorotetrahydro-1H-pyrrolo[1,2-a]pyrrol-7a(5H)-yl)methoxy)-4,6-dioxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate ES and Intermediate EM | Step 1: cataCXium A Pd G3 was used instead of $Pd(OAc)_2$/(R)-MOP. Step 2 Temperature was 45° C. instead of rt |
| 351 | 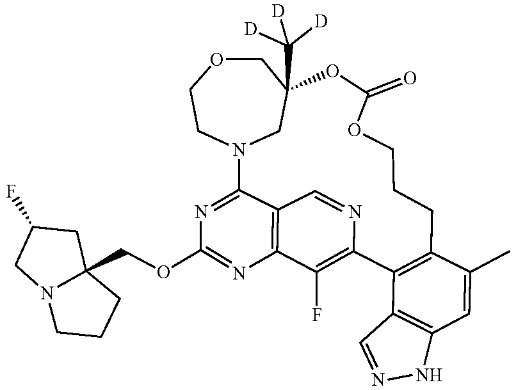 [SMILES: [2H]C([2H])([2H])[C@]12COCCN(C1)c1nc(OC[C@@]34CCCN3C[C@H](F)C4)nc3c(F)c(ncc13)-c1c(c(C)cc3[nH]ncc13)CCCOC(=O)O2] (26R)-32-fluoro-4-(((2R,7aS)-2-fluorotetrahydro-1H-pyrrolo[1,2-a]pyrrol-7a(5H)-yl)methoxy)-18-methyl-26-(~2~H_3_)methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate ET | Step 1: cataCXium A Pd G3 was used. Step 2 Temperature was 45° C. Chiral separation after Step 3. Details included below. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 352 | 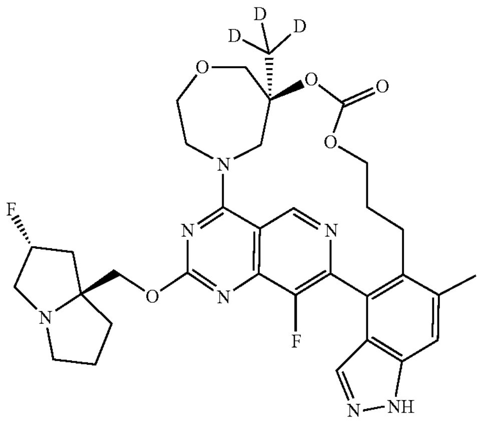 [SMILES: [2H]C([2H])([2H])[C@@]12COCCN(C1)c1nc(OC[C@@]34CCCN3C[C@H](F)C4)nc3c(F)c(ncc13)-c1c(c(C)cc3[nH]ncc13)CCCOC(=O)O2] (26S)-32-fluoro-4-(((2R,7aS)-2-fluorotetrahydro-1H-pyrrolo[1,2-a]pyrrol-7a(5H)-yl)methoxy)-18-methyl-26-(~2~H_3_)methyl-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one | NA | Step 1: Intermediate ET | Step 1: cataCXium A Pd G3 was used. Step 2 Temperature was 45~60° C. Chiral separation after Step 3. Details included below. |
| 353 | 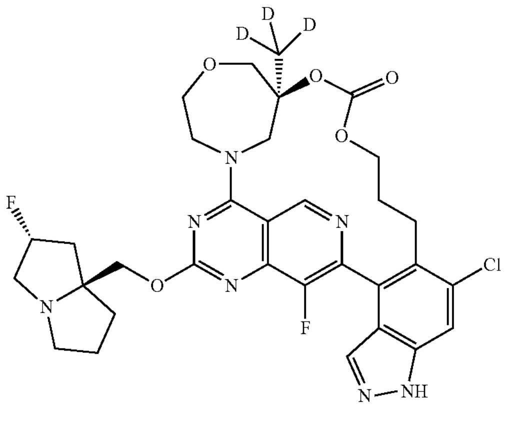 [SMILES: [2H]C([2H])([2H])[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2] (26S)-18-chloro-32-fluoro-4-(((2R,7aS)-2-fluorotetrahydro-1H-pyrrolo[1,2-a]pyrrol-7a(5H)-yl)methoxy)-26-(~2~H_3_)methyl-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate ET and Intermediate FFF | Step 1: cataCXium A Pd G3 was used. Step 2 Temperature was 45~60° C. Chiral separation after Step 3. Details included below. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 354 | 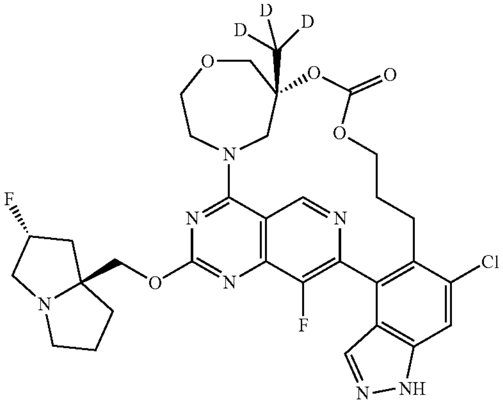 [SMILES: [2H]C([2H])([2H])[C@]12COCCN(C1)c1nc(OC[C@@]34CCCN3C[C@H](F)C4)nc3c(F)c(ncc13)-c1c(c(Cl)cc3[nH]ncc13)CCCOC(=O)O2] (26R)-18-chloro-32-fluoro-4-(((2R,7aS)-2-fluorotetrahydro-1H-pyrrolo[1,2-a]pyrrol-7a(5H)-yl)methoxy)-26-(~2~H_3_)methyl-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate ET and Intermediate FFF | Step 1: cataCXium A Pd G3 was used. Step 2 Temperature was 45~60° C. Chiral separation after Step 3. Details included below. |
| 355 | 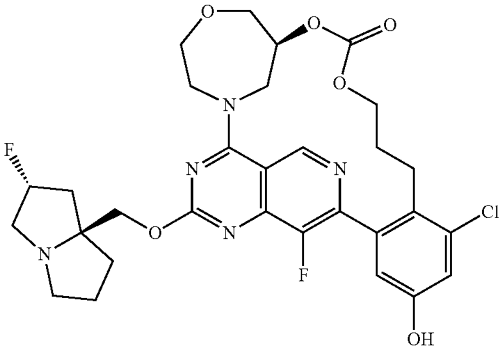 [SMILES: O=C1OCCCc2c(Cl)cc(O)cc2-c2ncc3c(nc(OC[C@@]45CCCN4C[C@H](F)C5)nc3c2F)N2CCOC[C@H](C2)O1] (23S)-15-chloro-29-fluoro-4-(((2R,7aS)-2-fluorotetrahydro-1H-pyrrolo[1,2-a]pyrrol-7a(5H)-yl)methoxy)-13-hydroxy-20,22,25-trioxa-1,3,5,9-tetraazapentacyclo[21.4.1.1~6,10~.0~2,7~.0~11,16~]nonacosa-2,4,6,8,10(29),11,13,15-octaen-21-one | NA | Step 1. Intermediate VV and Intermediate EU | Step 1: cataCXium A Pd G3 was used instead of $Pd(OAc)_2$/(R)-MOP. Step 2 Temperature was 25~40° C. instead of rt |
| 356 | 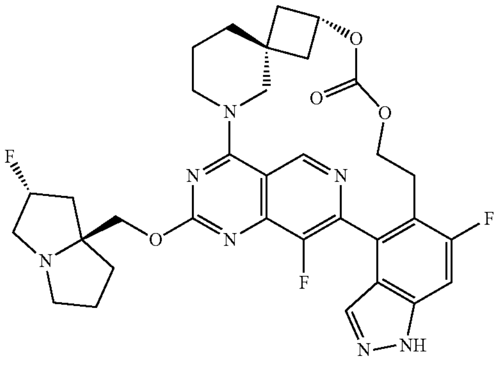 [SMILES: O=C1OCCc2c(F)cc3[nH]ncc3c2-c2ncc3c(nc(OC[C@@]45CCCN4C[C@H](F)C5)nc3c2F)N2CCC[C@]3(C2)C[C@H](C3)O1] (1R,3S)-10,32-difluoro-24-(((2R,7aS)-2-fluorotetrahydro-1H-pyrrolo[1,2-a]pyrrol-7a(5H)-yl)methoxy)-4,6-dioxa- | NA | Step 1. Intermediate EX and Intermediate EW | Step 1: cataCXium A Pd G3 was used instead of $Pd(OAc)_2$/(R)-MOP. Step 2 Temperature was 20~60° C. instead of rt |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | 13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-5-one | | | |
| 357 | 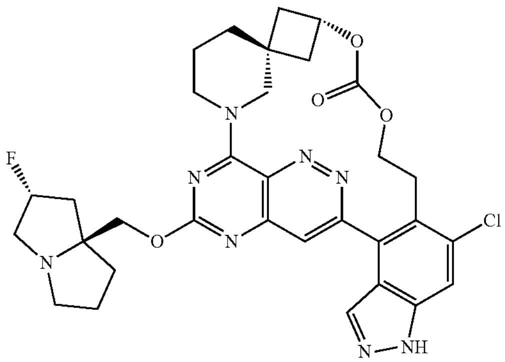 [SMILES: O=C1OCCc2c(Cl)cc3[nH]ncc3c2-c2cc3nc(OC[C@@]45CCCN4C[C@H](F)C5)nc(c3nn2)N2CCC[C@]3(C2)C[C@H](C3)O1] (1R,3S)-10-chloro-24-(((2R,7aS)-2-fluorotetrahydro-1H-pyrrolo[1,2-a]pyrrol-7a(5H)-yl)methoxy)-4,6-dioxa-13,14,19,20,23,25,27-heptaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate EY and Intermediate EM | Step 1: cataCXium A Pd G3 was used instead of $Pd(OAc)_2$/ (R)-MOP. Step 2 Temperature was 45~60° C. instead of rt |
| 358 | 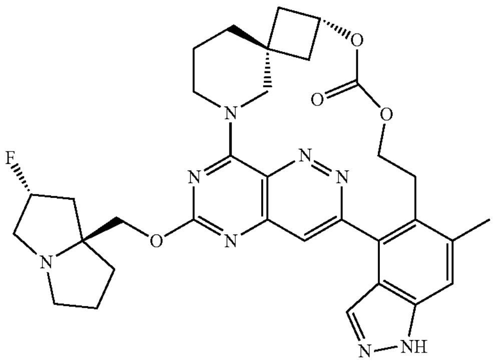 [SMILES: Cc1cc2[nH]ncc2c2c1CCOC(=O)O[C@H]1C[C@]3(CCCN(C3)c3nc(OC[C@@]45CCCN4C[C@H](F)C5)nc4cc-2nnc34)C1] (1R,3S)-24-(((2R,7aS)-2-fluorotetrahydro-1H-pyrrolo[1,2-a]pyrrol-7a(5H)-yl)methoxy)-10-methyl-4,6-dioxa-13,14,19,20,23,25,27-heptaazaheptacyclo[25.3.1.1~1,3~.1~18,22~.0~9,17~.0~12,16~.0~21,26~]tritriaconta-9,11,14,16,18(32),19,21,23,25-nonaen-5-one | NA | Step 1: Intermediate EY and Intermediate BN | Step 1: cataCXium A Pd G3 was used instead of $Pd(OAc)_2$/ (R)-MOP. Step 2 Temperature was 45~60° C. instead of rt |
| 359 | 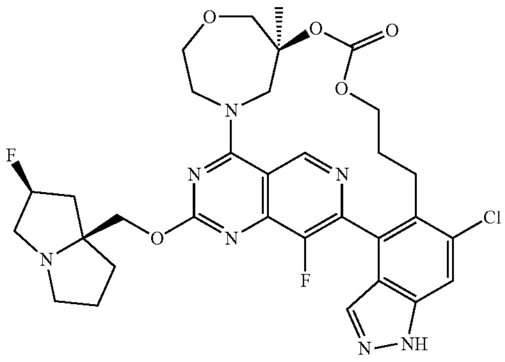 [SMILES: C[C@@]12COCCN(C1)c1nc(OC[C@@]34CCCN3C[C@@H](F)C4)nc3c(F)c(ncc13)-c1c(c(Cl)cc3[nH]ncc13)CCCOC(=O)O2] | NA | Step 1: Intermediate EZ and Intermediate FFF | Step 1: cataCXium A Pd G3 was used instead of $Pd(OAc)_2$/ (R)-MOP. Step 2 Temperature was 45~60° C. instead of rt |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | (26S)-18-chloro-32-fluoro-4-(((2S,7aS)-2-fluorotetrahydro-1H-pyrrolo[1,2-a]pyrrol-7a(5H)-yl)methoxy)-26-methyl-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | | | |
| 360 | 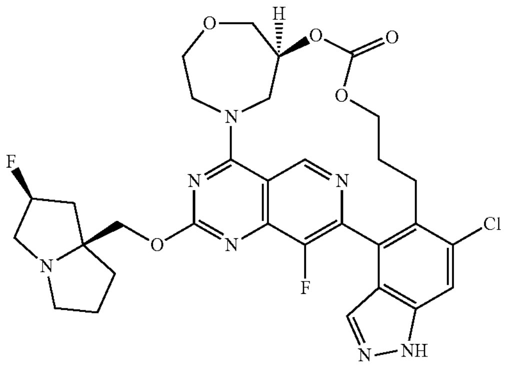 [SMILES: O=C1OCCCc2c(Cl)cc3[nH]ncc3c2-c2ncc3c(nc(OC[C@@]45CCCN4C[C@@H](F)C5)nc3c2F)N2CCOC[C@H](C2)O1] (26S)-18-chloro-32-fluoro-4-(((2S,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate EZ and Intermediate FFF | Step 1: cataCXium A Pd G3 was used instead of $Pd(OAc)_2$/(R)-MOP. Step 2 Temperature was 45° C. instead of rt |
| 361 | 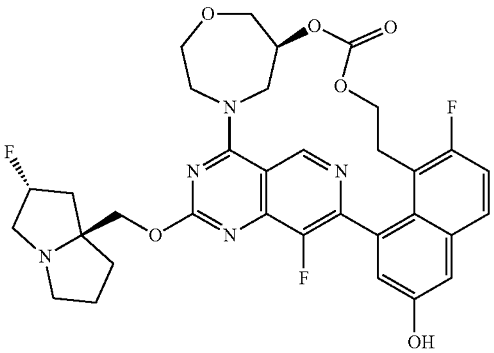 [SMILES: O=C1OCCc2c(F)ccc3cc(O)cc(c23)-c2ncc3c(nc(OC[C@@]45CCCN4C[C@H](F)C5)nc3c2F)N2CCOC[C@H](C2)O1] (16S)-23,32-difluoro-8-(((2R,7aS)-2-fluorotetrahydro-1H-pyrrolo[1,2-a]pyrrol-7a(5H)-yl)methoxy)-28-hydroxy-14,17,19-trioxa-3,7,9,11-tetraazahexacyclo[20.7.1.1~2,6~.1~11,16~.0~5,10~.0~26,30~]dotriaconta-1(30),2(32),3,5,7,9,22,24,26,28-decaen-18-one | NA | Step 1. Intermediate VV and Intermediate EO | Step 1: cataCXium A Pd G3 was used instead of $Pd(OAc)_2$/(R)-MOP. Step 2 Temperature was 25~60° C. instead of rt |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| 362 | 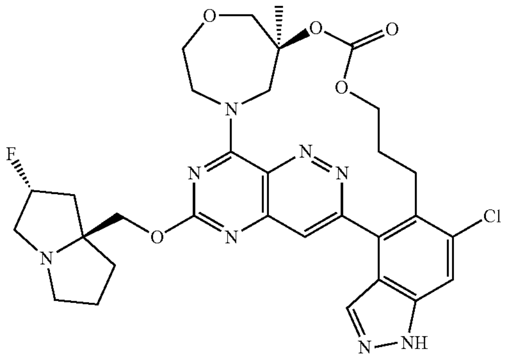 [SMILES: C[C@@]12COCCN(C1)c1nc(OC[C@@]34CCCN3C[C@H](F)C4)nc3cc(nnc13)-c1c(c(Cl)cc3[nH]ncc13)CCCOC(=O)O2] (26R)-18-chloro-4-(((2R,7aS)-2-fluorotetrahydro-1H-pyrrolo[1,2-a]pyrrol-7a(5H)-yl)methoxy)-26-methyl-23,25,28-trioxa-1,3,5,8,9,14,15-heptaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate FA and Intermediate FFF | Step 1: cataCXium A Pd G3 was used. Step 2 Temperature was 45~60° C. Chiral separation after Step 3. Details included below. |
| 363 | 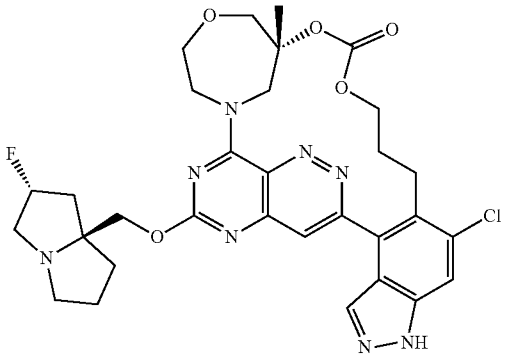 [SMILES: C[C@]12COCCN(C1)c1nc(OC[C@@]34CCCN3C[C@H](F)C4)nc3cc(nnc13)-c1c(c(Cl)cc3[nH]ncc13)CCCOC(=O)O2] (26S)-18-chloro-4-(((2R,7aS)-2-fluorotetrahydro-1H-pyrrolo[1,2-a]pyrrol-7a(5H)-yl)methoxy)-26-methyl-23,25,28-trioxa-1,3,5,8,9,14,15-heptaazahexacyclo[24.4.1.1~6,10~.0~2,7~.0~11,19~.0~12,16~]dotriaconta-2,4,6(32),7,9,11,13,16,18-nonaen-24-one | NA | Step 1: Intermediate FA and Intermediate FFF | Step 1: cataCXium A Pd G3 was used. Step 2 Temperature was 45~60° C. Chiral separation after Step 3. Details included below. |
| 364 | 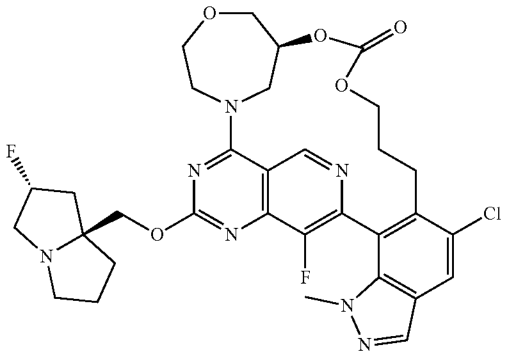 [SMILES: Cn1ncc2cc(Cl)c3c(c21)-c1ncc2c(nc(OC[C@@]45CCCN4C[C@H](F)C5)nc2c1F)N1CCOC[C@H](C1)OC(=O)OCCC3] (26S)-18-chloro-32-fluoro-4-(((2R,7aS)-2-fluorotetrahydro-1H-pyrrolo[1,2-a]pyrrol-7a(5H)-yl)methoxy)-13-methyl-23,25,28-trioxa-1,3,5,9,13,14- | NA | Step 1. Intermediate VV and Intermediate FC | Step 1: cataCXium A Pd G3 was used. Step 2 Temperature was 80° C. Step 3 was not performed. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | hexaazahexacyclo[24.4.1.1~6,10~.0~2,7~.0~11, 19~.0~12,16~]dotriaconta-2,4,6,8,10(32),11,14,16,18-nonaen-24-one | | | |
| 365 | 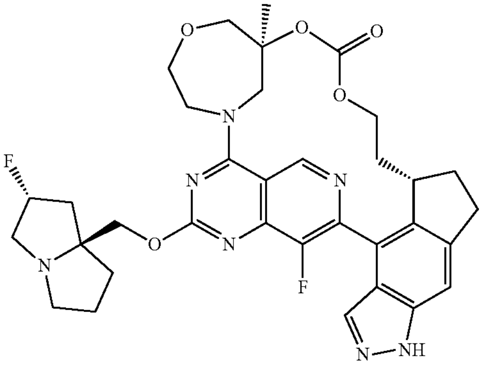 [SMILES: C[C@@]12COCCN(C1)c1nc(OC[C@@]34CCCN3C[C@H](F)C4)nc3c(F)c(ncc13)-c1c3c(cc4[nH]ncc14)CC[C@H]3CCOC(=O)O2] (16S,22S)-34-fluoro-8-(((2R,7aS)-2-fluorotetrahydro-1H-pyrrolo[1,2-a]pyrrol-7a(5H)-yl)methoxy)-16-methyl-14,17,19-trioxa-3,7,9,11,28,29-hexaazaheptacyclo[20.9.1.1~2,6~.1~11,16~.0~5,10~.0~25,32~.0~27,31~]tetratriaconta-1(31),2(34),3,5,7,9,25(32),26,29-nonaen-18-one | NA | Step 1: Intermediate YYYY and Intermediate FD | Step 1: cataCXium A Pd G3 was used. Step 2 Temperature was 25~80° C. Chiral separation after Step 3. Details included below. |
| 366 | 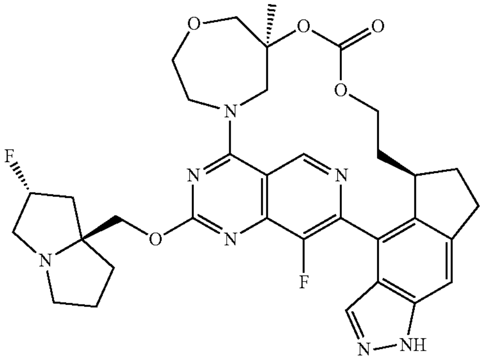 [SMILES: C[C@@]12COCCN(C1)c1nc(OC[C@@]34CCCN3C[C@H](F)C4)nc3c(F)c(ncc13)-c1c3c(cc4[nH]ncc14)CC[C@@H]3CCOC(=O)O2] (16S,22R)-34-fluoro-8-(((2R,7aS)-2-fluorotetrahydro-1H-pyrrolo[1,2-a]pyrrol-7a(5H)-yl)methoxy)-16-methyl-14,17,19-trioxa-3,7,9,11,28,29-hexaazaheptacyclo[20.9.1.1~2,6~.1~11,16~.0~5,10~.0~25,32~.0~27,31~]tetratriaconta-1(31),2(34),3,5,7,9,25(32),26,29-nonaen-18-one | NA | Step 1: Intermediate YYYY and Intermediate FD | Step 1: cataCXium A Pd G3 was used. Step 2 Temperature was 25~80° C. Chiral separation after Step 3. Details included below. |
| 367 | 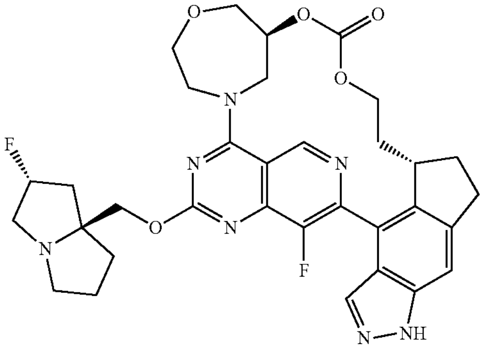 [SMILES: O=C1OCC[C@@H]2CCc3cc4[nH]ncc4c(c32)-c2ncc3c(nc(OC[C@@]45CCCN4C[C@H](F)C5)nc3c2F)N2CCOC[C@H](C2)O1] | NA | Step 1. Intermediate VV and Intermediate FD | Step 1: cataCXium A Pd G3 was used instead of Pd(OAc)$_2$/(R)-MOP. Chiral separation after Step 3. Details included below. |

TABLE 29-continued

| Additional Examples 92 to 98, 100 to 102, 179 to 212 and 303 to 368. Prepared in an Analogous Manner to Example 38. | | | | |
|---|---|---|---|---|
| Ex.# | Structure & Name | Salt Form | Reagent | Method Change |
| | (16S,22S)-34-fluoro-8-(((2R,7aS)-2-fluorotetrahydro-1H-pyrrolo[1,2-a]pyrrol-7a(5H)-yl)methoxy)-14,17,19-trioxa-3,7,9,11,28,29-hexaazaheptacyclo[20.9.1.1~2,6~.1~11,16~.0~5,10~.0~25,32~.0~27,31~]tetratriaconta-1(31),2(34),3,5,7,9,25(32),26,29-nonaen-18-one | | | |
| 368 | 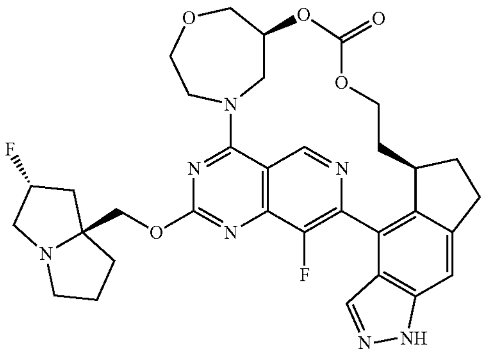 [SMILES: O=C1OCC[C@H]2CCc3cc4[nH]ncc4c(c32)-c2ncc3c(nc(OC[C@@]45CCCN4C[C@H](F)C5)nc3c2F)N2CCOC[C@H](C2)O1] (16S,22R)-34-fluoro-8-(((2R,7aS)-2-fluorotetrahydro-1H-pyrrolo[1,2-a]pyrrol-7a(5H)-yl)methoxy)-14,17,19-trioxa-3,7,9,11,28,29-hexaazaheptacyclo[20.9.1.1~2,6~.1~11,16~.0~5,10~.0~25,32~.0~27,31~]tetratriaconta-1(31),2(34),3,5,7,9,25(32),26,29-nonaen-18-one | NA | Step 1. Intermediate VV and Intermediate FD | Step 1: cataCXium A Pd G3 was used instead of $Pd(OAc)_2$/(R)-MOP. Chiral separation after Step 3. Details included below. |

TABLE 30

| Conditions for Chiral SFC Separation. | | |
|---|---|---|
| Separation | SFC Conditions | Peak to Ex# |
| 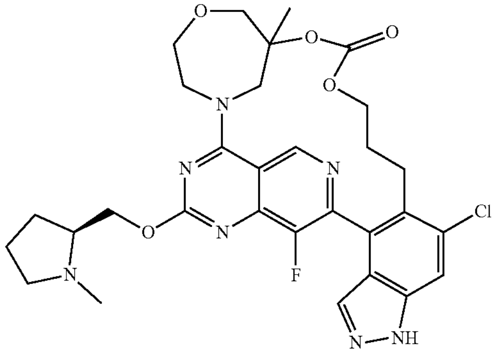 [SMILES: CN1CCC[C@H]1COc1nc2c3cnc(c(F)c3n1)-c1c(c(Cl)cc3[nH]ncc13)CCCOC(=O)OC1(C)COCCN2C1] | Column: Chiralcel OD (2 × 15 cm, 5 μm)<br>Mobile phase: 35% MeOH with 0.2% DEA<br>Flowrate: 120 mL/min.<br>Yield: 300 mg sample was submitted to generate 106 mg of peak 1 with an ee of 99% and 102 mg of peak 2 with an ee of 99%. | Peak 1: Example 180<br>Peak 2: Example 181 |

TABLE 30-continued

Conditions for Chiral SFC Separation.

| Separation | SFC Conditions | Peak to Ex# |
|---|---|---|
| 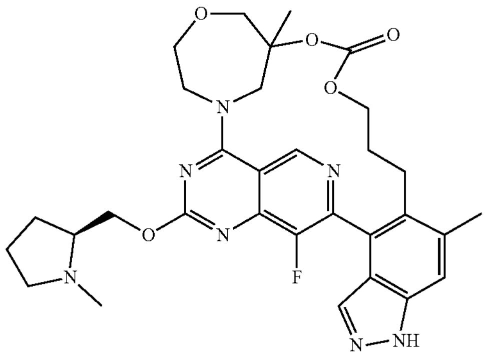 [SMILES: Cc1cc2[nH]ncc2c2c1CCCOC(=O)OC1(C)COCCN(C1)c1nc(OC[C@@H]3CCCN3C)nc3c(F)c-2ncc13] | Column: Chiralcel OD (2 × 15 cm, 5 μm)<br>Mobile phase: 35% MeOH with 0.2% DEA<br>Flowrate: 120 mL/min.<br>Yield: 250 mg sample was submitted to generate 65 mg of peak 1 with an ee of 99% and 75 mg of peak 2 with an ee of 99%. | Peak 1:<br>Example 182<br>Peak 2:<br>Example 183 |
| 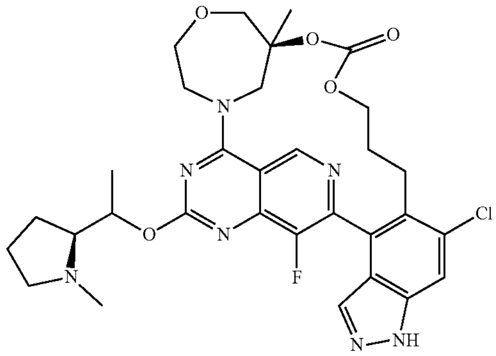 [SMILES: CC(Oc1nc2c3cnc(c(F)c3n1)-c1c(c(Cl)cc3[nH]ncc13)CCCOC(=O)O[C@]1(C)COCCN2C1)[C@@H]1CCCN1C] | Column: ChiralPak ID, 2 × 15 cm, 5 μm<br>Mobile phase: 55% MeOH with 0.2% DEA<br>Flowrate: 65 mL/min.<br>Yield: 289.7 mg sample was submitted to generate 140 mg of peak 1 with an ee of 99% and 37 mg of peak 2 with an ee of 92%. | Peak 1:<br>Example 203<br>Peak 2:<br>Example 204 |
| 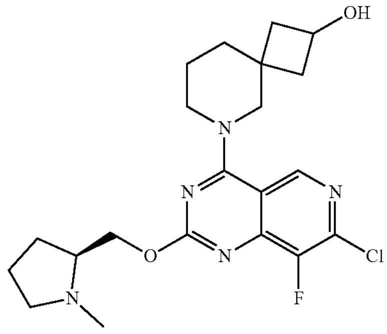 [SMILES: CN1CCC[C@H]1COc1nc(N2CCCC3(CC(O)C3)C2)c2cnc(Cl)c(F)c2n1] | Column: Chiralcel OX, 2 × 15 cm, 5 μm<br>Mobile phase: 40% iPrOH w/ 0.2% DEA<br>Flowrate: 120 mL/min.<br>Yield: 700 mg sample was submitted to generate 273.6 mg of peak 1 with an ee of 99% and 330.3 mg of peak 2 with an ee of 99%. Separated intermediate CQ (peak 2) was used to produce Example 212. | Peak 1:<br>Peak 2:<br>Example 212 |
| 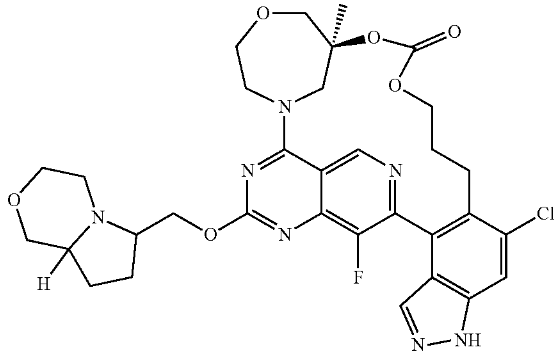 [SMILES: C[C@@]12COCCN(C1)c1nc(OCC3CCC4COCCN43)nc3c(F)c(ncc13)-c1c(c(Cl)cc3[nH]ncc13)CCCOC(=O)O2] | Column: (S,S) Whelk-0, 2 × 25 cm, 5 μm<br>Mobile phase: 55% EtOH with 0.2% DEA<br>Flowrate: 70 mL/min.<br>Yield: 700 mg sample was submitted to generate 16 mg of peak 1 with an ee of >99% and 15 mg of peak 2 with an ee of 98%. | Peak 1:<br>Example 308<br>Peak 2:<br>Example 309 |

TABLE 30-continued

| Conditions for Chiral SFC Separation. | | |
|---|---|---|
| Separation | SFC Conditions | Peak to Ex# |
| 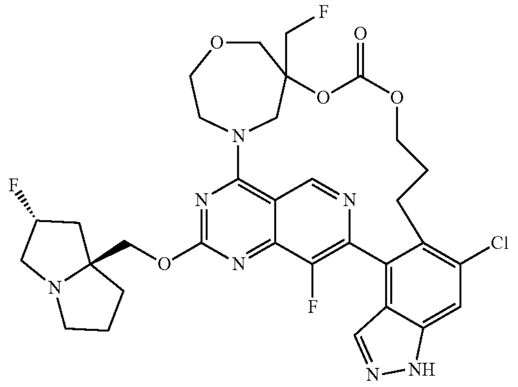 [SMILES: O=C1OCCCc2c(Cl)cc3[nH]ncc3c2-c2ncc3c(nc(OC[C@@]45CCCN4C[C@H](F)C5)nc3c2F)N2CCOCC(CF)(C2)O1] | Column: Chiralcel OD, 2 × 25 cm, 5 μm<br>Mobile phase: 40% MeOH with 0.2% DEA<br>Flowrate: 80 mL/min.<br>Yield: 25 mg sample was submitted to generate 8 mg of peak 1 with an ee of >99% and 9 mg of peak 2 with an ee of >99%. | Peak 1: Example 310<br>Peak 2: Example 311 |
| 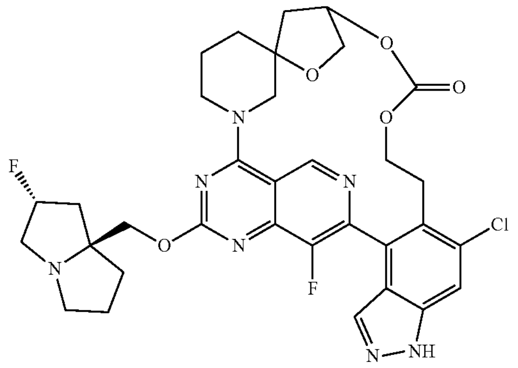 [SMILES: O=C1OCCc2c(Cl)cc3[nH]ncc3c2-c2ncc3c(nc(OC[C@@]45CCCN4C[C@H](F)C5)nc3c2F)N2CCCC3(CC(CO3)O1)C2] | Column: Chiralcel OD, 2 × 25 cm, 5 μm<br>Mobile phase: 40% MeOH with 0.2% DEA<br>Flowrate: 80 mL/min.<br>Yield: 80 mg sample was submitted to generate 32 mg of peak 1 with an ee of >99% and 30 mg of peak 2 with an ee of 98%. | Peak 1: Example 314<br>Peak 2: Example 315 |
| 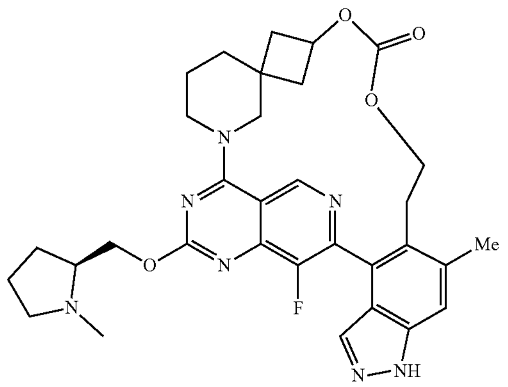 [SMILES: Cc1cc2[nH]ncc2c2c1CCOC(=O)OC1CC3(CCCN(C3)c3nc(OC[C@@H]4CCCN4C)nc4c(F)c-2ncc34)C1] | Column: (S,S) Whelk-0, 2 × 25 cm, 5 μm<br>Mobile phase: 55% EtOH with 0.2% DEA<br>Flowrate: 80 mL/min.<br>Yield: 58 mg sample was submitted to generate 29 mg of peak 1 with an ee of 99% and 25 mg of peak 2 with an ee of 94.5%. | Peak 1/2: Example 325<br>Peak 2: Example 326 |
| 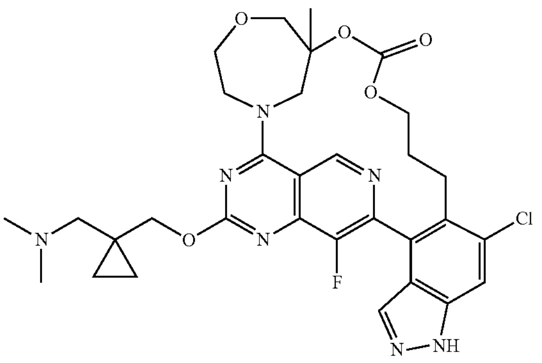 [SMILES: CN(C)CC1(COc2nc3c4cnc(c(F)c4n2)-c2c(c(Cl)cc4[nH]ncc24)CCCOC(=O)OC2(C)COCCN3C2)CC1] | Column: (S,S) Whelk-0, 2 × 25 cm, 5 μm<br>Mobile phase: 45% EtOH with 0.2% DEA<br>Flowrate: 80 mL/min.<br>Yield: 485 mg sample was submitted to generate 60 mg of peak 1 with an ee of >99% and 65 mg of peak 2 with an ee of >99%. | Peak 1/2: Example 332<br>Peak 2: Example 331 |

TABLE 30-continued

Conditions for Chiral SFC Separation.

| Separation | SFC Conditions | Peak to Ex# |
|---|---|---|
| 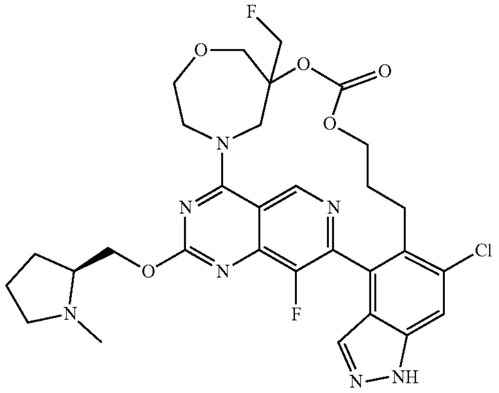 [SMILES: CN1CCC[C@H]1COc1nc2c3cnc(c(F)c3n1)-c1c(c(Cl)cc3[nH]ncc13)CCCOC(=O)OC1(CF)COCCN2C1] | Column: Chiralcel OD, 2 × 25 cm, 5 μm<br>Mobile phase: 40% MeOH with 0.2% DEA<br>Flowrate: 80 mL/min.<br>Yield: 221 mg sample was submitted to generate 70 mg of peak 1 with an ee of 99% and 69 mg of peak 2 with an ee of 99%. | Peak 1: Example 337<br>Peak 2: Example 338 |
| 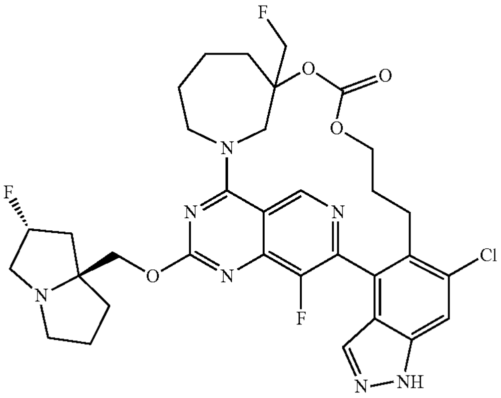 [SMILES: O=C1OCCCc2c(Cl)cc3[nH]ncc3c2-c2ncc3c(nc(OC[C@@]45CCCN4C[C@H](F)C5)nc3c2F)N2CCCCC(CF)(C2)O1] | Column: (S,S) Whelk-0, 2 × 25 cm, 5 μm<br>Mobile phase: 45% MeOH with 0.2% DEA<br>Flowrate: 80 mL/min.<br>Yield: 221 mg sample was submitted to generate 46 mg of peak 1 with an ee of 99% and 37 mg of peak 2 with an ee of 99%. | Peak 1: Example 339<br>Peak 2: Example 340 |
| 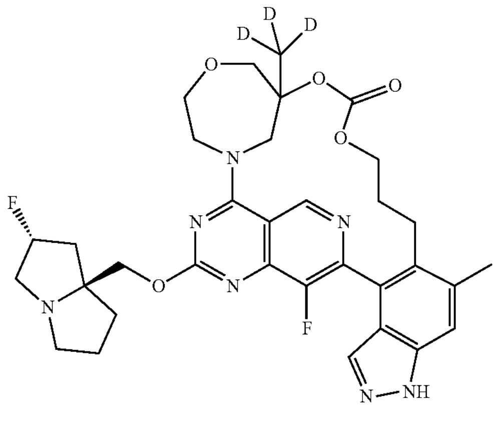 [SMILES: [2H]C([2H])([2H])C12COCCN(C1)c1nc(OC[C@@]34CCCN3C[C@H](F)C4)nc3c(F)c(ncc13)-c1c(c(C)cc3[nH]ncc13)CCCOC(=O)O2] | Column: Daicel Chiralcel OD, 3 × 25 cm, 10 μm<br>Mobile phase: 47% IPA (0.1% $NH_3H_2O$)<br>Flowrate: 75 mL/min<br>Yield: 500 mg sample was submitted to generate mg of peak 1 with an ee of 100% and mg of peak 2 with an ee of 97%. | Peak 1: Example 352<br>Peak 2: Example 351 |

TABLE 30-continued

Conditions for Chiral SFC Separation.

| Separation | SFC Conditions | Peak to Ex# |
|---|---|---|
| 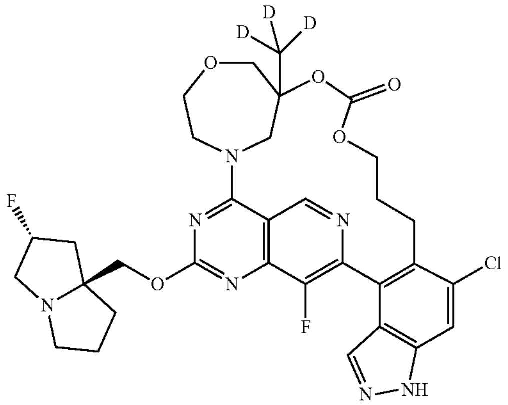 [SMILES: [2H]C([2H])([2H])C12COCCN(C1)c1nc(OC[C@@]34CCCN3C[C@H](F)C4)nc3c(F)c(ncc13)-c1c(c(Cl)cc3[nH]ncc13)CCCOC(=O)O2] | Column: Daicel Chiralcel OD, 3 × 25 cm, 10 μm<br>Mobile phase: 50% IPA(0.1% $NH_3H_2O$)<br>Flowrate: 70 g/min<br>Yield: 330 mg sample was submitted to generate 91 mg of, 1 with an ee of % and 72 mg of peak 2 with an ee of %. | Peak 1: Example 354<br>Peak 2: Example 355 |
| 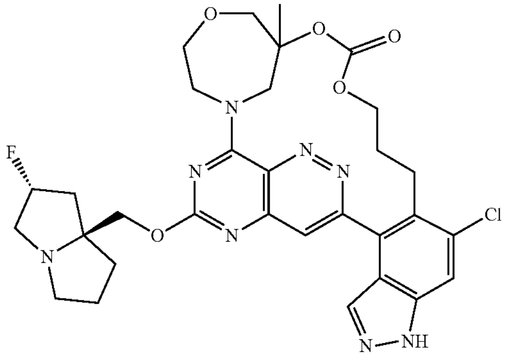 [SMILES: CC12COCCN(C1)c1nc(OC[C@@]34CCCN3C[C@H](F)C4)nc3cc(nnc13)-c1c(c(Cl)cc3[nH]ncc13)CCCOC(=O)O2] | Column: Daicel Chiralcel OD, 3 × 25 cm, 10 μm<br>Mobile phase: 50% IPA(0.1% $NH_3H_2O$)<br>Flowrate: 80 g/min<br>Yield: 60 mg sample was submitted to generate 34 mg of peak 1 with an ee of 100% and 10 mg of peak 2 with an ee of 95%. | Peak 1: Example 363<br>Peak 2: Example 362 |
| 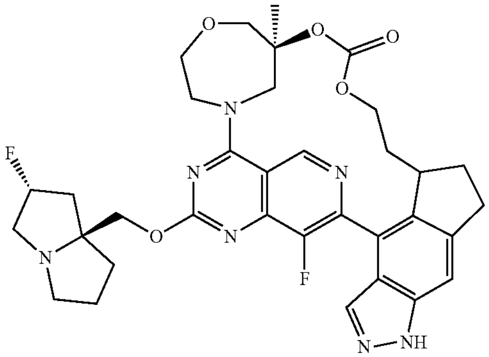 [SMILES: C[C@@]12COCCN(C1)c1nc(OC[C@@]34CCCN3C[C@H](F)C4)nc3c(F)c(ncc13)-c1c3c(cc4[nH]ncc14)CCC3CCOC(=O)O2] | Column: Daicel Chiralpak AD, 3 × 25 cm, 10 μm<br>Mobile phase: 50% IPA(0.1% $NH_3H_2O$)<br>Yield: 140 mg sample was submitted to generate 49 mg of peak 1 with an ee of 100% and 56 mg of peak 2 with an ee of 99%. | Peak 1: Example 366<br>Peak 2: Example 365 |
| 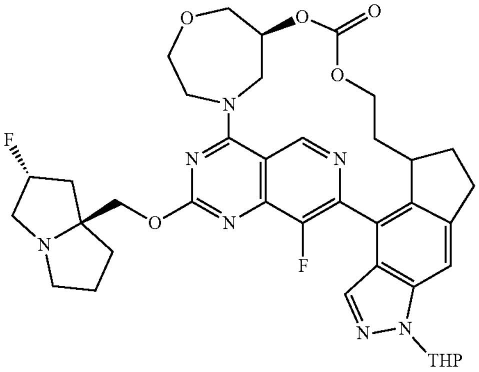 | Column: Chiralpak AD, 3 × 36 cm, 3 μm<br>Mobile phase: IPA (0.2% $NH_3$, 7 M in MeOH)<br>Yield: 26.4 mg of peak 1 with an ee of 100% and 52.4 mg of peak 2 with an ee of 99%. | Peak 1: Example 368<br>Peak 2: Example 367 |

TABLE 31

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| 92 | 608.1 | $^1H$ NMR (400 MHz, METHANOL-$d_4$) δ ppm 9.39 (s, 1 H), 7.66 (s, 1 H), 7.56 (s, 1 H), 5.41-5.60 (m, 2 H), 4.86-5.06 (m, 2 H), 4.81-4.85 (m, 1 H), 4.71-4.77 (m, 1 H), 4.25-4.36 (m, 1 H), 4.02-4.19 (m, 1 H), 3.85-4.00 (m, 2 H), 3.60-3.82 (m, 2 H), 3.35-3.44 (m, 1 H), 3.21 (s, 3 H), 2.77-2.88 (m, 1 H), 2.59 (s, 5 H), 2.30-2.56 (m, 2 H), 2.01-2.16 (m, 1 H), 1.82-1.97 (m, 2 H), 1.42-1.82 (m, 4 H). $^{19}F$ NMR (376 MHz, METHANOL-$d_4$) δ ppm −77.38 (s), −142.04 (br s), −174.12 (br s). |
| 93 | 637.8 | $^1H$ NMR (400 MHz, METHANOL-$d_4$) δ ppm 9.36 (s, 1 H), 7.79 (s, 1 H), 7.55 (s, 1 H), 5.52-5.76 (m, 1 H), 4.91-5.26 (m, 4 H), 4.68-4.82 (m, 2 H), 4.29-4.39 (m, 1 H), 3.89-4.15 (m, 4 H), 3.66-3.76 (m, 1 H), 3.46-3.57 (m, 1 H), 3.17-3.31 (m, 1 H), 2.62-2.89 (m, 2 H), 2.56 (s, 4 H), 2.29-2.48 (m, 4 H), 2.06-2.29 (m, 3 H), 1.41-1.67 (m, 2 H). $^{19}F$ NMR (376 MHz, METHANOL-$d_4$) δ ppm −77.26 (s), −141.72 (d, J = 31.2 Hz), −174.11 (d, J = 26.9 Hz), −186.03 (d, J = 18.2 Hz). |
| 94 | 634.2 | $^1H$ NMR (400 MHz, METHANOL-$d_4$) δ ppm 9.32 (s, 1 H) 7.81 (s, 1 H) 7.55 (s, 1 H) 5.49-5.73 (m, 1 H) 5.07-5.20 (m, 2 H) 4.79-4.83 (m, 1 H) 4.62-4.79 (m, 2 H) 4.21-4.36 (m, 1 H) 3.83-4.13 (m, 4 H) 3.62-3.76 (m, 1 H) 3.44-3.54 (m, 1 H) 3.23-3.31 (m, 1 H) 2.60-2.86 (m, 2 H) 2.56 (s, 5 H) 2.32-2.46 (m, 3 H) 2.12-2.25 (m, 2 H) 1.64-1.79 (m, 2 H) 1.49-1.64 (m, 2 H) 0.90 (d, J = 6.84 Hz, 3 H). $^{19}F$ NMR (376 MHz, METHANOL-$d_4$) δ ppm −77.48 (s), −141.88 (s), −174.10 (s). |
| 95 | 638.0 | $^1H$ NMR (400 MHz, METHANOL-$d_4$) δ ppm 9.37 (s, 1 H), 7.75 (d, J = 0.6 Hz, 1 H), 7.55 (s, 1 H), 5.74-5.92 (m, 1 H), 5.48-5.70 (m, 1 H), 5.27-5.37 (m, 1 H), 4.97-5.12 (m, 2 H), 4.60-4.73 (m, 1 H), 4.17-4.32 (m, 1 H), 3.88-4.14 (m, 4 H), 3.64-3.75 (m, 1 H), 3.45-3.61 (m, 2 H), 2.54-2.73 (m, 7 H), 2.42-2.53 (m, 2 H), 2.31-2.41 (m, 3 H), 2.23-2.31 (m, 1 H), 2.12-2.22 (m, 1 H), 1.62-1.77 (m, 2 H). $^{19}F$ NMR (377 MHz, METHANOL-$d_4$) δ ppm −77.28 (s), −142.16 (d, J = 41.6 Hz), −174.08 (d, J = 26.9 Hz), −182.32-−182.03 (m). |
| 96 | 646.2 | $^1H$ NMR (400 MHz, METHANOL-$d_4$) δ ppm 9.35 (s, 1 H), 7.76 (s, 1 H), 7.56 (s, 1 H), 5.27-5.71 (m, 3 H), 4.63-4.78 (m, 2 H), 3.83-4.14 (m, 4 H), 3.62-3.75 (m, 1 H), 3.44-3.58 (m, 1 H), 2.57 (s, 18 H), 1.53-1.78 (m, 4 H). $^{19}F$ NMR (376 MHz, METHANOL-$d_4$) δ ppm −77.47 (s), −141.95-−141.85 (m), −174.11-−173.99 (m). |
| 97 | 636.2 | $^1H$ NMR (400 MHz, METHANOL-$d_4$) δ ppm 9.30-9.51 (m, 1 H), 7.65-7.73 (m, 1 H), 7.51-7.61 (m, 1 H), 5.47-5.69 (m, 2 H), 4.91-4.99 (m, 1 H), 4.81-4.85 (m, 1 H), 4.68-4.74 (m, 2 H), 4.22-4.35 (m, 1 H), 3.84-4.16 (m, 7 H), 3.71-3.82 (m, 1 H), 3.55-3.68 (m, 1 H), 3.41-3.54 (m, 2 H), 2.53-2.88 (m, 7 H), 2.28-2.49 (m, 3 H), 2.11-2.26 (m, 1 H), 1.79-1.92 (m, 1 H), 1.66-1.78 (m, 1 H). $^{19}F$ NMR (376 MHz, METHANOL-$d_4$) δ ppm −77.32 (s), −142.29-−141.32 (m), −174.94-−173.41 (m). |
| 98 | 634.0 | $^1H$ NMR (400 MHz, METHANOL-$d_4$) δ ppm 9.31-9.46 (m, 1 H), 7.63-7.72 (m, 1 H), 7.51-7.60 (m, 1 H), 5.48-5.68 (m, 2 H), 4.86-4.94 (m, 1 H), 4.75-4.79 (m, 1 H), 4.67-4.77 (m, 2 H), 3.84-4.11 (m, 5 H), 3.72-3.82 (m, 1 H), 3.45-3.56 (m, 1 H), 3.35-3.43 (m, 1 H), 2.54-2.87 (m, 7 H), 2.29-2.49 (m, 4 H), 2.13-2.27 (m, 1 H), 2.02-2.12 (m, 1 H), 1.82-1.98 (m, 2 H), 1.56-1.81 (m, 3 H), 1.45-1.55 (m, 1 H). $^{19}F$ NMR (376 MHz, METHANOL-$d_4$) δ ppm −77.41 (s), −142.57-−141.59 (m), −174.80-−173.55 (m). |
| 100 | 654.0 | $^1H$ NMR (400 MHz, METHANOL-$d_4$) δ ppm 9.40 (s, 1 H), 7.82-7.89 (m, 1 H), 7.71-7.80 (m, 1 H), 5.50-5.68 (m, 2 H), 4.86-4.94 (m, 1 H), 4.76-4.79 (m, 1 H), 4.73 (s, 2 H), 3.75-4.12 (m, 6 H), 3.44-3.57 (m, 1 H), 3.35-3.41 (m, 1 H), 2.98-3.10 (m, 1 H), 2.55-2.85 (m, 3 H), 2.30-2.48 (m, 4 H), 2.15-2.28 (m, 1 H), 2.02-2.14 (m, 1 H), 1.85-1.97 (m, 3 H), 1.43-1.76 (m, 3 H). $^{19}F$ NMR (376 MHz, METHANOL-$d_4$) δ ppm −77.34-−77.21 (m), −141.99-−141.90 (m), −174.11-−174.05 (m). |
| 101 | 618.0 | $^1H$ NMR (400 MHz, METHANOL-$d_4$) δ ppm 9.09 (s, 1 H) 7.88 (s, 1 H) 7.52 (s, 1 H) 6.76-6.85 (m, 1 H) 5.17-5.43 (m, 2 H) 4.90-5.05 (m, 2 H) 4.67-4.76 (m, 1 H) 4.38-4.45 (m, 1 H) 4.25-4.32 (m, 1 H) 4.00-4.16 (m, 3 H) 3.34-3.40 (m, 1 H) 3.23-3.31 (m, 3 H) 3.02-3.10 (m, 1 H) 2.45 (s, 3 H) 2.28-2.36 (m, 1 H) 2.04-2.10 (m, 2 H) 1.90-1.98 (m, 2 H) 1.62-1.69 (m, 1 H) 1.35 (br d, J = 8.57 Hz, 4 H). $^{19}F$ NMR (376 MHz, METHANOL-$d_4$) δ ppm −141.96 (s) −173.67 (s). |
| 102 | 655.9 | $^1H$ NMR (400 MHz, DMSO-$d_6$) δ ppm 12.66-13.47 (m, 1 H), 10.73 (br d, J = 1.9 Hz, 1 H), 8.08 (br d, J = 10.2 Hz, 1 H), 7.65 (s, 1 H), 7.53 (s, 1 H), 5.49-5.73 (m, 1 H), 5.26 (br d, J = 17.1 Hz, 1 H), |

TABLE 31-continued

Analytical Data for Examples 92 to 98, 100 to 102, 179 to 212 and 303 to 368.

| Cmpd.# | MS m/z (ESI): $(M + H)^+$ | $^1$H and $^{19}$F NMR |
|---|---|---|
| | | 4.82-4.89 (m, 1 H), 4.64 (d, J = 11.9 Hz, 1 H), 4.53 (d, J = 11.7 Hz, 1 H), 4.49 (br dd, J = 13.7, 3.7 Hz, 1 H), 4.27 (td, J = 11.3, 4.3 Hz, 1 H), 3.95-4.05 (m, 3 H), 3.77-3.93 (m, 4 H), 3.68-3.76 (m, 2 H), 3.47-3.57 (m, 1 H), 3.22-3.38 (m, 2 H), 2.60-2.71 (m, 2 H), 2.55-2.59 (m, 1 H), 2.31-2.49 (m, 3 H), 2.13-2.27 (m, 2 H), 2.02-2.13 (m, 1 H), 1.70-1.86 (m, 1 H), 1.40-1.54 (m, 1 H). $^{19}$F NMR (376 MHz, DMSO-$d_6$) δ ppm −74.08 (s), −116.66 (s), −124.60 (s), −172.69 (s). |
| 179 | 652.0 | $^1$H NMR (400 MHz, METHANOL-$d_4$) δ ppm 9.24 (s, 1 H) 7.82 (s, 2 H) 5.52-5.62 (m, 1 H) 5.26-5.47 (m, 1 H) 5.05-5.20 (m, 2 H) 4.27-4.53 (m, 2 H) 3.99-4.14 (m, 1 H) 3.69-3.84 (m, 2 H) 3.54-3.64 (m, 1 H) 3.36 (br s, 3 H) 3.07-3.16 (m, 1 H) 2.86-3.00 (m, 1 H) 1.74-2.60 (m, 9 H) 1.30-1.55 (m, 2 H) 0.62-0.75 (m, 1 H) 0.26-0.42 (m, 1 H). $^{19}$F NMR (376 MHz, METHANOL-$d_4$) δ ppm −141.70 (s) −173.80 (d, J = 26.00 Hz). |
| 180 | 626.2 | 1H NMR (600 MHz, DMSO-$d_6$) δ ppm 9.40 (s, 1 H), 7.84 (s, 1 H), 7.75 (s, 1 H), 5.66 (br d, J = 17.5 Hz, 1 H), 4.59 (br d, J = 12.9 Hz, 1 H), 4.45 (dd, J = 10.8, 4.9 Hz, 1 H), 4.23 (dd, J = 10.8, 6.4 Hz, 1 H), 4.07-4.15 (m, 1 H), 3.98-4.06 (m, 1 H), 3.77 (br d, J = 17.5 Hz, 1 H), 3.51-3.67 (m, 4 H), 3.31-3.33 (m, 1 H), 3.06 (d, J = 12.3 Hz, 1 H), 2.93-2.99 (m, 1 H), 2.89 (ddd, J = 13.9, 5.1, 4.9 Hz, 1 H), 2.36-2.39 (m, 2 H), 2.21 (q, J = 8.8 Hz, 1 H), 1.91-2.00 (m, 1 H), 1.73-1.82 (m, 2 H), 1.60-1.71 (m, 3 H), 1.49 (s, 3 H). |
| 181 | 626.2 | 1H NMR (600 MHz, DMSO-$d_6$) δ ppm 9.40 (s, 1 H), 7.84 (s, 1 H), 7.76 (s, 1 H), 5.67 (br d, J = 17.5 Hz, 1 H), 4.59 (br d, J = 13.1 Hz, 1 H), 4.45 (dd, J = 10.9, 5.0 Hz, 1 H), 4.26 (dd, J = 10.7, 6.3 Hz, 1 H), 4.12 (td, J = 12.0, 2.7 Hz, 1 H), 3.99-4.05 (m, 1 H), 3.77 (d, J = 17.5 Hz, 1 H), 3.62-3.67 (m, 2 H), 3.58-3.60 (m, 1 H), 3.51-3.57 (m, 1 H), 3.33 (br s, 1 H), 3.06 (d, J = 12.5 Hz, 1 H), 2.87-2.98 (m, 2 H), 2.36 (s, 2 H), 2.15-2.25 (m, 1 H), 1.90-2.00 (m, 1 H), 1.74-1.82 (m, 2 H), 1.61-1.72 (m, 3 H), 1.49 (s, 3 H). |
| 182 | 606.2 | 1H NMR (600 MHz, DMSO-$d_6$) δ ppm 9.38 (s, 1 H), 7.60 (s, 1 H), 7.50 (s, 1 H), 5.67 (br d, J = 17.5 Hz, 1 H), 4.58 (br d, J = 12.9 Hz, 1 H), 4.45 (dd, J = 10.7, 5.0 Hz, 1 H), 4.22 (dd, J = 10.7, 6.3 Hz, 1 H), 4.12 (td, J = 11.9, 2.6 Hz, 1 H), 3.99-4.05 (m, 1 H), 3.66-3.80 (m, 2 H), 3.58-3.63 (m, 2 H), 3.50-3.57 (m, 1 H), 3.28-3.35 (m, 1 H), 3.07 (br d, J = 12.3 Hz, 1 H), 2.93-2.98 (m, 1 H), 2.70 (ddd, J = 13.9, 5.4, 5.2 Hz, 1 H), 2.37 (s, 3 H), 2.20 (q, J = 8.7 Hz, 1 H), 1.91-2.00 (m, 1 H), 1.60-1.76 (m, 5 H), 1.49 (s, 3 H). |
| 183 | 606.2 | 1H NMR (600 MHz, DMSO-$d_6$) δ ppm 9.39 (s, 1 H), 7.61 (s, 1 H), 7.50 (s, 1 H), 5.67 (br d, J = 17.5 Hz, 1 H), 4.58 (br d, J = 13.1 Hz, 1 H), 4.45 (dd, J = 10.8, 4.9 Hz, 1 H), 4.25 (dd, J = 10.7,6.3 Hz, 1 H), 4.13 (td, J = 12.0, 2.6 Hz, 1 H), 4.02 (dd, J = 12.0, 4.1 Hz, 1 H), 3.67 - 3.80 (m, 2 H), 3.58-3.64 (m, 2 H), 3.50-3.57 (m, 1 H), 3.31 (s, 1 H), 3.07 (br d, J = 12.3 Hz, 1 H), 2.93-2.97 (m, 1 H), 2.71 (ddd, J = 13.9, 5.4, 5.2 Hz, 1 H), 2.36 (s, 3 H), 2.20 (q, J = 8.8 Hz, 1 H), 1.92-1.99 (m, 1 H), 1.61-1.76 (m, 5 H), 1.49 (s, 3 H). |
| 184 | 654.0 | $^1$H NMR (400 MHz, METHANOL-$d_4$) δ ppm 9.44 (s, 1 H), 7.78 (d, J = 1.0 Hz, 1 H), 7.43-7.50 (m, 1 H), 5.78-5.88 (m, 1 H), 5.51-5.71 (m, 1 H), 4.76-4.83 (m, 1 H), 4.66-4.76 (m, 2 H), 4.21-4.31 (m, 1 H), 3.87-4.12 (m, 4 H), 3.79-3.87 (m, 1 H), 3.58-3.74 (m, 4 H), 3.44-3.55 (m, 1 H), 3.16-3.24 (m, 1 H), 2.91-3.01 (m, 1 H), 2.69-2.87 (m, 1 H), 2.56-2.68 (m, 1 H), 2.32-2.49 (m, 4 H), 2.12-2.28 (m, 1 H), 1.85-1.97 (m, 1 H), 1.70-1.83 (m, 1 H), 1.60 (s, 3 H). |
| 185 | 654.0 | $^1$H NMR (400 MHz, METHANOL-$d_4$) δ ppm 9.37-9.53 (m, 1 H), 7.83-7.91 (m, 1 H), 7.69-7.81 (m, 1 H), 5.47-5.59 (m, 1 H), 4.92-5.00 (m, 1 H), 4.63-4.83 (m, 2 H), 4.20-4.37 (m, 2 H), 3.71-4.18 (m, 11 H), 3.51-3.68 (m, 3 H), 3.39-3.49 (m, 1 H), 2.98-3.08 (m, 1 H), 2.47-2.68 (m, 2 H), 2.07-2.30 (m, 3 H), 1.82-1.94 (m, 2 H). |
| 186 | 616.5 | $^1$H NMR (400 MHz, $CDCl_3$-d) δ ppm 9.17 (s, 1 H), 7.50 (dd, J = 8.0, 1.2 Hz 1 H), 7.42 (dd, J = 7.6, 1.2 Hz, 1 H), 7.33 (t, J = 7.0 Hz, 1 H), 5.17-5.43 (m, 2 H), 4.75-5.02 (m, 1 H), 4.79 (d, J = 13.6 Hz, 1 H), 4.25-4.39 (m, 2 H), 4.09-4.23 (m, 3 H), 3.70-3.93 (m, 3 H), 3.32-3.46 (m, 2 H), 3.15-3.23 (m, 3 H), 2.95-3.09 (m, 1 H), 2.51-2.62 (m, 1 H), 2.14-2.42 (m, 3 H), 1.92-2.10 (m, 3 H), 1.75-1.92 (m, 3 H), 1.19-1.32 (m, 1 H). |
| 187 | 673.1 | $^1$H NMR (METHANOL-$d_4$, 400 MHz) δ ppm 7.99 (dd, J = 10.1, 1.3 Hz, 1 H), 7.85 (s, 1 H), 7.74 (s, 1 H), 5.70-5.51 (m, 1 H), 5.41 (br d, J = 17.0 Hz, 1 H), 4.95-4.89 (m, 1 H), 4.74-4.62 (m, 3 H), 4.35 (td, J = 11.7, 4.3 Hz, 1 H), 4.12-4.02 (m, 3 H), 4.01-3.89 (m, 4 H), 3.84-3.75 (m, 1 H), 3.65-3.46 (m, 2 H), 3.37 (br d, J = 7.3 Hz, 1 H), 3.04-2.94 (m, 1 H), 2.85-2.68 (m, 1 H), 2.68-2.56 (m, 2 |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| | | H), 2.49-2.32 (m, 3 H), 2.29-2.10 (m, 1 H), 1.97-1.84 (m, 1 H), 1.69-1.82(m, 1 H). $^{19}F$ NMR (METHANOL-$d_4$, 376 MHz) δ ppm −77.38, −116.94, −125.88, −174.24. |
| 188 | 673.1 | $^1H$ NMR (400 MHz, DMSO-$d_6$) δ ppm 13.19-13.88 (m, 1 H), 10.60-10.88 (m, 1 H), 8.17-8.33 (m, 1 H), 7.90 (d, J = 10.8 Hz, 2 H), 5.51-5.67 (m, 1 H), 4.55-4.65 (m, 3 H), 4.25-4.32 (m, 1 H), 3.91-4.04 (m, 3 H), 3.84-3.90 (m, 2 H), 3.71-3.83 (m, 4 H), 3.25-3.35 (m, 1 H), 2.65-2.75 (m, 1 H), 2.52-2.63 (m, 1 H), 2.30-2.43 (m, 3 H), 2.12-2.26 (m, 3 H), 1.95-2.09 (m, 2 H), 1.62-1.75 (m, 1 H). $^{19}F$ NMR (DMSO-d6, 376 MHz) δ ppm −74.33, −115.78, −125.33, −173.00. |
| 189 | 655.2 | $^1H$ NMR (400 MHz, DMSO-$d_6$) δ ppm 13.13-13.64 (m, 1 H), 10.72 (br d, J = 4.1 Hz, 1 H), 8.09 (d, J = 8.5 Hz, 1 H), 7.82 (s, 1 H), 7.74 (d, J = 0.6 Hz, 1 H), 7.29 (dd, J = 8.5, 6.6 Hz, 1 H), 5.48-5.76 (m, 1 H), 5.28 (br d, J = 17.2 Hz, 1 H), 4.80 (br s, 1 H), 4.63-4.73 (m, 1 H), 4.54 (d, J = 11.8 Hz, 1 H), 4.49 (br dd, J = 13.8, 3.8 Hz, 1 H), 4.25 (td, J = 11.5, 4.1 Hz, 1 H), 3.96-4.04 (m, 2 H), 3.92 (br d, J = 14.5 Hz, 2 H), 3.75-3.86 (m, 2 H), 3.66-3.75 (m, 2 H), 3.48-3.60 (m, 1 H), 3.28-3.38 (m, 1 H), 3.23 (dd, J = 13.2, 7.2 Hz, 1 H), 2.78-2.90 (m, 1 H), 2.61-2.70 (m, 1 H), 2.52-2.57 (m, 1 H), 2.32-2.41 (m, 1 H), 2.13-2.27 (m, 2 H), 2.00-2.11 (m, 1 H), 1.74-1.87 (m, 1 H), 1.52-1.67 (m, 1 H). $^{19}F$ NMR (376 MHz, DMSO-$d_6$) δ ppm −74.29, −129.42, −172.74. |
| 190 | 650.2 | $^1H$ NMR (400 MHz, DMSO-$d_6$) δ ppm 13.03 (br s, 1 H), 9.40 (s, 1 H), 8.15 (s, 1 H), 7.61 (s, 1 H), 7.51 (s, 1 H), 5.68 (br d, J = 16.8 Hz, 1 H), 5.17-5.45 (m, 1 H), 4.58 (br d, J = 12.6 Hz, 1 H), 4.08-4.22 (m, 3 H), 3.99-4.08 (m, 1 H), 3.65-3.83 (m, 2 H), 3.48-3.64 (m, 3 H), 2.98-3.16 (m, 4 H), 2.80-2.90 (m, 1 H), 2.71 (dt, J = 13.7, 4.8 Hz, 1 H), 2.55 (s, 1 H), 2.50 (br s, 3 H), 2.30-2.43 (m, 1 H), 1.99-2.27 (m, 3 H), 1.58-1.92 (m, 5 H), 1.50 (s, 3 H). $^{19}F$ NMR (DMSO-$d_6$, 376 MHz) δ ppm −141.68, −172.08. |
| 191 | 669.8 | $^1H$ NMR (400 MHz, METHANOL-$d_4$) δ ppm 9.44 (s, 1 H), 7.85 (s, 1 H), 7.75 (s, 1 H), 5.84 (d, J = 17.3 Hz, 1 H), 5.49-5.70 (m, 1 H), 4.69-4.75 (m, 2 H), 4.25 (td, J = 12.1, 3.0 Hz, 1 H), 4.02-4.14 (m, 2 H), 3.76-4.00 (m, 5 H), 3.58-3.73 (m, 3 H), 3.46-3.54 (m, 1 H), 3.21 (d, J = 12.5 Hz, 1 H), 3.04 (ddd, J = 14.1, 5.1, 5.0 Hz, 1 H), 2.50-2.88 (m, 3 H), 2.33-2.48 (m, 3 H), 2.16-2.25 (m, 1 H), 1.85-1.96 (m, 2 H), 1.60 (s, 3 H). $^{19}F$ NMR (376 MHz, METHANOL-$d_4$) δ ppm −77.34 (s), −141.87 (s), −174.1 (s). Stereochemistry of Example 191 was confirmed by X-Ray crystallography analysis. |
| 192 | 656.1 | $^1H$ NMR (400 MHz, DMSO-$d_6$) δ ppm 12.80-13.40 (m, 1 H), 10.57-10.94 (m, 1 H), 8.06 (d, J = 8.6 Hz, 1 H), 7.59 (d, J = 0.8 Hz, 1 H), 7.48 (s, 1 H), 7.24 (dd, J = 8.6, 6.9 Hz, 1 H), 5.48-5.74 (m, 1 H), 5.28 (br d, J = 16.7 Hz, 1 H), 4.80 (br t, J = 5.4 Hz, 1 H), 4.66 (d, J = 11.7 Hz, 1 H), 4.54 (d, J = 11.7 Hz, 1 H), 4.48 (br dd, J = 13.4, 3.1 Hz, 1 H), 4.26 (td, J = 11.4, 4.1 Hz, 2 H), 3.96-4.04 (m, 3 H), 3.91 (br d, J = 14.4 Hz, 2 H), 3.77-3.86 (m, 3 H), 3.64-3.70 (m, 1 H), 3.47-3.57 (m, 1 H), 3.28-3.37 (m, 1 H), 3.24 (dd, J = 13.3, 7.2 Hz, 1 H), 2.56-2.70 (m, 2 H), 2.32-−2.45 (m, 3 H), 2.12-2.25 (m, 2 H), 2.00-2.11 (m, 1 H), 1.67-1.82 (m, 1 H), 1.38-1.54 (m, 1 H). $^{19}F$ NMR (DMSO-$d_6$, 376 MHz) δ ppm −74.24, −129.65, −172.78. |
| 193 | 646.2 | $^1H$ NMR (400 MHz, METHANOL-$d_4$) δ ppm 9.23-9.33 (m, 1 H), 7.57-7.74 (m, 2 H), 5.45-5.71 (m, 1 H), 4.90-5.17 (m, 2 H), 4.61-4.77 (m, 4 H), 3.70-4.12 (m, 6 H), 3.49-3.58 (m, 1 H), 3.15-3.29 (m, 3 H), 2.60-2.83 (m, 3 H), 2.52 (s, 3 H), 2.20-2.48 (m, 5 H), 1.97-2.05 (m, 1 H), 1.79-1.93 (m, 2 H), 1.72-1.78 (m, 3 H), 1.31-1.40 (m, 2 H). $^{19}F$ NMR (376 MHz, METHANOL-d4) δ ppm −77.34 (s), −143.15-−143.19 (m), −174.22-−174.03 (m). Stereochemistry of Example 193 was confirmed by X-Ray crystallography analysis. |
| 194 | 646.0 | $^1H$ NMR (400 MHz, METHANOL-$d_4$) δ ppm 9.36-9.65 (m, 1 H), 7.80-7.95 (m, 1 H), 7.53-7.66 (m, 1 H), 5.41-5.80 (m, 1 H), 4.98-5.23 (m, 2 H), 4.61-4.77 (m, 1 H), 4.59-4.75 (m, 2 H), 4.39-4.47 (m, 1 H), 4.26-4.36 (m, 1 H), 3.90-4.20 (m, 4 H), 3.65-3.75 (m, 1 H), 3.48-3.58 (m, 1 H), 3.16-3.25 (m, 1 H), 2.83-2.93 (m, 1 H), 2.60-2.81 (m, 2 H), 2.50-2.54 (m, 3 H), 2.32-2.48 (m, 3 H), 2.08-2.28 (m, 2 H), 1.81-1.93 (m, 2 H), 1.62-1.79 (m, 3 H), 1.32-1.49 (m, 3 H). $^{19}F$ NMR (376 MHz, METHANOL-$d_4$) δ ppm −78.20-−76.93 (m), −141.68 (s), −175.12-−173.74 (m). |
| 195 | 626.95 | $^1H$ NMR (400 MHz, METHANOL-$d_4$) δ ppm 9.35-9.58 (m, 1 H), 7.87 (br s, 2 H), 5.52 (br d, J = 16.9 Hz, 1 H), 4.93-4.99 (m, 1 H), 4.69-4.82 (m, 1 H), 4.40-4.54 (m, 2 H), 4.18-4.32 (m, 1 H), |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| | | 3.94-4.16 (m, 3 H), 3.73-3.91 (m, 2 H), 3.54-3.69 (m, 1 H), 3.42-3.50 (m, 2 H), 3.11-3.27 (m, 2 H), 3.04 (s, 6 H), 2.57-2.69 (m, 1 H), 1.82-1.94 (m, 2 H), 1.69 (br d, J = 7.5 Hz, 1 H), 1.28-1.51 (m, 2 H), 0.98-1.07 (m, 3 H), 0.86-0.96 (m, 2 H). $^{19}F$ NMR (376 MHz, METHANOL-$d_4$) δ ppm −79.21-−75.97 (m), −144.16-−141.23 (m). |
| 196 | 585.0 | $^1H$ NMR (400 MHz, METHANOL-$d_4$) δ ppm 9.41-9.49 (m, 1 H), 7.82 (d, J = 19.6 Hz, 2 H), 5.77-5.84 (m, 1 H), 5.53 (br d, J = 16.9 Hz, 1 H), 4.93-5.03 (m, 1 H), 4.82-4.91 (m, 1 H), 4.00-4.26 (m, 7 H), 3.77-3.97 (m, 3 H), 3.63 (ddd, J = 14.0, 11.1, 5.4 Hz, 1 H), 3.42 (dd, J = 13.5, 7.2 Hz, 1 H), 3.04 (dt, J = 14.0, 5.3 Hz, 1 H), 2.58-2.70 (m, 1 H), 2.33-2.46 (m, 1 H), 2.22-2.32 (m, 1 H), 1.80-1.99 (m, 2 H). $^{19}F$ NMR (376 MHz, METHANOL-$d_4$) δ ppm −77.60 (s), −141.24-−141.16 (s). |
| 197 | 585.0 | $^1H$ NMR (400 MHz, METHANOL-$d_4$) δ ppm 9.40-9.49 (m, 1 H), 7.82 (d, J = 18.8 Hz, 2 H), 5.79 (td, J = 4.1, 2.2 Hz, 1 H), 5.54 (br d, J = 17.1 Hz, 1 H), 4.94-5.02 (m, 1 H), 4.85 (br dd, J = 13.8, 3.8 Hz, 1 H), 4.18-4.29 (m, 1 H), 4.00-4.18 (m, 6 H), 3.94 (td, J = 8.3, 4.5 Hz, 1 H), 3.75-3.89 (m, 2 H), 3.65 (ddd, J = 13.7, 11.4, 5.3 Hz, 1 H), 3.44 (dd, J = 13.3, 7.2 Hz, 1 H), 3.04 (dt, J = 14.0, 5.4 Hz, 1 H), 2.64 (dt, J = 14.1, 7.2 Hz, 1 H), 2.26-2.47 (m, 2 H), 1.81-1.97 (m, 2 H). $^{19}F$ NMR (376 MHz, METHANOL-$d_4$) δ ppm −77.62 (s), −141.18 (s). |
| 198 | 638.0 | $^1H$ NMR (400 MHz, METHANOL-$d_4$) δ ppm 9.40- 9.51 (m, 1 H), 7.81-7.89 (m, 1 H), 7.78 (s, 1 H), 5.52 (br d, J = 17.3 Hz, 1 H), 4.95 (br s, 1 H), 4.83 (br d, J = 4.8 Hz, 1 H), 4.62-4.75 (m, 2 H), 4.28 (td, J = 11.7, 4.5 Hz, 1 H), 3.98-4.16 (m, 3 H), 3.84-3.94 (m, 1 H), 3.68-3.84 (m, 3 H), 3.62 (ddd, J = 13.9, 11.1, 5.5 Hz, 1 H), 3.40-3.52 (m, 1 H), 3.03 (dt, J = 14.0, 5.5 Hz, 1 H), 2.56-2.71 (m, 1 H), 2.08-2.46 (m, 8 H), 1.83-1.96 (m, 2 H). $^{19}F$ NMR (376 MHz, METHANOL-$d_4$) δ ppm −77.18 (s), −141.66 (s). |
| 199 | 672.1 | $^1H$ NMR (METHANOL-$d_4$, 400 MHz) δ 9.36 (s, 1H), 7.82 (s, 1H), 7.77 (s, 1H), 5.66 (br d, 1H, J = 17.3 Hz), 5.5-5.6 (m, 1H), 5.3-5.5 (m, 1H), 4.84 (br dd, 1H, J = 3.3, 14.0 Hz), 4.45 (d, 2H, J = 7.1 Hz), 4.24 (dt, 1H, J = 3.8, 11.8 Hz), 4.0-4.2 (m, 5H), 3.5-3.6 (m, 2H), 3.4-3.5 (m, 3H), 3.39 (dd, 1H, J = 7.7, 13.2 Hz), 3.19 (dt, 1H, J = 5.6, 9.8 Hz), 3.04 (td, 1H, J = 5.6, 14.1 Hz), 2.6-2.7 (m, 1H), 2.4-2.5 (m, 1H), 2.3-2.4 (m, 1H), 2.2-2.3 (m, 1H), 2.1-2.2 (m, 2H), 1.9-2.1 (m, 3H). $^{19}F$ NMR (METHANOL-$d_4$, 376 MHz) δ ppm −141.40 (s), −173.82 (s). |
| 200 | 630.2 | $^1H$ NMR (METHANOL-$d_4$, 400 MHz) δ ppm 9.27 (s, 1H), 7.57 (dd, 1H, J = 2.1, 7.1 Hz), 7.4-7.5 (m, 2H), 5.75 (d, 1H, J = 17.1 Hz), 5.2-5.4 (m, 1H), 4.72 (dd, 1H, J = 2.1, 13.6 Hz), 4.30 (q, 2H, J = 10.7 Hz), 4.2-4.3 (m, 1H), 4.04 (dd, 1H, J = 4.2, 12.3 Hz), 3.7-3.8 (m, 2H), 3.6-3.7 (m, 2H), 3.55 (ddd, 1H, J = 4.4, 12.2, 13.5 Hz), 3.2-3.3 (m, 2H), 3.1-3.2 (m, 2H), 3.02 (dt, 1H, J = 5.9, 9.4 Hz), 2.94 (td, 1H, J = 5.5, 13.7 Hz), 2.4-2.5 (m, 1H), 2.3-2.4 (m, 1H), 2.2-2.3 (m, 1H), 2.1-2.2 (m, 1H), 2.0-2.1 (m, 2H), 1.8-2.0 (m, 3H), 1.56 (s, 3H). $^{19}F$ NMR (CHLOROFORM-d, 376 MHz) δ ppm −139.44 (s), −173.3 (s). |
| 201 | 618.25 | $^1H$ NMR (400 MHz, CHLOROFORM-d) δ ppm 9.13 (s, 1 H), 8.00 (dd, J = 8.2, 1.5 Hz, 1 H), 7.83-7.91 (m, 1 H), 7.54-7.59 (m, 1 H), 7.48-7.53 (m, 1 H), 7.42 (dd, J = 8.0, 7.2 Hz, 1 H), 7.24-7.27 (m, 1 H), 5.46 (br d, J = 16.7 Hz, 1 H), 5.18-5.37 (m, 1 H), 4.91 (br t, J = 6.7 Hz, 1 H), 4.76 (dd, J = 13.8, 2.7 Hz, 1 H), 4.12-4.30 (m, 6 H), 3.96-4.08 (m, 1 H), 3.82 (dd, J = 16.8, 2.2 Hz, 1 H), 3.46 (dd, J = 13.4, 7.3 Hz, 1 H), 3.33-3.42 (m, 1 H), 3.20-3.30 (m, 2 H), 3.11-3.18 (m, 1 H), 2.83-3.02 (m, 3 H), 2.26 (br d, J = 4.4 Hz, 1 H), 2.13-2.22 (m, 2 H), 1.86-2.00 (m, 3 H). $^{19}F$ NMR (376 MHz, CHLOROFORM-d) δ ppm −136.20 (s), −173.07 (s). |
| 202 | 610.0 | $^1H$ NMR (400 MHz, METHANOL-$d_4$) δ ppm 9.40 (s, 1 H), 7.81-7.88 (m, 1 H), 7.70-7.78 (m, 1 H), 5.45-5.61 (m, 1 H), 4.92-4.99 (m, 1 H), 4.90-4.92 (m, 1 H), 4.77-4.84 (m, 1 H), 4.65-4.74 (m, 1 H), 3.72-4.00 (m, 5 H), 3.36-3.41 (m, 1 H), 3.23-3.30 (m, 1 H), 3.13 (s, 3 H), 3.00-3.09 (m, 1 H), 2.60-2.71 (m, 1 H), 2.29-2.51 (m, 2 H), 2.20-2.29 (m, 1 H), 2.04-2.20 (m, 3 H), 1.84-1.96 (m, 3 H), 1.56-1.77 (m, 2 H), 1.42-1.56 (m, 1 H). $^{19}F$ NMR (376 MHz, METHANOL-$d_4$) δ ppm −77.38 (s), −141.87 (s) |
| 203 | 625.9 | $^1H$ NMR (500 MHz, METHANOL-$d_4$) δ ppm 9.44 (s, 1 H), 7.85 (d, J = 0.9 Hz, 1 H), 7.73-7.80 (m, 1 H), 5.47-5.58 (m, 1 H), 5.33-5.44 (m, 1 H), 4.93-5.00 (m, 1 H), 4.72-4.81 (m, 1 H), 4.21-4.32 (m, 1 H), 3.99-4.18 (m, 3 H), 3.77-3.92 (m, 3 H), 3.67-3.74 (m, 1 H), 3.57-3.67 (m, 1 H), 3.42-3.52 (m, 1 H), 3.26-3.31 (m, 1 H), 3.19 (s, 3 H), 2.96-3.09 (m, 1 H), 2.58-2.70 (m, 1 H), 2.39-2.50 (m, 1 H), 2.18-2.29 (m, 1 H), 2.06-2.19 (m, 1 H), |

TABLE 31-continued

Analytical Data for Examples 92 to 98, 100 to 102, 179 to 212 and 303 to 368.

| Cmpd.# | MS m/z (ESI): $(M + H)^+$ | $^1$H and $^{19}$F NMR |
|---|---|---|
| | | 1.96-2.05 (m, 1 H), 1.81-1.95 (m, 2 H), 1.59 (d, J = 6.2 Hz, 3 H). $^{19}$F NMR (471 MHz, METHANOL-$d_4$) δ ppm −77.37 (br s), −141.51 (br s). |
| 204 | 625.9 | $^1$H NMR (METHANOL-$d_4$, 400 MHz) δ ppm 9.46 (s, 1H), 7.8-7.9 (m, 1H), 7.7-7.8 (m, 1H), 5.7-5.8 (m, 1H), 5.5-5.6 (m, 1H), 4.9-5.0 (m, 1H), 4.7-4.8 (m, 1H), 4.2-4.3 (m, 1H), 4.0-4.1 (m, 3H), 3.8-3.9 (m, 1H), 3.7-3.8 (m, 3H), 3.6-3.7 (m, 1H), 3.5-3.5 (m, 1H), 3.2-3.3 (m, 1H), 3.13 (s, 3H), 3.0-3.1 (m, 1H), 2.5-2.7 (m, 1H), 2.3-2.5 (m, 2H), 2.2-2.3 (m, 1H), 2.1-2.2 (m, 1H), 1.9-1.9 (m, 2H), 1.53 (d, 3H, J = 6.4 Hz). $^{19}$F NMR (376 MHz, METHANOL-$d_4$) δ ppm −77.20 (s), −142.02 (s). |
| 205 | 602.1 | $^1$H NMR (400 MHz, METHANOL-$d_4$) δ ppm 9.51 (s, 1 H), 7.67-7.91 (m, 1 H), 7.54-7.66 (m, 1 H), 4.90-5.20 (m, 3 H), 4.60-4.81 (m, 2 H), 3.86-4.48 (m, 2 H), 3.64-3.86 (m, 2 H), 3.12 (br s, 6 H), 2.67-2.97 (m, 1 H), 2.34-2.58 (m, 4 H), 1.93-2.30 (m, 4 H), 1.60-1.91 (m, 5 H), 1.23-1.53 (m, 1 H), 0.96-1.12 (m, 1 H). $^{19}$F NMR (376 MHz, METHANOL-$d_4$) δ ppm −77.30 (s), −141.82-−141.31 (m), −143.28-−142.72 (m). |
| 206 | 590.0 | $^1$H NMR (400 MHz, METHANOL-$d_4$) δ ppm 9.39 (s, 1 H), 7.63-7.71 (m, 1 H), 7.52-7.60 (m, 1 H), 5.46-5.57 (m, 1 H), 4.89-4.98 (m, 2 H), 4.76-4.83 (m, 1 H), 4.65-4.75 (m, 1 H), 3.82-3.99 (m, 3 H), 3.71-3.82 (m, 2 H), 3.35-3.42 (m, 1 H), 3.22-3.30 (m, 1 H), 3.13 (s, 3 H), 2.77-2.88 (m, 1 H), 2.59 (s, 4 H), 2.30-2.49 (m, 2 H), 2.19-2.30 (m, 1 H), 2.04-2.19 (m, 3 H), 1.82-1.96 (m, 2 H), 1.56-1.82 (m, 3 H), 1.41-1.56 (m, 1 H). $^{19}$F NMR (376 MHz, METHANOL-$d_4$) δ ppm −77.44 (s), −141.80 (s). |
| 207 | 612.0 | $^1$H NMR (400 MHz, METHANOL-$d_4$) δ ppm 9.44 (s, 1 H), 7.80-7.88 (m, 1 H), 7.72-7.80 (m, 1 H), 5.46-5.57 (m, 1 H), 4.92-5.02 (m, 2 H), 4.81-4.85 (m, 1 H), 4.62-4.72 (m, 1 H), 4.22-4.36 (m, 1 H), 3.98-4.18 (m, 3 H), 3.84-3.99 (m, 2 H), 3.73-3.84 (m, 2 H), 3.54-3.69 (m, 1 H), 3.39-3.51 (m, 1 H), 3.24-3.30 (m, 1 H), 3.14 (s, 3 H), 2.96-3.07 (m, 1 H), 2.54-2.70 (m, 1 H), 2.35-2.50 (m, 1 H), 2.07-2.35 (m, 3 H), 1.80-1.95 (m, 2 H). $^{19}$F NMR (376 MHz, METHANOL-$d_4$) δ ppm −77.31 (s), −141.60 (s). |
| 208 | 639.8 | $^1$H NMR (METHANOL-$d_4$, 400 MHz) δ 9.35 (s, 1H), 7.81 (s, 1H), 7.43 (d, 1H, J = 10.2 Hz), 5.45 (br d, 1H, J = 16.9 Hz), 5.2-5.4 (m, 1H), 4.9-4.9 (m, 1H), 4.76 (br d, 2H, J = 11.7 Hz), 4.2-4.4 (m, 3H), 4.0-4.1 (m, 2H), 3.9-4.0 (m, 1H), 3.8-3.8 (m, 1H), 3.7-3.7 (m, 1H), 3.5-3.6 (m, 1H), 3.1-3.3 (m, 3H), 2.9-3.1 (m, 2H), 2.4-2.6 (m, 1H), 2.1-2.4 (m, 3H), 1.7-2.0 (m, 5H). |
| 209 | 652.0 | $^1$H NMR (METHANOL-$d_4$, 400 MHz) δ ppm 9.50 (s, 1H), 7.92 (s, 1H), 7.81-7.84 (m, 1H), 5.90 (br d, J = 17.3 Hz, 1H), 4.73-4.81 (m, 2H), 4.29-4.37 (m, 1H), 4.18 (br d, J = 4.2 Hz, 1H), 3.86-3.94 (m, 2H), 3.74-3.82 (m, 4H), 3.64-3.72 (m, 1H), 3.27 (br d, J = 12.3 Hz, 1H), 3.05-3.15 (m, 1H), 2.59-2.69 (m, 1H), 2.42 (dt, J = 12.6, 6.3 Hz, 2H), 2.36 (br s, 5H), 2.15-2.24 (m, 3H), 1.93-2.07 (m, 3H), 1.67 (s, 3H). $^{19}$F NMR (METHANOL-$d_4$, 376 MHz) δ ppm −77.36-−77.31 (m), −141.81-−141.74 ppm (m). |
| 210 | 493.0 | $^1$H NMR (400 MHz, METHANOL-$d_4$) δ ppm 9.65 (s, 1 H), 7.72 (s, 1 H), 7.61 (s, 1 H), 5.65 (br, d, J = 16.6 Hz, 1 H), 5.13 (dd, J = 13.6, 4.9 Hz, 1 H), 4.97 (br s, 1 H), 4.86-4.91 (m, 1 H), 4.03-4.22 (m, 4 H), 3.75-3.91 (m, 3 H), 3.63 (dd, J = 13.8, 5.7 Hz, 1 H), 2.90 (dt, J = 14.3, 5.5 Hz, 1 H), 2.78 (s, 3 H), 2.57-2.65 (m, 4 H), 1.85-1.96 (m, 1 H), 1.68-1.78 (m, 1 H). $^{19}$F NMR (376 MHz, METHANOL-$d_4$) δ ppm −77.44-−77.35 (m), −140.70-−140.68 (m). |
| 211 | 489.0 | $^1$H NMR (400 MHz, METHANOL-$d_4$) δ ppm 9.56 (s, 1 H), 8.14 (s, 1 H), 7.67 (s, 1 H), 5.41 (br d, J = 11.5 Hz, 1 H), 5.22 (br d, J = 14.2 Hz, 1 H), 4.90-5.05 (m, 1 H), 4.22 (d, J = 15.3 Hz, 1 H), 3.84 (d, J = 11.1 Hz, 1 H), 3.45-3.53 (m, 1 H), 3.07 (dd, J = 11.2, 8.3 Hz, 1 H), 2.79 (s, 3 H), 2.70 (s, 3 H), 2.45 (br dd, J = 8.9, 3.7 Hz, 1 H), 2.05-2.17 (m, 1 H), 1.81-2.00 (m, 3 H), 1.58 (td, J = 9.6, 4.8 Hz, 1 H), 1.28 (dd, J = 10.0, 7.7 Hz, 1 H), 0.17-0.23 (m, 1 H). $^{19}$F NMR (376 MHz, METHANOL-$d_4$) δ ppm −77.27-−77.22 (m), −136.91-−136.85 (m). |
| 212 | 622.0 | $^1$H NMR (500 MHz, METHANOL-$d_4$) δ ppm 9.30 (s, 1 H), 7.91 (d, J = 0.91 Hz, 1 H), 7.82 (s, 1 H), 5.02-5.09 (m, 1 H), 4.89-4.96 (m, 2 H), 4.77-4.82 (m, 1 H), 4.65-4.74 (m, 2 H), 3.69-3.99 (m, 4 H), 3.41-3.50 (m, 1 H), 3.17-3.30 (m, 2 H), 3.12 (s, 3 H), 2.70-2.81 (m, 1 H), 2.37-2.51 (m, 1 H), 2.18-2.30 (m, 2 H), 2.07-2.18 (m, 2 H), 1.97-2.06 (m, 1 H), 1.83-1.91 (m, 1 H), 1.70-1.80 (m, 4 H), 0.98-1.12 (m, 1 H). 1H not oberved. $^{19}$F NMR (471 MHz, METHANOL-$d_4$) δ ppm −77.42 (br s) −142.93 (br s). Stereochemistry of Example 212 was confirmed by X-Ray crystallography analysis. |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| 303 | 638.2 | $^1H$ NMR (METHANOL-$d_4$, 400 MHz) δ ppm 9.55 (s, 1H), 7.77 (d, 1H, J = 0.8 Hz), 7.7-7.8 (m, 1H), 7.50 (s, 1H), 5.4-5.6 (m, 2H), 4.8-5.0 (m, 1H), 4.74 (br d, 1H, J = 3.8 Hz), 4.60 (s, 2H), 4.26 (dt, 1H, J = 4.3, 11.7 Hz), 4.1-4.1 (m, 1H), 4.0-4.1 (m, 1H), 3.9-4.0 (m, 2H), 3.8-3.9 (m, 2H), 3.7-3.8 (m, 2H), 3.5-3.6 (m, 1H), 3.4-3.5 (m, 2H), 2.9-2.9 (m, 1H), 2.8-2.9 (m, 1H), 2.6-2.7 (m, 1H), 2.5-2.6 (m, 1H), 2.3-2.4 (m, 1H), 2.2-2.3 (m, 2H), 2.1-2.2 (m, 1H), 1.8-1.9 (m, 2H). $^{19}F$ NMR (METHANOL-$d_4$, 376 MHz) δ ppm −76.84 (s), −173.98 (s). |
| 304 | 650.2 | $^1H$ NMR (METHANOL-$d_4$, 400 MHz) δ ppm 9.23 (s, 1H), 8.10 (dd, 1H, J = 1.3, 8.2 Hz), 8.0-8.1 (m, 1H), 7.6-7.6 (m, 1H), 7.5-7.5 (m, 1H), 7.40 (t, 1H, J = 9.2 Hz), 5.77 (d, 1H, J = 17.1 Hz), 5.2-5.4 (m, 1H), 4.70 (dd, 1H, J = 2.7, 13.8 Hz), 4.3-4.4 (m, 3H), 4.0-4.1 (m, 2H), 3.9-3.9 (m, 1H), 3.7-3.8 (m, 2H), 3.5-3.6 (m, 1H), 3.3-3.4 (m, 2H), 3.2-3.3 (m, 2H), 3.18 (s, 1H), 3.0-3.1 (m, 1H), 2.4-2.5 (m, 1H), 2.3-2.4 (m, 1H), 2.2-2.3 (m, 1H), 2.1-2.2 (m, 1H), 2.0-2.0 (m, 2H), 1.8-2.0 (m, 1H), 1.60 (s, 3H). $^{19}F$ NMR (METHANOL-$d_4$, 376 MHz) δ ppm −115.17 (s), −138.39 (s), −173.65 (s). |
| 305 | 643.1 | $^1H$ NMR (400 MHz, DMSO-$d_6$) δ ppm 13.42 (br d, J = 11.4 Hz, 1 H), 9.22-9.39 (m, 1 H), 8.12 (d, J = 10.8 Hz, 1 H), 7.88 (s, 1 H), 7.81 (s, 1 H), 5.26 (br d, J = 17.0 Hz, 1 H), 4.84 (br t, J = 4.8 Hz, 1 H), 4.42-4.52 (m, 1 H), 4.39 (d, J = 11.8 Hz, 1 H), 4.20-4.30 (m, 1 H), 4.16 (d, J = 11.6 Hz, 1 H), 3.96-4.06 (m, 2 H), 3.83-3.92 (m, 3 H), 3.76-3.78 (m, 1 H), 3.49 (br d, J = 5.0 Hz, 1 H), 3.16-3.30 (m, 3 H), 2.88 (t, J = 5.4 Hz, 6 H), 2.40-2.47 (m, 1 H), 1.77-1.92 (m, 1 H), 1.52-1.68 (m, 1 H), 0.75-0.91 (m, 3 H). $^{19}F$ NMR (DMSO-$d_6$, 376 MHz) δ ppm −74.23, −117.70, −124.76. |
| 306 | 643.1 | $^1H$ NMR (400 MHz, DMSO-$d_6$) δ ppm 12.79-13.74 (m, 1 H), 9.05-9.42 (m, 1 H), 8.13-8.30 (m, 1 H), 7.76-8.03 (m, 1 H), 4.25-4.40 (m, 5 H), 3.92-4.06 (m, 4 H), 3.74-3.81 (m, 3 H), 3.17-3.30 (m, 2 H), 2.87 (d, J = 4.8 Hz, 6 H), 2.64-2.71 (m, 1 H), 2.32-2.35 (m, 2 H), 1.59-1.72 (m, 1 H), 0.85-0.92 (m, 2 H), 0.75-0.82 (m, 3 H). $^{19}F$ NMR (376 MHz, DMSO-$d_6$) δ ppm −74.00, −125.44, −171.58. |
| 307 | 652.3 | $^1H$ NMR (METHANOL-$d_4$, 400 MHz) δ ppm 9.27 (s, 1H), 7.88 (s, 1H), 7.79 (s, 1H), 5.0-5.1 (m, 1H), 4.86 (br s, 3H), 4.6-4.7 (m, 2H), 4.2-4.2 (m, 1H), 4.1-4.2 (m, 1H), 3.8-3.9 (m, 3H), 3.4-3.5 (m, 1H), 3.40 (d, 4H, J = 3.1 Hz), 3.2-3.2 (m, 1H), 3.15 (br s, 3H), 2.7-2.8 (m, 1H), 2.5-2.6 (m, 1H), 2.1-2.2 (m, 2H), 2.0-2.0 (m, 1H), 1.8-1.9 (m, 1H), 1.74 (br dd, 4H, J = 4.9, 10.8 Hz), 1.0-1.1 (m, 1H). $^{19}F$ NMR (METHANOL-$d_4$, 376 MHz) δ ppm −77.4 (m), −143.1 (m). |
| 308 | 667.9 | $^1H$ NMR (METHANOL-$d_4$, 400 MHz) 8 9.33 (s, 1H), 7.80 (d, 2H, J = 9.0 Hz), 5.77 (d, 1H, J = 17.3 Hz), 4.54 (dd, 1H, J = 6.3, 11.1 Hz), 4.41 (dd, 1H, J = 4.8, 11.1 Hz), 4.2-4.3 (m, 1H), 4.0-4.1 (m, 1H), 3.7-3.8 (m, 2H), 3.7-3.7 (m, 2H), 3.6-3.7 (m, 3H), 3.5-3.6 (m, 1H), 3.3-3.4 (m, 1H), 3.1-3.2 (m, 2H), 3.0-3.1 (m, 3H), 2.5-2.6 (m, 1H), 2.1-2.3 (m, 2H), 1.8-1.9 (m, 3H), 1.7-1.8 (m, 1H), 1.57 (s, 3H), 1.4-1.5 (m, 2H). |
| 309 | 667.9 | $^1H$ NMR (METHANOL-$d_4$, 400 MHz) δ ppm 9.34 (s, 1H), 7.81 (s, 1H), 7.77 (s, 1H), 5.78 (d, 1H, J = 17.1 Hz), 4.54 (dd, 1H, J = 6.5, 11.1 Hz), 4.41 (dd, 1H, J = 4.9, 11.2 Hz), 4.26 (s, 1H), 4.0-4.1 (m, 1H), 3.7-3.8 (m, 3H), 3.7-3.7 (m, 3H), 3.6-3.7 (m, 3H), 3.5-3.6 (m, 1H), 3.3-3.4 (m, 1H), 3.1-3.2 (m, 2H), 3.1-3.1 (m, 1H), 3.0-3.0 (m, 2H), 2.5-2.6 (m, 1H), 2.2-2.3 (m, 1H), 1.8-1.9 (m, 3H), 1.7-1.8 (m, 1H), 1.6-1.6 (m, 3H), 1.5-1.6 (m, 1H). |
| 310 | 688.2 | $^1H$ NMR (600 MHz, DMSO-$d_6$) δ ppm 9.44 (s, 1 H) 7.60-7.96 (m, 2 H) 5.47-5.70 (m, 1 H) 5.18-5.42 (m, 1 H) 4.80-5.09 (m, 1 H) 4.46-4.66 (m, 2 H) 4.14 (br d, J = 11.74 Hz, 4 H) 3.67-3.93 (m, 4 H) 3.45-3.58 (m, 1 H) 3.31-3.36 (m, 1 H) 3.03 (s, 5 H) 2.35-2.44 (m, 1 H) 2.11 (br s, 3 H) 1.72-1.90 (m, 5 H). |
| 311 | 688.2 | $^1H$ NMR (600 MHz, DMSO-$d_6$) δ ppm 9.44 (s, 1 H) 7.85 (s, 2 H) 5.52-5.68 (m, 1 H) 5.16-5.43 (m, 1 H) 4.83-5.10 (m, 1 H) 4.44-4.67 (m, 2 H) 3.99-4.23 (m, 4 H) 3.77-3.91 (m, 2 H) 3.72 (br s, 2 H) 3.46-3.56 (m, 1 H) 3.31-3.38 (m, 1 H) 2.80-3.12 (m, 5 H) 2.32-2.45 (m, 1 H) 2.01-2.20 (m, 3 H) 1.80 (br d, J = 12.18 Hz, 5 H). |
| 312 | 696.0 | $^1H$ NMR (400 MHz, METHANOL-$d_4$) δ ppm 9.31 (s, 1 H) 7.60-7.93 (m, 2 H) 5.45-5.69 (m, 1 H) 5.04-5.24 (m, 1 H) 4.80-4.84 (m, 1 H) 4.60-4.75 (m, 2 H) 4.45-4.53 (m, 1 H) 3.76-4.23 (m, 10 H) 3.59-3.67 (m, 1 H) 3.38-3.47 (m, 1 H) 3.04-3.15 (m, 1 H) 2.79-2.88 (m, 1 H) 2.49-2.77 (m, 2 H) 2.10-2.44 (m, 6 H) 1.86-1.99 (m, 1 H) 1.69-1.84 (m, 2 H) 1.49-1.60 (m, 1 H). $^{19}F$ NMR (376 MHz, METHANOL-d4) δ ppm −141.53-−140.38 (m) −174.78-−173.21 (m). |
| 313 | 696.0 | $^1H$ NMR (400 MHz, METHANOL-$d_4$) δ ppm 9.26 (s, 1 H) 7.46-7.94 (m, 2 H) 5.05-5.50 (m, 2 H) 4.80-4.87 (m, 2 H) 4.26-4.69 |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| | | (m, 4 H) 3.76-4.22 (m, 6 H) 3.37-3.72 (m, 3 H) 3.03-3.19 (m, 2 H) 2.68-2.90 (m, 1 H) 1.84-2.48 (m, 9 H) 1.50-1.81 (m, 3 H). $^{19}F$ NMR (376 MHz, METHANOL-$d_4$) δ ppm −141.21-−138.80 (m) −173.76 (d, J = 13.01 Hz). |
| 314 | 688.2 | 1H NMR (600 MHz, DMSO-$d_6$) δ ppm 9.23 (s, 1 H) 7.87 (s, 2 H) 5.21-5.38 (m, 1 H) 4.72-5.08 (m, 1 H) 4.48-4.64 (m, 1 H) 4.20-4.44 (m, 1 H) 3.98-4.19 (m, 3 H) 3.65-3.91 (m, 3 H) 3.32-3.46 (m, 1 H) 3.03 (br s, 2 H) 2.69-2.89 (m, 1 H) 1.99-2.18 (m, 3 H) 1.74-1.93 (m, 7 H) 1.47-1.68 (m, 2 H). |
| 315 | 688.2 | $^1H$ NMR (600 MHz, DMSO-$d_6$) δ ppm 9.22 (s, 1 H) 7.66-7.96 (m, 2 H) 5.21-5.39 (m, 1 H) 4.89-5.11 (m, 1 H) 4.31-4.81 (m, 2 H) 3.64-4.25 (m, 6 H) 3.31-3.46 (m, 2 H) 3.08-3.20 (m, 1 H) 2.69-2.88 (m, 1 H) 1.99-2.19 (m, 3 H) 1.72-1.91 (m, 7 H) 1.45-1.69 (m, 2 H). |
| 316 | 682.0 | $^1H$ NMR (400 MHz, METHANOL-$d_4$) δ ppm 9.58-9.68 (m, 1 H) 7.84-7.97 (m, 2 H) 5.26-5.45 (m, 2 H) 4.39 (s, 5 H) 4.13-4.24 (m, 2 H) 3.87-3.94 (m, 1 H) 3.77-3.85 (m, 1 H) 3.59-3.73 (m, 2 H) 3.37-3.55 (m, 4 H) 3.06-3.18 (m, 1 H) 2.76-2.85 (m, 1 H) 2.06-2.48 (m, 7 H) 1.85-2.02 (m, 2 H) 1.49-1.58 (m, 1 H) 1.31-1.41 (m, 1 H). $^{19}F$ NMR (376 MHz, METHANOL-$_4$) δ ppm −141.54 (d, J = 4.33 Hz) −173.78 (d, J = 19.94 Hz). |
| 317 | 682.0 | $^1H$ NMR (400 MHz, METHANOL-$d_4$) δ ppm 9.40 (s, 1 H) 7.79-7.92 (m, 2 H) 5.35-5.58 (m, 2 H) 4.64-4.74 (m, 2 H) 4.26-4.58 (m, 6 H) 3.82-4.10 (m, 5 H) 3.44-3.50 (m, 1 H) 3.21-3.29 (m, 1 H) 2.78-2.92 (m, 1 H) 2.21 (br dd, J = 14.21, 6.90 Hz, 10 H) 1.84-1.93 (m, 1 H) 1.14-1.25 (m, 1 H). $^{19}F$ NMR (376 MHz, METHANOL-$d_4$) δ ppm −142.87-−142.16 (m) −174.23-−173.61 (m). |
| 318 | 643.9 | $^1H$ NMR (400 MHz, MeOH-$d_4$) δ ppm 9.36 (s, 1 H), 7.82 (d, J = 7.1 Hz, 2 H), 5.79 (d, J = 17.3 Hz, 1 H), 5.08-5.28 (m, 1 H), 4.75 (br d, J = 13.8 Hz, 1 H), 4.56 (t, J = 5.0 Hz, 2 H), 4.29 (br d, J = 2.9 Hz, 1 H), 4.03-4.11 (m, 1 H), 3.75-3.83 (m, 2 H), 3.65-3.72 (m, 2 H), 3.45-3.62 (m, 2 H), 3.13-3.21 (m, 2 H), 3.03 (br d, J = 14.0 Hz, 1 H), 2.58-2.74 (m, 2 H), 2.57 (s, 3 H), 2.21-2.35 (m, 1 H), 2.03 (s, 1 H), 1.90 (br dd, J = 8.3, 4.3 Hz, 2 H), 1.58 (s, 3 H). $^{19}F$ NMR (376 MHz, MeOH-$d_4$) δ ppm −141.39 (s), −171.89 (s) |
| 319 | 655.9 | $^1H$ NMR (400 MHz, MeOH-$d_4$) δ ppm 9.35 (s, 1 H), 7.83 (s, 2 H), 5.79 (d, J = 17.3 Hz, 1 H), 4.74 (br dd, J = 13.7, 2.0 Hz, 1 H), 4.53 (dd, J = 5.2, 2.1 Hz, 2 H), 4.29 (br d, J = 2.9 Hz, 1 H), 4.06 (dd, J = 12.3, 4.2 Hz, 1 H), 3.94-4.01 (m, 1 H), 3.74-3.82 (m, 2 H), 3.63-3.72 (m, 3 H), 3.51-3.63 (m, 1 H), 3.35-3.44 (m, 1 H), 3.33 (t, J = 1.7 Hz, 2 H), 3.17 (d, J = 12.5 Hz, 1 H), 2.96-3.06 (m, 2 H), 2.54-2.63 (m, 1 H), 2.52 (s, 3 H), 2.39 (dd, J = 10.5, 5.2 Hz, 1 H), 1.85-2.08 (m, 4 H), 1.58 (s, 3 H). $^{19}F$ NMR (376 MHz, MeOH-$d_4$) δ ppm −141.33 (s). |
| 320 | 639.8 | $^1H$ NMR (400 MHz, MeOH-$d_4$) δ ppm 9.22 (s, 1 H), 7.86 (d, J = 17.8 Hz, 2 H), 5.23-5.31 (m, 1 H), 5.09-5.20 (m, 1 H), 5.03 (br d, J = 13.2 Hz, 1 H), 4.90 (br d, J = 12.8 Hz, 1 H), 4.68 (t, J = 6.6 Hz, 1 H), 4.47-4.62 (m, 2 H), 3.73-3.92 (m, 2 H), 3.39-3.61 (m, 2 H), 3.10-3.24 (m, 2 H), 2.72-2.84 (m, 1 H), 2.57 (s, 4 H), 2.24-2.39 (m, 1 H), 2.18 (s, 1 H), 1.92-2.12 (m, 2 H), 1.66-1.91 (m, 5 H), 1.05 (dd, J = 14.0, 5.0 Hz, 1 H). $^{19}F$ NMR (376 MHz, MeOH-$d_4$) δ ppm −142.65 (d, J = 3.5 Hz), −171.83 (d, J = 42.5 Hz). |
| 321 | 619.9 | $^1H$ NMR (400 MHz, MeOH-$d_4$) δ ppm 9.22 (s, 1 H), 7.73 (s, 1 H), 7.60 (s, 1 H), 5.23-5.30 (m, 1 H), 5.13 (br s, 1 H), 5.07 (br d, J = 13.6 Hz, 1 H), 4.90 (br d, J = 12.8 Hz, 1 H), 4.69 (t, J = 6.6 Hz, 1 H), 4.46-4.62 (m, 2 H), 3.79 (br d, J = 11.7 Hz, 2 H), 3.44-3.61 (m, 1 H), 3.11-3.29 (m, 3 H), 2.61-2.83 (m, 2 H), 2.57 (s, 3 H), 2.52 (d, J = 0.6 Hz, 3 H), 2.24-2.40 (m, 1 H), 2.14-2.23 (m, 1 H), 2.03 (s, 2 H), 1.77 (br d, J = 6.9 Hz, 5 H), 1.02-1.11 (m, 1 H). $^{19}F$ NMR (376 MHz, MeOH-$d_4$) δ ppm −142.72 (d, J = 4.3 Hz), −171.82 (d, J = 41.6 Hz). |
| 322 | 681.85 | $^1H$ NMR (400 MHz, METHANOL-$d_4$) δ ppm 9.19 (s, 1 H) 7.85 (m, 2 H) 5.23-5.44 (m, 1 H) 4.72-4.77 (m, 1 H) 4.30-4.39 (m, 3 H) 3.98 (br d, J = 14.00 Hz, 1 H) 3.81-3.83 (m, 1 H) 3.39-3.57 (m, 3 H) 3.28 (br d, J = 4.60 Hz, 1 H) 3.04-3.13 (m, 2 H) 2.82-2.93 (m, 1 H) 2.39 (br s, 1 H) 2.24-2.35 (m, 2 H) 1.85-2.23 (m, 10 H) 1.44 (s, 3 H). $^{19}F$ NMR (376 MHz, METHANOL-$d_4$) δ ppm −141.69 (s), −173.73 (s). |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| 323 | 680.0 | $^1H$ NMR (400 MHz, METHANOL-$d_4$) δ ppm 1.24-1.42 (m, 1 H) 1.67-2.62 (m, 16 H) 2.82-2.92 (m, 1 H) 3.28 (br d, J = 5.64 Hz, 2 H) 3.49-3.71 (m, 3 H) 3.88-4.00 (m, 2 H) 4.19-4.29 (m, 1 H) 4.42-4.59 (m, 2 H) 4.82-4.89 (m, 2 H) 4.92-5.04 (m, 1 H) 5.24-5.57 (m, 1 H) 7.59-7.90 (m, 2 H) 9.16-9.35 (m, 1 H). $^{19}F$ NMR (376 MHz, METHANOL-$d_4$) δ ppm −174.16-−173.51 (m) −139.92-−139.33 (m). |
| 324 | 670.0 | $^1H$ NMR (400 MHz, METHANOL-$d_4$) δ ppm 1.36 (br dd, J = 11.18, 5.75 Hz, 2 H) 1.64 (br dd, J = 10.35, 4.91 Hz, 2 H) 1.90-2.05 (m, 1 H) 2.07-2.17 (m, 2 H) 2.18-2.56 (m, 3 H) 2.67-2.84 (m, 1 H) 3.02-3.24 (m, 2 H) 3.36-3.64 (m, 5 H) 3.73-3.84 (m, 1 H) 3.98-4.24 (m, 4 H) 4.34 (td, J = 11.50, 4.39 Hz, 1 H) 4.40-4.56 (m, 2 H) 4.73 (br s, 1 H) 5.08 (br s, 1 H) 5.29-5.51 (m, 2 H) 7.62-7.69 (m, 1 H) 7.79 (s, 1 H) 9.41-9.48 (m, 1 H). $^{19}F$ NMR (376 MHz, METHANOL-$d_4$) δ ppm −174.51-−173.26 (m, 1 F) −140.75-−138.39 (m). |
| 325 | 602.1 | $^1H$ NMR (METHANOL-$d_4$, 400 MHz) δ ppm 9.46 (s, 1H), 7.90 (s, 1H), 7.60 (s, 1H), 5.0-5.2 (m, 2H), 4.5-4.7 (m, 2H), 4.3-4.5 (m, 2H), 4.1-4.2 (m, 1H), 3.6-3.7 (m, 1H), 3.1-3.2 (m, 2H), 2.9-3.0 (m, 1H), 2.7-2.8 (m, 4H), 2.52 (s, 3H), 2.2-2.3 (m, 1H), 2.1-2.1 (m, 1H), 1.8-2.0 (m, 5H), 1.6-1.8 (m, 3H), 1.4-1.5 (m, 1H), 1.3-1.4 (m, 1H). $^{19}F$ NMR (METHANOL-$d_4$, 376 MHz) δ ppm −76.93 (s), −141.27 (d, J = 8.7 Hz) |
| 326 | 602.1 | $^1H$ NMR. (METHANOL-$d_4$, 400 MHz) δ ppm 9.2-9.3 (m, 1H), 7.7-7.8 (m, 1H), 7.6-7.6 (m, 1H), 4.9-5.1 (m, 3H), 4.5-4.7 (m, 3H), 3.7-3.8 (m, 2H), 3.4-3.4 (m, 1H), 3.1-3.3 (m, 3H), 2.79 (s, 5H), 2.52 (d, 3H, J = 0.6 Hz), 2.2-2.3 (m, 2H), 1.9-2.1 (m, 4H), 1.8-1.9 (m, 1H), 1.7-1.8 (m, 4H), 1.0-1.1 (m, 1H). $^{19}F$ NMR (METHANOL-$d_4$, 376 MHz) δ ppm −76.93 (s), −142.88 (br s). |
| 327 | 654.2 | $^1H$ NMR (DMSO-$d_6$, 600 MHz) δ ppm 9.4-9.4 (m, 1H), 7.9-7.9 (m, 1H), 7.8-7.8 (m, 1H), 5.2-5.4 (m, 2H), 5.0-5.0 (m, 1H), 4.0-4.2 (m, 2H), 3.7-3.9 (m, 2H), 3.6-3.7 (m, 1H), 3.3-3.4 (m, 2H), 3.0-3.2 (m, 3H), 2.8-2.9 (m, 1H), 2.7-2.8 (m, 1H), 2.1-2.2 (m, 2H), 2.0-2.1 (m, 1H), 1.8-1.9 (m, 1H), 1.7-1.8 (m, 6H), 1.6-1.6 (m, 1H), 1.50 (s, 3H), 1.2-1.3 (m, 1H). |
| 328 | 625.9 | $^1H$ NMR (400 MHz, METHANOL-$d_4$) δ ppm 9.44 (s, 1 H) 7.82-7.87 (m, 1 H) 7.74-7.80 (m, 1 H) 5.47-5.57 (m, 1 H) 4.88-4.99 (m, 2 H) 4.62-4.71 (m, 1 H) 4.23-4.34 (m, 1 H) 3.96-4.17 (m, 4 H) 3.84-3.93 (m, 1 H) 3.76-3.84 (m, 2 H) 3.55-3.66 (m, 1 H) 3.40-3.48 (m, 1 H) 3.09-3.19 (m, 3 H) 2.99-3.08 (m, 1 H) 2.88-2.99 (m, 1 H) 2.46-2.71 (m, 2 H) 2.22-2.36 (m, 1 H) 2.01-2.16 (m, 1 H) 1.84-1.94 (m, 2 H) 1.17-1.27 (m, 3 H). $^{19}F$ NMR (METHANOL-$d_4$, 376 MHz) δ ppm −77.22 (s), −141.59 (br s). |
| 329 | 623.8 | $^1H$ NMR (400 MHz, METHANOL-$d_4$) δ ppm 9.45 (s, 1 H) 7.81-7.89 (m, 1 H) 7.70-7.81 (m, 1 H) 5.46-5.56 (m, 1 H) 4.84-5.07 (m, 3 H) 4.61-4.71 (m, 1 H) 4.19-4.34 (m, 1 H) 3.97-4.16 (m, 3 H) 3.83-3.95 (m, 1 H) 3.75-3.83 (m, 1 H) 3.53-3.72 (m, 3 H) 3.39-3.53 (m, 1 H) 3.18 (s, 3 H) 2.92-3.08 (m, 1 H) 2.67 (s, 1 H) 2.30-2.53 (m, 2 H) 1.93-2.04 (m, 1 H) 1.82-1.93 (m, 2 H) 1.24-1.37 (m, 1 H) 0.89-1.07 (m, 1 H). $^{19}F$ NMR (376 MHz, METHANOL-$d_4$) δ ppm −77.42 (s) −141.69 (s) |
| 330 | 623.9 | $^1H$ NMR (400 MHz, METHANOL-$d_4$) δ ppm 9.44 (s, 1 H) 7.82-7.87 (m, 1 H) 7.76-7.80 (m, 1 H) 5.46-5.57 (m, 1 H) 4.93-4.98 (m, 1 H) 4.71-. 4.81 (m, 2 H) 4.53-4.62 (m, 1 H) 4.39-4.49 (m, 1 H) 4.21-4.35 (m, 1 H) 3.98-4.18 (m, 3 H) 3.74-3.93 (m, 2 H) 3.56-3.67 (m, 1 H) 3.36-3.49 (m, 2 H) example 383.23 (s, 3 H) 2.97-3.07 (m, 1 H) 2.77-2.88 (m, 1 H) 2.57-2.66 (m, 1 H) 2.02-2.20 (m, 2 H) 1.79-1.95 (m, 2 H) 1.11-1.30 (m, 2 H). $^{19}F$ NMR (376 MHz, METHANOL-$d_4$) δ ppm −77.31 (s) −141.61-−141.53(m). |
| 331 | 640.2 | $^1H$ NMR (400 MHz, METHANOL-$d_4$) δ ppm 9.34-9.37 (m, 1 H), 7.66-7.99 (m, 1 H), 7.63-7.87 (m, 1 H), 5.63-5.88 (m, 1 H), 4.21-4.58 (m, 3 H), 3.93-4.14 (m, 1 H), 3.39-3.84 (m, 5 H), 3.10 (s, 2 H), 2.57-2.69 (m, 2 H), 2.30-2.34 (m, 6 H), 1.89-1.96 (m, 1 H), 1.52-1.63 (m, 3 H), 1.30-1.40 (m, 4 H), 0.68-0.79 (m, 2 H), 0.52-0.59 (m, 2 H). $^{19}F$ NMR (376 MHz, METHANOL-$d_4$) δ ppm −141.53 (s). |
| 332 | 640.2 | $^1H$ NMR (400 MHz, METHANOL-$d_4$) δ ppm 9.34-9.36 (m, 1 H), 7.67-7.88 (m, 2 H), 5.73-5.86 (m, 1 H), 4.48-4.55 (m, 1 H), 4.26-4.35 (m, 2 H), 4.02-4.12 (m, 1 H), 3.47-3.83 (m, 5H), 3.11-3.25 (m, 2 H), 2.93-3.09 (m, 1 H), 2.55-2.63 (m, 2 H), 2.31-2.36 (m, 6 H), 1.85-1.95 (m, 2 H), 1.57-1.62 (m, 3 H), 1.30-1.39 (m, 4 H), 0.51-0.62 (m, 2 H). $^{19}F$ NMR (376 MHz, METHANOL-$d_4$) δ ppm −141.53 (s). |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| 333 | 666.9 | $^1H$ NMR (400 MHz, METHANOL-$d_4$) δ ppm 9.46-9.59 (m, 1 H), 7.81-8.11 (m, 2 H), 5.52-5.76 (m, 1 H), 5.00-5.19 (m, 2 H), 4.57-4.84 (m, 2 H), 4.17-4.45 (m, 3 H), 3.91-4.11 (m, 3 H), 3.62-3.75 (m, 1 H), 3.36-3.56 (m, 3 H), 3.15-3.25 (m, 1 H), 2.77-2.94 (m, 1 H), 2.10-2.74 (m, 6 H), 1.82-1.92 (m, 2 H), 1.60-1.77 (m, 3 H), 1.30-1.49 (m, 4 H). $^{19}F$ NMR (377 MHz, METHANOL-$d_4$) δ ppm −81.34-−75.04 (m, 6 F), −142.22-−141.73 (m), −174.43-−173.94 (m). |
| 334 | 636.0 | $^1H$ NMR (400 MHz, METHANOL-$d_4$) δ ppm 9.23-9.32 (m, 1 H), 7.71 (s, 2 H), 4.86-5.11 (m, 2 H), 4.65-4.73 (m, 1 H), 4.38-4.53 (m, 2 H), 3.75-3.93 (m, 2 H), 3.42-3.52 (m, 2 H), 3.26 (br d, J = 13.6 Hz, 2 H), 2.95-3.07 (m, 6 H), 2.71-2.81 (m, 1 H), 2.14-2.28 (m, 1 H), 1.96-2.09 (m, 1 H), 1.84-1.92 (m, 1 H), 1.65-1.82 (m, 4 H), 1.24-1.39 (m, 1 H), 0.96-1.11 (m, 3 H), 0.82-0.94 (m, 2 H). $^{19}F$ NMR (376 MHz, METHANOL-$d_4$) δ ppm −77.42 (s), −143.60 (s). |
| 335 | 670.0 | $^1H$ NMR (400 MHz, METHANOL-$d_4$) δ ppm 9.40-9.48 (m, 1 H), 7.96-8.08 (m, 2 H), 5.46-5.54 (m, 1 H), 5.31 (br d, J = 8.8 Hz, 1 H), 5.14-5.14 (m, 1 H), 4.95-5.01 (m, 1 H), 4.24-4.37 (m, 3 H), 4.00-4.19 (m, 4 H), 3.72-3.83 (m, 1 H), 3.55 (s, 3 H), 3.40-3.45 (m, 1 H), 2.94-3.27 (m, 4 H), 2.08-2.63 (m, 4 H), 2.00-2.06 (m, 2 H), 1.88-1.94 (m, 2 H), 1.32-1.39 (m, 4H). $^{19}F$ NMR (376 MHz, METHANOL-$d_4$) δ ppm −139.28-−138.71 (m, 1 F), −173.77-−173.63 (m, 1 F). |
| 336 | 672.0 | $^1H$ NMR (600 MHz, DMSO-$d_6$) δ ppm 9.39 (s, 1 H), 7.89 (s, 1 H), 7.80 (s, 1 H), 5.33 (br s, 1 H), 5.22-5.27 (m, 2 H), 5.01 (br d, J = 13.1 Hz, 1 H), 4.96 (d, J = 10.0 Hz, 1 H), 4.88 (d, J = 10.1 Hz, 1 H), 4.79 (d, J = 10.1 Hz, 1 H), 4.71 (d, J = 10.1 Hz, 1 H), 4.18 (d, J = 10.3 Hz, 1 H), 4.07 (d, J = 10.4Hz, 1 H), 3.84-3.90 (m, 2 H), 3.69-3.73 (m, 1 H), 3.32-3.36 (m, 1 H), 3.05-3.19 (m, 2 H), 3.01-3.05 (m, 1 H), 2.81-2.86 (m, 1 H), 2.66-2.72 (m, 1 H), 2.05-2.13 (m, 1 H), 1.93-2.03 (m, 2 H), 1.84-1.87 (m, 1 H), 1.66-1.82 (m, 6 H), 1.32-1.39 (m, 1 H). |
| 338 | 644.0 | $^1H$ NMR (600 MHz, DMSO-$d_6$) δ ppm 9.44 (s, 1 H), 7.85 (s, 1 H), 7.75 (s, 1 H), 5.57 (br d, J = 17.6 Hz, 1 H), 5.01 (br d, J = 9.2 Hz, 1 H), 4.93 (br d, J = 9.1 Hz, 1 H), 4.53-4.63 (m, 2 H), 4.44-4.51 (m, 2 H), 4.26 (dd, J = 10.7, 6.3 Hz, 1 H), 4.14 (td, J = 12.1, 2.6 Hz, 1 H), 4.01-4.07 (m, 1 H), 3.87 (d, J = 12.8 Hz, 1 H), 3.79 (br d, J = 17.8 Hz, 1 H), 3.66-3.75 (m, 2 H), 3.46-3.57 (m, 1 H), 3.37-3.40 (m, 1 H), 2.87-2.99 (m, 3 H), 2.37-2.42 (m, 1 H), 2.36 (s, 2 H), 2.17-2.22 (m, 1 H), 1.90-2.01 (m, 1 H), 1.81 (tdd, J = 14.7, 14.7, 5.6, 5.5 Hz, 2 H), 1.62-1.73 (m, 3 H). |
| 339 | 686.0 | $^1H$ NMR (600 MHz, DMSO-$d_6$) δ ppm 9.38 (s, 1 H), 7.84 (s, 1 H), 7.72 (s, 1 H), 5.56 (br d, J = 17.8 Hz, 1 H), 5.34 (br s, 1 H), 5.25 (br s, 1 H), 5.00 (br d, J = 9.4 Hz, 1 H), 4.92 (br d, J = 10.1 Hz, 1 H), 4.58 (br d, J = 10.6 Hz, 2 H), 4.51 (d, J = 10.3 Hz, 1 H), 4.22 (br d, J = 9.0 Hz, 1 H), 4.11 (br d, J = 9.4 Hz, 1 H), 3.65-3.72 (m, 2 H), 3.58-3.64 (m, 1 H), 3.31-3.32 (m, 2 H), 3.20-3.25 (m, 1 H), 2.88-2.94 (m, 1 H), 2.21-2.31 (m, 1 H), 2.12-2.18 (m, 1 H), 2.09 (br s, 1 H), 1.99-2.07 (m, 2 H), 1.73-1.89 (m, 7 H), 1.51-1.61 (m, 1 H), 1.21-1.32 (m, 1 H), 1.07-1.18 (m, 2 H), 0.83-0.88 (m, 1 H). |
| 340 | 686.2 | $^1H$ NMR (600 MHz, DMSO-$d_6$) δ ppm 9.38 (s, 1 H), 7.84 (s, 1 H), 7.73 (s, 1 H), 5.56 (br d, J = 17.6 Hz, 1 H), 5.33-5.24 (d, 1 H), 5.00-4.92 (dd, 1 H), 4.58 (m, 2 H), 4.10-4.18 (m, 2 H), 3.58-3.74 (m, 3 H), 3.30-3.33 (m, 3 H), 3.03-3.12 (m, 2 H), 2.91 (dt, J = 14.0, 4.9 Hz, 1 H), 2.80-2.86 (m, 1 H), 1.96-2.13 (m, 5 H), 1.73-1.88 (m, 7 H), 1.52-1.62 (m, 1 H), 1.19-1.31 (m, 1H), 1.07-1.14 (m, 1 H). |
| 341 | 652.3 | $^1H$ NMR (CHLOROFORM-$d_4$, 400 MHz) δ ppm 9.29 (s, 1H), 7.65 (s, 1H), 7.62 (s, 1H), 5.47 (d, J = 17.01 Hz, 1H), 5.24-5.40 (m, 1H), 4.88-4.98 (m, 1H), 4.77 (d, J = 13.26 Hz, 1H), 4.20-4.35 (m, 3H), 4.10-4.17 (m, 2H), 3.96-4.04 (m, 1H), 3.87-3.92(m, 1H), 3.72-3.79 (m, 1H), 3.15-3.40 (m, 5H), 2.98-3.08 (m, 1H), 2.80-2.89 (m, 1H), 2.42-2.52 (m, 1H), 2.26-2.35 (m, 2H), 2.21 (s, 3H), 1.98 (d, J = 4.63 Hz, 3H), 1.87 (d, J = 3.00 Hz, 2H), 1.71-1.78 (m, 1H), 1.63-1.65 (m, 1H), 1.35-1.45 (m, 1H). $^{19}F$ NMR (CHLOROFORM-d, 376 MHz) δ −173.03 (s). |
| 342 | 652.3 | $^1H$ NMR (CHLOROFORM-$d_4$, 400 MHz) δ ppm 9.38 (s, 1H), 7.76 (s, 1H), 7.62 (s, 1H), 5.23-5.40 (m, 1H), 4.68-4.96 (m, 1H), 4.37-4.51(m, 2H), 4.27-4.31(m, 1H), 4.09-4.15 (m, 2H), 3.92-4.05 (m, 2H), 3.85-3.91(m, 1H), 3.51-3.67 (m, 2H), 3.34-3.46 (m, 2H), 3.23-3.31 (m, 1H), 2.98-3.07 (m, 1H), 2.60-2.72 (m, 1H), 2.21 (s, 3H), 1.94-2.07 (m, 5H), 1.60-1.84 (m, 6H), 0.94-0.99 (m, 1H). $^{19}F$ NMR (CHLOROFORM-d, 376 MHz) δ ppm −173.15 (s). |

TABLE 31-continued

| Analytical Data for Examples 92 to 98, 100 to 102, 179 to 212 and 303 to 368. | | |
|---|---|---|
| Cmpd.# | MS m/z (ESI): $(M + H)^+$ | $^1H$ and $^{19}F$ NMR |
| 343 | 648.3 | $^1H$ NMR (400 MHz, DMSO-$d_6$) δ ppm 13.32 (s, 1H), 9.37 (s, 1H), 7.72-7.99 (m, 2H), 7.45 (s, 1H), 5.13-5.47 (m, 1H), 4.48-4.97 (m, 4H), 4.02-4.24 (m, 2H), 3.65-3.92 (m, 2H), 2.95-3.24 (m, 6H), 2.79-2.90 (m, 1H), 1.95-2.22 (m, 5H), 1.74-1.89 (m, 4H), 1.58-1.71 (m, 5H). $^{19}F$ NMR (376 MHz, DMSO-$d_6$) δ ppm −73.45 (s). |
| 344 | 622.3 | $^1H$ NMR (400 MHz, CHLOROFORM-d) δ ppm 9.14 (s, 1H), 7.58-7.68 (m, 1H), 7.10-7.24 (m, 3H), 5.77 (d, J = 17.2 Hz, 1H), 4.67 (d, J = 12.0 Hz, 2H), 4.43-4.56 (m, 1H), 4.13-4.30 (m, 2H), 3.97-4.12 (m, 2H), 3.72-3.82 (m, 1H), 3.63 (d, J = 17.2 Hz, 1H), 3.31-3.43 (m, 3H), 3.19-3.30 (m, 2H), 2.94-3.10 (m, 1H), 2.85 (s, 1H), 2.66 (s, 3H), 2.39 (t, J = 8.0 Hz, 2H), 2.11-2.18 (m, 1H), 1.81-1.92 (m, 1H), 1.20-1.30 (m, 2H). $^{19}F$ NMR (CHLOROFORM-d, 377 MHz) δ ppm −118.19 (s), −135.45 (s). |
| 345 | 666.3 | $^1H$ NMR (400 MHz, CHLOROFORM-d) δ ppm 9.10 (s, 1H), 7.52-7.62 (m, 1H), 7.12-7.17 (m, 3H), 5.76 (d, J = 16.8 Hz, 1H), 5.28 (d, J = 53.2 Hz, 1H), 4.67 (d, J = 13.2 Hz, 1H), 4.18-4.37 (m, 4H), 4.12-4.17 (m, 1H), 3.97-4.07 (m, 1H), 3.69- 3.83 (m, 2H), 3.62 (d, J = 17.2 Hz, 1H), 3.26-3.43 (m, 4H), 3.14-3.24 (m, 2H), 2.96-3.06 (m, 1H), 2.17-2.49 (m, 4H), 1.86-2.13 (m, 5H), 1.25 (t, J = 7.2 Hz, 1H). $^{19}F$ NMR (CHLOROFORM-d, 376 MHz) δ ppm −172.21 (s), −135.34 (s), −118.44 (s). |
| 346 | 652.3 | $^1H$ NMR (400 MHz, CHLOROFORM-d) δ ppm 9.46 (s, 1H), 7.76 (s, 1H), 7.62 (s, 1H), 7.47 (s, 1H), 5.20-5.40 (m, 1H), 4.86 (d, J = 17.6Hz, 1H), 4.69-4.80 (m, 1H), 4.21-4.39 (m, 3H), 3.99-4.00 (m, 1H), 3.80-3.91 (m, 1H), 3.56-3.73 (m, 4H), 3.15-3.45 (m, 6H), 2.98-3.00 (m, 1H), 2.75-2.93 (m, 3H), 2.13-2.34 (m, 4H), 1.85-2.03 (m, 6H), 1.22-1.30 (m, 1H). $^{19}F$ NMR (CHLOROFORM-d, 376 MHz) δ ppm −172.91 (s). |
| 347 | 597.2 | $^1H$ NMR (400 MHz, CHLOROFORM-d) δ ppm 9.03 (s, 1H), 7.80 (s, 1H), 7.67 (s, 1H), 5.32 (d, J = 17.2 Hz, 1H), 4.89-5.95 (m, 1H), 4.62 (d, J = 13.6 Hz, 1H), 4.14-4.22 (m, 3H), 4.03 (s, 3H), 3.81-3.87 (m, 3H), 3.36-3.44 (m, 1H), 3.18-3.25 (m, 1H), 2.97-3.03 (m, 1H), 2.76-2.82 (m, 1H), 2.58 (s, 4H), 2.41 (s, 3H), 1.85-1.91 (m, 3H). |
| 348 | 597.2 | $^1H$ NMR (400 MHz, CHLOROFORM-d) δ ppm 9.04 (s, 1H), 7.79 (s, 1H), 7.69 (s, 1H), 5.33 (d, J = 16.8 Hz, 1H), 4.91 (t, J = 7.2 Hz, 1H), 4.87-4.79 (m, 1H), 4.62 (d, J = 13.6 Hz, 1H), 4.21-4.15 (m, 3H), 3.87-3.80 (m, 3H), 3.45-3.35 (m, 1H), 3.27-3.17 (m, 3H), 3.07-2.95 (m, 3H), 2.89 (d, J = 12.4 Hz, 1H), 2.82-2.73 (m, 1H), 1.89 (t, J = 12.4 Hz, 3H), 1.29-1.24 (m, 4H). |
| 349 | 628.3 | $^1H$ NMR (400 MHz, CHLOROFORM-d) δ ppm 9.36 (s, 1H), 7.89 (s, 1H), 7.47 (s, 1H), 7.43 (s, 1H), 5.24-5.43 (m, 1H), 4.69-4.72 (m, 1H), 4.25-4.43 (m, 2H), 3.70-3.78 (m, 1H), 3.25-3.42 (m, 2H), 3.00-3.22 (m, 4H), 2.79-2.91 (m, 1H), 3.46 (s, 3H), 2.23-2.40 (m, 4H), 1.92-2.12 (m, 7H), 1.30 (s, 1H), 1.22-1.28 (m, 4H). $^{19}F$ NMR (376 MHz, CHLOROFORM-d) δ ppm −173.01 (s). |
| 350 | 666.3 | $^1H$ NMR (CHLOROFORM-d, 400 MHz) δ ppm 9.14 (s, 1H), 7.86 (s, 1H), 7.71 (s, 1H), 5.25-5.43 (m, 1H), 4.88-5.10 (m, 2H), 4.81 (t, J = 11.38, 4.25 Hz, 1H), 4.70 (t, J = 6.57 Hz, 1H), 4.23-4.52 (m, 2H), 3.85 (t, J = 10.57 Hz, 1H), 3.57 (d, J = 13.13 Hz, 1H), 3.34-3.44 (m, 2H), 3.14-3.32 (m, 1H), 2.89-3.07 (m, 2H), 2.83 (s, 2H), 2.62-2.75 (m, 2H), 2.37 (t, J = 8.13 Hz, 2H), 1.98-2.04 (m, 2H), 1.96-1.90(m, 3H), 1.74-1.83 (m, 3H), 1.59-1.66 (m, 3H). |
| 351 | 653.4 | $^1H$ NMR (400 MHz, CHLOROFORM-d) δ ppm 9.26 (s, 1H), 7.73 (s, 1H), 7.43 (s, 1H), 5.79 (d, J = 17.2 Hz, 1H), 5.21-5.42 (m, 1H), 4.76 (d, J = 12.4 Hz, 1H), 4.23-4.37 (m, 2H), 4.16 (d, J = 10.4 Hz, 1H), 4.03-4.10 (m, 1H), 3.83 (t, J = 10.6 Hz, 1H), 3.66 (d, J = 12.0 Hz, 2H), 3.60 (d, J = 17.2 Hz, 1H), 3.36-3.46 (m, 1H), 3.24-3.32 (m, 2H), 3.13-3.20 (m, 2H), 2.94-3.03 (m, 1H), 2.73-2.82 (m, 1H), 2.62-2.70 (m, 1H), 2.53 (s, 3H), 2.24-2.30 (m, 1H), 2.07-2.17 (m, 2H), 1.82-1.98 (m, 5H). $^{19}F$ NMR (377 MHz, CHLOROFORM-$d_4$) δ ppm −139.33 (s), −173.23 (s). |
| 352 | 653.4 | $^1H$ NMR (400 MHz, CHLOROFORM-d) δ ppm 9.26 (s, 1H), 7.74 (s, 1H), 7.43 (s, 1H), 5.79 (d, J = 16.8 Hz, 1H), 5.21-5.42 (m, 1H), 4.76 (d, J = 12.8 Hz, 1H), 4.23-4.33 (m, 2H), 4.04-4.12 (m, 1H), 3.83 (t, J = 10.6 Hz, 1H), 3.68-3.74 (m, 2H), 3.60 (d, J = 17.2 Hz, 1H), 3.37-3.53 (m, 2H), 3.24-3.35 (m, 1H), 3.17 (d, J = 12.4 Hz, 1H), 3.03-3.13 (m, 1H), 2.74-2.82 (m, 1H), 2.63-2.70 (m, 1H), 2.53 (s, 3H), 2.20-2.38 (m, 3H), 2.01 (s, 2H), 1.85-1.92 (m, 2H), 1.62-1.72 (m, 3H). $^{19}F$ NMR (377 MHz, CHLOROFORM-$d_6$) δ ppm −75.52 (s), −139.28 (s). |
| 353 | 673.3 | $^1H$ NMR (CHLOROFORM-d, 400 MHz) δ ppm 10.58 (s, 1H), 9.26 (s, 1H), 7.77 (s, 1H), 7.69 (s, 1H), 5.78 (d, J = 17.2 Hz, 1H), 5.20-5.40 (m, 1H), 4.76 (d, J = 13.2 Hz, 1H), 4.20-4.35 (m, 3H), 4.00-4.10 (m, 1H), 3.73-3.82 (m, 1H), 3.55-3.72 (m, 3H), 3.33-3.45 (m, |

TABLE 31-continued

Analytical Data for Examples 92 to 98, 100 to 102, 179 to 212 and 303 to 368.

| Cmpd.# | MS m/z (ESI): $(M + H)^+$ | $^1H$ and $^{19}F$ NMR |
|---|---|---|
| | | 2H), 3.13-3.33 (m, 3H), 2.95-3.08 (m, 2H), 2.55-2.69 (m, 1H), 2.13-2.38 (m, 3H), 1.96-2.06 (m, 2H), 1.85-1.96 (m, 3H). $^{19}F$ NMR (CHLOROFORM-$d_4$, 376 MHz) 8-139.00 (s), −172.96 (s). |
| 354 | 673.3 | $^1H$ NMR (CHLOROFORM-d, 400 MHz) δ ppm 10.62 (s, 1H), 9.26 (s, 1H), 7.76 (s, 1H), 7.69 (s, 1H), 5.78 (d, J = 17.2 Hz, 1H), 5.22-5.40 (m, 1H), 4.75 (d, J = 12.4 Hz, 1H), 4.18-4.39 (m, 3H), 4.02-4.08 (m, 1H), 3.73-3.83 (m, 1H), 3.55-3.72 (m, 3H), 3.35-3.45 (m, 2H), 3.20-3.33 (m, 2H), 3.15 (d, J = 12.4 Hz, 1H), 2.96-3.08 (m, 2H), 2.58-2.68 (m, 1H), 2.13-2.38 (m, 3H), 1.95-2.04 (m, 2H), 1.86-1.95 (m, 3H). $^{19}F$ NMR (CHLOROFORM-$d_4$, 376 MHz) δ −139.02 (s), −173.09 (s). |
| 355 | 632.3 | $^1H$ NMR (400 MHz, CHLOROFORM-d) δ ppm 9.12 (s, 1H), 6.98 (d, J = 2.0Hz, 1H), 6.85 (d, J = 2.4Hz, 1H), 5.27-5.44 (m, 2H), 4.88 (t, J = 6.0Hz, 1H), 4.79 (d, J = 1.6Hz, 1H), 4.41-4.52 (m, 1H), 4.31-4.39 (m, 1H), 4.10-4.22 (m, 3H), 3.82-3.91 (m, 2H), 3.70-3.78 (m, 2H), 3.29-3.42 (m, 2H), 3.06-3.23 (m, 2H), 2.72-2.84 (m, 1H), 2.24-2.43 (m, 4H), 1.99-2.15 (m, 4H), 1.75-1.89 (m, 2H). $^{19}F$ NMR (CHLOROFORM-d, 376 MHz ) δ ppm −138.44 (s), −172.39 (s). |
| 356 | 650.3 | $^1H$ NMR (400 MHz, CHLOROFORM-d) δ ppm 9.15 (s, 1H), 7.93 (s, 1H), 7.32 (d, J = 9.6 Hz, 1H), 5.31 (d, J = 56.4 Hz, 1H), 5.02 (d, J = 12.8 Hz, 1H), 4.93 (d, J = 12.0 Hz, 1H), 4.82 (d, J = 11.2 Hz, 1H), 4.71 (t, J = 6.4 Hz, 1H), 4.19-4.42 (m, 2H), 3.58 (d, J = 13.2 Hz, 1H), 3.26 (d, J = 14.8 Hz, 2H), 3.02 (d, J = 8.4 Hz, 2H), 2.70-2.83 (m, 1H), 2.18-2.42 (m, 4H), 2.08-2.15 (m, 1H), 1.87-2.06 (m, 5H), 1.46-1.89 (m, 7H), 1.01-1.09 (m, 1H). $^{19}F$ NMR (CHLOROFORM-d, 376 MHz ) δ ppm −116.18 (s), −141.03 (s), −173.13 (s). |
| 357 | 649.3 | $^1H$ NMR (400 MHz, CHLOROFORM-d) δ ppm 7.72 (m, 2H), 7.59 (s, 1H) ,5.22-5.39 (m, 1H), 4.75-4.80 (m, 1H), 4.24-4.35 (m, 1H), 4.15-4.25 (m, 1H), 3.72-3.80 (m, 1H), 3.26-3.38 (m, 2H), 3.16-3.25 (m, 2H), 2.90-3.08 (m, 2H), 2.06-2.37 (m, 6H), 1.80-2.04 (m, 7H), 1.74 (s, 2H), 1.18-1.31 (m, 4H). $^{19}F$ NMR (CHLOROFORM-d, 376 MHz) δ ppm −173.08 (s). |
| 358 | 629.3 | $^1H$ NMR (400 MHz, CHLOROFORM-d) δ ppm 7.75 (s, 1H), 7.59 (s, 1H) ,7.49 (s, 1H), 5.22-5.40 (m, 1H), 4.75-4.85 (m 1H), 4.09-4.41 (m, 3H), 3.17-3.48 (m, 4H), 2.83-3.09 (m, 4H), 2.49 (s, 3H), 2.09-2.41 (m, 7H), 1.87-2.05 (m, 6H), 1.26 (s, 3H), 0.82-0.93 (m, 1H). $^{19}F$ NMR (CHLOROFORM-d, 377 MHz) δ ppm −173.12 (s). |
| 359 | 670.3 | $^1H$ NMR (DMSO-$d_6$, 400 MHz) δ ppm 13.34 (s, 1H), 9.41 (s, 1H), 7.85 (s, 1H), 7.75 (s, 1H), 5.67 (d, J = 17.3 Hz, 1H), 5.26-5.47 (m, 1H), 4.58 (d, J = 13.2 Hz, 1H), 3.98-4.29 (m, 4H), 3.77 (d, J = 17.2 Hz, 1H), 3.48-3.68 (m, 4H), 3.07 (d, J = 12.4 Hz, 1H), 2.83-3.00 (m, 3H), 2.27-2.47 (m, 2H), 1.61-2.00 (m, 8H), 1.49 (s, 3H), 1.23 (s, 1H). $^{19}F$ NMR (376 MHz, DMSO-$d_6$) δ −141.63 (s), −172.41 (s). |
| 360 | 656.2 | $^1H$ NMR (DMSO-$d_6$, 400 MHz) δ ppm 13.34 (s, 1H), 9.45 (s, 1H), 7.84 (s, 1H), 7.77 (s, 1H), 5.27-5.46 (m, 2H), 4.83 (s, 1H), 4.55-4.65 (m, 1H), 4.18-4.24 (m, 1H), 4.07-4.16 (m, 2H), 3.89-4.04 (m, 3H), 3.63-3.78 (m, 2H), 3.47-3.59 (m, 1H), 3.22-3.29 (m, 1H), 2.74-3.00 (m, 3H), 2.52-2.60 (m, 2H), 2.41-2.47 (m, 1H), 2.24-2.38 (m, 1H), 1.63-1.98 (m, 7H). $^{19}F$ NMR (DMSO-$d_6$, 376 MHz) δ −141.43 (s), −172.35 (s). |
| 361 | 652.2 | $^1H$ NMR (400 MHz, CHLOROFORM-d) δ ppm 9.04 (s, 1H), 7.47-7.58 (m, 1H), 7.21 (s, 1H), 7.08-7.17 (m, 2H), 5.16-5.50 (m, 2H), 4.87-5.02 (m, 1H), 4.71 (d, J = 14.0 Hz, 1H), 4.06-4.30 (m, 7H), 3.66-3.91 (m, 1H), 3.39-3.49 (m, 1H), 3.26-3.38 (m, 2H), 3.10-3.23 (m, 2H), 2.95-3.07 (m, 1H), 2.31-2.50 (m, 2H), 2.17-2.29 (m, 1H), 1.95-2.12 (m, 3H), 1.83-1.93 (m, 1H), 1.13-1.42 (m, 2H). $^{19}F$ NMR (376 MHz, CHLOROFORM-d) δ ppm −118.34 (s), −135.11 (s), −172.10 (s). |
| 362 | 633.3 | $^1H$ NMR (400 MHz, CHLOROFORM-d) δ ppm 7.71 (s, 2H), 7.55-7.63 (m, 2H), 5.21-5.40 (m, 1H), 5.17 (d, J = 13.2 Hz, 1H), 4.44 (t, J = 9.2 Hz, 1H), 4.17-4.32 (m, 2H), 4.10-4.16 (m, 1H), 3.93-4.06 (m, 1H), 3.71-3.82 (m, 2H), 3.56 (d, J = 16.4 Hz, 1H), 3.26-3.40 (m, 3H), 3.21 (s, 1H), 2.97-3.08 (m, 1H), 2.82-2.92 (m, 1H), 2.36-2.52 (m, 2H), 2.24-2.34 (m, 1H), 2.10-2.21 (m, 2H), 1.89-2.06 (m, 4H), 1.77 (s, 3H), 1.20-1.29 (m, 2H). $^{19}F$ NMR (377 MHz, CHLOROFORM-d) δ ppm −173.07 (s). |

TABLE 31-continued

| Analytical Data for Examples 92 to 98, 100 to 102, 179 to 212 and 303 to 368. | | |
|---|---|---|
| Cmpd.# | MS m/z (ESI): $(M + H)^+$ | $^1H$ and $^{19}F$ NMR |
| 363 | 633.3 | $^1H$ NMR (400 MHz, CHLOROFORM-d) δ ppm 7.72 (s, 2H), 7.57-7.65 (m, 2H), 5.15-5.39 (m, 2H), 4.45 (t, J = 9.2 Hz, 1H), 4.26 (d, J = 10.4 Hz, 1H), 4.12-4.18 (m, 2H), 3.96-4.07 (m, 1H), 3.71-3.80 (m, 2H), 3.56 (d, J = 16.4 Hz, 1H), 3.37 (d, J = 12.4 Hz, 2H), 3.24-3.35 (m, 2H), 3.18 (d, J = 9.2 Hz, 1H), 2.98-3.06 (m, 1H), 2.83-2.90 (m, 1H), 2.38-2.52 (m, 2H), 2.23-2.32 (m, 1H), 2.12-2.20 (m, 2H), 1.92-2.00 (m, 2H), 1.83-1.91 (m, 1H), 1.77 (s, 3H), 1.20-1.29 (m, 2H). $^{19}F$ NMR (377 MHz, CHLOROFORM-d) δ ppm −173.18 (s). |
| 364 | 670.2 | $^1H$ NMR (CHLOROFORM-d, 400 MHz) δ ppm 9.27 (s, 1H), 7.95 (s, 1H), 7.88 (s, 1H), 5.20-5.50 (m, 3H), 4.90-5.08 (m, 1H), 4.79 (d, J = 24.0Hz, 1H), 4.22 (d, J = 12.0Hz, 3H), 4.04-4.09 (m, 1H), 3.90-3.98 (m, 1H), 3.54 (s, 3H), 3.40-3.48 (m, 1H), 3.20-3.30 (m, 3H), 3.17 (d, J = 12.0Hz, 1H), 2-2.90-3.01 (m, 2H), 2.50-2.62 (m, 1H), 2.24-2.30 (m, 2H), 2.12-2.20 (m, 2H), 1.87 (d, J = 56.0Hz, 2H), 0.83-0.91 (m, 4H). $^{19}F$ NMR (CHLOROFORM-d, 376 MHz) δ −136.06 (s), −173.31 (s). |
| 365 | 662.3 | $^1H$ NMR (400 MHz, CHLOROFORM-d) δ ppm 9.23 (s, 1H), 7.91 (s, 1H), 7.44 (s, 1H), 5.74 (d, J = 16.8 Hz, 1H), 5.22-5.40 (s, 1H), 4.71 (d, J = 13.2 Hz, 1H), 4.21-4.38 (m, 3H), 4.02-4.10 (m, 1H), 3.53-3.76 (m, 4H), 3.25-3.48 (m, 4H), 3.12-3.24 (m, 3H), 2.93-3.08 (m, 2H), 2.36-2.45 (m, 1H), 2.12-2.33 (m, 3H), 1.82-2.03 (m, 5H), 1.67-1.80 (m, 3H), 1.60-1.64 (m, 1 H), 1.46-1.55 (m, 1H). $^{19}F$ NMR (CHLOROFORM-d, 376 MHz) δ ppm −140.17 (s), −172.94 (s). |
| 366 | 662.3 | $^1H$ NMR (400 MHz, CHLOROFORM-d, 400 MHz) δ ppm 9.89-10.50 (m, 1H), 9.48 (s, 1H), 7.99 (s, 1H), 7.38 (s, 1H), 5.46-5.56 (m, 1H), 5.28 (d, J = 54.4 Hz, 1H), 4.89 (d, J = 14.0 Hz, 1H), 4.22-4.38 (m, 2H), 4.09-4.20 (m, 3H), 3.95-4.07 (m, 2H), 3.62-3.86 (m, 3H), 3.27-3.45 (m, 4H), 2.95-3.18 (m, 3H), 2.14-2.46 (m, 4H), 1.88-2.04 (m, 3H), 1.76-1.86 (m, 2H), 1.65-1.69 (m, 4H). $^{19}F$ NMR (CHLOROFORM-d, 376 MHz) δ ppm −138.76(s), −172.96 (s). |
| 367 | 648.2 | $^1H$ NMR (400 MHz, CHLOROFORM-d) δ ppm 10.10 (s, 1H), 9.22 (s, 1H), 7.94 (s, 1H), 7.45 (s, 1H), 5.25-5.47 (m, 2H), 4.91 (t, J = 6.4 Hz, 1H), 4.76 (d, J = 13.2 Hz, 1H), 4.34-4.52 (m, 1H), 4.11-4.28 (m, 3H), 3.77-3.96 (m, 2H), 3.67 (t, J = 11.2 Hz, 1H), 3.26-3.49 (m, 4H), 3.15-3.25 (m, 2H), 2.96-3.11 (m, 2H), 2.20-2.48 (m, 4H), 1.97-2.16 (m, 3H), 1.81-1.96 (m, 2H), 1.64-1.79 (m, 3H). |
| 368 | 648.2 | $^1H$ NMR (400 MHz, CHLOROFORM-d) δ ppm 10.10 (s, 1H), 9.31 (s, 1H), 7.95 (d, J = 1.6 Hz, 1H), 7.40 (s, 1H), 5.24-5.50 (m, 2H), 5.11 (t, J = 6.4 Hz, 1H), 4.80-4.98 (m, 1H), 4.41-4.51 (m, 1H), 4.30-4.40 (m, 1H), 4.18-4.27 (m, 3H), 3.96-4.02 (m, 1H), 3.61-3.72 (m, 3H), 3.25-3.47 (m, 4H), 2.98-3.21 (m, 3H), 2.23-2.50 (m, 4H), 2.04-2.15 (m, 2H), 1.88-1.92 (m, 1H), 1.67-1.75 (m, 2H), 1.11-1.29 (m, 2 H). |

(26S)-18-Chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one (Example 99)

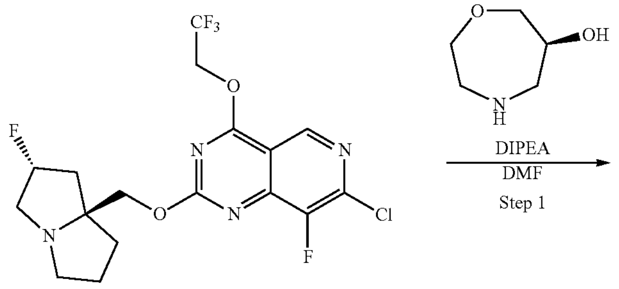

-continued
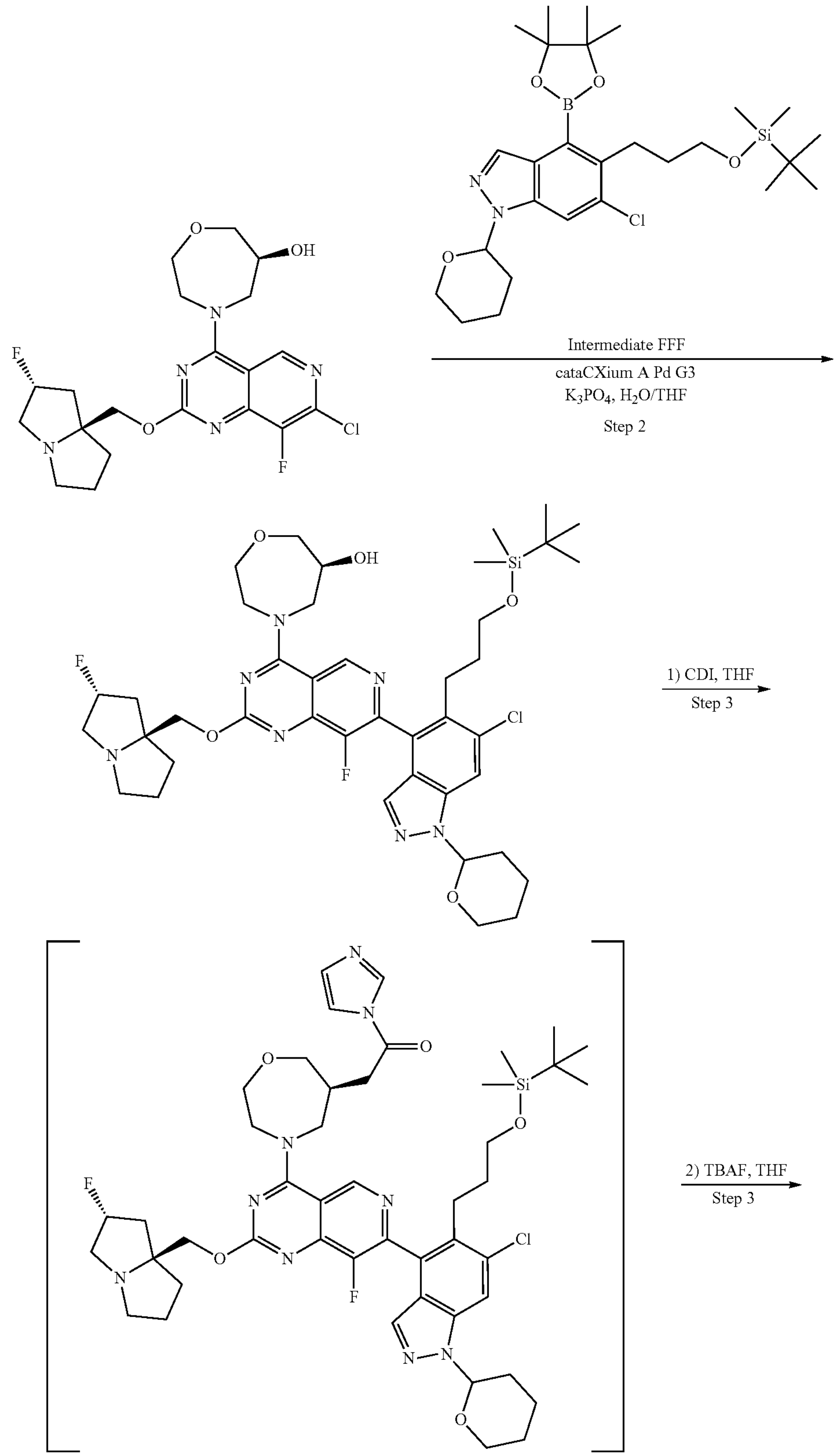

-continued

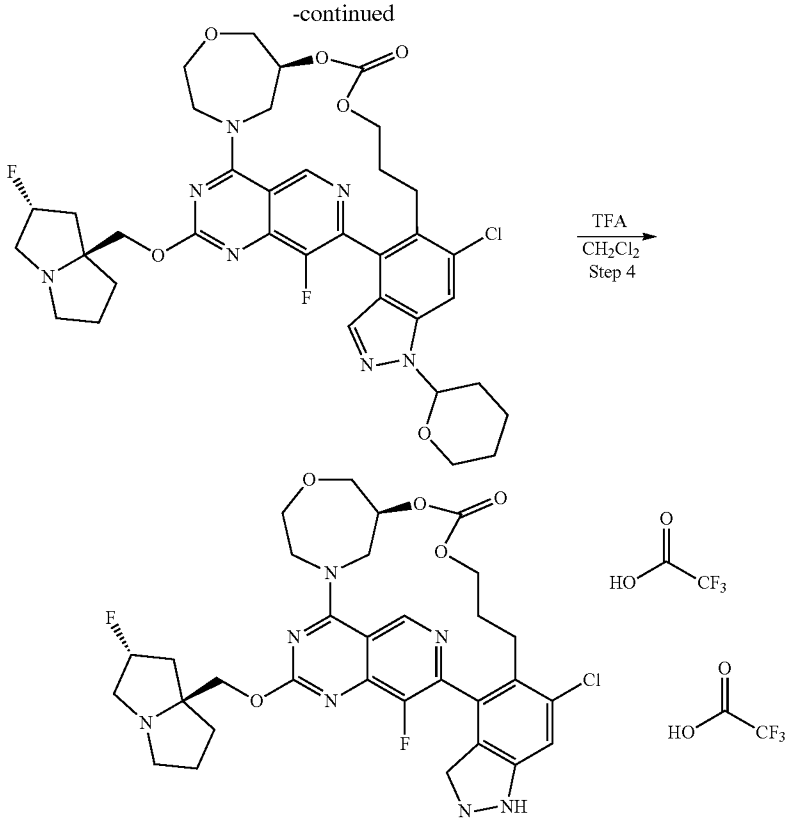

Example 99

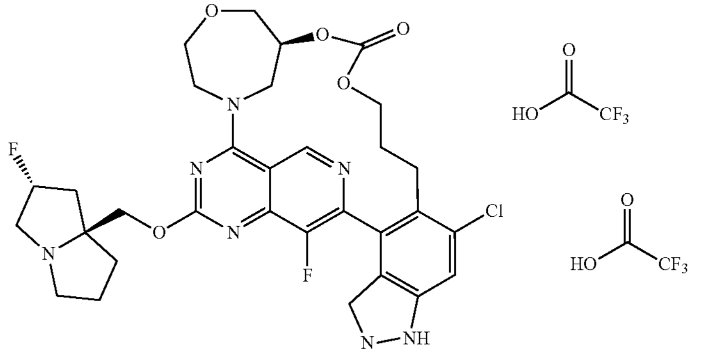

Example 99

Step 1. (S)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol. A 40-mL vial was charged with DIPEA (3.2 mL, 18.2 mmol), (S)-[1,4]oxazepan-6-ol (1.1 mL, 9.12 mmol, J&W Pharmlab), 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (2.00 g, 4.56 mmol, Step 2 in Intermediate AA) and N,N-dimethylformamide (20 mL). The reaction mixture was stirred at rt for 1 h. Water and DCM were added. The organic layer was separated, dried over $Na_2SO_4$, filtered, and concentrated. The residue was purified by column chromatography on silica gel, eluting with 0-85% 3:1 EtOAc/EtOH (with 2% triethylamine) in heptane, to yield (S)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol (1.40 g, 3.07 mmol, 67% yield). m/z (ESI): 456.0 $(M+H)^+$.

Step 2. (6S)-4-(7-(5-(3-((tert-Butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol. A 40 mL vial was charged with (S)-4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol (0.40 g, 0.88 mmol), 5-(3-((tert-butyldimethylsilyl)oxy)propyl)-6-chloro-1-(tetrahydro-2H-pyran-2-yl)-4-(4,4,5,5-tetramethyl-1,3,2-dioxaborolan-2-yl)-1H-indazole (0.70 g, 1.32 mmol, Intermediate FFF), potassium phosphate (0.75 g, 3.51 mmol), cataCXium A Pd G3 (0.13 g, 0.18 mmol). The vial was purged with nitrogen gas and then the reactants were suspended in degassed tetrahydrofuran (7.5 mL) and water (1.5 mL). The vial was then sealed, and the reaction mixture was heated to 80° C. for 2 h. After cooling to rt, the crude mixture was purified by column chromatography on silica gel, eluting with a gradient of 0-85% 3:1 EtOAc/EtOH (with 2% triethylamine) in heptane, to yield (6S)-4-(7-(5-(3-((tert-butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol (0.49 g, 0.59 mmol, 68% yield). m/z (ESI): 828.2 $(M+H)^+$.

Step 3. (26S)-18-Chloro-32-fluoro-4-(((2R,7aS)-2-fluorotetrahydro-1H-pyrrolo[1,2-a]pyrrol-7a(5H)-yl)methoxy)-N-(tetrahydro-2H-pyran-2-yl)-23,25,28-trioxa-1,3,5,9,14,15-hexaazahexacyclo[24.4.1.1~6,10~.0~2,7~.0~11,19~.0~12,16~]-dotriaconta-2,4,6,8,10(32),11,13,16,18-nonaen-24-one. A 40 mL vial was charged with (6S)-4-(7-(5-(3-((tert-butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol (0.49 g, 0.59 mmol) and 1,1'-carbonyldiimidazole (0.24 g, 1.49 mmol) and tetrahydrofuran (6 mL). The reaction mixture was allowed to stir at 40° C. until complete transformation to (6S)-4-(7-(5-(3-((tert-butyldimethylsilyl)oxy)propyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-yl 1H-imidazole-1-carboxylate was observed. m/z (ESI): 922.8 $(M+H)^+$.

The mixture was then diluted with THF (15 mL) and tetrabutylammonium fluoride (1.0 M in THF, 1.5 mL, 1.5 mmol) was added and the reaction mixture was allowed to stir at 40° C. until completion. The reaction was then concentrated under reduced pressure and the crude oil that was purified by column chromatography on silica gel, eluting with a gradient of 0-85% of a 3:1 EtOAc:EtOH (with 2% triethylamine) in heptane, to yield (26S)-18-chloro-32-fluoro-4-(((2R,7aS)-2-fluorotetrahydro-1H-pyrrolo[1,2-a]pyrrol-7a(5H)-yl)methoxy)-N-(tetrahydro-2H-pyran-2-yl)-23,25,28-trioxa-1,3,5,9,14,15-hexaazahexacyclo[24.4.1.1~6,10~.0~2,7~.0~11,19~.0~12,16~]-dotriaconta-2,4,6,8,10(32),11,13,16,18-nonaen-24-one (0.32 g, 0.43 mmol, 72% yield). m/z (ESI): 740.8 $(M+H)^+$.

Step 4. (26S)-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one. (26S)-18-Chloro-32-fluoro-4-(((2R,7aS)-2-fluorotetrahydro-1H-pyrrolo[1,2-a]pyrrol-7a(5H)-yl)methoxy)-N-(tetrahydro-2H-pyran-2-yl)-23,25,28-trioxa-1,3,5,9,14,15-hexaazahexacyclo[24.4.1.1~6,10~.0~2,7~.0~11,19~.0~12,16~]-dotriaconta-2,4,6,8,10(32),11,13,16,18-nonaen-24-one (0.32 g, 0.43 mmol) dissolved in DCM (2.1 mL) was treated with trifluoroacetic acid (2.1 mL) and the reaction mixture was stirred at rt for 1 h. The volatiles were removed under reduced pressure and the crude product was purified by reverse phase chromatography to yield (26S)-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one bis(2,2,2-trifluoroacetate) as white solid (0.14 g, 0.16 mmol, 36% yield). m/z (ESI): 655.9 $(M+H)^+$. $^1H$ NMR (400 MHz, METHANOL-$d_4$) δ ppm 9.37-9.54 (m, 1H), 7.82-7.89 (m, 1H), 7.78 (s, 1H), 5.47-5.70 (m, 2H), 4.91-4.98 (m, 1H), 4.80-4.85 (m, 1H), 4.72 (s, 2H), 4.22-4.34 (m, 1H), 3.84-4.16 (m, 7H), 3.74-3.83 (m, 1H), 3.55-3.67 (m, 1H), 3.41-3.55 (m, 2H), 2.96-3.07 (m, 1H), 2.55-2.84 (m, 3H), 2.29-2.49 (m, 3H), 2.12-2.27 (m, 1 H), 1.80-1.93 (m, 2H). $^{19}F$ NMR (376 MHz, METHANOL-$d_4$) δ ppm −77.32 (TFA), −141.67 (s), −174.08 (s). Stereochemistry of Example 99 was confirmed by X-Ray crystallography analysis.

(26S)-15-Acetyl-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaaza-hexacyclo[24.4.1.1~6,10~.0~2,7~.0~11,19~.0~12,16~]dotriaconta-2,4,6(32),7,9,11,13,16,18-nonaen-24-one (Example 213)

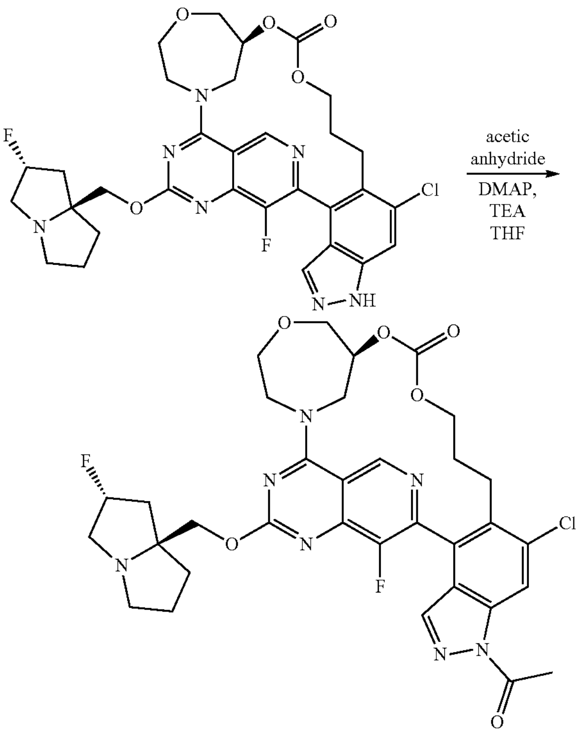

Example 213

A vial was charged with (26S)-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one (0.10 g, 0.15 mmol), DMAP (3.7 mg, 0.03 mmol), triethylamine (47 μL, 0.34 mmol) and tetrahydrofuran (1.5 mL). Acetic anhydride (29 μL, 0.30 mmol) was then added dropwise and the reaction mixture was stirred at 0° C. to rt overnight. The reaction was diluted with water and extracted with EtOAc. The combined organic layers were dried with $Na_2SO_4$, filtered, and concentrated under reduced pressure. The residue was purified by column chromatography on silica gel, eluting with a gradient of 0-70% (3:1 EtOAc/EtOH+2% TEA) in heptane, to provide (26S)-15-acetyl-18-chloro-32-fluoro-4-(((2R,7aS)-2-fluorotetrahydro-1H-pyrrolo[1,2-a]pyrrol-7a(5H)-yl)methoxy)-23,25,28-trioxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one (55 mg, 0.079 mmol, 52% yield) as white solid. $^1H$ NMR (400 MHz, METHANOL-$d_4$) δ ppm 9.37-9.43 (m, 1H), 8.63 (s, 1H), 8.02 (d, J=0.8 Hz, 1H), 5.47 (d, J=16.9 Hz, 1H), 5.22-5.41 (m, 1H), 4.91-5.00 (m, 1H), 4.22-4.39 (m, 3H), 4.01 (dd, J=17.1, 2.9 Hz, 1H), 3.76-3.88 (m, 2H), 3.57 (ddd, J=13.7, 11.3, 4.9 Hz, 1H), 3.35-3.40 (m, 1H), 3.14-3.30 (m, 3H), 2.98-3.11 (m, 2H), 2.78 (s, 3H), 2.70 (dt, J=14.4, 7.1 Hz, 1H), 2.11-2.41 (m, 3H), 1.98-2.08 (m, 3H), 1.81-1.94 (m, 3H). $^{19}$F NMR (376 MHz, METHANOL-$d_4$) δ ppm −141.01-−140.94 (m), −173.66 (s). m/z (ESI): 697.9 $(M+H)^+$.

(26S)-18-Chloro-32-fluoro-4-(((2S,7aS)-2-(2-propyn-1-yloxy)tetrahydro-1H-pyrrolo[1,2-a]pyrrol-7a(5H)-yl)methoxy)-23,25,28-trioxa-1,3,5,9,14,15 hexaazahexacyclo[24.4.1.1~6,10~.0~2,7~.0~11,19~.0~12,16~]dotriaconta-2,4,6,8,10(32),11,13,16,18-nonaen-24-one (Example 369)

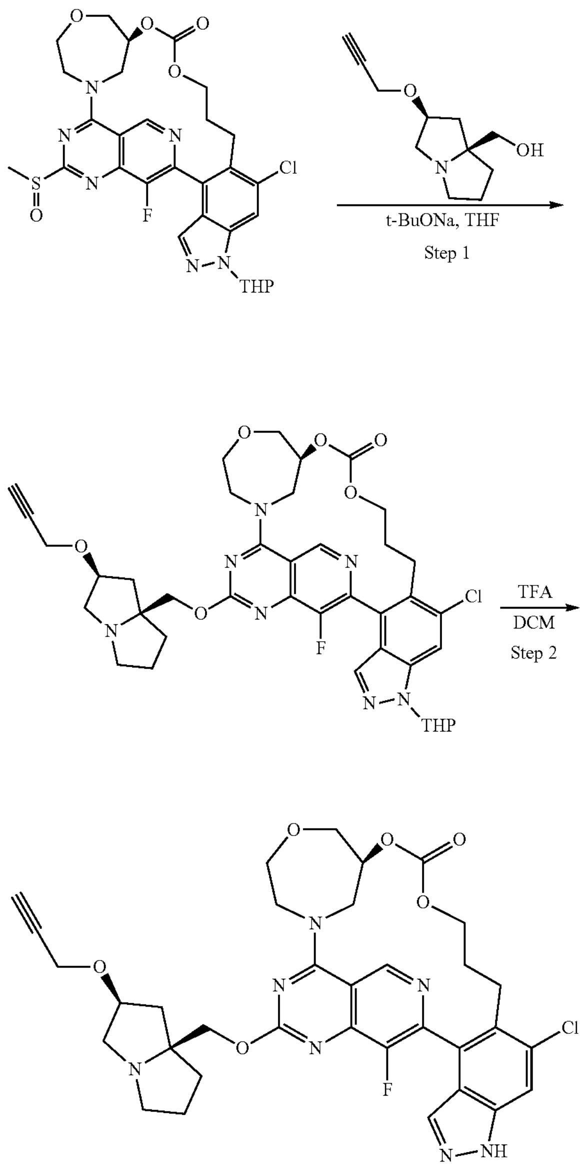

Example 369

Step 1. (26S)-18-Chloro-32-fluoro-4-(((2S,7aS)-2-(2-propyn-1-yloxy)tetrahydro-1H-pyrrolo[1,2-a]pyrrol-7a(5H)-yl)methoxy)-N-(tetrahydro-2H-pyran-2-yl)-23,25,28-trioxa-1,3,5,9,14,15 hexaazahexacyclo[24.4.1.1~6,10~.0~2,7~.0~11,19~.0~12,16~]dotriaconta-2,4,6,8,10(32),11,13,16,18-nonaen-24-one. A solution of ((2S, 7aS)-2-(prop-2-yn-1-yloxy)tetrahydro-1H-pyrrolizin-7a(5H)-yl)methanol (0.24 g, 1.24 mmol, Intermediate FG) in tetrahydrofuran (20 mL) was degassed, flushed with nitrogen, and cooled the solution to −65° C. Then t-BuONa (2 M in THF, 0.31 mL, 0.62 mmol) was added and the mixture was stirred at −65° C. for 20 min. (16S)-36-chloro-28-fluoro-22-(methylsulfinyl)-31-(tetrahydro-2H-pyran-2-yl)-31H-7,9-dioxa-1(4,6)-oxazepana-2(4,7)-pyrido[4,3-d]pyrimidina-3(4,5)-indazolacyclononaphan-8-one (0.20 g, 0.31 mmol, Intermediate FE) was added, and the mixture was stirred at −65° C. for 40 min. The reaction mixture was filtered, the filtrate was concentrated under reduced pressure. The residue was purified by preparative-TLC silica gel plate, eluting with 16% of ethyl alcohol in DCM, to provide (26S)-18-chloro-32-fluoro-4-(((2S,7aS)-2-(2-propyn-1-yloxy)tetrahydro-1H-pyrrolo[1,2-a]pyrrol-7a(5H)-yl)methoxy)-N-(tetrahydro-2H-pyran-2-yl)-23,25,28-trioxa-1,3,5,9,14,15 hexaazahexacyclo[24.4.1.1~6,10~.0~2,7~.0~11,19~.0~12,16~]dotriaconta-2,4,6,8,10(32),11,13,16,18-nonaen-24-one (0.13 g) as yellow solid. m/z (ESI): 776.0 $(M+H)^+$.

Step 2. (26S)-18-Chloro-32-fluoro-4-(((2S,7aS)-2-(2-propyn-1-yloxy)tetrahydro-1H-pyrrolo[1,2-a]pyrrol-7a(5H)-yl)methoxy)-23,25,28-trioxa-1,3,5,9,14,15 hexaazahexacyclo[24.4.1.1~6,10~.0~2,7~.0~11,19~.0~12,16~]dotriaconta-2,4,6,8,10(32),11,13,16,18-nonaen-24-one. To the solution of (26S)-18-chloro-32-fluoro-4-(((2S,7aS)-2-(2-propyn-1-yloxy)tetrahydro-1H-pyrrolo[1,2-a]pyrrol-7a(5H)-yl)methoxy)-N-(tetrahydro-2H-pyran-2-yl)-23,25,28-trioxa-1,3,5,9,14,15 hexaazahexacyclo[24.4.1.1~6,10~.02,7~.0~11,19~.0~12,16~]dotriaconta-2,4,6,8,10(32),11,13,16,18-nonaen-24-one (0.10 g, 0.13 mmol) in dichloromethane (3 mL) was added TFA (1.0 mL, 13 mmol) dropwise at 0° C. The reaction mixture was stirred at 0° C. for 2 h. The reaction was combined with another batch (30 mg scale) and basified with aq. $NaHCO_3$ to pH=7-8, and extracted with DCM. The combined organic layers were dried over $Na_2SO_4$, filtered, and concentrated under reduced pressure. The residue was purified by prep-TLC silica gel plate, eluting with 16% of ethyl alcohol in DCM, to provide (26S)-18-chloro-32-fluoro-4-(((2S,7aS)-2-(2-propyn-1-yloxy)tetrahydro-1H-pyrrolo[1,2-a]pyrrol-7a(5H)-yl)methoxy)-23,25,28-trioxa-1,3,5,9,14,15 hexaazahexacyclo[24.4.1.1~6,10~.0~2,7~.0~11,19~.0~12,16~]dotriaconta-2,4,6,8,10(32),11,13,16,18-nonaen-24-one (60 mg, 52% yield) as a yellow solid. m/z (ESI): 692.3 $(M+H)^+$. $^1$H NMR (400 MHz, CHLOROFORM-d) δ ppm 9.24 (s, 1H), 7.79 (s, 1H), 7.71 (s, 1H), 5.41 (d, J=16.0 Hz, 1H), 4.89-4.99 (m, 1H), 4.81 (d, J=12.0 Hz, 1H), 4.39-4.49 (m, 2H), 4.29-4.39 (m, 1H), 4.09-4.22 (m, 5H), 3.74-3.93 (m, 3H), 3.31-3.45 (m, 2H), 3.13-3.30 (m, 2H), 2.95-3.09 (m, 1H), 2.82-2.93 (m, 1H), 2.64-2.77 (m, 2H), 2.33-2.44 (m, 2H), 2.13-2.24 (m, 1H), 1.84-1.99 (m, 6H). $^{19}$F NMR (CHLOROFORM-d, 376 MHz) δ ppm −138.51 (s).

(26S)-18-Chloro-32-fluoro-4-((1-methyl-4-piperidinyl)oxy)-23,25,28-trioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaen-24-one trifluoroacetate (Example 370)

Example 370

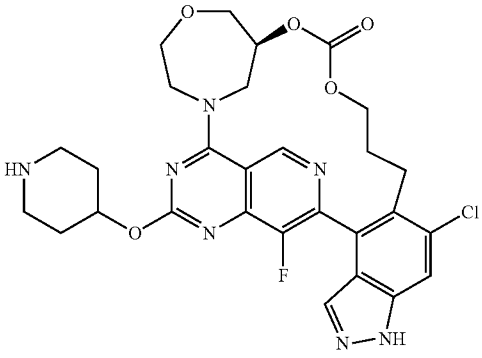

The title compound was prepared in an analogous manner to Example 369 using 1-methylpiperidin-4-ol (CAS #: 106-52-5, Aldrich) in Step 1. m/z (ESI): 612.2 $(M+H)^+$. $^1H$ NMR (CHLOROFORM-d, 400 MHz,) δ ppm 9.27 (s, 1H), 7.64-7.87 (m, 2H), 5.33-5.53 (m, 2H), 4.91-5.03 (m, 1H), 4.75 (d, J=16.0 Hz, 1H), 4.08-4.27 (m, 3H), 3.85-3.95 (m, 1H), 3.75-3.85 (m, 2H), 3.37-3.53 (m, 1H), 3.16-3.25 (m, 1H), 2.84-3.16 (m, 5H), 2.54-2.75 (m, 4H), 2.25-2.40 (m, 3H), 2.15 (s, 3H), 1.80-1.95 (m, 2H). $^{19}F$ NMR (CHLOROFORM-d, 376 MHz) δ ppm −75.55 (s), −138.62 (s).

(17R)-30-Fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and (17S)-30-fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (Example 39)

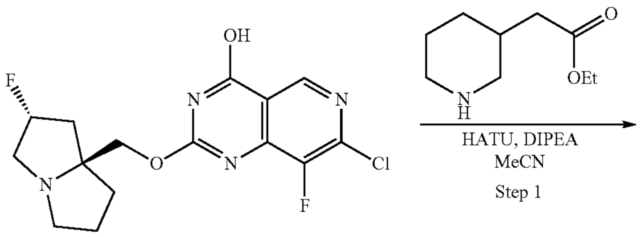

Intermediate Z

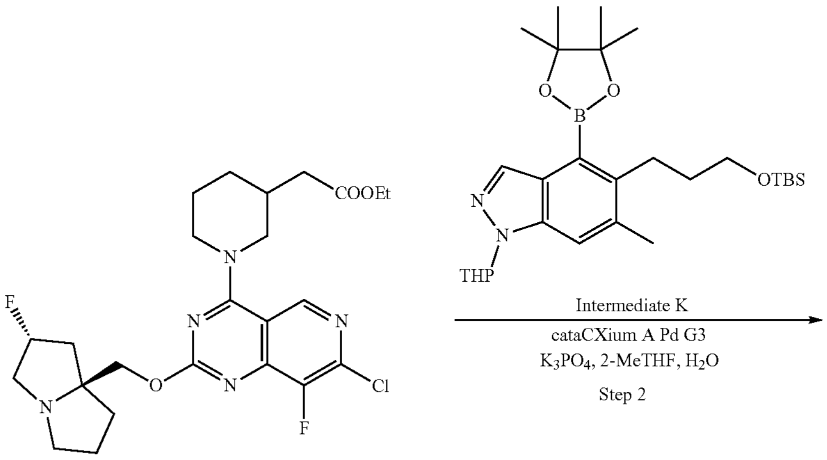

-continued

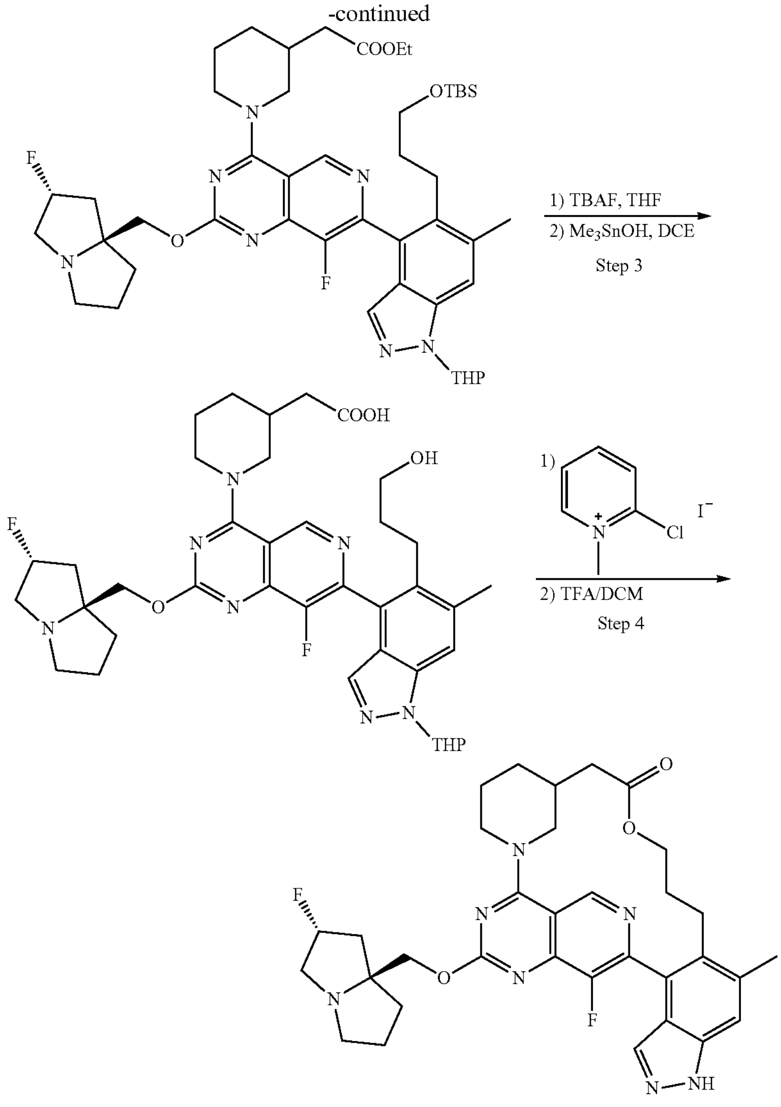

Example 39

Step 1. Ethyl 2-(1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate. To a solution of 7-chloro-8-fluoro-2-(((2R,7aS)-2-fluorotetrahydro-1H-pyrrolizin-7a(5H)-yl)methoxy)pyrido[4,3-d]pyrimidin-4-ol (2.00 g, 5.60 mmol, Intermediate Z) and DIPEA (2.0 mL, 11.2 mmol) in acetonitrile (22 mL) was added HATU (2.35 g, 6.17 mmol). The reaction mixture was stirred at rt for 15 min, and 2-(piperidin-3-yl)-acetic acid ethyl ester (1.10 mL, 6.17 mmol) was added. The reaction mixture was stirred at rt for 16 h and was partitioned between water and ethyl acetate. The organic layer was separated, dried ($Na_2SO_4$) and concentrated. The crude product was purified by column chromatography on silica gel, eluting with 0-100% (3:1 ethyl acetate/ethanol with 2% TEA) in heptane, to provide ethyl 2-(1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (0.72 g, 1.41 mmol, 25% yield) as yellow oil. m/z (ESI): 510.0 $(M+H)^+$.

Step 2. Ethyl 2-(1-(7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate. To a suspension of ethyl 2-(1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (0.10 g, 0.20 mmol) and 5-(3-((tert-butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole (0.10 g, 0.20 mmol, Intermediate K) in 2-methyltetrahydrofuran (1.8 mL) and water (0.18 mL) were added potassium phosphate (0.10 g, 0.49 mmol) and cataCXium A Pd G3 (29 mg, 0.039 mmol). The reaction mixture was sparged with argon and stirred at 80° C. for 16 h. After cooling to rt, the reaction mixture was partitioned between water and EtOAc. The organic layer was separated, dried ($Na_2SO_4$) and concentrated. The crude product was purified by column chromatography on silica gel, eluting with 0-100% (3:1 ethyl acetate/ethanol with 2% TEA) in heptane, to provide ethyl 2-(1-(7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro- 1H-pyrrolizin-7a(5H)-yl)methoxy)pyrido[4,3-d]pyrimidin-4-yl)piperidin-3-yl)acetate (0.12 g, 0.14 mmol, 72% yield) as yellow oil. m/z (ESI): 862.0 $(M+H)^+$.

Step 3. 2-(1-(8-Fluoro-2-(((2R,7aS)-2-fluorotetrahydro-1H-pyrrolizin-7a(5H)-yl)methoxy)-7-(5-(3-hydroxypropyl)-6-methyl-1-(tetrahydro-2H-pyran-2-yl)-1H-indazol-4-yl)pyrido[4,3-d]pyrimidin-4-yl)piperidin-3-yl)acetic acid. To a solution of ethyl 2-(1-(7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)acetate (0.12 g, 0.14 mmol) in tetrahydrofuran (14 mL) cooled to 0° C. was added TBAF (1 M in THF, 0.32 mL, 0.32 mmol). The reaction was allowed to slowly warm to rt with stirring for 4 h. The reaction mixture was quenched with saturated aqueous ammonium chloride solution and extracted with EtOAc. The organic layer was separated, dried ($Na_2SO_4$) and concentrated. The crude product was purified by column chromatography on silica gel, eluting with 0-100% (3:1 ethyl acetate/ethanol with 2% TEA) in heptane, to provide the mono-deprotected intermediate.

To a solution of the above material in 1,2-dichloroethane (1.0 mL) was added trimethyltin hydroxide (0.19 g, 1.07 mmol, AA Blocks). The reaction mixture was stirred at 70° C. for 9 h, cooled to rt, diluted with DCM, and passed through a pad of silica gel with 9:1 DCM/methanol as eluent to remove the tin residues. The filtrate was concentrated to provide 2-(1-(8-fluoro-2-(((2R,7aS)-2-fluorotetrahydro-1H-pyrrolizin-7a(5H)-yl)methoxy)-7-(5-(3-hydroxypropyl)-6-methyl-1-(tetrahydro-2H-pyran-2-yl)-1H-indazol-4-yl)pyrido[4,3-d]pyrimidin-4-yl)piperidin-3-yl)acetic acid (65 mg, 0.09 mmol, 84% yield) as tan solid. m/z (ESI): 720.0 $(M+H)^+$.

Step 4. (17R)-30-Fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and (17S)-30-fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one. To a solution of 2-(1-(8-fluoro-2-(((2R,7aS)-2-fluorotetrahydro-1H-pyrrolizin-7a(5H)-yl)methoxy)-7-(5-(3-hydroxypropyl)-6-methyl-1-(tetrahydro-2H-pyran-2-yl)-1H-indazol-4-yl)pyrido[4,3-d]pyrimidin-4-yl)piperidin-3-yl)acetic acid (33 mg, 0.046 mmol) in 1,2-dichloroethane (1.1 mL) were added triethylamine (64 μL, 0.46 mmol) and 2-chloro-1-methylpyridinium iodide (70 mg, 0.28 mmol). The reaction mixture was stirred at 60° C. for 16 h. After cooling to rt, the reaction mixture was partitioned between water and DCM. The crude product was purified by column chromatography on silica gel, eluting with 0-100% (3:1 ethyl acetate/ethanol+2% TEA) in heptane, to provide a mixture of N-(tetrahydro-2H-pyran-2-yl)-(17R)-30-fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and N-(tetrahydro-2H-pyran-2-yl)-(17S)-30-fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (19 mg, 0.027 mmol) as brown oil.

To a solution of the above material dissolved in DCM (0.5 mL) was added TFA (63 μL, 0.81 mmol). The reaction mixture was stirred at rt for 2 h, partitioned between water and DCM. The organic layer was separated, dried ($Na_2SO_4$) and concentrated. The crude product was purified by column chromatography on silica gel, eluting with 0-100% (3:1 ethyl acetate/ethanol with 2% TEA) in heptane, to provide (17R)-30-fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one and (17S)-30-fluoro-24-(((2R,7aS)-2-fluorotetrahydro-1H-pyrrolo[1,2-a]pyrrol-7a(5H)-yl)methoxy)-9-methyl-14-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-one (6.0 mg, 9.71 μmol, 36% yield) as colorless oil. m/z (ESI): 618.0 $(M+H)^+$. $^1H$ NMR (400 MHz, METHANOL-$d_4$) δ ppm 9.14 (s, 1H), 9.11-9.17 (m, 1H), 7.77 (s, 1H), 7.53 (s, 1H), 5.17-5.42 (m, 1H), 4.21-4.42 (m, 2H), 3.98 (br d, J=13.38 Hz, 1H), 3.57-3.71 (m, 1H), 3.17-3.28 (m, 4H), 2.98-3.07 (m, 1H), 2.78 (m, 1H), 2.50-2.61 (m, 4H), 2.35-2.41 (m, 1H), 2.20-2.28 (m, 1H), 2.11-2.16 (m, 1H), 1.93 (s, 4H), 1.63-1.86 (m, 6H), 1.10-1.21 (m, 4H). $^{19}F$ NMR (376 MHz, METHANOL-$d_4$) δ ppm −141.94 (s), −173.64 (s).

TABLE 32

Additional Examples 40 and 103 to 108. Prepared in an Analogous Manner to Example 39.

| Ex.# | Structure & Name | Salt Form | Reagent | Method Change |
|---|---|---|---|---|
| 40 | 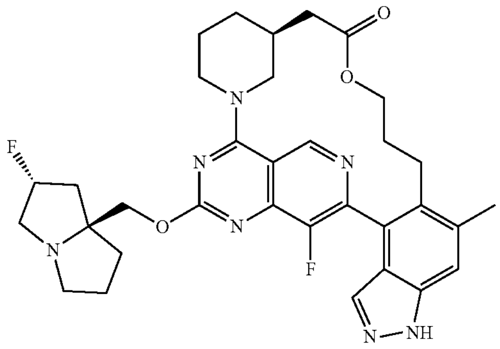 [SMILES: Cc1cc2[nH]ncc2c2c1CCCOC(=O)C[C@@H]1CCCN(C1)c1nc(OC[C@@]34CCCN3C[C@H](F)C4)nc3c(F)c-2ncc13] | NA | Step 1. Ethyl (S)-2-(piperidin-3-yl)acetate hydrochloride (CAS#: 2365423-82-8, J&W PharmLabs) | |

TABLE 32-continued

Additional Examples 40 and 103 to 108. Prepared in an Analogous Manner to Example 39.

| Ex.# | Structure & Name | Salt Form | Reagent | Method Change |
|---|---|---|---|---|
| 103 | 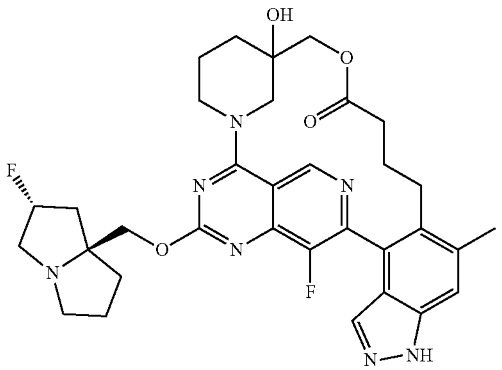 [SMILES: Cc1cc2[nH]ncc2c2c1CCCC(=O)OCC1(O)CCCN(C1)c1nc(OC[C@@]34CCCN3C[C@H](F)C4)nc3c(F)c-2ncc13] | NA | Step 1. 3-(Hydroxy-methyl) piperidin-3-ol hydrochloride (Advanced ChemBlocks Inc.) Step 2. Intermediate HHH | |
| 104 | 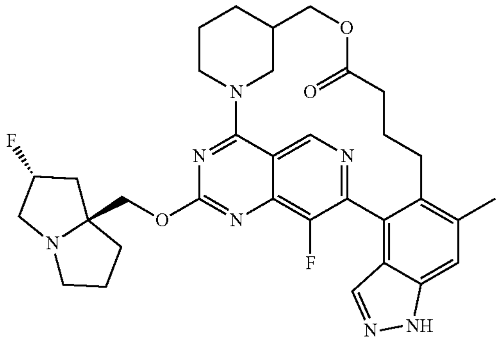 [SMILES: Cc1cc2[nH]ncc2c2c1CCCC(=O)OCC1CCCN(C1)c1nc(OC[C@@]34CCCN3C[C@H](F)C4)nc3c(F)c-2ncc13] | NA | Step 1. 3-(Hydroxy-methyl) piperidine (Ambeed, Inc.) Step 2. Intermediate HHH | Step 4 (1): 1.3 eq 2,3,4,5,6-pentafluoro benzoyl chloride (AmBeed) and 3 eq triethylamine (Sigma-Aldrich), 90° C., 18 h in Toluene: MeCN 10:1 |
| 105 | 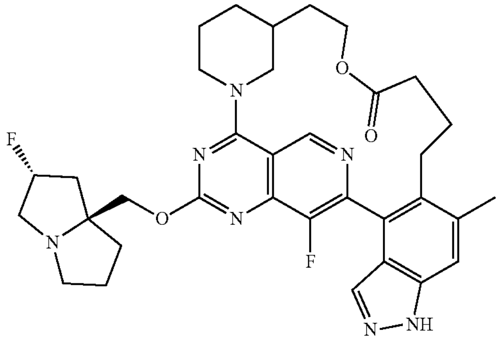 [SMILES: Cc1cc2[nH]ncc2c2c1CCCC(=O)OCCC1CCCN(C1)c1nc(OC[C@@]34CCCN3C[C@H](F)C4)nc3c(F)c-2ncc13] | NA | Step 1. 2-(3-Piperidyl) ethanol, HCl (Combi-Blocks Inc.) Step 2. Intermediate HHH | Step 2: TBS protection of first intermediate prior to Suzuki coupling. Step 4 (1): 1.3 eq 2,3,4,5,6-pentafluoro benzoyl chloride and 3 eq triethylamine (Sigma-Aldrich), 90° C., 18 h in toluene: MeCN 10:1 |
| 106 | 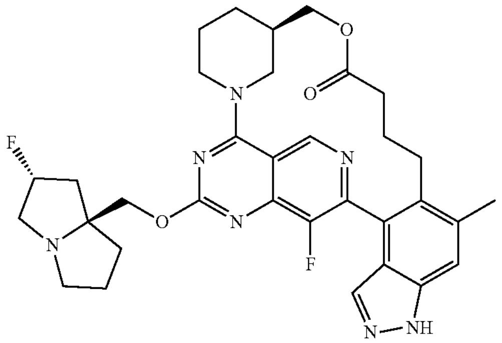 [SMILES: Cc1cc2[nH]ncc2c2c1CCCC(=O)OC[C@@H]1CCCN(C1)c1nc(OC[C@@]34CCCN3C[C@H](F)C4)nc3c(F)c-2ncc13] | NA | Step 1: (R)-piperidin-3-ylmethanol hydrochloride (Combi-Blocks Inc.) Step 2. Intermediate HHH | Step 4 (1): 1.3 eq 2,3,4,5,6-pentafluoro benzoyl chloride and 3 eq triethylamine (Sigma-Aldrich), 90° C., 18 h in toluene: MeCN 10:1 |

TABLE 32-continued

Additional Examples 40 and 103 to 108. Prepared in an Analogous Manner to Example 39.

| Ex.# | Structure & Name | Salt Form | Reagent | Method Change |
|---|---|---|---|---|
| 107 | 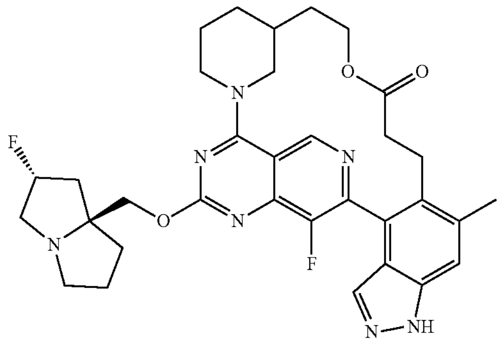 [SMILES: Cc1cc2[nH]ncc2c2c1CCC(=O)OCCC1CCCN(C1)c1nc(OC[C@@]34CCCN3C[C@H](F)C4)nc3c(F)c-2ncc13] | NA | Step 1: 2-(3-Piperidyl) ethanol, HCl (Combi-Blocks Inc.) Step 2. Intermediate III | Step 2: TBS protection of first intermediate prior to Suzuki coupling. Step 4 (1): 1.3 eq 2,3,4,5,6-pentafluoro benzoyl chloride and 3 eq triethylamine, 90° C., 3 h in toluene: MeCN 10:1 |
| 108 | 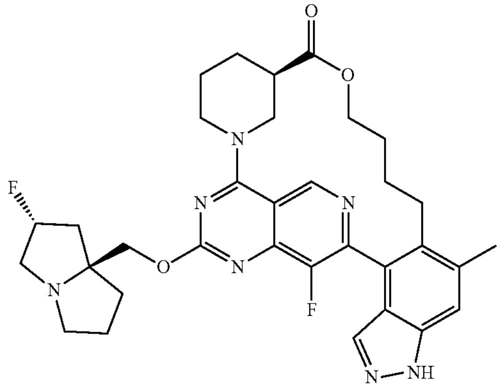 [SMILES: Cc1cc2[nH]ncc2c2c1CCCCOC(=O)[C@@H]1CCCN(C1)c1nc(OC[C@@]34CCCN3C[C@H](F)C4)nc3c(F)c-2ncc13] | Bis (2,2,2-trifluoro-acetate) | Step 1. (R)-3-methyl piperidinecar-boxylate (CAS# 164323-85-7, Combi-Blocks) Step 2. Intermediate JJJ | Step 3. (1) Not performed (2) LiOH, THF/water Step 4 (1): 1.3 eq 2,3,4,5,6-pentafluoro benzoyl chloride and 3 eq triethylamine, 90° C., 1.5 h in toluene: MeCN 10:1 |

TABLE 33

Analytical Data for Examples 40 and 103 to 108.

| Cmpd.# | MS m/z (ESI): $(M + H)^+$ | $^1H$ NMR |
|---|---|---|
| 40 | 618.1 | $^1H$ NMR (400 MHz, METHANOL-$d_4$) δ ppm 9.13 (s, 1 H), 7.79 (s, 1 H), 7.53 (s, 1 H), 5.20-5.44 (m, 1 H), 5.09 (br d, J = 12.75 Hz, 1 H), 4.76 (br s, 1 H), 4.40 (d, J = 10.66 Hz, 1 H), 4.28 (d, J = 10.66 Hz, 1 H), 4.13 (br s, 1 H), 3.97 (br d, J = 13.59 Hz, 1 H), 3.65 (br s, 1 H), 3.13-3.22 (m, 2 H), 3.05 (br d, J = 5.43 Hz, 1 H), 2.68 (s, 1 H) 2.48-2.63 (m, 4 H), 2.12-2.44 (m, 5 H), 1.89-2.10 (m, 5 H), 1.58-1.83 (m, 6 H), 1.30 (t, J = 7.32 Hz, 1 H). $^{19}F$ NMR (376 MHz, METHANOL-$d_4$) δ ppm −141.90 (s), −173.62 (s). |

TABLE 33-continued

Analytical Data for Examples 40 and 103 to 108.

| Cmpd.# | MS m/z (ESI): $(M + H)^+$ | $^1H$ NMR |
|---|---|---|
| 103 | 634.3 | $^1H$ NMR (400 MHz, METHANOL-$d_4$) δ ppm 9.31 (s, 1 H), 8.52 (s, 1 H), 7.81 (s, 1 H), 7.54 (s, 1 H), 5.27-5.48 (m, 1 H), 4.93-5.06 (m, 2 H), 4.31-4.48 (m, 2 H), 3.51-3.61 (m, 2 H), 3.34-3.51 (m, 4 H), 3.08-3.23 (m, 2 H), 2.86 (br s, 1 H), 2.56-2.63 (m, 1 H), 2.55 (s, 3 H), 2.28-2.50 (m, 2 H), 2.20 (br d, J = 8.7 Hz, 1 H), 2.01-2.14 (m, 3 H), 1.84-2.00 (m, 5 H), 1.70-1.84 (m, 2 H), 1.30-1.43 (m, 1 H). $^{19}F$ NMR (376 MHz, METHANOL-$d_4$) δ ppm −141.24 (d, J = 10.4 Hz), −173.78 (d, J = 7.8 Hz). |
| 104 | 618.3 | $^1H$ NMR (400 MHz, METHANOL-$d_4$) δ ppm 9.23 (s, 1 H), 8.50 (s, 1 H), 7.79 (s, 1 H), 7.53 (s, 1 H), 5.30-5.49 (m, 1 H), 5.03 (br d, J = 12.5 Hz, 1 H), 4.90 (br d, J = 14.2 Hz, 1 H), 4.35-4.51 (m, 2 H), 3.93 (br d, J = 13.8 Hz, 1 H), 3.39-3.62 (m, 5 H), 3.21-3.29 (m, 1 H), 3.12-3.21 (m, 1 H), 2.82 (s, 1 H), 2.57-2.68 (m, 1 H), 2.54 (s, 3 H), 2.28-2.51 (m, 2 H), 2.19-2.28 (m, 1 H), 1.93-2.18 (m, 7 H), 1.77-1.90 (m, 2 H), 1.73 (br d, J = 13.2 Hz, 1 H), 1.65 (br d, J = 12.5 Hz, 1 H), 1.30-1.44 (m, 1 H). $^{19}F$ NMR (376 MHz, METHANOL-$d_4$) δ ppm −141.60 (br d, J = 19.1 Hz), −173.81 (d, J = 6.1 Hz). |
| 105 | 632.4 | $^1H$ NMR (400 MHz, METHANOL-$d_4$) δ ppm 8.91-9.28 (m, 1 H), 7.68 (br s, 1 H), 7.50 (s, 1 H), 5.20-5.52 (m, 1 H), 4.80-5.01 (m, 1 H), 4.30-4.54 (m, 3 H), 4.05-4.18 (m, 1 H), 3.82-4.03 (m, 1 H), 3.33-3.53 (m, 3 H), 3.06-3.25 (m, 2 H), 2.76-2.99 (m, 1 H), 2.54 (s, 3 H), 2.39-2.50 (m, 1 H), 2.28-2.38 (m, 2 H), 2.14-2.27 (m, 3 H), 2.02-2.13 (m, 3 H), 1.89-2.01 (m, 3 H), 1.83 (br s, 3 H), 1.59-1.75 (m, 2 H), 1.34-1.58 (m, 3 H). $^{19}F$ NMR (376 MHz, METHANOL-$d_4$) δ ppm −142.11 (br d, J = 43.4 Hz), −173.76 (br s). |
| 106 | 618.3 | $^1H$ NMR (400 MHz, METHANOL-$d_4$) δ ppm 9.23 (s, 1 H), 7.80 (s, 1 H), 7.53 (s, 1 H), 5.26-5.48 (m, 1 H), 5.01 (br d, J = 12.3 Hz, 1 H), 4.88 (br d, J = 14.0 Hz, 1 H), 4.47 (d, J = 11.1 Hz, 1 H), 4.33-4.41 (m, 1 H), 3.90 (br d, J = 14.0 Hz, 1 H), 3.35-3.57 (m, 5 H), 3.23 (br t, J = 12.5 Hz, 1 H), 3.10-3.19 (m, 1 H), 2.83 (dt, J = 14.3, 5.1 Hz, 1 H), 2.56-2.70 (m, 1 H), 2.54 (s, 3 H), 2.46-2.52 (m, 1 H), 2.18-2.44 (m, 3 H), 1.93-2.15 (m, 7 H), 1.78-1.89 (m, 2 H), 1.72 (br d, J = 12.8 Hz, 1 H), 1.64 (br d, J = 13.0 Hz, 1 H), 1.31-1.43 (m, 1 H). $^{19}F$ NMR (376 MHz, METHANOL-$d_4$) δ ppm −141.54 (s, 1 F), −173.78 (s, 1 F). Stereochemistry of Example 106 was confirmed by X-Ray crystallography analysis. |
| 107 | 618.4 | $^1H$ NMR (400 MHz, METHANOL-$d_4$) δ ppm 9.15 (s, 1 H), 8.52 (s, 1 H), 7.82 (s, 1 H), 7.52 (s, 1 H), 5.26-5.49 (m, 1 H), 4.89-4.98 (m, 1 H), 4.30-4.49 (m, 2 H), 4.07-4.20 (m, 1 H), 3.85 (br t, J = 10.9 Hz, 1 H), 3.34-3.52 (m, 3 H), 3.12 (td, J = 9.7, 6.1 Hz, 1 H), 2.89-3.02 (m, 1 H), 2.59-2.73 (m, 1 H), 2.56 (s, 3 H), 2.41-2.51 (m, 1 H), 2.26-2.39 (m, 3 H), 2.14-2.24 (m, 1 H), 2.02-2.13 (m, 3 H), 1.90-2.00 (m, 2 H), 1.83 (br s, 3 H), 1.51-1.66 (m, 2 H), 1.33-1.48 (m, 3 H). $^{19}F$ NMR (376 MHz, METHANOL-$d_4$) δ ppm −144.30 (br s), −173.79 (s). |
| 108 | 618.0 | $^1H$ NMR (400 MHz, METHANOL-$d_4$) δ ppm 9.29 (s, 1 H), 7.81 (s, 1 H), 7.55 (s, 1 H), 5.50-5.81 (m, 1 H), 5.19-5.33 (m, 1 H), 4.94-5.08 (m, 1 H), 4.62-4.78 (m, 2 H), 3.78-4.21 (m, 5 H), 3.45-3.59 (m, 1 H), 3.18-3.30 (m, 1 H), 2.85-3.03 (m, 1 H), 2.56 (s, 14 H), 1.81-1.96 (m, 1 H), 1.62-1.75 (m, 1 H), 1.30-1.54 (m, 3 H), 0.98-1.18 (m, 1 H). |

(15R)-22,31-Difluoro-8-(((2R,7aS)-2-fluorotetrahydro-1H-pyrrolo[1,2-a]pyrrol-7a(5H)-yl)methoxy)-27-hydroxy-16-oxa-3,7,9,11-tetraazahexacyclo [19.7.1.1~2,6~.1~11,15~.0~5,10~.0~25,29~] hentriaconta-1(28),2(31),3,5,7,9,21,23,25(29),26-decaen-17-one 2,2,2-trifluoroacetate salt (Example 41)

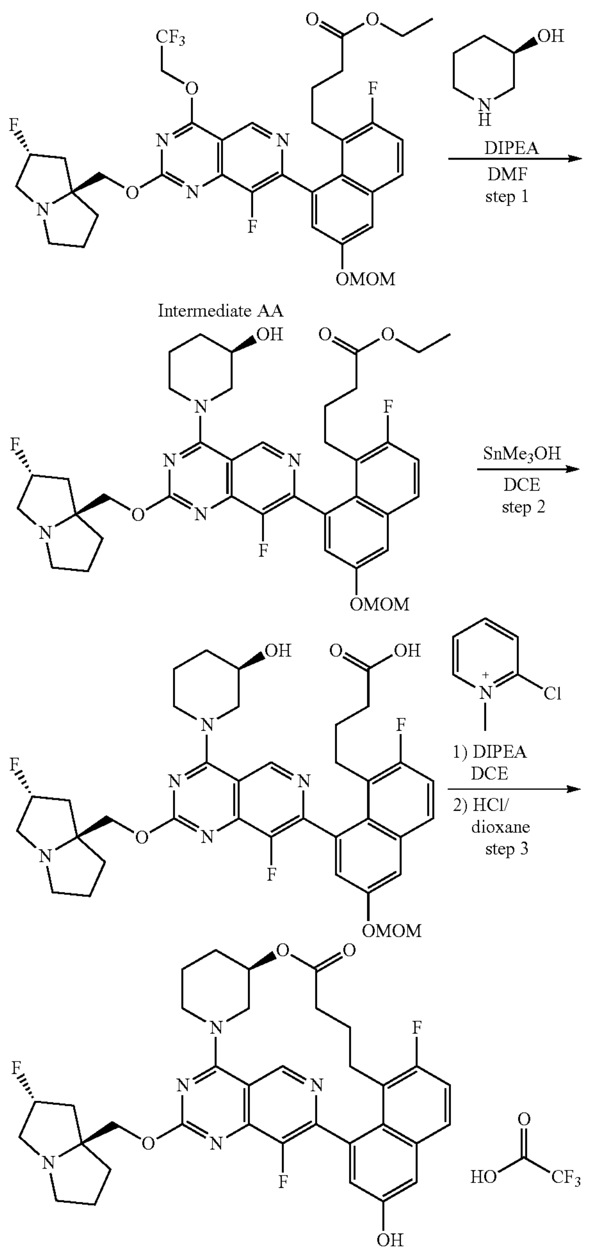

Intermediate AA

Example 41

Step 1. Ethyl 4-(2-fluoro-8-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-(methoxymethoxy)naphthalen-1-yl)butanoate. Ethyl 4-(2-fluoro-8-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-6-(methoxymethoxy)naphthalen-1-yl)butanoate (0.26 g, 0.36 mmol, Intermediate AA) was dissolved in DMF (1.5 mL) and (3R)-piperidin-3-ol (55 mg, 0.54 mmol) and DIPEA (0.19 mL, 1.1 mmol) was added. The mixture was stirred at 60° C. for 1 h, cooled to rt and treated with water and saturated aqueous $NH_4Cl$. The aqueous layer was extracted with EtOAc, and the combined organic layers were dried over $Na_2SO_4$, filtered and volatiles were removed in vacuo. The mixture was purified via column chromatography, eluting with 0-100% (3:1 EtOAc/EtOH with 2% $Et_3N$) in heptane, to provide ethyl 4-(2-fluoro-8-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-(methoxymethoxy)naphthalen-1-yl)butanoate (0.22 g, 0.30 mmol, 84% yield). m/z (ESI): $(M+H)^+$ 724.2.

Step 2: 4-(2-Fluoro-8-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-(methoxymethoxy)naphthalen-1-yl)butanoic acid. Ethyl 4-(2-fluoro-8-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-(methoxymethoxy)naphthalen-1-yl)butanoate (0.22 g, 0.30 mmol) was dissolved in DCE (5.0 mL) and trimethyltin hydroxide (0.55 g, 3.04 mmol) was added. The mixture was stirred at 70° C. for 20 h. The mixture was then filtered and purified via reverse phase column chromatography, eluting with 0-100% $MeCN/H_2O$+0.1% TFA to provide 4-(2-fluoro-8-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-(methoxymethoxy)naphthalen-1-yl)butanoic acid (0.10 g, 0.15 mmol, 49% yield). m/z (ESI): $(M+H)^+$ 696.0.

Step 3. (15R)-22,31-Difluoro-8-(((2R,7aS)-2-fluorotetrahydro-1H-pyrrolo[1,2-a]pyrrol-7a(5H)-yl)methoxy)-27-hydroxy-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate salt. 4-(2-Fluoro-8-(8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-6-(methoxymethoxy)naphthalen-1-yl)butanoic acid (0.10 g, 0.14 mmol) was co-evaporated with toluene. The residue was dissolved in DCE (15 mL), and 2-chloro-1-methylpyridinium iodide (0.22 g, 0.86 mmol) and TEA (0.2 mL, 1.44 mmol) were added. The reaction mixture was stirred at rt for 5 min and then heated to 60° C. for 16 h. Volatiles were removed in vacuo and the residue was purified via column chromatography, eluting with 0-100% (3:1 EtOAc:EtOH+2% $Et_3N$) in heptane, to provide (15R)-22,31-difluoro-8-(((2R,7aS)-2-fluorotetrahydro-1H-pyrrolo[1,2-a]pyrrol-7a(5H)-yl)methoxy)-27-(methoxymethoxy)-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one, which was redissolved in THF (1.5 mL) and treated with 4 M HCl in dioxane (0.5 mL, 2 mmol). The reaction mixture was stirred at rt for 2 h, volatiles were removed in vacuo and the mixture was purified via reverse phrase preparative HPLC, to provide (15R)-22,31-difluoro-8-(((2R,7aS)-2-fluorotetrahydro-1H-pyrrolo[1,2-a]pyrrol-7a(5H)-yl)methoxy)-27-hydroxy-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one 2,2,2-trifluoroacetate salt (45 mg, 0.06 mmol, 42% yield). m/z (ESI): (M+H)+634.0. $^1H$ NMR (400 MHz, METHANOL-$d_4$) δ ppm 9.23 (s, 1H), 7.73 (dd, J=9.1, 6.0 Hz, 1H), 7.35 (d, J=2.5 Hz, 1H), 7.23-7.30 (m, 2H), 5.53-

5.70 (m, 1H), 5.08-5.17 (m, 2H), 5.00-5.04 (m, 1H), 4.65-4.77 (m, 2H), 3.87-4.11 (m, 4H), 3.46-3.54 (m, 1H), 3.29 (br s, 1H), 2.69-2.85 (m, 1H), 2.61-2.69 (m, 1H), 2.49-2.59 (m, 1H), 2.32-2.49 (m, 4H), 2.20-2.31 (m, 2H), 2.02-2.14 (m, 2H), 1.88-1.94 (m, 1H), 1.71-1.79 (m, 1H), 1.43-1.57 (m, 1H), 1.30-1.40 (m, 1H), 1.14 (ddd, J=16.0, 8.6, 4.1 Hz, 1H). $^{19}F$ NMR (376 MHz, METHANOL-$d_4$) δ ppm −77.33 (s), −118.96 (s), −138.99 (s), −174.16-−174.00 (m).

TABLE 34

Additional Examples 42 and 109. Prepared in an Analogous Manner to Example 41.

| Ex.# | Structure & Name | Salt Form | Reagent | Method Change |
|---|---|---|---|---|
| 42 | 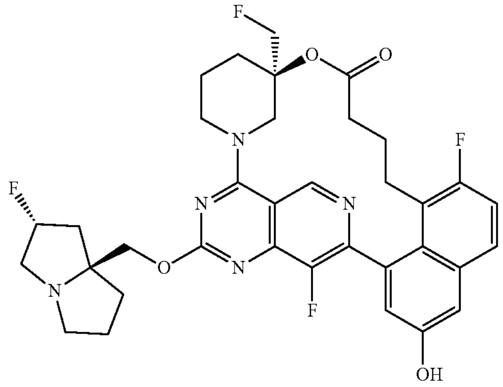 [SMILES: O=C1CCCc2c(F)ccc3cc(O)cc(c23)-c2ncc3c(nc(OC[C@@]45CCCN4C[C@H](F)C5)nc3c2F)N2CCC[C@](CF)(C2)O1] | bis (2,2,2-trifluoro-acetate) | Step 1. (R)-3-(fluoromethyl) piperidin-3-ol (LabNetwork) | |
| 109 | 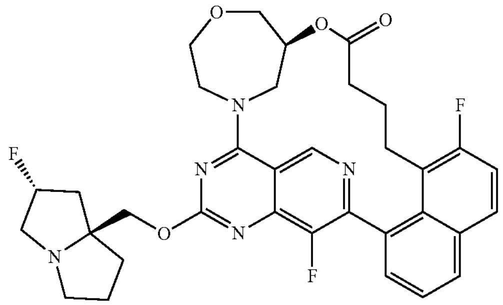 [SMILES: O=C1CCCc2c(F)ccc3cccc(c23)-c2ncc3c(nc(OC[C@@]45CCCN4C[C@H](F)C5)nc3c2F)N2CCOC[C@H](C2)O1] | NA | Step 1. Intermediate BB and (S)-[1,4]oxazepan-6-ol | |

TABLE 35

Analytical Data for Examples 42 and 109.

| Cmpd.# | MS m/z (ESI): $(M + H)^+$ | $^1H$ NMR |
|---|---|---|
| 42 | 666.2 | $^1H$ NMR (400 MHz, METHANOL-$d_4$) δ ppm 9.40 (s, 1 H), 7.72 (dd, J = 9.0, 5.9 Hz, 1 H), 7.34 (d, J = 2.5 Hz, 1 H), 7.29 (d, J = 2.7 Hz, 1 H), 7.25 (t, J = 9.5 Hz, 1 H), 5.54-5.71 (m, 1 H), 5.48 (br d, J = 14.6 Hz, 1 H), 5.25 (br d, J = 12.5 Hz, 1 H), 4.90-5.07 (m, 1 H), 4.72 (d, J = 19.2 Hz, 2 H), 4.48-4.65 (m, 1 H), 3.94-4.11 (m, 2 H), 3.90 (br d, J = 15.0 Hz, 2 H), 3.46-3.56 (m, 1 H), 3.21-3.29 (m, 1 H), 2.69-2.85 (m, 1 H), 2.58-2.68 (m, 1 H), 2.43-2.50 (m, 1 H), 2.35-2.42 (m, 2 H), 2.30 (br d, J = 11.7 Hz, 2 H), 2.21 (br s, 2 H), 2.04-2.14 (m, 1 H), 1.86-1.97 (m, 2 H), 1.74-1.82 (m, 1 H), 1.46-1.59 (m, 1 H), 1.18-1.39 (m, 3 H). $^{19}F$ NMR (376 MHz, METHANOL-$d_4$) δ ppm −77.35 (s), −118.90 (s), −139.58 (s), −174.08 (s), −234.02 (s). |
| 109 | 634.0 | $^1H$ NMR (400 MHz, METHANOL-$d_4$) δ ppm 9.37 (s, 1 H), 8.05-8.21 (m, 1 H), 7.93-8.05 (m, 1 H), 7.56-7.66 (m, 1 H), 7.46-7.55 (m, 1 H), 7.31-7.44 (m, 1 H), 5.02-5.76 (m, 2 H), 4.69-4.78 (m, 2 H), 4.32-4.47 (m, 1 H), 3.85-4.14 (m, 4 H), 3.58-3.77 (m, 1 H), 3.41-3.57 (m, 1 H), 3.06-3.26 (m, 1 H), 2.13-2.88 (m, 7 H), 0.96-1.79 (m, 2 H). |

(15R)-22,31-Difluoro-8-(((2R,7aS)-2-fluorotetrahydro-1H-pyrrolo[1,2-a]pyrrol-7a(5H)-yl)methoxy)-27-hydroxy-15-methyl-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (Example 43)
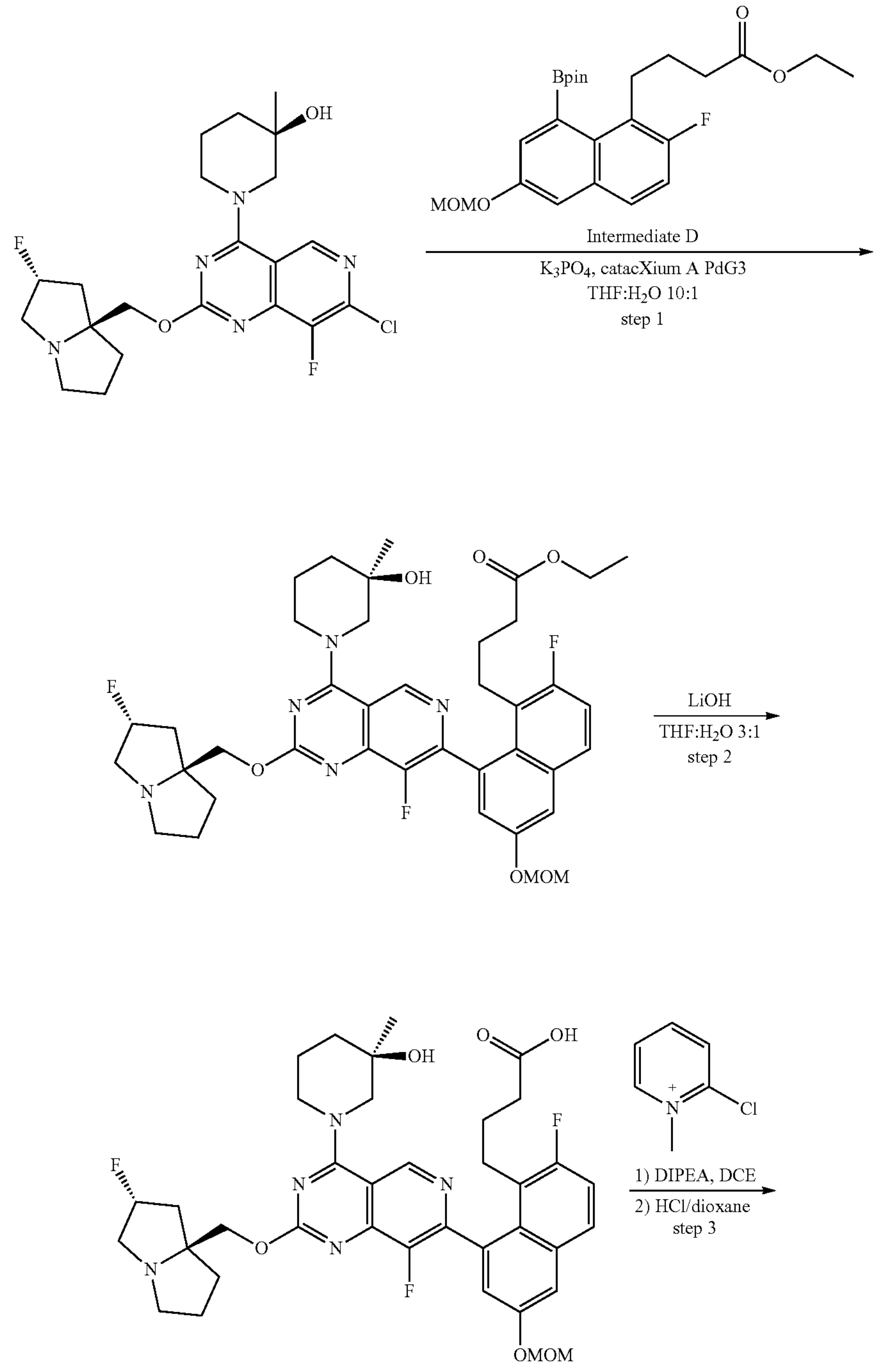

-continued

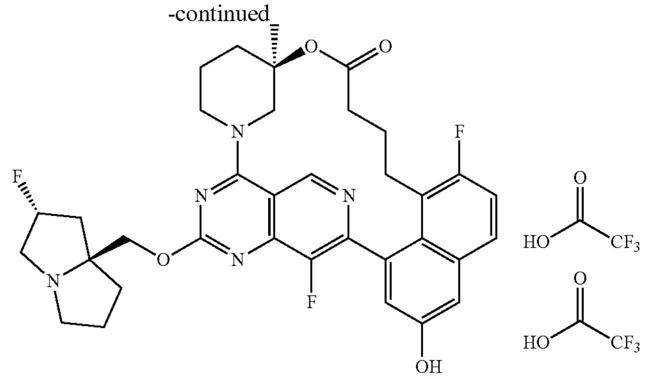

Example 43

Step 1: Ethyl 4-(2-fluoro-8-(8-fluoro-2-(((2R,7aS)-2-fluorotetrahydro-1H-pyrrolizin-7a(5H)-yl)methoxy)-4-((R)-3-hydroxy-3-methylpiperidin-1-yl)pyrido[4,3-d]pyrimidin-7-yl)-6-(methoxymethoxy)naphthalen-1-yl)butanoate. (R)-1-(7-Chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol (0.50 g, 1.10 mmol, Intermediate U), ethyl 4-(2-fluoro-6-(methoxymethoxy)-8-(4,4,5,5-tetramethyl-1,3,2-dioxaborolan-2-yl)naphthalen-1-yl)butanoate (0.54 g, 1.21 mmol, Intermediate D), potassium phosphate hydrate (0.76 g, 3.3 mmol), and cataCXium A Pd G3 (0.16 g, 0.22 mmol) were dissolved in THF (5.0 mL) and water (0.5 mL) and degassed for 10 min. The mixture was then heated to 80° C. for 4 h. Volatiles were removed in vacuo and the crude material was purified via column chromatography, eluting with 0-100% (3:1 EtOAc:EtOH+2% $Et_3N$) in heptane, to provide ethyl 4-(2-fluoro-8-(8-fluoro-2-(((2R,7aS)-2-fluorotetrahydro-1H-pyrrolizin-7a(5H)-yl)methoxy)-4-((R)-3-hydroxy-3-methylpiperidin-1-yl)pyrido[4,3-d]pyrimidin-7-yl)-6-(methoxymethoxy)naphthalen-1-yl)butanoate (0.59 g, 0.80 mmol, 73% yield). m/z (ESI): $(M+H)^+$ 738.2.

Step 2: 4-(2-Fluoro-8-(8-fluoro-2-(((2R,7aS)-2-fluorotetrahydro-1H-pyrrolizin-7a(5H)-yl)methoxy)-4-((R)-3-hydroxy-3-methylpiperidin-1-yl)pyrido[4,3-d]pyrimidin-7-yl)-6-(methoxymethoxy)naphthalen-1-yl)butanoic acid. Ethyl 4-(2-fluoro-8-(8-fluoro-2-(((2R,7aS)-2-fluorotetrahydro-1H-pyrrolizin-7a(5H)-yl)methoxy)-4-((R)-3-hydroxy-3-methylpiperidin-1-yl)pyrido[4,3-d]pyrimidin-7-yl)-6-(methoxymethoxy)naphthalen-1-yl)butanoate (0.59 g, 0.80 mmol), lithium hydroxide monohydrate (0.17 g, 4.0 mmol) were dissolved in THF (3.0 mL) and water (1.0 mL). The reaction mixture was heated to 40° C. for 4 h. 1 N aqueous hydrochloric acid (4.0 mL, 4.0 mmol) was added slowly and the residue was purified via reverse phase preparative HPLC, to provide 4-(2-fluoro-8-(8-fluoro-2-(((2R,7aS)-2-fluorotetrahydro-1H-pyrrolizin-7a(5H)-yl)methoxy)-4-((R)-3-hydroxy-3-methylpiperidin-1-yl)pyrido[4,3-d]pyrimidin-7-yl)-6-(methoxymethoxy)naphthalen-1-yl)butanoic acid (0.27 g, 0.38 mmol, 48% yield). m/z (ESI): $(M+H)^+$ 710.3.

Step 3. (15R)-22,31-Difluoro-8-(((2R,7aS)-2-fluorotetrahydro-1H-pyrrolo[1,2-a]pyrrol-7a(5H)-yl)methoxy)-27-hydroxy-15-methyl-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate). 4-(2-Fluoro-8-(8-fluoro-2-(((2R,7aS)-2-fluorotetrahydro-1H-pyrrolizin-7a(5H)-yl)methoxy)-4-((R)-3-hydroxy-3-methylpiperidin-1-yl)pyrido[4,3-d]pyrimidin-7-yl)-6-(methoxymethoxy)naphthalen-1-yl)butanoic acid (0.27 g, 0.38 mmol) was dissolved in DCE (30 mL), 2-chloro-1-methylpyridinium iodide (0.48 g, 1.86 mmol) and TEA (0.44 mL, 3.10 mmol) were added. The reaction mixture was stirred at rt for 5 min and then heated to 60° C. for 16 h. Volatiles were removed in vacuo and the residue was purified via column chromatography, eluting with 0-100% (3:1 EtOAc:EtOH+2% $Et_3N$) in heptane, to provide (15R)-22,31-difluoro-8-(((2R,7aS)-2-fluorotetrahydro-1H-pyrrolo[1,2-a]pyrrol-7a(5H)-yl)methoxy)-27-(methoxymethoxy)-15-methyl-16-oxa-3,7,9,11-tetraazahexacyclo[19.7.1.1~2,6~.1~11,15~.0~5,10~.025,29~]hentriaconta-1(28),2(31),3,5,7,9,21,23,25(29),26-decaen-17-one (65 mg, 0.09 mmol, 30% yield), which was redissolved in THF (1.5 mL) and treated with 4 M HCl/dioxane (0.5 mL, 0.5 mmol). The reaction mixture was stirred at rt for 2 h, volatiles were removed in vacuo and the mixture was purified by reverse phrase preparative HPLC to provide (15R)-22,31-difluoro-8-(((2R,7aS)-2-fluorotetrahydro-1H-pyrrolo[1,2-a]pyrrol-7a(5H)-yl)methoxy)-27-hydroxy-15-methyl-16-oxa-3,7,9,11-tetraazahexacyclo[19.7.1.1~2,6~.1~11,15~.0~5,10~.0~25,29~]hentriaconta-1(28),2(31),3,5,7,9,21,23,25(29),26-decaen-17-one bis(2,2,2-trifluoroacetate) (40 mg, 0.05 mmol, 15% yield). m/z (ESI): (M+H)+648.0. $^1H$ NMR (400 MHz, METHANOL-$d_4$) δ ppm 9.38 (s, 1H), 7.72 (dd, J=9.0, 5.9 Hz, 1H), 7.31-7.36 (m, 2H), 7.25 (t, J=9.6 Hz, 1H), 5.48-5.69 (m, 2H), 5.23 (br d, J=12.8 Hz, 1H), 4.65-4.77 (m, 2H), 3.88-4.11 (m, 3H), 3.80 (d, J=14.8 Hz, 1H), 3.49 (td, J=10.7, 6.0 Hz, 1H), 3.16-3.25 (m, 1H), 2.67 (s, 2H), 2.31-2.49 (m, 5H), 2.06-2.26 (m, 3H), 1.68-1.92 (m, 3H), 1.51 (s, 3H), 1.26-1.49 (m, 3H). $^{19}F$ NMR (376 MHz, METHANOL-$d_4$) δ ppm −77.39 (s), −118.63 (s), −140.02-−139.99 (m), −174.09 (s).

(17R)-30-Fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~0.0~2,10~0.0~3,7~0.0~22,27~]hentriaconta-1(30),2,4,7,9,22,24,26,28-nonaen-17-ol, and (17S)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol bis(2,2,2-trifluoroacetate) (Example 44)
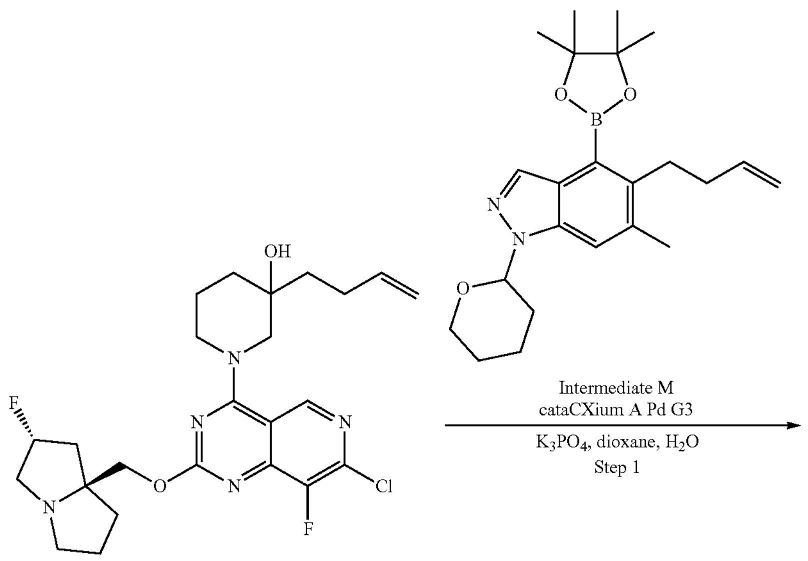
Intermediate R
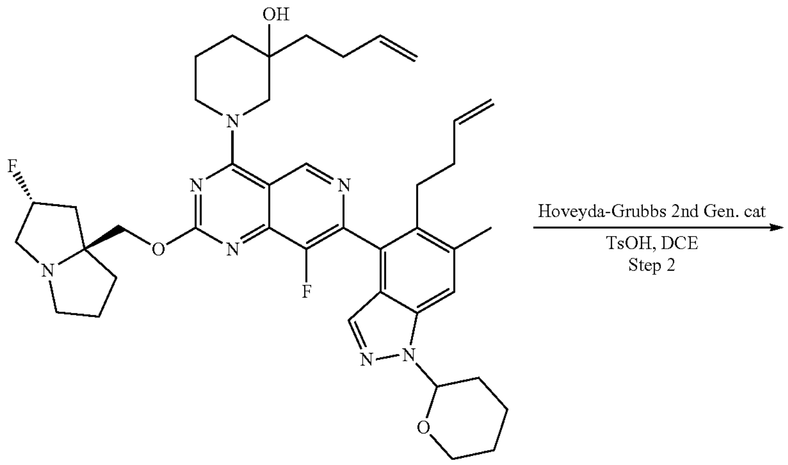

-continued

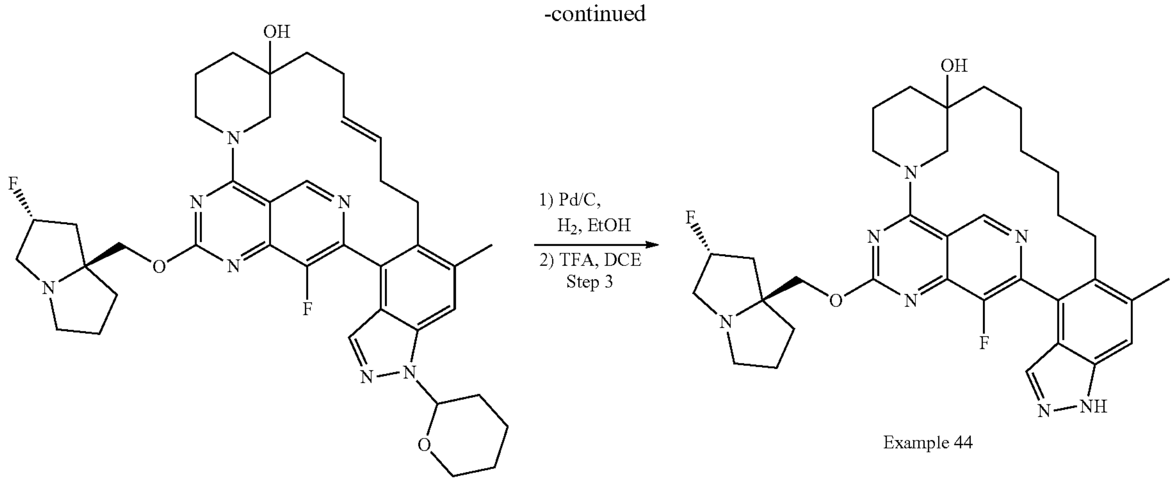

Example 44

Step 1. 3-(But-3-en-1-yl)-1-(7-(5-(but-3-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. To a vial was added 3-(but-3-en-1-yl)-1-(7-chloro-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.10 g, 0.20 mmol, Intermediate R), 5-(but-3-en-1-yl)-6-methyl-1-(tetrahydro-2H-pyran-2-yl)-4-(4,4,5,5-tetramethyl-1,3,2-dioxaborolan-2-yl)-1H-indazole (0.12 g, 0.30 mmol, Intermediate M), $K_3PO_4$ (0.14 g, 0.61 mmol), cataCXium A Pd G3 (15 mg, 0.02 mmol), and dioxane (2 mL), water (0.2 mL). The vial purged with nitrogen for 10 min, sealed, and heated to 80° C. for 4 h. After cooling to rt, the mixture was purified by column chromatography on silica gel, eluting with 0-100% (3:1 EtOAc:EtOH) in heptanes to give 3-(but-3-en-1-yl)-1-(7-(5-(but-3-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.14 g, 0.19 mmol, 93% yield). m/z (ESI): 728.4 $(M+H)^+$.

Step 2. (E)-28-Fluoro-22-(((2R,7aS)-2-fluorotetrahydro-1H-pyrrolizin-7a(5H)-yl)methoxy)-16-methyl-11-(tetrahydro-2H-pyran-2-yl)-11H-2(7,4)-pyrido[4,3-d]pyrimidina-1(4,5)-indazola-3(1,3)-piperidinacyclononaphan-6-en-33-ol. To a round-bottom flask was added 3-(but-3-en-1-yl)-1-(7-(5-(but-3-en-1-yl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.12 g, 0.16 mmol), TsOH (36 mg, 0.19 mmol) and DCE (100 mL). The flask was purged with nitrogen for 10 min, then Hoveyda-Grubbs catalyst $2^{nd}$ generation (20 mg, 0.032 mmol) was added. The reaction was heated to 80° C. for 18 h. Upon completion, the reaction was cooled to rt and purged with nitrogen for 15 min. The mixture was then concentrated and purified via reverse phase chromatography to give (E)-28-fluoro-22-(((2R,7aS)-2-fluorotetrahydro-1H-pyrrolizin-7a(5H)-yl)methoxy)-16-methyl-11-(tetrahydro-2H-pyran-2-yl)-11H-2(7,4)-pyrido[4,3-d]pyrimidina-1(4,5)-indazola-3(1,3)-piperidinacyclononaphan-6-en-33-ol (79 mg, 0.11 mmol, 71% yield) as brown oil.

Step 3. (17R)-30-Fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol, and (17S)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol bis(2,2,2-trifluoroacetate). To a vial was added (E)-28-fluoro-22-(((2R,7aS)-2-fluorotetrahydro-1H-pyrrolizin-7a(5H)-yl)methoxy)-16-methyl-11-(tetrahydro-2H-pyran-2-yl)-11H-2(7,4)-pyrido[4,3-d]pyrimidina-1(4,5)-indazola-3(1,3)-piperidinacyclononaphan-6-en-33-ol (79 mg, 0.11 mmol) in EtOH (2 mL), followed by Pd/C (2.4 mg, 0.023 mmol). The vial was placed in a hydrogenation vessel, purged with $N_2$ for 10 min, then hydrogenated under 40 psi H2 for 16 h. The mixture was diluted with EtOAc, passed through a celite/silica gel plug, and rinsed with 3:1 EtOAc:EtOAH with 2% TEA to give a crude mixture of N-(tetrahydro-2H-pyran-2-yl)-(17R)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol and N-(tetrahydro-2H-pyran-2-yl)-(17S)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol as yellow oil. The oil was redissolved in DCE (3 mL) and TFA (0.44 mL, 5.64 mmol) was added. The mixture was stirred at rt for 30 min. Upon completion, the mixture was concentrated to dryness and purified via reverse phase chromatography to give (17R)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol, and (17S)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-17-ol bis(2,2,2-trifluoroacetate) (15 mg, 0.018 mmol, 16% yield) as white solid. m/z (ESI): 618.1 $(M+H)^+$. $^1H$ NMR (400 MHz, METHANOL-$d_4$): δ ppm 9.39 (s, 1H), 7.75 (s, 1H), 7.54 (s, 1H), 5.53-5.69 (m, 1H), 5.08 (br d, J=13.4 Hz, 1H), 4.71 (dd, J=14.9, 11.8 Hz, 2H), 3.93 (br d, J=16.3 Hz, 3H), 3.45-3.63 (m, 3H), 3.13-3.24 (m, 1H), 2.34-2.59 (m, 10H), 1.76-1.90 (m, 4H), 1.23-1.49 (m, 4H), 1.00-1.18 (m, 3H), 0.88 (br s, 2H), 0.39-0.63 (m, 2H). $^{19}$F NMR (376 MHz, METHANOL-$d_4$): 6 ppm −77.34 (s), −141.92 (br d, J=12.1 Hz), −174.17--173.79 (m).

(11S,13R,18R)-9-Chloro-31-fluoro-25-(((2R,7aS)-2-fluorotetrahydro-1H-pyrrolo[1,2-a]pyrrol-7a(5H)-yl)methoxy)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) (Example 45) & (11R,13S,18R)-9-chloro-31-fluoro-25-(((2R,7aS)-2-fluorotetrahydro-1H-pyrrolo[1,2-a]pyrrol-7a(5H)-yl)methoxy)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) (Example 46)

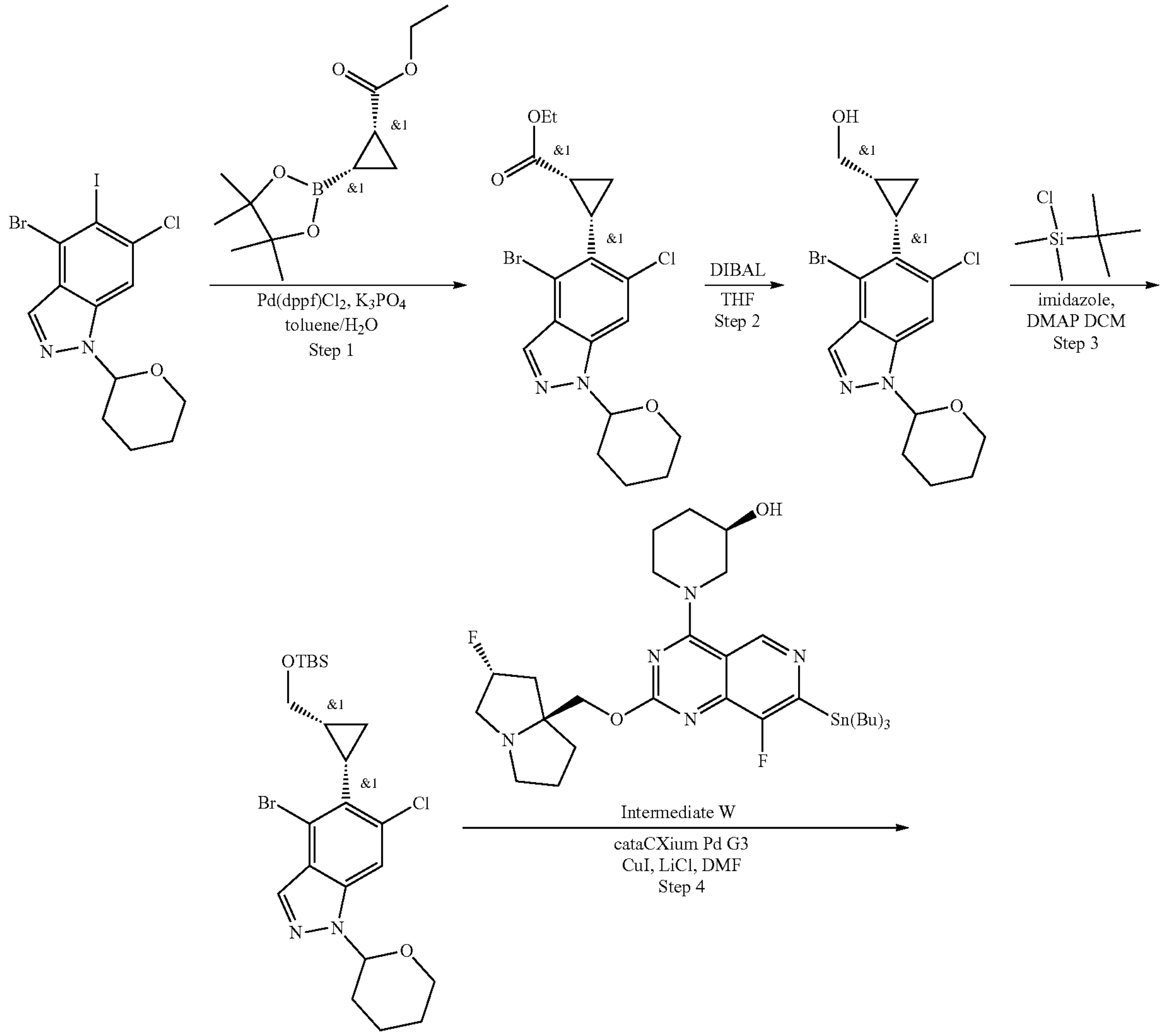

-continued

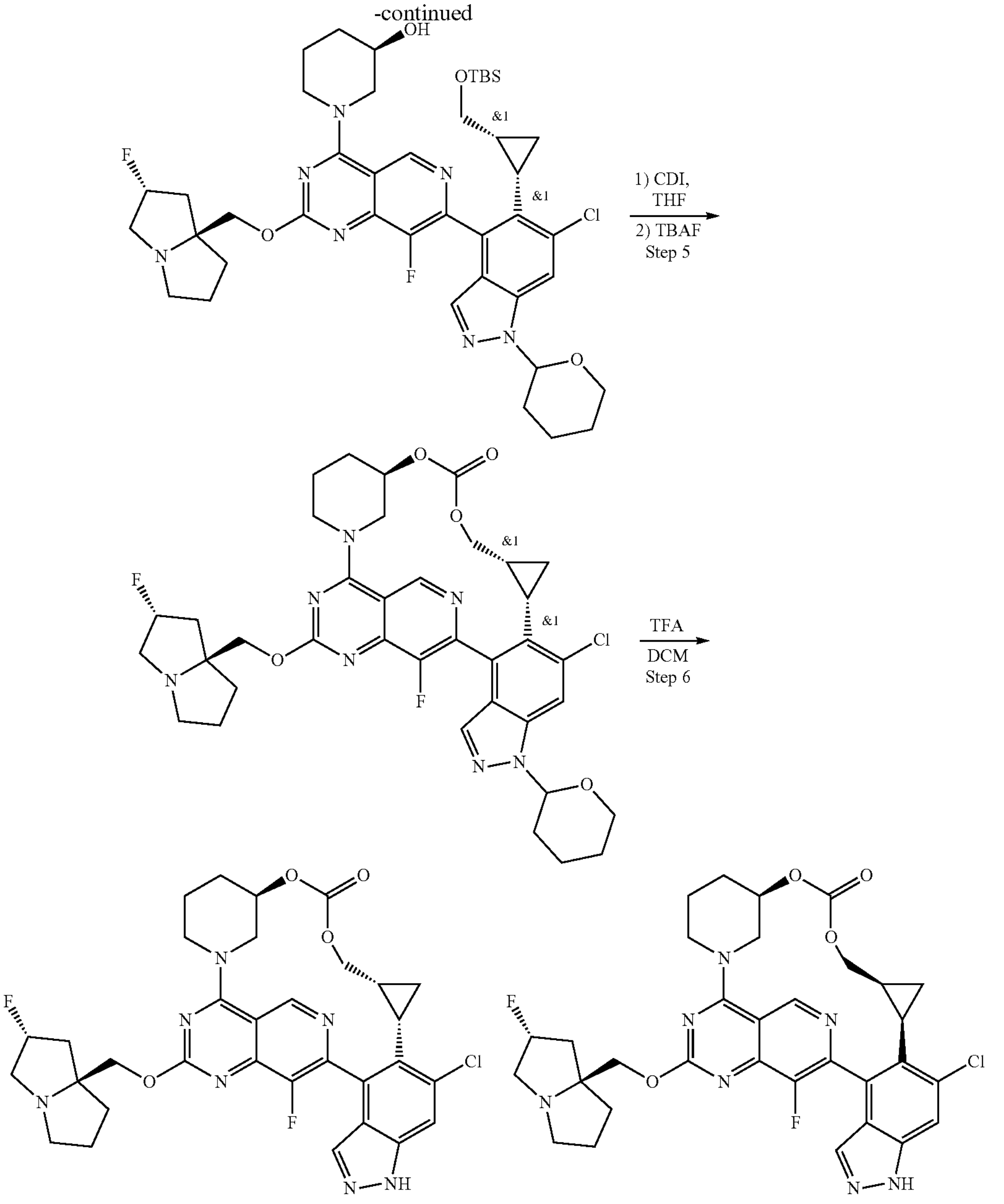

Example 45

Example 46

Step 1. rac-Ethyl (1R,2S)-2-(4-bromo-6-chloro-1-(tetrahydro-2H-pyran-2-yl)-1H-indazol-5-yl)cyclopropane-1-carboxylate. A vial was charged with 4-bromo-6-chloro-5-iodo-1-(tetrahydro-2H-pyran-2-yl)-1H-indazole (0.75 g, 1.70 mmol, Lab Network), rac-ethyl (1R,2S)-2-(tetramethyl-1,3,2-dioxaborolan-2-yl)cyclopropane-1-carboxylate (0.49 mL, 2.04 mmol, Enamine), 1,1'-bis(diphenylphosphino)ferrocene-palladium dichloride (0.12 g, 0.17 mmol), potassium phosphate tribasic (1.26 g, 5.95 mmol) in toluene (5 mL) and water (1 mL). The reaction mixture was flushed with nitrogen and heated at 100° C. for 16 h. After cooling to rt, the reaction mixture was concentrated and the residue purified by column chromatography on silica gel, eluting with a gradient of 0-60% EtOAc/heptane to provide rac-ethyl (1R,2S)-2-(4-bromo-6-chloro-1-(tetrahydro-2H-pyran-2-yl)-1H-indazol-5-yl)cyclopropane-1-carboxylate (0.24 g, 0.56 mmol, 33% yield) as white solid. m/z (ESI): 448.8 $(M+Na)^+$.

Step 2. rac-((1R,2S)-2-(4-Bromo-6-chloro-1-(tetrahydro-2H-pyran-2-yl)-1H-indazol-5-yl)cyclopropyl)methanol. To a stirred solution of rac-ethyl (1R,2S)-2-(4-bromo-6-chloro-1-(tetrahydro-2H-pyran-2-yl)-1H-indazol-5-yl)cyclopropane-1-carboxylate (0.95 g, 2.23 mmol) in tetrahydrofuran (6 mL) at −78° C. was added diisobutylaluminum hydride solution (1.0 M in DCM, 5.6 mL, 5.6 mmol) slowly. The resulting mixture was allowed to warm to rt and stirred for another 30 min. The reaction mixture was poured slowly into Rochelle's salt aqueous solution in an ice bath and extracted with EtOAc. The combined organic layers were dried ($Na_2SO_4$) and concentrated. The residue was purified by column chromatography on silica gel, eluting with a gradient of 0-60% EtOAc/heptane to afford rac-((1R,2S)-2-(4-bromo-6-chloro-1-(tetrahydro-2H-pyran-2-yl)-1H-indazol-5-yl)cyclopropyl)methanol (0.69 g, 1.78 mmol, 80% yield) as white solid. m/z (ESI): 384.8 $(M+H)^+$.

Step 3. rac-4-Bromo-5-((1R,2S)-2-(((tert-butyldimethylsilyl)oxy)methyl)cyclopropyl)-6-chloro-1-(tetrahydro-2H-pyran-2-yl)-1H-indazole. The mixture of rac-((1R,2S)-2-(4-bromo-6-chloro-1-(tetrahydro-2H-pyran-2-yl)-1H-indazol-5-yl)cyclopropyl)methanol (0.19 g, 0.49 mmol), tert-butyldimethylsilyl chloride (89 mg, 0.59 mmol), imidazole (83 mg, 1.23 mmol), and DMAP (6.0 mg, 0.049 mmol) in dichloromethane (3 mL) was stirred at rt for 1 h. The reaction mixture was purified by column chromatography on silica gel, eluting with a gradient of 0-20% EtOAc/heptane to provide rac-4-bromo-5-((1R,2S)-2-(((tert-butyldimethylsilyl)oxy)methyl)cyclopropyl)-6-chloro-1-(tetrahydro-2H-pyran-2-yl)-1H-indazole (0.23 g, 0.46 mmol, 94% yield) as colorless sticky oil. m/z (ESI): 498.9 $(M+H)^+$.

Step 4. rac-(3R)-1-((7S)-7-(5-((1R,2S)-2-(((tert-Butyldimethylsilyl)oxy)methyl)cyclopropyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol. In a vial, a suspension of (R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-ol (0.48 g, 0.69 mmol, Intermediate W), rac-4-bromo-5-((1R,2S)-2-(((tert-butyldimethylsilyl)oxy)methyl)cyclopropyl)-6-chloro-1-(tetrahydro-2H-pyran-2-yl)-1H-indazole (0.23 g, 0.46 mmol), cataCXium A Pd G3 (67 mg, 0.092 mmol), copper(I) iodide (44 mg, 0.23 mmol), and lithium chloride (39 mg, 0.92 mmol) in DMF (3 mL) was flushed with nitrogen and heated at 100° C. for 2 h. After cooling to rt, the reaction mixture was diluted with water and extracted with EtOAc. The combined organic layers were dried ($Na_2SO_4$) and concentrated. The residue was purified by column chromatography on silica gel, eluting with a gradient of 0-80% (3:1 EtOAc/EtOH, with 2% $Et_3N$) in heptane, to provide rac-(3R)-1-((7S)-7-(5-((1R,2S)-2-(((tert-butyldimethylsilyl)oxy)methyl)cyclopropyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (0.17 g, 0.21 mmol, 45% yield) as white solid. m/z (ESI): 823.8 $(M+H)^+$.

Step 5. rac-(11S,13R,18R)-9-Chloro-31-fluoro-25-(((2R,7aS)-2-fluorotetrahydro-1H-pyrrolo[1,2-a]pyrrol-7a(5H)-yl)methoxy)-N-(tetrahydro-2H-pyran-2-yl)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one. To a stirred solution of rac-(3R)-1-((7S)-7-(5-((1S,2R)-2-(((tert-butyldimethylsilyl)oxy)methyl)cyclopropyl)-6-chloro-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol (80 mg, 0.097 mmol) in tetrahydrofuran (1 mL) was added 1,1'-carbonyldiimidazole (39 mg, 0.24 mmol). The reaction mixture was stirred at rt for 16 h, then diluted with THF (10 mL) and treated with tetrabutylammonium fluoride (0.24 mL, 0.24 mmol). The resulting mixture was stirred at rt for 5 h. The reaction mixture was concentrated and purified by preparative HPLC, followed by column chromatography on silica gel, eluting with a gradient of 0-50% (20% MeOH in DCM) in DCM to provide rac-(11S,13R,18R)-9-chloro-31-fluoro-25-(((2R,7aS)-2-fluorotetrahydro-1H-pyrrolo[1,2-a]pyrrol-7a(5H)-yl)methoxy)-N-(tetrahydro-2H-pyran-2-yl)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one (16 mg, 0.022 mmol, 22% yield) as white solid. m/z (ESI, +ve ion): 735.9 $(M+H)^+$.

Step 6. (11S,13R,18R)-9-Chloro-31-fluoro-25-(((2R,7aS)-2-fluorotetrahydro-1H-pyrrolo[1,2-a]pyrrol-7a(5H)-yl)methoxy)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) (Example 45) & ((11R,13S,18R)-9-chloro-31-fluoro-25-(((2R,7aS)-2-fluorotetrahydro-1H-pyrrolo[1,2-a]pyrrol-7a(5H)-yl)methoxy)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) (Example 46). To a stirred solution of rac-(11S,13R,18R)-9-chloro-31-fluoro-25-(((2R,7aS)-2-fluorotetrahydro-1H-pyrrolo[1,2-a]pyrrol-7a(5H)-yl)methoxy)-N-(tetrahydro-2H-pyran-2-yl)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one (16 mg, 0.022 mmol) in dichloromethane (0.5 mL) was added trifluoroacetic acid (40 μL, 0.54 mmol). The resulting mixture was stirred at rt for 2 h. The reaction mixture was concentrated and the residue was purified by reverse phase preparative HPLC to (11S,13R,18R)-9-chloro-31-fluoro-25-(((2R,7aS)-2-fluorotetrahydro-1H-pyrrolo[1,2-a]pyrrol-7a(5H)-yl)methoxy)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) as white solid. m/z (ESI): 652.3 $(M+H)^+$. $^1$H NMR (400 MHz, METHANOL-$d_4$) δ ppm 9.37 (s, 1H), 8.17 (s, 1H), 7.89 (s, 1H), 5.53-5.74 (m, 1H), 5.10-5.22 (m, 2H), 4.85-4.88 (m, 1H), 4.74-4.78 (m, 1H), 4.64-4.72 (m, 1H), 3.92-4.12 (m, 4H), 3.79 (d, J=10.9 Hz, 1H), 3.50 (br dd, J=10.2, 5.4 Hz, 1H), 3.06 (dd, J=11.1, 8.2 Hz, 1H), 2.60-2.87 (m, 2H), 2.30-2.49 (m, 5H), 2.17-2.25 (m, 1H), 2.02-2.11 (m, 2H), 1.86-1.98 (m, 1H), 1.58-1.71 (m, 2H), 1.23 (br dd, J=9.8, 7.5 Hz, 1H), 0.32 (br d, J=7.3 Hz, 1H). Also isolated was ((11R,13S,18R)-9-chloro-31-fluoro-25-(((2R,7aS)-2-fluorotetrahydro-1H-pyrrolo[1,2-a]pyrrol-7a(5H)-yl)methoxy)-15,17-dioxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) as white solid. m/z (ESI): 652.3 $(M+H)^+$. $^1$H NMR (400 MHz, METHANOL-$d_4$) δ ppm 9.20-9.38 (m, 1H), 7.76-7.84 (m, 1H), 5.51-5.72 (m, 1H), 4.84-5.09 (m, 3H), 4.66-4.79 (m, 2H), 4.34-4.43 (m, 1H), 3.87-4.12 (m, 4H), 3.72-3.83 (m, 1H), 3.35-3.60 (m, 2H), 3.03 (dd, J=12.3, 10.0 Hz, 1H), 2.54-2.86 (m, 2H), 2.30-2.50 (m, 3H), 2.01-2.29 (m, 4H), 1.84-1.98 (m, 1H), 1.53-1.75 (m, 1H), 1.09-1.22 (m, 1H), 0.89 (dt, J=9.2, 5.3 Hz, 1H), 0.68-0.74 (m, 1H). Stereochemistry of Example 45 was confirmed by X-Ray crystallography analysis.

TABLE 36

| Additional Examples 110 to 116, 121 to 125, 214 to 216 and 371. Prepared in an Analogous Manner to Example 46. | | | | |
|---|---|---|---|---|
| Ex.# | Structure & Name | Salt Form | Reagent | Method Change |
| 110 | 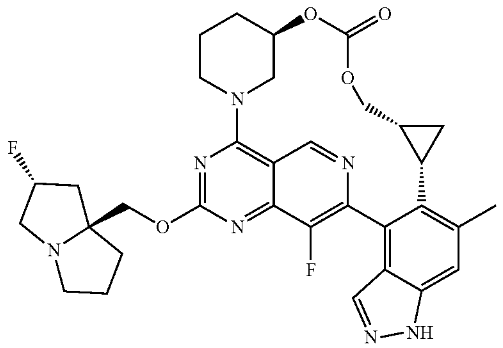 [SMILES: Cc1cc2[nH]ncc2c2c1[C@H]1C[C@H]1COC(=O)O[C@@H]1CCCN(C1)c1nc(OC[C@@]34CCCN3C[C@H](F)C4)nc3c(F)c-2ncc13] | bis (2,2,2-trifluoro-acetate) | Step 1. 4-bromo-5-iodo-6-methyl-1-(tetrahydro-2H-pyran-2-yl)-1H-indazole (Advanced ChemBlocks) | |
| 111 | 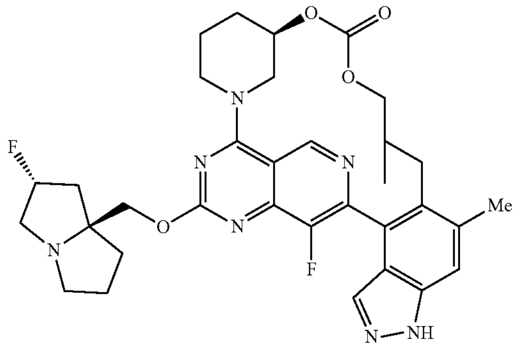 [SMILES: Cc1cc2[nH]ncc2c2c1CC(C)COC(=O)O[C@@H]1CCCN(C1)c1nc(OC[C@@]34CCCN3C[C@H](F)C4)nc3c(F)c-2ncc13] | bis (2,2,2-trifluoro-acetate) | Step 4. Intermediate ZZ | Steps 1-3 were not performed. |
| 214 | 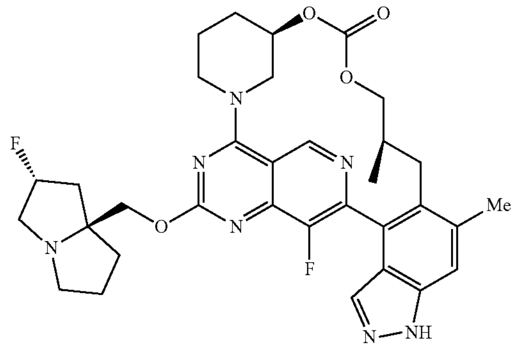 [SMILES: Cc1cc2[nH]ncc2c2c1C[C@@H](C)COC(=O)O[C@@H]1CCCN(C1)c1nc(OC[C@@]34CCCN3C[C@H](F)C4)nc3c(F)c-2ncc13] | NA | Step 4. Intermediate ZZ | Steps 1-3 were not performed. Chiral separation after Step 6. Details included below. |
| 215 | 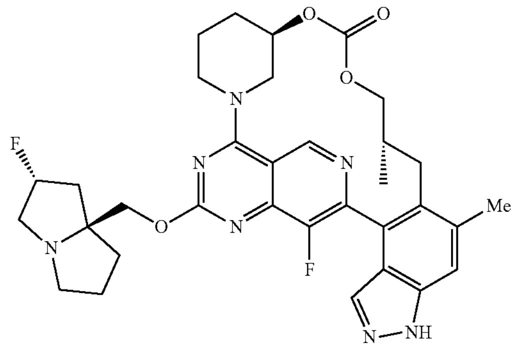 [SMILES: Cc1cc2[nH]ncc2c2c1C[C@H](C)COC(=O)O[C@@H]1CCCN(C1)c1nc(OC[C@@]34CCCN3C[C@H](F)C4)nc3c(F)c-2ncc13] | NA | Step 4. Intermediate ZZ | Steps 1-3 were not performed. Chiral separation after Step 6. Details included below. |

TABLE 36-continued

| Ex.# | Structure & Name | Salt Form | Reagent | Method Change |
|---|---|---|---|---|
| | Additional Examples 110 to 116, 121 to 125, 214 to 216 and 371. Prepared in an Analogous Manner to Example 46. | | | |
| 112 | 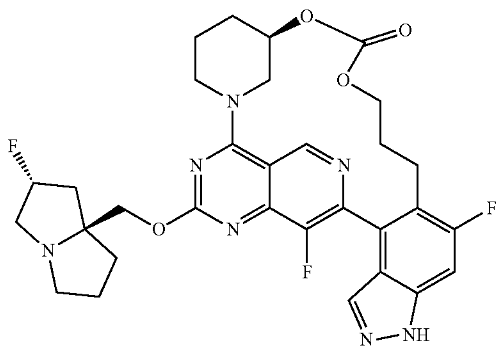 [SMILES: O=C1OCCCc2c(F)cc3[nH]ncc3c2-c2ncc3c(nc(OC[C@@]45CCCN4C[C@H](F)C5)nc3c2F)N2CCC[C@H](C2)O1] | bis (2,2,2-trifluoro-acetate) | Step 4. Intermediate KKK | Steps 1-3 were not performed. |
| 113 | 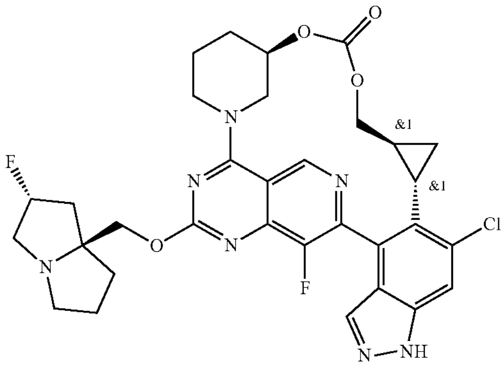 [SMILES: O=C1OC[C@H]2C[C@@H]2c2c(Cl)cc3[nH]ncc3c2-c2ncc3c(nc(OC[C@@]45CCCN4C[C@H](F)C5)nc3c2F)N2CCC[C@H](C2)O1] | bis (2,2,2-trifluoro-acetate) | Step 1. rac-ethyl (1R,2R)-2-(tetramethyl-1,3,2-dioxaborolan-2-yl) cyclopropane-1-carboxylate (CAS#: 2135443-03-5) | |
| 114 | 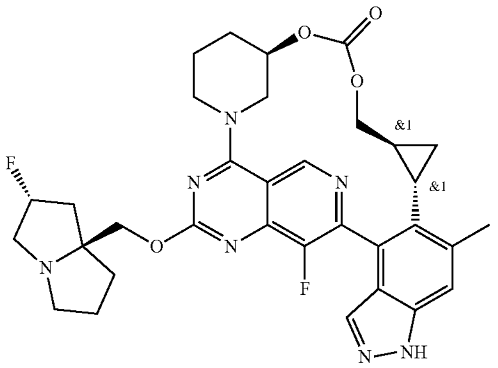 [SMILES: Cc1cc2[nH]ncc2c2c1[C@H]1C[C@@H]1COC(=O)O[C@@H]1CCCN(C1)c1nc(OC[C@@]34CCCN3C[C@H](F)C4)nc3c(F)c-2ncc13] | (2,2,2-trifluoro-acetate) | Step 1. 4-bromo-6-methyl-5-iodo-1-(tetrahydro-2H-pyran-2-yl)-1H-indazole CAS#: 2791273-76-0 and rac-ethyl (1R,2R)-2-(tetramethyl-1,3,2-dioxaborolan-2-yl) cyclopropane-1-carboxylate (CAS#: 2135443-03-5) | |
| 115 | 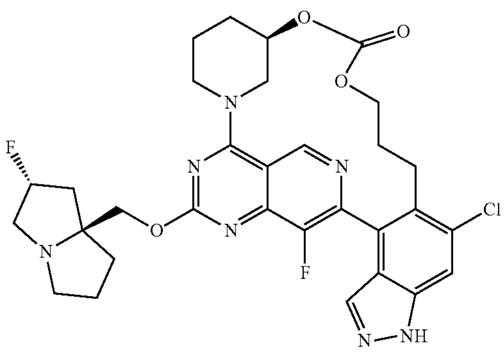 [SMILES: O=C1OCCCc2c(Cl)cc3[nH]ncc3c2-c2ncc3c(nc(OC[C@@]45CCCN4C[C@H](F)C5)nc3c2F)N2CCC[C@H](C2)O1] | bis (2,2,2-trifluoro-acetate) | Step 4: Intermediate FFF | Steps 1-3 were not performed. |

TABLE 36-continued

Additional Examples 110 to 116, 121 to 125, 214 to 216 and 371. Prepared in an Analogous Manner to Example 46.

| Ex.# | Structure & Name | Salt Form | Reagent | Method Change |
|---|---|---|---|---|
| 116 | 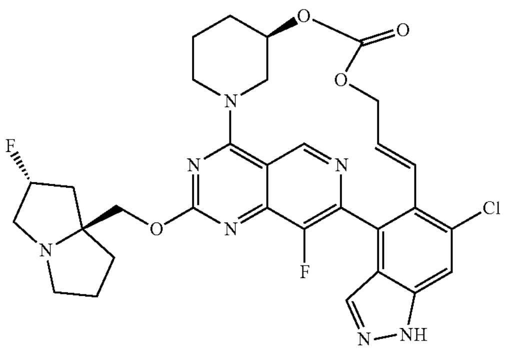 [SMILES: O=C1OC/C=C/c2c(Cl)cc3[nH]ncc3c2-c2ncc3c(nc(OC[C@@]45CCCN4C[C@H](F)C5)nc3c2F)N2CCC[C@H](C2)O1] | bis (2,2,2-trifluoro-acetate) | Step 4: Intermediate LLL | Steps 1-3 were not performed. |
| 121 | 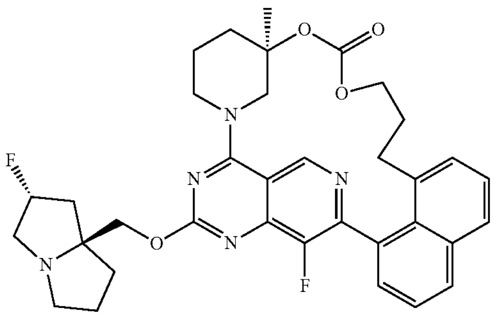 [SMILES: C[C@@]12CCCN(C1)c1nc(OC[C@@]34CCCN3C[C@H](F)C4)nc3c(F)c(ncc13)-c1cccc3cccc(c13)CCCOC(=O)O2] | bis (2,2,2-trifluoro-acetate) | Step 4. Intermediate MMM and Intermediate NNN | Steps 1-3 were not performed. |
| 122 | 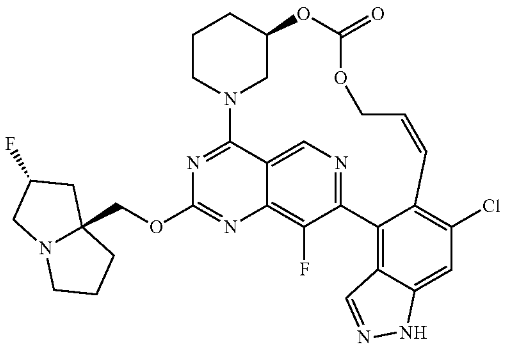 [SMILES: O=C1OC/C=C\c2c(Cl)cc3[nH]ncc3c2-c2ncc3c(nc(OC[C@@]45CCCN4C[C@H](F)C5)nc3c2F)N2CCC[C@H](C2)O1] | NA | Step 4. Intermediate OOO | Steps 1-3 were not performed. |
| 123 | 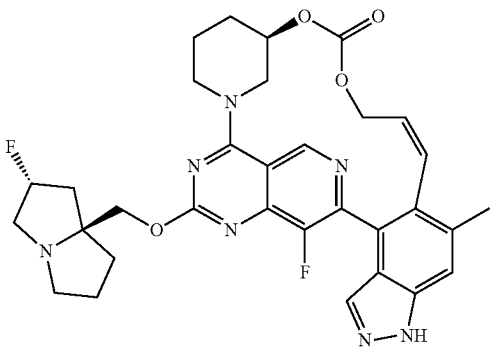 [SMILES: Cc1cc2[nH]ncc2c2c1/C=C\COC(=O)O[C@@H]1CCCN(C1)c1nc(OC[C@@]34CCCN3C[C@H](F)C4)nc3c(F)c-2ncc13] | NA | Step 4. Intermediate PPP | Steps 1-3 were not performed. |

TABLE 36-continued

| Additional Examples 110 to 116, 121 to 125, 214 to 216 and 371. Prepared in an Analogous Manner to Example 46. | | | | |
|---|---|---|---|---|
| Ex.# | Structure & Name | Salt Form | Reagent | Method Change |
| 124 | 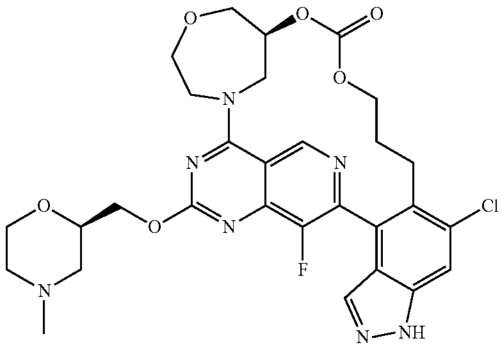 [SMILES: CN1CCO[C@@H](COc2nc3c4cnc(c(F)c4n2)-c2c(c(Cl)cc4[nH]ncc24)CCCOC(=O)O[C@@H]2COCCN3C2)C1] | 2,2,2-trifluoro-acetate | Step 4. Intermediate FFF and Intermediate QQQ | Steps 1-3 were not performed. Step 4: $K_3PO_4$ in 2-Me THF/Water was used instead of CuI, LiCl in DMF |
| 125 | 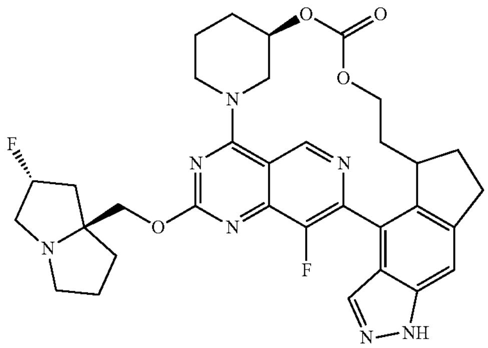 [SMILES: O=C1OCCC2CCc3cc4[nH]ncc4c(c32)-c2ncc3c(nc(OC[C@@]45CCCN4C[C@H](F)C5)nc3c2F)N2CCC[C@H](C2)O1] | NA | Step 4. Intermediate RRR | Steps 1-3 were not performed. |
| 216 | 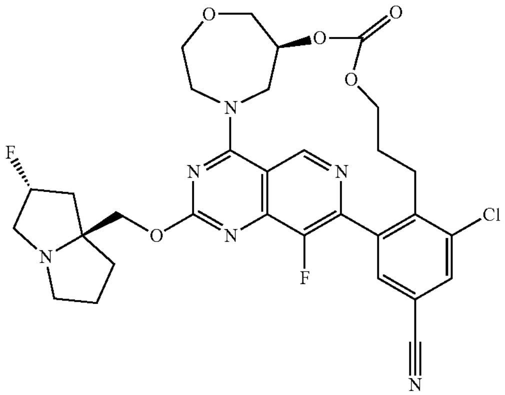 [SMILES: N#Cc1cc(Cl)c2c(c1)-c1ncc3c(nc(OC[C@@]45CCCN4C[C@H](F)C5)nc3c1F)N1CCOC[C@H](C1)OC(=O)OCCC2] | NA | Step 4. Intermediate BK and Intermediate BJ | Steps 1-3 were not performed. |
| 371 | 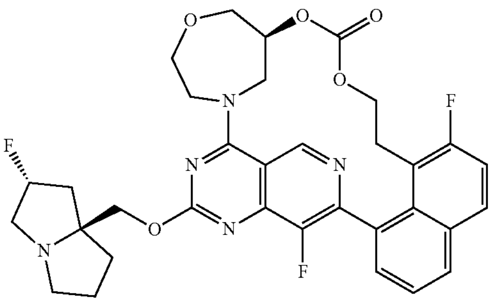 [SMILES: O=C1OCCc2c(F)ccc3cccc(c23)-c2ncc3c(nc(OC[C@@]45CCCN4C[C@H](F)C5)nc3c2F)N2CCOC[C@H](C2)O1] | | Step 4. Intermediate BK and Step 1 of Intermediate DN | Steps 1-3 & 6 were not performed. |

TABLE 37

| Conditions for Chiral SFC Separation. | | | |
|---|---|---|---|
| Separation | Conditions | m/z (ESI, +ve ion)+ | Final products |
| 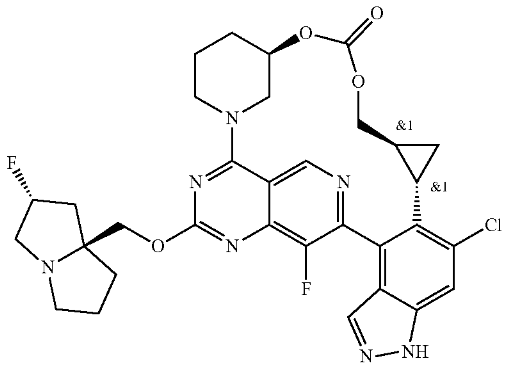 [SMILES: O=C1OC[C@H]2C[C@@H]2c2c(Cl)cc3[nH]ncc3c2-c2ncc3c(nc(OC[C@@]45CCCN4C[C@H](F)C5)nc3c2F)N2CCC[C@H](C2)O1] | Column: Chiralcel OD, 2 x 25 cm, 5 μm column Mobile phase: 40% MeOH with 0.2% TEA<br>Flowrate: 80 mL/min.<br>Yield: 57 mg sample was submitted to generate 18 mg of peak 1 with an ee of 99% and 20 mg of peak 2 with an ee of 99%. | 652.2 | Peak 1: 117<br>Peak 2: 118 |
| 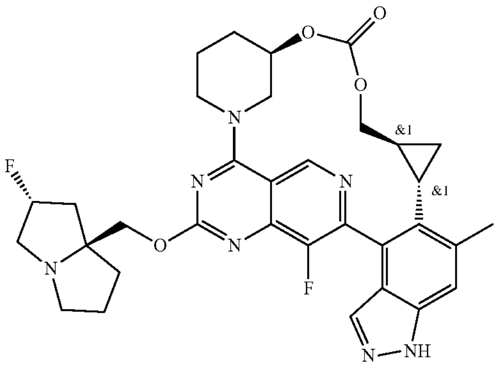 [SMILES: Cc1cc2[nH]ncc2c2c1[C@H]1C[C@@H]1COC(=O)O[C@@H]1CCCN(C1)c1nc(OC[C@@]34CCCN3C[C@H](F)C4)nc3c(F)c-2ncc13] | Column: Chiralcel OD, 2 x 25 cm, 5 μm column<br>Mobile phase: 30% MeOH with 0.2% TEA<br>Flowrate: 80 mL/min.<br>Yield: 19.7 mg sample was submitted to generate 6 mg of peak 1 with an ee of 99% and 7 mg of peak 2 with an ee of 99%. | 632.2 | Peak 1: 119<br>Peak 2: 120 |
| 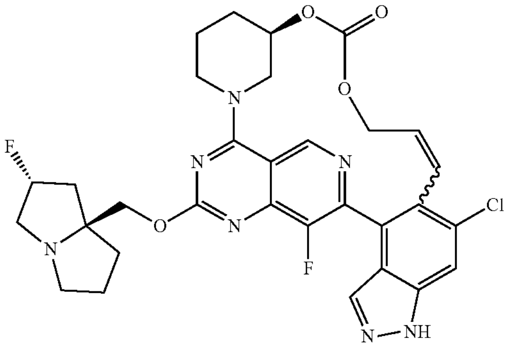 [SMILES: O=C1OCC=Cc2c(Cl)cc3[nH]ncc3c2-c2ncc3c(nc(OC[C@@]45CCCN4C[C@H](F)C5)nc3c2F)N2CCC[C@H](C2)O1] | Column: Chiralcel OD, 21 x 150 mm, 5 μm column<br>Mobile phase: 50% methanol with 0.2% triethylamine<br>Flowrate: 125 mL/min.<br>Yield: 12 mg sample was submitted to generate 4 mg of peak 1 with a ee of >99% and 3 mg of peak 2 with a ee of >96%. | 638.2 | Peak 1: 116<br>Peak 2: 122 |
| 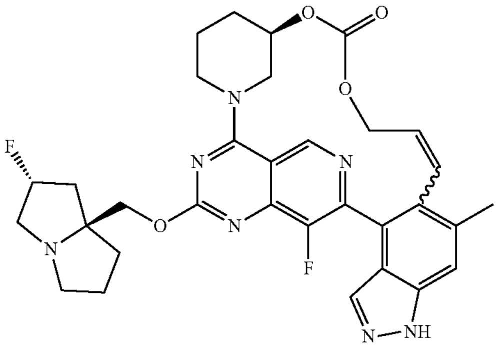 [SMILES: Cc1cc2[nH]ncc2c2c1C=CCOC(=O)O[C@@H]1CCCN(C1)c1nc(OC[C@@]34CCCN3C[C@H](F)C4)nc3c(F)c-2ncc13] | Column: (R,R) Whelk-01, 21 x 250 mm, 5 μm column<br>Mobile phase: 50% methanol with 0.2% triethylamine<br>Flowrate: 80 mL/min.<br>Yield: 20 mg sample was submitted to to generate 9 mg of peak 1 with an ee of >96% and 7 mg of peak 2 with an ee of >90%. | 618.2 | Peak 2: 123 |

TABLE 37-continued

| Conditions for Chiral SFC Separation. | | | |
|---|---|---|---|
| Separation | Conditions | m/z (ESI, +ve ion)$^+$ | Final products |
| 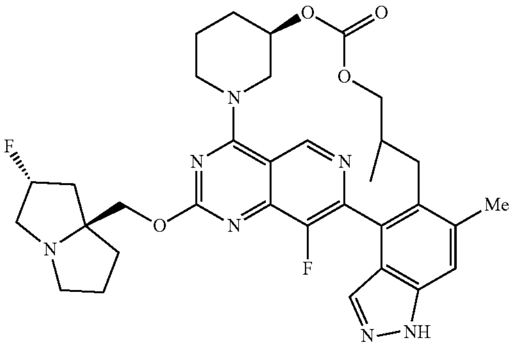 [SMILES: Cc1cc2[nH]ncc2c2c1CC(C)COC(=O)O[C@@H]1CCCN(C1)c1nc(OC[C@@]34CCCN3C[C@H](F)C4)nc3c(F)c-2ncc13] | Column: Chiralcel OD, 2 x 15 cm, 5 μm column<br>Mobile phase: 40% MeOH with 0.2% TEA<br>Flowrate: 100 mL/min.<br>Yield: 11.4 mg sample was submitted to generate 3 mg of peak 1 with an ee of 99% and 3 mg of peak 2 with an ee of 99%. | | Peak 1: Ex. 214<br>Peak 2: Ex. 215 |

TABLE 38

Analytical Data for Examples 110 to 116, 121 to 125, 214 to 216 and 371.

| Cmpd.# | MS m/z (ESI): (M + H)$^+$ | $^1$H and $^{19}$F NMR |
|---|---|---|
| 110 | 632.2 | $^1$H NMR (400 MHz, METHANOL-$d_4$) δ ppm 9.35 (s, 1 H), 8.09 (s, 1 H), 7.61 (s, 1 H), 5.49-5.74 (m, 1 H), 5.14 (br t, J = 16.6 Hz, 2 H), 4.83-4.90 (m, 1 H), 4.76 (s, 1 H), 4.64-4.71 (m, 1 H), 3.87-4.11 (m, 4 H), 3.78 (d, J = 11.1 Hz, 1 H), 3.45-3.57 (m, 1 H), 3.24-3.31 (m, 1 H), 3.11 (dd, J = 11.1, 7.9 Hz, 1 H), 2.56-2.90 (m, 5 H), 2.33-2.48 (m, 4 H), 2.13-2.25 (m, 1 H), 2.00-2.13 (m, 2 H), 1.86-1.99 (m, 1 H), 1.68 (br d, J = 9.4 Hz, 1 H), 1.54 (td, J = 9.6, 4.8 Hz, 1 H), 1.14-1.23 (m, 1 H), 0.14-0.21 (m, 1 H). |
| 111 | 634.0 | $^1$H NMR (400 MHz, METHANOL-$d_4$) δ ppm 9.21-9.35 (m, 1 H), 7.67-7.82 (m, 1 H), 7.48-7.58 (m, 1 H), 5.50-5.73 (m, 1 H), 4.90-5.28 (m, 3 H), 4.72-4.77 (m, 2 H), 4.61-4.74 (m, 1 H), 3.76-4.32 (m, 5 H), 3.50 (br s, 2 H), 2.61-2.91 (m, 3 H), 2.57 (s, 3 H), 2.28-2.50 (m, 4 H), 2.14-2.28 (m, 1 H), 1.85-2.14 (m, 3 H), 1.65-1.79 (m, 1 H), 1.35-1.55 (m, 1 H), 0.71-0.93 (m, 3 H). $^{19}$F NMR (376 MHz, METHANOL-$d_4$) δ ppm −77.40 (s), −142.03 (s), −174.16-−174.02 (m). |
| 214 | 634.0 | $^1$H NMR (400 MHz, METHANOL-$d_4$) δ ppm 9.19 (s, 1 H), 7.74-7.82 (m, 1 H), 7.53 (s, 1 H), 5.20-5.46 (m, 1 H), 4.89-5.06 (m, 3 H), 4.38-4.49 (m, 1 H), 4.14-4.35 (m, 2 H), 3.97-4.06 (m, 1 H), 3.45-3.53 (m, 1 H), 3.20-3.27 (m, 2 H), 3.11-3.19 (m, 1 H), 3.01-3.11 (m, 1 H), 2.60-2.69 (m, 1 H), 2.56 (s, 3 H), 2.28-2.50 (m, 3 H), 2.15-2.29 (m, 2 H), 2.01-2.10 (m, 4 H), 1.86-1.98 (m, 2 H), 1.61-1.69 (m, 1 H), 1.43-1.52 (m, 1 H), 0.72-0.81 (m, 3 H). $^{19}$F NMR (376 MHz, METHANOL-$d_4$) δ ppm −76.98-−76.87 (m), −141.58 (s), −173.64 (s). |
| 215 | 634.0 | $^1$H NMR (400 MHz, METHANOL-$d_4$) δ ppm 9.17-9.31 (m, 1 H), 7.77-7.86 (m, 1 H), 7.46-7.64 (m, 1 H), 5.25-5.48 (m, 1 H), 5.09-5.25 (m, 2 H), 4.83-4.96 (m, 1 H), 4.24-4.50 (m, 2 H), 3.79-4.09 (m, 2 H), 3.50-3.61 (m, 1 H), 3.34-3.46 (m, 2 H), 3.02-3.13 (m, 1 H), 2.65-2.77 (m, 1 H), 2.56 (s, 4 H), 2.29-2.48 (m, 2 H), 2.15-2.29 (m, 2 H), 1.99-2.12 (m, 3 H), 1.86-1.99 (m, 3 H), 1.51-1.77 (m, 3 H), 0.83-0.91 (m, 3 H). $^{19}$F NMR (376 MHz, METHANOL-d4) δ ppm −140.86 (br d, J = 6.1 Hz), −153.18-−152.96 (m), −173.67 (s). |
| 112 | 624.0 | $^1$H NMR (400 MHz, METHANOL-$d_4$) δ ppm 9.32 (s, 1 H), 7.91 (s, 1 H), 7.37-7.48 (m, 1 H), 5.43-5.73 (m, 1 H), 4.90-5.21 (m, 3 H), 4.63-4.76 (m, 2 H), 3.84-4.13 (m, 5 H), 3.65-3.75 (m, 1 H), 3.44-3.57 (m, 1 H), 3.24-3.31 (m, 1 H), 2.55-2.91 (m, 3 H), 2.32-2.51 (m, 4 H), 1.90-2.28 (m, 4 H), 1.58-1.81 (m, 3 H). $^{19}$F NMR (376 MHz, METHANOL-$d_4$) δ ppm −77.29 (s), −120.17 (s), −142.12 (s), −174.09 (s). |
| 113 | 651.9 | $^1$H NMR (400 MHz, METHANOL-$d_4$) δ ppm 9.21-9.36 (m, 1 H), 7.59-7.85 (m, 2 H), 5.50-5.72 (m, 1 H), 4.93 (br s, 3 H), 4.66-4.77 (m, 2 H), 3.67-4.47 (m, 6 H), 3.45-3.58 (m, 1 H), 3.35-3.43 (m, 1 H), 2.96-3.12 (m, 1 H), 2.55-2.89 (m, 2 H), 2.34- |

TABLE 38-continued

Analytical Data for Examples 110 to 116, 121 to 125, 214 to 216 and 371.

| Cmpd.# | MS m/z (ESI): $(M + H)^+$ | $^1H$ and $^{19}F$ NMR |
|---|---|---|
| | | 2.51 (m, 3 H), 2.01-2.30 (m, 4 H), 1.62-1.99 (m, 2 H), 1.06-1.20 (m, 1 H), 0.65-1.04 (m, 2 H). $^{19}F$ NMR (376 MHz, METHANOL-$d_4$) δ ppm −77.32 (s), −141.09 (d, J = 179.5 Hz), −174.26-−173.99 (m). |
| 114 | 631.9 | $^1H$ NMR (400 MHz, METHANOL-$d_4$) δ ppm 9.21-9.35 (m, 1 H), 7.49-7.74 (m, 2 H), 5.51-5.73 (m, 1 H), 4.87-5.25 (m, 3 H), 4.65-4.78 (m, 2 H), 3.70-4.47 (m, 6 H), 3.45-3.59 (m, 1 H), 3.36-3.44 (m, 1 H), 2.66 (s, 5 H), 2.33-2.52 (m, 3 H), 2.02-2.30 (m, 4 H), 1.85-1.99 (m, 1 H), 1.61-1.77 (m, 1 H), 1.03-1.22 (m, 1 H), 0.74-0.96 (m, 1 H), 0.52-0.71 (m, 1 H). $^{19}F$ NMR (376 MHz, METHANOL-$d_4$) δ ppm −77.34 (s), −141.48 (s), −174.15 (s). |
| 115 | 640.0 | $^1H$ NMR (400 MHz, METHANOL-$d_4$) δ ppm 9.33 (s, 1 H), 7.88 (d, J = 0.8 Hz, 1 H), 7.77-7.86 (m, 1 H), 5.46-5.74 (m, 1 H), 5.07-5.20 (m, 2 H), 4.91-4.97 (m, 1 H), 4.62-4.81 (m, 2 H), 4.13-4.26 (m, 1 H), 3.87-4.10 (m, 4 H), 3.62-3.77 (m, 1 H), 3.44-3.56 (m, 1 H), 2.67 (s, 3 H), 2.52-2.65 (m, 2 H), 2.31-2.48 (m, 3 H), 2.16-2.27 (m, 1 H), 1.97-2.15 (m, 2 H), 1.88-1.97 (m, 1 H), 1.54-1.76 (m, 3 H). $^{19}F$ NMR (377 MHz, METHANOL-d4) δ ppm −77.36 (s), −142.04 (s), −174.14 (s). |
| 116 | 637.8 | $^1H$ NMR (400 MHz, METHANOL-$d_4$) δ ppm 9.17-9.23 (m, 1 H) 7.90-7.97 (m, 1 H) 7.79-7.84 (m, 1 H) 6.78-6.86 (m, 1 H) 5.51-5.73 (m, 1 H) 5.18-5.30 (m, 1 H) 4.92-5.11 (m, 2 H) 4.82-4.86 (m, 1 H) 4.65-4.78 (m, 3 H) 4.00-4.15 (m, 3 H) 3.84-3.99 (m, 3 H) 3.44-3.57 (m, 1 H) 2.68-2.85 (m, 1 H) 2.67 (s, 1 H) 2.33-2.50 (m, 3 H) 2.00-2.28 (m, 3 H) 1.92-1.99 (m, 1 H) 1.64-1.75 (m, 1 H). $^{19}F$ NMR (376 MHz, METHANOL-$d_4$) δ ppm −77.32 (s), −142.34 (s), −174.12 (s). |
| 117 | 562.2 | $^1H$ NMR (600 MHz, DMSO-$d_6$) δ ppm 13.10-13.37 (m, 1 H) 9.25 (s, 1 H) 7.74-7.81 (m, 1 H) 7.69-7.75 (m, 1 H) 5.19-5.36 (m, 1 H) 4.62-4.85 (m, 3 H) 4.13-4.26 (m, 2 H) 3.92-4.10 (m, 2 H) 3.31-3.40 (m, 2 H) 2.97-3.16 (m, 3 H) 2.77-2.85 (m, 1 H) 1.97-2.19 (m, 6 H) 1.73-1.88 (m, 4 H) 1.50-1.60 (m, 1 H) 0.89-0.99 (m, 1 H) 0.78-0.85 (m, 1 H) 0.53-0.61 (m, 1 H). |
| 118 | 562.2 | $^1H$ NMR (600 MHz, DMSO-$d_6$) δ ppm 9.30 (s, 1 H) 7.78 (s, 1 H) 7.68 (s, 1 H) 5.19-5.39 (m, 1 H) 4.96-5.06 (m, 1 H) 4.82 (br s, 2 H) 4.04-4.27 (m, 2 H) 3.89-4.02 (m, 2 H) 3.57-3.72 (m, 1 H) 3.31-3.34 (m, 1 H) 3.16-3.26 (m, 1 H) 2.78-3.17 (m, 1 H) 1.74-2.22 (m, 9 H) 1.54-1.61 (m, 1 H) 0.90-1.02 (m, 2 H) 0.67-0.74 (m, 1 H). |
| 119 | 632.2 | $^1H$ NMR (600 MHz, DMSO-$d_6$) δ ppm 12.95-13.01 (m, 1 H), 9.26 (s, 1 H), 7.52 (s, 1 H), 7.39-7.48 (m, 1 H), 5.22-5.42 (m, 1 H), 4.93-5.10 (m, 1 H), 4.79-4.90 (m, 2 H), 4.05-4.23 (m, 2 H), 3.91-4.01 (m, 2 H), 3.61-3.70 (m, 1 H), 3.29-3.36 (m, 1 H), 3.18-3.28 (m, 1 H), 2.98-3.16 (m, 1 H), 2.81-2.91 (m, 1 H), 1.73-2.25 (m, 11 H), 1.52-1.62 (m, 1 H), 1.20-1.30 (m, 1 H), 0.91-1.00 (m, 1 H), 0.77-0.88 (m, 1 H), 0.53-0.63 (m, 1 H). |
| 120 | 632.2 | $^1H$ NMR (600 MHz, DMSO-$d_6$) δ ppm 9.23 (s, 1 H), 7.60 (s, 1 H), 7.45 (s, 1 H), 5.20-5.36 (m, 1 H), 4.78 (br s, 3 H), 4.15-4.26 (m, 2 H), 4.06 (s, 2 H), 3.31-3.39 (m, 1 H), 2.99-3.13 (m, 3 H), 2.79-2.86 (m, 1 H), 2.06-2.20 (m, 2 H), 1.97-2.05 (m, 5 H), 1.71-1.89 (m, 4 H), 1.41-1.62 (m, 2 H), 1.24 (br s, 3 H), 0.88-0.95 (m, 1 H), 0.64-0.76 (m, 1 H), 0.38-0.49 (m, 1 H). |
| 121 | 630.2 | $^1H$ NMR (400 MHz, METHANOL-$d_4$) δ ppm 9.32 (s, 1 H), 8.04-8.15 (m, 1 H), 7.86-7.94 (m, 1 H), 7.60 (s, 2 H), 7.44-7.55 (m, 2 H), 5.48-5.74 (m, 1 H), 5.28-5.37 (m, 1 H), 4.94-5.05 (m, 1 H), 4.70 (s, 2 H), 4.09-4.20 (m, 1 H), 3.82-4.07 (m, 5 H), 3.48 (br dd, J = 5.7, 4.3 Hz, 1 H), 3.21-3.31 (m, 1 H), 2.29-2.84 (m, 8 H), 2.06-2.28 (m, 3 H), 1.79-1.95 (m, 2 H), 1.60-1.75 (m, 2 H), 1.57 (s, 3 H). $^{19}F$ NMR (376 MHz, METHANOL-$d_4$) δ ppm −77.48-−77.36 (m), −140.05-−139.98 (m), −174.15-−174.11 (m). |
| 122 | 638.2 | $^1H$ NMR (400 MHz, METHANOL-$d_4$) δ ppm 9.23 (s, 1 H), 8.15 (d, J = 0.6 Hz, 1 H), 7.84 (s, 1 H), 6.80 (br d, J = 11.7 Hz, 1 H), 5.60 (td, J = 11.8, 3.4 Hz, 1 H), 5.21-5.43 (m, 1 H), 5.00-5.18 (m, 2 H), 4.38 (d, J = 10.5 Hz, 1 H), 4.23 (d, J = 10.5 Hz, 1 H), 4.00-4.08 (m, 1 H), 3.86-3.97 (m, 2 H), 3.17-3.28 (m, 4 H), 3.03 (td, J = 9.5, 5.7 Hz, 1 H), 2.30-2.43 (m, 1 H), 2.11-2.30 (m, 3 H), 1.98-2.10 (m, 4 H), 1.84-1.96 (m, 2 H), 1.63 (br d, J = 9.0 Hz, 1 H). $^{19}F$ NMR (376 MHz, METHANOL-$d_4$) δ ppm −137.92 (s), −173.63 (s). |
| 123 | 618.2 | $^1H$ NMR (400 MHz, METHANOL-$d_4$) δ ppm 9.25 (s, 1 H), 8.08 (s, 1 H), 7.57 (s, 1 H), 6.79 (br d, J = 12.0 Hz, 1 H), 5.35-5.61 (m, 2 H), 5.04-5.19 (m, 2 H), 4.51-4.61 (m, 1 H), 4.42 (br d, J = 11.6 Hz, 1 H), 4.00-4.04 (m, 1 H), 3.89-3.99 (m, 2 H), 3.10-3.29 (m, 4 H), 2.46-2.51 (m, 1 H), 2.44 (s, 3 H), 2.16-2.31 (m, 3 H), |

TABLE 38-continued

| Analytical Data for Examples 110 to 116, 121 to 125, 214 to 216 and 371. | | |
|---|---|---|
| Cmpd.# | MS m/z (ESI): $(M + H)^+$ | $^1H$ and $^{19}F$ NMR |
| | | 2.05-2.11 (m, 8 H), 1.64-1.68 (m, 1 H). $^{19}F$ NMR (376 MHz, METHANOL-$d_4$) δ ppm −138.34 (s), −173.66 (s). |
| 124 | 628.3 | $^1H$ NMR (400 MHz, METHANOL-$d_4$) δ ppm 9.37 (s, 1 H), 7.81 (s, 1 H), 7.76-7.79 (m, 1 H), 5.46 (br d, J = 17.1 Hz, 1 H), 4.88-4.97 (m, 1 H), 4.73 (br d, J = 3.6 Hz, 1 H), 4.60-4.69 (m, 1 H), 4.56 (dd, J = 11.7, 4.8 Hz, 1 H), 4.18-4.32 (m, 1 H), 4.09-4.15 (m, 2 H), 3.96-4.06 (m, 2 H), 3.82-3.89 (m, 1 H), 3.73-3.82 (m, 2 H), 3.48-3.64 (m, 2 H), 3.42 (br d, J = 12.1 Hz, 1 H), 3.33-3.38 (m, 1 H), 3.18-3.25 (m, 1 H), 2.95-3.05 (m, 1 H), 2.82-2.94 (m, 2 H), 2.77 (s, 3 H), 2.57-2.69 (m, 2 H), 1.83-1.92 (m, 2 H). $^{19}F$ NMR (376 MHz, METHANOL-$d_4$) δ ppm −76.93 (s), −141.31 (s). |
| 125 | 632.4 | $^1H$ NMR (600 MHz, DMSO-$d_6$) δ ppm 9.49-9.26 (m, 1H), 7.96-7.74 (m, 1H), 7.56-7.35 (m, 1H), 5.68-5.41 (m, 1H), 5.06-4.77 (m, 3H), 4.74-4.36 (m, 2H), 4.32-3.97 (m, 2H), 3.89-3.54 (m, 2H), 3.30 (s, 5H), 3.25-2.87 (m, 3H), 2.23-1.98 (m, 4H), 1.93-1.72 (m, 4H), 1.70-1.40 (m, 3H), 1.32-1.07 (m, 1H), 0.71-0.55 (m, 1H). |
| 216 | 641.2 | $^1H$ NMR (METHANOL-$d_4$, 400 MHz) 8 9.34 (s, 1H), 7.9-8.0 (m, 1H), 7.86 (d, 1H, J = 1.7 Hz), 5.2-5.5 (m, 2H), 4.9-5.0 (m, 1H), 4.6-4.8 (m, 1H), 4.3-4.4 (m, 2H), 4.1-4.3 (m, 1H), 4.07 (dt, 2H, J = 5.2, 13.1 Hz), 3.9-4.0 (m, 1H), 3.8-3.9 (m, 1H), 3.7-3.8 (m, 1H), 3.55 (ddd, 1H, J = 5.1, 11.4, 13.8 Hz), 3.3-3.4 (m, 2H), 3.3-3.3 (m, 1H), 3.08 (br d, 1H, J = 5.6 Hz), 2.8-3.0 (m, 1H), 2.5-2.6 (m, 1H), 2.2-2.4 (m, 2H), 2.1-2.2 (m, 1H), 2.0-2.1 (m, 3H), 1.9-2.0 (m, 1H), 1.7-1.9 (m, 2H). $^{19}F$ NMR (METHANOL-$d_4$, 376 MHz) δ −141.31 (s), −173.75 (s). Stereochemistry of Example 216 was confirmed by X-Ray crystallography analysis. |
| 371 | 636.3 | $^1H$ NMR (400 MHz, CHLOROFORM-d) δ ppm 9.12 (s, 1H), 6.98 (d, J = 2.0Hz, 1H), 6.85 (d, J = 2.4Hz, 1H), 5.27-5.44 (m, 2H), 4.88 (t, J = 6.0Hz, 1H), 4.79 (d, J = 1.6Hz, 1H), 4.41-4.52 (m, 1H), 4.31-4.39 (m, 1H), 4.10-4.22 (m, 3H), 3.82-3.91 (m, 2H), 3.70-3.78 (m, 2H), 3.29-3.42 (m, 2H), 3.06-3.23 (m, 2H), 2.72-2.84 (m, 1H), 2.24-2.43 (m, 4H), 1.99-2.15 (m, 4H), 1.75-1.89 (m, 2H). $^{19}F$ NMR (CHLOROFORM-d, 376 MHz) δ ppm −138.44 (s), −172.39 ( s). |

(17R)-30-Fluoro-24-(((2R,7aS)-2-fluorotetrahydro-1H-pyrrolo[1,2-a]pyrrol-7a(5H)-yl)methoxy)-9-methyl-13,15-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one bis(2,2,2-trifluoroacetate) (Example 126)

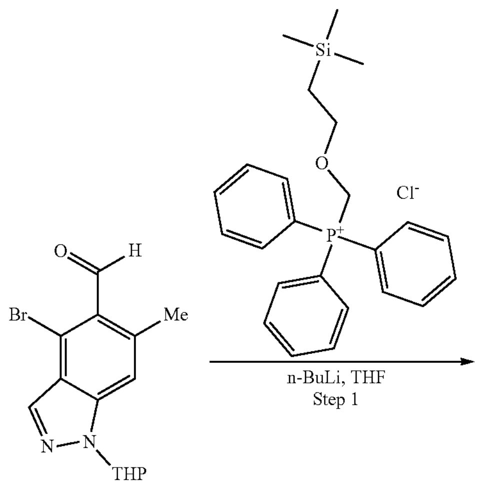

-continued

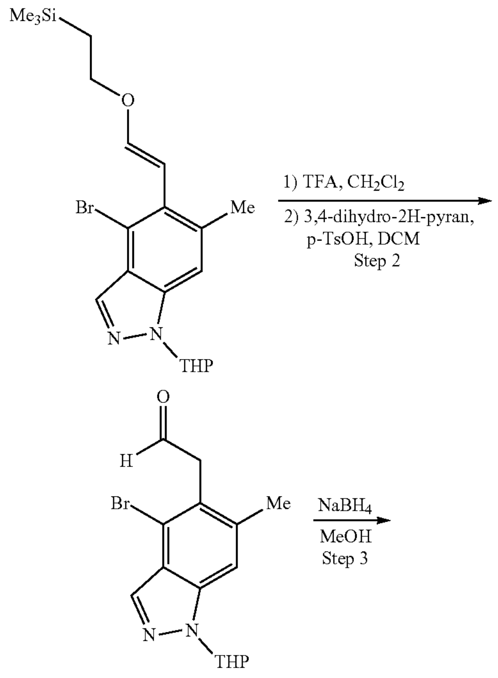

-continued

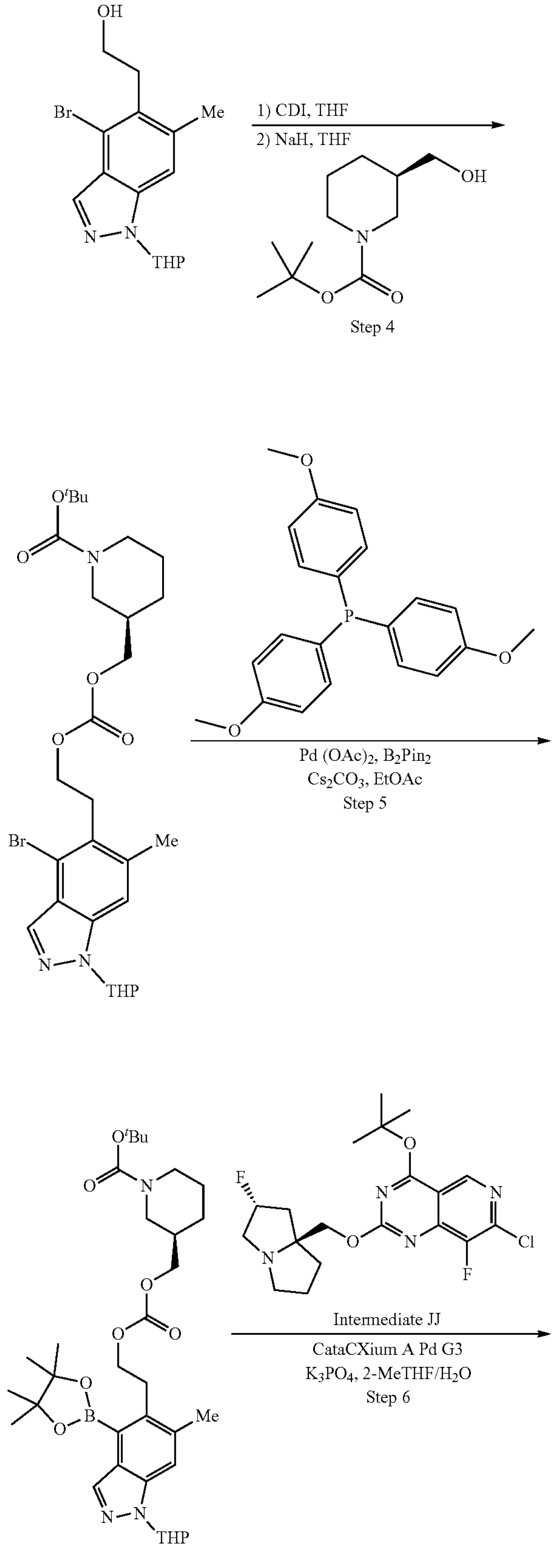

-continued

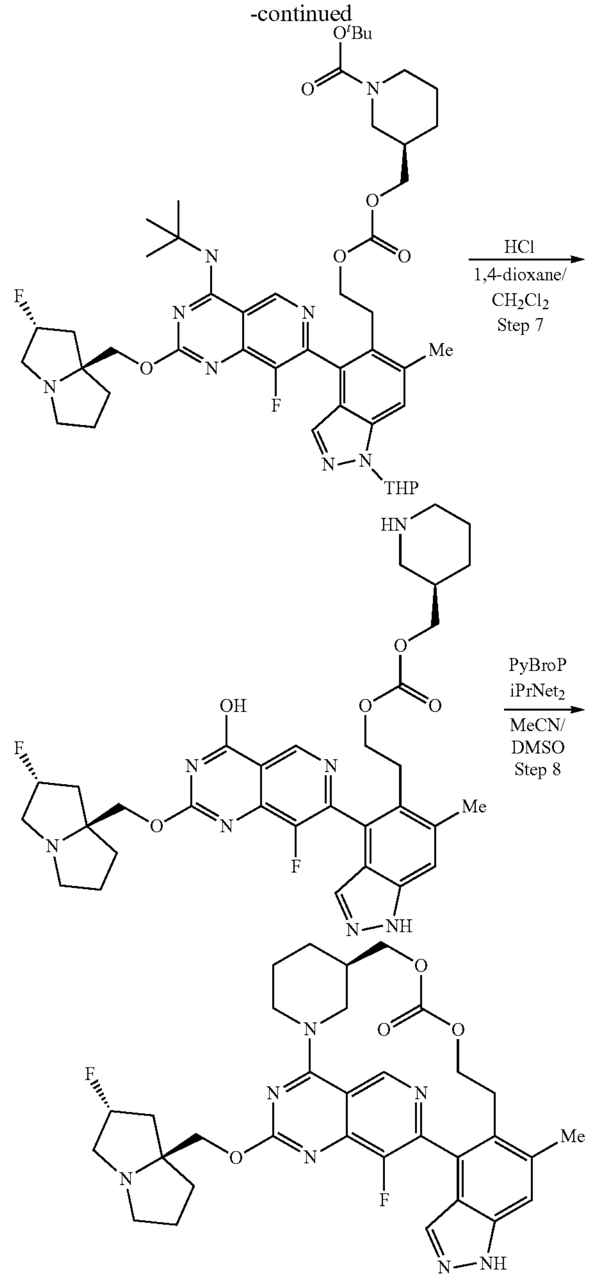

Example 126

Step 1. (E)-4-Bromo-6-methyl-1-(tetrahydro-2H-pyran-2-yl)-5-(2-(2-(trimethylsilyl)ethoxy)vinyl)-1H-indazole. A suspension of (trimethylsilyl)ethoxymethyl triphenylphosphonium chloride (2.65 g, 6.19 mmol, Ambeed, Inc.) in tetrahydrofuran (20 mL) was cooled to 0° C., n-butyl lithium (2.5 M in hexanes, 2.6 mL, 6.4 mmol) was added and the reaction was allowed to stir 0° C. for 40 min. A solution of 4-bromo-6-methyl-1-(tetrahydro-2H-pyran-2-yl)-1H-indazole-5-carbaldehyde (1.00 g, 3.09 mmol, Intermediate RRRR) in tetrahydrofuran (10 mL) was then added dropwise and the reaction was stirred at 0° C. for 15 min, then allowed to warm to rt with stirring for another 2.5 h. The reaction was quenched via the addition of saturated aqueous ammonium chloride. The aqueous layer was extracted with $CH_2Cl_2$, and the combined organic layers were dried with sodium sulfate, filtered, and concentrated. The crude oil was the purified by column chromatography on silica gel, eluting with a gradient of 0-15% EtOAc in heptane, to provide (E)-4-bromo-6-methyl-1-(tetrahydro-2H-pyran-2-yl)-5-(2-(2-(trimethylsilyl)ethoxy)vinyl)-1H-indazole (1.30 g, 3.00 mmol, 96% yield) as clear oil. m/z (ESI): 436.9/439.0 $(M+H)^+$.

Step 2. 2-(4-Bromo-6-methyl-1-(tetrahydro-2H-pyran-2-yl)-1H-indazol-5-yl)acetaldehyde. To a stirring solution of (E)-4-bromo-6-methyl-1-(tetrahydro-2H-pyran-2-yl)-5-(2-(2-(trimethylsilyl)ethoxy)vinyl)-1H-indazole (1.20 g, 2.70 mmol) in dichloromethane (12 mL) was added trifluoroacetic acid (1.7 mL) and the reaction was allowed to stir at rt for 1 h. The reaction was concentrated under reduced pressure and the residue was partitioned between EtOAc and saturated aqueous sodium bicarbonate. The aqueous layer was extracted with EtOAc, and the combined organic layers were dried with sodium sulfate, filtered, and concentrated. The crude oil was then dissolved in dichloromethane (12 mL) and p-toluenesulfonic acid monohydrate (26 mg, 0.13 mmol) and 3,4-dihydro-2H-pyran (0.75 mL, 8.1 mmol) were added. The reaction mixture was stirred at rt for 16 h, then concentrated under reduced pressure. The residue was purified by column chromatography on silica gel, eluting with a gradient of 0-30% EtOAc in heptane, to provide 2-(4-bromo-6-methyl-1-(tetrahydro-2H-pyran-2-yl)-1H-indazol-5-yl)acetaldehyde (0.45 g, 1.30 mmol, 50% yield) as clear oil. m/z (ESI): 337.1/339.1 $(M+H)^+$.

Step 3. 2-(4-Bromo-6-methyl-1-(tetrahydro-2H-pyran-2-yl)-1H-indazol-5-yl)ethan-1-ol. A solution of 2-(4-bromo-6-methyl-1-(tetrahydro-2H-pyran-2-yl)-1H-indazol-5-yl)acetaldehyde (0.45 g, 1.30 mmol) in methanol (13 mL) was cooled to 0° C. and then sodium borohydride (63 mg, 1.7 mmol) was added. The reaction mixture was stirred at rt for 30 min, then quenched by addition of saturated aqueous ammonium chloride. The aqueous layer was extracted with EtOAc, and the combined organic layers were dried with sodium sulfate, filtered, and concentrated. The crude oil was purified by column chromatography on silica gel, eluting with a gradient of 0-40% EtOAc in heptane, to provide 2-(4-bromo-6-methyl-1-(tetrahydro-2H-pyran-2-yl)-1H-indazol-5-yl)ethan-1-ol (0.35 g, 1.00 mmol, 78% yield) as white solid. m/z (ESI): 339.0/341.0 $(M+H)^+$.

Step 4. tert-Butyl (3R)-3-((((2-(4-bromo-6-methyl-1-(tetrahydro-2H-pyran-2-yl)-1H-indazol-5-yl)ethoxy)carbonyl)oxy)methyl)piperidine-1-carboxylate. To a stirred solution of 2-(4-bromo-6-methyl-1-(tetrahydro-2H-pyran-2-yl)-1H-indazol-5-yl)ethan-1-ol (0.18 g, 0.52 mmol) in tetrahydrofuran (1 mL) was added 1,1'-carbonyldiimidazole (0.13 g, 0.77 mmol). The reaction mixture was stirred at rt. In a separate vial a solution of (R)-1-Boc-3-(hydroxymethyl)piperidine (0.22 g, 1.03 mmol) in tetrahydrofuran (1.5 mL) was cooled to 0° C. and sodium hydride, 60% dispersion in mineral oil (62 mg, 1.5 mmol) was added. The resulting mixture was stirred at 0° C. for 30 min. The solution of 2-(4-bromo-6-methyl-1-(tetrahydro-2H-pyran-2-yl)-1H-indazol-5-yl)ethan-1-ol in THF was added to the solution containing (R)-1-Boc-3-(hydroxymethyl)piperidine and the mixture was stirred at 0° C. for 30 min. The reaction mixture was quenched via slow addition of saturated aqueous ammonium chloride and was allowed to warm to rt. The aqueous layer was extracted with $CH_2Cl_2$, and the combined organic layers were dried with sodium sulfate, filtered, and concentrated. The crude oil was purified sequentially by column chromatography on silica gel, eluting with a gradient of 0-40% EtOAc/heptane, then via reverse phase chromatography using a gradient of 10-100% MeCN (0.1% formic acid) in water (0.1% formic acid) to afford tert-butyl (3R)-3-((((2-(4-bromo-6-methyl-1-(tetrahydro-2H-pyran-2-yl)-1H-indazol-5-yl)ethoxy)carbonyl)oxy)methyl)piperidine-1-carboxylate (0.30 g, 0.50 mmol, 100% yield) as light yellow oil. m/z (ESI, +ve ion): 479.95/481.0 $(M+H-tBu)^+$.

Step 5. tert-Butyl (3R)-3-((((2-(6-methyl-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)methyl)piperidine-1-carboxylate. A vial was charged with tert-butyl (3R)-3-((((2-(4-bromo-6-methyl-1-(tetrahydro-2H-pyran-2-yl)-1H-indazol-5-yl)ethoxy)carbonyl)oxy)methyl)piperidine-1-carboxylate (0.26 g, 0.45 mmol), tris(4-methoxyphenyl) phosphine (16 mg, 0.045 mmol), palladium acetate (5.1 mg, 0.023 mmol), 4,4,4',4',5,5,5',5'-octamethyl-2,2'-bi(1,3,2-dioxaborolane) (0.14 g, 0.55 mmol, Ambeed, Inc.), cesium carbonate (0.22 g, 0.68 mmol), and ethyl acetate (1 mL). The reaction mixture was sparged with nitrogen gas and heated to 80° C. for 1 h. After cooling to rt, the mixture was filtered through celite, and the filtrate concentrated under reduced pressure. The crude oil was purified by column chromatography on silica gel, eluting with a gradient of 0-40% EtOAc in heptane, to provide tert-butyl (3R)-3-((((2-(6-methyl-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)methyl)piperidine-1-carboxylate (0.23 g, 0.37 mmol, 81% yield) as clear oil. m/z (ESI): 628.2 $(M+H)^+$.

Step 6. tert-Butyl (3R)-3-((((2-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)ethoxy)carbonyl)oxy)methyl)piperidine-1-carboxylate. A 20 mL vial was charged with 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (0.15 g, 0.36 mmol, Intermediate JJ), cataCXium A Pd G3 (40 mg, 0.054 mmol), potassium phosphate (0.23 g, 1.09 mmol), and tert-butyl (3R)-3-((((2-(6-methyl-1-(tetrahydro-2H-pyran-2-yl)-4-(4,4,5,5-tetramethyl-1,3,2-dioxaborolan-2-yl)-1H-indazol-5-yl)ethoxy)carbonyl)oxy)methyl)piperidine-1-carboxylate (0.27 g, 0.44 mmol). The vial was purged with nitrogen and then the reactants were suspended in degassed 2-methyltetrahydrofuran (3.5 mL) and water (0.35 mL). The reaction mixture was heated to 80° C. for 2.5 h. After cooling to rt, the reaction was concentrated under reduced pressure and the crude oil was purified by column chromatography on silica gel, eluting with a gradient of 0-50% of a 3:1 EtOAc/EtOH (with 2% triethylamine) in heptane to provide tert-butyl (3R)-3-((((2-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)ethoxy)carbonyl)oxy)methyl)piperidine-1-carboxylate (0.21 g, 0.24 mmol, 67% yield) as light yellow solid. m/z (ESI): 878.2 $(M+H)^+$.

Step 7. 2-(4-(8-Fluoro-2-(((2R,7aS)-2-fluorotetrahydro-1H-pyrrolizin-7a(5H)-yl)methoxy)-4-hydroxypyrido[4,3-d]pyrimidin-7-yl)-6-methyl-1H-indazol-5-yl)ethyl (((R)-piperidin-3-yl)methyl) carbonate. A vial was charged with tert-butyl (3R)-3-((((2-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)ethoxy)carbonyl)oxy)methyl)piperidine-1-carboxylate (0.21 g, 0.24 mmol) and dichloromethane (5 mL). Hydrogen chloride, 4 N solution in 1,4-dioxane (1.5 mL, 6.0 mmol) was added, then the reaction was vigorously stirred at rt for 3.5 h. The reaction was concentrated under reduced pressure and the crude product was dissolved in MeOH, and eluted through a PL-$HCO_3$ tube (flushed with MeOH) to provide 2-(4-(8-fluoro-2-(((2R,7aS)-2-fluorotetrahydro-1H-pyrrolizin-7a(5H)-yl)

methoxy)-4-hydroxypyrido[4,3-d]pyrimidin-7-yl)-6-methyl-1H-indazol-5-yl)ethyl (((R)-piperidin-3-yl)methyl) carbonate (0.16 g, 0.25 mmol, 100% yield, 80% purity) as orange glass. m/z (ESI): 637.9 $(M+H)^+$.

Step 8. (17R)-30-Fluoro-24-(((2R,7aS)-2-fluorotetrahydro-1H-pyrrolo[1,2-a]pyrrol-7a(5H)-yl)methoxy)-9-methyl-13,15-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one bis(2,2,2-trifluoroacetate). A vial equipped was charged with bromotripyrrolidinophosphonium hexafluorophosphate (72 mg, 0.15 mmol), DIPEA (0.11 mL, 0.64 mmol) in acetonitrile (23 mL). A solution of 2-(4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-6-methyl-1H-indazol-5-yl)ethyl (((R)-piperidin-3-yl)methyl) carbonate (82 mg, 0.13 mmol) in dimethyl sulfoxide (2.5 mL) was added via syringe pump over 30 min, then the reaction was stirred at rt for 48 h. The reaction mixture was concentrated under reduced pressure and the crude material was then purified via reverse phase HPLC using a gradient of 10-100% MeCN (0.1% TFA) in water (0.1% TFA) over 15 min, to provide (17R)-30-fluoro-24-(((2R,7aS)-2-fluorotetrahydro-1H-pyrrolo[1,2-a]pyrrol-7a(5H)-yl)methoxy)-9-methyl-13,15-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one bis(2,2,2-trifluoroacetate) (21 mg, 0.025 mmol, 20% yield) as white solid. m/z (ESI): 620.2 $(M+H)^+$. $^1H$ NMR (400 MHz, METHANOL-$d_4$) δ ppm 9.33 (s, 1H), 7.80-7.86 (m, 1H), 7.57-7.64 (m, 1H), 5.47-5.72 (m, 1H), 4.98-5.10 (m, 2H), 4.63-4.76 (m, 2H), 4.51-4.60 (m, 1H), 3.85-4.09 (m, 4H), 3.66-3.81 (m, 2H), 3.45-3.56 (m, 1H), 3.36-3.41 (m, 1H), 3.26-3.30 (m, 1H), 3.05-3.24 (m, 2H), 2.57-2.87 (m, 2H), 2.53 (s, 3H), 2.32-2.49 (m, 3H), 1.97-2.27 (m, 3H), 1.76-1.95 (m, 1H), 1.63-1.76 (m, 2H). $^{19}F$ NMR (376 MHz, METHANOL-$d_4$) δ ppm −77.38 (s), −142.63 (s), −174.11 (s).

TABLE 39

Additional Example 217 to 222. Prepared in an Analogous Manner to Example 126.

| Ex.# | Structure & Name | Salt Form | Reagent | Method Change |
|---|---|---|---|---|
| 217 | 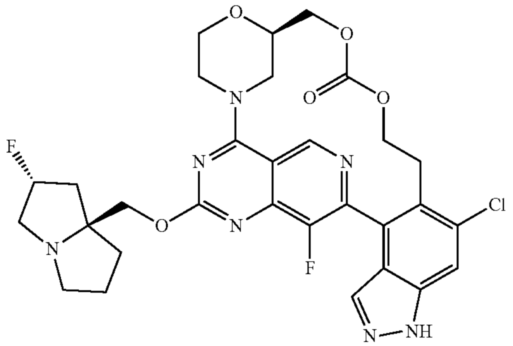 [SMILES: O=C1OCCc2c(Cl)cc3[nH]ncc3c2-c2ncc3c(nc(OC[C@@]45CCCN4C[C@H](F)C5)nc3c2F)N2CCO[C@@H](CO1)C2] | bis (2,2,2-trifluoro-acetate) | Step 1. Intermediate ZZZ, step 2. Step 4-2. (R)-2-hydroxymethyl morpholine-4-carboxylic acid tert-butyl ester (CAS#: 135065-71-3) | |
| 218 | 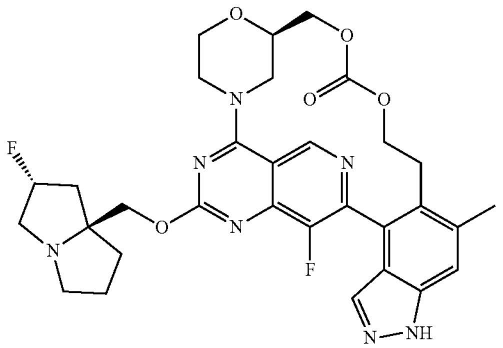 [SMILES: Cc1cc2[nH]ncc2c2c1CCOC(=O)OC[C@H]1CN(CCO1)c1nc(OC[C@@]34CCCN3C[C@H](F)C4)nc3c(F)c-2ncc13] | bis (2,2,2-trifluoro-acetate) | Step 4-2. (R)-2-hydroxymethyl morpholine-4-carboxylic acid tert-butyl ester (CAS#: 135065-71-3) | |
| 219 | 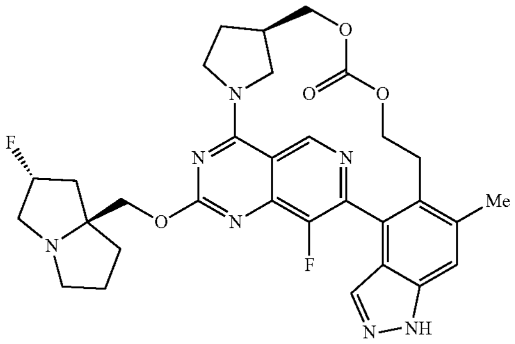 [SMILES: Cc1cc2[nH]ncc2c2c1CCOC(=O)OC[C@@H]1CCN(C1)c1nc(OC[C@@]34CCCN3C[C@H](F)C4)nc3c(F)c-2ncc13] | bis (2,2,2-trifluoro-acetate) | Step 4-2: (R)-3-hydroxymethyl-pyrrolidine-1-carboxylic acid tert-butyl ester (CAS: 138108-72-2, Combi-Blocks Inc.) | |

TABLE 39-continued

| Additional Example 217 to 222. Prepared in an Analogous Manner to Example 126. | | | | |
|---|---|---|---|---|
| Ex.# | Structure & Name | Salt Form | Reagent | Method Change |
| 220 | 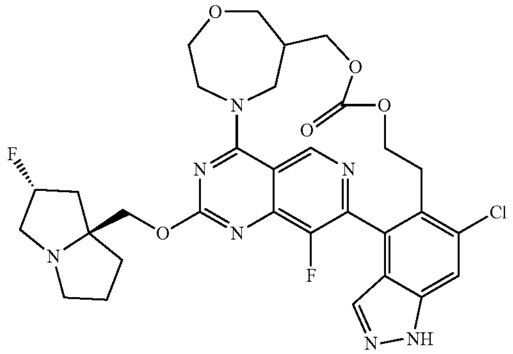 [SMILES: O=C1OCCc2c(Cl)cc3[nH]ncc3c2-c2ncc3c(nc(OC[C@@]45CCCN4C[C@H](F)C5)nc3c2F)N2CCOCC(CO1)C2] | NA | Step 1. Intermediate ZZZ, step 2 Step 4-2. tert-butyl 6-(hydroxy-methyl)-1,4-oxazepane-4-carboxylate (CAS: 1063734-19-9) | |
| 221 | 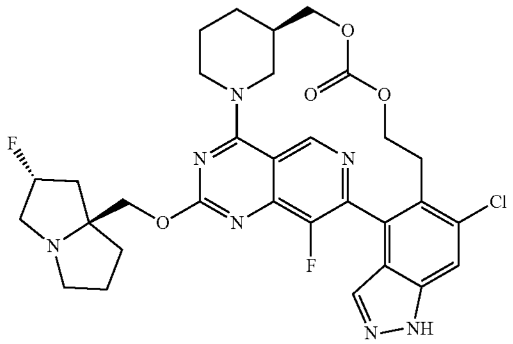 [SMILES: O=C1OCCc2c(Cl)cc3[nH]ncc3c2-c2ncc3c(nc(OC[C@@]45CCCN4C[C@H](F)C5)nc3c2F)N2CCC[C@@H](CO1)C2] | tris (2,2,2-trifluoro-acetate) | Step 1. Intermediate ZZZ, step 2 | |
| 222 | 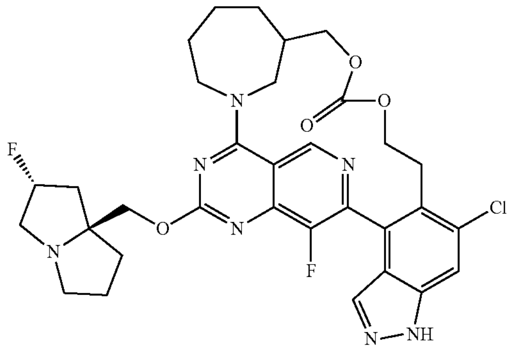 [SMILES: O=C1OCCc2c(Cl)cc3[nH]ncc3c2-c2ncc3c(nc(OC[C@@]45CCCN4C[C@H](F)C5)nc3c2F)N2CCCCC(CO1)C2] | bis (2,2,2-trifluoro-acetate) | Step 1. Intermediate ZZZ, step 2. Step 4. tert-butyl 3-(hydroxymethyl) azepane-1-carboxylate (CAS: 876147-43-2) | |

TABLE 40

| Analytical Data for Examples 217 to 222. | | |
|---|---|---|
| Cmpd.# | MS m/z (ESI): $(M + H)^+$ | $^1H$ NMR |
| 217 | 642.1 | $^1H$ NMR (400 MHz, METHANOL-$d_4$) δ ppm 9.33 (s, 1 H), 7.82-8.01 (m, 2 H), 5.50-5.74 (m, 1 H), 5.00 (br d, J = 12.3 Hz, 1 H), 4.83 (br s, 1 H), 4.66-4.76 (m, 2 H), 4.49 (br d, J = 11.5 Hz, 1 H), 4.26 (dd, J = 14.5, 3.4 Hz, 1 H), 3.90-4.08 (m, 5 H), 3.79-3.89 (m, 2 H), 3.70-3.79 (m, 2 H), 3.59-3.69 (m, 1 H), 3.47-3.56 (m, 1 H), 3.37-3.44 (m, 1 H), 3.05-3.19 (m, 1 H), 2.55-2.90 (m, 2 H), 2.32-2.50 (m, 3 H), 2.16-2.28 (m, 1 H). 19F NMR (METHANOL-$d_4$, 376 MHz) δ ppm −77.35, −142.08, −174.11. |
| 218 | 622.3 | $^1H$ NMR (400 MHz, METHANOL-$d_4$) δ ppm 9.31 (s, 1 H), 7.85 (s, 1 H), 7.60 (s, 1 H), 5.52-5.71 (m, 1 H), 5.00 (br d, J = 13.0 Hz, 1 H), 4.83 (br d, J = 8.2 Hz, 1 H), 4.65-4.72 (m, 1 H), 4.38-4.51 (m, 1 H), 4.26 (dd, J = 14.6, 3.8 Hz, 1 H), 4.04-4.20 (m, 1 H), |

TABLE 40-continued

| Analytical Data for Examples 217 to 222. | | |
|---|---|---|
| Cmpd.# | MS m/z (ESI): $(M + H)^+$ | $^1$H NMR |
| | | 3.89-4.03 (m, 5 H), 3.72-3.89 (m, 4 H), 3.62 (td, J = 12.5, 3.7 Hz, 1 H), 3.46-3.56 (m, 1 H), 3.04-3.24 (m, 2 H), 2.56-2.91 (m, 3 H), 2.53 (s, 3 H), 2.31-2.49 (m, 3 H), 2.14-2.29 (m, 1 H). $^{19}$F NMR (376 MHz, METHANOL-$d_4$) δ ppm −77.20, −142.10, −174.10. |
| 219 | 606.0 | $^1$H NMR (METHANOL-$d_4$, 400 MHz) δ ppm 9.13 (s, 1H), 7.9-8.0 (m, 1H), 7.5-7.6 (m, 1H), 5.5-5.7 (m, 1H), 4.7-4.8 (m, 2H), 4.3-4.4 (m, 1H), 4.00 (s, 4H), 3.8-3.9 (m, 2H), 3.7-3.8 (m, 3H), 3.5-3.5 (m, 1H), 3.1-3.2 (m, 2H), 2.6-2.9 (m, 4H), 2.57 (s, 3H), 2.3-2.5 (m, 4H), 2.1-2.3 (m, 1H), 1.7-1.8 (m, 1H). $^{19}$F NMR (376 MHz, METHANOL-$d_4$) δ ppm −77.32 (s), −142.18 (s), −174.15 (s). |
| 220 | 656.2 | $^1$H NMR (400 MHz, METHANOL-$d_4$) δ ppm 9.37 (s, 1 H), 7.82-7.90 (m, 2 H), 5.17-5.42 (m, 2 H), 4.53-4.66 (m, 2 H), 4.39-4.50 (m, 1 H), 4.23-4.37 (m, 2 H), 3.93-4.02 (m, 1 H), 3.66-3.89 (m, 6 H), 3.35-3.52 (m, 1 H), 3.17-3.30 (m, 4 H), 2.98-3.16 (m, 2 H), 2.19-2.41 (m, 2 H), 2.09-2.19 (m, 2 H), 1.96-2.07 (m, 2 H), 1.79-1.96 (m, 1 H). $^{19}$F NMR (376 MHz, METHANOL-$d_4$) δ ppm −142.64 (d, J = 4.3 Hz), −173.65 (d, J = 48.5 Hz). |
| 221 | 639.8 | $^1$H NMR (400 MHz, METHANOL-$d_4$) δ ppm 9.34 (s, 1 H), 7.91-7.97 (m, 1 H), 7.85-7.91 (m, 1 H), 5.53-5.74 (m, 1 H), 5.00-5.13 (m, 2 H), 4.63-4.77 (m, 2 H), 4.51-4.61 (m, 1 H), 3.79-4.14 (m, 6 H), 3.65-3.73 (m, 1 H), 3.48-3.56 (m, 1 H), 3.39-3.46 (m, 1 H), 3.08-3.17 (m, 1 H), 2.57-2.90 (m, 2 H), 2.33-2.53 (m, 3 H), 2.03-2.26 (m, 3 H), 1.78-1.92 (m, 1 H), 1.64-1.78 (m, 2 H), 1.30-1.35 (m, 1 H). $^{19}$F NMR (376 MHz, METHANOL-$d_4$) δ ppm −75.71--73.56 (m), −77.38 (s), −142.54 (s), −174.11 (s). |
| 222 | 654.0 | $^1$H NMR (400 MHz, METHANOL-$d_4$) δ ppm 9.34-9.47 (m, 1 H), 7.89 (s, 2 H), 5.49-5.74 (m, 1 H), 4.93-5.07 (m, 1 H), 4.51-4.81 (m, 4 H), 3.81-4.19 (m, 6 H), 3.37-3.63 (m, 4 H), 2.55-2.99 (m, 3 H), 2.34-2.53 (m, 3 H), 2.12-2.24 (m, 2 H), 1.85-2.07 (m, 2 H), 1.56-1.83 (m, 2 H), 1.09-1.47 (m, 2 H). $^{19}$F NMR (376 MHz, METHANOL-$d_4$) δ ppm −77.36 (s), −143.58--143.27 (m), −174.12 (br d, J = 14.7 Hz). |

(11R,13S,18R)-9-Chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one, (11S,13R,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one (Example 127)

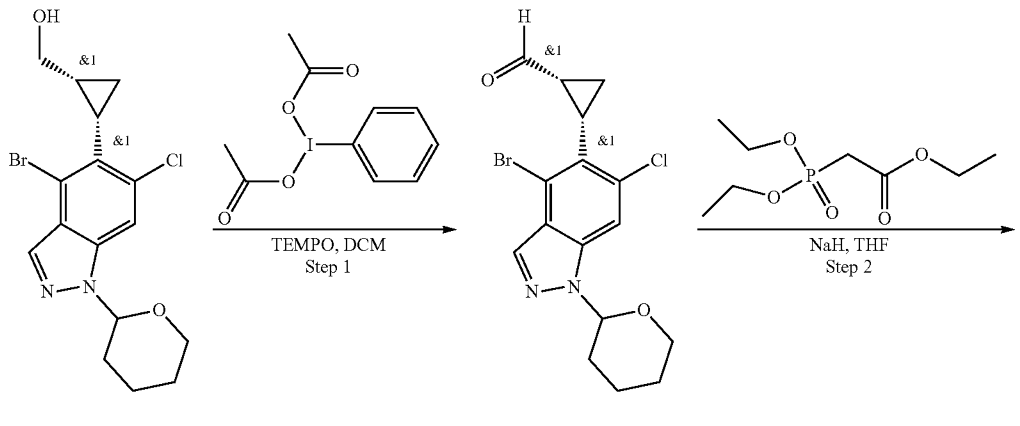

-continued
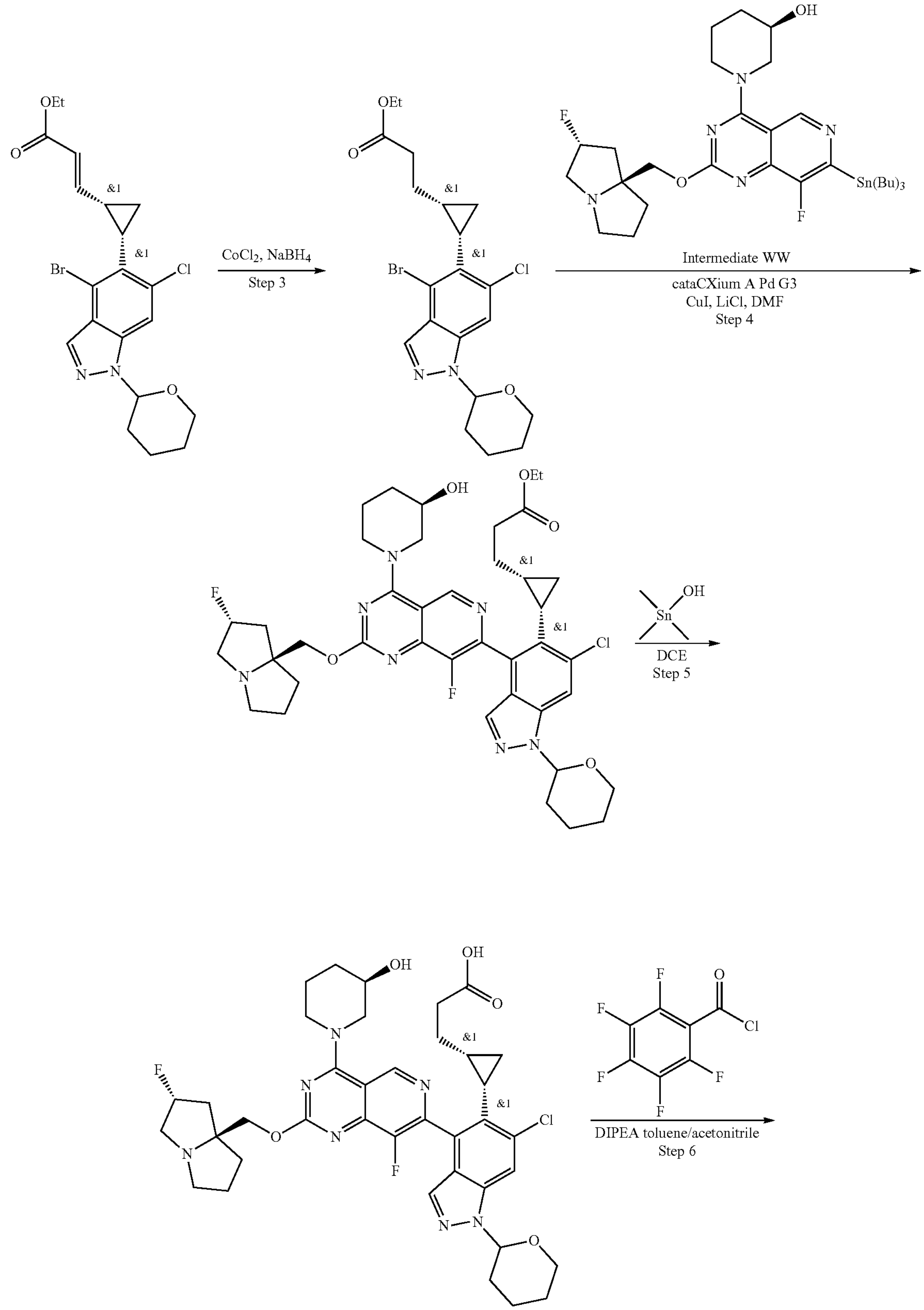

-continued

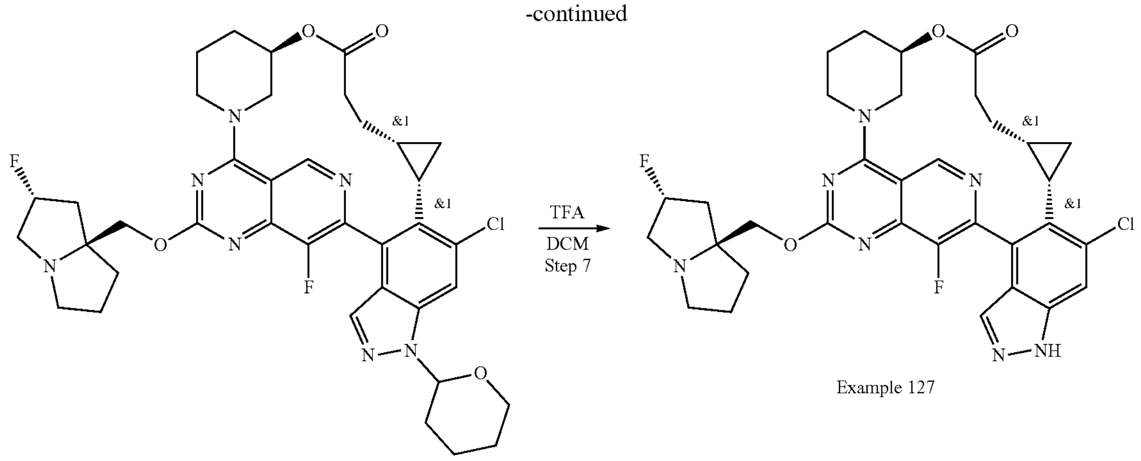

Example 127

Step 1. rac-(1R,2S)-2-(4-Bromo-6-chloro-1-(tetrahydro-2H-pyran-2-yl)-1H-indazol-5-yl)cyclopropane-1-carbaldehyde. To a stirred solution of rac-((1R,2S)-2-(4-bromo-6-chloro-1-(tetrahydro-2H-pyran-2-yl)-1H-indazol-5-yl)cyclopropyl)methanol (0.22 g, 0.58 mmol, Step 2 in Example 46) and (diacetoxyiodo)benzene (0.22 g, 0.69 mmol) in dichloromethane (3 mL) was added tempo (purified by sublimation, 9.0 mg, 0.058 mmol). The resulting mixture was stirred at rt for 2 h. The mixture was purified by column chromatography on silica gel, eluting with 0-40% EtOAc/heptane to afford rac-(1R,2S)-2-(4-bromo-6-chloro-1-(tetrahydro-2H-pyran-2-yl)-1H-indazol-5-yl)cyclopropane-1-carbaldehyde (0.19 g, 0.49 mmol, 84% yield) as white solid. m/z (ESI, +ve ion): 404.8 $(M+Na)^+$.

Step 2. rac-Ethyl (E)-3-((1R,2R)-2-(4-bromo-6-chloro-1-(tetrahydro-2H-pyran-2-yl)-1H-indazol-5-yl)cyclopropyl)acrylate. To a stirred solution of triethyl phosphonoacetate (0.12 mL, 0.59 mmol) in tetrahydrofuran (2 mL) was added sodium hydride (60% in mineral oil, 23 mg, 0.59 mmol) slowly at 0° C. The reaction mixture was stirred at 0° C. for 0.5 h, rac-(1R,2S)-2-(4-bromo-6-chloro-1-(tetrahydro-2H-pyran-2-yl)-1H-indazol-5-yl)cyclopropane-1-carbaldehyde (0.19 g, 0.49 mmol) in tetrahydrofuran (2 mL) was added. The resulting mixture was stirred at rt for 0.5 h, then was quenched with water and extracted with EtOAc. The organic layer was dried ($Na_2SO_4$) and concentrated and the residue was purified by column chromatography, eluting with a gradient of 0-30% EtOAc/heptane to afford rac-ethyl (E)-3-((1R,2R)-2-(4-bromo-6-chloro-1-(tetrahydro-2H-pyran-2-yl)-1H-indazol-5-yl)cyclopropyl)acrylate (0.21 g, 0.45 mmol, 93% yield) as colorless sticky oil. m/z (ESI, +ve ion): 474.8 $(M+Na)^+$.

Step 3. rac-Ethyl 3-((1R,2S)-2-(4-bromo-6-chloro-1-(tetrahydro-2H-pyran-2-yl)-1H-indazol-5-yl)cyclopropyl)propanoate. The mixture of rac-ethyl (E)-3-((1R,2R)-2-(4-bromo-6-chloro-1-(tetrahydro-2H-pyran-2-yl)-1H-indazol-5-yl)cyclopropyl)acrylate (198 mg, 0.47 mmol) and cobalt (II) chloride (11 mg, 0.087 mmol) in methanol (4 mL) was stirred at rt for 0.5 h. To this mixture was added sodium borohydride (66 mg, 1.7 mmol) in N,N-dimethylformamide (2 mL) slowly. The resulting mixture was stirred at rt for 0.5 h. The reaction mixture was poured into ice water and extracted with DCM. The organic layer was dried ($Na_2SO_4$) and concentrated. The residue was purified by column chromatography, eluting with a gradient of 0-20% EtOAc/heptane to afford rac-ethyl 3-((1R,2S)-2-(4-bromo-6-chloro-1-(tetrahydro-2H-pyran-2-yl)-1H-indazol-5-yl)cyclopropyl)propanoate (0.14 g, 0.30 mmol, 69% yield) as white solid. m/z (ESI, +ve ion): 477.1 $(M+Na)^+$.

Step 4. rac-Ethyl 3-((1R,2S)-2-(6-chloro-4-((S)-8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)cyclopropyl)propanoate. In a vial, a suspension of (R)-1-(8-fluoro-2-(((2R,7aS)-2-fluorotetrahydro-1H-pyrrolizin-7a(5H)-yl)methoxy)-7-(tributylstannyl)pyrido[4,3-d]pyrimidin-4-yl)piperidin-3-ol (0.32 g, 0.45 mmol, Intermediate W), rac-ethyl 3-((1R,2S)-2-(4-bromo-6-chloro-1-(tetrahydro-2H-pyran-2-yl)-1H-indazol-5-yl)cyclopropyl)propanoate (0.14 g, 0.30 mmol), cataCXium A Pd G3 (44 mg, 0.061 mmol), copper(I) iodide (29 mg, 0.15 mmol), and lithium chloride (26 mg, 0.61 mmol) in N,N-dimethylformamide (3 mL) was flushed with nitrogen and heated at 100° C. for 2 h. The reaction mixture was diluted with water and extracted with EtOAc. The organic layer was dried ($Na_2SO_4$) concentrated. The residue was purified by column chromatography, eluting with a gradient of 0-80% 3:1 (EtOAc/EtOH, with 2% $Et_3N$)/heptane to afford rac-ethyl 3-((1R,2S)-2-(6-chloro-4-((S)-8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)cyclopropyl)propanoate (0.15 g, 0.19 mmol, 61% yield) as yellow sticky solid. m/z (ESI, +ve ion): 780.3 $(M+H)^+$.

Step 5. rac-3-((1R,2S)-2-(6-Chloro-4-((S)-8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)cyclopropyl)propanoic acid. To a solution of rac-ethyl 3-((1R,2S)-2-(6-chloro-4-((S)-8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)cyclopropyl)propanoate (0.15 g, 0.19 mmol) in 1,2-dichloroethane (2 mL) was added trimethyltin hydroxide (0.34 g, 1.87 mmol). The resulting mixture was stirred at 70° C. overnight. The precipitate was filtered off and washed with DCM. The filtrate was concentrated and purified by reverse-phase C18 column, eluting with $CH_3CN$ (0.1% formic acid)/water (0.1% formic acid), to afford rac-3-((1R,2S)-2-(6-chloro-4-((S)-8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2- yl)-1H-indazol-5-yl)cyclopropyl)propanoic acid (66 mg, 0.088 mmol, 47% yield) as white solid. m/z (ESI, +ve ion): 752.4 (M+H)+.

Step 6. N-(Tetrahydro-2H-pyran-2-yl)-(11R,13S,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one and N-(Tetrahydro-2H-pyran-2-yl)-(11S,13R,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one. The mixture of rac-3-((1R,2S)-2-(6-chloro-4-((S)-8-fluoro-2-(((2R,7aS)-2-fluorotetrahydro-1H-pyrrolizin-7a(5H)-yl)methoxy)-4-((R)-3-hydroxypiperidin-1-yl)pyrido[4,3-d]pyrimidin-7-yl)-1-(tetrahydro-2H-pyran-2-yl)-1H-indazol-5-yl)cyclopropyl)propanoic acid (66 mg, 0.088 mmol) and Hunig's base (38 μL, 0.22 mmol) in acetonitrile (4 mL) and toluene (40 mL) was heated to 90° C. and stirred for 30 min. To this mixture was added 2,3,4,5,6-pentafluorobenzoyl chloride (15 μL, 0.11 mmol) slowly. The resulting mixture was stirred at 90° C. for 4 h. The reaction was concentrated and purified by reverse phase HPLC to afford N-(tetrahydro-2H-pyran-2-yl)-(11R,13S,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one and N-(tetrahydro-2H-pyran-2-yl)-(11S,13R,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one (28 mg, 0.038 mmol, 44% yield) as white solid. m/z (ESI, +ve ion): 734.0 (M+H)+.

Step 7. (11R,13S,18R)-9-Chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one, (11S,13R,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one. To a stirred solution of N-(tetrahydro-2H-pyran-2-yl)-(11R,13S,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one and N-(tetrahydro-2H-pyran-2-yl)-(11S,13R,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one (28 mg, 0.038 mmol) in dichloromethane (1 mL) was added trifluoroacetic acid (71 μL, 0.95 mmol). The resulting mixture was stirred at rt for 2 h. The reaction mixture was concentrated and purified by reverse phase HPLC to afford (11R,13S,18R)-9-chloro-31-fluoro-25-(((2R,7aS)-2-fluoro-tetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one, (11S,13R,18R)-9-chloro-31-fluoro-25-(((2R,7aS)-2-fluorotetrahydro-1H-pyrrolo[1,2-a]pyrrol-7a(5H)-yl)methoxy)-17-oxa-5,6,22,24,26,30-hexaazaheptacyclo[25.3.1.1~18,22~.0~2,10~.0~3,7~.0~11,13~.0~23,28~]dotriaconta-1(31),2,4,7,9,23,25,27,29-nonaen-16-one bis(2,2,2-trifluoroacetate) as white solid. $^1$H NMR (400 MHz, METHANOL-$d_4$) δ ppm 9.27 (s, 1H), 8.25 (d, J=0.8 Hz, 1H), 7.86 (s, 1H), 5.53-5.75 (m, 1H), 5.22 (br d, J=13.2 Hz, 1H), 5.11 (br s, 1H), 4.85-4.97 (m, 1H), 4.73-4.78 (m, 1H), 4.66-4.72 (m, 1H), 3.88-4.12 (m, 4H), 3.35-3.55 (m, 1H), 3.24-3.31 (m, 1H), 2.57-2.91 (m, 2H), 2.33-2.50 (m, 3H), 2.21 (br dd, J=5.9, 3.3 Hz, 1H), 1.95-2.16 (m, 4H), 1.87 (br d, J=14.0 Hz, 1H), 1.70-1.80 (m, 1H), 1.47-1.56 (m, 2H), 0.68-0.77 (m, 1H), 0.27-0.42 (m, 2H), −0.45-−0.36 (m, 1H). m/z (ESI, +ve ion): 649.9 (M+H)+.

(11S,13R,18R)-9-Chloro-31-fluoro-25-(((2R,7aS)-2-fluorotetrahydro-1H-pyrrolo[1,2-a]pyrrol-7a(5H)-yl)methoxy)-17-methyl-5,6,17,22,24,26,30-heptaaza-heptacyclo[25.3.1.1~18,22~.0~2,10~.0~3,7~.0~11,13~.0~23,28~]dotriaconta-1(31),2,4,7,9,23,25,27,29-nonaen-16-one bis (2,2,2-trifluoroaceate) (Example 128)

Example 128

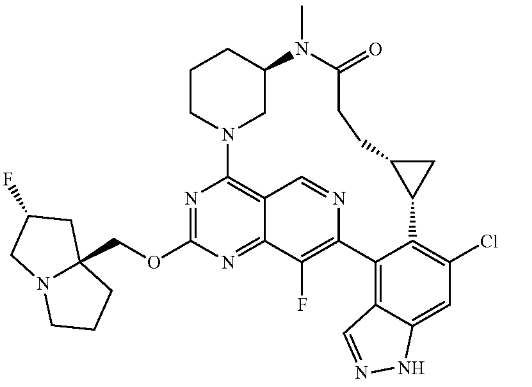

The title compound was synthesized in analagous manner as described above, using Intermediate SSS in Step 4. $^1$H NMR (400 MHz, METHANOL-$d_4$) δ ppm 9.24 (s, 1H), 8.26 (s, 1H), 7.85 (s, 1H), 5.49-5.75 (m, 1H), 4.94 (br d, J=13.0 Hz, 1H), 4.70-4.76 (m, 2H), 4.62 (br d, J=13.6 Hz, 1H), 3.89-4.10 (m, 4H), 3.43-3.57 (m, 1H), 3.23-3.29 (m, 1H), 3.11-3.21 (m, 1H), 2.74-2.79 (m, 3H), 2.58-2.71 (m, 2H), 2.36-2.52 (m, 3H), 2.10-2.28 (m, 4H), 1.85-2.01 (m, 4H), 1.44-1.52 (m, 1H), 0.62-0.72 (m, 1H), 0.36-0.43 (m, 1H), −0.01-0.13 (m, 1H), −0.55-−0.45 (m, 1H). m/z (ESI, +ve ion): 662.8 (M+H)+.

(17R)-30-Fluoro-24-(((2R,7aS)-2-fluorotetrahydro-1H-pyrrolo[1,2-a]pyrrol-7a(5H)-yl)methoxy)-9-methyl-15-oxa-5,6,21,23,25,29-hexaazahexacyclo[24.3.1.1~17,21~0.0~2,10~.0~3,7~.0~22,27~]hentriaconta-1(30),2,4,7,9,22,24,26,28-nonaene bis(2,2,2-trifluoroacetate) (Example 129)
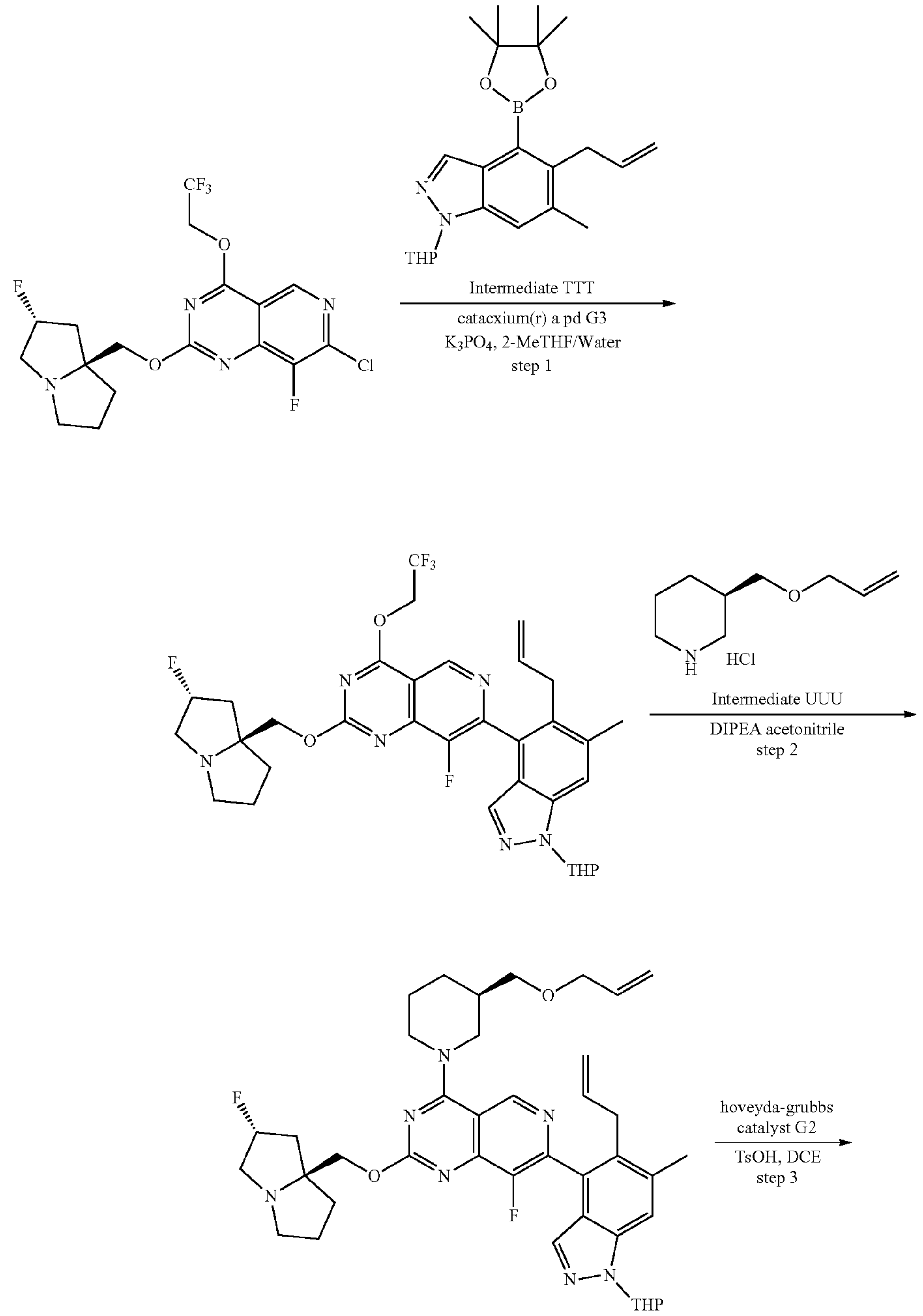

-continued

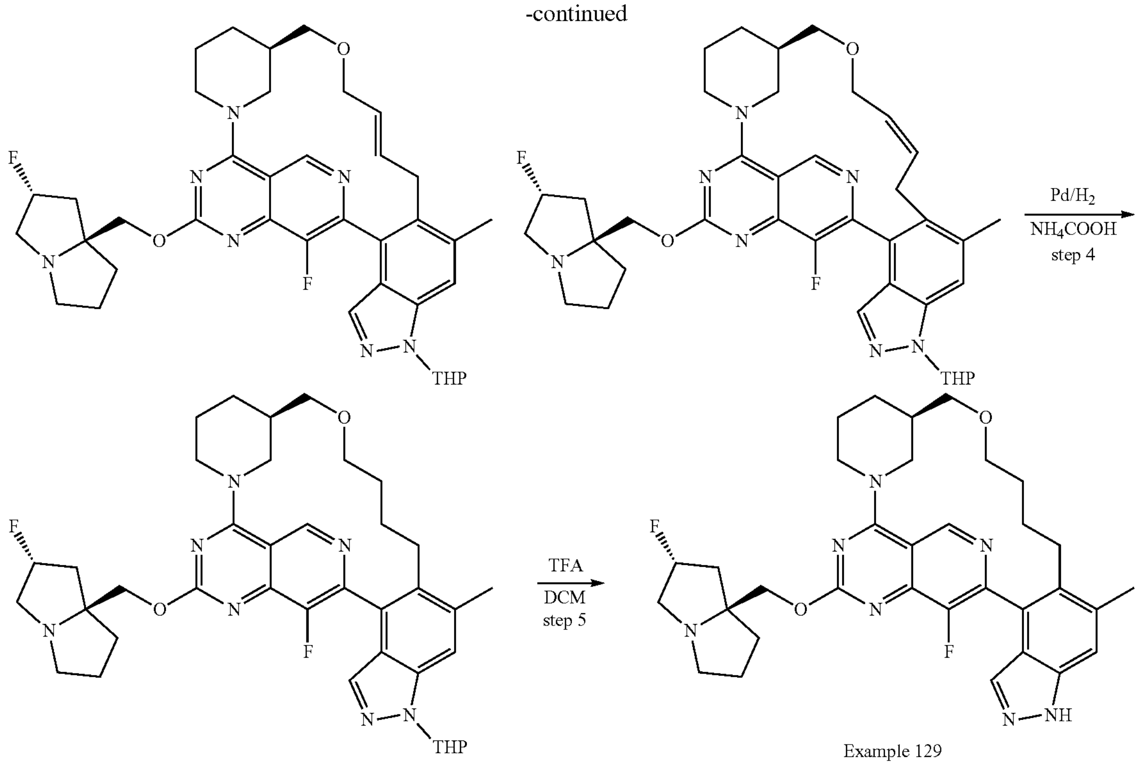

Example 129

Step 1. 7-(5-Allyl-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine. A vial was charged with 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (1.05 g, 2.39 mmol, Intermediate AA, Step 2), 5-allyl-6-methyl-1-(tetrahydro-2H-pyran-2-yl)-4-(4,4,5,5-tetramethyl-1,3,2-dioxaborolan-2-yl)-1H-indazole (1.00 g, 2.63 mmol, Intermediate TTT), potassium triphosphate (1.52 g, 7.18 mmol), cataCXium A Pd G3 (0.17 g, 0.24 mmol), 2-methyltetrahydrofuran (11 mL) and water (1.1 mL) under nitrogen. The reaction mixture was heated to 80° C. for 2 h. After cooling to rt, the reaction was concentrated and the crude material was purified by column chromatography on silica gel column, eluting with a gradient of 0-80% 3:1 EtOAc/EtOH (with 1% TEA) in heptane, to provide 7-(5-allyl-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (1.38 g, 2.1 mmol, 88% yield) as tan oil. m/z (ESI): 659.0 $(M+H)^+$.

Step 2. 7-(5-Allyl-6-methyl-1-(tetrahydro-2H-pyran-2-yl)-1H-indazol-4-yl)-4-((R)-3-((allyloxy)methyl)piperidin-1-yl)-8-fluoro-2-(((2R,7aS)-2-fluorotetrahydro-1H-pyrrolizin-7a(5H)-yl)methoxy)pyrido[4,3-d]pyrimidine. A 20-mL round-bottom flask was charged with 7-(5-allyl-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.49 g, 0.74 mmol), (R)-3-((allyloxy)methyl)piperidine hydrochloride (0.36 g, 1.86 mmol, Intermediate UUU) and DIPEA (0.65 mL, 3.7 mmol) in acetonitrile (3 mL). The reaction mixture was stirred at 60° C. for 3 h. After cooling to rt, the reaction mixture was fully concentrated and the crude material was injected into a C18 column (50 g), eluting with a gradient of 5-100% (0.1% formic acid MeCN)/(0.1% formic acid water) over 15 min. The desired fractions were basified with saturated aqueous sodium bicarbonate and extracted with EtOAc. The combined organic phases were concentrated under reduced pressure to provide 7-(5-allyl-6-methyl-1-(tetrahydro-2H-pyran-2-yl)-1H-indazol-4-yl)-4-((R)-3-((allyloxy)methyl)piperidin-1-yl)-8-fluoro-2-(((2R,7aS)-2-fluorotetrahydro-1H-pyrrolizin-7a(5H)-yl)methoxy)pyrido[4,3-d]pyrimidine (0.40 g, 0.56 mmol, 75% yield) as off-white solid. m/z (ESI): 714.0 $(M+H)^+$.

Step 3. (12E,17R)-30-Fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaazahexacyclo[24.3.1.1~17,21~.0~2,10~.0~3,7~.0~22,27~]hentriaconta-1(30),2,4,7,9,12,22,24,26,28-decaene and (12Z,17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaazahexacyclo[24.3.1.1~17,21~.0~2,10~.0~3,7~.0~22,27~]hentriaconta-1(30),2,4,7,9,12,22,24,26,28-decaene. To a 500-mL round-bottom flask was added 7-(5-allyl-6-methyl-1-(tetrahydro-2H-pyran-2-yl)-1H-indazol-4-yl)-4-((R)-3-((allyloxy)methyl)piperidin-1-yl)-8-fluoro-2-(((2R,7aS)-2-fluorotetrahydro-1H-pyrrolizin-7a(5H)-yl)methoxy)pyrido[4,3-d]pyrimidine (0.34 g, 0.48 mmol) and TsOH (0.11 g, 0.57 mmol) in 1,2-dichloroethane (227 mL). The reaction mixture was purged with $N_2$ and then Hoveyda-Grubbs catalyst 2nd generation (0.12 g, 0.19 mmol) was added. The reaction mixture was stirred under nitrogen at 80° C. for 6 h. After cooing to rt, the mixture was fully concentrated and the crude material was purified by column chromatography on silica gel, eluting with a gradient of 0-20% 2M $NH_3$-MeOH in DCM, to provide a mixture of (12E,17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaazahexacyclo[24.3.1.1~17,21~.0~2,10~.0~3,7~.0~22,27~]hentriaconta-1(30),2,4,7,9,12,22,24,26,28-decaene and (12Z,17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaaza-hexacyclo[24.3.1.1~17,21~.0~2,10~.0~3,7~.0~22,27~]hentriaconta-1(30),2,4,7,9,12,22,24,26,28-decaene (68 mg, 0.099 mmol, 21% yield) as white solid. m/z (ESI): 686.0 $(M+H)^+$.

Step 4. (17R)-30-Fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene. To a 8-mL vial was added (12E,17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaazahexacyclo[24.3.1.1~17,21~.0~2,10~.0~3,7~.0~22,27~]hentriaconta-1(30),2,4,7,9,12,22,24,26,28-decaene and (12Z,17R)-30-fluoro-24-(((2R,7aS)-2-fluorotetrahydro-1H-pyrrolo[1,2-a]pyrrol-7a(5H)-yl)methoxy)-9-methyl-(N-tetrahydro-2H-pyran-2-yl)-15-oxa-5,6,21,23,25,29-hexaazahexacyclo[24.3.1.1~17,21~.0~2,10~.0~3,7~.0~22,27~]hentriaconta-1(30),2,4,7,9,12,22,24,26,28-decaene (20 mg, 0.029 mmol), ammonium formate (18 mg, 0.29 mmol), palladium on activated carbon (3.1 mg, 2.9 μmol) in EtOH (0.3 mL). The reaction was stirred at 50° C. for 16 h. After cooling to rt, the catalyst was filtered through a pad of celite and the filtrate was concentrated, diluted with water, and extracted with EtOAc. The organic extract was washed with saturated NaCl, dried over $MgSO_4$, filtered, and concentrated in vacuo to give crude material. m/z (ESI): 688.0 $(M+H)^+$.

Step 5. (17R)-30-Fluoro-24-(((2R,7aS)-2-fluorotetrahydro-1H-pyrrolo[1,2-a]pyrrol-7a(5H)-yl)methoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene bis(2,2,2-trifluoroacetate). The material from last step dissolved in 1 mL of DCE was treated with 0.5 mL of TFA. The reaction mixture was stirred at rt for 1 h, concentrated, and the product was purified by reverse phase prep-HPLC to give (17R)-30-fluoro-24-(((2R,7aS)-2-fluorotetrahydro-1H-pyrrolo[1,2-a]pyrrol-7a(5H)-yl)methoxy)-9-methyl-15-oxa-5,6,21,23,25,29-hexaaza-hexacyclo[24.3.1.1~17,21~.0~2,10~.0~3,7~.0~22,27~]hentriaconta-1(30),2,4,7,9,22,24,26,28-nonaene bis(2,2,2-trifluoroacetate) as white solid. m/z (ESI): 604.0 $(M+H)^+$. $^1$H NMR (400 MHz, METHANOL-$d_4$): δ ppm 9.26 (s, 1H), 7.78 (s, 1H), 7.54 (s, 1H), 5.49-5.80 (m, 1H), 4.94-5.14 (m, 2H), 4.60-4.80 (m, 2H), 3.86-4.17 (m, 4H), 3.42-3.61 (m, 1H), 3.22-3.31 (m, 1H), 2.97-3.14 (m, 2H), 2.55 (s, 12H), 2.14-2.26 (m, 1H), 1.73-2.10 (m, 3H), 1.63-1.73 (m, 2H), 1.12-1.55 (in, 4H). $^{19}$F NMR (376 MHz, METHANOL-$d_4$): 6 ppm −77.24 (s), −143.34 (s), −174.06 (s). Stereochemistry of Example 129 was confirmed by X-Ray crystallography analysis.

TABLE 41

Additional Example 130 to 134. Prepared in an Analogous Manner to Example 129.

| Ex.# | Structure & Name | Salt Form | Reagent | Method Change |
|---|---|---|---|---|
| 130 | 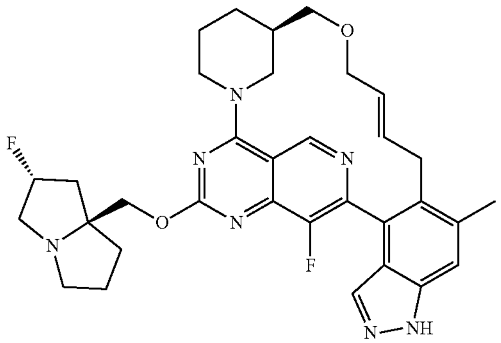 [SMILES: Cc1cc2[nH]ncc2c2c1C/C=C/COC[C@@H]1CCCN(C1)c1nc(OC[C@@]34CCCN3C[C@H](F)C4)nc3c(F)c-2ncc13] | bis (2,2,2-trifluoro-aceate) | | Step 4 was not performed. |
| 131 | 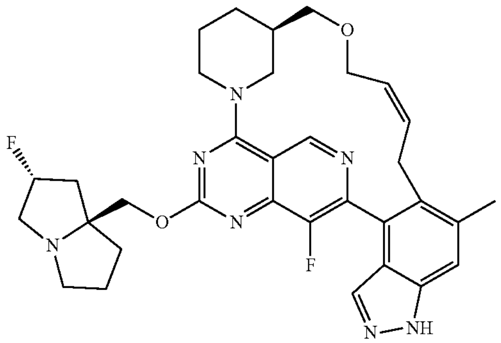 [SMILES: Cc1cc2[nH]ncc2c2c1C/C=C\COC[C@@H]1CCCN(C1)c1nc(OC[C@@]34CCCN3C[C@H](F)C4)nc3c(F)c-2ncc13] | bis (2,2,2-trifluor oaceate) | | Step 4 was not performed. |

TABLE 41-continued

Additional Example 130 to 134. Prepared in an Analogous Manner to Example 129.

| Ex.# | Structure & Name | Salt Form | Reagent | Method Change |
|---|---|---|---|---|
| 132 | 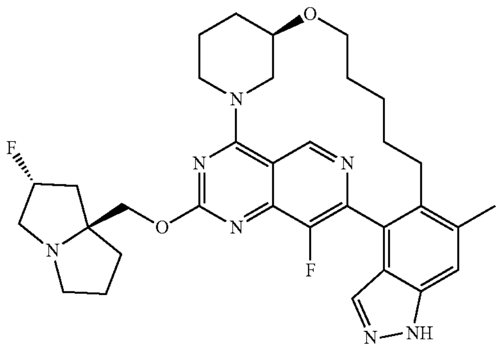 [SMILES: Cc1cc2[nH]ncc2c2c1CCCCCO[C@@H]1CCCN(C1)c1nc(OC[C@@]34CCCN3C[C@H](F)C4)nc3c(F)c-2ncc13] | bis (2,2,2-trifluoro-aceate) | Step 3. Intermediate VVV | Steps 1 & 2 were not performed. |
| 133 | 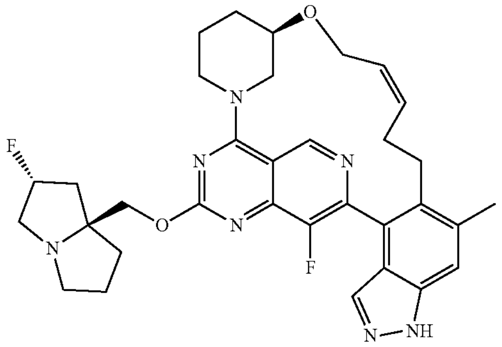 [SMILES: Cc1cc2[nH]ncc2c2c1CC/C=C\CO[C@@H]1CCCN(C1)c1nc(OC[C@@]34CCCN3C[C@H](F)C4)nc3c(F)c-2ncc13] | bis (2,2,2-trifluoro-aceate) | Step 3. Intermediate VVV | Steps 1, 2 & 4 were not performed. |
| 134 | 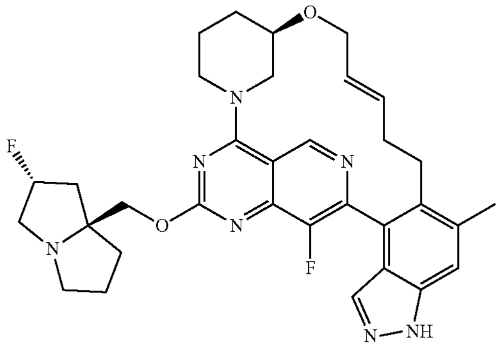 [SMILES: Cc1cc2[nH]ncc2c2c1CC/C=C/CO[C@@H]1CCCN(C1)c1nc(OC[C@@]34CCCN3C[C@H](F)C4)nc3c(F)c-2ncc13] | bis (2,2,2-trifluoro-aceate) | Step 3. Intermediate VVV | Steps 1, 2 & 4 were not performed. |

TABLE 42

Analytical Data for Examples 130 to 134.

| Cmpd.# | MS m/z (ESI): $(M + H)^+$ | $^1H$ NMR |
|---|---|---|
| 130 | 602.0 | $^1H$ NMR (400 MHz, METHANOL-$d_4$) δ ppm 9.22 (s, 1 H), 7.58-7.62 (m, 2 H), 5.52-5.78 (m, 1 H), 5.23-5.36 (m, 1 H), 4.99-5.19 (m, 3 H), 4.59-4.77 (m, 2 H), 3.83-4.14 (m, 4 H), 3.68-3.79 (m, 1 H), 3.54-3.62 (m, 2 H), 3.41-3.54 (m, 1 H), 3.12-3.31 (m, 3 H), 2.89-3.06 (m, 2 H), 2.54 (s, 6 H), 2.30-2.47 (m, 3 H), 2.16-2.27 (m, 1 H), 1.82-2.13 (m, 3 H), 1.57-1.74 (m, 2 H). |
| 131 | 602.0 | $^1H$ NMR (400 MHz, METHANOL-$d_4$) δ ppm 9.28 (s, 1 H), 7.53-7.83 (m, 2 H), 5.50-5.76 (m, 1 H), 5.02-5.40 (m, 4 H), 4.56-4.78 (m, 2 H), 3.78-4.25 (m, 4 H), 3.36-3.64 (m, 4 H), 3.13-3.31(m, 2 H), 2.91--3.10 (m, 1 H), 2.50-2.87 (m, 6 H), 2.32-2.50 (m, 3 H), 2.12-2.27 (m, 1 H), 1.97-2.10 (m, 2 H), 1.76-1.93 (m, 1 H), 1.57-1.72 (m, 2 H). |

TABLE 42-continued

Analytical Data for Examples 130 to 134.

| Cmpd.# | MS m/z (ESI): $(M + H)^+$ | $^1H$ NMR |
|---|---|---|
| 132 | 604.0 | $^1H$ NMR (400 MHz, METHANOL-$d_4$) δ ppm 9.33 (s, 1 H), 7.78 (d, J = 0.8 Hz, 1 H), 7.53 (s, 1 H), 5.52-5.74 (m, 1 H), 4.98-5.09 (m, 2 H), 4.73-4.78 (m, 1 H), 4.66 (d, J = 12.3 Hz, 1 H), 3.85-4.12 (m, 4 H), 3.35-3.54 (m, 3 H), 3.23-3.31 (m, 1 H), 2.96-3.03 (m, 1 H), 2.83-2.91 (m, 1 H), 2.56-2.81 (m, 6 H), 2.34-2.47 (m, 3 H), 2.14-2.24 (m, 1 H), 2.04-2.14 (m, 1 H), 1.83-1.96 (m, 2 H), 1.58-1.64 (m, 1 H), 1.39-1.49 (m, 1 H), 1.04-1.22 (m, 3 H), 0.89-0.99 (m, 1 H), 0.40-0.50 (m, 1 H). |
| 133 | 602.0 | $^1H$ NMR (400 MHz, METHANOL-$d_4$) δ ppm 9.29-9.38 (m, 1 H), 7.81-7.88 (m, 1 H), 7.52-7.58 (m, 1 H), 5.53-5.72 (m, 1 H), 4.95-5.19 (m, 4 H), 4.58-4.74 (m, 2 H), 3.90-4.12 (m, 4 H), 3.63 (dd, J = 12.0, 8.0 Hz, 1 H), 3.45-3.57 (m, 2 H), 3.14-3.31 (m, 1 H), 3.04 (dt, J = 14.2, 6.0 Hz, 1 H), 2.50-2.70 (m, 6 H), 2.33-2.47 (m, 4 H), 2.16-2.25 (m, 1 H), 1.85-2.14 (m, 5 H), 1.59-1.78 (m, 1 H). |
| 134 | 602.0 | $^1H$ NMR (400 MHz, METHANOL-$d_4$) δ ppm 9.33-9.39 (m, 1 H), 7.84-7.87 (m, 1 H), 7.52-7.57 (m, 1 H), 5.51-5.73 (m, 1 H), 5.22-5.30 (m, 1 H), 4.95-5.20 (m, 3 H), 4.70-4.76 (m, 1 H), 4.62-4.70 (m, 1 H), 3.85-4.10 (m, 4 H), 3.46-3.64 (m, 3 H), 3.35-3.43 (m, 1 H), 3.15-3.31 (m, 1 H), 2.90-3.07 (m, 1 H), 2.54-2.85 (m, 5 H), 2.32-2.49 (m, 4 H), 2.14-2.26 (m, 1 H), 1.99-2.11 (m, 1 H), 1.81-1.97 (m, 3 H), 1.63 (br d, J = 12.3 Hz, 1 H), 1.39-1.55 (m, 1 H). |

(17R)-9-Chloro-30-fluoro-24-(((2R,7aS)-2-fluorotetrahydro-1H-pyrrolo[1,2-a]pyrrol-7a(5H)-yl)methoxy)-15,18-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene trifluoroacetate (Example 135)

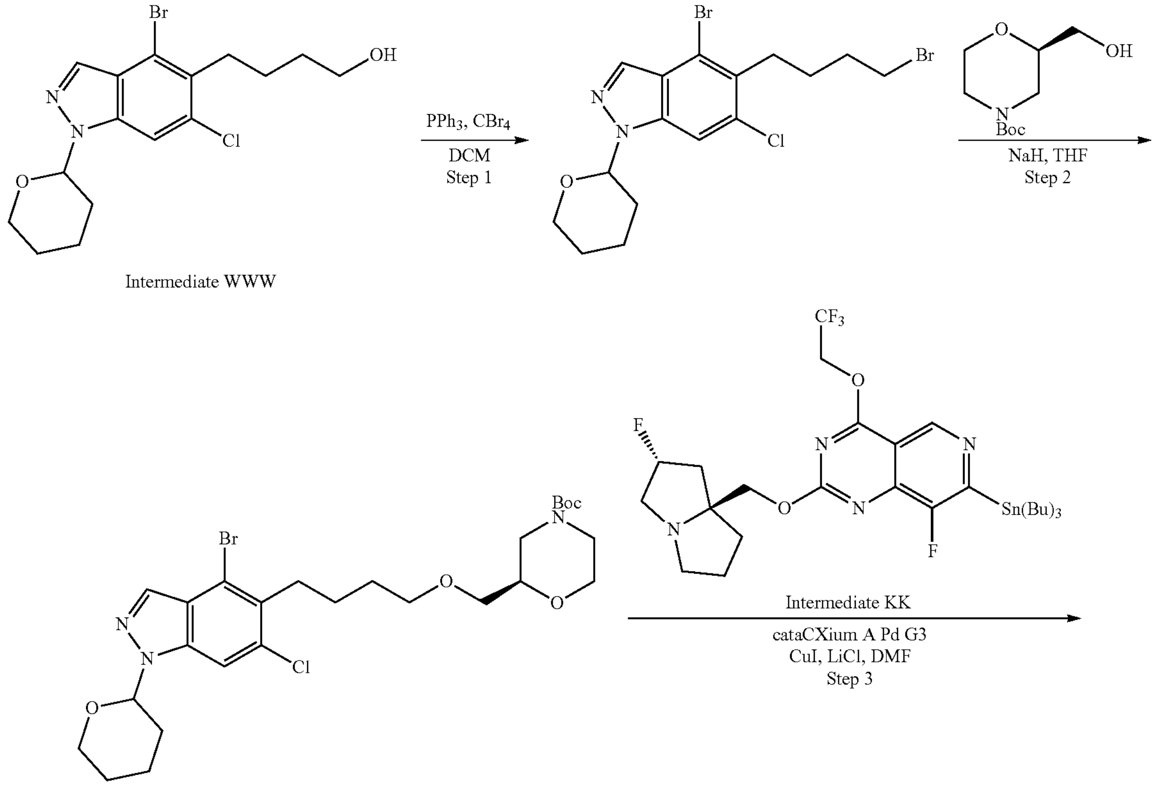

-continued

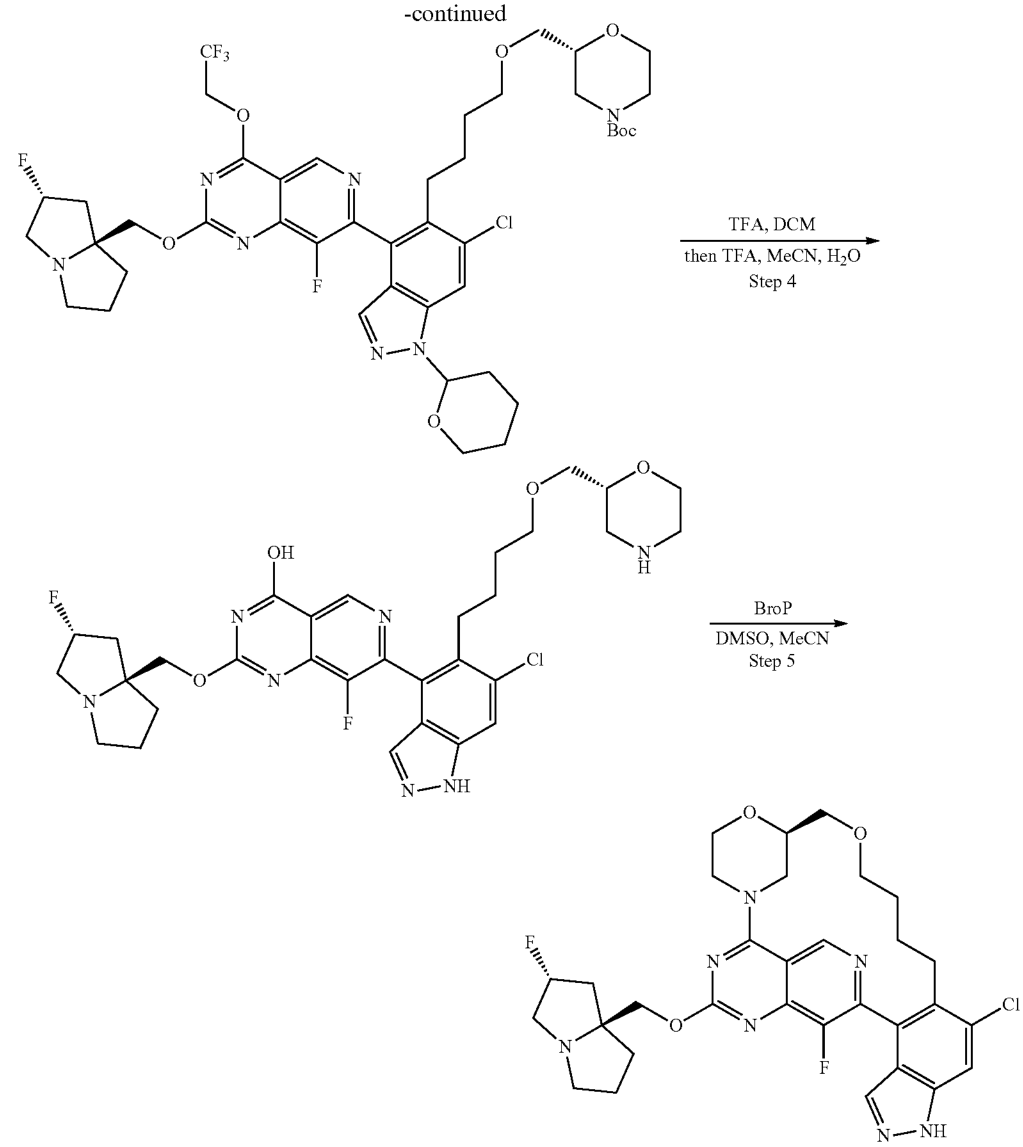

Example 135

Step 1. 4-Bromo-5-(4-bromobutyl)-6-chloro-1-(tetrahydro-2H-pyran-2-yl)-1H-indazole. To a solution of triphenylphosphine (2.44 g, 9.29 mmol) in dichloromethane (40 mL) was added carbon tetrabromide (3.59 g, 10.8 mmol). The reaction mixture was stirred at rt for 10 min, then 4-(4-bromo-6-chloro-1-(tetrahydro-2H-pyran-2-yl)-1H-indazol-5-yl)butan-1-ol (3 g, 7.74 mmol, Intermediate WWW) was added. The reaction mixture was stirred for 1.5 h. The solution was filtered, and the filtrate was concentrated. The crude residue was purified by flash column chromatography on silica gel, eluting with 0-20% EtOAc in heptane to give 4-bromo-5-(4-bromobutyl)-6-chloro-1-(tetrahydro-2H-pyran-2-yl)-1H-indazole (3.15 g, 6.99 mmol, 90% yield) as colorless oil. m/z (ESI): 448.8 $(M+H)^+$.

Step 2. tert-Butyl (2R)-2-((4-(4-bromo-6-chloro-1-(tetrahydro-2H-pyran-2-yl)-1H-indazol-5-yl)butoxy)methyl) morpholine-4-carboxylate. To a solution of (R)-tert-butyl 2-(hydroxymethyl)morpholine-4-carboxylate (0.32 g, 1.47 mmol) in tetrahydrofuran (9 mL) was added sodium hydride, 60% dispersion in mineral oil (85 mg, 2.13 mmol). After 10 min, a solution of 4-bromo-5-(4-bromobutyl)-6-chloro-1-(tetrahydro-2H-pyran-2-yl)-1H-indazole (0.60 g, 1.33 mmol) in tetrahydrofuran (4.5 mL) was added. The reaction was stirred at 50° C. for 48 h. After cooling to rt, the reaction was quenched with saturated ammonium chloride solution and then extracted with EtOAc. The organic layer was dried over $Na_2SO_4$, filtered, and concentrated. The crude material was purified by flash column chromatography on silica gel, eluting with a gradient of 0-50% EtOAc in heptane to give tert-butyl (2R)-2-((4-(4-bromo-6-chloro-1-(tetrahydro-2H-pyran-2-yl)-1H-indazol-5-yl)butoxy) methyl)morpholine-4-carboxylate (0.36 g, 0.62 mmol, 46% yield) as yellow oil. m/z (ESI): 486.0 $(M-Boc+H)^+$.

Step 3. tert-Butyl (2R)-2-((4-(6-chloro-4-(8-fluoro-2-(((2R,7aS)-2-fluorotetrahydro-1H-pyrrolizin-7a(5H)-yl) methoxy)-4-(2,2,2-trifluoroethoxy)pyrido[4,3-d]pyrimidin-7-yl)-1-(tetrahydro-2H-pyran-2-yl)-1H-indazol-5-yl) butoxy)methyl)morpholine-4-carboxylate. A vial was charged with tert-butyl (2R)-2-((4-(4-bromo-6-chloro-1-(tetrahydro-2H-pyran-2-yl)-1H-indazol-5-yl)butoxy)

methyl)morpholine-4-carboxylate (0.36 g, 0.62 mmol), cataCXium A Pd G3 (90 mg, 0.12 mmol), copper iodide (59 mg, 0.31 mmol), lithium chloride (52 mg, 1.20 mmol), 8-fluoro-2-(((2R,7aS)-2-fluorotetrahydro-1H-pyrrolizin-7a(5H)-yl)methoxy)-7-(tributylstannyl)-4-(2,2,2-trifluoroethoxy)pyrido[4,3-d]pyrimidine (0.86 g, 1.24 mmol, Intermediate KK), and degassed N,N-dimethylformamide (6.2 mL). The reaction mixture was heated to 100° C. for 3 h. After cooling to rt, the reaction mixture was purified by reverse phase column chromatography (10-100% (MeCN/$H_2O$+0.1% formic acid). The desired fractions were basified with saturated aqueous sodium bicarbonate and extracted with EtOAc. The combined organic phases were concentrated to provide tert-butyl (2R)-2-((4-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)butoxy)methyl)morpholine-4-carboxylate (0.21 g, 0.23 mmol, 37% yield). m/z (ESI): $(M+H)^+$ 910.7.

Step 4. 7-(6-Chloro-5-(4-(((R)-morpholin-2-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol. To a 20 mL flask was charged with tert-butyl (2R)-2-((4-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)butoxy)methyl)morpholine-4-carboxylate (0.21 g, 0.23 mmol) in dichloromethane (2.5 mL). TFA (0.9 mL, 12 mmol) was added, and the reaction mixture was stirred at rt for 30 min. The mixture was concentrated, and the residue was diluted with acetonitrile (2.5 mL) and water (2.5 mL), and treated with TFA (0.9 mL, 12 mmol) again. The reaction mixture was then stirred at room temperature for 40 min. The content was concentrated and the crude material was purified by reverse phase flash column chromatography (5-80% MeCN/$H_2O$+0.1% formic acid) to give 7-(6-chloro-5-(4-(((R)-morpholin-2-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol (95 mg, 0.15 mmol, 64% yield) as yellow solid. m/z (ESI): 643.9 $(M+H)^+$.

Step 5. (17R)-9-Chloro-30-fluoro-24-(((2R,7aS)-2-fluorotetrahydro-1H-pyrrolo[1,2-a]pyrrol-7a(5H)-yl)methoxy)-15,18-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene 2,2,2-trifluoroacetate. A vial was charged with bromotris(dimethylamino)phosphonium hexafluorophosphate (86 mg, 0.22 mmol), DIPEA (0.13 mL, 0.74 mmol) in acetonitrile (30 mL). A solution of 7-(6-chloro-5-(4-(((R)-morpholin-2-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol (95 mg, 0.15 mmol) in dimethyl sulfoxide (2 mL) was added via syringe pump over 40 min, then the reaction was stirred at rt for 16 h. The reaction was concentrated and the residue was purified by reverse phase preparative HPLC to afford (17R)-9-chloro-30-fluoro-24-(((2R,7aS)-2-fluorotetrahydro-1H-pyrrolo[1,2-a]pyrrol-7a(5H)-yl)methoxy)-15,18-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene 2,2,2-trifluoroacetate (43 mg, 0.058 mmol, 39% yield) as white solid. m/z (ESI): 625.9 $(M+H)^+$. $^1H$ NMR (400 MHz, METHANOL-$d_4$) δ ppm 9.26-9.33 (m, 1H), 7.83-7.90 (m, 1H), 7.82 (s, 1H), 5.52-5.72 (m, 1H), 4.84-5.04 (m, 2H), 4.63-4.76 (m, 3H), 4.20 (dd, J=13.9, 3.9 Hz, 1H), 3.88-4.12 (m, 4H), 3.74-3.85 (m, 2H), 3.46-3.65 (m, 3H), 3.23 (br dd, J=9.1, 3.9 Hz, 1H), 3.04-3.16 (m, 1H), 2.93-3.03 (m, 1H), 2.78-2.92 (m, 2H), 2.54-2.75 (m, 3H), 2.33-2.51 (m, 4H), 2.14 (s, 1H), 1.22-1.50 (m, 4H). $^{19}F$ NMR (376 MHz, METHANOL-$d_4$) δ ppm −73.94 (s), −75.82 (s), −77.31 (s), −143.02 (s), −174.08 (s). Stereochemistry of Example 135 was confirmed by X-Ray crystallography analysis.

TABLE 43

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 136 | 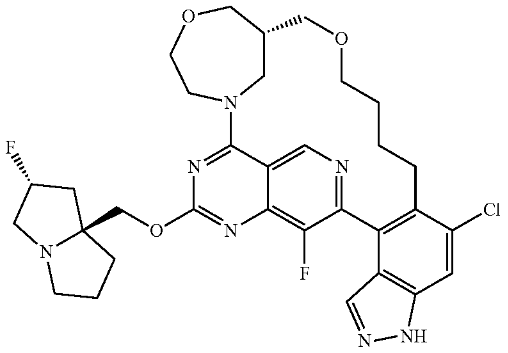 [SMILES: Fc1c2ncc3c(nc(OC[C@@]45CCCN4C[C@H](F)C5)nc13)N1CCOC[C@H](COCCCCc3c(Cl)cc4[nH]ncc4c3-2)C1] (26S)-18-chloro-32-fluoro-4-(((2R,7aS)-2-fluorotetrahydro-1H-pyrrolo[1,2-a]pyrrol-7a(5H)-yl)methoxy)-24,28-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaene | NA | Step 2. tert-butyl 6-(hydroxy-methyl)-1,4-oxazepane-4-carboxylate (CAS#: 1063734-19-9, AA Blocks LLC.) | Chiral separation by SFC in Step 5. Details included below. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 137 | 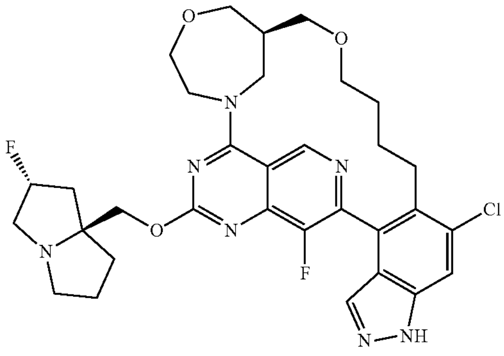 [SMILES: Fc1c2ncc3c(nc(OC[C@@]45CCCN4C[C@H](F)C5)nc13)N1CCOC[C@@H](COCCCCc3c(Cl)cc4[nH]ncc4c3-2)C1] (26R)-18-chloro-32-fluoro-4-(((2R,7aS)-2-fluorotetrahydro-1H-pyrrolo[1,2-a]pyrrol-7a(5H)-yl)methoxy)-24,28-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaene | NA | Step 2: tert-butyl 6-(hydroxy-methyl)-1,4-oxazepane-4-carboxylate (CAS#: 1063734-19-9, AA Blocks LLC.) | Chiral separation by SFC in Step 5. Details included below. |
| 138 | 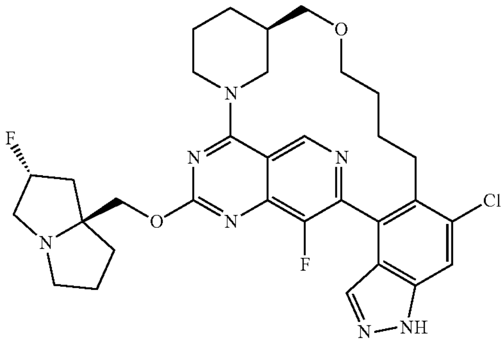 [SMILES: Fc1c2ncc3c(nc(OC[C@@]45CCCN4C[C@H](F)C5)nc13)N1CCC[C@@H](COCCCCc3c(Cl)cc4[nH]ncc4c3-2)C1] (17R)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7,~.0~22,27~]hentriaconta-1(30),2,4,7,9,22,24,26,28-nonaene | 2,2,2-trifluoro-aceate | Step 2: tert-butyl (R)-3-(hydroxymethyl) piperidine-1-carboxylate (CAS#: 140695-85-8, Ambeed, Inc.) | |
| 139 | 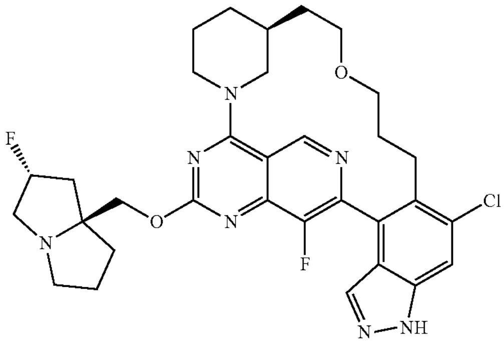 [SMILES: Fc1c2ncc3c(nc(OC[C@@]45CCCN4C[C@H](F)C5)nc13)N1CCC[C@@H](CCOCCCc3c(Cl)cc4[nH]ncc4c3-2)C1] (17S)-9-chloro-30-fluoro-24-(((2R,7aS)-2-fluorotetrahydro-1H-pyrrolo[1,2-a]pyrrol-7a(5H)-yl)methoxy)-14-oxa-5,6,21,23,25,29-hexaazahexacyclo[24.3.1.1~17,21~.0~2,10~.0~3,7,~.0~22,27~]hentriaconta-1(30),2,4,7,9,22,24,26,28-nonaene | bis (2,2,2-trifluoro-acetate) | Step 3. Intermediate YYY | Step 1 & 2 was not performed. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 140 | 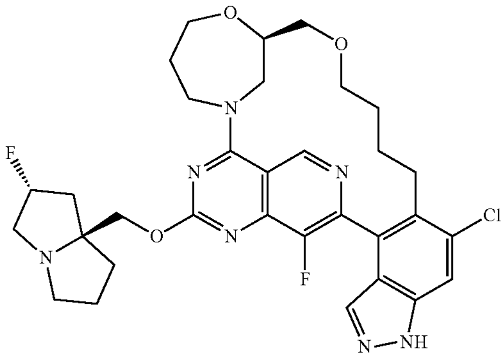 [SMILES: Fc1c2ncc3c(nc(OC[C@@]45CCCN4C[C@H](F)C5)nc13)N1CCCO[C@@H](COCCCCc3c(Cl)cc4[nH]ncc4c3-2)C1] (26S)-18-chloro-32-fluoro-4-(((2R,7aS)-2-fluorotetrahydro-1H-pyrrolo[1,2-a]pyrrol-7a(5H)-yl)methoxy)-24,27-dioxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaene | | Step 1. tert-butyl (2R)-2-(hydroxy-methyl)-1,4-oxazepane-4-carboxylate (CAS#: 911223-23-9) | |
| 141 | 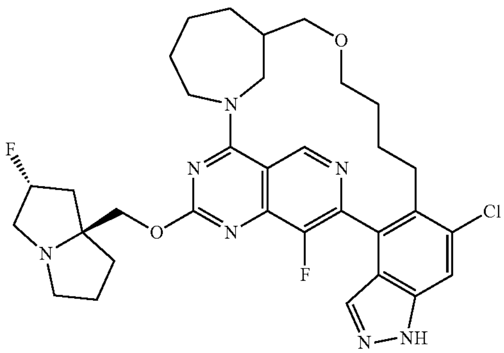 [SMILES: Fc1c2ncc3c(nc(OC[C@@]45CCCN4C[C@H](F)C5)nc13)N1CCCCC(COCCCCc3c(Cl)cc4[nH]ncc4c3-2)C1] (26S)-18-chloro-32-fluoro-4-(((2R,7aS)-2-fluorotetrahydro-1H-pyrrolo[1,2-a]pyrrol-7a(5H)-yl)methoxy)-24-oxa-1,3,5,9,14,15-hexaazahexacyclo[24.4.1.1~6,10~.0~2,7~.0~11,19~.0~12,16~]dotriaconta-2,4,6,8,10(32),11,13,16,18-nonaene | bis (2,2,2-trifluoro-aceate | Step 1. tert-butyl 3-(hydroxymethyl) azepane-1-carboxylate-97% (CAS: 876147-43-2) | |
| 142 | 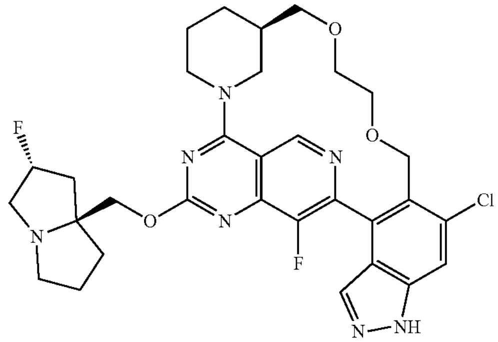 [SMILES: Fc1c2ncc3c(nc(OC[C@@]45CCCN4C[C@H](F)C5)nc13)N1CCC[C@@H](COCCOCc3c(Cl)cc4[nH]ncc4c3-2)C1] (17R)-9-chloro-30-fluoro-24-(((2R,7aS)-2-fluorotetrahydro-1H-pyrrolo[1,2-a]pyrrol-7a(5H)-yl)methoxy)-12,15-dioxa-5,6,21,23,25,29-hexaazahexacyclo[24.3.1.1~17,21~.0~2,10~.0~3,7,~.0~22,27~]hentriaconta-1(30),2,4,7,9,22,24,26,28-nonaene | 2,2,2-trifluoro-aceate | Step 3. Intermediate AAAA | Steps 1 & 2 were not performed. Step 4. No $2^{nd}$ TFA in $CH_3CN$ deprotection was performed. Step 5. $Cs_2CO_3$, DMF (0.01M), 90° C. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 143 | 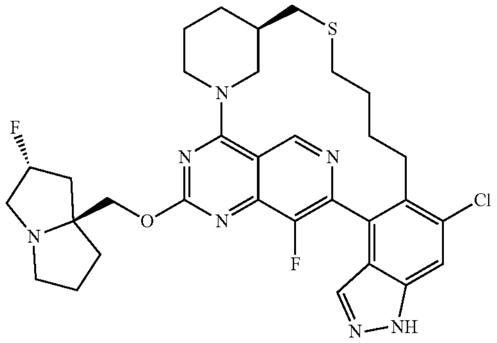 [SMILES: Fc1c2ncc3c(nc(OC[C@@]45CCCN4C[C@H](F)C5)nc13)N1CCC[C@@H](CSCCCCc3c(Cl)cc4[nH]ncc4c3-2)C1] (17R)-9-chloro-30-fluoro-24-(((2R,7aS)-2-fluorotetrahydro-1H-pyrrolo[1,2-a]pyrrol-7a(5H)-yl)methoxy)-15-thia-5,6,21,23,25,29-hexaazahexacyclo[24.3.1.1~17,21~.0~2,10~.0~3,7,~.0~22,27~]hentriaconta-1(30),2,4,7,9,22,24,26,28-nonaene | bis (2,2,2-trifluoro-acetate) | Step 3. Intermediate CCCC | Steps 1 & 2 were not performed. |
| 144 | 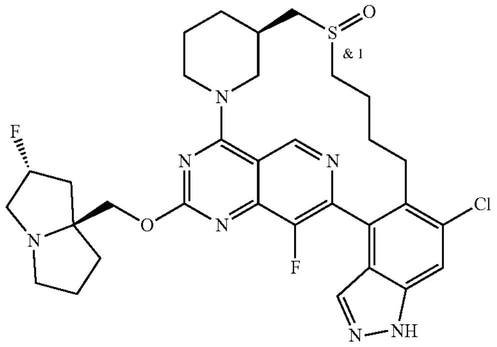 [SMILES: O=S1CCCCc2c(Cl)cc3[nH]ncc3c2-c2ncc3c(nc(OC[C@@]45CCCN4C[C@H](F)C5)nc3c2F)N2CCC[C@H](C2)C1] (15R,17R)-9-chloro-30-fluoro-24-(((2R,7aS)-2-fluorotetrahydro-1H-pyrrolo[1,2-a]pyrrol-7a(5H)-yl)methoxy)-15-thia-5,6,21,23,25,29-hexaazahexacyclo[24.3.1.1~17,21~.0~2,10~.0~3,7,~.0~22,27~]hentriaconta-1(30),2,4,7,9,22,24,26,28-nonaene 15-oxide | bis (2,2,2-trifluoro-acetate) | Step 3. Intermediate DDDD | Steps 1 & 2 were not performed. |
| 145 | 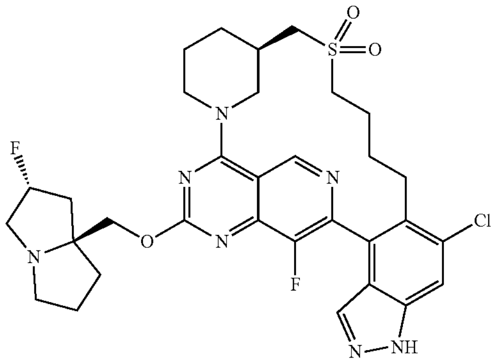 [SMILES: O=S1(=O)CCCCc2c(Cl)cc3[nH]ncc3c2-c2ncc3c(nc(OC[C@@]45CCCN4C[C@H](F)C5)nc3c2F)N2CCC[C@H](C2)C1] (17R)-9-chloro-30-fluoro-24-(((2R,7aS)-2-fluorotetrahydro-1H-pyrrolo[1,2-a]pyrrol-7a(5H)-yl)methoxy)-15-thia-5,6,21,23,25,29-hexaazahexacyclo[24.3.1.1~17,21~.0~2,10~.0~3,7,~.0~22,27~]hentriaconta-1(30),2,4,7,9,22,24,26,28-nonaene 15,15-dioxide | 2,2,2-trifluoro-acetate | Step 3. Intermediate EEEE | Steps 1 & 2 were not performed. |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 146 | 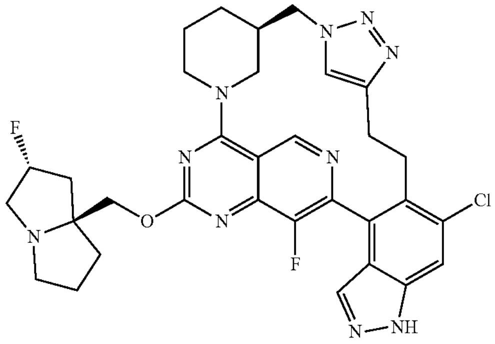 [SMILES: Fc1c2ncc3c(nc(OC[C@@]45CCCN4C[C@H](F)C5)nc13)N1CCC[C@H](C1)Cn1cc(nn1)CCc1c(Cl)cc3[nH]ncc3c1-2] (18R)-9-chloro-31-fluoro-25-(((2R,7aS)-2-fluorotetrahydro-1H-pyrrolo[1,2-a]pyrrol-7a(5H)-yl)methoxy)-5,6,14,15,16,22,24,26,30-nonaazaheptacyclo[25.3.1.1~13,16~.1~18,22~.0~2,10~.0~3,7~.0~23,28~]tritriaconta-1(31),2,4,7,9,13(33),14,23,25,27,29-undecaene | 2,2,2-trifluoro-acetate | Step 3. Intermediate GGGG | Steps 1 & 2 were not performed. |
| 147 | 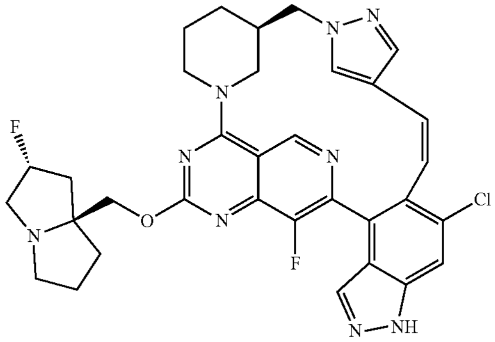 [SMILES: Fc1c2ncc3c(nc(OC[C@@]45CCCN4C[C@H](F)C5)nc13)N1CCC[C@H](C1)Cn1cc(cn1)/C=C\c1c(Cl)cc3[nH]ncc3c1-2] (11Z,18R)-9-chloro-31-fluoro-25-(((2R,7aS)-2-fluorotetrahydro-1H-pyrrolo[1,2-a]pyrrol-7a(5H)-yl)methoxy)-5,6,15,16,22,24,26,30-octaazaheptacyclo[25.3.1.1~13,16~.1~18,22~.0~2,10~.0~3,7~.0~23,28~]tritriaconta-1(31),2,4,7,9,13(33),14,23,25,27,29-dodecaene | NA | Step 3. Intermediate HHHH | Steps 1 & 2 were not performed. |
| 148 | 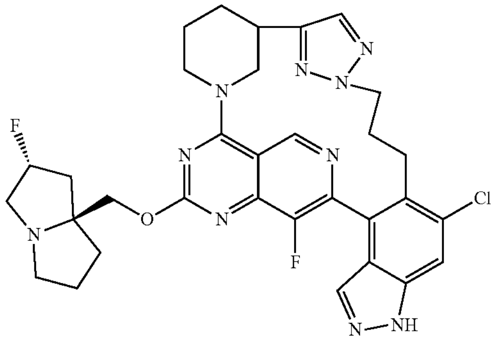 [SMILES: Fc1c2ncc3c(nc(OC[C@@]45CCCN4C[C@H](F)C5)nc13)N1CCCC(C1)c1cnn(n1)CCCc1c(Cl)cc3[nH]ncc3c1-2] 9-chloro-31-fluoro-25-(((2R,7aS)-2-fluorotetrahydro-1H-pyrrolo[1,2-a]pyrrol-7a(5H)-yl)methoxy)-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene | NA | Step 3. Intermediate IIII | Steps 1 & 2 were not performed. Step 4. No 2$^{nd}$ TFA in $CH_3CN$ deprotection was performed. Step 5. $Cs_2CO_3$, DMF (0.01M), 90° C. |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 149 | 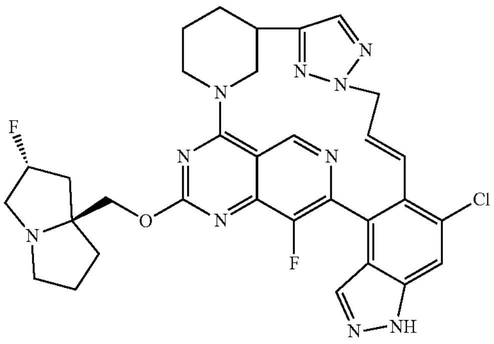 [SMILES: Fc1c2ncc3c(nc(OC[C@@]45CCCN4C[C@H](F)C5)nc13)N1CCCC(C1)c1cnn(n1)C/C=C/c1c(Cl)cc3[nH]ncc3c1-2] (11E)-9-chloro-31-fluoro-25-(((2R,7aS)-2-fluorotetrahydro-1H-pyrrolo[1,2-a]pyrrol-7a(5H)-yl)methoxy)-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,11,15,17(33),23,25,27,29-dodecaene | NA | Step 3. Intermediate JJJJ | Steps 1 & 2 were not performed. Step 4. No 2$^{nd}$ TFA in $CH_3CN$ deprotection was performed. Step 5. $Cs_2CO_3$, DMF (0.01M), 90° C. |
| 223 | 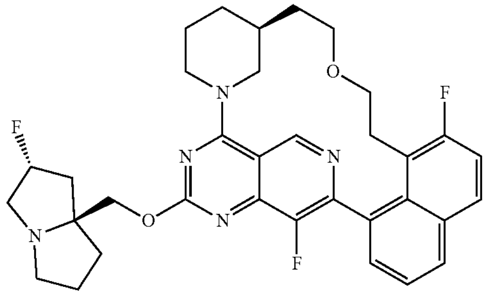 [SMILES: Fc1ccc2cccc3c2c1CCOCC[C@@H]1CCCN(C1)c1nc(OC[C@@]24CCCN2C[C@H](F)C4)nc2c(F)c-3ncc12] (15S)-22,31-difluoro-8-(((2R,7aS)-2-fluorotetrahydro-1H-pyrrolo[1,2-a]pyrrol-7a(5H)-yl)methoxy)-18-oxa-3,7,9,11-tetraazahexacyclo[19.7.1.1~2,6~.1~11,15~.0~5,10~.0~25,29~]hentriaconta-21(29),2(31),3,5,7,9,21,23,25,27-decaene | NA | Step 3. Intermediate BV | Steps 1 & 2 were not performed. Step 3. Pd(P'Bu$_3$), dioxane, 110° C. was used Step 4. 1M HCl in dioxane was used |
| 224 | 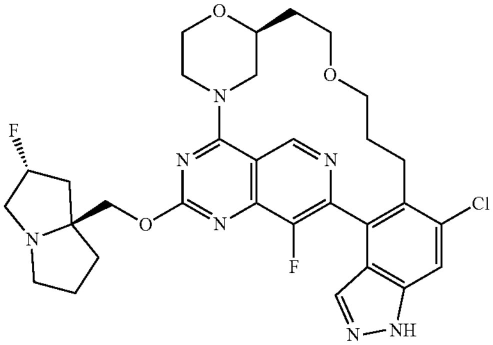 [SMILES: Fc1c2ncc3c(nc(OC[C@@]45CCCN4C[C@H](F)C5)nc13)N1CCO[C@@H](CCOCCCc3c(Cl)cc4[nH]ncc4c3-2)C1] (17S)-9-chloro-30-fluoro-24-(((2R,7aS)-2-fluorotetrahydro-1H-pyrrolo[1,2-a]pyrrol-7a(5H)-yl)methoxy)-14,18-dioxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene | NA | Step 2. 1,1-Dimethylethyl (2S)-2-(2-hydroxyethyl)-4-morpholinecarboxylate and Intermediate BW | Step 1 was not performed. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 225 | 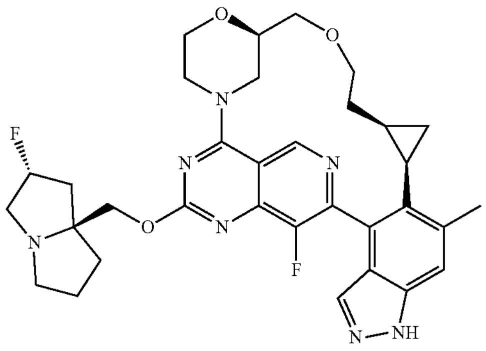 [SMILES: Cc1cc2[nH]ncc2c2c1[C@@H]1C[C@@H]1CCOC[C@H]1CN(CCO1)c1nc(OC[C@@]34CCCN3C[C@H](F)C4)nc3c(F)c-2ncc13] (11R,13R,18R)-31-fluoro-25-(((2R,7aS)-2-fluorotetrahydro-1H-pyrrolo[1,2-a]pyrrol-7a(5H)-yl)methoxy)-9-methyl-16,19-dioxa-5,6,22,24,26,30-hexaazahexacyclo[25.3.1.1~18,22~.0~2,10~.0~3,7~.0~11,13~.0~23,28~]dotriaconta-1(31),2,4,7,9,23,25,27,29-nonaene | NA | Step 2. Intermediate BT | Step 1 was not performed. Chiral separation after Step 5. Details included below. |
| 226 | 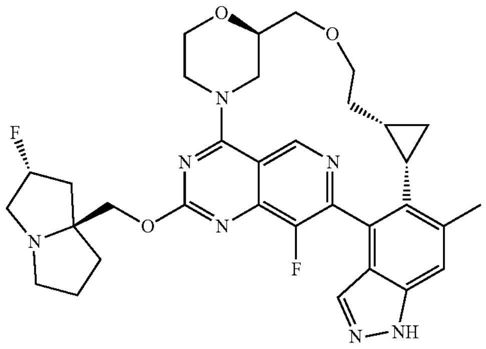 [SMILES: Cc1cc2[nH]ncc2c2c1[C@H]1C[C@H]1CCOC[C@H]1CN(CCO1)c1nc(OC[C@@]34CCCN3C[C@H](F)C4)nc3c(F)c-2ncc13] (11S,13S,18R)-31-fluoro-25-(((2R,7aS)-2-fluorotetrahydro-1H-pyrrolo[1,2-a]pyrrol-7a(5H)-yl)methoxy)-9-methyl-16,19-dioxa-5,6,22,24,26,30-hexaazahexacyclo[25.3.1.1~18,22~.0~2,10~.0~3,7~.0~11,13~.0~23,28~]dotriaconta-1(31),2,4,7,9,23,25,27,29-nonaene | NA | Step 2. Intermediate BT | Step 1 was not performed. Chiral separation after Step 5. Details included below. |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 227 | 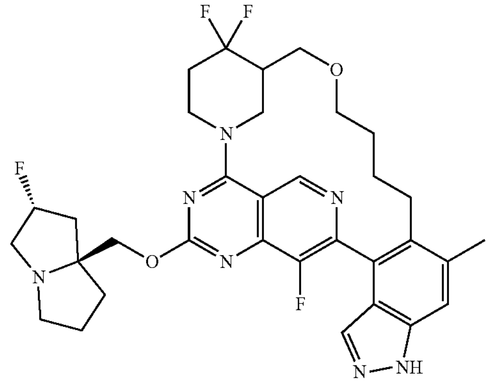 [SMILES: Cc1cc2[nH]ncc2c2c1CCCCOCC1CN(CCC1(F)F)c1nc(OC[C@@]34CCCN3C[C@H](F)C4)nc3c(F)c-2ncc13] (17R)-18,18,30-trifluoro-24-(((2R,7aS)-2-fluorotetrahydro-1H-pyrrolo[1,2-a]pyrrol-7a(5H)-yl)methoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene | Bis (2,2,2-trifluoro-aceate | Step 2. tert-butyl 4,4-difluoro-3-(hydroxymethyl) piperidine-1-carboxylate (CAS# 1303973-24-1, Enamine) | Step 1 was not performed. |
| 228 | 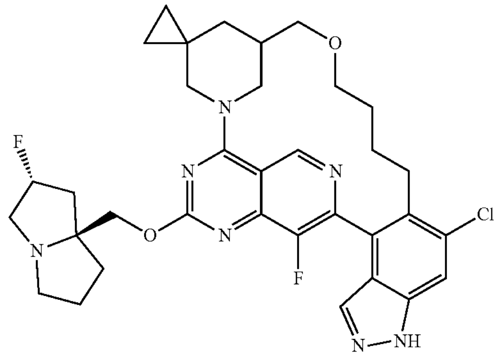 [SMILES: Fc1c2ncc3c(nc(OC[C@@]45CCCN4C[C@H](F)C5)nc13)N1CC(COCCCCc3c(Cl)cc4[nH]ncc4c3-2)CC2(CC2)C1] (17'R)-9'-chloro-30'-fluoro-24'-(((2R,7aS)-2-fluorotetrahydro-1H-pyrrolo[1,2-a]pyrrol-7a(5H)-yl)methoxy)-15'-oxa-5',6',21',23',25',29'-hexaazaspiro[cyclopropane-1,19'-hexacyclo[24.3.1.1~17,21~.0~2,10~.0~3,7~.0~22,27~]hentriacontane]-1'(30),2',4',7',9',22',24',26',28'-nonaene | Bis (2,2,2-trifluoro-aceate | Step 2. {5-azaspiro[2.5] octan-7-yl}methanol-hydrochloride (CAS#: 2751614-72-7, Enamine) | Step 1 was not performed. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 229 | 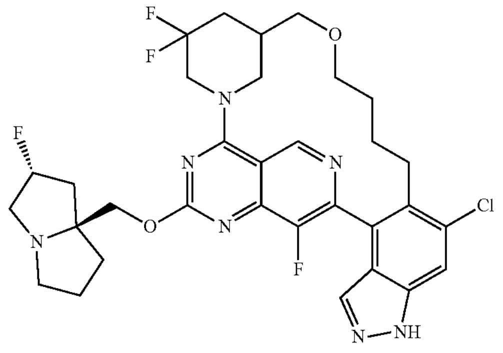 [SMILES: Fc1c2ncc3c(nc(OC[C@@]45CCCN4C[C@H](F)C5)nc13)N1CC(COCCCCc3c(Cl)cc4[nH]ncc4c3-2)CC(F)(F)C1] (17S)-9-chloro-19,19,30-trifluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene | Bis (2,2,2-trifluoro-aceate | Step 2. tert-butyl 3,3-difluoro-5-(hydroxymethyl) piperidine-1-carboxylate (CAS#: 1262412-64-5, Enamine) | Step 1 was not performed. |
| 230 | 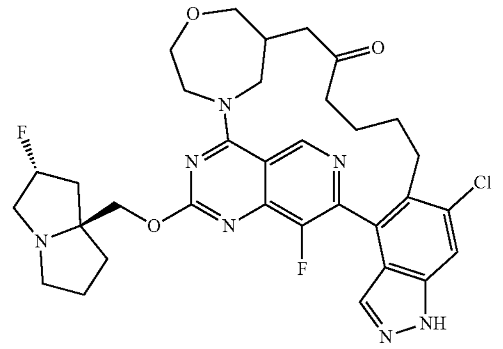 [SMILES: O=C1CCCCc2c(Cl)cc3[nH]ncc3c2-c2ncc3c(nc(OC[C@@]45CCCN4C[C@H](F)C5)nc3c2F)N2CCOCC(C1)C2] (26R)-18-Chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one and (26S)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | bis (2,2,2-trifluoro-acetate) | Step 3. Intermediate BX and Intermediate BY | Step 1-2 was not performed. |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 231 | 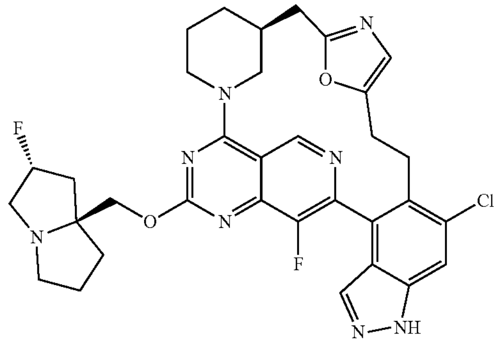 [SMILES: Fc1c2ncc3c(nc(OC[C@@]45CCCN4C[C@H](F)C5)nc13)N1CCC[C@@H](Cc3ncc(o3)CCc3c(Cl)cc4[nH]ncc4c3-2)C1] (18S)-9-chloro-31-fluoro-25-(((2R,7aS)-2-fluorotetrahydro-1H-pyrrolo[1,2-a]pyrrol-7a(5H)-yl)methoxy)-33-oxa-5,6,15,21,24,26,30-heptaazaheptacyclo[25.3.1.1~13,16~.1~18,22~.0~2,10~.0~3,7~.0~23,28~]tritriaconta-1(31),2,4,7,9,13,15,23,25,27,29-undecaene | bis (2,2.2-trifluoro-acetate) | Step 3. Intermediate BX and Intermediate BZ | Step 1-2 was not performed. Step 4. 4M HCl in dioxane was use instead of TFA |
| 232 | 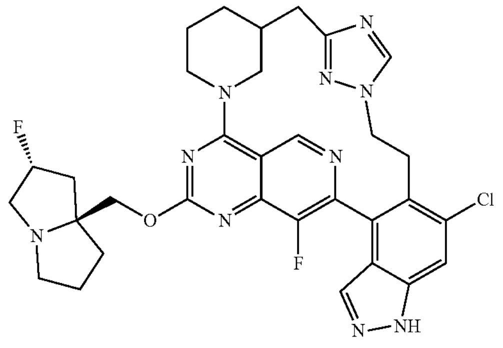 [SMILES: Fc1c2ncc3c(nc(OC[C@@]45CCCN4C[C@H](F)C5)nc13)N1CCCC(Cc3ncn(n3)CCc3c(Cl)cc4[nH]ncc4c3-2)C1] 9-chloro-31-fluoro-25-(((2R,7aS)-2-fluorotetrahydro-1H-pyrrolo[1,2-a]pyrrol-7a(5H)-yl)methoxy)-5,6,13,15,22,24,26,30,33-nonaazaheptacyclo[25.3.1.1~13,16~.1~18,22~.0~2,10~.0~3,7~.0~23,28~]tritriaconta-1(31),2,4,7,9,14,16(33),23,25,27,29-undecaene | bis (2,2,2-trifluoro-acetate) | Step 3. Intermediate BX and Intermediate CA | Step 1-2 was not performed. Step 4. 4M HCl in dioxane was use instead of TFA |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 233 | 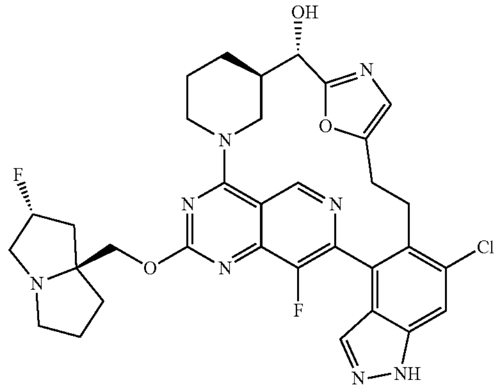 [SMILES: O[C@@H]1c2ncc(o2)CCc2c(Cl)cc3[nH]ncc3c2-c2ncc3c(nc(OC[C@@]45CCCN4C[C@H](F)C5)nc3c2F)N2CCC[C@@H]1C2] (17S,18R)-9-chloro-31-fluoro-25-(((2R,7aS)-2-fluorotetrahydro-1H-pyrrolo[1,2-a]pyrrol-7a(5H)-yl)methoxy)-33-oxa-5,6,15,22,24,26,30-heptaazaheptacyclo[25.3.1.1~13,16~.1~18,22~.0~2,10~.0~3,7~.0~23,28~]tritriaconta-1(31),2,4,7,9,13,15,23,25,27,29-undecaene-17-ol | | Step 3. Intermediate BX and Intermediate CB | Step 1-2 was not performed. Step 4. 4M HCl in dioxane was used. Step 6. TBAF, THF at 0° C. was added. |
| 234 | 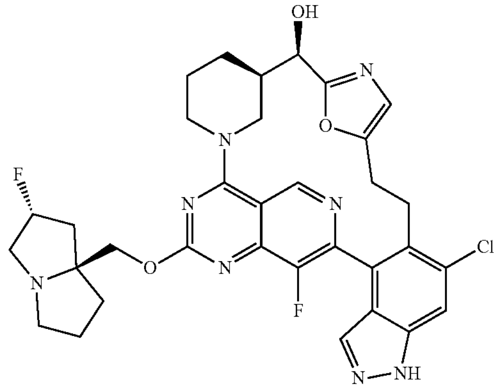 [SMILES: O[C@H]1c2ncc(o2)CCc2c(Cl)cc3[nH]ncc3c2-c2ncc3c(nc(OC[C@@]45CCCN4C[C@H](F)C5)nc3c2F)N2CCC[C@@H]1C2] (17R,18R)-9-chloro-31-fluoro-25-(((2R,7aS)-2-fluorotetrahydro-1H-pyrrolo[1,2-a]pyrrol-7a(5H)-yl)methoxy)-33-oxa-5,6,15,22,24,26,30-heptaazaheptacyclo[25.3.1.1~13,16~.1~18,22~.0~2,10~.0~3,7~.0~23,28~]tritriaconta-1(31),2,4,7,9,13,15,23,25,27,29-undecaene-17-ol | bis (2,2,2-trifluoro-acetate) | Step 3. Intermediate BX and CB | Step 1-2 was not performed. Step 4. 4M HCl in dioxane was use instead of TFA. Step 6. TBAF, THF at 0° C. was added. |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 372 | 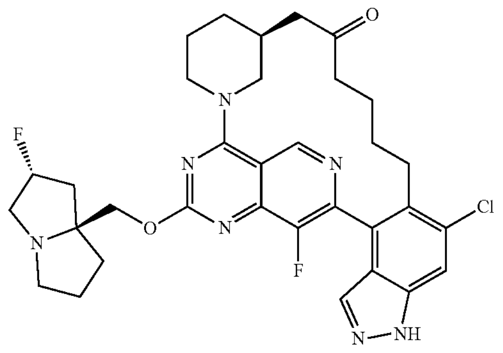 [SMILES: O=C1CCCCc2c(Cl)cc3[nH]ncc3c2-c2ncc3c(nc(OC[C@@]45CCCN4C[C@H](F)C5)nc3c2F)N2CCC[C@@H](C1)C2] (17S)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaene-15-one | Bis (2,2,2-trifluoro-acetate) | Step 3. Intermediate BX and Intermediate FH | |
| 373 | 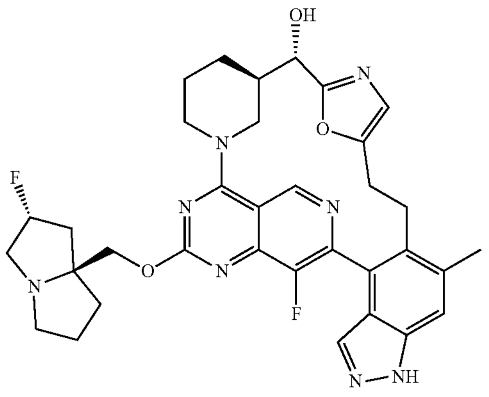 [SMILES: Cc1cc2[nH]ncc2c2c1CCc1cnc(o1)[C@@H](O)[C@@H]1CCCN(C1)c1nc(OC[C@@]34CCCN3C[C@H](F)C4)nc3c(F)c-2ncc13] (17R,18R)-31-fluoro-25-(((2R,7aS)-2-fluorotetrahydro-1H-pyrrolo[1,2-a]pyrrol-7a(5H)-yl)methoxy)-9-methyl-33-oxa-5,6,15,22,24,26,30-heptaazaheptacyclo[25.3.1.1~13,16~.1~18,22~.0~2,10~.0~3,7~.0~23,28~]tritriaconta-1(31),2,4,7,9,13,15,23,25,27,29-undecaene-17-ol | trifluoro-aceate | Step 3. Intermediate BX and Intermediate FJ | |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 374 | 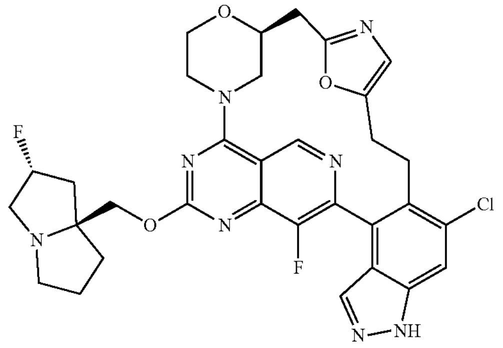 [SMILES: Fc1c2ncc3c(nc(OC[C@@]45CCCN4C[C@H](F)C5)nc13)N1CCO[C@@H](Cc3ncc(o3)CCc3c(Cl)cc4[nH]ncc4c3-2)C1] (18S)-9-chloro-31-fluoro-25-(((2R,7aS)-2-fluorotetrahydro-1H-pyrrolo[1,2-a]pyrrol-7a(5H)-yl)methoxy)-19,33-dioxa-5,6,15,22,24,26,30-heptaazaheptacyclo[25.3.1.1~13,16~.1~18,22~.0~2,10~.0~3,7~.0~23,28~]tritriaconta-1(31),2,4,7,9,13,15,23,25,27,29-undecaene | NA | Step 3. Intermediate BX and Intermediate FL | Step 4. 4M HCl in DCM was use instead of TFA. |
| 375 | 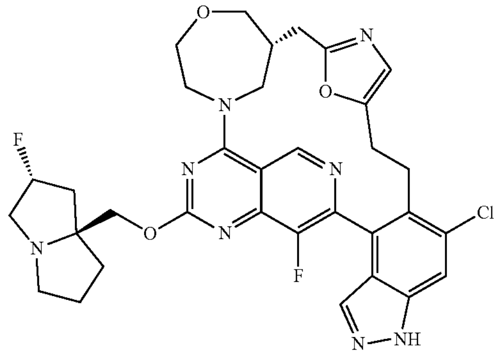 [SMILES: Fc1c2ncc3c(nc(OC[C@@]45CCCN4C[C@H](F)C5)nc13)N1CCOC[C@H](Cc3ncc(o3)CCc3c(Cl)cc4[nH]ncc4c3-2)C1] (27R)-18-chloro-34-fluoro-4-(((2R,7aS)-2-fluorotetrahydro-1H-pyrrolo[1,2-a]pyrrol-7a(5H)-yl)methoxy)-29,33-dioxa-1,3,5,9,14,15,24-heptaazaheptacyclo[25.4.1.1~6,10~.1~22,25~.0~2,7~.0~11,19~.0~12,16~]tetratriaconta-2,4,6,8,10(34),11,13,16,18,22,24-undecaene | NA | Step 3. Intermediate BX and Intermediate FM | Step 4. 4M HCl in DCM was use instead of TFA. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 376 | 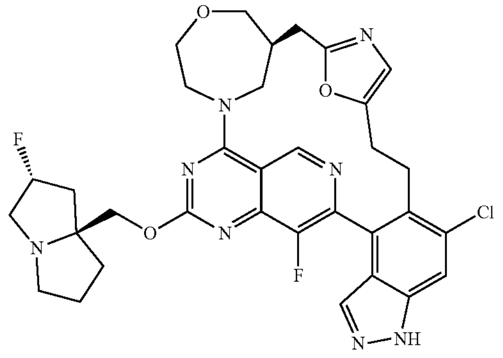 [SMILES: Fc1c2ncc3c(nc(OC[C@@]45CCCN4C[C@H](F)C5)nc13)N1CCOC[C@@H](Cc3ncc(o3)CCc3c(Cl)cc4[nH]ncc4c3-2)C1] (27S)-18-chloro-34-fluoro-4-(((2R,7aS)-2-fluorotetrahydro-1H-pyrrolo[1,2-a]pyrrol-7a(5H)-yl)methoxy)-29,33-dioxa-1,3,5,9,14,15,24-heptaazaheptacyclo[25.4.1.1~6,10~.1~22,25~.0~2,7~.0~11,19~.0~12,16~]tetratriaconta-2,4,6,8,10(34),11,13,16,18,22,24-undecaene | NA | Step 3. Intermediate BX and Intermediate FM | Step 4. 4M HCl in DCM was use instead of TFA. |
| 377 | 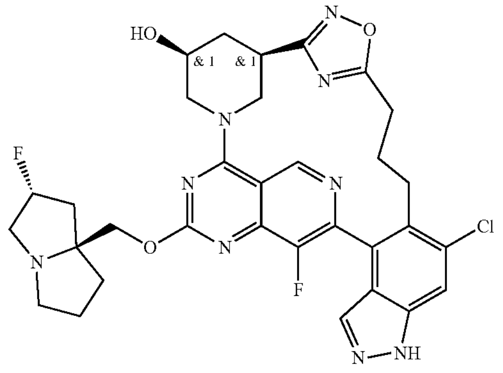 [SMILES: O[C@H]1C[C@@H]2CN(C1)c1nc(OC[C@@]34CCCN3C[C@H](F)C4)nc3c(F)c(ncc13)-c1c(c(Cl)cc3[nH]ncc13)CCCc1nc2no1] (rac-18R,20S)-9-chloro-31-fluoro-25-(((2R,7aS)-2-fluorotetrahydro-1H-pyrrolo[1,2-a]pyrrol-7a(5H)-yl)methoxy)-15-oxa-5,6,16,22,24,26,30,33-octaazaheptacyclo[25.3.1.1~14,17~.1~18,22~.0~2,10~.0~3,7~.0~23,28~]tritriaconta-1(31),2,4,7,9,14(33),16,23,25,27,29-undecaen-20-ol | NA | Step 6. Intermediate FZ and Intermediate BX | Step 1-5 were not performed. Step 6. CuI, LiCl in DMF was used. TMAF was used after Step 8. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 378 | 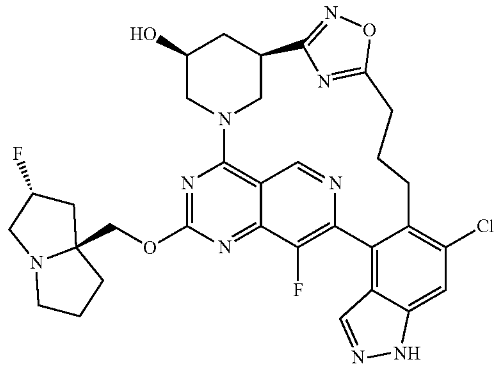 [SMILES: O[C@H]1C[C@@H]2CN(C1)c1nc(OC[C@@]34CCCN3C[C@H](F)C4)nc3c(F)c(ncc13)-c1c(c(Cl)cc3[nH]ncc13)CCCc1nc2no1] (18R,20S)-9-chloro-31-fluoro-25-(((2R,7aS)-2-fluorotetrahydro-1H-pyrrolo[1,2-a]pyrrol-7a(5H)-yl)methoxy)-15-oxa-5,6,16,22,24,26,30,33-octaazaheptacyclo[25.3.1.1~14,17~.1~18,22~.0~2,10~.0~3,7~.0~23,28~]tritriaconta-1(31),2,4,7,9,14(33),16,23,25,27,29-undecaen-20-ol | NA | Step 6. Intermediate FZ and Intermediate BX | Step 1-5 were not performed. Step 6. CuI, LiCl in DMF was used. TMAF was used after Step 8. |
| 379 | 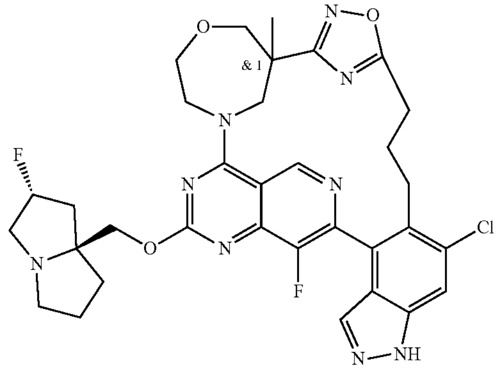 [SMILES: CC12COCCN(C1)c1nc(OC[C@@]34CCCN3C[C@H](F)C4)nc3c(F)c(ncc13)-c1c(c(Cl)cc3[nH]ncc13)CCCc1nc2no1] (1RS)-10-chloro-33-fluoro-24-(((2R,7aS)-2-fluorotetrahydro-1H-pyrrolo[1,2-a]pyrrol-7a(5H)-yl)methoxy)-1-methyl-4,30-dioxa-3,13,14,19,23,25,27,34-octaazaheptacyclo[25.4.1.1~2,5~.1~18,22~.0~9,17~.0~12,16~.0~21,26~]tetratriaconta-2,5(34),9,11,14,16,18(33),19,21,23,25-undecaene | formate | Step 6. Intermediate GA and Intermediate BX | Step 1-5 were not performed. |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 380 | 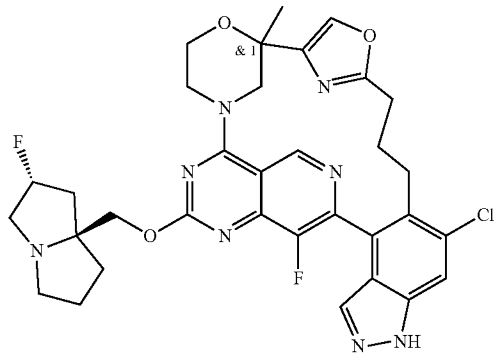 [SMILES: CC12CN(CCO1)c1nc(OC[C@@]34CCCN3C[C@H](F)C4)nc3c(F)c(ncc13)-c1c(c(Cl)cc3[nH]ncc13)CCCc1nc2co1] (18RS)-9-chloro-31-fluoro-25-(((2R,7aS)-2-fluorotetrahydro-1H-pyrrolo[1,2-a]pyrrol-7a(5H)-yl)methoxy)-18-methyl-15,19-dioxa-5,6,22,24,26,30,33-heptaazaheptacyclo[25.3.1.1~14,17~.1~18,22~.0~2,10~.0~3,7~.0~23,28~]tritriaconta-1(31),2,4,7,9,14(33),16,23,25,27,29-undecaene | bis(tri-fluro-acetate) | Step 6. Intermediate GB and Intermediate BX | Step 1-5 were not performed. |
| 381 | 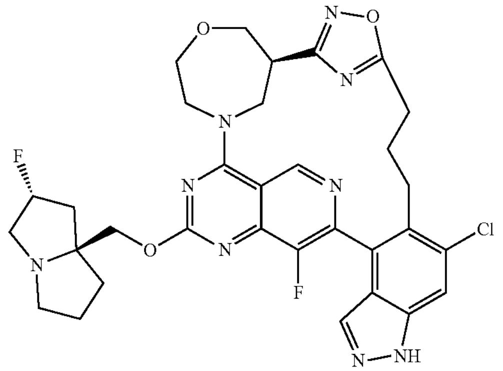 [SMILES: Fc1c2ncc3c(nc(OC[C@@]45CCCN4C[C@H](F)C5)nc13)N1CCOC[C@H](C1)c1noc(n1)CCCc1c(Cl)cc3[nH]ncc3c1-2] (1RS)-10-chloro-33-fluoro-24-(((2R,7aS)-2-fluorotetrahydro-1H-pyrrolo[1,2-a]pyrrol-7a(5H)-yl)methoxy)-4,30-dioxa-3,13,14,19,23,25,27,34-octaazaheptacyclo[25.4.1.1~2,5~.1~18,22~.0~9,17~.0~12,16~.0~21,26~]tetratriaconta-2,5(34),9,11,14,16,18(33),19,21,23,25-undecaene | formate | Step 6. Intermediate GC and Intermediate BX | Step 1-5 were not performed. |

TABLE 43-continued

| Additional Examples 136 to 149, 223 to 234 and 372 to 384. Prepared in an Analogous Manner to Example 135. | | | | |
|---|---|---|---|---|
| Ex.# | Structure & Name | Salt Form | Reagent | Method Change |
| 382 | 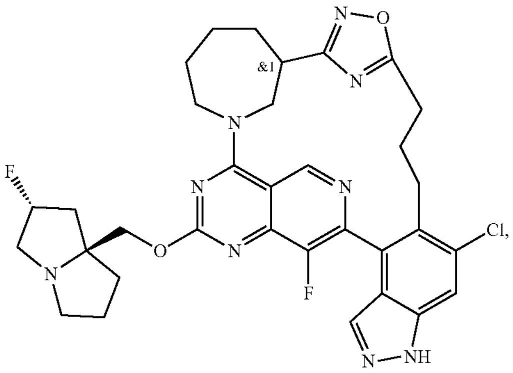 [SMILES: Fc1c2ncc3c(nc(OC[C@@]45CCCN4C[C@H](F)C5)nc13)N1CCCCC(C1)c1noc(n1)CCCc1c(Cl)cc3[nH]ncc3c1-2] (1RS)-10-chloro-33-fluoro-24-(((2R,7aS)-2-fluorotetrahydro-1H-pyrrolo[1,2-a]pyrrol-7a(5H)-yl)methoxy)-4-oxa-3,13,14,19,23,25,27,34-octaazaheptacyclo[25.4.1.1~2,5~.1~18,22~.0~9,17~.0~12,16~.0~21,26~]tetratriaconta-2,5(34),9,11,14,16,18(33),19,21,23,25-undecaene | NA | Step 6. Intermediate GD and Intermediate BX | Step 1-5 were not performed. |
| 383 | 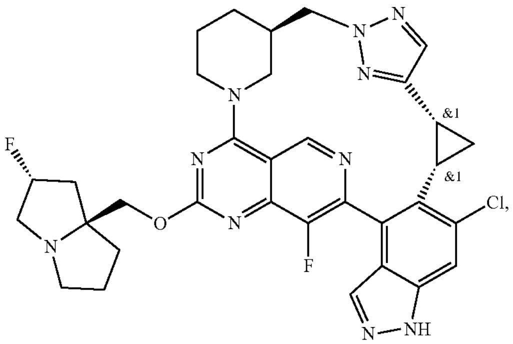 [SMILES: Fc1c2ncc3c(nc(OC[C@@]45CCCN4C[C@H](F)C5)nc13)N1CCC[C@H](C1)Cn1ncc(n1)[C@@H]1C[C@@H]1c1c(Cl)cc3[nH]ncc3c1-2] (11R,13S,19R)rel-9-chloro-32-fluoro-26-(((2R,7aS)-2-fluorotetrahydro-1H-pyrrolo[1,2-a]pyrrol-7a(5H)-yl)methoxy)-5,6,16,17,23,25,27,31,34-nonaazaoctacyclo[26.3.1.1~14,17~.1~19,23~.0~2,10~.0~3,7~.0~11,13~.0~24,29~]tetratriaconta-1(32),2,4,7,9,14(34),15,24,26,28,30-undecaene | bis (2,2,2-trifluoro-acetate) | Step 3. Intermediate BX and Intermediate FK | Step 4. 4M HCl in DCM was use instead of TFA |

TABLE 43-continued

Additional Examples 136 to 149, 223 to 234 and 372 to 384. Prepared in an Analogous Manner to Example 135.

| Ex.# | Structure & Name | Salt Form | Reagent | Method Change |
|---|---|---|---|---|
| 384 | 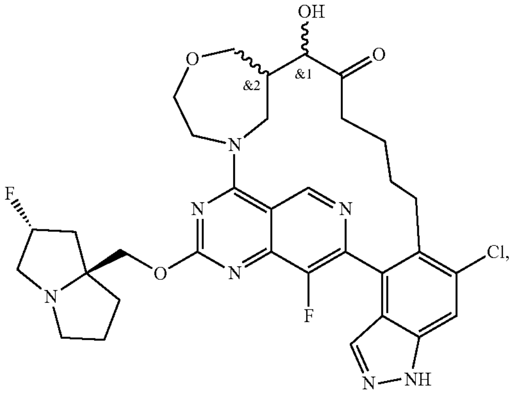 [SMILES: O=C1CCCCc2c(Cl)cc3[nH]ncc3c2-c2ncc3c(nc(OC[C@@]45CCCN4C[C@H](F)C5)nc3c2F)N2CCOCC(C2)C1O] (25R,26S)-18-chloro-32-fluoro-4-(((2R,7aS)-2-fluorotetrahydro-1H-pyrrolo[1,2-a]pyrrol-7a(5H)-yl)methoxy)-25-hydroxy-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one | NA | Step 6. Intermediate GE and Intermediate BX | Step 1-5 were not performed. |

TABLE 44

Conditions for Chiral SFC Separation.

| Separation | Conditions | Final products |
|---|---|---|
| 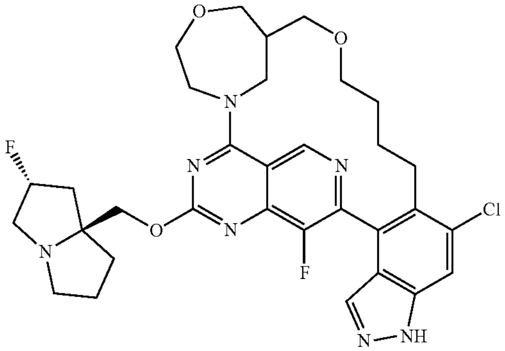 [SMILES: Fc1c2ncc3c(nc(OC[C@@]45CCCN4C[C@H](F)C5)nc13)N1CCOCC(COCCCCc3c(Cl)cc4[nH]ncc4c3-2)C1] | Column: Chiralcel OD (21 × 250 mm, 5 μm) Mobile phase: 40% MeOH with 0.2% DEA Flowrate: 100 mL/min. Yield: 46.6 mg sample was submitted to generate 15.0 mg of peak 1 with an ee of >99% and 14.9 mg of peak 2 with an ee of >99%. | Peak 1: Example 136 Peak 2: Example 137 |
| 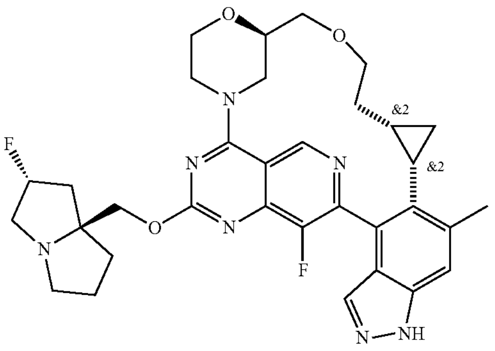 [SMILES: Cc1cc2[nH]ncc2c2c1[C@H]1C[C@H]1CCOC[C@H]1CN(CCO1)c1nc(OC[C@@]34CCCN3C[C@H](F)C4)nc3c(F)c-2ncc13] | Column: (S,S) Whelk-0, 2 × 15 cm, 5 μm Mobile phase: 50% MeOH with 0.2% DEA Flowrate: 100 mL/min. Yield: 22 mg sample was submitted to generate 10 mg of peak 1 with an ee of >99% and 6 mg of peak 2 with an ee of >99%. | Peak 1: Example 226 Peak 2: Example 225 |

TABLE 44-continued

| Conditions for Chiral SFC Separation. | | |
|---|---|---|
| Separation | Conditions | Final products |
| 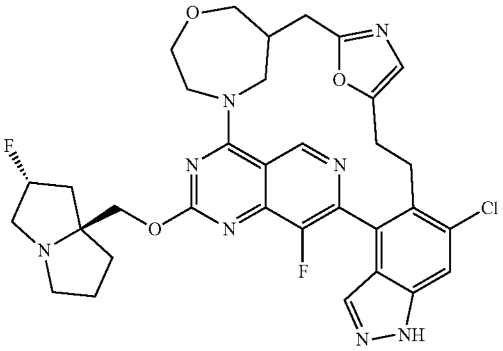 [SMILES: Fc1c2ncc3c(nc(OC[C@@]45CCCN4C[C@H](F)C5)nc13)N1CCOCC(Cc3ncc(o3)CCc3c(Cl)cc4[nH]ncc4c3-2)C1] | Column: (S,S) Whelk-0 (2 × 15 cm, 5 μm)<br>Mobile phase: 45% MeOH with 0.2% DEA<br>Flowrate: 110 mL/min.<br>Yield: 42 mg sample was submitted to generate 13 mg of peak 1 with an ee of >99% and 13 mg of peak 2 with an ee of >99%. | Peak 1: Example 375<br>Peak 2: Example 376 |

TABLE 45

| Analytical Data for Examples 136 to 149, 223 to 234 and 372 to 384. | | |
|---|---|---|
| Cmpd.# | MS m/z (ESI): $(M + H)^+$ | $^1H$ and $^{19}F$ NMR |
| 136 | 640.0 | $^1H$ NMR (400 MHz, METHANOL-$d_4$) δ ppm 9.31-9.37 (m, 1 H), 7.81 (s, 2 H), 5.35-5.42 (m, 1 H), 5.19-5.29 (m, 2 H), 4.53-4.62 (m, 1 H), 4.23 (br d, J = 2.7 Hz, 3 H), 3.94-4.02 (m, 1 H), 3.82-3.90 (m, 1 H), 3.68-3.80 (m, 2 H), 3.47-3.64 (m, 1 H), 3.12-3.27 (m, 7 H), 2.91-3.06 (m, 4 H), 2.63 (t, J = 10.5 Hz, 1 H), 2.41-2.54 (m, 2 H), 2.12-2.37 (m, 3 H), 1.84-2.07 (m, 4 H), 1.55-1.66 (m, 1 H), 1.29-1.51 (m, 4 H). $^{19}F$ NMR (376 MHz, METHANOL-$d_4$) δ ppm −142.75 (s), −173.74 (s). |
| 137 | 640.0 | $^1H$ NMR (400 MHz, METHANOL-$d_4$) δ ppm 9.30-9.40 (m, 1 H), 7.81 (s, 2 H), 5.18-5.47 (m, 2 H), 4.52-4.65 (m, 2 H), 4.19-4.44 (m, 3 H), 3.70-4.03 (m, 4 H), 3.43-3.65 (m, 1 H), 2.87-3.21 (m, 9 H), 2.17-2.70 (m, 6 H), 1.83-2.09 (m, 5 H), 1.54-1.66 (m, 1 H), 1.26-1.48 (m, 5 H). $^{19}F$ NMR (376 MHz, METHANOL-$d_4$) δ ppm −142.75 (s), −173.65 (s). |
| 138 | 624.0 | $^1H$ NMR (400 MHz, METHANOL-$d_4$) δ ppm 9.23-9.33 (m, 1 H), 7.84 (d, J = 16.1 Hz, 2 H), 5.51-5.75 (m, 1 H), 5.03 (br d, J = 13.4 Hz, 2 H), 4.60-4.76 (m, 2 H), 3.84-4.16 (m, 4 H), 3.46-3.57 (m, 1 H), 3.29 (br s, 1 H), 2.97-3.13 (m, 2 H), 2.77-2.96 (m, 2 H), 2.69 (s, 3 H), 2.40 (br s, 5 H), 2.12-2.26 (m, 1 H), 1.95 (s, 2 H), 1.67 (br s, 4 H), 1.31 (br s, 6 H). $^{19}F$ NMR (376 MHz, METHANOL-$d_4$) δ ppm −77.48-−77.21 (m), −143.24 (br s), −174.20-−173.90 (m). |
| 139 | 624.0 | $^1H$ NMR (400 MHz, METHANOL-$d_4$) δ ppm 9.18 (s, 1 H), 7.72-7.95 (m, 2 H), 5.46-5.77 (m, 1 H), 4.84-5.18 (m, 2 H), 4.57-4.76 (m, 2 H), 3.80-4.10 (m, 4 H), 3.35-3.57 (m, 3 H), 3.06-3.28(m, 3 H), 2.58-2.84 (m, 3 H), 2.28-2.49 (m, 3 H), 1.94-2.25 (m, 2 H), 1.58-1.91 (m, 6 H), 1.13-1.53 (m, 3 H). |
| 140 | 640.0 | $^1H$ NMR (400 MHz, METHANOL-$d_4$) δ ppm 9.19-9.41 (m, 1 H), 7.69-7.88 (m, 1 H), 5.48-5.75 (m, 1 H), 4.92-5.12 (m, 1 H), 4.74 (br d, J = 5.0 Hz, 2 H), 4.54-4.79 (m, 1 H), 3.78-4.22 (m, 7 H), 3.44-3.62 (m, 2 H), 3.05-3.29 (m, 2 H), 2.78-3.04 (m, 1 H), 2.61-2.74 (m, 2 H), 2.61-2.76 (m, 3 H), 2.17-2.57 (m, 7 H), 1.86-1.97 (m, 1 H), 1.57-1.69 (m, 1 H), 1.10-1.52 (m, 3 H). $^{19}F$ NMR (376 MHz, METHANOL-$d_4$) δ ppm −79.17-−76.17 (m), −145.50-−142.80 (m), −174.31-−173.71 (m). |
| 141 | 638.1 | $^1H$ NMR (400 MHz, METHANOL-$d_4$) δ ppm 9.18-9.46 (m, 1 H), 7.80 (d, J = 14.6 Hz, 2 H), 5.51-5.70 (m, 1 H), 4.94-5.11 (m, 1 H), 4.65-4.79 (m, 2 H), 3.79-4.12 (m, 4 H), 3.36-3.63 (m, 2H), 2.79-3.27 (m, 4 H), 1.95-2.79 (m, 12 H), 1.12-1.92 (m, 10 H). $^{19}F$ NMR (376 MHz, METHANOL-$d_4$) δ ppm −80.41-−72.46 (m), −146.03-−142.79 (m), −175.45-−173.10 (m). |
| 142 | 625.9 | $^1H$ NMR (400 MHz, DMSO-$d_6$) δ ppm 13.38 (br s, 1 H), 9.13 (s, 1 H), 8.21 (s, 1 H), 7.85 (s, 1 H), 7.81-7.83 (m, 1 H), 5.18-5.38 (m, 1 H), 4.82 (d, J = 13.68 Hz, 1 H), 4.70 (d, J = 13.27 Hz, 1 H), 4.65 (d, J = 12.65 Hz, 1 H), 4.52-4.62 (m, 1 H), 4.13-4.18 (m, 1 H), 4.06 (d, J = 10.37 Hz, 1 H), 3.75 (d, J = 13.48 Hz, 1 H), 2.98-3.23 (m, 8 H), 2.79-2.87 (m, 1 H), 2.32-2.44 (m, 3 H), 2.11- |

TABLE 45-continued

| Analytical Data for Examples 136 to 149, 223 to 234 and 372 to 384. | | |
|---|---|---|
| Cmpd.# | MS m/z (ESI): $(M + H)^+$ | $^1H$ and $^{19}F$ NMR |
| | | 2.22 (m, 1 H), 1.98-2.08 (m, 3 H), 1.84-1.90 (m, 2 H), 1.75-1.81 (m, 2 H), 1.48-1.58 (m, 2 H). $^{19}F$ NMR (377 MHz, DMSO-$d_6$) δ ppm −172.11 (s), −143.47 (s), −73.40 (s). |
| 143 | 640.9 | $^1H$ NMR (400 MHz, METHANOL-$d_4$) δ ppm 9.29-9.51 (m, 1 H), 7.58-7.90 (m, 2 H), 5.50-5.78 (m, 1 H), 4.85-5.46 (m, 2 H), 4.59-4.77 (m, 3 H), 3.64-4.14 (m, 4 H), 3.47-3.57 (m, 1H), 3.16-3.31 (m, 1 H), 2.32-2.92 (m, 9 H), 2.05-2.31 (m, 3 H), 1.82-1.97 (m, 3 H), 1.66-1.76 (m, 1 H), 1.17-1.60 (m, 6 H). $^{19}F$ NMR (376 MHz, METHANOL-$d_4$) δ ppm −79.53--72.17 (m,), −145.14--141.61 (m), −175.45--173.39 (m). |
| 144 | 656.0 | $^1H$ NMR (400 MHz, METHANOL-$d_4$) δ ppm 9.12-9.44 (m, 1 H), 7.67-7.89 (m, 2 H), 5.43-5.77 (m, 1 H), 4.96-5.07 (m, 1 H), 4.55-4.77 (m, 2 H), 3.75-4.16 (m, 4 H), 3.42-3.66 (m, 2 H), 3.14-3.30 (m, 1 H), 2.60-2.97 (m, 6 H), 2.21-2.53 (m, 6 H), 1.53-2.08 (m, 10 H). $^{19}F$ NMR (376 MHz, METHANOL-$d_4$) δ ppm −78.16--72.79 (m), −143.58--140.89 (m), −174.94--172.55 (m). |
| 145 | 672.7 | $^1H$ NMR (400 MHz, METHANOL-$d_4$) δ ppm 9.19-9.28 (m, 1 H), 7.82-7.88 (m, 1 H), 7.74-7.82 (m, 1 H), 5.28-5.48 (m, 1 H), 4.95-5.16 (m, 1 H), 4.29-4.49 (m, 2 H), 3.41-3.65 (m, 2 H), 3.05-3.26 (m, 3 H), 2.80-2.94 (m, 3 H), 2.56-2.69 (m, 2 H), 1.52-2.49 (m, 19 H). $^{19}F$ NMR (376 MHz, METHANOL-$d_4$) δ ppm −78.49--76.18 (m), −143.20--140.69 (m), −174.37--173.14 (m). |
| 146 | 647.1 | $^1H$ NMR (400 MHz, DMSO-$d_6$) δ ppm 13.18-13.50 (m, 1 H), 10.35-10.86 (m, 1 H), 8.57-9.00 (m, 1 H), 7.87 (s, 2 H), 7.75 (s, 1 H), 5.44-5.71 (m, 1 H), 4.56-4.85 (m, 2 H), 4.28--4.47 (m, 1 H), 4.12-4.22 (m, 2 H), 3.86 (br d, J = 14.9 Hz, 4 H), 3.27-3.45 (m, 2 H), 3.07-3.24 (m, 2 H), 2.89 (br d, J = 2.3 Hz, 1 H), 2.31-2.36 (m, 2 H), 2.01-2.22 (m, 6 H), 1.86-1.98 (m, 2 H), 1.66-1.79 (m, 2 H). $^{19}F$ NMR (376 MHz, DMSO-$d_6$) δ ppm −74.14 (s), −142.28 (s), −173.02 (s). |
| 147 | 643.8 | $^1H$ NMR (METHANOL-$d_4$, 400 MHz) δ ppm 8.76 (s, 1H), 8.72 (s, 1H), 8.15 (d, 1H, J = 0.8 Hz), 8.07 (d, 1H, J = 1.0 Hz), 7.89 (d, 1H, J = 1.0 Hz), 7.86 (d, 1H, J = 0.8 Hz), 7.20 (s, 1H), 6.78 (s, 2H), 6.73 (s, 1H), 6.5-6.5 (m, 1H), 6.20 (s, 1H), 5.39 (br d, 1H, J = 3.5 Hz), 5.25 (br d, 2H, J = 6.2 Hz), 4.68 (br s, 1H), 4.65 (br s, 1H), 4.3-4.4 (m, 2H), 4.25 (s, 2H), 4.21 (s, 1H), 4.18 (s, 1H), 3.8-3.9 (m, 7H), 3.6-3.7 (m, 1H), 3.36 (s, 7H), 3.2-3.3 (m, 14H), 3.02 (br dd, 4H, J = 5.5, 8.6 Hz), 2.35 (br d, 1H, J = 4.6 Hz), 2.1-2.3 (m, 11H), 1.9-2.1 (m, 17H), 1.7-1.8 (m, 5H), 1.30 (br s, 3H). $^{19}F$ NMR (METHANOL-$d_4$, 377 MHz) δ −138.2-138.1 (m), −140.6--140.5 (m), −173.66 (s), −173.78 (s). Stereochemistry of Example 147 was confirmed by X-Ray crystallography analysis. |
| 148 | 646.8 | $^1H$ NMR (METHANOL-$d_4$, 400 MHz) δ ppm 9.11 (d, 1H, J = 1.9 Hz), 7.81 (s, 1H), 7.76 (s, 1H), 7.00 (d, 1H, J = 13.2 Hz), 5.4-5.8 (m, 1H), 5.1-5.2 (m, 1H), 4.9-5.0 (m, 1H), 4.6-4.7 (m, 2H), 4.2-4.3 (m, 3H), 3.8-4.1 (m, 3H), 3.5-3.6 (m, 1H), 3.3-3.4 (m, 2H), 2.6-2.9 (m, 4H), 2.1-2.5 (m, 6H), 2.0-2.1 (m, 1H), 1.8-1.9 (m, 2H), 1.7-1.8 (m, 1H). $^{19}F$ NMR (METHANOL-d4, 376 MHz) δ −142.95 (d, J = 65.9 Hz), −174.22 (d, J = 29.5 Hz). |
| 149 | 644.8 | $^1H$ NMR (METHANOL-$d_4$, 400 MHz) δ ppm 9.12 (d, 1H, J = 1.9 Hz), 7.83 (d, 2H, J = 8.8 Hz), 7.19 (d, 1H, J = 9.2 Hz), 6.93 (dd, 1H, J = 3.1, 15.9 Hz), 5.6-5.7 (m, 1H), 5.5-5.6 (m, 1H), 5.3-5.4 (m, 1H), 5.1-5.1 (m, 1H), 4.98 (br d, 1H, J = 12.5 Hz), 4.8-4.9 (m, 3H), 4.5-4.7 (m, 2H), 4.28 (br d, 1H, J = 14.2 Hz), 3.8-4.1 (m, 4H), 3.4-3.5 (m, 4H), 2.6-2.7 (m, 1H), 2.3-2.4 (m, 3H), 2.2-2.2 (m, 1H), 1.8-1.9 (m, 1H). $^{19}F$ NMR (METHANOL-d4, 376 MHz) δ −142.95 (d, J = 65.9 Hz), −174.22 (d, J = 29.5 Hz). |
| 223 | 604.2 | $^1H$ NMR (400 MHz, METHANOL-$d_4$) δ ppm 9.20 (s, 1H), 8.07-8.09 (m, 1 H), 7.96-7.99 (m, 1 H), 7.60-7.66 (m, 2 H), 7.36 (t, J = 9.6 Hz, 1 H), 5.49 (s, 1 H), 5.34 (d, J = 54.4 Hz, 1 H), 5.09 (d, J = 13.6 Hz, 1 H), 4.92-4.95 (m, 2 H), 4.34 (s, 2 H), 3.55-3.57 (m, 1 H), 3.45-3.46 (m, 1 H), 3.37-3.38 (m, 2 H), 3.28-3.29 (m, 3 H), 3.07-3.10 (m, 1 H), 2.85-2.94 (m, 1 H), 2.25-2.35 (m, 2 H), 2.16-2.19 (m, 1 H), 2.05-2.09 (m, 1 H), 1.75-1.85 (m, 3 H), 1.55-1.73 (m, 4 H), 1.42-1.54 (m, 2 H), 1.26-1.31 (m, 1 H). |
| 224 | 625.9 | $^1H$ NMR (400 MHz, DMSO-$d_6$) δ ppm 13.32 (br s, 1 H), 9.15 (s, 1 H), 7.91-8.01 (m, 1 H), 7.79 (s, 1 H), 5.26-5.51 (m, 1 H), 4.72 (br t, J = 12.4 Hz, 2 H), 4.16-4.52 (m, 3 H), 3.93 (br d, J = 9.0 Hz, 1 H), 3.69-3.83 (m, 1 H), 3.62 (br d, J = 10.9 Hz, 1 H), 3.21-3.46 (m, 8 H), 3.06 (br t, − = 8.6 Hz, 1 H), 2.54-2.67 (m, 1 H), 2.09-2.38 (m, 3 H), 1.82-2.00 (m, 4 H), 1.66-1.80 (m, 1 H), 1.45--1.62 (m, 3 H). $^{19}F$ NMR (376 MHz, DMSO-$d_6$) δ ppm −144.08 (m, 1 F), −172.36 (s, 1 F). |

TABLE 45-continued

Analytical Data for Examples 136 to 149, 223 to 234 and 372 to 384.

| Cmpd.# | MS m/z (ESI): $(M + H)^+$ | $^1H$ and $^{19}F$ NMR |
| --- | --- | --- |
| 225 | 618.3 | $^1H$ NMR (600 MHz, DMSO-$d_6$) δ ppm 9.23 (s, 1 H), 8.02 (s, 1 H), 7.51 (s, 1 H), 5.18-5.41 (m, 1 H), 4.78 (br d, J = 13.2 Hz, 1 H), 4.60-4.61 (m, 1 H), 4.59 (br d, J = 13.9 Hz, 1 H), 4.18 (d, J = 10.4 Hz, 1 H), 4.03-4.12 (m, 2 H), 3.64-3.81 (m, 3 H), 3.41-3.48 (m, 1 H), 3.25-3.34 (m, 1 H), 3.00-3.13 (m, 2 H), 2.78-2.88 (m, 2 H), 2.04-2.20 (m, 3 H), 1.91-2.03 (m, 2 H), 1.73-1.89 (m, 3 H), 1.37-1.52 (m, 1 H), 1.27-1.30 (m, 1 H), 1.20-1.28 (m, 2 H), 0.86 (t, J = 7.0 Hz, 1 H), 0.50-0.58 (m, 1 H), 0.34-0.46 (m, 1 H), 0.03-0.08 (m, 1 H), −0.19--0.13 (m, 1 H). $^{19}F$ NMR (376 MHz, DMSO-$d_6$) δ ppm −141.36 (s, 1 F), −172.18 (s, 1 F). |
| 226 | 618.3 | $^1H$ NMR (600 MHz, DMSO-$d_6$) δ ppm 9.16 (s, 1 H), 7.95 (s, 1 H), 7.49 (s, 1 H), 5.21-5.34 (m, 1 H), 4.61 (br d, J = 13.1 Hz, 1 H), 4.53 (br d, J = 14.2 Hz, 1 H), 4.14-4.18 (m, 1 H), 4.08 (d, J = 10.3 Hz, 1 H), 3.78-3.88 (m, 2 H), 3.66-3.78 (m, 1 H), 3.43-3.54 (m, 2 H), 3.30-3.41 (m, 1 H), 3.29 (s, 1 H), 3.15-3.26 (m, 1 H), 2.98-3.13 (m, 3 H), 2.78-2.86 (m, 2 H), 1.98-2.19 (m, 4 H), 1.73-1.94 (m, 5 H), 1.13 (td, J = 8.6, 4.0 Hz, 1 H), 0.53-0.59 (m, 1 H), 0.05-0.19 (m, 2 H), −0.06-0.01 (m, 1 H), −0.61 (br t, J = 12.1 Hz, 1 H). $^{19}F$ NMR (376 MHz, DMSO-$d_6$) δ ppm −141.36 (s, 1 F), −172.18 (s, 1 F). |
| 227 | 659.8 | $^1H$ NMR (400 MHz, METHANOL-$d_4$) δ ppm 9.32 (s, 1 H), 7.79 (s, 1 H), 7.55 (s, 1 H), 5.47-5.81 (m, 1 H), 4.99-5.14 (m, 2 H), 4.60-4.80 (m, 2 H), 3.82-4.17 (m, 4 H), 3.37-3.61 (m, 2 H), 3.23-3.31 (m, 1 H), 2.98-3.07 (m, 1 H), 2.25-2.80 (m, 13 H), 2.03-2.30 (m, 3 H), 1.13-1.53 (m, 4 H). |
| 228 | 649.8 | $^1H$ NMR (400 MHz, METHANOL-$d_4$) δ ppm 9.31 (s, 1 H), 7.82-7.84 (m, 2 H), 5.45-5.77 (m, 1 H), 5.10-5.21 (m, 1 H), 4.46-4.76 (m, 3 H), 3.83-4.20 (m, 4 H), 3.56-3.67 (m, 1 H), 3.43-3.55 (m, 1 H), 2.29-3.19 (m, 13 H), 2.06-2.23 (m, 2 H), 1.26-1.54 (m, 4 H), 0.90-1.08 (m, 2 H), 0.50-0.65 (m, 1 H), 0.22-0.38 (m, 2 H). |
| 229 | 659.8 | $^1H$ NMR (400 MHz, METHANOL-$d_4$) δ ppm 9.38 (s, 1 H), 7.83 (s, 2 H), 5.55-5.65 (m, 2 H), 5.03-5.27 (m, 1 H), 4.65-4.75 (m, 2 H), 3.80-4.20 (m, 4 H), 3.42-3.71 (m, 2 H), 3.10-3.21 (m, 1 H), 2.98-3.09 (m, 1 H), 2.57-2.96 (m, 4 H), 2.00-2.53 (m, 9 H), 1.17-1.52 (m, 4 H). |
| 230 | 652.3 | $^1H$ NMR (400 MHz, METHANOL-$d_4$) δ ppm 9.27 (s, 1 H), 7.83 (s, 1 H), 7.67-7.75 (m, 1 H), 5.46-5.80 (m, 1 H), 5.06-5.29 (m, 1 H), 4.61-4.79 (m, 3 H), 4.28-4.50 (m, 1 H), 3.76-4.11 (m, 7 H), 3.47-3.65 (m, 3 H), 2.82-3.00 (m, 1 H), 2.60-2.78 (m, 2 H), 2.29-2.51 (m, 6 H), 2.10-2.24 (m, 2 H), 2.00-2.12 (m, 1 H), 1.20-1.69 (m, 6 H). $^{19}F$ NMR (376 MHz, METHANOL-$d_4$) δ ppm −77.36 (s), −146.18--138.77 (m), −174.12 (s). |
| 231 | 647.1 | $^1H$ NMR (400 MHz, METHANOL-$d_4$) δ ppm 9.42 (s, 1 H), 9.15 (s, 2 H), 7.93 (s, 1 H), 7.87 (s, 4 H), 7.85 (s, 1 H), 6.77 (s, 1 H), 6.53 (s, 2 H), 5.51-5.72 (m, 4 H), 4.95-5.08 (m, 4 H), 4.64-4.84 (m, 7 H), 3.87-4.12 (m, 14 H), 3.36-3.66 (m, 8 H), 3.29 (br s, 5 H), 3.01-3.11 (m, 2 H), 2.55-2.83 (m, 14 H), 2.29-2.54 (m, 15 H), 2.11-2.28 (m, 6 H), 1.87-2.05 (m, 7 H), 1.74-1.84 (m, 2 H). 100 H's/35 H's (spectrum/structure). $^{19}F$ NMR (376 MHz, METHANOL-$d_4$) δ ppm −144.08 (s), −145.13 (s), −175.36 (s). Title compound exhibited two sets of signals with a ratio of about 1:2 in $^1H$ NMR and $^{19}F$ NMR. The integration was based on the minor atropisomer. |
| 232 | 647.2 | $^1H$ NMR (400 MHz, METHANOL-$d_4$) δ ppm 9.38 (s, 1 H), 9.11 (s, 1 H), 8.52 (s, 1 H), 8.28 (s, 1 H), 7.96 (s, 1 H), 7.90-7.93 (m, 1 H), 7.89 (s, 1 H), 7.88 (s, 1 H), 5.93 (br d, J = 13.27 Hz, 1 H), 5.52 5.71 (m, 2 H), 4.99-5.08 (m, 2 H), 4.68-4.80 (m, 4 H), 4.42-4.63 (m, 3 H), 4.29 (br s, 2 H), 3.86-4.13 (m, 8 H), 3.36-3.55 (m, 7 H), 3.15 (br s, 1 H), 2.66-2.87 (m, 3 H), 2.59-2.64 (m, 2 H), 2.33-2.57 (m, 11 H), 2.14-2.26 (m, 3 H), 1.88-2.08 (m, 5 H), 1.63-1.87 (m, 4 H). $^{19}F$ NMR (376 MHz, METHANOL-$d_4$) δ ppm −144.25 (br s), −144.97 (s), −175.12 (d, J = 5.20 Hz), −175.20 (d, J = 5.20 Hz). |
| 233 | 663.2 | $^1H$ NMR (500 MHz, METHANOL-$d_4$) δ ppm 8.95 (s, 1 H), 7.85 (s, 1 H), 7.84 (s, 1 H), 6.50 (s, 1 H), 5.24-5.38 (m, 1 H), 4.38 (d, J = 10.38 Hz, 1 H), 4.25-4.36 (m, 1 H), 4.23 (d, J = 10.38 Hz, 1 H), 3.94-4.01 (m, 1 H), 3.91 (d, J = 11.16 Hz, 1 H), 3.14-3.29 (m, 5 H), 2.95-3.09 (m, 3 H), 2.76-2.87 (m, 2 H), 2.39-2.47 (m, 1 H), 2.31-2.37 (m, 1 H), 2.26 (br s, 4 H), 1.99 (br dd, J = 11.42, 6.49 Hz, 4 H), 1.84-1.95 (m, 2 H), 1.63-1.77 (m, 1 H). $^{19}F$ NMR (471 MHz, METHANOL-$d_4$) δ ppm −142.10 (s), −173.67 (s). Stereochemistry of Example 233 was confirmed by X-Ray crystallography analysis. |
| 234 | 663.2 | $^1H$ NMR (500 MHz, METHANOL-$d_4$) δ ppm 9.42 (s, 1 H), 9.19 (s, 1 H), 7.93 (s, 1 H), 7.85 (s, 4 H), 6.83 (s, 1 H), 6.69 (s, 1 H), 5.50- |

TABLE 45-continued

| Analytical Data for Examples 136 to 149, 223 to 234 and 372 to 384. | | |
|---|---|---|
| Cmpd.# | MS m/z (ESI): $(M + H)^+$ | $^1H$ and $^{19}F$ NMR |
| | | 5.68 (m, 1 H), 4.99-5.08 (m, 2 H), 4.75-4.82 (m, 5 H), 4.73 (s, 1 H), 4.65-4.69 (m, 3 H), 4.61 (s, 1 H), 3.97-4.10 (m, 6 H), 3.92 (br d, J = 15.96 Hz, 4 H), 3.44-3.52 (m, 4 H), 3.26-3.31 (m, 3 H), 3.04-3.19 (m, 11 H), 2.59-2.68 (m, 5 H), 2.47 (br d, J = 9.86 Hz, 1 H), 2.33-2.43 (m, 8 H), 2.19 (br dd, J = 10.25, 5.58 Hz, 3 H), 2.04-2.10 (m, 3 H), 1.94-2.02 (m, 5 H), 1.86-1.91 (m, 2 H), 1.67-1.74 (m, 6 H). $^{19}F$ NMR (471 MHz, METHANOL-$d_4$) δ ppm −143.91 (br s), −144.19 (br s), −174.11 (br s), −174.16 (br s). |
| 372 | 636.0 | $^1H$ NMR (400 MHz, METHANOL-$d_4$) δ ppm 9.15 (s, 1 H), 7.80 (s, 2 H), 5.41-5.82 (m, 1 H), 4.97-5.18 (m, 1 H), 4.61-4.78 (m, 3 H), 3.87-4.16 (m, 5 H), 3.44-3.55 (m, 1 H), 3.13-3.26 (m, 1 H), 2.56-2.93 (m, 3 H), 2.34-2.53 (m, 5 H), 1.99-2.31 (m, 6 H), 1.46-1.92 (m, 6 H), 1.26 (s, 4 H). $^{19}F$ NMR (376 MHz, METHANOL-$d_4$) δ −77.08 (s), −141.99 (s), −174.05 (s). |
| 373 | 643.3 | $^1H$ NMR (METHANOL-$d_4$, 400 MHz) δ ppm 8.9-9.1 (m, 1H), 7.7-7.8 (m, 1H), 7.56 (s, 1H), 6.51 (s, 1H), 5.2-5.4 (m, 1H), 4.9-5.0 (m, 1H), 4.39 (d, 1H, J = 10.7 Hz), 4.25 (d, 1H, J = 10.7 Hz), 3.9-4.0 (m, 2H), 2.9-3.3 (m, 6H), 2.7-2.9 (m, 2H), 2.65 (s, 1H), 2.60 (s, 3H), 2.1-2.4 (m, 6H), 1.9-2.1 (m, 6H). |
| 374 | 649.2 | $^1H$ NMR (400 MHz, METHANOL-$d_4$) δ ppm 9.35 (s, 1 H), 9.15 (s, 1 H), 7.98 (s, 1 H), 7.92 (s, 1 H), 7.84 (s, 1 H), 7.83 (s, 1 H), 6.79 (s, 1 H), 6.62 (s, 1 H), 5.22-5.49 (m, 4 H), 4.97 (br s, 1 H), 4.94 (br s, 1 H), 4.65-4.75 (m, 1 H), 4.36-4.46 (m, 2 H), 4.23-4.35 (m, 6 H), 4.00-4.19 (m, 4 H), 3.82-3.93 (m, 3 H), 3.49-3.66 (m, 4 H), 3.35-3.37 (m, 1 H), 3.29 (d, J = 2.90 Hz, 1 H), 3.20 (br s, 3 H), 3.25 (br s, 2 H), 2.96-3.06 (m, 7 H), 2.94 (s, 1 H), 2.90-2.92 (m, 1 H), 2.88 (d, J = 2.28 Hz, 1 H), 2.79-2.81 (m, 1 H), 2.78-2.96 (m, 1 H), 2.74 (br d, J = 7.05 Hz, 1 H), 2.53-2.78 (m, 1 H), 2.32-2.51 (m, 2 H), 2.20-2.32 (m, 3 H), 2.10-2.20 (m, 2 H), 1.96-2.09 (m, 7 H), 1.92 (br d, J = 6.22 Hz, 1 H). $^{19}F$ NMR (376 MHz, METHANOL-$d_4$) δ ppm −142.26 (s), −143.11 (s), −173.67 (s), −173.68 (s). |
| 375 | 663.2 | $^1H$ NMR (400 MHz, METHANOL-$d_4$) δ ppm 9.23 (s, 1 H), 8.98 (s, 1 H), 7.86 (s, 1 H), 7.74 (s, 1 H), 6.43 (s, 1 H), 5.23-5.41 (m, 2 H), 4.42-4.61 (m, 2 H), 4.30-4.37 (m, 1 H), 4.23-4.29 (m, 1 H), 4.03-4.11 (m, 1 H), 3.82-3.94 (m, 2 H), 3.68-3.81 (m, 2 H), 3.36-3.44 (m, 1 H), 3.19-3.29 (m, 3 H), 2.87-3.10 (m, 3 H), 2.67-2.78 (m, 1 H), 2.50-2.59 (m, 2 H), 2.22-2.40 (m, 2 H), 2.11-2.20 (m, 2 H), 1.86-2.05 (m, 4 H). $^{19}F$ NMR (376 MHz, METHANOL-$d_4$) δ ppm −142.38 (s), −173.73 (s). |
| 376 | 663.2 | $^1H$ NMR (400 MHz, METHANOL-$d_4$) δ ppm 8.98 (s, 1 H), 7.87 (s, 1 H), 7.75 (s, 1 H), 6.43 (s, 1 H), 5.23-5.42 (m, 2 H), 4.42-4.61 (m, 2 H), 4.26-4.35 (m, 2 H), 4.07 (br d, J = 11.20 Hz, 1 H), 3.69-3.93 (m, 4 H), 3.37-3.45 (m, 1 H), 3.17-3.26 (m, 3 H), 2.87-3.06 (m, 3 H), 2.66-2.78 (m, 1 H), 2.48-2.60 (m, 2 H), 2.12-2.37 (m, 4 H), 1.99-2.07 (m, 2 H), 1.82-1.94 (m, 1 H), 1.31 (s, 1 H), 1.22 (s, 1 H). $^{19}F$ NMR (376 MHz, METHANOL-d4) δ ppm −142.38 (s), −173.62 (s). |
| 377 | 664.2 | $^1H$ NMR (400 MHz, METHANOL-$d_4$) δ ppm 9.14-9.29 (m, 1 H), 7.68-7.89 (m, 2 H), 5.22-5.54 (m, 3 H), 4.47-4.59 (m, 1 H), 4.12-4.42 (m, 3 H), 3.39-3.62 (m, 5 H), 3.09-3.20 (m, 1 H), 2.76-2.89 (m, 3 H), 2.63-2.71 (m, 1 H), 1.84-2.52 (m, 10 H), 1.57-1.72 (m, 1 H), 1.31-1.41 (m, 1 H). $^{19}F$ NMR (376 MHz, METHANOL-$d_4$) δ ppm −142.41-−140.47 (m), −174.71-−173.10 m). |

TABLE 45-continued

| Analytical Data for Examples 136 to 149, 223 to 234 and 372 to 384. | | |
|---|---|---|
| Cmpd.# | MS m/z (ESI): $(M + H)^+$ | $^1H$ and $^{19}F$ NMR |
| 378 | 664.0 | $^1H$ NMR (400 MHz, METHANOL-$d_4$) δ ppm 9.10-9.31 (m, 1 H), 7.68-7.91 (m, 2 H), 5.09-5.52 (m, 3 H), 4.05-4.64 (m, 4 H), 3.40-3.61 (m, 5 H), 3.20 (br d, J = 2.1 Hz, 1 H), 2.65-2.89 (m, 4 H), 1.89-2.50 (m, 9 H), 1.52-1.72 (m, 1 H), 1.28-1.40 (m, 2 H). $^{19}F$ NMR (376 MHz, METHANOL-$d_4$) δ ppm −142.20-−141.46 (m), −174.26-−173.42 (m). |
| 379 | 678.0 | $^1H$ NMR (400 MHz, METHANOL-$d_4$) δ ppm 9.16-9.30 (m, 1 H), 7.79-7.88 (m, 1 H), 7.72 (s, 1 H), 5.22-5.49 (m, 2 H), 4.67-4.75 (m, 1 H), 4.25-4.49 (m, 3 H), 4.12-4.24 (m, 1 H), 4.00-4.10 (m, 1 H), 3.85-3.97 (m, 2 H), 3.58-3.72 (m, 1 H), 3.36-3.53 (m, 3 H), 3.02-3.19 (m, 2 H), 2.68-2.89 (m, 2 H), 1.93-2.60 (m, 9 H), 1.36-1.42 (m, 3 H), 1.27-1.35 (m, 1 H). $^{19}F$ NMR (376 MHz, METHANOL-$d_4$) δ ppm −141.93-−140.44 (m), −174.35-−173.40 (m) |
| 380 | 663.0 | $^1H$ NMR (400 MHz, METHANOL-$d_4$) δ ppm 9.32-9.38 (m, 1 H), 7.79-7.89 (m, 2 H), 7.33-7.41 (m, 1 H), 5.50-5.71 (m, 1 H), 5.25-5.33 (m, 1 H), 5.05-5.13 (m, 1 H), 4.59-4.72 (m, 2 H), 3.84-4.21 (m, 7 H), 3.44-3.62 (m, 2 H), 2.93-3.10 (m, 1 H), 2.33-2.81 (m, 9 H), 2.15-2.24 (m, 1 H), 1.74-1.86 (m, 1 H), 1.40-1.53 (m, 4 H), 1.32-1.36 (m, 1 H). $^{19}F$ NMR (376 MHz, METHANOL-$d_4$) δ ppm −77.96-−76.90 (m), −143.38-−141.79 (m), −175.21-−173.80 (m). |
| 381 | 664.8 | $^1H$ NMR (400 MHz, METHANOL-$d_4$) δ ppm 9.16-9.29 (m, 1 H), 7.76-7.86 (m, 1 H), 7.73 (s, 1 H), 5.15-5.45 (m, 2 H), 4.64-4.77 (m, 1 H), 4.13-4.43 (m, 6 H), 3.78-3.93 (m, 1 H), 3.54-3.73 (m, 2 H), 3.15-3.29 (m, 3 H), 2.95-3.10 (m, 2 H), 2.81-2.92 (m, 1 H), 2.63-2.79 (m, 2 H), 2.46-2.58 (m, 1 H), 2.10-2.42 (m, 3 H), 1.97-1.97 (m, 1 H), 1.91-2.07 (m, 4 H), 1.09-1.10 (m, 1 H), 1.05-1.21 (m, 1 H). $^{19}F$ NMR (376 MHz, METHANOL-$d_4$) δ ppm −142.22-−139.70 (m), −174.36-−172.35 (m). |
| 382 | 662.2 | $^1H$ NMR (400 MHz, METHANOL-$d_4$) δ ppm 9.15-9.25 (m, 1 H), 8.43-8.63 (m, 1 H), 7.75-7.85 (m, 1 H), 7.59-7.76 (m, 1 H), 5.26-5.55 (m, 2 H), 4.33-4.49 (m, 2 H), 4.14-4.31 (m, 1 H), 3.36-3.52 (m, 3 H), 3.02-3.21 (m, 2 H), 2.67-2.91 (m, 2 H), 1.77-2.56 (m, 15 H), 1.27-1.41 (m, 1 H). $^{19}F$ NMR (376 MHz, METHANOL-$d_4$) δ ppm −141.86-−140.27 (m), −175.37-−173.14 (m). |
| 383 | 659.2 | $^1H$ NMR (400 MHz, METHANOL-$d_4$) δ ppm 8.80 (s, 2 H), 8.72 (s, 1 H), 8.17 (s, 2 H), 8.09 (s, 1 H), 7.96 (s, 1 H), 7.94 (s, 2 H), 6.49 (s, 2 H), 6.19 (s, 1 H), 5.51-5.76 (m, 2 H), 5.06-5.13 (m, 2 H), 4.81 (s, 1 H), 4.78 (s, 1 H), 4.71 (d, J = 4.56 Hz, 1 H), 4.68 (s, 1 H), 4.66-4.82 (m, 1 H), 3.91-4.17 (m, 19 H), 3.48-3.58 (m, 5 H), 3.37 (br s, 1 H), 2.56-2.83 (m, 15 H), 2.32-2.52 (m, 10 H), 1.98-2.30 (m, 5 H), 1.74-1.94 (m, 7 H), 1.32 (br s, 3 H), 0.74-0.87 (m, 3 H). $^{19}F$ NMR (376 MHz, METHANOL-$d_4$) δ ppm −141.31 (s), −142.04 (s), −175.38 (s), −175.41 (s). |
| 384 | 667.9 | $^1H$ NMR (400 MHz, METHANOL-$d_4$) δ ppm 9.05-9.27 (m, 1 H), 7.61-7.85 (m, 2 H), 5.20-5.44 (m, 1 H), 4.84-5.00 (m, 1 H), 4.47-4.64 (m, 1 H), 4.12-4.46 (m, 3 H), 3.68-4.10 (m, 5 H), 3.41-3.64 (m, 1 H), 3.14-3.29 (m, 3 H), 2.89-3.07 (m, 2 H), 1.83-2.61 (m, 10 H), 1.19-1.82 (m, 6 H). $^{19}F$ NMR (376 MHz, METHANOL-$d_4$) δ ppm −144.54-−139.31 (m), −175.32-−171.39 (m). |

(24R,26R)-18-Chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol, (24R,26S)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol, (24S,26R)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol, and (24S,26S)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol (Example 235)

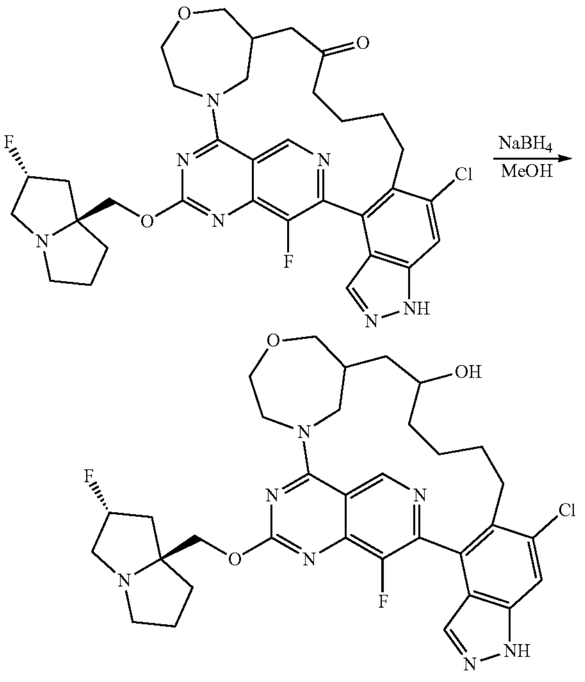

Example 235

A 2 mL vial was charged with (26R)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one and (26S)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-one (Example 230, 6 mg, 6.82 μmol) and methanol (0.35 mL). Sodium borohydride (10.0 mg, 0.27 mmol) was added, and the reaction mixture was stirred at rt for 1 h. The mixture was quenched with a few drops of water and most of the methanol was evaporated under reduced pressure. The residue was purified by reverse phase HPLC, eluting with 9-95% MeCN (0.1% TFA as the additive) in water (0.1% TFA as the additive), to provide after lyophilization (24R,26R)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol, (24R,26S)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol, (24S,26R)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol, and (24S,26S)-18-chloro-32-fluoro-4-(((2R,7aS)-2-fluorotetrahydro-1H-pyrrolo[1,2-a]pyrrol-7a(5H)-yl)methoxy)-28-oxa-1,3,5,9,14,15-hexaazahexacyclo[24.4.1.1~6,10~.0~2,7~.0~11,19~.0~12,16~]dotriaconta-2,4,6(32),7,9,11,13,16,18-nonaen-24-ol (2.5 mg, 2.8 μmol, 42% yield) as white solid. $^1$H NMR (400 MHz, METHANOL-$d_4$) δ ppm 9.34-9.70 (m, 1H), 7.64-7.88 (m, 2H), 5.47-5.74 (m, 1H), 5.00-5.23 (m, 1H), 4.56-4.78 (m, 3H), 3.36-4.41 (m, 11H), 1.89-3.25 (m, 9H), 0.32-1.87 (m, 8H). $^{19}$F NMR (376 MHz, METHANOL-$d_4$) δ ppm −78.10–−77.22 (m), −141.99–−141.45 (m), −174.33–−173.84 (m). m/z (ESI): 655.0 (M+H)$^+$.

(15R,17S)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-ol bis(2,2,2-trifluoroacetate) salt and (15S,17S)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-15-ol bis(2,2,2-trifluoroacetate) salt (Example 385)

Example 385

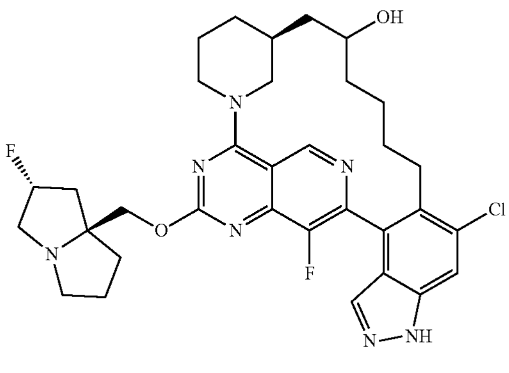

This compound was prepared analogous to Example 235 using Example 372 as starting material. $^1$H NMR (400 MHz, METHANOL-$d_4$) δ ppm 9.34-9.39 (m, 1H), 9.31 (s, 1H), 9.12-9.41 (m, 1H), 7.81 (d, J=4.1 Hz, 2H), 5.41-5.80 (m, 1H), 4.91-5.03 (m, 2H), 4.72 (d, J=16.2 Hz, 2H), 3.85-4.16 (m, 4H), 3.37-3.68 (m, 3H), 3.16-3.29 (m, 1H), 2.58-2.93 (m, 3H), 2.31-2.54 (m, 3H), 2.15-2.29 (m, 2H), 1.33-1.92 (m, 10H). $^{19}$F NMR (376 MHz, METHANOL-$d_4$) δ ppm −77.21 (s), −142.77–−141.92 (m), −174.08 (s). m/z (ESI): 638.0 (M+H)$^+$.

(17R)-9-Chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one and (17S)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one (Example 236)
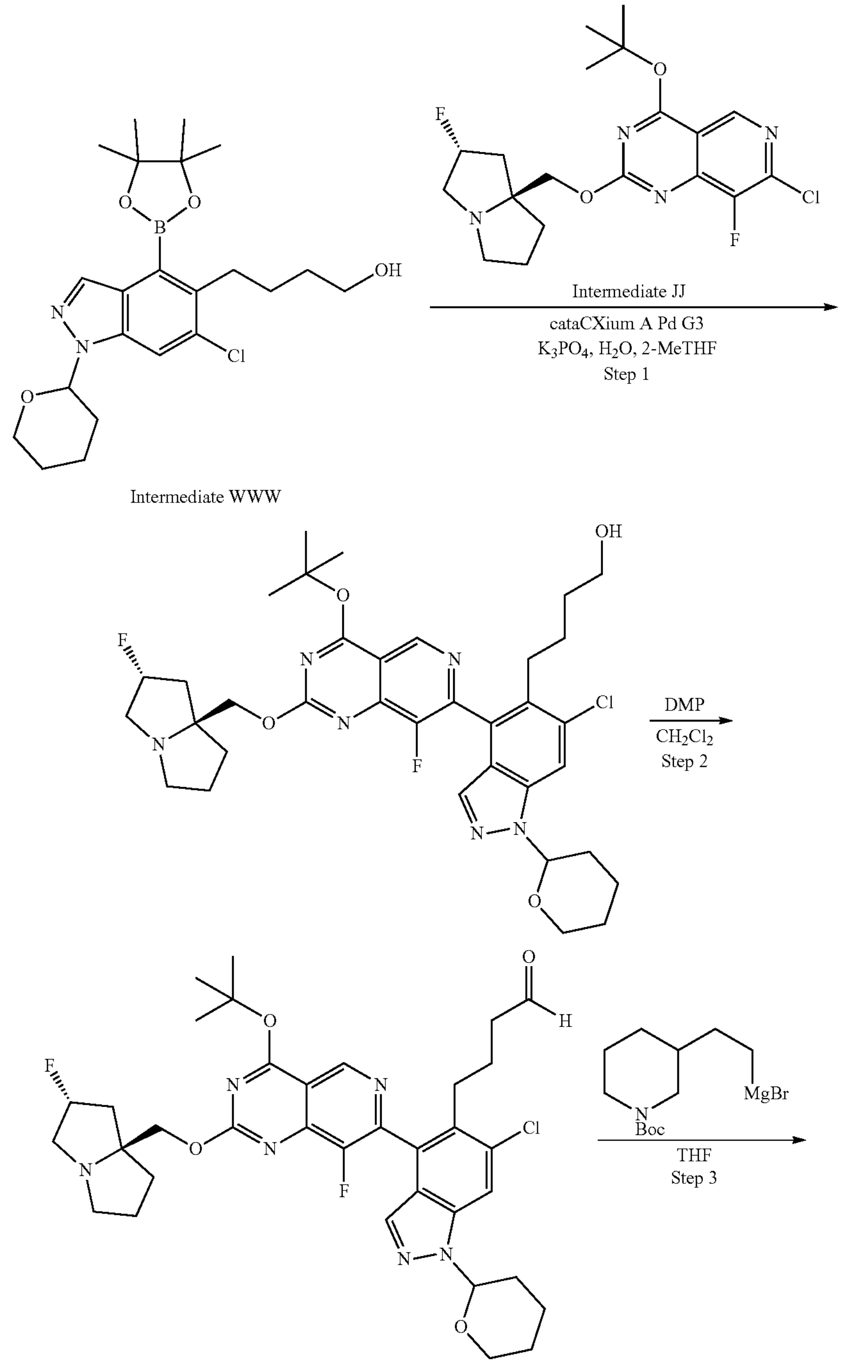

-continued

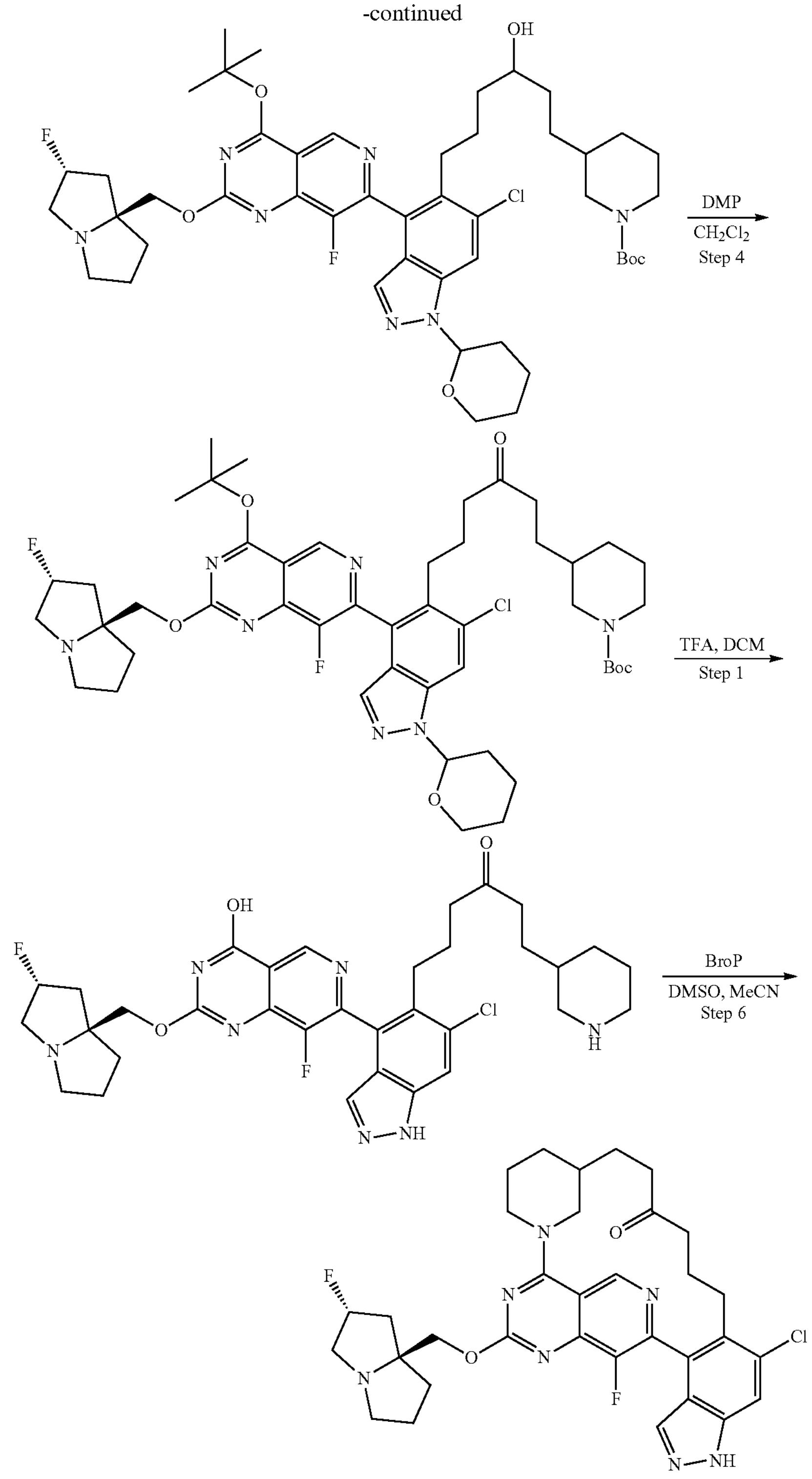

Example 236

Step 1. 4-(4-(4-(tert-Butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butan-1-ol. A vial was charged with 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (0.30 g, 0.72 mmol, Intermediate JJ), 4-(6-chloro-1-(tetrahydro-2H-pyran-2-yl)-4-(4,4,5,5-tetramethyl-1,3,2-dioxaborolan-2-yl)-1H-indazol-5-yl)butan-1-ol (0.26 g, 0.60 mmol, Intermediate WWW), cataCXium A Pd G3 (43.6 mg, 0.060 mmol), potassium triphosphate (0.38 g, 1.79 mmol), 2-methyltetrahydrofuran (2.7 mL) and water (0.27 mL) under nitrogen atmosphere. The mixture was heated to 65° C. for 4 h. After cooling to rt, the reaction mixture was filtered, and the filtrate was concentrated. The crude residue was purified by flash column chromatography on silica gel, eluting with a gradient of 0-100% EtOAc in heptane, to give 4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butan-1-ol (0.24 g, 0.35 mmol, 58% yield) as colorless oil. m/z (ESI): 685.0 $(M+H)^+$.

Step 2. 4-(4-(4-(tert-Butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butanal. A screw-cap vial was charged with 4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butan-1-ol (0.24 g, 0.35 mmol) in DCM (1.8 mL). Dess-Martin periodinane (0.26 g, 0.61 mmol) was added and the reaction mixture was stirred at rt for 18 h. The reaction mixture was diluted with saturated $NaHCO_3$ and extracted with EtOAc. The organic extract was washed with saturated NaCl, dried over $MgSO_4$, filtered, and concentrated. The crude material was purified by column chromatography on silica gel, eluting with a gradient of 0-100% 3:1 EtOAc:EtOAc with 1% TEA in heptane, to provide 4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butanal (0.20 g, 0.29 mmol, 84% yield) as yellow solid. m/z (ESI): 682.8 $(M+H)^+$.

Step 3. tert-Butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-hydroxyhexyl)piperidine-1-carboxylate. To a 50-mL round-bottom flask was added 4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butanal (0.20 g, 0.293 mmol) in THF (1.5 mL). At −78° C., (2-(1-(tert-butoxycarbonyl)piperidin-3-yl)ethyl)magnesium bromide (0.5 M solution in THF, 2.3 mL, 1.15 mmol) was added to the solution and the reaction mixture was stirred for 2 h at this temperature. The cold bath was removed, and the reaction mixture was diluted with sat. $NaHCO_3$ solution and extracted with EtOAc. The organic extract was washed with sat'd NaCl and dried over $MgSO_4$, filtered, and concentrated. The crude material was purified by column chromatography on silica gel, eluting with a gradient of 0-100% 3:1 EtOAc:EtOH with 1% TEA in heptane, to provide tert-butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-hydroxyhexyl)piperidine-1-carboxylate (0.10 g, 0.11 mmol, 38% yield) as colorless oil. m/z (ESI): 895.9 $(M+H)^+$.

Step 4. tert-Butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-oxohexyl)piperidine-1-carboxylate. A vial was charged with tert-butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-hydroxyhexyl)piperidine-1-carboxylate (100 mg, 0.11 mmol) in DCM (1.1 mL). Dess-Martin periodinane (71 mg, 0.17 mmol) was added and the mixture was stirred at rt for 16 h, then diluted with Sat. $NaHCO_3$ and extracted with EtOAc. The organic extract was washed with satd NaCl and dried over $MgSO_4$, filtered, and concentrated. The crude material was purified by column chromatography on silica gel, eluting with a gradient of 0-20% methanol in DCM, to provide tert-butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-oxohexyl)piperidine-1-carboxylate (70 mg, 0.078 mmol, 70% yield) as yellow solid. m/z (ESI): 894.0 $(M+H)^+$.

Step 5. 6-(6-Chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-(piperidin-3-yl)hexan-3-one. To a 25-mL round-bottom flask was added tert-butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-oxohexyl)piperidine-1-carboxylate (70 mg, 0.078 mmol) and hydrogen chloride solution, (4 M in dioxane, 0.98 mL, 3.92 mmol) in DCE (1.6 mL). The reaction mixture was stirred at rt for 2 h, fully concentrated and the crude purified by reverse phase chromatography using C18 column, eluting with a gradient of 5-100% (0.1% formic acid MeCN)/(0.1% formic acid water), to give 6-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-(piperidin-3-yl)hexan-3-one after lypholization and free basing the amine via the use of an SCX column. m/z (ESI): 653.8 $(M+H)^+$.

Step 6. (17R)-9-Chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one and (17S)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one. A 100-mL round-bottom flask was charged with 6-(6-chloro-4-(8-fluoro-2-(((2R,7aS)-2-fluorotetrahydro-1H-pyrrolizin-7a(5H)-yl)methoxy)-4-hydroxypyrido[4,3-d]pyrimidin-7-yl)-1H-indazol-5-yl)-1-(piperidin-3-yl)hexan-3-one (25 mg, 0.038 mmol) and Hunigs base (47 μL, 0.27 mmol) in acetonitrile (3.2 mL) and dimethyl sulfoxide (0.65 mL). Bromotripyrrolidinophosphonium hexafluorophosphate (29 mg, 0.061 mmol) was added and the reaction mixture was stirred at rt for 2 h. The solution was fully concentrated and the crude material was purified by reverse phase HPLC to give (17R)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one and (17S)-9-chloro-30-fluoro-24-(((2R,7aS)-2-fluorotetrahydro-1H-pyrrolo[1,2-a]pyrrol-7a(5H)-yl)methoxy)-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-one (11 mg, 0.013 mmol, 33% yield) as white solid. m/z (ESI): 635.8 $(M+H)^+$. $^1H$ NMR (400 MHz, METHANOL-$d_4$) δ ppm 9.30 (s, 1H), 7.81-7.95 (m, 2H), 5.50-5.77 (m, 1H), 5.04-5.15 (m, 1H), 4.62-4.81 (m, 3H), 3.82-4.16 (m, 4H), 3.38-3.58 (m, 2H), 3.20-3.31 (m, 1H), 2.56-2.87 (m, 5H), 2.13-2.52 (m, 8H), 1.59-2.10 (m, 9H), 1.39-1.57 (m, 2H), 0.99-1.33 (m, 2H).

(14R,17S)-30-Fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-ol and (14S,17R)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-ol (Example 237 and 238)

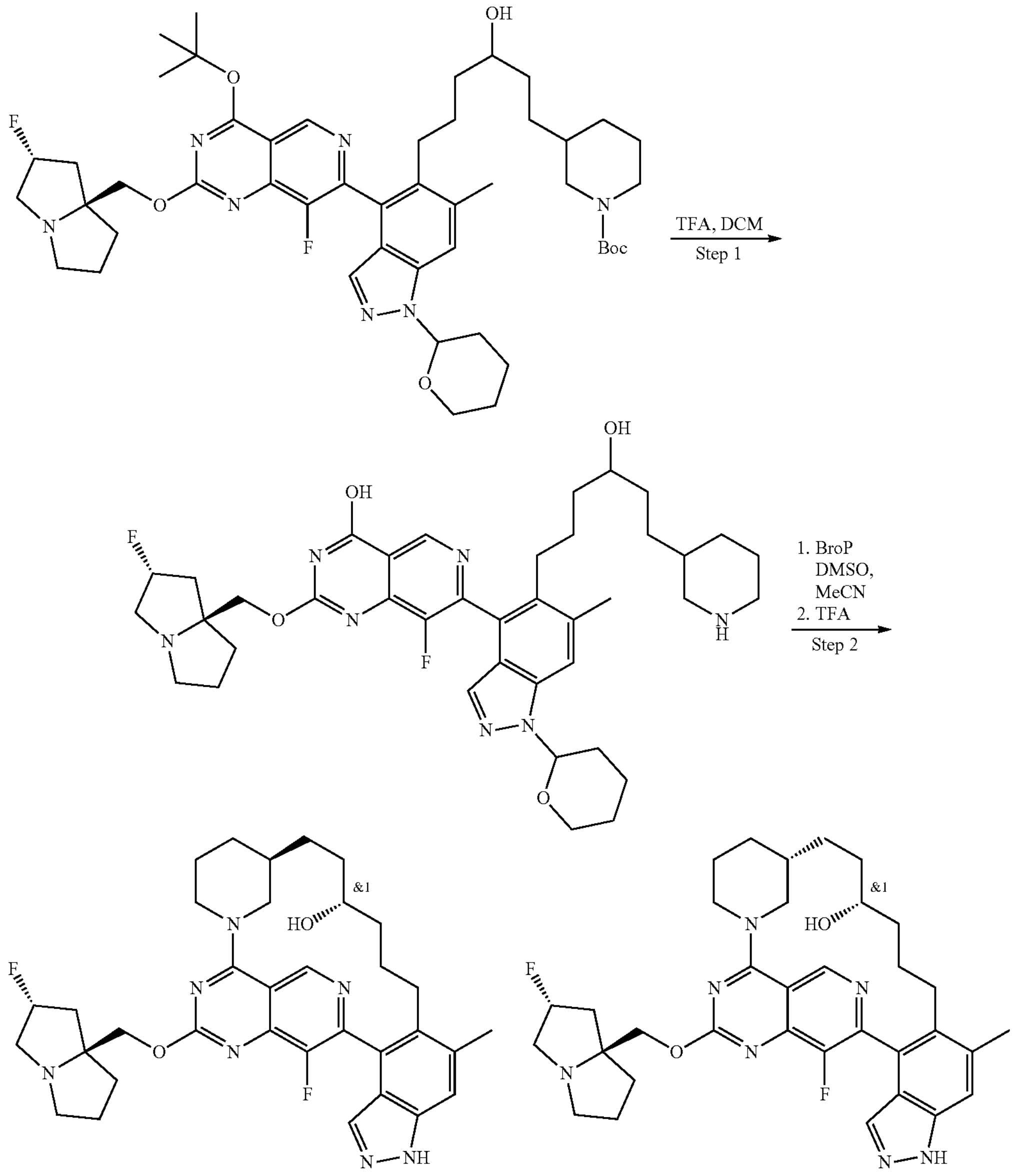

Example 237

Example 238

Step 1. 8-Fluoro-2-(((2R,7aS)-2-fluorotetrahydro-1H-pyrrolizin-7a(5H)-yl)methoxy)-7-(5-(4-hydroxy-6-(piperidin-3-yl)hexyl)-6-methyl-1-(tetrahydro-2H-pyran-2-yl)-1H-indazol-4-yl)pyrido[4,3-d]pyrimidin-4-ol. To a 25-mL round-bottomed flask was added tert-butyl 3-(6-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-3-hydroxyhexyl)piperidine-1-carboxylate (Step 3 in Example 230, 0.11 g, 0.12 mmol) in DCM (0.75 mL). At 0° C., TFA (0.47 mL, 6.10 mmol) was added, and the reaction mixture was stirred for 1 h. The reaction mixture was quenched with 5 N aqueous sodium hydroxide (1.1 mL, 5.5 mmol) and extracted with DCM. The organic layer was dried over $MgSO_4$, filtered, and concentrated. The crude was purified by reverse phase C18 column, eluting with a gradient of 5-100% (0.1% formic acid MeCN) in (0.1% formic acid water) to provide 8-fluoro-2-(((2R,7aS)-2-fluorotetrahydro-1H-pyrrolizin-7a(5H)-yl)methoxy)-7-(5-(4-hydroxy-6-(piperidin-3-yl)hexyl)-6-methyl-1-(tetrahydro-2H-pyran-2-yl)-1H-indazol-4-yl)pyrido[4,3-d]pyrimidin-4-ol (25 mg, 0.035 mmol, 29% yield) after lyophilization and converting to the free amine by passing through a SCX column. m/z (ESI): 719.9 $(M+H)^+$.

Step 2. (14R,17S)-30-Fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-ol and (14S,17R)-30-Fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-ol. A 100-mL round-bottom flask was charged with 8-fluoro-2-(((2R,7aS)-2-fluorotetrahydro-1H-pyrrolizin-7a(5H)-yl)methoxy)-7-(5-(4-hydroxy-6-(piperidin-3-yl)hexyl)-6-methyl-1-(tetrahydro-2H-pyran-2-yl)-1H-indazol-4-yl)pyrido[4,3-d]pyrimidin-4-ol (25 mg, 0.035 mmol), acetonitrile (2.9 mL) and Hunig's base (42 μL, 0.24 mmol) in acetonitrile (2.9 mL) and dimethyl sulfoxide (0.6 mL). Bromotripyrrolidinophosphonium hexafluorophosphate (26 mg, 0.056 mmol) was added and the reaction mixture was stirred at rt for 3 h. The crude mixture was purified by reverse phase C18 column, eluting with a gradient of 5-100% (0.1% formic acid MeCN) in (0.1% formic acid water) to give the desired product as well as the phosphine oxide. The material was dissolved in 1 mL of DCE and was treated with 0.5 mL of TFA. After stirring at rt for for 2 h, the solution was fully concentrated and the material was purified by prep-HPLC to (14R,17S)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-ol (peak #1: $^1$H NMR (400 MHz, METHANOL-$d_4$) δ ppm 9.34 (s, 1H), 7.73 (s, 1H), 7.55 (s, 1H), 5.49-5.78 (m, 1H), 5.04-5.14 (m, 1H), 4.60-4.80 (m, 2H), 3.83-4.20 (m, 4H), 3.50-3.56 (m, 1H), 3.11-3.29 (m, 1H), 2.31-2.93 (m, 11H), 2.00-2.27 (m, 2H), 1.80-1.98 (m, 2H), 1.20-1.78 (m, 8H), 0.78-1.05 (m, 3H), 0.43-0.69 (m, 1H)) and (14S,17R)-30-fluoro-24-(((2R,7aS)-2-fluorotetrahydro-1H-pyrrolo[1,2-a]pyrrol-7a(5H)-yl)methoxy)-9-methyl-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-14-ol (peak #2: $^1$H NMR (400 MHz, METHANOL-$d_4$) δ ppm 9.17-9.38 (m, 1H), 7.67-7.88 (m, 1H), 7.38-7.61 (m, 1H), 5.41-5.79 (m, 1H), 4.95-5.10 (m, 2H), 4.59-4.83 (m, 2H), 3.81-4.15 (m, 5H), 3.41-3.58 (m, 2H), 3.15-3.27 (m, 1H), 2.90-3.06 (m, 1H), 2.51-2.85 (m, 9H), 2.31-2.43 (m, 3H), 2.11-2.25 (m, 2H), 1.92-2.08 (m, 2H), 1.61-1.89 (m, 4H), 0.91-1.58 (m, 8H)) with the same mass. m/z (ESI): 618.0 $(M+H)^+$. The chiral centers were randomly assigned.

(17R)-9-Chloro-13,13,30-trifluoro-24-(((2R,7aS)-2-fluorotetrahydro-1H-pyrrolo[1,2-a]pyrrol-7a(5H)-yl)methoxy)-15,18-dioxa-5,6,21,23,25,29 hexaazahexacyclo[24.3.1.1~17,21~.0~2,10~.0~3,7~.0~22,27~]hentriaconta-1(30),2,4,7,9,22,24,26,28-nonaene (Example 150)

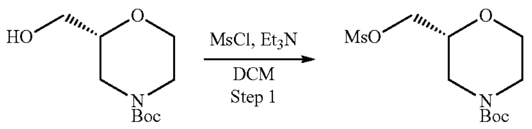

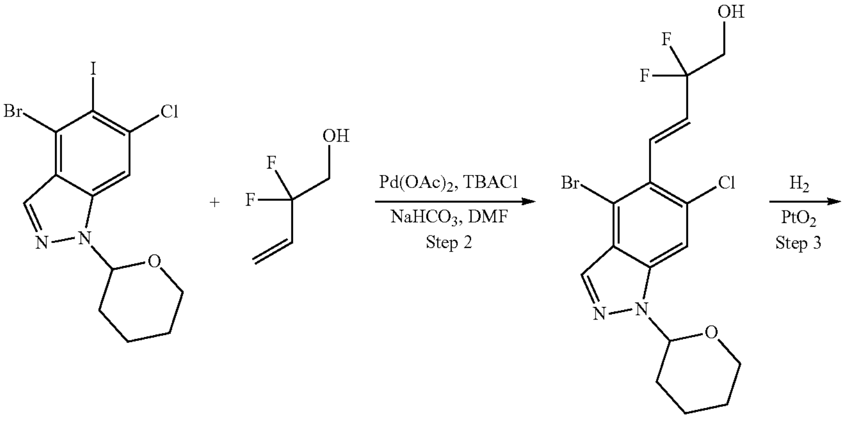

-continued
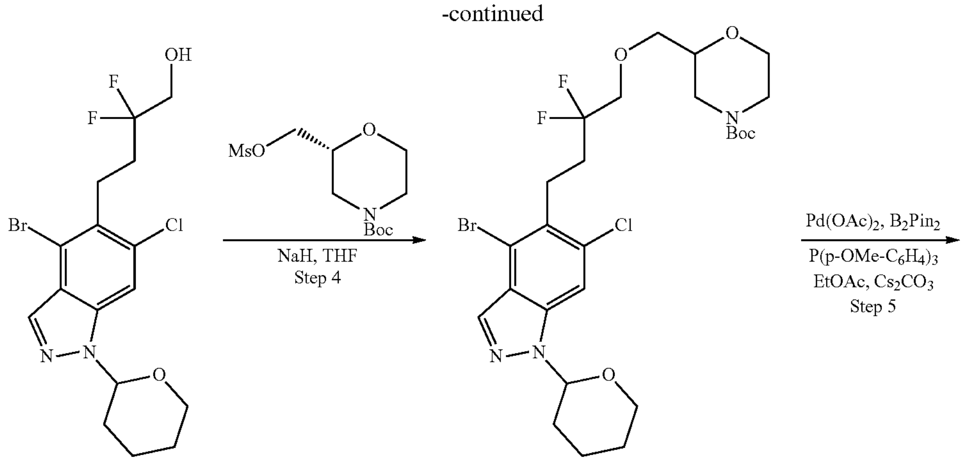
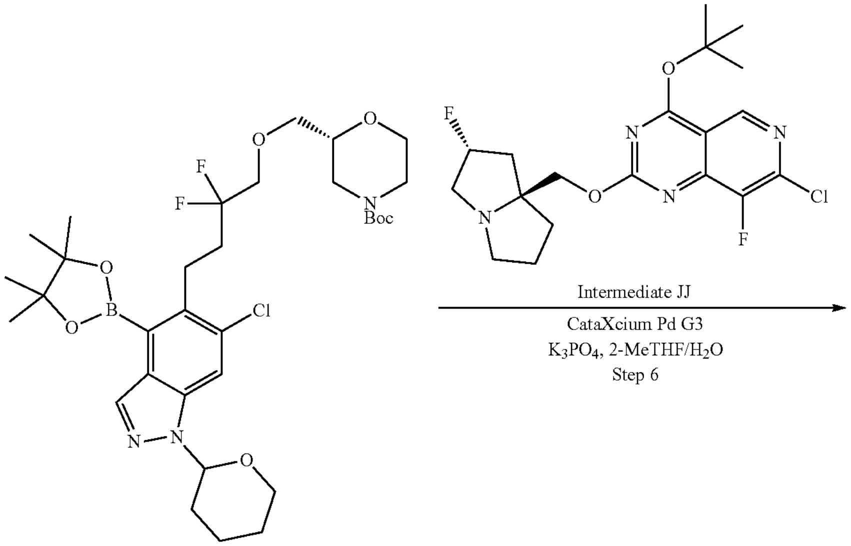
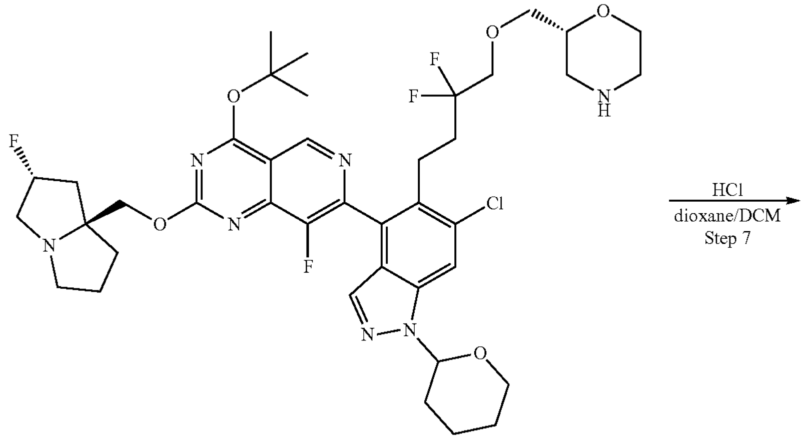

-continued

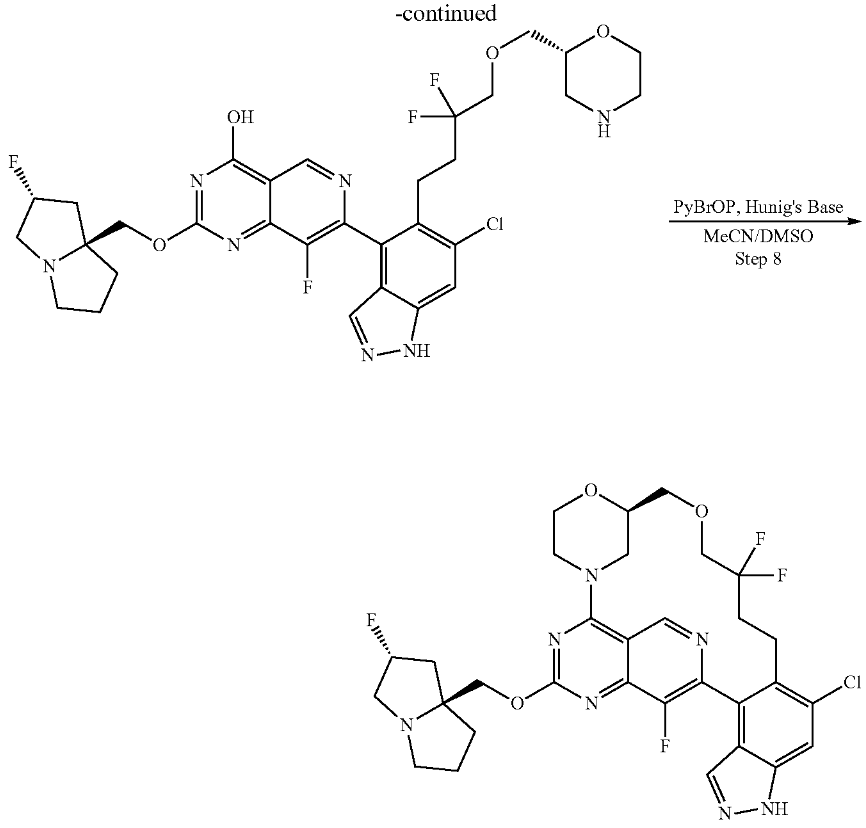

Example 150

Step 1. tert-Butyl (R)-2-(((methylsulfonyl)oxy)methyl) morpholine-4-carboxylate. To a 40 mL vial was charged with (R)—N-Boc-2-hydroxymethylmorpholine (1.00 g, 4.60 mmol) and triethylamine (0.97 mL, 6.9 mmol) in dichloromethane (30 mL). was added dropwise. Methanesulfonyl chloride (0.43 mL, 5.5 mmol) was added dropwise, and the reaction mixture was stirred at rt for 1.5 h. The reaction was fully concentrated, and the residue was purified by column chromatography on silica gel, eluting with 0-70% EtOAc in heptane, to give tert-butyl (R)-2-(((methylsulfonyl)oxy)methyl)morpholine-4-carboxylate (0.84 g, 2.8 mmol, 62% yield) as off-yellow oil. m/z (ESI): 196.1 $(M-Boc+H)^+$.

Step 2. (E)-4-(4-Bromo-6-chloro-1-(tetrahydro-2H-pyran-2-yl)-1H-indazol-5-yl)-2,2-difluorobut-3-en-1-ol. To a 20 mL vial was added 4-bromo-6-chloro-5-iodo-1-(tetrahydro-2H-pyran-2-yl)-1H-indazole (0.52 g, 1.19 mmol, Lab Network), tetrabutylammonium chloride (0.33 mL, 1.19 mmol), sodium bicarbonate (0.25 g, 2.97 mmol), and N,N-dimethylformamide (6 mL). The solution was degassed by sparging with nitrogen for 15 min, then palladium acetate (53 mg, 0.24 mmol) was added. The reaction mixture was placed on a preheated block and to it was added 2,2-difluorobut-3-en-1-ol (0.14 mL, 1.3 mmol) dropwise. The reaction mixture was heated for 35 min, cooled to rt, was then diluted with saturated aqueous sodium chloride, and extracted with EtOAc. The combined organics were washed with saturated aqueous sodium chloride, dried ($Na_2SO_4$) and concentrated. The residue was purified by column chromatography on silica gel, eluting with 0-55% EtOAc in heptane, to give (E)-4-(4-bromo-6-chloro-1-(tetrahydro-2H-pyran-2-yl)-1H-indazol-5-yl)-2,2-difluorobut-3-en-1-ol (0.23 g, 0.55 mmol, 46% yield) as yellow solid. m/z (ESI): 422.0 $(M+H)^+$.

Step 3. 4-(4-Bromo-6-chloro-1-(tetrahydro-2H-pyran-2-yl)-1H-indazol-5-yl)-2,2-difluorobutan-1-ol. To a 60 mL ChemGlass reactor was charged with (E)-4-(4-bromo-6-chloro-1-(tetrahydro-2H-pyran-2-yl)-1H-indazol-5-yl)-2,2-difluorobut-3-en-1-ol (0.23 g, 0.55 mmol) and platinum oxide (12 mg, 0.055 mmol). This was purged with nitrogen and then ethanol (20 mL) was added. The reaction was pressurized with hydrogen gas (50 psi) and allowed to stir at rt for 3 h. The solution was filtered through celite, and the filtrate was concentrated. The crude oil was purified by column chromatography on silica gel, eluting with 0-45% EtOAc in heptane, to give 4-(4-bromo-6-chloro-1-(tetrahydro-2H-pyran-2-yl)-1H-indazol-5-yl)-2,2-difluorobutan-1-ol (0.10 g, 0.24 mmol, 44% yield) as white solid. m/z (ESI): 423.8 $(M+H)^+$.

Step 4. tert-Butyl (2R)-2-((4-(4-bromo-6-chloro-1-(tetrahydro-2H-pyran-2-yl)-1H-indazol-5-yl)-2,2-difluorobutoxy)methyl)morpholine-4-carboxylate. To a 20 mL vial was charged with 4-(4-bromo-6-chloro-1-(tetrahydro-2H-pyran-2-yl)-1H-indazol-5-yl)-2,2-difluorobutan-1-ol (0.14 g, 0.33 mmol) in tetrahydrofuran (0.25 mL). Sodium hydride, 60% dispersion in mineral oil (21 mg, 0.53 mmol) was added and the reaction mixture was stirred at rt for 15 min. To this was added tert-butyl (R)-2-(((methylsulfonyl)oxy)methyl)morpholine-4-carboxylate (0.19 g, 0.66 mmol). The reaction was heated at 65° C. for 72 h. After cooling to rt, the mixture was diluted with saturated aqueous ammonium chloride and concentrated. The crude oil was purified by column chromatography on silica gel, eluting with a gradient of 0-60% EtOAc in heptane, to give tert-butyl (2R)-2-((4-(4-bromo-6-chloro-1-(tetrahydro-2H-pyran-2-yl)-1H-indazol-5-yl)-2,2-difluorobutoxy)methyl)morpholine-4-carboxylate (0.14 g, 0.23 mmol, 70% yield) as yellow oil. m/z (ESI): 522.8 $(M\text{-}Boc+H)^+$.

Step 5. tert-Butyl (2R)-2-((4-(6-chloro-1-(tetrahydro-2H-pyran-2-yl)-4-(4,4,5,5-tetramethyl-1,3,2-dioxaborolan-2-yl)-1H-indazol-5-yl)-2,2-difluorobutoxy)methyl)morpholine-4-carboxylate. To a 4 mL vial was charged with tert-butyl (2R)-2-((4-(4-bromo-6-chloro-1-(tetrahydro-2H-pyran-2-yl)-1H-indazol-5-yl)-2,2-difluorobutoxy)methyl) morpholine-4-carboxylate (0.14 g, 0.23 mmol), 4,4,4',4',5,5,5',5'-octamethyl-2,2'-bi(1,3,2-dioxaborolane) (70 mg, 0.27 mmol), tris(4-methoxyphenyl)phosphine (8 mg, 0.023 mmol), palladium acetate (2.6 mg, 0.011 mmol), cesium carbonate (0.11 g, 0.34 mmol), and EtOAc (1 mL). The reaction mixture was sparged with nitrogen and then heated to 80° C. for 3.5 h. After cooling to rt, the reaction was diluted with ethyl acetate, filtered, and concentrated. The crude material was purified by column chromatography on silica gel column, eluting with a gradient of 0-70% EtOAc in heptane, to give tert-butyl (2R)-2-((4-(6-chloro-1-(tetrahydro-2H-pyran-2-yl)-4-(4,4,5,5-tetramethyl-1,3,2-dioxaborolan-2-yl)-1H-indazol-5-yl)-2,2-difluorobutoxy)methyl) morpholine-4-carboxylate (60 mg, 0.09 mmol, 39% yield). m/z (ESI): 670.0 $(M+H)^+$.

Step 6. tert-Butyl (2R)-2-((4-(4-(4-(tert-Butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-2,2-difluorobutoxy)methyl)morpholine-4-carboxylate. A vial was charged with tert-butyl (2R)-2-((4-(6-chloro-1-(tetrahydro-2H-pyran-2-yl)-4-(4,4,5,5-tetramethyl-1,3,2-dioxaborolan-2-yl)-1H-indazol-5-yl)-2,2-difluorobutoxy)methyl) morpholine-4-carboxylate (60 mg, 0.09 mmol), 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (44 mg, 0.11 mmol, Intermediate JJ), potassium phosphate tribasic (57 mg, 0.27 mmol), cataCXium A Pd G3 (13 mg, 0.018 mmol), water (80 μL) and 2-methyltetrahydrofuran (0.8 mL). The reaction mixture was heated at 80° C. for 1.5 h. After cooling to rt, the reaction mixture was diluted with water and extracted with EtOAc. The combined organic phases were washed with brine, dried over anhydrous sodium sulfate, filtered, and concentrated under reduced pressure. The crude material was purified by column chromatography on silica gel, eluting with a gradient of 0-65% 3:1 EtOAc/EtOH (with 2% triethylamine) in heptane, to provide tert-butyl (2R)-2-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)-2,2-difluorobutoxy)methyl)morpholine-4-carboxylate (44 mg, 0.048 mmol, 53% yield) as off-white solid. m/z (ESI): 920.8 $(M+H)^+$.

Step 7. 7-(6-Chloro-5-(3,3-difluoro-4-(((R)-morpholin-2-yl)methoxy)butyl)-1H-indazol-4-yl)-8-fluoro-2-(((2R,7aS)-2-fluorotetrahydro-1H-pyrrolizin-7a(5H)-yl)methoxy) pyrido[4,3-d]pyrimidin-4-ol. A vial was charged with tert-butyl (2R)-2-((4-(4-(4-(tert-butoxy)-8-fluoro-2-(((2R,7aS)-2-fluorotetrahydro-1H-pyrrolizin-7a(5H)-yl)methoxy) pyrido[4,3-d]pyrimidin-7-yl)-6-chloro-1-(tetrahydro-2H-pyran-2-yl)-1H-indazol-5-yl)-2,2-difluorobutoxy)methyl) morpholine-4-carboxylate (0.31 g, 0.36 mmol) and dichloromethane (3.5 mL), then sonicated until all solids were dissolved. Hydrogen chloride (4 N solution in 1,4-dioxane, 4.4 mL, 17.6 mmol) was added, then the slurry was stirred vigorously for 35 min. The reaction was concentrated to dryness and the crude product was dissolved in MeOH and put through a 5 g Bond Elut SCX column with MeOH washing. The SCX column was then eluted with 2 M ammonia in MeOH to provide 7-(6-chloro-5-(3,3-difluoro-4-(((R)-morpholin-2-yl)methoxy)butyl)-1H-indazol-4-yl)-8-fluoro-2-(((2R,7aS)-2-fluorotetrahydro-1H-pyrrolizin-7a (5H)-yl)methoxy)pyrido[4,3-d]pyrimidin-4-ol (0.18 g, 0.29 mmol, 81% yield) as yellow solid. m/z (ESI): 681.0 $(M+H)^+$.

Step 8. (17R)-9-Chloro-13,13,30-trifluoro-24-(((2R,7aS)-2-fluorotetrahydro-1H-pyrrolo[1,2-a]pyrrol-7a(5H)-yl) methoxy)-15,18-dioxa-5,6,21,23,25,29 hexaazahexacyclo [24.3.1.1~17,21~.0~2,10~.0~3,7~.0~22,27~]hentriaconta-1 (30),2,4,7,9,22,24,26,28-nonaene diformate. In a 40 mL vial was charged with 7-(6-chloro-5-(3,3-difluoro-4-(((R)-morpholin-2-yl)methoxy)butyl)-1H-indazol-4-yl)-8-fluoro-2-(((2R,7aS)-2-fluorotetrahydro-1H-pyrrolizin-7a(5H)-yl) methoxy)pyrido[4,3-d]pyrimidin-4-ol (31 mg, 0.046 mmol), acetonitrile (4 mL), dimethyl sulfoxide (0.8 mL), and N,N-diisopropylethylamine (18 μL, 0.14 mmol). To this was added bromotris(dimethylamino)phosphonium hexafluorophosphate (28 mg, 0.073 mmol). The reaction mixture was stirred at rt for 1.5 h, was then concentrated. The residue was purified by reverse phase preparative HPLC using a gradient of 5-90% acetonitrile with 0.1% TFA in water with 0.1% TFA, followed by reverse phase chromatography using a C18 column, eluting with 5-75% acetonitrile with 0.1% formic acid in water with 0.1% formic acid, to provide (17R)-9-chloro-13,13,30-trifluoro-24-(((2R,7aS)-2-fluorotetrahydro-1H-pyrrolo[1,2-a]pyrrol-7a(5H)-yl)methoxy)-15,18-dioxa-5,6,21,23,25,29 hexaazahexacyclo [24.3.1.1~17,21~.0~2,10~.0~3,7~.0~22,27~]hentriaconta-1 (30),2,4,7,9,22,24,26,28-nonaene diformate (12 mg, 0.016 mmol, 35% yield) as white solid. m/z (ESI): 662.8 $(M+H)^+$. $^1H$ NMR (400 MHz, METHANOL-$d_4$) δ ppm 9.23 (s, 1H), 9.16-9.27 (m, 1H), 8.54 (s, 2H), 7.82-8.00 (m, 2H), 4.88-5.85 (m, 3H), 4.28-4.49 (m, 2H), 4.14-4.26 (m, 1H), 3.76-4.00 (m, 4H), 3.51-3.63 (m, 2H), 3.07-3.17 (m, 3H), 2.19-2.49 (m, 5H), 1.93-2.14 (m, 5H), 1.55-1.86 (m, 4H), 1.49-1.51 (m, 1H). $^{19}F$ NMR (376 MHz, METHANOL-$d_4$) δ ppm −101.10-−102.20 (m), −110.5-−111.7 (m), −142.94 (s), −174.93-−172.52 (m).

TABLE 46

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 151 | 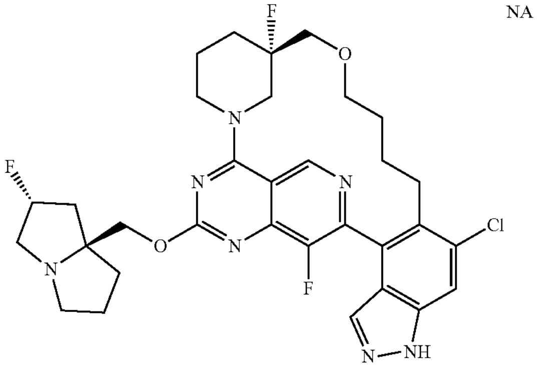 (17S)-9-chloro-17,30-difluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 5. Inermediate KKKK | Steps 1-4 were not performed. |
| 152 | 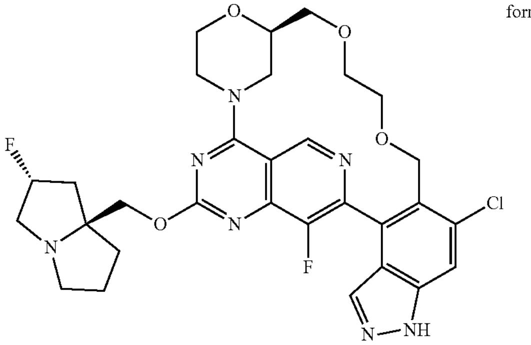 (17R)-9-chloro-30-fluoro-24-(((2R,7aS)-2-fluorotetrahydro-1H-pyrrolo[1,2-a]pyrrol-7a(5H)-yl) methoxy)-12,15,18-trioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | formate | Step 5. Intermediate AAAA Step 6. Intermediate AA, Step 2 | Steps 1-4 were not performed. Step 5. KOAc, Pd(dppf)$_2$, dioxane, 100° C. Step 7. TFA, DCM Step 8. $Cs_2CO_3$, DMF (0.01M), 90 ° C. |
| 153 | 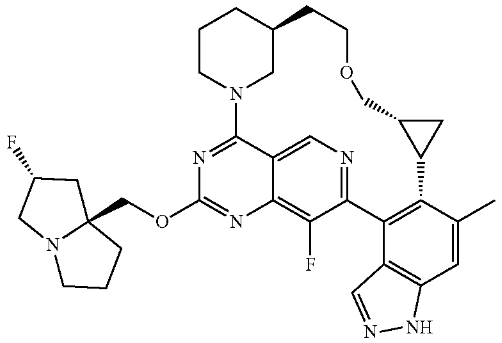 (11S,13R,18S)-31-fluoro-25-(((2R,7aS)-2-fluorotetrahydro-1H-pyrrolo[1,2-a]pyrrol-7a(5H)-yl) methoxy)-9-methyl-15-oxa-5,6,22,24,26,30-hexaazaheptacyclo [25.3.1.1~18,22~.0~2,10~.0~3,7~.0~11,13~.0~23,28~] dotriaconta-1(31),2,4,7,9,23,25,27,29-nonaene | NA | Step 4. Intermediate MMMM | Steps 1-4 were not performed. Step 6. TFA/DCM |

TABLE 46-continued

| Additional Examples 151 to 157, 239 to 259 and 386 to 397. Prepared in an Analogous Manner to Example 150. | | | | |
|---|---|---|---|---|
| Ex. # | Structure & Name | Salt Form | Reagent | Method Change |
| 154 | 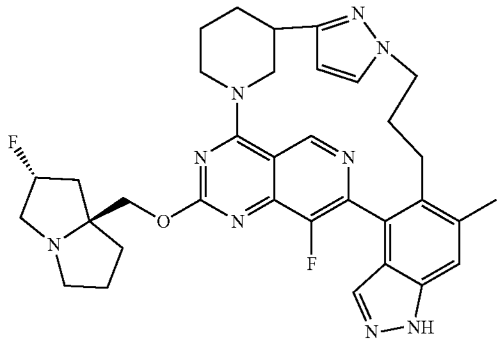 [SMILES: Cc1cc2[nH]ncc2c2c1CCCn1ccc(n1)C1CCCN(C1)c1nc(OC[C@@]34CCCN3C[C@H](F)C4)nc3c(F)c-2ncc13] (18S)-31-fluoro-25-(((2R,7aS)-2-fluorotetrahydro-1H-pyrrolo[1,2-a]pyrrol-7a(5H)-yl)methoxy)-9-methyl-5,6,14,22,24,26,30,33-octaazaheptacyclo [25.3.1.1~14,17~.1~18,22~.0~2,10~.0~3,7~.0~23,28~] tritriaconta-1(31),2,4,7,9,15,17(33),23,25,27,29-undecaene | bis(2,2,2-trifluoroacetate) | Step 6. Intermediate NNNN and Intermediate AA, Step 2 | Steps 1-5 were not performed. Step 7. TFA, DCM Then TFA, $CH_3CN/H_2O$ |
| 155 | 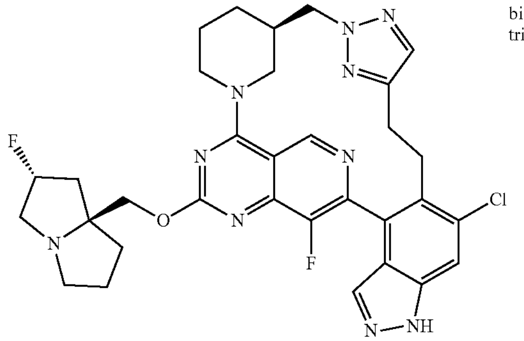 (11Z,18R)-9-chloro-31-fluoro-25-(((2R,7aS)-2-fluorotetrahydro-1H-pyrrolo[1,2-a]pyrrol-7a(5H)-yl) methoxy)-5,6,15,16,22,24,26,30,33-nonaazaheptacyclo [25.3.1.1~13,16~.1~18,22~.0~2,10~.0~3,7~.0~23,28~] tritriaconta-1(31),2,4,7,9,11,13(33),14,23,25,27,29-dodecaen | bis(2,2,2-trifluoroacetate) | Step 6. Intermediate OOOO and Intermediate AA, Step 2 | Steps 1-5 were not performed. |
| 156 | 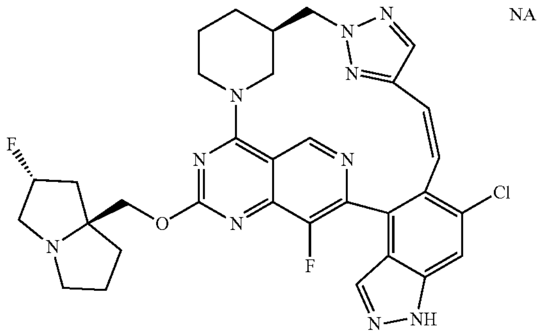 (18R)-9-chloro-31-fluoro-25-(((2R,7aS)-2-fluorotetrahydro-1H-pyrrolo[1,2-a]pyrrol-7a(5H)-yl) methoxy)-5,6,15,16,22,24,26,30,33-nonaazaheptacyclo [25.3.1.1~13,16~.1~18,22~.0~2,10~.0~3,7~.0~23,28~] tritriaconta-1(31),2,4,7,9,13(33),14,23,25,27,29-undecaene | NA | Step 6. Intermediate PPPP and Intermediate AA, Step 2 | Steps 1-5 were not performed. |

TABLE 46-continued

| Additional Examples 151 to 157, 239 to 259 and 386 to 397. Prepared in an Analogous Manner to Example 150. | | | | |
|---|---|---|---|---|
| Ex. # | Structure & Name | Salt Form | Reagent | Method Change |
| 157 | 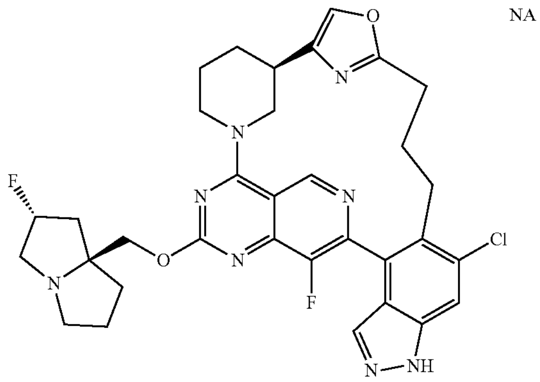 (18R)-9-chloro-31-fluoro-25-(((2R,7aS)-2-fluorotetrahydro-1H-pyrrolo[1,2-a]pyrrol-7a(5H)-yl) methoxy)-15-oxa-5,6,22,24,26,30,33-heptaazaheptacyclo [25.3.1.1~14,17~.1~18,22~.0~2,10~.0~3,7~.0~23,28~] tritriaconta-1(31),2,4,7,9,14(33),16,23,25,27,29-undecaene | NA | Step 6. Intermediate QQQQ | Steps 1-5 were not performed. |
| 239 | 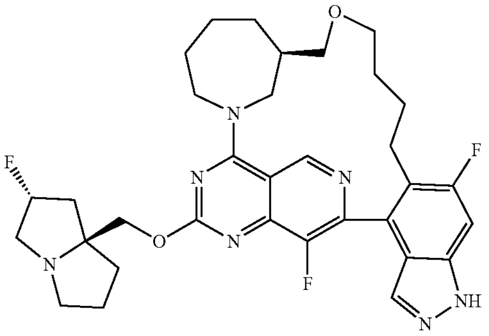 [SMILES: Fc1cc2[nH]ncc2c2c1CCCCOC[C@@H]1CCCCN(C1)c1nc(OC[C@@]34CCCN3C[C@H](F)C4)nc3c(F)c-2ncc13] (26R)-18,32-difluoro-4-(((2R,7aS)-2-fluorotetrahydro-1H-pyrrolo[1,2-a]pyrrol-7a(5H)-yl) methoxy)-24-oxa-1,3,5,9,14,15-hexaazahexacyclo [24.4.1.1~6, 10~.0~2,7~.0~11,19~.0~12,16~] dotriaconta-2,4,6(32),7,9,11,13,16,18-nonaene | NA | Step 6. Intermediate CD | Steps 1-5 were not performed. Chiral separation after Step 8. Details included below. |
| 240 | 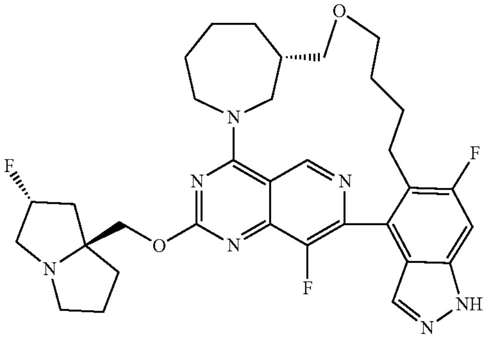 [SMILES: Fc1cc2[nH]ncc2c2c1CCCCOC[C@H]1CCCCN(C1)c1nc(OC[C@@]34CCCN3C[C@H](F)C4)nc3c(F)c-2ncc13] (26S)-18,32-difluoro-4-(((2R,7aS)-2-fluorotetrahydro-1H-pyrrolo[1,2-a]pyrrol-7a(5H)-yl) methoxy)-24-oxa-1,3,5,9,14,15-hexaazahexacyclo [24.4.1.1~6,10~.0~2,7~.0~11,19~.0~12,16~] dotriaconta-2,4,6(32),7,9,11,13,16,18-nonaene | NA | Step 6. Intermediate CD | Steps 1-5 were not performed. Chiral separation after Step 8. Details included below. |

TABLE 46-continued

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 241 | 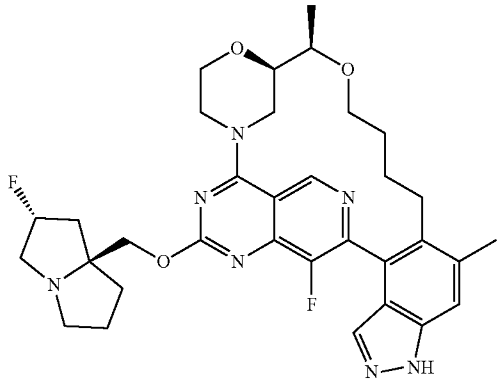 [SMILES: Cc1cc2[nH]ncc2c2c1CCCCO[C@H](C)[C@H]1CN(CCO1)c1nc(OC[C@@]34CCCN3C[C@H](F)C4)nc3c(F)c-2ncc13] (16R,17R)-30-fluoro-24-(((2R,7aS)-2-fluorotetrahydro-1H-pyrrolo[1,2-a]pyrrol-7a(5H)-yl)methoxy)-9,16-dimethyl-15,18-dioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 6. Intermediate CE | Steps 1-5 were not performed. Chiral separation after Step 8. Details included below. |
| 242 | 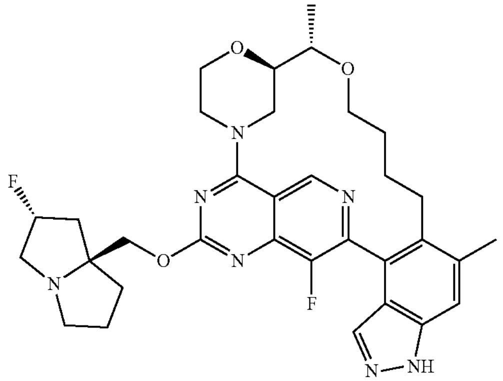 [SMILES: Cc1cc2[nH]ncc2c2c1CCCCO[C@@H](C)[C@H]1CN(CCO1)c1nc(OC[C@@]34CCCN3C[C@H](F)C4)nc3c(F)c-2ncc13] (16S,17R)-30-fluoro-24-(((2R,7aS)-2-fluorotetrahydro-1H-pyrrolo[1,2-a]pyrrol-7a(5H)-yl)methoxy)-9,16-dimethyl-15,18-dioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 6. Intermediate CE | Steps 1-5 were not performed. Chiral separation after Step 8. Details included below. |
| 243 | 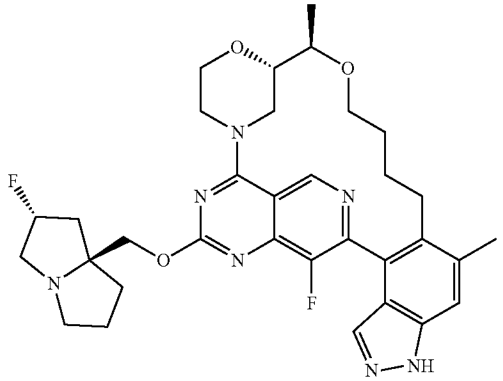 [SMILES: Cc1cc2[nH]ncc2c2c1CCCCO[C@H](C)[C@@H]1CN(CCO1)c1nc(OC[C@@]34CCCN3C[C@H](F)C4)nc3c(F)c-2ncc13] (16R,17S)-30-fluoro-24-(((2R,7aS)-2-fluorotetrahydro-1H-pyrrolo[1,2-a]pyrrol-7a(5H)-yl)methoxy)-9,16-dimethyl-15,18-dioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 6. Intermediate CE | Steps 1-5 were not performed. Chiral separation after Step 8. Details included below. |

TABLE 46-continued

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 244 | 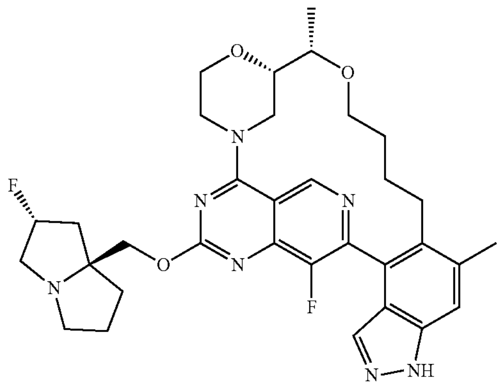 [SMILES: Cc1cc2[nH]ncc2c2c1CCCCO[C@@H](C)[C@@H]1CN(CCO1)c1nc(OC[C@@]34CCCN3C[C@H](F)C4)nc3c(F)c-2ncc13] (16S,17S)-30-fluoro-24-(((2R,7aS)-2-fluorotetrahydro-1H-pyrrolo[1,2-a]pyrrol-7a(5H)-yl)methoxy)-9,16-dimethyl-15,18-dioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 6. Intermediate CE | Steps 1-5 were not performed. Chiral separation after Step 8. Details included below. |
| 245 | 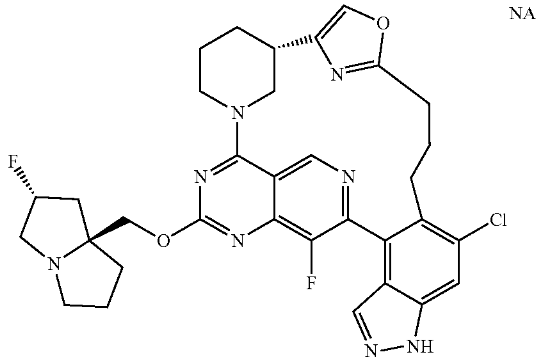 (18S)-9-chloro-31-fluoro-25-(((2R,7aS)-2-fluorotetrahydro-1H-pyrrolo[1,2-a]pyrrol-7a(5H)-yl)methoxy)-15-oxa-5,6,22,24,26,30,33-heptaazaheptacyclo [25.3.1.1~14,17~.1~18,22~.0~2,10~.0~3,7~.0~23,28~] tritriaconta-1(31),2,4,7,9,14(33),16,23,25,27,29-undecaene | NA | Step 6. Intermediate CF | Steps 1-5 were not performed. Chiral separation after Step 8. Details included below. |
| 246 | 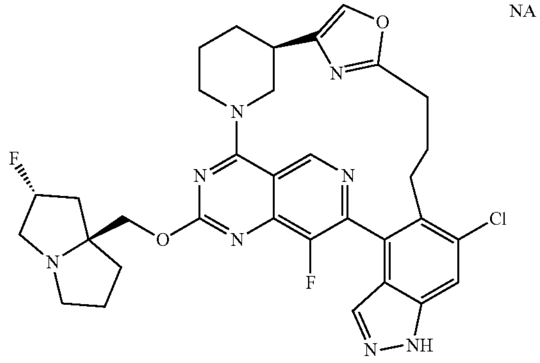 (18R)-9-chloro-31-fluoro-25-(((2R,7aS)-2-fluorotetrahydro-1H-pyrrolo[1,2-a]pyrrol-7a(5H)-yl)methoxy)-15-oxa-5,6,22,24,26,30,33-heptaazaheptacyclo [25.3.1.1~14,17~.1~18,22~.0~2,10~.0~3,7~.0~23,28~] tritriaconta-1(31),2,4,7,9,14(33),16,23,25,27,29-undecaene | NA | Step 6. Intermediate CF | Steps 1-5 were not performed. Chiral separation after Step 8. Details included below. |

TABLE 46-continued

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 247 | 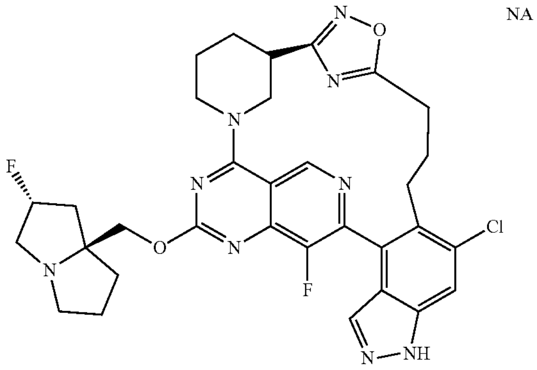<br>(18R)-9-chloro-31-fluoro-25-(((2R,7aS)-2-fluorotetrahydro-1H-pyrrolo[1,2-a]pyrrol-7a(5H)-yl) methoxy)-15-oxa-5,6,16,22,24,26,30,33-octaazaheptacyclo [25.3.1.1~14,17~.1~18,22~.0~2,10~.0~3,7~.0~23,28~] tritriaconta-1(31),2,4,7,9,14(33),16,23,25,27,29-undecaene | NA | Step 6.<br>Intermediate CG and Intermediate BX | Steps 1-5 were not performed.<br>Step 6.<br>CuI, LiCl in DMF was used instead of $K_3PO_4$ in 2-Me THF/water |
| 248 | 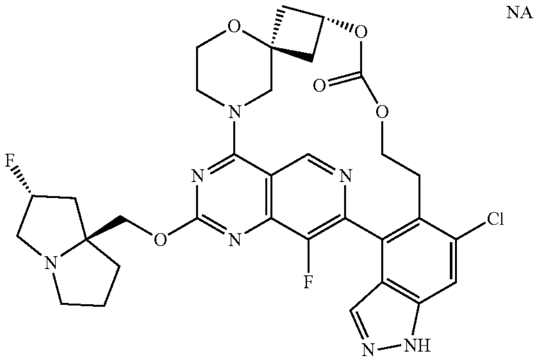<br>(1R,3R)-10-chloro-32-fluoro-24-(((2R,7aS)-2-fluorotetrahydro-1H-pyrrolo[1,2-a]pyrrol-7a(5H)-yl) methoxy)-4,6,30-trioxa-13,14,19,23,25,27-hexaazaheptacyclo [25.3.1.1~1,3~.1~18,22~.0~9,17~.0~12,16~.0~21,26~] tritriaconta-9,11,14,16,18(32),19,21,23,25-nonaen-5-one | NA | Step 6.<br>Intermediate CH | Steps 1-5 were not performed. |
| 249 | 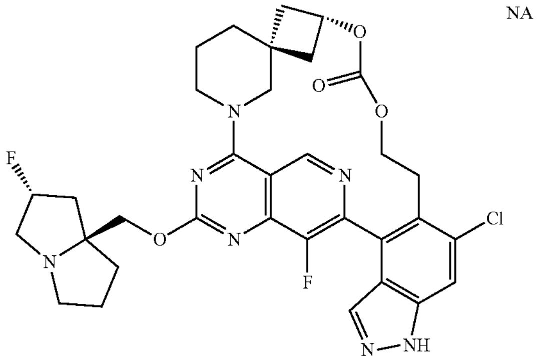<br>(1S,3R)-10-chloro-32-fluoro-24-(((2R,7aS)-2-fluorotetrahydro-1H-pyrrolo[1,2-a]pyrrol-7a(5H)-yl) methoxy)-4,6-dioxa-13,14,19,23,25,27-hexaazaheptacyclo [25.3.1.1~1,3~.1~18,22~.0~9,17~.0~12,16~.0~21,26~] tritriaconta-9,11,14,16,18(32),19,21,23,25-nonaen-5-one | NA | Step 6.<br>Intermediate CI | Steps 1-5 were not performed. |

TABLE 46-continued

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 250 | 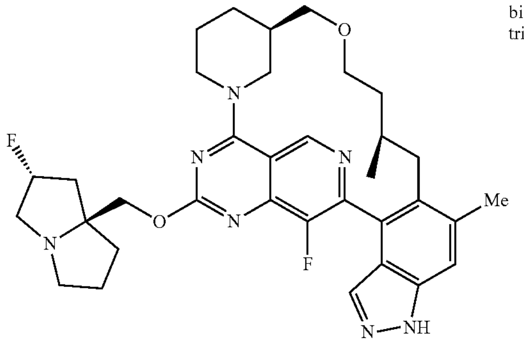 (12R,17R)-30-fluoro-24-(((2R,7aS)-2-fluorotetrahydro-1H-pyrrolo[1,2-a]pyrrol-7a(5H)-yl)methoxy)-9,12-dimethyl-15-oxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | bis(2,2,2-trifluoroacetate) | Step 5. Intermediate CJ | Steps 1-4 were not performed. |
| 251 | 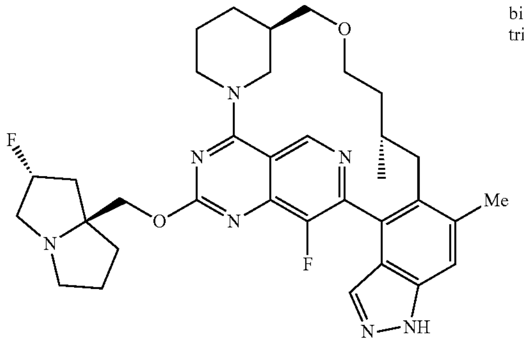 (12S,17R)-30-fluoro-24-(((2R,7aS)-2-fluorotetrahydro-1H-pyrrolo[1,2-a]pyrrol-7a(5H)-yl)methoxy)-9,12-dimethyl-15-oxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | bis(2,2,2-trifluoroacetate) | Step 5. Intermediate CJ | Steps 1-4 were not performed. |
| 252 | 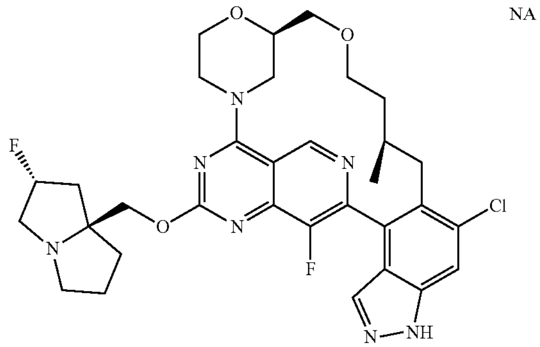 (12R,17R)-9-chloro-30-fluoro-24-(((2R,7aS)-2-fluorotetrahydro-1H-pyrrolo[1,2-a]pyrrol-7a(5H)-yl)methoxy)-12-methyl-15,18-dioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 5. Intermediate CK | Steps 1-4 were not performed. |

TABLE 46-continued

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 253 | 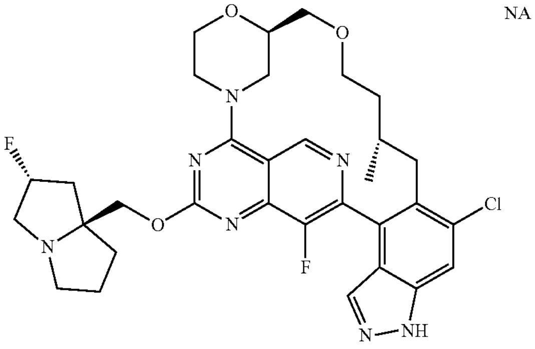 (12S,17R)-9-chloro-30-fluoro-24-(((2R,7aS)-2-fluorotetrahydro-1H-pyrrolo[1,2-a]pyrrol-7a(5H)-yl)methoxy)-12-methyl-15,18-dioxa-5,6,21,23,25,29-hexaazahexacyclo [24.3.1.1~17,21~.0~2,10~.0~3,7~.0~22,27~] hentriaconta-1(30),2,4,7,9,22,24,26,28-nonaene | NA | Step 5. Intermediate CK | Steps 1-4 were not performed. Steps 1-3 were not performed. |
| 254 | 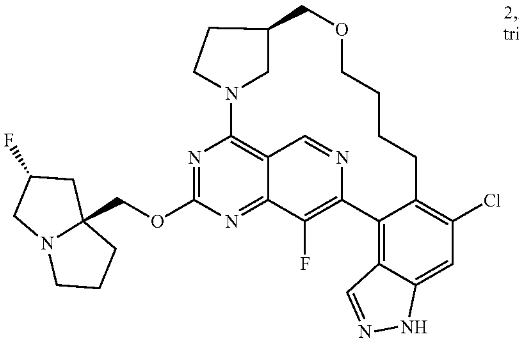 (17R)-9-chloro-29-fluoro-23-(((2R,7aS)-2-fluorotetrahydro-1H-pyrrolo[1,2-a]pyrrol-7a(5H)-yl) methoxy)-15-oxa-5,6,20,22,24,28-hexaazahexacyclo [23.3.1.1~17,20~.0~2,10~.0~3,7~.0~21,26~] triaconta-1(29),2,4,7,9,21,23,25,27-nonaene | 2,2,2-trifluoroacetate | Step 4. (R)-1-Boc-3-hydroxymethyl pyrrolidine (CAS#: 138108-72-2) and Intermediate WWW | |
| 255 | 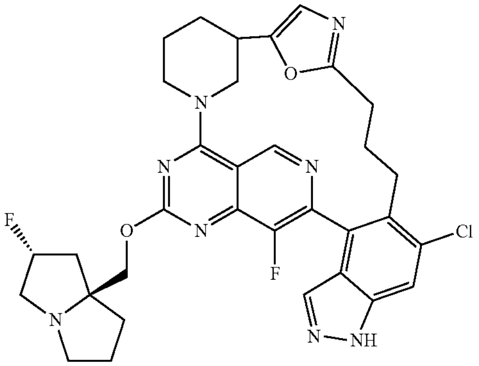 [SMILES: Fc1c2ncc3c(nc(OC[C@@]45CCCN4C[C@H](F)C5)nc13)N1CCCC(C1)c1cnc(o1)CCCc1c(Cl)cc3[nH]ncc3c1-2] (18R)-9-chloro-31-fluoro-25-(((2R,7aS)-2-fluorotetrahydro-1H-pyrrolo[1,2-a]pyrrol-7a(5H)-yl) methoxy)-33-oxa-5,6,15,22,24,26,30-heptaazaheptacyclo [25.3.1.1~14,17~.1~18,22~.0~2,10~.0~3,7~.0~23,28~] tritriaconta-1(31),2,4,7,9,14,16,23,25,27,29-undecaene, (18S)-9-chloro-31-fluoro-25-(((2R,7aS)-2-fluorotetrahydro-1H-pyrrolo[1,2-a]pyrrol-7a(5H)-yl) methoxy)-33-oxa-5,6,15,22,24,26,30-heptaazaheptacyclo [25.3.1.1~14,17~.1~18,22~.0~2,10~.0~3,7~.0~23,28~] tritriaconta-1(31),2,4,7,9,14,16,23,25,27,29-undecaene | NA | Step 5. Intermediate CL | Steps 1-4 were not performed. |

TABLE 46-continued

| Additional Examples 151 to 157, 239 to 259 and 386 to 397. Prepared in an Analogous Manner to Example 150. | | | | |
|---|---|---|---|---|
| Ex. # | Structure & Name | Salt Form | Reagent | Method Change |
| 386 | 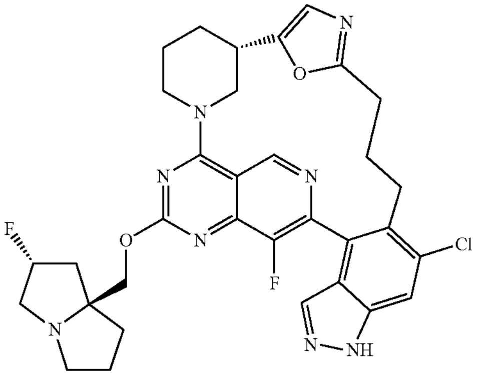 [SMILES: Fc1c2ncc3c(nc(OC[C@@]45CCCN4C[C@H](F)C5)nc13)N1CCC[C@@H](C1)c1cnc(o1)CCCc1c(Cl)cc3[nH]ncc3c1-2] (18S)-9-chloro-31-fluoro-25-(((2R,7aS)-2-fluorotetrahydro-1H-pyrrolo[1,2-a]pyrrol-7a(5H)-yl) methoxy)-33-oxa-5,6,15,22,24,26,30-heptaazaheptacyclo [25.3.1.1~14,17~.1~18,22~.0~2,10~.0~3,7~.0~23,28~] tritriaconta-1(31),2,4,7,9,14,16,23,25,27,29-undecaene | NA | Step 5. Intermediate CL | Steps 1-4 were not performed. Chiral separation after Step 8. Details included below. |
| 387 | 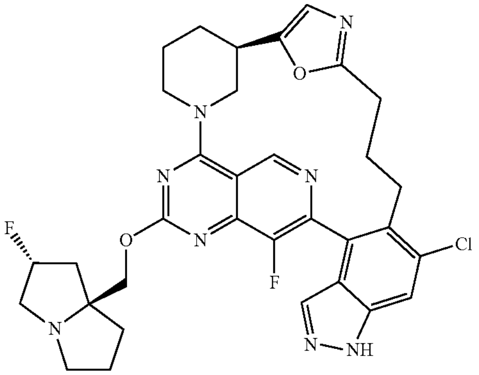 [SMILES: Fc1c2ncc3c(nc(OC[C@@]45CCCN4C[C@H](F)C5)nc13)N1CCC[C@H](C1)c1cnc(o1)CCCc1c(Cl)cc3[nH]ncc3c1-2] (18R)-9-chloro-31-fluoro-25-(((2R,7aS)-2-fluorotetrahydro-1H-pyrrolo[1,2-a]pyrrol-7a(5H)-yl) methoxy)-33-oxa-5,6,15,22,24,26,30-heptaazaheptacyclo [25.3.1.1~14,17~.1~18,22~.0~2,10~.0~3,7~.0~23,28~] tritriaconta-1(31),2,4,7,9,14,16,23,25,27,29-undecaene | NA | Step 5. Intermediate CL | Steps 1-4 were not performed. Chiral separation after Step 8. Details included below. |
| 256 | 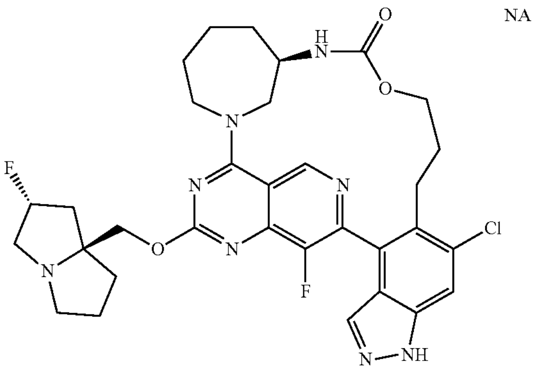 (26R)-18-chloro-32-fluoro-4-(((2R,7aS)-2-fluorotetrahydro-1H-pyrrolo[1,2-a]pyrrol-7a(5H)-yl) methoxy)-23-oxa-1,3,5,9,14,15,25-heptaazahexacyclo [24.4.1.1~6,10~.0~2,7~.0~11,19~.0~12,16~]dotriaconta-2,4,6(32),7,9,11,13,16,18-nonaen-24-one | NA | Step 5. Intermediate CM | Steps 1-4 were not performed. |

TABLE 46-continued

| Additional Examples 151 to 157, 239 to 259 and 386 to 397. Prepared in an Analogous Manner to Example 150. | | | | |
|---|---|---|---|---|
| Ex. # | Structure & Name | Salt Form | Reagent | Method Change |
| 257 | 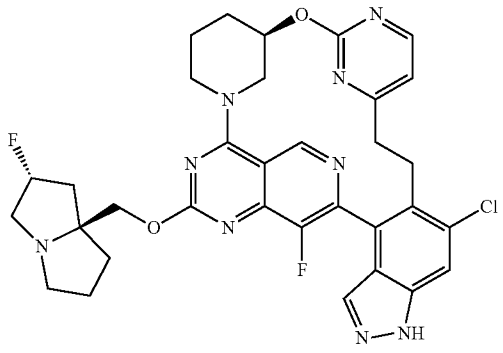 [SMILES: Fc1c2ncc3c(nc(OC[C@@]45CCCN4C[C@H](F)C5)nc13)N1CCC[C@H](C1)Oc1nccc(n1)CCc1c(Cl)cc3[nH]ncc3c1-2] (19R)-9-chloro-32-fluoro-26-(((2R,7aS)-2-fluorotetrahydro-1H-pyrrolo[1,2-a]pyrrol-7a(5H)-yl) methoxy)-18-oxa-5,6,16,23,25,27,31,34-octaazaheptacyclo [26.3.1.1~13,17~.1~19,23~.0~2, 10~.0~3,7~.0~24,29~] tetratriaconta-1(32),2,4,7,9,13(34),14,16,24,26,28,30-dodecaene | NA | Step 5. Intermediate CN | Steps 1-4 were not performed. |
| 258 | 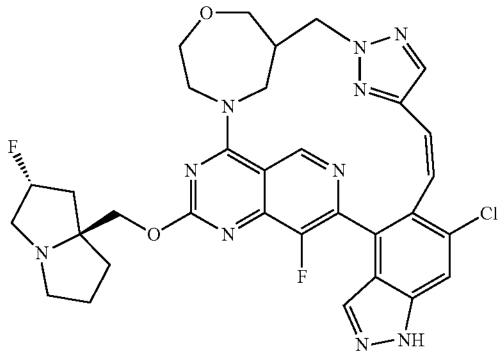 [SMILES: Fc1c2ncc3c(nc(OC[C@@]45CCCN4C[C@H](F)C5)nc13)N1CCOCC(C1)Cn1ncc(n1)/C=C\c1c(Cl)cc3[nH]ncc3c1-2] (20Z)-18-chloro-34-fluoro-4-(((2R,7aS)-2-fluorotetrahydro-1H-pyrrolo[1,2-a]pyrrol-7a(5H)-yl) methoxy)-29-oxa-1,3,5,9,14,15,24,25,33-nonaazaheptacyclo [25.4.1.1~6,10~.1~22,25~.0~2,7~.0~11,19~.0~12,16~] tetratriaconta-2,4,6,8,10(34),11,13,16,18,20,22(33),23-dodecaene | bis(2,2,2-trifluoroacetate) | Step 5. Intermediate CO | Steps 1-4 were not performed. |
| 259 | 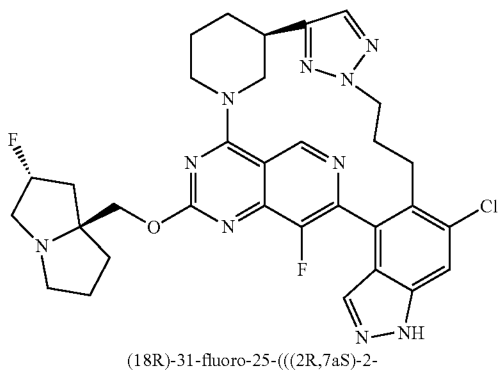 (18R)-31-fluoro-25-(((2R,7aS)-2-fluorotetrahydro-1H-pyrrolo[1,2-a]pyrrol-7a(5H)-yl) methoxy)-9-methyl-5,6,14,15,22,24,26,30,33-nonaazaheptacyclo [25.3.1.1~14,17~.1~18,22~.0~2,10~.0~3,7~.0~23,28~] tritriaconta-1(31),2,4,7,9,15,17(33),23,25,27,29-undecaene | NA | Step 5. Intermediate CP | Steps 1-4 were not performed. |

TABLE 46-continued

| Ex. # | Structure & Name | Salt Form | Reagent | Method Change |
|---|---|---|---|---|
| | Additional Examples 151 to 157, 239 to 259 and 386 to 397. Prepared in an Analogous Manner to Example 150. | | | |
| 388 | 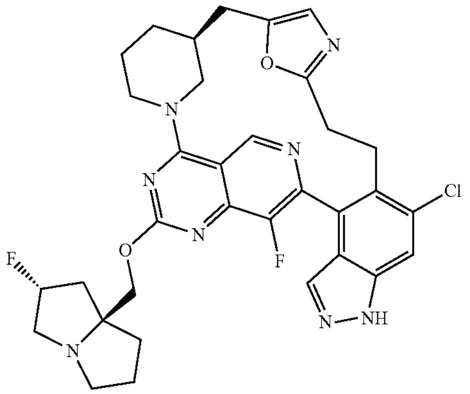 [SMILES: Fc1c2ncc3c(nc(OC[C@@]45CCCN4C[C@H](F)C5)nc13)N1CCC[C@@H](Cc3cnc(o3)CCc3c(Cl)cc4[nH]ncc4c3-2)C1] (18S)-9-chloro-31-fluoro-25-(((2R,7aS)-2-fluorotetrahydro-1H-pyrrolo[1,2-a]pyrrol-7a(5H)-yl) methoxy)-15-oxa-5,6,22,24,26,30,33-heptaazaheptacyclo [25.3.1.1~13,16~.1~18,22~.0~2,10~.0~3,7~.0~23,28~] tritriaconta-1(31),2,4,7,9,13,16(33),23,25,27,29-undecaene | | Step 6. Intermediate FV | |
| 389 | 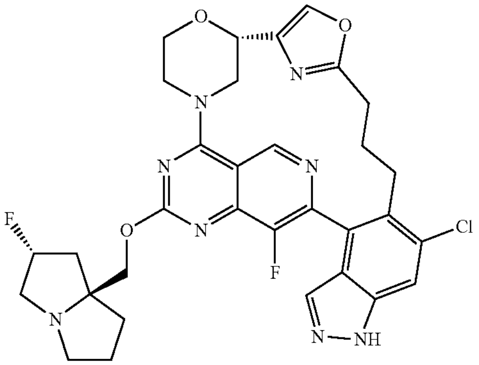 [SMILES: Fc1c2ncc3c(nc(OC[C@@]45CCCN4C[C@H](F)C5)nc13)N1CCO[C@@H](C1)c1coc(n1)CCCc1c(Cl)cc3[nH]ncc3c1-2] (18S)-9-chloro-31-fluoro-25-(((2R,7aS)-2-fluorotetrahydro-1H-pyrrolo[1,2-a]pyrrol-7a(5H)-yl) methoxy)-15,19-dioxa-5,6,22,24,26,30,33-heptaazaheptacyclo [25.3.1.1~14,17~.1~18,22~.0~2,10~.0~3,7~.0~23,28~] tritriaconta-1(31),2,4,7,9,14(33),16,23,25,27,29-undecaene | | Step 6. Intermediate FW | |
| 390 | 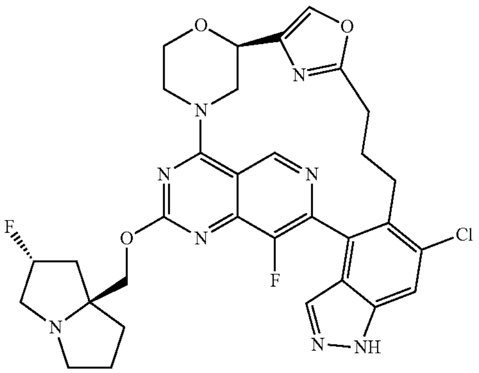 [SMILES: Fc1c2ncc3c(nc(OC[C@@]45CCCN4C[C@H](F)C5)nc13)N1CCO[C@H](C1)c1coc(n1)CCCc1c(Cl)cc3[nH]ncc3c1-2] (18R)-9-chloro-31-fluoro-25-(((2R,7aS)-2-fluorotetrahydro-1H-pyrrolo[1,2-a]pyrrol-7a(5H)-yl) methoxy)-15,19-dioxa-5,6,22,24,26,30,33-heptaazaheptacyclo [25.3.1.1~14,17~.1~18,22~.0~2,10~.0~3,7~.0~23,28~] tritriaconta-1(31),2,4,7,9,14(33),16,23,25,27,29-undecaene | | Step 6. Intermediate FW | |

TABLE 46-continued

Additional Examples 151 to 157, 239 to 259 and 386 to 397.
Prepared in an Analogous Manner to Example 150.

| Ex. # | Structure & Name | Salt Form | Reagent | Method Change |
|---|---|---|---|---|
| 391 | 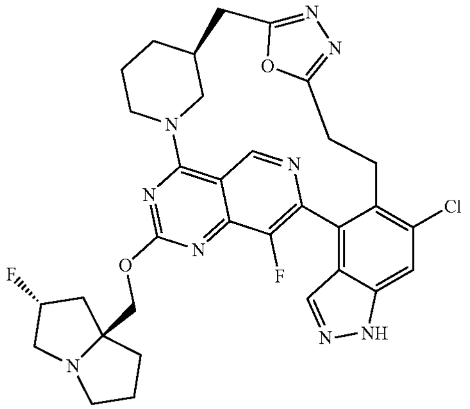 [SMILES: Fc1c2ncc3c(nc(OC[C@@]45CCCN4C[C@H](F)C5)nc13)N1CCC[C@@H](Cc3nnc(o3)CCc3c(Cl)cc4[nH]ncc4c3-2)C1] (18S)-9-chloro-31-fluoro-25-(((2R,7aS)-2-fluorotetrahydro-1H-pyrrolo[1,2-a]pyrrol-7a(5H)-yl) methoxy)-33-oxa-5,6,14,15,22,24,26,30-octaazaheptacyclo [25.3.1.1~13,16~.1~18,22~.0~2,10~.0~3,7~.0~23,28~] tritriaconta-1(31),2,4,7,9,13,15,23,25,27,29-undecaene | Trifluoroacetate | Step 6. Intermediate FX | |
| 392 | 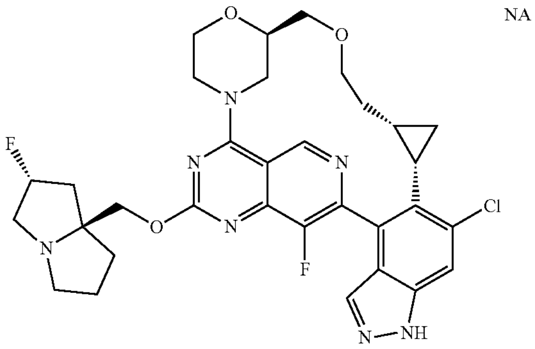 (11S,13S,18R)-9-chloro-31-fluoro-25-(((2R,7aS)-2-fluorotetrahydro-1H-pyrrolo[1,2-a]pyrrol-7a(5H)-yl) methoxy)-16,19-dioxa-5,6,22,24,26,30-hexaazaheptacyclo [25.3.1.1~18,22~.0~2,10~.0~3,7~.0~11,13~.0~23,28~] dotriaconta-1(31),2,4,7,9,23,25,27,29-nonaene | NA | Step 4. Intermediate FU and (R)-tert-butyl 2-(hydroxymethyl) morpholine-4-carboxylate (CAS#: 135065-71-3) | Chiral separation performed after Step 8. Details included below. |
| 393 | 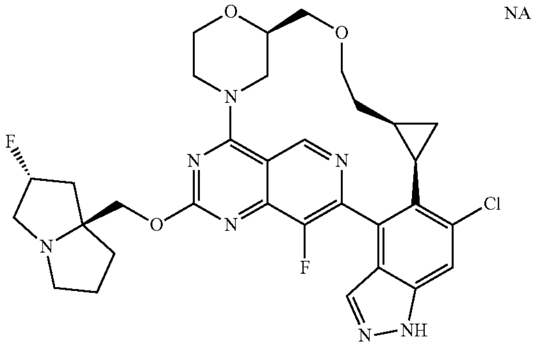 (11R,13R,18R)-9-chloro-31-fluoro-25-(((2R,7aS)-2-fluorotetrahydro-1H-pyrrolo[1,2-a]pyrrol-7a(5H)-yl) methoxy)-16,19-dioxa-5,6,22,24,26,30-hexaazaheptacyclo [25.3.1.1~18,22~.0~2,10~.0~3,7~.0~11,13~.0~23,28~] dotriaconta-1(31),2,4,7,9,23,25,27,29-nonaene | NA | Step 4. Intermediate FU and (R)-tert-butyl 2-(hydroxymethyl) morpholine-4-carboxylate (CAS#: 135065-71-3) | Chiral separation performed after Step 8. Details included below. |

TABLE 46-continued

| Additional Examples 151 to 157, 239 to 259 and 386 to 397. Prepared in an Analogous Manner to Example 150. | | | | |
|---|---|---|---|---|
| Ex. # | Structure & Name | Salt Form | Reagent | Method Change |
| 394 | 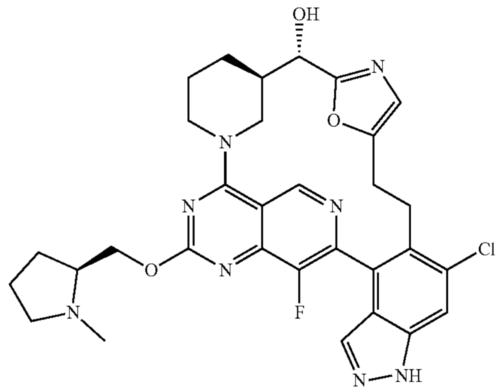 [SMILES: CN1CCC[C@H]1COc1nc2c3cnc(c(F)c3n1)-c1c(c(Cl)cc3[nH]ncc13)CCc1cnc(o1)[C@@H](O)[C@@H]1CCCN2C1] (17S,18R)-9-chloro-31-fluoro-25-(((2S)-1-methylpyrrolidin-2-yl)methoxy)-33-oxa-5,6,15,22,24,26,30-heptaazaheptacyclo [25.3.1.1~13,16~.1~18,22~.0~2,10~.0~3,7~.0~23,28~] tritriaconta-1(31),2,4,7,9,13,15,23,25,27,29-undecaen-17-ol | NA | Step 2. Intermediate FY and Intermediate FN | |
| 395 | 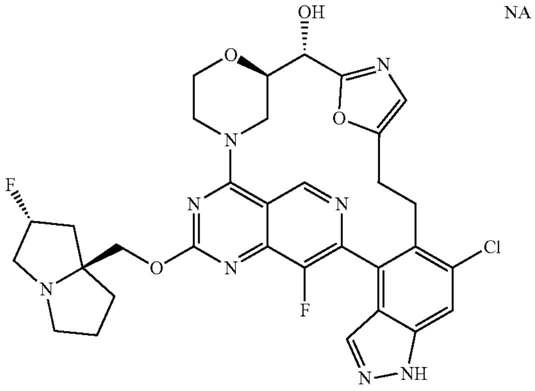 (17R,18R)-9-chloro-31-fluoro-25-(((2R,7aS)-2-fluorotetrahydro-1H-pyrrolo[1,2-a]pyrrol-7a(5H)-yl)methoxy)-19,33-dioxa-5,6,15,22,24,26,30-heptaazaheptacyclo [25.3.1.1~13,16~.1~18,22~.0~2,10~.0~3,7~.0~23,28~] tritriaconta-1(31),2,4,7,9,13,15,23,25,27,29-undecaen-17-ol | NA | Step 6. Intermediate FO | |
| 396 | 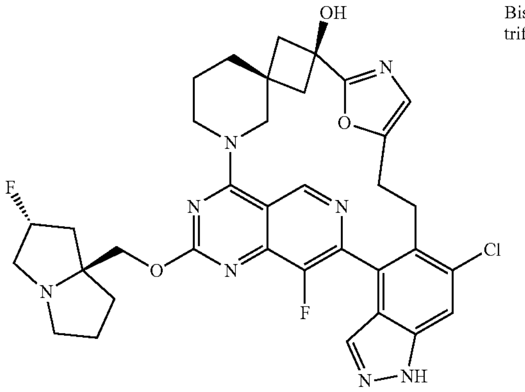 (1S,3R)-11-chloro-33-fluoro-25-(((2R,7aS)-2-fluorotetrahydro-1H-pyrrolo[1,2-a]pyrrol-7a(5H)-yl)methoxy)-34-oxa-5,14,15,20,24,26,28-heptaazaoctacyclo [26.3.1.1~1,3~.1~4,7~.1~19,23~.0~10,18~.0~13,17~.0~22,27~] pentatriaconta-4,6,10,12,15,17,19(33),20,22,24,26-undecaen-3-ol | Bis(2,2,2-trifluoroacetate) | Step 6. Intermediate FP | |

TABLE 46-continued

Additional Examples 151 to 157, 239 to 259 and 386 to 397. Prepared in an Analogous Manner to Example 150.

| Ex. # | Structure & Name | Salt Form | Reagent | Method Change |
|---|---|---|---|---|
| 397 | 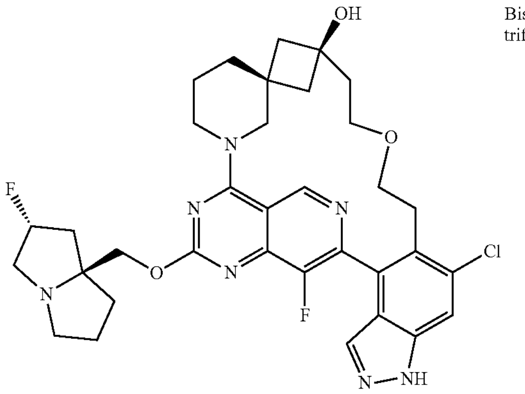 (1S,3R)-10-chloro-32-fluoro-24-(((2R,7aS)-2-fluorotetrahydro-1H-pyrrolo[1,2-a]pyrrol-7a(5H)-yl)methoxy)-6-oxa-13,14,19,23,25,27-hexaazaheptacyclo [25.3.1.1~1,3~.1~18,22~.0~9,17~.0~12,16~.0~21,26~] tritriaconta-9,11,14,16,18(32),19,21,23,25-nonaen-3-ol | Bis(2,2,2-trifluoroacetate) | Step 6. Intermediate FQ | |

TABLE 47

Conditions for Chiral SFC Separation.

| Separation | Conditions | Final products |
|---|---|---|
| 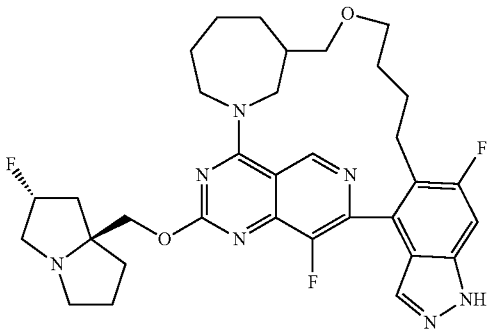 [SMILES: Fc1cc2[nH]ncc2c2c1CCCCOCC1CCCCN(C1)c1nc(OC[C@@]34CCCN3C[C@H](F)C4)nc3c(F)c-2ncc13] | Column: Chiralcel OD, (21 × 250 mm, 5 μm) Mobile phase: 20% MeOH with 0.2% TEA Flowrate: 150 mL/min. Yield: 38 mg sample was submitted to generate 9 mg of peak 1 with an ee of >96% and 14 mg of peak 2 with an ee of >90%. | Peak 1: Ex. 239 Peak 2: Ex. 240 |
| 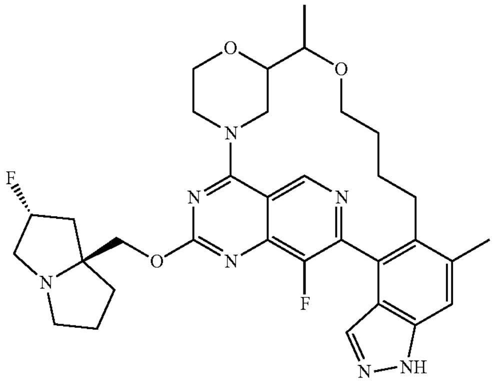 [SMILES: Cc1cc2[nH]ncc2c2c1CCCCOC(C)C1CN(CCO1)c1nc(OC[C@@]34CCCN3C[C@H](F)C4)nc3c(F)c-2ncc13] | Column: Chiralcel OD, (21 × 250 mm, 5 μm) Mobile phase: 35% 1:1 MeCN:MeOH with 0.2% TEA in water Flowrate: 80 mL/min. Yield: 55 mg sample was submitted to generate 13 mg of peak 1 with a de of 99%, 7 mg of peak 2 with a de of 91%, 9 mg of peak 3 with a de of 90%, and 8 mg of peak 4 with a de of 99%. | Peak 1: Ex. 241 Peak 2: Ex. 242 Peak 3: Ex. 243 Peak 4: Ex. 244 |

TABLE 47-continued

Conditions for Chiral SFC Separation.

| Separation | Conditions | Final products |
|---|---|---|
| 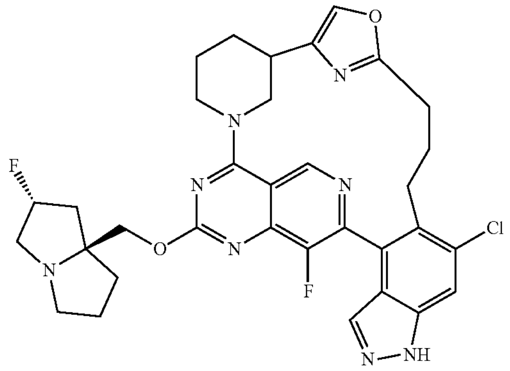 [SMILES: Fc1c2ncc3c(nc(OC[C@@]45CCCN4C[C@H](F)C5)nc13)N1CCCC(C1)c1coc(n1)CCCc1c(Cl)cc3[nH]ncc3c1-2] | Column: Chiralcel OJ, (2 × 25 cm, 5 μm)<br>Mobile phase: 15% MeOH with 0.2% triethylamine<br>Flowrate: 80 mL/min.<br>Yield: 27 mg sample was submitted to generate 3 mg of peak 1 with an ee of >99% and 8 mg of peak 2 with an ee of >99%. | Peak 1:<br>Ex. 245<br>Peak 2:<br>Ex. 246 |
| 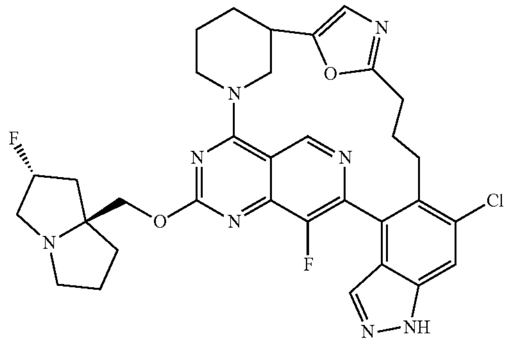 [SMILES: Fc1c2ncc3c(nc(OC[C@@]45CCCN4C[C@H](F)C5)nc13)N1CCCC(C1)c1cnc(o1)CCCc1c(Cl)cc3[nH]ncc3c1-2] | Column: Chiralcel OD, 2 × 25 cm, 5 μm<br>Mobile phase: 40% MeOH with 0.2% DEA<br>Flowrate: 80 mL/min.<br>Yield: 20 mg sample was submitted to generate 8 mg of peak 1 with an ee of 99% and 5 mg of peak 2 with an ee of 99%. | Peak 1:<br>Example 386<br>Peak 2:<br>Example 387 |
| 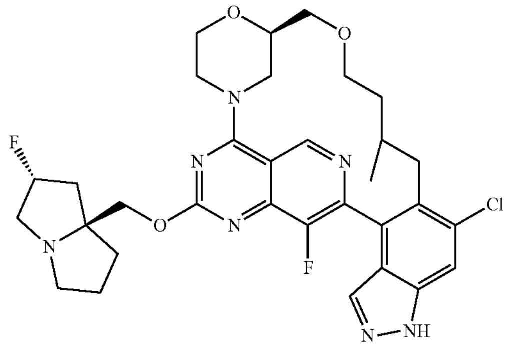 [SMILES: CC1CCOC[C@H]2CN(CCO2)c2nc(OC[C@@]34CCCN3C[C@H](F)C4)nc3c(F)c(ncc23)-c2c(c(Cl)cc3[nH]ncc23)C1] | Column: Chiralcel OD, 2 × 15 cm, 5 m column<br>Mobile phase: 40% MeOH with 0.2% DEA<br>Flowrate: 75 mL/min.<br>Yield: 67 mg sample was submitted to generate 13 mg of peak 1 with an ee of >99% and 15 mg of peak 2 with an ee of >99%. | Peak 1:<br>Ex. 252<br>Peak 2:<br>Ex. 253 |
| 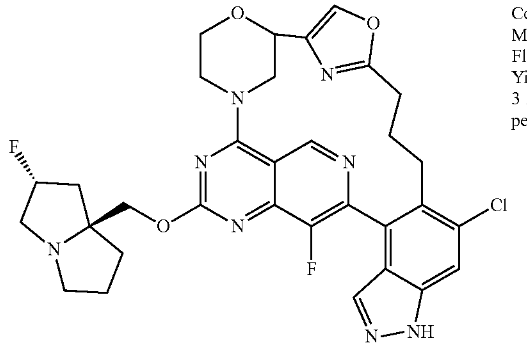 | Column: Chiralcel OD, 2 × 25 cm, 5 μm<br>Mobile phase: 15% MeOH with 0.2% DEA<br>Flowrate: 80 mL/min<br>Yield: 20 mg sample was submitted to generate 3 mg of peak 1 with an ee of >99% and 4 mg of peak 2 with an ee of >99%. | Peak 1:<br>Example 389<br>Peak 2:<br>Example 390 |

TABLE 47-continued

| Conditions for Chiral SFC Separation. | | |
|---|---|---|
| Separation | Conditions | Final products |
| 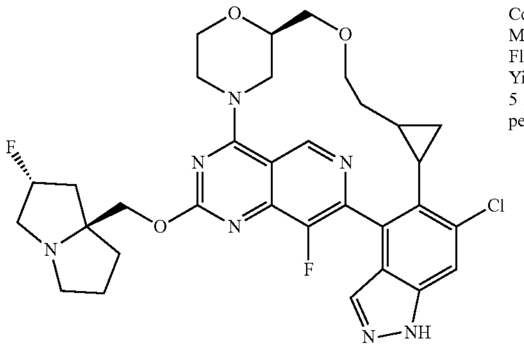 | Column: (S,S) Whelk-0 (2 × 15 cm, 5 μm)<br>Mobile phase: 50% MeOH with 0.2% DEA<br>Flowrate: 80 mL/min.<br>Yield: 32 mg sample was submitted to generate 5 mg of peak 1 with an ee of 99% and 3 mg of peak 2 with an ee of 99%. | Peak 1: Example 393<br>Peak 2: Example 392 |

TABLE 48

Analytical Data for Example 151 to 157, 239 to 259 and 386 to 397.

| Cmpd. # | MS m/z (ESI): $(M + H)^+$ | $^1H$ and $^{19}F$ NMR |
|---|---|---|
| 151 | 642.0 | $^1H$ NMR (400 MHz, METHANOL-$d_4$) δ ppm 9.36 (s, 1 H), 7.77-7.92 (m, 2 H), 5.49-5.73 (m, 1 H), 5.08-5.28 (m, 1 H), 4.84-5.03 (m, 1 H), 4.62-4.75 (m, 2 H), 3.94 (br d, J = 17.14 Hz, 3 H), 3.69-3.80 (m, 1 H), 3.50 (br d, J = 1.46 Hz, 1 H), 3.11-3.29 (m, 5 H), 2.92-3.10 (m, 2 H), 2.59-2.75 (m, 2 H), 2.32-2.55 (m, 4 H), 2.12-2.28 (m, 1 H), 1.93-2.08 (m, 2 H), 1.83-1.92 (m, 4 H), 1.21-1.42 (m, 3 H). $^{19}F$ NMR (376 MHz, METHANOL-$d_4$) 8 ppm −77.03 (s) −143.29--142.16 (m) −150.90 (s) −174.59--173.71 (m). |
| 152 | 627.8 | $^1H$ NMR (400 MHz, DMSO-$d_6$) δ ppm 13.38 (br s, 1 H), 9.16 (s, 1 H), 8.38 (s, 1 H), 7.87 (s, 1H), 7.82 (s, 1 H), 5.18-5.40 (m, 1 H), 4.67 (d, J = 13.8 Hz, 2 H), 4.54-4.68 (m, 2 H), 4.18 (d, J = 10.2 Hz, 1 H), 4.04-4.14 (m, 2 H), 3.73 (br s, 3 H), 3.36-3.52 (m, 3 H), 2.98-3.15 (m, 5 H), 2.75-2.92 (m, 2 H), 1.95-2.24 (m, 4 H), 1.68-1.93 (m, 4 H). $^{19}F$ NMR (376 MHz, DMSO-$d_6$) δ ppm −172.13 (s), −143.04 (s). |
| 153 | 616.2 | $^1H$ NMR (400 MHz, METHANOL-$d_4$) δ ppm 9.07-9.16 (m, 1 H), 8.04 (s, 1 H), 7.55 (s, 1 H), 5.22-5.44 (m, 1 H), 4.94-5.06 (m, 2 H), 4.18-4.46 (m, 2 H), 3.80-3.93 (m, 1 H), 3.12-3.28 (m, 4 H), 2.82-3.07 (m, 2 H), 2.65 (s, 3 H), 2.43-2.57 (m, 1 H), 2.08-2.43 (m, 4 H), 1.84-2.06 (m, 5 H), 1.54-1.71 (m, 3 H), 1.18-1.44 (m, 4 H), 0.83-1.06 (m, 3 H). $^{19}F$ NMR (376 MHz, METHANOL-$d_4$) δ ppm −173.65 (s), −140.30 (s). Stereochemistry of Example 153 was confirmed by X-Ray crystallography analysis. |
| 154 | 626.0 | $^1H$ NMR (400 MHz, METHANOL-$d_4$) δ ppm 1.54-1.75 (m, 1 H) 1.79-1.92 (m, 1 H) 1.99-2.06 (m, 1 H) 2.17-2.29 (m, 2 H) 2.34-2.50 (m, 6 H), 2.59 (s, 4 H) 2.61-2.70 (m, 2 H) 3.09-3.21 (m, 2 H) 3.36-3.41 (m, 1 H) 3.48-3.52 (m, 1 H) 3.86-4.04 (m, 6 H) 4.21-4.28 (m, 1 H) 4.61-4.69 (m, 1 H) 4.70-4.78 (m, 2 H) 5.00 (br d, J = 14.10 Hz, 1 H) 5.10 (br d, J = 13.27 Hz, 1 H) 5.50-5.67 (m, 1 H) 5.68-5.72 (m, 1 H) 7.15 (dd, J = 3.63, 2.18 Hz, 1 H) 7.52 (s, 1 H) 7.65 (s, 1 H) 9.08 (d, J = 1.66 Hz, 1 H). $^{19}F$ NMR (376 MHz, METHANOL-$d_4$) δ ppm −174.15 (d, J = 5.20 Hz) −143.36 (d, J = 51.15 Hz). |
| 155 | 644.7 | $^1H$ NMR (500 MHz, METHANOL-$d_4$) δ ppm 1.52-1.57 (m, 1 H) 1.62-1.72 (m, 2 H) 1.78-1.91 (m, 6 H) 1.94-2.08 (m, δ H) 2.14-2.25 (m, 6 H) 2.32-2.50 (m, 11 H) 2.60-2.70 (m, 4 H) 2.75-2.88 (m, 4 H) 3.25-3.29 (m, 2 H) 3.35-3.40 (m, 2 H) 3.46-3.54 (m, 4 H) 3.81-4.17 (m, 13 H) 4.64-4.78 (m, 9 H) 5.11 (br d, J = 12.46 Hz, 1 H) 5.53-5.61 (m, 2 H) 5.62-5.72 (m, 2 H) 6.34 (d, J = 12.98 Hz, 2 H) 6.37 (d, J = 12.72 Hz, 1 H) 6.78 (dd, J = 12.78, 1.36 Hz, 1 H) 6.82 (s, 1 H) 6.86 (d, J = 13.36 Hz, 2 H) 6.91 (s, 2 H) 7.92 (d, J = 0.78 Hz, 2 H) 7.94 (d, J = 0.78 Hz, 1 H) 8.09 (s, 1 H) 8.18 (s, 2 H) 8.74 (s, 1 H) 8.82 (s, 2 H). $^{19}F$ NMR (471 MHz, METHANOL-$d_4$) δ ppm −175.33 (br s) −175.27 (br s) −142.35 (br s) −140.12 (br s). |
| 156 | 647.2 | $^1H$ NMR (DMSO-$d_6$, 600 MHz) δ ppm 9.18 (s, 1H), 8.96 (s, 1H), 7.94 (br s, 1H), 7.82 (br d, 1H, J = 4.3 Hz), 7.50 (d, 1H, J = 5.7 Hz), |

TABLE 48-continued

Analytical Data for Example 151 to 157, 239 to 259 and 386 to 397.

| Cmpd. # | MS m/z (ESI): $(M + H)^+$ | $^1H$ and $^{19}F$ NMR |
|---|---|---|
| | | 5.3-5.3 (m, 1H), 5.24 (br s, 1H), 4.2-4.2 (m, 2H), 4.1-4.2 (m, 2H), 4.00 (br d, 1H, J = 13.6 Hz), 3.90 (br t, 1H, J = 13.2 Hz), 3.74 (br d, 1H, J = 11.9 Hz), 3.0-3.1 (m, 3H), 2.90 (br d, 1H, J = 9.4 Hz), 2.8-2.9 (m, 1H), 2.74 (br d, 1H, J = 13.8 Hz), 2.1-2.1 (m, 1H), 2.0-2.1 (m, 3H), 1.97 (br d, 1H, J = 6.3 Hz), 1.8-1.9 (m, 6H), 1.70 (br d, 1H, J = 14.1 Hz), 1.5-1.6 (m, 1H). $^{19}F$ NMR (DMSO-$d_6$, 376 MHz) δ −177.22 (s), −148.19 (s). Stereochemistry of Example 156 was confirmed by X-Ray crystallography analysis. |
| 157 | 648.0 | $^1H$ NMR (400 MHz, METHANOL-$d_4$) δ ppm 9.05-9.16 (m, 1 H), 7.82 (d, J = 17.6 Hz, 2 H), 7.20 (s, 1 H), 5.19-5.44 (m, 1 H), 5.01 (br d, J = 13.2 Hz, 2 H), 4.09-4.38 (m, 3 H), 3.28 (br s, 1 H), 3.16-3.21 (m, 1 H), 2.98-3.08 (m, 2 H), 2.48-2.85 (m, 4 H), 2.14-2.39 (m, 5 H), 1.84-2.09 (m, 6 H), 1.73-1.82 (m, 1 H), 1.30-1.53 (m, 3 H). $^{19}F$ NMR (376 MHz, METHANOL-$d_4$) δ ppm −143.17-−139.98 (m), −174.84-−172.51 (m). Stereochemistry of Example 157 was confirmed by X-Ray crystallography analysis. |
| 239 | 622.2 | $^1H$ NMR (400 MHz, METHANOL-$d_4$) δ ppm 9.04-9.38 (m, 1 H), 7.64-8.01 (m, 1 H), 7.32-7.53 (m, 1 H), 5.19-5.45 (m, 1 H), 4.24-4.41 (m, 2 H), 2.95-3.31 (m, 7 H), 2.42-2.94 (m, 3 H), 2.10-2.41 (m, 5 H), 1.87-2.07 (m, 5 H), 1.51-1.84 (m, 4 H), 0.57-1.45 (m, δ H). $^{19}F$ NMR (376 MHz, METHANOL-$d_4$) δ ppm −121.48-−118.24 (m), −146.11-−142.22 (m), −176.57-−172.68 (m). |
| 240 | 622.2 | $^1H$ NMR (400 MHz, METHANOL-$d_4$) δ ppm 9.14-9.34 (m, 1 H), 7.70-7.90 (m, 1 H), 7.37-7.44 (m, 1 H), 5.16-5.43 (m, 1 H), 4.26-4.37 (m, 2 H), 2.85-3.32 (m, 10 H), 1.71-2.75 (m, 10 H), 1.28-1.71 (m, 6 H), 0.43-1.25 (m, 4 H). $^{19}F$ NMR (376 MHz, METHANOL-$d_4$) δ ppm −119.24 (s), −145.14-−142.22 (m), −174.95-−172.36 (m). |
| 241 | 620.1 | $^1H$ NMR (400 MHz, METHANOL-$d_4$) δ ppm 9.17 (s, 1 H), 7.78 (s, 1 H), 7.51 (s, 1 H), 5.26-5.42 (m, 1 H), 4.81-4.91 (m, 2 H), 4.67-4.75 (m, 1 H), 4.29-4.39 (m, 3 H), 4.09-4.22 (m, 2 H), 3.75-4.00 (m, 3 H), 3.36-3.62 (m, 3 H), 2.95-3.27 (m, 6 H), 2.41-2.53 (m, 4 H), 2.19-2.39 (m, 5 H), 1.57-1.66 (m, 3 H), 1.05-1.13 (m, 3 H). $^{19}F$ NMR (376 MHz, METHANOL-$d_4$) δ ppm −146.85-−141.45 (m), −176.11-−172.06 (m). |
| 242 | 620.1 | $^1H$ NMR (400 MHz, METHANOL-$d_4$) δ ppm 9.17-9.32 (m, 1 H), 7.74-7.94 (m, 1 H), 7.43-7.66 (m, 1 H), 5.18-5.42 (m, 1 H), 4.88-5.04 (m, 2 H), 4.19-4.37 (m, 2 H), 4.00-4.15 (m, 1 H), 3.70-3.90 (m, 2 H), 3.50-3.59 (m, 1 H), 3.19-3.27 (m, 4 H), 2.98-3.07 (m, 2 H), 2.68-2.76 (m, 1 H), 2.51-2.57 (m, 3 H), 2.29-2.47 (m, 2 H), 1.90-2.27 (m, 7 H), 1.24-1.45 (m, 5 H), 1.05-1.10 (m, 3 H). $^{19}F$ NMR (376 MHz, METHANOL-$d_4$) δ ppm −144.15-−141.00 (m), −175.21-−172.51 (m). |
| 243 | 620.1 | $^1H$ NMR (400 MHz, METHANOL-$d_4$) δ ppm 9.06-9.31 (m, 1 H), 7.63-7.95 (m, 1 H), 7.32-7.59 (m, 1 H), 5.16-5.44 (m, 1 H), 4.82-4.88 (m, 1 H), 4.67-4.75 (m, 1 H), 4.21-4.44 (m, 2 H), 3.73-3.99 (m, 3 H), 3.40-3.56 (m, 2 H), 3.01-3.31 (m, 6 H), 2.42-2.56 (m, 4 H), 1.83-2.41 (m, δ H), 1.51-1.65 (m, 1 H), 1.20-1.46 (m, 4 H), 1.04-1.13 (m, 3 H). $^{19}F$ NMR (376 MHz, METHANOL-$d_4$) δ ppm −143.44 (s), −173.64 (s). |
| 244 | 620.1 | $^1H$ NMR (400 MHz, METHANOL-$d_4$) δ ppm 9.21 (s, 1 H), 7.83 (s, 1 H), 7.54 (s, 1 H), 5.17-5.43 (m, 1 H), 4.87-5.02 (m, 2 H), 4.20-4.37 (m, 2 H), 4.20-4.42 (m, 2 H), 4.05-4.15 (m, 1 H), 3.67-3.89 (m, 2 H), 3.49-3.65 (m, 1 H), 3.18-3.27 (m, 4 H), 2.96-3.07 (m, 2 H), 2.66-2.74 (m, 1 H), 2.47-2.56 (m, 3 H), 1.99-2.44 (m, 7 H), 1.24-1.47 (m, 5 H), 1.07 (d, J = 5.9 Hz, 3 H). $^{19}F$ NMR (376 MHz, METHANOL-$d_4$) δ ppm −144.60-−141.00 (m), −176.56-−170.26 (m). |
| 245 | 647.0 | $^1H$ NMR (400 MHz, METHANOL-$d_4$) δ ppm 9.12 (s, 1 H), 7.81 (s, 2 H), 7.26 (s, 1 H), 5.24-5.46 (m, 1 H), 4.96-5.05 (m, 2 H), 4.39-4.49 (m, 1 H), 4.09-4.29 (m, 2 H), 3.37-3.44 (m, 1 H), 3.02-3.28 (m, 3 H), 2.77-2.89 (m, 1 H), 1.70-2.73 (m, 15 H), 1.31-1.52 (m, 3 H). $^{19}F$ NMR (376 MHz, METHANOL-$d_4$) δ ppm −142.25-−141.53 (m), −173.83-−172.93 (m). |
| 246 | 647.9 | $^1H$ NMR (400 MHz, METHANOL-$d_4$) δ ppm 9.05-9.16 (m, 1 H), 7.82 (d, J = 17.6 Hz, 2 H), 7.20 (s, 1 H), 5.19-5.44 (m, 1 H), 5.01 (br d, J = 13.2 Hz, 2 H), 4.09-4.38 (m, 3 H), 3.28 (br s, 1 H), 3.16-3.21 (m, 1 H), 2.98-3.08 (m, 2 H), 2.48-2.85 (m, 4 H), 2.14-2.39 (m, 5 H), 1.84-2.09 (m, 6 H), 1.73-1.82 (m, 1 H), 1.30-1.53 (m, 3 H). $^{19}F$ NMR (376 MHz, METHANOL-$d_4$) δ ppm −143.17-−139.98 (m), −174.84-−172.51 (m). |
| 247 | 648.0 | $^1H$ NMR (400 MHz, METHANOL-$d_4$) δ ppm 9.05-9.19 (m, 1 H), 7.74-7.88 (m, 2 H), 5.09-5.44 (m, 3 H), 4.13-4.44 (m, 3 |

TABLE 48-continued

Analytical Data for Example 151 to 157, 239 to 259 and 386 to 397.

| Cmpd. # | MS m/z (ESI): $(M + H)^+$ | $^1H$ and $^{19}F$ NMR |
|---|---|---|
| | | H), 3.13-3.26 (m, 4 H), 2.96-3.07 (m, 1 H), 2.68-2.88 (m, 5 H), 2.37-2.54 (m, 1 H), 2.32-2.32 (m, 1 H), 2.15-2.33 (m, 3 H), 1.90-2.08 (m, 4 H), 1.67-1.79 (m, 1 H), 1.49-1.62 (m, 1 H), 1.30-1.37 (m, 2 H). $^{19}F$ NMR (376 MHz, METHANOL-$d_4$) δ ppm −142.73-−140.79 (m), −173.74-−172.45 (m). |
| 248 | 668.0 | $^1H$ NMR (400 MHz, METHANOL-$d_4$) δ ppm 9.17-9.26 (m, 1 H), 7.87-7.92 (m, 1 H), 7.78-7.86 (m, 1 H), 5.22-5.45 (m, 1 H), 4.83-4.89 (m, 2 H), 4.74 (s, 1 H), 4.24-4.39 (m, 2 H), 4.02 (br d, J = 13.6 Hz, 1 H), 3.76-3.91 (m, 3 H), 3.44-3.61 (m, 2 H), 2.94-3.31 (m, 3 H), 2.93-3.30 (m, 1 H), 2.63-2.75 (m, 1 H), 2.18-2.49 (m, 4 H), 1.85-2.16 (m, 5 H), 1.30-1.38 (m, 2 H), 0.89-0.99 (m, 1 H). $^{19}F$ NMR (376 MHz, METHANOL-$d_4$) δ ppm −145.79-−140.93 (m), −174.95-−172.36 (m). |
| 249 | 665.95 | $^1H$ NMR (400 MHz, METHANOL-$d_4$) δ ppm 9.10-9.30 (m, 1 H), 7.83-8.03 (m, 2 H), 5.18-5.44 (m, 1 H), 4.99-5.09 (m, 1 H), 4.61-4.81 (m, 2 H), 4.20-4.40 (m, 2 H), 3.43-3.92 (m, 10 H), 3.18-3.27 (m, 2 H), 2.98-3.10 (m, 1 H), 2.66-2.83 (m, 1 H), 2.13-2.37 (m, 4 H), 1.99-2.04 (m, 2 H), 1.67-1.94 (m, 6 H). $^{19}F$ NMR (376 MHz, METHANOL-$d_4$) δ ppm −143.83-−140.91 (m), −176.30-−173.05 (m). Stereochemistry of Example 249 was confirmed by X-Ray crystallography analysis. |
| 250 | 618.2 | $^1H$ NMR (400 MHz, METHANOL-$d_4$) δ ppm 9.24 (s, 1 H), 7.73 (s, 1 H), 7.55 (s, 1 H), 5.51-5.71 (m, 1 H), 4.94-5.03 (m, 2 H), 4.62-4.78 (m, 2 H), 3.84-4.13 (m, 4 H), 3.44-3.55 (m, 1 H), 3.24-3.31 (m, 1 H), 2.98-3.12 (m, 2 H), 2.60-2.87 (m, 4 H), 2.56 (s, 8 H), 2.13-2.27 (m, 1 H), 1.94-2.09 (m, 2 H), 1.80-1.93 (m, 1 H), 1.59-1.71 (m, 2 H), 1.17-1.42 (m, 3 H), 0.72-0.81 (m, 3 H). $^{19}F$ NMR (376 MHz, METHANOL-$d_4$) δ ppm −77.32 (s), −143.45 (s), −174.07 (s). |
| 251 | 618.2 | $^1H$ NMR (400 MHz, METHANOL-$d_4$) δ ppm 9.29 (s, 1 H), 7.74-7.79 (m, 1 H), 7.50-7.58 (m, 1 H), 5.46-5.71 (m, 1 H), 4.95-5.18 (m, 2 H), 4.60-4.77 (m, 2 H), 3.82-4.12 (m, 4 H), 3.47-3.57 (m, 1 H), 3.25-3.31 (m, 2 H), 3.10-3.19 (m, 1 H), 2.94-3.10 (m, 2 H), 2.77-2.94 (m, 1 H), 2.55 (s, 5 H), 2.32-2.53 (m, 4 H), 2.14-2.26 (m, 1 H), 1.96-2.12 (m, 2 H), 1.79-1.93 (m, 1 H), 1.57-1.73 (m, 2 H), 1.21-1.45 (m, 2 H), 0.60-0.80 (m, 1 H), 0.53 (d, J = 6.7 Hz, 2 H), 0.45-0.60 (m, 1 H). $^{19}F$ NMR (376 MHz, METHANOL-$d_4$) δ ppm −77.32 (s), −141.12 (s), −143.45 (s), −174.07 (s). |
| 252 | 639.8 | $^1H$ NMR (DMSO-$d_6$, 600 MHz) δ ppm 9.2-9.3 (m, 1H), 7.6-7.9 (m, 2H), 6.5-7.3 (m, 1H), 5.2-5.4 (m, 1H), 4.6-4.8 (m, 2H), 4.0-4.2 (m, 3H), 3.7-3.9 (m, 3H), 3.4-3.6 (m, 1H), 3.0-3.2 (m, 5H), 2.7-2.9 (m, 3H), 2.0-2.2 (m, 4H), 1.8-1.9 (m, 3H), 1.1-1.3 (m, 4H), 0.4-0.5 (m, 3H). |
| 253 | 639.8 | $^1H$ NMR (400 MHz, METHANOL-$d_4$) δ ppm 9.17 (s, 1 H), 7.84 (s, 1 H), 7.79 (s, 1 H), 5.20-5.40 (m, 1 H), 4.88 (br d, J = 13.2 Hz, 1 H), 4.22-4.37 (m, 2 H), 4.08-4.16 (m, 1 H), 3.90-4.00 (m, 1 H), 3.69-3.78 (m, 2 H), 3.54 (td, J = 12.4, 3.6 Hz, 1 H), 2.87-3.27 (m, 7 H), 2.50-2.74 (m, 3 H), 1.83-2.39 (m, 6 H), 1.18-1.37 (m, 4 H), 1.15 (d, J = 6.1 Hz, 3 H). $^{19}F$ NMR (376 MHz, METHANOL-$d_4$) δ ppm −142.53 (s, 1 F), −173.69 (s, 1 F). |
| 254 | 610.0 | $^1H$ NMR (400 MHz, METHANOL-$d_4$) δ ppm 9.21 (s, 1 H), 7.93 (s, 1 H), 7.75-7.80 (m, 1 H), 5.47-5.72 (m, 1 H), 4.61-4.78 (m, 4 H), 3.76-4.11 (m, 5 H), 3.44-3.55 (m, 2 H), 3.17 (br dd, J = 9.3, 4.3 Hz, 1 H), 2.12-2.82 (m, 12 H), 1.40-1.55 (m, 2 H), 1.26-1.31 (m, 1 H), 1.02-1.25 (m, 2 H). 33 H's/35 H's (spectrum/structure) $^{19}F$ NMR (376 MHz, METHANOL-$d_4$) δ ppm −77.24 (s), −144.22 (m), −174.04 (m). |
| 255 | 647.1 | $^1H$ NMR (METHANOL-$d_4$, 400 MHz) δ ppm 9.1-9.2 (m, 1H), 7.8-8.5 (m, 2H), 6.37 (d, 1H, J = 4.8 Hz), 5.2-5.5 (m, 1H), 4.9-5.1 (m, 2H), 4.1-4.4 (m, 3H), 3.0-3.3 (m, 7H), 2.9-3.0 (m, 1H), 2.0-2.6 (m, 12H), 1.7-1.8 (m, 1H), 1.5-1.6 (m, 1H). Two sets of peaks, 32H/33H. $^{19}F$ NMR (METHANOL-$d_4$, 376 MHz) δ −147.6-−138.2 (m), −175.0-−172.2 (m). |
| 386 | 647.05 | $^1H$ NMR (DMSO-$d_6$, 600 MHz) δ ppm 13.30 (s, 1H), 9.24 (br s, 1H), 7.81 (d, 2H, J = 6.6 Hz), 6.30 (s, 1H), 5.2-5.5 (m, 1H), 4.7-5.2 (m, 4H), 4.2-4.3 (m, 2H), 4.1-4.2 (m, 3H), 3.3-3.3 (m, 1H), 2.9-3.2 (m, 1H), 2.79 (ddd, 1H, J = 5.2, 8.5, 13.9 Hz), 2.3-2.4 (m, 3H), 2.1-2.2 (m, 1H), 2.0-2.1 (m, 1H), 1.92 (br d, 2H, J = 13.6 Hz), 1.7-1.8 (m, 3H), 1.4-1.5 (m, 5H) |

TABLE 48-continued

| Analytical Data for Example 151 to 157, 239 to 259 and 386 to 397. | | |
|---|---|---|
| Cmpd. # | MS m/z (ESI): $(M + H)^+$ | $^1H$ and $^{19}F$ NMR |
| 387 | 647.05 | $^1H$ NMR (DMSO-$d_6$, 600 MHz) δ ppm 13.29 (s, 1H), 9.22 (s, 1H), 7.82 (s, 2H), 6.29 (s, 1H), 5.2-5.4 (m, 1H), 4.8-5.0 (m, 3H), 4.0-4.3 (m, 4H), 3.3-3.4 (m, 1H), 3.2-3.3 (m, 1H), 3.17 (br s, 1H), 2.8-2.8 (m, 1H), 2.3-2.4 (m, 2H), 2.1-2.2 (m, 2H), 2.0-2.1 (m, 3H), 1.9-2.0 (m, 2H), 1.7-1.8 (m, 5H), 1.4-1.6 (m, 2H). |
| 256 | 653.2 | $^1H$ NMR (DMSO-$d_6$, 500 MHz) δ ppm 13.29 (s, 1H), 9.34 (s, 1H), 7.81 (s, 1H), 7.73 (s, 1H), 6.79 (d, 1H, J = 6.2 Hz), 5.3-5.4 (m, 1H), 5.2-5.3 (m, 1H), 4.55 (br dd, 1H, J = 4.4, 12.7 Hz), 4.19 (d, 1H, J = 10.4 Hz), 3.8-3.9 (m, 1H), 3.6-3.6 (m, 1H), 3.48 (ddd, 2H, J = 2.5, 7.6, 10.6 Hz), 3.0-3.2 (m, 4H), 2.7-2.9 (m, 2H), 2.5-2.6 (m, 1H), 2.0-2.1 (m, 3H), 1.7-1.9 (m, 7H), 1.5-1.6 (m, 1H), 1.2-1.3 (m, 1H), 1.12 (s, 3H). |
| 257 | 660.2 | $^1H$ NMR (400 MHz, METHANOL-$d_4$) δ ppm 8.81 (s, 1H), 8.17 (d, J = 4.8 Hz, 1H), 7.89 (s, 1H), 7.8-7.8 (m, 1H), 6.21 (d, J = 5.0 Hz, 1H), 5.4-5.5 (m, 1H), 5.2-5.3 (m, 2H), 4.45 (d, J = 10.6 Hz, 1H), 4.25 (d, J = 10.6 Hz, 1H), 4.02 (d, J = 15.5 Hz, 1H), 3.5-3.5 (m, 1H), 3.2-3.3 (m, 3H), 3.0-3.1 (m, 2H), 2.8-3.0 (m, 1H), 2.8-2.8 (m, 1H), 2.4-2.5 (m, 1H), 2.3-2.3 (m, 2H), 2.0-2.2 (m, 8H), 1.9-2.0 (m, 1H), 1.7-1.8 (m, 1H). $^{19}F$ NMR (376 MHz, METHANOL-$d_4$) δ ppm −142.23 (s), −175.27 (s). |
| 258 | 661.0 | $^1H$ NMR (400 MHz, METHANOL-$d_4$) δ ppm 8.7-8.8 (m, 1H), 8.05 (s, 1H), 7.93 (s, 1H), 6.82 (s, 2H), 6.2-6.3 (m, 1H), 5.5-5.7 (m, 1H), 4.6-4.8 (m, 3H), 4.2-4.3 (m, 1H), 4.0-4.1 (m, 3H), 3.9-4.0 (m, 9H), 3.4-3.5 (m, 4H), 2.6-2.6 (m, 1H), 2.6-2.8 (m, 1H), 2.42 (br s, 1H), 2.3-2.4 (m, 3H), 1.8-2.1 (m, 1H). $^{19}F$ NMR (376 MHz, METHANOL-$d_4$) δ ppm −142.6-−142.5 (m), −175.5-−175.4 (m). |
| 259 | 647.2 | $^1H$ NMR (400 MHz, METHANOL-$d_4$) δ ppm 9.0-9.1 (m, 1H), 7.81 (d, J = 1.9 Hz, 2H), 7.0-7.0 (m, 1H), 5.2-5.4 (m, 1H), 5.1-5.2 (m, 1H), 4.94 (br d, J = 14.5 Hz, 1H), 4.41 (d, J = 10.6 Hz, 1H), 4.2-4.3 (m, 4H), 3.1-3.3 (m, 4H), 3.0-3.1 (m, 1H), 2.6-2.8 (m, 2H), 2.1-2.4 (m, 6H), 1.7-2.1 (m, 7H). $^{19}F$ NMR (376 MHz, METHANOL-$d_4$) δ ppm −142.20 (s), −173.72 (s). |
| 388 | 647.05 | $^1H$ NMR (METHANOL-$d_4$, 400 MHz) δ ppm 8.9-9.3 (m, 1H), 7.8-7.9 (m, 1H), 7.2-7.4 (m, 1H), 5.93 (br d, 1H, J = 13.5 Hz), 5.2-5.4 (m, 1H), 4.51 (s, 1H), 4.2-4.4 (m, 1H), 3.2-3.3 (m, 4H), 2.8-3.1 (m, 3H), 2.1-2.7 (m, 9H), 1.6-2.0 (m, 9H).$^{19}F$ NMR (METHANOL-$d_4$, 377 MHz) δ −143.55 (s), −173.70 (d, J = 4.3 Hz). |
| 389 | 649.15 | $^1H$ NMR (METHANOL-$d_4$, 400 MHz) δ ppm 9.17 (s, 1H), 7.82 (s, 1H), 7.79 (s, 1 H), 7.41 (d, 1H, J = 1.3 Hz), 5.2-5.4 (m, 1H), 5.0-5.1 (m, 2H), 4.81 (br d, 1H, J = 4.4 Hz), 4.42 (dd, 1H, J = 4.5, 14.3 Hz), 4.2-4.3 (m, 3H), 3.9-4.0 (m, 1H), 3.60 (ddd, 1H, J = 3.8, 10.3, 13.5 Hz), 3.2-3.3 (m, 2H), 3.0-3.1 (m, 1H), 2.6-2.8 (m, 2H), 2.5-2.6 (m, 2H), 1.8-2.4 (m, 8H), 1.4-1.5 (m, 1H). |
| 390 | 649.15 | $^1H$ NMR (METHANOL-$d_4$, 400 MHz) δ ppm 9.18 (s, 1H), 7.83 (s, 1H), 7.79 (s, 1H), 7.39 (d, 1H, J = 1.0 Hz), 5.2-5.4 (m, 1H), 5.0-5.1 (m, 2H), 4.81 (br d, 1H, J = 4.4 Hz), 4.2-4.4 (m, 3H), 3.8-3.9 (m, 2H), 3.5-3.7 (m, 3H), 3.3-3.4 (m, 1H), 3.2-3.3 (m, 3H), 3.0-3.1 (m, 1H), 2.6-2.9 (m, 2H), 2.5-2.6 (m, 1H), 2.1-2.4 (m, 3H), 1.9-2.0 (m, 3H). $^{19}F$ NMR (METHANOL-$d_4$, 376 MHz) δ −141.79 (s), −173.71 (s). |
| 391 | 648.25 | $^1H$ NMR (METHANOL-$d_4$, 400 MHz) δ ppm 9.0-9.4 (m, 1H), 7.92 (br d, 1H, J = 19.9 Hz), 7.84 (br d, 1H, J = 4.2 Hz), 4.9-5.4 (m, 2H), 4.2-4.7 (m, 3H), 3.98 (br d, 1H, J = 14.4 Hz), 3.3-3.6 (m, 2H), 3.1-3.3 (m, 5H), 2.9-3.1 (m, 2H), 2.6-2.8 (m, 2H), 2.0-2.5 (m, 6H), 1.6-2.0 (m, 5H). |
| 392 | 638.0 | $^1H$ NMR (400 MHz, METHANOL-$d_4$) δ ppm 9.22 (s, 1H), 8.20 (s, 1H), 7.84 (s, 1H), 5.45-5.22 (m, 1H), 4.96 (br d, J = 13.2 Hz, 1H), 4.20-4.09 (m, 1H), 4.05-3.91 (m, 1H), 3.82-3.72 (m, 2H), 3.66-3.48 (m, 2H), 3.44-3.39 (m, 1H), 3.28-3.17 (m, 3H), 3.11-2.94 (m, 2H), 2.44-2.22 (m, 4H), 2.11-1.88 (m, 5H), 1.49 (td, J = 9.1, 4.8 Hz, 1H), 1.40-1.30 (m, 3H), 0.97-0.90 (m, 1H), 0.79-0.56 (m, 2H), 0.37-0.25 (m, 1H). $^{19}F$ NMR (376 MHz, METHANOL-$d_4$) δ ppm −139.16 (s), −173.69 (s). |
| 393 | 638.0 | $^1H$ NMR (400 MHz, METHANOL-$d_4$) δ ppm 9.14 (s, 1H), 8.14 (s, 1H), 7.83 (s, 1H), 5.49-5.21 (m, 2H), 5.04-4.87 (m, 1H), 4.02-3.88 (m, 2H), 3.66-3.47 (m, 4H), 3.28-3.12 (m, 5H), 3.10-2.97 (m, 2H), 2.93-2.79 (m, 1H), 2.42-2.11 (m, 5H), 2.08-1.86 (m, 5H), 1.44-1.25 (m, 2H), 0.74-0.59 (m, 1H), 0.40-0.30 (m, 1H). $^{19}F$ NMR (376 MHz, METHANOL-$d_4$) δ ppm −140.68 (s), −173.74 (s). |
| 394 | 619.0 | $^1H$ NMR (400 MHz, METHANOL-$d_4$) δ ppm 8.97 (s, 1 H), 7.86 (s, 1 H), 7.86 (s, 1 H), 6.52 (s, 1 H), 4.60 (dd, J = 11.08, 5.85 Hz, 1 H), 4.46 (dd, J = 10.97, 5.54 Hz, 1 H), 3.99 (dd, J = 14.63, 3.34 Hz, 1 H), 3.93 (d, J = 11.50 Hz, 1 H), 3.37-3.46 (m, 2 H), 3.11 (dd, J = 9.72, 4.08 Hz, 1 H), 3.00-3.06 (m, 1 H), 2.79-2.89 (m, 4 H), 2.55 (s, 3 |

TABLE 48-continued

Analytical Data for Example 151 to 157, 239 to 259 and 386 to 397.

| Cmpd. # | MS m/z (ESI): $(M + H)^+$ | $^1H$ and $^{19}F$ NMR |
|---|---|---|
| | | H), 2.43-2.47 (m, 1 H), 2.39 (q, J = 9.06 Hz, 2 H), 2.27-2.32 (m, 1 H), 2.11-2.17 (m, 1 H), 2.00 (br dd, J = 8.99, 6.48 Hz, 2 H), 1.81-1.91 (m, 4 H), 1.71-1.81 (m, 2 H). |
| 395 | 665.2 | $^1H$ NMR (500 MHz, DMSO-$d_6$) δ ppm 9.39 (s, 1 H), 8.01 (s, 1 H), 7.84 (s, 1 H), 6.88 (s, 1 H), 5.33 (br s, 1 H), 5.21-5.24 (m, 1 H), 4.77 (br d, J = 13.62 Hz, 1 H), 4.66 (s, 1 H), 4.17-4.25 (m, 2 H), 4.11-4.17 (m, 1 H), 4.07 (d, J = 10.38 Hz, 1 H), 3.98-4.05 (m, 1 H), 3.69-3.76 (m, 1 H), 3.54 (br d, J = 9.86 Hz, 1 H), 3.42 (br d, J = 10.12 Hz, 1 H), 3.09 (br d, J = 10.25 Hz, 2 H), 3.02 (s, 1 H), 2.91-2.98 (m, 1 H), 2.80-2.88 (m, 3 H), 2.12 (br d, J = 4.02 Hz, 1 H), 2.07 (br d, J = 10.12 Hz, 1 H), 1.99-2.04 (m, 1 H), 1.83-1.91 (m, 2 H), 1.73-1.82 (m, 3 H). $^{19}F$ NMR (471 MHz, DMSO-$d_6$) δ ppm −143.19 (s), −172.10 (s). |
| 396 | 688.9 | $^1H$ NMR (400 MHz, METHANOL-$d_4$) δ ppm 9.20 (s, 1H), 7.88 (s, 1H), 7.81 (s, 1H), 6.63 (s, 1H), 5.71-5.47 (m, 1H), 5.02-4.97 (m, 1H), 4.72-4.63 (m, 2H), 4.14-3.98 (m, 1H), 3.98-3.76 (m, 4H), 3.49 (br t, J = 9.0 Hz, 1H), 3.23-3.14 (m, J = 7.9 Hz, 2H), 3.13-3.05 (m, 1H), 2.94-2.49 (m, 5H), 2.48-2.34 (m, 4H), 2.31-1.97 (m, 4H), 1.95-1.86 (m, 2H), 1.86-1.76 (m, 3H). $^{19}F$ NMR (376 MHz, METHANOL-$d_4$) δ −144.25 (d, J = 6.9 Hz), −175.51 (d, J = 32.9 Hz). |
| 397 | 666.3 | $^1H$ NMR (400 MHz, METHANOL-$d_4$) δ ppm 9.53-9.10 (m, 1H), 8.16-7.46 (m, 2H), 5.83-5.43 (m, 1H), 5.10-4.95 (m, 1H), 4.75-4.61 (m, 2H), 4.15-3.84 (m, 3H), 3.77-3.60 (m, 2H), 3.59-3.44 (m, 2H), 3.25-3.05 (m, 3H), 2.99-2.12 (m, 9H), 2.07-1.17 (m, 11H). 1H not observed. $^{19}F$ NMR (376 MHz, METHANOL-$d_4$) δ −77.21 (s, 6F), −141.88 (d, J = 7.8 Hz, 1F), −174.02 (s, 1F). Stereochemistry of Example 153 was confirmed by X-Ray crystallography analysis. |

(1S,3R)-10-Chloro-32-fluoro-24-(((2R,7aS)-2-fluorotetrahydro-1H-pyrrolo[1,2-a]pyrrol-7a(5H)-yl)methoxy)-4-oxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaene bis(2,2,2-trifluoroacetate) (Example 260)

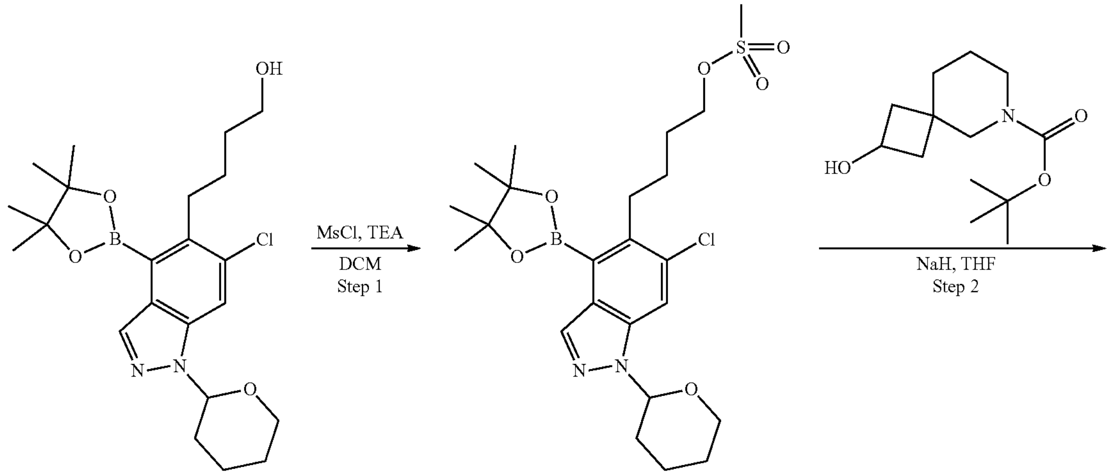

-continued
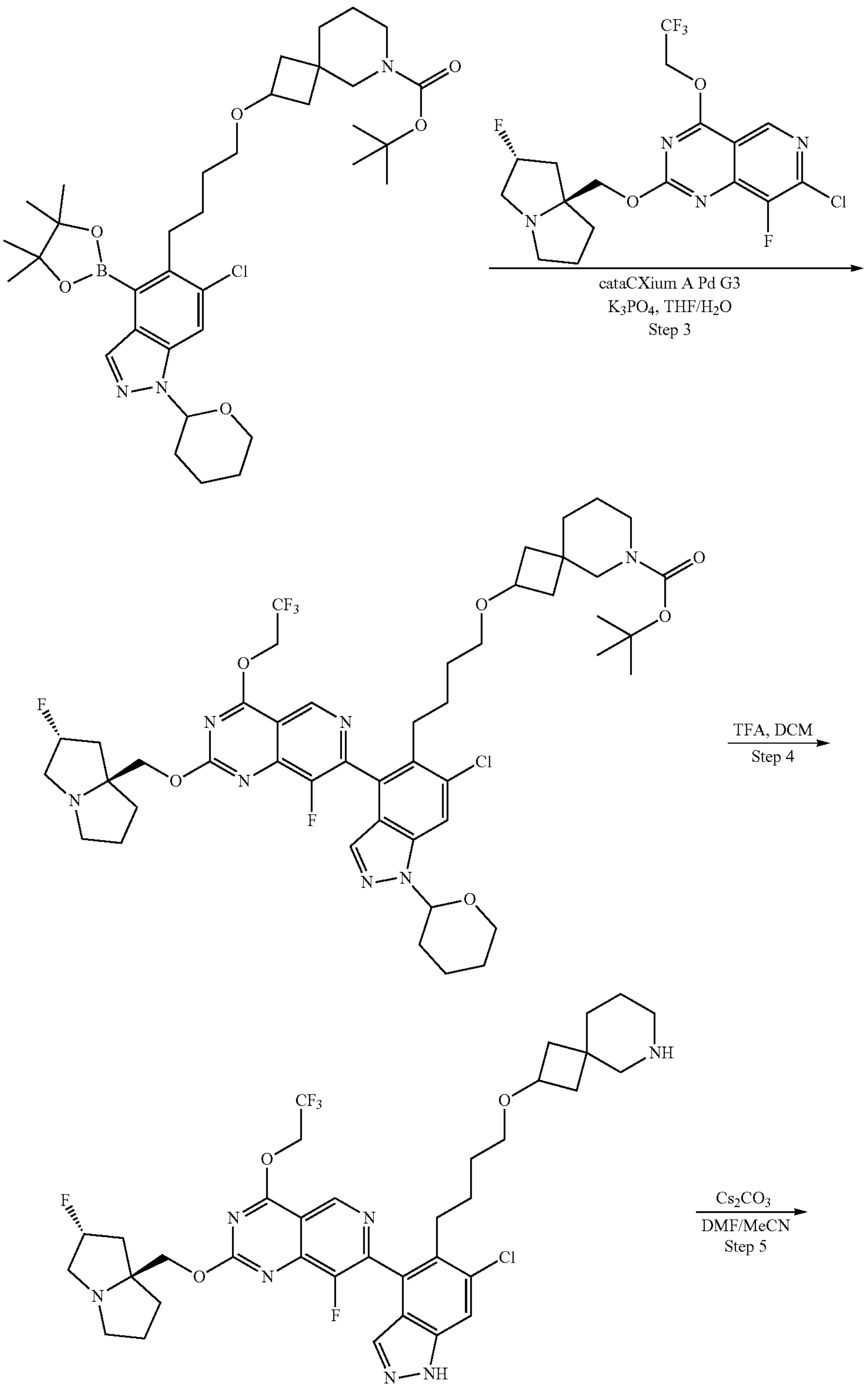

-continued

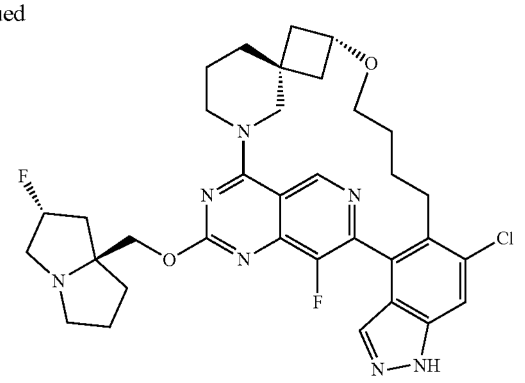

Example 260

Step 1. 4-(6-Chloro-1-(tetrahydro-2H-pyran-2-yl)-4-(4,4,5,5-tetramethyl-1,3,2-dioxaborolan-2-yl)-1H-indazol-5-yl) butyl methanesulfonate. A 40 mL vial was charged 4-(6-chloro-1-(tetrahydro-2H-pyran-2-yl)-4-(4,4,5,5-tetramethyl-1,3,2-dioxaborolan-2-yl)-1H-indazol-5-yl) butan-1-ol (1.16 g, 2.67 mmol), dichloromethane (15 mL), and triethylamine (0.75 mL, 5.34 mmol). To this vial was added dropwise methanesulfonyl chloride (0.31 mL, 4.0 mmol). The reaction was stirred at rt for 3 h. The crude mixture was purified by flash column chromatography on silica gel, eluting with a gradient of 0-85% ethyl acetate in heptane, to give 4-(6-chloro-1-(tetrahydro-2H-pyran-2-yl)-4-(4,4,5,5-tetramethyl-1,3,2-dioxaborolan-2-yl)-1H-indazol-5-yl)butyl methanesulfonate (0.80 g, 1.56 mmol, 58% yield) as colorless oil. m/z (ESI): 513.2 $(M+H)^+$.

Step 2. tert-Butyl 2-(4-(6-chloro-1-(tetrahydro-2H-pyran-2-yl)-4-(4,4,5,5-tetramethyl-1,3,2-dioxaborolan-2-yl)-1H-indazol-5-yl)butoxy)-6-azaspiro[3.5]nonane-6-carboxylate. To a 40 mL vial was charged with 6-Boc-2-hydroxy-6-azaspiro[3.5]nonane (0.75 g, 3.11 mmol, Combi-Blocks Inc.), tetrahydrofuran (4.0 mL), and sodium hydride (60% in mineral oil, 124 mg, 3.11 mmol). This was allowed to stir at rt for 15 minutes, then 4-(6-chloro-1-(tetrahydro-2H-pyran-2-yl)-4-(4,4,5,5-tetramethyl-1,3,2-dioxaborolan-2-yl)-1H-indazol-5-yl)butyl methanesulfonate (0.80 g, 1.56 mmol) was added as a solution in tetrahydrofuran (4.0 mL). The solution was warmed to 50° C. for 4 h. After cooling to rt, the reaction mixture was carefully quenched with saturated ammonium chloride and concentrated. The crude oil was purified by flash column chromatography on silica gel, eluting with 0-75% ethyl acetate in heptane, to give tert-butyl 2-(4-(6-chloro-1-(tetrahydro-2H-pyran-2-yl)-4-(4,4,5,5-tetramethyl-1,3,2-dioxaborolan-2-yl)-1H-indazol-5-yl) butoxy)-6-azaspiro[3.5]nonane-6-carboxylate (0.75 g, 1.14 mmol, 73% yield) as yellow oil. m/z (ESI): 658.2 $(M+H)^+$.

Step 3. tert-Butyl 2-(4-(6-chloro-4-(8-fluoro-2-(((2R,7aS)-2-fluorotetrahydro-1H-pyrrolizin-7a(5H)-yl) methoxy)-4-(2,2,2-trifluoroethoxy)pyrido[4,3-d]pyrimidin-7-yl)-1-(tetrahydro-2H-pyran-2-yl)-1H-indazol-5-yl) butoxy)-6-azaspiro[3.5]nonane-6-carboxylate. A 40-mL vial was charged with phosphoric acid (potassium) (0.97 g, 4.56 mmol), cataCXium A Pd G3 (0.17 g, 0.23 mmol), tert-butyl 2-(4-(6-chloro-1-(tetrahydro-2H-pyran-2-yl)-4-(4,4,5,5-tetramethyl-1,3,2-dioxaborolan-2-yl)-1H-indazol-5-yl)butoxy)-6-azaspiro[3.5]nonane-6-carboxylate (0.90 g, 1.37 mmol), 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.50 g, 1.14 mmol), tetrahydrofuran (5.0 mL) and water (0.5 mL). The reaction mixture was stirred at 80° C. for 3 h. After cooling to rt, the crude mixture was purified by column chromatography on silica gel, eluting with a gradient of 0-85% 3:1 EtOAc:EtOH (with 2% triethylamine) in heptane, to yield tert-butyl 2-(4-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)butoxy)-6-azaspiro[3.5]nonane-6-carboxylate (0.93 g, 0.99 mmol, 87% yield). m/z (ESI): 934.2 $(M+H)^+$.

Step 4. 7-(5-(4-((6-Azaspiro[3.5]nonan-2-yl)oxy)butyl)-6-chloro-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine. To the solution of tert-butyl 2-(4-(6-chloro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)-1-(tetrahydro-2H-pyran-2-yl)-1H-indazol-5-yl)butoxy)-6-azaspiro[3.5]nonane-6-carboxylate (0.93 g, 0.99 mmol) in dichloromethane (5.0 mL) was was added trifluoroacetic acid (5.0 mL). The reaction mixture was stirred at rt for 1 h. The volatiles were removed under reduced pressure and the crude product was purified by reverse phase chromatography to yield 0.26 g of 7-(5-(4-((6-azaspiro[3.5]nonan-2-yl) oxy)butyl)-6-chloro-1H-indazol-4-yl)-8-fluoro-2-(((2R,7aS)-2-fluorotetrahydro-1H-pyrrolizin-7a(5H)-yl) methoxy)-4-(2,2,2-trifluoroethoxy)pyrido[4,3-d]pyrimidine as TFA salt which was used in the subsequent step without further purification. m/z (ESI): 750.2 $(M+H)^+$.

Step 5. (1S,3R)-10-Chloro-32-fluoro-24-(((2R,7aS)-2-fluorotetrahydro-1H-pyrrolo[1,2-a]pyrrol-7a(5H)-yl) methoxy)-4-oxa-13,14,19,23,25,27-hexaazaheptacyclo [25.3.1.1~1,3~.1~18,22~.0~9,17~.0~12,16~.0~21,26~] tritriaconta-9,11,14,16,18(32),19,21,23,25-nonaene bis(2,2,2-trifluoroacetate). A suspension of 7-(5-(4-((6-azaspiro [3.5]nonan-2-yl)oxy)butyl)-6-chloro-1H-indazol-4-yl)-8-fluoro-2-(((2R,7aS)-2-fluorotetrahydro-1H-pyrrolizin-7a (5H)-yl)methoxy)-4-(2,2,2-trifluoroethoxy)pyrido[4,3-d] pyrimidine (0.26 g, 0.34 mmol) and cesium carbonate (0.56 g, 1.71 mmol) in N,N-dimethylformamide (3.3 mL) and acetonitrile (65 mL) was heated to 80° C. with stirring for 1 h. The volatiles were removed under reduced pressure and the crude product was purified by reverse phase HPLC to yield (1S,3R)-10-chloro-32-fluoro-24-(((2R,7aS)-2-fluorotetrahydro-1H-pyrrolo[1,2-a]pyrrol-7a(5H)-yl)methoxy)-4-oxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaene bis(2,2,2- trifluoroacetate) (16 mg, 0.018 mmol, 5% yield) as off-white solid after lyophilization. m/z (ESI): 650.2 $(M+H)^+$. $^1H$ NMR (400 MHz, METHANOL-$d_4$) δ ppm 9.18-9.36 (m, 1H), 7.81-7.86 (m, 1H), 7.72-7.79 (m, 1H), 5.47-5.75 (m, 1H), 5.03-5.13 (m, 1H), 4.89-5.01 (m, 1H), 4.62-4.75 (m, 2H), 3.88-4.12 (m, 3H), 3.73-3.87 (m, 2H), 3.44-3.57 (m, 1H), 3.12-3.24 (m, 1H), 2.93-3.03 (m, 1H), 2.76-2.86 (m, 2H), 2.56-2.75 (m, 2H), 2.33-2.51 (m, 4H), 2.15-2.30 (m, 1H), 2.04-2.14 (m, 1H), 1.58-1.80 (m, 7H), 1.33-1.53 (m, 3H), 1.01-1.13 (in, 1H). $^{19}F$ NMR (376 MHz, METHANOL-$d_4$) δ ppm −77.29 (s), −142.58--142.49 (in), −174.14--173.98 (in). Stereochemistry of Example 260 was confirmed by X-Ray crystallography analysis.

TABLE 49

Additional Examples 261 to 264 and 398 to 405.
Prepared in an Analogous Manner to Example 260.

| Ex. # | Structure & Name | Salt Form | Reagent | Method Change |
|---|---|---|---|---|
| 261 | 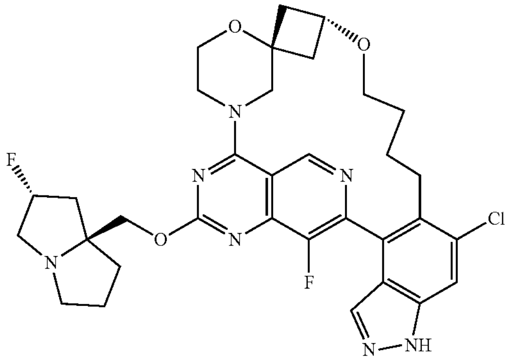 [SMILES: Fc1c2ncc3c(nc(OC[C@@]45CCCN4C[C@H](F)C5)nc13)N1CCO[C@]3(C1)C[C@@H](C3)OCCCCc1c(Cl)cc3[nH]ncc3c1-2] (1S,3S)-10-chloro-32-fluoro-24-(((2R,7aS)-2-fluorotetrahydro-1H-pyrrolo[1,2-a]pyrrol-7a(5H)-yl) methoxy)-4,30-dioxa-13,14,19,23,25,27-hexaazaheptacyclo [25.3.1.1~1,3~.1~18,22~.0~9,17~.0~12,16~.0~21,26~] tritriaconta-9,11,14,16,18(32),19,21,23,25-nonaene | NA | Step 2. tert-butyl 2-hydroxy-5-oxa-8-azaspiro[3.5] nonane-8-carboxylate (CAS#: 2309427-24-3) | Achiral separation after Step 5. Details included below. |
| 262 | 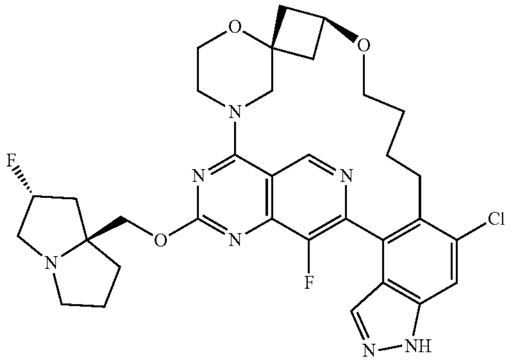 [SMILES: Fc1c2ncc3c(nc(OC[C@@]45CCCN4C[C@H](F)C5)nc13)N1CCO[C@]3(C1)C[C@H](C3)OCCCCc1c(Cl)cc3[nH]ncc3c1-2] (1R,3R)-10-chloro-32-fluoro-24-(((2R,7aS)-2-fluorotetrahydro-1H-pyrrolo[1,2-a]pyrrol-7a(5H)-yl)methoxy)-4,30-dioxa-13,14,19,23,25,27-hexaazaheptacyclo [25.3.1.1~1,3~.1~18,22~.0~9,17~.0~12,16~.0~21,26~] tritriaconta-9,11,14,16,18(32),19,21,23,25-nonaene | NA | Step 2. tert-butyl 2-hydroxy-5-oxa-8-azaspiro[3.5] nonane-8-carboxylate (CAS#: 2309427-24-3) | Achiral separation after Step 5. Details included below. |

TABLE 49-continued

| Ex. # | Structure & Name | Salt Form | Reagent | Method Change |
|---|---|---|---|---|
| | Additional Examples 261 to 264 and 398 to 405. Prepared in an Analogous Manner to Example 260. | | | |
| 263 | 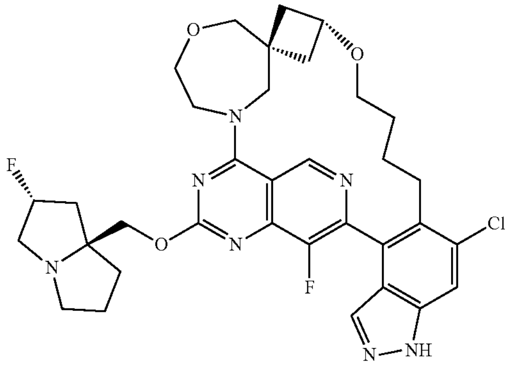 [SMILES: Fc1c2ncc3c(nc(OC[C@@]45CCCN4C[C@H](F)C5)nc13)N1CCOC[C@]3(C1)C[C@@H](C3)OCCCCc1c(Cl)cc3[nH]ncc3c1-2] (1S,3S)-10-chloro-33-fluoro-24-(((2R,7aS)-2-fluorotetrahydro-1H-pyrrolo[1,2-a]pyrrol-7a(5H)-yl)methoxy)-4,30-dioxa-13,14,19,23,25,27-hexaazaheptacyclo [25.4.1.1~1,3~.1~18,22~.0~9,17~.0~12,16~.0~21,26~] tetratriaconta-9,11,14,16,18(33),19,21,23,25-nonaene | trifluoroacetate | Step 2. tert-butyl 2-hydroxy-6-oxa-9-azaspiro[3.6] decane-9-carboxylate (CAS#: 2803863-99-0) | |
| 264 | 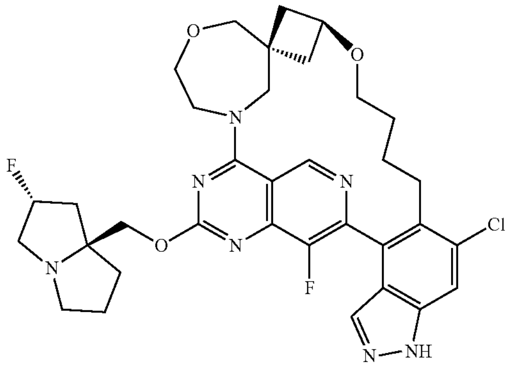 [SMILES: Fc1c2ncc3c(nc(OC[C@@]45CCCN4C[C@H](F)C5)nc13)N1CCOC[C@]3(C1)C[C@H](C3)OCCCCc1c(Cl)cc3[nH]ncc3c1-2] (1R,3R)-10-chloro-33-fluoro-24-(((2R,7aS)-2-fluorotetrahydro-1H-pyrrolo[1,2-a]pyrrol-7a(5H)-yl)methoxy)-4,30-dioxa-13,14,19,23,25,27-hexaazaheptacyclo [25.4.1.1~1,3~.1~18,22~.0~9,17~.0~12,16~.0~21,26~] tetratriaconta-9,11,14,16,18(33),19,21,23,25-nonaene | trifluoroacetate | Step 2. tert-butyl 2-hydroxy-6-oxa-9-azaspiro[3.6] decane-9-carboxylate (CAS#: 2803863-99-0) | |
| 398 | 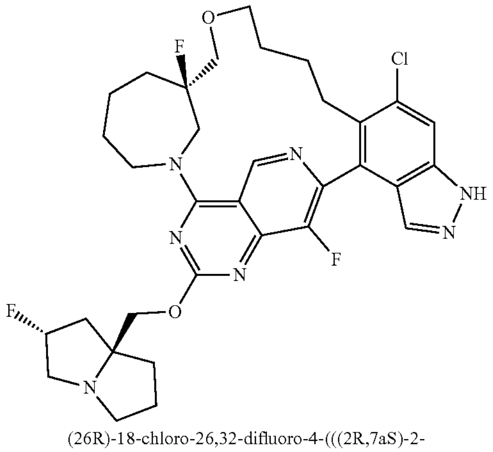 (26R)-18-chloro-26,32-difluoro-4-(((2R,7aS)-2-fluorotetrahydro-1H-pyrrolo[1,2-a]pyrrol-7a(5H)-yl) methoxy)-24-oxa-1,3,5,9,14,15-hexaazahexacyclo [24.4.1.1~6,10~.0~2,7~.0~11,19~.0~12,16~] dotriaconta-2,4,6,8,10(32),11,13,16,18-nonaene | NA | Step 2. tert-butyl 3-fluoro-3-(hydroxymethyl) azepane-1-carboxylate (CAS#: 1784405-24-8) | Chiral separation after Step 5. Details included below. |

TABLE 49-continued

Additional Examples 261 to 264 and 398 to 405.
Prepared in an Analogous Manner to Example 260.

| Ex. # | Structure & Name | Salt Form | Reagent | Method Change |
|---|---|---|---|---|
| 399 | 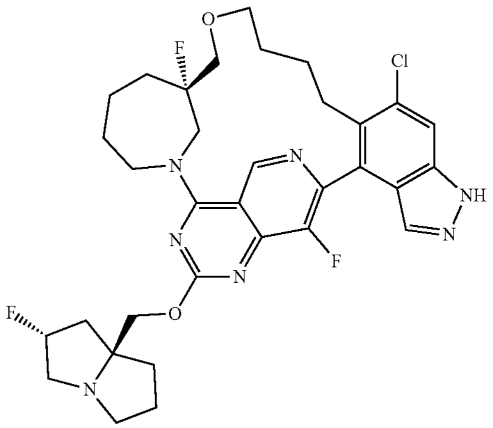 [SMILES: Fc1c2ncc3c(nc(OC[C@@]45CCCN4C[C@H](F)C5)nc13)N1CCCC[C@@](F)(COCCCCc3c(Cl)cc4[nH]ncc4c3-2)C1] (26S)-18-chloro-26,32-difluoro-4-(((2R,7aS)-2-fluorotetrahydro-1H-pyrrolo[1,2-a]pyrrol-7a(5H)-yl) methoxy)-24-oxa-1,3,5,9,14,15-hexaazahexacyclo [24.4.1.1~6,10~.0~2,7~.0~11,19~.0~12,16~] dotriaconta-2,4,6,8,10(32),11,13,16,18-nonaene | NA | Step 2. tert-butyl 3-fluoro-3-(hydroxymethyl) azepane-1-carboxylate (CAS#: 1784405-24-8) | Chiral separation after Step 5. Details included below. |
| 400 | 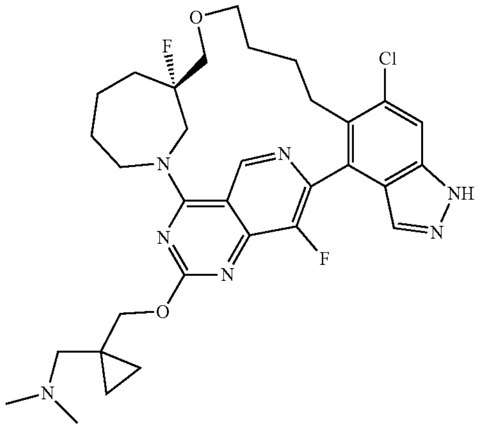 [SMILES: CN(C)CC1(COc2nc3c4cnc(c(F)c4n2)-c2c(c(Cl)cc4[nH]ncc24)CCCCOC[C@]2(F)CCCCN3C2)CC1] 1-(1-((((26R)-18-chloro-26,32-difluoro-24-oxa-1,3,5,9,14,15-hexaazahexacyclo [24.4.1.1~6,10~.0~2,7~.0~11,19~.0~12,16~] dotriaconta-2,4,6,8,10(32),11,13,16,18-nonaen-4-yl)oxy)methyl)cyclopropyl)-N,N-dimethylmethanamine | NA | Step 2. tert-butyl 3-fluoro-3-(hydroxymethyl) azepane-1-carboxylate (CAS#: 1784405-24-8) Step 3. Intermediate EF | Chiral separation after Step 5. Details included below. |

TABLE 49-continued

| Additional Examples 261 to 264 and 398 to 405. Prepared in an Analogous Manner to Example 260. | | | | |
|---|---|---|---|---|
| Ex. # | Structure & Name | Salt Form | Reagent | Method Change |
| 401 | 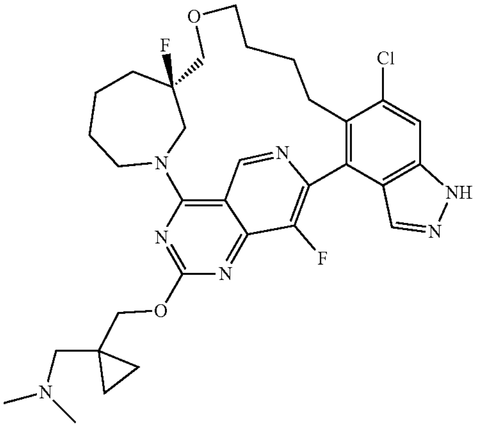 [SMILES: CN(C)CC1(COc2nc3c4cnc(c(F)c4n2)-c2c(c(Cl)cc4[nH]ncc24)CCCCOC[C@@]2(F)CCCCN3C2)CC1] 1-(1-((((26S)-18-chloro-26,32-difluoro-24-oxa-1,3,5,9,14,15-hexaazahexacyclo [24.4.1.1~6,10~.0~2,7~.0~11,19~.0~12,16~] dotriaconta-2,4,6,8,10(32),11,13,16,18-nonaen-4-yl)oxy)methyl)cyclopropyl)-N,N-dimethylmethanamine | NA | Step 2. tert-butyl 3-fluoro-3-(hydroxymethyl) azepane-1-carboxylate (CAS#: 1784405-24-8) Step 3. Intermediate EF | Chiral separation after Step 5. Details included below. |
| 402 | 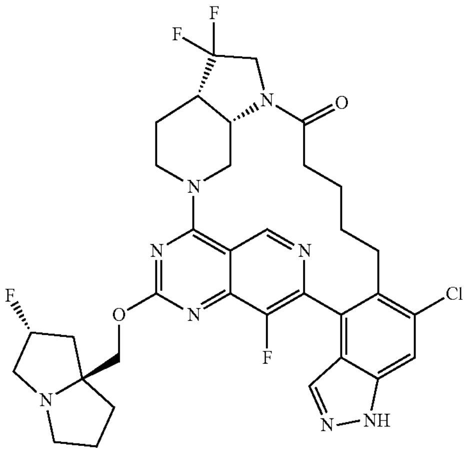 [SMILES: O=C1CCCCc2c(Cl)cc3[nH]ncc3c2-c2ncc3c(nc(OC[C@@]45CCCN4C[C@H](F)C5)nc3c2F)N2CC[C@H]3[C@@H](C2)N1CC3(F)F] (28S,32S)-18-chloro-27,27,33-trifluoro-4-(((2R,7aS)-2-fluorotetrahydro-1H-pyrrolo[1,2-a] pyrrol-7a(5H)-yl)methoxy)-1,3,5,9,14,15,25-heptaazaheptacyclo [23.5.2.1~6,10~.0~2,7~.0~11,19~.0~12,16~.0~28,32~] tritriaconta-2,4,6,8,10(33),11,13,16,18-nonaen-24-one | NA | Step 3. Intermediate FR | Chiral separation after Step 5. Details included below. |

TABLE 49-continued

| Ex. # | Structure & Name | Salt Form | Reagent | Method Change |
|---|---|---|---|---|
| | Additional Examples 261 to 264 and 398 to 405. Prepared in an Analogous Manner to Example 260. | | | |
| 403 | 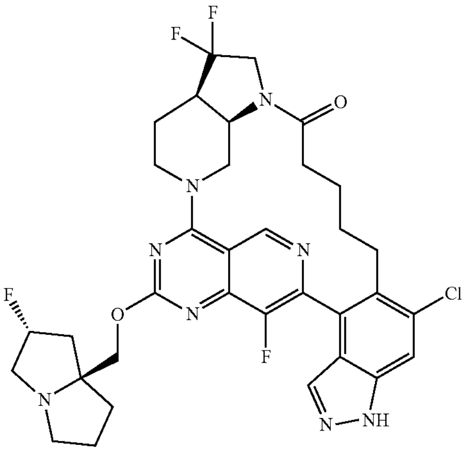 [SMILES: O=C1CCCCc2c(Cl)cc3[nH]ncc3c2-c2ncc3c(nc(OC[C@@]45CCCN4C[C@H](F)C5)nc3c2F)N2CC[C@@H]3[C@H](C2)N1CC3(F)F] (28R,32R)-18-chloro-27,27,33-trifluoro-4-(((2R,7aS)-2-fluorotetrahydro-1H-pyrrolo[1,2-a]pyrrol-7a(5H)-yl)methoxy)-1,3,5,9,14,15,25-heptaazaheptacyclo[23.5.2.1~6,10~.0~2,7~.0~11,19~.0~12,16~.0~28,32~]tritriaconta-2,4,6,8,10(33),11,13,16,18-nonaen-24-one | NA | Step 3. Intermediate FR | Chiral separation after Step 5. Details included below. |
| 404 | 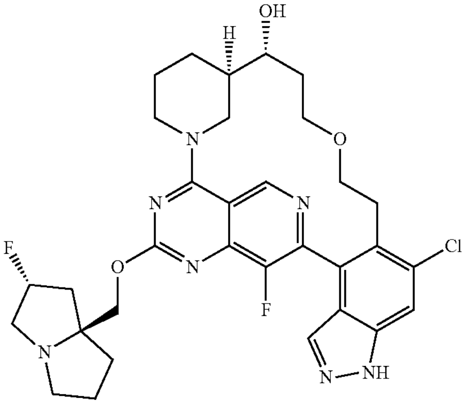 [SMILES: O[C@@H]1CCOCCc2c(Cl)cc3[nH]ncc3c2-c2ncc3c(nc(OC[C@@]45CCCN4C[C@H](F)C5)nc3c2F)N2CCC[C@@H]1C2] (16R,17R)-9-Chloro-30-fluoro-24-(((2R,7aS)-2-fluorotetrahydro-1H-pyrrolo[1,2-a]pyrrol-7a(5H)-yl)methoxy)-13-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-16-ol | trifluoroacetate | Step 3. Intermediate FS | 4N HCl in dioxane was used after Step 5 to remove TBS protecting group |
| 405 | 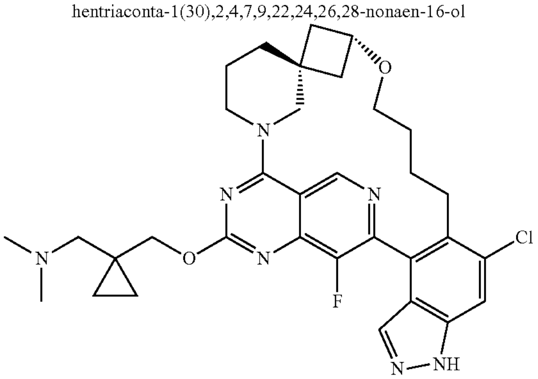 1-(1-((((1S,3R)-10-chloro-32-fluoro-4-oxa-13,14,19,23,25,27-hexaazaheptacyclo[25.3.1.1~1,3~.1~18,22~.0~9,17~.0~12,16~.0~21,26~]tritriaconta-9,11,14,16,18(32),19,21,23,25-nonaen-24-yl)oxy)methyl)cyclopropyl)-N,N-dimethylmethanamine | Bis (2,2,2-trifluoroaceate) | Step 3. Intermediate EF | Chiral separation after Step 5. Details included below. |

TABLE 50

| Conditions for Chiral/Achiral Separation. | | |
|---|---|---|
| Separation | Conditions | Final products |
| 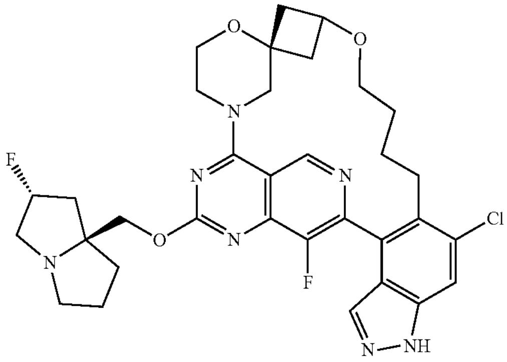 | Column: XBridge C18, (19 × 100 mm, 5 μm)<br>Mobile phase: 40-80% $CH_3CN$ with 0.1% $NH_4OH$ in water with 0.1% $NH_4OH$<br>Flowrate: 80 mL/min.<br>Yield: 50 mg sample was submitted to generate 5 mg of peak 1 with an ee of >98% and 3 mg of peak 2 with an ee of >99%. | Peak 1: Ex. 261<br>Peak 2: Example Ex. 262 |
| 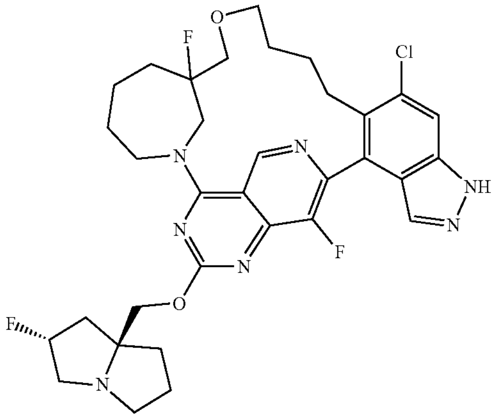 [SMILES: Fc1c2ncc3c(nc(OC[C@@]45CCCN4C[C@H](F)C5)nc13)N1CCCCC(F)(COCCCCc3c(Cl)cc4[nH]ncc4c3-2)C1] | Column: (S,S) Whelk-0 (2 × 25 cm, 5 μm)<br>Mobile phase: 35% MeOH with 0.2% DEA<br>Flowrate: 90 mL/min.<br>Yield: 34 mg sample was submitted to generate 5 mg of peak 1 with an ee of >99% and 6 mg of peak 2 with an ee of 91%. | Peak 1: Example 399<br>Peak 2: Example 398 |
| 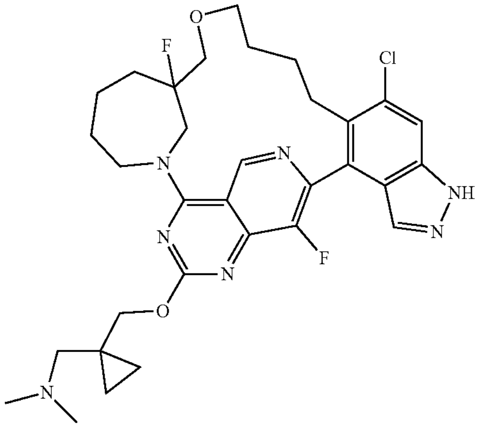 [SMILES: CN(C)CC1(COc2nc3c4cnc(c(F)c4n2)-c2c(c(Cl)cc4[nH]ncc24)CCCCOCC2(F)CCCCN3C2)CC1] | Column: ChiralPak AD (2 × 25 cm, 5 μm)<br>Mobile phase: 35% iPrOH with 0.2% DEA<br>Flowrate: 80 mL/min.<br>Yield: 26 mg sample was submitted to generate 5 mg of peak 1 with an ee of >99% and 5 mg of peak 2 with an ee of 88%. | Peak 1: Example 401<br>Peak 2: Example 400 |

TABLE 50-continued

| Conditions for Chiral/Achiral Separation. | | |
|---|---|---|
| Separation | Conditions | Final products |
| 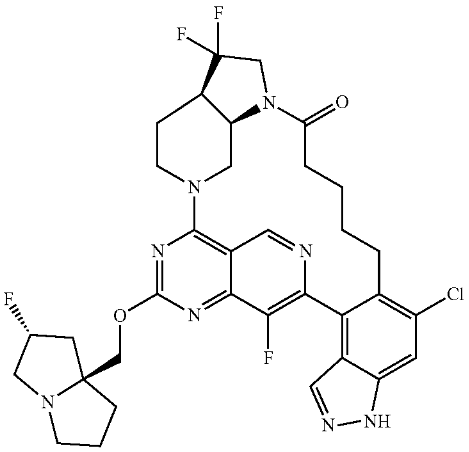 [SMILES: O=C1CCCCc2c(Cl)cc3[nH]ncc3c2-c2ncc3c(nc(OC[C@@]45CCCN4C[C@H](F)C5)nc3c2F)N2CC[C@@H]3[C@H](C2)N1CC3(F)F] | Column: Chiralel OD (2 × 15 cm, 5 μm)<br>Mobile phase: 45% iPrOH with 0.2% DEA<br>Flowrate: 100 mL/min.<br>Yield: 22 mg sample was submitted to generate 5 mg of peak 1 with an ee of 91% and 5 mg of peak 2 with an ee of >99%. | Peak 1: Example 402<br>Peak 2: Example 403 |

TABLE 51

| Analytical Data for Examples 261 to 264 and 398 to 405. | | |
|---|---|---|
| Cmpd. # | MS m/z (ESI): $(M + H)^+$ | $^1H$ and $^{19}F$ NMR |
| 261 | 652.2 | $^1H$ NMR (400 MHz, METHANOL-$d_4$) δ ppm 9.20 (s, 1 H), 7.74-7.87 (m, 2 H), 5.18-5.43 (m, 1 H), 4.82-4.91 (m, 4 H), 4.57-4.57 (m, 1 H), 4.21-4.40 (m, 2 H), 3.97 (br d, J = 12.96 Hz, 1 H), 3.79-3.90 (m, 3 H), 3.39-3.56 (m, 1 H), 3.11-3.29 (m, 3 H), 2.90-3.09 (m, 2 H), 2.74-2.86 (m, 2 H), 2.10-2.48 (m, 5 H), 1.87-2.09 (m, 4 H), 1.82 (br dd, J = 12.65, 6.17 Hz, 1 H), 1.56-1.73 (m, 1 H), 1.33-1.51 (m, 4 H). $^{19}F$ NMR (376 MHz, METHANOL-$d_4$) δ ppm −141.92 (d, J = 1.73 Hz), −173.71 (d, J = 8.67 Hz). |
| 262 | 652.2 | $^1H$ NMR (400 MHz, METHANOL-$d_4$) δ ppm 9.15-9.24 (m, 1 H), 7.81 (s, 1 H), 7.64 (s, 1 H), 5.16-5.44 (m, 1 H), 4.51 (br s, 2 H), 4.20-4.39 (m, 2 H), 3.92-4.18 (m, 3 H), 3.83 (br s, 1 H), 3.58-3.77 (m, 2 H), 3.40-3.48 (m, 1 H), 3.12-3.28 (m, 5 H), 2.91-3.11 (m, 3 H), 2.19-2.46 (m, 4 H), 2.08-2.19 (m, 1 H), 1.94-2.08 (m, 2 H), 1.71-1.94 (m, 3 H), 1.54-1.71 (m, 3 H), 1.48 (br d, J = 5.85 Hz, 3 H). $^{19}F$ NMR (376 MHz, METHANOL-$d_4$) δ ppm −139.48-−138.33 (m), −174.45-−173.31 (m). |
| 263 | 666.0 | $^1H$ NMR (400 MHz, METHANOL-$d_4$) δ ppm 9.50 (s, 1 H), 7.66-7.86 (m, 2 H), 5.46-5.71 (m, 1 H), 5.26 (br d, J = 14.84 Hz, 1 H), 4.62-4.75 (m, 3 H), 4.28-4.48 (m, 2 H), 3.86-4.00 (m, 6 H), 3.75-3.85 (m, 3 H), 3.57-3.75 (m, 4 H), 3.09-3.20 (m, 2 H), 3.05 (br dd, J = 5.23, 4.60 Hz, 1 H), 2.90 (ddd, J = 13.74, 10.09, 3.97 Hz, 1 H), 2.53-2.82 (m, 3 H), 2.32-2.48 (m, 5 H), 2.12-2.28 (m, 2 H), 1.92-2.10 (m, 3 H), 1.75 (br d, J = 12.54 Hz, 2 H), 1.27-1.68 (m, 7 H), 1.06 (br d, J = 13.17 Hz, 1 H). $^{19}F$ NMR (376 MHz, METHANOL-$d_4$) δ ppm −77.08 (s), −142.46 (d, J = 19.08 Hz), −174.08 (br d, J = 32.07 Hz). |
| 264 | 666.0 | $^1H$ NMR (400 MHz, METHANOL-$d_4$) δ ppm 9.61 (s, 1 H), 7.78-7.88 (m, 2 H), 7.73-7.77 (m, 1 H), 5.45-5.75 (m, 1 H), 5.07-5.30 (m, 2 H), 4.61-4.76 (m, 6 H), 3.83-4.02 (m, 13 H), 3.67-3.79 (m, 6 H), 3.43-3.61 (m, 4 H), 3.00-3.13 (m, 2 H), 2.83-2.96 (m, 2 H), 2.55-2.83 (m, 3 H), 2.29-2.55 (m, 5 H), 1.98-2.29 (m, 2 H), 1.70-1.87 (m, 2 H), 1.53-1.68 (m, 3 H), 1.35-1.53 (m, 4 H), 1.17-1.35 (m, 4 H). $^{19}F$ NMR (376 MHz, METHANOL-$d_4$) δ ppm −76.99 (br s), −140.77 (d, J = 13.87 Hz), −174.08 (br d, J = 37.28 Hz). |

TABLE 51-continued

| Analytical Data for Examples 261 to 264 and 398 to 405. | | |
|---|---|---|
| Cmpd. # | MS m/z (ESI): $(M + H)^+$ | $^1H$ and $^{19}F$ NMR |
| 398 | 655.9 | $^1H$ NMR (600 MHz, DMSO-$d_6$) δ ppm 9.41 (s, 1 H), 7.70-7.91 (m, 2 H), 5.12-5.41 (m, 2 H), 4.40 (br d, J = 11.74 Hz, 1 H), 4.02-4.23 (m, 3 H), 3.71 (br t, J = 13.86 Hz, 1 H), 3.40-3.56 (m, 1 H), 3.31-3.40 (m, 3 H), 3.15-3.24 (m, 1 H), 2.99-3.12 (m, 3 H), 2.79-2.89 (m, 2 H), 2.02-2.19 (m, 4 H), 1.97-2.02 (m, 1 H), 1.69-1.94 (m, 7 H), 1.45-1.64 (m, 4 H), 1.29-1.42 (m, 3 H), 1.24 (br s, 3 H). |
| 399 | 655.9 | $^1H$ NMR (600 MHz, DMSO-$d_6$) δ ppm 9.41 (s, 1 H), 7.67-7.89 (m, 2 H), 5.11-5.29 (m, 2 H), 4.40 (br d, J = 11.15 Hz, 1 H), 4.02-4.24 (m, 2 H), 3.71 (br t, J = 14.16 Hz, 1 H), 3.41-3.58 (m, 1 H), 3.32-3.37 (m, 1 H), 3.20 (br t, J = 10.27 Hz, 1 H), 3.00-3.12 (m, 4 H), 2.74-2.92 (m, 2 H), 2.12-2.13 (m, 1 H), 1.96-2.13 (m, 3 H), 1.72-1.94 (m, 7 H), 1.50-1.68 (m, 1 H), 1.44-1.66 (m, 3 H), 1.29-1.43 (m, 3 H), 1.14-1.29 (m, 3 H). |
| 400 | 626.0 | $^1H$ NMR (400 MHz, METHANOL-$d_4$) δ ppm 9.34 (s, 1 H), 7.80 (br d, J = 5.43 Hz, 2 H), 5.33-5.50 (m, 1 H), 5.18-5.36 (m, 1 H), 4.30-4.67 (m, 3 H), 4.02-4.18 (m, 1 H), 3.71-3.87 (m, 1 H), 3.43-3.56 (m, 2 H), 3.21-3.30 (m, 2 H), 3.10-3.20 (m, 1 H), 2.95-3.07 (m, 1 H), 2.54-2.80 (m, 3 H), 2.15-2.34 (m, 1 H), 1.86-2.05 (m, 3 H), 1.38-1.80 (m, 7 H), 1.29-1.37 (m, 2 H), 1.18 (d, J = 6.27 Hz, 1 H), 0.78 (br s, 2 H), 0.61 (br s, 2 H). $^{19}F$ NMR (376 MHz, METHANOL-$d_4$) δ ppm −143.06 (br d, J = 4.33 Hz), −153.09 (br d, J = 4.33 Hz). |
| 401 | 626.0 | $^1H$ NMR (400 MHz, METHANOL-$d_4$) δ ppm 9.34 (s, 1 H), 7.80 (br d, J = 5.43 Hz, 2 H), 5.17-5.36 (m, 1 H), 4.53-4.69 (m, 1 H), 4.44-4.53 (m, 1 H), 4.29-4.44 (m, 1 H), 4.04-4.19 (m, 1 H), 3.69-3.88 (m, 1 H), 3.46-3.53 (m, 1 H), 3.15 (dt, J = 3.19, 1.65 Hz, 2 H), 2.93-3.06 (m, 1 H), 2.53-2.78 (m, 2 H), 2.36-2.45 (m, 6 H), 2.17-2.33 (m, 1 H), 1.85-2.05 (m, 2 H), 1.38-1.79 (m, 6 H), 1.25-1.36 (m, 3 H), 1.24 (s, 1 H), 1.18 (d, J = 6.27 Hz, 1 H), 0.77 (br s, 2 H), 0.60 (br s, 2 H). $^{19}F$ NMR (376 MHz, METHANOL-$d_4$) δ ppm −143.05 (br d, J = 2.60 Hz), −153.09 (br s). |
| 402 | 699.0 | $^1H$ NMR (600 MHz, DMSO-$d_6$) δ ppm 9.53 (s, 1 H), 9.21 (s, 1 H), 7.79 (s, 2 H), 5.19-5.46 (m, 2 H), 4.54-4.75 (m, 1 H), 4.05-4.26 (m, 2 H), 3.88-4.00 (m, 2 H), 3.66-3.88 (m, 1 H), 3.31-3.37 (m, 1 H), 3.01-3.15 (m, 1 H), 2.79-3.01 (m, 1 H), 2.64-2.79 (m, 1 H), 1.94-2.34 (m, 6 H), 1.73-1.94 (m, 5 H), 1.73-1.90 (m, 1 H), 1.46-1.58 (m, 1 H), 1.33-1.46 (m, 2 H), 0.98-1.22 (m, 1 H), 0.95-1.33 (m, 2 H), 0.77-0.93 (m, 1 H). |
| 403 | 699.0 | $^1H$ NMR (600 MHz, DMSO-$d_6$) δ ppm 9.53 (s, 1 H), 9.21 (s, 1 H), 7.79 (s, 2 H), 5.19-5.46 (m, 2 H), 4.54-4.75 (m, 1 H), 4.05-4.26 (m, 2 H), 3.88-4.00 (m, 2 H), 3.66-3.88 (m, 1 H), 3.31-3.37 (m, 1 H), 3.01-3.15 (m, 1 H), 2.79-3.01 (m, 1 H), 2.64-2.79 (m, 1 H), 1.94-2.34 (m, 6 H), 1.73-1.88 (m, 5 H), 1.46-1.58 (m, 1 H), 1.33-1.46 (m, 2 H), 1.32 (br d, J = 6.75 Hz, 1 H), 1.02-1.31 (m, 2 H), 0.77-0.93 (m, 1 H). |
| 404 | 604.3 | $^1H$ NMR (400 MHz, DMSO-$d_6$) δ ppm 13.06-13.63 (m, 1 H), 10.66 (br d, J = 5.6 Hz, 1 H), 9.39-9.51 (m, 1 H), 7.87 (d, J = 11.7 Hz, 1 H), 5.41-5.75 (m, 1 H), 4.53-4.99 (m, 5 H), 3.84-3.97 (m, 3 H), 3.19-3.36 (m, 6 H), 2.79-3.04 (m, 2 H), 2.43 (br d, J = 9.6 Hz, 2 H), 2.31-2.38 (m, 2 H), 1.97-2.28 (m, 5 H), 1.61-1.73 (m, 2 H), 1.45-1.57 (m, 2 H), 1.22-1.36 (m, 1 H), 0.94-1.10 (m, 1 H). $^{19}F$ NMR (376 MHz, DMSO-$d_6$) δ ppm −74.11, −141.44, −172.87. |
| 405 | 620.0 | $^1H$ NMR (400 MHz, METHANOL-$d_4$) δ ppm 9.21-9.33 (m, 1 H), 7.83-7.84 (m, 1 H), 7.75-7.77 (m, 1 H), 5.02-5.13 (m, 1 H), 4.88-4.98 (m, 1 H), 4.42-4.56 (m, 2 H), 3.72-3.87 (m, 2 H), 3.38-3.48 (m, 1 H), 3.25-3.31 (m, 1 H), 3.13-3.22 (m, 1 H), 3.02 (s, 7 H), 2.81 (br s, 2 H), 2.37-2.51 (m, 1 H), 2.03-2.15 (m, 1 H), 1.59-1.82 (m, 7 H), 1.45 (br s, 3 H), 1.06-1.14 (m, 1 H), 0.96-1.04 (m, 2 H), 0.84-0.95 (m, 2 H). $^{19}F$ NMR (376 MHz, METHANOL-$d_4$) δ ppm −77.49-−77.39 (m, 6 F), −143.06-−142.98 (m, 1 F). |

(17R,19S)-9-Chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt and (17S,19R)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt (Example 265)
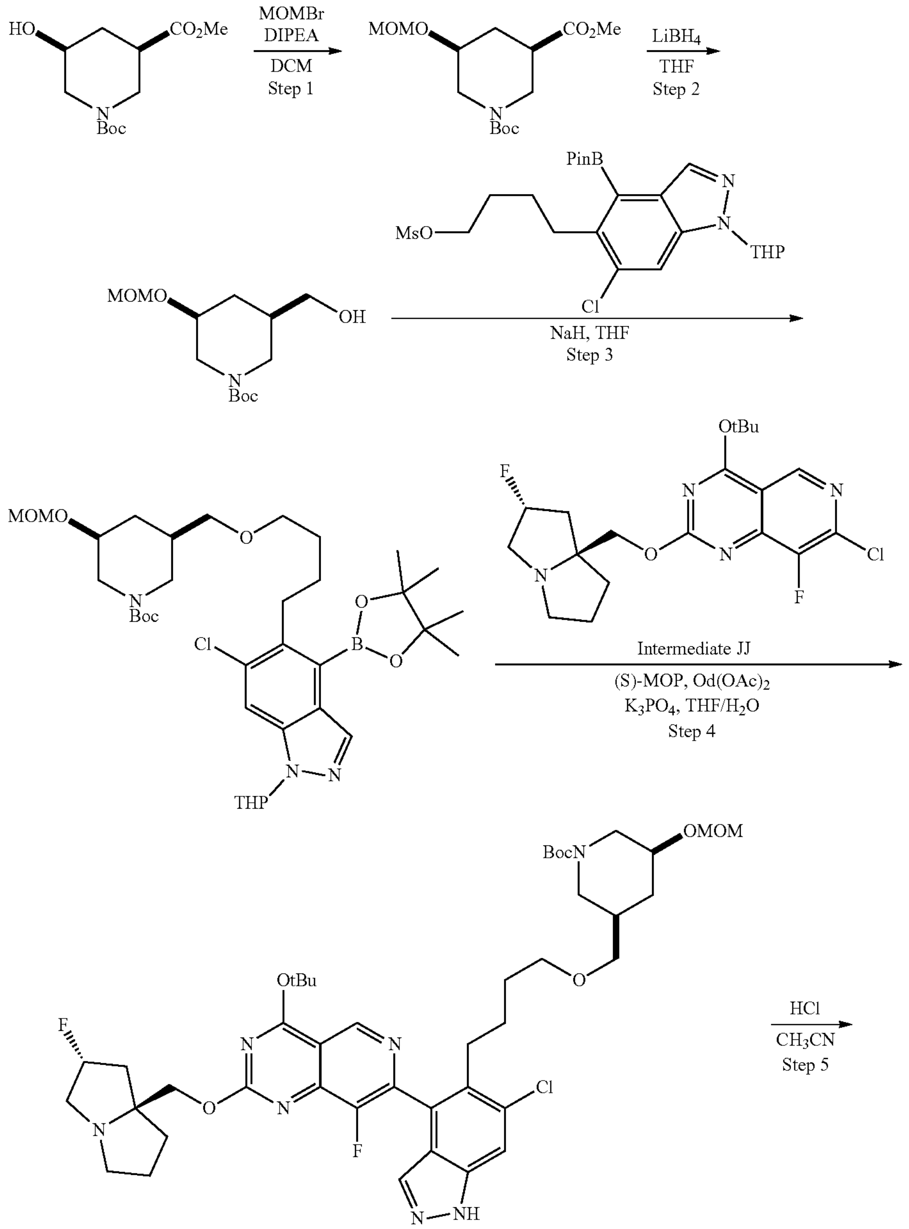

-continued

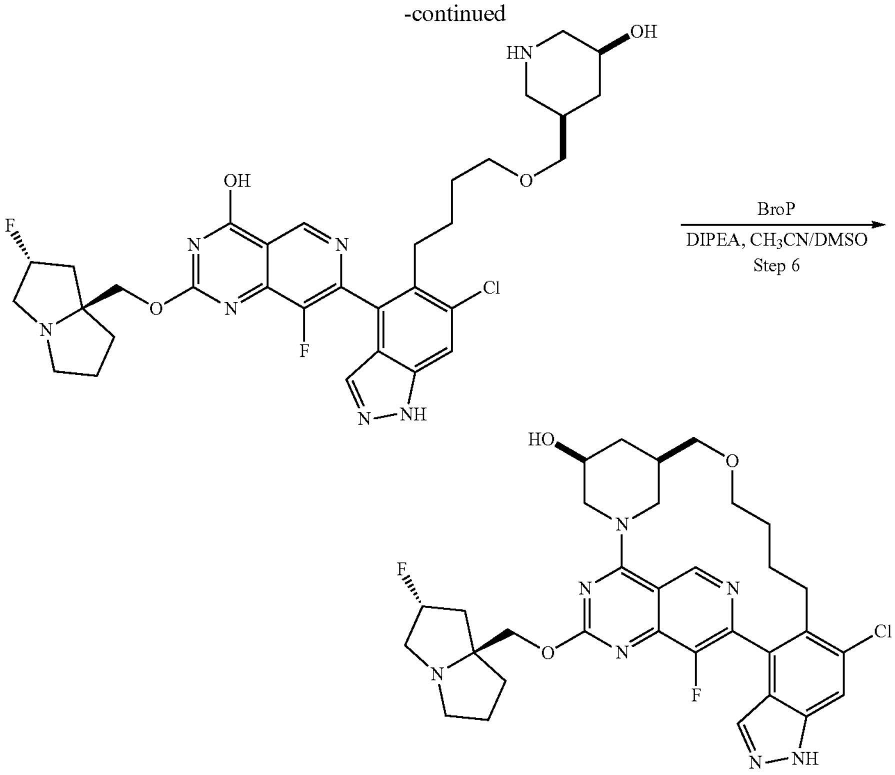

Example 265

Step 1. rac-1-(tert-Butyl) 3-methyl (3R,5S)-5-(methoxymethoxy)piperidine-1,3-dicarboxylate. A vial was charged with rac-1-(tert-butyl) 3-methyl (3R,5S)-5-hydroxypiperidine-1,3-dicarboxylate (1.0 g, 3.9 mmol, eNovation), N-ethyl-N-isopropylpropan-2-amine (2.0 mL, 11.6 mmol) and dichloromethane (13 mL). The reaction mixture was cooled to 0° C. with an ice-water bath. Bromo(methoxy)methane (0.63 mL, 7.7 mmol) was added slowly, and the reaction mixture was stirred at 0° C. for 5 h. The reaction was carefully quenched with saturated aqueous sodium bicarbonate. The organic phase was separated, and the aqueous phase was extracted with DCM. The combined organic phases were washed with brine, dried over anhydrous sodium sulfate, filtered, and concentrated under reduced pressure to provide rac-1-(tert-butyl) 3-methyl (3R,5S)-5-(methoxymethoxy)piperidine-1,3-dicarboxylate (1.00 g, 3.30 mmol, 100% yield) as orange oil. m/z (ESI): 326.2 $(M+Na)^+$. $^1H$ NMR (400 MHz, CHLOROFORM-d) δ ppm 4.68 (s, 2H) 4.02-4.44 (m, 2H) 3.70 (s, 3H) 3.48-3.61 (m, 1H) 3.38 (s, 3H) 2.30-2.82 (m, 4H) 1.50-1.63 (m, 1H) 1.46 (s, 9H).

Step 2. rac-tert-Butyl (3R,5S)-3-(hydroxymethyl)-5-(methoxymethoxy)piperidine-1-carboxylate. A vial was charged with rac-1-(tert-butyl) 3-methyl (3R,5S)-5-(methoxymethoxy)piperidine-1,3-dicarboxylate (1.0 g, 3.3 mmol) and tetrahydrofuran (11 mL), then cooled to 0° C. with an ice-water bath. Lithium borohydride (2.0 M in THF, 3.6 mL, 7.2 mmol) was added and the reaction mixture was stirred and warmed to rt for 30 min. The reaction mixture was carefully quenched with saturated aqueous ammonium chloride. The phases were separated, then the aqueous phase was extracted with EtOAc. The combined organic phases were washed with brine, dried over anhydrous sodium sulfate, filtered, and concentrated under reduced pressure to provide rac-tert-butyl (3R,5S)-3-(hydroxymethyl)-5-(methoxymethoxy)piperidine-1-carboxylate (0.92 g, 3.3 mmol, 100%) as light-yellow oil. m/z (ESI): 298.2 $(M+Na)^+$. $^1H$ NMR (400 MHz, CHLOROFORM-d) δ ppm 4.70 (d, J=3.76 Hz, 2H) 3.86-4.40 (m, 2H) 3.50-3.68 (m, 3H) 3.40 (s, 3H) 2.49-3.07 (m, 2H) 2.06-2.17 (m, 1H) 1.75-1.88 (m, 1H) 1.48 (s, 9H) 1.25-1.37 (m, 1H).

Step 3. rac-tert-Butyl (3R,5S)-3-((4-(6-chloro-1-(tetrahydro-2H-pyran-2-yl)-4-(4,4,5,5-tetramethyl-1,3,2-dioxaborolan-2-yl)-1H-indazol-5-yl)butoxy)methyl)-5-(methoxymethoxy)piperidine-1-carboxylate. A vial was charged with rac-tert-butyl (3R,5S)-3-(hydroxymethyl)-5-(methoxymethoxy)piperidine-1-carboxylate (2.15 g, 7.8 mmol), sodium hydride (60 wt % in mineral oil, 0.31 g, 7.8 mmol) and tetrahydrofuran (20 mL). The mixture was stirred at rt for 15 min, then a solution of 4-(6-chloro-1-(tetrahydro-2H-pyran-2-yl)-4-(4,4,5,5-tetramethyl-1,3,2-dioxaborolan-2-yl)-1H-indazol-5-yl)butyl methanesulfonate (Step 1 from Example 260, 2.00 g, 3.90 mmol) in THF (5.0 mL) was added. The reaction mixture was heated to 50° C. for 3 h. After cooling to rt, the reaction mixture was carefully quenched with saturated aqueous ammonium chloride. The phases were separated, then the aqueous layer was extracted with EtOAc. The combined organic phases were washed with brine, dried over anhydrous sodium sulfate, filtered, and concentrated under reduced pressure. The crude residue was purified by column chromatography on silica gel, eluting with a gradient of 0-50% (3:1 EtOAc/EtOH with 2% TEA)/heptane, to provide rac-tert-butyl (3R,5S)-3-((4-(6-chloro-1-(tetrahydro-2H-pyran-2-yl)-4-(4,4,5,5-tetramethyl-1,3,2-dioxaborolan-2-yl)-1H-indazol-5-yl)butoxy)methyl)-5-(methoxymethoxy)piperidine-1-carboxylate (2.3 g, 3.3 mmol, 85% yield) as colorless oil. m/z (ESI): 692.2 $(M+H)^+$.

Step 4. tert-Butyl (3R,5S)-3-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butoxy)methyl)-5-(methoxymethoxy)piperidine-1-carboxylate and tert-butyl (3S,5R)-3-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butoxy)methyl)-5-(methoxymethoxy)piperidine-1-carboxylate. A vial was charged with potassium phosphate tribasic (1.3 g, 6.1 mmol), (S)-(−)-2-(diphenylphosphino)-2-methoxy-1-,1-binaphthyl(S)-MOP (0.46 g, 1.0 mmol), palladium acetate (0.11 mg, 0.5 mmol), rac-tert-butyl (3R,5S)-3-((4-(6-chloro-1-(tetrahydro-2H-pyran-2-yl)-4-(4,4,5,5-tetramethyl-1,3,2-dioxaborolan-2-yl)-1H-indazol-5-yl)butoxy)methyl)-5-(methoxymethoxy)piperidine-1-carboxylate (1.7 g, 2.4 mmol), 4-(tert-butoxy)-7-chloro-8-fluoro-2-(((2R,7aS)-2-fluorotetrahydro-1H-pyrrolizin-7a(5H)-yl)methoxy)pyrido[4,3-d]pyrimidine (1.0 g, 2.4 mmol, Intermediate JJ), water (2.2 mL) and 2-methyltetrahydrofuran (22 mL). The reaction mixture was heated to 80° C. for 1.5 h. After cooling to rt, the reaction mixture was diluted with water and extracted with EtOAc. The combined organic phases were washed with brine, dried over anhydrous sodium sulfate, filtered, and concentrated under reduced pressure. The crude material was purified by column chromatography on silica gel, eluting with a gradient of 0-80% (3:1 EtOAc/EtOH with 2% TEA)/heptane, to provide tert-butyl (3R,5S)-3-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butoxy)methyl)-5-(methoxymethoxy)piperidine-1-carboxylate and tert-butyl (3S,5R)-3-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butoxy)methyl)-5-(methoxymethoxy)piperidine-1-carboxylate (0.50 g, 0.53 mmol, 21% yield) as light-yellow foam. m/z (ESI): 942.2 $(M+H)^+$.

Step 5. 7-(6-Chloro-5-(4-(((3R,5S)-5-hydroxypiperidin-3-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol and 7-(6-chloro-5-(4-(((3S,5R)-5-hydroxypiperidin-3-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol. A round-bottom flask was charged with tert-butyl (3R,5S)-3-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butoxy)methyl)-5-(methoxymethoxy)piperidine-1-carboxylate and tert-butyl (3S,5R)-3-((4-(4-(4-(tert-butoxy)-8-fluoro-2-(((2R,7aS)-2-fluorotetrahydro-1H-pyrrolizin-7a(5H)-yl)methoxy)pyrido[4,3-d]pyrimidin-7-yl)-6-chloro-1-(tetrahydro-2H-pyran-2-yl)-1H-indazol-5-yl)butoxy)methyl)-5-(methoxymethoxy)piperidine-1-carboxylate (0.50 g, 0.53 mmol) and acetonitrile (5.5 mL), then sonicated until everything dissolved. Hydrogen chloride (4 N solution in 1,4-dioxane, 2.7 mL, 10.8 mmol) was added, followed by 5 mL isopropyl alcohol. The reaction mixture was stirred at rt for 2 h, and was concentrated to dryness to provide 7-(6-chloro-5-(4-(((3R,5S)-5-hydroxypiperidin-3-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol and 7-(6-chloro-5-(4-(((3S,5R)-5-hydroxypiperidin-3-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol as light-yellow solid. m/z (ESI): 671.0 $(M+H)^+$.

Step 6. (17R,19S)-9-Chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt and (17S,19R)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt. A vial was charged with 7-(6-chloro-5-(4-(((3R,5S)-5-hydroxypiperidin-3-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol and 7-(6-chloro-5-(4-(((3S,5R)-5-hydroxypiperidin-3-yl)methoxy)butyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-ol (0.35 g, 0.53 mmol), dimethyl sulfoxide (12 mL), acetonitrile (100 mL) and DIPEA (0.9 mL, 5.3 mmol). Bromotris(dimethylamino)phosphonium hexafluorophosphate (1.0 g, 2.7 mmol) was added in one portion, and the reaction mixture was stirred at rt for 5 min. The precipitate was filtered off and the filtrate was concentrated under reduced pressure. The crude material (in DMSO) was injected into a C18 column (220 g), eluting with a gradient of 5-60% (0.1% TFA MeCN)/(0.1% TFA water) over 20 min. The desired fractions were lyophilized to provide (17R,19S)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt and (17S,19R)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt (85 mg, 0.13 mmol, 25% yield) as white solid. m/z (ESI): 639.9 $(M+H)^+$. $^1H$ NMR (400 MHz, METHANOL-$d_4$) δ ppm 9.30 (s, 1H) 7.82 (s, 2H) 5.48-5.73 (m, 1H) 5.05-5.42 (m, 2H) 4.83-4.90 (m, 1H) 4.56-4.68 (m, 1H) 3.82-4.22 (m, 5H) 3.38-3.56 (m, 2H) 3.03-3.18 (m, 3H) 2.33-2.93 (m, 8H) 2.09-2.29 (m, 2H) 1.98-2.04 (m, 1H) 1.68-1.76 (m, 1H) 1.25-1.51 (m, 4H). $^{19}F$ NMR (376 MHz, METHANOL-$d_4$) δ ppm −77.29 (s, 1 F) −77.33 (s, 1 F) −143.62 (s, 1 F) −143.67 (s, 1 F) −174.01 (s, 1 F) −174.02 (s, 1 F).

(17S,19R)-9-Chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol (Example 406) and (17R,19S)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol (Example 407)

Example 406

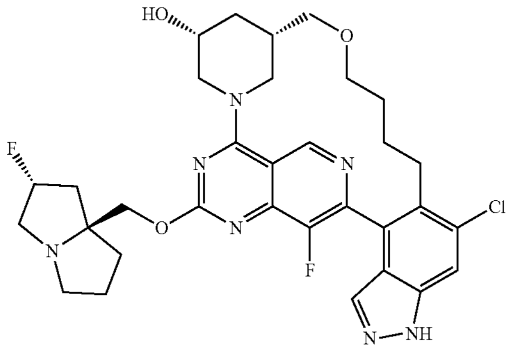

Example 407

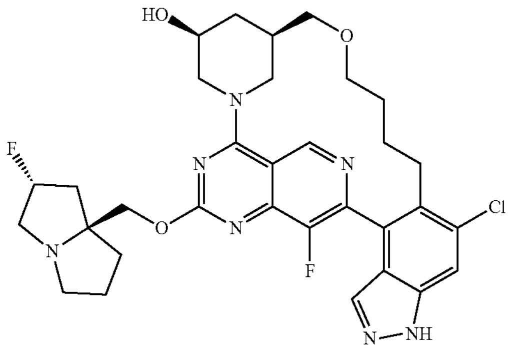

The material from Example 265 was purified via SFC using a Chiralcel OD, 2×25 cm, 5 μm column with a mobile phase of 35% MeOH with 0.2% DEA with a flowrate of 70 mL/min to generate 14.5 mg of peak 1 with an ee of >99% as (17S,19R)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol $^1$H NMR (400 MHz, METHANOL-$d_4$) δ ppm 9.07-9.32 (m, 1H) 7.70-7.94 (m, 2H), 4.90-5.44 (m, 3H), 4.11-4.50 (m, 3H), 3.77-3.89 (m, 1H), 3.36-3.43 (m, 1H), 2.93-3.28 (m, 7H), 2.81-2.92 (m, 1H), 1.85-2.62 (m, 10H), 1.65-1.76 (m, 1H), 1.27-1.49 (m, 4H). 2H not observed. $^{19}$F NMR (376 MHz, METHANOL-$d_4$) δ ppm −143.02 (s) −173.60 (s). m/z (ESI): 640.2 $(M+H)^+$ and 24.0 mg of peak 2 with an ee of >99% as (17R,19S)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol $^1$H NMR (400 MHz, METHANOL-$d_4$) δ ppm 9.07-9.32 (m, 1H), 7.70-7.94 (m, 2H), 4.90-5.44 (m, 3H), 4.11-4.50 (m, 3H), 3.77-3.89 (m, 1H), 3.36-3.43 (m, 1H), 2.93-3.28 (m, 7 H), 2.81-2.92 (m, 1H), 1.85-2.62 (m, 10H), 1.65-1.76 (m, 1H), 1.27-1.49 (m, 4H). 2H not observed. $^{19}$F NMR (376 MHz, METHANOL-$d_4$) δ ppm −143.02 (s) −173.60 (s). m/z (ESI): 640.2 $(M+H)^+$. Stereochemistry of Example 407 was confirmed by X-Ray crystallography analysis.

(17S,19S)-9-Chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt and (17R,19R)-9-chloro-30-fluoro-24-(((2R,7aS)-2-fluorotetrahydro-1H-pyrrolo[1,2-a]pyrrol-7a(5H)-yl)methoxy)-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaen-19-ol 2,2,2-trifluoroacetate salt (Example 408)

Example 408

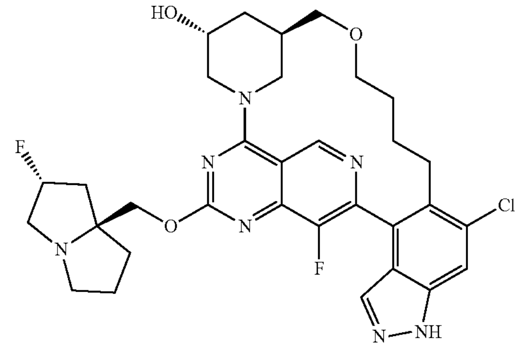

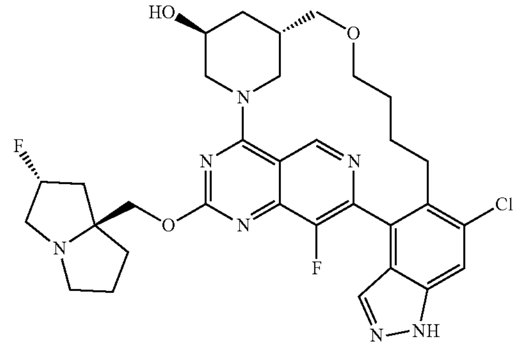

This compound was prepared in analogous fashion as Example 265 using rel-1-(tert-butyl) 3-methyl (3R,5R)-5-hydroxypiperidine-1,3-dicarboxylate (CAS #: 1638765-16-8, PharmaBlock). $^1$H NMR (400 MHz, METHANOL-$d_4$) δ ppm 9.33 (s, 1H), 7.93-8.04 (m, 1H), 7.78 (d, J=0.8 Hz, 1H), 5.51-5.75 (m, 1H), 5.36-5.47 (m, 1H), 5.04-5.21 (m, 1H), 4.88-5.04 (m, 2H), 4.48-4.68 (m, 1H), 3.75-4.19 (m, 5H), 3.36-3.52 (m, 6H), 3.06-3.24 (m, 1H), 2.25-2.94 (m, 9H), 1.75-2.05 (m, 5H), 1.30-1.70 (m, 3H), 0.80-1.12 (m, 1H), 0.37-0.71 (m, 1H). $^{19}$F NMR (376 MHz, METHANOL-$d_4$) δ ppm −77.09 (s), −143.55-−143.64 (m), −173.87-−174.11 (m). m/z (ESI): 640.3 $(M+H)^+$.

(17R)-30-Fluoro-24-((6R,8aR)-hexahydro-1H-pyrrolo[2,1-c][1,4]oxazin-6-ylmethoxy)-9-methyl-15-oxa-5,6,21,23,25,29-hexaazahexacyclo[24.3.1.1~17,21~0.0~2,10~.0~3,7~.0~22,27~]hentriaconta-1(30),2,4,7,9,22,24,26,28-nonaene and (17R)-30-fluoro-24-((6S,8aS)-hexahydro-1H-pyrrolo[2,1-c][1,4]oxazin-6-ylmethoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene (Example 266)

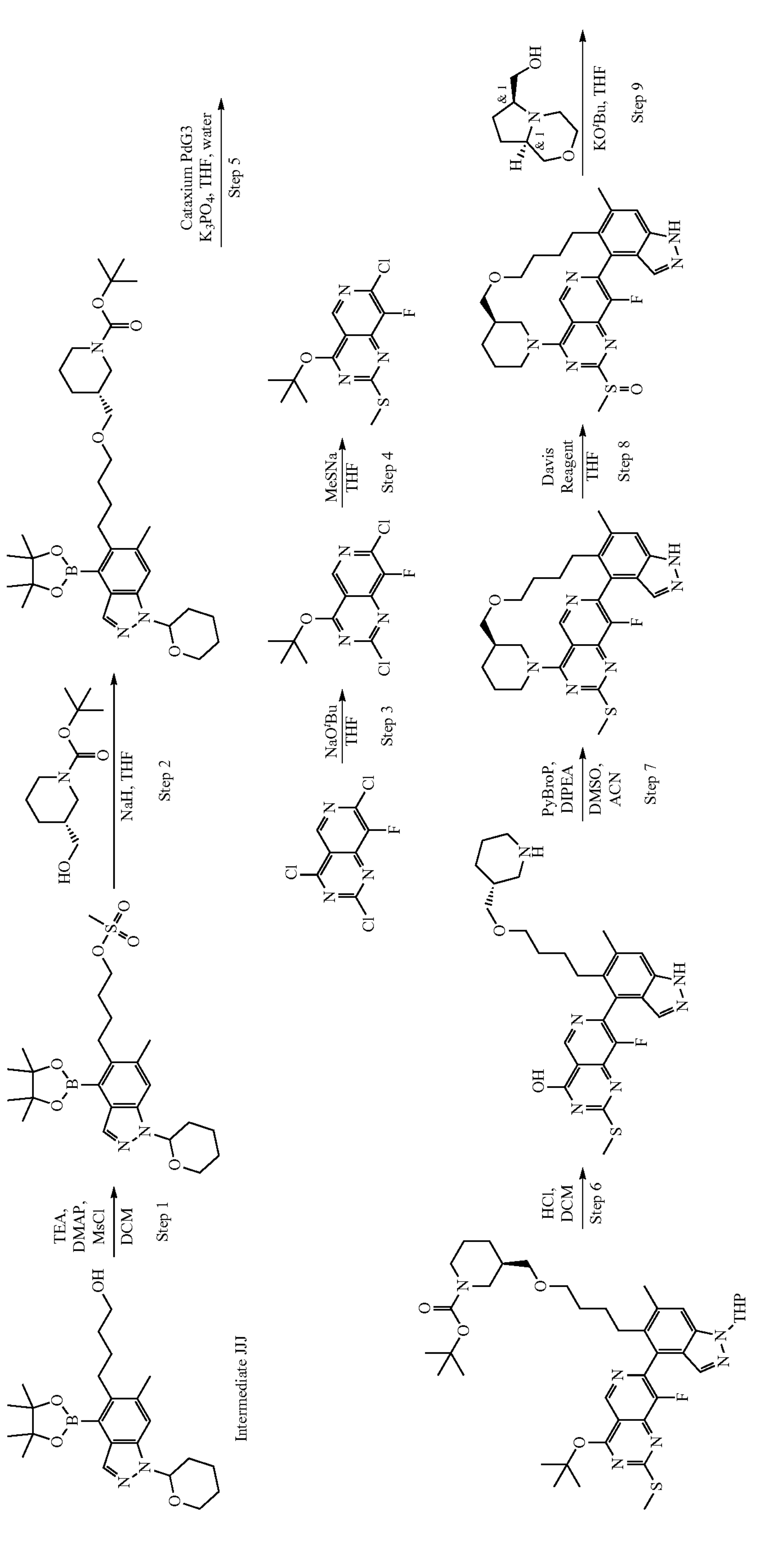
Intermediate JJJ
TEA,
DMAP,
MsCl
DCM
Step 1
NaH, THF
Step 2
Cataxium PdG3
$K_3PO_4$, THF, water
Step 5
NaO$^t$Bu
THF
Step 3
MeSNa
THF
Step 4
HCl,
DCM
Step 6
PyBroP,
DIPEA
DMSO,
ACN
Step 7
Davis
Reagent
THF
Step 8
KO$^t$Bu, THF
Step 9

-continued
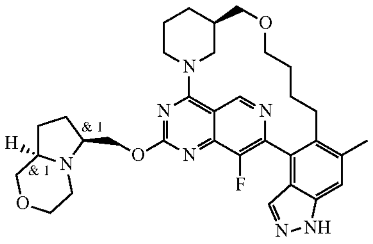
Example 266

Step 1. 4-(6-Methyl-1-(tetrahydro-2H-pyran-2-yl)-4-(4,4,5,5-tetramethyl-1,3,2-dioxaborolan-2-yl)-1H-indazol-5-yl)butyl methanesulfonate. To a 40-mL vial was added 4-(6-methyl-1-(tetrahydro-2H-pyran-2-yl)-4-(4,4,5,5-tetramethyl-1,3,2-dioxaborolan-2-yl)-1H-indazol-5-yl)butan-1-ol (0.59 mg, 1.43 mmol, Intermediate JJJ) and triethylamine (0.6 mL, 4.3 mmol) in dichloromethane (5 mL). Methanesulfonyl chloride (0.22 mL, 2.9 mmol) and N,N-dimethylpyridin-4-amine (35 mg, 0.29 mmol) was added sequentially. After stirring at rt for 1.5 h, more MsCl (0.1 mL, 1.3 mmol) and triethylamine (0.2 mL, 1.4 mmol) were added, and the reaction was stirred for another 3 h. The mixture was quenched with water, the organic layer was separated, and the aqueous layer was extracted with dichloromethane. The combined organic layers were dried over sodium sulfate and concentrated. The crude material was purified by column chromatography on silica gel, eluting with a gradient of 0-100% EtOAc in heptane, to provide 4-(6-methyl-1-(tetrahydro-2H-pyran-2-yl)-4-(4,4,5,5-tetramethyl-1,3,2-dioxaborolan-2-yl)-1H-indazol-5-yl)butyl methanesulfonate (0.40 g, 0.81 mmol, 57% yield) as pale colorless oil. m/z (ESI): 493.3 $(M+H)^+$.

Step 2. tert-Butyl (3R)-3-((4-(6-methyl-1-(tetrahydro-2H-pyran-2-yl)-4-(4,4,5,5-tetramethyl-1,3,2-dioxaborolan-2-yl)-1H-indazol-5-yl)butoxy)methyl)piperidine-1-carboxylate. A 4 mL vial was charged with tert-butyl (R)-3-(hydroxymethyl)piperidine-1-carboxylate (0.35 g, 1.62 mmol, Combi-Blocks), tetrahydrofuran (4 mL), and sodium hydride (60 wt % in mineral oil, 64.7 mg, 1.62 mmol). The mixture was allowed to stir at rt for 30 minutes. 4-(6-Methyl-1-(tetrahydro-2H-pyran-2-yl)-4-(4,4,5,5-tetramethyl-1,3,2-dioxaborolan-2-yl)-1H-indazol-5-yl)butyl methanesulfonate (0.40 g, 0.81 mmol) in THF (4 mL) was added. The mixture was warmed to 50° C. for 5 h. After cooling to rt, the reaction mixture was carefully quenched with saturated aqueous ammonium chloride and concentrated. The crude oil was purified by column chromatography on silica gel, eluting with a gradient of 0-75% ethyl acetate in heptane, to give tert-butyl (3R)-3-((4-(6-methyl-1-(tetrahydro-2H-pyran-2-yl)-4-(4,4,5,5-tetramethyl-1,3,2-dioxaborolan-2-yl)-1H-indazol-5-yl)butoxy)methyl)piperidine-1-carboxylate (0.28 g, 0.46 mmol, 56% yield) as colorless oil. m/z (ESI): 612.4 $(M+H)^+$.

Step 3. 4-(tert-Butoxy)-2,7-dichloro-8-fluoropyrido[4,3-d]pyrimidine. 2,4,7-Trichloro-8-fluoropyrido[4,3-d]pyrimidine (5.15 g, 20.4 mmol, Enamine) was azeotropically dried with toluene on a rotary evaporator. THF (30 mL) was added under a nitrogen atmosphere. The mixture was cooled to −78° C. and (tert-butoxy)sodium (2 M in THF, 11.2 mL, 22.4 mmol) was added. The reaction mixture was stirred at −78° C. After 30 minutes the mixture was concentrated under reduced pressure. The crude material was purified by column chromatography on silica gel, eluting with a gradient of 0-50% EtOAc in heptane, to provide 4-(tert-butoxy)-2,7-dichloro-8-fluoropyrido[4,3-d]pyrimidine (4.88 g, 16.8 mmol, 82% yield) as beige solid. m/z (ESI): 234.0 $(M-tBu+2H)^+$.

Step 4. 4-(tert-Butoxy)-7-chloro-8-fluoro-2-(methylthio)pyrido[4,3-d]pyrimidine. A 100 mL round-bottom flask was charged with 4-(tert-butoxy)-2,7-dichloro-8-fluoropyrido[4,3-d]pyrimidine (1.45 g, 5.00 mmol), tetrahydrofuran (50 mL) and cooled to 0° C. Sodium thiomethoxide (0.41 g, 5.25 mmol,) was added and the mixture was allowed to warm to rt with stirring. After 5 h the mixture was diluted with water and extracted with DCM. The combined organic layers were washed with brine, dried over sodium sulfate, filtered, and concentrated. The residue was purified by column chromatography on silica gel, eluting with a gradient of 0-60% EtOAc in heptane, to yield 4-(tert-butoxy)-7-chloro-8-fluoro-2-(methylthio)pyrido[4,3-d]pyrimidine (1.0 g, 3.30 mmol, 66% yield) as yellow solid. m/z (ESI): 244.5 $(M-tBu+2H)^+$.

Step 5. tert-butyl (3R)-3-((4-(4-(4-(tert-butoxy)-8-fluoro-2-(methylthio)pyrido[4,3-d]pyrimidin-7-yl)-6-methyl-1-(tetrahydro-2H-pyran-2-yl)-1H-indazol-5-yl)butoxy)methyl)piperidine-1-carboxylate. A mixture of tert-butyl (3R)-3-((4-(6-methyl-1-(tetrahydro-2H-pyran-2-yl)-4-(4,4,5,5-tetramethyl-1,3,2-dioxaborolan-2-yl)-1H-indazol-5-yl)butoxy)methyl)piperidine-1-carboxylate (0.28 g, 0.45 mmol), 4-(tert-butoxy)-7-chloro-8-fluoro-2-(methylthio)pyrido[4,3-d]pyrimidine (0.25 g, 0.70 mmol), cataCXium A Pd G3 (0.068 g, 0.093 mmol), and potassium phosphate tribasic (0.30 g, 1.40 mmol) in tetrahydrofuran (3 mL) and water (1.5 mL) was heated in a vial at 80° C. for 3 h. After cooling to rt, the reaction mixture was diluted with water and extracted with DCM. The combined organic layers were dried with sodium sulfate, filtered, and concentrated under reduced pressure. The residue was purified by column chromatography on silica gel, eluting with a gradient of 0-100% EtOAc in heptane, to afford tert-butyl (3R)-3-((4-(4-(4-(tert-butoxy)-8-fluoro-2-(methylthio)pyrido[4,3-d]pyrimidin-7-yl)-6-methyl-1-(tetrahydro-2H-pyran-2-yl)-1H-indazol-5-yl)butoxy)methyl)piperidine-1-carboxylate (0.19 g, 0.25 mmol, 56% yield. m/z (ESI): 751.4 $(M+H)^+$.

Step 6. 8-Fluoro-7-(6-methyl-5-(4-(((R)-piperidin-3-yl)methoxy)butyl)-1H-indazol-4-yl)-2-(methylthio)pyrido[4,3-d]pyrimidin-4-ol. A vial was charged with tert-butyl (3R)-3-((4-(4-(4-(tert-butoxy)-8-fluoro-2-(methylthio)pyrido[4,3-d]pyrimidin-7-yl)-6-methyl-1-(tetrahydro-2H-pyran-2-yl)-1H-indazol-5-yl)butoxy)methyl)piperidine-1-carboxylate (1.00 g, 1.33 mmol) and dichloromethane (13 mL). The mixture was solubilized by sonication. HCl in 1,4-dioxane (4 M, 16.6 mL, 66.6 mmol) was added, and the slurry was vigorously stirred for 20 h. The mixture was concentrated to dryness under reduced pressure. The residue was dissolved in MeOH, and eluted through SCX columns (flushed with MeOH and eluted with 2 M ammonia in MeOH), to provide 8-fluoro-7-(6-methyl-5-(4-(((R)-piperidin-3-yl)methoxy)butyl)-1H-indazol-4-yl)-2-(methylthio)pyrido[4,3-d]pyrimidin-4-ol (0.54 g, 1.05 mmol, 79% yield) as yellow solid. m/z (ESI): 511.2 $(M+H)^+$.

Step 7. (17R)-30-Fluoro-24-(methylthio)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene. A round-bottom flask was charged with bromotripyrrolidinophosphonium hexafluorophosphate (0.59 g, 1.26 mmol), Hunig's base (0.92 mL, 5.26 mmol) in acetonitrile (200 mL). A solution of 8-fluoro-7-(6-methyl-5-(4-(((R)-piperidin-3-yl)methoxy)butyl)-1H-indazol-4-yl)-2-(methylthio)pyrido[4,3-d]pyrimidin-4-ol (0.54 g, 1.05 mmol) in dimethyl sulfoxide (13 mL) was added dropwise, then the reaction was stirred at rt for 24 h. More bromotripyrrolidinophosphonium hexafluorophosphate (0.12 g, 0.26 mmol) was added and the reaction was further stirred at rt for 4 h. Water was added, and the acetonitrile was evaporated. The aqueous phase was extracted with EtOAc, and the organic layers were combined, dried over sodium sulfate, filtered, and concentrated. The crude mixture was then purified by column chromatography on silica gel, eluting with a gradient of 10-70% 3:1 EtOAc:EtOH in heptane, to yield (17R)-30-fluoro-24-(methylthio)-9-methyl-15-oxa-5,6,21,23,25,29-hexaazahexacyclo[24.3.1.1~17,21~.0~2,10~.0~3,7~.0~22,27~]hentriaconta-1

(30),2,4,7,9,22,24,26,28-nonaene (0.14 g, 0.29 mmol, 28% yield) as white solid. m/z (ESI): 492.2 $(M+H)^+$.

Step 8. (17R)-30-Fluoro-24-(methylsulfinyl)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene To a vial was added (17R)-30-fluoro-24-(methylthio)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene (0.22 g, 0.44 mmol) in tetrahydrofuran (4.5 mL). 3-Phenyl-2-(phenylsulfonyl)-1,2-oxaziridine (0.17 g, 0.66 mmol) was added and the reaction mixture was stirred at rt for 3 h. More 3-phenyl-2-(phenylsulfonyl)-1,2-oxaziridine (0.12 g, 0.44 mmol) was added and the reaction mixture was further stirred for 3.5 h. The crude was purified by column chromatography on silica gel, eluting with a gradient of 10-100% 3:1 EtOAc:EtOH in heptane, to yield (17R)-30-fluoro-24-(methylsulfinyl)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene (0.15 g, 0.29 mmol, 66% yield) as white to yellowish solid. m/z (ESI): 509.2 $(M+H)^+$.

Step 9. (17R)-30-Fluoro-24-((6R,8aR)-hexahydro-1H-pyrrolo[2,1-c][1,4]oxazin-6-ylmethoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene and (17R)-30-fluoro-24-((6S,8aS)-hexahydro-1H-pyrrolo[2,1-c][1,4]oxazin-6-ylmethoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene. To a vial was charged with [cis-3,4,6,7,8,8a-hexahydro-1H-pyrrolo[2,1-c][1,4]oxazin-6-yl]methanol (28 mg, 0.18 mmol, Pharmablock, Inc.) and tetrahydrofuran (1.0 mL). The mixture was cooled to −78° C. and potassium tert-butoxide solution (1.0 M in THF, 0.18 mL, 0.18 mmol) was added dropwise. The solution was stirred for 10 min. (17R)-30-Fluoro-24-(methylsulfinyl)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene (70 mg, 0.14 mmol) in tetrahydrofuran (1.5 mL) was added dropwise. The mixture was stirred for another 15 min and the reaction was quenched with saturated aqueous sodium bicarbonate solution, water and extracted with EtOAc. The combined organics were dried over sodium sulfate, filtered, and concentrated. The crude material was purified by column chromatography on silica gel, eluting with a gradient of 0-100% 3:1 EtOAc/EtOAH with 1% triethylamine in heptane, followed by C18 reversed phase column with a gradient of 0-100% 0.1% TFA in MeCN/0.1% TFA in water, to give (17R)-30-fluoro-24-((6R,8aR)-hexahydro-1H-pyrrolo[2,1-c][1,4]oxazin-6-ylmethoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene and (17R)-30-fluoro-24-((6S,8aS)-hexahydro-1H-pyrrolo[2,1-c][1,4]oxazin-6-ylmethoxy)-9-methyl-15-oxa-5,6,21,23,25,29-hexaazahexacyclo[24.3.1.1~17,21~.0~2,10~.0~3,7~.0~22,27~]hentriaconta-1(30),2,4,7,9,22,24,26,28-nonaene (28 mg, 0.047 mmol, 34% yield) as white solid after lyophilization. $^1H$ NMR (400 MHz, METHANOL-$d_4$) δ ppm 9.18 (s, 1H), 8.40-8.68 (m, 1H), 7.70-8.00 (m, 1H), 7.41-7.61 (m, 1H), 4.93-5.11 (m, 2H), 4.32-4.71 (m, 2H), 3.60-3.95 (m, 5H), 3.39-3.49 (m, 1H), 2.93-3.32 (m, 7H), 2.67 (br t, J=10.2 Hz, 1H), 2.44-2.59 (m, 5H), 2.15-2.36 (m, 1H), 1.02-2.10 (m, 12H). $^{19}F$ NMR (376 MHz, METHANOL-$d_4$) δ ppm −142.94 (d, J=9.5 Hz, 1 F). m/z (ESI): 602.4 $(M+H)^+$. 31-Fluoro-25-(((2R,7aS)-2-fluorotetrahydro-1H-pyrrolo[1,2-a]pyrrol-7a(5H)-yl)methoxy)-9-methyl-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene (Example 158)

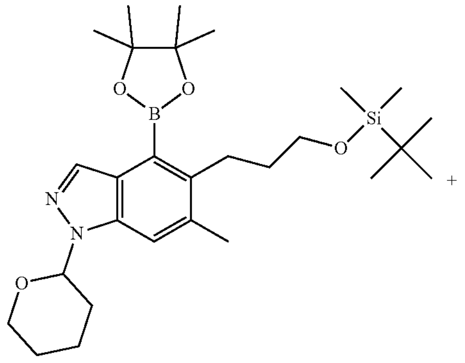

Intermediate K

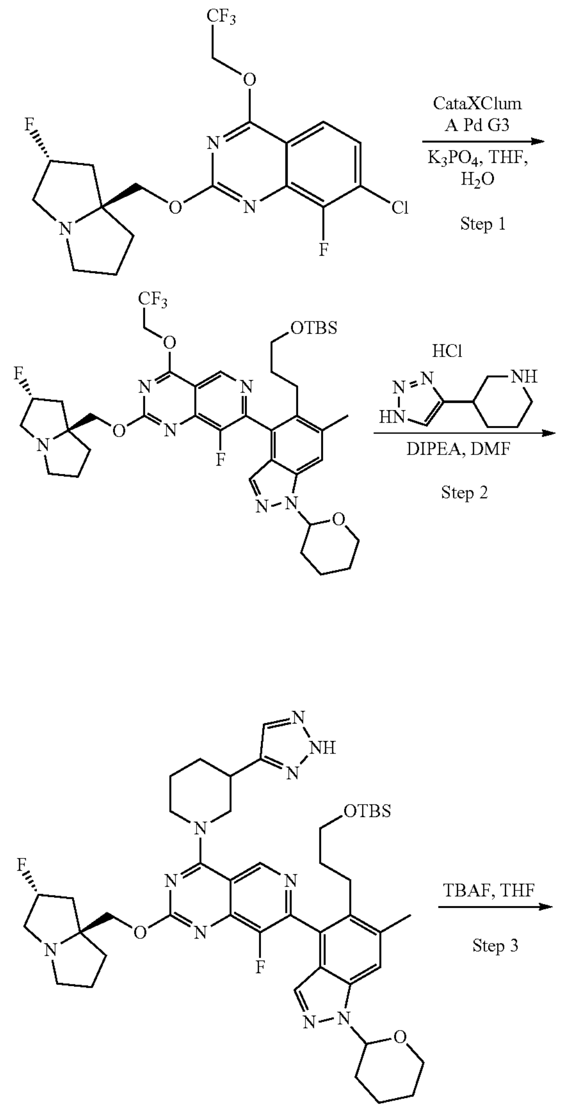

-continued

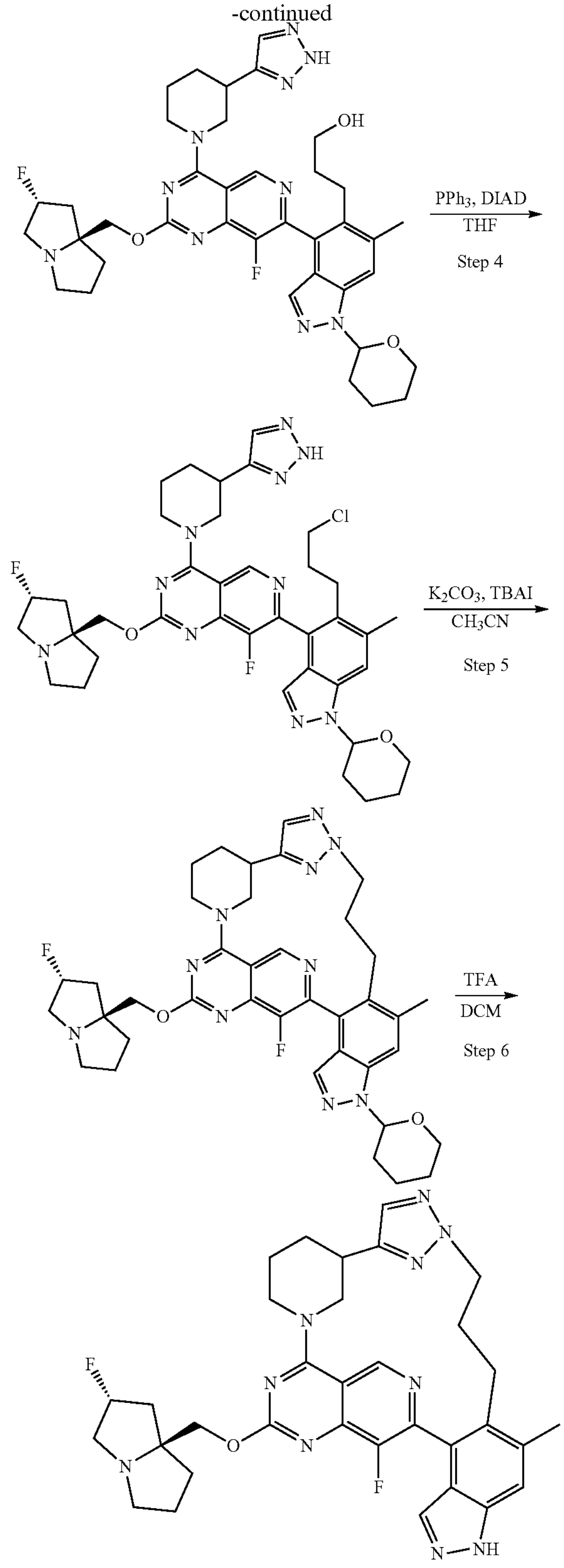

Example 158

Step 1. 7-(5-(3-((tert-Butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine. In a 10-mL microwave vial was charged with 7-chloro-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.45 g, 1.03 mmol, Intermediate AA, Step 2), 5-(3-((tert-butyldimethylsilyl)oxy)propyl)-6-methyl-1-(tetrahydro-2H-pyran-2-yl)-4-(4,4,5,5-tetramethyl-1,3,2-dioxaborolan-2-yl)-1H-indazole (0.53 g, 1.03 mmol, Intermediate K), potassium phosphate (0.65 g, 3.08 mmol), cataCXium A Pd G3 (0.15 g, 0.21 mmol) in THF (4.5 mL) and water (0.5 mL). The reaction mixture was purged with nitrogen for 10 min and then irradiated in microwave at 80° C. for 1.5 h. After cooling to rt, the crude mixture was directly purified by column chromatography on silica gel, eluting with 6-20% MeOH in DCM, to give 7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.25 g, 0.32 mmol, 31% yield) as colorless film. m/z (ESI): 791.2 $(M+H)^+$.

Step 2. 4-(3-(2H-1,2,3-Triazol-4-yl)piperidin-1-yl)-7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine. To a mixture of 7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (0.25 g, 0.32 mmol) and 3-(1H-1,2,3-triazol-4-yl)piperidine hydrochloride (0.12 g, 0.62 mmol, Enamine) in MeCN (5 mL) was added 1,1-dimethyltriethylamine (0.12 mL, 0.7 mmol). The resulting mixture was stirred at rt for 16 h, then in a 45° C. sand bath for 2.5 h. The crude mixture was directly purified by column chromatography on silica gel, eluting with 1-20% MeOH in DCM, to give 4-(3-(2H-1,2,3-triazol-4-yl)piperidin-1-yl)-7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (50 mg, 0.06 mmol, 19% yield) as white solid. m/z (ESI): 843.2 $(M+H)^+$.

Step 3. 3-(4-(4-(3-(2H-1,2,3-Triazol-4-yl)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)propan-1-ol. In a stirred solution of 4-(3-(2H-1,2,3-triazol-4-yl)piperidin-1-yl)-7-(5-(3-((tert-butyldimethylsilyl)oxy)propyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (0.11 g, 0.13 mmol) in THF (5 mL) was added tetrabutylammonium fluoride solution (1 M in tetrahydrofuran, 0.4 mL, 0.4 mmol). The resulting mixture was stirred at rt for 16 h. The volatiles were removed in vacuo and the residue was purified by column chromatography on silica gel, eluting with 2-20% MeOH in DCM, to give crude 3-(4-(4-(3-(2H-1,2,3-triazol-4-yl)piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)propan-1-ol (0.14 g, contaminated by tetrabutylammonium salt) as white solid. The material was used without further purification. m/z (ESI): 729.2 $(M+H)^+$.

Step 4. 4-(3-(2H-1,2,3-Triazol-4-yl)piperidin-1-yl)-7-(5-(3-chloropropyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine. To a stirred suspension of 3-(4-(4-(3-(2H-1,2,3-triazol-4-yl)

piperidin-1-yl)-8-fluoro-2-(((2R,7aS)-2-fluorotetrahydro-1H-pyrrolizin-7a(5H)-yl)methoxy)pyrido[4,3-d]pyrimidin-7-yl)-6-methyl-1-(tetrahydro-2H-pyran-2-yl)-1H-indazol-5-yl)propan-1-ol (0.14 g, 0.19 mmol) and triphenylphosphine (71 mg, 0.27 mmol) in THF (50 mL) was added a solution of (E)-diisopropyl diazene-1,2-dicarboxylate (54 mg, 0.27 mmol) in THF (1 mL) slowly. The resulting mixture was stirred at rt for 16 h. The volatiles were removed in vacuo and the residue was purified by column chromatography on silica gel, eluting with 2-20% MeOH in DCM, to give 4-(3-(2H-1,2,3-triazol-4-yl)piperidin-1-yl)-7-(5-(3-chloropropyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (85 mg, 0.11 mmol, 59% yield) as white solid. m/z (ESI): 747.0 $(M+H)^+$.

Step 5. 31-Fluoro-25-(((2R,7aS)-2-fluorotetrahydro-1H-pyrrolo[1,2-a]pyrrol-7a(5H)-yl)methoxy)-9-methyl-6-(tetrahydro-2H-pyran-2-yl)-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene. A mixture of 4-(3-(2H-1,2,3-triazol-4-yl)piperidin-1-yl)-7-(5-(3-chloropropyl)-6-methyl-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido[4,3-d]pyrimidine (85 mg, 0.11 mmol), potassium carbonate (0.16 g, 1.14 mmol), and tetrabutylammonium iodide (21 mg, 0.057 mmol) in MeCN (16 mL) in a 20-mL microwave reaction vessel was subjected to irradiation for 2 h at 85° C. followed by 1 h at 80° C. After cooling to rt, the volatiles were removed in vacuo and the residue was purified by column chromatography on silica gel, eluting with 2-20% (20% MeOH/DCM with 1% TEA) in DCM, to provide 31-fluoro-25-(((2R,7aS)-2-fluorotetrahydro-1H-pyrrolo[1,2-a]pyrrol-7a(5H)-yl)methoxy)-9-methyl-6-(tetrahydro-2H-pyran-2-yl)-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene (25 mg, 0.035 mmol, 31% yield) as off-white solid. m/z (ESI): 711.2 $(M+H)^+$.

Step 6. 31-Fluoro-25-(((2R,7aS)-2-fluorotetrahydro-1H-pyrrolo[1,2-a]pyrrol-7a(5H)-yl)methoxy)-9-methyl-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene. To a stirred solution of 31-fluoro-25-(((2R,7aS)-2-fluorotetrahydro-1H-pyrrolo[1,2-a]pyrrol-7a(5H)-yl)methoxy)-9-methyl-6-(tetrahydro-2H-pyran-2-yl)-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene (20 mg, 0.028 mmol) in DCM (3 mL) was added 2,2,2-trifluoroacetic acid (2.5 mL, 33 mmol). The resulting mixture was stirred at rt for 6.5 h. The volatiles were removed and the residue was purified by column chromatography on silica gel, eluting with 6-20% (20% MeOH/DCM with 1% TEA) in DCM, followed by preparative reverse-phase HPLC (Gemini™ Prep C18, 10 μm column; Phenomenex, Torrance, CA; gradient elution of 10-95% MeCN in water, where both solvents contain 0.1% TFA), to give 31-fluoro-25-(((2R,7aS)-2-fluorotetrahydro-1H-pyrrolo[1,2-a]pyrrol-7a(5H)-yl)methoxy)-9-methyl-5,6,14,15,22,24,26,30,33-nonaazaheptacyclo[25.3.1.1~14,17~.1~18,22~.0~2,10~.0~3,7~.0~23,28~]tritriaconta-1(31),2,4,7,9,15,17(33),23,25,27,29-undecaene (8 mg, 0.013 mmol, 46% yield) as white solid as a TFA salt. $^1H$ NMR (METHANOL-$d_4$, 400 MHz) δ ppm 9.09 (d, 1H, J=1.9 Hz), 7.66 (s, 1H), 7.53 (s, 1H), 7.00 (d, 1H, J=13.6 Hz), 5.4-5.7 (m, 1H), 5.13 (br d, 1H, J=12.5 Hz), 4.98 (br d, 1H, J=14.2 Hz), 4.6-4.8 (m, 3H), 4.2-4.3 (m, 3H), 3.8-4.1 (m, 3H), 3.4-3.6 (m, 1H), 3.3-3.4 (m, 2H), 2.0-2.9 (m, 13H), 1.6-1.9 (m, 3H). $^{19}F$ NMR (METHANOL-$d_4$, 376 MHz) δ ppm −142.92 (d, J=71.1 Hz), −174.24 (d, J=33.8 Hz). m/z (ESI): 627.2 $(M+H)^+$.

All the compounds exemplified as TFA or other acid salts were neutralized with saturated $NaHCO_3$ solution and extracted with DCM to generate the free base. Or, the above-mentioned salts were dissolved in MeOH and eluted through a SCX column with additional MeOH wash. The SCX column was dried, then eluted with 2.0 M ammonia MeOH to provide the free base.

Biological Evaluation

Provided in this section is the biological evaluation of the specific examples provided herein.

KRAS G12D TR-FRET Assay

Compounds of interest were prepared in a dose-response titration in DMSO, and 80 nL were added via Labcyte Echo to each well of a 384-well plate (Perkin Elmer 6008280). The His-tagged KRAS G12D protein (Amgen) was diluted to 20 nM in Assay Buffer (20 mM HEPES, pH 7.4, 10 mM $MgCl_2$, 50 mM NaCl, 0.1% BSA, 0.01% Tween-20, 10 μM GDP) and 2 μL was added to the appropriate wells of the 384-well plate. The plate was incubated for 30 minutes at room temperature. Biotinylated KRPep-2d substrate (Amgen) was diluted to 20 nM in Assay Buffer and 2 μL was added to all wells and incubated for 1 hour at room temperature. Detection Reagent (0.4 nM LANCE Eu-W1024 Anti-6×His (Perkin Elmer AD0401), 5 nM streptavidin-d2 (Cisbio 610SADLA)) was prepared in Assay Buffer, then 4 μL was added to the plate and incubated for 1 hour at room temperature. Plates were read using PerkinElmer EnVision (ex: 320 nm, em1: 665 nm, em2: 615 nm) and em1/em2 data was used to generate curve fits using a 4-parameter logistic model to calculate $IC_{50}$ values.

KRAS G12D Coupled Nucleotide Exchange Assay

Purified GDP-bound KRAS protein (aa 1-169), containing both G12D and C118A amino acid substitutions and an N-terminal His-tag, was pre-incubated in assay buffer (25 mM HEPES pH 7.4, 10 mM $MgCl_2$, and 0.01% Triton X-100) with a compound dose-response titration for 2 hours. Following compound pre-incubation, purified SOS protein (aa 564-1049) and GTP (Roche 10106399001) were added to the assay wells and incubated for an additional 30 min. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 10 minutes. The assay plates were then read on a PerkinElmer EnVision Multilabel Reader, using AlphaScreen® technology, and data were analyzed using a 4-parameter logistic model to calculate $IC_{50}$ values.

Phospho-ERK1/2 MSD Assay

AsPC-1 (ATCC® CRL-1682™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, AsPC-1 cells were seeded in 96-well cell culture plates at a density of 25,000 cells/well and incubated at 37° C., 5% $CO_2$. A compound dose-response titration was diluted in growth media, added to appropriate wells of a cell culture plate, and then incubated at 37° C., 5% $CO_2$ for 2 hours. Following compound treatment, cells were washed with ice-cold Dulbecco's phosphate-buffered saline, no $Ca^{2+}$ or $Mg^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate $IC_{50}$ values.

AsPC-1 and SW620 CTG Assay Protocols

AsPC-1 (human pancreatic adenocarcinoma; ATCC CRL-1682) or SW620 (human colon adenocarcinoma; ATCC CCL-227) cells were cultured in RPMI 1640 medium containing 10% fetal bovine serum and 1× penicillin/streptomycin/L-glutamine. Cells were seeded in 384-well plates at a density of 3.33E+04 cells/mL and incubated at 37° C., 5% $CO_2$, overnight. Serially-diluted compound or DMSO was added to the cells, and plates were incubated at 37° C., 5% $CO_2$ for 72 h. Cell viability was measured using a CellTiter-Glo® Luminescent Cell Viability Assay kit (Promega) according to the manufacturer's protocol. The luminescence signal of treated samples was normalized to DMSO control, and data were analyzed using a 4-parameter logistic model to calculate $IC_{50}$ values.

MIA PaCa-2 CTG Assay Protocol

MIA PaCa-2 (human pancreatic carcinoma; ATCC CRL-1420) cells were cultured in RPMI 1640 medium containing 10% fetal bovine serum and 1× penicillin/streptomycin/L-glutamine. Cells were seeded in 384-well plates at a density of 1.67E+04 cells/mL and incubated at 37° C., 5% $CO_2$, overnight. Serially-diluted compound or DMSO was added to the cells, and plates were incubated at 37° C., 5% $CO_2$ for 72 h. Cell viability was measured using a CellTiter-Glo® Luminescent Cell Viability Assay kit (Promega) according to the manufacturer's protocol. The luminescence signal of treated samples was normalized to DMSO control, and data were analyzed using a 4-parameter logistic model to calculate $IC_{50}$ values.

TABLE 52

Biochemical and cellular activity of examples.

| Ex. # | KRAS G12D Binding $IC_{50}$ (μM) | KRAS G12D Coupled Exchange $IC_{50}$ (μM) | 2 h p-ERK (AsPC-1 cells), $IC_{50}$ (μM) | G12D/C/V Cell Proliferation CTG (72 h) AsPC-1 \|Mia PaCa-2\| SW620 (μM) |
|---|---|---|---|---|
| 1 | 0.005 | 0.004 | 0.196 | 1.93\|NT\|NT |
| 2 | 0.050 | 0.024 | 1.400 | 4.11\|NT\|NT |
| 3 | 0.001 | 0.0001 | 0.023 | 0.285\|0.075\|NT |
| 4 | 0.004 | 0.002 | 0.003 | 0.014\|0.005\|0.007 |
| 5 | 0.001 | 0.001 | 0.023 | 0.471\|0.062\|NT |
| 6 | 0.154 | 0.125 | NT | NT |
| 7 | 0.015 | 0.015 | 0.26 | NT |
| 8 | 0.008 | 0.006 | 0.06 | NT\|NT\|0.579 |
| 9 | 0.302 | 0.292 | NT | NT |
| 10 | 0.004 | 0.002 | 0.084 | 0.574\|0.157\|NT |
| 11 | 0.012 | 0.008 | 0.155 | 1.05\|NT\|NT |
| 12 | 0.006 | 0.003 | 0.052 | 0.49\|NT\|0.427 |
| 13 | 0.238 | 0.342 | NT | NT |
| 14 | 0.344 | 0.296 | NT | NT |
| 15 | 0.004 | 0.003 | 0.019 | 0.141\|NT\|0.08 |
| 16 | 0.006 | 0.005 | 0.092 | 1.2\|NT\|NT |
| 17 | 0.011 | 0.007 | 0.046 | 0.405\|NT\|NT |
| 18 | 0.006 | 0.003 | 0.012 | 0.082\|0.029\|0.032 |
| 19 | 0.007 | 0.005 | 1.86 | 5.0\|NT\|NT |

TABLE 52-continued

Biochemical and cellular activity of examples.

| Ex. # | KRAS G12D Binding $IC_{50}$ (μM) | KRAS G12D Coupled Exchange $IC_{50}$ (μM) | 2 h p-ERK (AsPC-1 cells), $IC_{50}$ (μM) | G12D/C/V Cell Proliferation CTG (72 h) AsPC-1 \|Mia PaCa-2\| SW620 (μM) |
|---|---|---|---|---|
| 20 | 0.02 | 0.022 | 0.823 | 2.22\|NT\|NT |
| 21 | 0.043 | 0.043 | NT | NT |
| 22 | 0.003 | 0.001 | 0.005 | 0.108\|0.01\|NT |
| 23 | 0.16 | 0.111 | NT | NT |
| 24 | 0.02 | 0.018 | 1.14 | NT |
| 25 | 0.01 | 0.007 | NT | NT |
| 26 | 0.124 | 0.109 | NT | NT |
| 27 | 0.007 | 0.005 | 0.18 | 0.661\|NT\|NT |
| 28 | 0.068 | 0.048 | NT | NT |
| 29 | 0.443 | 0.513 | NT | NT |
| 30 | 0.119 | 0.141 | 1.46 | NT |
| 31 | 0.007 | 0.005 | 0.033 | NT\|0.17\|0.133 |
| 32 | 0.005 | 0.003 | 0.043 | 0.422\|NT\|NT |
| 33 | 0.006 | 0.004 | 0.077 | 0.809\|NT\|NT |
| 34 | 0.22 | 0.177 | NT | NT |
| 35 | 0.001 | 0.001 | 0.019 | 0.277\|0.09\|NT |
| 36 | 0.003 | 0.001 | 0.008 | 0.111\|NT\|NT |
| 37 | 0.005 | 0.004 | 0.058 | NT |
| 38 | 0.002 | 0.002 | 0.02 | 0.443\|NT\|0.076 |
| 39 | 0.012 | 0.008 | 0.016 | 0.191\|NT\|NT |
| 40 | 0.005 | 0.003 | 0.008 | 0.09\|NT\|NT |
| 41 | 0.003 | 0.002 | 0.003 | 0.047\|NT\|NT |
| 42 | 0.004 | 0.002 | 0.038 | 0.414\|NT\|NT |
| 43 | 0.004 | 0.002 | 0.013 | 0.092\|NT\|NT |
| 44 | 0.16 | 0.266 | NT | NT |
| 45 | 0.002 | 0.001 | 0.001 | 0.05\|0.01\|0.01 |
| 46 | 0.012 | 0.01 | NT | NT |
| 47 | 0.004 | 0.002 | 0.036 | 0.35\|0.20\|NT |
| 48 | 0.014 | 0.013 | 0.931 | NT |
| 49 | 0.007 | 0.005 | 0.116 | NT |
| 50 | 0.007 | 0.004 | 0.169 | NT |
| 51 | 0.010 | 0.005 | 0.356 | NT |
| 52 | 0.019 | 0.012 | 0.403 | NT |
| 53 | 0.008 | 0.004 | 0.074 | 0.48\|NT\|0.15 |
| 54 | 0.006 | 0.003 | 0.135 | 1.64\|NT\|NT |
| 55 | 0.019 | 0.014 | 1.380 | NT |
| 56 | 0.020 | 0.011 | 2.320 | NT |
| 57 | 0.221 | 0.194 | NT | NT |
| 58 | 0.349 | 0.368 | NT | NT |
| 59 | 0.651 | 0.481 | NT | NT |
| 60 | 0.013 | 0.006 | 0.012 | NT |
| 61 | 0.079 | 0.034 | 0.070 | NT |
| 62 | 0.003 | 0.002 | 0.004 | 0.07\|NT\|0.01 |
| 63 | 0.009 | 0.002 | 0.059 | 0.46\|NT\|NT |
| 64 | 0.098 | 0.081 | NT | NT |
| 65 | 0.006 | 0.002 | 0.024 | 0.32\|0.16\|0.052 |
| 66 | 0.034 | 0.026 | 4.700 | NT |
| 67 | 0.046 | 0.034 | 1.660 | NT |
| 68 | 0.033 | 0.016 | 0.931 | NT |
| 69 | 0.030 | 0.020 | 1.140 | NT |
| 70 | 0.277 | 0.274 | NT | NT |
| 71 | 0.306 | 0.119 | NT | NT |
| 72 | 0.003 | 0.001 | 0.016 | 0.23\|0.20\|NT |
| 73 | 0.029 | 0.020 | 2.070 | NT |
| 74 | 0.003 | 0.002 | 0.016 | NT |
| 75 | 0.020 | 0.013 | 0.213 | NT |
| 76 | 0.015 | 0.009 | 0.820 | 1.71\|NT\|NT |
| 77 | 0.014 | 0.007 | 0.745 | 2.14\|NT\|NT |
| 78 | 3.810 | 2.100 | NT | NT |
| 79 | 0.004 | 0.003 | 0.004 | 0.06\|NT\|NT |
| 80 | 0.055 | 0.047 | NT | NT |
| 81 | 0.279 | 0.212 | NT | NT |
| 82 | 0.002 | 0.001 | 0.002 | 0.04\|0.01\|NT |
| 83 | 0.004 | 0.003 | 0.015 | 0.16\|0.04\|NT |
| 84 | 0.002 | 0.001 | 0.004 | 0.05\|0.02\|NT |
| 85 | 0.005 | 0.004 | 0.058 | 0.48\|0.40\|NT |
| 86 | 0.061 | 0.057 | NT | NT |
| 87 | 0.024 | 0.023 | 0.421 | NT |
| 88 | 0.019 | 0.011 | 1.585 | NT |
| 89 | 0.039 | 0.013 | NT | NT |
| 90 | 0.012 | 0.011 | 0.167 | NT |
| 91 | 0.004 | 0.002 | 0.027 | 0.28\|NT\|NT |

TABLE 52-continued

<table>
<tr><th colspan="5">Biochemical and cellular activity of examples.</th></tr>
<tr><th>Ex. #</th><th>KRAS G12D Binding $IC_{50}$ (μM)</th><th>KRAS G12D Coupled Exchange $IC_{50}$ (μM)</th><th>2 h p-ERK (AsPC-1 cells), $IC_{50}$ (μM)</th><th>G12D/C/V Cell Proliferation CTG (72 h) AsPC-1 |Mia PaCa-2| SW620 (μM)</th></tr>
<tr><td>92</td><td>0.013</td><td>0.011</td><td>0.317</td><td>NT</td></tr>
<tr><td>93</td><td>0.014</td><td>0.005</td><td>0.180</td><td>1.25|NT|NT</td></tr>
<tr><td>94</td><td>0.010</td><td>0.006</td><td>0.222</td><td>1.00|NT|NT</td></tr>
<tr><td>95</td><td>0.038</td><td>0.036</td><td>2.460</td><td>NT</td></tr>
<tr><td>96</td><td>0.067</td><td>0.054</td><td>1.380</td><td>NT</td></tr>
<tr><td>97</td><td>0.002</td><td>0.001</td><td>0.009</td><td>0.08|0.02|0.0208</td></tr>
<tr><td>98</td><td>0.004</td><td>0.002</td><td>0.017</td><td>0.14|0.05|</td></tr>
<tr><td>99</td><td>0.003</td><td>0.002</td><td>0.002</td><td>0.03|0.001|0.01</td></tr>
<tr><td>100</td><td>0.002</td><td>0.001</td><td>0.004</td><td>0.06|NT|0.01</td></tr>
<tr><td>101</td><td>0.093</td><td>0.070</td><td>1.340</td><td>NT</td></tr>
<tr><td>102</td><td>0.003</td><td>0.002</td><td>0.010</td><td>0.09|NT|0.0226</td></tr>
<tr><td>103</td><td>0.031</td><td>0.032</td><td>1.990</td><td>NT</td></tr>
<tr><td>104</td><td>0.007</td><td>0.002</td><td>0.038</td><td>0.86|0.30|NT</td></tr>
<tr><td>105</td><td>0.014</td><td>0.008</td><td>0.245</td><td>1.94|NT|NT</td></tr>
<tr><td>106</td><td>0.004</td><td>0.001</td><td>0.029</td><td>0.27|NT|NT</td></tr>
<tr><td>107</td><td>0.070</td><td>0.042</td><td>NT</td><td>NT</td></tr>
<tr><td>108</td><td>0.024</td><td>0.014</td><td>0.386</td><td>NT</td></tr>
<tr><td>109</td><td>0.180</td><td>0.196</td><td>NT</td><td>NT</td></tr>
<tr><td>110</td><td>0.003</td><td>0.002</td><td>0.004</td><td>0.08|0.02|0.01</td></tr>
<tr><td>111</td><td>0.015</td><td>0.011</td><td>0.187</td><td>NT</td></tr>
<tr><td>112</td><td>0.005</td><td>0.003</td><td>0.048</td><td>0.36|NT|0.137</td></tr>
<tr><td>113</td><td>0.010</td><td>0.003</td><td>0.109</td><td>1.18|NT|NT</td></tr>
<tr><td>114</td><td>0.019</td><td>0.012</td><td>0.346</td><td>NT</td></tr>
<tr><td>115</td><td>0.003</td><td>0.001</td><td>0.010</td><td>0.06|0.06|0.0274</td></tr>
<tr><td>116</td><td>0.017</td><td>0.012</td><td>0.270</td><td>NT</td></tr>
<tr><td>117</td><td>0.569</td><td>0.413</td><td>NT</td><td>NT</td></tr>
<tr><td>118</td><td>0.007</td><td>0.004</td><td>0.110</td><td>0.63|NT|NT</td></tr>
<tr><td>119</td><td>2.12</td><td>1.86</td><td>NT</td><td>NT</td></tr>
<tr><td>120</td><td>0.010</td><td>0.008</td><td>0.229</td><td>NT</td></tr>
<tr><td>121</td><td>0.508</td><td>0.422</td><td>NT</td><td>NT</td></tr>
<tr><td>122</td><td>0.005</td><td>0.003</td><td>0.008</td><td>0.25|0.10|NT</td></tr>
<tr><td>123</td><td>0.008</td><td>0.004</td><td>0.104</td><td>0.65|NT|NT</td></tr>
<tr><td>124</td><td>0.020</td><td>0.015</td><td>0.479</td><td>NT</td></tr>
<tr><td>125</td><td>0.009</td><td>0.005</td><td>0.066</td><td>0.41|NT|NT</td></tr>
<tr><td>126</td><td>0.002</td><td>0.001</td><td>0.010</td><td>0.16|0.06|NT</td></tr>
<tr><td>127</td><td>0.004</td><td>0.003</td><td>0.013</td><td>0.23|0.12|NT</td></tr>
<tr><td>128</td><td>0.068</td><td>0.046</td><td>0.248</td><td>1.26|NT|NT</td></tr>
<tr><td>129</td><td>0.004</td><td>0.002</td><td>0.020</td><td>0.17|0.09|0.0674</td></tr>
<tr><td>130</td><td>0.005</td><td>0.002</td><td>0.032</td><td>0.23|NT|NT</td></tr>
<tr><td>131</td><td>0.006</td><td>0.003</td><td>0.041</td><td>0.37|0.23|NT</td></tr>
<tr><td>132</td><td>0.070</td><td>0.067</td><td>NT</td><td>NT</td></tr>
<tr><td>133</td><td>0.241</td><td>0.240</td><td>NT</td><td>NT</td></tr>
<tr><td>134</td><td>0.056</td><td>0.059</td><td>NT</td><td>NT</td></tr>
<tr><td>135</td><td>0.003</td><td>0.002</td><td>0.017</td><td>0.25|NT|0.0551</td></tr>
<tr><td>136</td><td>0.007</td><td>0.003</td><td>0.077</td><td>0.67|NT|NT</td></tr>
<tr><td>137</td><td>0.004</td><td>0.002</td><td>0.047</td><td>0.42|NT|0.0967</td></tr>
<tr><td>138</td><td>0.004</td><td>0.002</td><td>0.013</td><td>5.00|NT|NT</td></tr>
<tr><td>139</td><td>0.006</td><td>0.003</td><td>0.114</td><td>0.91|NT|NT</td></tr>
<tr><td>140</td><td>0.005</td><td>0.004</td><td>0.083</td><td>0.65|0.10|NT</td></tr>
<tr><td>141</td><td>0.002</td><td>0.001</td><td>0.006</td><td>0.12|0.02|0.0202</td></tr>
<tr><td>142</td><td>0.017</td><td>0.015</td><td>0.247</td><td>NT</td></tr>
<tr><td>143</td><td>0.003</td><td>0.002</td><td>0.109</td><td>0.98|0.48|NT</td></tr>
<tr><td>144</td><td>0.146</td><td>0.079</td><td>NT</td><td>NT</td></tr>
<tr><td>145</td><td>0.068</td><td>0.063</td><td>4.670</td><td>5.00|NT|NT</td></tr>
<tr><td>146</td><td>0.077</td><td>0.065</td><td>NT</td><td>NT</td></tr>
<tr><td>147</td><td>0.016</td><td>0.013</td><td>0.298</td><td>NT</td></tr>
<tr><td>148</td><td>0.007</td><td>0.005</td><td>0.042</td><td>0.46|NT|0.165</td></tr>
<tr><td>149</td><td>0.060</td><td>0.034</td><td>0.033</td><td>0.47|NT|0.154</td></tr>
<tr><td>150</td><td>0.033</td><td>0.017</td><td>0.306</td><td>NT</td></tr>
<tr><td>151</td><td>0.004</td><td>0.002</td><td>0.013</td><td>0.20|0.07|0.0387</td></tr>
<tr><td>152</td><td>0.071</td><td>0.056</td><td>NT</td><td>NT</td></tr>
<tr><td>153</td><td>0.003</td><td>0.003</td><td>0.009</td><td>0.21|NT|0.0325</td></tr>
<tr><td>154</td><td>0.002</td><td>0.004</td><td>0.252</td><td>3.36|0.23|NT</td></tr>
<tr><td>155</td><td>0.006</td><td>0.005</td><td>0.052</td><td>0.72|NT|0.302</td></tr>
<tr><td>156</td><td>0.012</td><td>0.003</td><td>0.110</td><td>0.72|NT|0.367</td></tr>
<tr><td>157</td><td>0.002</td><td>0.001</td><td>0.007</td><td>0.06|NT|NT</td></tr>
<tr><td>158</td><td>0.020</td><td>0.006</td><td>0.278</td><td>NT</td></tr>
<tr><td>159</td><td>0.006</td><td>0.005</td><td>0.0796</td><td>NT</td></tr>
<tr><td>160</td><td>0.004</td><td>0.003</td><td>0.0718</td><td>0.587|0.420|NT</td></tr>
<tr><td>161</td><td>0.006</td><td>0.004</td><td>0.0198</td><td>0.225|NT|NT</td></tr>
<tr><td>162</td><td>0.037</td><td>0.020</td><td>1.8300</td><td>NT</td></tr>
<tr><td>163</td><td>2.840</td><td>1.570</td><td>NT</td><td>NT</td></tr>
<tr><td>164</td><td>0.010</td><td>0.007</td><td>0.2360</td><td>3.100|NT|NT</td></tr>
<tr><td>165</td><td>12.700</td><td>4.430</td><td>NT</td><td>NT</td></tr>
<tr><td>166</td><td>0.005</td><td>0.003</td><td>0.0162</td><td>0.068|0.090|NT</td></tr>
<tr><td>167</td><td>0.044</td><td>0.020</td><td>1.5900</td><td>5.000|NT|NT</td></tr>
<tr><td>168</td><td>0.003</td><td>0.001</td><td>0.0013</td><td>0.010|NT|0.003</td></tr>
<tr><td>169</td><td>0.616</td><td>0.339</td><td>NT</td><td>NT</td></tr>
<tr><td>170</td><td>2.490</td><td>1.540</td><td>NT</td><td>NT</td></tr>
<tr><td>171</td><td>0.006</td><td>0.004</td><td>0.1060</td><td>1.090|NT|NT</td></tr>
<tr><td>172</td><td>1.770</td><td>1.030</td><td>NT</td><td>NT</td></tr>
<tr><td>173</td><td>1.570</td><td>1.110</td><td>NT</td><td>NT</td></tr>
<tr><td>174</td><td>0.005</td><td>0.003</td><td>0.0535</td><td>NT</td></tr>
<tr><td>175</td><td>0.005</td><td>0.004</td><td>0.0277</td><td>0.123|NT|NT</td></tr>
<tr><td>176</td><td>0.287</td><td>0.179</td><td>NT</td><td>NT</td></tr>
<tr><td>177</td><td>0.003</td><td>0.003</td><td>0.0163</td><td>0.178|0.100|0.039</td></tr>
<tr><td>178</td><td>0.079</td><td>0.044</td><td>NT</td><td>NT</td></tr>
<tr><td>179</td><td>0.009</td><td>0.005</td><td>0.0788</td><td>NT</td></tr>
<tr><td>180</td><td>1.510</td><td>0.689</td><td>NT</td><td>NT</td></tr>
<tr><td>181</td><td>0.006</td><td>0.003</td><td>0.0188</td><td>NT|0.010|0.008</td></tr>
<tr><td>182</td><td>7.570</td><td>3.620</td><td>NT</td><td>NT</td></tr>
<tr><td>183</td><td>0.008</td><td>0.004</td><td>0.0493</td><td>0.164|0.050|0.044</td></tr>
<tr><td>184</td><td>0.004</td><td>0.002</td><td>0.0118</td><td>0.120|NT|NT</td></tr>
<tr><td>185</td><td>0.006</td><td>0.005</td><td>0.0120</td><td>0.038|0.033|NT</td></tr>
<tr><td>186</td><td>0.012</td><td>0.009</td><td>0.2000</td><td>1.950|NT|NT</td></tr>
<tr><td>187</td><td>0.004</td><td>0.002</td><td>0.0046</td><td>0.076|0.015|NT</td></tr>
<tr><td>188</td><td>0.071</td><td>0.044</td><td>NT</td><td>NT</td></tr>
<tr><td>189</td><td>0.003</td><td>0.002</td><td>0.0049</td><td>0.115|0.024|NT</td></tr>
<tr><td>190</td><td>0.004</td><td>0.002</td><td>0.0045</td><td>0.005|0.004|0.004</td></tr>
<tr><td>191</td><td>0.003</td><td>0.002</td><td>0.0019</td><td>0.008|0.001|0.002</td></tr>
<tr><td>192</td><td>0.004</td><td>0.002</td><td>0.0218</td><td>0.375|0.067|NT</td></tr>
<tr><td>193</td><td>0.049</td><td>0.024</td><td>0.0239</td><td>0.060|NT|NT</td></tr>
<tr><td>194</td><td>0.005</td><td>0.003</td><td>0.0013</td><td>0.006|0.007|0.004</td></tr>
<tr><td>195</td><td>0.004</td><td>0.002</td><td>0.0060</td><td>0.067|0.031|0.050</td></tr>
<tr><td>196</td><td>0.167</td><td>0.214</td><td>NT</td><td>NT</td></tr>
<tr><td>197</td><td>0.090</td><td>0.105</td><td>NT</td><td>NT</td></tr>
<tr><td>198</td><td>0.002</td><td>0.001</td><td>0.0081</td><td>0.108|0.016|0.014</td></tr>
<tr><td>199</td><td>0.004</td><td>0.003</td><td>0.0157</td><td>0.046|NT|0.022</td></tr>
<tr><td>200</td><td>0.010</td><td>0.004</td><td>0.2620</td><td>NT|0.320|NT</td></tr>
<tr><td>201</td><td>0.009</td><td>0.008</td><td>0.171</td><td>NT</td></tr>
<tr><td>202</td><td>0.006</td><td>0.003</td><td>0.0411</td><td>0.494|0.113|NT</td></tr>
<tr><td>203</td><td>0.017</td><td>0.008</td><td>0.1710</td><td>NT</td></tr>
<tr><td>204</td><td>0.034</td><td>0.016</td><td>0.4290</td><td>NT</td></tr>
<tr><td>205</td><td>0.011</td><td>0.006</td><td>0.0361</td><td>NT</td></tr>
<tr><td>206</td><td>0.014</td><td>0.009</td><td>0.2110</td><td>2.230|NT|NT</td></tr>
<tr><td>207</td><td>0.004</td><td>0.002</td><td>0.0147</td><td>0.196|NT|0.058</td></tr>
<tr><td>208</td><td>0.003</td><td>0.002</td><td>0.0207</td><td>0.262|0.038|NT</td></tr>
<tr><td>209</td><td>0.005</td><td>0.003</td><td>0.0039</td><td>0.003|NT|0.003</td></tr>
<tr><td>210</td><td>0.435</td><td>0.431</td><td>NT</td><td>NT</td></tr>
<tr><td>211</td><td>0.617</td><td>0.268</td><td>NT</td><td>NT</td></tr>
<tr><td>212</td><td>0.004</td><td>0.003</td><td>0.0053</td><td>0.079|0.024|0.02</td></tr>
<tr><td>213</td><td>0.046</td><td>0.015</td><td>0.0049</td><td>0.005|NT|NT</td></tr>
<tr><td>214</td><td>0.022</td><td>0.018</td><td>0.4960</td><td>NT</td></tr>
<tr><td>215</td><td>0.015</td><td>0.012</td><td>0.1080</td><td>NT</td></tr>
<tr><td>216</td><td>0.074</td><td>0.055</td><td>NT</td><td>NT</td></tr>
<tr><td>217</td><td>0.004</td><td>0.002</td><td>0.0230</td><td>0.455|0.049|NT</td></tr>
<tr><td>218</td><td>0.004</td><td>0.003</td><td>0.0278</td><td>NT</td></tr>
<tr><td>219</td><td>0.019</td><td>0.010</td><td>0.3690</td><td>NT</td></tr>
<tr><td>220</td><td>0.006</td><td>0.003</td><td>0.0589</td><td>0.816|0.064|NT</td></tr>
<tr><td>221</td><td>0.004</td><td>0.001</td><td>0.0071</td><td>0.209|NT|0.075</td></tr>
<tr><td>222</td><td>0.003</td><td>0.002</td><td>0.0094</td><td>0.287|0.052|NT</td></tr>
<tr><td>223</td><td>0.642</td><td>0.343</td><td>NT</td><td>NT</td></tr>
<tr><td>224</td><td>0.063</td><td>0.039</td><td>NT</td><td>NT</td></tr>
<tr><td>225</td><td>9.62</td><td>4.77</td><td>NT</td><td>NT</td></tr>
<tr><td>226</td><td>0.007</td><td>0.005</td><td>0.0778</td><td>0.412|0.130|NT</td></tr>
<tr><td>227</td><td>0.035</td><td>0.012</td><td>0.6110</td><td>3.910|NT|NT</td></tr>
<tr><td>228</td><td>0.012</td><td>0.008</td><td>0.1810</td><td>0.487|NT|NT</td></tr>
<tr><td>229</td><td>0.027</td><td>0.012</td><td>0.3420</td><td>NT</td></tr>
<tr><td>230</td><td>0.012</td><td>0.009</td><td>0.0951</td><td>0.174|NT|NT</td></tr>
<tr><td>231</td><td>0.006</td><td>0.004</td><td>0.0116</td><td>0.029|0.042|NT</td></tr>
<tr><td>232</td><td>0.031</td><td>0.018</td><td>1.3450</td><td>NT</td></tr>
<tr><td>233</td><td>0.004</td><td>0.003</td><td>0.0010</td><td>0.002|NT|0.001</td></tr>
<tr><td>234</td><td>0.077</td><td>0.009</td><td>NT</td><td>NT</td></tr>
<tr><td>235</td><td>0.240</td><td>0.125</td><td>NT</td><td>NT</td></tr>
</table>

TABLE 52-continued

Biochemical and cellular activity of examples.

| Ex. # | KRAS G12D Binding $IC_{50}$ (μM) | KRAS G12D Coupled Exchange $IC_{50}$ (μM) | 2 h p-ERK (AsPC-1 cells), $IC_{50}$ (μM) | G12D/C/V Cell Proliferation CTG (72 h) AsPC-1 \|Mia PaCa-2\| SW620 (μM) |
|---|---|---|---|---|
| 236 | 0.055 | 0.019 | 0.9500 | NT |
| 237 | 0.019 | 0.010 | 0.2790 | 5.000\|NT\|NT |
| 238 | 0.045 | 0.024 | 0.8610 | 5.000\|NT\|NT |
| 239 | 0.006 | 0.005 | 0.0829 | 0.527\|NT\|NT |
| 240 | 0.003 | 0.002 | 0.0219 | 0.230\|0.140\|0.080 |
| 241 | 1.290 | 1.410 | NT | NT |
| 242 | 1.140 | 1.050 | NT | NT |
| 243 | 4.480 | 4.070 | NT | NT |
| 244 | 0.027 | 0.030 | NT | NT |
| 245 | 0.583 | 0.344 | NT | NT |
| 246 | 0.002 | 0.002 | 0.0101 | 0.112\|0.082\|NT |
| 247 | 0.009 | 0.005 | 0.0312 | 0.446\|NT\|NT |
| 248 | 0.004 | 0.002 | 0.0078 | 0.013\|0.007\|NT |
| 249 | 0.004 | 0.001 | 0.0007 | 0.005\|0.002\|0.003 |
| 250 | 0.013 | 0.006 | 0.1280 | 1.060\|NT\|NT |
| 251 | 0.015 | 0.008 | 0.3810 | NT |
| 252 | 0.028 | 0.017 | 0.9260 | NT |
| 253 | 0.009 | 0.006 | 0.0678 | 1.200\|NT\|NT |
| 254 | 0.019 | 0.012 | 0.5450 | 3.970\|NT\|NT |
| 255 | 0.010 | 0.009 | 0.0775 | NT |
| 256 | 0.004 | 0.005 | 0.0094 | 0.229\|NT\|NT |
| 257 | 0.262 | 0.178 | NT | NT |
| 258 | 0.013 | 0.006 | 0.0829 | 0.996\|NT\|NT |
| 259 | 0.004 | 0.003 | 0.0253 | 0.215\|0.126\|NT |
| 260 | 0.004 | 0.002 | 0.0032 | 0.040\|0.026\|0.008 |
| 261 | 0.006 | 0.005 | 0.0402 | 0.270\|0.028\|NT |
| 262 | 3.265 | 2.420 | NT | NT |
| 263 | 0.006 | 0.004 | 0.0424 | NT |
| 264 | 0.038 | 0.024 | 0.3685 | NT |
| 265 | 0.003 | 0.002 | 0.005 | 0.03\|0.07\|NT |
| 266 | 0.014 | 0.006 | 0.1810 | 2.080\|NT\|NT |
| 267 | 0.004 | 0.002 | 0.0335 | 0.080\|0.121\|NT |
| 268 | 0.007 | 0.004 | 0.246 | 1.350\|NT\|NT |
| 269 | 0.016 | 0.011 | 0.25 | 0.606\|NT\|NT |
| 270 | 0.007 | 0.002 | 0.123 | 0.606\|0.675\|NT |
| 271 | 0.013 | 0.002 | 0.5 | NT |
| 272 | 0.011 | 0.003 | 0.25 | 1.760\|NT\|NT |
| 273 | 0.003 | 0.002 | 1.1 | 5.000\|NT\|NT |
| 274 | 0.032 | 0.016 | 1.78 | 5.000\|NT\|NT |
| 275 | 0.006 | 0.003 | 0.0531 | 0.778\|NT\|NT |
| 276 | 0.498 | 0.153 | NT | NT |
| 277 | 0.003 | 0.002 | 0.011 | 0.088\|0.060\|NT |
| 278 | 19.3 | 5.9 | NT | NT |
| 279 | 0.333 | 0.071 | NT | NT |
| 280 | 0.01 | 0.003 | 0.099 | 0.475\|NT\|NT |
| 281 | 0.005 | 0.002 | 0.0079 | 0.104\|0.090\|NT |
| 282 | 0.007 | 0.003 | 0.133 | 1.190\|NT\|NT |
| 283 | 3.27 | 1 | 10 | NT |
| 284 | 0.005 | 0.002 | 0.0413 | 0.788\|NT\|NT |
| 285 | 1.91 | 0.61 | NT | NT |
| 286 | 0.081 | 0.015 | 1.25 | NT |
| 287 | 1.23 | 0.376 | NT | NT |
| 288 | 0.007 | 0.002 | 0.102 | 0.427\|NT\|NT |
| 289 | 0.01 | 0.006 | 0.11 | 0.613\|NT\|NT |
| 290 | 0.004 | 0.002 | 0.0031 | 0.036\|0.032\|NT |
| 291 | 0.026 | 0.005 | 1.23 | NT |
| 292 | 0.004 | 0.002 | 0.0171 | 0.178\|NT\|NT |
| 293 | 50 | 16.4 | NT | NT |
| 294 | 0.02 | 0.009 | 0.0551 | NT |
| 295 | 2.25 | 1.08 | NT | NT |
| 296 | 0.004 | 0.004 | 0.0126 | 0.150\|0.053\|NT |
| 297 | 8.07 | 5.98 | NT | NT |
| 298 | 0.007 | 0.003 | 0.0913 | 0.592\|NT\|NT |
| 299 | 0.03 | 0.021 | 0.467 | 5.000\|NT\|NT |
| 300 | 0.01 | 0.005 | 0.0232 | 0.281\|NT\|NT |
| 301 | 0.005 | 0.003 | 0.0605 | 0.954\|NT\|NT |
| 302 | 1.27 | 0.831 | NT | NT |
| 303 | 0.004 | 0.002 | 0.01 | 0.155\|0.075\|NT |
| 304 | 0.015 | 0.004 | 0.103 | NT\|0.380\|NT |
| 305 | 0.004 | 0.003 | 0.0177 | 0.061\|0.134\|NT |
| 306 | 0.695 | 0.45 | NT | NT |
| 307 | 0.004 | 0.002 | 0.012 | 0.134\|0.062\|NT |
| 308 | 0.006 | 0.003 | 0.0163 | 0.022\|NT\|NT |
| 309 | 0.01 | 0.004 | 0.0716 | 0.153\|NT\|NT |
| 310 | 2.265 | 1.488 | NT | NT |
| 311 | 0.005 | 0.003 | 0.0042 | 0.036\|0.007\|0.006 |
| 312 | 0.004 | 0.002 | 0.342 | 1.080\|NT\|NT |
| 313 | 0.019 | 0.011 | 0.462 | 1.210\|NT\|NT |
| 314 | 0.021 | 0.011 | 0.59 | NT |
| 315 | 0.003 | 0.002 | 0.0208 | 0.023\|NT\|NT |
| 316 | 0.004 | 0.003 | 0.0067 | 0.054\|0.013\|0.010 |
| 317 | 0.05 | 0.035 | NT | NT |
| 318 | 0.005 | 0.003 | 0.0351 | 0.183\|0.033\|NT |
| 319 | 0.006 | 0.003 | 0.0267 | 0.134\|NT\|NT |
| 320 | 0.004 | 0.003 | 0.0138 | 0.137\|0.080\|NT |
| 321 | 0.005 | 0.002 | 0.025 | 0.186\|0.162\|NT |
| 322 | 0.366 | 0.156 | 0.589 | |
| 323 | 0.005 | 0.002 | 0.0305 | 0.318\|NT\|NT |
| 324 | 0.061 | 0.042 | NT | NT |
| 325 | 0.099 | 0.065 | NT | NT |
| 326 | 0.004 | 0.002 | 0.0168 | 0.114\|NT\|0.066 |
| 327 | 0.004 | 0.002 | 0.0084 | 0.013\|NT\|0.024 |
| 328 | 0.005 | 0.003 | 0.029 | 0.050\|NT\|NT |
| 329 | 0.014 | 0.007 | 0.206 | 0.402\|0.530\|NT |
| 330 | 0.004 | 0.002 | 0.02 | 0.128\|0.054\|NT |
| 331 | 0.005 | 0.003 | 0.0154 | 0.115\|NT\|NT |
| 332 | 3.24 | 2.11 | NT | NT |
| 333 | 0.314 | 0.127 | NT | NT |
| 334 | 0.002 | 0.001 | 0.008 | 0.117\|NT\|0.031 |
| 335 | 0.044 | 0.009 | 1.26 | NT |
| 336 | 0.003 | 0.003 | 0.012 | 0.031\|NT\|0.049 |
| 337 | 2.44 | 0.79 | NT | NT |
| 338 | 0.007 | 0.002 | 0.0415 | 0.268\|0.035\|NT |
| 339 | 1.35 | 0.501 | 0.826 | NT |
| 340 | 0.004 | 0.001 | 0.0025 | 0.042\|0.017\|NT |
| 341 | 0.01 | 0.006 | 0.0655 | 0.889\|NT\|NT |
| 342 | 0.047 | 0.023 | 0.332 | 3.060\|NT\|NT |
| 343 | 0.022 | 0.013 | 0.0452 | 0.953\|NT\|NT |
| 344 | 0.008 | 0.003 | 0.0057 | 0.156\|NT\|NT |
| 345 | 0.003 | 0.001 | 0.0007 | 0.016\|NT\|NT |
| 346 | 0.005 | 0.002 | 0.0134 | 0.297\|NT\|NT |
| 347 | 0.027 | 0.007 | 0.2 | NT |
| 348 | 0.013 | 0.004 | 0.298 | 2.225\|NT\|NT |
| 349 | 0.005 | 0.002 | 0.0304 | 0.645\|NT\|NT |
| 350 | 0.006 | 0.003 | 0.0581 | 0.545\|NT\|NT |
| 351 | 0.464 | 0.149 | NT | NT |
| 352 | 0.006 | 0.002 | 0.0082 | 0.103\|NT\|NT |
| 353 | 0.003 | 0.001 | 0.0019 | 0.022\|0.003\|NT |
| 354 | 1.59 | 0.531 | NT | NT |
| 355 | 0.002 | 0.001 | 0.0052 | 0.082\|NT\|NT |
| 356 | 0.004 | 0.003 | 0.0082 | 0.094\|NT\|NT |
| 357 | 0.014 | 0.01 | 0.234 | 1.970\|NT\|NT |
| 358 | 0.024 | 0.016 | 0.384 | NT |
| 359 | 0.012 | 0.004 | 0.101 | 0.410\|0.107\|NT |
| 360 | 0.01 | 0.003 | 0.118 | 0.457\|0.344\|NT |
| 361 | 0.003 | 0.001 | 0.0004 | 0.007\|0.005\| |
| 362 | 0.008 | 0.005 | 0.133 | 1.450\|NT\|NT |
| 363 | 20.2 | 5.63 | NT | NT |
| 364 | 0.102 | 0.02 | NT | NT |
| 365 | 0.003 | 0.001 | 0.0067 | 0.141\|0.011\|NT |
| 366 | 0.938 | 0.631 | NT | NT |
| 367 | 0.004 | 0.002 | 0.0092 | 0.139\|0.026\|NT |
| 368 | 1.23 | 0.783 | NT | NT |
| 369 | 0.013 | 0.008 | 0.363 | 5.000\|NT\|NT |
| 370 | 0.036 | 0.018 | 0.708 | NT |
| 371 | 0.008 | 0.004 | 0.239 | NT |
| 372 | 0.003 | 0.002 | 0.0044 | 0.017\|0.020\|NT |
| 373 | 0.007 | 0.003 | 0.007 | 0.021\|0.005\|NT |
| 374 | 0.005 | 0.004 | 0.0327 | 0.127\|NT\|NT |
| 375 | 0.027 | 0.015 | 0.673 | 3.120\|NT\|NT |
| 376 | 0.016 | 0.011 | 0.35 | 2.060\|NT\|NT |
| 377 | 0.005 | 0.002 | 0.0099 | 0.125\|NT\|NT |
| 378 | 0.034 | 0.015 | 0.0477 | 0.782\|NT\|NT |
| 379 | 0.009 | 0.003 | 0.0853 | 0.404\|NT\|NT |

TABLE 52-continued

| Biochemical and cellular activity of examples. | | | | |
|---|---|---|---|---|
| Ex. # | KRAS G12D Binding $IC_{50}$ (μM) | KRAS G12D Coupled Exchange $IC_{50}$ (μM) | 2 h p-ERK (AsPC-1 cells), $IC_{50}$ (μM) | G12D/C/V Cell Proliferation CTG (72 h) AsPC-1 \|Mia PaCa-2\| SW620 (μM) |
| 380 | 0.155 | 0.029 | 1.69 | NT |
| 381 | 0.005 | 0.001 | 0.0104 | NT\|0.012\|NT |
| 382 | 0.005 | 0.003 | 0.0168 | 1.480\|NT\|NT |
| 383 | 0.013 | 0.008 | 0.0754 | NT |
| 384 | 0.01 | 0.006 | 0.0223 | 0.109\|NT\|NT |
| 385 | 0.031 | 0.016 | 0.137 | 0.211\|NT\|NT |
| 386 | 3.73 | 1.81 | NT | NT |
| 387 | 0.008 | 0.004 | 0.0663 | NT |
| 388 | 0.013 | 0.005 | 0.264 | NT |
| 389 | 3.96 | 1.021 | NT | NT |
| 390 | 0.005 | 0.003 | 0.0095 | 0.074\|NT\|NT |
| 391 | 0.004 | 0.002 | 0.0363 | 0.265\|0.183\|NT |
| 392 | 0.006 | 0.004 | 0.0315 | 0.291\|NT\|NT |
| 393 | 1.81 | 1.17 | NT | NT |
| 394 | 0.005 | 0.002 | 0.003 | 0.058\|0.010\|NT |
| 395 | 1.17 | 0.198 | NT | NT |
| 396 | 0.007 | 0.003 | 0.0012 | 0.002\|NT\|NT |
| 397 | 0.004 | 0.002 | 0.0014 | 0.012\|0.003\|NT |
| 398 | 0.004 | 0.002 | 0.0268 | 0.035\|0.170\|NT |
| 399 | 0.004 | 0.002 | 0.0259 | 0.044\|0.105\|NT |
| 400 | 0.015 | 0.008 | 0.371 | 0.817\|NT\|NT |
| 401 | 0.005 | 0.003 | 0.289 | 0.386\|NT\|NT |
| 402 | 0.097 | 0.046 | NT | NT |
| 403 | 0.003 | 0.002 | 0.18 | 0.639\|NT\|NT |
| 404 | 0.01 | 0.006 | 0.236 | 1.570\|NT\|NT |
| 405 | 0.005 | 0.004 | 0.0412 | 0.174\|NT\|NT |
| 406 | 0.021 | 0.004 | 0.261 | 1.940\|NT\|NT |
| 407 | 0.006 | 0.001 | 0.0025 | 0.049\|NT\|NT |
| 408 | 0.024 | 0.018 | 0.0524 | NT |

NT: not tested.

Tumor Pharmacodynamic Assays

Inhibitor pharmacodynamic effects were assessed in PANC 04.03 tumor-bearing mice. PANC 04.03 tumor cells (5.0E+06 cells) were injected subcutaneously into the flank of female athymic nude mice in a mixture with Matrigel (BD Bioscience). Mice received a single oral dose of either vehicle or inhibitor (100 mg/kg) when the average tumor size reached ~300-600 $mm^3$ (n=3/group) and harvested 2 hours later. Tumor samples were collected, snap frozen, and processed for analysis by pulverizing with a cryoPREP® Dry Impactor (Covaris). Pulverized samples were resuspended in RIPA lysis buffer containing protease and phosphatase inhibitors and homogenized. Cleared lysates were analyzed using phospho-ERK1/2 and total ERK1/2 whole cell lysate kits (Meso Scale Discovery) according to the manufacturer's protocol. Phospho-ERK1/2 signal was normalized to total ERK1/2 signal for a given sample, and percent inhibition of p-ERK was calculated relative to the vehicle group. Data are showing in Table 53 below.

TABLE 53

| Tumor Pharmacodynamic Assay Data | | |
|---|---|---|
| Ex. # | Conc. (mg/kg) | p-ERK (% inhibition) 2 hr. |
| 7 | 100 | 21 |
| 15 | 100 | 0 |
| 97 | 100 | 85 |
| 99 | 100 | 91 |
| 166 | 100 | 63 |
| 168 | 100 | 65 |
| 181 | 100 | 65 |
| 190 | 100 | 86 |
| 191 | 100 | 91 |
| 194 | 100 | 88 |
| 209 | 100 | 63 |
| 212 | 100 | 85 |
| 233 | 100 | 23 |
| 248 | 100 | 85 |
| 249 | 100 | 90 |
| 265 | 100 | 83 |

What is claimed is:

1. A compound, wherein the compound is:

| Compound |
|---|
| 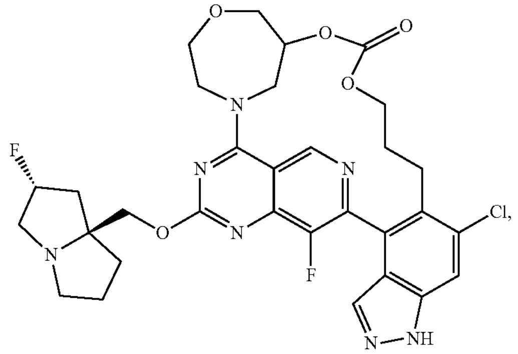 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] |
| 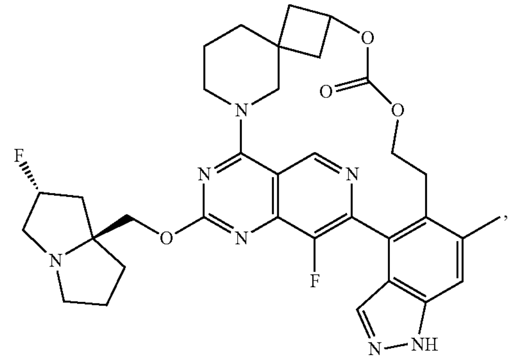 [SMILES: Cc1cc2[nH]ncc2c2c1CCOC(=O)OC1CC3(CCCN(C3)c3nc(OC[C@@]45CCCN4C[C@H](F)C5)nc4c(F)c-2ncc34)C1] |
| 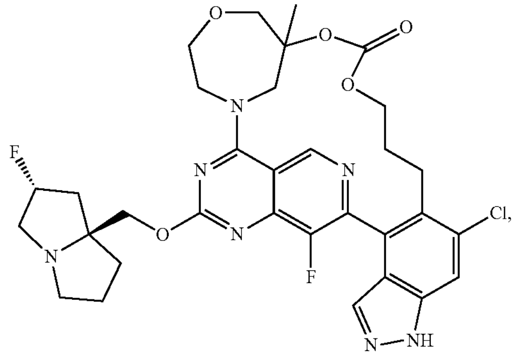 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2] |

-continued
| Compound |
| --- |
| 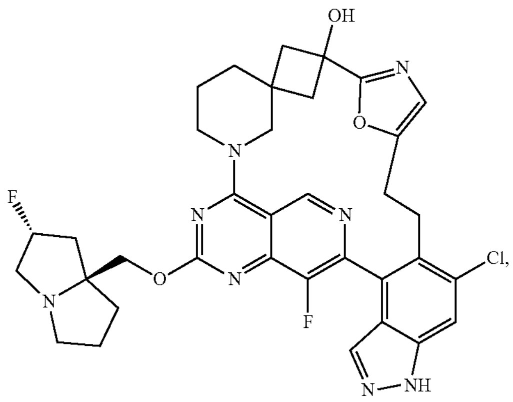 [SMILES: OC12CC3(CCCN(C3)c3nc(OC[C@@]45CCCN4C[C@H](F)C5)nc4c(F)c(ncc34)-c3c(c(Cl)cc4[nH]ncc34)CCc3cnc1o3)C2] , |
| 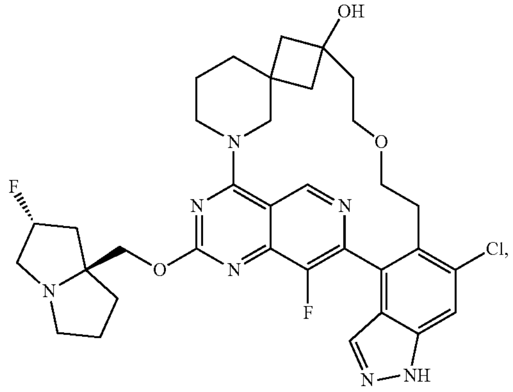 [SMILES: OC12CCOCCc3c(Cl)cc4[nH]ncc4c3-c3ncc4c(nc(OC[C@@]56CCCN5C[C@H](F)C6)nc4c3F)N3CCCC(C3)(C1)C2] , |
| 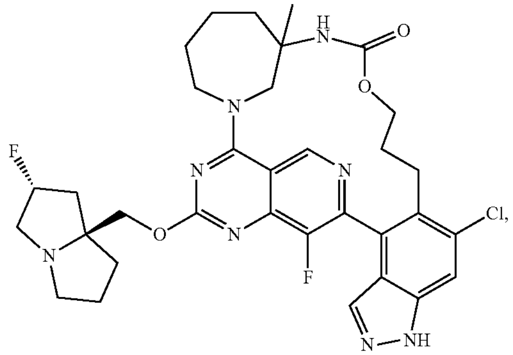 [SMILES: CC12CCCCN(C1)c1nc(OC[C@@]34CCCN3C[C@H](F)C4)nc3c(F)c(ncc13)-c1c(c(Cl)cc3[nH]ncc13)CCCOC(=O)N2] , |
| 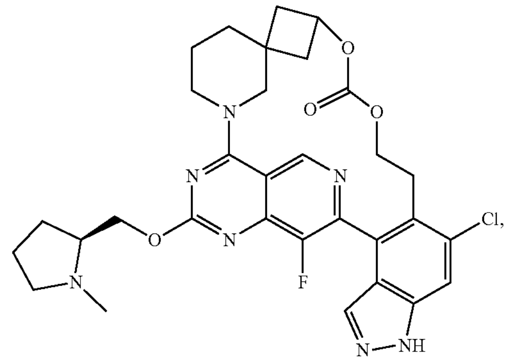 [SMILES: CN1CCC[C@H]1COc1nc2c3cnc(c(F)c3n1)-c1c(c(Cl)cc3[nH]ncc13)CCOC(=O)OC1CC3(CCCN2C3)C1] , |
-continued
| Compound |
| --- |
| 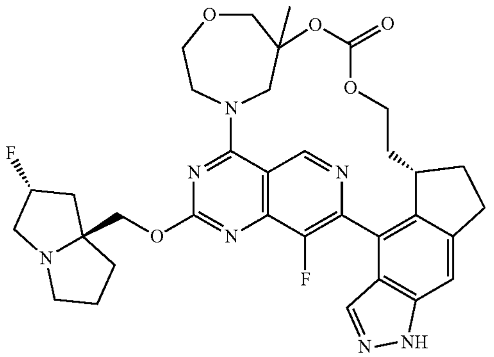 , |
| 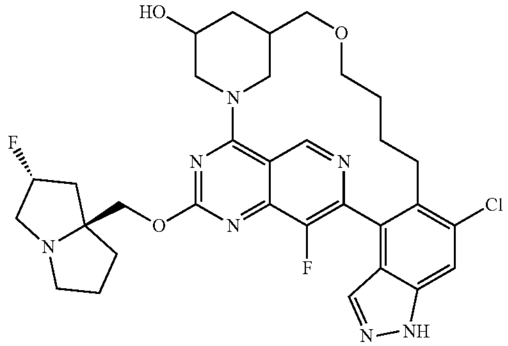 or |
| or |
| 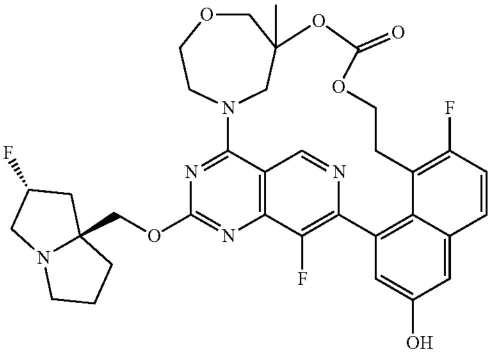 ; |
or a pharmaceutically acceptable salt thereof.
2. A compound, wherein the compound is
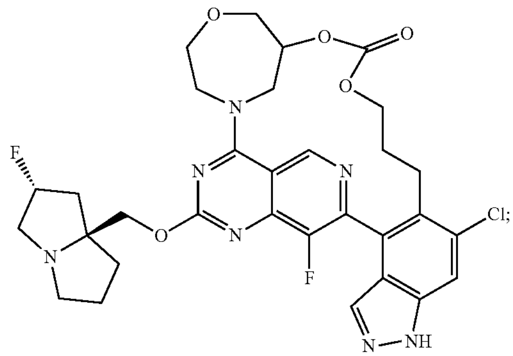 [SMILES: O=C1OCCCc2c(Cl)cc3[nH]ncc3c2-c2ncc3c(nc(OC[C@@]45CCCN4C[C@H](F)C5)nc3c2F)N2CCOCC(C2)O1] ;

or a pharmaceutically acceptable salt thereof.

3. The compound or salt of claim 1, wherein the compound is

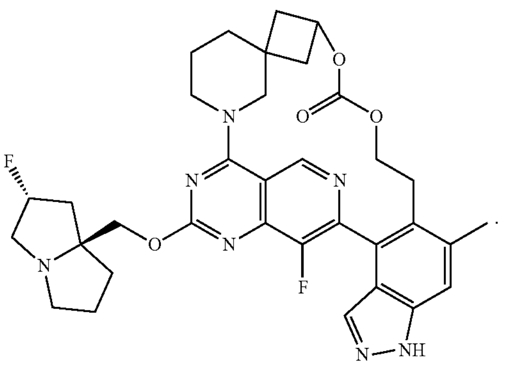 [SMILES: Cc1cc2[nH]ncc2c2c1CCOC(=O)OC1CC3(CCCN(C3)c3nc(OC[C@@]45CCCN4C[C@H](F)C5)nc4c(F)c-2ncc34)C1 ; "."]

4. The compound or salt of claim 1, wherein the compound is

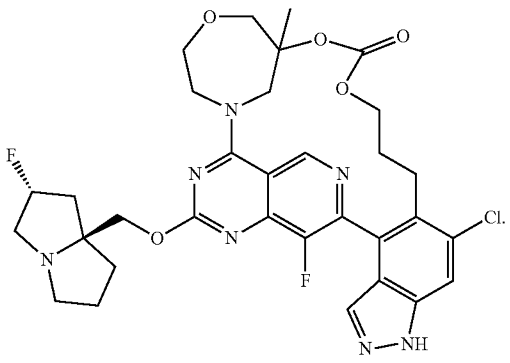 [SMILES: CC12COCCN(C1)c1nc(OC[C@@]34CCCN3C[C@H](F)C4)nc3c(F)c(ncc13)-c1c(c(Cl)cc3[nH]ncc13)CCCOC(=O)O2]

5. The compound or salt of claim 1, wherein the compound is

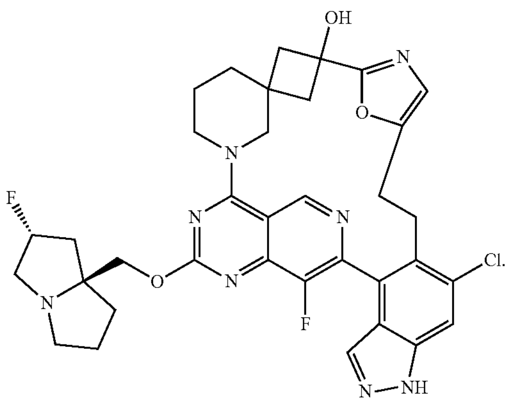 [SMILES: OC12CC3(CCCN(C3)c3nc(OC[C@@]45CCCN4C[C@H](F)C5)nc4c(F)c(ncc34)-c3c(c(Cl)cc4[nH]ncc34)CCc3cnc1o3)C2]

6. The compound or salt of claim 1, wherein the compound is

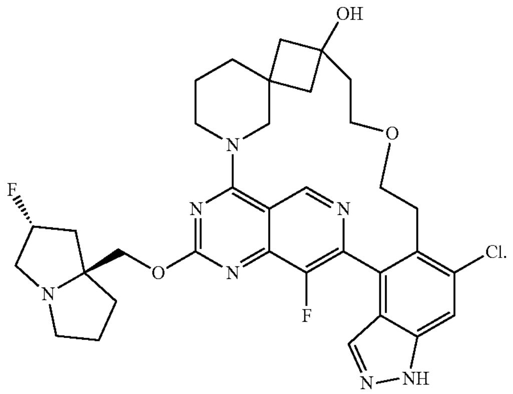 [SMILES: OC12CCOCCc3c(Cl)cc4[nH]ncc4c3-c3ncc4c(nc(OC[C@@]56CCCN5C[C@H](F)C6)nc4c3F)N3CCCC(C3)(C1)C2]

7. The compound or salt of claim 1, wherein the compound is

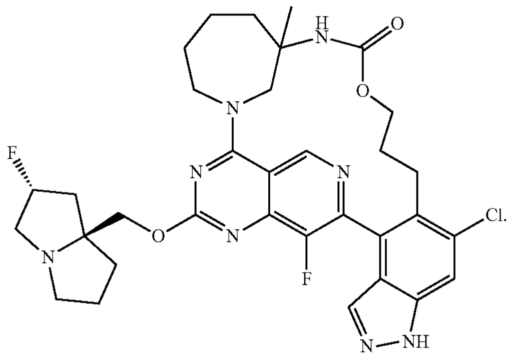 [SMILES: CC12CCCCN(C1)c1nc(OC[C@@]34CCCN3C[C@H](F)C4)nc3c(F)c(ncc13)-c1c(c(Cl)cc3[nH]ncc13)CCCOC(=O)N2]

8. The compound or salt of claim 1, wherein the compound is

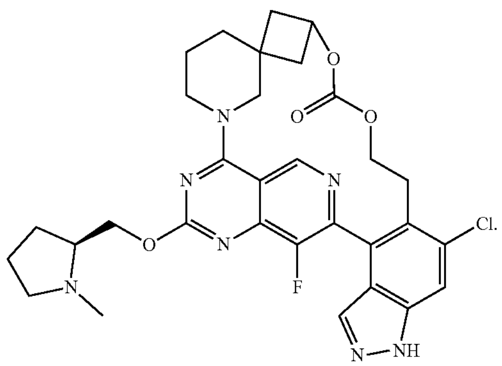 [SMILES: CN1CCC[C@H]1COc1nc2c3cnc(c(F)c3n1)-c1c(c(Cl)cc3[nH]ncc13)CCOC(=O)OC1CC3(CCCN2C3)C1]

9. The compound or salt of claim 1, wherein the compound is

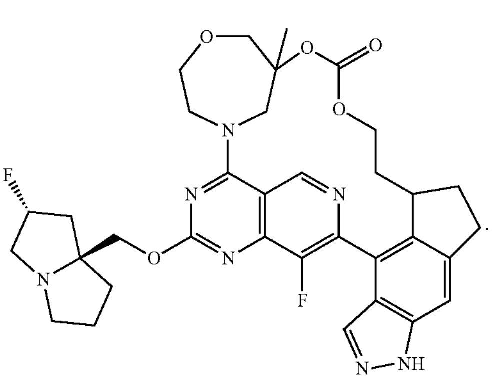 [SMILES: CC12COCCN(C1)c1nc(OC[C@@]34CCCN3C[C@H](F)C4)nc3c(F)c(ncc13)-c1c3c(cc4[nH]ncc14)CCC3CCOC(=O)O2]
10. The compound or salt of claim 1, wherein the compound is
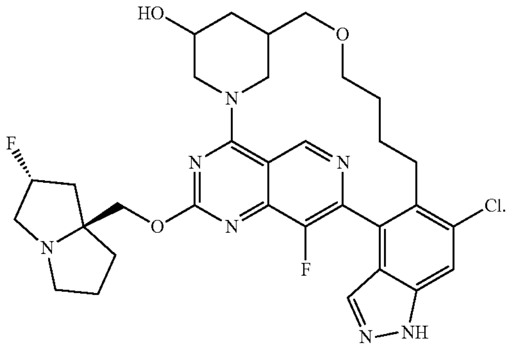 [SMILES: OC1CC2COCCCCc3c(Cl)cc4[nH]ncc4c3-c3ncc4c(nc(OC[C@@]56CCCN5C[C@H](F)C6)nc4c3F)N(C1)C2]
11. The compound or salt of claim 1, wherein the compound is
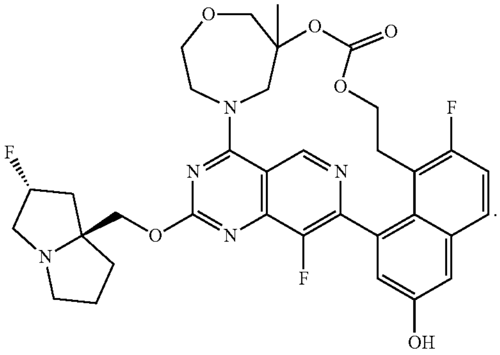 [SMILES: CC12COCCN(C1)c1nc(OC[C@@]34CCCN3C[C@H](F)C4)nc3c(F)c(ncc13)-c1cc(O)cc3ccc(F)c(c13)CCOC(=O)O2]
12. A compound, wherein the compound is:
| Compound |
| --- |
| 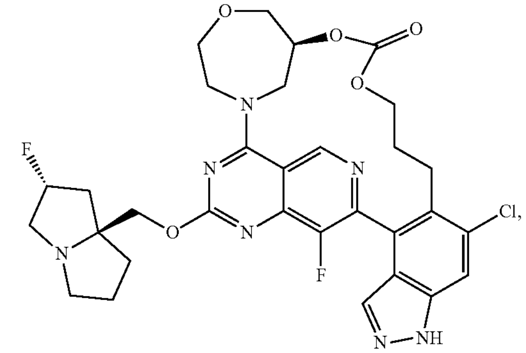 [SMILES: O=C1OCCCc2c(Cl)cc3[nH]ncc3c2-c2ncc3c(nc(OC[C@@]45CCCN4C[C@H](F)C5)nc3c2F)N2CCOC[C@H](C2)O1] |
| 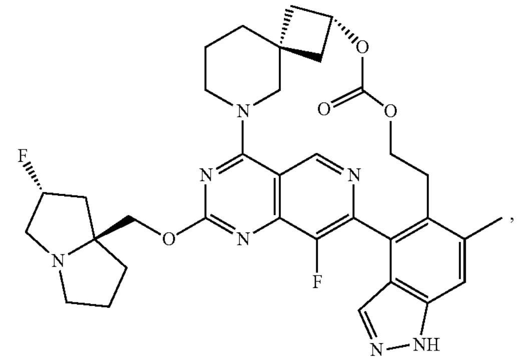 [SMILES: Cc1cc2[nH]ncc2c2c1CCOC(=O)O[C@H]1C[C@]3(CCCN(C3)c3nc(OC[C@@]45CCCN4C[C@H](F)C5)nc4c(F)c-2ncc34)C1] |
| 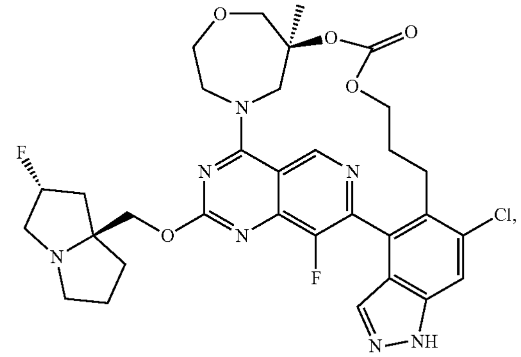 [SMILES: C[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2] |
| 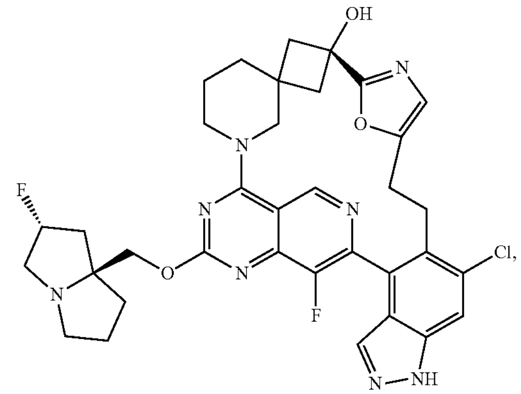 |

-continued
| Compound |
| --- |
| 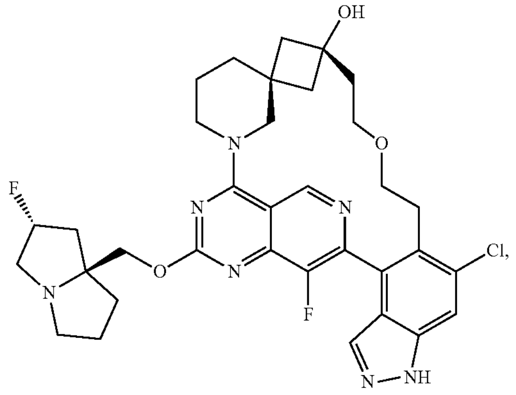 [SMILES: O[C@]12CCOCCc3c(Cl)cc4[nH]ncc4c3-c3ncc4c(nc(OC[C@@]56CCCN5C[C@H](F)C6)nc4c3F)N3CCC[C@@](C3)(C1)C2] |
| 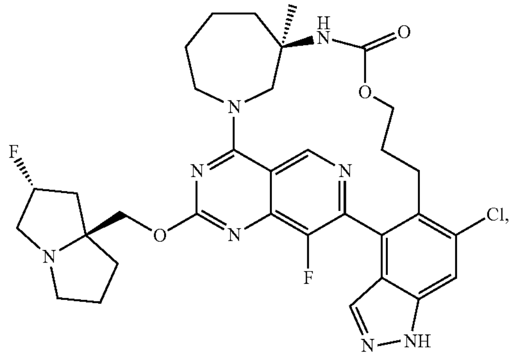 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCOC(=O)N2] |
| 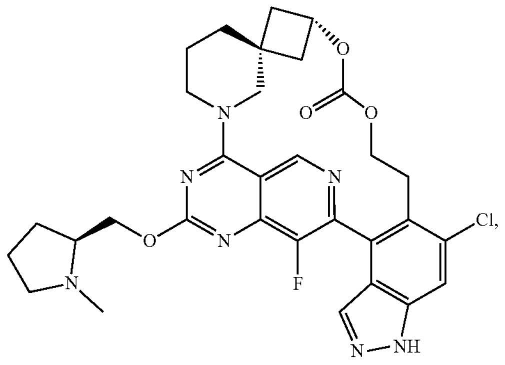 [SMILES: CN1CCC[C@H]1COc1nc2c3cnc(c(F)c3n1)-c1c(c(Cl)cc3[nH]ncc13)CCOC(=O)O[C@H]1C[C@]3(CCCN2C3)C1] |
| 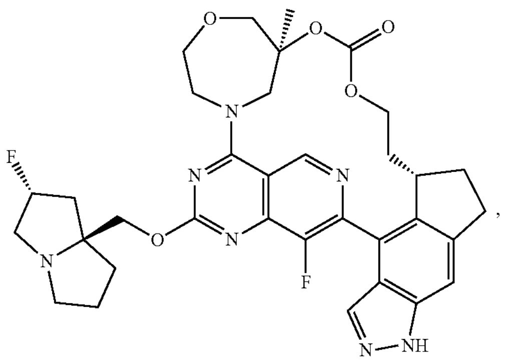 [SMILES: C[C@@]12COCCN(C1)c1nc(OC[C@@]34CCCN3C[C@H](F)C4)nc3c(F)c(ncc13)-c1c3c(cc4[nH]ncc14)CC[C@H]3CCOC(=O)O2] |
-continued
| Compound |
| --- |
| 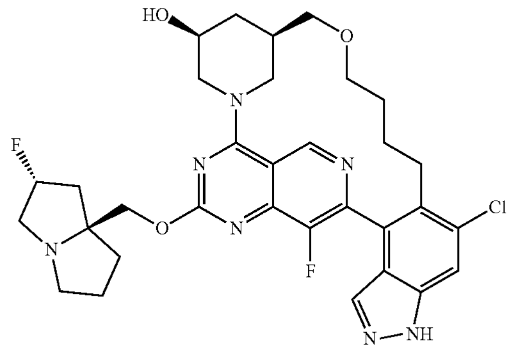 [SMILES: O[C@H]1C[C@H]2COCCCCc3c(Cl)cc4[nH]ncc4c3-c3ncc4c(nc(OC[C@@]56CCCN5C[C@H](F)C6)nc4c3F)N(C1)C2] |
| or |
| 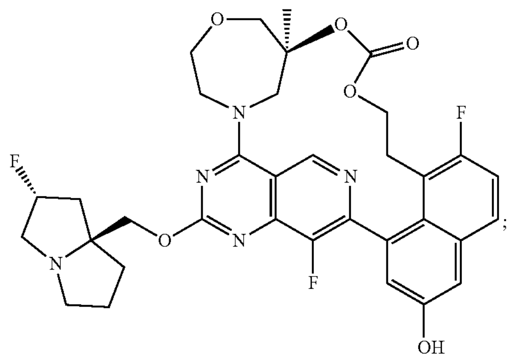 [SMILES: C[C@@]12COCCN(C1)c1nc(OC[C@@]34CCCN3C[C@H](F)C4)nc3c(F)c(ncc13)-c1cc(O)cc3ccc(F)c(c13)CCOC(=O)O2] |
or a pharmaceutically acceptable salt thereof.
13. The compound or salt of claim 12, wherein the compound is
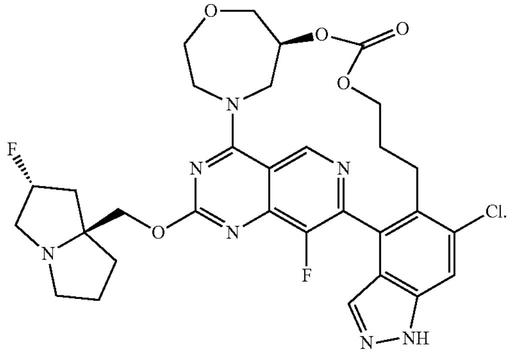
or a pharmaceutically acceptable salt thereof.
14. The compound or salt of claim 12, wherein the compound is

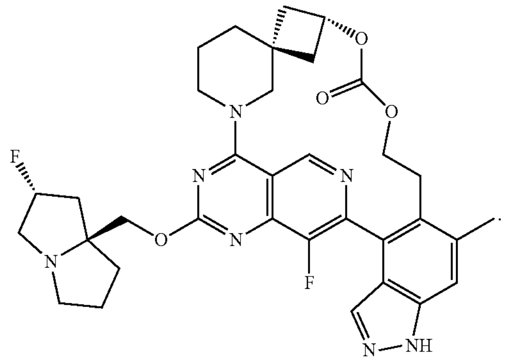 [SMILES: Cc1cc2[nH]ncc2c2c1CCOC(=O)O[C@H]1C[C@]3(CCCN(C3)c3nc(OC[C@@]45CCCN4C[C@H](F)C5)nc4c(F)c-2ncc34)C1]

15. The compound or salt of claim 12, wherein the compound is

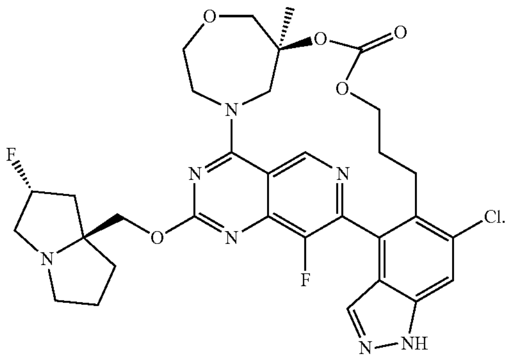 [SMILES: C[C@@]12COCCN(C1)c1nc(OC[C@@]34CCCN3C[C@H](F)C4)nc3c(F)c(ncc13)-c1c(c(Cl)cc3[nH]ncc13)CCCOC(=O)O2]

or a pharmaceutically acceptable salt thereof.

16. The compound or salt of claim 12, wherein the compound is

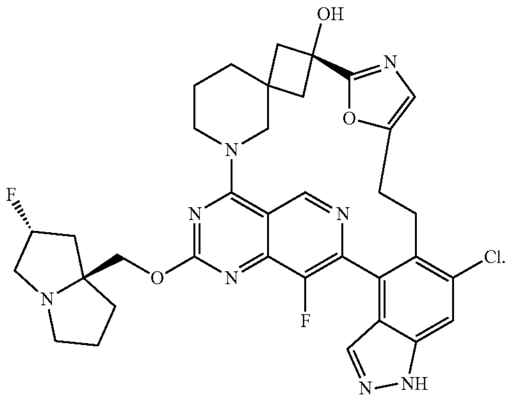

17. The compound or salt of claim 12, wherein the compound is

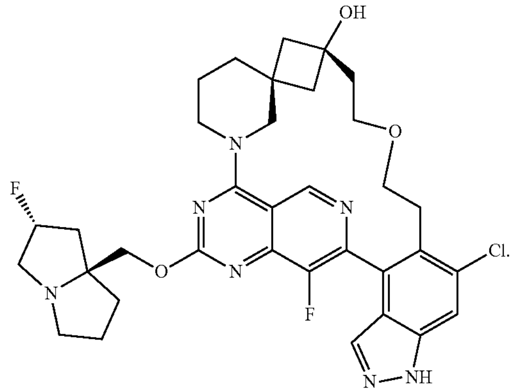 [SMILES: O[C@]12CCOCCc3c(Cl)cc4[nH]ncc4c3-c3ncc4c(nc(OC[C@@]56CCCN5C[C@H](F)C6)nc4c3F)N3CCC[C@@](C3)(C1)C2]

18. The compound or salt of claim 12, wherein the compound is

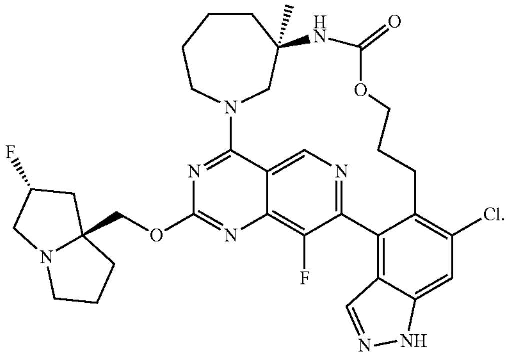 [SMILES: C[C@@]12CCCCN(C1)c1nc(OC[C@@]34CCCN3C[C@H](F)C4)nc3c(F)c(ncc13)-c1c(c(Cl)cc3[nH]ncc13)CCCOC(=O)N2]

19. The compound or salt of claim 12, wherein the compound is

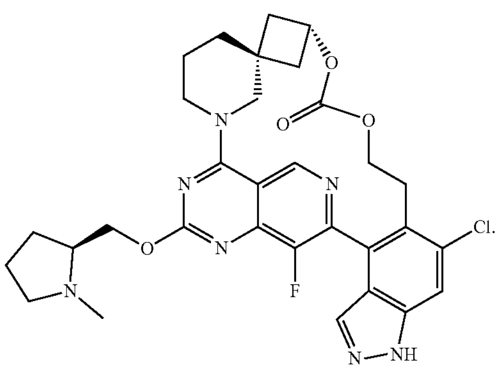 [SMILES: CN1CCC[C@H]1COc1nc2c3cnc(c(F)c3n1)-c1c(c(Cl)cc3[nH]ncc13)CCOC(=O)O[C@H]1C[C@]3(CCCN2C3)C1]

20. The compound or salt of claim 12, wherein the compound is

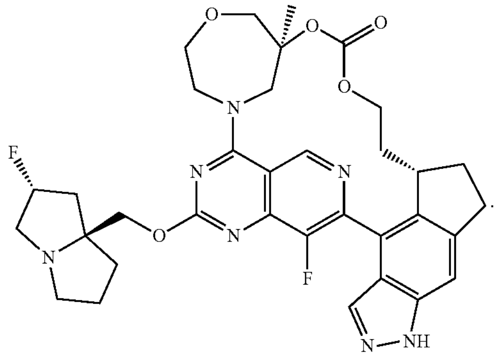 [SMILES: C[C@@]12COCCN(C1)c1nc(OC[C@@]34CCCN3C[C@H](F)C4)nc3c(F)c(ncc13)-c1c3c(cc4[nH]ncc14)CC[C@H]3CCOC(=O)O2]

21. The compound or salt of claim 12, wherein the compound is

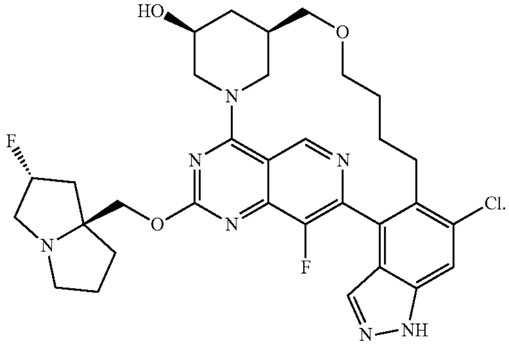 [SMILES: O[C@H]1C[C@H]2COCCCCc3c(Cl)cc4[nH]ncc4c3-c3ncc4c(nc(OC[C@@]56CCCN5C[C@H](F)C6)nc4c3F)N(C1)C2]

22. The compound or salt of claim 12, wherein the compound is

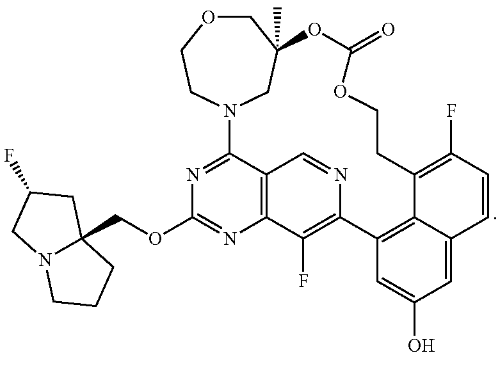 [SMILES: C[C@@]12COCCN(C1)c1nc(OC[C@@]34CCCN3C[C@H](F)C4)nc3c(F)c(ncc13)-c1cc(O)cc3ccc(F)c(c13)CCOC(=O)O2]

23. A pharmaceutical composition comprising the compound or salt according to claim 1 and a pharmaceutically acceptable excipient.

24. A method of treating cancer in a subject in need thereof, the method comprising administering to the subject a therapeutically effective amount of the compound or salt according to claim 1 or a pharmaceutical composition according to claim 23.

25. The method according to claim 24, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelionma, thyroid cancer, leukemia, or melanoma.

26. The method according to claim 24, wherein the cancer is non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

27. The method according to claim 26, wherein the cancer is non-small cell lung cancer.

28. The method according to claim 26, wherein the cancer is colorectal cancer.

29. The method according to claim 26, wherein the cancer is pancreatic cancer.

30. A pharmaceutical composition comprising the compound or salt according to claim 12 and a pharmaceutically acceptable excipient.

31. A method of treating cancer in a subject in need thereof, the method comprising administering to the subject a therapeutically effective amount of the compound or salt according to claim 12 or a therapeutically effective amount of the pharmaceutical composition according to claim 30.

32. The method according to claim 31, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

33. The method according to claim 31, wherein the cancer is non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

34. The method according to claim 33, wherein the cancer is non-small cell lung cancer.

35. The method according to claim 33, wherein the cancer is colorectal cancer.

36. The method according to claim 33, wherein the cancer is pancreatic cancer.

37. A pharmaceutical composition comprising the compound or salt according to claim 13 and a pharmaceutically acceptable excipient.

38. A method of treating cancer in a subject in need thereof, the method comprising administering to the subject a therapeutically effective amount of the compound or salt according to claim 13 or a therapeutically effective amount of the pharmaceutical composition according to claim 37.

39. The method according to claim 38, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

40. The method according to claim 38, wherein the cancer is non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

41. The method according to claim 40, wherein the cancer is non-small cell lung cancer.

42. The method according to claim 40, wherein the cancer is colorectal cancer.

43. The method according to claim 40, wherein the cancer is pancreatic cancer.

44. The method according to claim 41, wherein the cancer is non-small cell lung cancer wherein one or more cells express a KRAS G12D, G12V, G12A, G12S, G13D, Q61H, Q61L or G12C mutant protein.

45. The method according to claim 41, wherein the cancer is non-small cell lung cancer wherein one or more cells express a KRAS G12D, G12V, G12A, G12S or G12C mutant protein.

46. The method according to claim 45, wherein the cancer is non-small cell lung cancer wherein one or more cells express a KRAS G12C mutant protein.

47. The method according to claim 45, wherein the cancer is non-small cell lung cancer wherein one or more cells express a KRAS G12D mutant protein.

48. The method according to claim 45, wherein the cancer is non-small cell lung cancer wherein one or more cells express a KRAS G12V mutant protein.

49. The method according to claim 45, wherein the cancer is non-small cell lung cancer wherein one or more cells express a KRAS G12A mutant protein.

50. The method according to claim 42, wherein the cancer is colorectal cancer wherein one or more cells express a KRAS G12D, G12V, G12A, G12S, G13D, Q61H, Q61L or G12C mutant protein.

51. The method according to claim 42, wherein the cancer is colorectal cancer wherein one or more cells express a KRAS G12D, G12V, G12A, G12S or G12C mutant protein.

52. The method according to claim 51, wherein the cancer is colorectal cancer wherein one or more cells express a KRAS G12D mutant protein.

53. The method according to claim 51, wherein the cancer is colorectal cancer wherein one or more cells express a KRAS G12V mutant protein.

54. The method according to claim 51, wherein the cancer is colorectal cancer wherein one or more cells express a KRAS G12A mutant protein.

55. The method according to claim 51, wherein the cancer is colorectal cancer wherein one or more cells express a KRAS G12C mutant protein.

56. The method according to claim 43, wherein the cancer is pancreatic cancer wherein one or more cells express a KRAS G12D, G12V, G12A, G12S, G13D, Q61H, Q61L or G12C mutant protein.

57. The method according to claim 43, wherein the cancer is pancreatic cancer wherein one or more cells express a KRAS G12D, G12V, G12A, G12S or G12C mutant protein.

58. The method according to claim 57, wherein the cancer is pancreatic cancer wherein one or more cells express a KRAS G12D mutant protein.

59. The method according to claim 57, wherein the cancer is pancreatic cancer wherein one or more cells express a KRAS G12V mutant protein.

60. The method according to claim 57, wherein the cancer is pancreatic cancer wherein one or more cells express a KRAS G12C mutant protein.

61. The method according to claim 57, wherein the cancer is pancreatic cancer wherein one or more cells express a KRAS G12A mutant protein.

* * * * *